(12) United States Patent
Cai et al.

(10) Patent No.: US 11,352,329 B2
(45) Date of Patent: *Jun. 7, 2022

(54) HIV PROTEASE INHIBITORS

(71) Applicant: Gilead Sciences, Inc., Foster City, CA (US)

(72) Inventors: Zhenhong R. Cai, Palo Alto, CA (US); Aesop Cho, Mountain View, CA (US); Ana Zurisadai Gonzalez Buenrostro, San Mateo, CA (US); Xiaochun Han, San Jose, CA (US); Salman Y. Jabri, San Francisco, CA (US); Ryan McFadden, Foster City, CA (US); Yingmei Qi, Foster City, CA (US); Johannes Voigt, Cambridge, MA (US); Jie Xu, Foster City, CA (US); Lianhong Xu, Palo Alto, CA (US); Hong Yang, Fremont, CA (US)

(73) Assignee: Gilead Sciences, Inc., Foster City, CA (US)

( * ) Notice: Subject to any disclaimer, the term of this patent is extended or adjusted under 35 U.S.C. 154(b) by 26 days.

This patent is subject to a terminal disclaimer.

(21) Appl. No.: 16/925,096

(22) Filed: Jul. 9, 2020

(65) Prior Publication Data
US 2021/0078959 A1    Mar. 18, 2021

Related U.S. Application Data

(63) Continuation of application No. 16/158,446, filed on Oct. 12, 2018, now Pat. No. 10,774,053.

(60) Provisional application No. 62/572,243, filed on Oct. 13, 2017.

(51) Int. Cl.
| | |
|---|---|
| C07D 247/00 | (2006.01) |
| A61P 31/18 | (2006.01) |
| C07D 401/10 | (2006.01) |
| C07D 403/14 | (2006.01) |
| C07D 233/88 | (2006.01) |
| C07D 487/04 | (2006.01) |
| C07D 417/10 | (2006.01) |
| C07D 471/04 | (2006.01) |
| C07D 417/14 | (2006.01) |
| C07D 491/107 | (2006.01) |
| C07D 401/14 | (2006.01) |
| C07D 405/14 | (2006.01) |
| C07D 413/14 | (2006.01) |
| C07D 403/10 | (2006.01) |
| C07D 413/10 | (2006.01) |
| A61K 45/06 | (2006.01) |

(52) U.S. Cl.
CPC ........... *C07D 247/00* (2013.01); *A61P 31/18* (2018.01); *C07D 233/88* (2013.01); *C07D 401/10* (2013.01); *C07D 401/14* (2013.01); *C07D 403/10* (2013.01); *C07D 403/14* (2013.01); *C07D 405/14* (2013.01); *C07D 413/10* (2013.01); *C07D 413/14* (2013.01); *C07D 417/10* (2013.01); *C07D 417/14* (2013.01); *C07D 471/04* (2013.01); *C07D 487/04* (2013.01); *C07D 491/107* (2013.01); *A61K 45/06* (2013.01)

(58) Field of Classification Search
None
See application file for complete search history.

(56) References Cited

U.S. PATENT DOCUMENTS

| | | |
|---|---|---|
| 5,243,054 A | 9/1993 | Naka et al. |
| 2006/0040999 A1 | 2/2006 | All et al. |
| 2007/0155750 A1 | 7/2007 | Neamati et al. |
| 2009/0186926 A1 | 7/2009 | Sheth et al. |
| 2011/0065916 A1 | 3/2011 | Spyvee et al. |
| 2014/0179751 A1 | 6/2014 | Graef et al. |

(Continued)

FOREIGN PATENT DOCUMENTS

| | | |
|---|---|---|
| TW | I360542 B | 3/2012 |
| WO | WO-2005/058311 A1 | 6/2005 |

(Continued)

OTHER PUBLICATIONS

International Search Report and Written Opinion dated Jan. 3, 2019 on International Application No. PCT/US2018/055554.

(Continued)

*Primary Examiner* — Samantha L Shterengarts

(57) ABSTRACT

The invention provides a compound of Formula I:

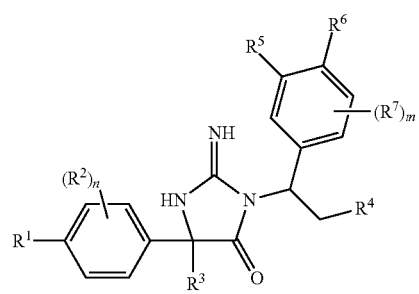

or a pharmaceutically acceptable salt thereof as described herein. The invention also provides pharmaceutical compositions comprising a compound of Formula I, processes for preparing compounds of Formula I, therapeutic methods for treating the proliferation of the HIV virus, treating AIDS or delaying the onset of AIDS symptoms in a mammal using compounds of Formula I.

5 Claims, No Drawings

Specification includes a Sequence Listing.

(56) References Cited

U.S. PATENT DOCUMENTS

2015/0376136 A1    12/2015  Chumakova et al.
2016/0024071 A1     1/2016  Garofalo et al.

FOREIGN PATENT DOCUMENTS

| WO | WO-2007/079186 A2 | 7/2007 |
| WO | WO-2007/081569 A2 | 7/2007 |
| WO | WO-2007/081571 A2 | 7/2007 |
| WO | WO-2007/092642 A2 | 8/2007 |
| WO | WO-2011/133719 A2 | 10/2011 |
| WO | WO-2014/145331 A1 | 9/2014 |
| WO | WO-2017/142821 A1 | 8/2017 |
| WO | WO-2018/106519 A1 | 6/2018 |
| WO | WO-2018/118829 A1 | 6/2018 |

OTHER PUBLICATIONS

Office Action dated Oct. 7, 2019 for Taiwan Appl. No. 107128405.
Office Action dated Jan. 2, 2020 for Gulf Cooperation Council Appl. No. 2018-36190.
Third Party Observation dated Feb. 14, 2020 for International Appl. No. PCT/US2018/055554.
Ali, A., et al., Discovery of HIV-1 Protease Inhibitors with Picomolar Affinities Incorporating N-Aryl-oxazolidinone-5-carboxamides as Novel P2 Ligands, Journal of Medicinal Chemistry, 2006, 49:7342-7356.
U.S. Appl. No. 16/849,747, filed Apr. 15, 2020, Aesop Cho, et al.
U.S. Appl. No. 16/849,201, dated Apr. 15, 2020, Bing Shi.

SEQUENCE LISTING

```
<160> NUMBER OF SEQ ID NOS: 2

<210> SEQ ID NO 1
<211> LENGTH: 6
<212> TYPE: PRT
<213> ORGANISM: Artificial Sequence
<220> FEATURE:
<223> OTHER INFORMATION: synthetic polypeptide substrate
<220> FEATURE:
<221> NAME/KEY: MOD_RES
<222> LOCATION: (1)..(1)
<223> OTHER INFORMATION: 2-aminobenzoyl
<220> FEATURE:
<221> NAME/KEY: misc_feature
<222> LOCATION: (3)..(3)
<223> OTHER INFORMATION: Xaa = norleucine (Nle)
<220> FEATURE:
<221> NAME/KEY: MOD_RES
<222> LOCATION: (4)..(4)
<223> OTHER INFORMATION: p-nitro

<400> SEQUENCE: 1

Thr Ile Xaa Phe Gln Arg
1               5

<210> SEQ ID NO 2
<211> LENGTH: 13
<212> TYPE: PRT
<213> ORGANISM: Artificial Sequence
<220> FEATURE:
<223> OTHER INFORMATION: synthetic polypeptide substrate
<220> FEATURE:
<221> NAME/KEY: MOD_RES
<222> LOCATION: (1)..(1)
<223> OTHER INFORMATION: 7-methoxycoumarin acetic acid (Mca)
<220> FEATURE:
<221> NAME/KEY: MOD_RES
<222> LOCATION: (12)..(12)
<223> OTHER INFORMATION: 2,4-dinitrophenyl (Dnp)

<400> SEQUENCE: 2

Ser Glu Val Asn Leu Asp Ala Glu Phe Arg Lys Arg Arg
1               5                   10
```

HIV PROTEASE INHIBITORS

CROSS REFERENCE TO RELATED APPLICATIONS

This Application is a continuation application of U.S. application Ser. No. 16/158,446, filed Oct. 12, 2018, now U.S. Pat. No. 10,774,053, which claims the benefit of U.S. Provisional Application 62/572,243 filed on Oct. 13, 2017. The entire contents of these applications are incorporated herein by reference in their entirety.

The present disclosure relates to novel compounds for use in the treatment of a Retroviridae viral infection including an infection caused by the HIV virus. The present disclosure also relates to intermediates for its preparation and to pharmaceutical compositions containing those compounds.

BACKGROUND

Human immunodeficiency virus (HIV) infection and related diseases are a major public health problem worldwide. Human immunodeficiency virus type 1 (HIV-1) encodes three enzymes which are required for viral replication: reverse transcriptase, protease, and integrase. Several protease inhibitors (PI) are presently approved for use in AIDS or HIV. Yet many PI inhibitors suffer from high rates of hepatic metabolism, which may require co-administration of a booster or more frequent dosing. Furthermore, viral resistance remains a problem. Accordingly, there is a need for new agents that inhibit the replication of HIV.

SUMMARY

The present disclosure provides compounds and methods for the treatment of an HIV infection. Accordingly, in one embodiment, the invention provides a compound of Formula I:

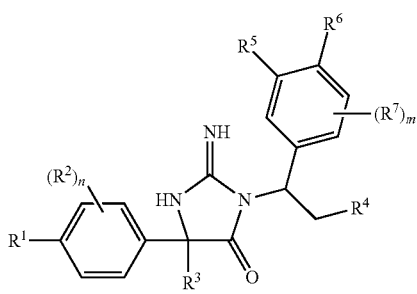

I where the variables ($R^1$, $R^2$, $R^3$, $R^4$, $R^5$, $R^6$, $R^7$, m, and n) shown are defined below.

$R^1$ is selected from the group consisting of hydrogen, halogen, cyano, $C_{2-6}$ alkynyl, $-OR^a$, 5-10 membered heteroaryl, 3-12 membered heterocyclyl, 5-10 membered aryl and 3-10 membered cycloalkyl, where each 5-10 membered heteroaryl, 3-12 membered heterocyclyl, 6-10 membered aryl and 3-10 membered cycloalkyl is optionally substituted with 1-5 $R^{20}$ groups.

Each $R^2$ is independently selected from the group consisting of hydrogen, $C_{1-6}$ alkyl, $-NR^aR^b$, halogen, cyano, or $-OR^a$, wherein the $C_{1-6}$ alkyl, is optionally substituted with 1-5 $R^{20}$ groups; or $R^1$ and $R^2$ together with the atoms to which they are attached form a heteroaryl optionally substituted with 1-5 $R^{20}$ groups. Here, n is either 0, 1, or 2.

$R^3$ is $C_{1-6}$ alkyl, $C_{2-6}$ alkynyl, or 3-10 membered cycloalkyl, each optionally substituted with 1-5 $R^{20}$ groups.

$R^4$ is selected from the group consisting of $-C(O)R^a$, $-C(O)OR^a$, $-C(O)NR^aR^b$, $-OC(O)NR^aR^b$, $-NR^aC(O)R^b$, $-NR^aC(O)OR^b$, $-S(O)_{0-2}R^a$, $-S(O)_2NR^aR^b$, $-NR^aS(O)_2R^b$, $-NR^aS(O)_{1-2}OR^b$, $-OS(O)_{1-2}NR^aR^b$ or $-OR^a$.

$R^5$ is selected from the group consisting of cyano, halo, and 5-10 membered heteroaryl, where the 5-10 membered heteroaryl is optionally substituted with 1-5 $R^{20}$ groups.

$R^6$ is hydrogen, halogen, cyano, $C_{1-3}$ haloalkoxy, $-C(O)NR^aR^b$, or 5-10 membered heteroaryl optionally substituted with 1-5 $R^{20}$ groups.

Each $R^7$ is independently selected from the group consisting of $C_{1-6}$ alkyl, $C_{1-6}$ alkoxy, $-NR^aR^b$, halogen, cyano, 5-10 membered aryl, 3-6 membered cycloalkyl, 5-10 membered heteroaryl and 3-12 membered heterocyclyl, where each $C_{1-6}$ alkyl, $C_{1-6}$ alkoxy, 5-10 membered aryl, 3-6 membered cycloalkyl, 5-10 membered heteroaryl and 3-12 membered heterocyclyl is optionally substituted with 1-5 $R^{20}$ groups. Here, m is either 0 or 1.

Each $R^a$ and $R^b$ is independently selected from the group consisting of H, $C_{1-6}$ alkyl, 3-10 membered cycloalkyl, 3-12 membered heterocyclyl, 6-10 membered aryl, 5-10 membered heteroaryl, each of which is optionally substituted with from one to five $R^{21}$ groups; or $R^a$ and $R^b$ together with the atoms to which they are attached form a 3-12 membered heterocyclyl optionally substituted with one to five $R^{21}$ groups.

Each $R^{20}$ is independently selected from the group consisting $C_{1-6}$ alkyl, $C_{1-6}$ haloalkyl, 3-10 membered cycloalkyl, $C_{1-6}$ alkoxy, 3-12 membered heterocyclyl, 6-10 membered aryl, 5-10 membered heteroaryl, halogen, oxo, $-OR^a$, $-C(O)R^a$, $-C(O)OR^a$, $-C(O)NR^aR^b$, $-OC(O)NR^aR^b$, $-NR^aR^b$, $-NR^aC(O)R^b$, $-NR^aC(O)OR^b$, $-S(O)_{0-2}R^a$, $-S(O)_2NR^aR^b$, $-NR^aS(O)_2R^b$, $-N_3$, $-CN$, or $-NO_2$, or two $R^{20}$ groups appended to the same group can join together to form a fused, spiro or bridged $C_3$-10 cylcloalkyl or 3-12 membered heterocyclyl ring, wherein each $C_{1-6}$ alkyl, 3-10 membered cycloalkyl, $C_{1-6}$ alkoxy, 3-12 membered heterocyclyl, 5-10 membered aryl, 5-10 membered heteroaryl is optionally substituted with from one to five halogen, oxo, $-OR^a$, $-C(O)R^a$, $-C(O)OR^a$, $-C(O)NR^aR^b$, $-OC(O)NR^aR^b$, $-NR^aR^b$, $-NR^aC(O)R^b$, $-NR^aC(O)OR^b$, $-S(O)_{0-2}R^a$, $-S(O)_2NR^aR^b$, $-NR^aS(O)_2R^b$, $-N_3$, $-CN$, 3-12 membered heterocyclyl, or $-NO_2$.

Each $R^{21}$ is independently selected from the group consisting of $C_{1-6}$ alkyl, $C_{1-6}$ haloalkyl, 3-10 membered cycloalkyl, $C_{1-6}$ alkoxy, 3-12 membered heterocyclyl, 6-10 membered aryl, 5-10 membered heteroaryl, hydroxyl, amino, $-S(O)_2-CH_3$, $C_{1-6}$ alkylamino, $-CN$ or halogen.

Each of the variations for Formula I disclosed above can further include pharmaceutically acceptable salt thereof.

Also provided is a pharmaceutical composition comprising a therapeutically effective amount of a compound disclosed herein, or a pharmaceutically acceptable salt thereof, and a pharmaceutically acceptable excipient. In certain embodiments, the pharmaceutical composition further comprising one, two, three, or four additional therapeutic agents.

Also provided is method of treating or preventing a human immunodeficiency virus (HIV) infection comprising administering a therapeutically effective amount of a compound disclosed herein, or a pharmaceutically acceptable salt thereof, to a subject in need thereof.

In certain embodiments, the current disclosure relates to an article of manufacture comprising a unit dosage of a compound disclosed herein, or a pharmaceutically acceptable salt thereof.

Also provided is a compound disclosed herein, or a pharmaceutically acceptable salt thereof, for use in therapy.

A compound disclosed herein, or a pharmaceutically acceptable salt thereof, for use in a method of treating or preventing a human immunodeficiency virus (HIV) infection comprising administering a therapeutically effective amount of said compound to a subject in need thereof, is also provided.

DETAILED DESCRIPTION

The following is a list of abbreviations and acronyms used throughout the application:
Abbreviation Meaning
° C. Degree Celsius
ATP Adenosine-5'-triphosphate
aq aqueous
AcOH Acetic acid
calc'd Calculated
compd Compound
d Doublet
dd Doublet of doublets
DCE 1,2-dichloroethane
DCM Dichloromethane
DIPEA N,N-diisopropylethylamine
DME 1,2-dimethoxyethane
DMF Dimethylformamide
DMSO Dimethylsulfoxide
dppf 1,1'-Bis(diphenylphosphino)ferrocene
EGTA Ethylene glycol tetraacetic acid
EtOAc Ethyl acetate
equiv/eq Equivalents
ESI Electrospray ionization
Ac Acetate
Et Ethyl
g Grams
HATU 2-(7-Aza-1H-Benzotriazole-1-yl)-1,1,3,3-tetramethyluronium hexafluorophosphate
hERG human Ether-à-go-go Related Gene
HPLC High-performance liquid chromatography
h/hr Hours
Hz Hertz
IC$_{50}$ The half maximal inhibitory concentration
J Coupling constant
Kg Kilogram
M Molar
m multiplet
m/z mass-to-charge ratio
M+ Mass peak
M+H Mass peak plus hydrogen
Me Methyl
MeOH Methyl alcohol/methanol
mg Milligram
MHz Megahertz
min/m Minute
ml/mL Milliliter
mM Millimolar
mmol Millimole
MS Mass spectroscopy
mw Microwave
N Normal
mol Mole
nM Nanomolar
nmol Nanomole
NMP N-methylpyrrolidinone
NMR Nuclear magnetic resonance
Ph Phenyl
ppm Parts per million
prep Preparative
Rf Retention factor
RP Reverse phase
RT/rt Room temperature
s Second
s Singlet
t Triplet
TEA Triethylamine
TFA Trifluoroacetic acid
TLC Thin layer chromatography
TMS trimethylsilyl
WT Wild type
δ Chemical shift
μg Microgram
μL/μl Microliter
μM Micromolar
μm Micrometer
μmol Micromole Unless defined otherwise, all technical and scientific terms used herein have the same meaning as commonly understood by one of ordinary skill in the art. It must be noted that as used herein and in the appended claims, the singular forms "a", "and", and "the" include plural referents unless the context clearly dictates otherwise. Thus, e.g., reference to "the compound" includes a plurality of such compounds and reference to "the assay" includes reference to one or more assays and equivalents thereof known to those skilled in the art, and so forth.

A dash at the front or end of a chemical group is a matter of convenience; chemical groups may be depicted with or without one or more dashes without losing their ordinary meaning. A wavy line drawn through a line in a structure indicates a point of attachment of a group, e.g.:

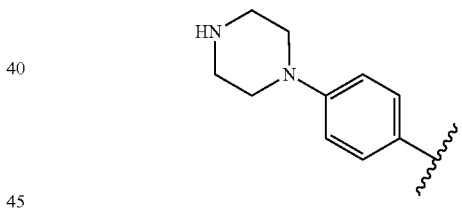

A dashed line indicates an optional bond. Where multiple substituent groups are identified the point of attachment is at the terminal substituent (e.g. for "alkylaminocarbonyl" the point of attachment is at the carbonyl substituent).

The prefix "$C_{x-y}$" indicates that the following group has from x (e.g. 1) to y (e.g. 6) carbon atoms, one or more of which, in certain groups (e.g. heteroalkyl, heteroaryl, heteroarylalkyl, etc), may be replaced with one or more heteroatoms or heteroatomic groups. For example, "$C_{1-6}$ alkyl" indicates that the alkyl group has from 1 to 6 carbon atoms. Likewise, the term "x-y membered" rings, wherein x and y are numerical ranges, such as "3 to 12-membered heterocyclyl", refers to a ring containing x-y atoms (e.g. 3-12), of which up to 80% may be heteroatoms, such as N, O, S, P, and the remaining atoms are carbon.

Also, certain commonly used alternative chemical names may or may not be used. For example, a divalent group such as a divalent "alkyl" group, a divalent "aryl" group, etc., may also be referred to as an "alkylene" group or an "alkylenyl" group, or alkylyl group, an "arylene" group or an "arylenyl" group, or arylyl group, respectively.

"A compound disclosed herein" or "a compound of the present disclosure" refers to the compounds of Formula (I), (Ia), (Ib), (Ic), (Id), and/or (Ie). Also included are the specific compounds of Examples 1-245.

"Alkyl" refers to any group derived from a linear or branched saturated hydrocarbon. Alkyl groups include, but are not limited to, methyl, ethyl, propyl such as propan-1-yl, propan-2-yl (iso-propyl), butyls such as butan-1-yl, butan-2-yl (sec-butyl), 2-methyl-propan-1-yl (iso-butyl), 2-methyl-propan-2-yl (t-butyl), pentyls, hexyls, octyls, dectyls, and the like. Unless otherwise specified, an alkyl group has from 1 to 10 carbon atoms, for example from 1 to 6 carbon atoms, for example from 1 to 4 carbon atoms.

"Alkenyl" refers to any group derived from a straight or branched hydrocarbon with at least one carbon-carbon double bond. Alkenyl groups include, but are not limited to, ethenyl (vinyl), propenyl (allyl), 1-butenyl, 1,3-butadienyl, and the like. Unless otherwise specified, an alkenyl group has from 2 to 10 carbon atoms, for example from 2 to 6 carbon atoms, for example from 2 to 4 carbon atoms.

"Alkynyl" refers to any group derived from a straight or branched hydrocarbon with at least one carbon-carbon triple bond and includes those groups having one triple bond and one double bond. Examples of alkynyl groups include, but are not limited to, ethynyl (—C≡C—), propargyl (—CH$_2$C≡C—), (E)-pent-3-en-1-ynyl, and the like. Unless otherwise specified, an alkynyl group has from 2 to 10 carbon atoms, for example from 2 to 6 carbon atoms, for example from 2 to 4 carbon atoms.

"Amino" refers to —NH$_2$. Amino groups may also be substituted as described herein, such as with alkyl, carbonyl or other amino groups. The term "alkylamino" refers to an amino group substituted with one or two alkyl substituents (e.g. dimethylamino or propylamino).

The term "aryl" as used herein refers to a single all carbon aromatic ring or a multiple condensed all carbon ring system wherein at least one of the rings is aromatic. For example, in certain embodiments, an aryl group has 6 to 20 carbon atoms, 6 to 14 carbon atoms, or 6 to 12 carbon atoms. Aryl includes a phenyl radical. Aryl also includes multiple condensed ring systems (e.g., ring systems comprising 2, 3 or 4 rings) having about 9 to 20 carbon atoms in which at least one ring is aromatic and wherein the other rings may be aromatic or not aromatic (i.e., carbocycle). Such multiple condensed ring systems are optionally substituted with one or more (e.g., 1, 2 or 3) oxo groups on any carbocycle portion of the multiple condensed ring system. The rings of the multiple condensed ring system can be connected to each other via fused, spiro and bridged bonds when allowed by valency requirements. It is also to be understood that when reference is made to a certain atom-range membered aryl (e.g., 6-10 membered aryl), the atom range is for the total ring atoms of the aryl. For example, a 6-membered aryl would include phenyl and a 10-membered aryl would include naphthyl and 1, 2, 3, 4-tetrahydronaphthyl. Aryl groups include, but are not limited to, those groups derived from acenaphthylene, anthracene, azulene, benzene, chrysene, a cyclopentadienyl anion, naphthalene, fluoranthene, fluorene, indane, perylene, phenalene, phenanthrene, pyrene and the like. Non-limiting examples of aryl groups include, but are not limited to, phenyl, indenyl, naphthyl, 1, 2, 3, 4-tetrahydronaphthyl, anthracenyl, and the like.

"Bridged" refers to a ring fusion wherein non-adjacent atoms on a ring are joined by a divalent substituent, such as an alkylenyl or heteroalkylenyl group or a single heteroatom. Quinuclidinyl and adamantanyl are examples of bridged ring systems.

The term "cycloalkyl" refers to a single saturated or partially unsaturated all carbon ring having 3 to 20 annular carbon atoms (i.e., C$_{3-20}$ cycloalkyl), for example from 3 to 12 annular atoms, for example from 3 to 10 annular atoms. The term "cycloalkyl" also includes multiple condensed, saturated and partially unsaturated all carbon ring systems (e.g., ring systems comprising 2, 3 or 4 carbocyclic rings). Accordingly, cycloalkyl includes multicyclic carbocycles such as a bicyclic carbocycles (e.g., bicyclic carbocycles having about 6 to 12 annular carbon atoms such as bicyclo [3.1.0]hexane and bicyclo[2.1.1]hexane), and polycyclic carbocycles (e.g tricyclic and tetracyclic carbocycles with up to about 20 annular carbon atoms). The rings of a multiple condensed ring system can be connected to each other via fused, spiro and bridged bonds when allowed by valency requirements. Non-limiting examples of monocyclic cycloalkyl include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, spiro [3.3]heptane, and 1-cyclohex-3-enyl.

"Halo" and "halogen" refer to fluoro, chloro, bromo and iodo.

"Haloalkyl" refers to an alkyl wherein one or more hydrogen atoms are each replaced by a halogen. Examples include, but are not limited to, —CH$_2$Cl, —CH$_2$F, —CH$_2$Br, —CFClBr, —CH$_2$CH$_2$Cl, —CH$_2$CH$_2$F, —CF$_3$, —CH$_2$CF$_3$, —CH$_2$CCl$_3$, and the like, as well as alkyl groups such as perfluoroalkyl in which all hydrogen atoms are replaced by fluorine atoms.

"Alkoxy" or "alkoxyl" refers to a moiety of the formula —O-alkyl, wherein the alkyl portion is as defined above. For example, C$_{1-4}$ alkoxy refers to a moiety having 1-4 carbon alkyl group attached to the oxygen. "Haloalkoxy" or "haloalkoxyl" refers to a moiety of the formula —O-haloalkyl, wherein the haloalkyl portion is as defined above. For example, C$_{1-4}$ alkoxy refers to a moiety having 1-4 carbon halo alkyl group attached to the oxygen.

"Heteroalkyl" refers to an alkyl in which one or more of the carbon atoms (and any associated hydrogen atoms) are each independently replaced with the same or different heteroatom or heteroatomic ngroup. Heteroatoms include, but are not limited to, N, P, O, S, etc. Heteroatomic groups include, but are not limited to, —NR—, —O—, —S—, —PH—, —P(O)$_2$—, —S(O)—, —S(O)$_2$—, and the like, where R is H, alkyl, aryl, cycloalkyl, heteroalkyl, heteroaryl or cycloheteroalkyl. Heteroalkyl groups include, but are not limited to, —OCH$_3$, —CH$_2$OCH$_3$, —SCH$_3$, —CH$_2$SCH$_3$, —NRCH$_3$, —CH$_2$NRCH$_3$, —CH$_2$OH and the like, where R is hydrogen, alkyl, aryl, arylalkyl, heteroalkyl, or heteroaryl, each of which may be optionally substituted. A heteroalkyl group comprises from 1 to 10 carbon and up to three or four hetero atoms, e.g., from 1 to 6 carbon and from 1 to 2 hetero atoms.

"Heteroaryl" refers to mono or multicyclic aryl group in which one or more of the aromatic carbon atoms (and any associated hydrogen atoms) are independently replaced with the same or different heteroatom or heteroatomic group, as defined above. Multicyclic ring systems are included in heteroaryl and may be attached at the ring with the heteroatom or the aryl ring. Heteroaryl groups include, but are not limited to, groups derived from acridine, benzoimidazole, benzothiophene, benzofuran, benzoxazole, benzothiazole, carbazole, carboline, cinnoline, furan, imidazole, imidazopyridine, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyridone, pyrimidine, pyrrole, pyrrolizine, quinazoline, quinoline, quinolizine, quinoxaline, tetrazole, thiadiazole, thiazole, thiophene, triazole, xanthene, and the like. Heteroaryl groups may have 5-12 members, 5-10 members, or 5-6 members.

The term "heterocyclyl" or "heterocycle" as used herein refers to a single saturated or partially unsaturated non-aromatic ring or a non-aromatic multiple ring system that has at least one heteroatom in the ring (i.e., at least one annular heteroatom selected from oxygen, nitrogen, and sulfur). Unless otherwise specified, a heterocyclyl group has from 5 to about 20 annular atoms, for example from 3 to 12 annular atoms, for example from 3 to 10 annular atoms, for example from 5 to 10 annular atoms or for example from 5 to 6 annular atoms. Thus, the term includes single saturated or partially unsaturated rings (e.g., 3, 4, 5, 6 or 7-membered rings) having from about 1 to 6 annular carbon atoms and from about 1 to 3 annular heteroatoms selected from the group consisting of oxygen, nitrogen and sulfur in the ring. The rings of the multiple condensed ring (e.g. bicyclic heterocyclyl) system can be connected to each other via fused, spiro and bridged bonds when allowed by valency requirements. Heterocycles include, but are not limited to, groups derived from azetidine, aziridine, imidazolidine, morpholine, oxirane (epoxide), oxetane, piperazine, piperidine, pyrazolidine, piperidine, pyrrolidine, pyrrolidinone, tetrahydrofuran, tetrahydrothiophene, dihydropyridine, tetrahydropyridine, tetrahydro-2H-thiopyran 1,1-dioxide, quinuclidine, N-bromopyrrolidine, N-chloropiperidine, and the like. Heterocycles include spirocycles, such as, for example, aza or oxo-spiroheptanes. Heterocyclyl groups also include partially unsaturated ring systems containing one or more double bonds, including fused ring systems with one aromatic ring and one non-aromatic ring, but not fully aromatic ring systems. Examples include dihydroquinolines, e.g. 3,4-dihydroquinoline, dihydroisoquinolines, e.g. 1,2-dihydroisoquinoline, dihydroimidazole, tetrahydroimidazole, etc., indoline, isoindoline, isoindolones (e.g. isoindolin-1-one), isatin, dihydrophthalazine, quinolinone, spiro[cyclopropane-1,1'-isoindolin]-3'-one, and the like. Additional examples of heterocycles include 3,8-diazabicyclo[3.2.1]octanyl, 2,5-diazabicyclo[2.2.1]heptanyl, 3,6-diazabicyclo[3.1.1]heptanyl, 3-oxa-7,9-diazabicyclo[3.3.1]nonanyl, and hexahydropyrazino[2,1-c][1,4]oxazinyl, for example.

"Hydrogen" or "H" used herein can be either hydrogen or the hydrogens within any group disclosed can be substituted with deuterium.

"Hydroxyl" and "hydroxy" are used interchangeably and refer to —OH. "Oxo" refers to

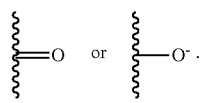

Where tautomeric forms of the compound exist, hydroxyl and oxo groups are interchangeable. In some embodiments, oxo refers to an oxygen linker:

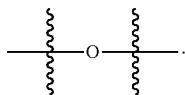

It is understood that combinations of chemical groups may be used and will be recognized by persons of ordinary skill in the art. For instance, the group "hydroxyalkyl" would refer to a hydroxyl group attached to an alkyl group. A great number of such combinations may be readily envisaged. Additional examples of substituent combinations used herein include: $C_{1-6}$ alkylamiocarbonyl (e.g. $CH_3CH_2NHC(O)$—) $C_{1-6}$ alkoxycarbonyl (e.g. $CH_3O$—C(O)—), 5-7 membered heterocyclyl-$C_{1-6}$ alkyl (e.g. piperazinyl-$CH_2$—), $C_{1-6}$ alkyl sulfonyl-5-7 membered heterocyclyl (e.g. $CH_3S(O)_2$-morpholinyl-), 5-7 membered heterocyclyl $C_{1-6}$ alkoxy 5-7 membered heterocyclyloxy, (4-7 membered heterocyclyl)-4-7 membered heterocyclyl (e.g. oxetanyl-pyrrolidinyl-), $C_{3-6}$ cycloalkylaminocarbonyl (e.g. cyclopropyl-NH—C(O)—), 5-7 membered heterocyclyl-$C_{2-6}$ alkynyl (e.g. N-piperazinyl-$CH_2C\equiv CCH_2$—), and $C_{6-10}$ aryl aminocarbonyl (e.g. phenyl-NH—C(O)—).

"Spiro" refers to a ring substituent which is joined by two bonds at the same carbon atom. Examples of spiro groups include 1,1-diethylcyclopentane, dimethyl-dioxolane, and 4-benzyl-4-methylpiperidine, wherein the cyclopentane and piperidine, respectively, are the spiro substituents. When substituents (R-groups) join together (e.g. when $R^7$ and $R^8$ join together) they may be taken from the same point of attachment to form a spiro ring.

The phrase "meta (3) position with respect to the point of attachment of the A ring" refers to the position on the ring where the substituent (e.g. —CN) is adjoined and is shown below with an arrow, wherein z represents a carbon atom or nitrogen:

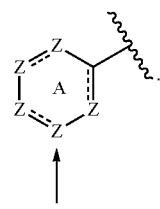

Similarly, para (4) position substitution refers to attachment of a substituent at the position indicated below, with respect to the point of attachment (e.g. of the B ring):

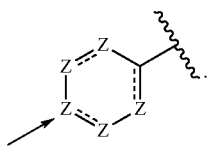

Similarly, ortho or 2-position refers to attachment of a substituent at the position indicated below, with respect to the point of attachment:

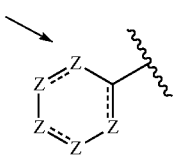

The compounds described herein include isomers, stereoisomers and the like. As used herein, the term "isomers" refers to different compounds that have the same molecular formula but differ in arrangement and configuration of the atoms. Also as used herein, the term "a stereoisomer" refers to any of the various stereo isomeric configurations which may exist for a given compound of the present invention and includes geometric isomers. It is understood that a substituent may be attached at a chiral center of a carbon atom. Therefore, the invention includes enantiomers, diastereomers or racemates of the compound.

The term "fused" refers to a ring which is bound to an adjacent ring.

"Enantiomers" are a pair of stereoisomers that are non-superimposable mirror images of each other. A 1:1 mixture of a pair of enantiomers is a "racemic" mixture.

The absolute stereochemistry is specified according to the Cahn-Ingold-Prelog R—S system. When a compound is a pure enantiomer the stereochemistry at each chiral carbon may be specified by either R or S. Resolved compounds whose absolute configuration is unknown can be designated (+) or (−) depending on the direction (dextro- or levorotatory) which they rotate plane polarized light at the wavelength of the sodium D line. Certain of the compounds described herein contain one or more asymmetric centers and may thus give rise to enantiomers, diastereomers, and other stereoisomeric forms that may be defined, in terms of absolute stereochemistry, as (R)— or (S)—. The present invention is meant to include all such possible isomers, including racemic and scalemic mixtures, optically pure forms and intermediate mixtures. Where chirality is not specified but is present, it is understood that the embodiment is directed to either the specific diastereomerically or enantiomerically enriched form; or a racemic or scalemic mixture of such compound(s). As used herein, "scalemic mixture" is a mixture of stereoisomers at a ratio other than 1:1. Optically active (R)- and (S)-isomers may be prepared using chiral synthons or chiral reagents, or resolved using conventional techniques. If the compound contains a double bond, the substituent may be E or Z configuration. If the compound contains a disubstituted cycloalkyl, the cycloalkyl substituent may have a cis- or trans-configuration. All tautomeric forms are also intended to be included. To the extent that compounds depicted herein are represented as having a particular stereochemistry, it is understood by one of skill in the art that such compounds may contain some detectable or undetectable levels of compounds sharing the same structure, but having different stereochemistry.

"$IC_{95}$" or "$EC_{95}$" refers to the inhibitory concentration required to achieve 95% of the maximum desired effect, which in many cases here is the inhibition of the HIV virus. This term is obtained using an in vitro assay evaluating the concentration-dependent inhibition of wild type HIV virus.

"$IC_{50}$" or "$EC_{50}$" refers to the inhibitory concentration required to achieve 50% of the maximum desired effect, which in many cases here is the inhibition of the HIV virus. This term is obtained using an in vitro assay evaluating the concentration-dependent inhibition of wild type HIV virus.

"Pharmaceutically acceptable" refers to compounds, salts, compositions, dosage forms and other materials which are useful in preparing a pharmaceutical composition that is suitable for veterinary or human pharmaceutical use.

"Pharmaceutically acceptable excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

"Pharmaceutically acceptable salt" refers to a salt of a compound that is pharmaceutically acceptable and that possesses (or can be converted to a form that possesses) the desired pharmacological activity of the parent compound. Such salts include acid addition salts formed with inorganic acids such as hydrochloric acid, hydrobromic acid, sulfuric acid, nitric acid, phosphoric acid, and the like; or formed with organic acids such as acetic acid, benzenesulfonic acid, benzoic acid, camphorsulfonic acid, citric acid, ethanesulfonic acid, fumaric acid, glucoheptonic acid, gluconic acid, lactic acid, maleic acid, malonic acid, mandelic acid, methanesulfonic acid, 2-naphthalenesulfonic acid, oleic acid, palmitic acid, propionic acid, stearic acid, succinic acid, tartaric acid, p-toluenesulfonic acid, trimethylacetic acid, and the like, and salts formed when an acidic proton present in the parent compound is replaced by either a metal ion, e.g., an alkali metal ion, an alkaline earth ion, or an aluminum ion; or coordinates with an organic base such as diethanolamine, triethanolamine, N-methylglucamine and the like. Also included in this definition are ammonium and substituted or quaternized ammonium salts. Representative non-limiting lists of pharmaceutically acceptable salts can be found in S. M. Berge et al., J. Pharma Sci., 66(1), 1-19 (1977), and Remington: The Science and Practice of Pharmacy, R. Hendrickson, ed., 21st edition, Lippincott, Williams & Wilkins, Philadelphia, Pa., (2005), at p. 732, Table 38-5, both of which are hereby incorporated by reference herein.

The present disclosure also provides for prodrugs of the compounds disclosed herein. A "prodrug" is defined in the pharmaceutical field as a biologically inactive derivative of a drug that upon administration to the human body is converted to the biologically active parent drug according to some chemical or enzymatic pathway.

"Subject" and "subjects" refers to humans, domestic animals (e.g., dogs and cats), farm animals (e.g., cattle, horses, sheep, goats and pigs), laboratory animals (e.g., mice, rats, hamsters, guinea pigs, pigs, pocket pets, rabbits, dogs, and monkeys), and the like.

As used herein, "treatment" or "treating" is an approach for obtaining beneficial or desired results. For purposes of the present disclosure, beneficial or desired results include, but are not limited to, alleviation of a symptom and/or diminishment of the extent of a symptom and/or preventing a worsening of a symptom associated with a disease or condition. In one embodiment, "treatment" or "treating" includes one or more of the following: a) inhibiting the disease or condition (e.g., decreasing one or more symptoms resulting from the disease or condition, and/or diminishing the extent of the disease or condition); b) slowing or arresting the development of one or more symptoms associated with the disease or condition (e.g., stabilizing the disease or condition, delaying the worsening or progression of the disease or condition); and/or c) relieving the disease or condition, e.g., causing the regression of clinical symptoms, ameliorating the disease state, delaying the progression of the disease, increasing the quality of life, and/or prolonging survival.

As used herein, "delaying" development of a disease or condition means to defer, hinder, slow, retard, stabilize and/or postpone development of the disease or condition. This delay can be of varying lengths of time, depending on the history of the disease and/or subject being treated. As is evident to one skilled in the art, a sufficient or significant delay can, in effect, encompass prevention, in that the subject does not develop the disease or condition. For example, a method that "delays" development of AIDS is a method that reduces the probability of disease development in a given time frame and/or reduces extent of the disease in a given time frame, when compared to not using the method. Such comparisons may be based on clinical studies, using a statistically significant number of subjects. For example, the development of AIDS can be detected using known methods, such as confirming a subject's $HIV^+$ status and assessing the subject's T-cell count or other indication of AIDS development, such as extreme fatigue, weight loss, persistent diarrhea, high fever, swollen lymph nodes in the neck, armpits or groin, or presence of an opportunistic condition that is known to be associated with AIDS (e.g., a condition that is generally not present in subjects with functioning immune systems but does occur in AIDS patients). Development may also refer to disease progression that may be initially undetectable and includes occurrence, recurrence and onset.

As used herein, "prevention" or "preventing" refers to a regimen that protects against the onset of the disease or disorder such that the clinical symptoms of the disease do not develop. Thus, "prevention" relates to administration of a therapy (e.g., administration of a therapeutic substance) to a subject before signs of the disease are detectable in the subject (e.g., administration of a therapeutic substance to a subject in the absence of detectable infectious agent (e.g., virus) in the subject). The subject may be an individual at risk of developing the disease or disorder, such as an individual who has one or more risk factors known to be associated with development or onset of the disease or disorder. Thus, the term "preventing HIV infection" refers to administering to a subject who does not have a detectable HIV infection an anti-HIV therapeutic substance. It is understood that the subject for anti-HIV preventative therapy may be an individual at risk of contracting the HIV virus. Further, it is understood that prevention may not result in complete protection against onset of the disease or disorder. In some instances, prevention includes reducing the risk of developing the disease or disorder. The reduction of the risk may not result in complete elimination of the risk of developing the disease or disorder.

As used herein, an "at risk" individual is an individual who is at risk of developing a condition to be treated. An individual "at risk" may or may not have detectable disease or condition, and may or may not have displayed detectable disease prior to the treatment of methods described herein. "At risk" denotes that an individual has one or more so-called risk factors, which are measurable parameters that correlate with development of a disease or condition and are known in the art. An individual having one or more of these risk factors has a higher probability of developing the disease or condition than an individual without these risk factor(s). For example, individuals at risk for AIDS are those having HIV.

As used herein, the term "therapeutically effective amount" or "effective amount" refers to an amount that is effective to elicit the desired biological or medical response, including the amount of a compound that, when administered to a subject for treating a disease, is sufficient to effect such treatment for the disease or to an amount that is effective to protect against the contracting or onset of a disease. The effective amount will vary depending on the compound, the disease, and its severity and the age, weight, etc., of the subject to be treated. The effective amount can include a range of amounts. As is understood in the art, an effective amount may be in one or more doses, i.e., a single dose or multiple doses may be required to achieve the desired treatment outcome. An effective amount may be considered in the context of administering one or more therapeutic agents, and a single agent may be considered to be given in an effective amount if, in conjunction with one or more other agents, a desirable or beneficial result may be or is achieved. Suitable doses of any co-administered compounds may optionally be lowered due to the combined action (e.g., additive or synergistic effects) of the compounds.

The compounds of the invention include solvates, hydrates, tautomers, stereoisomers and salt forms thereof.

Provided are also compounds in which from 1 to n specified or unspecified hydrogen atoms attached to a carbon atom may be replaced by a deuterium atom or D, in which n is the number of hydrogen atoms in the molecule. As known in the art, the deuterium atom is a non-radioactive isotope of the hydrogen atom. Such compounds exhibit may increase resistance to metabolism, and thus may be useful for increasing the half-life of the compounds when administered to a mammal. See, e.g., Foster, "Deuterium Isotope Effects in Studies of Drug Metabolism," Trends Pharmacol. Sci., 5(12):524-527 (1984). Such compounds are synthesized by means well known in the art, for example by employing starting materials in which one or more hydrogen atoms have been replaced by deuterium.

Examples of isotopes that can be incorporated into the disclosed compounds also include isotopes of hydrogen, carbon, nitrogen, oxygen, phosphorous, fluorine, chlorine, and iodine, such as $^2H$, $^3H$, $^{11}C$, $^{13}C$, $^{14}C$, $^{13}N$, $^{15}N$, $^{15}O$, $^{17}O$, $^{18}O$, $^{31}P$, $^{32}P$, $^{35}S$, $^{18}F$, $^{36}Cl$, $^{123}I$, and $^{125}I$, respectively. Substitution with positron emitting isotopes, such as $^{11}C$, $^{18}F$, $^{15}O$ and $^{13}N$, can be useful in Positron Emission Topography (PET) studies for examining substrate receptor occupancy. Isotopically-labeled compounds of Formula (Ia) or (Ib), can generally be prepared by conventional techniques known to those skilled in the art or by processes analogous to those described in the Examples as set out below using an appropriate isotopically-labeled reagent in place of the non-labeled reagent previously employed.

Additionally, the compounds described herein may be covalently bound to a polyethylene glycol (PEG) substituent, i.e. "pegylated" in order to enhance pharmacokinetic and metabolic profiles.

As referenced herein, darunavir is a HIV protease inhibitor having the structure:

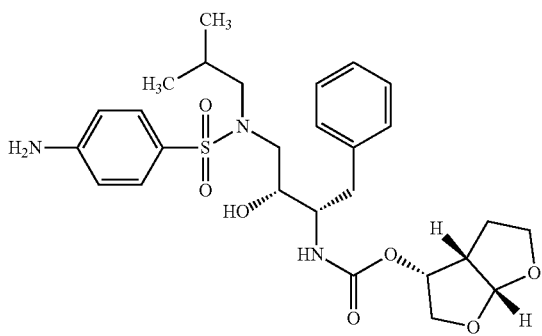 [SMILES: CC(C)CN(C[C@@H](O)[C@H](Cc1ccccc1)NC(=O)O[C@H]1CO[C@H]2OCC[C@H]21)S(=O)(=O)c1ccc(N)cc1]

and having the IUPAC name [(3aS,4R,6aR)-2,3,3a,4,5,6a-hexahydrofuro[2,3-b]furan-4-yl] N-[(2S,3R)-4-[(4-aminophenyl)sulfonyl-(2-methylpropyl)amino]-3-hydroxy-1-phenylbutan-2-yl]carbamate. Darunavir (DRV) is marketed under the brand name PREZISTA®.

As referenced herein, atazanavir is a HIV protease inhibitor having the structure:

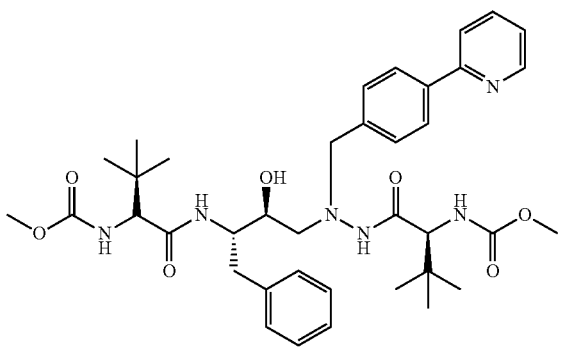

and having the IUPAC name methyl N-[(2S)-1-[2-[(2S,3S)-2-hydroxy-3-[[(2S)-2-(methoxycarbonylamino)-3,3-dimethylbutanoyl]amino]-4-phenylbutyl]-2-[(4-pyridin-2-ylphenyl)methyl]hydrazinyl]-3,3-dimethyl-1-oxobutan-2-yl]carbamate. Atazanavir (ATV) is marked under the brand name REYATAZ®.

Compounds

In some embodiments, a compound of Formula I is provided:

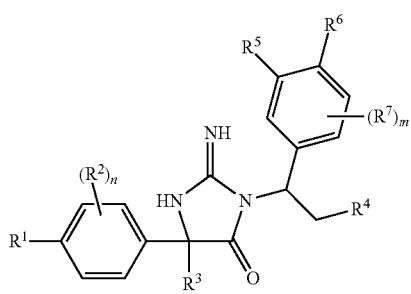

wherein,
n is 0-2;
m is 0-1;
$R^1$ is selected from the group consisting of hydrogen, halogen, cyano, $C_{2-6}$ alkynyl, —$OR^a$, 5-10 membered heteroaryl, 3-12 membered heterocyclyl, 5-10 membered aryl and 3-10 membered cycloalkyl, wherein each $C_{2-6}$ alkynyl, 5-10 membered heteroaryl, 3-12 membered heterocyclyl, 6-10 membered aryl and 3-10 membered cycloalkyl is optionally substituted with 1-5 $R^{20}$ groups;

each $R^2$ is independently selected from the group consisting of hydrogen, $C_{1-6}$ alkyl, —$NR^aR^b$, halogen, cyano, and —$OR^a$, wherein the $C_{1-6}$ alkyl is optionally substituted with 1-5 $R^{20}$ groups; or $R^1$ and $R^2$ together with the atoms to which they are attached form a heteroaryl optionally substituted with 1-5 $R^{20}$ groups;

$R^3$ is $C_{1-6}$ alkyl, $C_{2-6}$ alkynyl, or 3-10 membered cycloalkyl, each optionally substituted with 1-5 $R^{20}$ groups;

$R^4$ is selected from the group consisting of —$C(O)R^a$, —$C(O)OR^a$, —$C(O)NR^aR^b$, —$OC(O)NR^aR^b$, —$NR^aC(O)R^b$, —$NR^aC(O)OR^b$, —$S(O)_{0-2}R^a$, —$S(O)_2NR^aR^b$, —$NR^aS(O)_2R^b$, —$NR^aS(O)_{1-2}OR^b$, —$OS(O)_{1-2}NR^aR^b$ and —$OR^a$;

$R^5$ is selected from the group consisting of cyano, halo, and 5-10 membered heteroaryl, where the 5-10 membered heteroaryl is optionally substituted with 1-5 $R^{20}$ groups;

$R^6$ is hydrogen, halogen, cyano, $C_{1-3}$ haloalkoxy, —$C(O)NR^aR^b$, or 5-10 membered heteroaryl optionally substituted with 1-5 $R^{20}$ groups;

each $R^7$ is independently selected from the group consisting of $C_{1-6}$ alkyl, $C_{1-6}$ alkoxy, —$NR^aR^b$, halogen, cyano, 5-10 membered aryl, 3-6 membered cycloalkyl, 5-10 membered heteroaryl and 3-12 membered heterocyclyl, wherein each $C_{1-6}$ alkyl, $C_{1-6}$ alkoxy, 5-10 membered aryl, 3-6 membered cycloalkyl, 5-10 membered heteroaryl and 3-12 membered heterocyclyl is optionally substituted with 1-5 $R^{20}$ groups;

each $R^a$ and $R^b$ is independently selected from the group consisting of H, $C_{1-6}$ alkyl, 3-10 membered cycloalkyl, 3-12 membered heterocyclyl, 6-10 membered aryl, and 5-10 membered heteroaryl, each of which is optionally substituted with from one to five $R^{21}$ groups; or $R^a$ and $R^b$ together with the atoms to which they are attached form a 3-12 membered heterocyclyl optionally substituted with one to five $R^{21}$ groups;

each $R^{20}$ is independently selected from the group consisting $C_{1-6}$ alkyl, $C_{2-6}$ alkynyl, $C_{1-6}$ haloalkyl, 3-10 membered cycloalkyl, $C_{1-6}$ alkoxy, 3-12 membered heterocyclyl, 6-10 membered aryl, 5-10 membered heteroaryl, halogen, oxo, —$OR^a$, —$C(O)R^a$, —$C(O)OR^a$, —$C(O)NR^aR^b$, —$OC(O)NR^aR^b$, —$NR^aR^b$, —$NR^aC(O)R^b$, —$NR^aC(O)OR^b$, —$S(O)_{0-2}R^a$, —$S(O)_2NR^aR^b$, —$NR^aS(O)_2R^b$, —$N_3$, —CN, and —$NO_2$, or two $R^{20}$ groups appended to the same group can join together to form a fused, spiro or bridged $C_{3-10}$ cylcloalkyl or 3-12 membered heterocyclyl ring, wherein each $C_{1-6}$ alkyl, $C_{2-6}$ alkynyl, 3-10 membered cycloalkyl, $C_{1-6}$ alkoxy, 3-12 membered heterocyclyl, 5-10 membered aryl, and 5-10 membered heteroaryl is optionally substituted with from one to five halogen, oxo, —$OR^a$, —$C(O)R^a$, —$C(O)OR^a$, —$C(O)NR^aR^b$, —$OC(O)NR^aR^b$, —$NR^aR^b$, —$NR^aC(O)R^b$, —$NR^aC(O)OR^b$, —$S(O)_{0-2}R^a$, —$S(O)_2NR^aR^b$, —$NR^aS(O)_2R^b$, —$N_3$, —CN, 3-12 membered heterocyclyl, $C_{1-6}$ haloalkyl, 6-10 membered aryl, and —$NO_2$; and each $R^{21}$ is independently selected from the group consisting of $C_{1-6}$ alkyl, $C_{1-6}$ haloalkyl, 3-10 membered cycloalkyl, $C_{1-6}$ alkoxy, 3-12 membered heterocyclyl, 6-10 membered aryl, 5-10 membered heteroaryl, hydroxyl, amino, —$S(O)_2$—$CH_3$, $C_{1-6}$ alkylamino, —CN and halogen;

or a pharmaceutically acceptable salt thereof.

In certain embodiments, a compound of Formula I is provided:

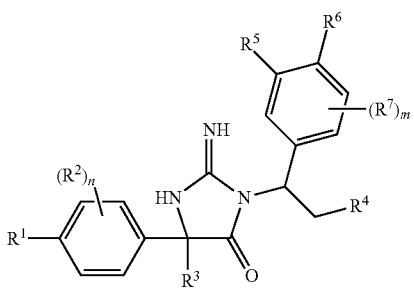

wherein, n is 0-2;

m is 0-1;

$R^1$ is selected from the group consisting of hydrogen, halogen, cyano, $C_{2-6}$ alkynyl, —$OR^a$, 5-10 membered heteroaryl, 3-12 membered heterocyclyl, 6-10 membered aryl and 3-10 membered cycloalkyl, wherein each 5-10 membered heteroaryl, 3-12 membered heterocyclyl, 6-10 membered aryl and 3-10 membered cycloalkyl is optionally substituted with 1-5 $R^{20}$ groups;

each $R^2$ is independently selected from the group consisting of hydrogen, $C_{1-6}$ alkyl, —$NR^aR^b$, halogen, cyano, or —$OR^a$, wherein the $C_{1-6}$ alkyl, is optionally substituted with 1-5 $R^{20}$ groups; or $R^1$ and $R^2$ together with the atoms to which they are attached form a heteroaryl optionally substituted with 1-5 $R^{20}$ groups;

$R^3$ is $C_{1-6}$ alkyl, $C_{2-6}$ alkynyl, or $C_{3-11}$) cycloalkyl, each optionally substituted with 1-5 $R^{20}$ groups;

$R^4$ is selected from the group consisting of —$C(O)R^a$, —$C(O)OR^a$, —$C(O)NR^aR^b$, —$OC(O)NR^aR^b$, —$NR^aC(O)R^b$, —$NR^aC(O)OR^b$, —$S(O)_{0-2}R^a$, —$S(O)_2NR^aR^b$, —$NR^aS(O)_2R^b$, —$NR^aS(O)_{1-2}OR^b$, —$OS(O)_{1-2}NR^aR^b$, or —$OR^a$;

$R^5$ is selected from the group consisting of cyano, halo, and 5-10 membered heteroaryl, where the 5-10 membered heteroaryl is optionally substituted with 1-5 $R^{20}$ groups;

$R^6$ is hydrogen, halo, —CN, —$C(O)NR^aR^b$, $C_{1-3}$ haloalkoxy, or 5-10 membered heteroaryl optionally substituted with 1-5 $R^{20}$ groups;

each $R^7$ is independently selected from the group consisting of $C_{1-6}$ alkyl, $C_{1-6}$ alkoxy, —$NR^aR^b$, halogen, cyano, 5-10 membered aryl, 3-6 membered cycloalkyl, 5-10 membered heteroaryl and 3-12 membered heterocyclyl, wherein each $C_{1-6}$ alkyl, $C_{1-6}$ alkoxy, 5-10 membered aryl, 3-6 membered cycloalkyl, 5-10 membered heteroaryl and 3-12 membered heterocyclyl is optionally substituted with 1-5 $R^{20}$ groups;

each $R^a$ and $R^b$ is independently selected from the group consisting of H, $C_{1-6}$ alkyl, $C_{1-6}$ haloalkyl, 3-10 membered cycloalkyl, 3-12 membered heterocyclyl, 6-10 membered aryl, 5-10 membered heteroaryl, each of which is optionally substituted with from one to five $R^{21}$ groups; or $R^a$ and $R^b$ together with the atoms to which they are attached form a 3-12 membered heterocyclyl optionally substituted with one to five $R^{21}$ groups;

each $R^{20}$ is independently selected from the group consisting $C_{1-6}$ alkyl, $C_{1-6}$ haloalkyl, 3-10 membered cycloalkyl, $C_{1-6}$ alkoxy, 3-12 membered heterocyclyl, 6-10 membered aryl, 5-10 membered heteroaryl, halogen, oxo, —$OR^a$, —$C(O)R^a$, —$C(O)OR^a$, —$C(O)NR^aR^b$, —$OC(O)NR^aR^b$, —$NR^aR^b$, —$NR^aC(O)R^b$, —$NR^aC(O)OR^b$, —$S(O)_{0-2}R^a$, —$S(O)_2NR^aR^b$, —$NR^aS(O)_2R^b$, —$N_3$, —CN, or —$NO_2$, or two $R^{20}$ groups appended to the same group can join together to form a fused, spiro or bridged $C_{3-10}$ cylcloalkyl or 3-12 membered heterocyclyl ring, wherein each $C_{1-6}$ alkyl, 3-10 membered cycloalkyl, $C_{1-6}$ alkoxy, 3-12 membered heterocyclyl, 6-10 membered aryl, 5-10 membered heteroaryl is optionally substituted with from one to five halogen, oxo, —$OR^a$, —$C(O)R^a$, —$C(O)OR^a$, —$C(O)NR^aR^b$, —$OC(O)NR^aR^b$, —$NR^aR^b$, —$NR^aC(O)R^b$, —$NR^aC(O)OR^b$, —$S(O)_{0-2}R^a$, —$S(O)_2NR^aR^b$, —$NR^aS(O)_2R^b$, —$N_3$, —CN, 3-12 membered heterocyclyl, or —$NO_2$; and each $R^{21}$ is independently selected from the group consisting of $C_{1-6}$ alkyl, $C_{1-6}$ haloalkyl, 3-10 membered cycloalkyl, $C_{1-6}$ alkoxy, 3-12 membered heterocyclyl, 6-10 membered aryl, 5-10 membered heteroaryl, hydroxyl, amino, —$S(O)_2$—$CH_3$, $C_{1-6}$ alkylamino, —CN or halogen;

or a pharmaceutically acceptable salt thereof.

In certain embodiments, a compound of formula ($I_a$) is provided:

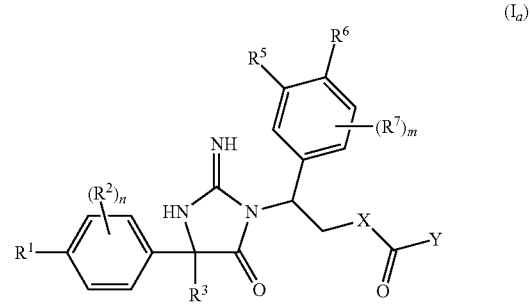

wherein, n is 0-2;

m is 0-1;

$R^1$ is selected from the group consisting of hydrogen, halogen, cyano, $C_{2-6}$ alkynyl, —$OR^a$, 5-10 membered heteroaryl, 3-12 membered heterocyclyl, 6-10 membered aryl and 3-10 membered cycloalkyl, wherein each 5-10 membered heteroaryl, 3-12 membered heterocyclyl, 6-10 membered aryl and 3-10 membered cycloalkyl is optionally substituted with 1-5 $R^{20}$ groups;

each $R^2$ is independently selected from the group consisting of hydrogen, cyano, $C_{1-6}$ alkyl, —$NR^aR^b$, halogen or —$OR^a$, wherein the $C_{1-6}$ alkyl, is optionally substituted with 1-5 $R^{20}$ groups; or wherein $R^1$ and $R^2$ together with the atoms to which they are attached, form a heteroaryl optionally substituted with 1-5 $R^{20}$ groups;

$R^3$ is $C_{1-6}$ alkyl, $C_{2-6}$ alkynyl, or $C_{3-10}$ cycloalkyl, each optionally substituted with 1-5 $R^{20}$ groups;

X is oxo or $NR^a$;

Y is —$NR^aR^b$;

$R^5$ is selected from the group consisting of cyano, halo, and 5-10 membered heteroaryl, where the 5-10 membered heteroaryl is optionally substituted with 1-5 $R^{20}$ groups;

$R^6$ is hydrogen, halogen, —CN, $C_{1-3}$ haloalkoxy, —$C(O)NR^aR^b$, or 5-10 membered heteroaryl optionally substituted with 1-5 $R^{20}$ groups;

each $R^7$ is independently selected from the group consisting of $C_{1-6}$ alkyl, $C_{1-6}$ alkoxy, —$NR^aR^b$, halogen, cyano, 5-10 membered aryl, 3-6 membered cycloalkyl, 5-10 membered heteroaryl and 3-12 membered heterocyclyl, wherein each $C_{1-6}$ alkyl, $C_{1-6}$ alkoxy, 5-10 membered aryl, 3-6 membered cycloalkyl, 5-10 membered heteroaryl and 3-12 membered heterocyclyl is optionally substituted with 1-5 $R^{20}$ groups;

each $R^a$ and $R^b$ is independently selected from the group consisting H, $C_{1-6}$ alkyl, 3-10 membered cycloalkyl, 3-12 membered heterocyclyl, 6-10 membered aryl, 5-10 membered heteroaryl, each of which is optionally substituted with from one to five $R^{21}$ groups; or $R^a$ and $R^b$ together with the atoms to which they are attached form a 3-12 membered heterocyclyl optionally substituted with one to five $R^{21}$ groups;

each $R^{20}$ is independently selected from the group consisting of $C_{1-6}$ alkyl, $C_{1-6}$ haloalkyl, 3-10 membered cycloalkyl, $C_{1-6}$ alkoxy, 3-12 membered heterocyclyl, 6-10 membered aryl, 5-10 membered heteroaryl, halogen, oxo, —OR$^a$, —C(O)R$^a$, —C(O)OR$^a$, —C(O)NR$^a$R$^b$, —OC(O)NR$^a$R$^b$, —NR$^a$R$^b$, —NR$^a$C(O)R$^b$, —NR$^a$C(O)OR$^b$, —S(O)$_{0-2}$R$^a$, —S(O)$_2$NR$^a$R$^b$, —NR$^a$S(O)$_2$R$^b$, —N$_3$, —CN, or —NO$_2$, or two $R^{20}$ groups appended to the same group can join together to form a fused, spiro or bridged $C_{3-10}$ cylcloalkyl or 3-12 membered heterocyclyl ring, wherein each $C_{1-6}$ alkyl, 3-10 membered cycloalkyl, $C_{1-6}$ alkoxy, 3-12 membered heterocyclyl, 6-10 membered aryl, 5-10 membered heteroaryl is optionally substituted with from one to five halogen, oxo, —OR$^a$, —C(O)R$^a$, —C(O)OR$^a$, —C(O)NR$^a$R$^b$, —OC(O)NR$^a$R$^b$, —NR$^a$R$^b$, —NR$^a$C(O)R$^b$, —NR$^a$C(O)OR$^b$, —S(O)$_{0-2}$R$^a$, —S(O)$_2$NR$^a$R$^b$, —NR$^a$S(O)$_2$R$^b$, —N$_3$, —CN, 3-12 membered heterocyclyl, or —NO$_2$; and each $R^{21}$ is independently selected from the group consisting of $C_{1-6}$ alkyl, $C_{1-6}$ haloalkyl, 3-10 membered cycloalkyl, $C_{1-6}$ alkoxy, 3-12 membered heterocyclyl, 6-10 membered aryl, 5-10 membered heteroaryl, hydroxyl, amino, —S(O)$_2$—CH$_3$, $C_{1-6}$ alkylamino, —CN or halogen;

or a pharmaceutically acceptable salt thereof.

In some embodiments, a compound of Formula (I$_b$) is provided:

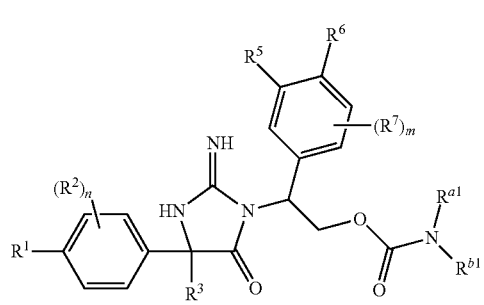

$I_b$ wherein,
n is 0-2;
m is 0-1;

$R^1$ is selected from the group consisting of hydrogen, halogen, cyano, $C_{2-6}$ alkynyl, —OR$^a$, 5-10 membered heteroaryl, 3-12 membered heterocyclyl, 6-10 membered aryl and 3-10 membered cycloalkyl, wherein each 5-10 membered heteroaryl, 3-12 membered heterocyclyl, 6-10 membered aryl and 3-10 membered cycloalkyl is optionally substituted with 1-5 $R^{20}$ groups;

each $R^2$ is independently selected from the group consisting of hydrogen, $C_{1-6}$ alkyl, —NR$^a$R$^b$, halogen, cyano, or —OR$^a$, wherein the $C_{1-6}$ alkyl, is optionally substituted with 1-5 $R^{20}$ groups; or wherein $R^1$ and $R^2$ together with the atoms to which they are attached form a heteroaryl optionally substituted with 1-5 $R^{20}$ groups;

$R^3$ is $C_{1-6}$ alkyl, $C_{1-6}$ alkynyl, or $C_{3-10}$ cycloalkyl, each optionally substituted with 1-5 $R^{20}$ groups;

$R^5$ is selected from the group consisting of cyano, halo, and 5-10 membered heteroaryl, where the 5-10 membered heteroaryl is optionally substituted with 1-5 $R^{20}$ groups;

$R^6$ is hydrogen, halogen, —CN, $C_{1-3}$ haloalkoxy, —C(O)NR$^a$R$^b$, or 5-10 membered heteroaryl optionally substituted with 1-5 $R^{20}$ groups;

each $R^7$ is independently selected from the group consisting of $C_{1-6}$ alkyl, $C_{1-6}$ alkoxy, —NR$^a$R$^b$, halogen, cyano, 5-10 membered aryl, 3-6 membered cycloalkyl, 5-10 membered heteroaryl and 3-12 membered heterocyclyl, wherein each $C_{1-6}$ alkyl, $C_{1-6}$ alkoxy, 5-10 membered aryl, 3-6 membered cycloalkyl, 5-10 membered heteroaryl and 3-12 membered heterocyclyl is optionally substituted with 1-5 $R^{20}$ groups;

each $R^a$ and $R^b$ is independently selected from the group consisting hydrogen, $C_{1-6}$ alkyl, 3-10 membered cycloalkyl, 3-12 membered heterocyclyl, 6-10 membered aryl, 5-10 membered heteroaryl, each of which is optionally substituted with from one to five $R^{21}$ groups; or $R^a$ and $R^b$ together with the atoms to which they are attached form a 3-12 membered heterocyclyl optionally substituted with one to five $R^{21}$ groups;

each $R^{20}$ is independently selected from the group consisting $C_{1-6}$ alkyl, $C_{1-6}$ haloalkyl, 3-10 membered cycloalkyl, $C_{1-6}$ alkoxy, 3-12 membered heterocyclyl, 6-10 membered aryl, 5-10 membered heteroaryl, halogen, oxo, —OR$^a$, —C(O)R$^a$, —C(O)OR$^a$, —C(O)NR$^a$R$^b$, —OC(O)NR$^a$R$^b$, —NR$^a$R$^b$, —NR$^a$C(O)R$^b$, —NR$^a$C(O)OR$^b$, —S(O)$_{0-2}$R$^a$, —S(O)$_2$NR$^a$R$^b$, —NR$^a$S(O)$_2$R$^b$, —N$_3$, —CN, or —NO$_2$, or two $R^{20}$ groups appended to the same group can join together to form a fused, spiro or bridged 3-10 membered cylcloalkyl or 3-12 membered heterocyclyl ring, wherein each $C_{1-6}$ alkyl, 3-10 membered cycloalkyl, $C_{1-6}$ alkoxy, 3-12 membered heterocyclyl, 6-10 membered aryl, 5-10 membered heteroaryl is optionally substituted with from one to five halogen, oxo, —OR$^a$, —C(O)R$^a$, —C(O)OR$^a$, —C(O)NR$^a$R$^b$, —OC(O)NR$^a$R$^b$, —NR$^a$R$^b$, —NR$^a$C(O)R$^b$, —NR$^a$C(O)OR$^b$, —S(O)$_{0-2}$R$^a$, —S(O)$_2$NR$^a$R$^b$, —NR$^a$S(O)$_2$R$^b$, —N$_3$, —CN, 3-12 membered heterocyclyl, or —NO$_2$;

$R^{a1}$ and $R^{b1}$ each independently selected from the group consisting of hydrogen, $C_{1-6}$ alkyl, 3-10 membered cycloalkyl, —S(O)$_2$R$^{21}$ each of which is optionally substituted with one to five $R^{21}$ groups; or wherein $R^{a1}$ and $R^{b1}$ are appended to the same group to form a 3-12 membered heterocyclyl optionally substituted with from one to five $R^{21}$ groups; and each $R^{21}$ is independently selected from the group consisting of $C_{1-6}$ alkyl, $C_{1-6}$ haloalkyl, 3-10 membered cycloalkyl, $C_{1-6}$ alkoxy, 3-12 membered heterocyclyl, 6-10 membered aryl, 5-10 membered heteroaryl, hydroxyl, amino, —S(O)$_2$—CH$_3$, $C_{1-6}$ alkylamino, —CN or halogen;

or a pharmaceutically acceptable salt thereof.

In some embodiments, a compound of Formula (I$_c$) is provided:

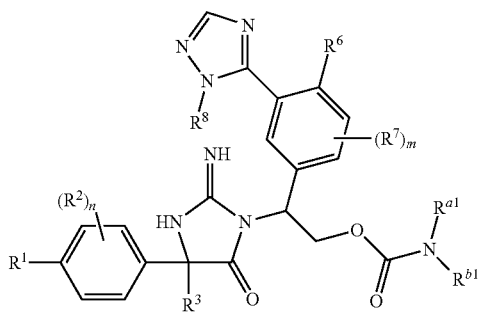

wherein, n is 0-2;

m is 0-1;

$R^1$ is selected from the group consisting of hydrogen, halogen, cyano, $C_{2-6}$ alkynyl, $-OR^a$, 5-10 membered heteroaryl, 3-12 membered heterocyclyl, 6-10 membered aryl and 3-10 membered cycloalkyl, wherein each 5-10 membered heteroaryl, 3-12 membered heterocyclyl, 6-10 membered aryl and 3-10 membered cycloalkyl is optionally substituted with 1-5 $R^{20}$ groups;

each $R^2$ is independently selected from the group consisting of hydrogen, cyano, $C_{1-6}$ alkyl, $-NR^aR^b$, halogen or $-OR^a$, wherein the $C_{1-6}$ alkyl, is optionally substituted with 1-5 $R^{20}$ groups; or wherein $R^1$ and $R^2$ together with the atoms to which they are attached, form a heteroaryl optionally substituted with 1-5 $R^{20}$ groups;

$R^3$ is $C_{1-6}$ alkyl, $C_{1-6}$ alkynyl, or 3-10 membered cycloalkyl, each optionally substituted with 1-5 $R^{20}$ groups;

$R^6$ is hydrogen, halogen, $-CN$, $C_{1-3}$ haloalkoxy, $-C(O)NR^aR^b$, or 5-10 membered heteroaryl optionally substituted with 1-5 $R^{20}$ groups;

each $R^7$ is independently selected from the group consisting of $C_{1-6}$ alkyl, $C_{1-6}$ alkoxy, $-NR^aR^b$, halogen, cyano, 5-10 membered aryl, 3-6 membered cycloalkyl, 5-10 membered heteroaryl and 3-12 membered heterocyclyl, wherein each $C_{1-6}$ alkyl, $C_{1-6}$alkoxy, 5-10 membered aryl, 3-6 membered cycloalkyl, 5-10 membered heteroaryl and 3-12 membered heterocyclyl is optionally substituted with 1-5 $R^{20}$ groups;

each $R^a$ and $R^b$ is independently selected from the group consisting H, $C_{1-6}$ alkyl, 3-10 membered cycloalkyl, 3-12 membered heterocyclyl, 6-10 membered aryl, 5-10 membered heteroaryl, each of which is optionally substituted with from one to five $R^{21}$ groups; or $R^a$ and $R^b$ together with the atoms to which they are attached form a 3-12 membered heterocyclyl optionally substituted with one to five $R^{21}$ groups;

each $R^{20}$ is independently selected from the group consisting $C_{1-6}$ alkyl, $C_{1-6}$ haloalkyl, 3-10 membered cycloalkyl, $C_{1-6}$ alkoxy, 3-12 membered heterocyclyl, 6-10 membered aryl, 5-10 membered heteroaryl, halogen, oxo, $-OR^a$, $-C(O)R^a$, $-C(O)OR^a$, $-C(O)NR^aR^b$, $-OC(O)NR^aR^b$, $-NR^aR^b$, $-NR^aC(O)R^b$, $-NR^aC(O)OR^b$, $-S(O)_{0-2}R^a$, $-S(O)_2NR^aR^b$, $-NR^aS(O)_2R^b$, $-N_3$, $-CN$, or $-NO_2$, or two $R^{20}$ groups appended to the same group can join together to form a fused, spiro or bridged $C_{3-10}$ cylcloalkyl or 3-12 membered heterocyclyl ring, wherein each $C_{1-6}$ alkyl, 3-10 membered cycloalkyl, $C_{1-6}$ alkoxy, 3-12 membered heterocyclyl, 6-10 membered aryl, 5-10 membered heteroaryl is optionally substituted with from one to five halogen, oxo, $-OR^a$, $-C(O)R^a$, $-C(O)OR^a$, $-C(O)NR^aR^b$, $-OC(O)NR^aR^b$, $-NR^aR^b$, $-NR^aC(O)R^b$, $-NR^aC(O)OR^b$, $-S(O)_{0-2}R^a$, $-S(O)_2NR^aR^b$, $-NR^aS(O)_2R^b$, $-N_3$, $-CN$, 3-12 membered heterocyclyl, or $-NO_2$;

$R^8$ is halogen, oxo, $-CN$, $C_{1-6}$ alkyl, $C_{1-6}$ haloalkyl, 3-6 membered cycloalkyl, $-COR^{21}$, $R^{a1}$ and $R^{b1}$ each independently selected from the group consisting of hydrogen, $C_{1-6}$ alkyl, 3-10 membered cycloalkyl, $-S(O)_2R^{21}$ each of which is optionally substituted with one to five $R^{21}$ groups; or wherein $R^{a1}$ and $R^{b1}$ are appended to the same group to form a 3-12 membered heterocyclyl optionally substituted with from one to five $R^{21}$ groups; and each $R^{21}$ is independently selected from the group consisting of $C_{1-6}$ alkyl, $C_{1-6}$ haloalkyl, 3-10 membered cycloalkyl, $C_{1-6}$ alkoxy, 3-12 membered heterocyclyl, 6-10 membered aryl, 5-10 membered heteroaryl, hydroxyl, amino, $-S(O)_2-CH_3$, $C_{1-6}$ alkylamino, $-CN$ or halogen;

or a pharmaceutically acceptable salt thereof.

In some embodiments, a compound of Formula ($I_d$) is provided:

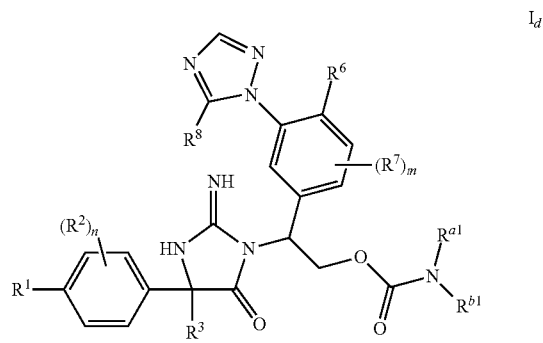

wherein, n is 0-2;

m is 0-1;

$R^1$ is selected from the group consisting of hydrogen, halogen, cyano, $C_{1-6}$ alkynyl, $-OR^{20}$, 5-10 membered heteroaryl, 3-12 membered heterocyclyl, 6-10 membered aryl and 3-10 membered cycloalkyl, wherein each 5-10 membered heteroaryl, 3-12 membered heterocyclyl, 6-10 membered aryl and 3-10 membered cycloalkyl is optionally substituted with 1-5 $R^{20}$ groups;

each $R^2$ is independently selected from the group consisting of hydrogen, $C_{1-6}$ alkyl, $-NR^aR^b$, halogen, cyano, or $-OR^a$, wherein the $C_{1-6}$ alkyl, is optionally substituted with 1-5 $R^{20}$ groups; or wherein $R^1$ and $R^2$ are linked to form a 5-10 membered heteroaryl optionally substituted with 1-5 $R^{20}$ groups;

$R^3$ is $C_{1-6}$ alkyl, $C_{1-6}$ alkynyl, or 3-10 membered cycloalkyl, each optionally substituted with 1-5 $R^{20}$ groups;

$R^6$ is halogen, $-CN$, $C_{1-3}$ haloalkoxy, $-C(O)NR^aR^b$, or $C_{3-6}$ heteroaryl optionally substituted with 1-5 $R^{20}$ groups;

each $R^7$ is independently selected from the group consisting of $C_{1-6}$ alkyl, $C_{1-6}$alkoxy, $-NR^aR^b$, halogen, cyano, 5-10 membered aryl, 3-6 membered cycloalkyl, 5-10 membered heteroaryl and 3-12 membered heterocyclyl, wherein each $C_{1-6}$ alkyl, $C_{1-6}$alkoxy, 5-10 membered aryl, 3-6 membered cycloalkyl, 5-10 membered heteroaryl and 3-12 membered heterocyclyl is optionally substituted with 1-5 $R^{20}$ groups;

each $R^a$ and $R^b$ is independently selected from the group consisting H; or $C_{1-6}$ alkyl, 3-10 membered cycloalkyl, 3-12 membered heterocyclyl, 6-10 membered aryl, 5-10 membered heteroaryl, each of which is optionally substituted with from one to five $R^{21}$ groups; or $R^a$ and $R^b$ together with the atoms to which they are attached form a 3-12 membered heterocyclyl optionally substituted with one to five $R^{21}$ groups;

each $R^{20}$ is independently selected from the group consisting $C_{1-6}$ alkyl, $C_{1-6}$ haloalkyl, 3-10 membered cycloalkyl, $C_{1-6}$ alkoxy, 3-12 membered heterocyclyl, 6-10 membered aryl, 5-10 membered heteroaryl, halogen, oxo, —$OR^a$, —$C(O)R^a$, —$C(O)OR^a$, —$C(O)NR^aR^b$, —$OC(O)NR^aR^b$, —$NR^aR^b$, —$NR^aC(O)R^b$, —$NR^aC(O)OR^b$, —$S(O)_{0-2}R^a$, —$S(O)_2NR^aR^b$, —$NR^aS(O)_2R^b$, —$N_3$, —CN, or —$NO_2$, or two $R^{20}$ groups appended to the same group can join together to form a fused, spiro or bridged $C_{3-10}$ cylcloalkyl or 3-12 membered heterocyclyl ring, wherein each $C_{1-6}$ alkyl, 3-10 membered cycloalkyl, $C_{1-6}$ alkoxy, 3-12 membered heterocyclyl, 6-10 membered aryl, 5-10 membered heteroaryl is optionally substituted with from one to five halogen, oxo, —$OR^a$, —$C(O)R^a$, —$C(O)OR^a$, —$C(O)NR^aR^b$, —$OC(O)NR^aR^b$, —$NR^aR^b$, —$NR^aC(O)R^b$, —$NR^aC(O)OR^b$, —$S(O)_{0-2}R^a$, —$S(O)_2NR^aR^b$, —$NR^aS(O)_2R^b$, —$N_3$, —CN, 3-12 membered heterocyclyl, or —$NO_2$;

$R^8$ is halogen, oxo, —CN, $C_{1-6}$ alkyl, $C_{1-6}$ haloalkyl, 3-10 membered cycloalkyl, —$COR^{21}$, $R^{a1}$ and $R^{b1}$ each independently selected from the group consisting of hydrogen, $C_{1-6}$ alkyl, 3-10 membered cycloalkyl, —$S(O)_2R^{21}$ each of which is optionally substituted with one to five $R^{21}$ groups; or wherein $R^{a1}$ and $R^{b1}$ are appended to the same group to form a 3-12 membered heterocyclyl optionally substituted with from one to five $R^{21}$ groups; and each $R^{21}$ is independently selected from the group consisting of $C_{1-6}$ alkyl, $C_{1-6}$ haloalkyl, 3-10 membered cycloalkyl, $C_{1-6}$ alkoxy, 3-12 membered heterocyclyl, 5-10 membered aryl, 5-10 membered heteroaryl, hydroxyl, amino, —$S(O)_2$—$CH_3$, $C_{1-6}$ alkylamino, —CN or halogen;

or a pharmaceutically acceptable salt thereof.

In some embodiments, $R^1$ is selected from the group consisting of hydrogen, halogen, $C_{2-6}$ alkynyl, —$OR^a$, 5-10 membered heteroaryl, 3-12 membered heterocyclyl, and 5-10 membered aryl, wherein each $C_{2-6}$ alkynyl, 5-10 membered heteroaryl, 3-12 membered heterocyclyl, and 6-10 membered aryl is optionally substituted with 1-5 $R^{20}$ groups.

In some embodiments, $R^1$ is selected from the group consisting of hydrogen, halogen, $C_{2-6}$ alkynyl, and —$OR^a$, wherein the $C_{2-6}$ alkynyl is optionally substituted with 1-5 $R^{20}$ groups.

In some embodiments, $R^1$ is selected from the group consisting of 5-10 membered heteroaryl, 3-12 membered heterocyclyl, and 5-10 membered aryl, wherein each 5-10 membered heteroaryl, 3-12 membered heterocyclyl, and 6-10 membered aryl is optionally substituted with 1-5 $R^{20}$ groups.

In some embodiments, $R^1$ is hydrogen.

In some embodiments, $R^1$ is cyano.

In some embodiments, $R^1$ is a halogen atom. In certain embodiments, $R^1$ is fluoro, chloro, or bromo. In certain embodiments, $R^1$ is chloro. In certain embodiments, $R^1$ is bromo.

In some embodiments, $R^1$ is $C_{2-6}$ alkynyl. In certain embodiments, $R^1$ is ethynyl, butynyl, propynyl, pentynyl, or hexynyl optionally substituted with 1-5 $R^{20}$ groups. In certain embodiments, $R^1$ is ethynyl, butynyl, propynyl, pentynyl, or hexynyl, each of which is optionally substituted with 1-5 $R^{20}$ groups. In certain embodiments $R^1$ is ethynyl further substituted with $C_{5-10}$ heteroaryl optionally substituted with $C_{1-3}$ haloalkyl. In certain embodiments, $R^1$ is ethynyl further substituted with pyrazolyl optionally substituted with $C_{1-3}$ haloalkyl. In certain embodiments, $R^1$ is 1-(difluoromethyl)-5-ethynyl-1H-pyrazolyl. In some embodiments, $R^1$ is butynyl optionally substituted with sulfonyl. In certain embodiments, $R^1$ is 3-methyl-3-(methylsulfonyl)but-1-ynyl.

In some embodiments, $R^1$ is $C_{1-3}$ haloalkyl. In certain embodiments, $R^1$ is trifluoromethyl. In other embodiments, $R^1$ is difluoromethyl or fluoromethyl.

In some embodiments, $R^1$ is —$OR^a$. In certain embodiments, $R^1$ is methoxy, ethoxy, isopropoxy, or tert-butoxy.

In some embodiments, $R^1$ is 5-10 membered heteroaryl. In certain embodiments, $R^1$ is 5-10 membered heteroaryl substituted with 1 or more $R^{20}$ groups. In certain embodiments, $R^1$ is 5-10 membered heteroaryl substituted with 1-2$R^{20}$ groups. In certain embodiments, $R^1$ is 5-10 membered heteroaryl substituted with 3-6 membered cycloalkyl.

In certain embodiments, $R^1$ is tetrahydrofuranyl, furanyl, pyrrolyl, pyrazolyl, triazolyl, tetrazolyl, thiophenyl, oxazolyl, thiazolyl, oxadiazolyl, isoxazolyl, thiadiazolyl, isothiazolyl, phenyl, pyridinyl, pyranyl, pyrimidinyl, pyridazinyl, or pyrazinyl, that can be further substituted independently with 1 or more $R^{20}$ groups selected from: $C_{1-6}$ alkyl, 3-10 membered cycloalkyl, $C_{1-6}$ alkoxy, 3-12 membered heterocyclyl, 5-10 membered aryl, 5-10 membered heteroaryl, halogen, oxo, —$OR^a$, —$C(O)R^a$, —$C(O)OR^a$, —$C(O)NR^aR^b$, —$OC(O)NR^aR^b$, —$NR^aR^b$, —$NR^aC(O)R^b$, —$NR^aC(O)OR^b$, —$S(O)_{0-2}R^a$, —$S(O)_2NR^aR^b$, —$NR^aS(O)_2R^b$, —$N_3$, —CN, or —$NO_2$, or two $R^{20}$ groups appended to the same group can join together to form a fused, spiro or bridged $C_{3-11}$) cylcloalkyl or 3-12 membered heterocyclyl ring, wherein each $C_{1-6}$ alkyl, 3-10 membered cycloalkyl, $C_{1-6}$ alkoxy, 3-12 membered heterocyclyl, 5-10 membered aryl, 5-10 membered heteroaryl is optionally substituted with from one to five halogen, oxo, —$OR^a$, —$C(O)R^a$, —$C(O)OR^a$, —$C(O)NR^aR^b$, —$OC(O)NR^aR^b$, —$NR^aR^b$, —$NR^aC(O)R^b$, —$NR^aC(O)OR^b$, —$S(O)_{0-2}R^a$, —$S(O)_2NR^aR^b$, —$NR^aS(O)_2R^b$, —$N_3$, —CN, 3-12 membered heterocyclyl, or —$NO_2$.

In some embodiments, $R^1$ is a five-membered heteroaryl substituted with 1-4 $R^{20}$ groups. In some embodiments, $R^1$ is a five-membered heteroaryl substituted with $C_{1-3}$ haloalkyl. In certain embodiments, $R^1$ is furanyl, pyrrolyl, imidazolyl, pyrazolyl, triazolyl, tetrazolyl, thiophenyl, oxazolyl, or thiazolyl. In some embodiments, $R^1$ is a five-membered heteroaryl substituted with $C_{1-6}$ alkyl. In some embodiments, $R^1$ is a five-membered heteroaryl substituted with a 3-6 membered cycloalkyl. In some embodiments, $R^1$ is a five-membered heteroaryl substituted with a 3-6 membered heterocycyl. In some embodiments, $R^1$ is a five-membered heteroaryl substituted with one or more halo atoms. In certain embodiments, $R^1$ is a five-membered heteroaryl substituted with a combination of with $C_{1-6}$ alkyl, $C_{1-3}$ haloalkyl, 3-6 membered cycloalkyl, or one or more halo atoms.

In some embodiments, $R^1$ is pyrazolyl substituted with 1-3 $R^{20}$ groups. In certain embodiments, $R^1$ is pyrazolyl substituted with $C_{1-3}$ haloalkyl. In certain embodiments, $R^1$ is pyrazolyl is substituted with difluoromethyl. In certain embodiments, $R^1$ is pyrazolyl substituted with trifluoroethyl. In certain embodiments, $R^1$ is pyrazolyl substituted with cyclopropyl. In certain embodiments, $R^1$ is pyrazolyl substituted with oxetanyl. In certain embodiments, $R^1$ is pyrazolyl substituted with one or more halo atoms. In certain embodiments, $R^1$ is fluoro substituted pyrazolyl. In certain embodiments, $R^1$ is pyrazolyl substituted with methyl or ethyl. In certain embodiments, $R^1$ is pyrazolyl substituted with trideuterated methyl. In some embodiments, $R^1$ is pyrazolyl substituted with sulfonyl. In certain embodiments, $R^1$ is pyrazolyl substituted with methylsulfonyl. In certain embodiments, $R^1$ is pyrazolyl substituted with cyclopropyl sulfonyl. In certain embodiments, $R^1$ is pyrazolyl independently substituted with one or more groups of $R^{20}$, such as halo, $C_{1-6}$ alkyl, 3-6 membered cycloalkyl, or $C_{1-3}$ haloalkyl. In certain embodiments, $R^1$ is unsubstituted pyrazolyl.

In some embodiments, $R^1$ is triazolyl substituted with 1 or 2 $R^{20}$ groups. In some embodiments, $R^1$ is triazolyl substituted with 3-6 membered cycloalkyl. In certain embodiments, $R^1$ is triazolyl substituted with cyclopropyl. In some embodiments, $R^1$ is triazolyl substituted with $C_{1-3}$ haloalkyl. In certain embodiments, $R^1$ is triazolyl substituted with difluoro or trifluoro methyl. In some embodiments, $R^1$ is triazolyl substituted with $C_{1-6}$ alkyl. In certain embodiments, $R^1$ is methyl, ethyl, or propyl substituted triazolyl. In certain embodiments, $R^1$ is triazolyl substituted with dimethyl propropyl or neopentyl. In certain embodiments, $R^1$ is triazolyl substituted with trideuterated methyl. In certain embodiments, $R^1$ is unsubstituted triazolyl.

In some embodiments, $R^1$ is tetrazolyl substituted with a $R^{20}$ group. In some embodiments, $R^1$ is $C_{1-6}$ alkyl substituted tetrazolyl. In certain embodiments, $R^1$ is methyl, ethyl, or propyl substituted tetrazolyl. In certain embodiments, $R^1$ is methyl substituted tetrazolyl. In certain embodiments, $R^1$ is unsubstituted tetrazolyl.

In some embodiments, $R^1$ is substituted or unsubstituted phenyl. In certain embodiments, $R^1$ is cyano substituted phenyl. In some embodiments, $R^1$ is $C_{1-3}$ alkoxy substituted phenyl. In some embodiments, $R^1$ is $C_{1-3}$ haloalkoxy substituted phenyl. In certain embodiments, $R^1$ is difluoromethoxy substituted phenyl. In some embodiments, $R^1$ is sulfonyl substituted phenyl. In certain embodiments, $R^1$ is methyl sulfonyl substituted phenyl.

In some embodiments, $R^1$ is a six-membered heteroaryl optionally substituted with 1-5 $R^{20}$ groups. In some embodiments, $R^1$ is pyridinyl. In certain embodiments, $R^1$ is cyano substituted pyridinyl. In some embodiments, $R^1$ is halo substituted pyridinyl. In certain embodiments, $R^1$ is fluoro pyridinyl. In some embodiments $R^1$ is $C_{1-3}$ haloalkyl substituted pyridinyl. In certain embodiments, $R^1$ is difluoromethyl substituted pyridinyl. In some embodiments, $R^1$ is trifluoromethyl substituted pyridinyl. In some embodiments, $R^1$ is pyridinyl substituted with 5-10 membered heterocycle which is optionally substituted with 1-5 $R^{21}$ groups. In certain embodiments, $R^1$ is pyridinyl substituted with hexahydropyridazinyl further optionally substituted with 1-5 $R^{21}$ groups. In certain embodiments, $R^1$ is 1-(oxetan-3-yl) hexahydropyridazinyl.

In some embodiments, $R^1$ is pyrazinyl optionally substituted with 1-4 $R^{20}$ groups. In some embodiments, $R^1$ is pyrimidinyl optionally substituted with 1-4 $R^{20}$ groups. In certain embodiments, $R^1$ is cyano substituted pyrimidinyl. In some embodiments, $R^1$ is halo substituted pyrimidinyl. In certain embodiments, $R^1$ is fluoro substituted pyrimidinyl.

In some embodiments, $R^1$ is a nine membered heterocycle optionally substituted with 1-5 $R^{20}$ groups. In certain embodiments, $R^1$ is benzo[d][1,3]dioxolyl optionally substituted with 1-5 $R^{20}$ groups. In certain embodiments, $R^1$ is 2,2-difluorobenzo[d][1,3]dioxolyl.

In certain embodiments, $R^1$ is 5,6,7,8-tetrahydro-[1,2,4]triazolo[4,3-a]pyrazinyl optionally substituted with 1-5 $R^{20}$ groups. In certain embodiments, $R^1$ is $C_{1-3}$ haloalkyl substituted 5,6,7,8-tetrahydro-[1,2,4]triazolo[4,3-a]pyrazinyl.

In certain embodiments, $R^1$ is 3-(trifluoromethyl)-5,6,7,8-tetrahydro-[1,2,4]triazolo[4,3-a]pyrazinyl.

In certain embodiments, $R^1$ is imidazo[1,2-a]pyridinyl.

In certain embodiments, $R^1$ is indene or imidazo-[1,2-a]pyridine.

In certain embodiments, $R^1$ is selected from the group consisting of:

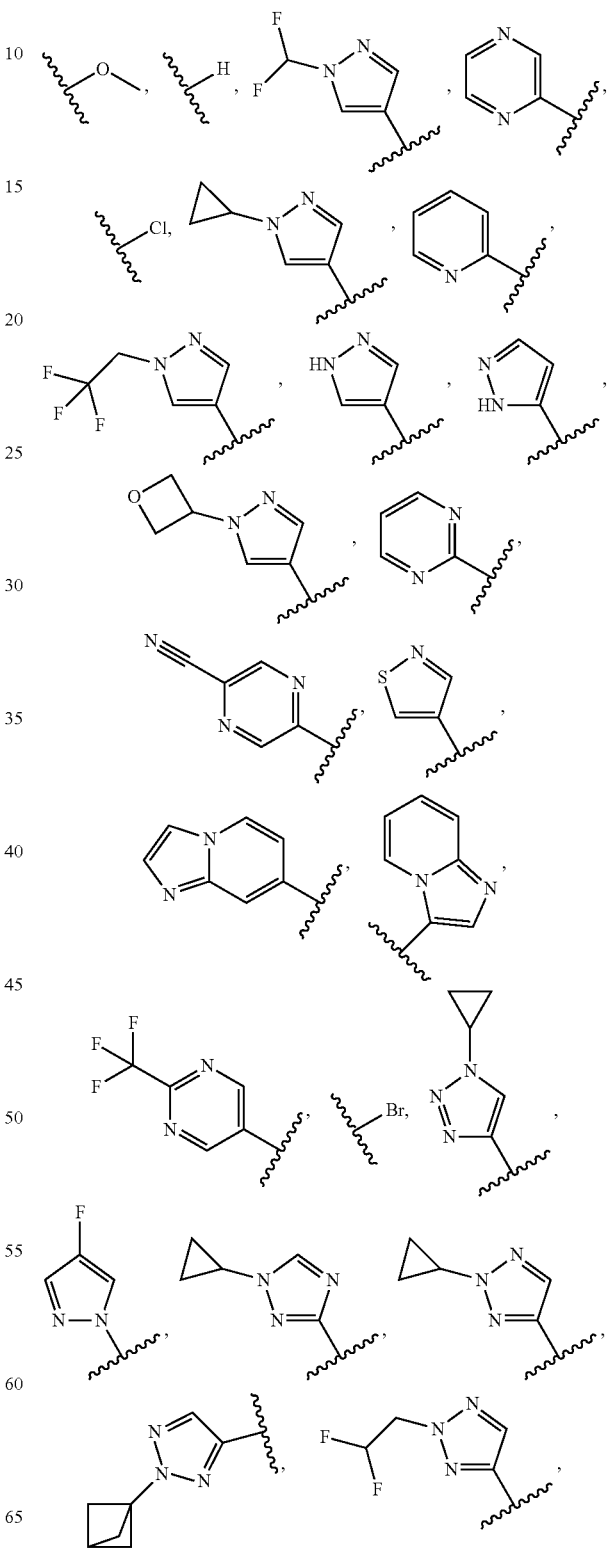

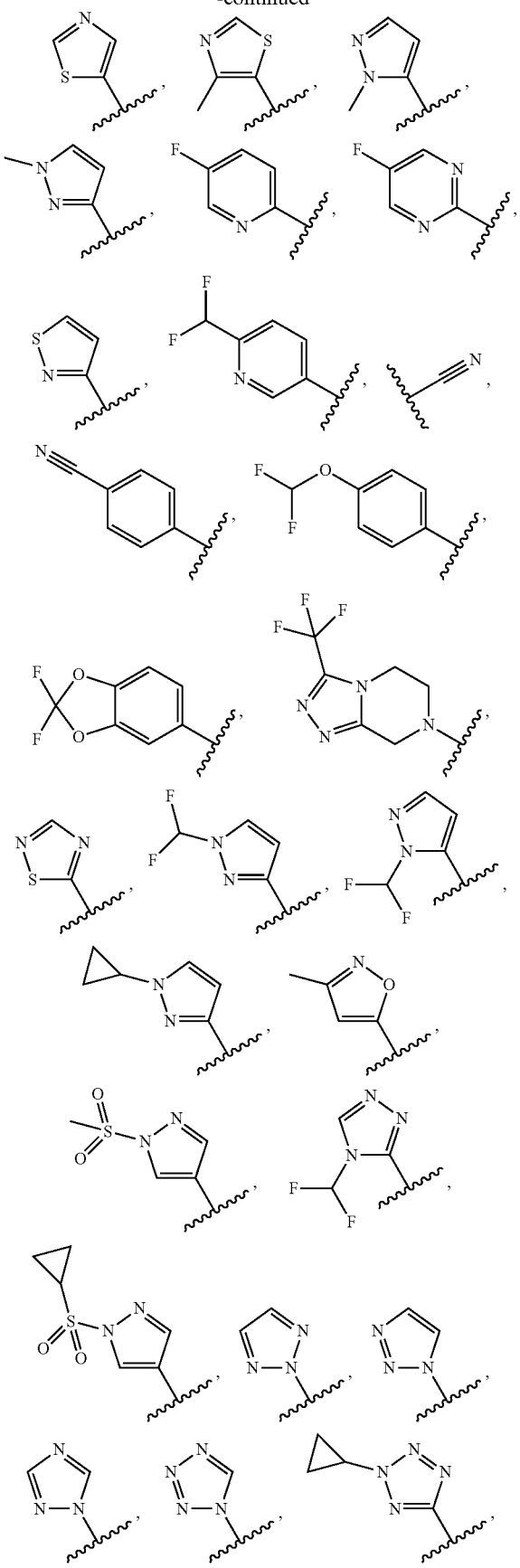
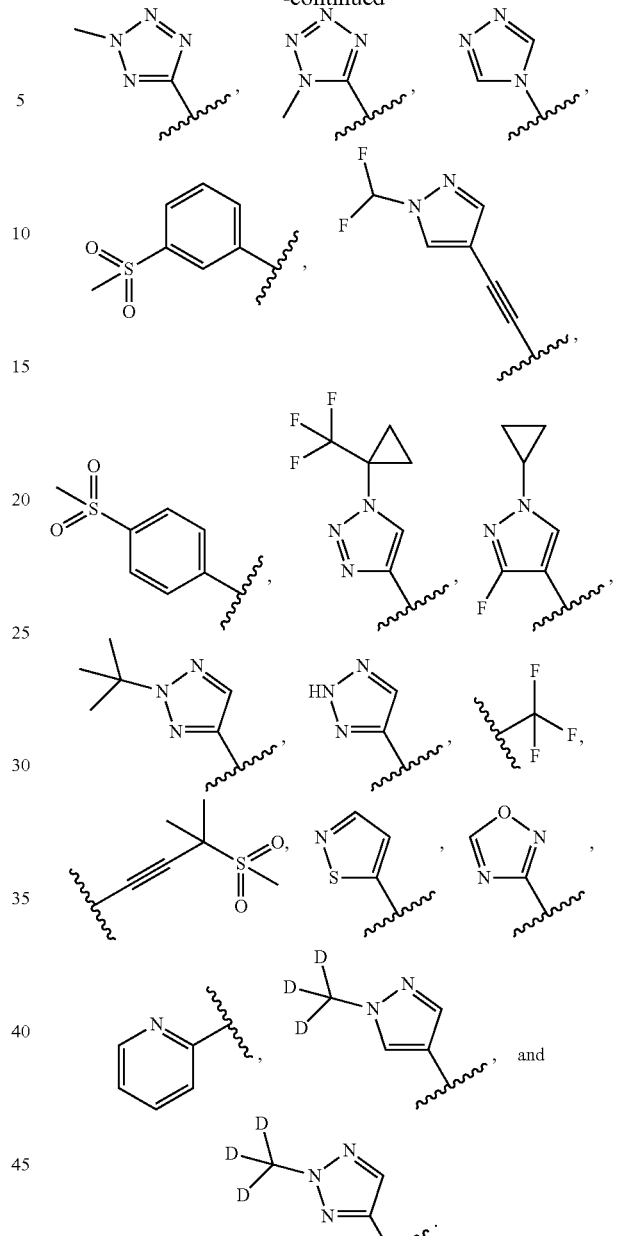

In some embodiments, $R^2$ is cyano. In some embodiments, $R^2$ is halo. In some embodiments, there is one $R^2$ group which is halo. In some embodiments, there are two $R^2$, each of which is independently selected halo atoms. In certain embodiments, $R^2$ is fluoro. In certain embodiments, there are two $R^2$ groups which are both fluoro. In certain embodiments, $R^2$ is absent or n is zero.

In some embodiments, $R^1$ and $R^2$ together with the atoms to which they are attached form a heteroaryl optionally substituted with 1-5 $R^{20}$ groups. In some embodiments, $R^1$ and $R^2$ together with the atoms to which they are attached form a 5-10 membered heteroaryl optionally substituted with 1-5 $R^{20}$ groups.

In some embodiments, $R^1$ and $R^2$ taken together with the carbons and/or heteroatom to which they are attached, form a heterocyclyl or a carbocyclyl, wherein the heterocyclyl formed by $R^1$ and $R^2$ is optionally substituted with one to five $R^{20}$ groups.

In some embodiments, $R^1$ and $R^2$ taken together with the carbons or heteroatom to which they are attached form a five-membered heterocycyl optionally substituted with one to five $R^{20}$ groups.

In certain embodiments, $R^1$ and $R^2$ taken together with the carbons or heteroatom to which they are attached form a pyrazoyl optionally substituted with one to three $R^{20}$ groups. In certain embodiments, $R^1$ and $R^2$ taken together with the carbons and/or heteroatom to which they are attached, form a pyrazoyl substituted with a 3-6 membered cycloalkyl. In certain embodiments, $R^1$ and $R^2$ taken together with the carbons or heteroatom to which they are attached, form a pyrazoyl substituted with a cyclopropyl. In certain embodiments, $R^1$ and $R^2$ taken together with the carbons and/or heteroatom to which they are attached, form a pyrazoyl substituted with a cyano group.

In some embodiments, $R^1$ and $R^2$ taken together with the carbons and/or heteroatom to which they are attached, form an imidazolyl optionally substituted with one to three $R^{20}$ groups. In certain embodiments, $R^1$ and $R^2$ taken together with the carbons and/or heteroatom to which they are attached, form imidazolyl.

In some embodiments, $R^1$ and $R^2$ taken together with the carbons and/or heteroatom to which they are attached, form a six-membered heteroaryl optionally substituted with one to five $R^{20}$ groups.

In certain embodiments, $R^1$ and $R^2$ taken together with the carbons and/or heteroatom to which they are attached, form a pyridinyl optionally substituted with one to five $R^{20}$ groups. In certain embodiments, $R^1$ and $R^2$ taken together with the carbons and/or heteroatom to which they are attached, form a pyridinyl substituted with $C_{1-3}$ haloalkyl. In certain embodiments, $R^1$ and $R^2$ taken together with the carbons and/or heteroatom to which they are attached, form a pyridinyl substituted with difluoromethyl.

In certain embodiments, $R^1$ and $R^2$ taken together with the carbons and/or heteroatom to which they are attached, form a pyridinyl substituted with $C_{1-3}$ alkyl. In certain embodiments, $R^1$ and $R^2$ taken together with the carbons or heteroatom to which they are attached, form a methyl substituted pyridinyl.

In certain embodiments, $R^1$ and $R^2$ taken together with the carbons and/or heteroatom to which they are attached, form a pyridinyl substituted with a 3-6 membered cycloalkyl. In certain embodiments, $R^1$ and $R^2$ taken together with the carbons and/or heteroatom to which they are attached, form a pyridinyl substituted with cyclopropyl.

In certain embodiments, $R^1$ and $R^2$ taken together with the carbons and/or heteroatom to which they are attached, form a pyridinyl substituted with one or more halo. In certain embodiments, $R^1$ and $R^2$ taken together with the carbons and/or heteroatom to which they are attached, form a pyridinyl substituted with bromo, fluoro, or chloro.

In certain embodiments, $R^1$ and $R^2$ taken together with the carbons and/or heteroatom to which they are attached form a pyridinyl substituted with $C_{2-6}$ alkynyl, where the $C_{2-6}$ alkynyl may further optionally be substituted with 5-10 membered aryl. In certain embodiments, $R^1$ and $R^2$ taken together with the carbons and/or heteroatom to which they are attached, form a pyridinyl substituted with ethynyl that is further substituted with 5-10 membered aryl. In certain embodiments, $R^1$ and $R^2$ taken together with the carbons or heteroatom to which they are attached, form a pyridinyl substituted with phenyl.

In certain embodiments, $R^1$ and $R^2$ taken together with the carbons and/or heteroatom to which they are attached, form a pyridinyl substituted with oxo and $C_{1-3}$ alkyl. In certain embodiments, $R^1$ and $R^2$ taken together with the carbons and/or heteroatom to which they are attached, form a pyridinyl substituted with oxo and methyl. In certain embodiments, $R^1$ and $R^2$ taken together with the carbons and/or heteroatom to which they are attached, form 1-methyl-5,6-dihydropyridin-2(1H)-onyl.

In certain embodiments, $R^1$ and $R^2$ taken together with the carbons and/or heteroatom to which they are attached form a pyridinyl substituted with a 5-10 membered heteroaryl, where the 5-10 membered heteroaryl can further be substituted with $C_{1-3}$ haloalkyl. In certain embodiments, $R^1$ and $R^2$ taken together with the carbons and/or heteroatom to which they are attached, form a pyridinyl substituted with pyrazoyl, where the pyrazoyl can be further substituted with $C_{1-3}$ haloalkyl. In certain embodiments, $R^1$ and $R^2$ taken together with the carbons and/or heteroatom to which they are attached, form a pyridinyl substituted with pyrazoyl, where the pyrazoyl can be further substituted with difluoromethyl. In certain embodiments, $R^1$ and $R^2$ taken together with the carbons and/or heteroatom to which they are attached, form a pyridinyl substituted with difluoromethyl pyrazolyl.

In certain embodiments, $R^1$ and $R^2$ taken together with the carbons and/or heteroatom to which they are attached, form groups consisting of:

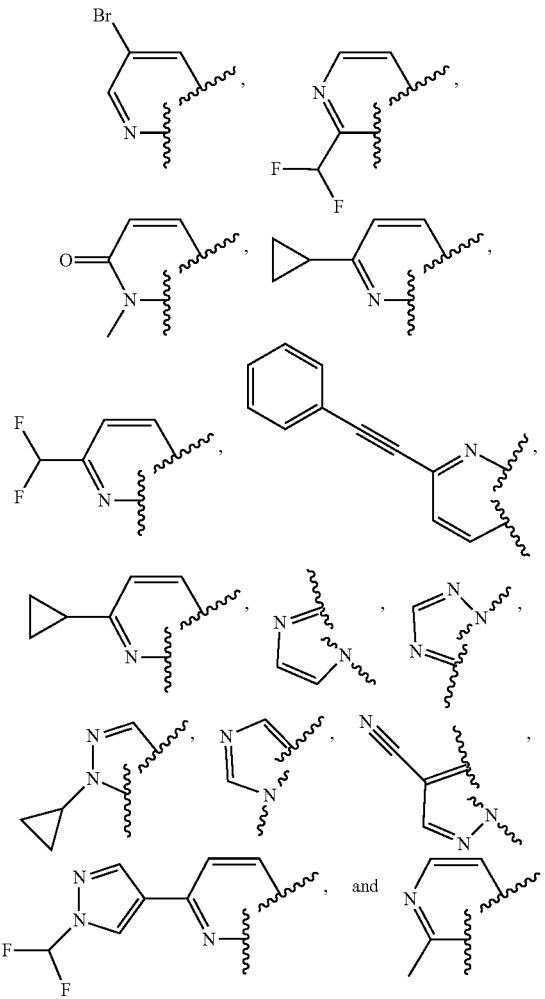

In some embodiments, $R^3$ is $C_{1-6}$ alkyl, $C_{2-6}$ alkynyl, or $C_{1-6}$ haloalkyl, where the $C_{1-6}$ alkyl and $C_{2-6}$ alkynyl can further substituted with 1-5 $R^{20}$ groups. In some embodiments, $R^3$ is $C_{1-6}$ alkyl or $C_{2-6}$ alkynyl, where the $C_{1-6}$ alkyl and $C_{2-6}$ alkynyl can further substituted with 1-5 $R^{20}$ groups.

In some embodiments, $R^3$ is $C_{1-6}$ alkyl, $C_{2-6}$ alkynyl, or $C_{1-6}$ haloalkyl, where the $C_{1-6}$ alkyl, $C_{2-6}$ alkynyl, and $C_{1-6}$ haloalkyl can further substituted with 1-5 $R^{20}$ groups.

In some embodiments, $R^3$ is propyl or butyl, each of which is substituted with 1-5 $R^{20}$ groups. In some embodiments, $R^3$ is propyl or butyl substituted with 1-5 $R^{20}$ groups.

In certain embodiments, $R^3$ is propyl substituted with a combination of $C_{1-3}$ alkyl, $C_{1-3}$ haloalkyl, a 3-6 membered cycloalkyl, cyano, or sulfonyl groups. In certain embodiments, $R^3$ is propyl substituted with a combination of $C_{1-3}$ alkyl, $C_{1-3}$ haloalkyl, a 3-6 membered cycloalkyl, cyano, or sulfonyl groups, where the $C_{1-3}$ alkyl, $C_{1-3}$ haloalkyl, a 3-6 membered cycloalkyl, cyano, or sulfonyl groups can further be substituted with one or more methyl, halo, or cyclopropyl.

In some embodiments, $R^3$ is methyl propyl or dimethylpropyl.

In some embodiments, $R^3$ is propyl, methylpropyl, or dimethylpropyl, each of which is further substituted with one or more halo.

In some embodiments, $R^3$ is propyl, methylpropyl, or dimethylpropyl that is further substituted with one or more halo. In certain embodiments, $R^3$ is fluoro substituted dimethylpropyl. In certain embodiments, $R^3$ is either a fluoro or chloro substituted methylpropyl. In certain embodiments, $R^3$ is 1,1-difluoro-2,2-dimethylpropyl. In certain embodiments, $R^3$ is 1,1,1-trifluoro-2,2 methylpropyl. In certain embodiments, $R^3$ is 1,1,1-trifluoro-2,2 methylpropyl or its stereoisomers. In certain embodiments, $R^3$ is 2-fluoro-2-methylpropyl. In certain embodiments, $R^3$ is 2-chloro-2-methylpropyl.

In some embodiments, $R^3$ is cyano substituted methylpropyl or dimethylpropyl. In certain embodiments, $R^3$ is 1-cyano-2-methylpropyl. In certain embodiments, $R^3$ is 1-cyano-2,2-dimethylpropyl. In certain embodiments, $R^3$ is 1-cyano-2,2-dimethylpropyl or its stereoisomers.

In some embodiments, $R^3$ is methyl propyl substituted with sulfonyl, where the sulfonyl can be further substituted with $C_{1-3}$ alkyl. In certain embodiments, $R^3$ is 1-methylsulfonyl-2-methylpropyl.

In some embodiments, $R^3$ is propyl substituted with $C_{1-3}$ alkyl, 3-6 membered cycloalkyl, or halo substituted 3-6 membered cycloalkyl. In certain embodiments, $R^3$ is 2-cyclopropyl propyl. In certain embodiments, $R^3$ is 2-cyclopropyl-2-methylpropyl. In certain embodiments, $R^3$ is propyl substituted with difluorocyclopropyl. In certain embodiments, $R^3$ is 2-difluorocyclopropyl-propyl, and its stereoisomers.

In some embodiments, $R^3$ is $C_{2-6}$ alkynyl that is optionally substituted with 1-5 $R^{20}$ groups. In certain embodiments, $R^3$ is $C_{2-4}$ alkynyl that is substituted with 3-6 membered cycloalkyl. In certain embodiments, $R^3$ is ethynyl that is substituted with 3-6 membered cycloalkyl. In certain embodiments, $R^3$ is 1-cyclopropyl ethynyl.

In some embodiments, $R^3$ is 3-10 membered cycloalkyl. In some embodiments, $R^3$ is 3-6 membered cycloalkyl. In some embodiments, $R^3$ is 3-6 membered cycloalkyl and its stereoisomers. In certain embodiments, $R^3$ is cyclopropyl. In certain embodiments, $R^3$ is cyclopropyl and its corresponding stereoisomers.

In some embodiments, $R^3$ is selected from a group consisting of:

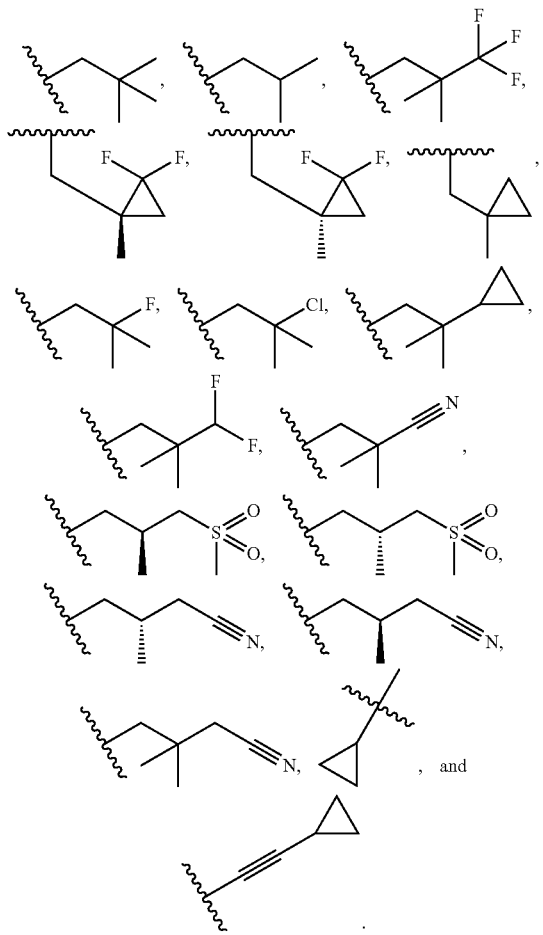

In some embodiments, $R^4$ is —C(O)$R^a$, —C(O)O$R^a$, —C(O)N$R^a R^b$, —OC(O)N$R^a R^b$, —N$R^a$C(O)$R^b$, —N$R^a$C(O)O$R^b$, —S(O)$_{0-2}R^a$, —S(O)$_2$N$R^a R^b$, —N$R^a$S(O)$_2 R^b$, or —O$R^a$.

In some embodiments, $R^4$ is —OC(O)N$R^a R^b$, —N$R^a$C(O)$R^b$, —N$R^a$C(O)O$R^b$, —N$R^a$S(O)$_2 R^b$, or —O$R^a$.

In some embodiments, $R^4$ is —OC(O)NH$R^b$ or —NHC(O)$R^b$.

In some embodiments, $R^4$ is —OC(O)NH$R^b$, where $R^b$ is cyclopropyl substituted with $C_{1-6}$ haloalkyl.

In some embodiments, $R^4$ is —NHC(O)$R^b$, where $R^b$ is cyclopropyl substituted with $C_{1-6}$ haloalkyl. In certain embodiments, $R^4$ is —NHC(O)$R^b$, where $R^b$ is cyclopropyl substituted with $CF_3$ or $CHF_2$.

In some embodiments, $R^4$ has a general formula of —OC(O)N$R^a R^b$, where $R^a$ and $R^b$ is selected from a group as follows: hydrogen, oxo, $C_{1-3}$ alkyl, 3-6 membered cycloalkyl, $C_{1-3}$ haloalkyl, $C_{4-6}$ heterocycyl, 5-10 membered aryl, or 5-10 membered heteroaryl, where either $R^a$ or $R^b$ can be further substituted with hydroxy, $C_{1-3}$ alkyl, or $C_{1-3}$ haloalkyl.

In some embodiments, $R^4$ has a general formula of —OC(O)N$R^a R^b$, where $R^a$ and $R^b$ is selected from a group as follows: hydrogen, $C_{1-3}$ alkyl, 3-6 membered cycloalkyl, $C_{4-6}$ heterocycyl, 6-10 membered aryl, and 5-10 membered heteroaryl, where either $R^a$ or $R^b$ can be further substituted with hydroxy, $C_{1-3}$ alkyl, or $C_{1-3}$ haloalkyl.

In certain embodiments, $R^a$ and $R^b$ are selected from hydrogen, oxo, methyl, ethyl, isobutyl, 1,1-dimethyl, 2-fluoro-ethyl, cyclopropyl, difluoroethyl, trifluoroethyl, oxetanyl, ethanol, phenyl, and pyrimidinyl, where the methyl, ethyl, isobutyl, 1,1-dimethyl, 2-fluoro-ethyl, cyclopropyl, difluoroethyl, trifluoroethyl, oxetanyl, ethanol, phenyl, and pyrimidinyl substitutents is optionally substituted with 1-5 $R^{21}$ groups.

In certain embodiments, $R^a$ and $R^b$ are selected from hydrogen, methyl, ethyl, isobutyl, 1,1-dimethyl, 2-fluoroethyl, cyclopropyl, difluoroethyl, trifluoroethyl, oxetanyl, ethanol, phenyl, and pyrimidinyl, where the methyl, ethyl, isobutyl, 1,1-dimethyl, 2-fluoro-ethyl, cyclopropyl, difluoroethyl, trifluoroethyl, oxetanyl, ethanol, phenyl, and pyrimidinyl substitutents are each optionally substituted with 1-5 $R^{21}$ groups.

In certain embodiments, when $R^a$ or $R^b$ is methyl, ethyl, isobutyl, 1,1-dimethyl, 2-fluoro-ethyl, cyclopropyl, difluoroethyl, trifluoroethyl, oxetanyl, ethanol, phenyl, and pyrimidinyl, $R^a$ and $R^b$ is optionally substituted with one or more $C_{1-3}$ alkyl or halo.

In certain embodiments, when $R^a$ or $R^b$ is methyl, ethyl, isobutyl, 1,1-dimethyl, 2-fluoro-ethyl, cyclopropyl, difluoroethyl, trifluoroethyl, oxetanyl, phenyl, and pyrimidinyl, $R^a$ and $R^b$ are each optionally substituted with one or more $C_{1-3}$ alkyl or halo.

In some embodiments, $R^a$ is hydrogen and $R^b$ is methyl, ethyl, isobutyl, 1,1-dimethyl, 2-fluoro-ethyl, cyclopropyl, difluoroethyl, trifluoroethyl, oxetanyl, phenyl, or pyrimidinyl, wherein $R^b$ is optionally substituted with one or more halo (e.g., F, Cl, or Br). In some embodiments, $R^a$ is hydrogen and $R^b$ is cyclopropyl optionally substituted with one or more halo (e.g., F, Cl, or Br).

In certain embodiments, $R^4$ is selected from the following: carbamoyl, dimethylcarbamoyl, isopropylcarbamoyl, cyclopropylcarbamoyl, 1-(trifluoromethyl)cyclopropyl carbamoyl, 1-methylcyclopropyl carbamoyl, 1-fluoro-2-methylpropan-2-yl carbamoyl, 1,1-difluoro-2-methylpropan-2-yl carbamoyl, 1,1,1-trifluoro-2-methylpropan-2-yl carbamoyl, tert-butylcarbamoyl, cyclopropyl (2,2-difluoroethyl)carbamoyl, 1-(difluoromethyl)cyclopropyl carbamoyl, oxetan-3-ylcarbamoyl, cyclopropyl(2,2,2-trifluoroethyl) carbamoyl, (1,3-dihydroxy-2-methylpropan-2-yl) carbamoyl, phenyl carbamoyl, pyridin-2-ylcarbamoyl, (1,1,1-trifluoropropan-2-yl) carbamoyl, (2,2-difluoroethyl) carbamoyl, (2,2,2-trifluoroethyl) carbamoyl, (1-(2,2-difluoroethyl)cyclopropyl) carbamoyl, (2,2-difluorocyclopropyl) carbamoyl, cyclopropyl(methyl)carbamoyl, (2,2-difluoropropyl) carbamoyl, (3-(trifluoromethyl)bicyclo[1.1.1] pentan-1-yl)carbamoyl, methyl (1-ethylcyclopropyl) carbamoyl, and (1-(trifluoromethyl)cyclopropyl)carbamoyl. In certain embodiments, the $R^4$ groups disclosed above includes corresponding stereoisomers, for example, (S)-(1,1,1-trifluoropropan-2-yl) carbamoyl.

In some embodiments, $R^4$ has a general formula —OC(O)$NR^aR^b$, where $R^a$ and $R^b$ is hydrogen or 3-6 membered cycloalkyl, that is further optionally substituted with one or more halo, and their corresponding stereoisomers.

In certain embodiments, $R^4$ is (2-(trifluoromethyl)cyclopropyl)carbamoyl. In other embodiments, $R^4$ can be the stereoisomers of (2-(trifluoromethyl)cyclopropyl)carbamoyl, such as ((1R,2R)-2-(trifluoromethyl)cyclopropyl)carbamoyl or ((1S,2S)-2-(trifluoromethyl)cyclopropyl)carbamoyl.

In certain embodiments, $R^4$ is (2-(difluoromethyl)cyclopropyl)carbamoyl. In other embodiments, $R^4$ can be stereoisomers of (2-(difluoromethyl)cyclopropyl)carbamoyl, such as ((1S,2S)-2-(difluoromethyl)cyclopropyl)carbamoyl or ((1R,2R)-2-(difluoromethyl)cyclopropyl)carbamoyl.

In certain embodiments, $R^4$ is (2,2-difluorocyclopropyl) carbamate. In other embodiments, $R^4$ can be stereoisomers of (2,2-difluorocyclopropyl)carbamoyl, such as (R)-(2,2-difluorocyclopropyl)carbamoyl or (S)-(2,2-difluorocyclopropyl)carbamoyl.

In certain embodiments, $R^4$ is (2-fluorocyclopropyl) carbamoyl. In other embodiments, $R^4$ can be stereoisomers of (2-fluorocyclopropyl) carbamoyl, such as ((1R,2S)-2-fluorocyclopropyl)carbamoyl, ((1S,2R)-2-fluorocyclopropyl) carbamoyl, ((1R,2R)-2-fluorocyclopropyl)carbamoyl, or ((1S,2S)-2-fluorocyclopropyl)carbamoyl.

In certain embodiments, $R^4$ is spiro[2.2]pentan-1-ylcarbamoyl. In other embodiments, $R^4$ can be stereoisomers of spiro[2.2]pentan-1-ylcarbamoyl, such as (R)-spiro[2.2]pentan-1-ylcarbamoyl or (S)-spiro[2.2]pentan-1-ylcarbamoyl.

In certain embodiments, $R^4$ is (1,1,1-trifluoropropan-2-yl)carbamoyl. In other embodiments, $R^4$ can be stereoisomers of (1,1,1-trifluoropropan-2-yl)carbamoyl, such as (R)-(1,1,1-trifluoropropan-2-yl)carbamoyl or (S)-(1,1,1-trifluoropropan-2-yl)carbamoyl.

In certain embodiments, $R^4$ is (1,1-difluoropropan-2-yl) carbamoyl. In other embodiments, $R^4$ can be stereoisomers of (1,1-difluoropropan-2-yl)carbamoyl, such as (S)-(1,1-difluoropropan-2-yl)carbamoyl or (R)-(1,1-difluoropropan-2-yl)carbamoyl.

In certain embodiments, $R^4$ is selected from the following: carbamoyloxy, dimethylcarbamoyloxy, isopropylcarbamoyloxy, cyclopropylcarbamoyloxy, 1-(trifluoromethyl) cyclopropyl carbamoyloxy, 1-methylcyclopropyl carbamoyloxy, 1-fluoro-2-methylpropan-2-yl carbamoyloxy, 1,1-difluoro-2-methylpropan-2-yl carbamoyloxy, 1,1,1-trifluoro-2-methylpropan-2-yl carbamoyloxy, tert-butylcarbamoyloxy, cyclopropyl (2,2-difluoroethyl) carbamoyloxy, 1-(difluoromethyl)cyclopropyl carbamoyloxy, oxetan-3-ylcarbamoyloxy, cyclopropyl(2,2,2-trifluoroethyl) carbamoyloxy, (1,3-dihydroxy-2-methylpropan-2-yl) carbamoyloxy, phenyl carbamoyloxy, pyridin-2-ylcarbamoyloxy, (1,1,1-trifluoropropan-2-yl) carbamoyloxy, (2,2-difluoroethyl) carbamoyloxy, (2,2,2-trifluoroethyl) carbamoyloxy, (1-(2,2-difluoroethyl)cyclopropyl) carbamoyloxy, (2,2-difluorocyclopropyl) carbamoyloxy, cyclopropyl(methyl)carbamoyloxy, (2,2-difluoropropyl) carbamoyloxy, (3-(trifluoromethyl)bicyclo [1.1.1] pentan-1-yl)carbamoyloxy, methyl (1-ethylcyclopropyl) carbamoyloxy, and (1-(trifluoromethyl)cyclopropyl)carbamoyloxy. In certain embodiments, the $R^4$ groups disclosed above includes corresponding stereoisomers, for example, (S)-(1,1,1-trifluoropropan-2-yl) carbamoyloxy.

In certain embodiments, $R^4$ is (2-(trifluoromethyl)cyclopropyl)carbamoyloxy. In other embodiments, $R^4$ can be the stereoisomers of (2-(trifluoromethyl)cyclopropyl)carbamoyloxy, such as ((1R,2R)-2-(trifluoromethyl)cyclopropyl) carbamoyloxy or ((1S,2S)-2-(trifluoromethyl)cyclopropyl) carbamoyloxy.

In certain embodiments, $R^4$ is (2-(difluoromethyl)cyclopropyl)carbamoyloxy. In other embodiments, $R^4$ can be stereoisomers of (2-(difluoromethyl)cyclopropyl)carbamoyloxy, such as ((1S,2S)-2-(difluoromethyl)cyclopropyl)carbamoyloxy or ((1R,2R)-2-(difluoromethyl)cyclopropyl)carbamoyloxy.

In certain embodiments, $R^4$ is (2,2-difluorocyclopropyl) carbamoyloxy. In other embodiments, $R^4$ can be stereoisomers of (2,2-difluorocyclopropyl)carbamoyloxy, such as (R)-(2,2-difluorocyclopropyl)carbamoyloxy or (S)-(2,2-difluorocyclopropyl)carbamoyloxy.

In certain embodiments, $R^4$ is (2-fluorocyclopropyl) carbamoyloxy. In other embodiments, $R^4$ can be stereoisomers of (2-fluorocyclopropyl) carbamoyloxy, such as ((1R,2S)-2-fluorocyclopropyl)carbamoyloxy, ((1S,2R)-2-fluorocyclopropyl)carbamoyloxy, ((1R,2R)-2-fluorocyclopropyl)carbamoyloxy, or ((1S,2S)-2-fluorocyclopropyl)carbamoyloxy.

In certain embodiments, $R^4$ is 1-(difluoromethyl)cyclopropyl carbamoyloxy.

In certain embodiments, $R^4$ is spiro[2.2]pentan-1-ylcarbamoyloxy. In other embodiments, $R^4$ can be stereoisomers of spiro[2.2]pentan-1-ylcarbamoyloxy, such as (R)-spiro[2.2]pentan-1-ylcarbamoyloxy or (S)-spiro[2.2]pentan-1-ylcarbamoyloxy.

In certain embodiments, $R^4$ is (1,1,1-trifluoropropan-2-yl)carbamoyloxy. In other embodiments, $R^4$ can be stereoisomers of (1,1,1-trifluoropropan-2-yl)carbamoyloxy, such as (R)-(1,1,1-trifluoropropan-2-yl)carbamoyloxy or (S)-(1,1,1-trifluoropropan-2-yl)carbamoyloxy.

In certain embodiments, $R^4$ is (1,1-difluoropropan-2-yl)carbamoyloxy. In other embodiments, $R^4$ can be stereoisomers of (1,1-difluoropropan-2-yl)carbamoyloxy, such as (S)-(1,1-difluoropropan-2-yl)carbamoyloxy or (R)-(1,1-difluoropropan-2-yl)carbamoyloxy.

In some embodiments, $R^4$ has a general formula of —OC(O)NR$^a$R$^b$, where R$^a$ and R$^b$ are linked together to from a 4-6 membered heterocycyl that is optionally substituted with one or more halo, $C_{1-3}$ alkyl, $C_{1-3}$ haloalkyl, cyano, or sulfonyl groups. In certain embodiments, $R^4$ is selected from the following: azetidine-1-carboxyl, 3,3-dimethylazetidine-1-carboxyl, 3-fluoro-3-methylazetidine-1-carboxyl, 3-(2-fluoropropan-2-yl)azetidine-1-carboxyl, 3-(1,1-difluoroethyl)azetidine-1-carboxyl, 3-(trifluoromethyl)azetidine-1-carboxyl, 3-hydrosulfonylazetidine-1-carboxyl, 3-(methylsulfonyl)azetidine-1-carboxyl, 3-cyano-3-methylazetidine-1-carboxyl, 2-methylazetidine-1-carboxyl, 5-azaspiro[2.3]hexane-5-carboxyl, 2-oxa-6-azaspiro[3.3]heptane-6-carboxyl, and 2-oxa-6-azaspiro[3.3]heptane-6-carboxyl.

In certain embodiments, $R^4$ is selected from the following: azetidine-1-carbonyloxy, 3,3-dimethylazetidine-1-carbonyloxy, 3-fluoro-3-methylazetidine-1-carbonyloxy, 3-(2-fluoropropan-2-yl)azetidine-1-carbonyloxy, 3-(1,1-difluoroethyl)azetidine-1-carbonyloxy, 3-(trifluoromethyl)azetidine-1-carbonyloxy, 3-hydrosulfonylazetidine-1-carbonyloxy, 3-(methylsulfonyl)azetidine-1-carbonyloxy, 3-cyano-3-methylazetidine-1-carbonyloxy, 2-methylazetidine-1-carbonyloxy, 5-azaspiro[2.3]hexane-5-carbonyloxy, 2-oxa-6-azaspiro[3.3]heptane-6-carbonyloxy, and 2-oxa-6-azaspiro[3.3]heptane-6-carbonyloxy.

In some embodiments, $R^4$ has a general formula of —NHC(O)R$^b$, where R$^b$ is $C_{1-3}$ alkyl or 3-6 membered cycloalkyl, where the $C_{1-3}$ alkyl or 3-6 membered cycloalkyl is further optionally substituted with halo, $C_{1-3}$ alkyl, $C_{1-3}$ haloalkyl, or a 3-6 membered cycloalkyl. In some embodiments, $R^4$ has a general formula of —NC(O)R$^a$, where R$^a$ is $C_{1-3}$ alkyl, $C_{1-3}$ haloalkyl, or 3-6 membered cycloalkyl, where the $C_{1-3}$ alkyl, $C_{1-3}$ haloalkyl, or 3-6 membered cycloalkyl is further optionally substituted with halo, $C_{1-3}$ alkyl, $C_{1-3}$ haloalkyl, or a 3-6 membered cycloalkyl. In certain embodiments, $R^4$ is 3,3,3-trifluoropropanamidyl. In certain embodiments, $R^4$ is 3,3,3-trifluoro-2-methylpropanamidyl. In other embodiments, $R^4$ can be stereoisomers of 3,3,3-trifluoro-2-methylpropanamidyl, such as (R)-3,3,3-trifluoro-2-methylpropanamidyl or (S)-3,3,3-trifluoro-2-methylpropanamidyl. In certain embodiments, $R^4$ is 2-cyclopropylacetamidyl. In certain embodiments, $R^4$ is isobutyramidyl.

In some embodiments, $R^4$ has a general formula —OR$^a$, where R$^a$ can be $C_{1-3}$ alkyl, 3-6 membered cycloalkyl, 5-10 membered aryl, or 5-10 membered heteroaryl, where the $C_{1-3}$ alkyl, 3-6 membered cycloalkyl, 5-10 membered aryl, and 5-10 membered heteroaryl each can further optionally be substituted with one or more halo or $C_{1-3}$ alkyl. In some embodiments, $R^4$ has a general formula —OR$^a$, where R$^a$ can be $C_{1-3}$ alkyl, $C_{1-3}$ haloalkyl, 3-6 membered cycloalkyl, 5-10 membered aryl, or 5-10 membered heteroaryl, where the $C_{1-3}$ alkyl, $C_{1-3}$ haloalkyl, 3-6 membered cycloalkyl, 5-10 membered aryl, or 5-10 membered heteroaryl can further optionally be substituted with one or more halo or $C_{1-3}$ alkyl. In certain embodiments, $R^4$ is 2,4-difluoro-phenoxy.

In some embodiments, $R^4$ has a general formula —NHS(O)$_2$R$^b$. In some embodiments, $R^4$ has a formula —NHS(O)$_2$R$^b$, where R$^b$ is $C_{1-3}$ alkyl or 3-6 membered cycloalkyl. In some embodiments, $R^4$ has a general formula —NS(O)$_{0-2}$R$^a$. In some embodiments, $R^4$ has a formula —NS(O)$_{0-2}$R$^a$, where R$^a$ is $C_{1-3}$ alkyl or 3-6 membered cycloalkyl. In certain embodiments, $R^4$ is cyclopropyl sulfonamidyl.

In some embodiments, $R^4$ has a general formula —NHC(O)OR$^b$. In some embodiments, $R^4$ has a general formula —NHC(O)OR$^b$, where R$^b$ is selected from $C_{1-3}$ alkyl, a 3-6 membered cycloalkyl, a 3-6 membered heterocycyl, a 5-10 membered aryl, or a 5-10 membered heteroaryl. In some embodiments, $R^4$ has a general formula —NHC(O)O-cyclopropyl. In some embodiments, $R^4$ has a general formula —NC(O)OR$^a$. In some embodiments, $R^4$ has a general formula —NC(O)OR$^a$, where R$^a$ is selected from $C_{1-3}$ alkyl, a 3-6 membered cycloalkyl, a 3-6 membered heterocycyl, a 5-10 membered aryl, or a 5-10 membered heteroaryl. In certain embodiments, $R^4$ is carbamate cyclopropyl.

In some embodiments, the halogen atoms of any group within $R^4$ can be replaced with deuterium atoms. In some embodiments, the hydrogen atoms of any group within $R^4$ can be replaced with deuterium atoms.

In other embodiments, $R^4$ has the following formula:

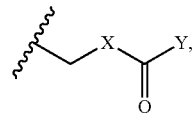

where X is either oxo or N, and Y has the general formula —NR$^a$R$^b$. In certain embodiments, X is oxo. In some embodiments, when X is oxo, it refers to X is an oxygen linker: —O—. In certain embodiments, Y is selected from hydrogen, $C_{1-3}$ alkyl, $C_{1-3}$ haloalkyl, 3-6 membered cycloalkyl, 4-10 membered heterocycyl, 5-10 membered aryl, sulfonyl, or amino, where the $C_{1-3}$ alkyl, $C_{1-3}$ haloalkyl, 3-6 membered cycloalkyl, 4-10 membered heterocycyl, 5-10 membered aryl, sulfonyl, or amino group is further optionally substituted with one or more $R^{20}$ groups.

In other embodiments, $R^4$ has the following formula:

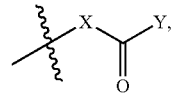

where X is either oxo or N, and Y has the general formula —NR$^a$R$^b$. In certain embodiments, X is oxo. In some embodiments, when X is oxo, it refers to X is an oxygen linker: —O—. In certain embodiments, Y is selected from hydrogen, $C_{1-3}$ alkyl, $C_{1-3}$ haloalkyl, 3-6 membered cycloalkyl, 4-10 membered heterocycyl, 5-10 membered aryl, sulfonyl, or amino, where the $C_{1-3}$ alkyl, $C_{1-3}$ haloalkyl, 3-6 membered cycloalkyl, 4-10 membered heterocycyl, 5-10 membered aryl, sulfonyl, or amino group is further optionally substituted with one or more $R^{20}$ groups.

In other embodiments, $R^4$ has the following formula:

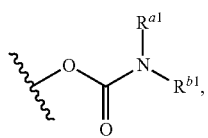

where $R^{a1}$ and $R^{b1}$ each independently selected from the group consisting of hydrogen, $C_{1-6}$ alkyl, 3-10 membered cycloalkyl, —S(O)$_2$R$^{21}$ each of which is optionally substituted with one to five $R^{21}$ groups, where each $R^{21}$ is independently selected from the group consisting of $C_{1-6}$ alkyl, $C_{1-6}$ haloalkyl, 3-10 membered cycloalkyl, $C_{1-6}$ alkoxy, 3-12 membered heterocyclyl, 6-10 membered aryl, 5-10 membered heteroaryl, hydroxyl, amino, —S(O)$_2$—CH$_3$, amino, —CN or halogen.

In some embodiments, $R^{a1}$ and $R^{b1}$ are appended to the same group to form a 3-12 membered heterocyclyl optionally substituted with from one to five $R^{21}$ groups.

In some embodiments, $R^4$ is selected from a group consisting of:

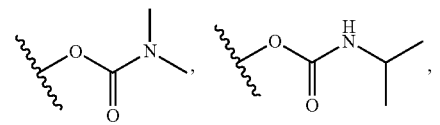

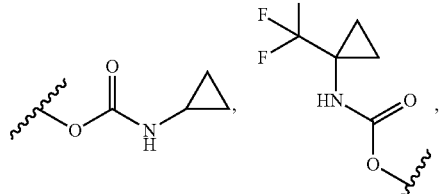

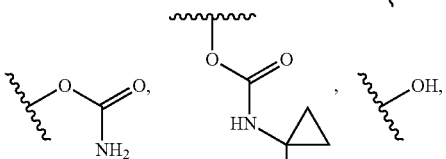

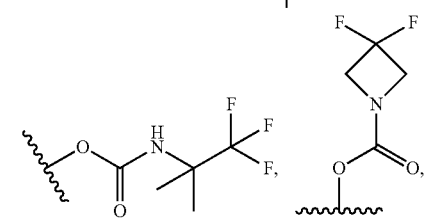

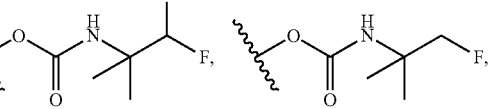

-continued

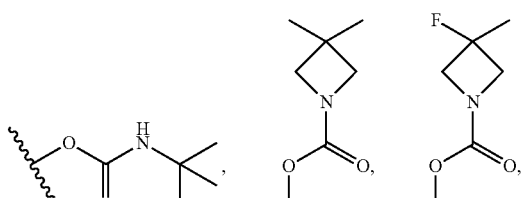

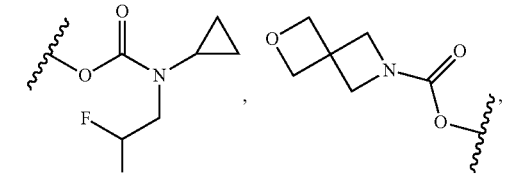

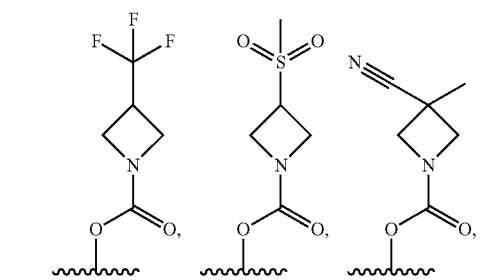

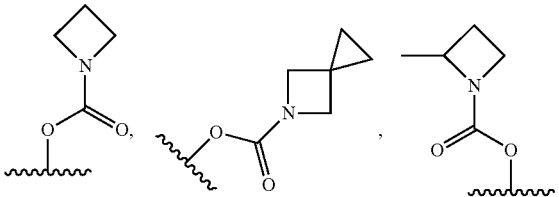

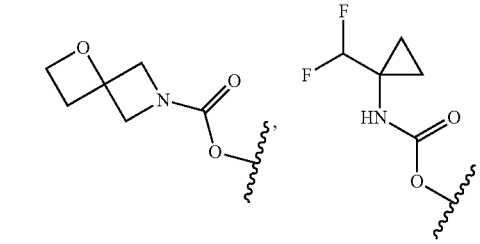

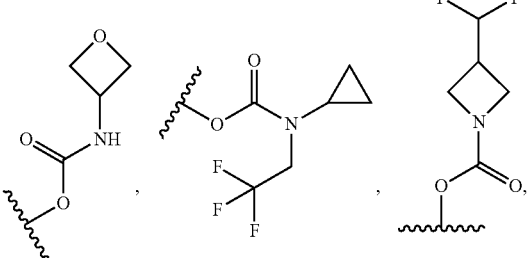

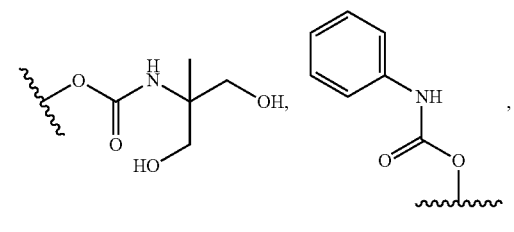

-continued
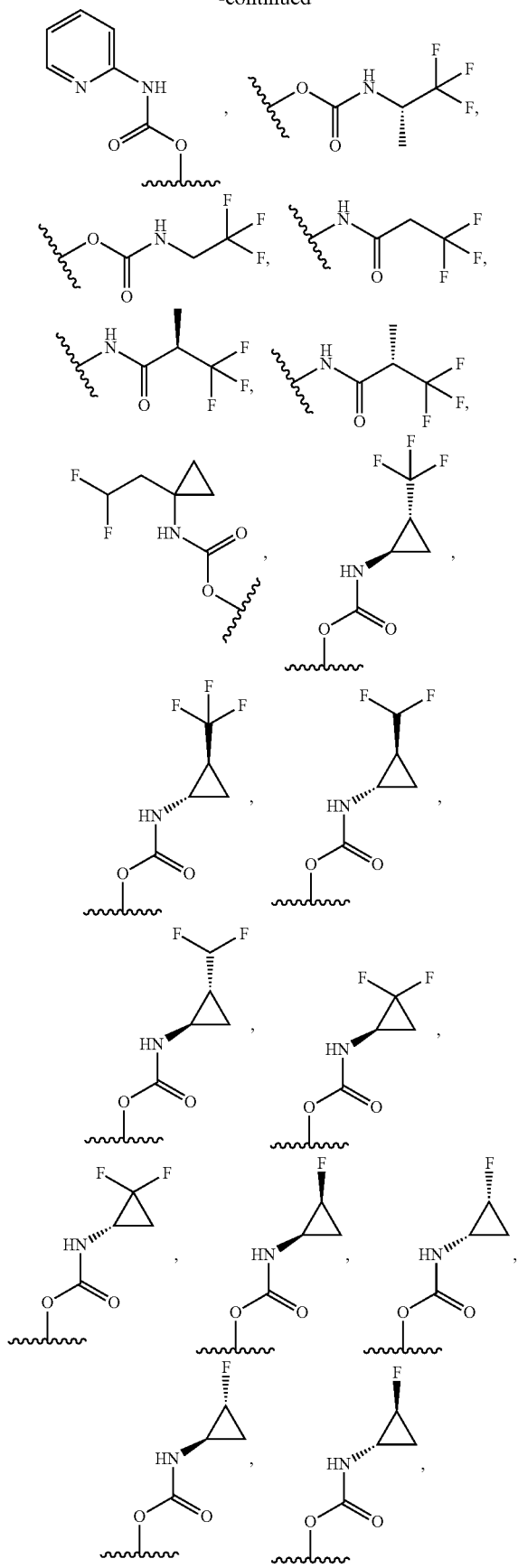
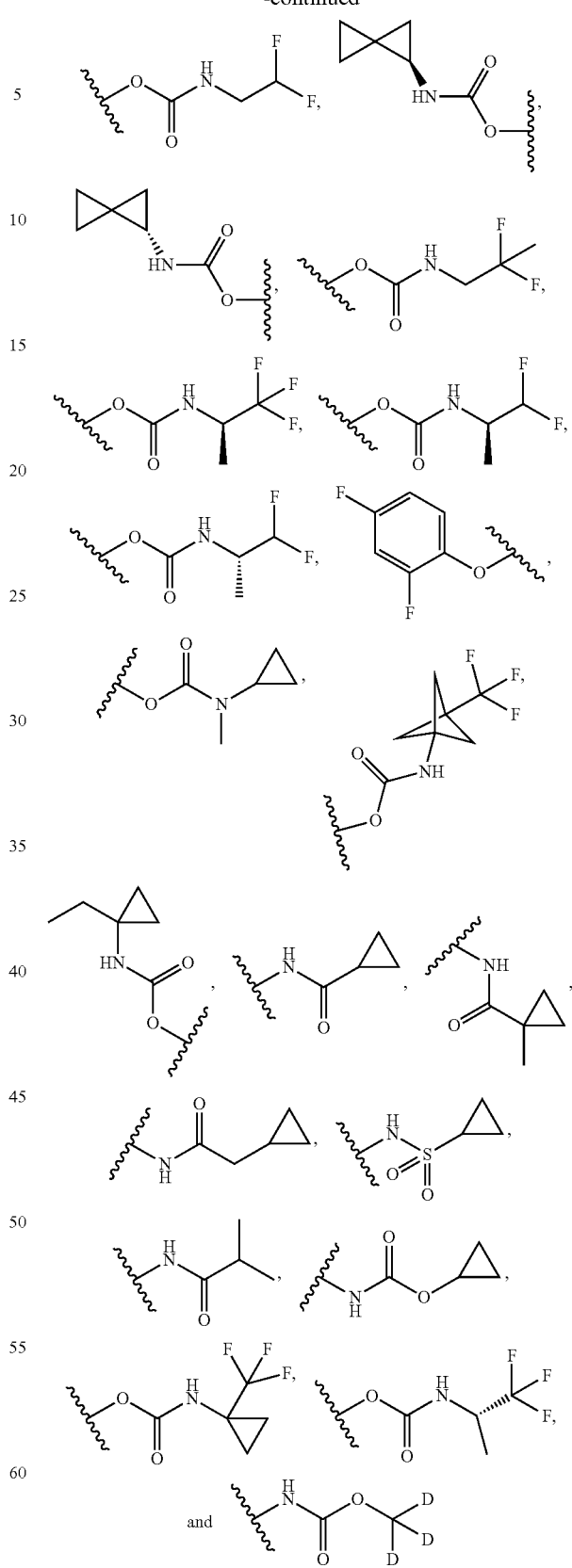
In some embodiments, R[4] is

In some embodiments, R⁴ is

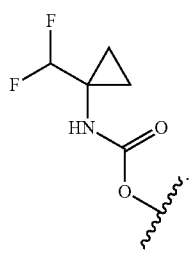

In some embodiments, R⁴ is

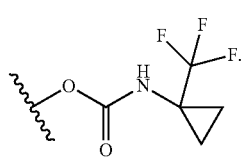 [SMILES: *OC(=O)NC1(C(F)(F)F)CC1]

In some embodiments, R⁴ is

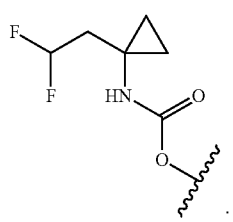 [SMILES: *OC(=O)NC1(CC(F)F)CC1]

In some embodiments, $R^5$ is a 5-10 membered heteroaryl, where the 5-10 membered heteroaryl is optionally substituted with 1-5 $R^{20}$ groups.

In some embodiments, $R^5$ is pyrazolyl is optionally substituted with 1-3 $R^{20}$ groups. In some embodiments, $R^5$ is pyrazolyl optionally substituted with 1, 2, or 3 groups selected from cyano, $C_{1-3}$ alkyl, $C_{1-6}$ haloalkyl, $C_{1-3}$ alkoxy, 3-6 membered cycloalkyl, 3-6 membered heterocycloalkyl, 5-10 membered aryl, and 5-10 membered heteroaryl. In some embodiments, $R^5$ is 5-10 membered heteroaryl substituted with $C_{1-6}$ haloalkyl, where $C_{1-6}$ haloalkyl is $CHF_2$.

In certain embodiments, $R^5$ is unsubstituted pyrazolyl. In certain embodiments, $R^5$ is 4-cyanopyrazolyl. In certain embodiments, $R^5$ is pyrazolyl substituted with $C_{1-3}$ haloalkyl. In certain embodiments, $R^5$ is fluoromethyl pyrazolyl, difluoromethyl pyrazolyl, or trifluoromethyl pyrazolyl. In certain embodiments, $R^5$ is difluoromethyl pyrazolyl.

In some embodiments, $R^5$ is imidazolyl is optionally substituted with 1-5 $R^{20}$ groups. In some embodiments, $R^5$ is imidazolyl optionally substituted with 1, 2, or 3 groups selected from cyano, $C_{1-3}$ alkyl, $C_{1-3}$ haloalkyl, $C_{1-3}$ alkoxy, 3-6 membered cycloalkyl, 3-6 membered heterocycloalkyl, 5-10 membered aryl, and 5-10 membered heteroaryl. In certain embodiments, $R^5$ is imidazolyl, 1-methyl-1H-imidazolyl, 4-chloro-1H-imidazolyl, 4,5-dichloro-1H-imidazolyl, and difluoromethyl imidazolyl.

In some embodiments, $R^5$ is triazolyl optionally substituted with 1-5 $R^{20}$ groups. In some embodiments, $R^5$ is triazolyl is optionally substituted with 1 or 2 groups selected from cyano, $C_{1-3}$ alkyl, $C_{1-3}$ haloalkyl, $C_{1-3}$ alkoxy, 3-6 membered cycloalkyl, 3-6 membered heterocycloalkyl, 5-10 membered aryl, and 5-10 membered heteroaryl. In certain embodiments, $R^5$ is triazolyl, methyl triazolyl, difluoromethyl triazolyl, and cyclopropyl triazolyl.

In some embodiments, $R^5$ is tetrazolyl optionally substituted with a $R^{20}$ group. In some embodiments, $R^5$ is tetrazolyl is optionally substituted with groups selected from cyano, $C_{1-3}$ alkyl, $C_{1-3}$ haloalkyl, $C_{1-3}$ alkoxy, 3-6 membered cycloalkyl, 3-6 membered heterocycloalkyl, 5-10 membered aryl, and 5-10 membered heteroaryl.

In some embodiments, $R^5$ is oxazolyl optionally substituted with 1-3 $R^{20}$ groups. In some embodiments, $R^5$ is oxazolyl is optionally substituted with 1,2, or 3 groups selected from cyano, $C_{1-3}$ alkyl, $C_{1-3}$ haloalkyl, $C_{1-3}$ alkoxy, 3-6 membered cycloalkyl, 3-6 membered heterocycloalkyl, 5-10 membered aryl, and 5-10 membered heteroaryl. In certain embodiments, $R^5$ is oxazolyl, methyloxazolyl, and phenyloxazolyl.

In some embodiments, $R^5$ is thiazolyl optionally substituted with 1-3 $R^{20}$ groups. In some embodiments, $R^5$ is thiazolyl is optionally substituted with 1, 2, or 3 groups selected from cyano, $C_{1-3}$ alkyl, $C_{1-3}$ haloalkyl, $C_{1-3}$ alkoxy, 3-6 membered cycloalkyl, 3-6 membered heterocycloalkyl, 5-10 membered aryl, and 5-10 membered heteroaryl. In certain embodiments, $R^5$ is thiazolyl, phenylthiazolyl, and morpholinyl thiazolyl.

In some embodiments, $R^5$ is thiadiazolyl optionally substituted with a $R^{20}$ group. In some embodiments, $R^5$ is thiadiazolyl is optionally substituted with any one of the following groups: cyano, $C_{1-3}$ alkyl, $C_{1-3}$ alkoxy, $C_{1-3}$ haloalkyl, 3-6 membered cycloalkyl, 3-6 membered heterocycloalkyl, 5-10 membered aryl, and 5-10 membered heteroaryl. In certain embodiments, $R^5$ is thiadiazolyl and cyclopropyl thiadiazolyl. In certain embodiments, $R^5$ is 1,3,4-thiadiazolyl. In certain embodiments, $R^5$ is 1,2,3-thiadiazolyl.

In some embodiments, $R^5$ is pyridinyl optionally substituted with 1-4 $R^{20}$ groups. In some embodiments, $R^5$ is pyridinyl optionally substituted with $C_{1-3}$ alkyl or halo. In certain embodiments, $R^5$ is pyridinyl or methylpyridinyl. In certain embodiments, $R^5$ is fluoropyridinyl or chloropyridinyl.

In some embodiments, $R^5$ is pyrimidinyl optionally substituted with 1-3 $R^{20}$ groups. In some embodiments, $R^5$ is pyrimidinyl optionally substituted with is optionally substituted with 1,2, or 3 groups selected from cyano, $C_{1-3}$ alkyl, $C_{1-3}$ alkoxy, $C_{1-3}$ haloalkyl, 3-6 membered cycloalkyl, 3-6 membered heterocycloalkyl, 5-10 membered aryl, and 5-10 membered heteroaryl. In certain embodiments, $R^5$ is pyrimidinyl. In certain embodiments, $R^5$ is pyrimidinyl substituted with $C_{1-3}$ alkoxy. In certain embodiments, $R^5$ is methoxypyrimidinyl.

In certain embodiments, $R^5$ is cyano.

In some embodiments, $R^5$ is halo. In certain embodiments, $R^5$ is fluoro.

In other embodiments, $R^5$ has the following structure:

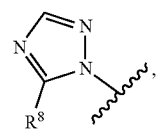

where $R^8$ is halogen, oxo, —CN, $C_{1-6}$ alkyl, $C_{1-6}$ haloalkyl, 3-6 membered cycloalkyl, or —$COR^M$, and where $R^{21}$ is independently selected from the group consisting of $C_{1-6}$ alkyl, $C_{1-6}$ haloalkyl, 3-10 membered cycloalkyl, $C_{1-6}$ alkoxy, 3-12 membered heterocyclyl, 5-10 membered aryl, 5-10 membered heteroaryl, hydroxyl, amino, —S(O)$_2$—CH$_3$, C$_{1-6}$ alkylamino, —CN or halogen.
In some embodiments, R$^5$ is selected from a group consisting of:
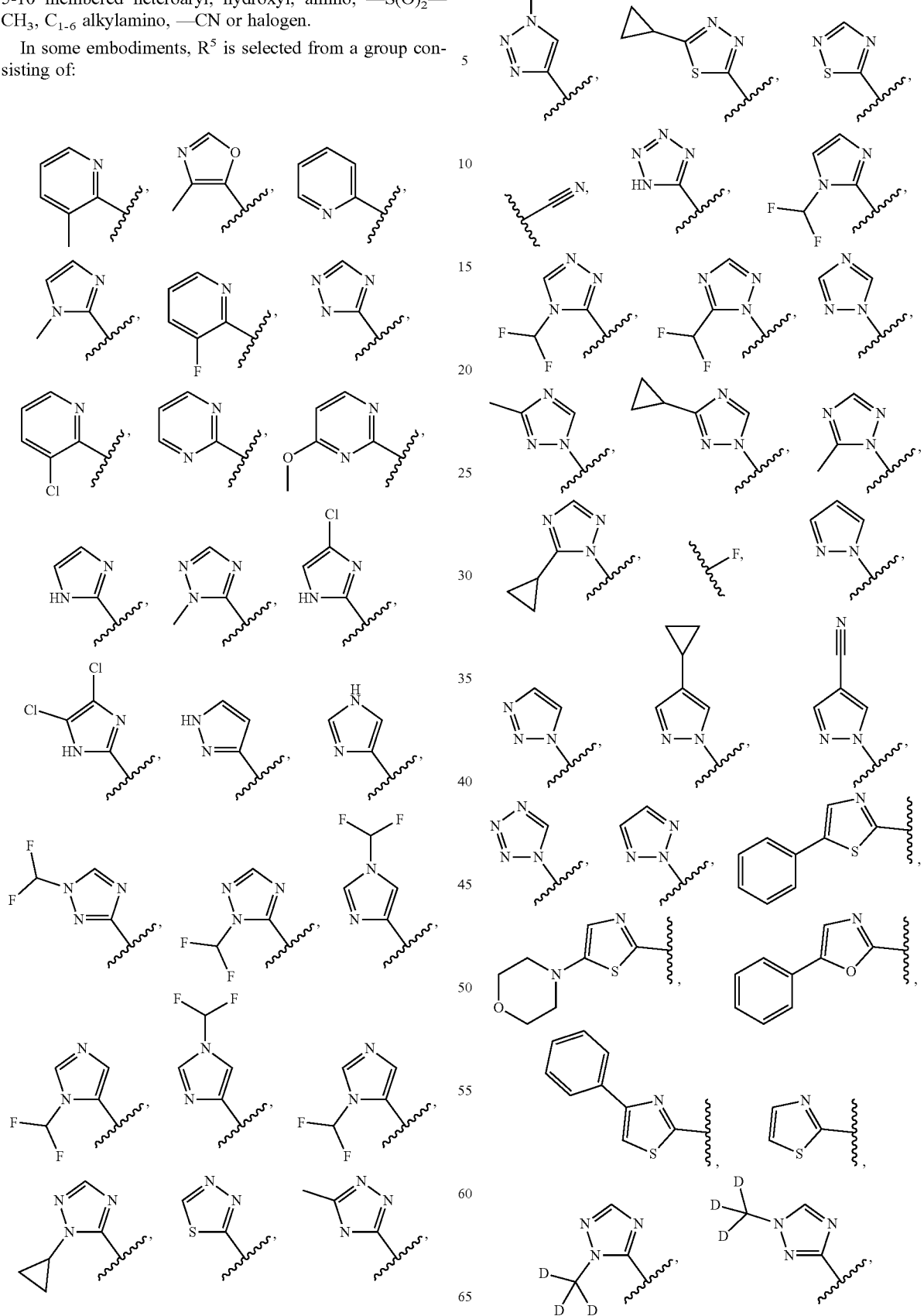

and 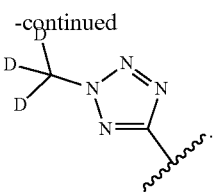

In some embodiments, $R^5$ is

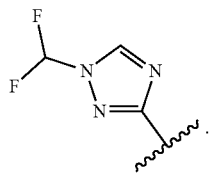 [SMILES: *c1ncn(C(F)F)n1]

In some embodiments, $R^5$ is

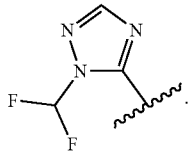

In some embodiments, $R^5$ is

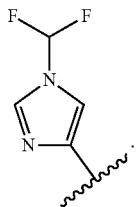

In some embodiments, $R^5$ is

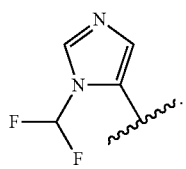

In some embodiments, $R^6$ is hydrogen, halo, —CN, $C_{1-3}$ haloalkoxy, —C(O)NR$^a$R$^b$, or 5-10 membered heteroaryl optionally substituted with 1-5 $R^{20}$ groups.

In some embodiments, $R^6$ is hydrogen, halo, —CN, $C_{1-3}$ haloalkoxy, —C(O)NR$^a$R$^b$, or $C_{5-10}$ heteroaryl optionally substituted with 1-5 $R^{20}$ groups.

In certain embodiments, $R^6$ is hydrogen.

In some embodiments, $R^6$ is halo. In certain embodiments, $R^6$ is chloro. In certain embodiments, $R^6$ is fluoro.

In certain embodiments, $R^6$ is cyano.

In certain embodiments, $R^6$ is a $C_{1-3}$ haloalkoxy. In certain embodiments, $R^6$ is fluoromethoxy. In certain embodiments, $R^6$ is difluoromethoxy. In certain embodiments, $R^6$ is trifluoromethoxy.

In some embodiments, $R^6$ has the general formula —C(O)NR$^a$R$^b$. In certain embodiments, $R^6$ has the formula —C(O)NR$^a$R$^b$, where $R^a$ and $R^b$ are independently hydrogen, $C_{1-3}$ alkyl, $C_{1-3}$ haloalkyl, or a 3-6 membered cycloalkyl. In certain embodiments, $R^6$ has the formula —C(O)NR$^a$R$^b$, where $R^a$ and $R^b$ are independently hydrogen, $C_{1-3}$ alkyl, or a 3-6 membered cycloalkyl. In certain embodiments, $R^6$ is —C(O)NR$^a$R$^b$ where $R^a$ and $R^b$ are both hydrogen. In certain embodiments, $R^6$ is formamidyl.

In some embodiments, $R^6$ is a 5-10 membered heteroaryl optionally substituted with 1-5 $R^{20}$ groups. In some embodiments, $R^6$ is furanyl, pyrrolyl, imidazolyl, pyrazolyl, triazolyl, oxazolyl, or thiazolyl that can be independently substituted with 1, 2, or 3 $C_{1-3}$ alkyl or $C_{1-3}$ haloalkyl groups. In certain embodiments, $R^6$ is triazolyl substituted that is independently substituted with 1 or 2 $C_{1-3}$ alkyl or $C_{1-3}$ haloalkyl groups. In certain embodiments, $R^6$ is fluoromethyl triazolyl. In certain embodiments, $R^6$ is difluoromethyl triazolyl. In certain embodiments, $R^6$ is trifluoromethyl triazolyl.

In some embodiments, $R^7$ is absent or $R^7$ is independently selected from the group consisting of $C_{1-6}$ alkyl, $C_{1-6}$ alkoxy, —NR$^a$R$^b$, halogen, cyano, 5-10 membered aryl, 3-6 membered cycloalkyl, 5-10 membered heteroaryl and 3-12 membered heterocyclyl, wherein each $C_{1-6}$ alkyl, $C_{1-6}$ alkoxy, 5-10 membered aryl, 3-6 membered cycloalkyl, 5-10 membered heteroaryl and 3-12 membered heterocyclyl is optionally substituted with 1-5 $R^{20}$ groups.

In some embodiments, $R^7$ is a 5-10 membered heteroaryl that is optionally substituted with 1-5 $R^{20}$ groups. In certain embodiments, $R^7$ is a five membered heteroaryl substituted with 1, 2, 3, or 4 $R^{20}$ groups. In certain embodiments, $R^7$ is furanyl, pyrrolyl, imidazolyl, pyrazolyl, triazolyl, oxazolyl, or thiazolyl that can be independently substituted with 1, 2, or 3 $C_{1-3}$ alkyl groups. In certain embodiments, $R^7$ is methyl oxazolyl.

In some embodiments, $R^1$ is absent. In some embodiments, m is 0. In some embodiments, m is 1.

In some embodiments, $R^8$ is $C_{1-6}$ haloalkyl. In some embodiments, $R^8$ is CHF$_2$. In some embodiments, $R^8$ is CH$_2$F. In some embodiments, $R^8$ is CF$_3$.

In one embodiment, the compound of the present disclosure is selected from the group consisting of:

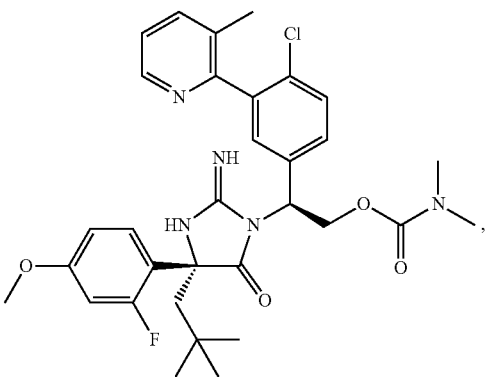

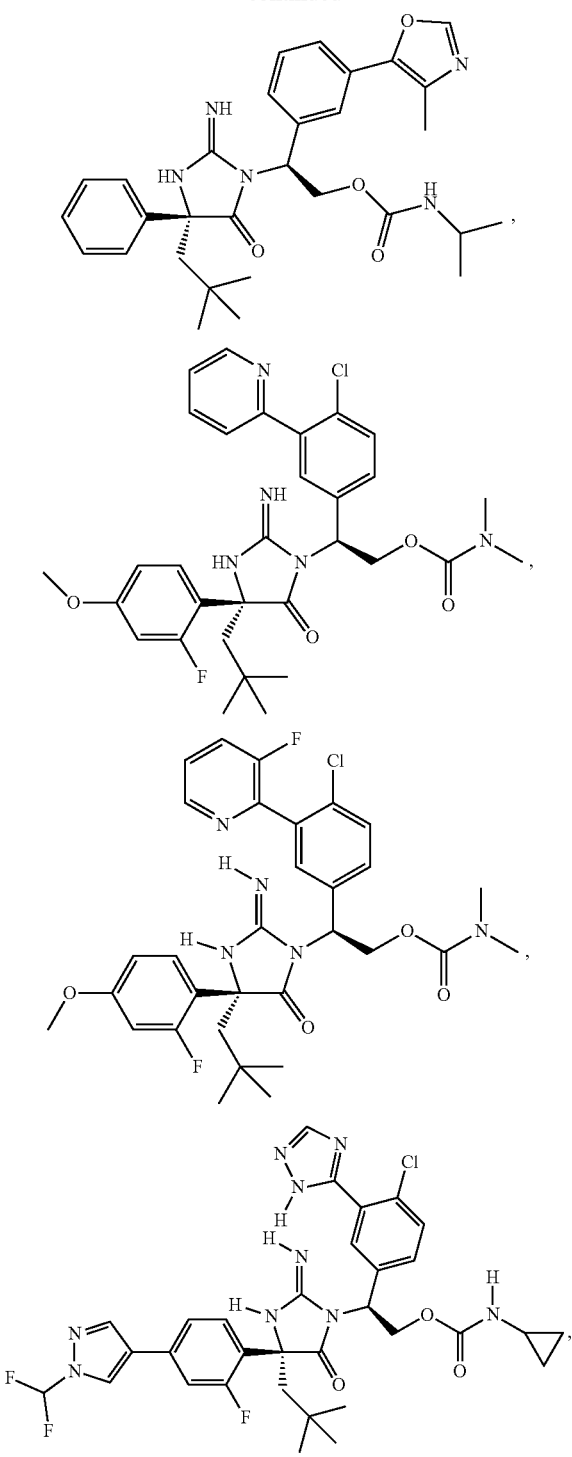
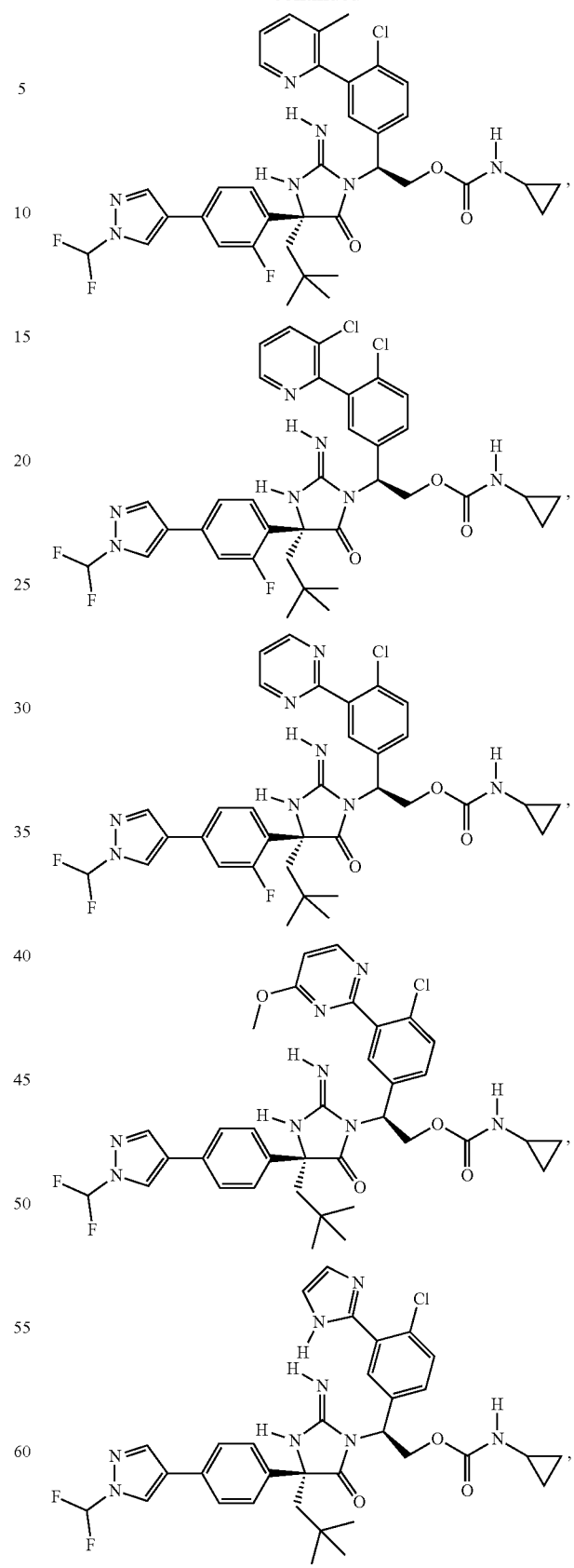

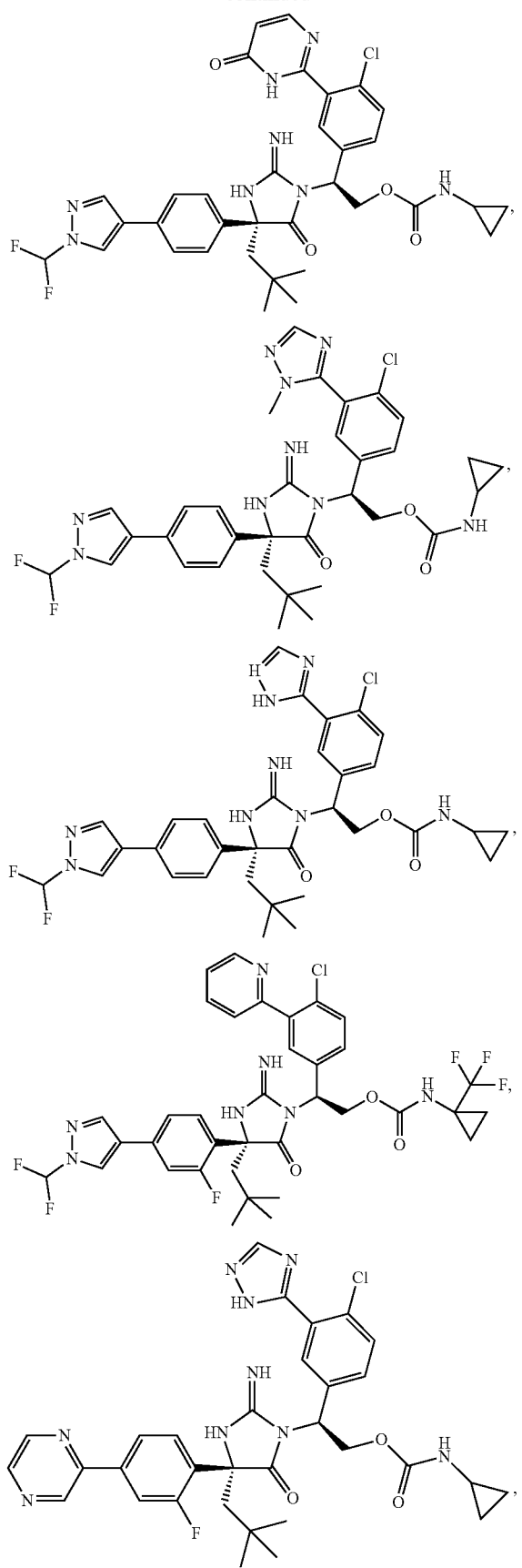
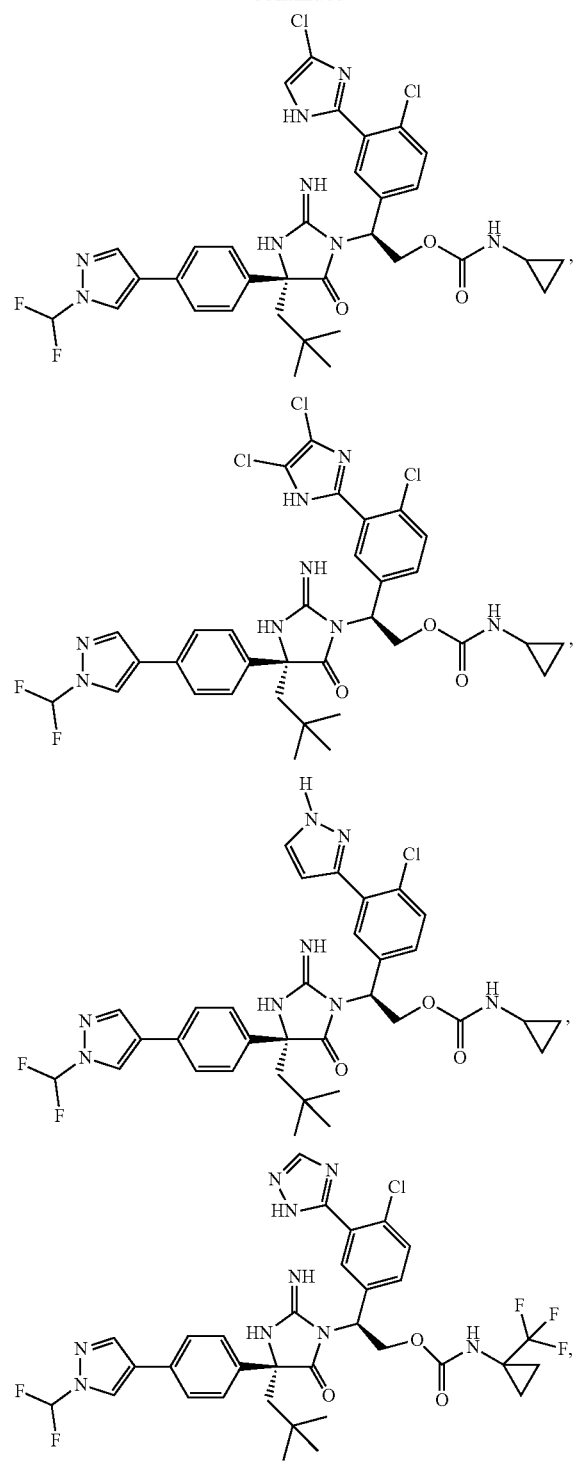

-continued

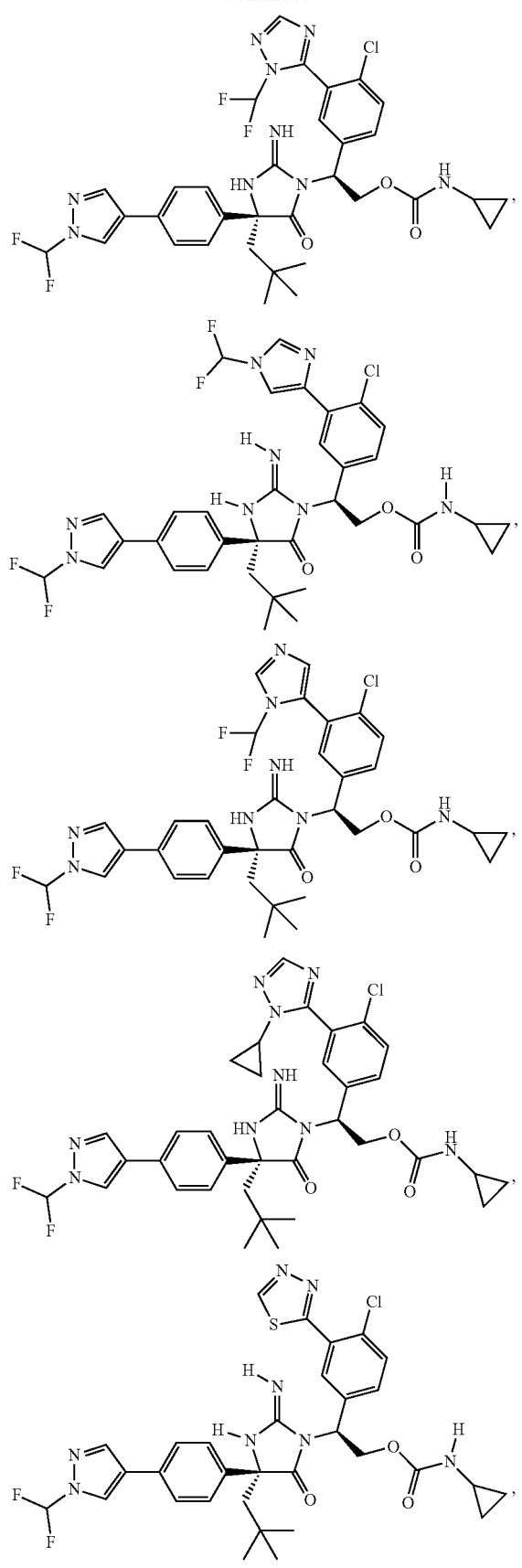
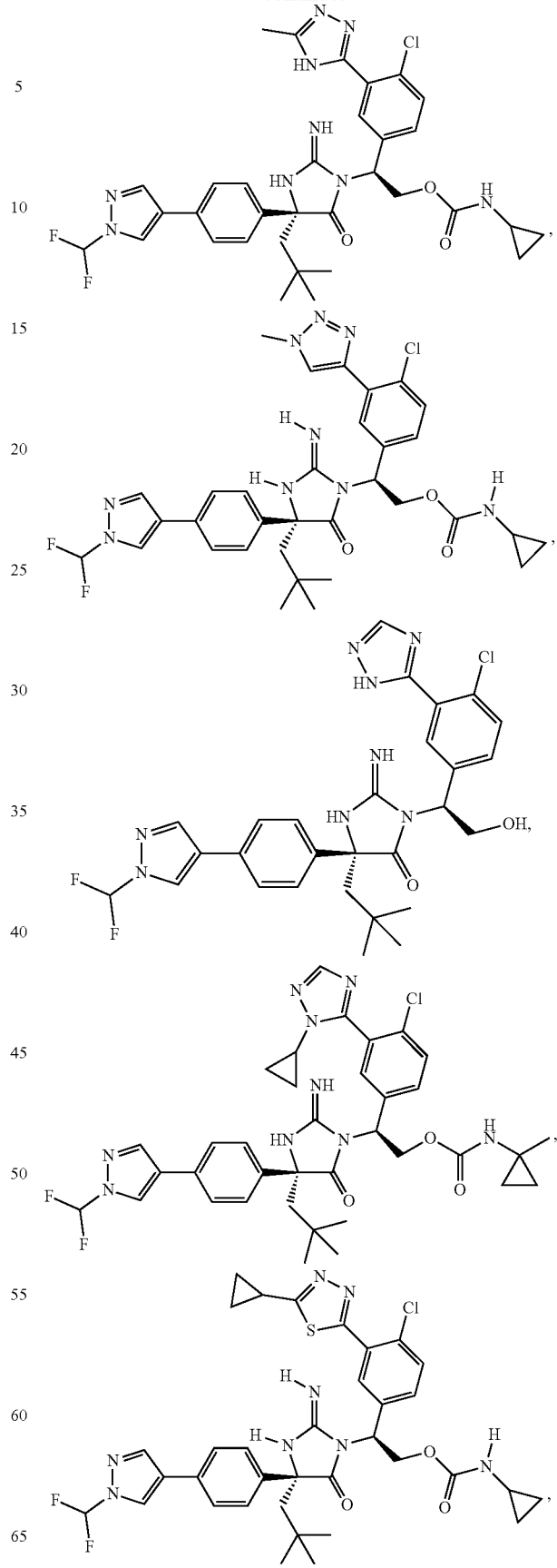

53
-continued
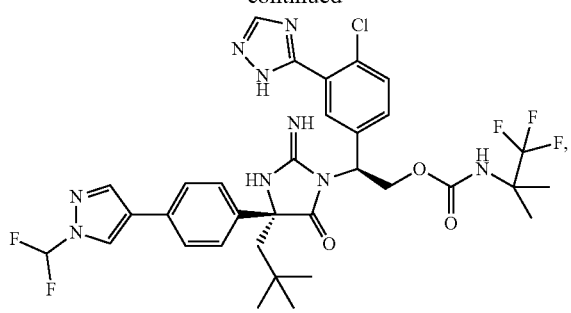
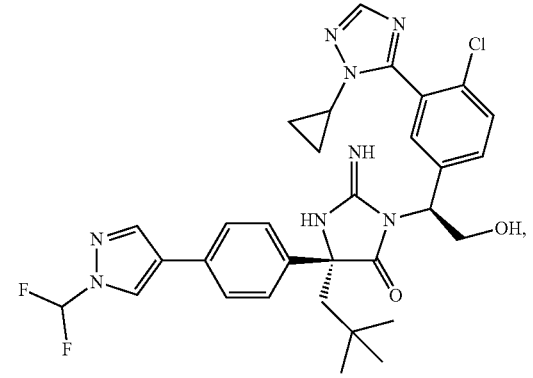
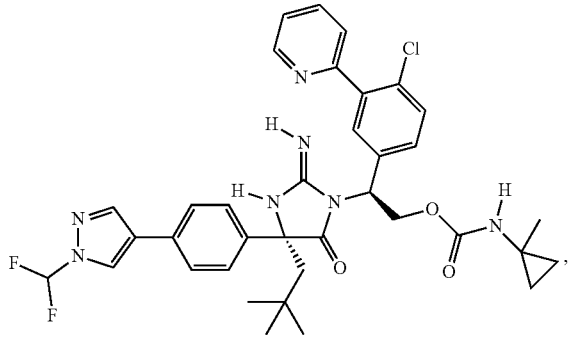
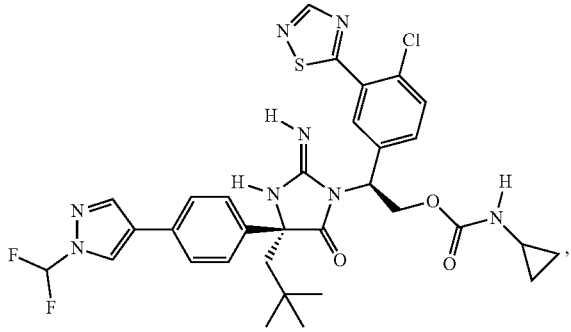
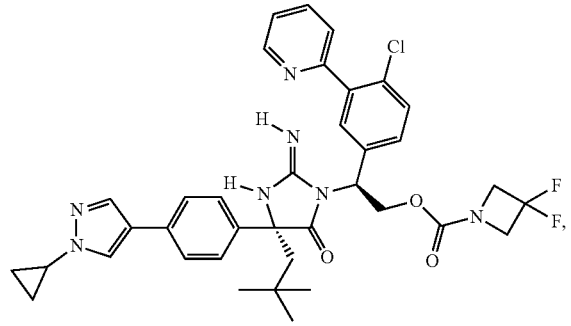
54
-continued
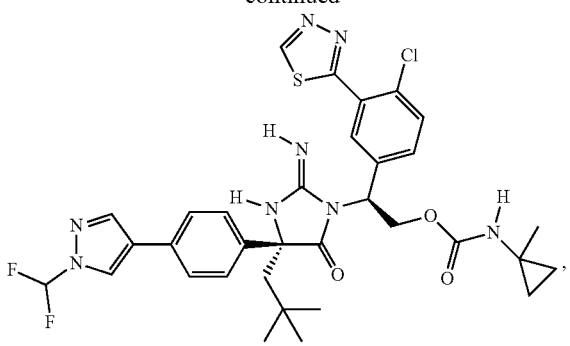
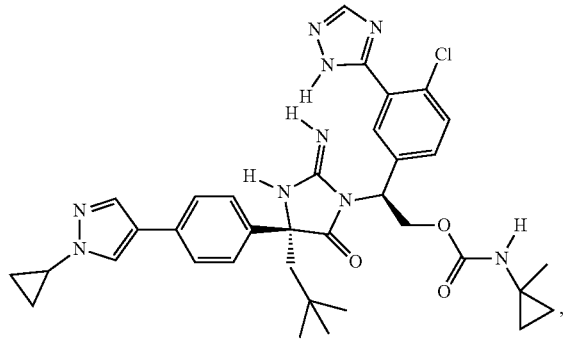
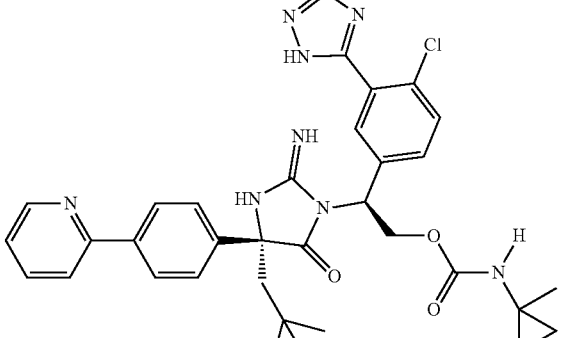
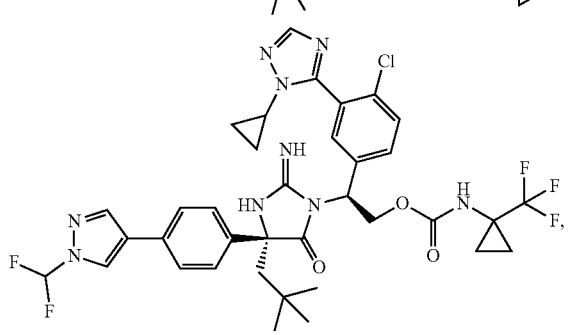
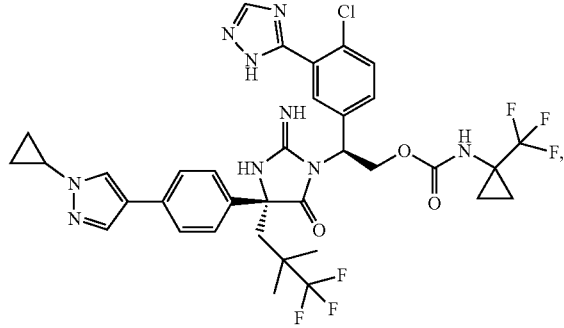

55
-continued
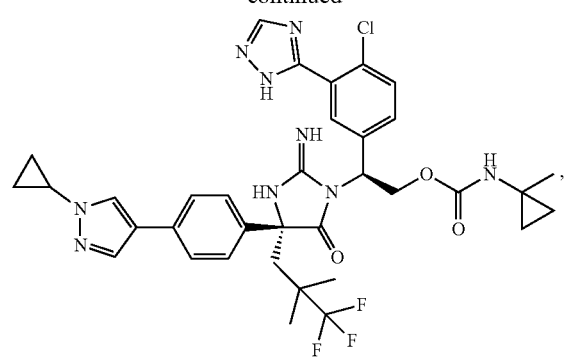
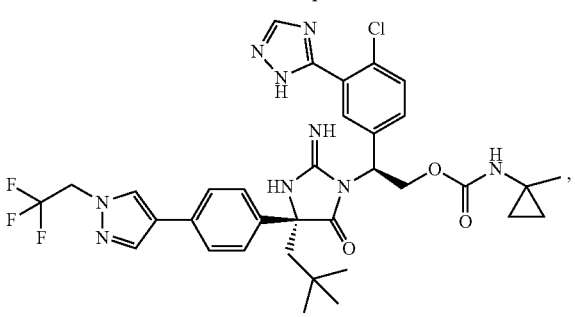
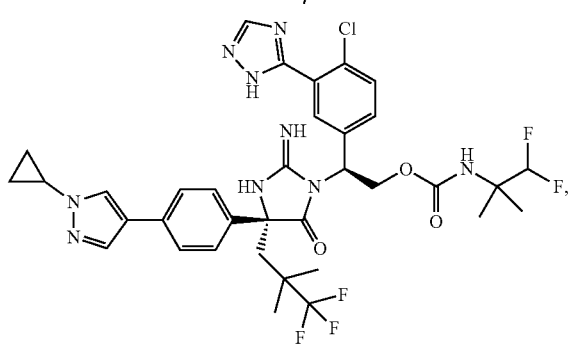
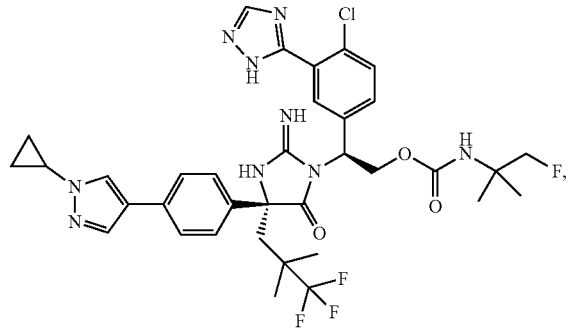
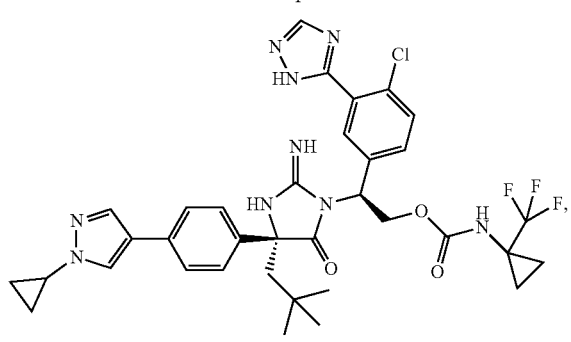
56
-continued
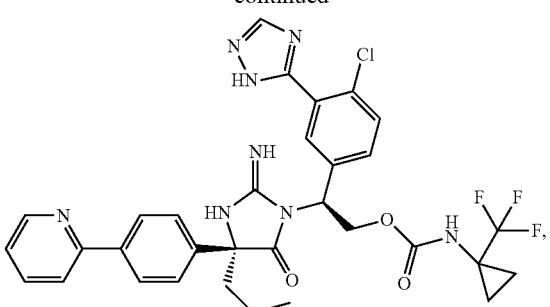
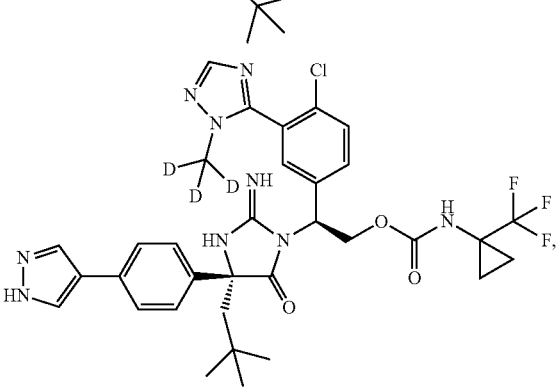
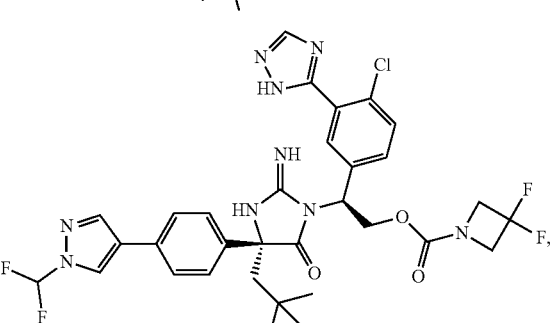
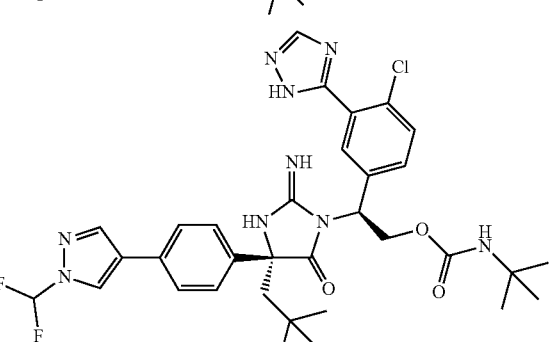
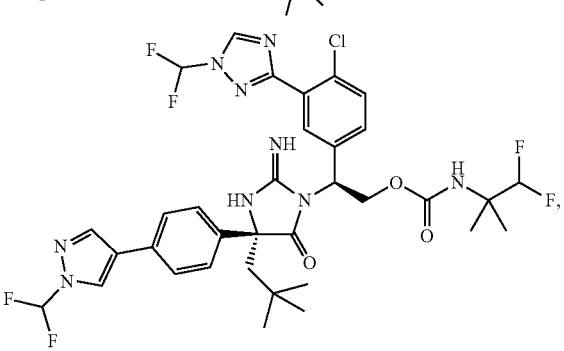

57
-continued
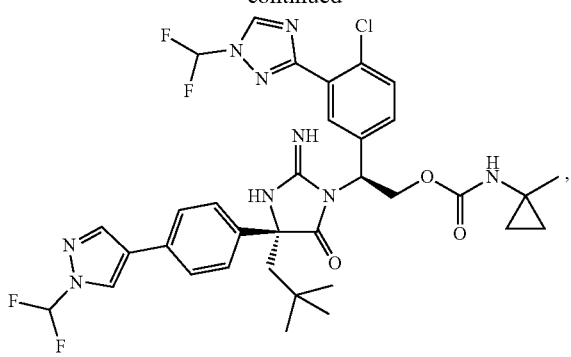
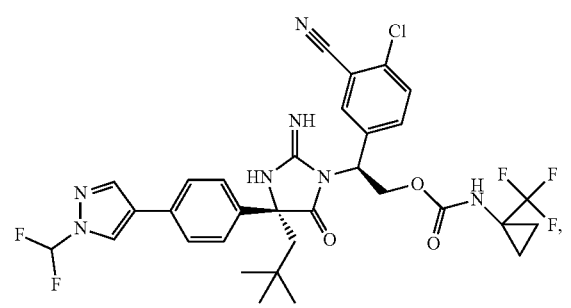
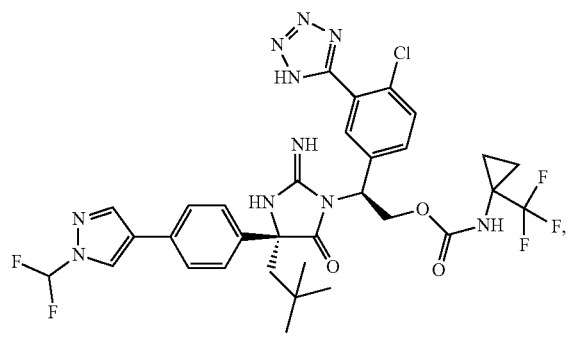
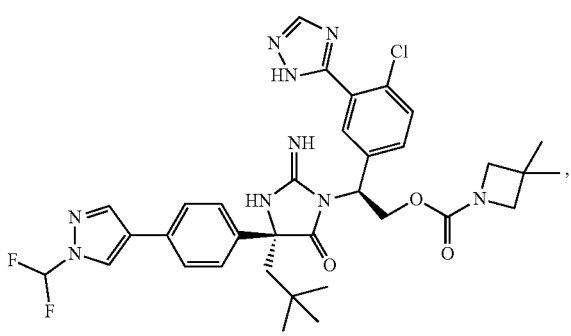
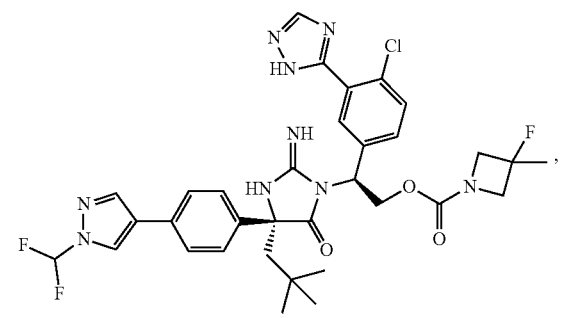
58
-continued
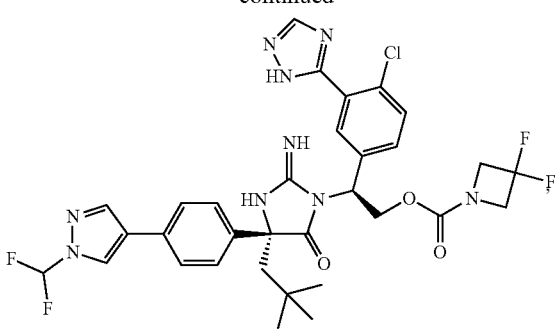
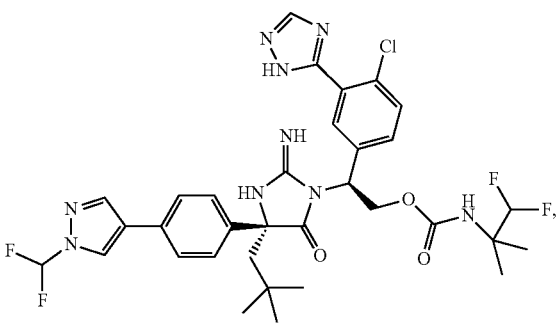
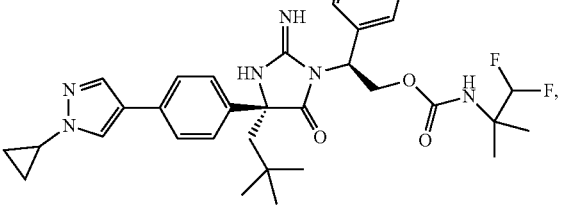
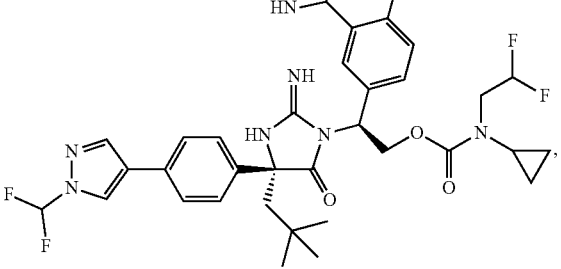
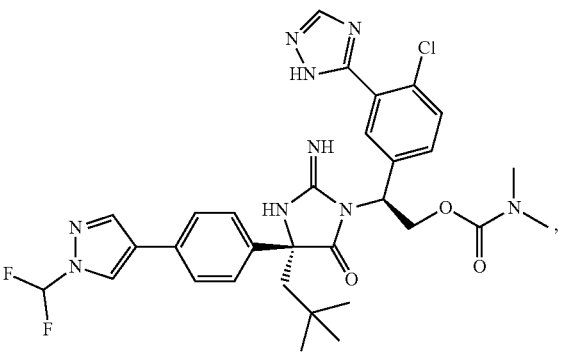

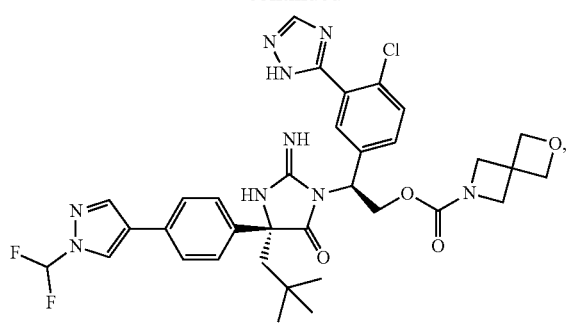
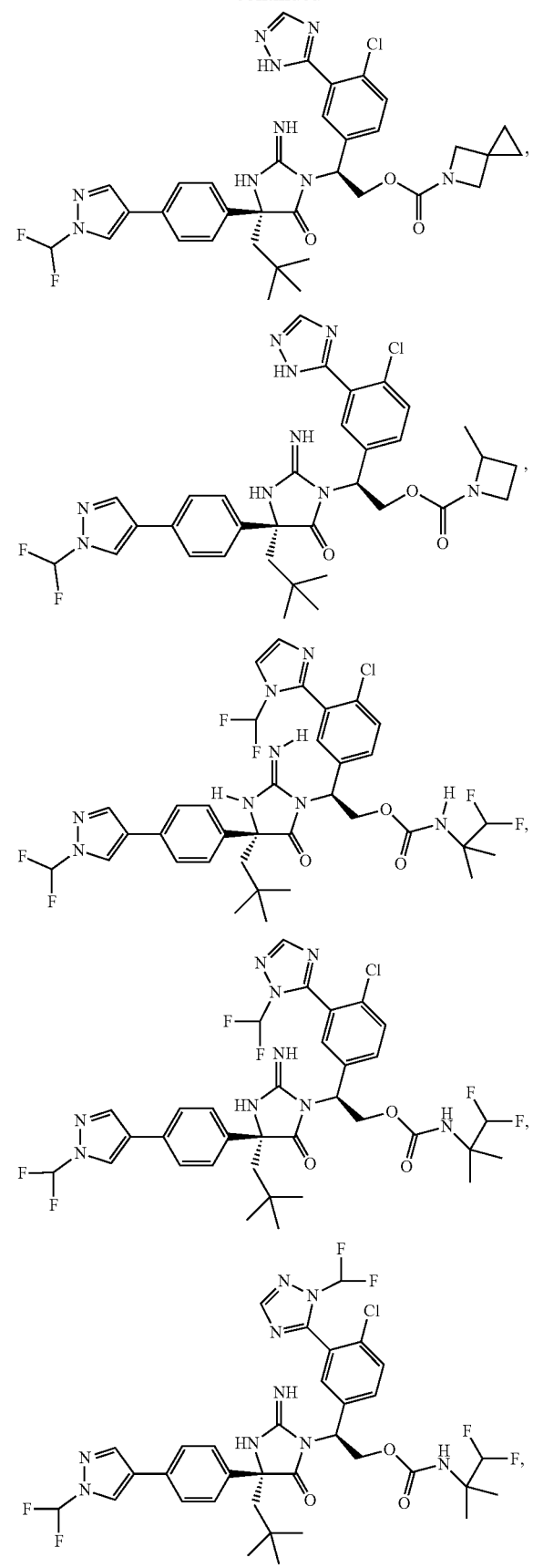

61
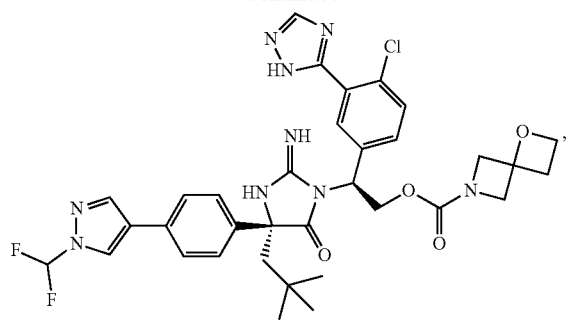
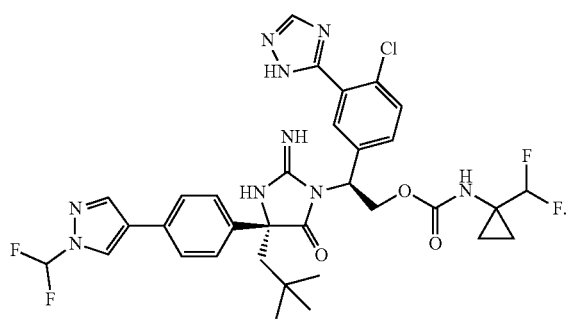
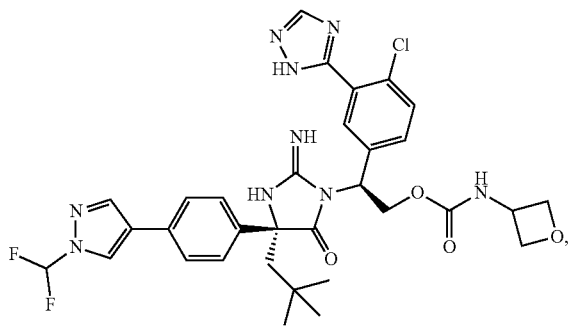
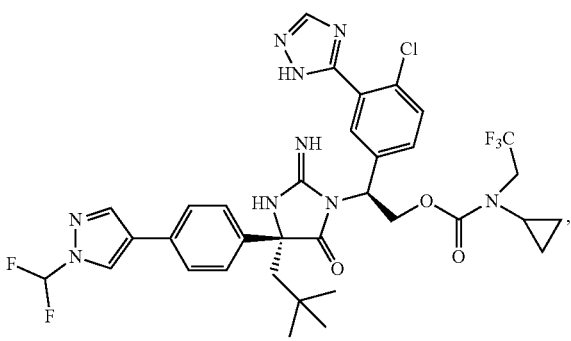
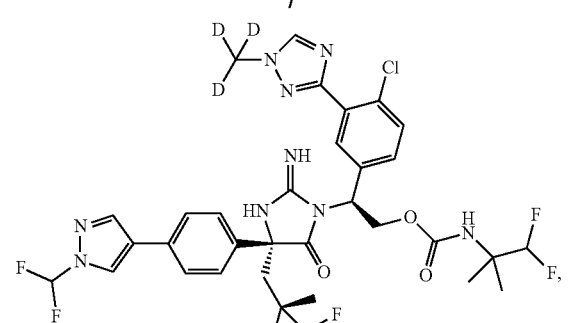
62
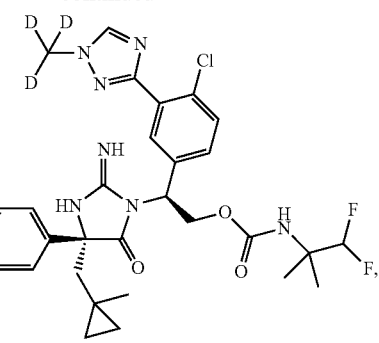
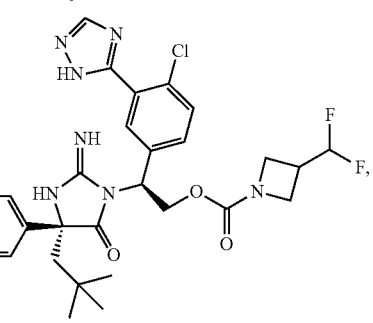
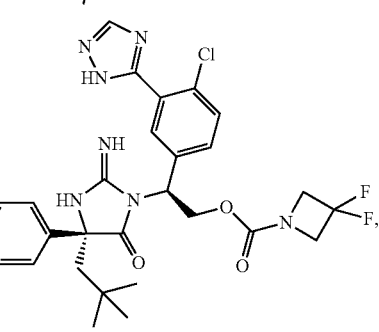
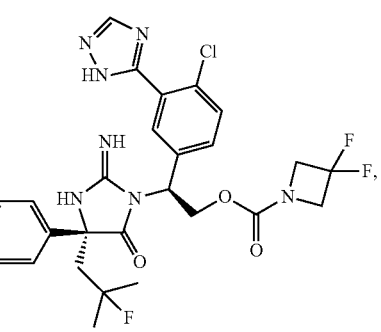
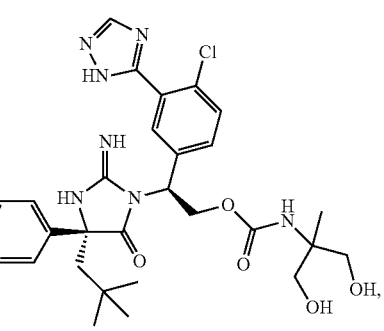

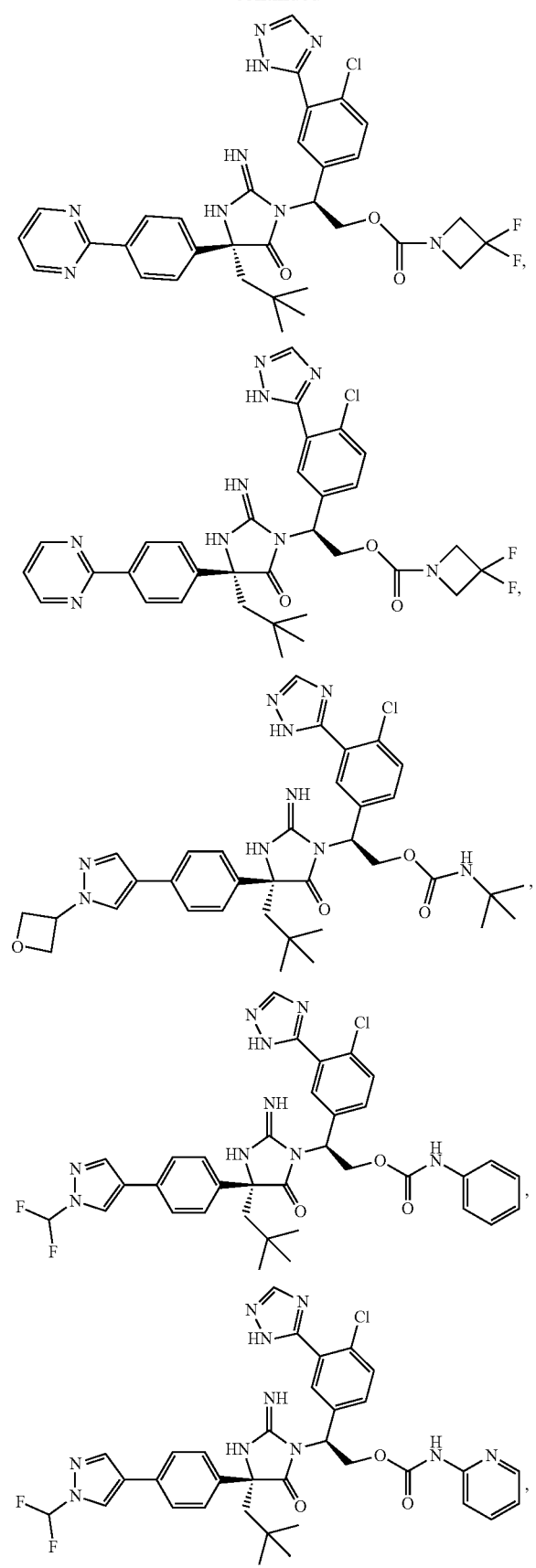
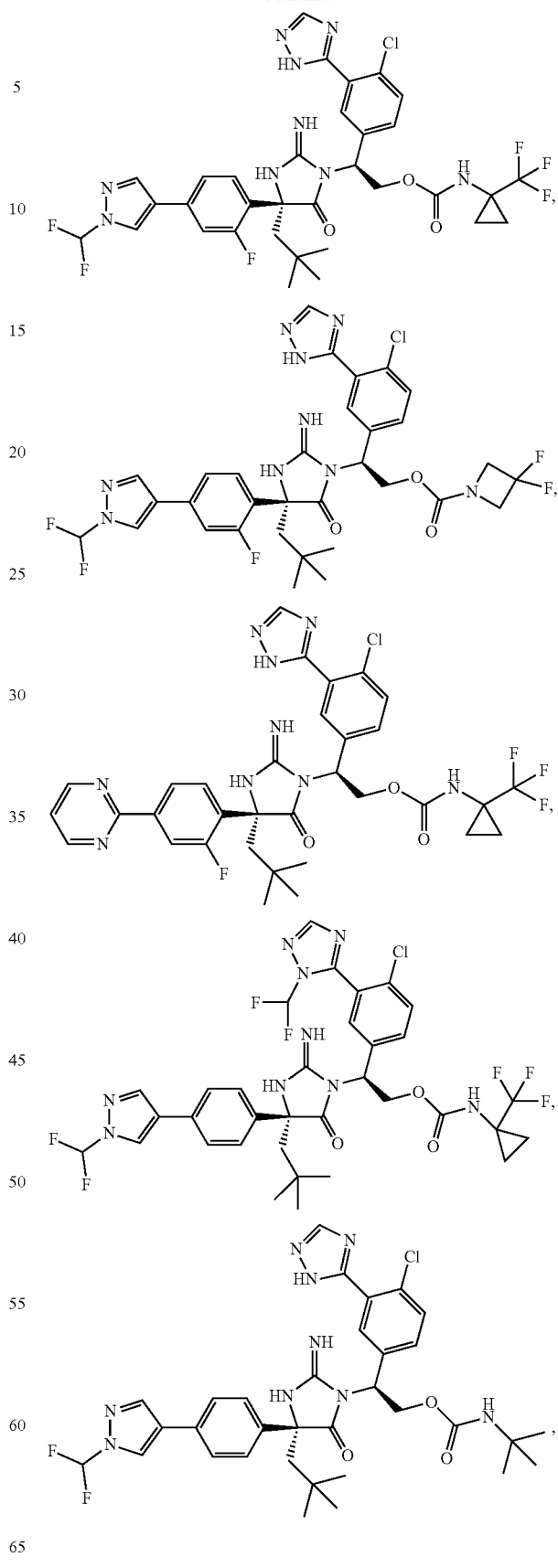

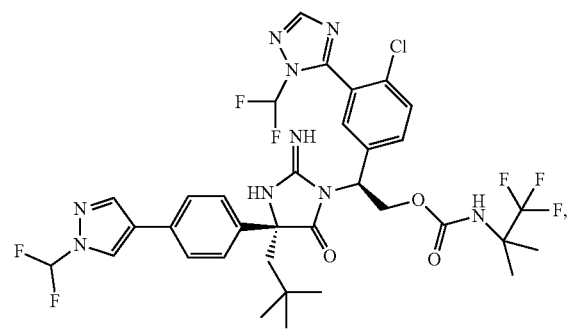
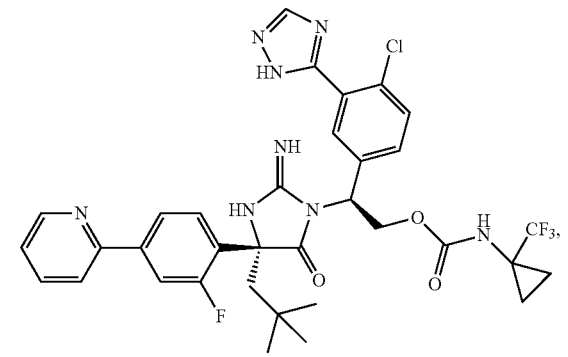
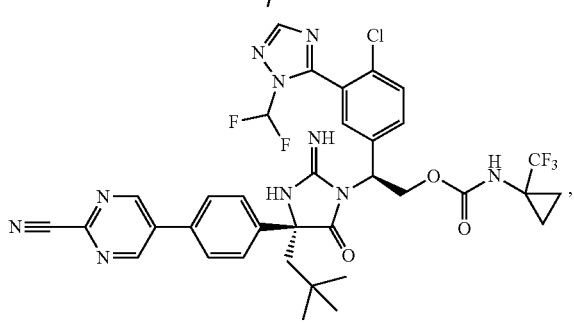
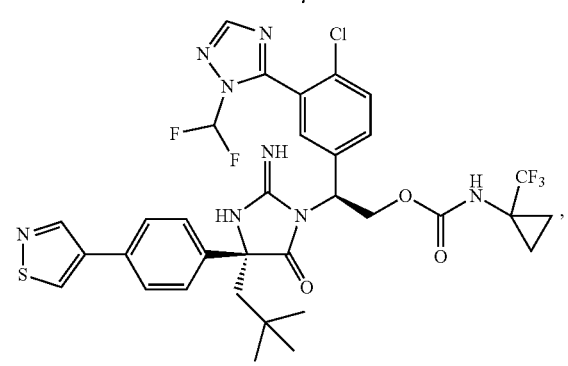
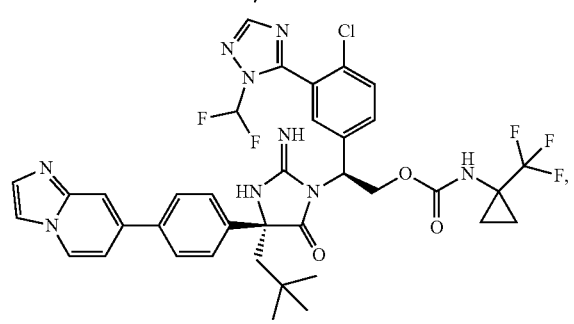
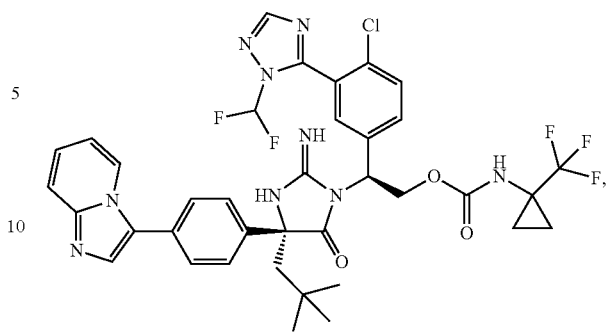
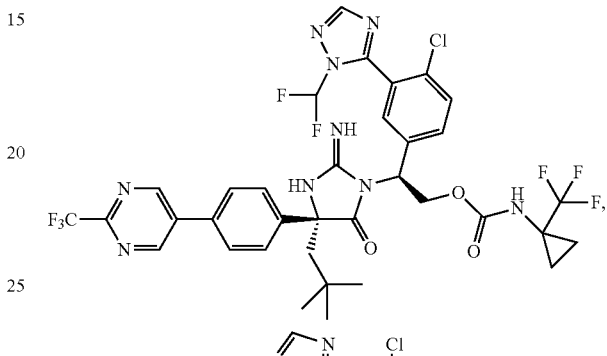
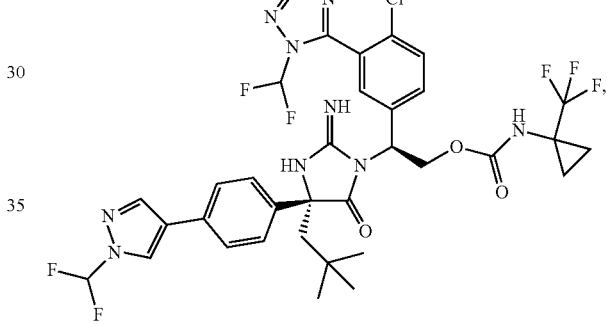
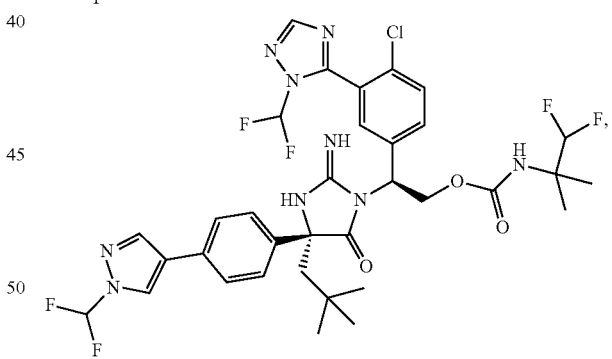
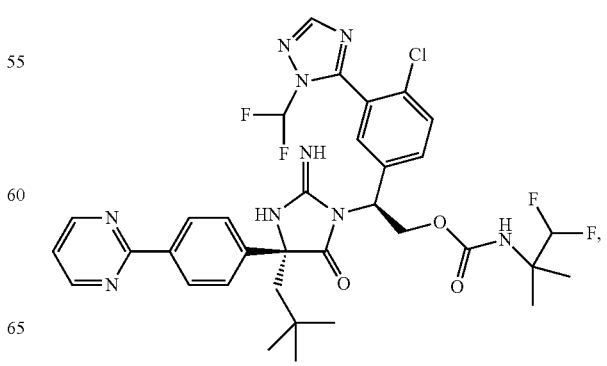

67
-continued
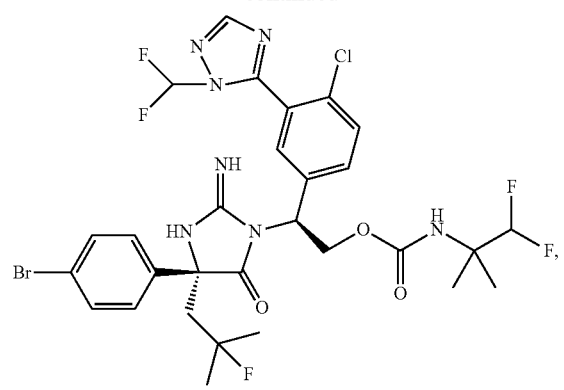
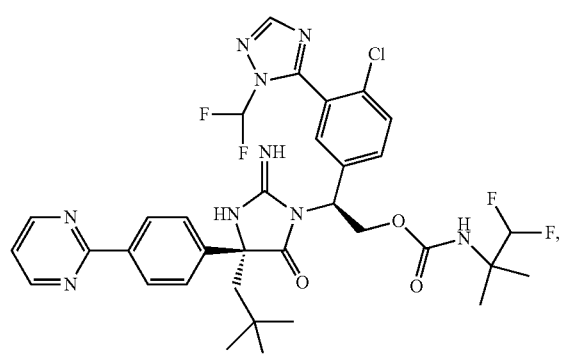
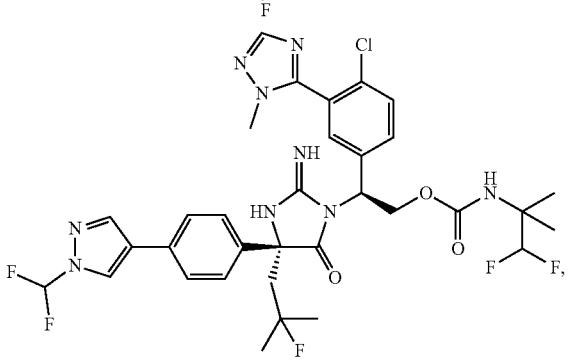
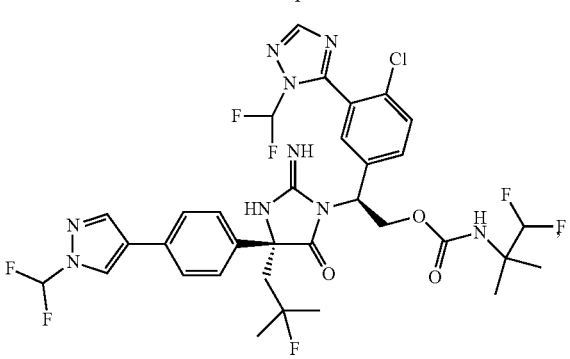
68
-continued
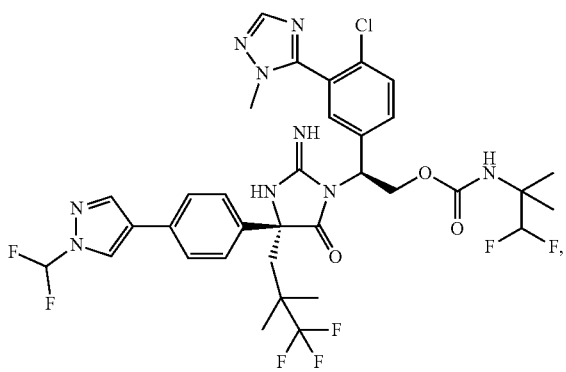
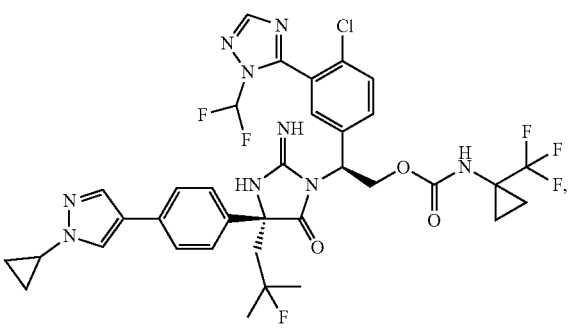
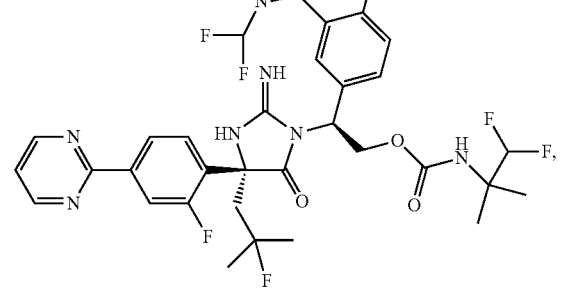
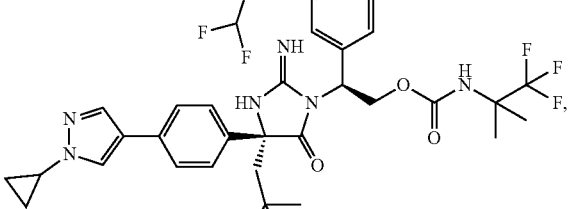
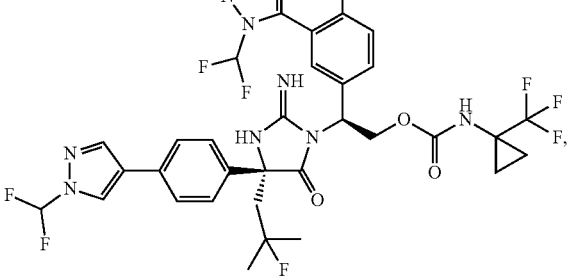

69
-continued
70
-continued
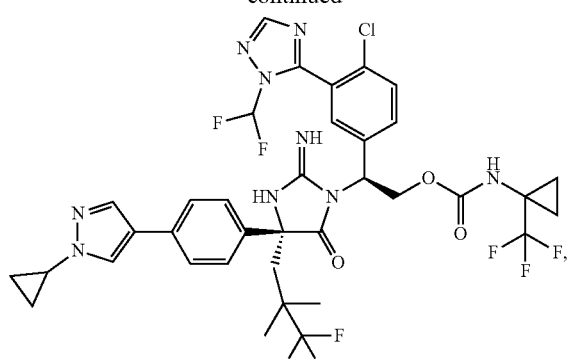
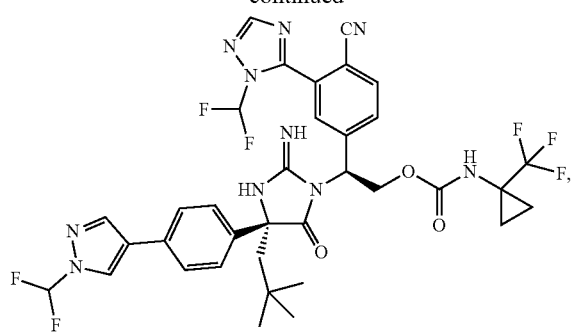

-continued
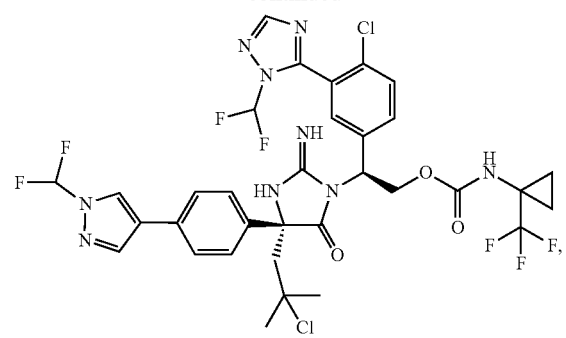
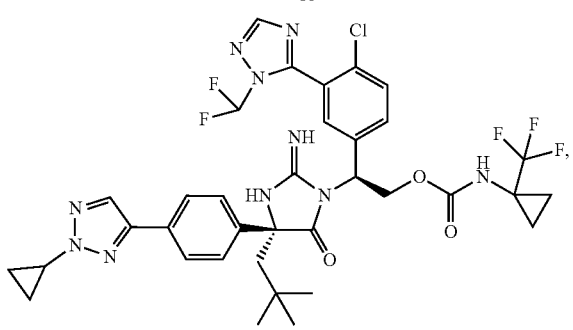
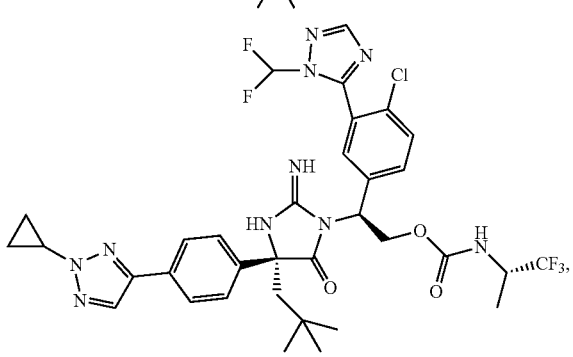
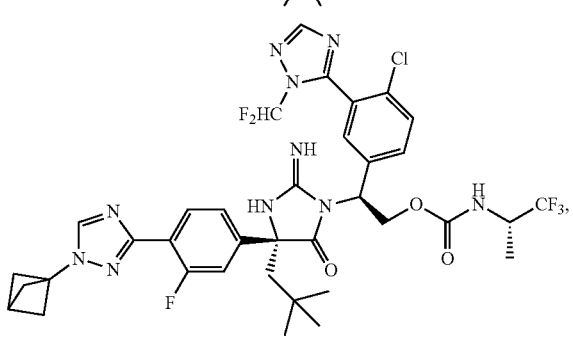
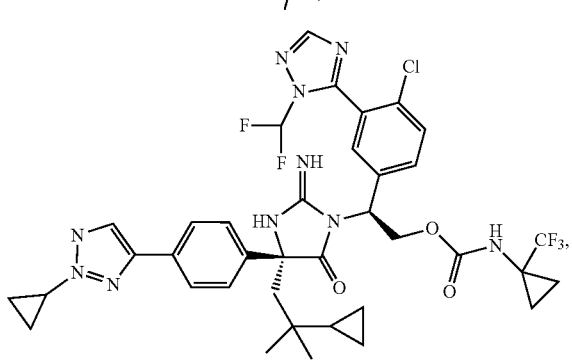
-continued
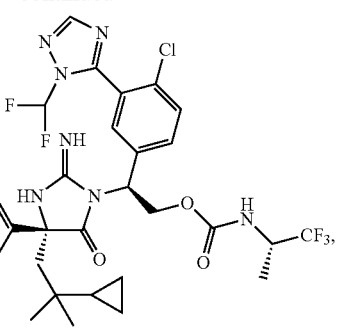
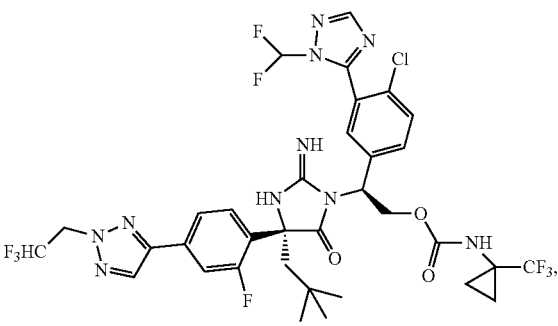
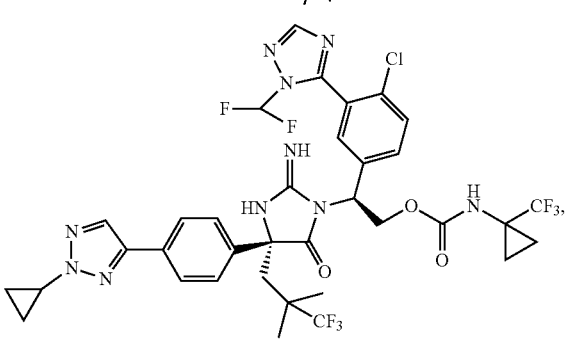
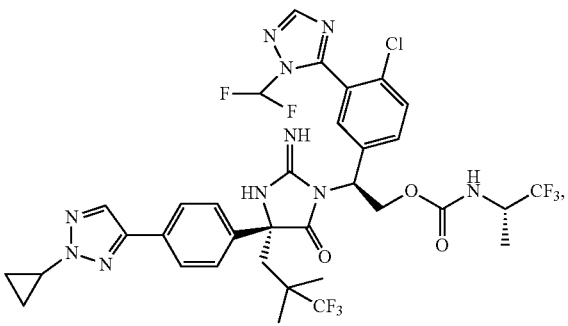
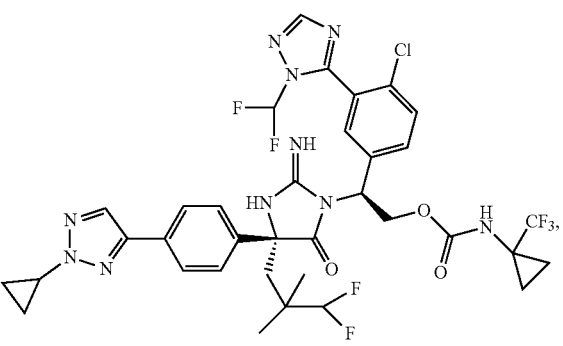

73
-continued
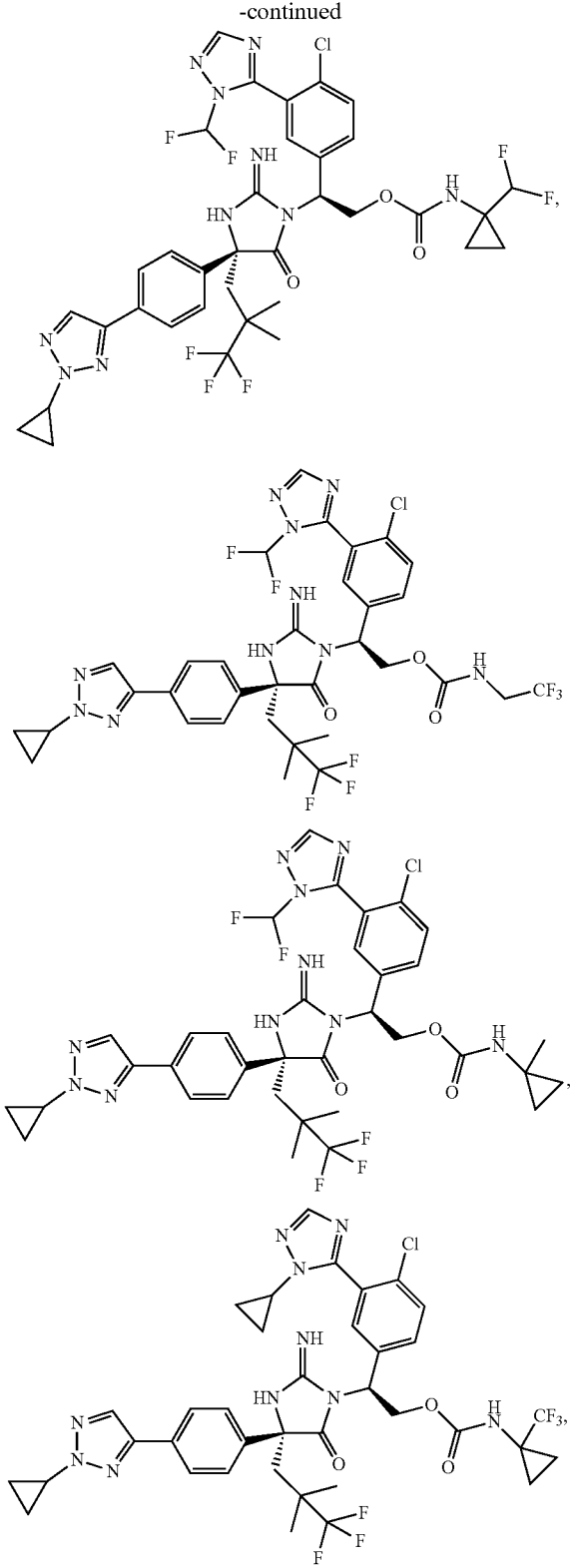
74
-continued
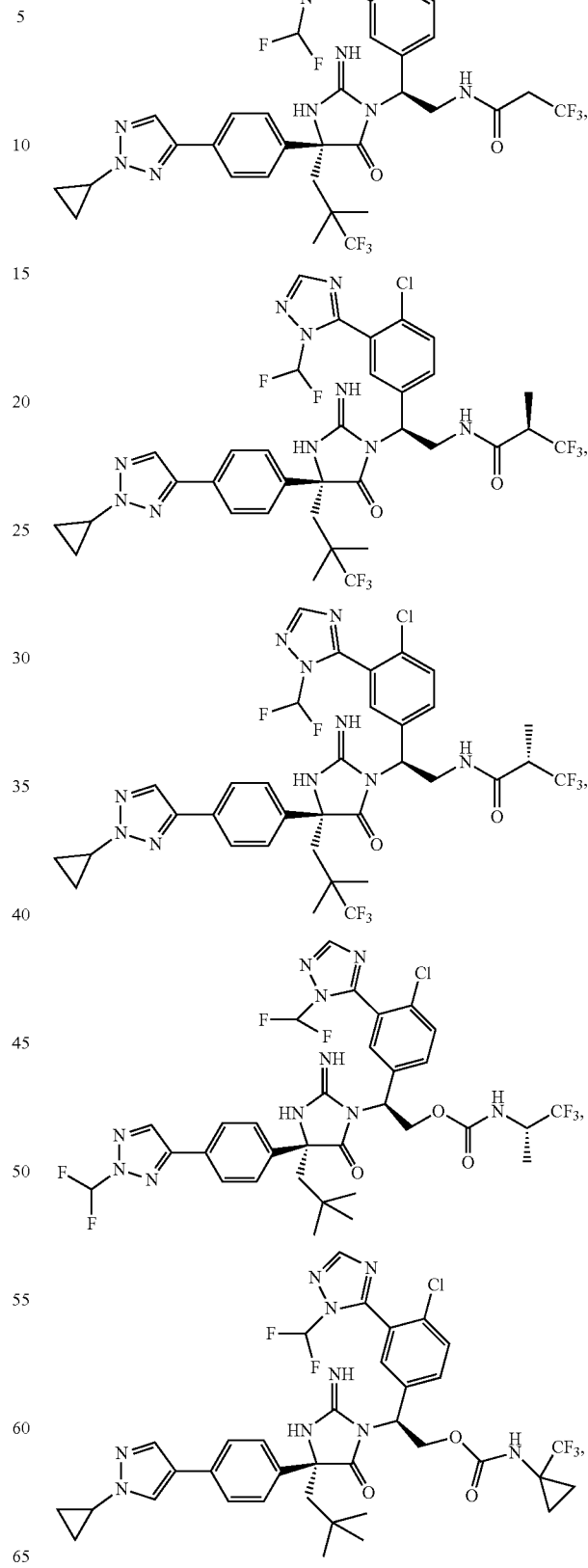

75
-continued
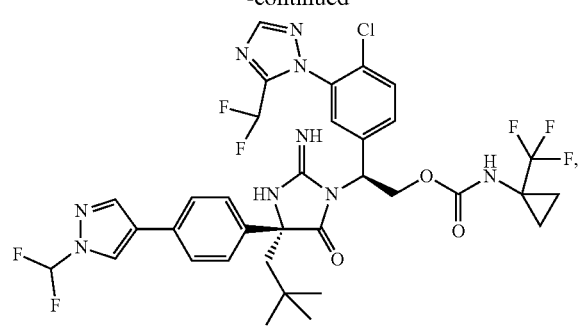
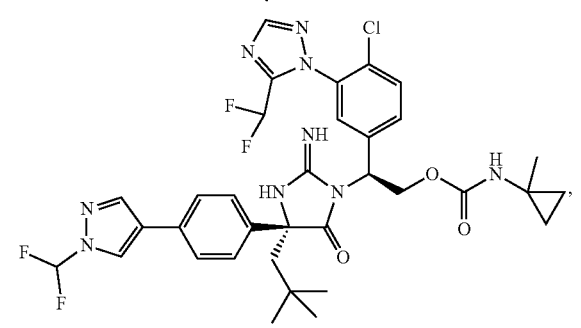
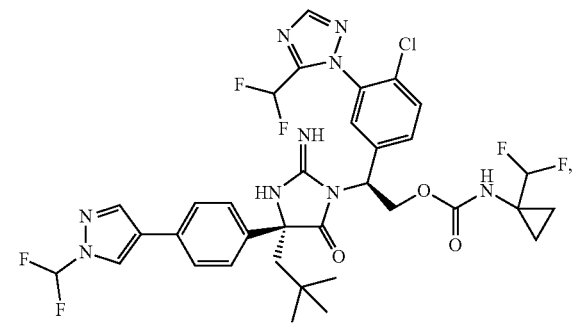
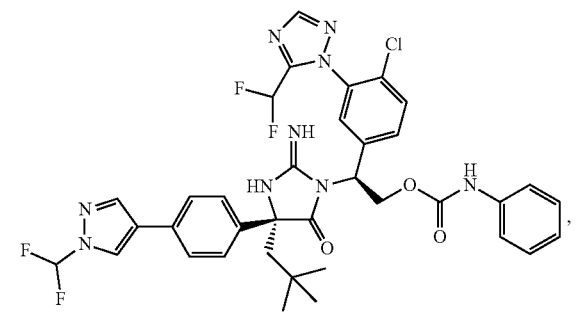
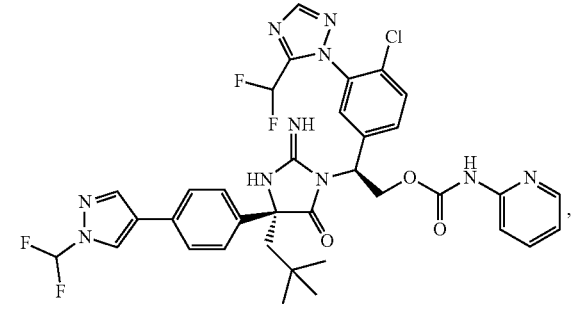
76
-continued
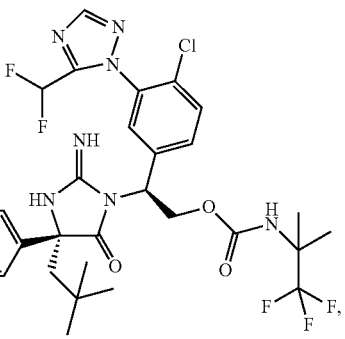
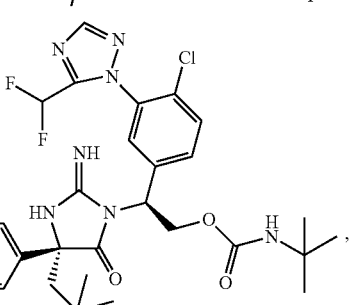
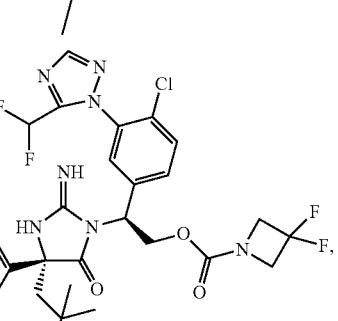
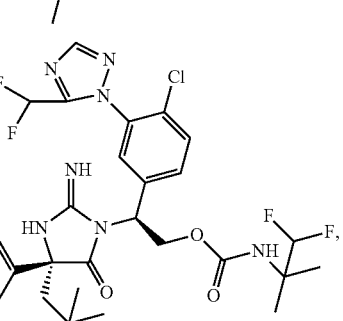
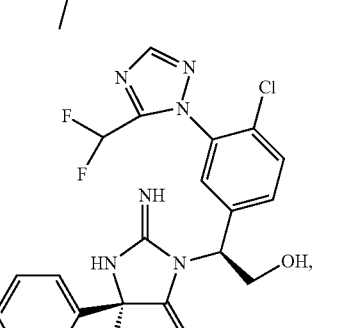
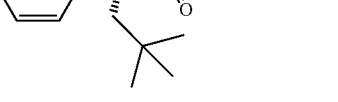

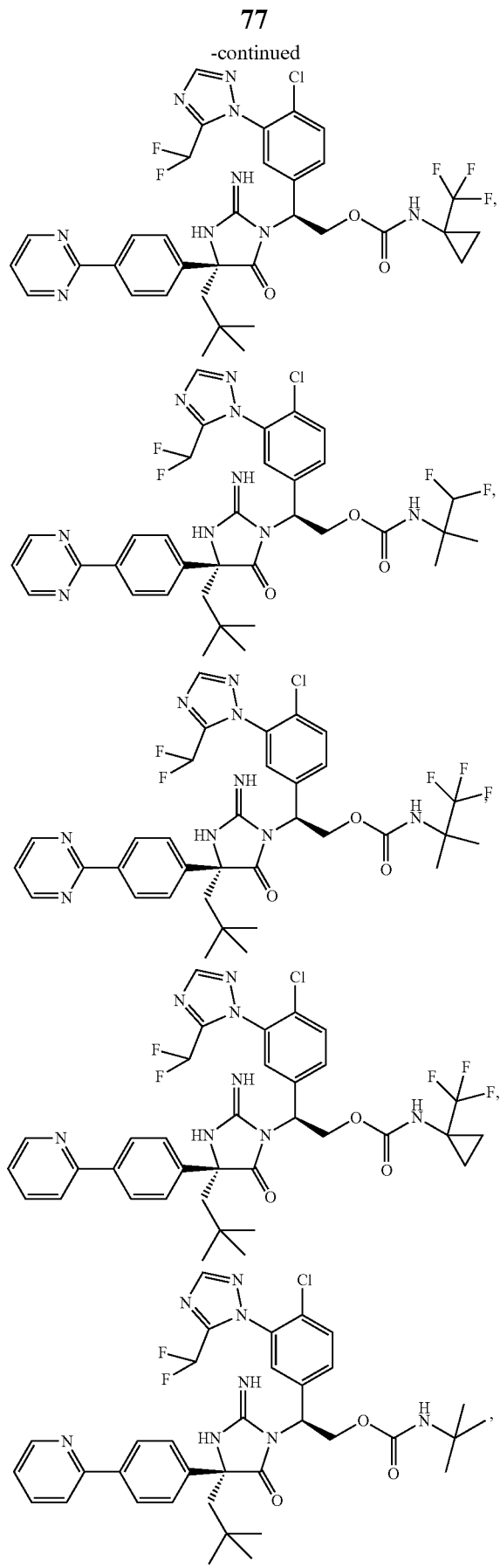
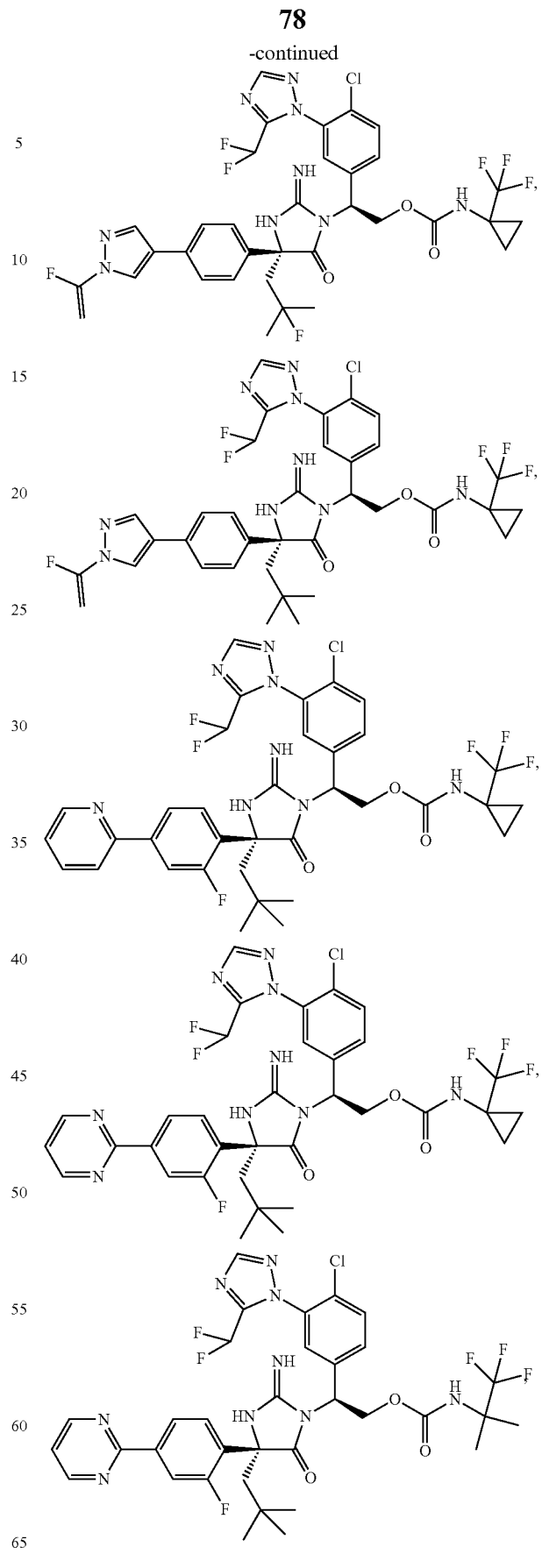

79
-continued
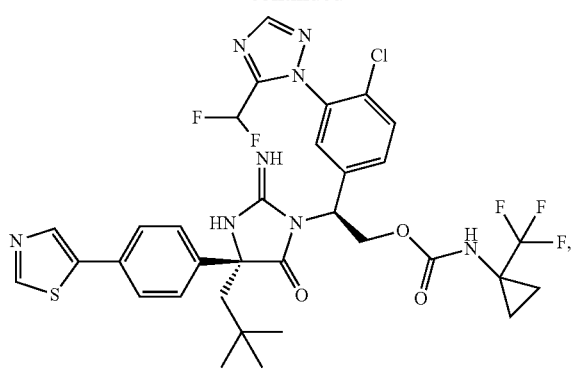
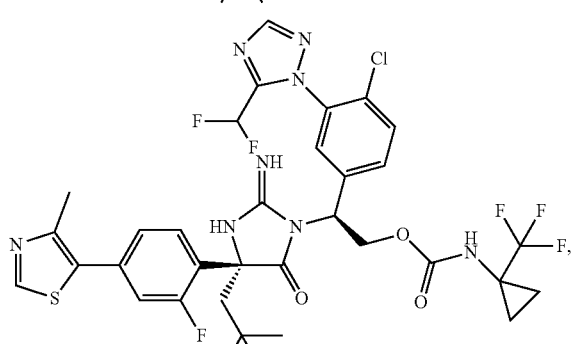
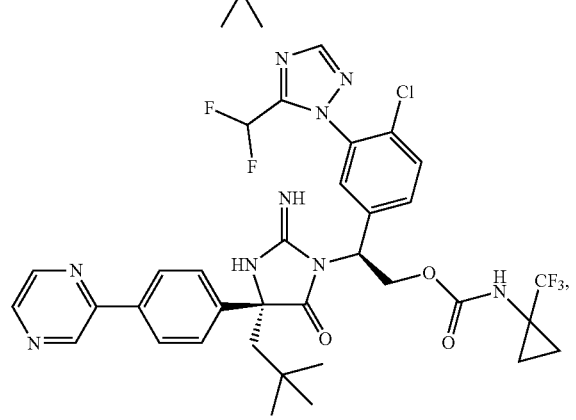
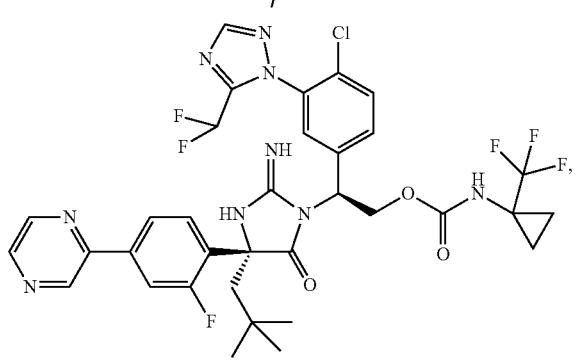
80
-continued
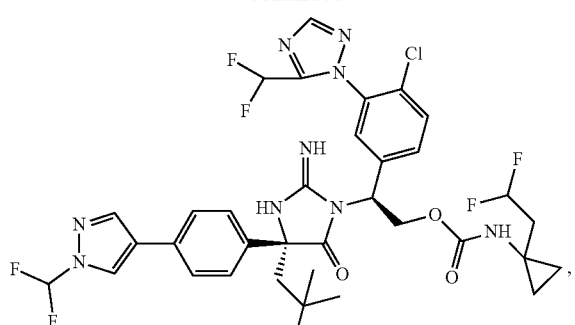
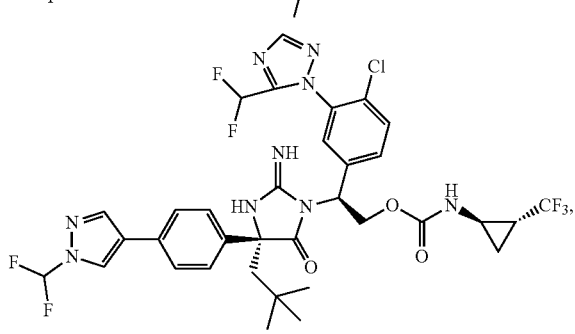
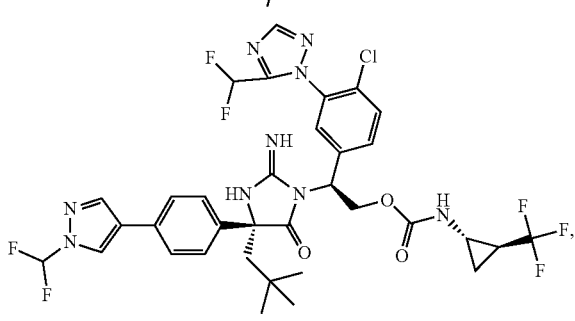
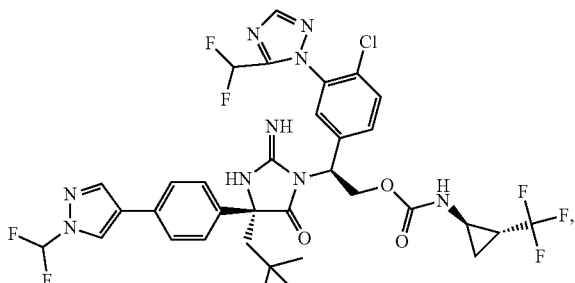
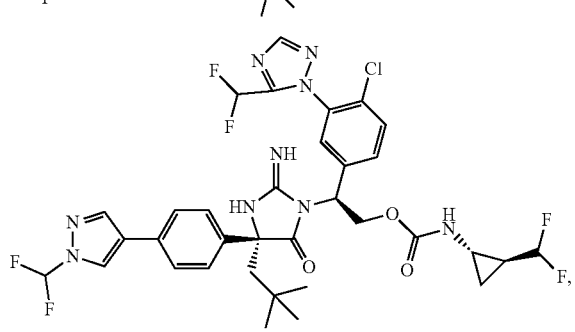

81
-continued
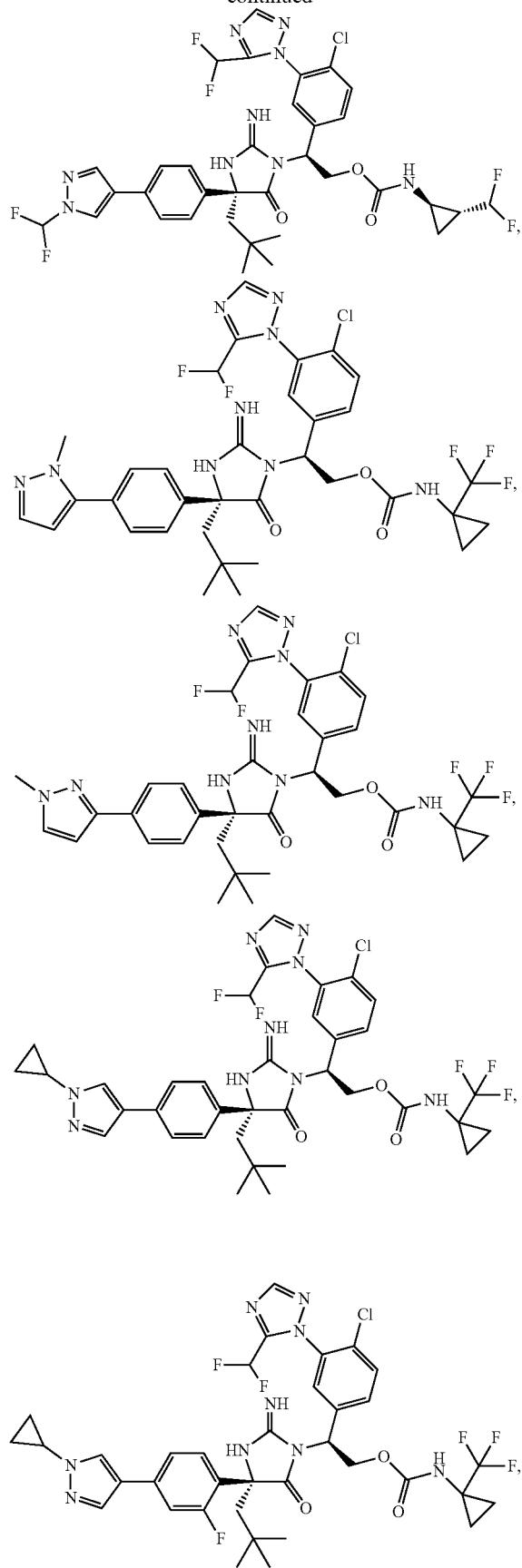
82
-continued
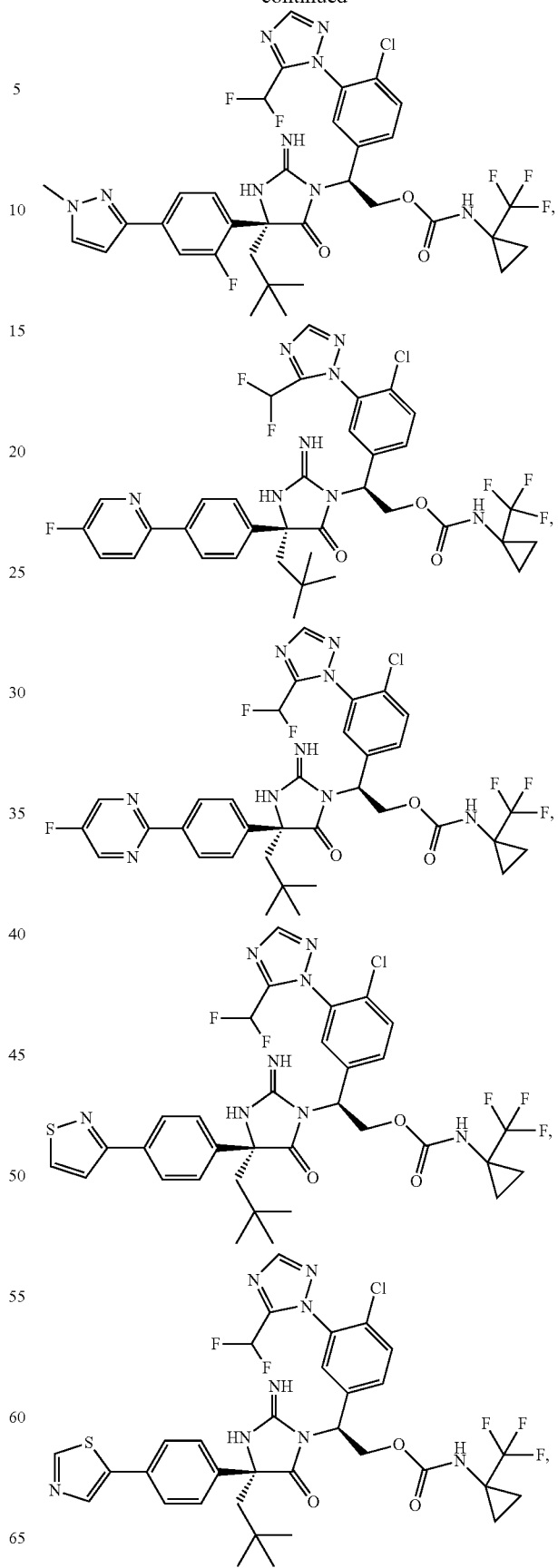

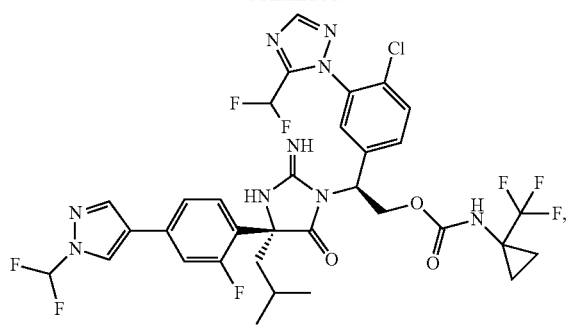
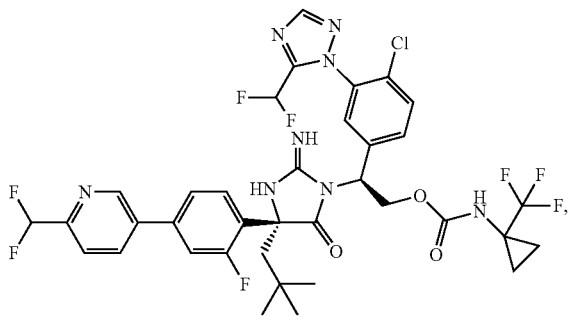
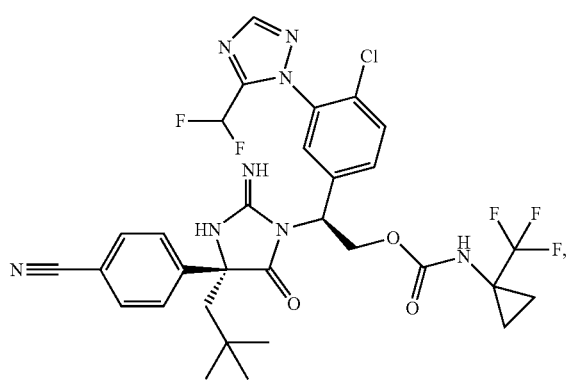
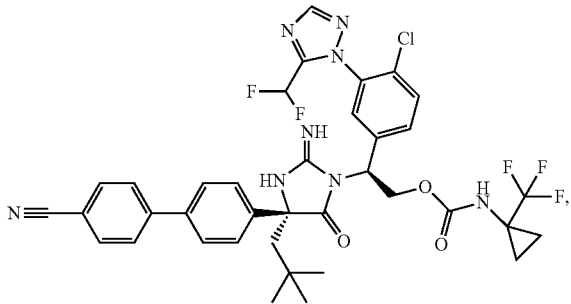
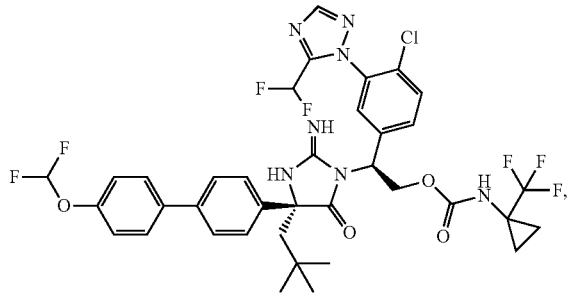
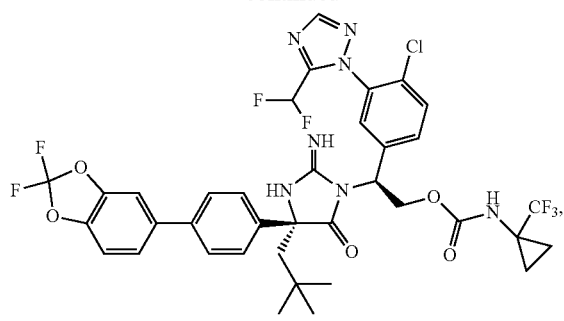
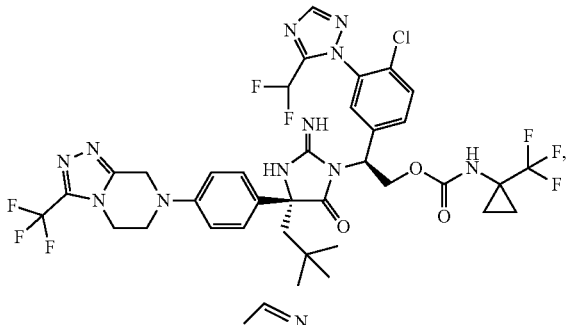
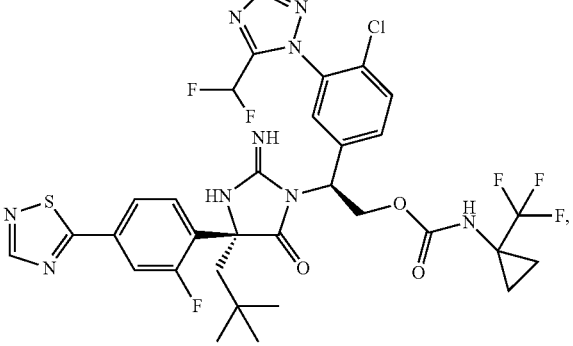
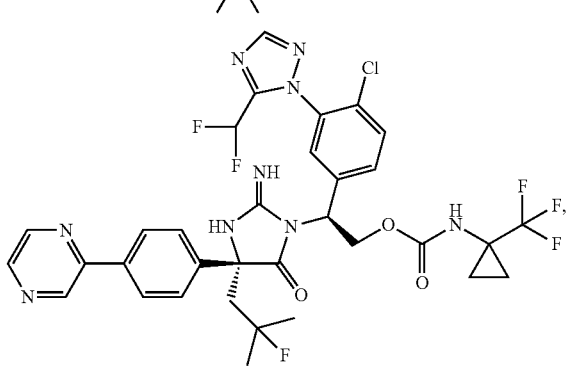
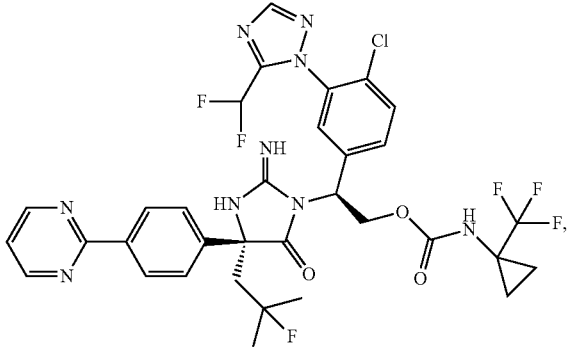

-continued
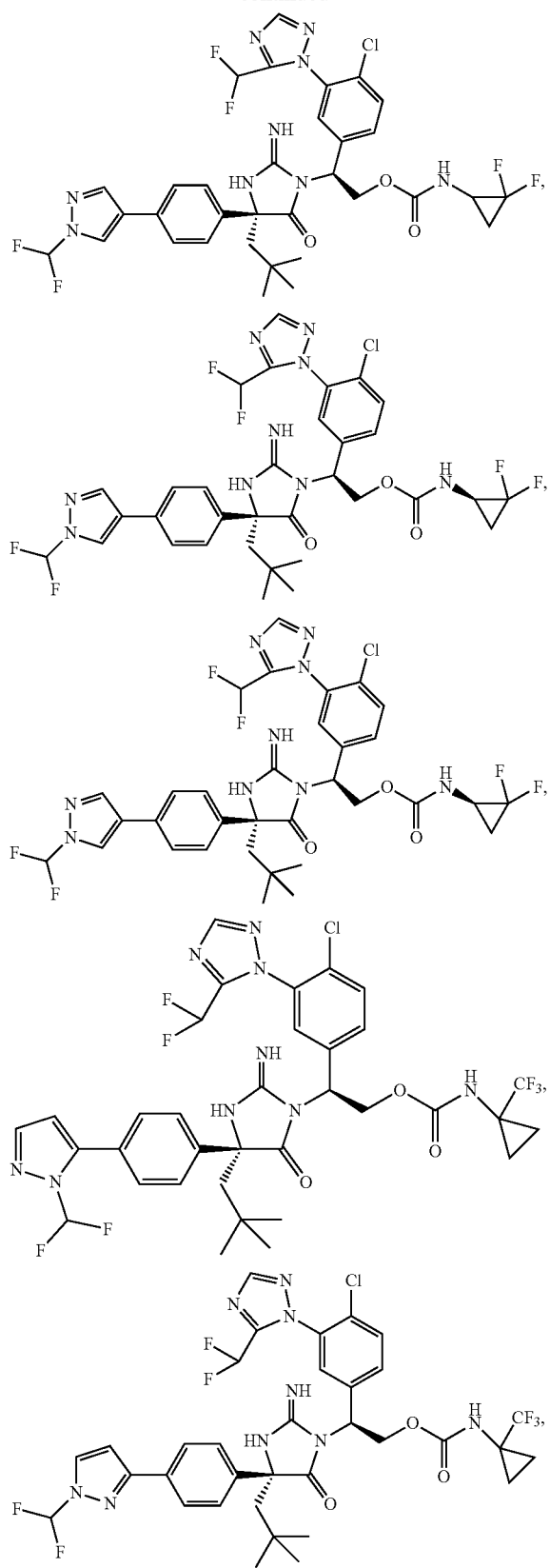
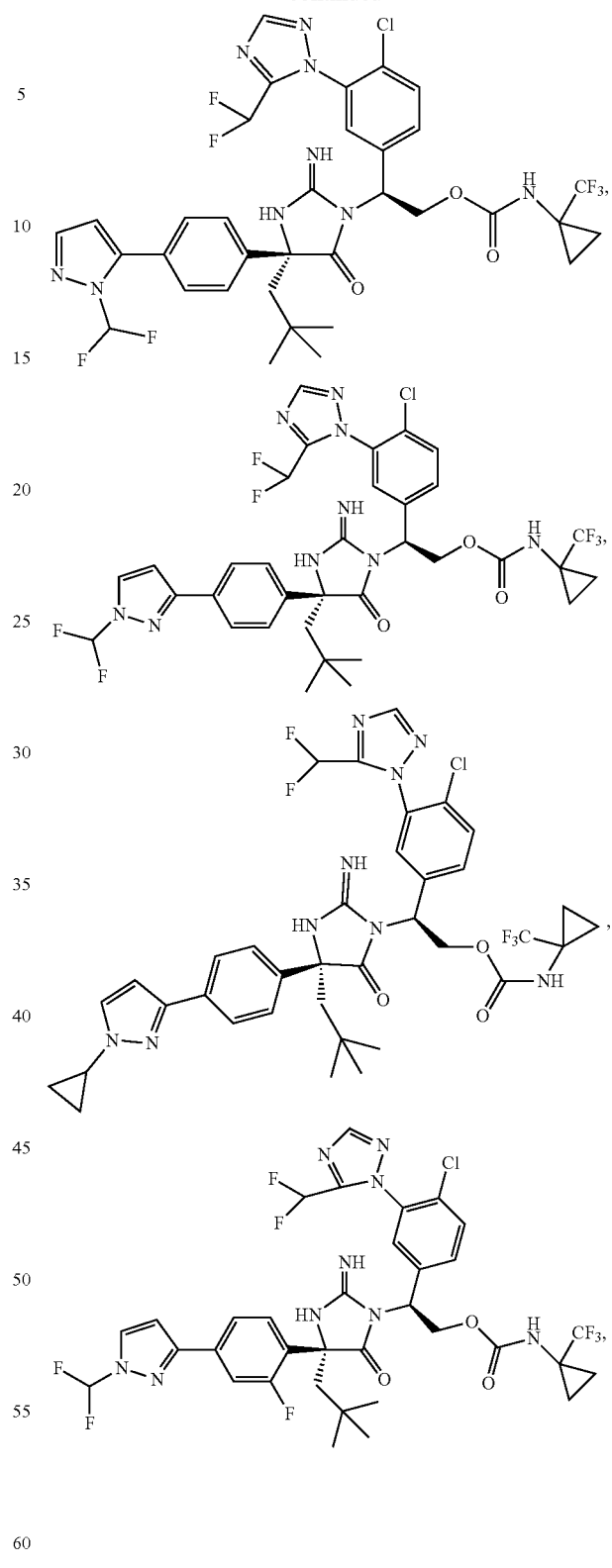

87
-continued
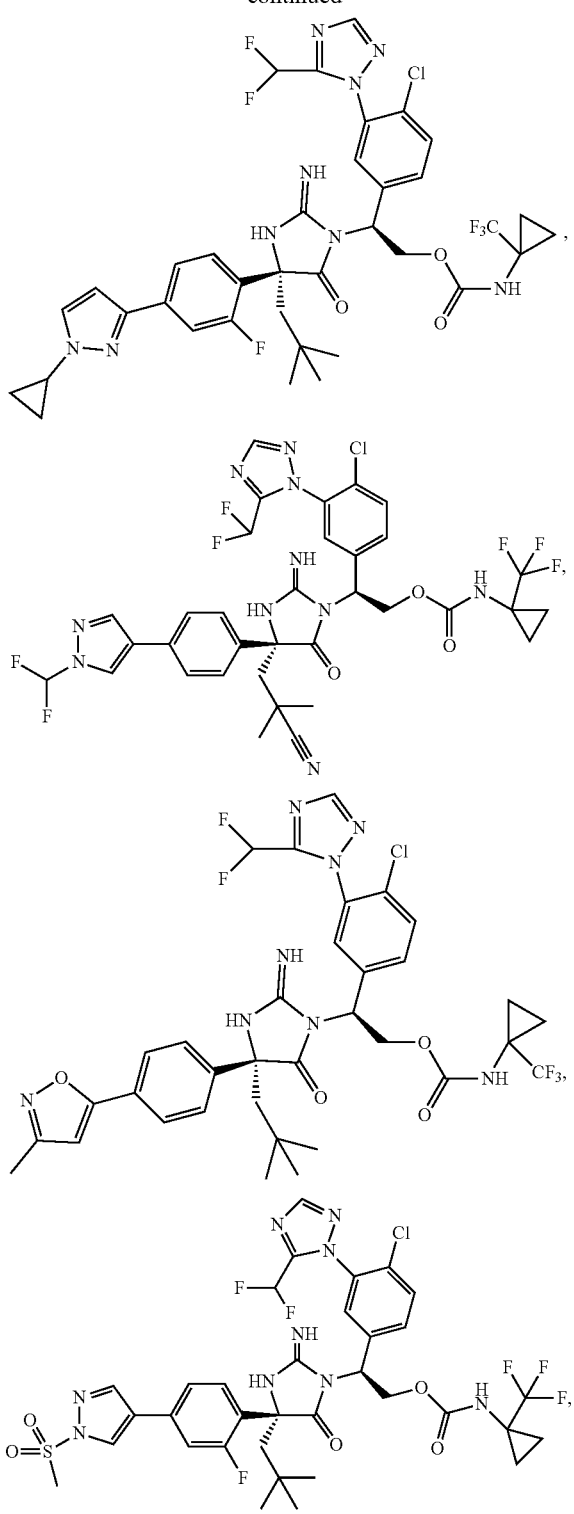
88
-continued
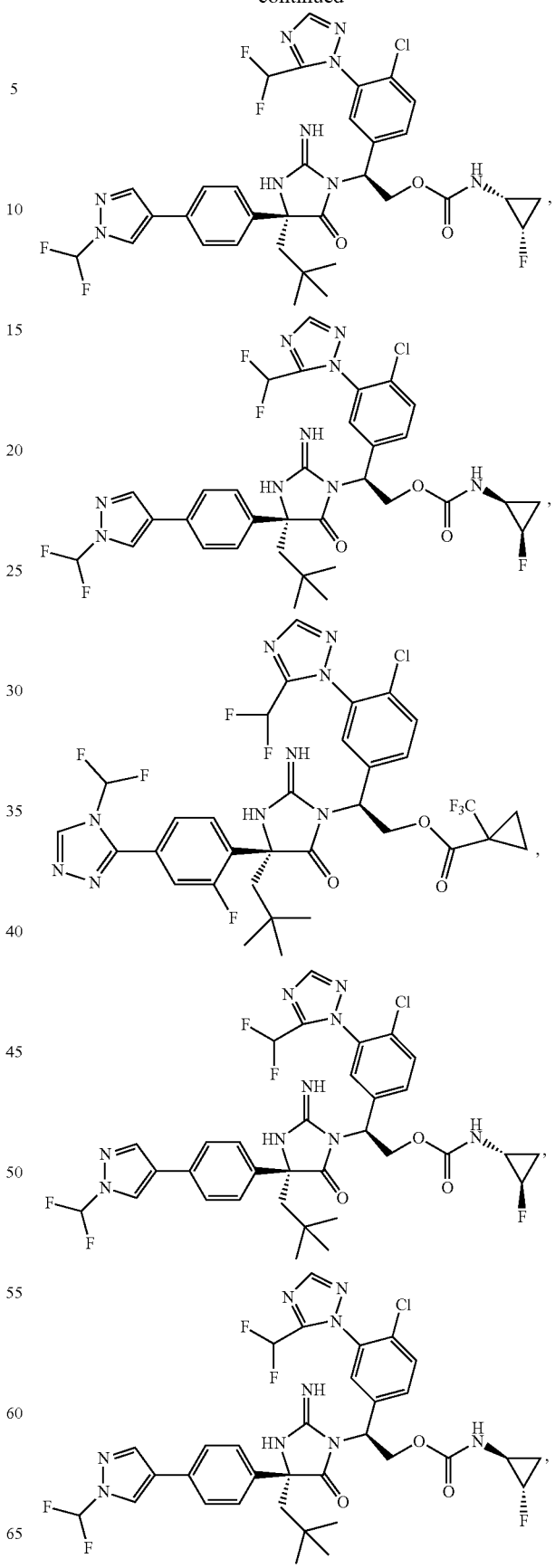

-continued
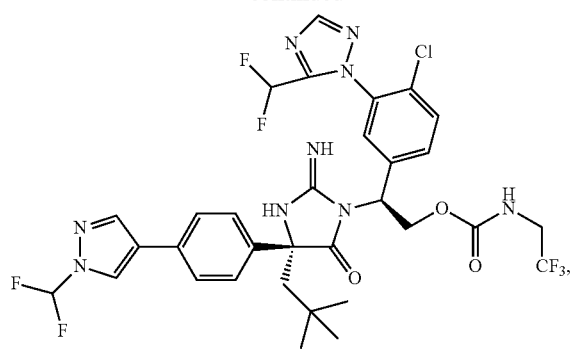
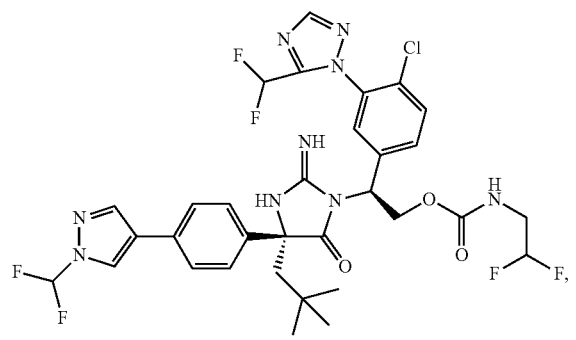
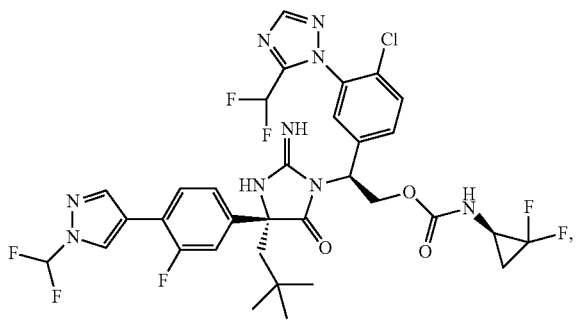
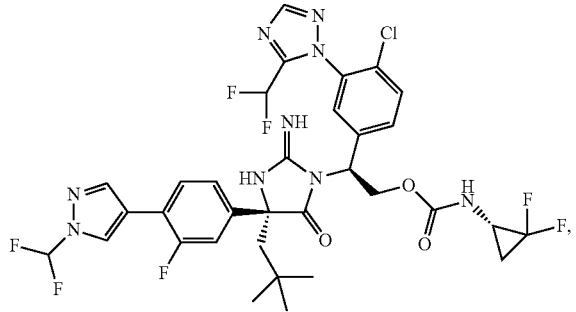
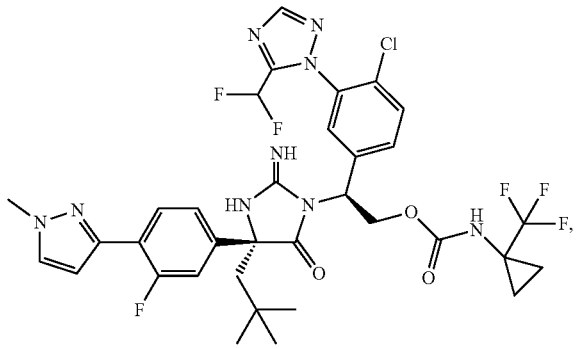
-continued
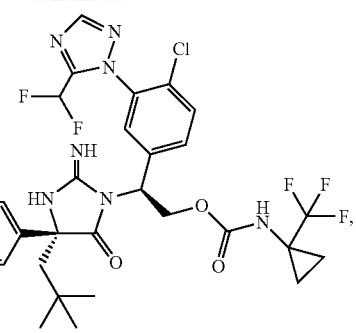
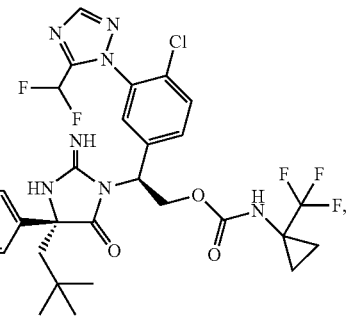
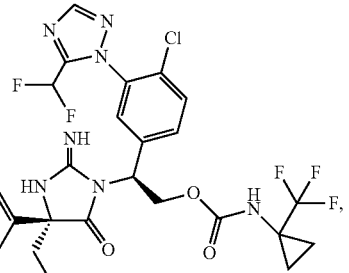
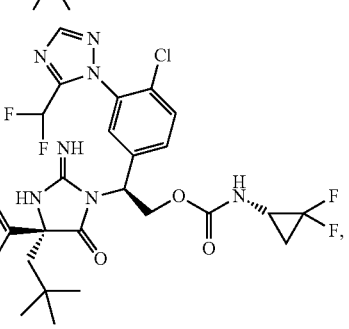
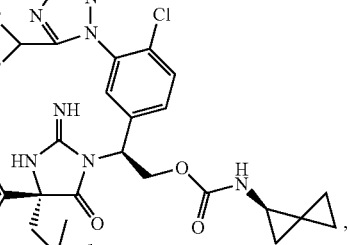

91
-continued
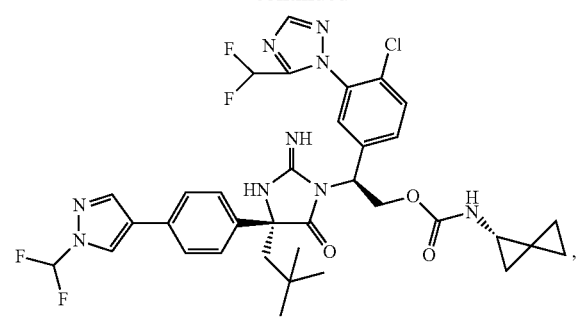
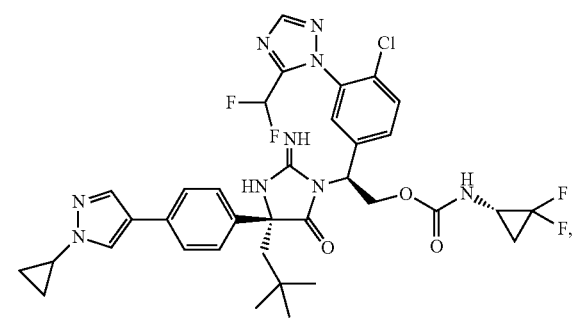
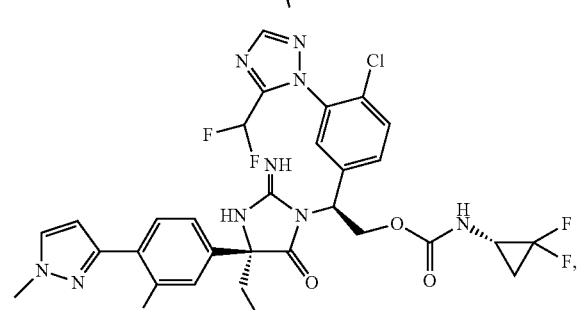
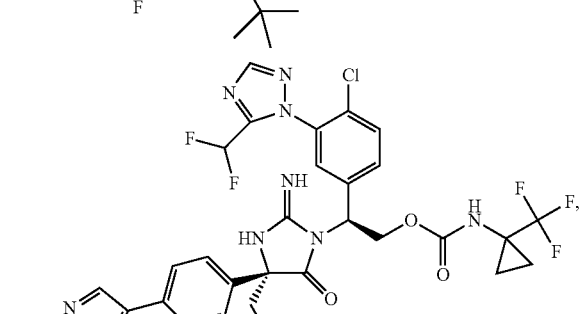
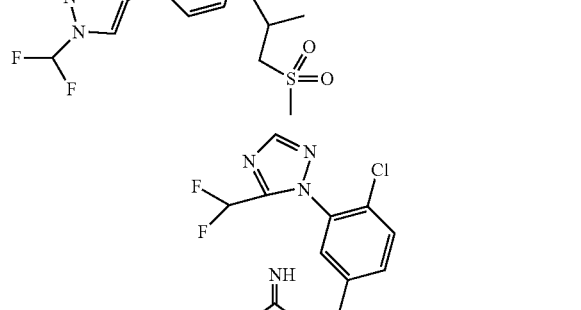
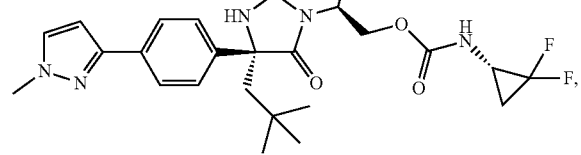
92
-continued
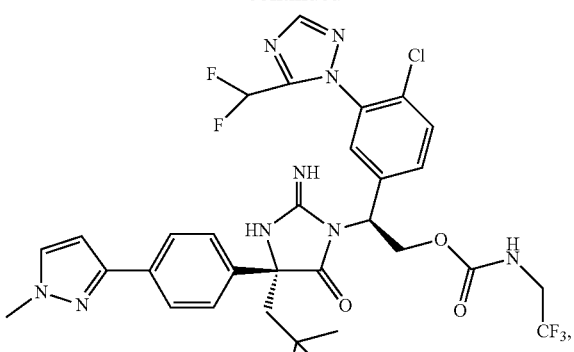
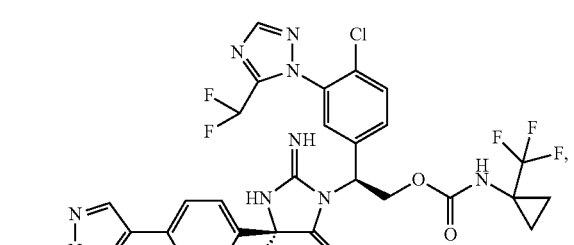
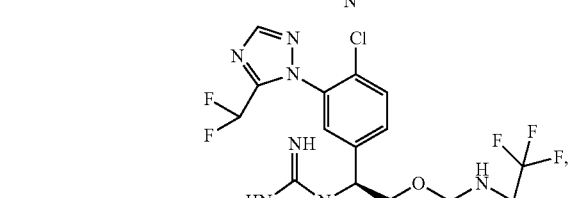
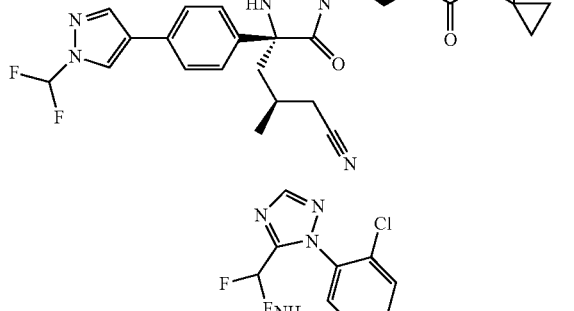
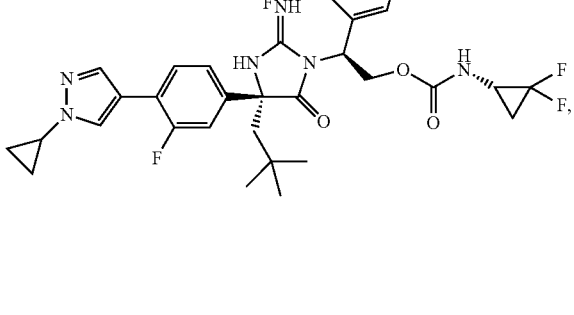

-continued
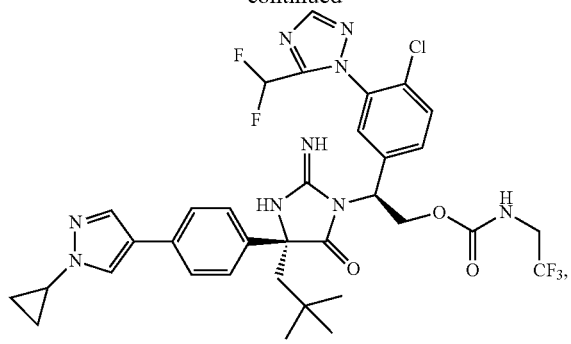
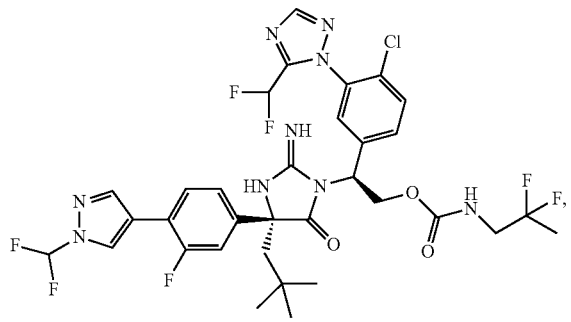
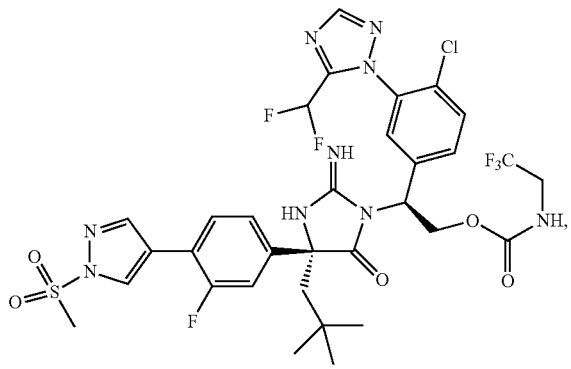
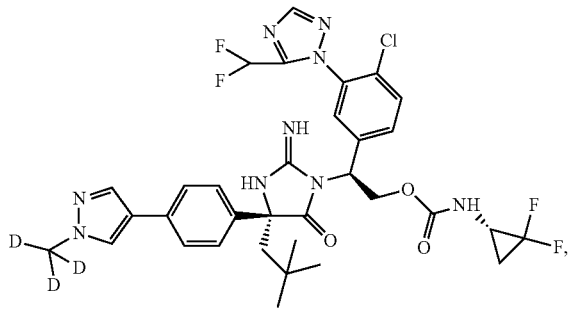
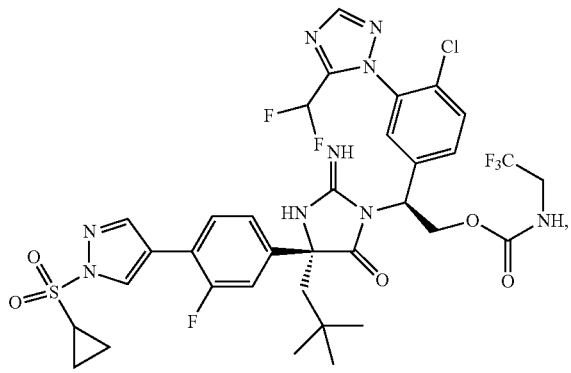
-continued
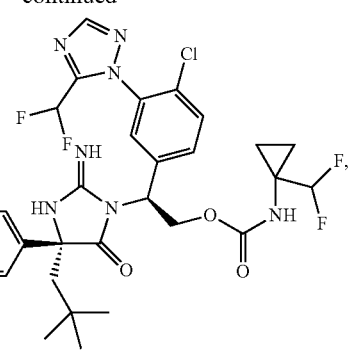
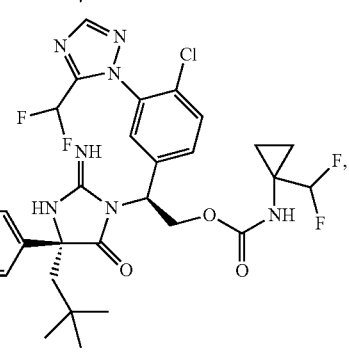
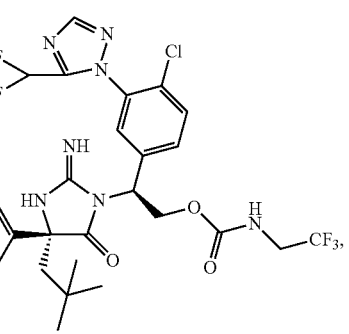
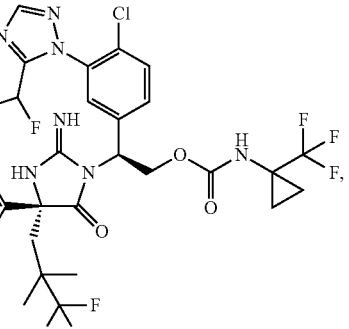
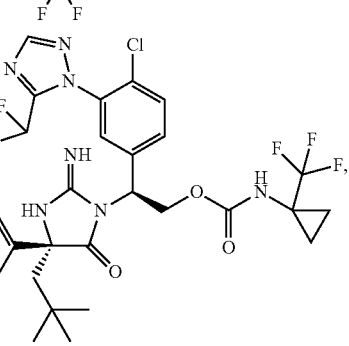

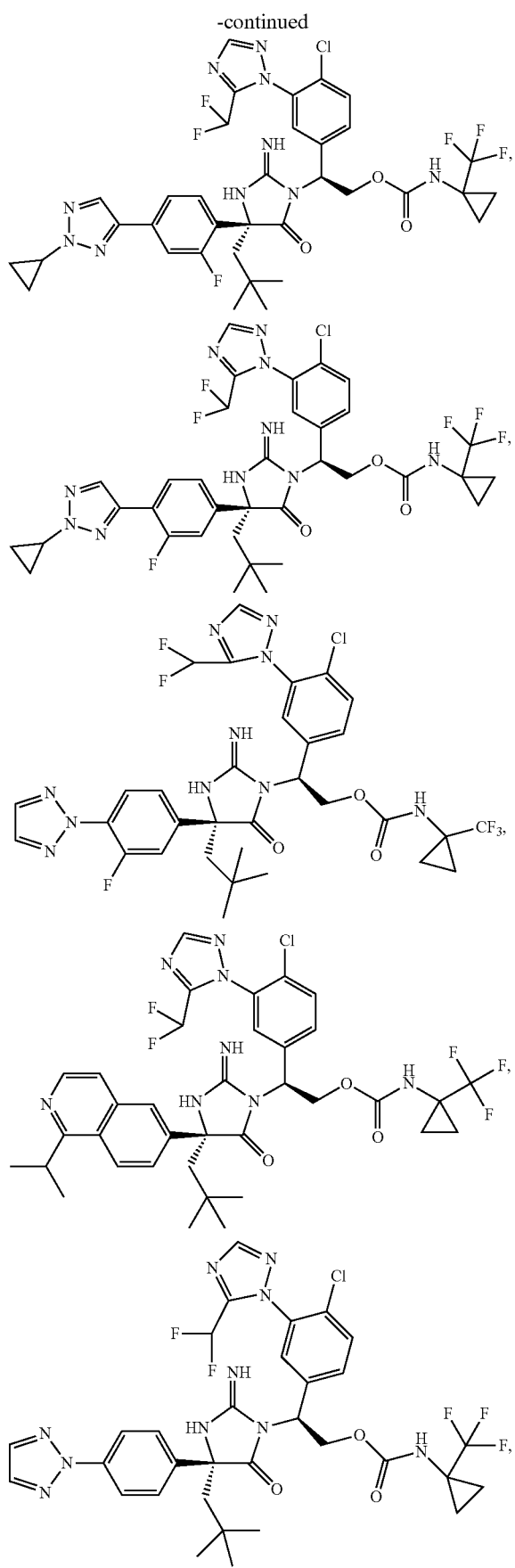
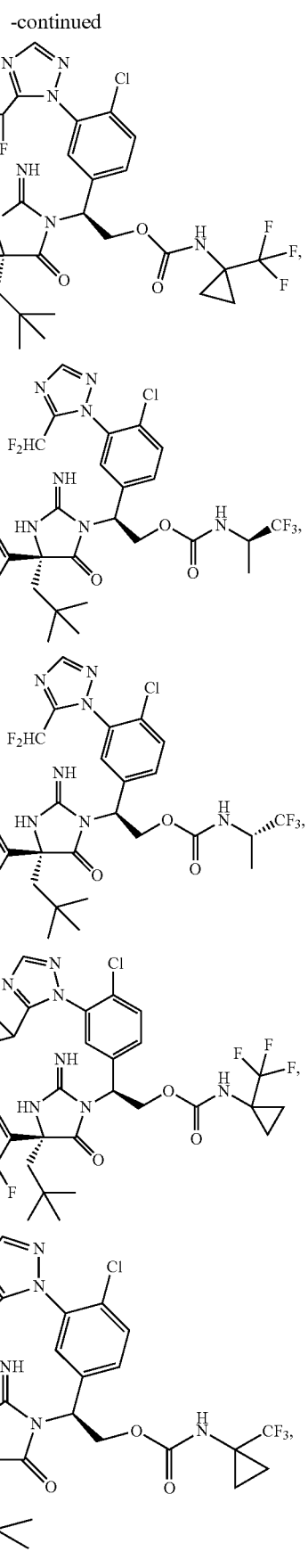

97
-continued
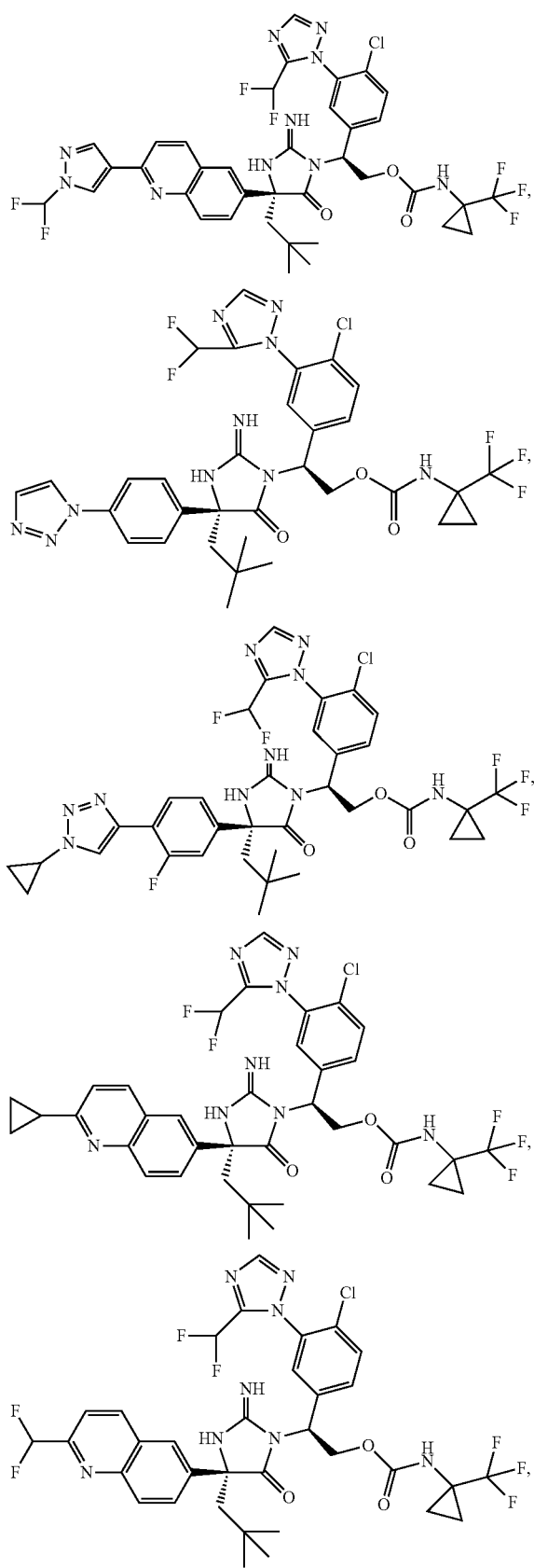
98
-continued
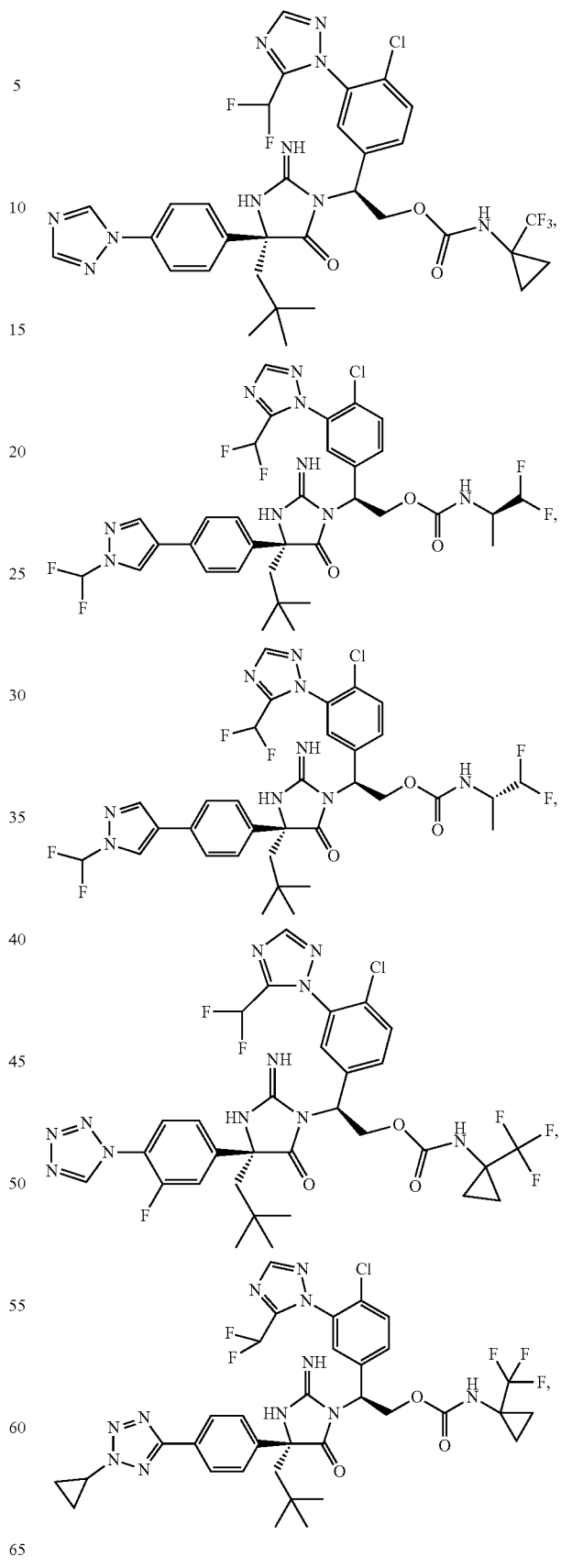

-continued
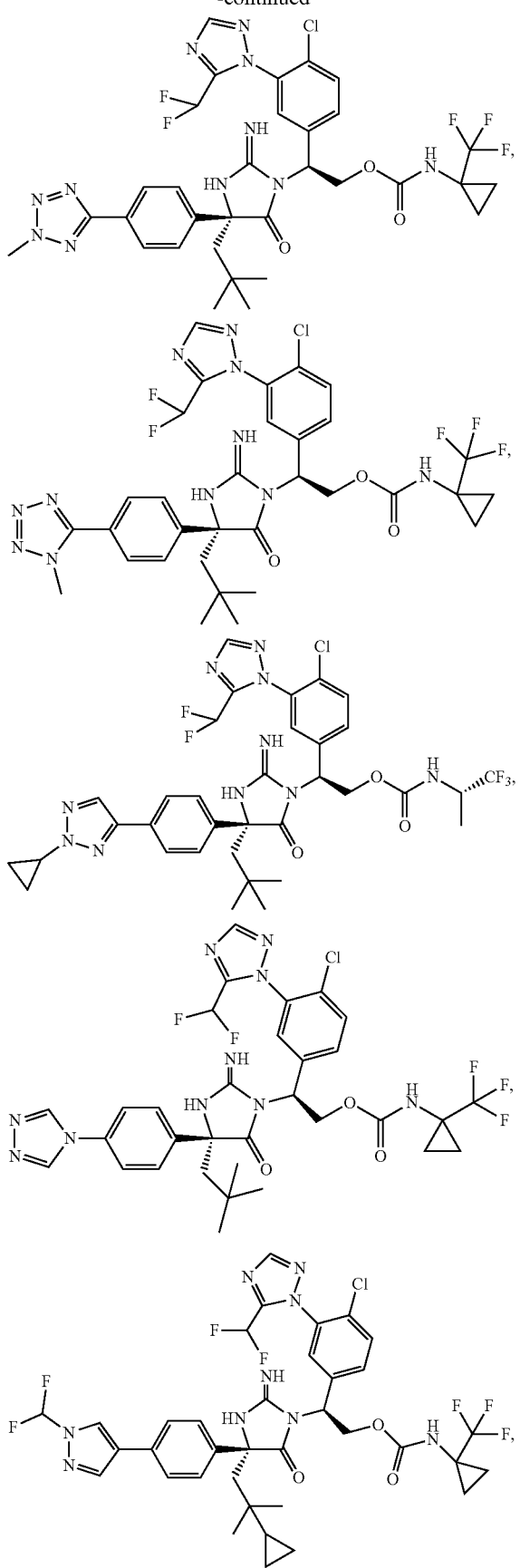
-continued
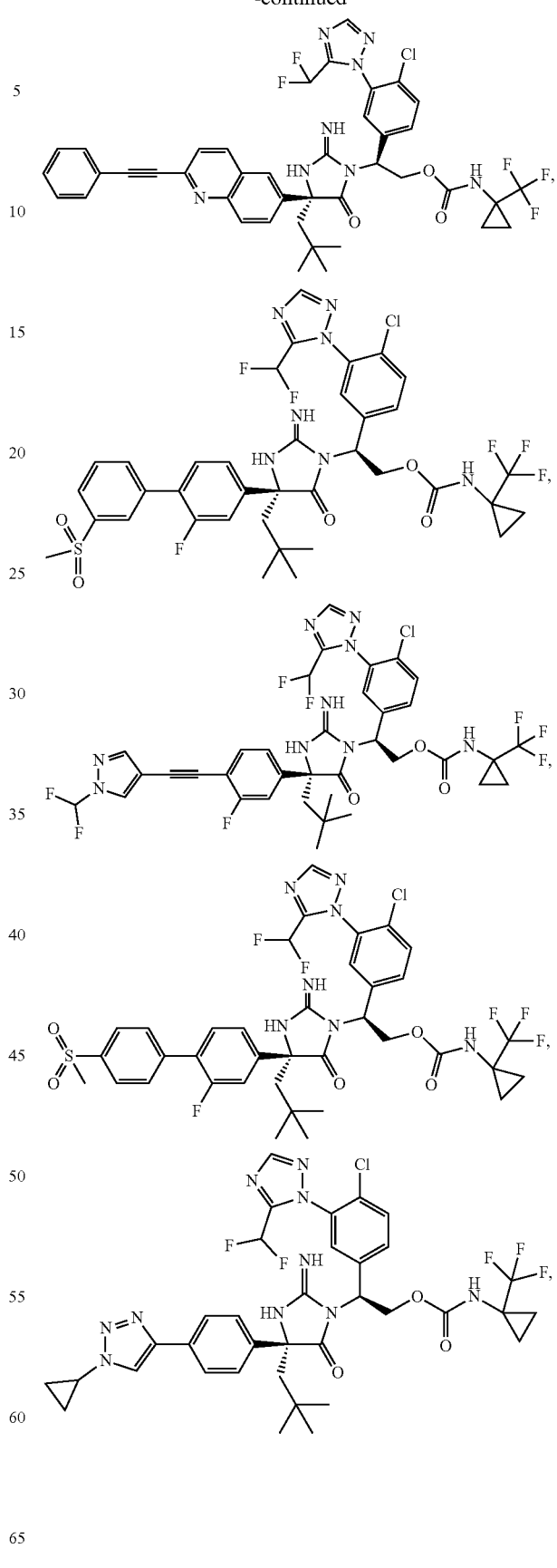

-continued
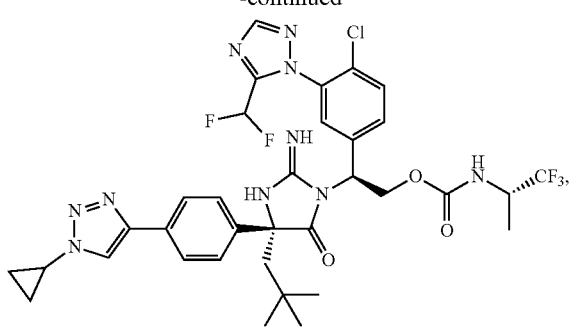
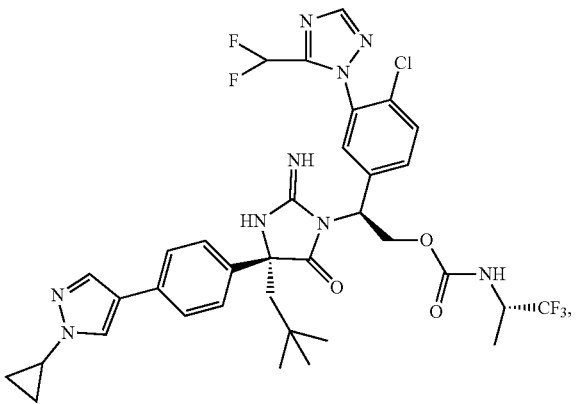
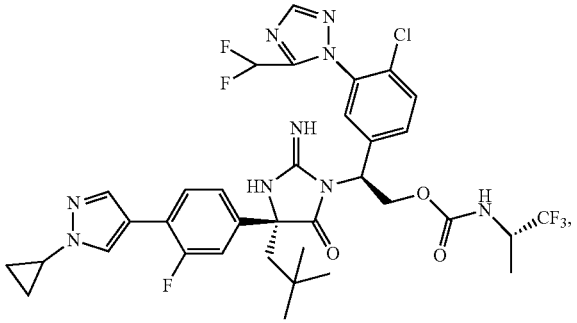
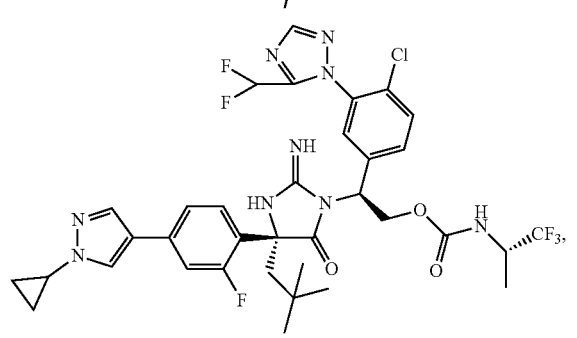
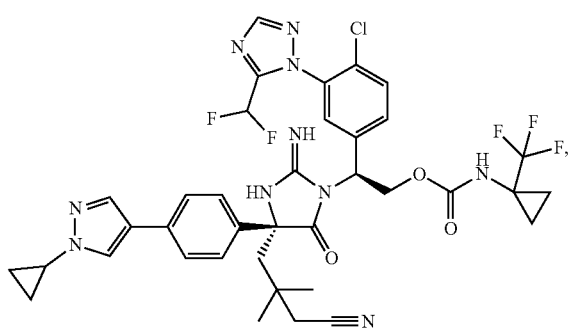
-continued
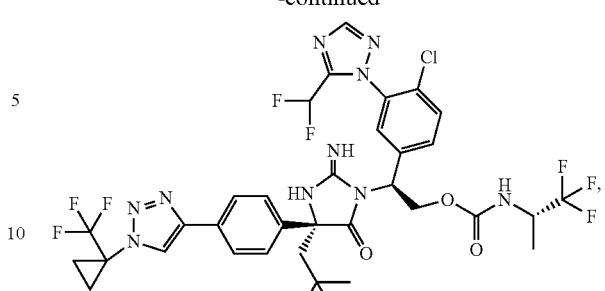
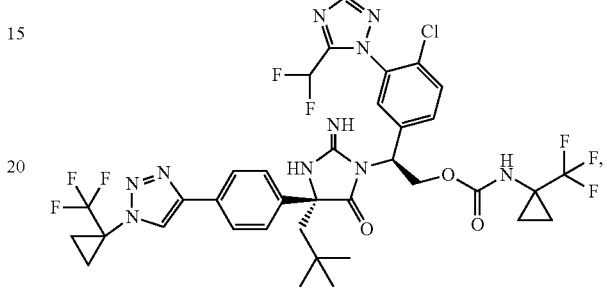
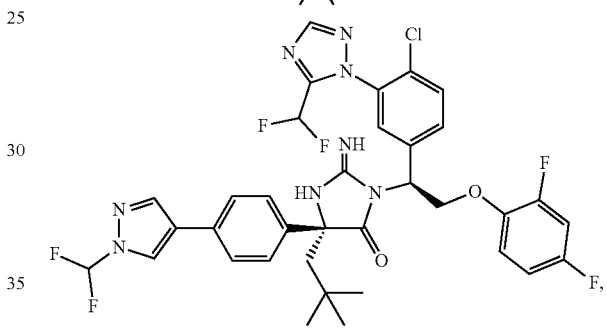
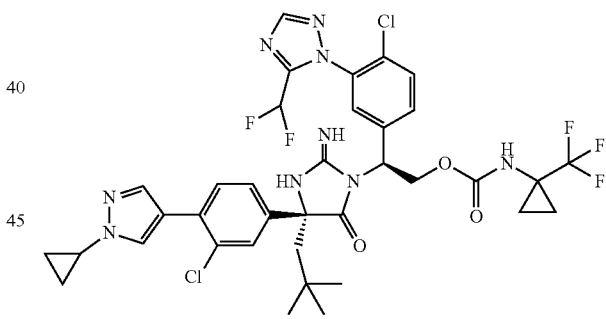
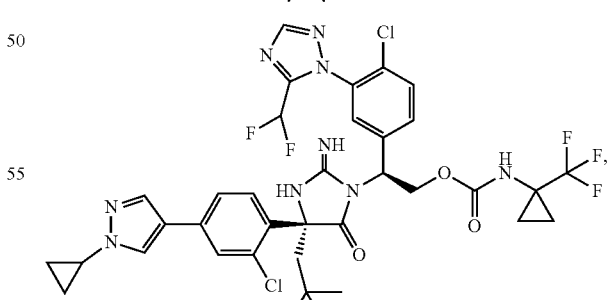

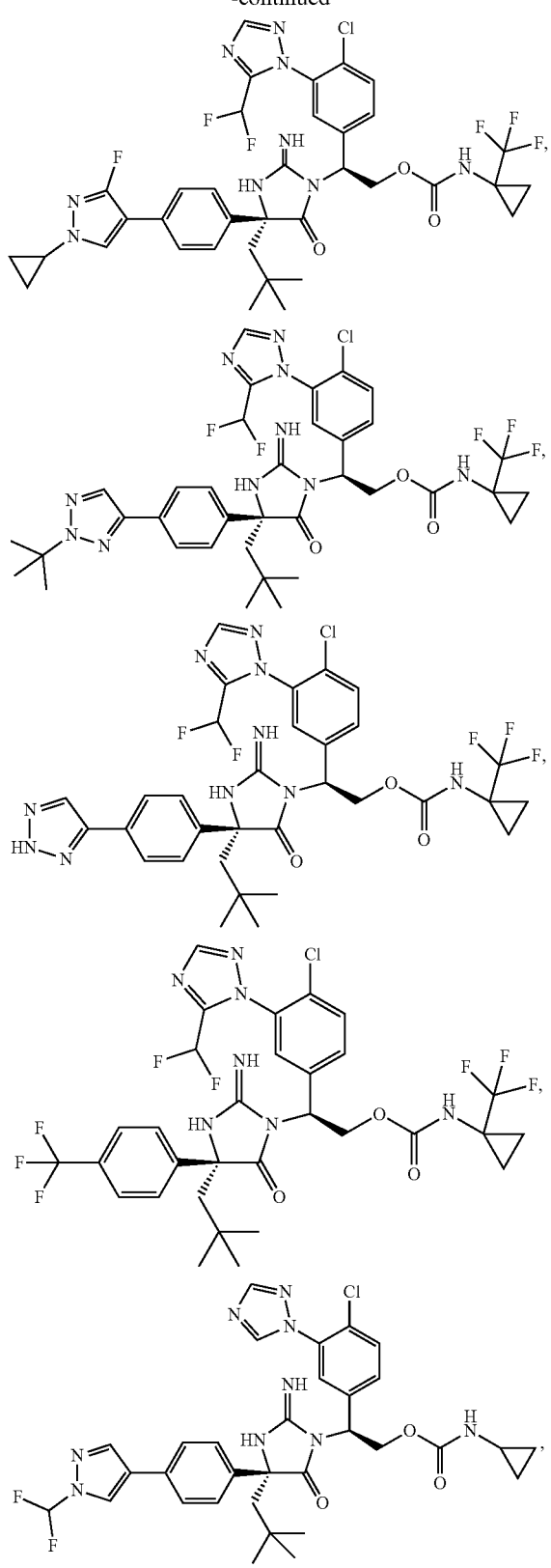
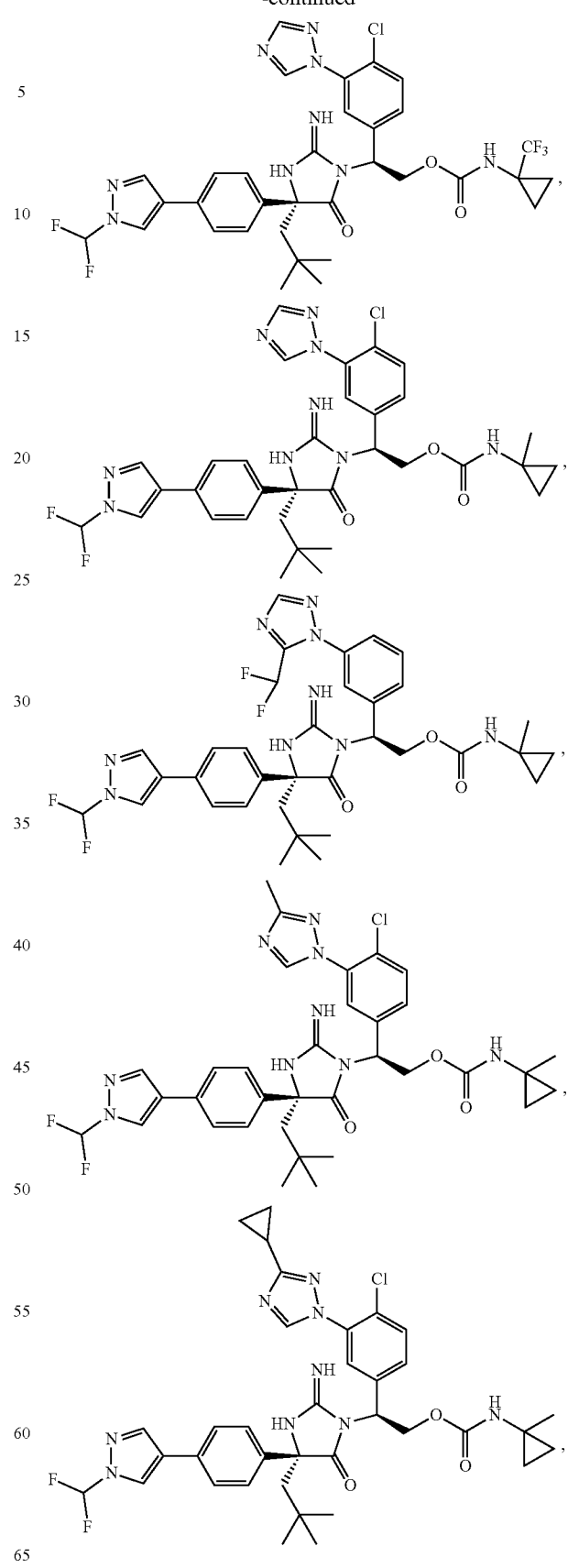

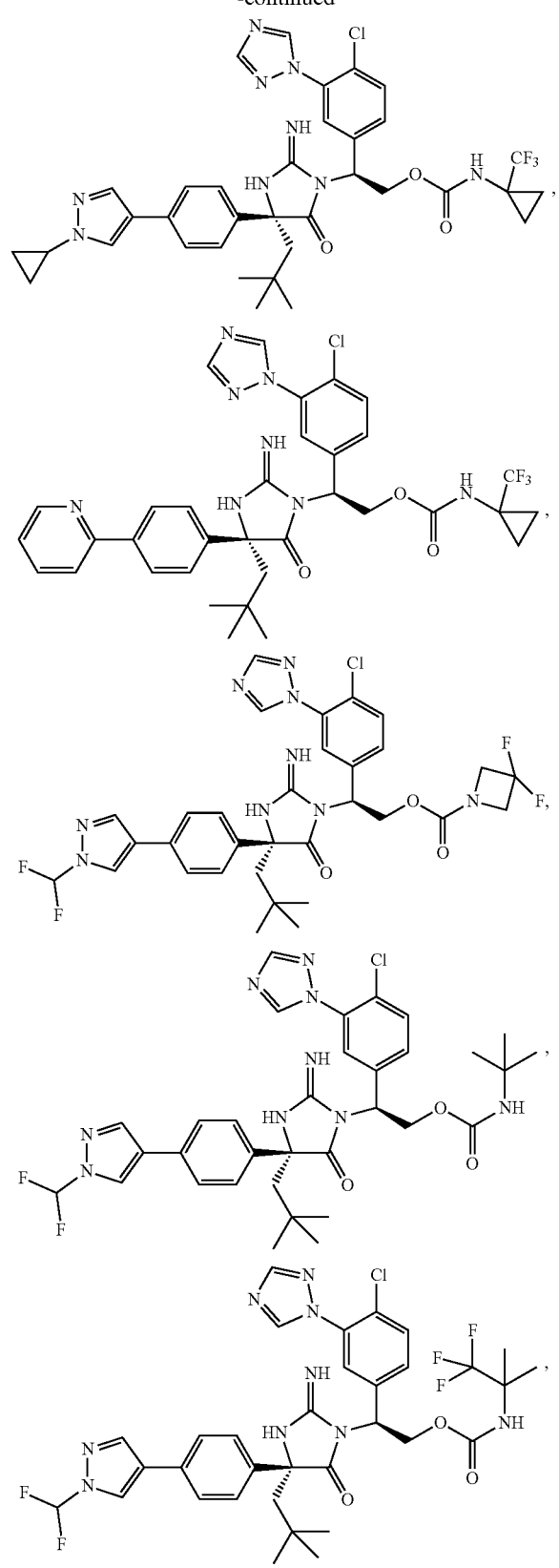
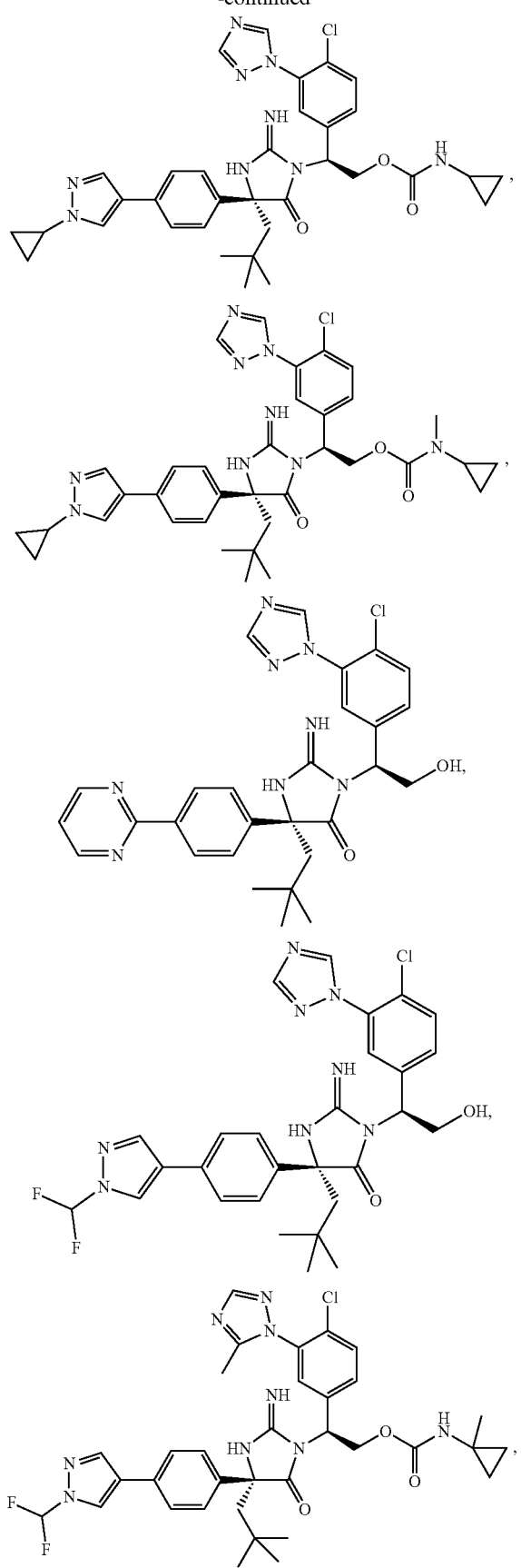

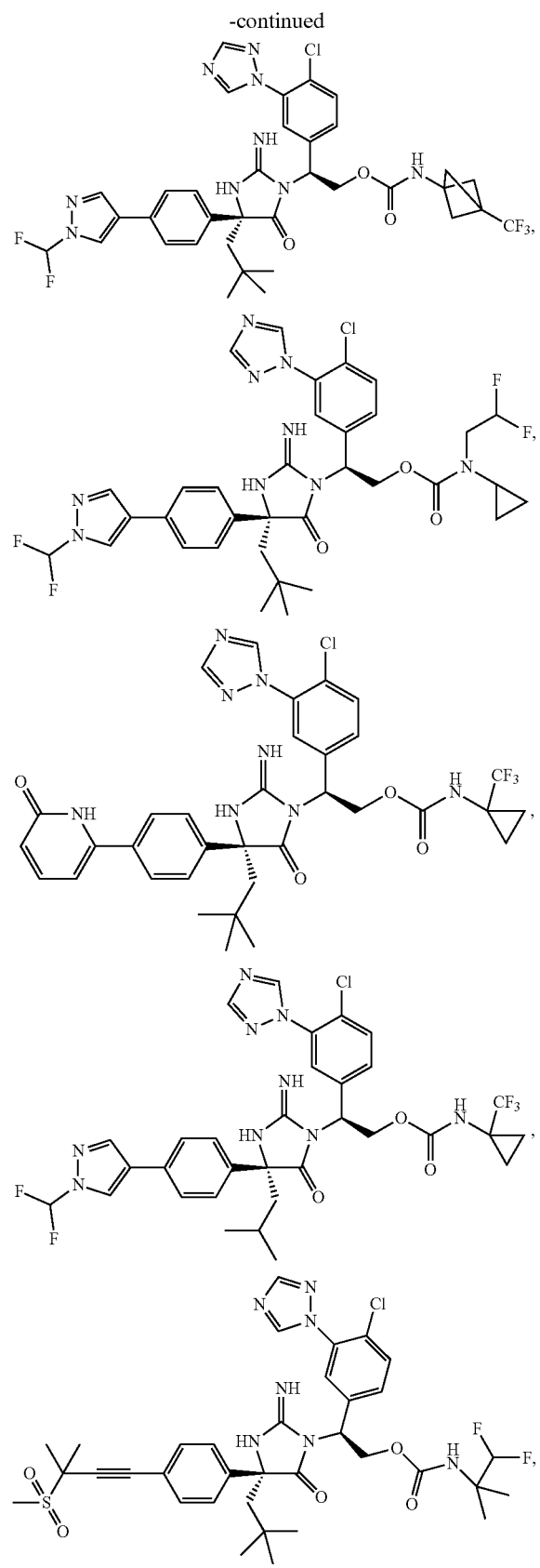
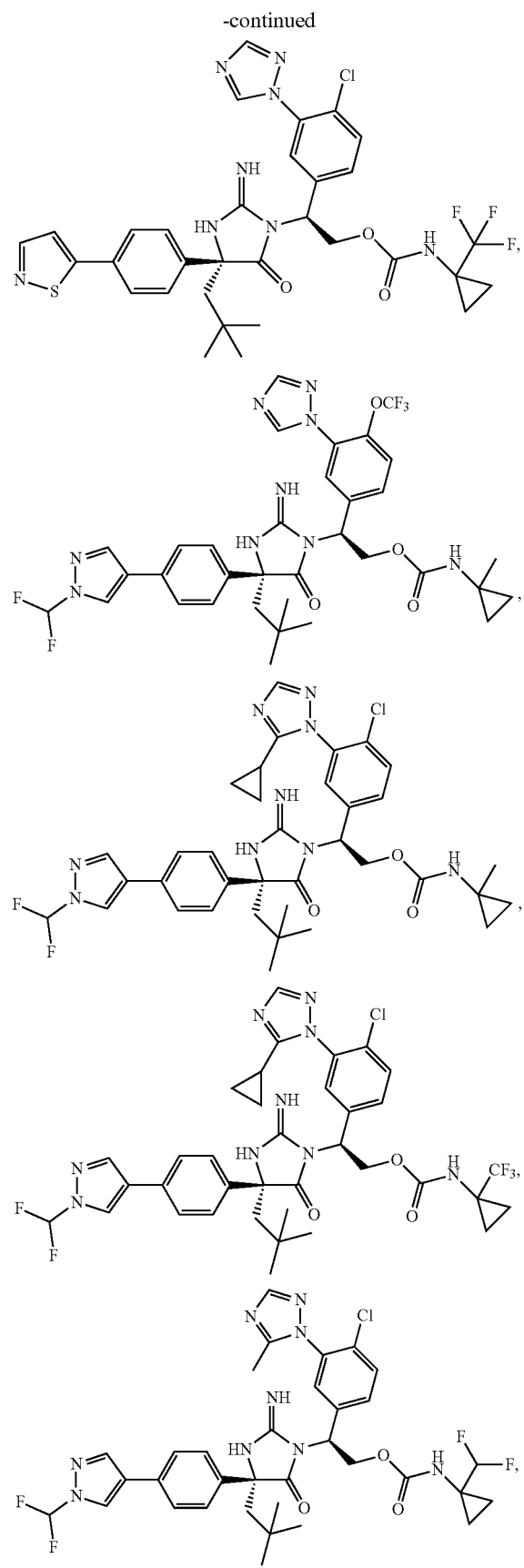

109
-continued
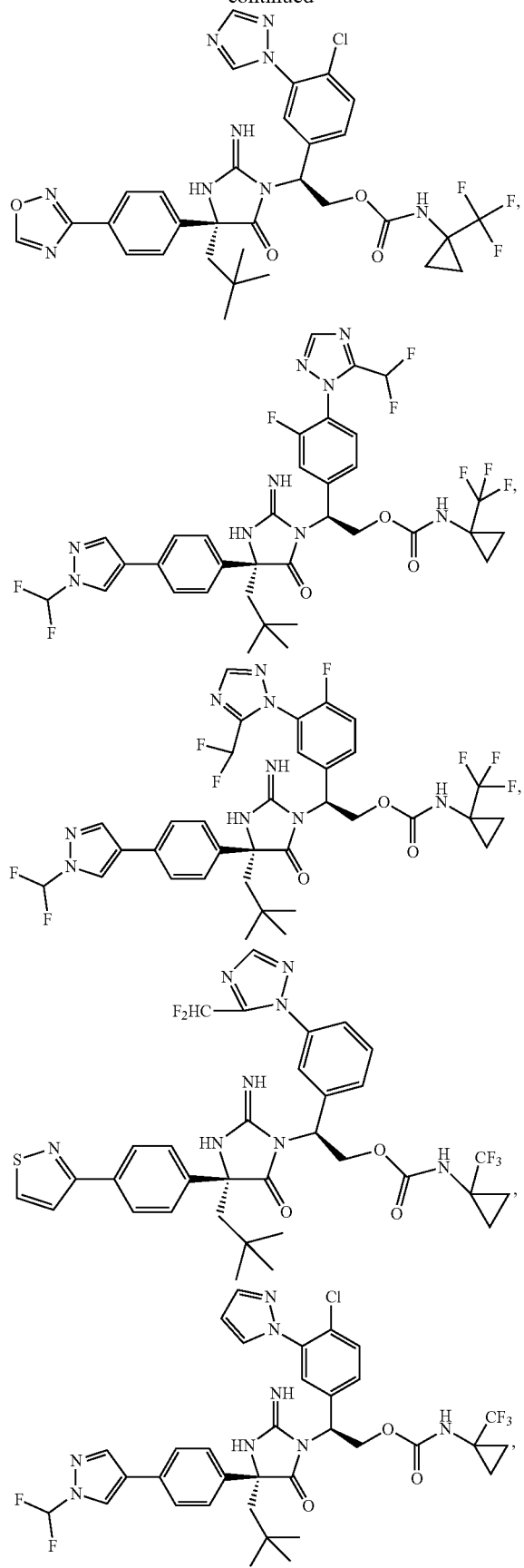
110
-continued
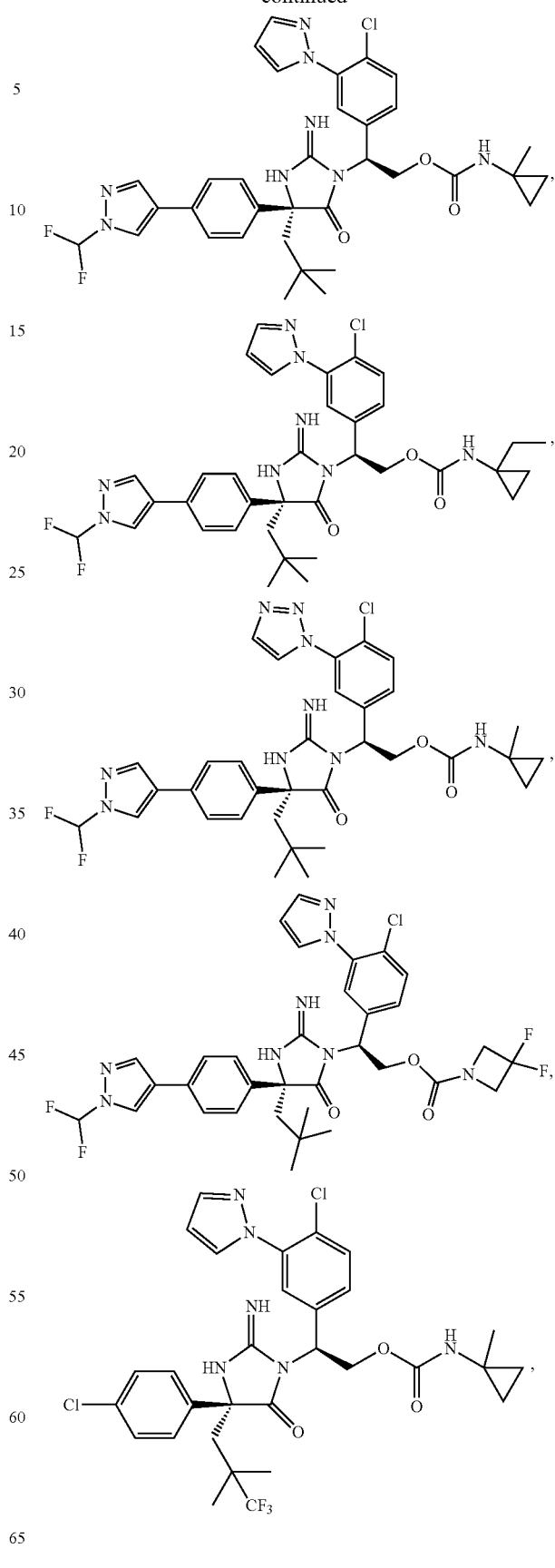

111
-continued
112
-continued
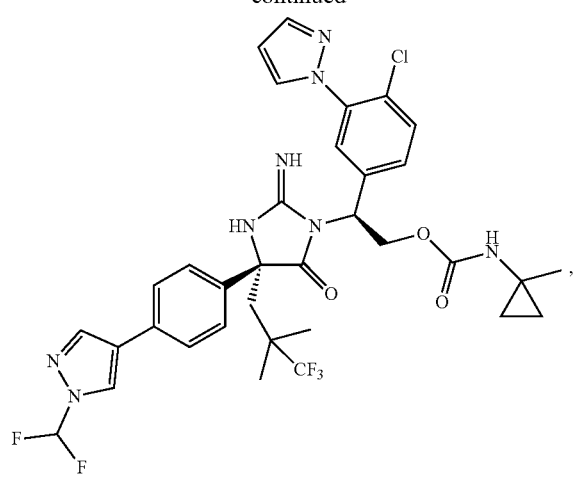
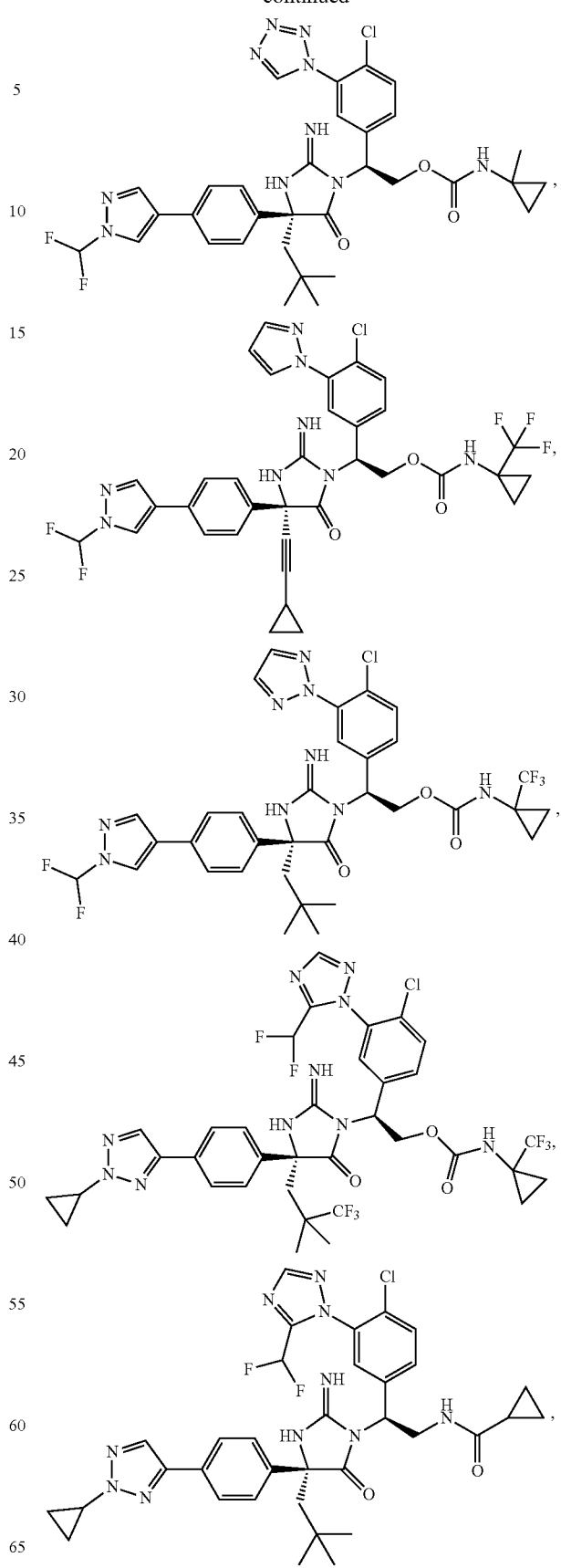

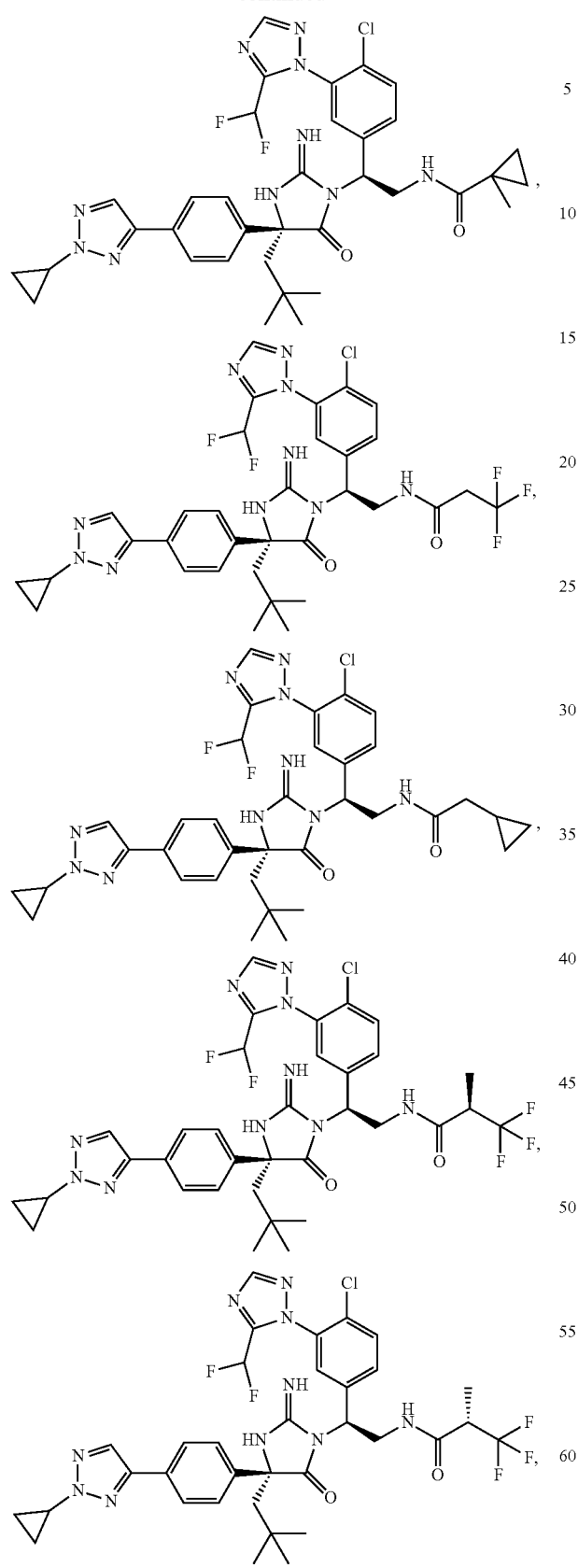
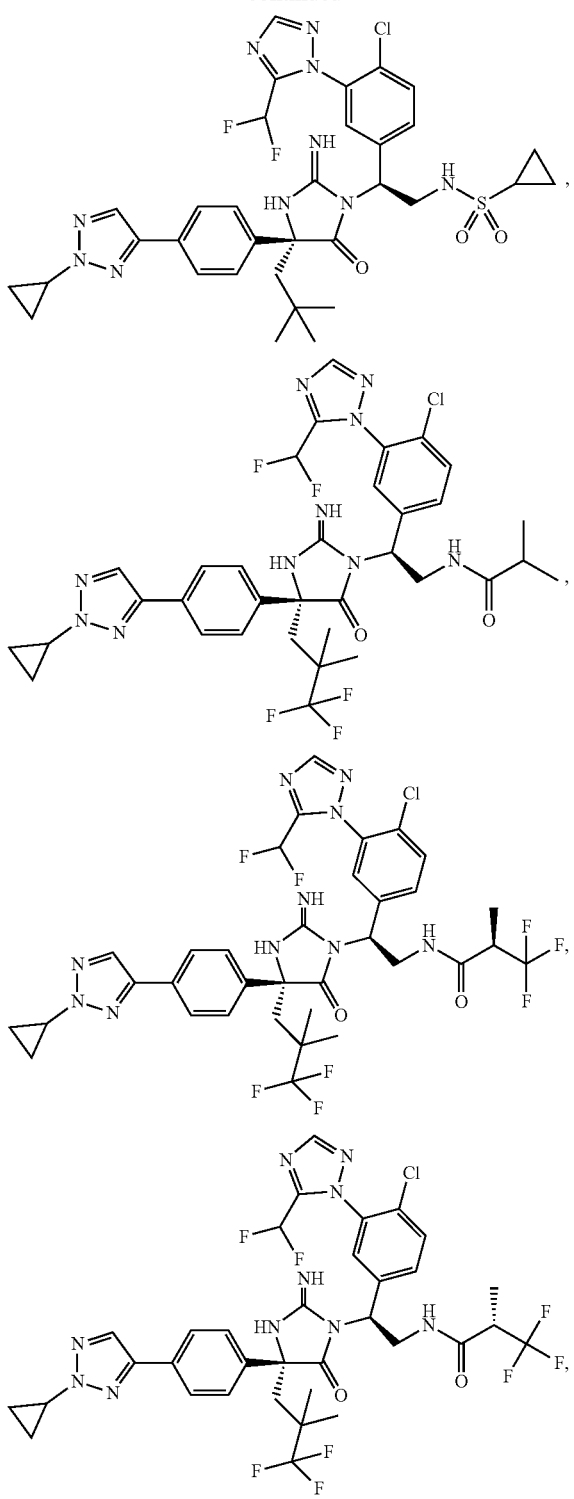

115
-continued
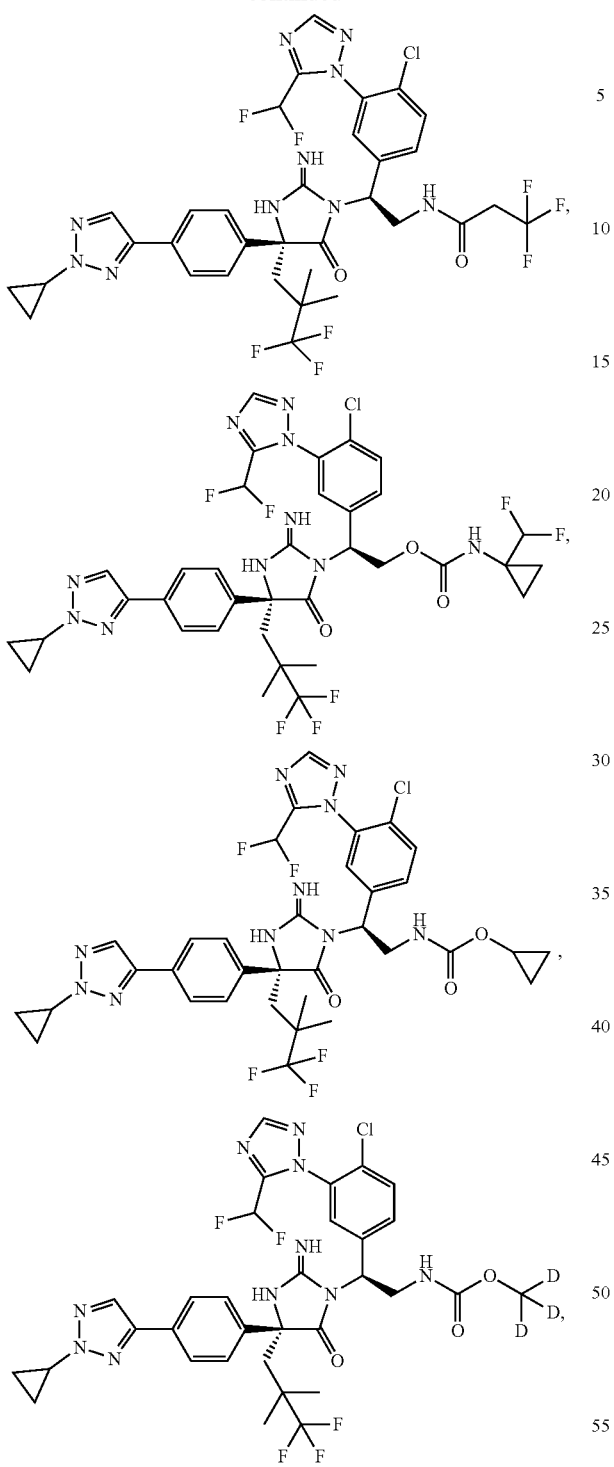
116
-continued
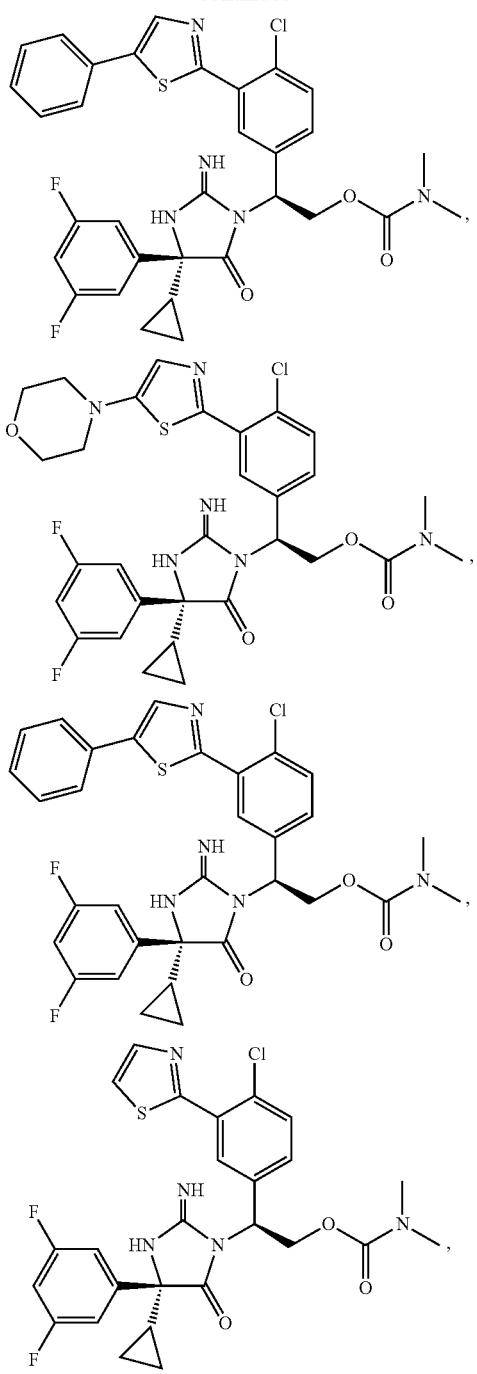

117
-continued
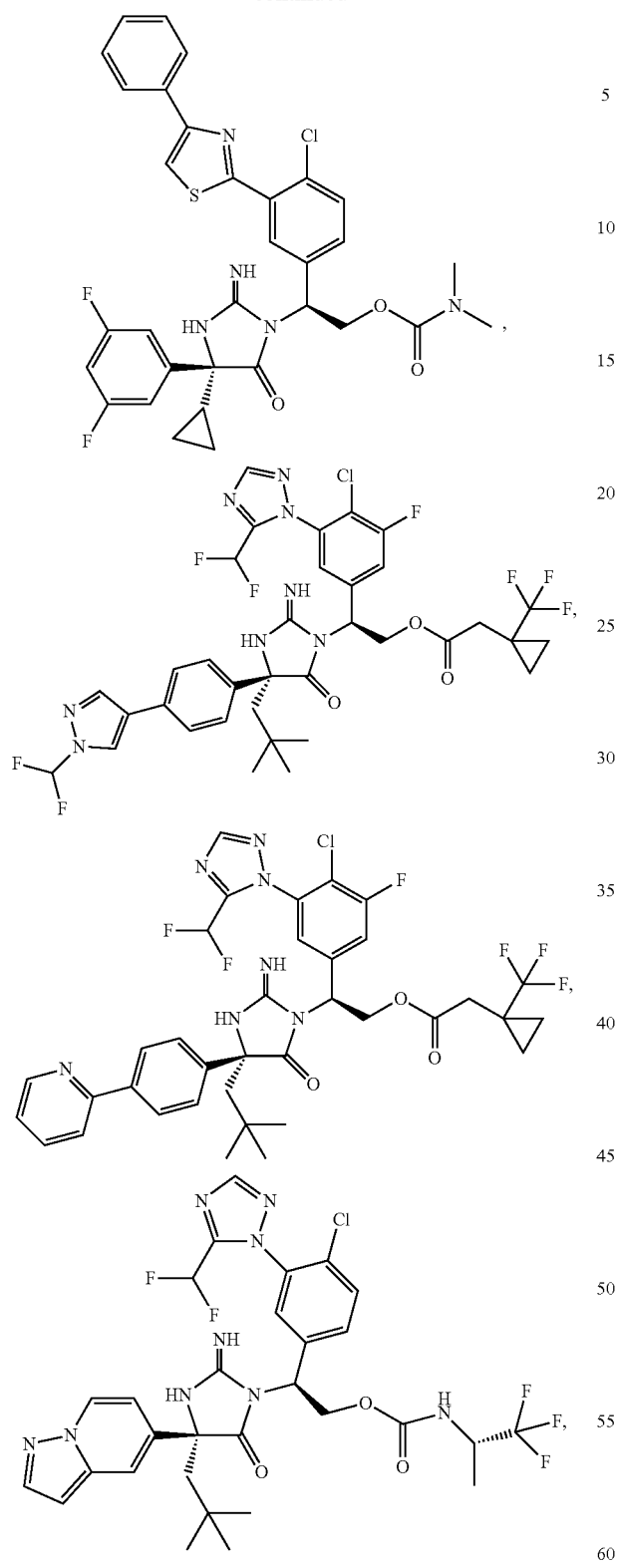
118
-continued
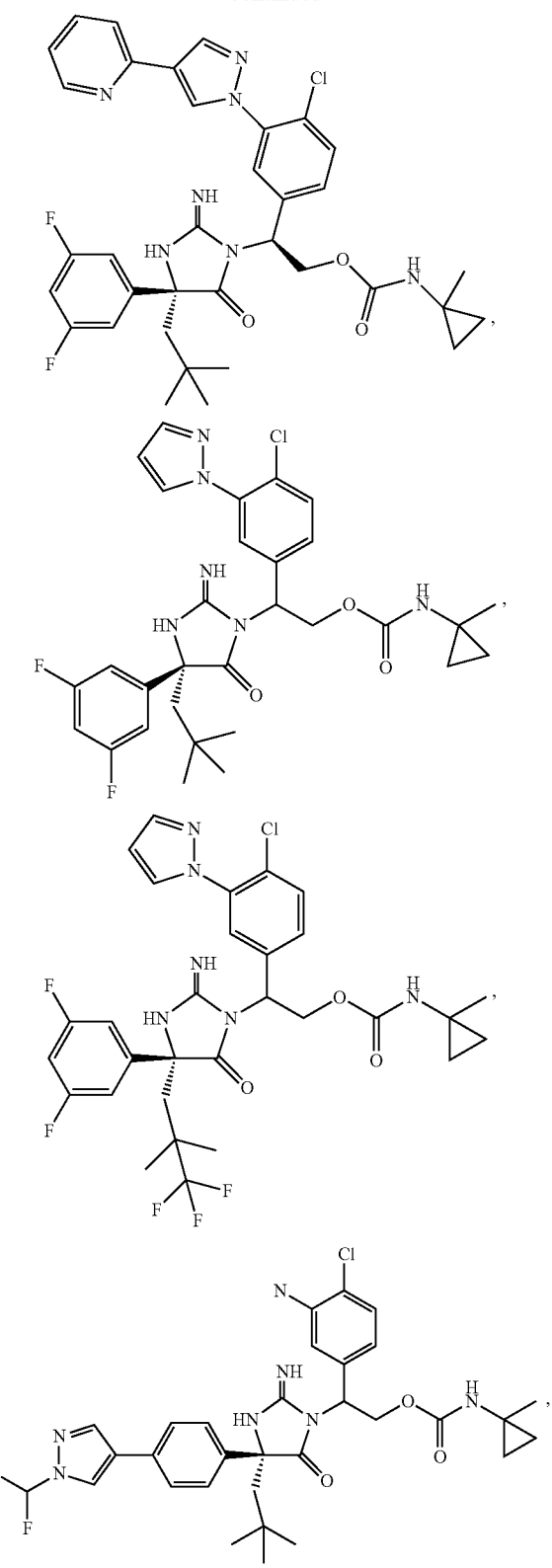

119
-continued
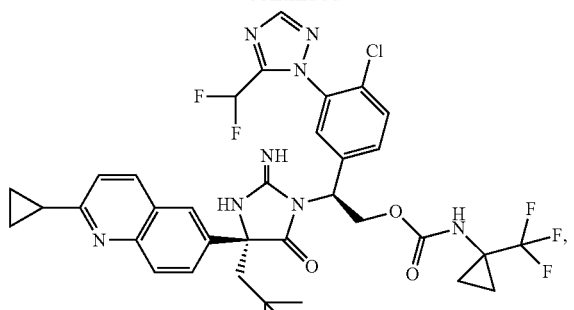
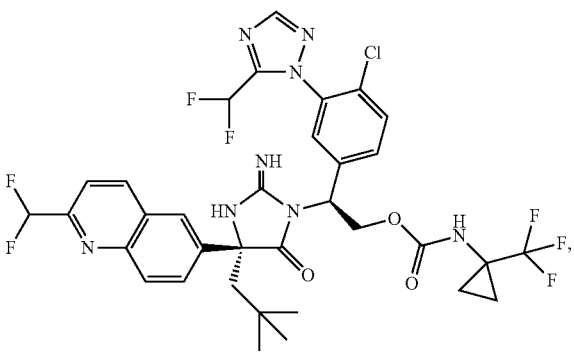
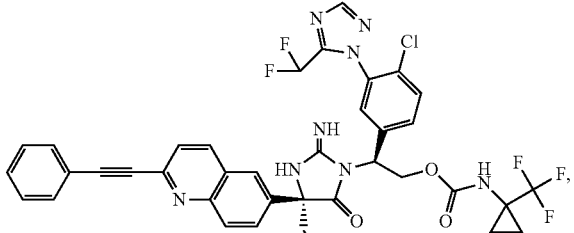
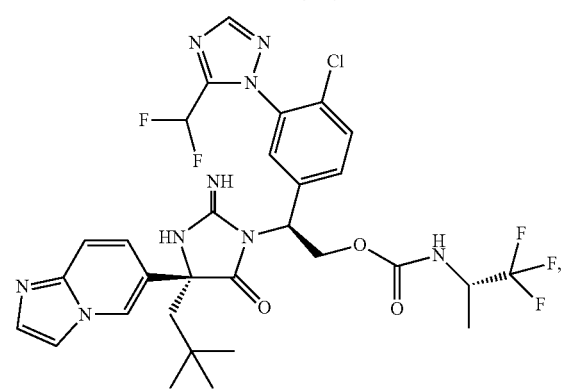
120
-continued
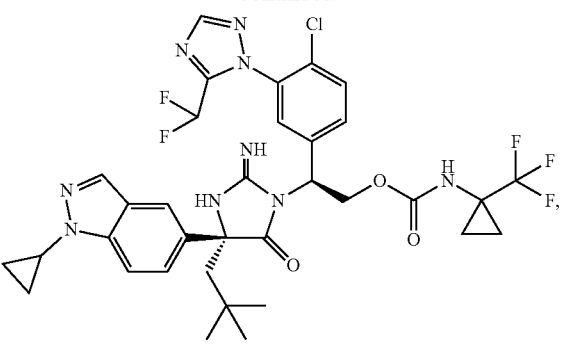
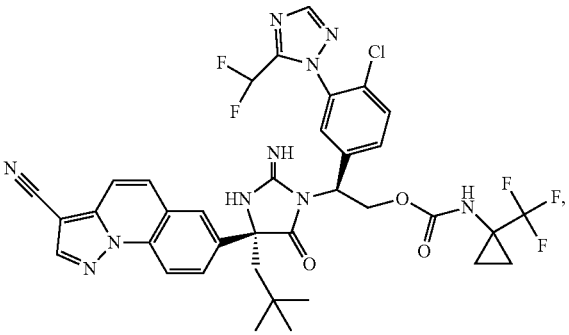
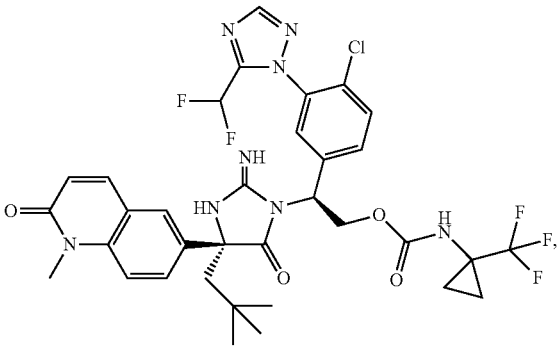

121
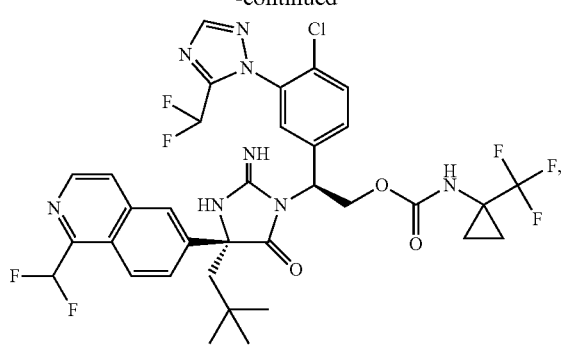
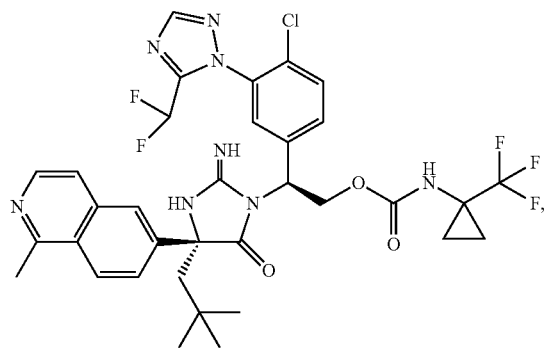
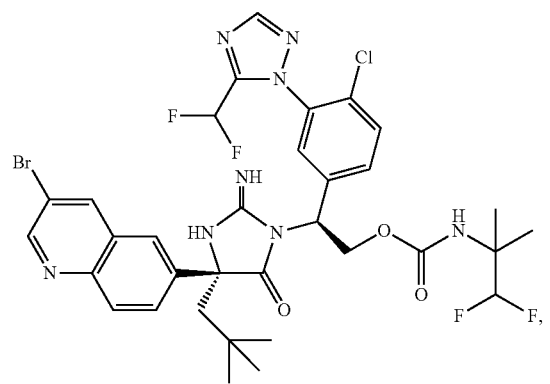
and
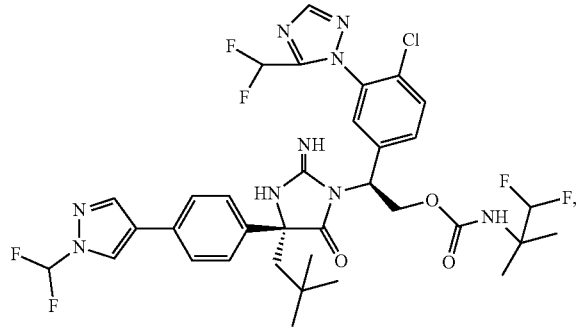
or a pharmaceutically acceptable salt thereof.
In another embodiment, the compound is:
122
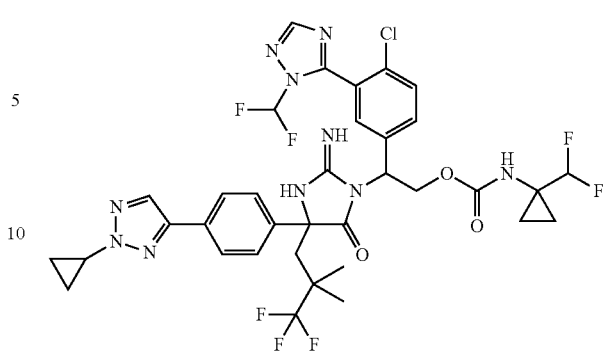
or a pharmaceutically acceptable salt thereof.
In another embodiment, the compound is:
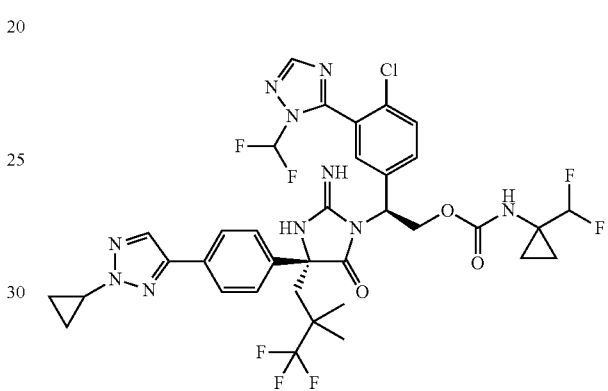
or a pharmaceutically acceptable salt thereof.
In another embodiment, the compound is:
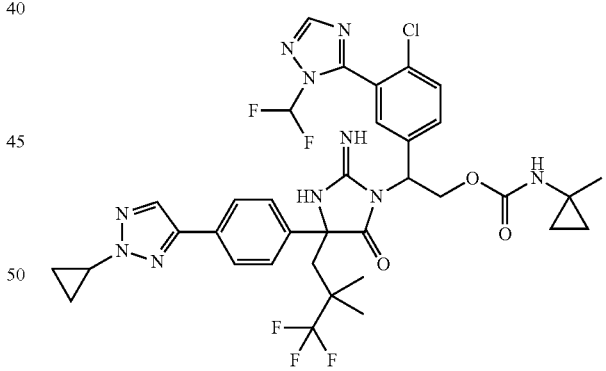
or a pharmaceutically acceptable salt thereof.
In another embodiment, the compound is:

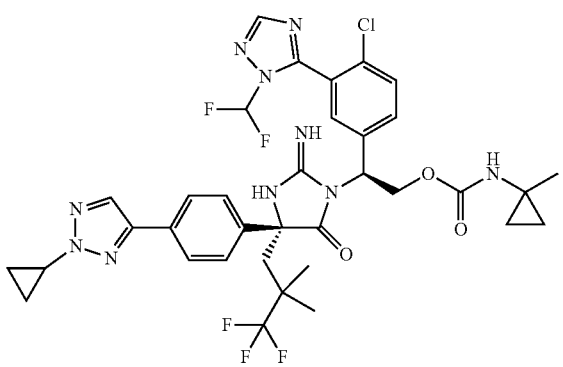 [SMILES: CC1(NC(=O)OC[C@H](c2ccc(Cl)c(-c3ncnn3C(F)F)c2)N2C(=N)N[C@](CC(C)(C)C(F)(F)F)(c3ccc(-c4cnn(C5CC5)n4)cc3)C2=O)CC1]

or a pharmaceutically acceptable salt thereof

Methods of Treatment

The pharmaceutical compositions of compounds of Formula (I) (including compounds of Formulae (Ia)-(Ie)) may be administered in either single or multiple doses by any of the accepted modes of administration of agents having similar utilities, for example as described in those patents and patent applications incorporated by reference, including rectal, buccal, intranasal and transdermal routes, by intra-arterial injection, intravenously, intraperitoneally, parenterally, intramuscularly, subcutaneously, orally, topically, as an inhalant, or via an impregnated or coated device such as a stent, for example, or an artery-inserted cylindrical polymer.

In one aspect, the compounds described herein may be administered orally. Oral administration may be via, for example, capsule or enteric coated tablets. In making the pharmaceutical compositions that include at least one compound of Formula (I), or a pharmaceutically acceptable salt, is usually diluted by an excipient and/or enclosed within such a carrier that can be in the form of a capsule, sachet, paper or other container. When the excipient serves as a diluent, it can be in the form of a solid, semi-solid, or liquid material (as above), which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, sterile injectable solutions, and sterile packaged powders.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include: lubricating agents such as talc, magnesium stearate, and mineral oil; wetting agents; emulsifying and suspending agents; preserving agents such as methyl and propylhydroxy-benzoates; sweetening agents; and flavoring agents.

The compositions that include at least one compound of Formula (I), or a pharmaceutically acceptable salt, can be formulated so as to provide quick, sustained or delayed release of the active ingredient after administration to the subject by employing procedures known in the art. Controlled-release drug delivery systems for oral administration include osmotic pump systems and dissolutional systems containing polymer-coated reservoirs or drug-polymer matrix formulations. Examples of controlled release systems are given in U.S. Pat. Nos. 3,845,770; 4,326,525; 4,902,514; and 5,616,345. Another formulation for use in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art. See, e.g., U.S. Pat. Nos. 5,023,252, 4,992,445 and 5,001,139. Such patches may be constructed for continuous, pulsatile, or on demand delivery of pharmaceutical agents.

The compositions may, in some embodiments, be formulated in a unit dosage form. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient (e.g., a tablet, capsule, ampule). The compounds are generally administered in a pharmaceutically effective amount. In some embodiments, for oral administration, each dosage unit contains from about 10 mg to about 1000 mg of a compound described herein, for example from about 50 mg to about 500 mg, for example about 50 mg, about 75 mg, about 100 mg, about 150 mg, about 200 mg, about 225 mg, about 250 mg, about 275 mg, about 300 mg, about 325 mg, about 350 mg, about 375 mg, about 400 mg, about 425 mg, about 450 mg, about 475 mg, or about 500 mg. In other embodiments, for parenteral administration, each dosage unit contains from 0.1 to 700 mg of a compound a compound described herein. It will be understood, however, that the amount of the compound actually administered usually will be determined by a physician, in the light of the relevant circumstances, including the condition to be treated, the chosen route of administration, the actual compound administered and its relative activity, the age, weight, and response of the individual subject, and the severity of the subject's symptoms.

In certain embodiments, dosage levels may be from 0.1 mg to 100 mg per kilogram of body weight per day, for example from about 1 mg to about 50 mg per kilogram, for example from about 5 mg to about 30 mg per kilogram. Such dosage levels may, in certain instances, be useful in the treatment of the above-indicated conditions. In other embodiments, dosage levels may be from about 10 mg to about 2000 mg per subject per day. The amount of active ingredient that may be combined with the vehicle to produce a single dosage form will vary depending upon the host treated and the particular mode of administration. Dosage unit forms may contain from 1 mg to 1000 mg of an active ingredient.

The compounds disclosed herein, or a pharmaceutically acceptable salt thereof, may be administered to a subject in accordance with an effective dosing regimen for a desired period of time or duration, such as at least about one day, at least about one week, at least about one month, at least about 2 months, at least about 3 months, at least about 4 months, at least about 6 months, or at least about 12 months or longer. In one variation, the compound is administered on a daily or intermittent schedule. In one variation, the compound is administered on a monthly schedule. In one variation, the compound is administered every two months. In one variation, the compound is administered every three months. In one variation, the compound is administered every four months. In one variation, the compound is administered every five months. In one variation, the compound is administered every 6 months.

The dosage or dosing frequency of a compound disclosed herein, or a pharmaceutically acceptable salt thereof, may be adjusted over the course of the treatment, based on the judgment of the administering physician. The compound may be administered to a subject (e.g., a human) in an effective amount. In certain embodiments, the compound is administered once daily.

For preparing solid compositions such as tablets, the principal active ingredient may be mixed with a pharmaceutical excipient to form a solid preformulation composition containing a homogeneous mixture of a compound of Formula (I), or a pharmaceutically acceptable salt, thereof. When referring to these preformulation compositions as homogeneous, the active ingredient may be dispersed evenly throughout the composition so that the composition may be readily subdivided into equally effective unit dosage forms such as tablets, pills and capsules.

The tablets or pills of the compounds described herein may be coated or otherwise compounded to provide a dosage form affording the advantage of prolonged action, or to protect from the acid conditions of the stomach. For example, the tablet or pill can comprise an inner dosage and an outer dosage component, the latter being in the form of an envelope over the former. The two components can be separated by an enteric layer that serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

In some embodiments, formulations suitable for parenteral administration (e.g., intramuscular (IM) and subcutaneous (SC) administration) will include one or more excipients. Excipients should be compatible with the other ingredients of the formulation and physiologically innocuous to the recipient thereof. Examples of suitable excipients are well known to the person skilled in the art of parenteral formulation and may be found e.g., in Handbook of Pharmaceutical Excipients (eds. Rowe, Sheskey & Quinn), 6th edition 2009.

In certain embodiments, a method of treating or preventing a human immunodeficiency virus (HIV) infection comprising administering a therapeutically effective amount of a compound disclosed herein, or a pharmaceutically acceptable salt thereof, to a subject in need thereof, is provided. In certain embodiments, a method of treating a human immunodeficiency virus (HIV) infection comprising administering a therapeutically effective amount of a compound disclosed herein, or a pharmaceutically acceptable salt thereof, to a subject in need thereof, is provided. In certain embodiments, the method comprises administering a compound disclosed herein, or a pharmaceutically acceptable salt thereof, in combination with one, two, three, or four additional therapeutic agents. In certain embodiments, the subject is at risk of contracting the HIV virus, such as a subject who has one or more risk factors known to be associated with contracting the HIV virus. In certain embodiments, the subject may have not previously received antiviral treatment (treatment naïve). In certain embodiments, the subject may have previously received antiviral treatment (treatment experienced). In certain embodiments, the subject may have previously received antiviral treatment and developed resistance to the previously received antiviral treatment.

In certain embodiments, a method of treating or preventing a human immunodeficiency virus (HIV) infection comprising administering a therapeutically effective amount of a compound disclosed herein, or a pharmaceutically acceptable salt thereof, to a subject in need thereof, in combination with a therapeutically effective amount of one or more (e.g., one, two, three, or four; or one or two; or one to three; or one to four) additional therapeutic agents selected from the group consisting of combination drugs for HIV, other drugs for treating HIV, HIV protease inhibitors, HIV non-nucleoside or non-nucleotide inhibitors of reverse transcriptase, HIV nucleoside or nucleotide inhibitors of reverse transcriptase, HIV integrase inhibitors, HIV non-catalytic site (or allosteric) integrase inhibitors, HIV entry inhibitors, HIV maturation inhibitors, latency reversing agents, compounds that target the HIV capsid, immune-based therapies, phosphatidylinositol 3-kinase (PI3K) inhibitors, HIV antibodies, bispecific antibodies and "antibody-like" therapeutic proteins, HIV p17 matrix protein inhibitors, IL-13 antagonists, peptidyl-prolyl cis-trans isomerase A modulators, protein disulfide isomerase inhibitors, complement C5a receptor antagonists, DNA methyltransferase inhibitor, HIV vif gene modulators, Vif dimerization antagonists, HIV-1 viral infectivity factor inhibitors, TAT protein inhibitors, HIV-1 Nef modulators, Hck tyrosine kinase modulators, mixed lineage kinase-3 (MLK-3) inhibitors, HIV-1 splicing inhibitors, Rev protein inhibitors, integrin antagonists, nucleoprotein inhibitors, splicing factor modulators, COMM domain containing protein 1 modulators, HIV ribonuclease H inhibitors, retrocyclin modulators, CDK-9 inhibitors, dendritic ICAM-3 grabbing nonintegrin 1 inhibitors, HIV GAG protein inhibitors, HIV POL protein inhibitors, Complement Factor H modulators, ubiquitin ligase inhibitors, deoxycytidine kinase inhibitors, cyclin dependent kinase inhibitors, proprotein convertase PC9 stimulators, ATP dependent RNA helicase DDX3X inhibitors, reverse transcriptase priming complex inhibitors, G6PD and NADH-oxidase inhibitors, pharmacokinetic enhancers, HIV gene therapy, and HIV vaccines, or any combinations thereof, is provided. In certain embodiments, the one or more (e.g., one, two, three, or four; or one or two; or one to three; or one to four) additional therapeutic agents are selected from the group consisting of HIV protease inhibiting compounds, HIV non-nucleoside inhibitors of reverse transcriptase, HIV non-nucleotide inhibitors of reverse transcriptase, HIV nucleoside inhibitors of reverse transcriptase, HIV nucleotide inhibitors of reverse transcriptase, HIV integrase inhibitors, gp41 inhibitors, CXCR4 inhibitors, gp120 inhibitors, CCR5 inhibitors, capsid polymerization inhibitors, pharmacokinetic enhancers, and other drugs for treating HIV, or any combinations thereof. In certain embodiments, the one or more additional therapeutic agent does not include a pharmacokinetic enhancer.

In certain embodiments, a method for inhibiting the replication of the HIV virus, treating AIDS or delaying the onset of AIDS in a subject (e.g., a human), comprising administering a compound disclosed herein, or a pharmaceutically acceptable salt thereof, to the subject is disclosed.

In certain embodiments, a compound of disclosed herein, or a pharmaceutically acceptable salt thereof for use in medical therapy of an HIV infection (e.g. HIV-1 or the replication of the HIV virus (e.g. HIV-1) or AIDS or delaying the onset of AIDS in a subject (e.g., a human)) is disclosed.

In certain embodiments, a compound disclosed herein, or a pharmaceutically acceptable salt thereof for use in the manufacture of a medicament for treating an HIV infection or the replication of the HIV virus or AIDS or delaying the onset of AIDS in a subject (e.g., a human) is disclosed. One embodiment relates to a compound disclosed herein, or a pharmaceutically acceptable salt thereof, for use in the prophylactic or therapeutic treatment of an HIV infection or AIDS or for use in the therapeutic treatment or delaying the onset of AIDS.

In certain embodiments, the use of a compound disclosed herein, or a pharmaceutically acceptable salt thereof, for the manufacture of a medicament for an HIV infection in a subject (e.g., a human) is disclosed. In certain embodiments, a compound disclosed herein, or a pharmaceutically acceptable salt thereof, for use in the prophylactic or therapeutic treatment of an HIV infection is disclosed.

In certain embodiments, in the methods of use, the administration is to a subject (e.g., a human) in need of the treatment. In certain embodiments, in the methods of use, the administration is to a subject (e.g., a human) who is at risk of developing AIDS.

The compounds disclosed herein, or a pharmaceutically acceptable salt thereof, for use in therapy is provided. In one embodiment, a compound disclosed herein, or a pharmaceutically acceptable salt thereof, is for use in a method of treating an HIV infection or the replication of the HIV virus or AIDS or delaying the onset of AIDS in a subject (e.g., a human).

The compounds disclosed herein, or a pharmaceutically acceptable salt thereof, for use in a method of treating or preventing HIV infection in a subject in need thereof is provided. In certain embodiments, a compound disclosed herein, or a pharmaceutically acceptable salt thereof, for use in a method of treating HIV infection in a subject in need thereof is provided. In certain embodiments, the subject in need thereof is a human who has been infected with HIV. In certain embodiments, the subject in need thereof is a human who has been infected with HIV but who has not developed AIDS. In certain embodiments, the subject in need thereof is a subject at risk for developing AIDS. In certain embodiments, the subject in need thereof is a human who has been infected with HIV and who has developed AIDS.

In one embodiment, a compound disclosed herein, or a pharmaceutically acceptable salt thereof, in combination with one or more (e.g. one, two, three, or four; or one or two; or one to three; or one to four) additional therapeutic agents as described herein for use in a method of treating or preventing HIV infection in a subject in need thereof is provided. In one embodiment, said additional therapeutic agents are selected from the group consisting of combination drugs for HIV, other drugs for treating HIV, HIV protease inhibitors, HIV non-nucleoside or non-nucleotide inhibitors of reverse transcriptase, HIV nucleoside or nucleotide inhibitors of reverse transcriptase, HIV integrase inhibitors, HIV non-catalytic site (or allosteric) integrase inhibitors, HIV entry inhibitors, HIV maturation inhibitors, latency reversing agents, compounds that target the HIV capsid, immune-based therapies, phosphatidylinositol 3-kinase (PI3K) inhibitors, HIV antibodies, bispecific antibodies and "antibody-like" therapeutic proteins, HIV p17 matrix protein inhibitors, IL-13 antagonists, peptidyl-prolyl cis-trans isomerase A modulators, protein disulfide isomerase inhibitors, complement C5a receptor antagonists, DNA methyltransferase inhibitor, HIV vif gene modulators, Vif dimerization antagonists, HIV-1 viral infectivity factor inhibitors, TAT protein inhibitors, HIV-1 Nef modulators, Hck tyrosine kinase modulators, mixed lineage kinase-3 (MLK-3) inhibitors, HIV-1 splicing inhibitors, Rev protein inhibitors, integrin antagonists, nucleoprotein inhibitors, splicing factor modulators, COMM domain containing protein 1 modulators, HIV ribonuclease H inhibitors, retrocyclin modulators, CDK-9 inhibitors, dendritic ICAM-3 grabbing nonintegrin 1 inhibitors, HIV GAG protein inhibitors, HIV POL protein inhibitors, Complement Factor H modulators, ubiquitin ligase inhibitors, deoxycytidine kinase inhibitors, cyclin dependent kinase inhibitors, proprotein convertase PC9 stimulators, ATP dependent RNA helicase DDX3X inhibitors, reverse transcriptase priming complex inhibitors, G6PD and NADH-oxidase inhibitors, pharmacokinetic enhancers, HIV gene therapy, and HIV vaccines, or any combinations thereof. In certain embodiments, said additional therapeutic agents are selected from the group consisting of HIV protease inhibiting compounds, HIV non-nucleoside inhibitors of reverse transcriptase, HIV non-nucleotide inhibitors of reverse transcriptase, HIV nucleoside inhibitors of reverse transcriptase, HIV nucleotide inhibitors of reverse transcriptase, HIV integrase inhibitors, gp41 inhibitors, CXCR4 inhibitors, gp120 inhibitors, CCR5 inhibitors, capsid polymerization inhibitors, pharmacokinetic enhancers, and other drugs for treating HIV, or any combinations thereof.

In one embodiment, a compound disclosed herein, or a pharmaceutically acceptable salt thereof, in combination with a first additional therapeutic agent selected from the group consisting of tenofovir alafenamide fumarate, tenofovir alafenamide, and tenofovir alafenamide hemifumarate, and a second additional therapeutic agent, wherein the second additional therapeutic agent is emtricitabine, is provided for use in a method of treating or preventing HIV infection in a subject in need thereof. In a particular embodiment, a compound disclosed herein, or a pharmaceutically acceptable salt thereof, in combination with a first additional therapeutic agent selected from the group consisting of tenofovir disoproxil fumarate, tenofovir disoproxil, and tenofovir disoproxil hemifumarate, and a second additional therapeutic agent, wherein the second additional therapeutic agent is emtricitabine, is provided for use in a method of treating or preventing HIV infection in a subject in need thereof.

In a particular embodiment, a compound disclosed herein or a pharmaceutically acceptable salt thereof, are provided for use to prevent HIV infection from taking hold if the individual is exposed to the virus and/or to keep the virus from establishing a permanent infection and/or to prevent the appearance of symptoms of the disease and/or to prevent the virus from reaching detectable levels in the blood, for example for pre-exposure prophylaxis (PrEP) or post-exposure prophylaxis (PEP). Accordingly, in certain embodiments, methods for reducing the risk of acquiring HIV (e.g., HIV-1 and/or HIV-2) are provided. For example, methods for reducing the risk of acquiring HIV (e.g., HIV-1 and/or HIV-2) comprise administration of a compound disclosed herein, or a pharmaceutically acceptable salt thereof. In certain embodiments, methods for reducing the risk of acquiring HIV (e.g., HIV-1 and/or HIV-2) comprise administration of a compound disclosed herein, or a pharmaceutically acceptable salt thereof, in combination with one or more additional therapeutic agents. In certain embodiments, methods for reducing the risk of acquiring HIV (e.g., HIV-1 and/or HIV-2) comprise administration of a pharmaceutical composition comprising a therapeutically effective amount of the compound disclosed herein, or pharmaceutically acceptable salt thereof, and a pharmaceutically acceptable excipient.

In certain embodiments, methods for reducing the risk of acquiring HIV (e.g., HIV-1 and/or HIV-2) comprise administration of a compound of disclosed herein, or a pharmaceutically acceptable salt thereof, in combination with safer sex practices. In certain embodiments, methods for reducing the risk of acquiring HIV (e.g., HIV-1 and/or HIV-2) comprise administration to an individual at risk of acquiring HIV. Examples of individuals at high risk for acquiring HIV include, without limitation, an individual who is at risk of sexual transmission of HIV.

In certain embodiments, the reduction in risk of acquiring HIV is at least about 40%, 50%, 60%, 70%, 80%, 90%, or 95%. In certain embodiments, the reduction in risk of acquiring HIV is at least about 75%. In certain embodiments, the reduction in risk of acquiring HIV is about 80%, 85%, or 90%.

In another embodiment, the use of a compound disclosed herein, or a pharmaceutically acceptable salt thereof, for the manufacture of a medicament for the treatment of an HIV infection in a human being having or at risk of having the infection is disclosed.

Also disclosed herein is a compound disclosed herein, or a pharmaceutically acceptable salt thereof, for use in the therapeutic treatment or delaying the onset of AIDS.

Also disclosed herein is a compound disclosed herein, or a pharmaceutically acceptable salt thereof, for use in the prophylactic or therapeutic treatment of an HIV infection.

In certain embodiments, a compound disclosed herein, or a pharmaceutically acceptable salt thereof can be used as a research tool (e.g. to study the inhibition of HIV reverse transcriptase in a subject or in vitro).

Kits that include a compound of Formula (I), or a pharmaceutically acceptable salt, thereof, and suitable packaging are provided. In one embodiment, a kit further includes instructions for use. In one aspect, a kit includes a compound of Formula (I), or a pharmaceutically acceptable salt thereof, and instructions for use of the compounds in the treatment of the diseases or conditions described herein.

Articles of manufacture that include a compound of Formula (I), or a pharmaceutically acceptable salt thereof, in a suitable container are provided. The container may be a vial, jar, ampoule, preloaded syringe, and intravenous bag.

Administration of HIV Combination Therapy

In certain embodiments, a compound disclosed herein is administered with one or more additional therapeutic agents. Co-administration of a compound disclosed herein with one or more additional therapeutic agents generally refers to simultaneous or sequential administration of a compound disclosed herein and one or more additional therapeutic agents, such that therapeutically effective amounts of the compound disclosed herein and the one or more additional therapeutic agents are both present in the body of the patient. When administered sequentially, the combination may be administered in two or more administrations.

Co-administration includes administration of unit dosages of the compounds disclosed herein before or after administration of unit dosages of one or more additional therapeutic agents. For example, the compound disclosed herein may be administered within seconds, minutes, or hours of the administration of the one or more additional therapeutic agents. In some embodiments, a unit dose of a compound disclosed herein is administered first, followed within seconds or minutes by administration of a unit dose of one or more additional therapeutic agents. Alternatively, a unit dose of one or more additional therapeutic agents is administered first, followed by administration of a unit dose of a compound disclosed herein within seconds or minutes. In other embodiments, a unit dose of a compound disclosed herein is administered first, followed, after a period of hours (e.g., 1-12 hours), by administration of a unit dose of one or more additional therapeutic agents. In yet other embodiments, a unit dose of one or more additional therapeutic agents is administered first, followed, after a period of hours (e.g., 1-12 hours), by administration of a unit dose of a compound disclosed herein.

In certain embodiments, a compound disclosed herein is combined with one or more additional therapeutic agents in a unitary dosage form for simultaneous administration to a patient, for example as a solid dosage form for oral administration.

In certain embodiments, a compound of Formula (I) is formulated as a tablet, which may optionally contain one or more other compounds useful for treating HIV. In certain embodiments, the tablet can contain another active ingredient for treating HIV, such as HIV protease inhibitors, HIV non-nucleoside or non-nucleotide inhibitors of reverse transcriptase, HIV nucleoside or nucleotide inhibitors of reverse transcriptase, HIV integrase inhibitors, HIV non-catalytic site (or allosteric) integrase inhibitors, pharmacokinetic enhancers, and combinations thereof.

In certain embodiments, such tablets are suitable for once daily dosing.

HIV Combination Therapy

In the above embodiments, the additional therapeutic agent may be an anti-HIV agent. HIV protease inhibitors, HIV non-nucleoside or non-nucleotide inhibitors of reverse transcriptase, HIV nucleoside or nucleotide inhibitors of reverse transcriptase, HIV integrase inhibitors, HIV non-catalytic site (or allosteric) integrase inhibitors, HIV entry inhibitors, HIV maturation inhibitors, latency reversing agents, compounds that target the HIV capsid, immune-based therapies, phosphatidylinositol 3-kinase (PI3K) inhibitors, HIV antibodies, bispecific antibodies and "antibody-like" therapeutic proteins, HIV p17 matrix protein inhibitors, IL-13 antagonists, peptidyl-prolyl cis-trans isomerase A modulators, protein disulfide isomerase inhibitors, complement C5a receptor antagonists, DNA methyltransferase inhibitor, HIV vif gene modulators, Vif dimerization antagonists, HIV-1 viral infectivity factor inhibitors, TAT protein inhibitors, HIV-1 Nef modulators, Hck tyrosine kinase modulators, mixed lineage kinase-3 (MLK-3) inhibitors, HIV-1 splicing inhibitors, Rev protein inhibitors, integrin antagonists, nucleoprotein inhibitors, splicing factor modulators, COMM domain containing protein 1 modulators, HIV ribonuclease H inhibitors, retrocyclin modulators, CDK-9 inhibitors, dendritic ICAM-3 grabbing nonintegrin 1 inhibitors, HIV GAG protein inhibitors, HIV POL protein inhibitors, Complement Factor H modulators, ubiquitin ligase inhibitors, deoxycytidine kinase inhibitors, cyclin dependent kinase inhibitors, proprotein convertase PC9 stimulators, ATP dependent RNA helicase DDX3X inhibitors, reverse transcriptase priming complex inhibitors, G6PD and NADH-oxidase inhibitors, pharmacokinetic enhancers, HIV gene therapy, HIV vaccines, and combinations thereof.

In some embodiments, the additional therapeutic agent is selected from the group consisting of combination drugs for HIV, other drugs for treating HIV, HIV protease inhibitors, HIV reverse transcriptase inhibitors, HIV integrase inhibitors, HIV non-catalytic site (or allosteric) integrase inhibitors, HIV entry (fusion) inhibitors, HIV maturation inhibitors, latency reversing agents, capsid inhibitors, immune-based therapies, PI3K inhibitors, HIV antibodies, and bispecific antibodies, and "antibody-like" therapeutic proteins, and combinations thereof.

HIV Combination Drugs

Examples of combination drugs include ATRIPLA® (efavirenz, tenofovir disoproxil fumarate, and emtricitabine); COMPLERA® (EVIPLERA®; rilpivirine, tenofovir disoproxil fumarate, and emtricitabine); STRIBILD® (elvitegravir, cobicistat, tenofovir disoproxil fumarate, and emtricitabine); TRUVADA® (tenofovir disoproxil fumarate and emtricitabine; TDF+FTC); DESCOVY® (tenofovir alafenamide and emtricitabine); ODEFSEY® (tenofovir alafenamide, emtricitabine, and rilpivirine); GENVOYA® (tenofovir alafenamide, emtricitabine, cobicistat, and elvitegravir); darunavir, tenofovir alafenamide hemifumarate, emtricitabine, and cobicistat; efavirenz, lamivudine, and tenofovir disoproxil fumarate; lamivudine and tenofovir disoproxil fumarate; tenofovir and lamivudine; tenofovir alafenamide and emtricitabine; tenofovir alafenamide hemifumarate and emtricitabine; tenofovir alafenamide hemifumarate, emtricitabine, and rilpivirine; tenofovir alafenamide hemifumarate, emtricitabine, cobicistat, and elvitegravir; COMBIVIR® (zidovudine and lamivudine; AZT+3TC); EPZICOM® (LIVEXA®; abacavir sulfate and lamivudine; ABC+3TC); KALETRA® (ALUVIA®; lopinavir and ritonavir); TRIUMEQ® (dolutegravir, abacavir, and lamivudine); TRIZIVIR® (abacavir sulfate, zidovudine, and lamivudine; ABC+AZT+3TC); atazanavir and cobicistat; atazanavir sulfate and cobicistat; atazanavir sulfate and ritonavir; darunavir and cobicistat; dolutegravir and rilpivirine; dolutegravir and rilpivirine hydrochloride; dolutegravir, abacavir sulfate, and lamivudine; lamivudine, nevirapine, and zidovudine; raltegravir and lamivudine; doravirine, lamivudine, and tenofovir disoproxil fumarate; doravirine, lamivudine, and tenofovir disoproxil; dolutegravir+lamivudine, lamivudine+abacavir+zidovudine, lamivudine+abacavir, lamivudine+tenofovir disoproxil fumarate, lamivudine+zidovudine+nevirapine, lopinavir+ritonavir, lopinavir+ritonavir+abacavir+lamivudine, lopinavir+ritonavir+zidovudine+lamivudine, tenofovir+lamivudine, and tenofovir disoproxil fumarate+emtricitabine+rilpivirine hydrochloride, lopinavir, ritonavir, zidovudine and lamivudine; Vacc-4x and romidepsin; and APH-0812.

Other HIV Drugs

Examples of other drugs for treating HIV include acemannan, alisporivir, BanLec, deferiprone, Gamimune, metenkefalin, naltrexone, Prolastin, REP 9, RPI-MN, VSSP, Hlviral, SB-728-T, 1,5-dicaffeoylquinic acid, rHIV7-shl-TAR-CCRSRZ, AAV-eCD4-Ig gene therapy, MazF gene therapy, BlockAide, ABX-464, AG-1105, APH-0812, BIT-225, CYT-107, HGTV-43, HPH-116, HS-10234, IMO-3100, IND-02, MK-1376, MK-8507, MK-8591, NOV-205, PA-1050040 (PA-040), PGN-007, SCY-635, SB-9200, SCB-719, TR-452, TEV-90110, TEV-90112, TEV-90111, TEV-90113, RN-18, Immuglo, and VIR-576.

HIV Protease Inhibitors

Examples of HIV protease inhibitors include amprenavir, atazanavir, brecanavir, darunavir, fosamprenavir, fosamprenavir calcium, indinavir, indinavir sulfate, lopinavir, nelfinavir, nelfinavir mesylate, ritonavir, saquinavir, saquinavir mesylate, tipranavir, DG-17, TMB-657 (PPL-100), T-169, BL-008, and TMC-310911.

HIV Reverse Transcriptase Inhibitors

Examples of HIV non-nucleoside or non-nucleotide inhibitors of reverse transcriptase include dapivirine, delavirdine, delavirdine mesylate, doravirine, efavirenz, etravirine, lentinan, nevirapine, rilpivirine, ACC-007, AIC-292, KM-023, PC-1005, and VM-1500.

Examples of HIV nucleoside or nucleotide inhibitors of reverse transcriptase include adefovir, adefovir dipivoxil, azvudine, emtricitabine, tenofovir, tenofovir alafenamide, tenofovir alafenamide fumarate, tenofovir alafenamide hemifumarate, tenofovir disoproxil, tenofovir disoproxil fumarate, tenofovir disoproxil hemifumarate, VIDEX® and VIDEX EC® (didanosine, ddl), abacavir, abacavir sulfate, alovudine, apricitabine, censavudine, didanosine, elvucitabine, festinavir, fosalvudine tidoxil, CMX-157, dapivirine, doravirine, etravirine, OCR-5753, tenofovir disoproxil orotate, fozivudine tidoxil, lamivudine, phosphazid, stavudine, zalcitabine, zidovudine, GS-9131, GS-9148, MK-8504, and KP-1461.

HIV Integrase Inhibitors

Examples of HIV integrase inhibitors include elvitegravir, curcumin, derivatives of curcumin, chicoric acid, derivatives of chicoric acid, 3,5-dicaffeoylquinic acid, derivatives of 3,5-dicaffeoylquinic acid, aurintricarboxylic acid, derivatives of aurintricarboxylic acid, caffeic acid phenethyl ester, derivatives of caffeic acid phenethyl ester, tyrphostin, derivatives of tyrphostin, quercetin, derivatives of quercetin, raltegravir, dolutegravir, JTK-351, bictegravir, AVX-15567, cabotegravir (long-acting injectable), diketo quinolin-4-1 derivatives, integrase-LEDGF inhibitor, ledgins, M-522, M-532, NSC-310217, NSC-371056, NSC-48240, NSC-642710, NSC-699171, NSC-699172, NSC-699173, NSC-699174, stilbenedisulfonic acid, T-169 and cabotegravir.

Examples of HIV non-catalytic site, or allosteric, integrase inhibitors (NCINI) include CX-05045, CX-05168, and CX-14442.

HIV Entry Inhibitors

Examples of HIV entry (fusion) inhibitors include cenicriviroc, CCR5 inhibitors, gp41 inhibitors, CD4 attachment inhibitors, gp120 inhibitors, and CXCR4 inhibitors.

Examples of CCR5 inhibitors include aplaviroc, vicriviroc, maraviroc, cenicriviroc, PRO-140, adaptavir (RAP-101), nifeviroc (TD-0232), anti-GP120/CD4 or CCR5 bispecific antibodies, B-07, MB-66, polypeptide C25P, TD-0680, and vMIP (Haimipu).

Examples of gp41 inhibitors include albuvirtide, enfuvirtide, BMS-986197, enfuvirtide biobetter, enfuvirtide biosimilar, HIV-1 fusion inhibitors (P26-Bapc), ITV-1, ITV-2, ITV-3, ITV-4, PIE-12 trimer and sifuvirtide.

Examples of CD4 attachment inhibitors include ibalizumab and CADA analogs

Examples of gp120 inhibitors include Radha-108 (receptol) 3B3-PE38, BanLec, bentonite-based nanomedicine, fostemsavir tromethamine, IQP-0831, and BMS-663068

Examples of CXCR4 inhibitors include plerixafor, ALT-1188, $N_{15}$ peptide, and vMIP (Haimipu).

HIV Maturation Inhibitors

Examples of HIV maturation inhibitors include BMS-955176 and GSK-2838232.

Latency Reversing Agents

Examples of latency reversing agents include histone deacetylase (HDAC) inhibitors, proteasome inhibitors such as velcade, protein kinase C (PKC) activators, Smyd2 inhibitors, BET-bromodomain 4 (BRD4) inhibitors, ionomycin, PMA, SAHA (suberanilohydroxamic acid, or suberoyl, anilide, and hydroxamic acid), AM-0015, ALT-803, NIZ-985, NKTR-255, IL-15 modulating antibodies, JQ1, disulfiram, amphotericin B, and ubiquitin inhibitors such as largazole analogs, and GSK-343.

Examples of HDAC inhibitors include romidepsin, vorinostat, and panobinostat.

Examples of PKC activators include indolactam, prostratin, ingenol B, and DAG-lactones.

Capsid Inhibitors

Examples of capsid inhibitors include capsid polymerization inhibitors or capsid disrupting compounds, HIV nucleocapsid p7 (NCp7) inhibitors such as azodicarbonamide, HIV p24 capsid protein inhibitors, AVI-621, AVI-101, AVI-201, AVI-301, and AVI-CAN1-15 series;

Immune-Based Therapies

Examples of immune-based therapies include toll-like receptors modulators such as tlr1, tlr2, tlr3, tlr4, tlr5, tlr6, tlr7, tlr8, tlr9, tlr10, tlr11, tlr12, and tlr13; programmed cell death protein 1 (Pd-1) modulators; programmed death-ligand 1 (Pd-L1) modulators; IL-15 agonists; DermaVir; interleukin-7; plaquenil (hydroxychloroquine); proleukin (aldesleukin, IL-2); interferon alfa; interferon alfa-2b; interferon alfa-n3; pegylated interferon alfa; interferon gamma; hydroxyurea; mycophenolate mofetil (MPA) and its ester derivative mycophenolate mofetil (MMF); ribavirin; rintatolimod, polymer polyethyleneimine (PEI); gepon; rintatolimod; IL-12; WF-10; VGV-1; MOR-22; BMS-936559; CYT-107, interleukin-15/Fc fusion protein, normferon, peginterferon alfa-2a, peginterferon alfa-2b, recombinant interleukin-15, RPI-MN, GS-9620, STING modulators, RIG-I modulators, NOD2 modulators, and IR-103.

Phosphatidylinositol 3-Kinase (PI3K) Inhibitors

Examples of PI3K inhibitors include idelalisib, alpelisib, buparlisib, CAI orotate, copanlisib, duvelisib, gedatolisib, neratinib, panulisib, perifosine, pictilisib, pilaralisib, puquitinib mesylate, rigosertib, rigosertib sodium, sonolisib, taselisib, AMG-319, AZD-8186, BAY-1082439, CLR-1401, CLR-457, CUDC-907, DS-7423, EN-3342, GSK-2126458, GSK-2269577, GSK-2636771, INCB-040093, LY-3023414, MLN-1117, PQR-309, RG-7666, RP-6530, RV-1729, SAR-245409, SAR-260301, SF-1126, TGR-1202, UCB-5857, VS-5584, XL-765, and ZSTK-474.

Alpha-4/Beta-7 Antagonists

Examples of Integrin alpha-4/beta-7 antagonists include PTG-100, TRK-170, abrilumab, etrolizumab, carotegrast methyl, and vedolizumab.

HIV Antibodies, Bispecific Antibodies, and "Antibody-Like" Therapeutic Proteins

Examples of HIV antibodies, bispecific antibodies, and "antibody-like" therapeutic proteins include DARTs®, DUOBODIES®, BITES®, XmAbs®, TandAbs®, Fab derivatives, bnABs (broadly neutralizing HIV-1 antibodies), BMS-936559, TMB-360, and those targeting HIV gp120 or gp41, antibody-Recruiting Molecules targeting HIV, anti-CD63 monoclonal antibodies, anti-GB virus C antibodies, anti-GP120/CD4, CCR5 bispecific antibodies, anti-nef single domain antibodies, anti-Rev antibody, camelid derived anti-CD18 antibodies, camelid-derived anti-ICAM-1 antibodies, DCVax-001, gp140 targeted antibodies, gp41-based HIV therapeutic antibodies, human recombinant mAbs (PGT-121), ibalizumab, Immuglo, MB-66

Examples of those targeting HIV in such a manner include bavituximab, UB-421, C2F5, 2G12, C4E10, C2F5+C2G12+C4E10, 8ANC195, 3BNC117, 3BNC60, 10-1074, PGT145, PGT121, PGT-151, PGT-133, MDX010 (ipilimumab), DH511, N6, VRC01 PGDM1400, A32, 7B2, 10E8, 10E8v4, CAP256-VRC26.25, DRVIA7, VRC-07-523, VRC-HIVMAB080-00-AB, VRC-HIVMAB060-00-AB, MGD-014 and VRC07. Example of HIV bispecific antibodies include MGD014.

Pharmacokinetic Enhancers

Examples of pharmacokinetic enhancers include cobicistat and ritonavir.

Additional Therapeutic Agents

Examples of additional therapeutic agents include the compounds disclosed in WO 2004/096286 (Gilead Sciences), WO 2006/015261 (Gilead Sciences), WO 2006/110157 (Gilead Sciences), WO 2012/003497 (Gilead Sciences), WO 2012/003498 (Gilead Sciences), WO 2012/145728 (Gilead Sciences), WO 2013/006738 (Gilead Sciences), WO 2013/159064 (Gilead Sciences), WO 2014/100323 (Gilead Sciences), US 2013/0165489 (University of Pennsylvania), US 2014/0221378 (Japan Tobacco), US 2014/0221380 (Japan Tobacco), WO 2009/062285 (Boehringer Ingelheim), WO 2010/130034 (Boehringer Ingelheim), WO 2013/006792 (Pharma Resources), US 20140221356 (Gilead Sciences), US 20100143301 (Gilead Sciences) and WO 2013/091096 (Boehringer Ingelheim).

HIV Vaccines

Examples of HIV vaccines include peptide vaccines, recombinant subunit protein vaccines, live vector vaccines, DNA vaccines, CD4-derived peptide vaccines, vaccine combinations, rgp120 (AIDSVAX), ALVAC HIV (vCP1521)/AIDSVAX B/E (gp120) (RV144), monomeric gp120 HIV-1 subtype C vaccine, Remune, ITV-1, Contre Vir, Ad5-ENVA-48, DCVax-001 (CDX-2401), Vacc-4x, Vacc-05, VAC-3S, multiclade DNA recombinant adenovirus-5 (rAd5), Pennvax-G, Pennvax-GP, HIV-TriMix-mRNA vaccine, HIV-LAMP-vax, Ad35, Ad35-GRIN, NAcGM3/VSSP ISA-51, poly-ICLC adjuvanted vaccines, TatImmune, GTU-multi-HIV (FIT-06), gp140[delta]V2.TV1+MF-59, rVSVIN HIV-1 gag vaccine, SeV-Gag vaccine, AT-20, DNK-4, ad35-Grin/ENV, TBC-M4, HIVAX, HIVAX-2, NYVAC-HIV-PT1, NYVAC-HIV-PT4, DNA-HIV-PT123, rAAV1-PG9DP, GOVX-B11, GOVX-B21, TV1-HIV-1, Ad-4 (Ad4-env Clade C+Ad4-mGag), EN41-UGR7C, EN41-FPA2, PreVaxTat, AE-H, MYM-V101, CombiHIVvac, ADVAX, MYM-V201, MVA-CMDR, DNA-Ad5 gag/pol/nef/nev (HVTN505), MVATG-17401, ETV-01, CDX-1401, rcAD26.MOS1.HIV-Env, Ad26.Mod.HIV vaccine, AGS-004, AVX-101, AVX-201, PEP-6409, SAV-001, ThV-01, TL-01, TUTI-16, VGX-3300, IHV-001, and virus-like particle vaccines such as pseudovirion vaccine, CombiVICH-vac, LFn-p24 B/C fusion vaccine, GTU-based DNA vaccine, HIV gag/pol/nef/env DNA vaccine, anti-TAT HIV vaccine, conjugate polypeptides vaccine, dendritic-cell vaccines, gag-based DNA vaccine, GI-2010, gp41 HIV-1 vaccine, HIV vaccine (PIKA adjuvant), I i-key/MHC class II epitope hybrid peptide vaccines, ITV-2, ITV-3, ITV-4, LIPO-5, multiclade Env vaccine, MVA vaccine, Pennvax-GP, pp71-deficient HCMV vector HIV gag vaccine, recombinant peptide vaccine (HIV infection), NCI, rgp160 HIV vaccine, RNActive HIV vaccine, SCB-703, Tat Oyi vaccine, TBC-M4, therapeutic HIV vaccine, UBI HIV gp120, Vacc-4x+romidepsin, variant gp120 polypeptide vaccine, rAd5 gag-pol env A/B/C vaccine, DNA.HTI and MVA.HTI.

HIV Combination Therapy

In a particular embodiment, a compound disclosed herein, or a pharmaceutically acceptable salt thereof, is combined with one, two, three, four or more additional therapeutic agents selected from ATRIPLA® (efavirenz, tenofovir disoproxil fumarate, and emtricitabine); COMPLERA® (EVIPLERA®; rilpivirine, tenofovir disoproxil fumarate, and emtricitabine); STRIBILD® (elvitegravir, cobicistat, tenofovir disoproxil fumarate, and emtricitabine); TRUVADA® (tenofovir disoproxil fumarate and emtricitabine; TDF+FTC); DESCOVY® (tenofovir alafenamide and emtricitabine); ODEFSEY® (tenofovir alafenamide, emtricitabine, and rilpivirine); GENVOYA® (tenofovir alafenamide, emtricitabine, cobicistat, and elvitegravir); adefovir; adefovir dipivoxil; cobicistat; emtricitabine; tenofovir; tenofovir disoproxil; tenofovir disoproxil fumarate; tenofovir alafenamide; tenofovir alafenamide hemifumarate; TRIUIMEQ® (dolutegravir, abacavir, and lamivudine); dolutegravir, abacavir sulfate, and lamivudine; raltegravir; raltegravir and lamivudine; maraviroc; enfuvirtide; ALUVIA® (KALETRA®; lopinavir and ritonavir); COMBIVIR® (zidovudine and lamivudine; AZT+3TC); EPZICOM® (LIVEXA®;

abacavir sulfate and lamivudine; ABC+3TC); TRIZIVIR® (abacavir sulfate, zidovudine, and lamivudine; ABC+AZT+3TC); rilpivirine; rilpivirine hydrochloride; atazanavir sulfate and cobicistat; atazanavir and cobicistat; darunavir and cobicistat; atazanavir; atazanavir sulfate; dolutegravir; elvitegravir; ritonavir; atazanavir sulfate and ritonavir; darunavir; lamivudine; prolastin; fosamprenavir; fosamprenavir calcium efavirenz; etravirine; nelfinavir; nelfinavir mesylate; interferon; didanosine; stavudine; indinavir; indinavir sulfate; tenofovir and lamivudine; zidovudine; nevirapine; saquinavir; saquinavir mesylate; aldesleukin; zalcitabine; tipranavir; amprenavir; delavirdine; delavirdine mesylate; Radha-108 (receptol); lamivudine and tenofovir disoproxil fumarate; efavirenz, lamivudine, and tenofovir disoproxil fumarate; phosphazid; lamivudine, nevirapine, and zidovudine; abacavir; and abacavir sulfate.

It will be appreciated by one of skill in the art that the additional therapeutic agents listed above may be included in more than one of the classes listed above. The particular classes are not intended to limit the functionality of those compounds listed in those classes.

In a specific embodiment, a compound disclosed herein, or a pharmaceutically acceptable salt thereof, is combined with an HIV nucleoside or nucleotide inhibitor of reverse transcriptase and an HIV non-nucleoside inhibitor of reverse transcriptase. In another specific embodiment, a compound disclosed herein, or a pharmaceutically acceptable salt thereof, is combined with an HIV nucleoside or nucleotide inhibitor of reverse transcriptase, and an HIV protease inhibiting compound. In an additional embodiment, a compound disclosed herein, or a pharmaceutically acceptable salt thereof, is combined with an HIV nucleoside or nucleotide inhibitor of reverse transcriptase, an HIV non-nucleoside inhibitor of reverse transcriptase, and a pharmacokinetic enhancer. In certain embodiments, a compound disclosed herein, or a pharmaceutically acceptable salt thereof, is combined with at least one HIV nucleoside inhibitor of reverse transcriptase, an integrase inhibitor, and a pharmacokinetic enhancer. In another embodiment, a compound disclosed herein, or a pharmaceutically acceptable salt thereof, is combined with two HIV nucleoside or nucleotide inhibitors of reverse transcriptase.

In a particular embodiment, a compound disclosed herein, or a pharmaceutically acceptable salt thereof, is combined with abacavir sulfate, bictegravir, tenofovir, tenofovir disoproxil, tenofovir disoproxil fumarate, tenofovir disoproxil hemifumarate, tenofovir alafenamide, or tenofovir alafenamide hemifumarate.

In a particular embodiment, a compound disclosed herein, or a pharmaceutically acceptable salt thereof, is combined with tenofovir, tenofovir disoproxil, tenofovir disoproxil fumarate, tenofovir alafenamide, or tenofovir alafenamide hemifumarate.

In a particular embodiment, a compound disclosed herein, or a pharmaceutically acceptable salt thereof, is combined with a first additional therapeutic agent selected from the group consisting of abacavir sulfate, bictegravir, tenofovir, tenofovir disoproxil, tenofovir disoproxil fumarate, tenofovir alafenamide, and tenofovir alafenamide hemifumarate, and a second additional therapeutic agent selected from the group consisting of emtricitabine and lamivudine.

In a particular embodiment, a compound disclosed herein, or a pharmaceutically acceptable salt thereof, is combined with a first additional therapeutic agent selected from the group consisting of tenofovir, tenofovir disoproxil, tenofovir disoproxil fumarate, tenofovir alafenamide, and tenofovir alafenamide hemifumarate, and a second additional therapeutic agent, wherein the second additional therapeutic agent is emtricitabine.

A compound as disclosed herein (e.g., any compound of Formula (I)) may be combined with one or more additional therapeutic agents in any dosage amount of the compound of Formula (I) (e.g., from 1 mg to 1000 mg of compound).

In certain embodiments, a compound disclosed herein, or a pharmaceutically acceptable salt thereof, is combined with 5-30 mg tenofovir alafenamide, in the form of tenofovir alafenamide fumarate, tenofovir alafenamide hemifumarate, or tenofovir alafenamide, or any salt of solvate form of tenofovir alafenamide. In certain embodiments, a compound disclosed herein, or a pharmaceutically acceptable salt thereof, is combined with 5-30 mg tenofovir alafenamide fumarate, tenofovir alafenamide hemifumarate, or tenofovir alafenamide, and 200 mg emtricitabine. In certain embodiments, a compound disclosed herein, or a pharmaceutically acceptable salt thereof, is combined with 5-10, 5-15, 5-20, 5-25, 25-30, 20-30, 15-30, or 10-30 mg tenofovir alafenamide fumarate, tenofovir alafenamide hemifumarate, or tenofovir alafenamide, and 200 mg emtricitabine. In certain embodiments, a compound disclosed herein, or a pharmaceutically acceptable salt thereof, is combined with 10 mg tenofovir alafenamide fumarate, tenofovir alafenamide hemifumarate, or tenofovir alafenamide, and 200 mg emtricitabine. In certain embodiments, a compound disclosed herein, or a pharmaceutically acceptable salt thereof, is combined with 25 mg tenofovir alafenamide fumarate, tenofovir alafenamide hemifumarate, or tenofovir alafenamide, and 200 mg emtricitabine. A compound as disclosed herein (e.g., a compound of formula (I)) may be combined with the agents provided herein in any dosage amount of the compound (e.g., from 1 mg to 1000 mg of compound) the same as if each combination of dosages were specifically and individually listed.

In certain embodiments, a compound disclosed herein, or a pharmaceutically acceptable salt thereof, is combined with 200-400 mg tenofovir disoproxil fumarate, tenofovir disoproxil hemifumarate, or tenofovir disoproxil, and 200 mg emtricitabine. In certain embodiments, a compound disclosed herein, or a pharmaceutically acceptable salt thereof, is combined with 200-250, 200-300, 200-350, 250-350, 250-400, 350-400, 300-400, or 250-400 mg tenofovir disoproxil fumarate, tenofovir disoproxil hemifumarate, or tenofovir disoproxil, and 200 mg emtricitabine. In certain embodiments, a compound disclosed herein, or a pharmaceutically acceptable salt thereof, is combined with 300 mg tenofovir disoproxil fumarate, tenofovir disoproxil hemifumarate, or tenofovir disoproxil, and 200 mg emtricitabine. A compound as disclosed herein (e.g., a compound of formula (I)) may be combined with the agents provided herein in any dosage amount of the compound (e.g., from 1 mg to 1000 mg of compound) the same as if each combination of dosages were specifically and individually listed.

In certain embodiments, a compound disclosed herein, or a pharmaceutically acceptable salt thereof, is combined with a HIV nucleoside or nucleotide inhibitor and an integrase inhibitor. In certain embodiments, a compound disclosed herein, or a pharmaceutically acceptable salt thereof, is combined with GS-9131 and bictegravir.

In one embodiment, kits comprising a compound disclosed herein, or a pharmaceutically acceptable salt thereof, in combination with one or more (e.g., one, two, three, one or two, or one to three) additional therapeutic agents are provided.

Certain embodiments of the methods disclosed herein exclude the administration of a pharmacokinetic enhancer. For example, in certain methods disclosed herein, the subject is not administered a pharmacokinetic enhancer, such as cobicistat or ritonavir, during the treatment with a compound disclosed herein, or a pharmaceutically acceptable salt thereof. Thus, in certain embodiments, a method of treating or preventing a human immunodeficiency virus (HIV) infection is provided, comprising administering a therapeutically effective amount of a compound disclosed herein, or a pharmaceutically acceptable salt thereof, to a subject in need thereof, wherein the treatment does not comprise administration of a pharmacokinetic enhancer. In certain embodiments, a method of treating or preventing a human immunodeficiency virus (HIV) infection is provided, comprising administering a therapeutically effective amount of a compound disclosed herein, or a pharmaceutically acceptable salt thereof, once daily to a subject in need thereof, wherein the treatment does not comprise administration of a pharmacokinetic enhancer.

Gene Therapy and Cell Therapy

Gene Therapy and Cell Therapy including the genetic modification to silence a gene; genetic approaches to directly kill the infected cells; the infusion of immune cells designed to replace most of the patient's own immune system to enhance the immune response to infected cells, or activate the patient's own immune system to kill infected cells, or find and kill the infected cells; genetic approaches to modify cellular activity to further alter endogenous immune responsiveness against the infection.

Examples of dendritic cell therapy include AGS-004.

Gene Editors

The genome editing system is selected from the group consisting of: a CRISPR/Cas9 system, a zinc finger nuclease system, a TALEN system, a homing endonucleases system, and a meganuclease system.

Examples of HIV targeting CRISPR/Cas9 systems include EBT101.

CAR-T Cell Therapy

A population of immune effector cells engineered to express a chimeric antigen receptor (CAR), wherein the CAR comprises an HIV antigen-binding domain. The HIV antigen include an HIV envelope protein or a portion thereof, gp120 or a portion thereof, a CD4 binding site on gp120, the CD4-induced binding site on gp120, N glycan on gp120, the V2 of gp120, the membrane proximal region on gp41. The immune effector cell is a T cell or an NK cell. In some embodiments, the T cell is a CD4+ T cell, a CD8+ T cell, or a combination thereof.

Examples of HIV CAR-T include VC-CAR-T.

TCR-T Cell Therapy

TCR-T cells are engineered to target HIV derived peptides present on the surface of virus-infected cells.

EXAMPLES

Methods for preparing the novel compounds described herein will be apparent to those of skill in the art with suitable procedures being described, for example, in the reaction schemes and examples below.

Section 1 provides exemplary synthetic schemes for assembling compounds of Formula I, preparation of intermediates as used herein, example syntheses and compounds. Section 2 shows biological activity.

1. Synthetic Examples

Preparation of Intermediates

Preparation of Isopropyl (R)-2-amino-2-(2-fluoro-4-methoxyphenyl)-4,4-dimethylpentanoate (Method I)

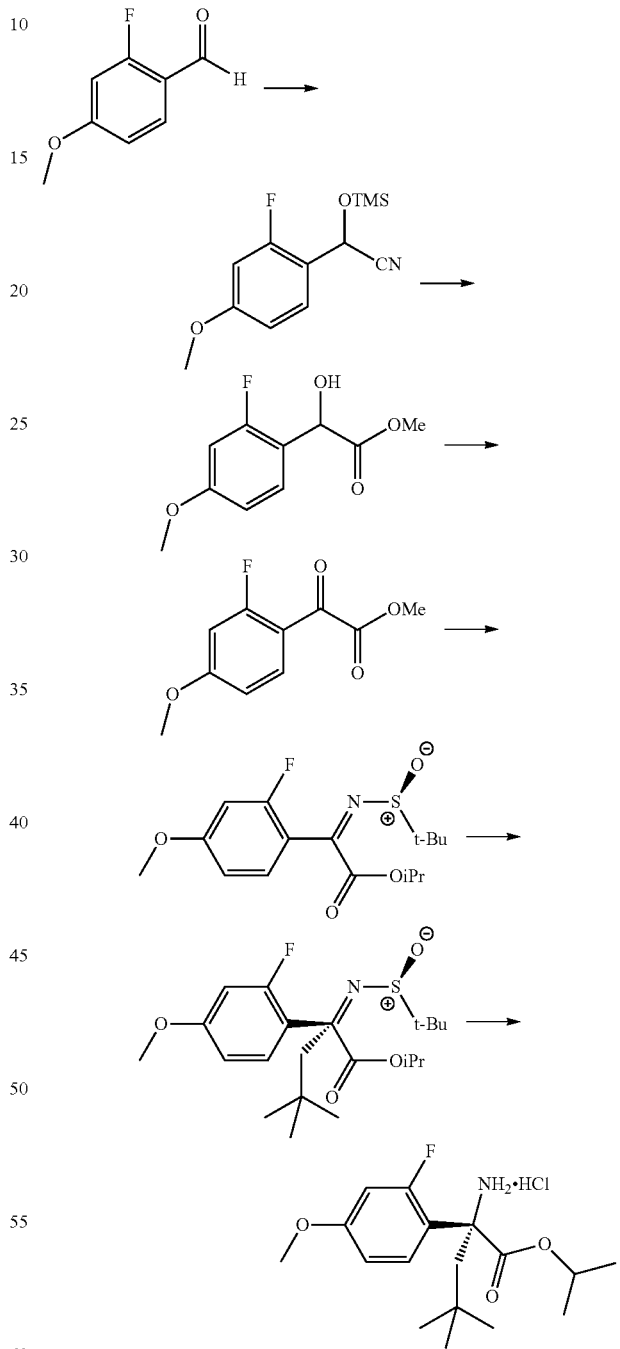

Preparation of 2-(2-fluoro-4-methoxyphenyl)-2-((trimethylsilyl)oxy)acetonitrile: TMSCN (486 mL, 3.9 mol) was added to a stirred solution of 2-fluoro-4-methoxybenzaldehyde (200 g, 1.3 mol) in DCM (2000 mL) at 0° C. under argon atmosphere. Then ZnI$_2$ (6.2 kg, 1.9 mol) was added portion wise to the reaction mixture, and stirred at rt for 3 h.

The reaction mixture was then diluted with DCM and washed with water. The organic layer was separated, dried over Na₂SO₄, filtered, and concentrated. The residue was used for the next step without further purification.

Preparation of methyl 2-(2-fluoro-4-methoxyphenyl)-2-hydroxyacetate: TMSCl (303 mL, 2.4 mol) was added to a stirred solution of 2-(2-fluoro-4-methoxyphenyl)-2-((trimethylsilyl)oxy)acetonitrile (300 g, 1.2 mol) in MeOH at 0° C. and the resulting reaction mixture was stirred at room temperature for 16 h. The mixture was then diluted with ethyl acetate and washed with water. The organic layer was separated and dried over anhydrous Na₂SO₄, filtered, and concentrated. The residue was purified by silica gel column chromatography, elution gradient 5-10% EtOAc in hexanes, to give the product.

Preparation of methyl 2-(2-fluoro-4-methoxyphenyl)-2-oxoacetate: Dess-Martin periodinane (387 g, 0.91 mol) was added to a solution of methyl 2-(2-fluoro-4-methoxyphenyl)-2-hydroxyacetate (150 g, 0.7 mol) in DCM (1500 mL) at 0° C. and stirred at rt for 1 h. The reaction mixture was then diluted with ethyl acetate, and washed with water and then with NaHCO₃ solution. The organic layer was separated, dried over Na₂SO₄, filtered, and concentrated. The residue was purified by silica gel column chromatography, elution gradient 5-10% EtOAc in hexanes, to give the compound.

Preparation of isopropyl (S)-2-((tert-butylsulfinyl)imino)-2-(2-fluoro-4-methoxyphenyl)acetate: Ti(Oi-Pr)₄ (150 mL, 0.49 mol) was added dropwise to a stirred solution of methyl 2-(2-fluoro-4-methoxyphenyl)-2-oxoacetate (80 g, 0.38 mol) and (S)-(−)-2-methyl-2-propanesulfinamide (59.4 g, 0.49 mol) in THF (1200 mL). The mixture was then refluxed for 16 h. After cooling to rt, the reaction mixture was diluted with EtOAc, and washed with water and then with brine. The organic layer was separated, dried over Na₂SO₄, filtered, and concentrated. The residue was purified through silica gel, elution gradient 10-15% EtOAc in hexanes, to give the product.

Preparation of isopropyl (R)-2-(((S)-tert-butylsulfinyl)amino)-2-(2-fluoro-4-methoxyphenyl)-4,4-dimethylpentanoate: neo-Pentylmagnesium bromide was prepared by the following procedure: neo-pentyl bromide (59 mL, 0.39 mol) was added dropwise to magnesium turnings (12.7 g, 0.52 mol; activated by washed with 1M HNO₃, followed by washed with H₂O, acetone, and dried for 5 h) in ether (900 mL) at rt and stirred for 15 min. The reaction mixture was heated to 40° C. for 2 h. The reaction mixture was cooled to rt and this magnesium reagent was ready for use. The magnesium reagent was added dropwise to a solution of isopropyl (S)-2-((tert-butyl sulfinyl)imino)-2-(2-fluoro-4-methoxyphenyl)acetate (45 g, 0.13 mol) in a mixture of DCM (200 mL) and THF (500 mL) at −78° C. and the resulting reaction mixture was stirred at −78° C. for 3 h. The reaction mixture was quenched with saturated aq NH₄Cl solution, diluted with EtOAc, and washed with water. The organic layer was separated, dried over Na₂SO₄, filtered, and concentrated. The residue was purified through silica gel column chromatography, elution gradient 40-80% EtOAc in hexanes, to give the product.

Preparation of isopropyl (R)-2-amino-2-(2-fluoro-4-methoxyphenyl)-4,4-dimethylpentanoate hydrochloride: To a solution of isopropyl (R)-2-(((S)-tert-butylsulfinyl)amino)-2-(2-fluoro-4-methoxyphenyl)-4,4-dimethylpentanoate (34 g, 0.081 mol) in DCM (350 mL) was added hydrogen chloride in 1,4-dioxane (4M, 150 mL) at 0° C. and stirred at rt for 1 h. The solvent was removed by distillation. The residue was triturated with hexanes and dried to give the product.

Unless otherwise stated, other α,α-disubstituted amino acid esters used in preparation of examples were prepared by Method I.

Preparation of Isopropyl 2-amino-2-(4-bromophenyl)-3-((S)-2,2-difluoro-1-methylcyclopropyl)propanoate and isopropyl 2-amino-2-(4-bromophenyl)-3-((R)-2,2-difluoro-1-methylcyclopropyl)propanoate

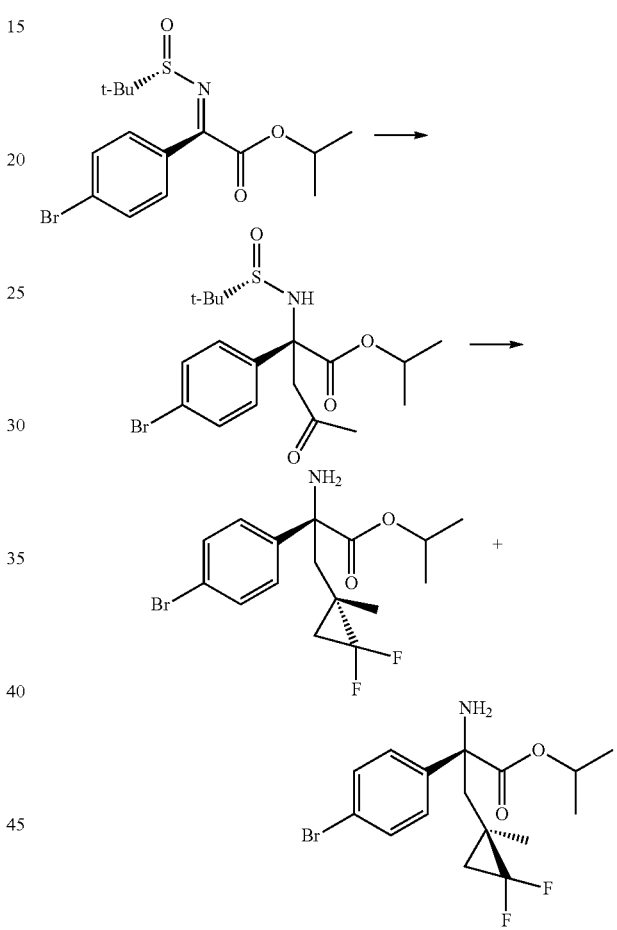

Preparation of isopropyl 2-(4-bromophenyl)-2-(((S)-tert-butylsulfinyl)amino)-4-methylpent-4-enoate: To a solution of isopropyl (S)-2-(4-bromophenyl)-2-((tert-butylsulfinyl)imino)acetate (1.8 g, 5 mmol) in DCM (100 mL) at −78° C. was added 2-methylallylmagnesium chloride solution in tetrahydrofuran (0.5 M, 19 mL) dropwise, and stirred at −78° C. for 15 min. Then saturated ammonium chloride was added to the mixture and the resulting mixture was allowed to reach rt. The organic phase was concentrated and the residue was purified by silica gel column chromatography (1-100% gradient EtOAc/hexanes) to give the product.

Preparation of isopropyl 2-amino-2-(4-bromophenyl)-3-((S)-2,2-difluoro-1-methylcyclopropyl)propanoate and isopropyl 2-amino-2-(4-bromophenyl)-3-((R)-2,2-difluoro-1-methylcyclopropyl)propanoate: To a solution of isopropyl 2-(4-bromophenyl)-2-(((S)-tert-butylsulfinyl)amino)-4-methylpent-4-enoate (332 mg, 0.071 mmol) in toluene (2 mL) was added tetrabutylammonium bromide (7 mg, 0.0023 mmol). Then to the mixture was added trimethyl(bromodifluoromethyl)silane (0.24 mL, 2 mmol). The reaction mixture was heated at 100° C. overnight. After cooling to rt, the crude mixture was purified by silica gel column chromatography (DCM/MeOH) and further purified by reverse phase HPLC (acetonitrile/water, both containing 0.1% TFA) to give the products isopropyl 2-amino-2-(4-bromophenyl)-3-((S)-2,2-difluoro-1-methylcyclopropyl)propanoate (53 mg, 18%) and isopropyl 2-amino-2-(4-bromophenyl)-3-((R)-2,2-difluoro-1-methylcyclopropyl)propanoate (41 mg, 14%). The structure of the two isomers is randomly assigned.

Preparation of Isopropyl 2-amino-2-(4-bromophenyl)-3-(1-methylcyclopropyl)propanoate

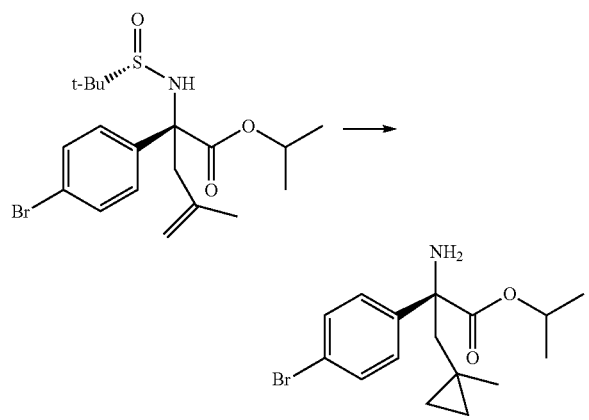

Preparation of isopropyl 2-amino-2-(4-bromophenyl)-3-(1-methylcyclopropyl)propanoate: The reaction mixture of isopropyl 2-(4-bromophenyl)-2-((S)-tert-butylsulfinyl)amino)-4-methylpent-4-enoate (0.2 g, 0.046 mmol), trifluoroacetic acid (0.28 mL, 4 mmol), diethylzinc in hexane (1.0M, 4 mL) and diiodomethane (0.3 mL, 4 mmol) in DCM (10 mL) was stirred at rt overnight. The reaction mixture was washed with water and extracted with EtOAc. The organic phase was dried over magnesium sulfate, filtered and concentrated. The residue was purified by silica gel column chromatography to give the product.

Preparation of Isopropyl (R)-2-(3-((benzyloxy)carbonyl)thioureido)-2-(4-bromophenyl)-4-fluoro-4-methylpentanoate

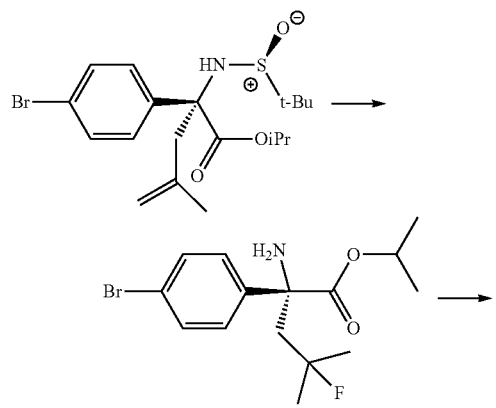

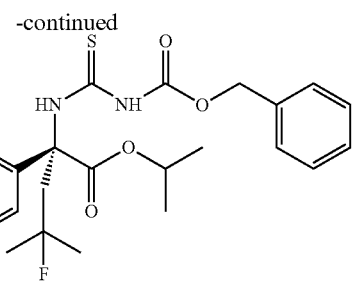

Preparation of isopropyl (R)-2-amino-2-(4-bromophenyl)-4-fluoro-4-methylpentanoate: A polypropylene bottle was charged with neat 60-70% HF-urea (10 mL) and cooled to 0° C. Then a solution of isopropyl (R)-2-(4-bromophenyl)-2-((S)-tert-butylsulfinyl)amino)-4-methylpent-4-enoate (1.20 g, 0.004 mol) in DCM (10 mL) was added over 5 min. The reaction was allowed to warm to 23° C. overnight. A separate polypropylene bottle was charged with 50% w/v aq KOH (50 mL) and DCM (50 mL) and then cooled to 0° C. Using a polypropylene pipette, the reaction mixture was added slowly over 5 min to the biphasic KOH system. The final pH was ~7.5. Additional 50% w/v aq KOH (10 mL) and DCM (100 mL) were added. The organic phase was collected and the aqueous layer was extracted with DCM (50 mL). The combined organics were concentrated to a total volume of ~60 mL and directly used for the next step.

Preparation of isopropyl (R)-2-(3-((benzyloxy)carbonyl)thioureido)-2-(4-bromophenyl)-4-fluoro-4-methylpentanoate: Saturated aq NaHCO$_3$ (60 mL) was added to the organic solution of isopropyl (R)-2-amino-2-(4-bromophenyl)-4-fluoro-4-methylpentanoate in DCM (60 mL) obtained from the previous step. A solution of O-benzyl carbonisothiocyanatidate (1.25 g, 6.48 mmol)) in DCM (10 mL) was then added at rt with rapid stirring. The two layers were separated and then aqueous layer was extracted with DCM (20 mL) for 16 h. The combined organic layers were dried (Na$_2$SO$_4$), filtered, and concentrated. The residue was purified by silica gel chromatography (0-100% gradient EtOAc/hexanes) to give the product.

Preparation of Isopropyl (R)-2-amino-2-(4-(2-cyclopropyl-2H-1,2,3-triazol-4-yl)phenyl)-5,5,5-trifluoro-4,4-dimethylpentanoate (Method II)

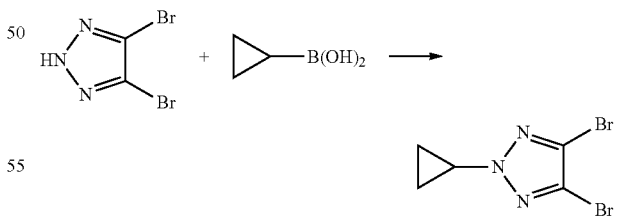

Preparation of 4,5-dibromo-2-cyclopropyl-2H-1,2,3-triazole: To a 20-L round-bottom flask were placed 4,5-dibromo-2H-1,2,3-triazole (500 g, 2.20 mol), DCE (5 L), 2-methylfuran (5 L), cyclopropylboronic acid (379 g, 4.41 mol), Cu(OAc)$_2$ (401 g, 2.20 mol), 2,2-bipyridyl (344 g, 2.21 mol) and sodium carbonate (467 g, 4.41 mol). The mixture was stirred overnight at 80° C. After the reaction was cooled to room temperature, the mixture was filtered. The filtrate was concentrated under vacuum, dissolved in 5

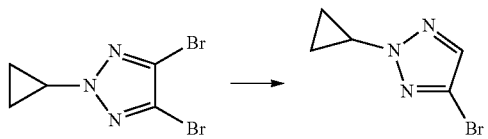 [SMILES: Brc1nn(C2CC2)nc1Br ; Brc1cnn(C2CC2)n1]

Preparation of 4-bromo-2-cyclopropyl-2H-1,2,3-triazole: To a 3000-mL 4-necked round-bottom flask was added a solution of 4,5-dibromo-2-cyclopropyl-2H-1,2,3-triazole (100 g, 375 mmol) in tetrahydrofuran (1000 mL) followed by addition of n-BuLi (2.5 M, 165 mL) dropwise with stirring at −78° C. and stirred for 30 min at the same temperature. The reaction was then quenched by the addition of 500 mL of water. The mixture was extracted with 2×1000 mL of EtOAc and the organic layers were combined, washed with 1×500 mL of brine, dried over anhydrous $Na_2SO_4$, and concentrated under vacuum. The residue was applied onto a silica gel column eluted with ethyl acetate/PE (1:100-1:30) to afford the product. $^1$H NMR: (300 MHz, $CDCl_3$): δ 7.50 (s, 1H), 3.97 (tt, J=7.5, 3.8 Hz, 1H), 1.38-1.27 (m, 2H), 1.13-1.02 (m, 2H).

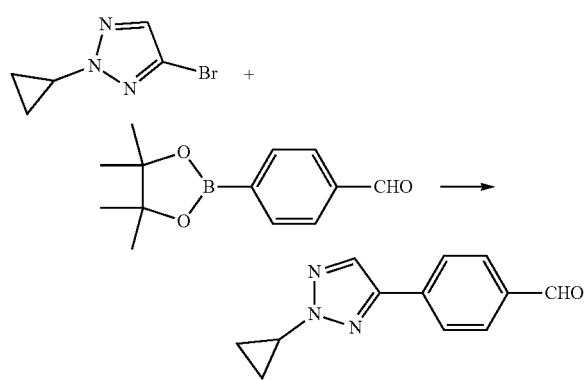

Preparation of 4-(2-cyclopropyl-2H-1,2,3-triazol-4-yl)benzaldehyde: To a mixture of 4-bromo-2-cyclopropyl-2H-1,2,3-triazole (38 g, 202 mmol) and 4-(4,4,5,5-tetramethyl-1,3,2-dioxaborolan-2-yl)benzaldehyde (56 g, 242 mmol) in ACN (190 mL) and $H_2O$ (190 mL) were added $K_3PO_4$ (107 g, 505 mmol) and $Pd(PPh_3)_4$ (11.6 g, 10.1 mmol) and stirred at 85° C. for 12 h.

After cooling, the reaction mixture was filtered and extracted with EtOAc (300 mL×2). The organic extracts were combined, dried over $Na_2SO_4$ and concentrated. The residue was purified by silica gel chromatography column eluted with petroleum ether/ethyl acetate=1/0~50/1 to obtain the product.

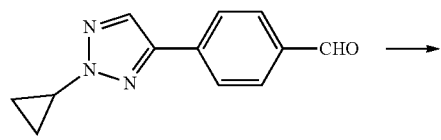

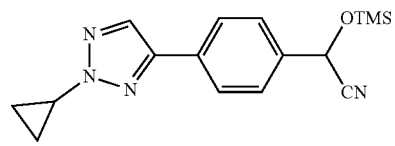

Preparation of 2-(4-(2-cyclopropyl-2H-1,2,3-triazol-4-yl)phenyl)-2-((trimethylsilyl)oxy)acetonitrile: To a solution of 4-(2-cyclopropyl-2H-1,2,3-triazol-4-yl)benzaldehyde (37 g, 17 mmol) and DABCO (580 mg, 5.2 mmol, 0.57 mL) in DCM (300 mL) was added TMSCN (51 g, 520 mmol, 65 mL) and stirred at 25° C. for 4 h. The mixture was treated with water (200 mL) and extracted with EtOAc (200 mL×2). The extracts were combined, dried over $Na_2SO_4$, filtered and concentrated to obtain the product (crude).

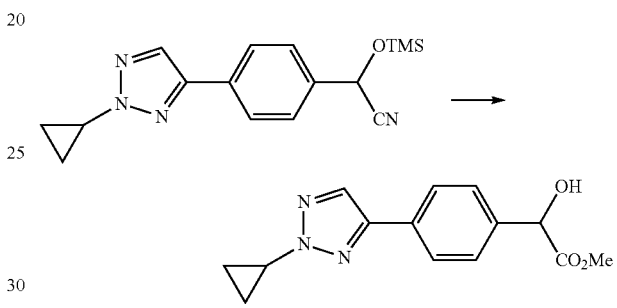

Preparation of methyl 2-(4-(2-cyclopropyl-2H-1,2,3-triazol-4-yl)phenyl)-2-hydroxyacetate: A mixture of 2-(4-(2-cyclopropyl-2H-1,2,3-triazol-4-yl)phenyl)-2-((trimethylsilyl)oxy)acetonitrile (60 g, 19 mmol) and HCl/MeOH (4 M, 600 mL) was stirred at 80° C. for 2 h. After cooling, the mixture was neutralized with aqueous $NaHCO_3$ until pH=~3-4. The resulting solid was filtered and the filter cake was dried. The dried solid was triturated with petroleum ether (100 mL) to afford the product.

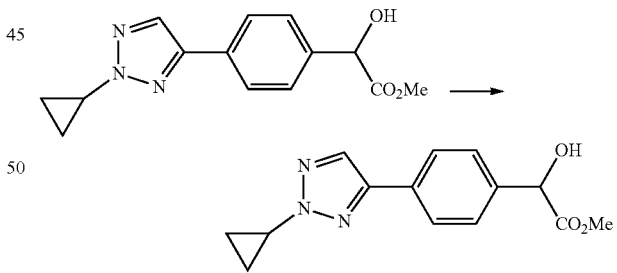

Preparation of methyl 2-(4-(2-cyclopropyl-2H-1,2,3-triazol-4-yl)phenyl)-2-oxoacetate: To a solution of methyl 2-(4-(2-cyclopropyl-2H-1,2,3-triazol-4-yl)phenyl)-2-hydroxyacetate (35 g, 128 mmol) in DCM (250 mL) was added Dess-Martin periodinane (108 g, 256 mmol, 79 mL), and stirred at 25° C. for 1 h. The mixture was filtered and the filtrate was poured into aq.$NaHCO_3$ (500 mL), and extracted with EtOAc (300 mL×2). The organic extract was dried over $Na_2SO_4$, concentrated and purified by silica gel chromatography column, eluted with petroleum ether/ethyl acetate (1/0~10/1) to afford the product.

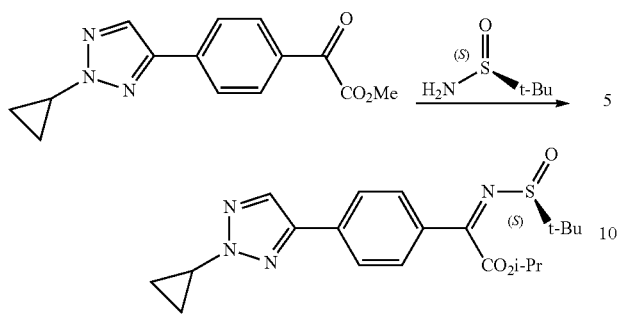

Preparation of isopropyl (S)-2-((tert-butylsulfinyl)imino)-2-(4-(2-cyclopropyl-2H-1,2,3-triazol-4-yl)phenyl)acetate:
To a mixture of methyl 2-(4-(2-cyclopropyl-2H-1,2,3-triazol-4-yl)phenyl)-2-hydroxyacetate (23 g, 84.8 mmol) and (S)-2-methylpropane-2-sulfinamide (12.3 g, 101 mmol) in n-heptane (160 mL) was added Ti(Oi-Pr)$_4$ (36 g, 127 mmol, 37 mL) and stirred at 80° C. for 12 h under N$_2$. After cooling, the reaction mixture was treated with water (150 mL) and stirred for 10 mins. The mixture was filtered through diatomite and the filter cake was washed with n-heptane (100 mL). The two phases were separated and the aqueous layer was further extracted with EtOAc (100 mL). The organic extracts were dried over Na$_2$SO$_4$, concentrated, purified by silica gel column chromatography, eluted with petroleum ether/ethyl acetate (1/0~50/1), to afford the product.

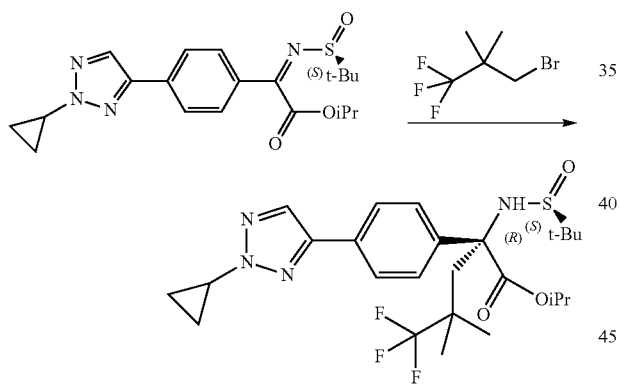

Preparation of isopropyl (R)-2-(((S)-tert-butylsulfinyl)amino)-2-(4-(2-cyclopropyl-2H-1,2,3-triazol-4-yl)phenyl)-5,5,5-trifluoro-4,4-dimethylpentanoate: To Mg turnings (4.41 g, 181 mmol) in THF (150 mL) at 25° C. was added BrCH$_2$CH$_2$Br (5.68 g, 30 mmol, 2.28 mL). Then, 3-bromo-1,1,1-trifluoro-2,2-dimethylpropane (31 g, 151 mmol) was added at 45° C. and stirred for 1 h at the same temperature. After cooling to rt, the mixture was used directly for the next reaction as Grignard reagent. This reagent was dropwise added to a solution of isopropyl (S)-2-((tert-butylsulfinyl)imino)-2-(4-(2-cyclopropyl-2H-1,2,3-triazol-4-yl)phenyl)acetate (24 g, 59 mmol) in DCM (150 mL) at −78° C. and then stirred at 25° C. for 12 h. The reaction was quenched aq. NH$_4$Cl (100 mL) and the mixture extracted with EtOAc (200 mL, 100 mL). The extract was dried over Na$_2$SO$_4$, concentrated and purified by silica gel column chromatography, eluted with petroleum ether/ethyl acetate (1/0~50/1), to afford the product.

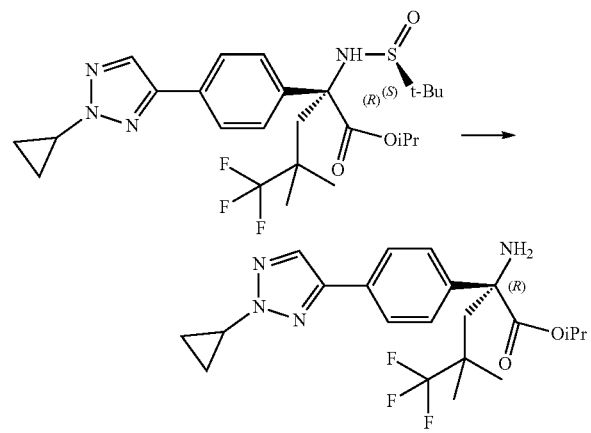

Preparation of isopropyl (R)-2-amino-2-(4-(2-cyclopropyl-2H-1,2,3-triazol-4-yl)phenyl)-5,5,5-trifluoro-4,4-dimethylpentanoate: A mixture of isopropyl (R)-2-(((S)-tert-butylsulfinyl)amino)-2-(4-(2-cyclopropyl-2H-1,2,3-triazol-4-yl)phenyl)-5,5,5-trifluoro-4,4-dimethylpentanoate (21 g, 39.7 mmol) and HCl/EtOAc (4 M, 200 mL) was stirred at 25° C. for 1 h. The reaction mixture was poured into aq. NaHCO$_3$ (250 mL), extracted with EtOAc (150 mL, 100 mL), dried over Na$_2$SO$_4$ and concentrated. The residue was purified by silica gel chromatography column, eluted with petroleum ether/ethyl acetate (1/0~50/1), to afford the product (10 g, 59%) as a white solid. MS cal.: 424.2, [M+1]+ =425.2; 1H NMR: (MeOD-d4, 400 MHz) δ 7.96 (s, 1H), 7.80 (d, J=8.4 Hz, 2H), 7.63 (d, J=8.8 Hz, 2H), 4.99-4.92 (m, 1H), 4.09-4.04 (m, 1H), 2.65 (d, J=14.8 Hz, 1H), 2.22 (d, J=14.8 Hz, 1H), 1.32-1.31 (m, 2H), 1.25 (s, 3H), 1.19-1.08 (m, 11H).

Preparation of Isopropyl (R)-2-(3-((benzyloxy)carbonyl)thioureido)-2-(4-bromophenyl)-4,4-dimethylpentanoate

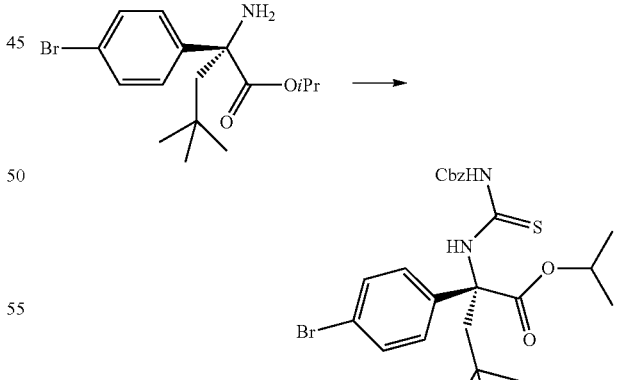

Preparation of isopropyl (R)-2-(3-((benzyloxy)carbonyl)thioureido)-2-(4-bromophenyl)-4,4-dimethylpentanoate: To a biphasic solution of isopropyl (R)-2-amino-2-(4-bromophenyl)-4,4-dimethylpentanoate (10 g, 28 mmol) in EtOAc (100 mL) and saturated NaHCO$_3$ solution (100 mL) was added O-benzyl carbonisothiocyanatidate (13.4 g, 70 mmol). The reaction mixture was stirred at rt for 2 h. The reaction mixture was diluted with EtOAc, and washed with water and then with brine. The organic phase was dried over Na₂SO₄, filtered, and concentrated. The residue was purified by silica gel column chromatography (EtOAc/hexanes) to give the product.

Preparation of Isopropyl (R)-2-amino-4,4-dimethyl-2-(4-(4,4,5,5-tetramethyl-1,3,2-dioxaborolan-2-yl)phenyl)pentanoate

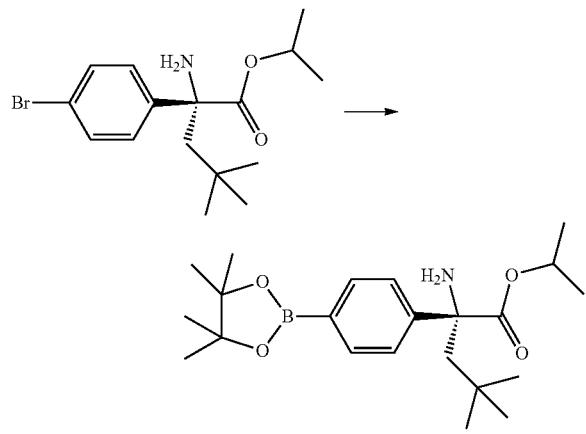

Preparation of isopropyl (R)-2-amino-4,4-dimethyl-2-(4-(4,4,5,5-tetramethyl-1,3,2-dioxaborolan-2-yl)phenyl)pentanoate: To a solution of isopropyl (R)-2-amino-2-(4-bromophenyl)-4,4-dimethylpentanoate (850 mg, 2.5 mmol) in 1,4-dioxane (8 mL) were added bis (pinacolato) diboron (1.26 g, 4.97 mmol), potassium acetate (731 mg, 7.4 mmol), palladium acetate (83.6 mg, 0.373 mmol) and 2-(dicyclohexylphosphino)-2',4',6'-triisopropylbiphenyl (XPhOS) (236 mg, 0.5 mmol). The reaction mixture was flushed with nitrogen for 10 min and then heated to 100° C. for 1.5 h. The reaction mixture was treated with water, extracted with EtOAc, dried over MgSO₄, filtered, concentrated, and purified by silica gel chromatography (EtOAc/hexanes) to give the product.

Preparation of Isopropyl (R)-2-(3-((benzyloxy)carbonyl)thioureido)-2-(4-(1-(difluoromethyl)-1H-pyrazol-4-yl)phenyl)-4,4-dimethylpentanoate (Method III)

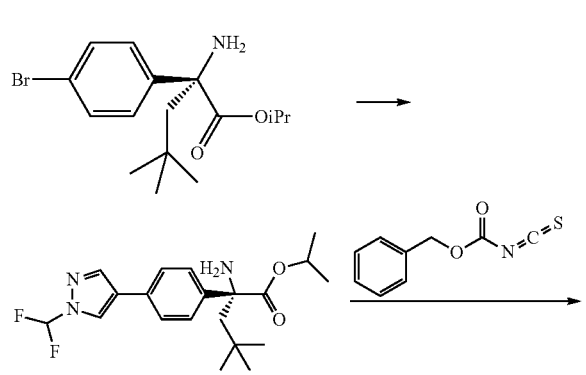

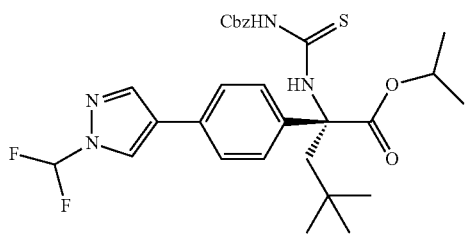

Preparation of isopropyl (R)-2-amino-2-(4-(1-(difluoromethyl)-1H-pyrazol-4-yl)phenyl)-4-methylpentanoate: A degassed mixture of isopropyl (R)-2-amino-2-(4-bromophenyl)-4,4-dimethylpentanoate (4.0 g, 11.7 mmol) in dioxane (120 mL), 1-(difluoromethyl)-4-(4,4,5,5-tetramethyl-1,3,2-dioxaborolan-2-yl)-1H-pyrazole (5.7 g, 23.3 mmol), tetrakis(triphenylphosphine)palladium(O) (2.7 g, 2.34 mmol), potassium carbonate (8.08 g, 58.4 mmol) and water (15 mL) was stirred at 100° C. for 2 h. The reaction mixture was cooled to rt, treated with saturated aq. NaHCO₃ and extracted with EtOAc. The mixture was stirred for 10 min. The layers were separated and the aqueous layer was further extracted with EtOAc. The combined organic layers were washed with saturated aqueous NH₄Cl, brine, dried (over Na₂SO₄), filtered, and concentrated in vacuo. The residue was purified by silica gel column chromatography (0-100% EtOAc/hexanes) to afford the product.

Preparation of isopropyl (R)-2-(3-((benzyloxy)carbonyl)thioureido)-2-(4-(1-(difluoromethyl)-1H-pyrazol-4-yl)phenyl)-4,4-dimethylpentanoate: To a gently stirred biphasic solution of the isopropyl (R)-2-amino-2-(4-(1-(difluoromethyl)-1H-pyrazol-4-yl)phenyl)-4-methylpentanoate (4.44 g, 11.7 mmol) in EtOAc (60 mL) and saturated aqueous sodium bicarbonate (NaHCO₃) (60 mL) was dropwise added a solution of the isothiocyanate (3.39 g, 17.5 mmol) in EtOAc (20 mL). The mixture was stirred for 1 h at rt. The ethyl acetate layer was separated, washed with brine, dried over MgSO₄, filtered, and concentrated. The residue was purified by silica gel chromatography to give the product.

Preparation of Isopropyl (R)-2-(3-((benzyloxy)carbonyl)thioureido)-4,4-dimethyl-2-(4-(pyridin-2-yl)phenyl)pentanoate

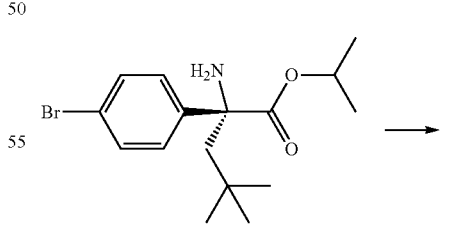

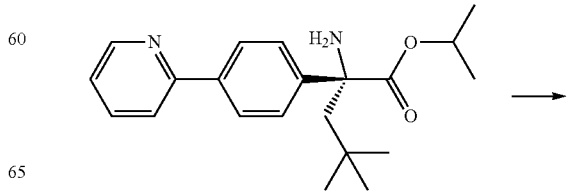

-continued

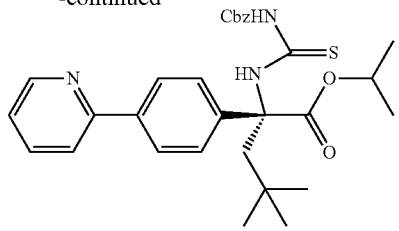

Preparation of isopropyl (R)-2-amino-4,4-dimethyl-2-(4-(pyridin-2-yl)phenyl)pentanoate: To a solution of isopropyl (R)-2-amino-2-(4-bromophenyl)-4,4-dimethylpentanoate (3.0 g, 8.76 mmol) and 2-(tributylstannyl)pyridine (5.85 g, 15.9 mmol) in 1,4-dioxane (45 mL) was added bis(tri-t-butylphosphine)palladium (896 mg, 1.76 mmol). The mixture was then purged with argon and then heated to 90° C. for 3 h. The reaction mixture was cooled to rt, then to the mixture was added 10% KF aqueous solution (45 mL) and ether (45 mL). The mixture was left stirring at rt for 2 h. The mixture was then filtered through Celite; the organic layer was concentrated in vacuo. The residue was purified by silica gel column chromatography (0-100% gradient EtOAc/hexanes) to give the product.

Preparation of isopropyl (R)-2-(3-((benzyloxy)carbonyl)thioureido)-4,4-dimethyl-2-(4-(pyridin-2-yl)phenyl)pentanoate: isopropyl (R)-2-(3-((benzyloxy)carbonyl)thioureido)-4,4-dimethyl-2-(4-(pyridin-2-yl)phenyl)pentanoate was prepared following the procedure to prepare isopropyl (R)-2-(3-((benzyloxy)carbonyl)thioureido)-2-(4-bromophenyl)-4,4-dimethylpentanoate.

Preparation of Benzyl Isopropyl (R)-2-(3-((benzyloxy)carbonyl)thioureido)-4,4-dimethyl-2-(4-(pyrimidin-2-yl)phenyl)pentanoate

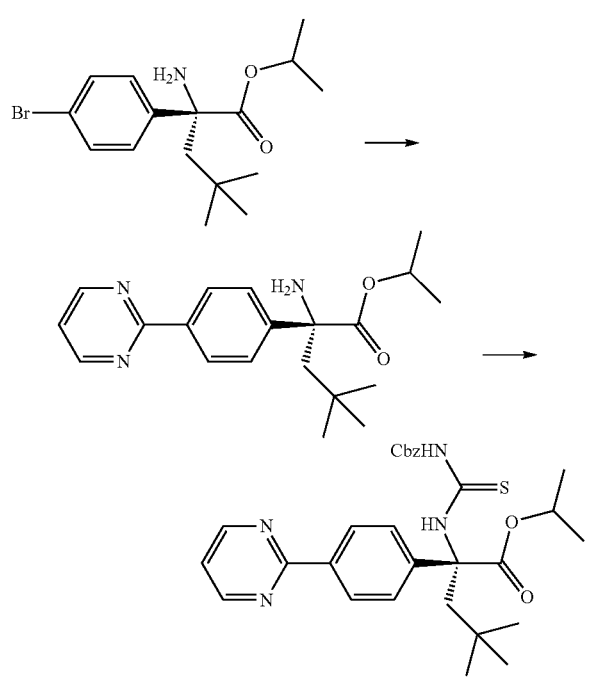

Preparation of isopropyl (R)-2-amino-4,4-dimethyl-2-(4-(pyrimidin-2-yl)phenyl)pentanoate:

To a solution of isopropyl (R)-2-amino-2-(4-bromophenyl)-4,4-dimethylpentanoate (1.10 g, 3.21 mmol) and 2-(tributylstannyl)pyrimidine (2.44 g, 6.61 mmol) in 1,4-dioxane (12 mL) was added bis(tri-t-butylphosphine) (0.33 g, 0.63 mmol). The mixture was then degassed with argon and heated to 90° C. for 3 h. The reaction mixture was cooled to rt, treated with 10% KF and ether, and left stirring overnight. The resulting precipitate was removed by filtration through Celite, and the filter cake was washed with EtOAc. The organic filtrate and the washing were combined and concentrated in vacuo. The residue was purified by silica gel chromatography (0-100% gradient EtOAc/hexanes) to give the product.

Preparation of isopropyl (R)-2-(3-((benzyloxy)carbonyl)thioureido)-4,4-dimethyl-2-(4-(pyrimidin-2-yl)phenyl)pentanoate: isopropyl (R)-2-(3-((benzyloxy)carbonyl)thioureido)-4,4-dimethyl-2-(4-(pyrimidin-2-yl)phenyl)pentanoate was prepared following the procedure used to prepare isopropyl (R)-2-(3-((benzyloxy)carbonyl)thioureido)-2-(4-(1-(difluoromethyl)-1H-pyrazol-4-yl)phenyl)-4,4-dimethylpentanoate.

Preparation of Isopropyl (R)-2-amino-2-(4-(1-cyclopropyl-1H-1,2,4-triazol-3-yl)-2-fluorophenyl)-4,4-dimethylpentanoate

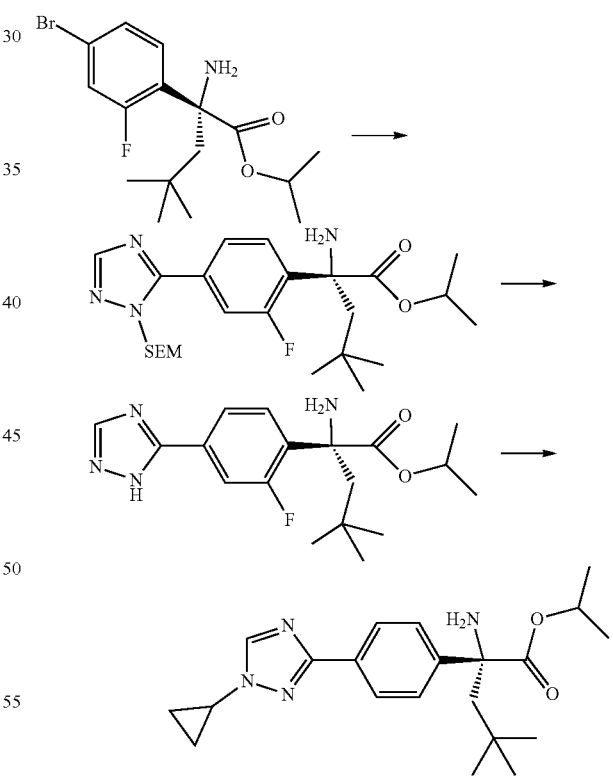

Preparation of isopropyl (R)-2-amino-2-(2-fluoro-4-(1-((2-(trimethylsilyl)ethoxy)methyl)-1H-1,2,4-triazol-5-yl)phenyl)-4,4-dimethylpentanoate: A mixture of isopropyl (R)-2-amino-2-(4-bromo-2-fluorophenyl)-4,4-dimethylpentanoate (1.0 g, 2.78 mmol), palladium(II) acetate (62 mg, 0.28 mmol), potassium carbonate (1.53 g, 11.1 mmol) and n-butyl-di-(1-adamantyl)phosphonium iodide (0.27 g, 0.56 mmol) was sparged with argon and then diluted with toluene (3 mL). Then 1-((2-(trimethylsilyl)ethoxy)methyl)-1H-1,2,4-triazole (0.66 g, 3.33 mmol) and 2,2-dimethylbutyric acid (0.21 mL, 1.67 mmol) were added. The biphasic mixture was flushed with argon for 15 min. Then the reaction mixture was stirred at 120° C. overnight. The reaction mixture was cooled and filtered through Celite. The filter cake was washed with EtOAc. The filtrate and the washing were combined and concentrated. The residue was purified by silica gel column chromatography (0-100% gradient EtOAc/hexanes) to give the product.

Preparation of isopropyl (R)-2-amino-2-(2-fluoro-4-(1H-1,2,4-triazol-5-yl)phenyl)-4,4-dimethylpentanoate: A solution of isopropyl (R)-2-amino-2-(2-fluoro-4-(1-((2-(trimethylsilyl)ethoxy)methyl)-1H-1,2,4-triazol-5-yl)phenyl)-4,4-dimethylpentanoate (0.8 g, 1.67 mmol) in TFA (5 mL) was stirred at rt for 10 min. The reaction mixture was concentrated down to remove most of TFA. The residue was treated with 1N HCl (8 mL) with stirring for 30 min. To the mixture was added acetic acid (AcOH) (10 mL) followed by sonication and stirred at rt for 1 h. The mixture was then heated at 55° C. for 18 h. The reaction mixture was concentrated down. The residue was treated with saturated NaHCO$_3$ solution and EtOAc. The two phases were separated and the aqueous phase was further extracted with EtOAc. The combined organic phase was washed with brine, concentrated down, and the residue was purified by silica gel column chromatography (0-100% gradient EtOAc/hexanes) to give the product.

Preparation of isopropyl (R)-2-amino-2-(4-(1-cyclopropyl-1H-1,2,4-triazol-3-yl)-2-fluorophenyl)-4,4-dimethylpentanoate: A mixture of isopropyl (R)-2-amino-2-(2-fluoro-4-(1H-1,2,4-triazol-5-yl)phenyl)-4,4-dimethylpentanoate (170 mg, 0.49 mmol), cyclopropylboronic acid (85%, 296 mg, 2.93 mmol), cupric acetate (266 mg, 1.45 mmol), N,N-diisopropylethylamine (0.51 mL, 2.98 mmol) and pyridine (0.32 mL, 3.9 mmol) was heated at 100° C. The reaction mixture was later cooled to rt, filtered off solid through a pile of Celite. The filtrate was diluted with EtOAc, washed with 3% lithium chloride solution and then with saturated ammonium chloride solution. The organic phase was dried over MgSO$_4$, filtered, and concentrated down. The residue was purified by silica gel column chromatography (0-100% gradient EtOAc/hexanes) to give the product.

Preparation of Isopropyl (R)-2-amino-2-(4-(4-(difluoromethyl)-4H-1,2,4-triazol-3-yl)-2-fluorophenyl)-4,4-dimethylpentanoate

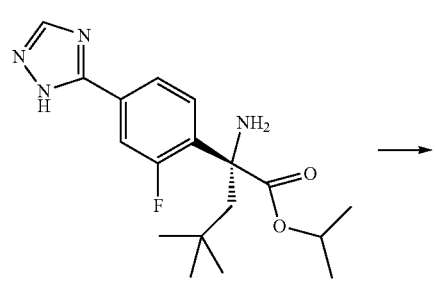

Preparation of isopropyl (R)-2-amino-2-(4-(4-(difluoromethyl)-4H-1,2,4-triazol-3-yl)-2-fluorophenyl)-4,4-dimethylpentanoate: To the solution of isopropyl (R)-2-amino-2-(2-fluoro-4-(1H-1,2,4-triazol-5-yl)phenyl)-4,4-dimethylpentanoate (120 mg, 0.34 mmol) in THF (2 mL) was added NaH (60%, 40 mg, 1 mmol) at 0° C. and stirred at 0° C. for 10 min. Then difluoroiodomethane solution in THF (10 wt. %, 0.69 mL, 0.52 mol) was added. The mixture was warmed to and stirred at rt for 30 min. The reaction mixture was concentrated down and purified by silica gel chromography to give the product (90 mg, 65%) and the other two regioisomeric difluoromethyl substituted products.

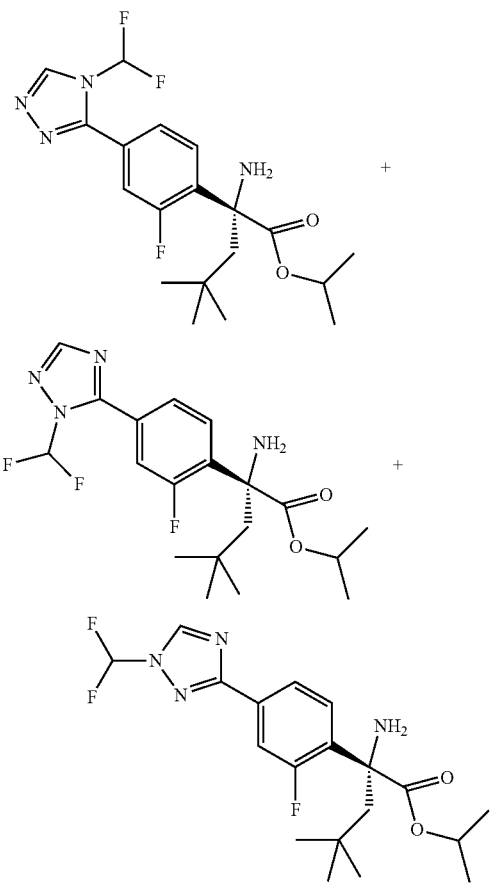

Preparation of Isopropyl (R)-2-amino-2-(4-(1-cyclopropyl-1H-1,2,4-triazol-3-yl)-2-fluorophenyl)-4,4-dimethylpentanoate

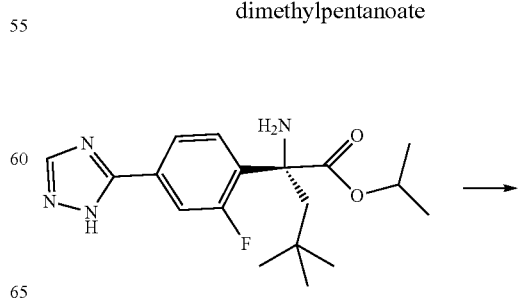

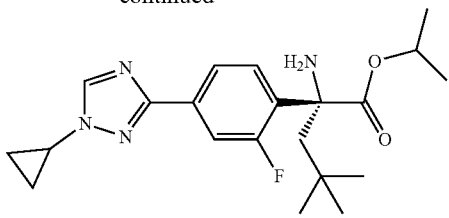

Preparation of isopropyl (R)-2-amino-2-(4-(1-cyclopropyl-1H-1,2,4-triazol-3-yl)-2-fluorophenyl)-4,4-dimethylpentanoate: A mixture of isopropyl (R)-2-amino-2-(2-fluoro-4-(1H-1,2,4-triazol-5-yl)phenyl)-4,4-dimethylpentanoate (170 mg, 0.49 mmol), cyclopropylboronic acid (85%, 296 mg, 2.93 mmol), cupric acetate (266 mg, 1.45 mmol), N,N-diisopropylethylamine (0.51 mL, 2.98 mmol) and pyridine (0.32 mL, 3.9 mmol) was heated at 100° C. The reaction mixture was later cooled to rt, filtered off solid through a pile of Celite. The filtrate was diluted with EtOAc, washed with 3% lithium chloride solution and then with saturated ammonium chloride solution. The organic phase was dried over MgSO$_4$, filtered, and concentrated down. The residue was purified by silica gel column chromatography (0-100% gradient EtOAc/hexanes) to give the product.

Preparation of Isopropyl (R)-2-amino-2-(3-fluoro-4-(2-(methyl-d3)-2H-1,2,3-triazol-4-yl)phenyl)-4,4-dimethylpentanoate

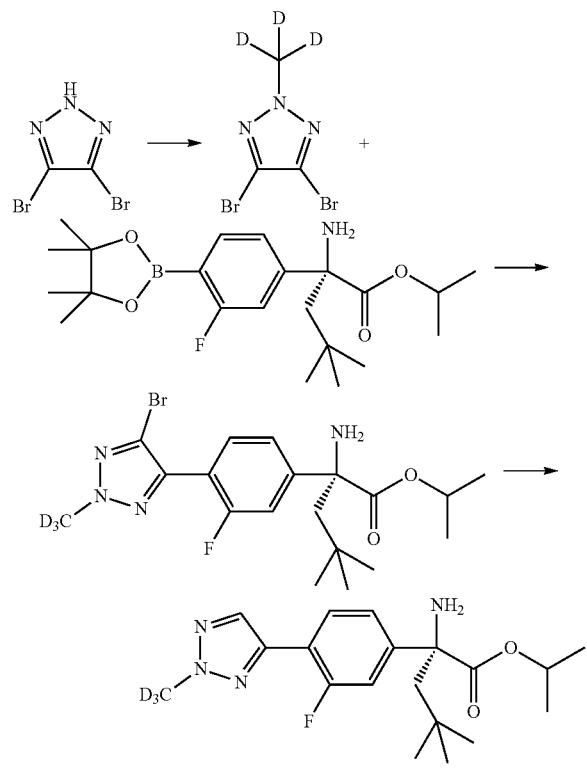

Preparation of 4,5-dibromo-2-(methyl-d$_3$)-2H-1,2,3-triazole: To a solution of 4,5-dibromo-2H-1,2,3-triazole (1500 mg, 6.6 mmol) in DMF (12 mL) at −20° C. were added iodomethane-d3 (0.82 ml, 13.2 mmol) and potassium carbonate (1736.2 mg, 12.6 mmol). The reaction mixture was allowed to warm up to rt and stirred over 3 days. The reaction mixture was treated with water and extracted with EtOAc. The organic phase was dried over MgSO$_4$, filtered, concentrated down and purified by silica gel column chromatography, eluting by EtOAc/hexanes, to give the product (376 mg, 23%).

Preparation of isopropyl (R)-2-amino-2-(4-(5-bromo-2-(methyl-d3)-2H-1,2,3-triazol-4-yl)-3-fluorophenyl)-4,4-dimethylpentanoate: A mixture of isopropyl (R)-2-amino-2-(3-fluoro-4-(4,4,5,5-tetramethyl-1,3,2-dioxaborolan-2-yl)phenyl)-4,4-dimethylpentanoate (140 mg, 0.34 mmol), 4,5-dibromo-2-(methyl-d$_3$)-2H-1,2,3-triazole (168 mg, 0.69 mmol),tetrakis(triphenylphosphine)palladium (60 mg, 0.050 mmol) and potassium carbonate (190 mg, 1.4 mmol) in dioxane (1.0 mL) and water (0.2 mL) was sparged with nitrogen. Then the reaction mixture was stirred at 90° C. for 1 h. The reaction mixture was cooled to rt and quenched by the addition of saturated aqueous NH$_4$Cl and EtOAc. The layers were separated and the aqueous layer was further extracted with EtOAc. The combined organic layers were washed with brine, dried (over Na$_2$SO$_4$), filtered, and concentrated in vacuo. The residue was purified by silica gel column chromatography, eluting by 0-100% EtOAc/hexanes, to afford the product.

Preparation of isopropyl (R)-2-amino-2-(3-fluoro-4-(2-(methyl-d3)-2H-1,2,3-triazol-4-yl)phenyl)-4,4-dimethylpentanoate: To a solution of isopropyl (R)-2-amino-2-(4-(5-bromo-2-(methyl-d3)-2H-1,2,3-triazol-4-yl)-3-fluorophenyl)-4,4-dimethylpentanoate (80 mg, 0.18 mmol) in EtOH (2 mL) was added palladium on carbon (5%, 71 mg, 0.02 mmol) and a hydrogen balloon was attached. The reaction mixture was stirred at rt until the reaction was complete. The reaction mixture was filtered over Celite and used directly for the next step.

Preparation of Isopropyl (R)-2-(4-(2H-1,2,3-triazol-2-yl)phenyl)-2-amino-4,4-dimethylpentanoate

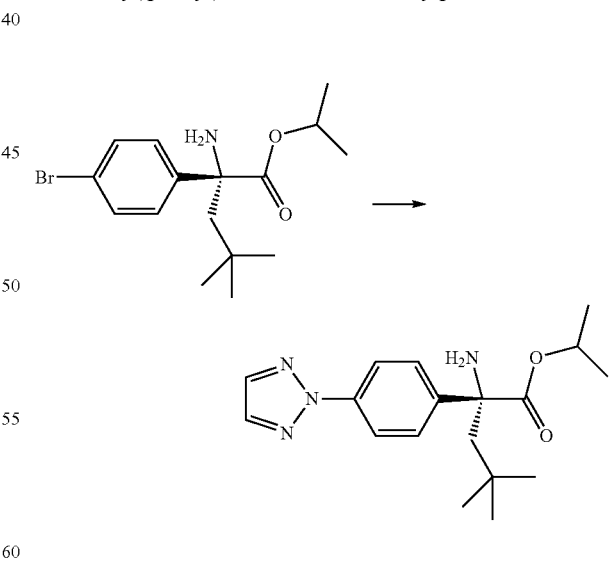

Preparation of isopropyl (R)-2-(4-(2H-1,2,3-triazol-2-yl)phenyl)-2-amino-4,4-dimethylpentanoate: To a solution of isopropyl (R)-2-amino-2-(4-bromophenyl)-4,4-dimethylpentanoate (0.50 g, 1.46 mmol) in Me-THF (8 mL) were added 2H-1,2,3-triazole (0.85 mL, 14.6 mmol), cesium carbonate (4.75 g, 14.6 mmol), tetramethyl t-BuXphos (0.70 g, 1.46 mmol) and bis(dibenzylideneacetone)palladium(O)

(0.42 g, 0.73 mmol). The mixture was degassed for 5 min. The reaction mixture was then heated at 90° C. for 20 h. The reaction was quenched by adding water, extracted with EtOAc. The organic phase was dried over MgSO₄, filtered, concentrated and purified by silica gel column chromatography (0-100% gradient EtOAc/hexanes) to give the product.

Preparation of Isopropyl (R)-2-(4-(4H-1,2,4-triazol-4-yl)phenyl)-2-amino-4,4-dimethylpentanoate

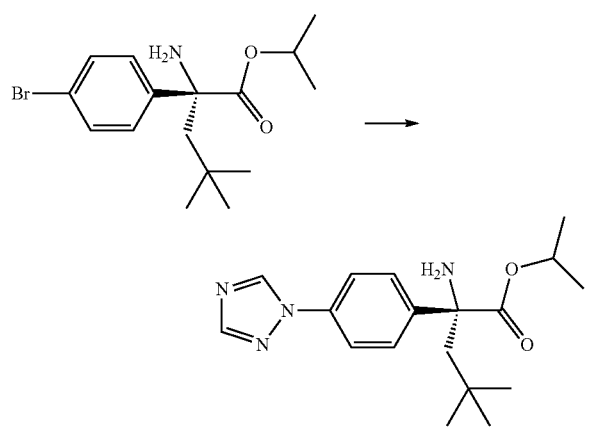

Preparation of isopropyl (R)-2-(4-(4H-1,2,4-triazol-4-yl)phenyl)-2-amino-4,4-dimethylpentanoate: To a solution of isopropyl (R)-2-amino-2-(4-bromophenyl)-4,4-dimethylpentanoate (1265 mg, 3.7 mmol) in DMF (4 mL) were added 4H-1,2,4-triazole (218 mg, 3 mmol), copper(II) acetate monohydrate) (62 mg, 0.31 mmol) and cesium carbonate (1950 mg, 6 mmol). The reaction mixture was heated at 90° C. for 1 d. The reaction mixture was diluted with saturated ammonium chloride solution and extracted with EtOAc. The organic phase was concentrated down and the residue was purified by silica gel column chromatography (0-100% gradient EtOAc/hexanes) to give the product.

Preparation of Isopropyl (R)-2-amino-2-(4-(1-cyclopropyl-1H-1,2,3-triazol-4-yl)phenyl)-4,4-dimethylpentanoate

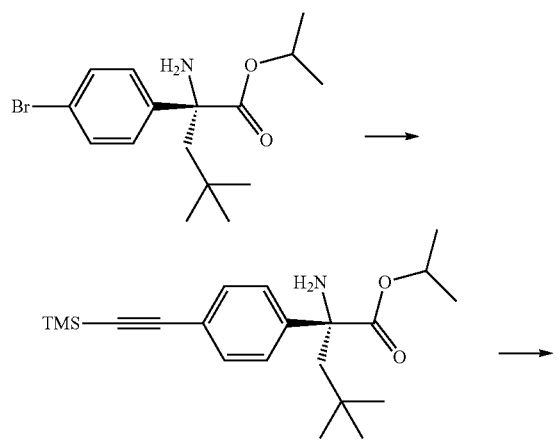

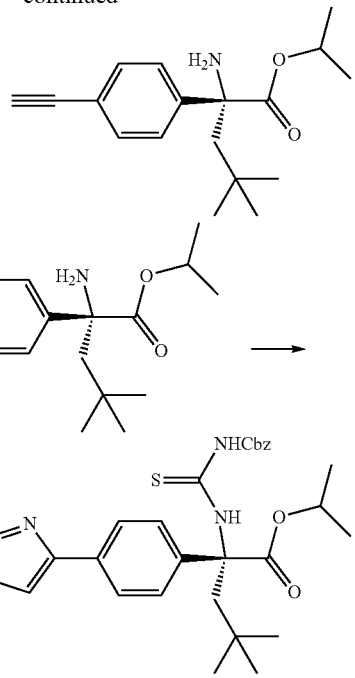

Preparation of isopropyl (R)-2-amino-4,4-dimethyl-2-(4-((trimethylsilyl)ethynyl)phenyl)pentanoate: A mixture of isopropyl (R)-2-amino-2-(4-bromophenyl)-4,4-dimethylpentanoate (1020 mg, 2.98 mmol), CuI (283.78 mg, 1.49 mmol), ethynyltrimethylsilane (1.27 mL, 8.94 mmol) and Pd(PPh₃)₄ (1720 mg, 1.49 mmol) in triethylamine (5.0 mL) was sparged with argon for 5 min. Then the reaction mixture was heated at 90° C. for 1.5 h. The reaction mixture was diluted with EtOAc and treated with water. The organic phase was separated and the aqueous phase was further extracted with EtOAc. The combined organic phase was washed with brine and concentrated down. The residue was purified by silica gel column chromatography (0-100% gradient EtOAc/hexanes) to give the product.

Preparation of isopropyl (R)-2-amino-2-(4-ethynylphenyl)-4,4-dimethylpentanoate: To a solution of isopropyl (R)-2-amino-4,4-dimethyl-2-(4-((trimethylsilyl)ethynyl)phenyl)pentanoate (850 mg, 2.36 mmol) in THF (8 mL) was added TBAF in THF (1.5 M, 1.58 mL) dropwise, and stirred at rt for 10 min under argon. The reaction mixture was diluted with EtOAc and washed with saturated ammonium chloride solution. The organic phase was separated and the aqueous phase was further extracted with EtOAc. The organic phases were combined, washed with water and concentrated. The residue was purified by silica gel column chromatography (0-100% gradient EtOAc/hexanes) to give the product.

Preparation of isopropyl (R)-2-amino-2-(4-(1-cyclopropyl-1H-1,2,3-triazol-4-yl)phenyl)-4,4-dimethylpentanoate: To a solution of isopropyl (R)-2-amino-2-(4-ethynylphenyl)-4,4-dimethylpentanoate (400 mg, 1.39 mmol) in THF (4 mL) under argon were added cyclopropyl azide (158 mg, 1.81 mmol) and copper(I)-thiophene-2-carboxylate (54 mg, 0.21 mmol). The reaction mixture was stirred at rt for 30 min. The reaction mixture was treated with saturated NaHCO₃ solution and extracted with EtOAc. The organic phase was washed with brine, concentrated, and purified by silica gel column chromatography (0-100% gradient EtOAc/hexanes) to give the product.

Preparation of Isopropyl (R)-2-amino-2-(4-(4-fluoro-1H-pyrazol-1-yl)phenyl)-4,4-dimethylpentanoate

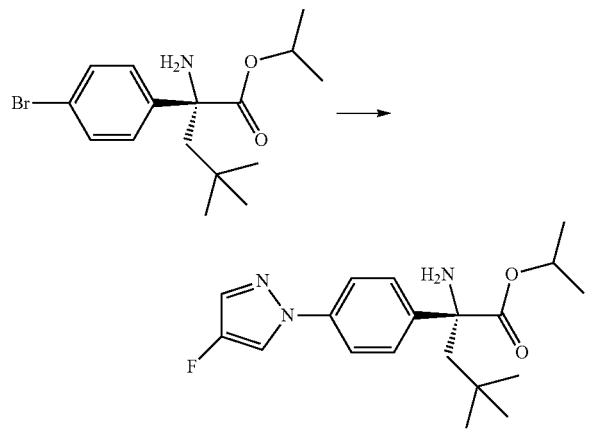

Preparation of isopropyl (R)-2-amino-2-(4-(4-fluoro-1H-pyrazol-1-yl)phenyl)-4,4-dimethylpentanoate: To a solution of isopropyl (R)-2-amino-2-(4-bromophenyl)-4,4-dimethylpentanoate (420 mg, 1.23 mmol) in dioxane (6 mL) were added 4-fluoro-1H-pyrazole (739 mg, 8.59 mmol), cesium carbonate (3.20 g, 9.82 mmol), 2-di-tert-butylphosphino-3,4,5,6-tetramethyl-2',4',6'-triisopropyl-1,1'-biphenyl (590 mg, 1.23 mmol) and bis(dibenzylideneacetone)palladium(O) (353 mg, 0.61 mmol). The reaction mixture was sparged with argon for 5 min, and heated at 90° C. for 1.5 h. Then to the mixture were added 4-fluoro-1H-pyrazole (317 mg, 3.68 mmol), cesium carbonate (1.60 g, 4.91 mmol), 2-di-tert-butylphosphino-3,4,5,6-tetramethyl-2',4',6'-triisopropyl-1,1'-biphenyl (354 mg, 0.74 mmol) and bis(dibenzylideneacetone)palladium(O) (212 mg, 0.23 mmol). The mixture was sparged and heated at 90° C. for 20 h. The reaction mixture was then purified by silica gel column chromatography (0-100% gradient EtOAc/hexanes) to give the product.

Preparation of (S)-2-amino-2-(4-chloro-3-(3-methylpyridin-2-yl)phenyl)ethan-1-ol (Method IV)

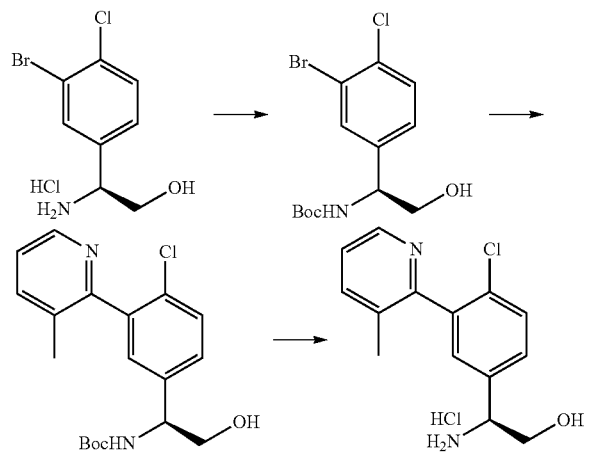

Preparation of tert-butyl (S)-(1-(3-bromo-4-chlorophenyl)-2-hydroxyethyl)carbamate: To a solution of (S)-2-amino-2-(3-bromo-4-chlorophenyl)ethan-1-ol hydrochloride (0.9 g, 3.14 mmol) in THF (15 mL) were added sequentially N,N-diisopropylethylamine (1.64 mL, 9.41 mmol) and di-tert-butyl dicarbonate (1.03 g, 4.7 mmol) and stirred at rt for 12 h. The reaction mixture was then quenched by addition of saturated ammonium chloride solution and extracted with EtOAc. The layers were separated and the aqueous layer was further extracted with EtOAc. The combined organic layers were washed with brine, dried (over $Na_2SO_4$), filtered, and concentrated. The residue was purified by silica gel column chromatography (0-100% EtOAc/hexanes) to afford the product.

Preparation of tert-butyl (S)-(1-(4-chloro-3-(3-methylpyridin-2-yl)phenyl)-2-hydroxyethyl)carbamate: To a sparged solution of tert-butyl (S)-(1-(3-bromo-4-chlorophenyl)-2-hydroxyethyl)carbamate (275 mg, 0.78 mmol) and bis(tri-t-butylphosphine)palladium (0) (80 mg, 0.16 mmol) in dioxane (7.5 mL) was added 3-methyl-2-(tributylstannyl)pyridine (450 mg, 1.18 mmol). The reaction mixture was stirred overnight at 90° C. The reaction mixture was cooled to rt, and saturated aqueous KF solution and diethylether were added to the mixture. The resulting reaction mixture was stirred for 3 h, and filtered through Celite. The organic layer was separated, and dried (over $Na_2SO_4$), filtered, and concentrated. The residue was purified by silica gel column chromatography (0-100% acetone/hexanes) to give the product.

Preparation of (S)-2-amino-2-(4-chloro-3-(3-methylpyridin-2-yl)phenyl)ethan-1-ol hydrochloride: To a solution of tert-butyl (S)-(1-(4-chloro-3-(3-methylpyridin-2-yl)phenyl)-2-hydroxyethyl)carbamate (283 mg, 0.78 mmol) in dioxane (2.0 mL) was added hydrochloric acid in dioxane (4M, 0.39 mL). The reaction mixture was stirred at rt for 72 h. The reaction mixture was diluted with toluene and concentrated down. This sequence was repeated twice, and then the crude product was carried to the next step with no further purification.

If not otherwise stated, amino alcohols used in preparation of examples were prepared by Method III.

Preparation of (S)-2-amino-2-(3-carbamoyl-4-chlorophenyl)ethyl cyclopropylcarbamate (Method V)

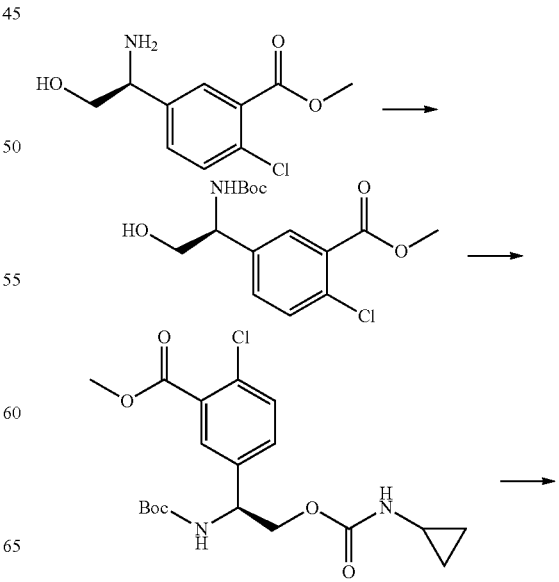

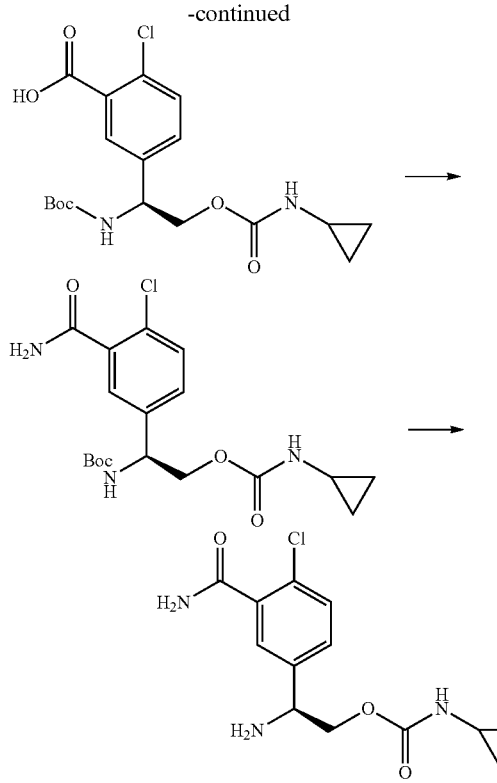

Preparation of methyl (S)-5-(1-((tert-butoxycarbonyl)amino)-2-hydroxyethyl)-2-chlorobenzoate: To a solution of methyl (S)-5-(1-amino-2-hydroxyethyl)-2-chlorobenzoate (3 g, 0.01 mol) and di-tert-butyl dicarbonate (2.85 g, 0.01 mol) in THF (100 mL) was added triethylamine (5.61 g, 0.04 mol). The reaction mixture was stirred at rt overnight. The reaction mixture was concentrated down and purified by silica gel column chromatography (0-100% gradient EtOAc/hexanes) to give the product.

Preparation of methyl (S)-5-(1-((tert-butoxycarbonyl)amino)-2-((cyclopropylcarbamoyl)oxy)ethyl)-2-chlorobenzoate: A mixture of methyl (S)-5-(1-((tert-butoxycarbonyl)amino)-2-hydroxyethyl)-2-chlorobenzoate (1.75 g, 0.01 mol), 1,1'-carbonyldiimidazole (3.02 g, 0.02 mol) and N,N-diisopropylethylamine (4.63 mL, 0.03 mol) in DCM (100 mL) was stirred at rt for 4 h. Then to the mixture was added cyclopropylamine (3.68 mL, 0.05 mol), and the reaction mixture was stirred at rt overnight. The reaction mixture was concentrated down and the residue was purified by silica gel column chromatography (0-100% gradient EtOAc/hexanes) to give the product.

Preparation of (S)-5-(1-((tert-butoxycarbonyl)amino)-2-((cyclopropylcarbamoyl)oxy)ethyl)-2-chlorobenzoic acid: The reaction mixture of methyl (S)-5-(1-((tert-butoxycarbonyl)amino)-2-((cyclopropylcarbamoyl)oxy)ethyl)-2-chlorobenzoate (2.78 g, 0.01 mol) and NaOH (2M, 10 mL) in THF (20 mL) and MeOH (20 mL) was stirred at rt for 2 h. Then to the mixture was added EtOAc and water. The mixture was filtered to collect some of the product. The filtrate was concentrated and the residue was purified by silica gel column chromatography (0-100% gradient EtOAc/hexanes) to afford the product.

Preparation of tert-butyl (S)-(1-(3-carbamoyl-4-chlorophenyl)-2-((cyclopropylcarbamoyl)oxy)ethyl)carbamate: To a solution of (S)-5-(1-((tert-butoxycarbonyl)amino)-2-((cyclopropylcarbamoyl)oxy)ethyl)-2-chlorobenzoic acid (1.25 g, 3 mmol) in DCM (50 mL) and THF (5 mL) was added 1,1'-carbonyldiimidazole (1.53 g, 0.01 mol). The reaction mixture was stirred at rt for 2 h. Then ammonia was bubbling in to the reaction mixture, and the reaction mixture was stirred at rt for 3 h. Then the reaction was washed with brine and extracted with EtOAc. The organic phase was dried (over MgSO₄), filtered, and concentrated down. The residue was purified by silica gel column chromatography (0-100% gradient EtOAc/hexanes) to give the product.

Preparation of (S)-2-amino-2-(3-carbamoyl-4-chlorophenyl)ethyl cyclopropylcarbamate: To a solution of tert-butyl (S)-(1-(3-carbamoyl-4-chlorophenyl)-2-((cyclopropylcarbamoyl)oxy)ethyl)carbamate (1.25 g, 3 mmol) in DCM (10 mL) was added trifluoracetic acid (10 mL). The reaction mixture was stirred at rt for 2 h. The reaction mixture was concentrated down and the residue was purified by silica gel column chromatography (0-100% gradient EtOAc/hexanes) to give the product.

Preparation of (S)-2-amino-2-(3-carbamoyl-4-chlorophenyl)ethyl 3,3-difluoroazetidine-1-carboxylate

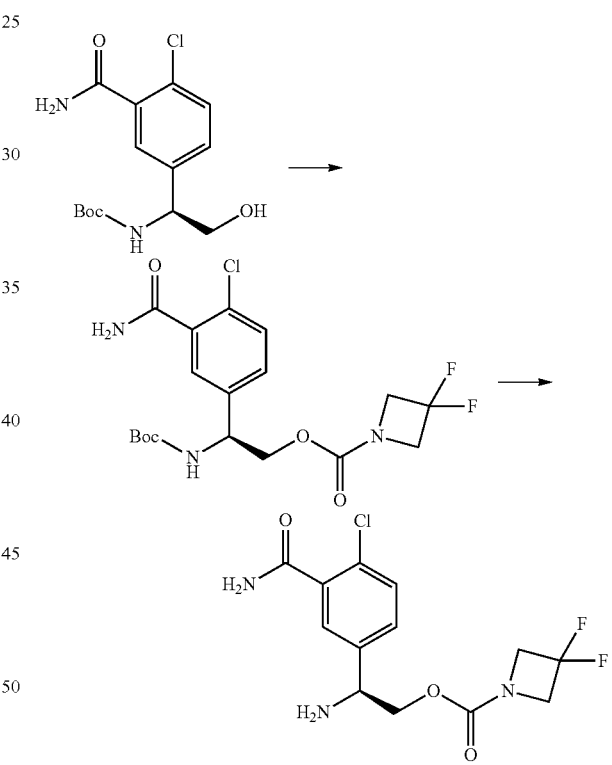

Preparation of (S)-2-amino-2-(3-carbamoyl-4-chlorophenyl)ethyl 3,3-difluoroazetidine-1-carboxylate: To a solution of tert-butyl (S)-(1-(3-carbamoyl-4-chlorophenyl)-2-hydroxyethyl)carbamate (100 mg, 0.32 mmol) in DCM (3 mL) were added 1,1'-carbonyldiimidazole (77.27 mg, 0.48 mmol) and N,N-diisopropylethylamine (166 µL, 0.95 mmol) and stirred at rt for 10 min. Then to the mixture was added 3,3-difluoroazetidine (130 µL, 1.59 mmol) and stirred at rt for 40 min. The reaction mixture was concentrated down and purified by silica gel column chromatography to give (S)-2-((tert-butoxycarbonyl)amino)-2-(3-carbamoyl-4-chlorophenyl)ethyl 3,3-difluoroazetidine-1-carboxylate (127 mg, 92%). Then, (S)-2-((tert-butoxycarbonyl)amino)-2-(3-carbamoyl-4-chlorophenyl)ethyl 3,3-difluoroazetidine-1-carboxylate (127 mg, 0.29 mmol) was dissolved in DCM (3.0 mL) and to the mixture was added HCl in dioxane (4 M, 0.37 mL). The mixture was stirred at rt for 40 min. The mixture was then concentrated down to give the product, which was used directly in the next reaction without purification.

Preparation of (S)-2-amino-2-(4-chloro-3-(4-methoxypyrimidin-2-yl)phenyl)ethan-1-ol (Method VI)

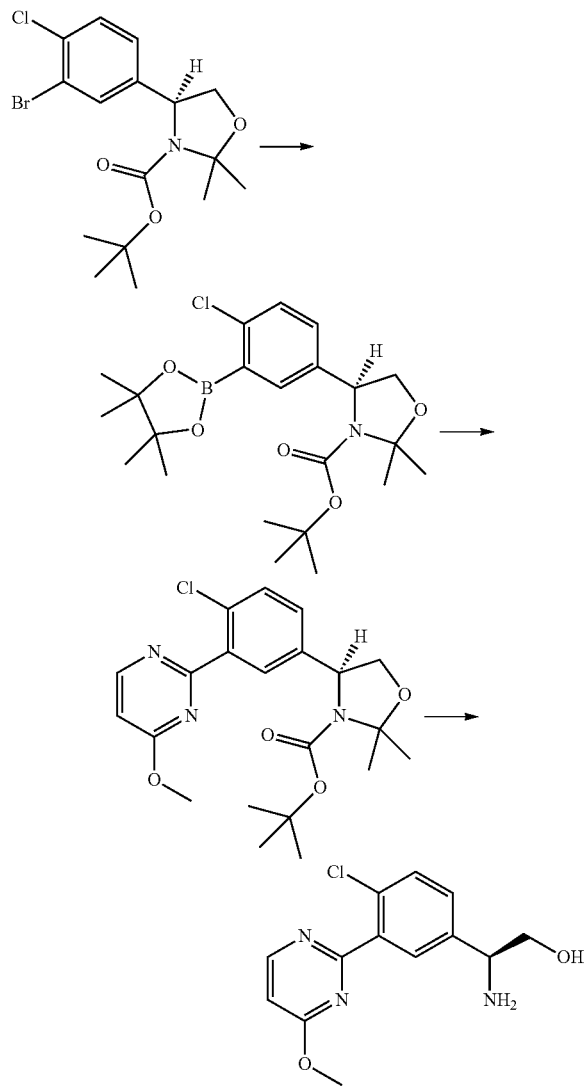

Preparation of tert-butyl (S)-4-(4-chloro-3-(4,4,5,5-tetramethyl-1,3,2-dioxaborolan-2-yl)phenyl)-2,2-dimethyloxazolidine-3-carboxylate: An argon-purged solution of tert-butyl (S)-4-(3-bromo-4-chlorophenyl)-2,2-dimethyloxazolidine-3-carboxylate (0.99 g, 3.0 mol) in dioxane (16.0 mL) was added to a vial containing potassium acetate (1.3 g, 13.3 mmol), 1,1'-bis(diphenylphosphino)ferrocene (200 mg, 0.27 mmol) and bis(pinacolato)diboron (1.3 g, 5.1 mmol) under argon. After stirring at rt for 5 min, the reaction mixture was heated at 90° C. for 16 h. The mixture was then cooled to rt, and poured into brine/EtOAc. The organic phase was collected and the aqueous layer was extracted with EtOAc. The combined organics were dried, filtered, and concentrated down. The residue was purified by silica gel column chromatography (0-100% gradient EtOAc/hexanes) to give the product.

Preparation of tert-butyl (S)-4-(4-chloro-3-(4-methoxypyrimidin-2-yl)phenyl)-2,2-dimethyloxazolidine-3-carboxylate: A solution of tert-butyl (S)-4-(4-chloro-3-(4,4,5,5-tetramethyl-1,3,2-dioxaborolan-2-yl)phenyl)-2,2-dimethyloxazolidine-3-carboxylate (100 mg, 0.15 mmol), 2-chloro-4-methoxypyrimidine (70 mg, 0.048 mmol), tetrakis(triphenylphosphine)palladium(0) (35 mg, 0.003 mmol) and potassium carbonate (100 mg, 0.072 mmol) in dioxane (2.0 mL) and $H_2O$ (0.5 mL) was heated at 90° C. for 16 h. The mixture was diluted with water and brine, extracted with EtOAc. The organic phase was dried ($Na_2SO_4$), filtered, and concentrated down. The residue was purified by silica gel column (0-100% gradient EtOAc/hexanes) to give the product.

Preparation of (S)-2-amino-2-(4-chloro-3-(4-methoxypyrimidin-2-yl)phenyl)ethan-1-ol: tert-butyl (S)-4-(4-chloro-3-(4-methoxypyrimidin-2-yl)phenyl)-2,2-dimethyloxazolidine-3-carboxylate (123 mg, 0.029 mmol) was treated with HCl in dioxane (4.0 M, 2.0 mL) at rt for 5 min. Then, $H_2O$ (2.0 mL) was added. After 10 min, more $H_2O$ was added and the mixture was lyophilized to give the product, which was used for the next reaction without further purification.

Preparation of (S)-2-amino-2-(4-chloro-3-(1-(difluoromethyl)-1H-imidazol-2-yl)phenyl)ethan-1-ol

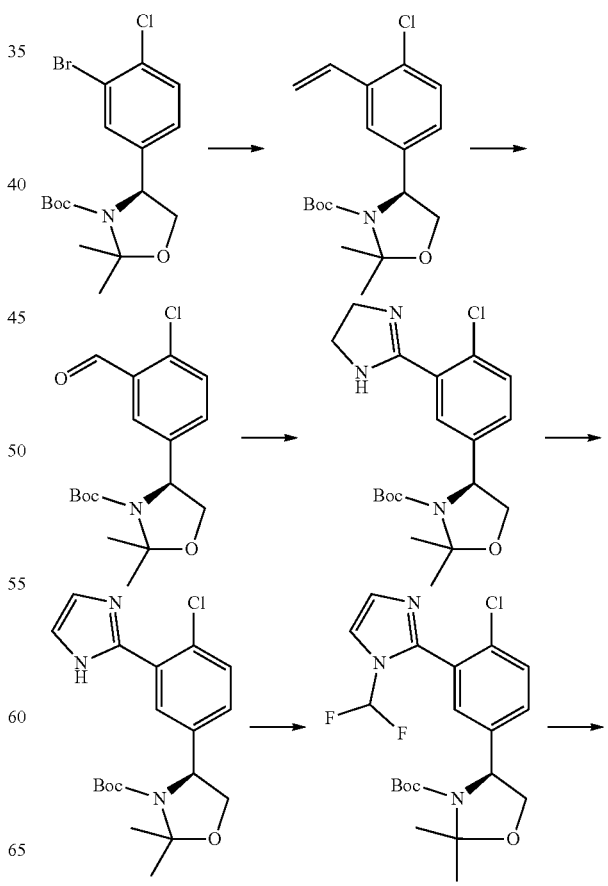

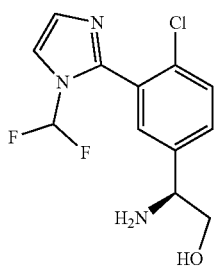

Preparation of tert-butyl (S)-4-(4-chloro-3-vinylphenyl)-2,2-dimethyloxazolidine-3-carboxylate: To the mixture of tert-butyl (S)-4-(3-bromo-4-chlorophenyl)-2,2-dimethyloxazolidine-3-carboxylate (530 mg, 1 mmol) and potassium trifluoro(vinyl)borate (363 mg, 3 mmol) in THF (10 mL) was added $PdCl_2$ (48 mg, 0.027 mmol), $PPh_3$ (213 mg, 0.081 mmol) and $Cs_2CO_3$ (2200 mg, 7 mmol). The mixture was sparged for 5 min with argon and heated at 75° C. for 17 h. The reaction mixture was treated with water and extracted with EtOAc. The organic phase was concentrated down and the residue was purified by silica gel column chromatography (0-100% gradient EtOAc/hexanes) to give the product.

Preparation of tert-butyl (S)-4-(4-chloro-3-formylphenyl)-2,2-dimethyloxazolidine-3-carboxylate: To a solution of tert-butyl (S)-4-(4-chloro-3-vinylphenyl)-2,2-dimethyloxazolidine-3-carboxylate (0.44 g, 1.31 mmol) in THF (25 mL) and $H_2O$ (20 mL) was added 2.5 wt. % $OsO_4$ in t-BuOH (0.27 mL, 0.03 mmol) and stirred at rt for 30 min. Then sodium periodate (0.84 g, 3.94 mmol) was added and stirred at rt for 45 min. The reaction mixture was washed with water and extracted with EtOAc. The organic phase was separated, dried, filtered and concentrated down. The residue was purified by silica gel column chromatography (eluted with 0-50% EtOAc/hexanes) to give the product.

Preparation of tert-butyl (S)-4-(4-chloro-3-(4,5-dihydro-1H-imidazol-2-yl)phenyl)-2,2-dimethyloxazolidine-3-carboxylate: To a solution of tert-butyl (S)-4-(4-chloro-3-formylphenyl)-2,2-dimethyloxazolidine-3-carboxylate (200 mg, 0.59 mmol) in t-BuOH (2.0 mL) at rt under argon was added ethylenediamine (39 mg, 0.65 mmol) and stirred at the same temperature for 30 min. Then to the mixture were added potassium carbonate (487 mg, 3.53 mmol) and iodine (156 mg, 1.47 mmol). The mixture was heated at 70° C. for 1 h, and then at rt overnight. Then to the mixture was added ethylenediamine (76 mg, 1.3 mmol) and stirred at rt for 30 min. Additional potassium carbonate (487 mg, 3.53 mmol) and iodine (156 mg, 1.47 mmol) were added and heated again at 77° C. for 3 h. To the mixture, water (3 mL) was added, the resulting orange red solution (two layers) was heated at 75° C. for 1 h. The crude reaction mixture was partitioned between DCM and water. The DCM layer was washed with $Na_2S_2O_3$ solution (1N) and then with water. The organic phase was dried over $Na_2SO_4$, filtered, concentrated down and the residue was directly used in the next step.

Preparation of tert-butyl (S)-4-(4-chloro-3-(1H-imidazol-2-yl)phenyl)-2,2-dimethyloxazolidine-3-carboxylate: To the crude tert-butyl (S)-4-(4-chloro-3-(4,5-dihydro-1H-imidazol-2-yl)phenyl)-2,2-dimethyloxazolidine-3-carboxylate (60%, 300 mg, 0.47 mmol) in DMSO (12 mL) were added potassium carbonate (131 mg, 0.95 mmol) and (diacetoxyiodo)benzene (183 mg, 0.57 mmol) and stirred at rt for 4 h. More potassium carbonate (130 mg, 0.95 mmol) and (diacetoxyiodo)benzene (183 mg, 0.57 mmol) were added and stirred at 45° C. overnight and then at 72° C. for 2 h. After cooling to rt, the mixture was washed with water and extracted with EtOAc. The organic phase was then washed sequentially with $Na_2S_2O_3$ solution, water and brine. The organic phase was concentrated down and residue was purified by silica gel column chromatography (0-100% gradient EtOAc/hexanes) to give the product.

Preparation of tert-butyl (S)-4-(4-chloro-3-(1-(difluoromethyl)-1H-imidazol-2-yl)phenyl)-2,2-dimethyloxazolidine-3-carboxylate: To a solution of tert-butyl (S)-4-(4-chloro-3-(1H-imidazol-2-yl)phenyl)-2,2-dimethyloxazolidine-3-carboxylate (93 mg, 0.024 mmol) in THF (2.0 mL) was added NaH (60%, 12.8 mg, 0.032 mmol) at 0° C. The mixture was stirred at 0° C. for 10 min. To the mixture was added iododifluoromethane in THF (10 wt. %, 0.59 mL, 0.029 mol), and stirred at 0° C. for 30 min. The reaction mixture was washed with water and extracted with EtOAc. The organic phase was washed with brine, concentrated down, purified by silica gel column chromatography (0-100% gradient EtOAc/hexanes) to give the product.

Preparation of (S)-2-amino-2-(4-chloro-3-(1-(difluoromethyl)-1H-imidazol-2-yl)phenyl)ethan-1-ol: The material of tert-butyl (S)-4-(4-chloro-3-(1-(difluoromethyl)-1H-imidazol-2-yl)phenyl)-2,2-dimethyloxazolidine-3-carboxylate (76 mg, 0.018 mmol) was treated with HCl in isopropyl alcohol (1M, 7 mL) was stirred at rt overnight. The mixture was then concentrated down and the residue was directly used in the next reaction.

Preparation of (S)-2-amino-2-(4-chloro-3-(1-(difluoromethyl)-1H-1,2,4-triazol-5-yl)phenyl)ethan-1-ol Hydrochloride

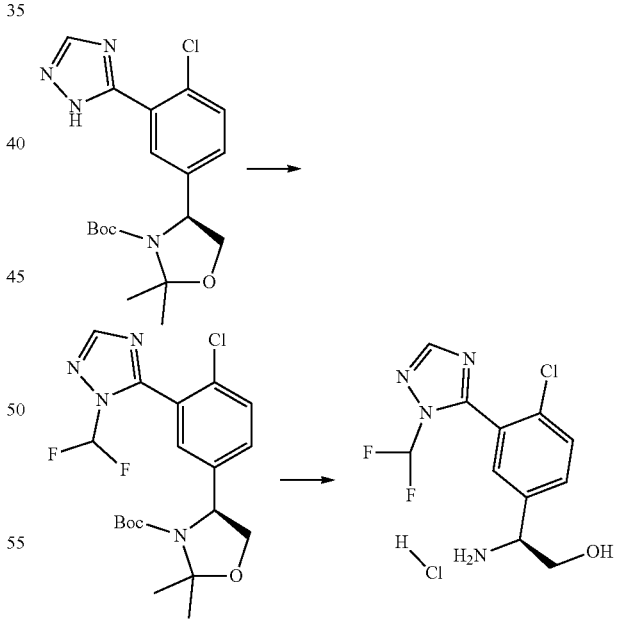

Preparation of tert-butyl (S)-4-(4-chloro-3-(1-(difluoromethyl)-1H-1,2,4-triazol-5-yl)phenyl)-2,2-dimethyloxazolidine-3-carboxylate: To a solution of tert-butyl (S)-4-(4-chloro-3-(1H-1,2,4-triazol-5-yl)phenyl)-2,2-dimethyloxazolidine-3-carboxylate (2.4 g, 6.3 mmol) in toluene (100 mL) was added potassium hydroxide solution (25% wt, 8 mL, 0.04 mol). Then to the mixture was added trimethyl(bromodifluoromethyl)silane (1.6 mL, 0.01 mol) in two portions. The reaction was stirred at 0° C. for 5 min and then stirred at rt for 1 h. The reaction mixture was treated with saturated ammonium chloride solution and extracted with EtOAc. The organic phase was washed with brine/ water, dried (over Na$_2$SO$_4$), filtered, concentrated, and purified by silica gel column chromatography (10% acetone in (1/1 hexanes/DCM)) to give the product.

Preparation of (S)-2-amino-2-(4-chloro-3-(1-(difluoromethyl)-1H-1,2,4-triazol-5-yl)phenyl)ethan-1-ol hydrochloride: tert-butyl (S)-4-(4-chloro-3-(1-(difluoromethyl)-1H-1,2,4-triazol-5-yl)phenyl)-2,2-dimethyloxazolidine-3-carboxylate (654 mg, 1.52 mmol) was treated with HCl in dioxane (4M, 5 mL) at rt for 2 h. The reaction mixture was concentrated down and the residue was dissolved in HCl in MeOH (1.25 M, 10 mL) overnight. The reaction mixture was concentrated down and used directly in the next reaction.

Alternatively, this intermediate was prepared by the following procedure.

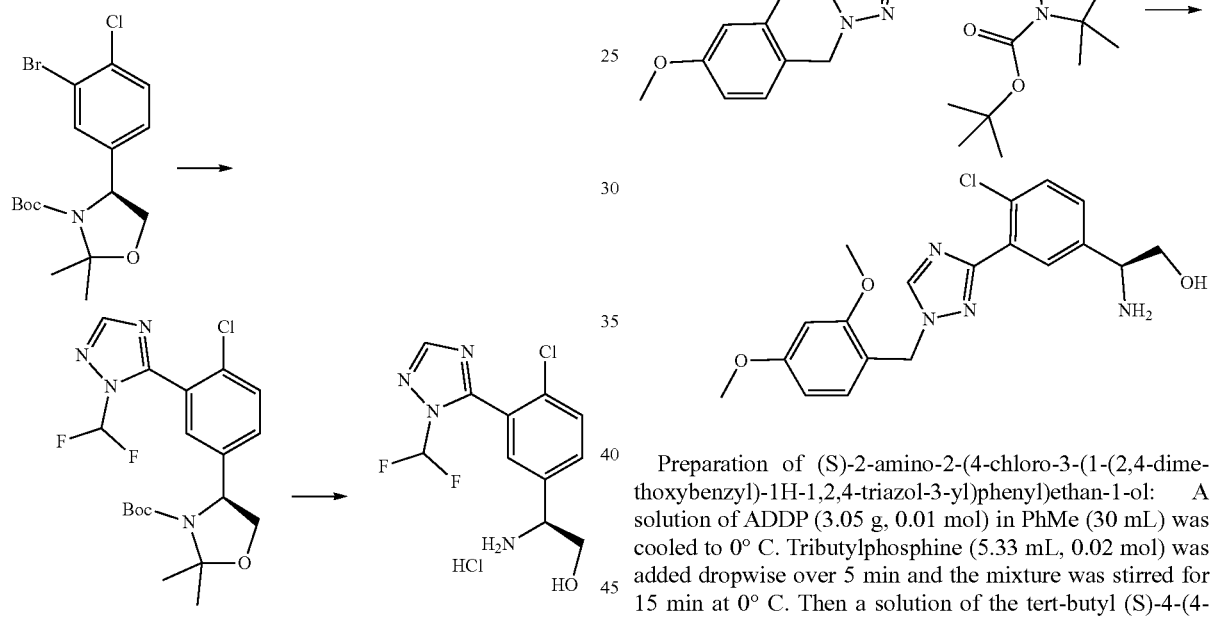

Preparation of tert-butyl (S)-4-(4-chloro-3-(1-(difluoromethyl)-1H-1,2,4-triazol-5-yl)phenyl)-2,2-dimethyloxazolidine-3-carboxylate: The mixture of tert-butyl (S)-4-(3-bromo-4-chlorophenyl)-2,2-dimethyloxazolidine-3-carboxylate (5 g, 0.013 mol), palladium(II) acetate (0.07 g, 0.64 mmol), n-butyl-di-(1-adamantyl)phosphonium iodide (0.62 g, 1.28 mmol) and potassium carbonate (5.31 g, 0.038 mol) was sparged with argon and then diluted with toluene (13 mL). Then 1-(difluoromethyl)-1H-1,2,4-triazole (1.83 g, 0.015 mol) were added. The biphasic mixture was sparged with argon for 15 min. Then the mixture was heated at 120° C. overnight. After cooling, the mixture was filtered through Celite and the filter cake was washed with EtOAc. The filtrate and the washing were combined, concentrated, and purified by silica gel column chromatography (0-100% gradient EtOAc/hexanes) to give the product.

Preparation of (S)-2-amino-2-(4-chloro-3-(1-(2,4-dimethoxybenzyl)-1H-1,2,4-triazol-3-yl)phenyl)ethan-1-ol

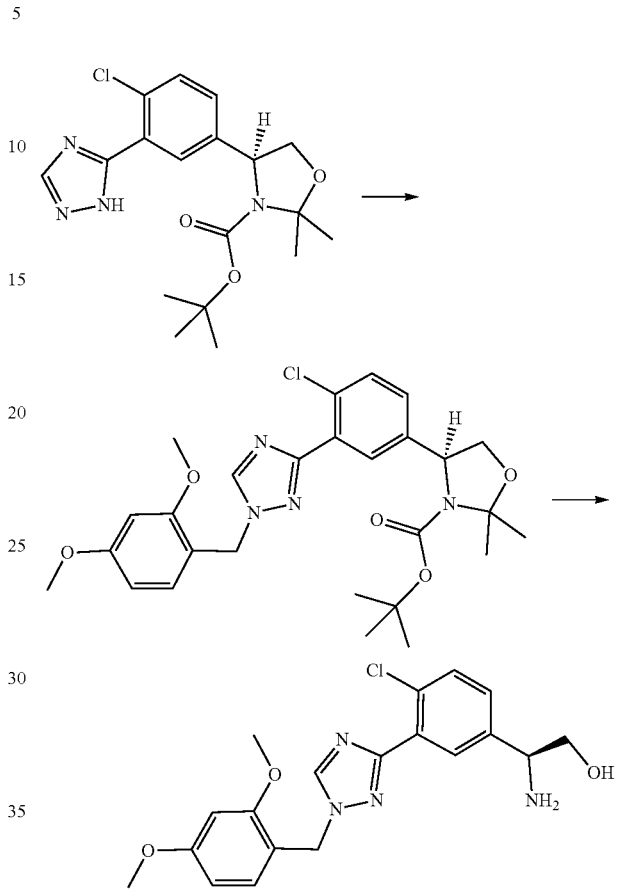

Preparation of (S)-2-amino-2-(4-chloro-3-(1-(2,4-dimethoxybenzyl)-1H-1,2,4-triazol-3-yl)phenyl)ethan-1-ol: A solution of ADDP (3.05 g, 0.01 mol) in PhMe (30 mL) was cooled to 0° C. Tributylphosphine (5.33 mL, 0.02 mol) was added dropwise over 5 min and the mixture was stirred for 15 min at 0° C. Then a solution of the tert-butyl (S)-4-(4-chloro-3-(1H-1,2,4-triazol-5-yl)phenyl)-2,2-dimethyloxazolidine-3-carboxylate (910 mg, 2 mmol) and 2,4-dimethoxybenzyl alcohol (1.01 g, 6 mmol) in CH$_3$CN (10 mL) was added to the reaction over a 1 min period, followed by a washing of PhMe (10 mL). The reaction mixture was kept at 0° C. for 15 min and then stirred at rt for 16 h. The reaction mixture was directly purified by silica gel column chromatography (EtOAc/hexanes) to give tert-butyl (S)-4-(4-chloro-3-(1-(2,4-dimethoxybenzyl)-1H-1,2,4-triazol-3-yl) phenyl)-2,2-dimethyloxazolidine-3-carboxylate (1.27 g, 2 mmol) which was treated with neat TFA (10 mL) at rt for 15 min. Then the mixture was concentrated down to 2 mL of TFA, and H$_2$O (50 mL) and DCM (50 mL) were added. The reaction was stirred vigorously for 1.5 h at rt. To the mixture was added 50% w/v aq KOH (3 mL). The resulting mixture was extracted with DCM. The organic phase was dried over Na$_2$SO$_4$, filtered, concentrated down and give the product.

Preparation of (S)-2-amino-2-(3-(1-(difluoromethyl)-1H-1,2,4-triazol-5-yl)-4-fluorophenyl)ethan-1-ol

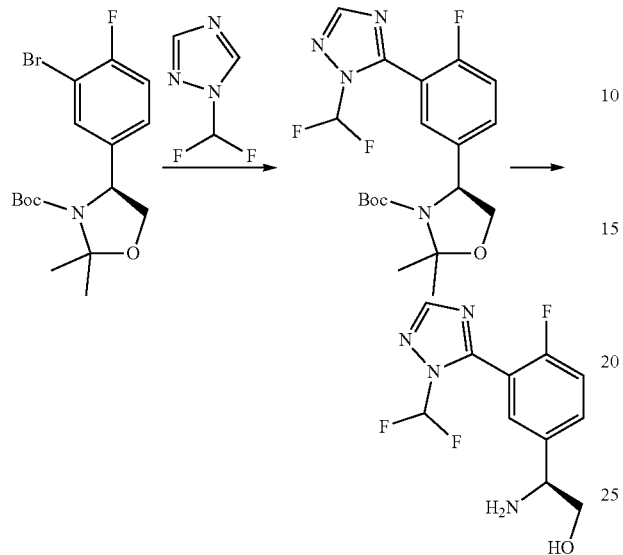

Preparation of (S)-2-amino-2-(3-(1-(difluoromethyl)-1H-1,2,4-triazol-5-yl)-4-fluorophenyl)ethan-1-ol: A mixture of tert-butyl (S)-4-(3-bromo-4-fluorophenyl)-2,2-dimethyloxazolidine-3-carboxylate (0.29 g, 0.762 mmol), palladium(II) acetate (0.016 g, 0.15 mmol), potassium carbonate (0.32 g, 1.7 mmol) and n-butyl-di-(1-adamantyl)phosphonium iodide (0.15 g, 0.30 mmol) was sparged with argon twice and then diluted with toluene (3 mL). Then 1-(difluoromethyl)-1H-1,2,4-triazole (0.27 g, 2.29 mol) and 2,2-dimethylbutyric acid (0.04 mL, 0.30 mmol) were added. The biphasic mixture was purged with argon for 15 min and stirred at 120° C. overnight. The reaction was cooled and filtered with Celite and the filter cake was washed with EtOAc. The filtrate and the washing were combined, concentrated, purified by silica gel column chromatography (EtOAc/hexanes) to give tert-butyl (S)-4-(3-(1-(difluoromethyl)-1H-1,2,4-triazol-5-yl)-4-fluorophenyl)-2,2-dimethyloxazolidine-3-carboxylate (0.27 g, 85%). This material treated with a mixture of TFA/water and stirred at rt for 3 h. The mixture was then concentrated down, stripping with toluene and used directly for the next reaction.

Preparation of (S)-2-amino-2-(4-chloro-3-(1-(methyl-d₃)-1H-tetrazol-5-yl)phenyl)ethan-1-ol

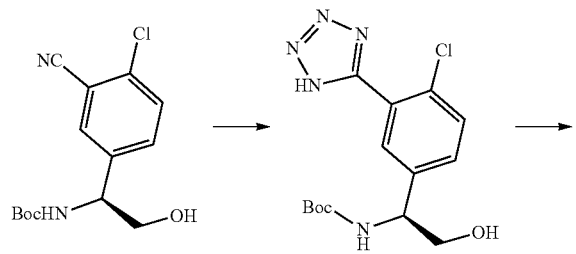

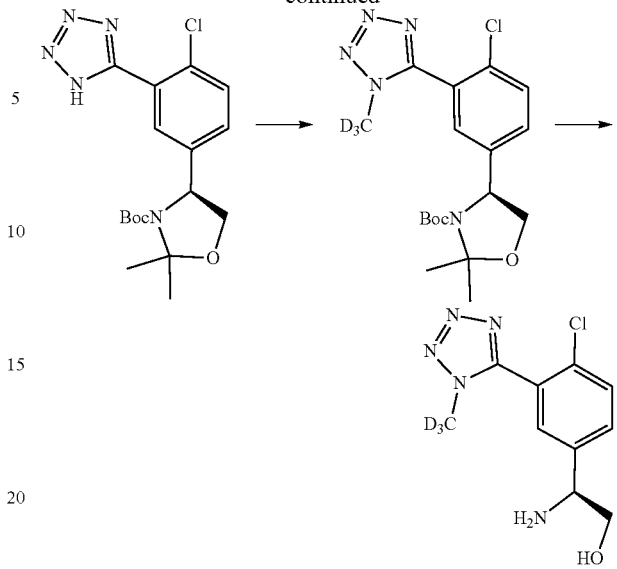

Preparation of tert-butyl (S)-(1-(4-chloro-3-(1H-tetrazol-5-yl)phenyl)-2-hydroxyethyl)carbamate: A mixture of tert-butyl (S)-(1-(4-chloro-3-cyanophenyl)-2-hydroxyethyl)carbamate (200 mg, 0.67 mmol), azidotrimethylsilane (0.36 mL, 2.7 mmol) and di-n-butyltin oxide (34 mg, 0.13 mmol) in toluene (5.0 mL) was stirred at 90° C. for 2 h. The reaction mixture was concentrated down and the residue was purified by silica gel column (1-100% gradient EtOAc/hexanes, followed by 1-50% gradient DCM/MeOH) to give the product.

Preparation of tert-butyl (S)-4-(4-chloro-3-(1H-tetrazol-5-yl)phenyl)-2,2-dimethyloxazolidine-3-carboxylate: A mixture of tert-butyl (S)-(1-(4-chloro-3-(1H-tetrazol-5-yl)phenyl)-2-hydroxyethyl)carbamate (0.07 g, 0.21 mmol), 2,2-dimethoxypropane (0.25 mL, 2.06 mmol) and para-toluenesulfonic acid monohydrate (3.9 mg, 0.021 mmol) in dichloromethane ($CH_2Cl_2$) (3 mL) was stirred at rt for 2 d. The reaction mixture was quenched by addition of saturated ammonium chloride solution and the mixture was extracted with $CH_2Cl_2$. The layers were separated and the aqueous layer was further extracted with $CH_2Cl_2$. The combined organic layers were washed with brine, dried (over $Na_2SO_4$), filtered, and concentrated in vacuo. The residue was purified by silica gel column chromatography (0-100% gradient EtOAc/hexanes) to give the product.

Preparation of tert-butyl (S)-4-(4-chloro-3-(1-(methyl-d₃)-1H-tetrazol-5-yl)phenyl)-2,2-dimethyloxazolidine-3-carboxylate: A mixture of tert-butyl (S)-4-(4-chloro-3-(1H-tetrazol-5-yl)phenyl)-2,2-dimethyloxazolidine-3-carboxylate (30 mg, 0.079 mmol), potassium carbonate (33 mg, 0.24 mmol) and iodomethane-d3 (0.05 mL, 0.79 mmol) in DMF (1.5 mL) was stirred at rt overnight. The reaction mixture was treated with water and extracted with EtOAc. The organic phase was dried over $MgSO_4$, filtered, and concentrated down. The residue was purified by silica gel column chromatography (0-100% gradient EtOAc/hexanes) to give the product.

Preparation of (S)-2-amino-2-(4-chloro-3-(1-(methyl-d₃)-1H-tetrazol-5-yl)phenyl)ethan-1-ol: A solution of tert-butyl (S)-4-(4-chloro-3-(1-(methyl-d₃)-1H-tetrazol-5-yl)phenyl)-2,2-dimethyloxazolidine-3-carboxylate (0.02 g, 0.05 mmol) in TFA (0.5 mL) was stirred at rt for 10 min. Then to the mixture was added a few drops of water and stirred at rt for 1 h. The reaction mixture was concentrated down, coevaporated with acetonitrile, and then the residue was dissolved in acetonitrile/water (1:1), lyophilized and used for the next reaction without further purification.

Preparation of (S)-2-amino-2-(4-chloro-3-(1-(difluoromethyl)-1H-1,2,4-triazol-5-yl)phenyl)ethyl (1-(trifluoromethyl)cyclopropyl)carbamate

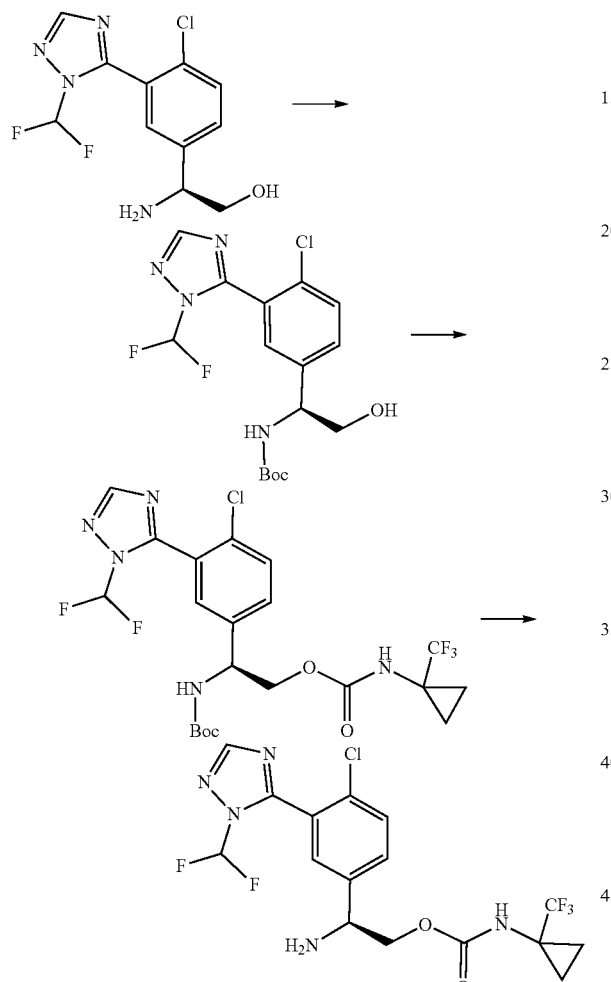

Preparation of tert-butyl (S)-(1-(4-chloro-3-(1-(difluoromethyl)-1H-1,2,4-triazol-5-yl)phenyl)-2-hydroxyethyl)carbamate: To a solution of (S)-2-amino-2-(4-chloro-3-(1-(difluoromethyl)-1H-1,2,4-triazol-5-yl)phenyl)ethan-1-ol (6.2 g, 0.02 mol) in THF (25 mL) were added Boc anhydride (7 g, 0.03 mol)) and N,N-diisopropylethylamine (11.2 mL, 0.06 mol) sequentially. The reaction was allowed to stir at room temperature for a couple of hours. The reaction mixture was partitioned between ethyl acetate and water. The organic layer was dried over magnesium sulfate, filtered, and concentrated. The residue was loaded into 80 g silica gel cartridge and purified via column chromatography eluting with a 0-100% gradient of ethyl acetate in hexanes to give the product.

Preparation of (S)-2-amino-2-(4-chloro-3-(1-(difluoromethyl)-1H-1,2,4-triazol-5-yl)phenyl)ethyl (1-(trifluoromethyl)cyclopropyl)carbamate: To a solution of tert-butyl (S)-(1-(4-chloro-3-(1-(difluoromethyl)-1H-1,2,4-triazol-5-yl)phenyl)-2-hydroxyethyl)carbamate (5 g, 12.9 mmol) in DCM (15 mL) were added 1-isocyanato-1-(trifluoromethyl)cyclopropane (0.73M in toluene) (70 mL, 51 mmol) and titanium (IV) tert-butoxide (5.0 mL, 12.9 mmol). The reaction mixture was stirred at room temperature for 3 h. After this time, the mixture was concentrated (up to 2 mL) and loaded into a 40 g silica gel cartridge, and purified via column chromatography eluting with a 0-100% gradient of ethyl acetate in hexanes. The product tert-butyl (S)-(1-(4-chloro-3-(1-(difluoromethyl)-1H-1,2,4-triazol-5-yl)phenyl)-2-(((1-(trifluoromethyl)cyclopropyl)carbamoyl)oxy)ethyl)carbamate was dissolved in 4M HCl/dioxane (24 mL) for 20 min. After this time, the crude mixture was concentrated and azeotroped with toluene (3×50 mL) to afford the product.

Preparation of (S)-2-amino-2-(4-chloro-3-(1-(difluoromethyl)-1H-1,2,4-triazol-5-yl)phenyl)ethyl (1-(difluoromethyl)cyclopropyl)carbamate

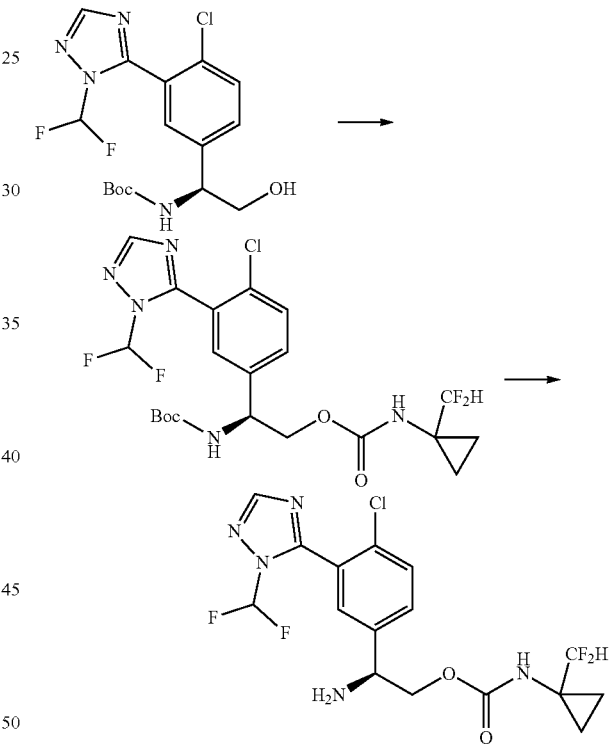

Preparation of tert-butyl (S)-(1-(4-chloro-3-(1-(difluoromethyl)-1H-1,2,4-triazol-5-yl)phenyl)-2-(((1-(difluoromethyl)cyclopropyl)carbamoyl)oxy)ethyl)carbamate: To a solution of 1-(difluoromethyl)-1-isocyanatocyclopropane in toluene (35 mmol in 50 ml toluene) was added a solution of tert-butyl (S)-(1-(4-chloro-3-(1-(difluoromethyl)-1H-1,2,4-triazol-5-yl)phenyl)-2-hydroxyethyl)carbamate (7.0 g, 18 mmol) in DCM (20 mL), followed by DIEA (3.13 mL, 18 mmol). Additional DCM (50 mL) was added. The reaction mixture was stirred at rt for 17 h. The mixture was then concentrated and the residue was purified by silica gel column chromatography (0-100% EtOAc/hexanes) to give the product.

Preparation of (S)-2-amino-2-(4-chloro-3-(1-(difluoromethyl)-1H-1,2,4-triazol-5-yl)phenyl)ethyl (1-(difluoromethyl)cyclopropyl)carbamate: A solution of tert-butyl (S)-(1-(4-chloro-3-(1-(difluoromethyl)-1H-1,2,4-triazol-5-yl)phenyl)-2-(((1-(difluoromethyl)cyclopropyl)carbamoyl)oxy)ethyl)carbamate (7.0 g, 13.4 mmol) in TFA (100 mL) was stirred at rt for 2 h. The mixture was then concentrated to dryness. The crude material was absorbed on silica gel and loaded unto a short silica gel column. Elution with 0-50% EtOAc/hexanes removed light yellow impurities. Then elution with 10% MeOH in EtOAc afforded the desired free base product.

Preparation of (S)-2-amino-2-(4-chloro-3-(5-(difluoromethyl)-1H-1,2,4-triazol-1-yl)phenyl)ethan-1-ol

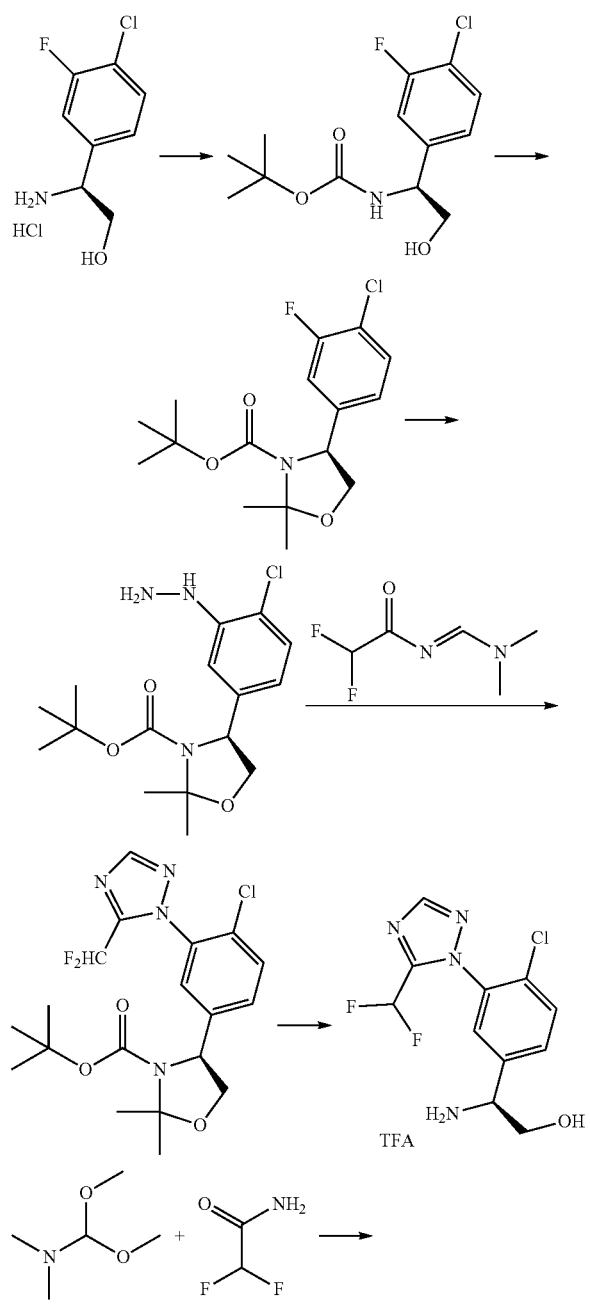

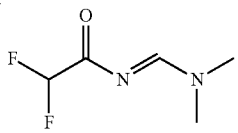

Preparation of tert-butyl (S)-(1-(4-chloro-3-fluorophenyl)-2-hydroxyethyl)carbamate: To a solution of the (S)-2-amino-2-(4-chloro-3-fluorophenyl)ethan-1-ol hydrochloride (3.0 g, 13.3 mmol) in THF (50 mL) were added Boc anhydride (3.6 g, 16.6 mmol) and N,N-diisopropylethylamine (3.86 g, 29.9 mmol). The mixture was stirred at rt overnight. The reaction mixture was treated with saturated aq NH$_4$Cl and extracted with EtOAc. The organic layer was separated and the aqueous layer was further extracted with EtOAc. The combined organic layers were washed with brine, dried (over Na$_2$SO$_4$), filtered, and concentrated in vacuo. The crude mixture was taken to the next reaction without further purification.

Preparation of tert-butyl (S)-4-(4-chloro-3-fluorophenyl)-2,2-dimethyloxazolidine-3-carboxylate: To a solution of tert-butyl (S)-(1-(4-chloro-3-fluorophenyl)-2-hydroxyethyl)carbamate in CH$_2$Cl$_2$ (50 mL) were added sequentially 2,2-dimethoxypropane (13.8 g, 133 mmol) and para-toluenesulfonic acid monohydrate (0.252 g, 1.33 mmol). The reaction mixture was maintained at rt overnight. The reaction mixture was treated with saturated aq. NH$_4$Cl and extracted with CH$_2$Cl$_2$. The two layers were separated and the aqueous layer was further extracted with CH$_2$Cl$_2$. The combined organic layers were washed with brine, dried (over Na$_2$SO$_4$), filtered, and concentrated in vacuo. The residue was purified by silica gel chromatography (eluting by EtOAc/hexanes) to afford the product (4.5 g, quantitative yield over 2 steps).

Preparation of tert-butyl (S)-4-(4-chloro-3-hydrazinylphenyl)-2,2-dimethyloxazolidine-3-carboxylate: A mixture of tert-butyl (S)-4-(4-chloro-3-fluorophenyl)-2,2-dimethyloxazolidine-3-carboxylate (2.29 g, 6.94 mmol) and hydrazine hydrate (20 g) was stirred at 100° C. in a capped pressure tube over weekend (3 days). The reaction mixture was treated with saturated NH$_4$Cl and extracted with EtOAc. The organic extract was washed by brine, dried (over Na$_2$SO$_4$), filtered, and concentrated in vacuo. The residue was purified by silica gel chromatography (eluting by EtOAc/hexanes) to give the product and the recovered unreacted starting material.

Preparation of tert-butyl (S)-4-(4-chloro-3-(5-(difluoromethyl)-1H-1,2,4-triazol-1-yl)phenyl)-2,2-dimethyloxazolidine-3-carboxylate: To a solution of the tert-butyl (S)-4-(4-chloro-3-hydrazinylphenyl)-2,2-dimethyloxazolidine-3-carboxylate (1.44 g, 4.21 mmol) in DMSO (12 mL) were sequentially added N-((dimethylamino)methylene)-2,2-difluoroacetamide (3.12 g, 21 mmol) and p-toluenesulfonic acid monohydrate (2.18 g, 12.6 mmol). The reaction mixture was stirred at rt. After 2 h, the reaction mixture was treated with saturated NH$_4$Cl (aq) and extracted with EtOAc. The organic layer was washed several times with diluted NH$_4$Cl (aq) to remove most of the polar byproducts. The organic layer was then dried (over Na$_2$SO$_4$), filtered, and concentrated in vacuo. The residue was dissolved in a minimum amount of EtOAc, and then hexanes was added slowly. The resulting solid was then collected by filtration, and dried under high vacuum to give the product.

Preparation of (S)-2-amino-2-(4-chloro-3-(5-(difluoromethyl)-1H-1,2,4-triazol-1-yl)phenyl)ethan-1-ol: tert-Butyl (S)-4-(4-chloro-3-(5-(difluoromethyl)-1H-1,2,4-triazol-1-yl)phenyl)-2,2-dimethyloxazolidine-3-carboxylate (0.60 g, 1.4 mmol) was dissolved in trifluoroacetic acid (12 mL) and the resulting purple pink solution was left stirring at rt for 10 min. Then to the mixture, water (2.5 mL) was added. After 4 h, the mixture was concentrated in vacuo, dissolved in CH₃CN/H₂O) (2:1), and freeze-dried. The crude product was used for the next reaction.

Preparation of N-((dimethylamino)methylene)-2,2-difluoroacetamide:

A suspension of 2,2-difluoroacetamide (5.0 g, 52.6 mmol) and N,N-dimethylformamide dimethyl acetal (9.4 g, 78.9 mmol) in toluene was stirred at rt for 1 h. The mixture became homogeneous was concentrated in vacuo. The residue was co-evaporated with toluene to remove the side product MeOH and unreacted dimethyl acetal. The resulting residue was purified by a short pad of silica gel column chromatography (just to remove polar impurities such as the unreacted dimethyl acetal starting material) to give the product.

Preparation of (S)-2-amino-2-(4-chloro-3-(5-(difluoromethyl)-1H-1,2,4-triazol-1-yl)phenyl)ethyl (1-(trifluoromethyl)cyclopropyl)carbamate

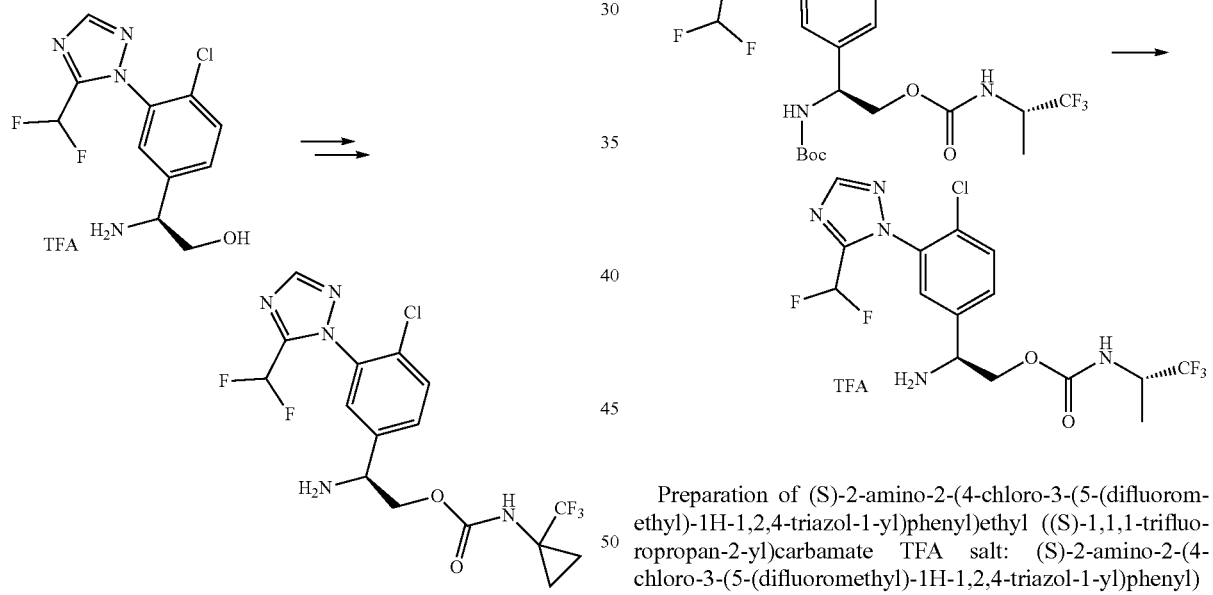

Preparation of (S)-2-amino-2-(4-chloro-3-(5-(difluoromethyl)-1H-1,2,4-triazol-1-yl)phenyl)ethyl (1-(trifluoromethyl)cyclopropyl)carbamate: (S)-2-amino-2-(4-chloro-3-(5-(difluoromethyl)-1H-1,2,4-triazol-1-yl)phenyl)ethyl (1-(trifluoromethyl)cyclopropyl)carbamate was prepared following the procedure to prepare (S)-2-amino-2-(4-chloro-3-(1-(difluoromethyl)-1H-1,2,4-triazol-5-yl)phenyl)ethyl (1-(trifluoromethyl)cyclopropyl)carbamate.

Preparation of (S)-2-amino-2-(4-chloro-3-(5-(difluoromethyl)-1H-1,2,4-triazol-1-yl)phenyl)ethyl ((S)-1,1,1-trifluoropropan-2-yl)carbamate TFA Salt

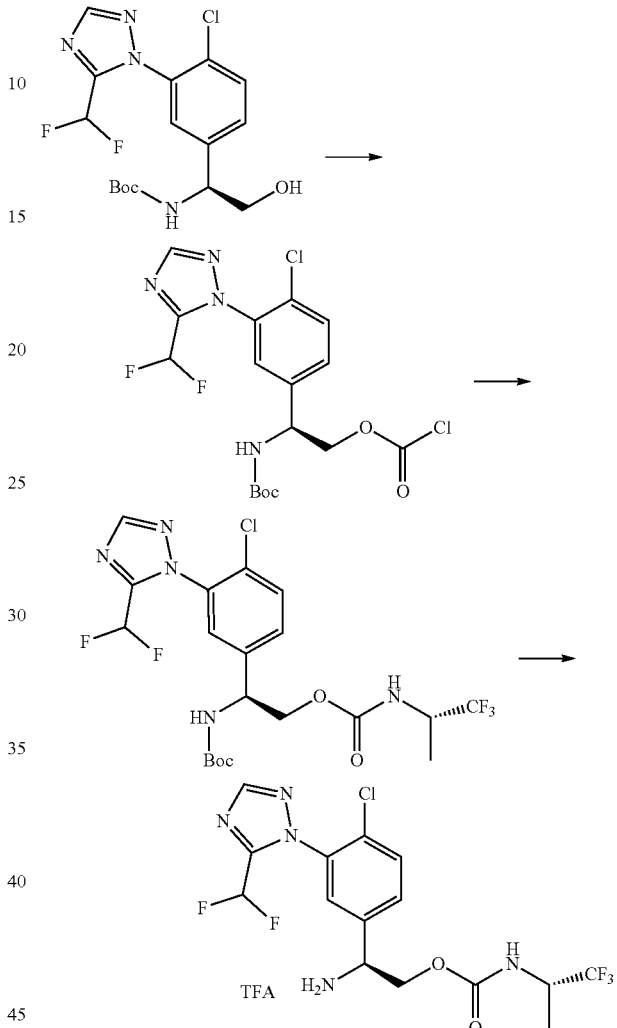

Preparation of (S)-2-amino-2-(4-chloro-3-(5-(difluoromethyl)-1H-1,2,4-triazol-1-yl)phenyl)ethyl ((S)-1,1,1-trifluoropropan-2-yl)carbamate TFA salt: (S)-2-amino-2-(4-chloro-3-(5-(difluoromethyl)-1H-1,2,4-triazol-1-yl)phenyl)ethyl ((S)-1,1,1-trifluoropropan-2-yl)carbamate TFA salt was prepared following the procedure to prepare Example 67, except that (S)-1,1,1-trifluoropropan-2-amine was used instead of 1-(difluoromethyl)cyclopropane-1-amine.

175

Preparation of (S)-2-amino-2-(4-chloro-3-(5-(difluoromethyl)-1H-1,2,4-triazol-1-yl)-5-fluorophenyl)ethan-1-ol TFA Salt

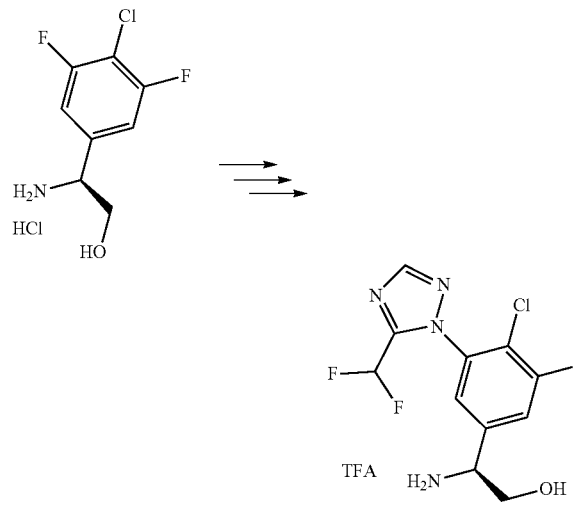

Preparation of (S)-2-amino-2-(4-chloro-3-(5-(difluoromethyl)-1H-1,2,4-triazol-1-yl)-5-fluorophenyl)ethan-1-ol TFA salt: (S)-2-amino-2-(4-chloro-3-(5-(difluoromethyl)-1H-1,2,4-triazol-1-yl)-5-fluorophenyl)ethan-1-ol TFA salt was prepared following the procedure to prepare (S)-2-amino-2-(4-chloro-3-(5-(difluoromethyl)-1H-1,2,4-triazol-1-yl)phenyl)ethan-1-ol TFA salt, except that (S)-2-amino-2-(4-chloro-3,5-difluorophenyl)ethan-1-ol hydrochloride was used instead of (S)-2-amino-2-(4-chloro-3-fluorophenyl)ethan-1-ol hydrochloride.

Preparation of (S)-2-amino-2-(4-chloro-3-(5-cyclopropyl-1H-1,2,4-triazol-1-yl)phenyl)ethan-1-ol

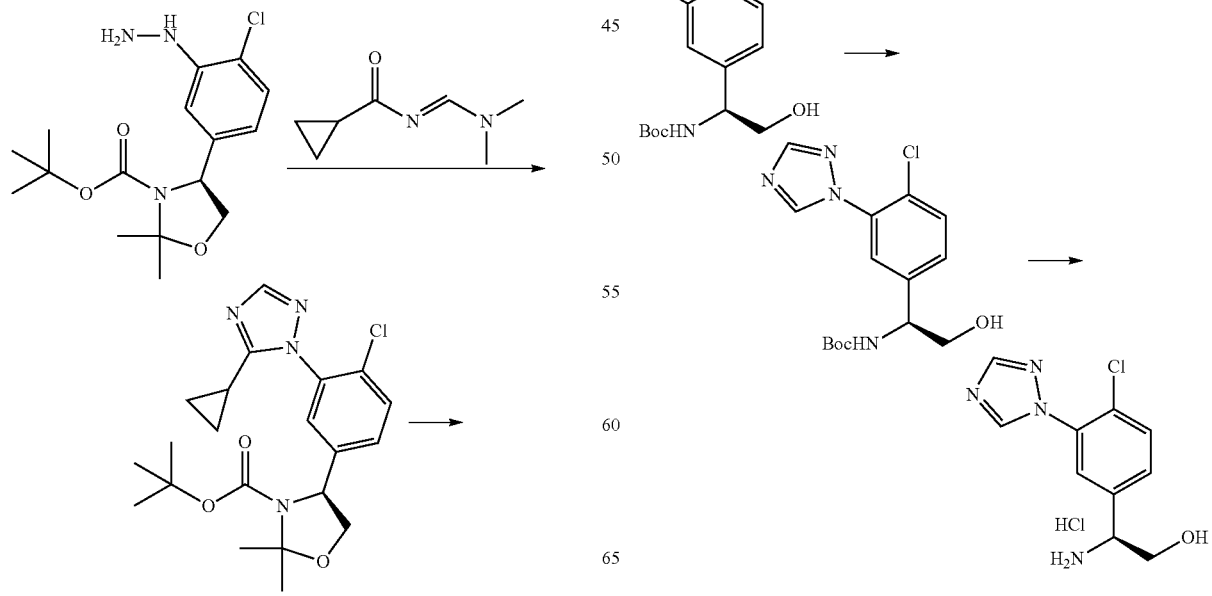

176

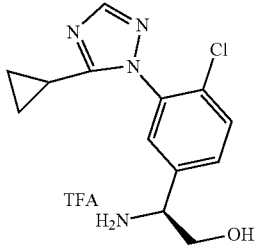

Preparation of tert-butyl (S)-4-(4-chloro-3-(5-(difluoromethyl)-1H-1,2,4-triazol-1-yl)phenyl)-2,2-dimethyloxazolidine-3-carboxylate: To a solution of tert-butyl (S)-4-(4-chloro-3-hydrazinylphenyl)-2,2-dimethyloxazolidine-3-carboxylate (100 mg, 0.29 mmol) in acetic acid (2.0 mL) was added N-dimethylamino)methylene)cyclopropanecarboxamide (246 mg, 1.76 mmol). The reaction mixture was stirred at rt overnight; The reaction mixture was diluted with toluene and concentrated. The residue was then quenched by adding saturated aq NaHCO₃ solution and extracted with EtOAc. The organic phase was washed with brine, dried (over Na₂SO₄), filtered and concentrated. The residue was purified by silica gel column chromatography (EtOAc/hexanes) to give the product (115 mg, 93%).

Preparation of (S)-2-amino-2-(4-chloro-3-(5-cyclopropyl-1H-1,2,4-triazol-1-yl)phenyl)ethan-1-ol: (S)-2-amino-2-(4-chloro-3-(5-cyclopropyl-1H-1,2,4-triazol-1-yl)phenyl)ethan-1-ol was prepared following the procedure to prepare (S)-2-amino-2-(4-chloro-3-(5-(difluoromethyl)-1H-1,2,4-triazol-1-yl)phenyl)ethan-1-ol, starting with tert-butyl (S)-4-(4-chloro-3-(5-(difluoromethyl)-1H-1,2,4-triazol-1-yl)phenyl)-2,2-dimethyloxazolidine-3-carboxylate.

Preparation of (S)-2-amino-2-(4-chloro-3-(1H-1,2,4-triazol-1-yl)phenyl)ethan-1-ol Hydrochloride Preparation of tert-butyl (S)-(1-(4-chloro-3-(1H-1,2,4-triazol-1-yl)phenyl)-2-hydroxyethyl)carbamate: A sparged mixture of bis(dibenzylideneacetone)palladium(O) (32.8 mg, 0.06 mmol) and 2-di-tert-butylphosphino-3,4,5,6-tetramethyl-2',4',6'-triisopropyl-1,1'-biphenyl (65.81 mg, 0.14 mmol) in dioxane (1 mL) was stirred at 120° C. for less than 5 min. After cooling to rt, this solution of activated catalyst was added to a sparged mixture of tert-butyl (S)-(1-(3-bromo-4-chlorophenyl)-2-hydroxyethyl)carbamate (200 mg, 0.57 mmol), 1,2,4-triazole (49 mg, 0.71 mmol) and cesium carbonate (372 mg, 1.14 mmol) in dioxane (1 mL). The reaction mixture was stirred at 90° C. overnight. The reaction mixture was diluted with ethyl acetate and filtered through a pad of Celite, and the filtrate was concentrated down. The residue was purified by silica gel column chromatography to (EtOAc/hexanes) to give the product.

Preparation of (S)-2-amino-2-(4-chloro-3-(1H-1,2,4-triazol-1-yl)phenyl)ethan-1-ol hydrochloride: To a solution of tert-butyl (S)-(1-(4-chloro-3-(1H-1,2,4-triazol-1-yl)phenyl)-2-hydroxyethyl)carbamate (140 mg, 0.41 mmol) in dioxane (4 mL) was added hydrochloride acid in dioxane (4M, 0.62 mL). The reaction was stirred at rt overnight. Then the reaction mixture was diluted with toluene and concentrated down. This sequence was repeated twice to afford the crude ammonium salt, which was carried forward without further purification.

Preparation of (S)-2-amino-2-(4-chloro-3-(3-methyl-1H-1,2,4-triazol-1-yl)phenyl)ethan-1-ol Hydrochloride

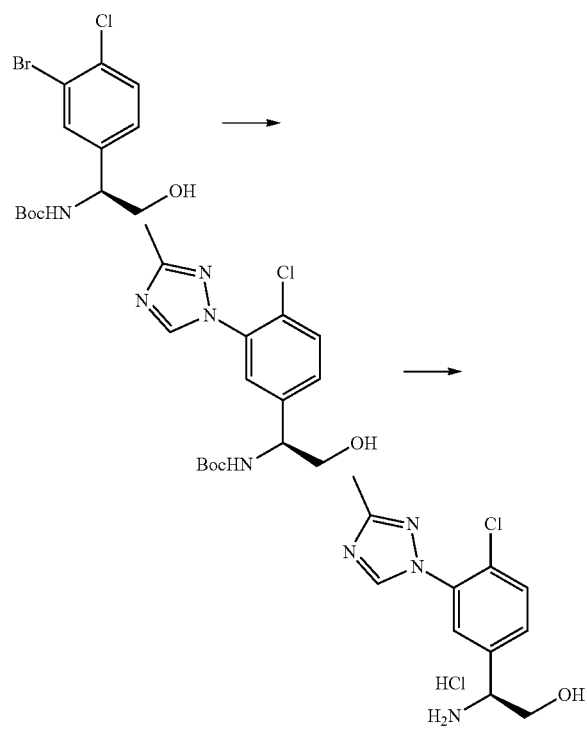

Preparation of (S)-2-amino-2-(4-chloro-3-(3-methyl-1H-1,2,4-triazol-1-yl)phenyl)ethan-1-ol hydrochloride: (S)-2-amino-2-(4-chloro-3-(3-methyl-1H-1,2,4-triazol-1-yl)phenyl)ethan-1-ol hydrochloride was prepared following the procedure to prepared (S)-2-amino-2-(4-chloro-3-(1H-1,2,4-triazol-1-yl)phenyl)ethan-1-ol hydrochloride.

Preparation of (S)-2-amino-2-(4-chloro-3-(1H-1,2,3-triazol-1-yl)phenyl)ethan-1-ol Hydrochloride

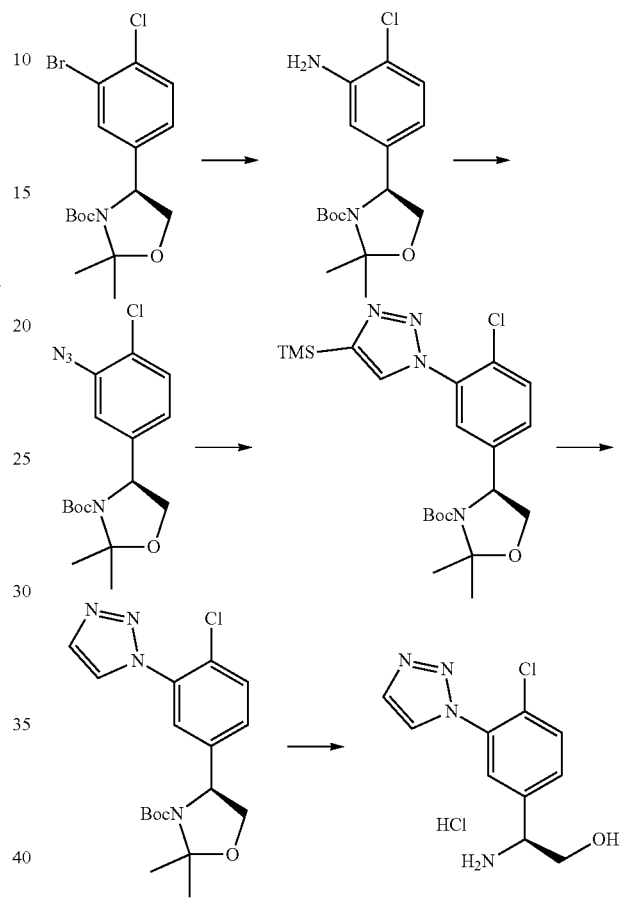

Preparation of tert-butyl (S)-4-(3-amino-4-chlorophenyl)-2,2-dimethyloxazolidine-3-carboxylate: A sparged solution of tert-butyl (S)-4-(3-bromo-4-chlorophenyl)-2,2-dimethyloxazolidine-3-carboxylate (200 mg, 0.51 mmol), sodium azide (67 mg, 1.02 mmol), copper(I) iodide (97 mg, 0.51 mmol), trans-N,N'-dimethyl-1,2-cyclohexanediamine (0.08 mL, 0.51 mmol) and (+)-sodium L-ascorbate (206 mg, 1.02 mmol) in ethanol (4 mL) and water (1.5 mL) was stirred for 12 h at 90° C. The reaction mixture was cooled to rt and filtered through a pad of Celite. The organic layer from the filtrate was separated and the aqeuous layer was extracted with EtOAc. The organic extracts were combined, dried (over sodium sulfate), filtered, and concentrated. The residue was purified by silica gel column chromatography (0-100% gradient EtOAc/hexanes) to give the product.

Preparation of tert-butyl (S)-4-(3-azido-4-chlorophenyl)-2,2-dimethyloxazolidine-3-carboxylate: To a solution of tert-butyl (S)-4-(3-amino-4-chlorophenyl)-2,2-dimethyloxazolidine-3-carboxylate in acetonitrile (5.0 mL) and THF (2.5 mL) was added azidotrimethylsilane (0.11 mL, 0.84 mmol) and tert-butyl nitrite (0.13 mL, 1.11 mmol) at 0° C. The reaction mixture was stirred at 0° C. for 1 h. The reaction mixture was concentrated down. The residue was purified by silica gel column chromatography (0-100% gradient EtOAc/hexanes) to give the product.

Preparation of tert-butyl (S)-4-(4-chloro-3-(4-(trimethylsilyl)-1H-1,2,3-triazol-1-yl)phenyl)-2,2-dimethyloxazolidine-3-carboxylate: To a solution of tert-butyl (S)-4-(3-azido-4-chlorophenyl)-2,2-dimethyloxazolidine-3-carboxylate (95 mg, 0.27 mmol) in toluene (2.7 mL) was added trimethylsilylacetylene (0.080 mL, 0.54 mmol). The reaction mixture heated at 110° C. for 1 h. The crude mixture was directly purified by silica gel column chromatography (0-100% gradient EtOAc/hexanes) to give the product.

Preparation of tert-butyl (S)-4-(4-chloro-3-(1H-1,2,3-triazol-1-yl)phenyl)-2,2-dimethyloxazolidine-3-carboxylate: To a solution of tert-butyl (S)-4-(4-chloro-3-(4-(trimethylsilyl)-1H-1,2,3-triazol-1-yl)phenyl)-2,2-dimethyloxazolidine-3-carboxylate (90 mg, 0.2 mmol) in THF (2.0 mL) was added tetrabutylammonium fluoride solution in THF (1 M, 0.3 mL). The reaction was stirred at rt for 3 h, then quenched by the addition of saturated ammonium chloride solution and EtOAc. The layers were separated and the aqueous layer was further extracted with EtOAc. The combined organic layers were washed with brine, dried (over $Na_2SO_4$), filtered and concentrated. The residue was purified by silica gel column chromatography (0-100% gradient EtOAc/hexanes) to give the product.

Preparation of (S)-2-amino-2-(4-chloro-3-(1H-1,2,3-triazol-1-yl)phenyl)ethan-1-ol hydrochloride: To a solution of tert-butyl (S)-4-(4-chloro-3-(1H-1,2,3-triazol-1-yl)phenyl)-2,2-dimethyloxazolidine-3-carboxylate (80 mg, 0.21 mmol) in dioxane (2.0 mL) was added hydrochloric acid in dioxane (4M, 0.21 mL). The reaction mixture was stirred at rt for 6 h, then diluted with toluene, and concentrated down. This sequence was repeated twice to afford the product in sufficient purity to carry forward.

Preparation of (S)-2-amino-2-(4-chloro-3-(1H-tetrazol-1-yl)phenyl)ethan-1-ol

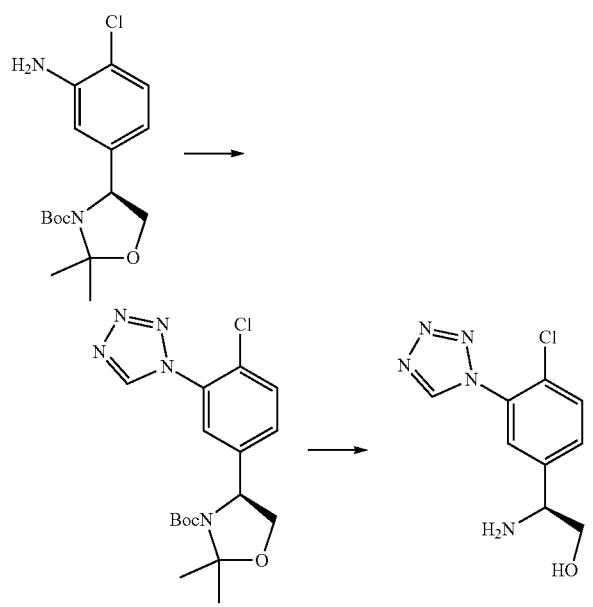

Preparation of tert-butyl (S)-4-(4-chloro-3-(1H-tetrazol-1-yl)phenyl)-2,2-dimethyloxazolidine-3-carboxylate: To a solution of tert-butyl (S)-4-(3-amino-4-chlorophenyl)-2,2-dimethyloxazolidine-3-carboxylate (150 mg, 0.46 mmol) in acetic acid (4 mL) was added sequentially trimethyl orthoformate (0.15 mL, 1.4 mmol) and sodium azide (90 mg, 1.4 mmol). The reaction mixture was stirred at rt for 3 h. The reaction mixture was diluted with toluene, and then concentrated in vacuo. This sequence was repeated twice. The residue was partitioned between sat. $NaHCO_3$ solution and EtOAc. The layers were separated and the aqueous layer was further extracted with EtOAc. The combined organic layers were washed with brine, dried (over $Na_2SO_4$), filtered and concentrated in vacuo. The residue was purified by silica gel column chromatography (0-100% EtOAc/hexanes) to give the product.

Preparation of (S)-2-amino-2-(4-chloro-3-(1H-tetrazol-1-yl)phenyl)ethan-1-ol: To a solution of tert-butyl (S)-4-(4-chloro-3-(1H-tetrazol-1-yl)phenyl)-2,2-dimethyloxazolidine-3-carboxylate (150 mg, 0.39 mmol) (80 mg, 0.21 mmol) in dioxane (4.0 mL) was added hydrochloric acid in dioxane (4M, 0.79 mL). The reaction mixture was stirred at rt for 6 h, then diluted with toluene and concentrated. This sequence was repeated twice to afford the product in sufficient purity to carry forward.

Preparation of (S)-2-amino-2-(4-chloro-3-(2H-1,2,3-triazol-2-yl)phenyl)ethan-1-ol Hydrochloride

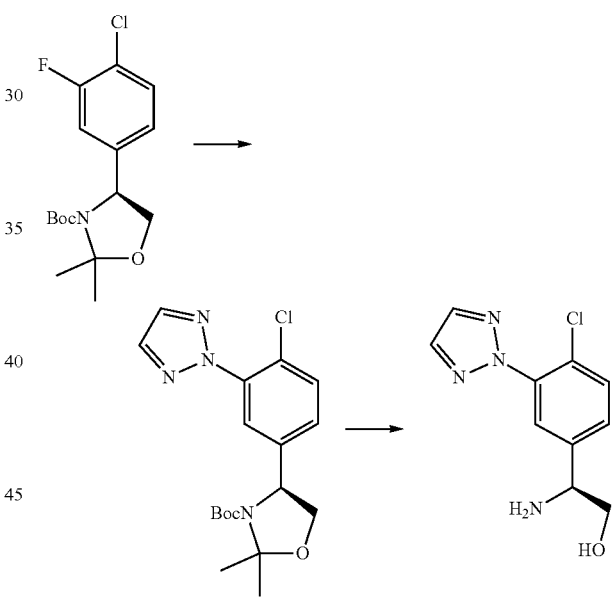

Preparation of tert-butyl (S)-4-(4-chloro-3-(2H-1,2,3-triazol-2-yl)phenyl)-2,2-dimethyloxazolidine-3-carboxylate: To a solution of tert-butyl (S)-4-(4-chloro-3-fluorophenyl)-2,2-dimethyloxazolidine-3-carboxylate (60 mg, 0.18 mmol) in NMP (5 mL) was added 1H-1,2,3-triazole (62.8 mg, 0.91 mmol) and cesium carbonate (296 mg, 0.91 mmol). The reaction mixture was degassed with nitrogen and heated at 100° C. for 16 h. The mixture was treated with water and extracted with EtOAc. The organic phase was washed with water and then with brine, dried (over $Na_2SO_4$), filtered and concentrated. The residue was purified by silica gel column chromatography (EtOAc/hexanes) to give the product (22 mg, 32%).

Preparation of (S)-2-amino-2-(4-chloro-3-(2H-1,2,3-triazol-2-yl)phenyl)ethan-1-ol hydrochloride: To a solution of tert-butyl (S)-4-(4-chloro-3-(2H-1,2,3-triazol-2-yl)phenyl)-2,2-dimethyloxazolidine-3-carboxylate (22 mg, 0.06 mmol)

in dioxane (1 mL) was added hydrogen chloride in dioxane solution (4.0 M, 1 mL). The reaction mixture was stirred for 3 h. The reaction mixture was then concentrated to give a solid, which was used for the next step directly.

Preparation of (S)-2-amino-2-(5-chloro-4-(1H-1,2,4-triazol-1-yl)pyridin-2-yl)ethan-1-ol

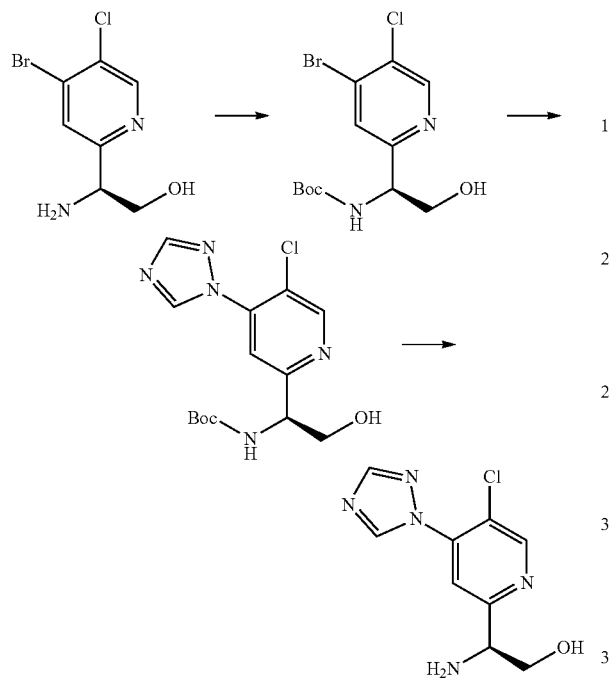

Preparation of tert-butyl (S)-(1-(4-bromo-5-chloropyridin-2-yl)-2-hydroxyethyl)carbamate: To a solution of (S)-2-amino-2-(4-bromo-5-chloropyridin-2-yl)ethan-1-ol (3.0 g, 0.012 mol) in THF (5 mL) and water (0.5 mL) was added di-tert-butyl dicarbonate (3.29 mL, 0.014 mol) and N,N-diisopropylethylamine (6.23 mL, 0.036 mol). The reaction was stirred at rt for 2 days. The crude mixture was treated with ethyl acetated and water. The organic phase was dried over magnesium sulfate, filtered, and concentrated. The residue was purified by silica gel column chromatography (0-100% gradient EtOAc/hexanes) to give the product.

Preparation of tert-butyl (S)-(1-(5-chloro-4-(1H-1,2,4-triazol-1-yl)pyridin-2-yl)-2-hydroxyethyl)carbamate: To a mixture of tert-butyl (S)-(1-(4-bromo-5-chloropyridin-2-yl)-2-hydroxyethyl)carbamate (0.2 g, 0.57 mmol), 1,2,4-triazole (0.08 g, 1.14 mmol) and cesium carbonate (0.15 g, 0.42 mmol) in dioxane (2 mL) was added a solution of bis(dibenzylideneacetone)palladium(O) (0.03 g, 0.052 mmol) and 2-di-tert-butylphosphino-3,4,5,6-tetramethyl-2',4',6'-triisopropyl-1,1'-biphenyl (0.07 g, 0.145 mmol) in dioxane (2 mL) which was pre-heated at 120° C. for 3 min. The reaction was then heated at 100° C. overnight. The mixture was treated with ethyl acetate and water. The organic layer was separated, dried over magnesium sulfate, filtered, and concentrated. The residue was purified by silica gel column chromatography (0-100% gradient EtOAc/hexanes) to give the product.

Preparation of (S)-2-amino-2-(5-chloro-4-(1H-1,2,4-triazol-1-yl)pyridin-2-yl)ethan-1-ol: To a solution of tert-butyl (S)-(1-(5-chloro-4-(1H-1,2,4-triazol-1-yl)pyridin-2-yl)-2- hydroxyethyl)carbamate (25 mg, 0.075 mmol) in dioxane (1 mL) was added hydrogen chloride in dioxane solution (4.0 M, 1 mL). The reaction mixture was stirred for 3 h. The reaction mixture was then concentrated to give the product, which was used for the next step directly.

Preparation of 1-(difluoromethyl)-1-isocyanatocyclopropane

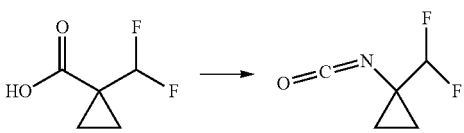 [SMILES: O=C(O)C1(C(F)F)CC1 ; O=C=NC1(C(F)F)CC1]

To a 2000-mL 3-necked round-bottom flask, purged and maintained with an inert atmosphere of nitrogen were placed a solution of 1-(difluoromethyl)cyclopropane-1-carboxylic acid (36 g, 265 mmol) in toluene (1000 mL), DPPA (76.4 g, 278 mmol) and TEA (29.4 g, 291 mmol). The mixture was stirred for 3 h at 100° C. in an oil bath. The crude product was purified by atmospheric distillation and the fraction was collected at 110° C. Fractions containing the desired product were collected and used for the next step.

Example 1: Preparation of Compound 1

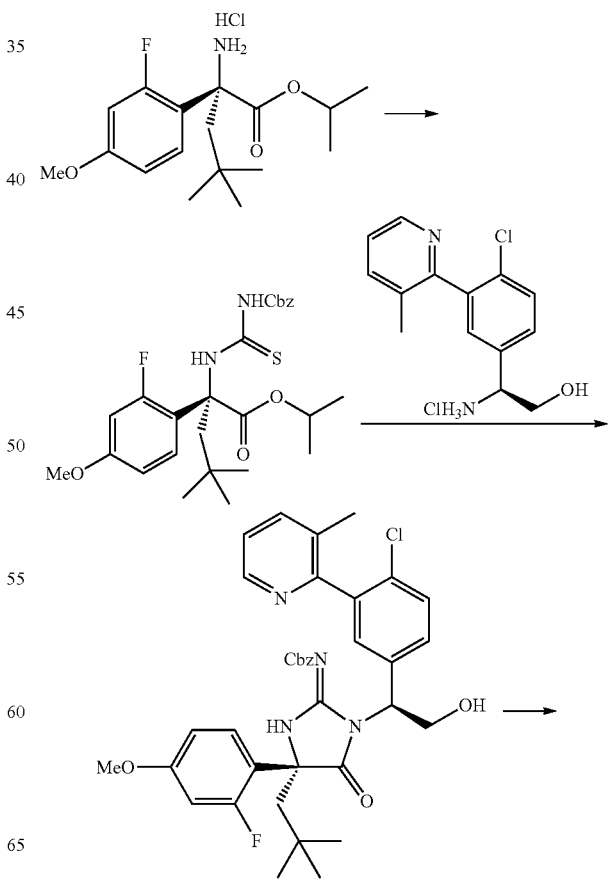

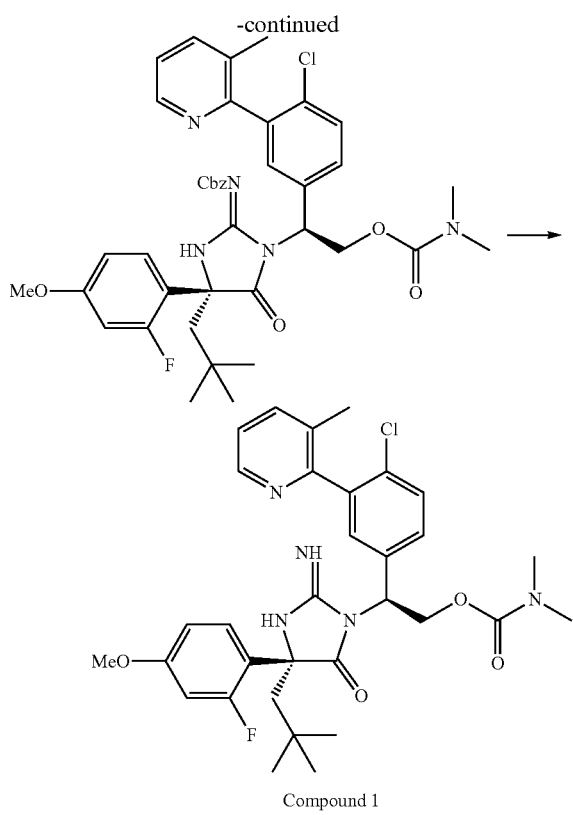

Compound 1

Preparation of isopropyl (R)-2-(3-((benzyloxy)carbonyl) thioureido)-2-(2-fluoro-4-methoxyphenyl)-4,4-dimethylpentanoate: To a biphasic solution of isopropyl (R)-2-amino-2-(2-fluoro-4-methoxyphenyl)-4,4-dimethylpentanoate hydrochloride (0.5 g, 1.44 mmol) in EtOAc (4 mL) and saturated sodium bicarbonate (3 mL) was added O-benzyl carbonisothiocyanatidate (0.28 g, 1.44 mmol, prepared according to the procedure described in Journal of Medicinal Chemistry, 56(2), 451-459; 2013). The reaction mixture was stirred for 30 min. The layers were separated and the aqueous layer was further extracted with EtOAc. The combined organic layers were washed with brine, dried (over $Na_2SO_4$), filtered, and concentrated in vacuo. The residue was purified by silica column chromatography (0-100% EtOAc/hexanes) to give the product.

Preparation of benzyl ((R)-1-((S)-1-(4-chloro-3-(3-methylpyridin-2-yl)phenyl)-2-hydroxyethyl)-4-(2-fluoro-4-methoxyphenyl)-4-neopentyl-5-oxoimidazolidin-2-ylidene) carbamate: To a solution of isopropyl (R)-2-(3-((benzyloxy) carbonyl)thioureido)-2-(2-fluoro-4-methoxyphenyl)-4,4-dimethylpentanoate (0.08 g, 0.17 mmol), (S)-2-amino-2-(4-chloro-3-(3-methylpyridin-2-yl)phenyl)ethan-1-ol hydrochloride (0.05 g, 0.17 mmol) and N-(3-dimethylaminopropyl)-N'-ethylcarbodiimide hydrochloride (0.05 g, 0.25 mmol) (EDCI) in DMF (1.0 mL) was added N,N-diisopropylethylamine (0.15 mL, 0.84 mmol). The reaction mixture was stirred at 55° C. overnight. The reaction mixture was quenched by addition of saturated ammonium chloride solution and EtOAc. The layers were separated and the aqueous layer was further extracted with EtOAc. The combined organic layers were washed with 10% lithium chloride (aq) and then with brine, dried (over $Na_2SO_4$), filtered, and concentrated. The residue was purified by silica gel column chromatography (0-100% EtOAc/hexanes) to give the product.

Preparation of (S)-2-((R)-2-(((benzyloxy)carbonyl) imino)-4-(2-fluoro-4-methoxyphenyl)-4-neopentyl-5-oxoimidazolidin-1-yl)-2-(4-chloro-3-(3-methylpyridin-2-yl) phenyl)ethyl dimethylcarbamate: To a solution of benzyl ((R)-1-((S)-1-(4-chloro-3-(3-methylpyridin-2-yl)phenyl)-2-hydroxyethyl)-4-(2-fluoro-4-methoxyphenyl)-4-neopentyl-5-oxoimidazolidin-2-ylidene)carbamate (23 mg, 0.03 mmol) in dichloromethane (0.3 mL) were added 1,1'-carbonyldiimidazole (8.3 mg, 0.05 mmol) and N,N-diisopropylethylamine (0.01 mL, 0.07 mmol). The reaction was stirred at rt for 2 h. Then, dimethylamine in THF (2M, 0.14 mL) was added to the reaction mixture and stirred at rt for 30 min. The reaction mixture was quenched by addition of saturated aqueous ammonium chloride solution and extracted with ethyl acetate. The combined organic layers were washed with brine, dried (over $Na_2SO_4$), filtered, and concentrated. The residue was purified by silica gel column chromatography (0-100% EtOAc/hexanes) to give the product.

Preparation of Compound 1: To a solution of (S)-2-((R)-2-(((benzyloxy)carbonyl)imino)-4-(2-fluoro-4-methoxyphenyl)-4-neopentyl-5-oxoimidazolidin-1-yl)-2-(4-chloro-3-(3-methylpyridin-2-yl)phenyl)ethyl dimethylcarbamate (23 mg, 0.03 mmol) in dichloromethane (0.5 mL) (placed in a water bath to prevent any exotherm) was added iodotrimethylsilane (0.01 mL, 0.06 mmol). The reaction was stirred at rt for 15 min. The reaction mixture was quenched by addition of saturated aqueous $NaHCO_3$ and EtOAc. The layers were separated and the aqueous layer was further extracted with EtOAc. The combined organic layers were washed with brine, dried (over $Na_2SO_4$), filtered, and concentrated. The residue was purified by silica gel column chromatography (0-100% EtOAc/(3:1 $CH_2Cl_2$/hexanes)) to give the product. LCMS-ESI+ (m/z): calc'd for $C_{32}H_{37}ClFN_5O_4$: 610.2 $[M+H]^+$. found: 610.1 $[M+H]^+$. 1H NMR (400 MHz, Methanol-d4) δ 8.50-8.24 (m, 1H), 7.85-7.64 (m, 1H), 7.62-7.43 (m, 2H), 7.38 (dd, J=7.8, 4.8 Hz, 2H), 7.22-6.99 (m, 1H), 6.72-6.53 (m, 1H), 6.54-6.32 (m, 1H), 5.63-5.42 (m, 1H), 5.20-4.96 (m, 1H), 4.75 (s, 2H), 3.74 (d, J=1.1 Hz, 3H), 2.87 (s, 3H), 2.82 (s, 3H), 2.19 (t, J=16.7 Hz, 1H), 2.10-1.87 (m, 4H), 0.95 (s, 9H).

Example 2: Preparation of Compound 2

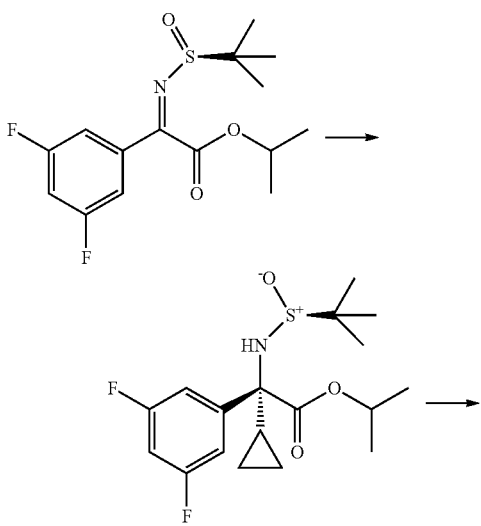

185
-continued

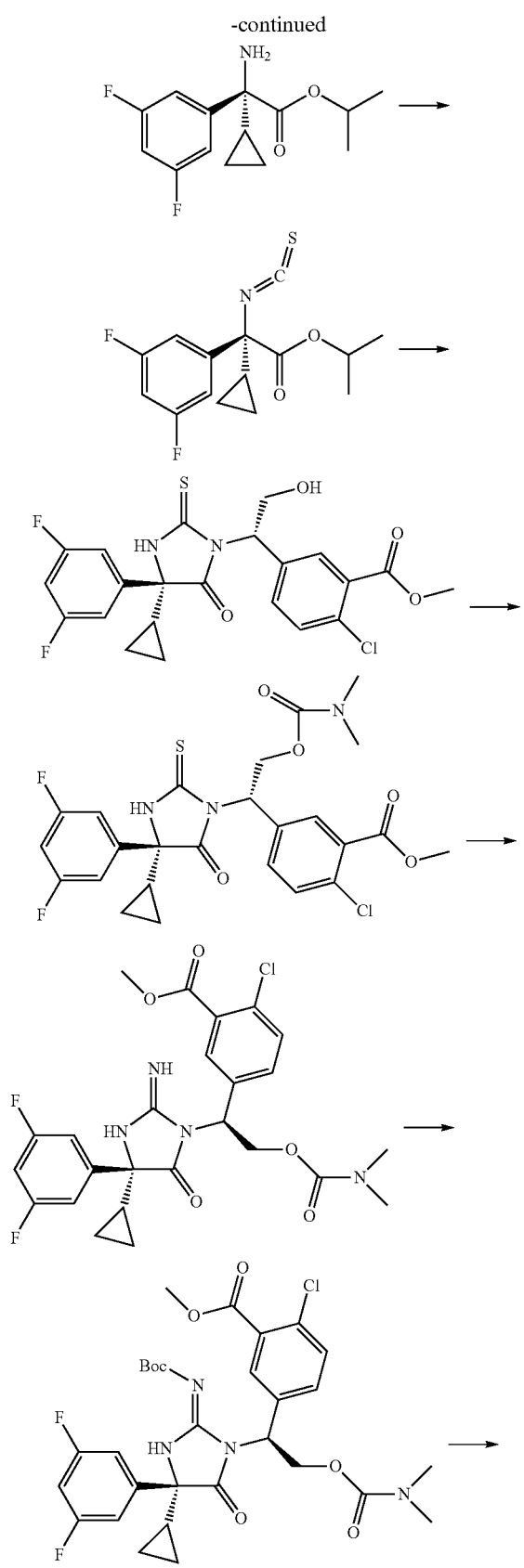

186
-continued

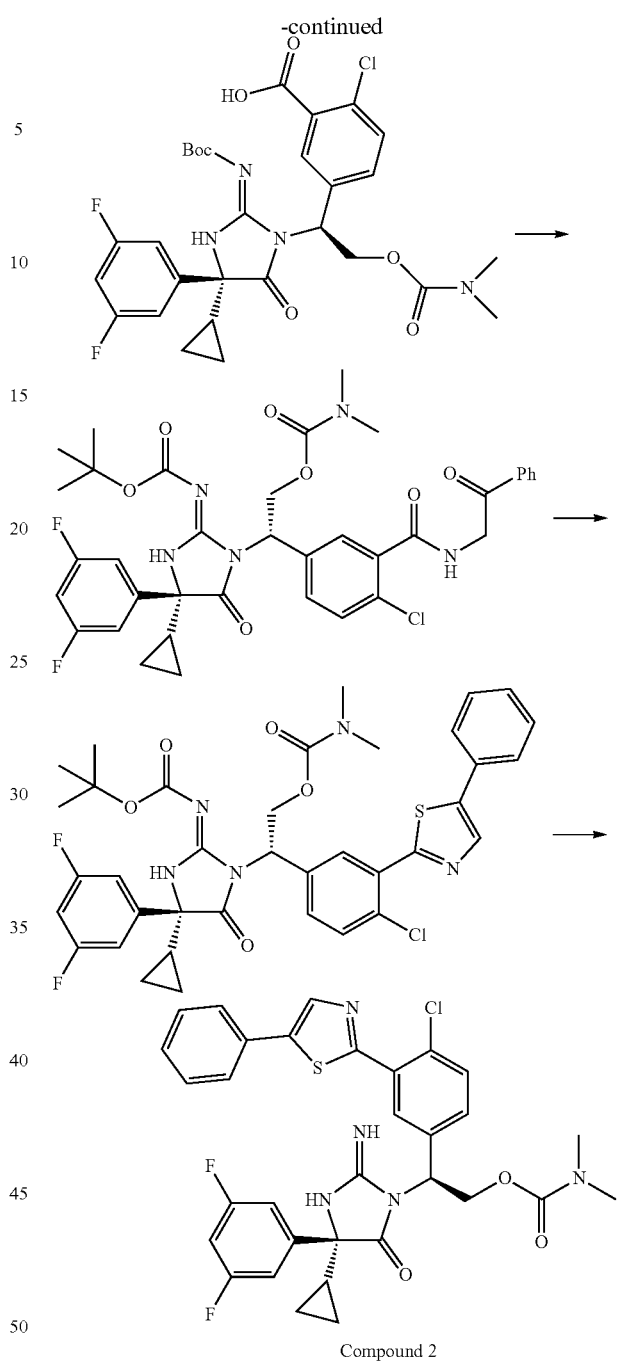

Compound 2

Preparation of isopropyl (R)-2-amino-2-cyclopropyl-2-(3,5-difluorophenyl)acetate: Isopropyl (R)-2-amino-2-cyclopropyl-2-(3,5-difluorophenyl)acetate was prepared following the procedure to prepare isopropyl (R)-2-amino-2-(2-fluoro-4-methoxyphenyl)-4,4-dimethylpentanoate, except that commercially available cyclopropylmagnesium bromide was used instead of neo-pentylmagnesium bromide.

Preparation of methyl isopropyl (R)-2-cyclopropyl-2-(3,5-difluorophenyl)-2-isothiocyanatoacetate: To a biphasic solution of isopropyl (R)-2-amino-2-cyclopropyl-2-(3,5-difluorophenyl)acetate (1.52 g, 3.97 mmol) in ethyl acetate (60 mL) and saturated NaHCO₃ solution (60 mL) was added thiophosgene (0.91 mL, 0.012 mol) at 0° C. The reaction mixture was allowed to warm to rt and stirred for 1 h. Then, the two layers were separated, and the organic phase was dried over sodium sulfate, and filtered. The filtrate was concentrated down and used in the next step without further purification.

Preparation of methyl 2-chloro-5-((S)-1-((R)-4-cyclopropyl-4-(3,5-difluorophenyl)-5-oxo-2-thioxoimidazolidin-1-yl)-2-hydroxyethyl)benzoate: A mixture of methyl isopropyl (R)-2-cyclopropyl-2-(3,5-difluorophenyl)-2-isothiocyanatoacetate (1.24 g, 3.97 mmol), methyl (S)-5-(1-amino-2-hydroxyethyl)-2-chlorobenzoate hydrochloride (1.37 g, 5.16 mmol), N,N-diisopropylethylamine (3.45 mL, 19.8 mmol) in 1-methyl-2-pyrrolidinone (8 mL) was heated at 95° C. for 1 h. The reaction mixture was diluted with water and extracted with EtOAc. The organic extract was washed by brine and concentrated. The residue was purified by silica gel column chromatography (0-100% gradient EtOAc/hexanes) to give the product.

Preparation of methyl 2-chloro-5-((S)-1-((R)-4-cyclopropyl-4-(3,5-difluorophenyl)-5-oxo-2-thioxoimidazolidin-1-yl)-2-((dimethylcarbamoyl)oxy)ethyl)benzoate: To a solution of methyl 2-chloro-5-((S)-1-((R)-4-cyclopropyl-4-(3,5-difluorophenyl)-5-oxo-2-thioxoimidazolidin-1-yl)-2-hydroxyethyl)benzoate (1.82 g, 3.78 mmol) in DCM (30 mL) were added N,N-diisopropylethylamine (1.61 mL, 9.26 mmol) and 1,1'-carbonyldiimidazole (1.05 g, 6.46 mmol). The reaction mixture was stirred at rt for 15 min. Then to the mixture was added dimethylamine in THF (2M, 9.46 mL). The reaction was stirred at rt for 5 min. The reaction mixture was diluted with EtOAc, and washed with water and then with brine. The organic phase was concentrated in vacuo. The residue was purified silica gel column chromatography (0-100% gradient EtOAc/hexanes) to give the product.

Preparation of methyl 2-chloro-5-((S)-1-((R)-4-cyclopropyl-4-(3,5-difluorophenyl)-2-imino-5-oxoimidazolidin-1-yl)-2-((dimethylcarbamoyl)oxy)ethyl)benzoate: To a solution of methyl 2-chloro-5-((S)-1-((R)-4-cyclopropyl-4-(3,5-difluorophenyl)-5-oxo-2-thioxoimidazolidin-1-yl)-2-((dimethylcarbamoyl)oxy)ethyl)benzoate (2.18 g, 3.95 mmol) in methanol (45 mL) were added $NH_4OH$ aqueous solution (13.8 mL, 0.12 mol) and t-BuOOH (75% in water, 7.62 mL, 59 mmol). The reaction was stirred at rt overnight. The reaction mixture was concentrated down and the residue was purified by silica gel column chromatography (EtOAc/hexanes) to give the product (1.05 g, 50%).

Preparation of methyl 5-((S)-1-((R)-2-((tert-butoxycarbonyl)imino)-4-cyclopropyl-4-(3,5-difluorophenyl)-5-oxoimidazolidin-1-yl)-2-((dimethylcarbamoyl)oxy)ethyl)-2-chlorobenzoate: To a solution of methyl 2-chloro-5-((S)-1-((R)-4-cyclopropyl-4-(3,5-difluorophenyl)-2-imino-5-oxoimidazolidin-1-yl)-2-((dimethylcarbamoyl)oxy)ethyl) benzoate (1.05 g, 1.96 mmol) in THF (15 mL) was added di-tert-butyl dicarbonate (0.9 mL, 3.93 mmol) and triethylamine (1.09 mL, 7.85 mmol) and stirred at rt for 18 h. The mixture was then concentrated down and the residue was purified by silica gel column chromatography (0-100% gradient EtOAc/hexanes) to give the product.

Preparation of 5-((S)-1-((R)-2-((tert-butoxycarbonyl)imino)-4-cyclopropyl-4-(3,5-difluorophenyl)-5-oxoimidazolidin-1-yl)-2-((dimethylcarbamoyl)oxy)ethyl)-2-chlorobenzoic acid: To a solution of methyl 5-((S)-1-((R)-2-((tert-butoxycarbonyl)imino)-4-cyclopropyl-4-(3,5-difluorophenyl)-5-oxoimidazolidin-1-yl)-2-((dimethylcarbamoyl)oxy)ethyl)-2-chlorobenzoate (1.0 g, 1.57 mmol) in THF (12 mL) and methanol (5 mL) was added sodium hydroxide solution (2M, 3.15 mL). The reaction was stirred at rt for 2 h. To the mixture, 1N HCl was added to quench the reaction. The reaction mixture was concentrated. The residue was dissolved in minimum amount of $CH_3CN$/water (1:1) and lyophilized to give the product.

Preparation of (S)-2-((R)-2-((tert-butoxycarbonyl)imino)-4-cyclopropyl-4-(3,5-difluorophenyl)-5-oxoimidazolidin-1-yl)-2-(4-chloro-3-((2-oxo-2-phenylethyl)carbamoyl)phenyl)ethyl dimethylcarbamate: To a solution of 5-((S)-1-((R)-2-((tert-butoxycarbonyl)imino)-4-cyclopropyl-4-(3,5-difluorophenyl)-5-oxoimidazolidin-1-yl)-2-((dimethylcarbamoyl)oxy)ethyl)-2-chlorobenzoic acid (40 mg, 0.064 mmol) in DCM (1 mL) and DMF (1 mL) were added O-(7-azabenzotriazol-1-yl)-N,N,N',N'-tetramethyluronium hexafluorophosphate (23 mg, 0.097 mol) and N,N-diisopropylethylamine (0.02 mL, 0.097 mmol). The reaction mixture was stirred at rt for 30 min. Then to the mixture was added 2-aminoacetophenone hydrochloride (17 mg, 0.097 mmol). The reaction was stirred at rt for 1 h. The reaction mixture was washed with brine and extracted with ethyl acetate. The organic layer were dried over magnesium sulfate, filtered and concentrated. The residue was purified by silica gel column chromatography (0-100% gradient EtOAc/hexanes) to give the product.

Preparation of (S)-2-((R)-2-((tert-butoxycarbonyl)imino)-4-cyclopropyl-4-(3,5-difluorophenyl)-5-oxoimidazolidin-1-yl)-2-(4-chloro-3-(5-phenylthiazol-2-yl)phenyl)ethyl dimethylcarbamate: To a solution of (S)-2-((R)-2-((tert-butoxycarbonyl)imino)-4-cyclopropyl-4-(3,5-difluorophenyl)-5-oxoimidazolidin-1-yl)-2-(4-chloro-3-((2-oxo-2-phenyl)ethyl)carbamoyl)phenyl)ethyl dimethylcarbamate (20 mg, 0.027 mmol) in THF (1 mL) was added Lawesson's reagent (16 mg, 0.041 mmol). The reaction was stirred at 60° C. overnight. The reaction mixture was concentrated down and the residue was purified by silica gel column chromatography (0-100% gradient EtOAc/hexanes) to give the product.

Preparation of Compound 2: To a solution of (S)-2-((R)-2-((tert-butoxycarbonyl)imino)-4-cyclopropyl-4-(3,5-difluorophenyl)-5-oxoimidazolidin-1-yl)-2-(4-chloro-3-(5-phenylthiazol-2-yl)phenyl)ethyl dimethylcarbamate (13 mg, 0.018 mmol) in DCM (1.5 mL) was added trifluoroacetic acid (0.3 mL). The reaction was stirred at rt for 30 min. The reaction mixture was concentrated down and the residue was purified by prep-TLC (eluting with 80% ethyl acetate and 20% hexanes) to give the product. LCMS-ESI+ (m/z): calc'd for $C_{32}H_{28}ClF_2N_5O_3S$: 636.2 $[M+H]^+$. found: 636.0 $[M+H]^+$. $^1$H NMR (400 MHz, Methanol-$d_4$) δ 8.16 (s, 1H), 8.14-8.10 (m, 1H), 7.73-7.68 (m, 2H), 7.60 (d, J=8.4 Hz, 1H), 7.50-7.43 (m, 4H), 7.42-7.37 (m, 1H), 7.20-7.13 (m, 2H), 6.84 (tt, J=9.0, 2.4 Hz, 1H), 5.57 (dd, J=10.0, 4.8 Hz, 1H), 5.07 (dd, J=11.2, 10.0 Hz, 1H), 4.78 (dd, J=11.2, 4.9 Hz, 1H), 2.86 (d, J=21.5 Hz, 6H), 1.72-1.57 (m, 1H), 0.55 (dtt, J=21.8, 9.6, 4.4 Hz, 4H).

Example 3: Preparation of Compound 3

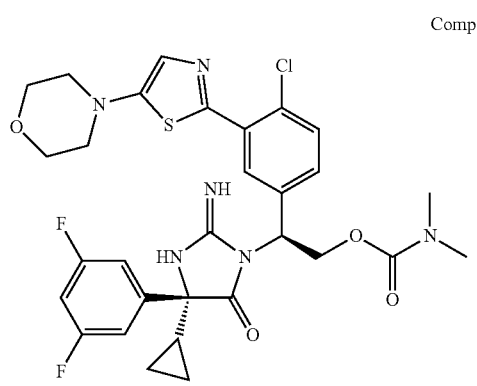

Compound 3

Compound 3 was prepared by following the procedure to prepare Compound 2, except that 2-amino-1-morpholin-4-ylethanone hydrochloride was used instead of 2-aminoacetophenone hydrochloride. LCMS-ESI+ (m/z): calc'd for $C_{30}H_{31}ClF_2N_6O_4S$: 645.2 [M+H]+. found: 645.2 [M+H]+. $^1$H NMR (400 MHz, Methanol-$d_4$) δ 7.97-7.93 (m, 1H), 7.52 (d, J=8.4 Hz, 1H), 7.37-7.32 (m, 1H), 7.20-7.13 (m, 2H), 7.13 (s, 1H), 6.95-6.87 (m, 1H), 5.55 (dd, J=10.0, 4.8 Hz, 1H), 5.05 (dd, J=11.3, 10.1 Hz, 1H), 4.75 (dd, J=11.3, 4.8 Hz, 1H), 3.89-3.81 (m, 4H), 3.24-3.17 (m, 4H), 2.85 (d, J=22.0 Hz, 6H), 1.65 (td, J=8.3, 4.2 Hz, 1H), 0.63-0.45 (m, 4H).

Example 4: Preparation of Compound 4

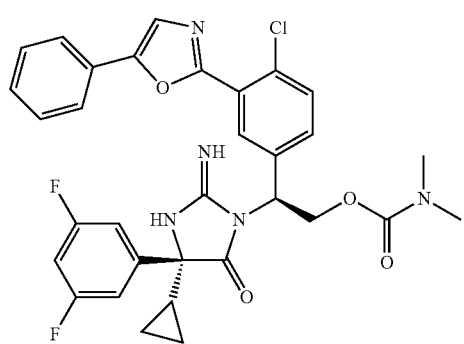

Compound 4

Compound 4 was prepared following the procedure to prepare Compound 2, except that (methoxycarbonylsulfamoyl)triethylammonium hydroxide (Burgess' reagent) and DCE were used instead of Lawesson's reagent and THF, respectively. LCMS-ESI+ (m/z): calc'd for $C_{32}H_{28}ClF_2N_5O_4$: 620.2 [M+H]+. found: 620.2 [M+H]+. 1H NMR (400 MHz, Methanol-$d_4$) δ 8.05-8.03 (m, 1H), 7.79-7.75 (m, 2H), 7.66 (s, 1H), 7.62 (d, J=8.4 Hz, 1H), 7.53-7.45 (m, 4H), 7.42-7.37 (m, 1H), 7.19-7.11 (m, 2H), 6.82 (t, J=9.0 Hz, 1H), 5.56 (d, J=8.3 Hz, 1H), 5.09 (t, J=10.6 Hz, 1H), 4.77 (dd, J=11.3, 4.9 Hz, 1H), 2.87 (d, J=20.4 Hz, 6H), 1.66 (s, 1H), 0.67-0.46 (m, 4H).

Example 5: Preparation of Compound 5

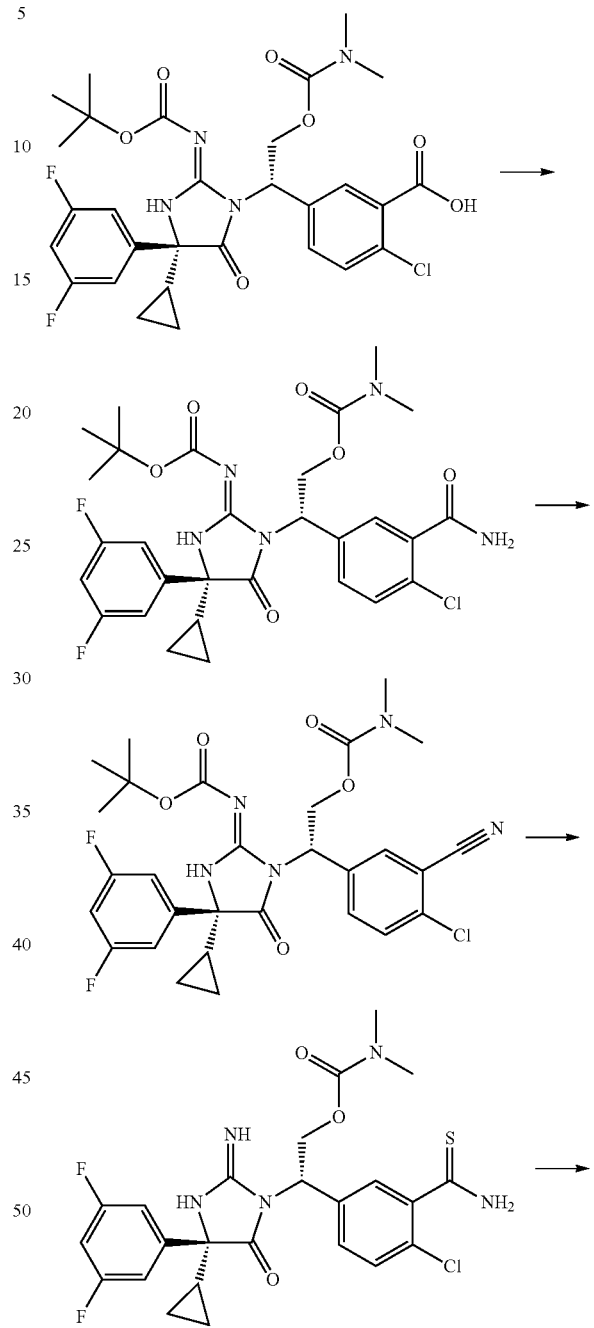

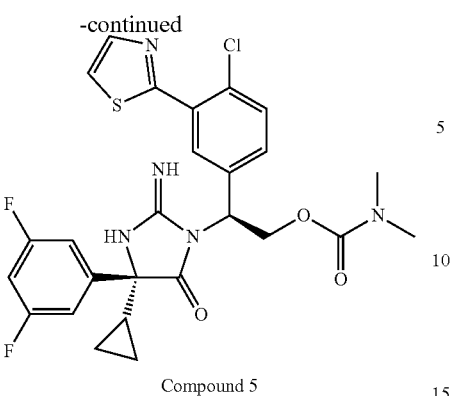

Compound 5

Preparation of (S)-2-((R)-2-((tert-butoxycarbonyl)imino)-4-cyclopropyl-4-(3,5-difluorophenyl)-5-oxoimidazolidin-1-yl)-2-(3-carbamoyl-4-chlorophenyl)ethyl dimethylcarbamate: To a solution of 5-((S)-1-((R)-2-((tert-butoxycarbonyl)imino)-4-cyclopropyl-4-(3,5-difluorophenyl)-5-oxoimidazolidin-1-yl)-2-((dimethylcarbamoyl)oxy)ethyl)-2-chlorobenzoic acid (20 mg, 0.032 mmol) in DCM (1.0 mL) was added N,N'-carbonyldiimidazole (5 mg, 0.032 mmol) and stirred at rt for 2 h. After this time, ammonia was bubbled to the mixture for 15 minutes and the reaction mixture was stirred overnight. The mixture was then partitioned between ethyl acetate and water. The organic layer was dried over magnesium sulfate, filtered, and concentrated. The residue was purified by silica gel column chromatography (eluting with (0-100% gradient EtOAc/hexanes) to give the product.

Preparation of (S)-2-((R)-2-((tert-butoxycarbonyl)imino)-4-cyclopropyl-4-(3,5-difluorophenyl)-5-oxoimidazolidin-1-yl)-2-(4-chloro-3-cyanophenyl)ethyl dimethylcarbamate: To a solution of (S)-2-((R)-2-((tert-butoxycarbonyl)imino)-4-cyclopropyl-4-(3,5-difluorophenyl)-5-oxoimidazolidin-1-yl)-2-(3-carbamoyl-4-chlorophenyl)ethyl dimethylcarbamate (20 mg, 0.032 mmol) in THF (1 mL) were added triethylamine (0.02 mL, 0.16 mmol) and trifluoroacetic anhydride (0.01 mL, 0.081 mmol). The reaction was stirred at rt for 1 h. The reaction mixture was then concentrated. The residue was purified by silica gel column chromatography (0-100% gradient EtOAc/hexanes) to give the product.

Preparation of (S)-2-(3-carbamothioyl-4-chlorophenyl)-2-((R)-4-cyclopropyl-4-(3,5-difluorophenyl)-2-imino-5-oxoimidazolidin-1-yl)ethyl dimethylcarbamate: To a solution of (S)-2-((R)-2-((tert-butoxycarbonyl)imino)-4-cyclopropyl-4-(3,5-difluorophenyl)-5-oxoimidazolidin-1-yl)-2-(4-chloro-3-cyanophenyl)ethyl dimethylcarbamate (40 mg, 0.065 mmol) in ethanol (1 mL) was added phosphorous pentasulfide (59 mg, 0.027 mmol). The reaction mixture was stirred at 60° C. overnight. The reaction mixture was concentrated down and the residue was purified by prep-TLC (eluting with 20% hexanes-80% ethyl acetate) to give the product (27 mg, 76%).

Preparation of Compound 5: To a solution of (S)-2-(3-carbamothioyl-4-chlorophenyl)-2-((R)-4-cyclopropyl-4-(3,5-difluorophenyl)-2-imino-5-oxoimidazolidin-1-yl)ethyl dimethylcarbamate (14 mg, 0.026 mmol) in ethanol (1 mL) was added chloroacetaldehyde (0.006 mL, 0.039 mmol). The reaction mixture was stirred at 60° C. overnight. The reaction mixture was concentrated down and the residue was purified by prep TLC plate (eluting with 70% ethyl acetate and 30% hexanes) to give the product. LCMS-ESI+ (m/z): calc'd calculated for $C_{26}H_{24}ClF_2N_5O_3S$: 560.1 [M+H]+. 1H found: 560.3 [M+H]+. 1H NMR (400 MHz, Methanol-$d_4$) δ 8.06 (s, 1H), 7.94 (d, J=3.3 Hz, 1H), 7.77 (d, J=3.3 Hz, 1H), 7.66-7.56 (m, 2H), 7.46 (s, 1H), 7.15 (td, J=8.5, 2.4 Hz, 2H), 4.79-4.61 (m, 1H), 3.31 (m, 3H), 2.86 (d, J=26.2 Hz, 6H), 1.62 (s, 1H), 0.98-0.81 (m, 4H).

Example 6: Preparation of Compound 6

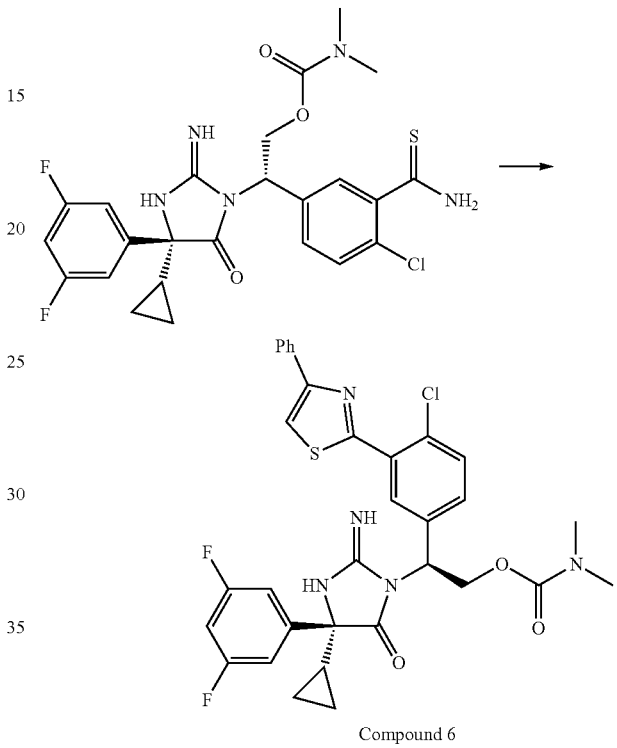

Compound 6

Compound 6 was prepared following the procedure to prepare Compound 5, except that 2-bromoacetophenone was used instead of chloroacetaldehyde. LCMS-ESI+ (m/z): calc'd for $C_{32}H_{28}ClF_2N_5O_3S$: 636.2 [M+H]+. found: 636.2 [M+H]+. 1H NMR (400 MHz, Methanol-$d_4$) δ 8.35 (s, 1H), 8.03-7.95 (m, 3H), 7.61 (d, J=8.4 Hz, 1H), 7.45 (td, J=7.8, 6.0 Hz, 3H), 7.38-7.33 (m, 1H), 7.18-7.11 (m, 2H), 6.76 (s, 1H), 5.57 (s, 1H), 5.08 (s, 1H), 4.79 (dd, J=11.2, 5.0 Hz, 1H), 2.85 (d, J=31.2 Hz, 6H), 1.62 (s, 1H), 0.51 (s, 4H).

Example 7: Preparation of Compound 7

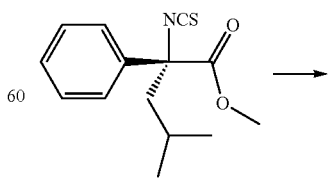

-continued

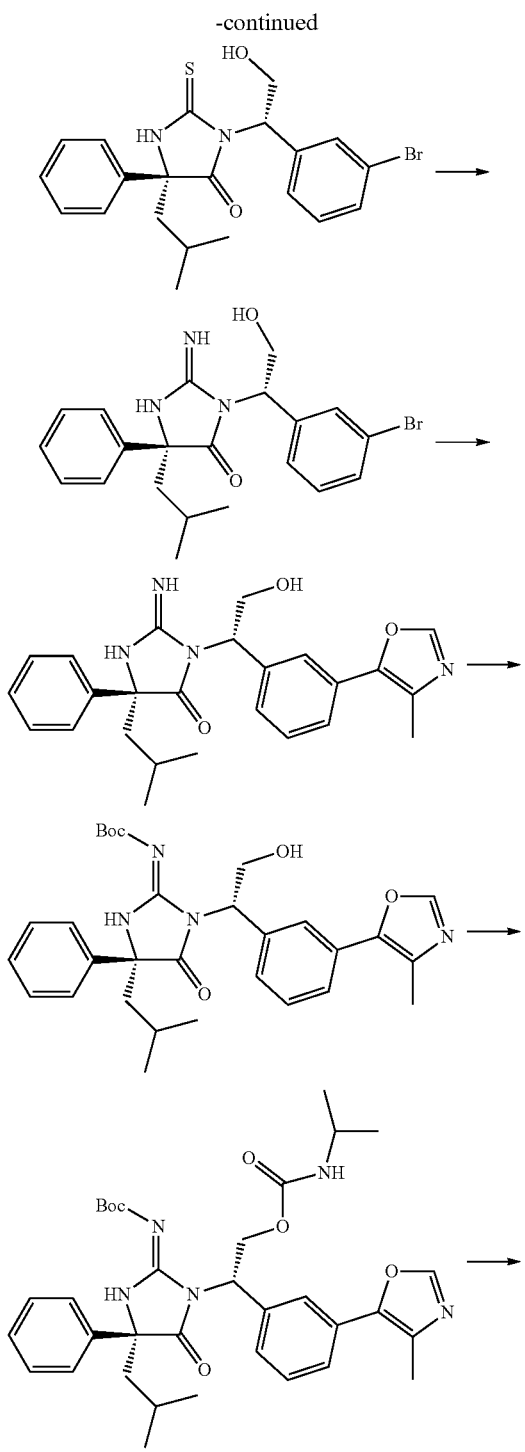

-continued

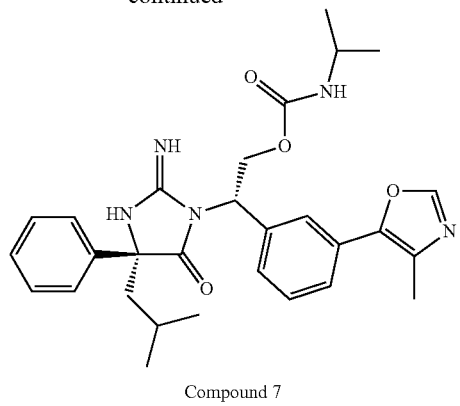

Compound 7

Preparation of methyl (R)-2-isothiocyanato-4-methyl-2-phenylpentanoate: Methyl (R)-2-isothiocyanato-4-methyl-2-phenylpentanoate was prepared following the procedure to prepare methyl isopropyl (R)-2-cyclopropyl-2-(3,5-difluorophenyl)-2-isothiocyanatoacetate described in Example 2.

Preparation of (R)-3-((S)-1-(3-bromophenyl)-2-hydroxyethyl)-5-isobutyl-5-phenyl-2-thioxoimidazolidin-4-one: A mixture of methyl (R)-2-isothiocyanato-4-methyl-2-phenylpentanoate (400 mg, 1.52 mmol), (S)-2-amino-2-(3-bromophenyl)ethan-1-ol hydrochloride (499 mg, 1.97 mmol) and N,N-diisopropylethylamine (660 μL, 3.8 mmol) in THF (8 mL) was stirred at 50° C. for 3 h. The reaction mixture was concentrated down and the residue was purified by silica gel column chromatography (0-100% gradient EtOAc/hexanes) to give the product.

Preparation of (R)-3-((S)-1-(3-bromophenyl)-2-hydroxyethyl)-2-imino-5-isobutyl-5-phenylimidazolidin-4-one: To a solution of (R)-3-((S)-1-(3-bromophenyl)-2-hydroxyethyl)-5-isobutyl-5-phenyl-2-thioxoimidazolidin-4-one (200 mg, 0.45 mmol) in methanol (5 mL) was added NH$_4$OH aqueous solution (30%, 1.56 mL, 0.013 mol) and t-BuOOH (70% in water, 0.86 mL, 6.7 mmol). The reaction mixture was stirred at rt for 4.5 h. The mixture was concentrated down and the residue was purified by reverse phase HPLC chromatography (CH$_3$CN/H$_2$O, both containing with 0.1% TFA) to give the product.

Preparation of (R)-3-((S)-2-hydroxy-1-(3-(4-methyloxazol-5-yl)phenyl)ethyl)-2-imino-5-isobutyl-5-phenylimidazolidin-4-one: A mixture of (R)-3-((S)-1-(3-bromophenyl)-2-hydroxyethyl)-2-imino-5-isobutyl-5-phenylimidazolidin-4-one (56 mg, 0.13 mmol), 4-methyloxazole-5-carboxylic acid (33 mg, 0.26 mmol), cesium carbonate (63.6 mg, 0.2 mmol), tetrabutyl ammonium chloride (36 mg, 0.13 mmol) and bis(tri-t-butylphosphine)palladium (0) (6.65 mg, 0.013 mmol) in DMF (1 mL) was stirred at rt and purged with argon for 10 min. The reaction mixture was then subjected to a microwave reactor at 170° C. for 10 min. To the mixture was added EtOAc and water. The organic layer was filtered through a short pad of Celite and concentrated. The residue was purified by reverse phase HPLC (acetonitrile/water, both containing with 0.1% TFA) to give the product.

Preparation of tert-butyl ((R)-1-((S)-2-hydroxy-1-(3-(4-methyloxazol-5-yl)phenyl)ethyl)-4-isobutyl-5-oxo-4-phenylimidazolidin-2-ylidene)carbamate: To a solution of (R)-3-((S)-2-hydroxy-1-(3-(4-methyloxazol-5-yl)phenyl)ethyl)-2-imino-5-isobutyl-5-phenylimidazolidin-4-one (20 mg, 0.046 mmol) in THF (0.5 mL) were added di-tert-butyl dicarbonate (0.02 mL, 0.07 mmol) and triethylamine (0.02 mL, 0.14 mmol). The reaction mixture was stirred at rt for 5 h. The mixture was then concentrated down. The residue was purified by silica gel column chromatography (0-100% gradient EtOAc/hexanes) to give the product.

Preparation of tert-butyl ((R)-4-isobutyl-1-((S)-2-((isopropylcarbamoyl)oxy)-1-(3-(4-methyloxazol-5-yl)phenyl)ethyl)-5-oxo-4-phenylimidazolidin-2-ylidene)carbamate: To a solution of tert-butyl ((R)-1-((S)-2-hydroxy-1-(3-(4-methyloxazol-5-yl)phenyl)ethyl)-4-isobutyl-5-oxo-4-phenylimidazolidin-2-ylidene)carbamate (31 mg, 0.058 mmol) in DCM (1 mL) was added 1,1'-carbonyldiimidazole (14 mg, 0.087 mmol) and N,N-diisopropylethylamine (20 µL, 0.12 mmol). The reaction was stirred at rt for 5 min. Then to the mixture was added isopropylamine (0.02 mL, 0.29 mmol) and stirred at rt for 15 min. The reaction mixture was partitioned between water and EtOAc. The organic phase was concentrated and the residue was used directly in the next step without purification.

Preparation of Compound 7: The solution of tert-butyl ((R)-4-isobutyl-1-((S)-2-((isopropylcarbamoyl)oxy)-1-(3-(4-methyloxazol-5-yl)phenyl)ethyl)-5-oxo-4-phenylimidazolidin-2-ylidene)carbamate (36 mg, 0.06 mmol) in DCM (0.5 mL) and TFA (0.5 mL) was stirred at rt for 30 min. The reaction mixture was concentrated and the residue was purified by reverse phase HPLC (acetonitrile/water, both containing 0.1% TFA) to give the product. LCMS-ESI+(m/z): calc'd calculated for $C_{29}H_{35}N_5O_4$: 518.3 [M+H]$^+$. found: 518.2 [M+H]$^+$. $^1$H NMR (400 MHz, Chloroform-d) δ 7.90 (s, 1H), 7.65-7.29 (m, 8H), 7.28-7.21 (m, 1H), 5.68 (dd, J=8.4, 4.2 Hz, 1H), 4.89 (dd, J=12.0, 8.3 Hz, 1H), 4.66 (dd, J=12.0, 4.2 Hz, 1H), 4.48 (d, J=8.0 Hz, 1H), 3.71-3.68 (m, 1H), 2.36 (s, 3H), 2.18 (d, J=6.2 Hz, 2H), 1.76-1.66 (m, 1H), 1.07 (dd, J=10.4, 6.6 Hz, 6H), 0.91 (dd, J=24.5, 6.6 Hz, 6H).

Example 8: Preparation of Compound 8

Compound 8

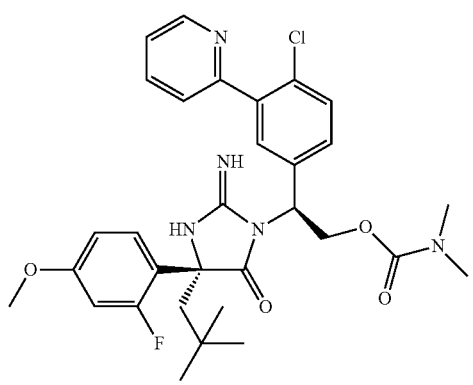

Compound 8 was prepared in a manner similar to that for Compound 1. LCMS-ESI+(m/z): calc'd for $C_{31}H_{35}ClFN_5O_4$: 596.2 [M+H]$^+$. found: 596.1 [M+H]$^+$. $^1$H NMR (400 MHz, Methanol-d$_4$) δ 8.58 (dd, J=5.0, 1.4 Hz, 1H), 7.90 (td, J=7.8, 1.8 Hz, 1H), 7.56-7.36 (m, 5H), 7.12 (t, J=9.1 Hz, 1H), 6.63 (dd, J=14.2, 2.6 Hz, 1H), 6.47 (dd, J=8.8, 2.6 Hz, 1H), 5.56 (dd, J=9.6, 4.8 Hz, 1H), 5.09 (dd, J=11.1, 9.7 Hz, 1H), 4.74 (dd, J=11.1, 4.8 Hz, 1H), 3.75 (s, 3H), 2.88 (s, 3H), 2.83 (s, 3H), 2.20 (d, J=14.7 Hz, 1H), 2.08 (d, J=14.7 Hz, 1H), 0.95 (s, 9H).

Example 9: Preparation of Compound 9

Compound 9

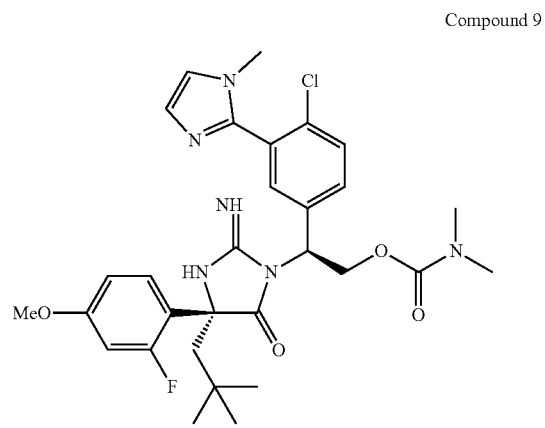 [SMILES: COc1ccc([C@@]2(CC(C)(C)C)NC(=N)N([C@H](COC(=O)N(C)C)c3ccc(Cl)c(-c4nccn4C)c3)C2=O)c(F)c1]

Compound 9 was prepared following the procedure to prepare Compound 1, except that (S)-2-amino-2-(4-chloro-3-(1-methyl-1H-imidazol-2-yl)phenyl)ethan-1-ol hydrochloride was used instead of (S)-2-amino-2-(3-(3-methylpyridin-2-yl)phenyl)ethan-1-ol hydrochloride. LCMS-ESI+ (m/z): calc'd calculated for $C_{30}H_{36}ClFN_6O_4$: 599.2 [M+H]$^+$. found: 599.2 [M+H]$^+$. $^1$H NMR (400 MHz, Methanol-d$_4$) δ 7.73 (s, 1H), 7.59-7.46 (m, 2H), 7.29 (s, 1H), 7.14 (t, J=9.1 Hz, 1H), 6.89 (s, 1H), 6.65 (dd, J=14.3, 2.6 Hz, 1H), 6.55 (dd, J=8.9, 2.6 Hz, 1H), 5.55 (dd, J=9.7, 4.7 Hz, 1H), 5.09 (t, J=10.4 Hz, 1H), 4.73 (dd, J=11.1, 4.7 Hz, 1H), 3.77 (s, 3H), 3.40 (s, 3H), 2.89 (s, 3H), 2.85 (s, 3H), 2.24 (d, J=14.8 Hz, 1H), 2.10 (d, J=14.8 Hz, 1H), 0.97 (s, 9H).

Example 10: Preparation of Compound 10

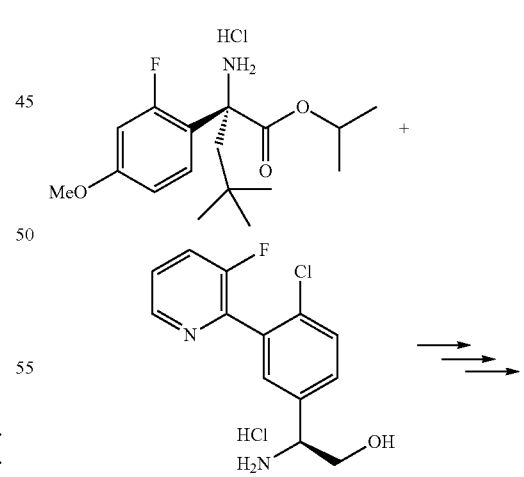

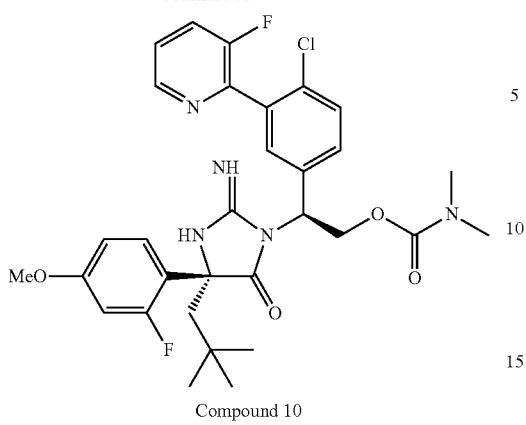

Compound 10

Compound 10 was prepared following the procedure to prepare Compound 1, except that (S)-2-amino-2-(4-chloro-3-(3-fluoropyridin-2-yl)phenyl)ethan-1-ol hydrochloride was used instead of (S)-2-amino-2-(4-chloro-3-(3-methylpyridin-2-yl)phenyl)ethan-1-ol hydrochloride. LCMS-ESI+ (m/z): calc'd for $C_{31}H_{34}ClF_2N_5O_4$: 614.2 [M+H]+. found: 614.2 [M+H]+. $^1$H NMR (400 MHz, Methanol-$d_4$) δ 8.47 (dd, J=3.9, 2.6 Hz, 1H), 7.75 (tt, J=9.3, 1.0 Hz, 1H), 7.65-7.50 (m, 3H), 7.37 (d, J=2.2 Hz, 1H), 7.16 (t, J=9.1 Hz, 1H), 6.73-6.55 (m, 2H), 5.66 (dd, J=9.8, 4.4 Hz, 1H), 5.13 (dd, J=11.5, 9.8 Hz, 1H), 4.80 (dd, J=11.5, 4.4 Hz, 1H), 3.78 (d, J=0.7 Hz, 3H), 2.93-2.88 (m, 6H), 2.35 (d, J=15.0 Hz, 1H), 2.26 (d, J=15.0 Hz, 1H), 1.00 (s, 9H).

Example 11: Preparation of Compound 11

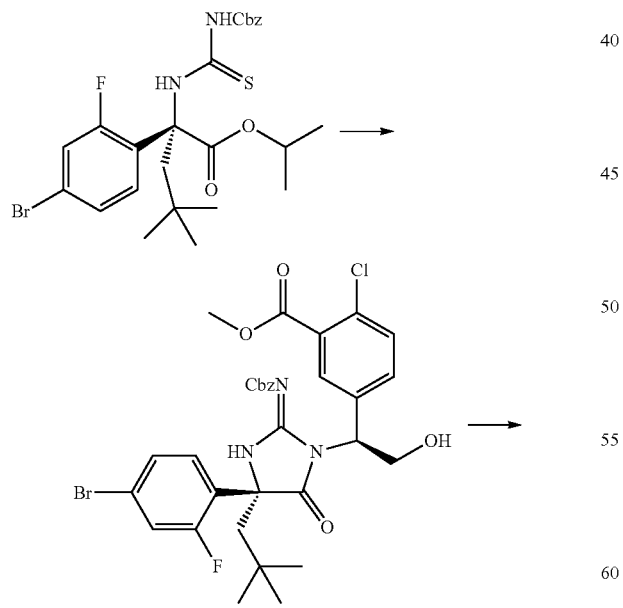

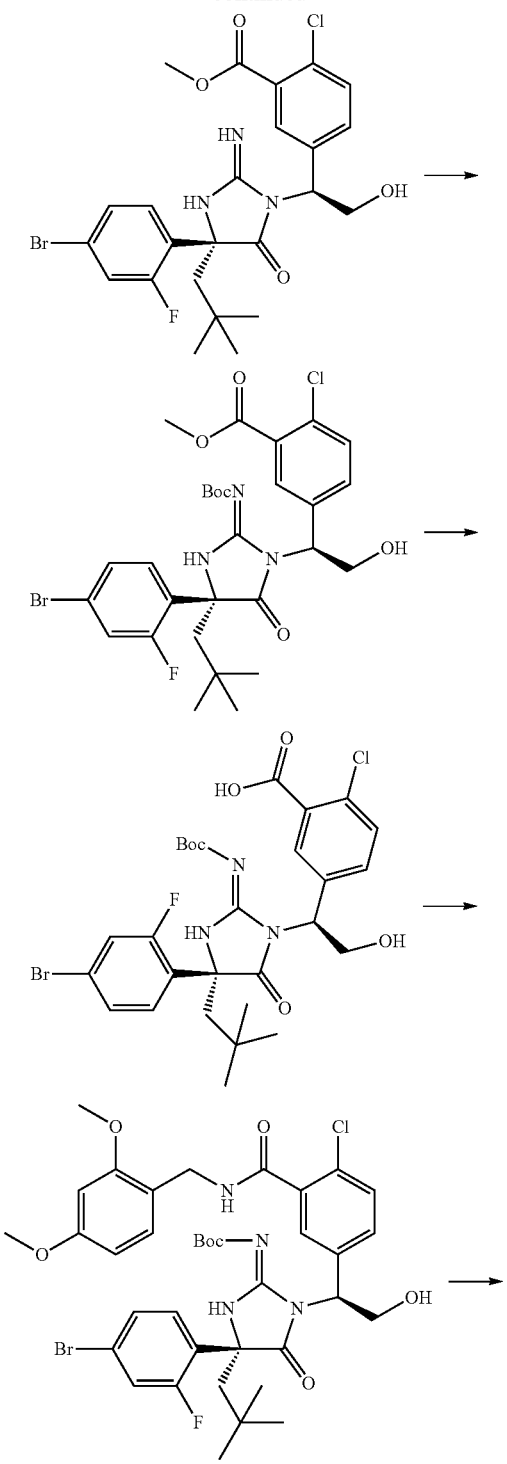

-continued

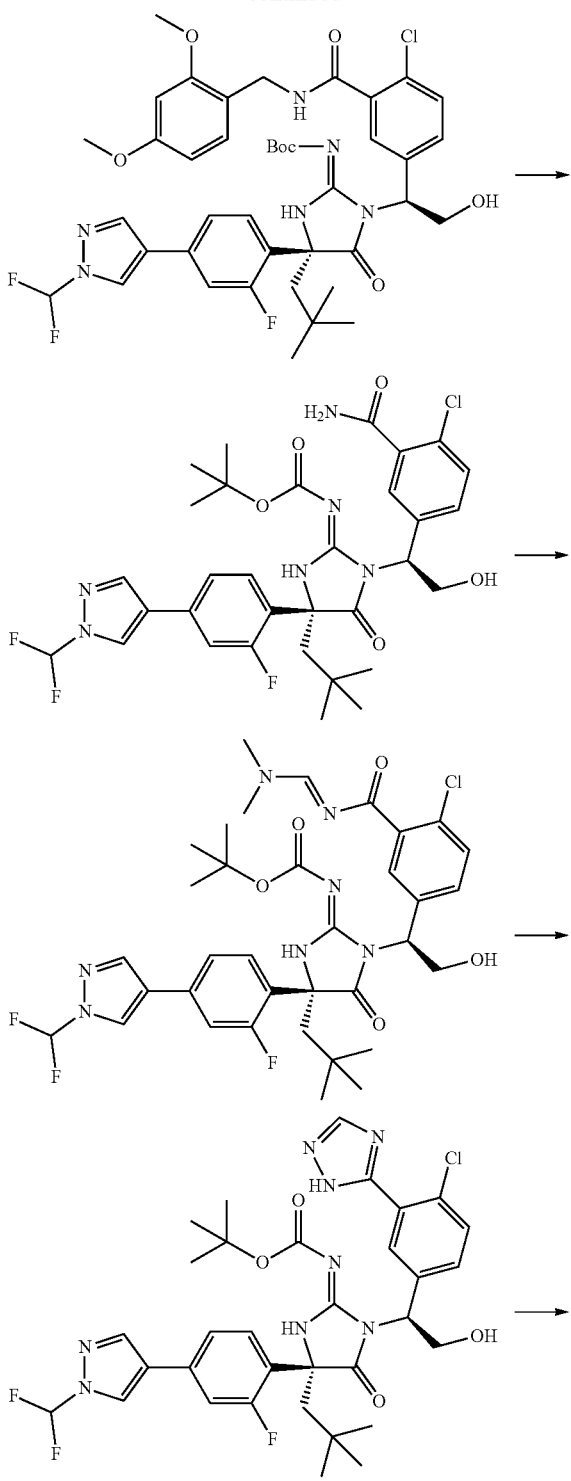

-continued

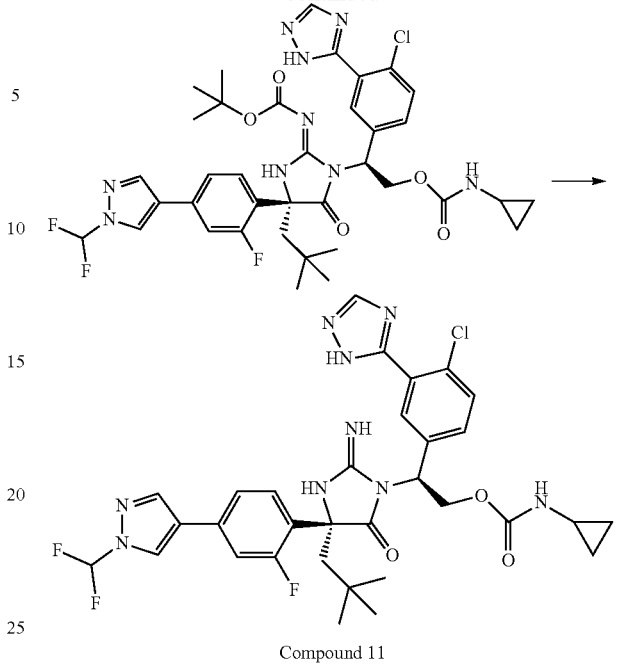

Compound 11

Preparation of methyl 5-((S)-1-((R)-2-(((benzyloxy)carbonyl)imino)-4-(4-bromo-2-fluorophenyl)-4-neopentyl-5-oxoimidazolidin-1-yl)-2-hydroxyethyl)-2-chlorobenzoate: methyl 5-((S)-1-((R)-2-(((benzyloxy)carbonyl)imino)-4-(4-bromo-2-fluorophenyl)-4-neopentyl-5-oxoimidazolidin-1-yl)-2-hydroxyethyl)-2-chlorobenzoate was prepared following the procedure to prepare benzyl ((R)-1-((S)-1-(4-chloro-3-(3-methylpyridin-2-yl)phenyl)-2-hydroxyethyl)-4-(2-fluoro-4-methoxyphenyl)-4-neopentyl-5-oxoimidazolidin-2-ylidene)carbamate in Example 1, except that methyl-5-(1-amino-2-hydroxyethyl)-2-chlorobenzoate hydrochloride was used instead of (S)-2-amino-2-(4-chloro-3-(3-methylpyridin-2-yl)phenyl)ethan-1-ol hydrochloride.

Preparation of methyl 5-((S)-1-((R)-4-(4-bromo-2-fluorophenyl)-2-imino-4-neopentyl-5-oxoimidazolidin-1-yl)-2-hydroxyethyl)-2-chlorobenzoate: To a solution of methyl 5-((S)-1-((R)-2-(((benzyloxy)carbonyl)imino)-4-(4-bromo-2-fluorophenyl)-4-neopentyl-5-oxoimidazolidin-1-yl)-2-hydroxyethyl)-2-chlorobenzoate (1.51 g, 2.19 mmol) in DCM (15 mL) was added iodotrimethylsilane (0.57 mL, 4.38 mmol). The reaction mixture was stirred at rt for 2 days, resulting in formation of the trimethylsilyl protected product, methyl 5-((S)-1-((R)-4-(4-bromo-2-fluorophenyl)-2-imino-4-neopentyl-5-oxoimidazolidin-1-yl)-2-((trimethylsilyl)oxy)ethyl)-2-chlorobenzoate. The reaction mixture was washed with saturated $NaHCO_3$ and extracted with EtOAc. The organic phase was separated, dried over $MgSO_4$, filtered, and concentrated. The residue was purified by silica gel column chromatography (0-100% gradient EtOAc/hexanes), during the purification trimethylsilyl group was removed to give the product.

Preparation of methyl 5-((S)-1-((R)-4-(4-bromo-2-fluorophenyl)-2-((tert-butoxycarbonyl)imino)-4-neopentyl-5-oxoimidazolidin-1-yl)-2-hydroxyethyl)-2-chlorobenzoate: The reaction mixture of methyl 5-((S)-1-((R)-4-(4-bromo-2-fluorophenyl)-2-imino-4-neopentyl-5-oxoimidazolidin-1-yl)-2-hydroxyethyl)-2-chlorobenzoate (1.0 g, 2.0 mmol), di-tert-butyl dicarbonate (0.47 g, 2.0 mmol) and N,N-diisopropylethylamine (1.57 mL, 0.01 mol) in THF (13 mL) was stirred at rt overnight. The reaction mixture was partitioned between saturated aqueous NaHCO₃ and EtOAc. The organic phase was separated, dried over MgSO₄, filtered, and concentrated. The residue was purified by silica gel column chromatography (0-100% gradient EtOAc/hexanes) to give the product.

Preparation of 5-((S)-1-((R)-4-(4-bromo-2-fluorophenyl)-2-((tert-butoxycarbonyl)imino)-4-neopentyl-5-oxoimidazolidin-1-yl)-2-hydroxyethyl)-2-chlorobenzoic acid: To a solution of methyl 5-((S)-1-((R)-4-(4-bromo-2-fluorophenyl)-2-((tert-butoxycarbonyl)imino)-4-neopentyl-5-oxoimidazolidin-1-yl)-2-hydroxyethyl)-2-chlorobenzoate (320 mg, 0.49 mmol) in dioxane (2.5 mL) and water (2.5 mL), was added lithium hydroxide solution (2M, 1.22 mL). The reaction mixture was stirred at rt for 1 h. The reaction was quenched by adding 2M hydrogen chloride solution and extracted with EtOAc. The organic extract was separated, dried over MgSO₄, filtered, and concentrated down. The residue was used in the next reaction without further purification.

Preparation of tert-butyl ((R)-4-(4-bromo-2-fluorophenyl)-1-((S)-1-(4-chloro-3-((2,4-dimethoxybenzyl)carbamoyl)phenyl)-2-hydroxyethyl)-4-neopentyl-5-oxoimidazolidin-2-ylidene)carbamate: To a solution of 5-((S)-1-((R)-4-(4-bromo-2-fluorophenyl)-2-((tert-butoxycarbonyl)imino)-4-neopentyl-5-oxoimidazolidin-1-yl)-2-hydroxyethyl)-2-chlorobenzoic acid (330 mg, 0.51 mmol) in DMF (5.0 mL) was added N,N-diisopropylethylamine (0.9 mL, 5.15 mmol), then added 2-(7-aza-1H-benzotriazole-1-yl)-1,1,3,3-tetramethyluronium hexafluorophosphate (HATU) (392 mg, 1.03 mmol). The reaction mixture was stirred at rt for 5 min. Then, to the mixture was added (2,4-dimethoxyphenyl)methanamine (0.39 mL, 2.57 mmol). The reaction mixture was stirred at rt for half an hour. The reaction mixture was partitioned between saturated aqueous NaHCO₃ and EtOAc. The organic phase was separated, dried over MgSO₄, filtered, and concentrated down. The residue was purified by silica gel column chromatography (0-100% gradient EtOAc/hexanes) to give the product.

Preparation of tert-butyl ((R)-1-((S)-1-(4-chloro-3-((2,4-dimethoxybenzyl)carbamoyl)phenyl)-2-hydroxyethyl)-4-(4-(1-(difluoromethyl)-1H-pyrazol-4-yl)-2-fluorophenyl)-4-neopentyl-5-oxoimidazolidin-2-ylidene)carbamate: A reaction mixture of tert-butyl ((R)-4-(4-bromo-2-fluorophenyl)-1-((S)-1-(4-chloro-3-((2,4-dimethoxybenzyl)carbamoyl)phenyl)-2-hydroxyethyl)-4-neopentyl-5-oxoimidazolidin-2-ylidene)carbamate (375 mg, 0.47 mmol), 1-(difluoromethyl)-4-(4,4,5,5-tetramethyl-1,3,2-dioxaborolan-2-yl)-1H-pyrazole (0.23 mL, 0.86 mmol), tetrakis (triphenylphosphine) palladium (0) (55 mg, 0.05 mmol) and potassium carbonate (197 mg, 1.42 mmol) in dioxane (5 mL) and water (1 mL) was stirred at 85° C. for 40 min. The reaction mixture was diluted with saturated NaHCO₃ solution and extracted with EtOAc. The organic extract was separated, dried over MgSO₄, filtered, and concentrated down. The residue was purified by silica gel column chromatography (0-100% gradient EtOAc/hexanes) to give the product.

Preparation of tert-butyl ((R)-1-((S)-1-(3-carbamoyl-4-chlorophenyl)-2-hydroxyethyl)-4-(4-(1-(difluoromethyl)-1H-pyrazol-4-yl)-2-fluorophenyl)-4-neopentyl-5-oxoimidazolidin-2-ylidene)carbamate: A solution of tert-butyl ((R)-1-((S)-1-(4-chloro-3-((2,4-dimethoxybenzyl)carbamoyl)phenyl)-2-hydroxyethyl)-4-(4-(1-(difluoromethyl)-1H-pyrazol-4-yl)-2-fluorophenyl)-4-neopentyl-5-oxoimidazolidin-2-ylidene)carbamate (15 mg, 0.18 mmol) in acetonitrile (3 mL) was treated with H₂O (3 mL) and ceric ammonium sulfate dihydrate (220 mg, 0.35 mmol). The reaction mixture was heated at 60° C. for 2 h. More ceric ammonium sulfate dihydrate (220 mg, 0.35 mmol) was added to the mixture and stirred at rt for 2 h. The reaction was diluted with H₂O, and extracted with EtOAc. The organic phase was washed with saturated NaHCO₃ solution, dried over Na₂SO₄, filtered, and concentrated. The residue was purified by silica gel column chromatography (0-100% gradient EtOAc/hexanes) to give the product.

Preparation of tert-butyl ((R)-1-((S)-1-(4-chloro-3-(((dimethylamino)methylene)carbamoyl)phenyl)-2-hydroxyethyl)-4-(4-(1-(difluoromethyl)-1H-pyrazol-4-yl)-2-fluorophenyl)-4-neopentyl-5-oxoimidazolidin-2-ylidene)carbamate: A solution of tert-butyl ((R)-1-((S)-1-(3-carbamoyl-4-chlorophenyl)-2-hydroxyethyl)-4-(4-(1-(difluoromethyl)-1H-pyrazol-4-yl)-2-fluorophenyl)-4-neopentyl-5-oxoimidazolidin-2-ylidene)carbamate (3 mg, 0.44 mmol) in THF (1.0 mL) was treated with Bredereck's reagent (15 uL, 0.22 mmol) at 70° C. for 1 h. The reaction was cooled to rt and used directly for the next reaction.

Preparation of tert-butyl ((R)-1-((S)-1-(4-chloro-3-(1H-1,2,4-triazol-5-yl)phenyl)-2-hydroxyethyl)-4-(4-(1-(difluoromethyl)-1H-pyrazol-4-yl)-2-fluorophenyl)-4-neopentyl-5-oxoimidazolidin-2-ylidene)carbamate: To a solution of tert-butyl ((R)-1-((S)-1-(4-chloro-3-(((dimethylamino)methylene)carbamoyl)phenyl)-2-hydroxyethyl)-4-(4-(1-(difluoromethyl)-1H-pyrazol-4-yl)-2-fluorophenyl)-4-neopentyl-5-oxoimidazolidin-2-ylidene)carbamate made from the previous step were sequentially added acetic acid (47 mg, 0.79 mmol) and hydrazine monohydrate (15.3 mg, 0.49 mmol). The reaction mixture was heated at 60° C. for 1 h. The reaction was cooled to rt, quenched to pH=8 with saturated aqueous NaHCO₃, extracted with EtOAc. The organic phase was washed with dilute aqeuous HCl, dried over (Na₂SO₄), filtered, and concentrated down. The residue was directly used in the next reaction.

Preparation of tert-butyl ((R)-1-((S)-1-(4-chloro-3-(1H-1,2,4-triazol-5-yl)phenyl)-2-((cyclopropylcarbamoyl)oxy)ethyl)-4-(4-(1-(difluoromethyl)-1H-pyrazol-4-yl)-2-fluorophenyl)-4-neopentyl-5-oxoimidazolidin-2-ylidene)carbamate: The residue of tert-butyl ((R)-1-((S)-1-(4-chloro-3-(1H-1,2,4-triazol-5-yl)phenyl)-2-hydroxyethyl)-4-(4-(1-(difluoromethyl)-1H-pyrazol-4-yl)-2-fluorophenyl)-4-neopentyl-5-oxoimidazolidin-2-ylidene)carbamate from the previous step was dissolved in DCM (1 mL). Hunig's base (33 mg, 0.26 mmol) and 1,1'-carbonyldiimidazole (20 mg, 0.12 mmol) were added. The reaction mixture was stirred at rt for half an hour. Then, to the mixture was added cyclopropylamine (24.7 mg, 0.44 mmol). The reaction mixture was stirred at rt. The reaction mixture was diluted with DCM (5 mL) and washed with diluted aq HCl solution. The organic phase was separated, concentrated down and the residue was used for the next reaction directly.

Preparation of Compound 11: To a solution of tert-butyl ((R)-1-((S)-1-(4-chloro-3-(1H-1,2,4-triazol-5-yl)phenyl)-2-((cyclopropylcarbamoyl)oxy)ethyl)-4-(4-(1-(difluoromethyl)-1H-pyrazol-4-yl)-2-fluorophenyl)-4-neopentyl-5-oxoimidazolidin-2-ylidene)carbamate from the previous step in DCM (5 mL) was added trifluoroacetic acid (1 mL). The reaction mixture was stirred at rt for 15 min. The reaction mixture was concentrated down and purified by reverse phase HPLC (eluting by acetonitrile in water, containing 0.1% TFA) to give the product. LCMS-ESI+ (m/z): calc'd for $C_{32}H_{33}ClF_3N_9O_3$: 684.2 [M+H]⁺. found: 684.3 [M+H]⁺. ¹H NMR (400 MHz, CD₃CN) δ 11.91 (s, broad, 1H), 8.32 (d, J=0.7 Hz, 1H), 8.28 (s, 1H), 8.04 (s, 1H), 7.89 (d, J=2.2 Hz, 1H), 7.60-7.14 (m, 8H), 5.92-5.84 (m, broad, 1H), 5.51-5.41 (m, broad, 1H), 5.01-4.92 (m, 1H), 4.72-4.62 (m, broad, 1H), 2.41-2.20 (m, 2H), 0.97 (s, 9H), 0.61 (d, J=7.0 Hz, 2H), 0.42 (d, J=3.6 Hz, 2H).

Example 12: Preparation of Compound 12

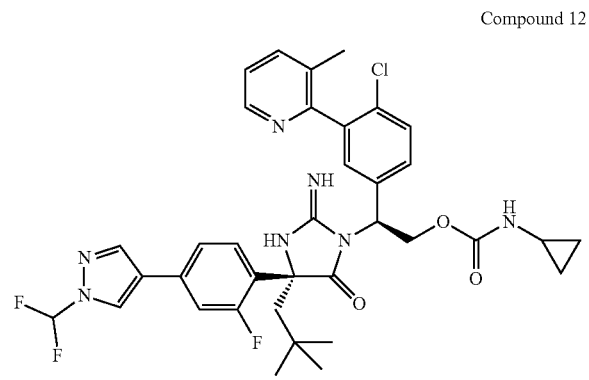 [SMILES: Cc1cccnc1-c1cc([C@@H](COC(=O)NC2CC2)N2C(=N)N[C@](CC(C)(C)C)(c3ccc(-c4cnn(C(F)F)c4)cc3F)C2=O)ccc1Cl]

Compound 12

Preparation of benzyl ((R)-4-(4-bromo-2-fluorophenyl)-1-((S)-1-(4-chloro-3-(3-methylpyridin-2-yl)phenyl)-2-hydroxyethyl)-4-neopentyl-5-oxoimidazolidin-2-ylidene)carbamate: To a solution of isopropyl (R)-2-(3-((benzyloxy)carbonyl)thioureido)-2-(4-bromo-2-fluorophenyl)-4,4-dimethylpentanoate (0.33 g, 0.60 mmol), (S)-2-amino-2-(4-chloro-3-(3-methylpyridin-2-yl)phenyl)ethan-1-ol hydrochloride (0.18 g, 0.60 mmol) and 1-(3-dimethylaminopropyl)-3-ethylcarbodiimide hydrochloride (0.23 g, 1.2 mmol) in DMF (4 mL) was added N,N-diisopropylethylamine (0.52 mL, 3.0 mmol). The reaction mixture was maintained at 65° C. for 12 h. The reaction mixture was quenched by addition of saturated $NH_4Cl$ solution and EtOAc. The layers were separated and the aqueous layer was further extracted with EtOAc. The combined organic layers were washed with brine, dried (over $Na_2SO_4$), filtered, and concentrated in vacuo. The residue was purified by silica gel column chromatography (0-100% EtOAc/hexanes) to give the product.

Preparation of benzyl ((R)-1-((S)-1-(4-chloro-3-(3-methylpyridin-2-yl)phenyl)-2-hydroxyethyl)-4-(4-(1-(difluoromethyl)-1H-pyrazol-4-yl)-2-fluorophenyl)-4-neopentyl-5-oxoimidazolidin-2-ylidene)carbamate: An argon-sparged solution of benzyl ((R)-4-(4-bromo-2-fluorophenyl)-1-((S)-1-(4-chloro-3-(3-methylpyridin-2-yl)phenyl)-2-hydroxyethyl)-4-neopentyl-5-oxoimidazolidin-2-ylidene)carbamate (75 mg, 0.1 mmol), 1-(difluoromethyl)-4-(4,4,5,5-tetramethyl-1,3,2-dioxaborolan-2-yl)-1H-pyrazole (101 mg, 0.42 mmol), tetrakis(triphenylphosphine)palladium (0) (24 mg, 0.02 mmol) and potassium carbonate (144 mg, 1.04 mmol) in dioxane (2 mL) and water (0.4 mL) was stirred at 90° C. for 1 h. The reaction mixture was cooled to rt, quenched by saturated aq $NH_4Cl$ solution, and extracted with EtOAc. The layers were separated and the aqueous layer was further extracted with EtOAc. The combined organic layers were washed with brine, dried (over $Na_2SO_4$), filtered and concentrated. The residue was purified by silica gel column chromatography (0-100% EtOAc/hexanes) to give the product.

Preparation of benzyl ((R)-1-((S)-1-(4-chloro-3-(3-methylpyridin-2-yl)phenyl)-2-((cyclopropylcarbamoyl)oxy)ethyl)-4-(4-(1-(difluoromethyl)-1H-pyrazol-4-yl)-2-fluorophenyl)-4-neopentyl-5-oxoimidazolidin-2-ylidene) carbamate: To a solution of benzyl ((R)-1-((S)-1-(4-chloro-3-(3-methylpyridin-2-yl)phenyl)-2-hydroxyethyl)-4-(4-(1-(difluoromethyl)-1H-pyrazol-4-yl)-2-fluorophenyl)-4-neopentyl-5-oxoimidazolidin-2-ylidene)carbamate (15 mg, 0.02 mmol) in dichloromethane (0.50 mL) was added 1,1'-carbonyldiimidazole (6.4 mg, 0.04 mmol) and N,N-diisopropylethylamine (0.017 mL, 0.099 mmol). The reaction was stirred at rt for 2 h. Then to the mixture was added cyclopropylamine (0.011 mL, 0.16 mmol) and stirred at rt for 12 h. The reaction mixture was quenched by addition of saturated ammonium chloride solution, and extracted with ethyl acetate (twice). The combined organic layers were washed with brine, dried (over $Na_2SO_4$), and concentrated. The residue was purified by silica gel column chromatography (0-100% EtOAc/hexanes) to give the product.

Preparation of Compound 12: To a solution of benzyl ((R)-1-((S)-1-(4-chloro-3-(3-methylpyridin-2-yl)phenyl)-2-((cyclopropylcarbamoyl)oxy)ethyl)-4-(4-(1-(difluoromethyl)-1H-pyrazol-4-yl)-2-fluorophenyl)-4-neopentyl-5-oxoimidazolidin-2-ylidene)carbamate (15 mg, 0.02 mmol) in dichloromethane (0.50 mL) was added iodotrimethylsilane (0.005 mL, 0.04 mmol). The reaction was maintained at rt for 1 h. Then the reaction mixture was quenched by addition of saturated ammonium chloride solution, and extracted with ethyl acetate (twice). The combined organic layers were washed with brine, dried (over $Na_2SO_4$), and concentrated down. The residue was purified by silica column chromatography (0-10% MeOH/(3/1 $CH_2Cl_2$/hexanes)) followed by reverse-phase chromatography (10-95% MeCN/$H_2O$, both containing 0.1% TFA) to give the product. LCMS-ESI+(m/z): calc'd for $C_{36}H_{37}ClF_3N_7O_3$: 708.3 [M+H]$^+$. found: 708.2 [M+H]$^+$. $^1$H NMR (400 MHz, Methanol-$d_4$) δ 8.62 (dd, J=22.9, 5.5 Hz, 1H), 8.54 (d, J=4.0 Hz, 1H), 8.32 (d, J=8.1 Hz, 0.5H), 8.20 (d, J=8.0 Hz, 0.5H), 8.12 (d, J=2.3 Hz, 1H), 7.88-7.59 (m, 4H), 7.58-7.30 (m, 5H), 5.87-5.59 (m, 1H), 5.14 (dt, J=29.7, 10.5 Hz, 1H), 4.80-4.55 (m, 1H), 2.58-2.45 (m, 1H), 2.46-2.28 (m, 2H), 2.20-2.05 (m, 3H), 2.04-1.91 (m, 1H), 1.02 (s, 9H), 0.74-0.60 (m, 2H), 0.57-0.39 (m, 2H).

Example 13: Preparation of Compound 13

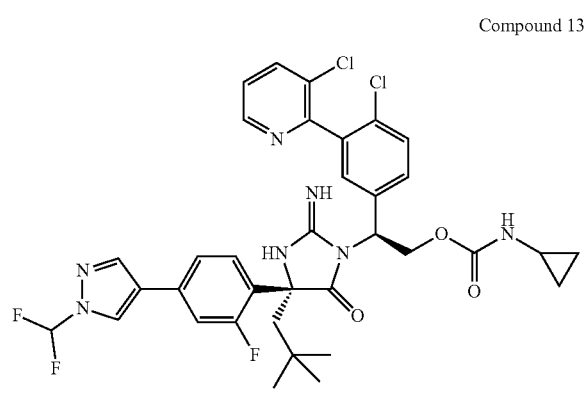 [SMILES: CC(C)(C)C[C@]1(c2ccc(-c3cnn(C(F)F)c3)cc2F)NC(=N)N([C@H](COC(=O)NC2CC2)c2ccc(Cl)c(-c3ncccc3Cl)c2)C1=O]

Compound 13

Preparation of (S)-2-amino-2-(4-chloro-3-(3-chloropyridin-2-yl)phenyl)ethan-1-ol hydrochloride: (S)-2-amino-2-(4-chloro-3-(3-chloropyridin-2-yl)phenyl)ethan-1-ol hydrochloride was prepared following the procedure to prepare (S)-2-amino-2-(4-chloro-3-(3-methylpyridin-2-yl)phenyl)ethan-1-ol hydrochloride, except that 3-chloro-2-(tributylstannyl)pyridine was used instead of 3-methyl-2-(tributylstannyl)pyridine.

Preparation of benzyl ((R)-1-((S)-1-(4-chloro-3-(3-chloropyridin-2-yl)phenyl)-2-((cyclopropylcarbamoyl)oxy)ethyl)-4-(4-(1-(difluoromethyl)-1H-pyrazol-4-yl)-2-fluorophenyl)-4-neopentyl-5-oxoimidazolidin-2-ylidene)carbamate: benzyl ((R)-1-((S)-1-(4-chloro-3-(3-chloropyridin-2-yl)phenyl)-2-((cyclopropylcarbamoyl)oxy)ethyl)-4-(4-(1-(difluoromethyl)-1H-pyrazol-4-yl)-2-fluorophenyl)-4-neopentyl-5-oxoimidazolidin-2-ylidene)carbamate was prepared following the procedure to prepare benzyl ((R)-1-((S)-1-(4-chloro-3-(3-methylpyridin-2-yl)phenyl)-2-((cyclopropylcarbamoyl)oxy)ethyl)-4-(4-(1-(difluoromethyl)-1H-pyrazol-4-yl)-2-fluorophenyl)-4-neopentyl-5-oxoimidazolidin-2-ylidene)carbamate described in Example 12, except that (S)-2-amino-2-(4-chloro-3-(3-chloropyridin-2-yl)phenyl)ethan-1-ol hydrochloride was used instead of (S)-2-amino-2-(4-chloro-3-(3-methylpyridin-2-yl)phenyl)ethan-1-ol hydrochloride.

Preparation of Compound 13: To a solution of benzyl ((R)-1-((S)-1-(4-chloro-3-(3-chloropyridin-2-yl)phenyl)-2-((cyclopropylcarbamoyl)oxy)ethyl)-4-(4-(1-(difluoromethyl)-1H-pyrazol-4-yl)-2-fluorophenyl)-4-neopentyl-5-oxoimidazolidin-2-ylidene)carbamate (6 mg, 0.01 mmol) in dichloromethane (0.5 mL) placed in an ice-water bath was added boron tribromide in DCM (1M, 0.02 mL) dropwise. The reaction mixture was stirred at rt for 30 min, quenched by addition of saturated NaHCO$_3$, and extracted with EtOAc. The layers were separated and the aqueous layer was further extracted with EtOAc. The combined organic layers were washed with brine, dried (over Na$_2$SO$_4$), filtered, and concentrated. The residue was purified by silica gel column chromatography (0-100% EtOAc/hexanes) to the product. LCMS-ESI+ (m/z): calc'd for $C_{35}H_{34}Cl_2F_3N_7O_3$: 728.2 [M+H]$^+$. found: 728.2 [M+H]$^+$. $^1$H NMR (400 MHz, Methanol-d$_4$) δ 8.55 (d, J=7.4 Hz, 1H), 8.46 (s, 1H), 8.42 (s, 1H), 8.09 (s, 1H), 7.71-7.10 (m, 8H), 5.66-5.39 (m, 1H), 5.07 (t, J=10.5, 9.4 Hz, 1H), 4.74-4.64 (m, OH), 2.47 (s, 1H), 2.23 (d, J=14.7 Hz, 1H), 2.12 (d, J=14.7 Hz, 1H), 0.97 (s, 9H), 0.63 (s, 2H), 0.43 (s, 2H).

Example 14: Preparation of Compound 14

Compound 14

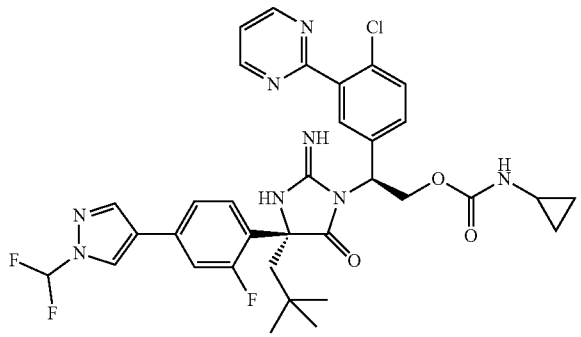

Preparation of (S)-2-amino-2-(4-chloro-3-(pyrimidin-2-yl)phenyl)ethan-1-ol hydrochloride: (S)-2-amino-2-(4-chloro-3-(pyrimidin-2-yl)phenyl)ethan-1-ol hydrochloride was prepared following the procedure to prepare (S)-2-amino-2-(4-chloro-3-(3-methylpyridin-2-yl)phenyl)ethan-1-ol hydrochloride, except that 2-(tributylstannyl)pyrimidine was used instead of 3-methyl-2-(tributylstannyl)pyridine.

Compound 14 was prepared following the procedure to prepare Compound 13, except that (S)-2-amino-2-(4-chloro-3-(pyrimidin-2-yl)phenyl)ethan-1-ol hydrochloride was used instead of (S)-2-amino-2-(4-chloro-3-(3-chloropyridin-2-yl)phenyl)ethan-1-ol hydrochloride. LCMS-ESI+ (m/z): calc'd for $C_{34}H_{34}ClF_3N_8O_3$: 695.2 [M+H]$^+$. found: 695.2 [M+H]$^+$. $^1$H NMR (400 MHz, Methanol-d$_4$) δ 8.81 (d, J=4.9 Hz, 2H), 8.51 (s, 1H), 8.10 (s, 1H), 5.74-5.59 (m, 1H), 5.16 (t, J=10.5 Hz, 1H), 4.80-4.62 (m, 1H), 2.49 (d, J=3.9 Hz, 1H), 2.39 (d, J=15.0 Hz, 1H), 2.32 (d, J=15.1 Hz, 1H), 1.03 (s, 9H), 0.75-0.61 (m, 2H), 0.46 (s, 2H).

Example 15: Preparation of Compound 15

Compound 15

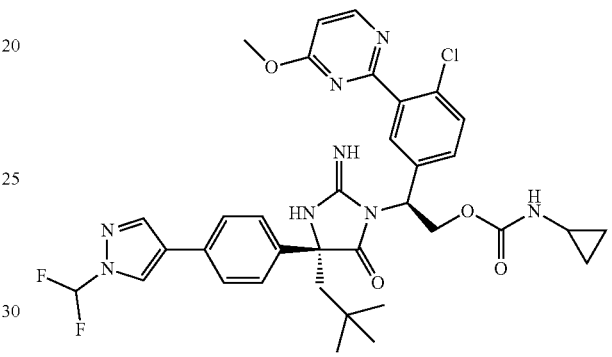

Compound 15 was prepared following the procedure to prepare Compound 13, except that (S)-2-amino-2-(4-chloro-3-(4-methoxypyrimidin-2-yl)phenyl)ethan-1-ol hydrochloride was used instead of (S)-2-amino-2-(4-chloro-3-(3-chloropyridin-2-yl)phenyl)ethan-1-ol hydrochloride. LCMS-ESI+ (m/z): calc'd for $C_{35}H_{37}ClF_2N_8O_4$: 707.3 [M+H]$^+$. found: 707.3 [M+H]$^+$. $^1$H NMR (400 MHz, CD3CN) δ 8.45 (d, J=5.9 Hz, 1H), 8.29 (s, 1H), 8.03 (s, 1H), 7.57-7.45 (m, 6H), 7.42 (t, JHF=59.9 Hz, 1H), 7.42-7.34 (m, 1H), 6.65 (d, J=5.9 Hz, 1H), 5.84-5.76 (m, 1H), 5.49-5.38 (m, 1H), 4.91 (t, J=10.6 Hz, 1H), 4.67 (d, J=11.8 Hz, 1H), 3.91 (s, 3H), 2.35-2.11 (m, 2H), 0.92 (s, 9H), 0.65-0.52 (m, 2H), 0.44-0.36 (m, 2H).

Preparation of tert-butyl (S)-4-(4-chloro-3-(4,4,5,5-tetramethyl-1,3,2-dioxaborolan-2-yl)phenyl)-2,2-dimethyloxazolidine-3-carboxylate: An argon-purged solution of tert-butyl (S)-4-(3-bromo-4-chlorophenyl)-2,2-dimethyloxazolidine-3-carboxylate (0.99 g, 3.0 mol) in dioxane (16.0 mL) was added to a vial containing potassium acetate (1.3 g, 13.3 mmol), 1,1'-bis(diphenylphosphino)ferrocene (200 mg, 0.27 mmol) and bis(pinacolato)diboron (1.3 g, 5.1 mmol) under argon. After stirring at rt for 5 min, the reaction mixture was heated at 90° C. for 16 h. The mixture was then cooled to rt, and poured into brine/EtOAc. The organic phase was collected and the aqueous layer was extracted with EtOAc. The combined organics were dried, filtered, and concentrated down. The residue was purified by silica gel column chromatography (0-100% gradient EtOAc/hexanes) to give the product.

Preparation of tert-butyl (S)-4-(4-chloro-3-(4-methoxypyrimidin-2-yl)phenyl)-2,2-dimethyloxazolidine-3-carboxylate: A solution of tert-butyl (S)-4-(4-chloro-3-(4,4,5,5-tetramethyl-1,3,2-dioxaborolan-2-yl)phenyl)-2,2-dimethyloxazolidine-3-carboxylate (100 mg, 0.15 mmol), 2-chloro-4-methoxypyrimidine (70 mg, 0.048 mmol), tetrakis(triphenylphosphine)palladium(O) (35 mg, 0.003 mmol) and potassium carbonate (100 mg, 0.072 mmol) in dioxane (2.0 mL) and H$_2$O (0.5 mL) was heated at 90° C. for 16 h. The mixture was diluted with water and brine, extracted with EtOAc. The organic phase was dried (Na$_2$SO$_4$), filtered, and concentrated down. The residue was purified by silica gel column chromatography (0-100% gradient EtOAc/hexanes) to give the product.

Preparation of (S)-2-amino-2-(4-chloro-3-(4-methoxypyrimidin-2-yl)phenyl)ethan-1-ol: tert-butyl (S)-4-(4-chloro-3-(4-methoxypyrimidin-2-yl)phenyl)-2,2-dimethyloxazolidine-3-carboxylate (123 mg, 0.029 mmol) was treated with HCl in dioxane (4.0 M, 2.0 mL) at rt for 5 min. Then, H$_2$O (2.0 mL) was added. After 10 min, more H$_2$O was added and the mixture was lyophilized, and used for the next reaction without further purification.

Example 16: Preparation of Compound 16

Compound 16

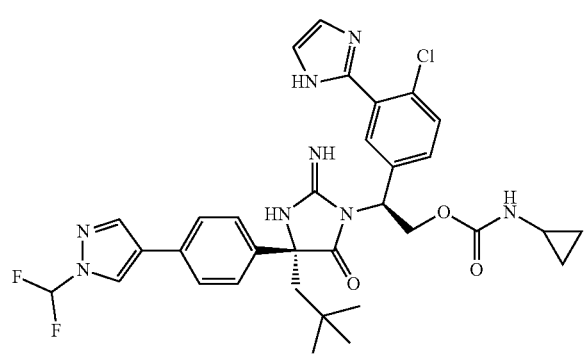

Preparation of (S)-2-amino-2-(4-chloro-3-(1H-imidazol-2-yl)phenyl)ethan-1-ol: (S)-2-amino-2-(4-chloro-3-(1H-imidazol-2-yl)phenyl)ethan-1-ol was prepared following the procedure to prepare (S)-2-amino-2-(4-chloro-3-(4-methoxypyrimidin-2-yl)phenyl)ethan-1-ol in Example 15 except that 2-iodo-1H-imidazole was used instead of 2-chloro-4-methoxypyrimidine.

Compound 16 was prepared following the procedure to Compound 15, except that (S)-2-amino-2-(4-chloro-3-(1H-imidazol-2-yl)phenyl)ethan-1-ol was used instead of (S)-2-amino-2-(4-chloro-3-(4-methoxypyrimidin-2-yl)phenyl)ethan-1-ol. LCMS-ESI+ (m/z): calc'd for C$_{33}$H$_{35}$ClF$_2$N$_8$O$_3$: 665.3 [M+H]+. found: 665.2 [M+H]+. $^1$H NMR (400 MHz, CD3CN) δ 8.30 (s, 1H), 8.08-7.98 (m, 2H), 7.64-7.40 (m, 9H), 7.38 (t, JHF=59.9 Hz, 1H), 5.94-5.86 (m, 1H), 5.65-5.52 (m, 1H), 4.99 (t, J=10.5 Hz, 1H), 4.61-4.53 (m, 1H), 2.31-2.15 (m, 2H), 0.91 (s, 9H), 0.64-0.54 (m, 2H), 0.43-0.34 (m, 2H).

Example 17: Preparation of Compound 17

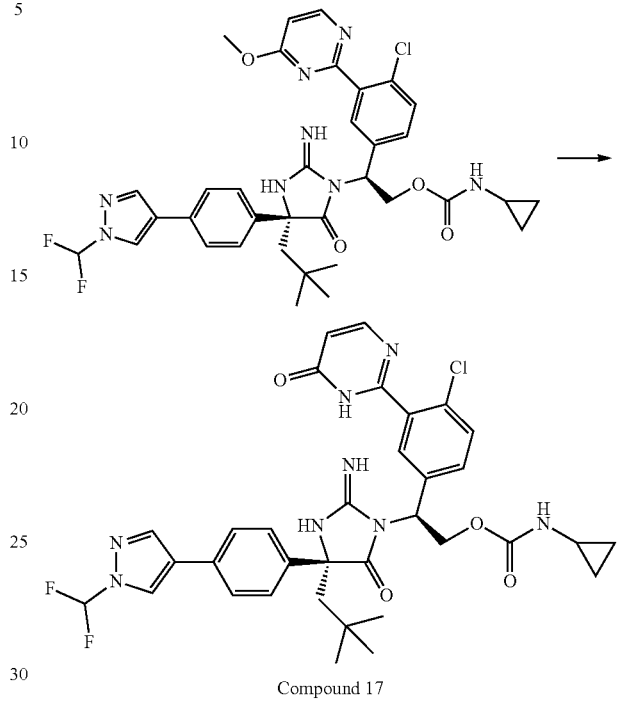

Compound 17

Preparation of Compound 17: A suspension of (S)-2-(4-chloro-3-(4-methoxypyrimidin-2-yl)phenyl)-2-((R)-4-(4-(1-(difluoromethyl)-1H-pyrazol-4-yl)phenyl)-2-imino-4-neopentyl-5-oxoimidazolidin-1-yl)ethyl cyclopropylcarbamate TFA salt (10 mg, 0.012 mmol) in aqueous HCl (1M, 1.0 mL) and dioxane (0.1 mL) and heated at 110° C. for 40 min. The reaction mixture was then cooled to rt, and H$_2$O (0.5 mL) and acetonitrile (1.5 mL) were added. The resulting solution was purified by reverse phase HPLC (acetonitrile/water, containing 0.1% TFA) to give the product. LCMS-ESI+ (m/z): calc'd for C$_{34}$H$_{35}$ClF$_2$N$_8$O$_4$: 693.3 [M+H]+. found: 693.2 [M+H]+. $^1$H NMR (400 MHz, CD3CN) δ 8.32 (d, J=0.7 Hz, 1H), 8.05 (s, 1H), 7.86 (d, J=6.8 Hz, 1H), 7.64-7.19 (m, 9H), 6.19 (d, J=6.8 Hz, 1H), 5.87-5.77 (m, 1H), 5.49-5.39 (m, 1H), 4.88 (t, J=10.5 Hz, 1H), 4.66 (d, J=11.7 Hz, 1H), 2.35-2.12 (m, 2H), 0.92 (s, 9H), 0.64-0.54 (m, 2H), 0.45-0.35 (m, 2H).

Example 18: Preparation of Compound 18

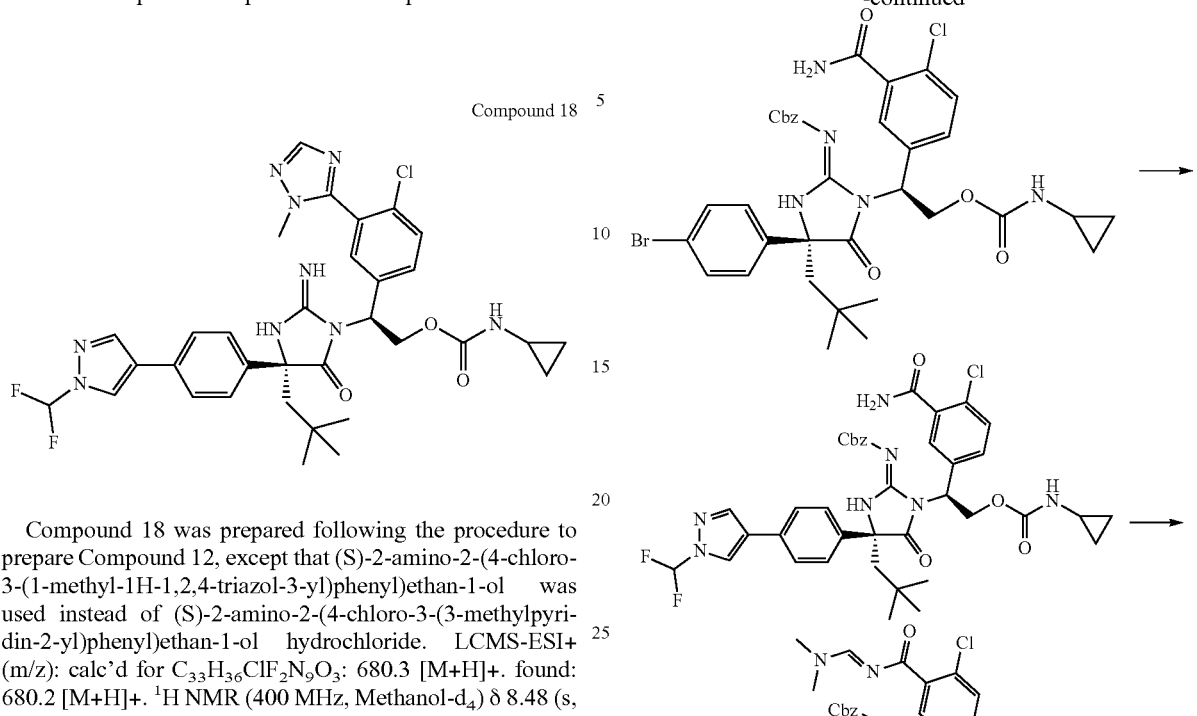

Compound 18

Compound 18 was prepared following the procedure to prepare Compound 12, except that (S)-2-amino-2-(4-chloro-3-(1-methyl-1H-1,2,4-triazol-3-yl)phenyl)ethan-1-ol was used instead of (S)-2-amino-2-(4-chloro-3-(3-methylpyridin-2-yl)phenyl)ethan-1-ol hydrochloride. LCMS-ESI+ (m/z): calc'd for $C_{33}H_{36}ClF_2N_9O_3$: 680.3 [M+H]+. found: 680.2 [M+H]+. $^1$H NMR (400 MHz, Methanol-$d_4$) δ 8.48 (s, 1H), 8.12 (s, 1H), 7.87 (s, 1H), 7.60 (dd, J=11.8, 8.5 Hz, 3H), 7.52 (t, J=59.8 Hz, 1H), 7.51 (d, J=6.61 Hz, 1H), 7.48-7.41 (m, 2H), 7.13 (s, 1H), 5.68-5.57 (m, 1H), 5.06 (dd, J=11.5, 9.4 Hz, 1H), 4.90-4.60 (m, 1H), 2.50 (d, J=15.1 Hz, 1H), 2.14 (d, J=15.2 Hz, 1H), 1.01 (s, 9H), 0.67 (d, J=6.8 Hz, 2H), 0.46 (q, J=3.8 Hz, 2H).

Preparation of (S)-2-amino-2-(4-chloro-3-(1-methyl-1H-1,2,4-triazol-3-yl)phenyl)ethan-1-ol: (S)-2-amino-2-(4-chloro-3-(1-methyl-1H-1,2,4-triazol-3-yl)phenyl)ethan-1-ol was prepared following the procedure to prepare (S)-2-amino-2-(4-chloro-3-(4-methoxypyrimidin-2-yl)phenyl)ethan-1-ol described in Example 15 except that 5-bromo-1-methyl-1H-1,2,4-triazole was used instead of 2-chloro-4-methoxypyrimidine.

Example 19: Preparation of Compound 19

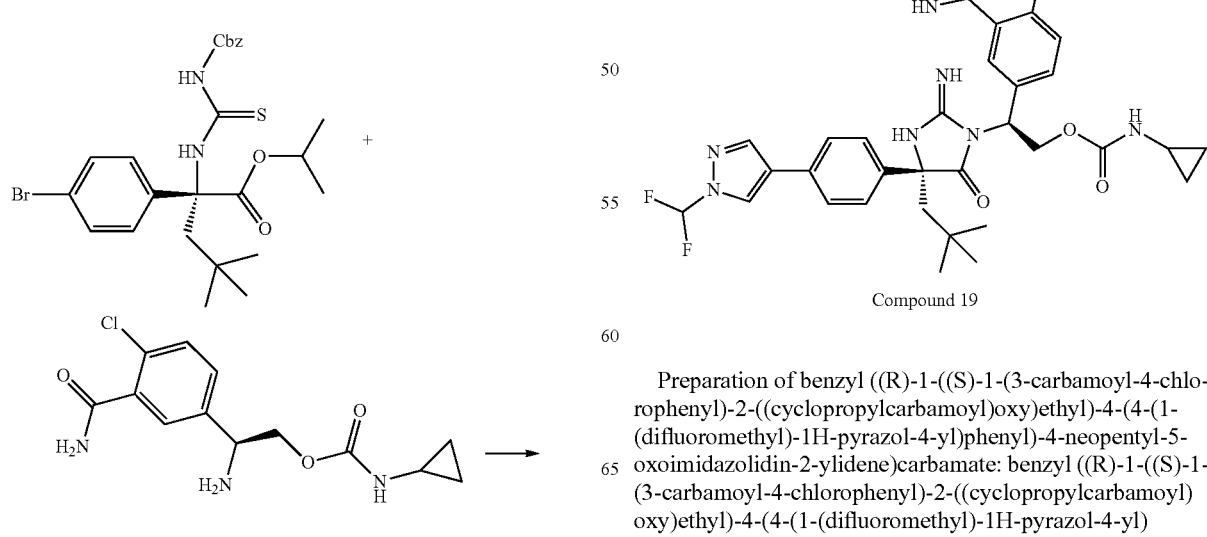

Compound 19

Preparation of benzyl ((R)-1-((S)-1-(3-carbamoyl-4-chlorophenyl)-2-((cyclopropylcarbamoyl)oxy)ethyl)-4-(4-(1-(difluoromethyl)-1H-pyrazol-4-yl)phenyl)-4-neopentyl-5-oxoimidazolidin-2-ylidene)carbamate: benzyl ((R)-1-((S)-1-(3-carbamoyl-4-chlorophenyl)-2-((cyclopropylcarbamoyl)oxy)ethyl)-4-(4-(1-(difluoromethyl)-1H-pyrazol-4-yl)

phenyl)-4-neopentyl-5-oxoimidazolidin-2-ylidene) carbamate was prepared following the procedure to prepare benzyl ((R)-1-((S)-1-(4-chloro-3-(3-methylpyridin-2-yl)phenyl)-2-hydroxyethyl)-4-(4-(1-(difluoromethyl)-1H-pyrazol-4-yl)-2-fluorophenyl)-4-neopentyl-5-oxoimidazolidin-2-ylidene)carbamate described in Example 12, except that (S)-2-amino-2-(3-carbamoyl-4-chlorophenyl)ethyl cyclopropylcarbamate was used instead of (S)-2-amino-2-(4-chloro-3-(3-methylpyridin-2-yl)phenyl)ethan-1-ol hydrochloride.

Preparation of (S)-2-((R)-2-(((benzyloxy)carbonyl)imino)-4-(4-(1-(difluoromethyl)-1H-pyrazol-4-yl)phenyl)-4-neopentyl-5-oxoimidazolidin-1-yl)-2-(4-chloro-3-(1H-1,2,4-triazol-5-yl)phenyl)ethyl cyclopropylcarbamate: (S)-2-((R)-2-(((benzyloxy)carbonyl)imino)-4-(4-(1-(difluoromethyl)-1H-pyrazol-4-yl)phenyl)-4-neopentyl-5-oxoimidazolidin-1-yl)-2-(4-chloro-3-(1H-1,2,4-triazol-5-yl)phenyl)ethyl cyclopropylcarbamate was prepared following the procedure to prepare tert-butyl ((R)-1-((S)-1-(4-chloro-3-(1H-1,2,4-triazol-5-yl)phenyl)-2-hydroxyethyl)-4-(4-(1-(difluoromethyl)-1H-pyrazol-4-yl)-2-fluorophenyl)-4-neopentyl-5-oxoimidazolidin-2-ylidene)carbamate described in Example 11, starting with benzyl ((R)-1-((S)-1-(3-carbamoyl-4-chlorophenyl)-2-((cyclopropylcarbamoyl)oxy)ethyl)-4-(4-(1-(difluoromethyl)-1H-pyrazol-4-yl)phenyl)-4-neopentyl-5-oxoimidazolidin-2-ylidene)carbamate.

Preparation of Compound 19: To a solution of benzyl ((R)-1-((S)-1-(3-carbamoyl-4-chlorophenyl)-2-((cyclopropylcarbamoyl)oxy)ethyl)-4-(4-(1-(difluoromethyl)-1H-pyrazol-4-yl)phenyl)-4-neopentyl-5-oxoimidazolidin-2-ylidene)carbamate (88 mg, 0.11 mmol) in DCM (5 mL) was added boron tribromide in DCM (1M, 1.0 mL) dropwise at 0° C. and stirred for 5 min. The reaction was then quenched by addition of methanol. The mixture was then concentrated down. The residue was purified by reverse phase HPLC (acetonitrile/water, both containing 0.1% TFA) to give the product. LCMS-ESI+(m/z): calc'd for $C_{32}H_{34}ClF_2N_9O_3$: 666.2 [M+H]+. found: 666.1 [M+H]+. $^1$H NMR (400 MHz, $CD_3CN$) δ 8.30 (s, 1H), 8.27 (s, 1H), 8.04 (s, 1H), 7.79-7.20 (m, 9H), 5.82-5.73 (m, 1H), 5.49-5.39 (m, 1H), 4.92 (t, J=10.7 Hz, 1H), 4.63 (d, J=11.4 Hz, 1H), 2.35-2.13 (m, 2H), 0.92 (s, 9H), 0.64-0.51 (m, 2H), 0.43-0.31 (m, 2H).

Example 20: Preparation of Compound 20

Compound 20

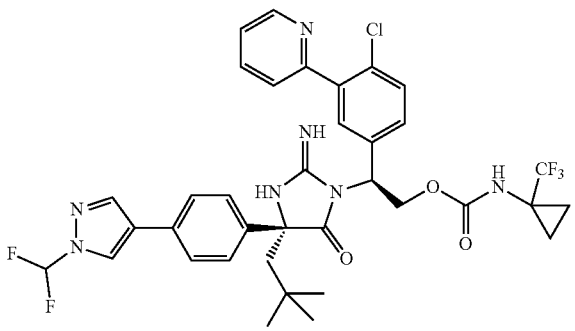

Preparation of benzyl ((R)-1-((S)-1-(4-chloro-3-(pyridin-2-yl)phenyl)-2-hydroxyethyl)-4-(4-(1-(difluoromethyl)-1H-pyrazol-4-yl)phenyl)-4-neopentyl-5-oxoimidazolidin-2-ylidene)carbamate: To a solution of isopropyl (R)-2-(3-((benzyloxy)carbonyl)thioureido)-2-(4-(1-(difluoromethyl)-1H-pyrazol-4-yl)phenyl)-4,4-dimethylpentanoate (36 mg, 0.063 mmol) and (S)-2-amino-2-(4-chloro-3-(pyridin-2-yl)phenyl)ethan-1-ol hydrochloride (18 mg, 0.063 mmol) in DMF (0.6 mL) were added sequentially N,N-diisopropylethylamine (0.055 mL, 0.32 mmol) and 1-(3-dimethylaminopropyl)-3-ethylcarbodiimide hydrochloride (24 mg, 0.13 mmol). The reaction mixture was stirred at 60° C. for 12 h. Then the reaction mixture was cooled to rt and quenched by addition of saturated ammonium chloride solution and EtOAc. The layers were separated and the aqueous layer was further extracted with EtOAc. The combined organic layers were washed with 10% LiCl, and then with brine, dried (over $Na_2SO_4$), filtered, and concentrated in vacuo. The residue was purified by silica gel column chromatography (0-100% EtOAc/hexanes) to give the product.

Preparation of benzyl ((R)-1-((S)-1-(4-chloro-3-(pyridin-2-yl)phenyl)-2-(((1-(trifluoromethyl)cyclopropyl)carbamoyl)oxy)ethyl)-4-(4-(1-(difluoromethyl)-1H-pyrazol-4-yl)phenyl)-4-neopentyl-5-oxoimidazolidin-2-ylidene)carbamate: 1-isocyanato-1-(trifluoromethyl)cyclopropane was prepared by the following procedure: A mixture of 1-trifluoromethylcyclopropane-1-carboxylic acid (0.45 g, 2.89 mmol), toluene (4.6 mL), diphenyl phosphoryl azide (0.84 g, 3.04 mmol) and triethylamine (0.32 g, 3.82 mmol) was stirred at 100° C. for 2 h. Then, the reaction mixture was allowed to cool to rt and used for the next step without purification. To a solution of benzyl ((R)-1-((S)-1-(4-chloro-3-(pyridin-2-yl)phenyl)-2-hydroxyethyl)-4-(4-(1-(difluoromethyl)-1H-pyrazol-4-yl)phenyl)-4-neopentyl-5-oxoimidazolidin-2-ylidene)carbamate (9 mg, 0.01 mmol) in dichloromethane (0.2 mL) were added sequentially a solution of 1-isocyanato-1-(trifluoromethyl)cyclopropane in toluene (0.65M, 0.19 mL) and titanium (IV) tert-butoxide (0.02 mL). The reaction mixture was maintained at rt for 90 min. The reaction mixture was directly purified by silica column chromatography (0-100% EtOAc/hexane) to give the product.

Preparation of Compound 20: To a solution of benzyl ((R)-1-((S)-1-(4-chloro-3-(pyridin-2-yl)phenyl)-2-(((1-(trifluoromethyl)cyclopropyl)carbamoyl)oxy)ethyl)-4-(4-(1-(difluoromethyl)-1H-pyrazol-4-yl)phenyl)-4-neopentyl-5-oxoimidazolidin-2-ylidene)carbamate (10 mg, 0.01 mmol) in dichloromethane (0.2 mL) was added boron tribromide in DCM (1M, 0.03 mL) at 0° C. The reaction mixture was maintained at 0° C. for 60 min. The reaction mixture was quenched by addition of saturated $NaHCO_3$ and extracted with EtOAc. The organic layer was washed with brine, dried (over $Na_2SO_4$), filtered, and concentrated in vacuo. The residue was purified by silica gel column chromatography (0-10% MeOH/(3:1 $CH_2Cl_2$/hexanes)) to give the product. LCMS-ESI+ (m/z): calc'd for $C_{36}H_{35}ClF_5N_7O_3$: 744.2 [M+H]+. found: 744.2 [M+H]+. $^1$H NMR (400 MHz, Methanol-$d_4$) δ 8.48-8.38 (m, 2H), 8.06 (s, 1H), 7.70-7.43 (m, 5H), 7.42-7.32 (m, 2H), 7.24 (d, J=7.9 Hz, 1H), 7.18 (q, J=6.9 Hz, 1H), 7.11 (d, J=2.1 Hz, 1H), 5.46 (dd, J=9.1, 5.6 Hz, 1H), 5.15-5.02 (m, 1H), 4.63 (dd, J=11.1, 5.5 Hz, 1H), 2.30 (d, J=14.6 Hz, 1H), 1.93 (d, J=14.7 Hz, 1H), 1.31-1.20 (m, 2H), 1.05 (s, 2H), 0.95 (s, 9H).

Example 21: Preparation of Compound 21

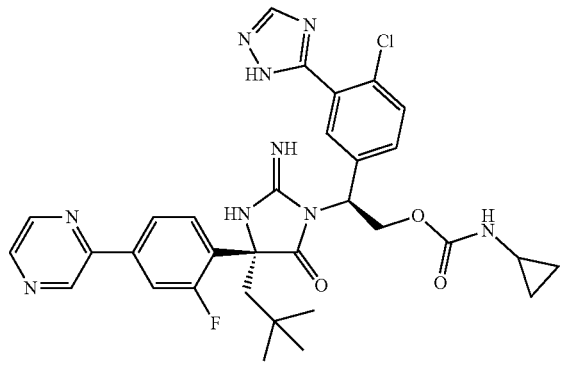

Compound 21

Preparation of methyl 5-((S)-1-((R)-2-(((benzyloxy)carbonyl)imino)-4-(4-bromo-2-fluorophenyl)-4-neopentyl-5-oxoimidazolidin-1-yl)-2-((cyclopropylcarbamoyl)oxy)ethyl)-2-chlorobenzoate: To a solution of methyl 5-((S)-1-((R)-2-(((benzyloxy)carbonyl)imino)-4-(4-bromo-2-fluorophenyl)-4-neopentyl-5-oxoimidazolidin-1-yl)-2-hydroxyethyl)-2-chlorobenzoate (1.39 g, 2.02 mmol) in DCM (40 mL) were added 1,1'-carbonyldiimidazole (490 mg, 3.03 mmol) and N,N-diisopropylethylamine (0.88 mL, 5.04 mmol). The reaction mixture was stirred at rt for 30 min. Then to the mixture was added cyclopropylamine (0.7 mL, 10 mmol) and the reaction mixture was stirred at rt overnight. The reaction mixture was diluted with EtOAc, and washed with $H_2O$ and then with brine. The organic phase was dried over $Na_2SO_4$, filtered, and concentrated. The residue was purified by silica gel column chromatography (0-100% gradient EtOAc/hexanes) to give the product.

Preparation of methyl 5-((S)-1-((R)-4-(4-bromo-2-fluorophenyl)-2-imino-4-neopentyl-5-oxoimidazolidin-1-yl)-2-((cyclopropylcarbamoyl)oxy)ethyl)-2-chlorobenzoate: To a solution of methyl 5-((S)-1-((R)-2-(((benzyloxy)carbonyl)imino)-4-(4-bromo-2-fluorophenyl)-4-neopentyl-5-oxoimidazolidin-1-yl)-2-((cyclopropylcarbamoyl)oxy)ethyl)-2-chlorobenzoate (968 mg, 1.25 mmol) in DCM (10 mL) was dropwise added iodotrimethylsilane (0.36 mL, 2.51 mmol). The reaction mixture was stirred at rt for 1 h. The reaction was quenched by addition of saturated $NaHCO_3$ solution, and the mixture was extracted with EtOAc. The organic extract was washed with brine, dried over $Na_2SO_4$, filtered, and concentrated. The residue was used directly in the next reaction without further purification.

Preparation of methyl 5-((S)-1-((R)-4-(4-bromo-2-fluorophenyl)-2-((tert-butoxycarbonyl)imino)-4-neopentyl-5-oxoimidazolidin-1-yl)-2-((cyclopropylcarbamoyl)oxy)ethyl)-2-chlorobenzoate: To a stirred suspension of methyl 5-((S)-1-((R)-4-(4-bromo-2-fluorophenyl)-2-imino-4-neopentyl-5-oxoimidazolidin-1-yl)-2-((cyclopropylcarbamoyl)oxy)ethyl)-2-chlorobenzoate (924 mg, 1.45 mmol) in THF (13 mL) was added N,N-diisopropylethylamine (2.52 ml, 14.5 mmol) and di-tert-butyl dicarbonate (949 mg, 4.35 mmol). The reaction mixture was stirred at rt overnight. The reaction mixture was treated with saturated aqueous $NaHCO_3$ and extracted with EtOAc. The organic phase was dried over $Na_2SO_4$, filtered, and concentrated. The residue was purified by silica gel column chromatography (0-100% gradient EtOAc/hexanes) to give the product.

Preparation of tert-butyl ((R)-4-(4-bromo-2-fluorophenyl)-1-((S)-1-(3-carbamoyl-4-chlorophenyl)-2-((cyclopropylcarbamoyl)oxy)ethyl)-4-neopentyl-5-oxoimidazolidin-2-ylidene)carbamate: tert-butyl ((R)-4-(4-bromo-2-fluorophenyl)-1-((S)-1-(3-carbamoyl-4-chlorophenyl)-2-((cyclopropylcarbamoyl)oxy)ethyl)-4-neopentyl-5-oxoimidazolidin-2-ylidene)carbamate was prepared following the procedure to prepare tert-butyl (S)-(1-(3-carbamoyl-4-chlorophenyl)-2-((cyclopropylcarbamoyl)oxy)ethyl)carbamate described in Example 19, starting with methyl 5-((S)-1-((R)-4-(4-bromo-2-fluorophenyl)-2-((tert-butoxycarbonyl)imino)-4-neopentyl-5-oxoimidazolidin-1-yl)-2-((cyclopropylcarbamoyl)oxy)ethyl)-2-chlorobenzoate.

Preparation of (S)-2-((R)-4-(4-bromo-2-fluorophenyl)-2-((tert-butoxycarbonyl)imino)-4-neopentyl-5-oxoimidazolidin-1-yl)-2-(4-chloro-3-(1H-1,2,4-triazol-5-yl)phenyl)ethyl cyclopropylcarbamate: (S)-2-((R)-4-(4-bromo-2-fluorophenyl)-2-((tert-butoxycarbonyl)imino)-4-neopentyl-5-oxoimidazolidin-1-yl)-2-(4-chloro-3-(1H-1,2,4-triazol-5-yl)phenyl)ethyl cyclopropylcarbamate was prepared following the procedure to prepare (S)-2-((R)-2-(((benzyloxy)carbonyl)imino)-4-(4-(1-(difluoromethyl)-1H-pyrazol-4-yl)phenyl)-4-neopentyl-5-oxoimidazolidin-1-yl)-2-(4-chloro-3-(1H-1,2,4-triazol-5-yl)phenyl)ethyl cyclopropylcarbamate described in Example 18, starting with tert-butyl ((R)-4-(4-bromo-2-fluorophenyl)-1-((S)-1-(3-carbamoyl-4-chlorophenyl)-2-((cyclopropylcarbamoyl)oxy)ethyl)-4-neopentyl-5-oxoimidazolidin-2-ylidene)carbamate.

Preparation of (S)-2-((R)-2-((tert-butoxycarbonyl)imino)-4-(2-fluoro-4-(pyrazin-2-yl)phenyl)-4-neopentyl-5-oxoimidazolidin-1-yl)-2-(4-chloro-3-(1H-1,2,4-triazol-5-yl)phenyl)ethyl cyclopropylcarbamate: To a solution of (S)-2-((R)-4-(4-bromo-2-fluorophenyl)-2-((tert-butoxycarbonyl)imino)-4-neopentyl-5-oxoimidazolidin-1-yl)-2-(4-chloro-3-(1H-1,2,4-triazol-5-yl)phenyl)ethyl cyclopropylcarbamate in dioxane (0.8 mL) were added 2-tributylstannylpyrazine (38 μL, 0.12 mmol), tetrakis(triphenylphosphine)palladium (4.64 mg, 0.004 mmol) and copper(I) iodide (0.76 mg, 0.004 mmol). The reaction mixture was degassed with nitrogen and was heated at 100° C. for 90 min. The reaction was cooled down, and diluted with EtOAc, washed with aqueous KF solution and then with brine. The organic phase was dried over $Na_2SO_4$, filtered, and concentrated in vacuo. The residue was purified by reverse phase prep HPLC (acetonitrile/$H_2O$, both containing 0.1% TFA) to give the product.

Compound 21 was then prepared following the procedure to prepare Compound 8, starting with (S)-2-((R)-2-((tert-butoxycarbonyl)imino)-4-(2-fluoro-4-(pyrazin-2-yl)phenyl)-4-neopentyl-5-oxoimidazolidin-1-yl)-2-(4-chloro-3-(1H-1,2,4-triazol-5-yl)phenyl)ethyl cyclopropylcarbamate. LCMS-ESI+ (m/z): calc'd for $C_{32}H_{34}ClFN_9O_3$: 646.2 [M+H]+. found: 646.2 [M+H]+. 1H NMR (400 MHz, $CD_3OD$) δ=9.18-9.09 (m, 1H), 8.75-8.66 (m, 1H), 8.59 (d, J=2.5, 1H), 8.39 (s, 1H), 7.98-7.78 (m, 2H), 7.73 (s, 1H), 7.65-7.40 (m, 3H), 5.78-5.54 (m, 1H), 5.16 (t, J=10.3, 1H), 4.78-4.65 (m, 1H), 2.49 (dt, J=7.1, 3.4, 1H), 2.39 (d, J=6.5, 2H), 1.05 (s, 9H), 0.72-0.60 (m, 2H), 0.54-0.39 (m, 2H).

Example 22: Preparation of Compound 22 and Compound 23

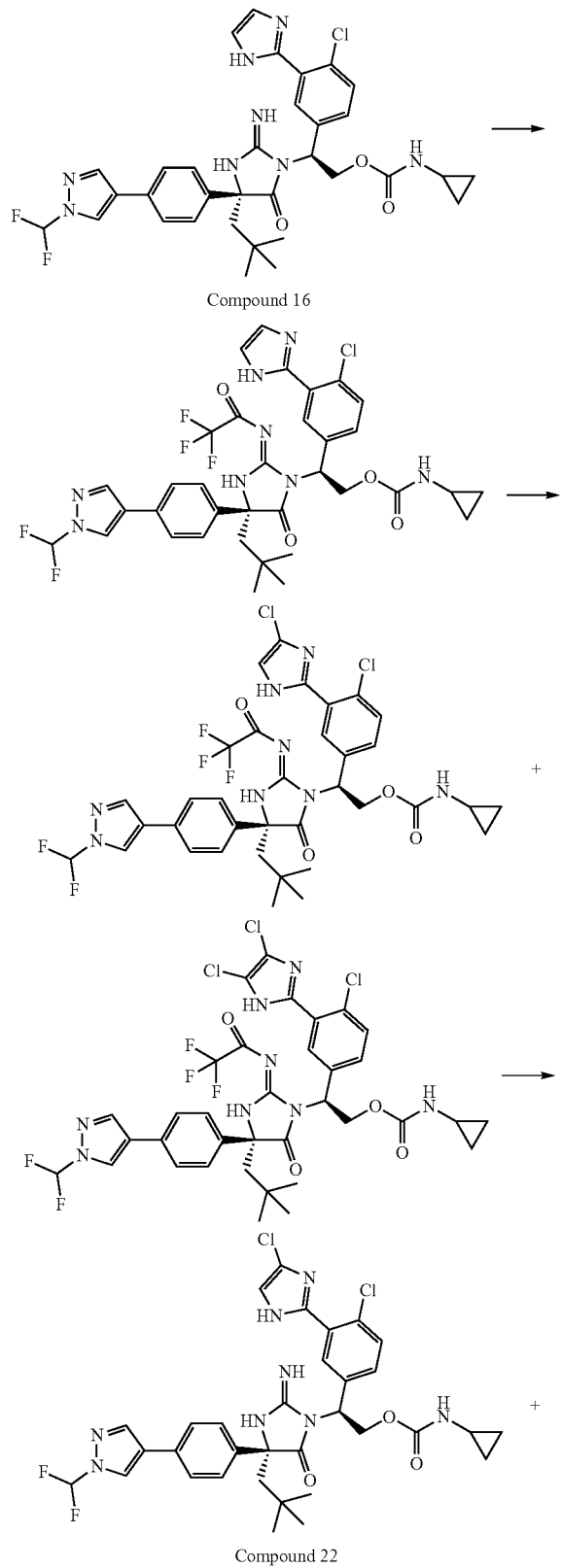

Compound 16

Compound 22

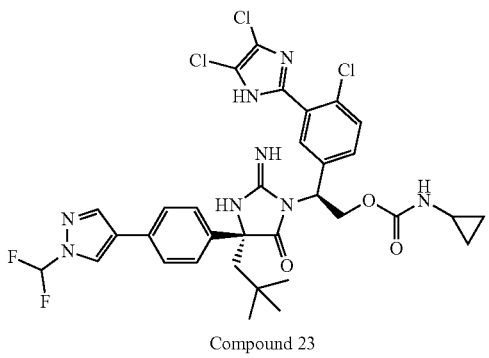

Compound 23

Preparation Compound 22 and Compound 23: To a solution of Compound 16, TFA salt (5 mg, 0.0064 mmol) in DCM (1.5 mL) was added 2,6-lutidine (20 μL, 0.0064 mmol). The reaction mixture was stirred at rt for 5 min. To the mixture was added a trifluoroacetic anhydride solution in DCM (0.14 M, 175 μL, 0.016 mmol), stirred at rt, resulting in formation of (S)-2-(4-chloro-3-(1H-imidazol-2-yl)phenyl)-2-((R)-4-(4-(1-(difluoromethyl)-1H-pyrazol-4-yl)phenyl)-4-neopentyl-5-oxo-2-((2,2,2-trifluoroacetyl)imino)imidazolidin-1-yl)ethyl cyclopropylcarbamate. To this solution was titrated Palau'Chlor solution in DCM (0.095 M, 100 μL, 0.0095 mmol). The reaction mixture was stirred at rt for 1.5 h. Then to the mixture was added more of the Palau'chlor solution (35 μL, 0.003 mmol). The mixture was stirred at rt for another 1 h, and a mixture of (S)-2-(4-chloro-3-(4-chloro-1H-imidazol-2-yl)phenyl)-2-((R)-4-(4-(1-(difluoromethyl)-1H-pyrazol-4-yl)phenyl)-4-neopentyl-5-oxo-2-(2,2,2-trifluoroacetyl)imino)imidazolidin-1-yl)ethyl cyclopropylcarbamate and (S)-2-(4-chloro-3-(4,5-dichloro-1H-imidazol-2-yl)phenyl)-2-((R)-4-(4-(1-(difluoromethyl)-1H-pyrazol-4-yl)phenyl)-4-neopentyl-5-oxo-2-((2,2,2-trifluoroacetyl)imino)imidazolidin-1-yl)ethyl cyclopropylcarbamate were formed. To the mixture was added cyclopropylamine (20 μL, 0.29 mmol). After 15 min, Hunig's base (20 μL, 0.11 mmol) was added and the reaction mixture was stirred at rt for 10 min. Then to the mixture was added MeOH (500 μL) and stirred at rt for 10 min. The reaction mixture was concentrated down and the residue was purified by reverse phase HPLC (acetonitrile/$H_2O$, both containing 0.1% TFA) to give Compound 22 and Compound 23. For Compound 22: LCMS-ESI+ (m/z): calc'd for $C_{33}H_{34}Cl_2F_2N_8O_3$: 699.2 [M+H]+. found: 699.2 [M+H]+. 1H NMR (400 MHz, $CD_3CN$) δ 8.29 (s, 1H), 8.04 (s, 1H), 7.81 (s, 1H), 7.59 (d, J=8.3 Hz, 2H), 7.52 (d, J=8.6 Hz, 2H), 7.45 (d, J=8.4 Hz, 1H), 7.38 (t, JHF=60.2 Hz, 1H), 7.28 (d, J=8.3 Hz, 1H), 7.06 (s, 1H), 5.85-5.67 (m, 1H), 5.52-5.36 (m, 1H), 4.93 (t, J=10.6 Hz, 1H), 4.66-4.58 (m, 1H), 2.33-2.13 (m, 2H), 0.93 (s, 9H), 0.65-0.52 (m, 2H), 0.43-0.34 (m, 2H). For Compound 23: LCMS-ESI+(m/z): calc'd for $C_{33}H_{33}Cl_3F_2N_8O_3$: 733.2 [M+H]+. found: 733.3 [M+H]+. 1H NMR (400 MHz, $CD_3CN$) δ 8.29 (s, 1H), 8.04 (s, 1H), 7.64 (s, 1H), 7.58 (d, J=8.4 Hz, 2H), 7.50 (d, J=8.5 Hz, 2H), 7.45 (d, J=8.4 Hz, 1H), 7.38 (t, JHF=60.0 Hz, 1H), 7.31 (d, J=8.5 Hz, 1H), 5.85-5.77 (m, 1H), 5.51-5.37 (m, 1H), 4.92 (t, J=10.5 Hz, 1H), 4.67-4.57 (m, 1H), 2.33-2.11 (m, 2H), 0.92 (s, 9H), 0.66-0.53 (m, 2H), 0.44-0.33 (m, 3H).

Example 23: Preparation of Compound 24

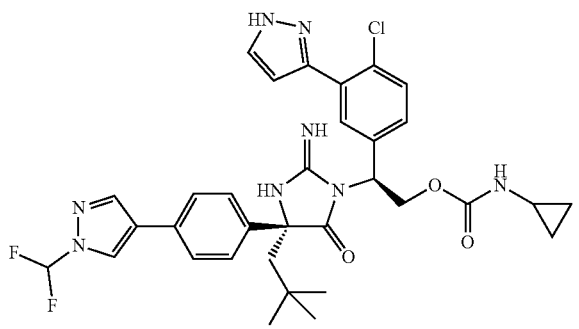

Compound 24

Preparation of (S)-2-(4-chloro-3-(1H-imidazol-2-yl)phenyl)-2-((R)-4-(4-(1-(difluoromethyl)-1H-pyrazol-4-yl)phenyl)-4-neopentyl-5-oxo-2-((2,2,2-trifluoroacetyl)imino)imidazolidin-1-yl)ethyl cyclopropylcarbamate: (S)-2-(4-chloro-3-(1H-imidazol-2-yl)phenyl)-2-((R)-4-(4-(1-(difluoromethyl)-1H-pyrazol-4-yl)phenyl)-4-neopentyl-5-oxo-2-((2,2,2-trifluoroacetyl)imino)imidazolidin-1-yl)ethyl cyclopropylcarbamate was prepared following the procedure to prepare benzyl ((R)-1-((S)-1-(4-chloro-3-(pyridin-2-yl)phenyl)-2-hydroxyethyl)-4-(4-(1-(difluoromethyl)-1H-pyrazol-4-yl)phenyl)-4-neopentyl-5-oxoimidazolidin-2-ylidene)carbamate described in Example 20, except that (S)-2-amino-2-(4-chloro-3-(1H-pyrazol-3-yl)phenyl)ethan-1-ol hydrochloride was used instead of (S)-2-amino-2-(4-chloro-3-(pyridin-2-yl)phenyl)ethan-1-ol hydrochloride. Compound 24 was prepared following the procedure to prepare Compound 20, starting with benzyl ((R)-1-((S)-1-(4-chloro-3-(1H-pyrazol-3-yl)phenyl)-2-hydroxyethyl)-4-(4-(1-(difluoromethyl)-1H-pyrazol-4-yl)phenyl)-4-neopentyl-5-oxoimidazolidin-2-ylidene)carbamate. LCMS-ESI+ (m/z): calc'd for $C_{33}H_{35}ClF_2N_8O_3$: 655.3 [M+H]+. found: 655.2 [M+H]+. $^1$H NMR (400 MHz, $CD_3CN$) δ 8.30 (s, 1H), 8.04 (s, 1H), 7.63-7.47 (m, 7H), 7.44 (d, J=8.4 Hz, 1H), 7.39 (t, JHF=60.0 Hz, 1H), 7.28-7.18 (m, 1H), 6.62 (d, J=2.3 Hz, 1H), 5.80-5.71 (m, 1H), 5.50-5.36 (m, 1H), 4.92 (t, J=10.6 Hz, 1H), 4.68-4.58 (m, 1H), 2.36-2.10 (m, 2H), 0.92 (s, 9H), 0.64-0.47 (m, 2H), 0.43-0.29 (m, 2H). Preparation of tert-butyl (S)-4-(4-chloro-3-(1H-pyrazol-3-yl)phenyl)-2,2-dimethyloxazolidine-3-carboxylate: A mixture of tert-butyl (S)-4-(3-bromo-4-chlorophenyl)-2,2-dimethyloxazolidine-3-carboxylate (0.19 g, 0.47 mmol), pyrazole-3-boronic acid (0.27 g, 2.0 mmol), $PdCl_2$(dppf) (0.02 g, 0.023 mmol) and potassium carbonate (330 mg, 2.0 mmol) in dioxane (2.5 mL) and water (0.5 mL) was heated at 90° C. for 16 h. The reaction mixture was diluted with brine and extracted with EtOAc (3×). The combined organic phases were washed with brine, dried (over $Na_2SO_4$), filtered, and concentrated. The residue was purified by silica gel column chromatography (0-100% gradient EtOAc/hexanes) to give the product.

Preparation of (S)-2-amino-2-(4-chloro-3-(1H-pyrazol-3-yl)phenyl)ethan-1-ol hydrochloride: (S)-2-amino-2-(4-chloro-3-(1H-pyrazol-3-yl)phenyl)ethan-1-ol hydrochloride was prepared following the procedure to prepare (S)-2-amino-2-(4-chloro-3-(1-methyl-1H-1,2,4-triazol-3-yl)phenyl)ethan-1-ol described in Example 18, starting with tert-butyl (S)-4-(4-chloro-3-(1H-pyrazol-3-yl)phenyl)-2,2-dimethyloxazolidine-3-carboxylate.

Example 24: Preparation of Compound 25

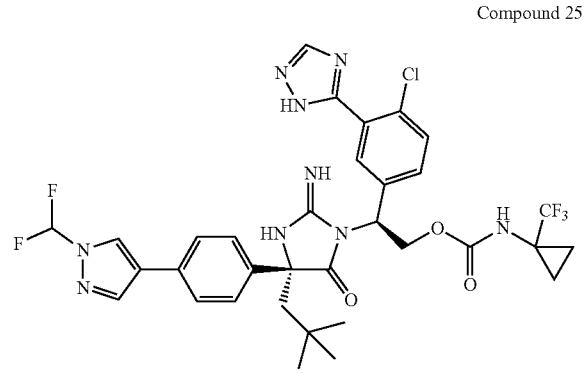 [SMILES: CC(C)(C)C[C@]1(c2ccc(-c3cnn(C(F)F)c3)cc2)NC(=N)N([C@H](COC(=O)NC2(C(F)(F)F)CC2)c2ccc(Cl)c(-c3ncn[nH]3)c2)C1=O]

Compound 25

Compound 25 was prepared following the procedure to prepare Compound 19, except that (S)-2-amino-2-(3-carbamoyl-4-chlorophenyl)ethyl (1-(trifluoromethyl)cyclopropyl)carbamate was used instead of (S)-2-amino-2-(3-carbamoyl-4-chlorophenyl)ethylcyclopropylcarbamate. LCMS-ESI+ (m/z): calc'd for $C_{33}H_{33}ClF_5N_9O_3$: 734.2 [M+H]+. found: 734.5 [M+H]+. $^1$H NMR (400 MHz, Methanol-$d_4$) δ 8.38 (s, 1H), 8.22 (s, 1H), 8.06 (s, 1H), 7.74-7.23 (m, 7H), 5.46 (s, 1H), 5.05 (t, J=9.9 Hz, 1H), 4.65 (dd, J=11.2, 5.9 Hz, 1H), 2.28 (d, J=14.7 Hz, 1H), 1.95 (d, J=14.6 Hz, 1H), 1.19 (d, J=21.8 Hz, 2H), 1.03 (s, 2H), 0.95 (s, 9H).

Preparation of (S)-2-amino-2-(3-carbamoyl-4-chlorophenyl)ethyl (1-(trifluoromethyl)cyclopropyl)carbamate: (S)-2-amino-2-(3-carbamoyl-4-chlorophenyl)ethyl (1-(trifluoromethyl)cyclopropyl)carbamate was prepared following the procedure to prepare (S)-2-amino-2-(3-carbamoyl-4-chlorophenyl)ethylcyclopropylcarbamate described in Example 19, except that preparation of methyl (S)-5-(1-((tert-butoxycarbonyl)amino)-2-((1-(trifluoromethyl)cyclopropyl)carbamoyl)oxy)ethyl)-2-chlorobenzoate was prepared using 1-isocyanato-1-(trifluoromethyl)cyclopropane and titanium (IV) tert-butoxide.

Example 25: Preparation of Compound 26

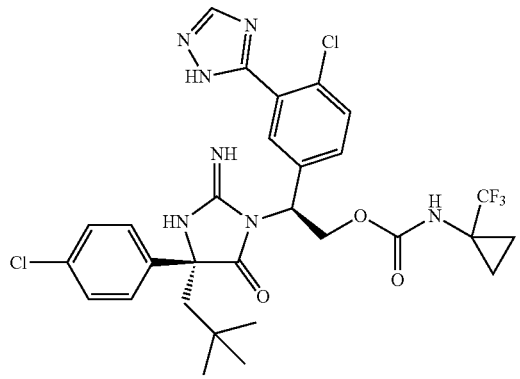

Compound 26

Compound 26 was prepared following the procedure to prepare Compound 25, starting with isopropyl (R)-2-(3-((benzyloxy)carbonyl)thioureido)-2-(4-chlorophenyl)-4,4-dimethylpentanoate, which was prepared following the procedure to prepare isopropyl (R)-2-(3-((benzyloxy)carbonyl)thioureido)-2-(4-bromophenyl)-4,4-dimethylpentanoate. LCMS-ESI+ (m/z): calc'd for $C_{29}H_{30}Cl_2F_3N_7O_3$: 652.2 [M+H]+. found: 652.3 [M+H]+. $^1$H NMR (400 MHz, Methanol-$d_4$) δ 8.38 (s, 1H), 7.42 (d, J=8.7 Hz, 4H), 7.38-7.27 (m, 1H), 7.20 (d, J=8.3 Hz, 2H), 5.60-5.32 (m, 1H), 5.04 (dd, J=11.1, 8.9 Hz, 1H), 4.64 (dd, J=11.1, 5.6 Hz, 1H), 2.23 (d, J=14.6 Hz, 1H), 1.90 (d, J=14.5 Hz, 1H), 1.23 (d, J=2.3 Hz, 2H), 1.04 (s, 2H), 0.93 (s, 9H).

Example 26: Preparation of Compound 27

Compound 27

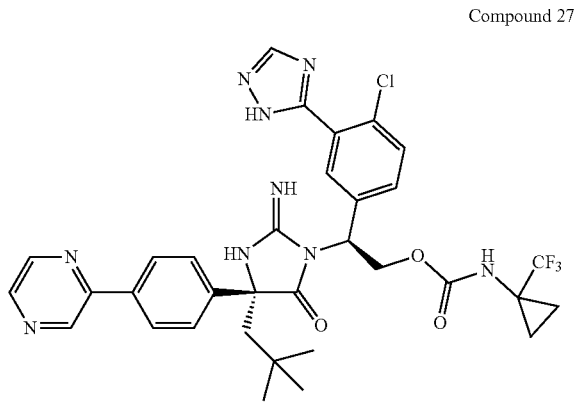 [SMILES: CC(C)(C)C[C@]1(c2ccc(-c3cnccn3)cc2)NC(=N)N([C@H](COC(=O)NC2(C(F)(F)F)CC2)c2ccc(Cl)c(-c3ncn[nH]3)c2)C1=O]

Compound 27 was prepared following the procedure to prepare Compound 21, starting with (S)-2-(3-carbamoyl-4-chlorophenyl)-2-((R)-2-imino-4-neopentyl-5-oxo-4-(4-(pyrazin-2-yl)phenyl)imidazolidin-1-yl)ethyl (1-(trifluoromethyl)cyclopropyl)carbamate. LCMS-ESI+ (m/z): calc'd for $C_{33}H_{33}ClF_3N_9O_3$: 696.2 [M+H]+. found: 696.2 [M+H]+. $^1$H NMR (400 MHz, Methanol-$d_4$) δ 9.10 (d, J=16.3 Hz, 1H), 8.70 (dq, J=4.4, 2.9, 2.2 Hz, 1H), 8.56 (dq, J=4.2, 2.6, 1.9 Hz, 1H), 8.30 (s, 1H), 8.20-7.97 (m, 3H), 7.70-7.53 (m, 2H), 7.53-7.41 (m, 1H), 7.40-7.21 (m, 1H), 5.63 (ddd, J=21.0, 9.6, 4.8 Hz, 1H), 5.12 (t, J=10.6 Hz, 1H), 4.77-4.54 (m, 1H), 2.49 (dd, J=14.8, 5.2 Hz, 1H), 2.21 (t, J=12.9 Hz, 1H), 1.37-0.86 (m, 13H).

Example 27: Preparation of Compound 28

Compound 28

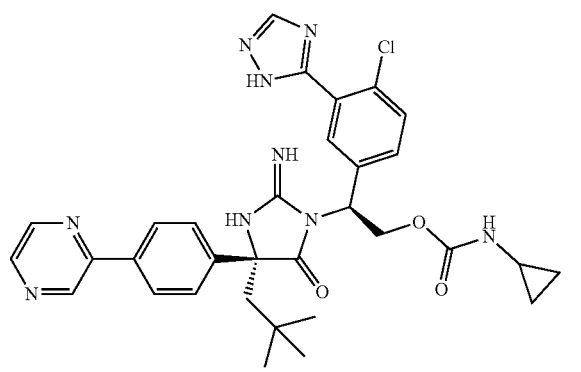

Compound 28 was prepared following the procedure to prepare Compound 27, except the use of methyl 5-((S)-1-((R)-2-((tert-butoxycarbonyl)imino)-4-neopentyl-5-oxo-4-(4-(pyrazin-2-yl)phenyl)imidazolidin-1-yl)-2-((cyclopropylcarbamoyl)oxy)ethyl)-2-chlorobenzoate, which was prepared following the procedure to prepare benzyl ((R)-1-((S)-1-(4-chloro-3-(3-methylpyridin-2-yl)phenyl)-2-((cyclopropylcarbamoyl)oxy)ethyl)-4-(4-(1-(difluoromethyl)-1H-pyrazol-4-yl)-2-fluorophenyl)-4-neopentyl-5-oxoimidazolidin-2-ylidene)carbamate described in Example 12, starting with methyl 5-((S)-1-((R,E)-2-((tert-butoxycarbonyl)imino)-4-neopentyl-5-oxo-4-(4-(pyrazin-2-yl)phenyl)imidazolidin-1-yl)-2-hydroxyethyl)-2-chlorobenzoate. LCMS-ESI+ (m/z): calc'd for $C_{32}H_{34}ClN_9O_3$: 628.2 [M+H]+. found: 628.2 [M+H]+. $^1$H NMR (400 MHz, Methanol-$d_4$) δ 9.23-8.99 (m, 1H), 8.70 (dt, J=3.0, 1.5 Hz, 1H), 8.57 (t, J=2.1 Hz, 1H), 8.30 (s, 1H), 8.17-7.98 (m, 2H), 7.68-7.24 (m, 5H), 5.63 (s, 1H), 5.25-5.01 (m, 1H), 4.70 (d, J=7.4 Hz, 1H), 2.50 (d, J=15.8 Hz, 2H), 2.18 (d, J=15.1 Hz, 1H), 1.01 (d, J=1.7 Hz, 9H), 0.55 (d, J=82.4 Hz, 4H).

Example 28: Preparation of Compound 29 and Compound 30

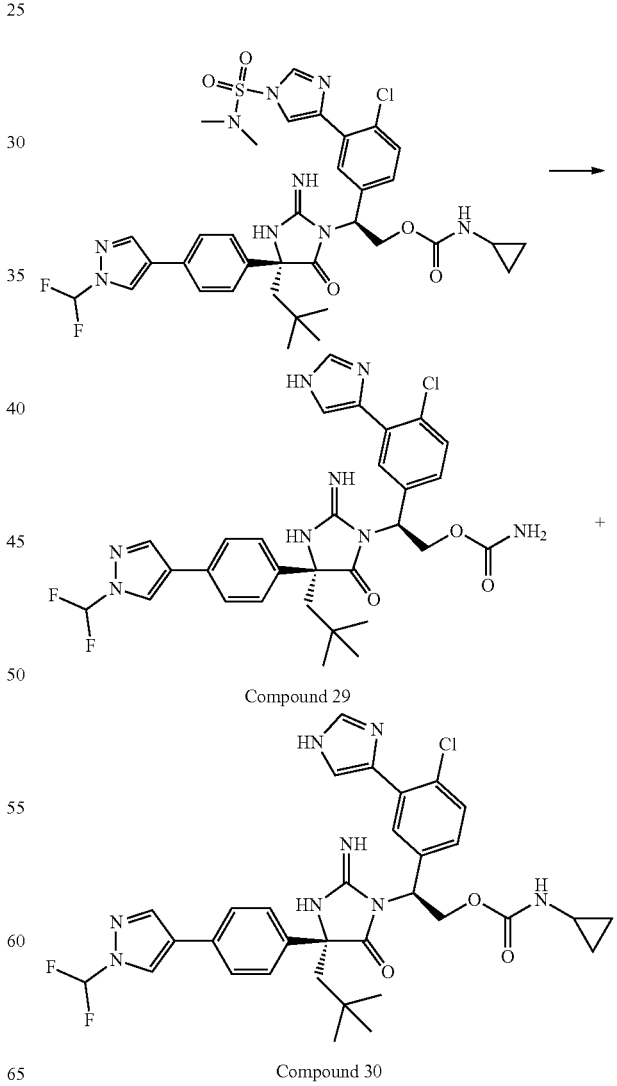

Compound 29

Compound 30

Preparation of (S)-2-(4-chloro-3-(1-(N,N-dimethylsulfamoyl)-1H-imidazol-4-yl)phenyl)-2-((R)-4-(4-(1-(difluoromethyl)-1H-pyrazol-4-yl)phenyl)-2-imino-4-neopentyl-5-oxoimidazolidin-1-yl)ethyl cyclopropylcarbamate: (S)-2-(4-chloro-3-(1-(N,N-dimethylsulfamoyl)-1H-imidazol-4-yl) phenyl)-2-((R)-4-(4-(1-(difluoromethyl)-1H-pyrazol-4-yl) phenyl)-2-imino-4-neopentyl-5-oxoimidazolidin-1-yl)ethyl cyclopropylcarbamate was prepared following the procedure to prepare Compound 24, except that (S)-4-(5-(1-amino-2-hydroxyethyl)-2-chlorophenyl)-N,N-dimethyl-1H-imidazole-1-sulfonamide was used instead of (S)-2-amino-2-(4-chloro-3-(1H-pyrazol-3-yl)phenyl)ethan-1-ol hydrochloride.

Preparation of Compound 29 and Compound 30: To a mixture of (S)-2-(4-chloro-3-(1-(N,N-dimethylsulfamoyl)-1H-imidazol-4-yl)phenyl)-2-((R)-4-(4-(1-(difluoromethyl)-1H-pyrazol-4-yl)phenyl)-2-imino-4-neopentyl-5-oxoimidazolidin-1-yl)ethyl cyclopropylcarbamate (6.5 mg, 0.008 mmol) in aqueous HCl solution (1M, 0.5 mL) and HCl solution in dioxane (4M, 0.5 mL) was added concentrated aqueous HCl solution (0.5 mL), and the reaction mixture was heated to 80° C. Then to the mixture was added concentrated aqueous HCl solution (0.5 mL) and the reaction mixture was heated to 90° C. until the reaction was complete. The reaction was cooled to rt and purified by reverse phase HPLC (acetonitrile/water, containing 0.1% TFA) to give the products Compound 29 and Compound 30. For Compound 29: LCMS-ESI+ (m/z): calc'd for $C_{30}H_{31}ClF_2N_8O_3$: 625.3 [M+H]+. found: 625.1 [M+H]+. $^1$H NMR (400 MHz, $CD_3CN$) δ 8.46 (d, J=1.3 Hz, 1H), 8.29 (d, J=0.7 Hz, 1H), 8.03 (s, 1H), 7.89 (d, J=2.2 Hz, 1H), 7.74 (d, J=1.2 Hz, 1H), 7.60-7.21 (m, 8H), 5.54 (dd, J=9.6, 4.8 Hz, 1H), 5.33 (s, broad, 2H), 5.00 (dd, J=11.5, 9.7 Hz, 1H), 4.59 (dd, J=11.5, 4.8 Hz, 1H), 2.34-2.11 (m, 2H), 0.93 (s, 9H). For Compound 30: LCMS-ESI+(m/z): calc'd for $C_{33}H_{35}ClF_2N_8O_3$: 665.3 [M+H]+. found: 665.1 [M+H]+. $^1$H NMR (400 MHz, $CD_3CN$) δ 8.43 (s, 1H), 8.30 (s, 1H), 8.04 (s, 1H), 7.91 (s, 1H), 7.76 (s, 1H), 7.61-7.20 (m, 8H), 5.93-5.85 (m, 1H), 5.61-5.50 (m, 1H), 5.01 (t, J=10.6 Hz, 1H), 4.66-4.50 (m, 1H), 2.32-2.13 (m, 2H), 0.91 (s, 9H), 0.64-0.53 (m, 2H), 0.43-0.35 (m, 2H).

Example 29: Preparation of Compound 31

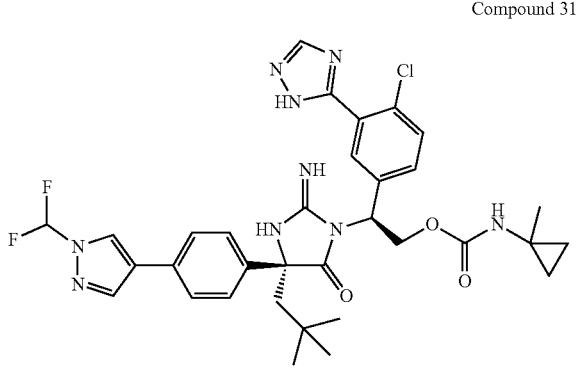 [SMILES: CC(C)(C)C[C@]1(c2ccc(-c3cnn(C(F)F)c3)cc2)NC(=N)N([C@H](COC(=O)NC2(C)CC2)c2ccc(Cl)c(-c3ncn[nH]3)c2)C1=O]

Compound 31

Compound 31 was prepared following the procedure to prepare Compound 25, except that (S)-2-amino-2-(3-carbamoyl-4-chlorophenyl)ethyl (1-methylcyclopropyl)carbamate was used instead of (S)-2-amino-2-(3-carbamoyl-4-chlorophenyl)ethyl (1-trifluoromethylcyclopropyl) carbamate. In addition, (S)-2-amino-2-(3-carbamoyl-4-chlorophenyl)ethyl (1-methylcyclopropyl)carbamate was prepared by using 1-methylcyclopropyl carboxylic acid instead of 1-trifluoromethylcyclopropyl carboxylic acid. LCMS-ESI+ (m/z): calc'd for $C_{33}H_{36}ClF_2N_9O_3$: 680.3 [M+H]+. found: 680.5 [M+H]+. $^1$H NMR (400 MHz, Methanol-$d_4$) δ 8.41 (s, 1H), 8.26 (s, 1H), 8.07 (s, 1H), 7.68-7.22 (m, 8H), 5.51 (d, J=7.8 Hz, 1H), 5.01 (t, J=10.3 Hz, 1H), 4.65 (dd, J=11.4, 5.3 Hz, 1H), 2.38 (d, J=14.9 Hz, 1H), 2.04 (d, J=14.9 Hz, 1H), 1.29 (s, 3H), 0.98 (s, 9H), 0.60 (d, J=45.0 Hz, 4H).

Example 30: Preparation of Compound 32

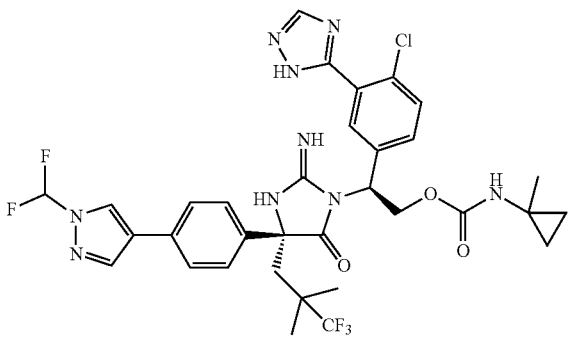

Compound 32

Preparation of isopropyl (R)-2-amino-2-(4-bromophenyl)-5,5,5-trifluoro-4,4-dimethylpentanoate: Isopropyl (R)-2-amino-2-(4-bromophenyl)-5,5,5-trifluoro-4,4-dimethylpentanoate was prepared following the procedure to prepare isopropyl (R)-2-amino-2-(4-bromophenyl)-4,4-dimethylpentanoate except that (3,3,3-trifluoro-2,2-dimethylpropyl) magnesium bromide was used instead of neo-pentylmagnesium bromide.

Compound 32 was then prepared following the procedure to prepare Compound 19, except that 2-amino-2-(3-carbamoyl-4-chlorophenyl)ethyl (1-methylcyclopropyl)carbamate was used instead of 2-amino-2-(3-carbamoyl-4-chlorophenyl)ethyl cyclopropylcarbamate. LCMS-ESI+ (m/z): calc'd for $C_{33}H_{33}ClF_5N_9O_3$: 734.3 [M+H]+. found: 734.5 [M+H]+. $^1$H NMR (400 MHz, Methanol-$d_4$) δ 8.39 (s, 1H), 8.22 (s, 1H), 8.07 (s, 1H), 7.57-7.45 (m, 5H), 7.43-7.23 (m, 2H), 5.41 (s, 1H), 5.01 (t, J=10.2 Hz, 1H), 4.60 (dd, J=11.2, 5.4 Hz, 1H), 2.50 (d, J=14.7 Hz, 1H), 2.20 (d, J=14.6 Hz, 1H), 1.26 (d, J=10.2 Hz, 3H), 1.15 (d, J=6.7 Hz, 6H), 0.64 (d, J=5.2 Hz, 2H), 0.54 (d, J=5.4 Hz, 2H).

Example 31: Preparation of Compound 33

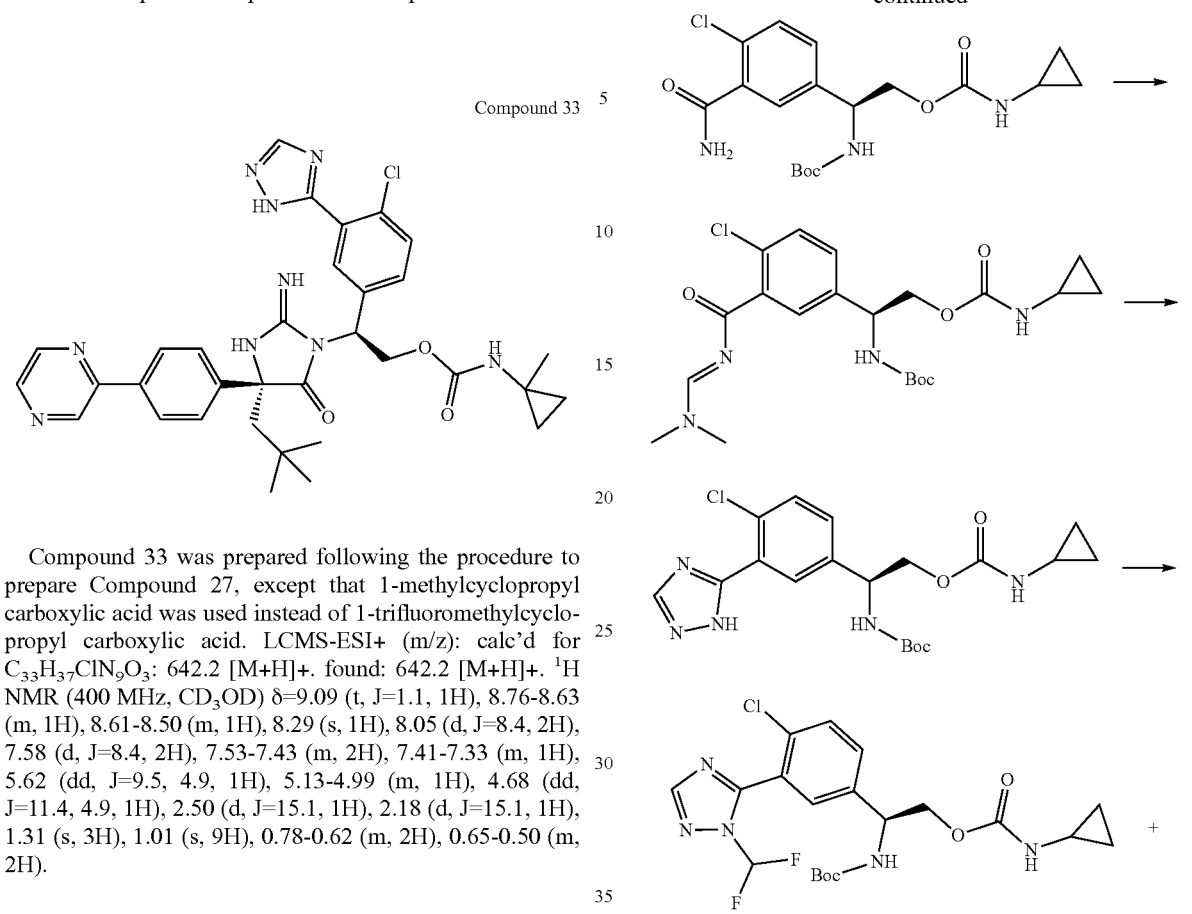

Compound 33

Compound 33 was prepared following the procedure to prepare Compound 27, except that 1-methylcyclopropyl carboxylic acid was used instead of 1-trifluoromethylcyclopropyl carboxylic acid. LCMS-ESI+ (m/z): calc'd for $C_{33}H_{37}ClN_9O_3$: 642.2 [M+H]+. found: 642.2 [M+H]+. $^1$H NMR (400 MHz, CD$_3$OD) δ=9.09 (t, J=1.1, 1H), 8.76-8.63 (m, 1H), 8.61-8.50 (m, 1H), 8.29 (s, 1H), 8.05 (d, J=8.4, 2H), 7.58 (d, J=8.4, 2H), 7.53-7.43 (m, 2H), 7.41-7.33 (m, 1H), 5.62 (dd, J=9.5, 4.9, 1H), 5.13-4.99 (m, 1H), 4.68 (dd, J=11.4, 4.9, 1H), 2.50 (d, J=15.1, 1H), 2.18 (d, J=15.1, 1H), 1.31 (s, 3H), 1.01 (s, 9H), 0.78-0.62 (m, 2H), 0.65-0.50 (m, 2H).

Example 32: Preparation of Compound 34 and Compound 35

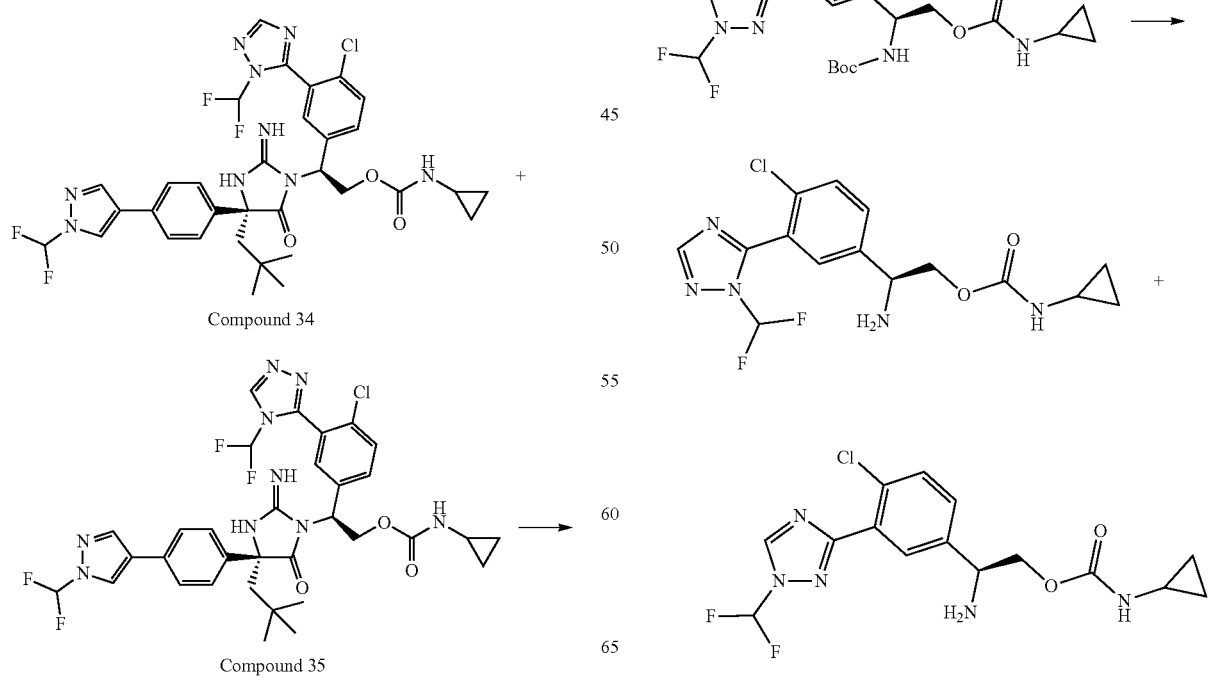

Compound 34

Compound 35

Compound 34 and Compound 35 were prepared by following the procedure to prepare Compound 24, except that the mixture of (S)-2-amino-2-(4-chloro-3-(1-(difluoromethyl)-1H-1,2,4-triazol-5-yl)phenyl)ethyl cyclopropylcarbamate and (S)-2-amino-2-(4-chloro-3-(1-(difluoromethyl)-1H-1,2,4-triazol-3-yl)phenyl)ethyl cyclopropylcarbamate were used instead of (S)-2-amino-2-(4-chloro-3-(1H-pyrazol-3-yl)phenyl)ethan-1-ol hydrochloride. For Compound 34: LCMS-ESI+(m/z): calc'd for $C_{33}H_{39}ClF_4N_9O_3$: 716.2 [M+H]+. found: 716.2 [M+H]+. $^1$H NMR (400 MHz, $CD_3CN$) δ 8.67 (s, 1H), 8.30 (s, 1H), 8.05 (s, 1H), 7.84-7.21 (m, 9H), 5.79-5.72 (m, 1H), 5.51-5.40 (m, 1H), 4.93 (t, J=10.6 Hz, 1H), 4.63 (d, J=11.7 Hz, 1H), 2.35-2.11 (m, 2H), 0.92 (s, 9H), 0.64-0.50 (m, 2H), 0.43-0.32 (m, 3H). For Compound 35: LCMS-ESI+ (m/z): calc'd for $C_{33}H_{39}ClF_4N_9O_3$: 716.2 [M+H]+. found: 716.2 [M+H]+. $^1$H NMR (400 MHz, $CD_3CN$) δ 8.71-7.19 (m, 12H), 5.86-5.74 (m, 1H), 5.60-5.49 (m, 1H), 4.94 (t, J=10.5 Hz, 1H), 4.65-4.57 (m, 1H), 2.32-2.14 (m, 2H), 0.92 (s, 4.5H), 0.89 (s, 4.5H), 0.63-0.52 (m, 2H), 0.45-0.33 (m, 2H).

Preparation of (S)-2-((tert-butoxycarbonyl)amino)-2-(4-chloro-3-(1H-1,2,4-triazol-5-yl)phenyl)ethyl cyclopropylcarbamate: (S)-2-((tert-butoxycarbonyl)amino)-2-(4-chloro-3-(1H-1,2,4-triazol-5-yl)phenyl)ethyl cyclopropylcarbamate was prepared starting with (S)-2-((tert-butoxycarbonyl)amino)-2-(3-carbamoyl-4-chlorophenyl)ethyl cyclopropylcarbamate. The triazole ring was constructed by a method similar to that described in preparation of Compound 11.

Preparation of a mixture of (S)-2-amino-2-(4-chloro-3-(1-(difluoromethyl)-1H-1,2,4-triazol-5-yl)phenyl)ethyl cyclopropylcarbamate and (S)-2-amino-2-(4-chloro-3-(1-(difluoromethyl)-1H-1,2,4-triazol-3-yl)phenyl)ethyl cyclopropylcarbamate: To a solution of (S)-2-((tert-butoxycarbonyl)amino)-2-(4-chloro-3-(1H-1,2,4-triazol-5-yl)phenyl)ethyl cyclopropylcarbamate (106 mg, 0.24 mmol) in DMF (4 mL) was added difluoromethyliodide in THF (10% v/v, 2.0 mL). Then to the mixture was added $Cs_2CO_3$ (400 mg, 1.21 mmol). The reaction mixture was heated at 60° C. for 1.5 h. The mixture was cooled down, and diluted with EtOAc and $H_2O$. The organic phase was collected, washed with $H_2O$, dried over $Na_2SO_4$, filtered, and concentrated. The residue was purified by silica gel column chromatography (0-100% gradient EtOAc/hexanes) to give the product.

Preparation of a mixture of (S)-2-amino-2-(4-chloro-3-(1-(difluoromethyl)-1H-1,2,4-triazol-5-yl)phenyl)ethyl cyclopropylcarbamate and (S)-2-amino-2-(4-chloro-3-(1-(difluoromethyl)-1H-1,2,4-triazol-3-yl)phenyl)ethyl cyclopropylcarbamate: The mixture of (S)-2-amino-2-(4-chloro-3-(1-(difluoromethyl)-1H-1,2,4-triazol-5-yl)phenyl)ethyl cyclopropylcarbamate and (S)-2-amino-2-(4-chloro-3-(1-(difluoromethyl)-1H-1,2,4-triazol-3-yl)phenyl)ethylcyclopropylcarbamate obtained from the previous step was treated with neat TFA (2 mL) at rt for 5 min. The reaction mixture was concentrated to dryness. The residue was treated with DCM and $H_2O$, followed by addition of 50% w/v aq KOH to give an aqueous phase pH of 13. The mixture was extracted with DCM (2×10 mL). The combined organic extracts were thoroughly dried ($Na_2SO_4$), filtered, concentrated, and used for the next reaction without further purification.

Example 33: Preparation of Compound 36

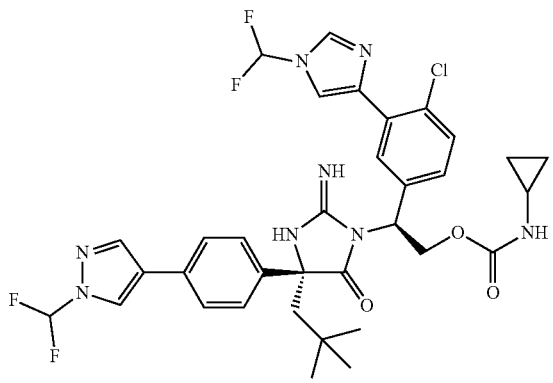

Compound 36

Compound 36 was prepared following the procedure to prepare Compound 34, except that (S)-2-amino-2-(4-chloro-3-(1-(difluoromethyl)-1H-imidazol-4-yl)phenyl)ethan-1-ol was used instead of (S)-2-amino-2-(4-chloro-3-(1H-pyrazol-3-yl)phenyl)ethan-1-ol hydrochloride. LCMS-ESI+ (m/z): calc'd for $C_{34}H_{35}ClF_4N_8O_3$: 715.3 [M+H]+. found: 715.2 [M+H]+. $^1$H NMR (400 MHz, $CD_3CN$) δ 8.29 (s, 1H), 8.07-7.96 (m, 3H), 7.62-7.14 (m, 9H), 5.79-5.70 (m, 1H), 5.52-5.39 (m, 1H), 4.94 (t, J=10.5 Hz, 1H), 4.69-4.56 (m, 1H), 2.36-2.14 (m, 2H), 0.93 (s, 9H), 0.65-0.51 (m, 2H), 0.43-0.31 (m, 2H).

Preparation of (S)-2-amino-2-(4-chloro-3-(1-(difluoromethyl)-1H-imidazol-4-yl)phenyl)ethan-1-ol: (S)-2-amino-2-(4-chloro-3-(1-(difluoromethyl)-1H-imidazol-4-yl)phenyl)ethan-1-ol was prepared following the procedure to prepare (S)-2-amino-2-(4-chloro-3-(4-methoxypyrimidin-2-yl)phenyl)ethan-1-ol described in Example 15, except that 1-(difluoromethyl)-4-iodo-1H-imidazole was used instead of 2-chloro-4-methoxypyrimidine and TFA was used instead of 4.0 M HCl in dioxane.

Example 34: Preparation of Compound 37

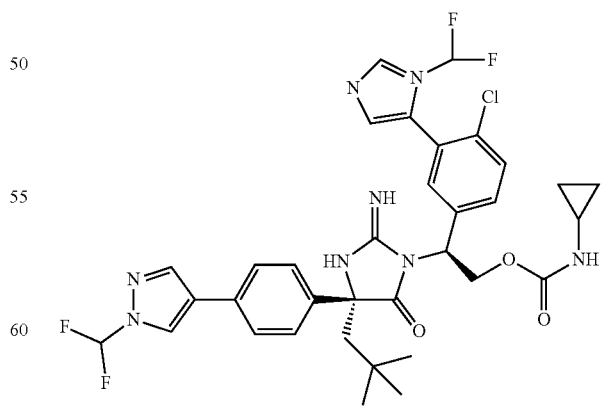

Compound 37

Compound 37 was prepared by following the procedure to prepare Compound 24, except that (S)-2-amino-2-(4-chloro-3-(1-(difluoromethyl)-1H-imidazol-5-yl)phenyl)ethan-1-ol (Method VI) was used instead of (S)-2-amino-2-(4-chloro-3-(1H-pyrazol-3-yl)phenyl)ethan-1-ol hydrochloride. LCMS-ESI+ (m/z): calc'd for $C_{34}H_{35}ClF_4N_8O_3$: 715.3 [M+H]+. found: 715.2 [M+H]+. $^1$H NMR (400 MHz, $CD_3CN$) δ 8.38-8.01 (m, 3H), 7.63-6.83 (m, 10H), 5.83-5.76 (m, 1H), 5.46-5.36 (m, 1H), 4.91 (t, J=10.3 Hz, 1H), 4.67-4.57 (m, 1H), 2.35-2.11 (m, 2H), 0.91 (s, 9H), 0.64-0.54 (m, 2H), 0.43-0.35 (m, 2H).

Example 35: Preparation of Compound 38

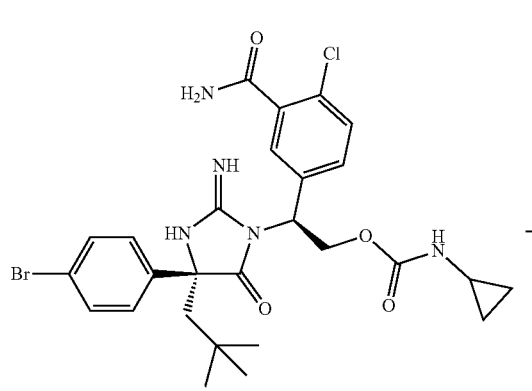

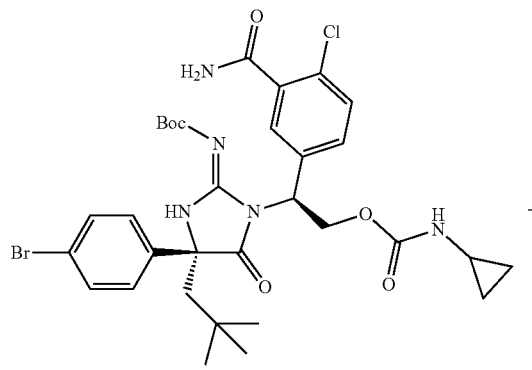

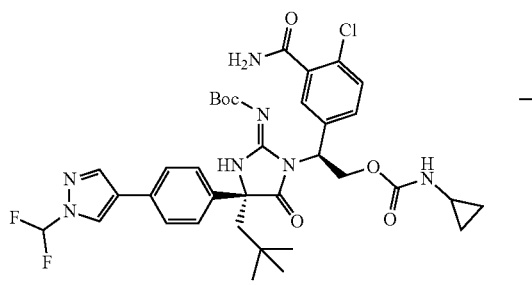

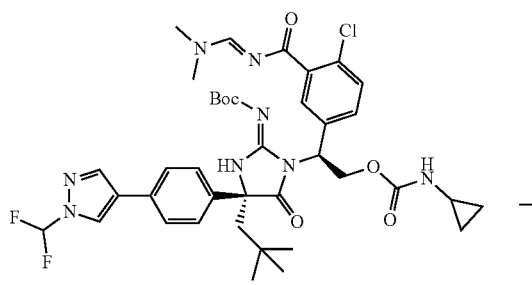

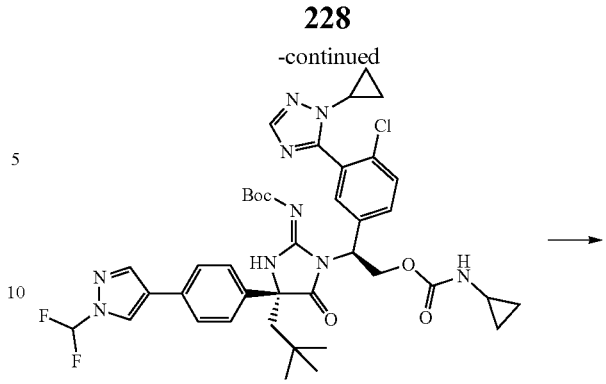

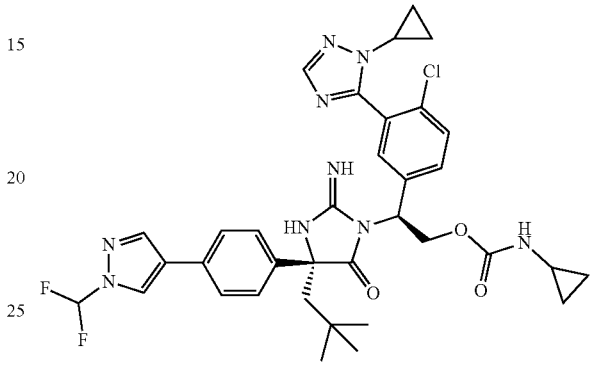

Compound 38

Preparation of (S)-2-((R)-4-(4-bromophenyl)-2-((tert-butoxycarbonyl)imino)-4-neopentyl-5-oxoimidazolidin-1-yl)-2-(3-carbamoyl-4-chlorophenyl)ethyl cyclopropylcarbamate: To a solution of (S)-2-((R)-4-(4-bromophenyl)-2-imino-4-neopentyl-5-oxoimidazolidin-1-yl)-2-(3-carbamoyl-4-chlorophenyl)ethyl cyclopropylcarbamate (128 mg, 0.212 mmol) in DCM (2 mL) was added triethylamine (0.25 mL, 1.79 mmol) and di-tert-butyl dicarbonate (92 mg, 0.42 mmol). The reaction mixture was stirred at rt overnight. The reaction mixture was purified by silica gel column chromatography (0-100% gradient EtOAc/hexanes) to give the product.

Preparation of (S)-2-((R)-2-((tert-butoxycarbonyl)imino)-4-(4-(1-(difluoromethyl)-1H-pyrazol-4-yl)phenyl)-4-neopentyl-5-oxoimidazolidin-1-yl)-2-(3-carbamoyl-4-chlorophenyl)ethyl cyclopropylcarbamate: An argon-purged mixture of (S)-2-((R)-4-(4-bromophenyl)-2-((tert-butoxycarbonyl)imino)-4-neopentyl-5-oxoimidazolidin-1-yl)-2-(3-carbamoyl-4-chlorophenyl)ethyl cyclopropylcarbamate (144 mg, 0.2 mmol), 1-(difluoromethyl)-4-(4,4,5,5-tetramethyl-1,3,2-dioxaborolan-2-yl)-1H-pyrazole (0.11 mL, 0.41 mmol), Pd(PPh$_3$)$_4$ (24 mg, 0.02 mmol) and potassium carbonate (141 mg, 1.02 mmol) in dioxane (2 mL) and water (0.4 mL) was heated at 85° C. for 20 min. The reaction mixture was cooled to rt, concentrated down, and purified by silica gel column chromatography (0-100% gradient EtOAc/hexanes) to give the product. Compound 38 was then prepared by following the procedure to prepare Compound 27, except that cyclopropylhydrazine HCl was used instead of hydrazine. LCMS-ESI+ (m/z): calc'd for $C_{35}H_{38}ClF_2N_9O_3$: 706.3 [M+H]+. found: 706.3 [M+H]+. $^1$H NMR (400 MHz, Methanol-d$_4$) δ 8.47 (s, 1H), 8.10 (s, 1H), 7.81 (s, 1H), 7.63-7.53 (m, 4H), 7.52 (t, J=59.8 Hz, 1H), 7.47-7.41 (m, 2H), 7.15 (s, 1H), 5.71-5.58 (m, 1H), 5.07 (dd, J=11.5, 9.5 Hz, 1H), 4.79-4.63 (m, 1H), 3.26-3.17 (m, 1H), 2.49 (d, J=15.1 Hz, 2H), 2.14 (d, J=15.1 Hz, 1H), 1.00 (s, 9H), 0.83-0.56 (m, 6H), 0.46 (t, J=3.5 Hz, 2H).

Example 36: Preparation of Compound 39

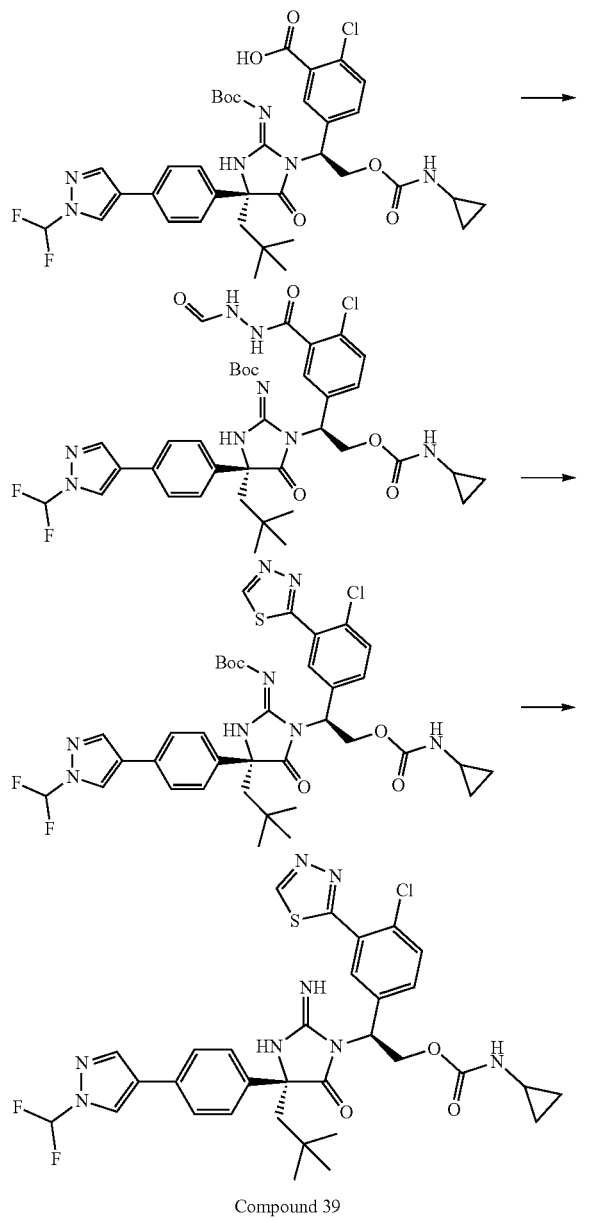

Compound 39

Preparation of tert-butyl ((R)-1-((S)-1-(4-chloro-3-(2-formylhydrazine-1-carbonyl)phenyl)-2-((cyclopropylcarbamoyl)oxy)ethyl)-4-(4-(1-(difluoromethyl)-1H-pyrazol-4-yl)phenyl)-4-neopentyl-5-oxoimidazolidin-2-ylidene) carbamate: To a mixture of 5-((S)-1-((R)-2-((tert-butoxycarbonyl)imino)-4-(4-(1-(difluoromethyl)-1H-pyrazol-4-yl)phenyl)-4-neopentyl-5-oxoimidazolidin-1-yl)-2-((cyclopropylcarbamoyl)oxy)ethyl)-2-chlorobenzoic acid (60 mg, 0.07 mmol) and formic hydrazide (7.9 mg, 0.13 mmol) in dry DMF (2 mL) was added N,N-diisopropylethylamine (34 μL, 0.2 mmol) and stirred at rt for a few minutes. To the mixture was added HATU (50 mg, 0.13 mmol). The reaction mixture was stirred at rt for 5 min. The reaction was quenched with saturated sodium bicarbonate solution and the mixture was extracted with EtOAc. The organic phase was washed by 5% lithium chloride solution and brine, dried over sodium sulfate, filtered, and concentrated. The residue was purified by silica gel column chromatography (0-100% gradient EtOAc/hexanes) to give the product.

Preparation of tert-butyl ((R)-1-((S)-1-(4-chloro-3-(1,3,4-thiadiazol-2-yl)phenyl)-2-((cyclopropylcarbamoyl)oxy)ethyl)-4-(4-(1-(difluoromethyl)-1H-pyrazol-4-yl)phenyl)-4-neopentyl-5-oxoimidazolidin-2-ylidene)carbamate: To a solution of tert-butyl ((R)-1-((S)-1-(4-chloro-3-(2-formylhydrazine-1-carbonyl)phenyl)-2-((cyclopropylcarbamoyl)oxy)ethyl)-4-(4-(1-(difluoromethyl)-1H-pyrazol-4-yl)phenyl)-4-neopentyl-5-oxoimidazolidin-2-ylidene)carbamate (30 mg, 0.04 mmol) in dry toluene (1.5 mL) was added Lawesson's reagent (19 mg, 0.05 mmol). The reaction mixture was stirred at 80° C. for 30 min. The reaction mixture was cooled to rt and purified by silica gel column chromatography (0-100% gradient EtOAc/hexanes) to give the product.

Preparation of Compound 39: To a solution of tert-butyl ((R)-1-((S)-1-(4-chloro-3-(1,3,4-thiadiazol-2-yl)phenyl)-2-((cyclopropylcarbamoyl)oxy)ethyl)-4-(4-(1-(difluoromethyl)-1H-pyrazol-4-yl)phenyl)-4-neopentyl-5-oxoimidazolidin-2-ylidene)carbamate (17 mg, 0.02 mmol) in DCM (0.5 mL) was added TFA (0.5 mL) and stirred at rt for 20 min. The reaction mixture was concentrated down, and purified by reverse phase HPLC (acetonitrile/water, both containing 0.1% TFA) to give the product. LCMS-ESI+ (m/z): calc'd for $C_{32}H_{33}ClF_2N_8O_3S$: 683.2 [M+H]+. found: 683.3 [M+H]+. $^1$H NMR (400 MHz, Methanol-$d_4$) δ 9.40 (s, 1H), 8.41 (s, 1H), 8.05 (s, 1H), 7.90 (s, 1H), 7.63-7.53 (m, 2H), 7.51 (t, J=59.8 Hz, 1H), 7.49 (d, J=8.0 Hz, 1H), 7.45-7.40 (m, 2H), 5.65 (dd, J=8.9, 5.0 Hz, 1H), 5.09 (dd, J=11.5, 9.5 Hz, 1H), 4.75 (dd, J=11.4, 5.0 Hz, 1H), 2.49 (d, J=15.1 Hz, 2H), 2.14 (d, J=15.2 Hz, 1H), 1.01 (s, 9H), 0.66 (d, J=6.8 Hz, 2H), 0.45 (d, J=3.4 Hz, 2H).

Example 37: Preparation of Compound 40

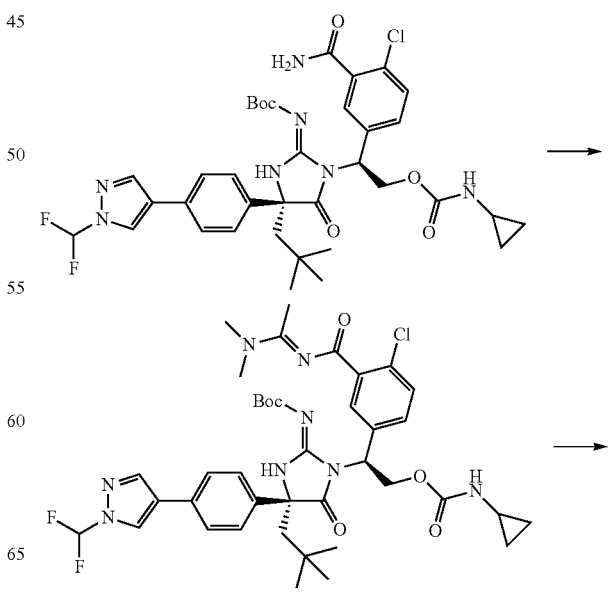

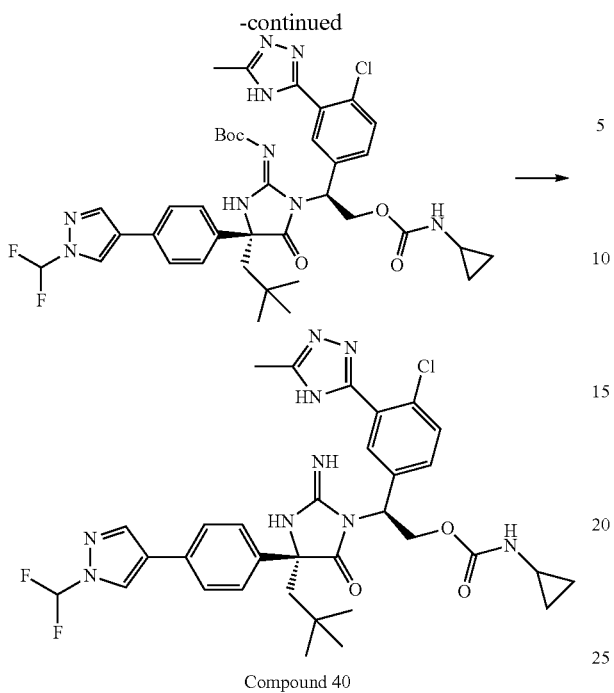

Compound 40

Preparation of tert-butyl ((R)-1-((S)-1-(4-chloro-3-((1-(dimethylamino)ethylidene)carbamoyl)phenyl)-2-((cyclopropylcarbamoyl)oxy)ethyl)-4-(4-(1-(difluoromethyl)-1H-pyrazol-4-yl)phenyl)-4-neopentyl-5-oxoimidazolidin-2-ylidene)carbamate: The reaction mixture of tert-butyl ((R)-1-((S)-1-(3-carbamoyl-4-chlorophenyl)-2-((cyclopropylcarbamoyl)oxy)ethyl)-4-(4-(1-(difluoromethyl)-1H-pyrazol-4-yl)phenyl)-4-neopentyl-5-oxoimidazolidin-2-ylidene)carbamate (50 mg, 0.07 mmol) and N,N-dimethylacetamide dimethylacetal (1.5 mL, 10.26 mmol) was stirred at rt for 90 min. The reaction mixture was concentrated down and used for the next reaction without further purification.

Preparation of tert-butyl ((R)-1-((S)-1-(4-chloro-3-(5-methyl-4H-1,2,4-triazol-3-yl)phenyl)-2-((cyclopropylcarbamoyl)oxy)ethyl)-4-(4-(1-(difluoromethyl)-1H-pyrazol-4-yl)phenyl)-4-neopentyl-5-oxoimidazolidin-2-ylidene)carbamate: To the crude mixture of tert-butyl ((R)-1-((S)-1-(4-chloro-3-((1-(dimethylamino)ethylidene)carbamoyl)phenyl)-2-((cyclopropylcarbamoyl)oxy)ethyl)-4-(4-(1-(difluoromethyl)-1H-pyrazol-4-yl)phenyl)-4-neopentyl-5-oxoimidazolidin-2-ylidene)carbamate (52 mg, 0.06 mmol) in THF (2 mL) was added acetic acid (200 uL) and hydrazine monohydrate (200 μL, 4.11 mmol). The reaction mixture was stirred at 60° C. for 15 min. The reaction mixture was cooled down. The mixture was treated with saturated NaHCO$_3$ solution, and extracted with EtOAc. The organic phase was separated, dried over sodium sulfate, filtered, and concentrated down. The residue was purified by silica gel column chromatography (0-100% gradient EtOAc/hexanes) to give the product.

Preparation of Compound 40: A solution of tert-butyl ((R)-1-((S)-1-(4-chloro-3-(5-methyl-4H-1,2,4-triazol-3-yl)phenyl)-2-((cyclopropylcarbamoyl)oxy)ethyl)-4-(4-(1-(difluoromethyl)-1H-pyrazol-4-yl)phenyl)-4-neopentyl-5-oxoimidazolidin-2-ylidene)carbamate in DCM (0.5 mL) was added TFA (0.5 mL) and stirred at rt for 1 h. The reaction mixture was concentrated down and purified by reverse phase HPLC (acetonitrile/H$_2$O, both containing 0.1% TFA) to give the product. LCMS-ESI+ (m/z): calc'd for C$_{33}$H$_{36}$ClF$_2$N$_9$O$_3$: 680.3 [M+H]+. found 680.2 [M+H]+. $^1$H NMR (400 MHz, Methanol-d$_4$) δ 8.45 (s, 1H), 8.08 (s, 1H), 7.62-7.55 (m, 2H), 7.51 (t, J=59.8 Hz, 1H), 7.49-7.39 (m, 4H), 7.34 (d, J=9.0 Hz, 1H), 5.70-5.54 (m, 1H), 5.09 (dd, J=11.5, 9.6 Hz, 1H), 4.69 (dd, J=11.5, 4.9 Hz, 1H), 2.46 (d, J=15.1 Hz, 2H), 2.34 (s, 3H), 2.14 (d, J=15.1 Hz, 1H), 1.00 (s, 9H), 0.65 (d, J=6.7 Hz, 2H), 0.50-0.31 (m, 2H).

Example 38: Preparation of Compound 41

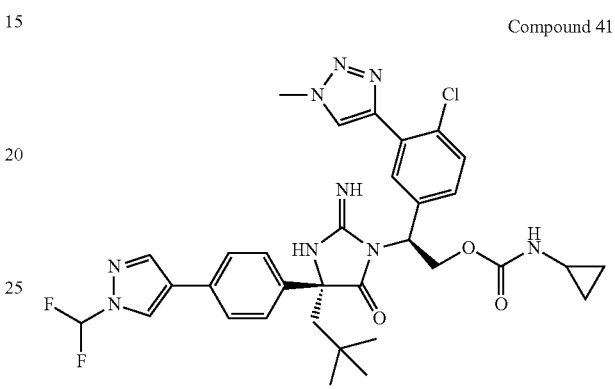

Compound 41

Compound 41 was prepared following the procedure to prepare Compound 12, except that (S)-2-amino-2-(4-chloro-3-(1-methyl-1H-1,2,3-triazol-4-yl)phenyl)ethan-1-ol (Method VI) was used instead of (S)-2-amino-2-(4-chloro-3-(3-methylpyridin-2-yl)phenyl)ethan-1-ol hydrochloride. LCMS-ESI+ (m/z): calc'd for C$_{33}$H$_{36}$ClF$_2$N$_9$O$_3$: 680.3 [M+H]+. found 680.3 [M+H]+. $^1$H NMR (400 MHz, Methanol-d$_4$) δ 8.42 (s, 1H), 8.32 (s, 1H), 8.06 (s, 1H), 7.71 (s, 1H), 7.55 (d, J=8.2 Hz, 2H), 7.52 (t, J=59.7 Hz, 1H), 7.48-7.39 (m, 3H), 7.27 (d, J=7.5 Hz, 1H), 5.67-5.50 (m, 1H), 5.08 (t, J=10.5 Hz, 1H), 4.72 (dd, J=11.7, 5.1 Hz, 1H), 3.97 (s, 3H), 2.48 (d, J=15.1 Hz, 2H), 2.13 (d, J=15.1 Hz, 1H), 1.01 (s, 9H), 0.74-0.57 (m, 2H), 0.45 (p, J=4.2 Hz, 2H).

Example 39: Preparation of Compound 42

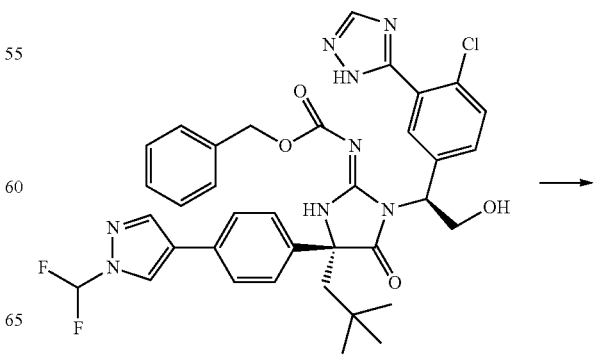

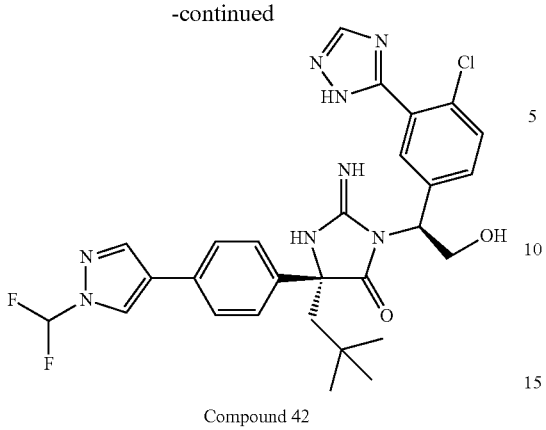

Compound 42

Preparation of Compound 42: To a solution of benzyl ((R)-1-((S)-1-(4-chloro-3-(1H-1,2,4-triazol-5-yl)phenyl)-2-hydroxyethyl)-4-(4-(1-(difluoromethyl)-1H-pyrazol-4-yl)phenyl)-4-neopentyl-5-oxoimidazolidin-2-ylidene)carbamate (12 mg, 0.016 mmol) in DCM (5 mL) was added boron tribromide in DCM (1M, 200 µL) slowly at 0° C. and stirred at the same temperature for 5 min. The reaction was quenched by addition of methanol. The mixture was concentrated down and the residue was purified by reverse phase HPLC (acetonitrile/water, both containing 0.1% TFA) to give the product (3.4 mg, 30%). LCMS-ESI+ (m/z): calc'd for $C_{28}H_{29}ClF_2N_8O_2$: 583.2 [M+H]+. found 583.3 [M+H]+. $^1$H NMR (400 MHz, CD$_3$CN) δ 8.32 (s, 1H), 8.27 (s, 1H), 8.07 (s, 1H), 7.87 (d, J=2.3 Hz, 1H), 7.68-7.19 (m, 7H), 5.44 (d, J=4.0 Hz, 1H), 4.31 (dd, J=12.5, 5.8 Hz, 1H), 4.14 (dd, J=12.5, 2.9 Hz, 1H), 2.29-2.16 (m, 2H), 0.84 (s, 9H).

Example 40: Preparation of Compound 43

Compound 43

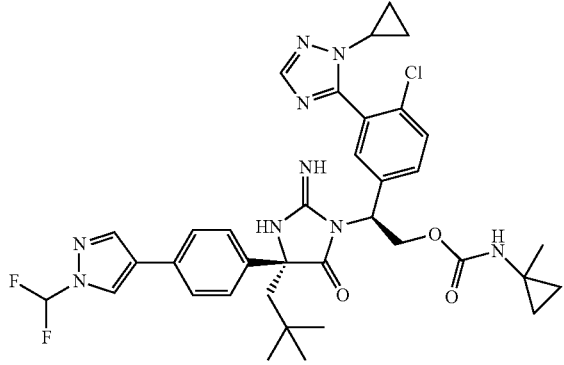

Compound 43 was prepared by following the procedure to prepare Compound 38, except that (S)-2-amino-2-(3-carbamoyl-4-chlorophenyl)ethyl (1-methylcyclopropyl)carbamate was used instead (S)-2-amino-2-(3-carbamoyl-4-chlorophenyl)ethylcyclopropylcarbamate. LCMS-ESI+ (m/z): calc'd for $C_{36}H_{40}ClF_2N_9O_3$: 720.3 [M+H]+. found 720.3 [M+H]+. 1H NMR (400 MHz, CD$_3$CN) δ 8.32 (s, 1H), 8.06 (s, 1H), 7.81 (s, 1H), 7.72-7.17 (m, 8H), 6.03-5.93 (m, 1H), 5.41 (dd, J=9.7, 4.4 Hz, 1H), 4.88 (t, J=10.6 Hz, 1H), 4.62 (dd, J=11.6, 4.5 Hz, 1H), 3.21 (app. tt, J=7.2, 4.0 Hz, 1H), 2.34-2.11 (m, 2H), 1.27 (s, 3H), 0.91 (s, 9H), 0.82-0.46 (m, 8H).

Example 41: Preparation of Compound 44

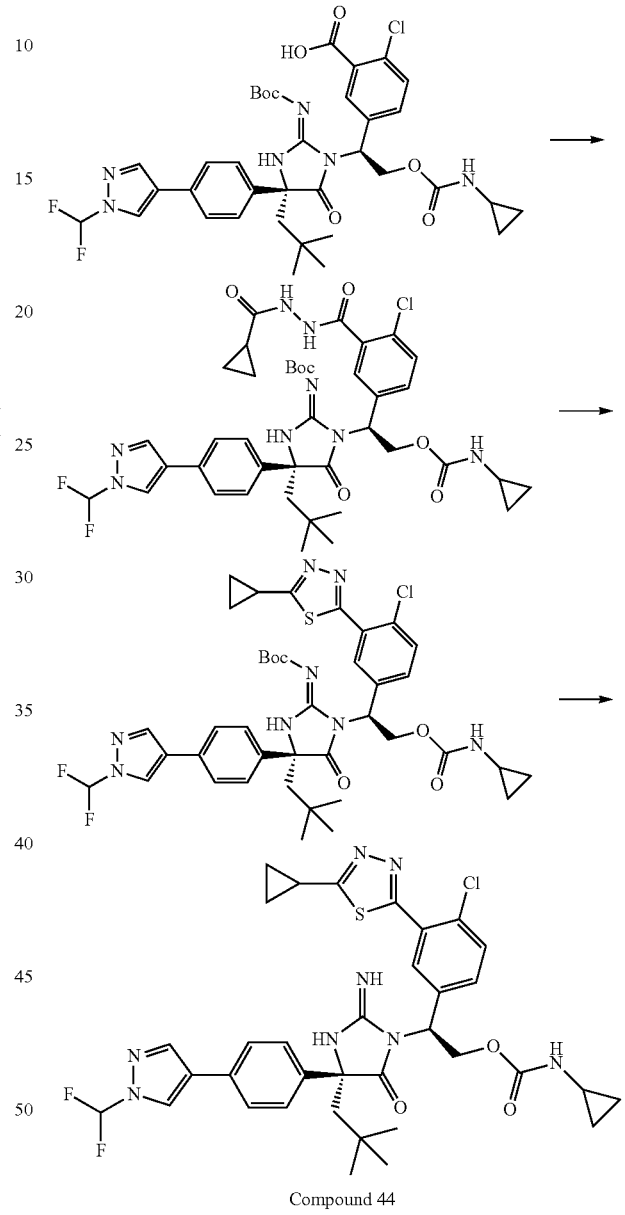

Compound 44

Compound 44 was prepared by following the procedure to prepare Compound 39, except that cyclopropanecarbohydrazide was used instead of formic hydrazide. LCMS-ESI+ (m/z): calc'd for $C_{35}H_{37}ClF_2N_8O_3S$: 723.2 [M+H]+. found 723.3 [M+H]+. $^1$H NMR (400 MHz, Methanol-d$_4$) δ 8.42 (s, 1H), 8.06 (s, 1H), 7.79 (s, 1H), 7.56 (dd, J=7.8, 5.6 Hz, 3H), 7.51 (t, J=59.7 Hz, 1H), 7.46 (d, J=8.7 Hz, 1H), 7.44-7.39 (m, 2H), 5.62 (t, J=7.3 Hz, 1H), 5.07 (dd, J=11.5, 9.5 Hz, 1H), 4.73 (dd, J=11.2, 5.1 Hz, 1H), 2.47 (d, J=15.1 Hz, 2H), 2.33 (ddd, J=13.2, 8.6, 4.9 Hz, 1H), 2.13 (d, J=15.1 Hz, 1H), 1.25 (dd, J=8.4, 2.8 Hz, 2H), 1.11-0.94 (m, 11H), 0.67 (d, J=6.7 Hz, 2H), 0.45 (p, J=4.0 Hz, 2H).

Example 42: Preparation of Compound 45

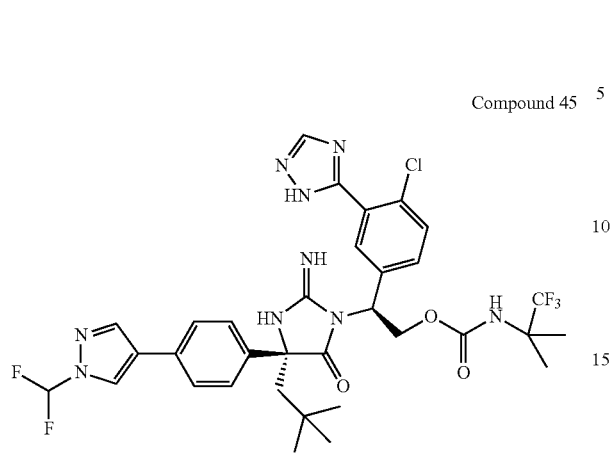

Compound 45

Preparation of 5-((S)-1-((R)-2-(((benzyloxy)carbonyl)imino)-4-(4-(1-(difluoromethyl)-1H-pyrazol-4-yl)phenyl)-4-neopentyl-5-oxoimidazolidin-1-yl)-2-(((1,1,1-trifluoro-2-methylpropan-2-yl)carbamoyl)oxy)ethyl)-2-chlorobenzoic acid: 5-((S)-1-((R)-2-(((benzyloxy)carbonyl)imino)-4-(4-(1-(difluoromethyl)-1H-pyrazol-4-yl)phenyl)-4-neopentyl-5-oxoimidazolidin-1-yl)-2-(((1,1,1-trifluoro-2-methylpropan-2-yl)carbamoyl)oxy)ethyl)-2-chlorobenzoic acid was prepared following the procedure to prepare 5-((S)-1-((R)-2-((tert-butoxycarbonyl)imino)-4-neopentyl-5-oxo-4-(4-(pyrazin-2-yl)phenyl)imidazolidin-1-yl)-2-(((1-methylcyclopropyl)carbamoyl)oxy)ethyl)-2-chlorobenzoic acid described in Example 26, except that 3,3,3-trifluoro-2,2-dimethylpropanoic acid was used instead of 1-(trifluoromethyl)cyclopropane-1-carboxylic acid. Compound 45 was then prepared in a manner similar to that for Compound 21. LCMS-ESI+: calc'd for $C_{33}H_{35}ClF_5N_9O_3$: 736.2 (M+H+). Found: 736.3 (M+H+). $^1$H NMR (400 MHz, Methanol-$d_4$) δ 8.38 (s, 1H), 8.22 (s, 1H), 8.05 (s, 1H), 7.74-7.25 (m, 8H), 5.44-5.46 (m, 1H), 5.01 (dd, J=11.1, 8.7 Hz, 1H), 4.70-4.55 (m, 1H), 2.28 (d, J=14.6 Hz, 1H), 1.96 (d, J=14.6 Hz, 1H), 1.56-1.30 (m, 6H), 0.95 (s, 9H).

Example 43: Preparation of Compound 46

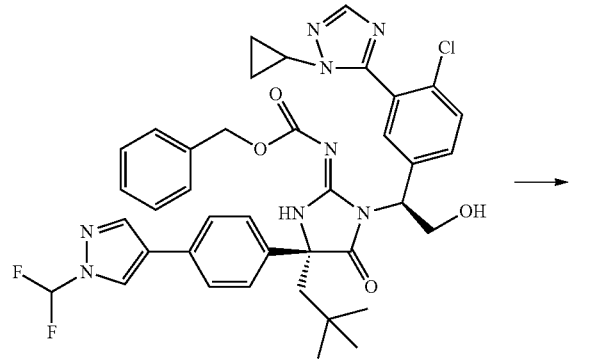

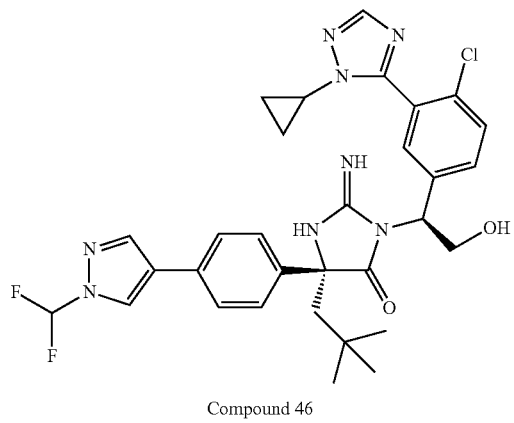

Compound 46

Preparation of Compound 46: To a solution of benzyl ((R)-1-((S)-1-(4-chloro-3-(1-cyclopropyl-1H-1,2,4-triazol-5-yl)phenyl)-2-hydroxyethyl)-4-(4-(1-(difluoromethyl)-1H-pyrazol-4-yl)phenyl)-4-neopentyl-5-oxoimidazolidin-2-ylidene)carbamate (59 mg, 0.078 mmol) in DCM (5 mL) was added boron tribromide in DCM (1M, 250 µL) at 0° C. and stirred at the same temperature for 3 min. Additional boron tribromide in DCM (1M, 350 µL) was added and stirred for another 3 min. The reaction was quenched by adding methanol. The mixture was then concentrated. The residue was purified by reverse phase HPLC (acetonitrile/water, both containing 0.1% TFA) to give the product. LCMS-ESI+: calc'd for $C_{31}H_{33}ClF_2N_8O_2$: 623.2 (M+H+). Found: 623.3 (M+H+). $^1$H NMR (400 MHz, CD$_3$CN) δ 8.33 (d, J=0.7 Hz, 1H), 8.07 (s, 1H), 7.89 (s, 1H), 7.70-7.21 (m, 8H), 5.39 (dd, J=6.1, 3.1 Hz, 1H), 4.29 (dd, J=12.3, 6.2 Hz, 1H), 4.16 (dd, J=12.3, 3.2 Hz, 1H), 3.40-3.31 (m, 1H), 2.28-2.10 (m, 2H), 0.99-0.71 (m, 13H).

Example 44: Preparation of Compound 47

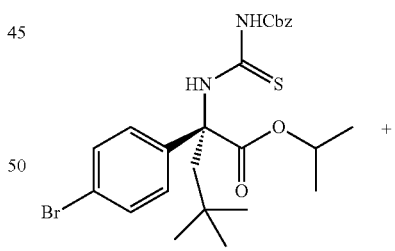

+

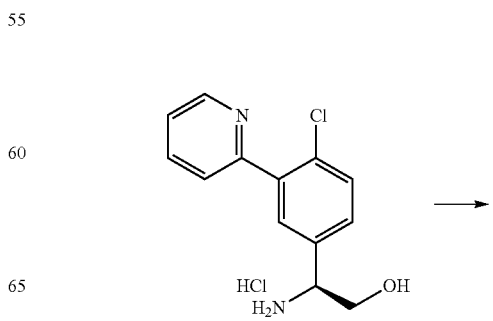

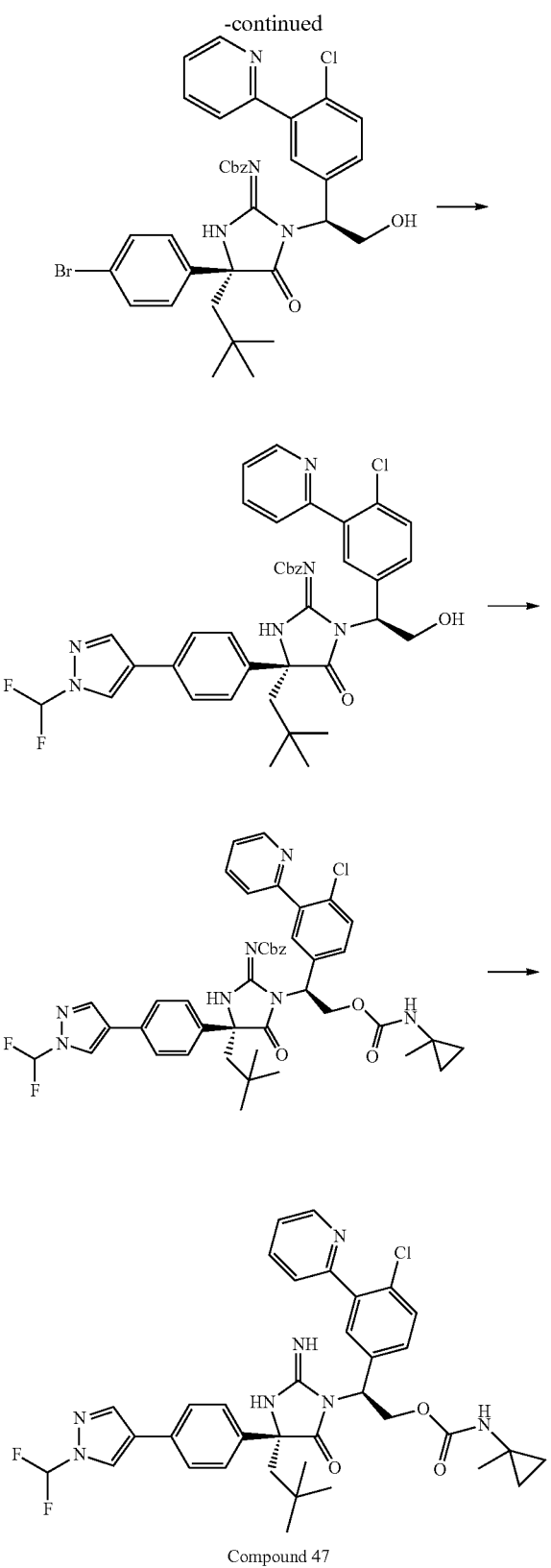

Compound 47

Preparation of benzyl ((R)-4-(4-bromophenyl)-1-((S)-1-(4-chloro-3-(pyridin-2-yl)phenyl)-2-hydroxyethyl)-4-neopentyl-5-oxoimidazolidin-2-ylidene)carbamate: To a solution of isopropyl (R)-2-(3-((benzyloxy)carbonyl)thioureido)-2-(4-bromophenyl)-4,4-dimethylpentanoate (0.2 g, 0.37 mmol) in DMF (2.0 mL) were added (S)-2-amino-2-(4-chloro-3-(pyridin-2-yl)phenyl)ethan-1-ol hydrochloride (0.15 g, 0.52 mmol), N,N-diisopropylethylamine (0.2 mL, 0.63 mol) and N-(3-dimethylaminopropyl)-N-ethylcarbodiimide hydrochloride (0.11 g, 0.56 mmol). The reaction mixture was stirred at 55° C. over 3 days. The reaction mixture was diluted with EtOAc and washed with saturated NaHCO₃ solution. The organic phase was separated, dried over MgSO₄, filtered, and concentrated. The residue was purified by silica gel column chromatography (eluting by 0-70% EtOAc/hexanes) to give the product.

Preparation of benzyl ((R)-1-((S)-1-(4-chloro-3-(pyridin-2-yl)phenyl)-2-hydroxyethyl)-4-(4-(1-(difluoromethyl)-1H-pyrazol-4-yl)phenyl)-4-neopentyl-5-oxoimidazolidin-2-ylidene)carbamate: A mixture of benzyl ((R)-4-(4-bromophenyl)-1-((S)-1-(4-chloro-3-(pyridin-2-yl)phenyl)-2-hydroxyethyl)-4-neopentyl-5-oxoimidazolidin-2-ylidene)carbamate (70 mg, 0.1 mmol), 1-(difluoromethyl)-4-(4,4,5,5-tetramethyl-1,3,2-dioxaborolan-2-yl)-1H-pyrazole (32 mg, 0.13 mmol), Pd(PPh₃)₄ (11.7 mg, 0.01 mmol) and K₂CO₃ (28 mg, 0.2 mmol) was stirred at 85° C. for 1 h and then 95° C. for another 1 h. The reaction mixture was diluted with EtOAc and washed with saturated NaHCO₃ solution. The organic phase was separated, dried over MgSO₄, filtered, and concentrated. The residue was purified by silica gel column chromatography (eluting with EtOAc/hexanes) to give the product (60 mg, 81%).

Preparation of benzyl ((R)-1-((S)-1-(4-chloro-3-(pyridin-2-yl)phenyl)-2-(((1-methylcyclopropyl)carbamoyl)oxy)ethyl)-4-(4-(1-(difluoromethyl)-1H-pyrazol-4-yl)phenyl)-4-neopentyl-5-oxoimidazolidin-2-ylidene)carbamate: The reaction mixture of benzyl ((R)-1-((S)-1-(4-chloro-3-(pyridin-2-yl)phenyl)-2-hydroxyethyl)-4-(4-(1-(difluoromethyl)-1H-pyrazol-4-yl)phenyl)-4-neopentyl-5-oxoimidazolidin-2-ylidene)carbamate (60 mg, 0.08 mmol), 1-isocyanato-1-methylcyclopropane in toluene (0.65M, 1.27 mL) and MoO₂Cl₂(DMF)₂ (57 mg, 0.16 mmol) was stirred at rt overnight. The reaction mixture was concentrated down and the residue was purified by silica gel column chromatography to give the product.

Preparation of Compound 47: To a solution of benzyl ((R)-1-((S)-1-(4-chloro-3-(pyridin-2-yl)phenyl)-2-(((1-methylcyclopropyl)carbamoyl)oxy)ethyl)-4-(4-(1-(difluoromethyl)-1H-pyrazol-4-yl)phenyl)-4-neopentyl-5-oxoimidazolidin-2-ylidene)carbamate (68 mg, 0.082 mmol) in DCM (1.0 mL) was added boron tribromide solution in DCM (1M, 0.41 mL) at 0° C. The reaction mixture was stirred at 0° C. for 40 min. The reaction mixture was diluted with DCM and washed with saturated NaHCO₃ solution. The organic phase was separated, dried over MgSO₄, filtered, and concentrated. The residue was purified by reverse phase HPLC (acetonitrile/water, both containing 0.1% TFA) to give the product. LCMS-ESI+: calc'd for $C_{33}H_{38}ClF_2N_7O_3$: 690.2 (M+H+). Found: 690.2 (M+H+). ¹H NMR (400 MHz, Methanol-d₄) δ 8.56 (d, J=5.3 Hz, 1H), 8.52-8.42 (m, 1H), 8.09 (s, 1H), 7.94 (td, J=7.8, 1.7 Hz, 1H), 7.77-7.31 (m, 8H), 7.16 (dd, J=10.6, 1.8 Hz, 2H), 5.63 (dd, J=9.8, 4.8 Hz, 1H), 5.05 (dd, J=11.4, 9.8 Hz, 1H), 4.66 (dd, J=11.4, 4.8 Hz, 1H), 2.43 (d, J=15.1 Hz, 1H), 2.13 (d, J=15.2 Hz, 1H), 1.32 (s, 3H), 0.98 (s, 9H), 0.77-0.64 (m, 2H), 0.59 (t, J=3.3 Hz, 2H).

Example 45: Preparation of Compound 48

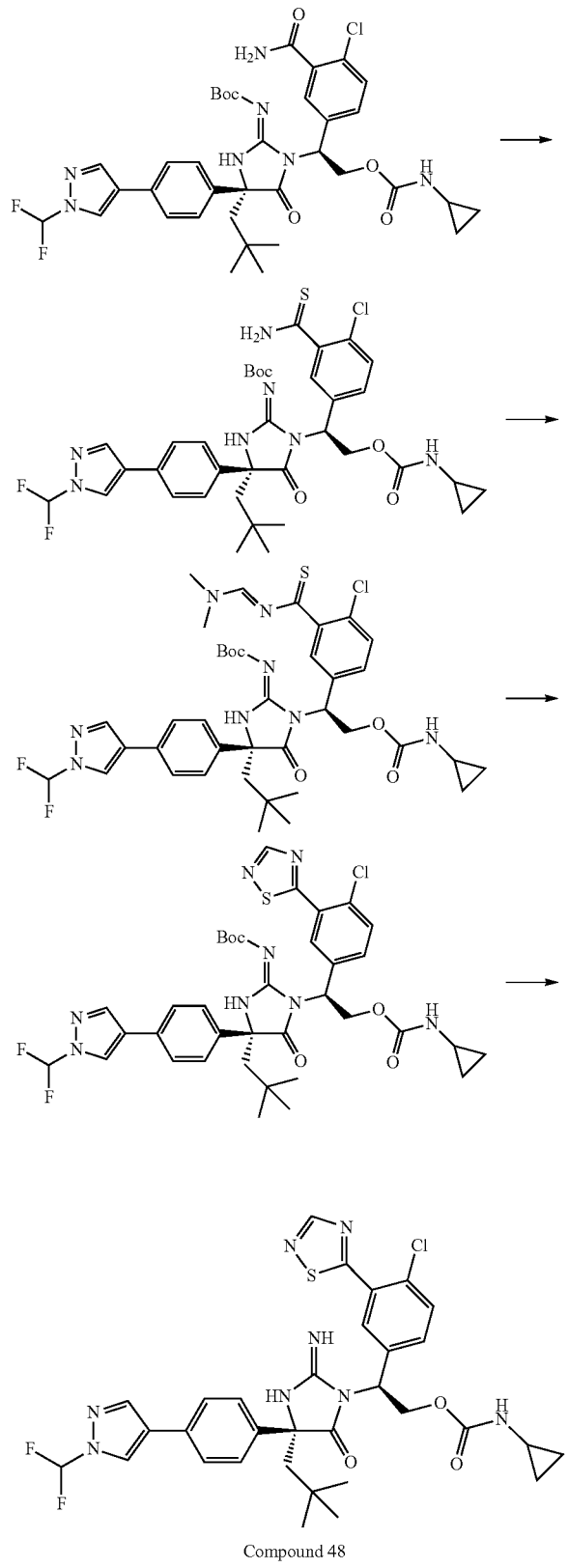

Compound 48

Preparation of tert-butyl ((R)-1-((S)-1-(3-carbamothioyl-4-chlorophenyl)-2-((cyclopropylcarbamoyl)oxy)ethyl)-4-(4-(1-(difluoromethyl)-1H-pyrazol-4-yl)phenyl)-4-neopentyl-5-oxoimidazolidin-2-ylidene)carbamate: A mixture of tert-butyl ((R)-1-((S)-1-(3-carbamoyl-4-chlorophenyl)-2-((cyclopropylcarbamoyl)oxy)ethyl)-4-(4-(1-(difluoromethyl)-1H-pyrazol-4-yl)phenyl)-4-neopentyl-5-oxoimidazolidin-2-ylidene)carbamate (88.7 mg, 0.12 mmol) and Lawesson's reagent (72.5 mg, 0.18 mmol) in toluene (1.5 mL) was heated at 80° C. for 20 min. The reaction was cooled to rt, and purified by silica gel column chromatography (0-100% gradient EtOAc/hexanes) to give the product.

Preparation of tert-butyl ((R)-1-((S)-1-(4-chloro-3-(((dimethylamino)methylene)carbamothioyl)phenyl)-2-((cyclopropylcarbamoyl)oxy)ethyl)-4-(4-(1-(difluoromethyl)-1H-pyrazol-4-yl)phenyl)-4-neopentyl-5-oxoimidazolidin-2-ylidene)carbamate: A mixture of tert-butyl ((R)-1-((S)-1-(3-carbamothioyl-4-chlorophenyl)-2-((cyclopropylcarbamoyl)oxy)ethyl)-4-(4-(1-(difluoromethyl)-1H-pyrazol-4-yl)phenyl)-4-neopentyl-5-oxoimidazolidin-2-ylidene)carbamate (52.8 mg, 0.07 mmol) in N,N-dimethylformamide dimethyl acetal (1 mL, 7.53 mmol) was stirred at rt for 5 min. The reaction mixture was concentrated down, and the residue was directly used without purification.

Preparation of tert-butyl ((R)-1-((S)-1-(4-chloro-3-(1,2,4-thiadiazol-5-yl)phenyl)-2-((cyclopropylcarbamoyl)oxy)ethyl)-4-(4-(1-(difluoromethyl)-1H-pyrazol-4-yl)phenyl)-4-neopentyl-5-oxoimidazolidin-2-ylidene)carbamate: To a solution of the crude tert-butyl ((R)-1-((S)-1-(4-chloro-3-(((E)-(dimethylamino)methylene)carbamothioyl)phenyl)-2-((cyclopropylcarbamoyl)oxy)ethyl)-4-(4-(1-(difluoromethyl)-1H-pyrazol-4-yl)phenyl)-4-neopentyl-5-oxoimidazolidin-2-ylidene)carbamate (56.6 mg, 0.07 mmol) in EtOH (0.5 mL) was added pyridine (34 µl, 0.42 mmol), and then added a solution of hydroxylamine-o-sulfonic acid (23.6 mg, 0.21 mmol) in EtOH (0.5 mL). The reaction mixture was stirred at rt for 10 min. The reaction mixture was concentrated down, and residue was purified by silica gel column chromatography (0-100% gradient EtOAc/hexanes) to give the product.

Preparation of Compound 48: A solution of tert-butyl ((R)-1-((S)-1-(4-chloro-3-(1,2,4-thiadiazol-5-yl)phenyl)-2-((cyclopropylcarbamoyl)oxy)ethyl)-4-(4-(1-(difluoromethyl)-1H-pyrazol-4-yl)phenyl)-4-neopentyl-5-oxoimidazolidin-2-ylidene)carbamate (27.1 mg, 0.03 mmol) in DCM (0.5 mL) and TFA (0.5 mL) was stirred at rt for 1 h. The reaction mixture was concentrated, and the residue was purified by reverse phase HPLC (acetonitrile/H$_2$O, both containing 0.1% TFA) to give the product. LCMS-ESI+: calc'd for $C_{32}H_{33}ClF_2N_8O_3S$: 683.2 (M+H+). Found: 683.4 (M+H+). $^1$H NMR (400 MHz, Methanol-d$_4$) δ 8.69 (s, 1H), 8.39 (s, 1H), 8.28 (s, 1H), 8.03 (s, 1H), 7.62 (d, J=8.4 Hz, 1H), 7.57 (d, J=8.4 Hz, 2H), 7.51 (s, 1H), 7.49 (t, J=59.8 Hz, 1H), 7.44 (d, J=8.4 Hz, 2H), 5.68 (d, J=5.8 Hz, 1H), 5.15-5.04 (m, 1H), 4.74 (dd, J=11.5, 4.8 Hz, 1H), 2.48 (d, J=15.1 Hz, 1H), 2.15 (d, J=15.1 Hz, 1H), 1.02 (s, 9H), 0.66 (d, J=6.9 Hz, 2H), 0.44 (d, J=4.0 Hz, 2H).

Example 46: Preparation of Compound 49

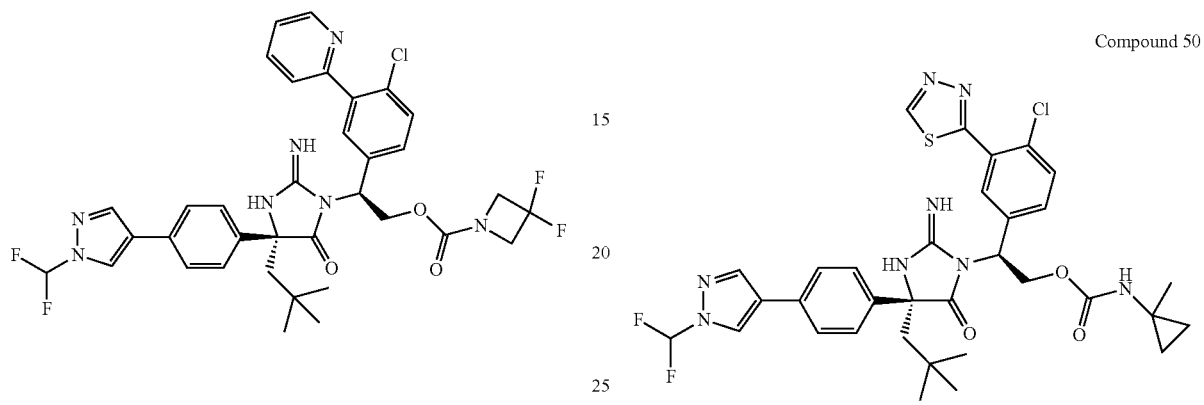

Compound 49

Compound 49 was prepared by following the procedure to prepare Compound 12 except that (S)-2-amino-2-(4-chloro-3-(pyridin-2-yl)phenyl)ethan-1-ol hydrochloride, 3,3-difluoroazetidine and boron tribromide were used instead of (S)-2-amino-2-(4-chloro-3-(3-methylpyridin-2-yl)phenyl)ethan-1-ol hydrochloride, cyclopropylamine and iodotrimethylsilane, respectively. LCMS-ESI+: calc'd for $C_{37}H_{38}ClF_2N_7O_3$: 702.2 (M+H+). Found: 702.3 (M+H+). $^1$H NMR (400 MHz, Methanol-$d_4$) δ 8.57 (dt, J=5.0, 1.3 Hz, 1H), 8.07 (s, 1H), 7.90 (td, J=7.8, 1.7 Hz, 1H), 7.81 (d, J=0.8 Hz, 1H), 7.60-7.30 (m, 8H), 7.19 (d, J=2.3 Hz, 1H), 5.67 (dd, J=9.9, 4.5 Hz, 1H), 5.06 (dd, J=11.5, 9.9 Hz, 1H), 4.89-4.90 (m, 1H), 4.28 (t, J=11.9 Hz, 4H), 3.72 (tt, J=7.4, 3.6 Hz, 1H), 2.45 (d, J=15.2 Hz, 1H), 2.10 (d, J=15.2 Hz, 1H), 1.19-1.12 (m, 2H), 1.12-1.05 (m, 2H), 1.00 (s, 9H).

Example 47: Preparation of Compound 50

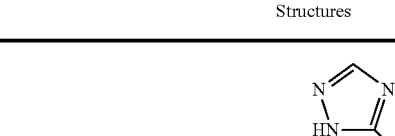

Compound 50

Compound 50 was prepared by following the procedure to prepare Compound 39. LCMS-ESI+: calc'd for $C_{33}H_{35}ClF_2N_8O_3S$: 697.2 (M+H+). Found: 697.4 (M+H+). $^1$H NMR (400 MHz, Methanol-$d_4$) δ 9.39 (s, 1H), 8.40 (s, 1H), 8.05 (s, 1H), 7.88 (d, J=2.3 Hz, 1H), 7.57 (t, J=8.2 Hz, 3H), 7.51 (t, J=59.8 Hz, 1H), 7.48 (dd, J=8.5, 2.4 Hz, 1H), 7.45-7.40 (m, 2H), 5.64 (dd, J=9.6, 5.1 Hz, 1H), 5.11-4.98 (m, 1H), 4.73 (dd, J=11.4, 5.1 Hz, 1H), 2.49 (d, J=15.1 Hz, 1H), 2.15 (d, J=15.1 Hz, 1H), 1.31 (s, 3H), 1.01 (s, 9H), 0.68 (d, J=5.0 Hz, 2H), 0.59 (t, J=3.3 Hz, 2H).

Unless otherwise stated, the following compounds were prepared in a similar manner as those disclosed above.

| Compound # | Structures | Mass data | NMR data |
|---|---|---|---|
| Compd 51 | ![structure] | LCMS-ESI+: calc'd for $C_{35}H_{40}ClN_9O_3$: 670.3 (M + H+); Found: 670.4 (M + H+). | $^1$H NMR (400 MHz, Chloroform-d) δ 12.71 (s, 1H), 8.25 (s, 1H), 7.91 (s, 1H), 7.72 (d, J = 16.2 Hz, 3H), 7.45 (q, J = 8.6 Hz, 6H), 7.24 (s, 2H), 5.65 (s, 1H), 5.12 (s, 1H), 4.81 (s, 1H), 4.67 (s, 2H), 3.63 (s, 2H), 2.42-2.03 (m, 2H), 1.26 (d, J = 5.5 Hz, 3H), 1.18-1.02 (m, 4H), 0.95 (s, 9H), 0.86 (s, 1H), 0.58 (d, J = 37.7 Hz, 4H). |

| Compound # | Structures | Mass data | NMR data |
|---|---|---|---|
| Compd 52 | 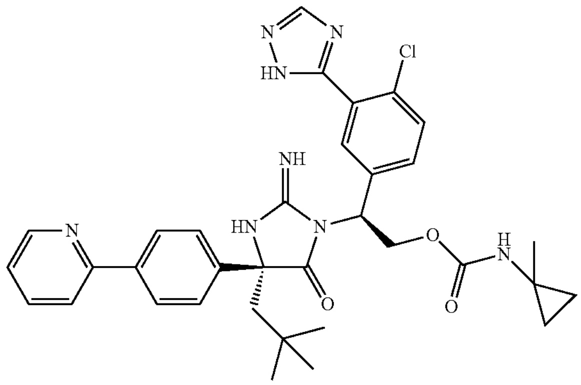 [SMILES: CC(C)(C)C[C@]1(c2ccc(-c3ccccn3)cc2)NC(=N)N([C@H](COC(=O)NC2(C)CC2)c2ccc(Cl)c(-c3ncn[nH]3)c2)C1=O] | LCMS-ESI+: calc'd for $C_{34}H_{37}ClN_8O_3$: 641.3 (M + H+); Found: 641.2 (M + H+). | $^1$H NMR (400 MHz, Chloroform-d) δ 8.75-8.60 (m, 1H), 8.14 (s, 1H), 7.89-7.55 (m, 7H), 7.42-7.27 (m, 2H), 5.55 (d, J = 16.5 Hz, 2H), 4.94-4.54 (m, 3H), 3.87-3.07 (m, 1H), 2.62-1.99 (m, 2H), 1.64 (s, 2H), 1.26 (d, J = 3.3 Hz, 8H), 0.97 (s, 9H), 0.86 (d, J = 15.8 Hz, 3H), 0.55 (d, J = 50.2 Hz, 4H). |
| Compd 53 | 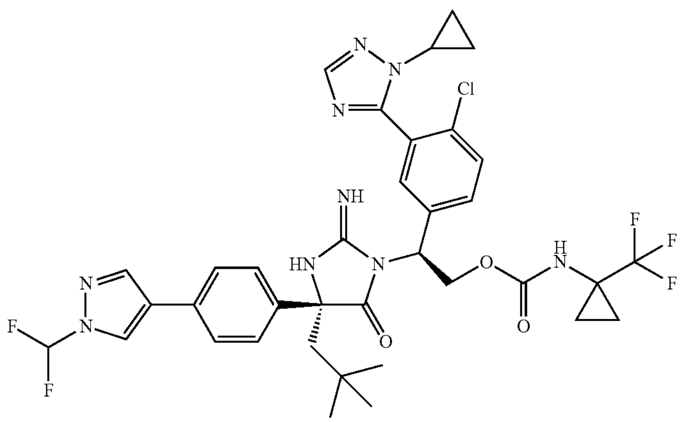 [SMILES: CC(C)(C)C[C@]1(c2ccc(-c3cnn(C(F)F)c3)cc2)NC(=N)N([C@H](COC(=O)NC2(C(F)(F)F)CC2)c2ccc(Cl)c(-c3ncnn3C3CC3)c2)C1=O] | LCMS-ESI+: calc'd for $C_{36}H_{37}ClF_5N_9O_3$: 774.3 (M + H+); Found: 774.4 (M + H+). | $^1$H NMR (400 MHz, CD3CN) δ 8.31 (s, 1H), 8.05 (s, 1H), 7.81 (s, 1H), 7.60-7.19 (m, 8H), 6.59 (s, 1H), 5.39 (dd, J = 9.7, 4.4 Hz, 1H), 4.95 (t, J = 10.6 Hz, 1H), 4.66 (dd, J = 11.4, 4.4 Hz, 1H), 3.26-3.12 (m, 1H), 2.34-2.09 (m, 2H), 1.33-1.22 (m, 2H), 1.11-1.02 (m, 2H), 0.91 (s, 9H), 0.81-0.55 (m, 4H). |
| Compd 54 | 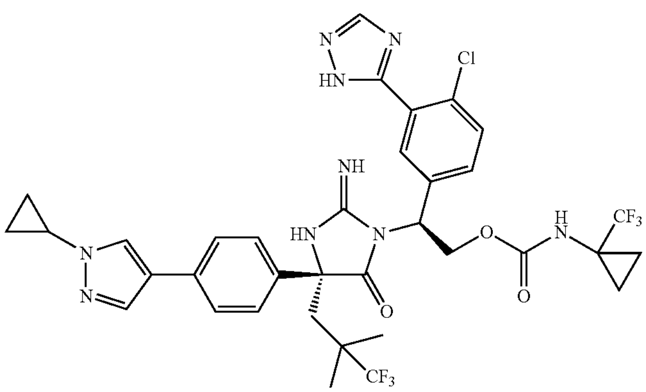 | LCMS-ESI+: calc'd for $C_{35}H_{34}ClF_6N_9O_3$: 778.2 (M + H+); Found: 778.0 (M + H+). | $^1$H NMR (400 MHz, Methanol-$d_4$) δ 9.41 (s, 1H), 8.41 (s, 1H), 8.19 (d, J = 0.9 Hz, 1H), 7.73-7.61 (m, 3H), 7.60-7.43 (m, 4H), 5.80 (dd, J = 9.7, 4.5 Hz, 1H), 5.16 (dd, J = 11.5, 9.8 Hz, 1H), 4.71 (dd, J = 11.5, 4.6 Hz, 1H), 3.82 (tt, J = 7.3, 3.8 Hz, 1H), 2.74 (d, J = 15.5 Hz, 1H), 2.46 (d, J = 15.5 Hz, 1H), 1.30-1.06 (m, 14H). |
| Compd 55 | 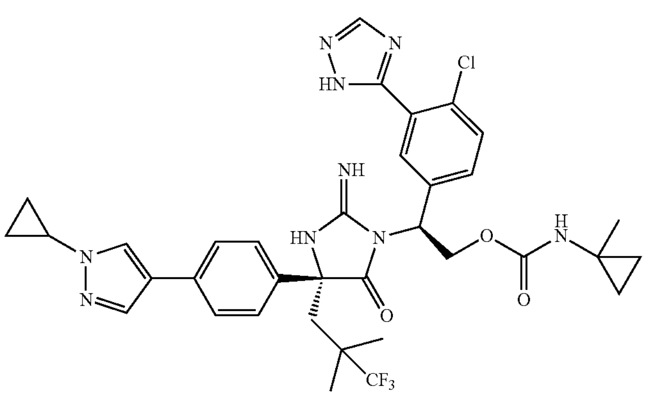 [SMILES: CC1(NC(=O)OC[C@H](c2ccc(Cl)c(-c3ncn[nH]3)c2)N2C(=N)N[C@](CC(C)(C)C(F)(F)F)(c3ccc(-c4cnn(C5CC5)c4)cc3)C2=O)CC1] | LCMS-ESI+: calc'd for $C_{35}H_{37}ClF_3N_9O_3$: 724.3 (M + H+); Found: 724.0 (M + H+). | $^1$H NMR (400 MHz, Methanol-$d_4$) δ 9.35 (s, 1H), 8.36 (s, 1H), 8.14 (d, J = 0.9 Hz, 1H), 7.68-7.37 (m, 8H), 5.73 (dd, J = 9.8, 4.6 Hz, 1H), 5.09 (t, J = 10.6 Hz, 1H), 4.67 (dd, J = 11.5, 4.7 Hz, 1H), 3.80 (tt, J = 7.3, 3.8 Hz, 1H), 2.78-2.65 (m, 1H), 2.46 (d, J = 15.5 Hz, 1H), 1.32 (s, 3H), 1.25-1.13 (m, 10H), 0.76-0.46 (m, 4H). |

-continued

| Compound # | Structures | Mass data | NMR data |
|---|---|---|---|
| Compd 56 | 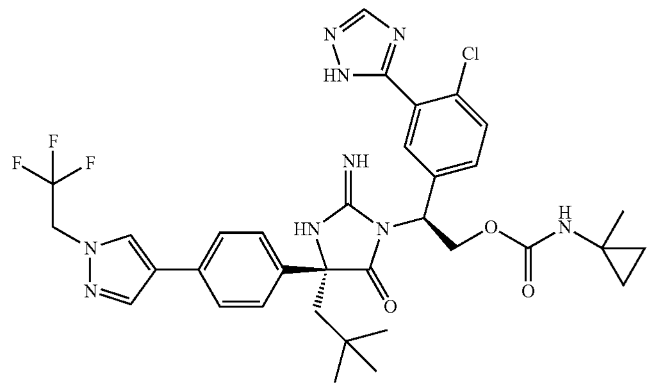 [SMILES: CC(C)(C)C[C@]1(c2ccc(-c3cnn(CC(F)(F)F)c3)cc2)NC(=N)N([C@H](COC(=O)NC2(C)CC2)c2ccc(Cl)c(-c3ncn[nH]3)c2)C1=O] | LCMS-ESI+: calc'd for C₃₅H₃₇ClF₃N₉O₃: 712.3 (M + H+); Found: 712.0 (M + H+). | ¹H NMR (400 MHz, Methanol-d₄) δ 8.12 (s, 1H), 7.94 (s, 1H), 7.61-7.11 (m, 7H), 5.12-4.88 (m, 3H), 4.67 (dd, J = 11.3, 5.2 Hz, 1H), 2.45 (d, J = 15.1 Hz, 1H), 2.12 (d, J = 15.2 Hz, 1H), 1.30 (s, 3H), 1.00 (s, 9H), 0.62 (d, J = 42.0 Hz, 4H). |
| Compd 57 | 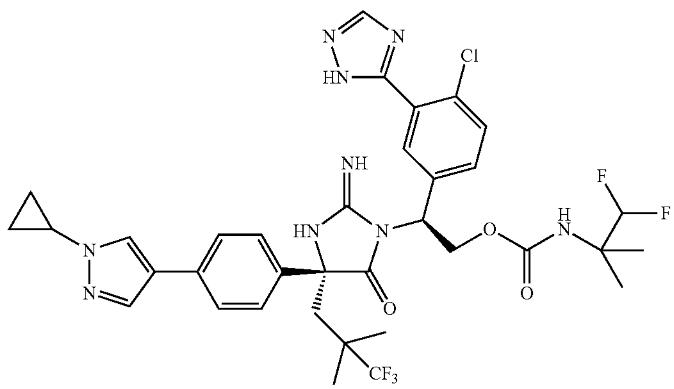 [SMILES: CC(C)(NC(=O)OC[C@H](c1ccc(Cl)c(-c2ncn[nH]2)c1)N1C(=N)N[C@](CC(C)(C)C(F)(F)F)(c2ccc(-c3cnn(C4CC4)c3)cc2)C1=O)C(F)F] | LCMS-ESI+: calc'd for C₃₅H₃₇ClF₅N₉O₃: 762.2 (M + H+); Found: 762.0 (M + H+). | ¹H NMR (400 MHz, Methanol-d₄) δ 8.72 (s, 1H), 8.14 (s, 1H), 7.89 (d, J = 0.9 Hz, 1H), 7.57-7.53 (m, 3H), 7.50 (d, J = 8.5 Hz, 1H), 7.40 (dd, J = 8.4, 6.2 Hz, 3H), 6.13 (t, J = 57.3 Hz, 1H), 5.68 (dd, J = 9.4, 4.9 Hz, 1H), 5.16-5.01 (m, 1H), 4.67 (dd, J = 11.7, 5.0 Hz, 1H), 3.72 (tt, J = 7.3, 3.9 Hz, 1H), 2.72 (d, J = 15.6 Hz, 1H), 2.49 (d, J = 15.5 Hz, 1H), 1.32 (s, 6H), 1.17 (d, J = 8.9 Hz, 8H), 1.13-1.05 (m, 2H). |
| Compd 58 | 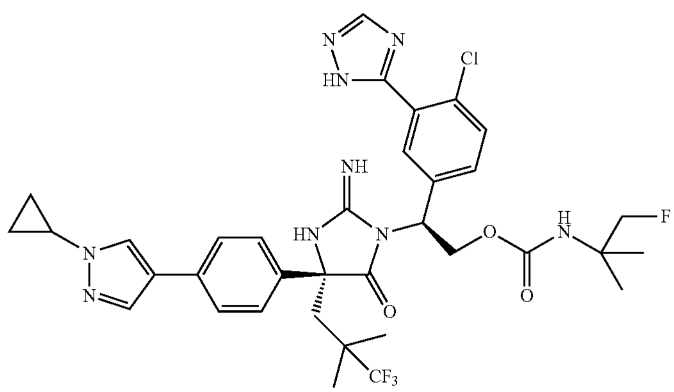 [SMILES: CC(C)(CF)NC(=O)OC[C@H](c1ccc(Cl)c(-c2ncn[nH]2)c1)N1C(=N)N[C@](CC(C)(C)C(F)(F)F)(c2ccc(-c3cnn(C4CC4)c3)cc2)C1=O] | LCMS-ESI+: calc'd for C₃₅H₃₈ClF₄N₉O₃: 744.3 (M + H+); Found: 744.0 (M + H+). | NMR (400 MHz, Methanol-d₄) δ 8.82 (s, 1H), 8.15 (s, 1H), 7.91 (d, J = 0.9 Hz, 1H), 7.60-7.53 (m, 3H), 7.51 (d, J = 8.5 Hz, 1H), 7.46-7.37 (m, 3H), 5.68 (dd, J = 9.5, 4.8 Hz, 1H), 5.15-5.02 (m, 1H), 4.65 (dd, J = 11.7, 4.8 Hz, 1H), 4.40 (d, J = 47.6 Hz, 2H), 3.73 (tt, J = 7.4, 3.9 Hz, 1H), 2.72 (d, J = 15.6 Hz, 1H), 2.49 (d, J = 15.5 Hz, 1H), 1.28 (d, J = 1.9 Hz, 6H), 1.17 (d, J = 11.7 Hz, 6H), 1.14-1.03 (m, 2H). |
| Compd 59 | 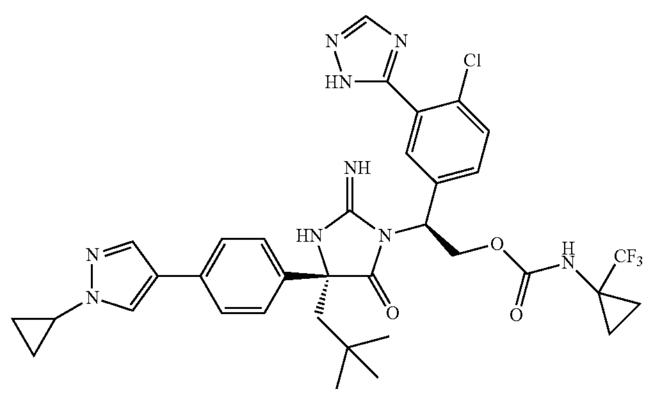 [SMILES: CC(C)(C)C[C@]1(c2ccc(-c3cnn(C4CC4)c3)cc2)NC(=N)N([C@H](COC(=O)NC2(C(F)(F)F)CC2)c2ccc(Cl)c(-c3ncn[nH]3)c2)C1=O] | LCMS-ESI+: calc'd for C₃₅H₃₇ClF₃N₉O₃: 724.3 (M + H+); Found: 724.4 (M + H+). | ¹H NMR (400 MHz, Methanol-d₄) δ 8.27 (s, 1H), 8.11 (s, 1H), 8.04 (s, 1H), 7.80 (s, 1H), 7.52-7.43 (m, 4H), 7.40-7.29 (m, 3H), 5.63 (dd, J = 9.6, 4.9 Hz, 1H), 5.11 (t, J = 10.5 Hz, 1H), 4.70 (dd, J = 11.4, 5.0 Hz, 1H), 3.69 (tt, J = 7.2, 3.9 Hz, 1H), 2.45 (d, J = 15.2 Hz, 1H), 2.14 (d, J = 15.1 Hz, 1H), 1.26 (t, J = 3.9 Hz, 2H), 1.19-1.10 (m, 2H), 1.08 (dd, J = 7.4, 4.6 Hz, 4H), 1.00 (s, 9H). |

| Compound # | Structures | Mass data | NMR data |
|---|---|---|---|
| Compd 60 | 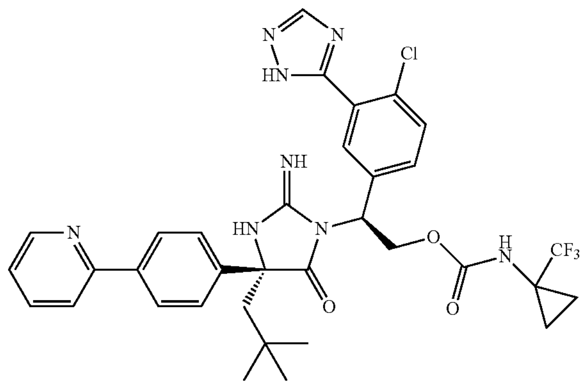 [SMILES: CC(C)(C)C[C@]1(c2ccc(-c3ccccn3)cc2)NC(=N)N([C@H](COC(=O)NC2(C(F)(F)F)CC2)c2ccc(Cl)c(-c3ncn[nH]3)c2)C1=O] | LCMS-ESI+: calc'd for C$_{34}$H$_{34}$ClF$_3$N$_8$O$_3$: 695.2 (M + H+); Found: 695.3 (M + H+). | $^1$H NMR (400 MHz, Methanol-d$_4$) δ 8.72 (dd, J = 5.3, 1.6 Hz, 1H), 8.31 (s, 1H), 8.22-8.13 (m, 2H), 8.01 (d, J = 8.1 Hz, 1H), 7.95-7.90 (m, 2H), 7.67-7.59 (m, 3H), 7.54 (d, J = 2.3 Hz, 1H), 7.46 (d, J = 8.4 Hz, 1H), 7.35 (dd, J = 8.5, 2.3 Hz, 1H), 5.64 (dd, J = 9.6, 4.8 Hz, 1H), 5.14 (t, J = 10.6 Hz, 1H), 4.71 (dd, J = 11.5, 4.9 Hz, 1H), 2.48 (d, J = 15.1 Hz, 1H), 2.20 (d, J = 15.1 Hz, 1H), 1.34-1.20 (m, 2H), 1.08 (s, 2H), 1.01 (s, 9H). |
| Compd 61 | 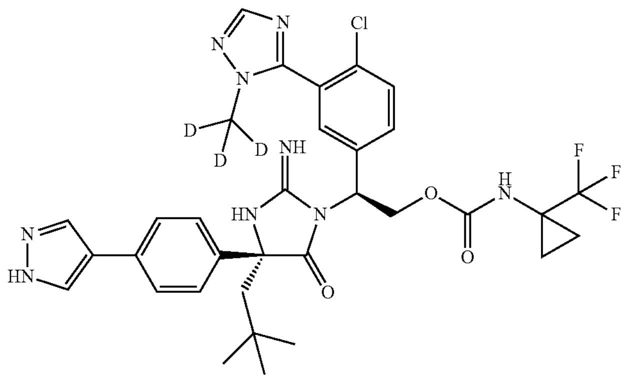 [SMILES: [2H]C([2H])([2H])n1ncnc1-c1cc([C@@H](COC(=O)NC2(C(F)(F)F)CC2)N2C(=N)N[C@](CC(C)(C)C)(c3ccc(-c4cn[nH]c4)cc3)C2=O)ccc1Cl] | LCMS-ESI+: calc'd for C$_{33}$H$_{32}$D$_3$ClF$_3$N$_9$O$_3$: 701.3 (M + H+); Found: 701.1 (M + H+). | $^1$H NMR (400 MHz, Methanol-d$_4$) δ 8.32 (s, 2H), 8.17 (s, 1H), 8.00 (s, 1H), 7.68-7.51 (m, 4H), 7.49-7.40 (m, 2H), 7.19 (s, 1H), 5.71 (dd, J = 9.6, 4.9 Hz, 1H), 5.09 (t, J = 10.6 Hz, 1H), 4.72 (dd, J = 11.5, 4.9 Hz, 1H), 2.49 (d, J = 15.2 Hz, 1H), 2.16 (d, J = 15.1 Hz, 1H), 1.27 (d, J = 6.5 Hz, 2H), 1.10 (s, 2H), 1.00 (s, 9H). |
| Compd 62 | 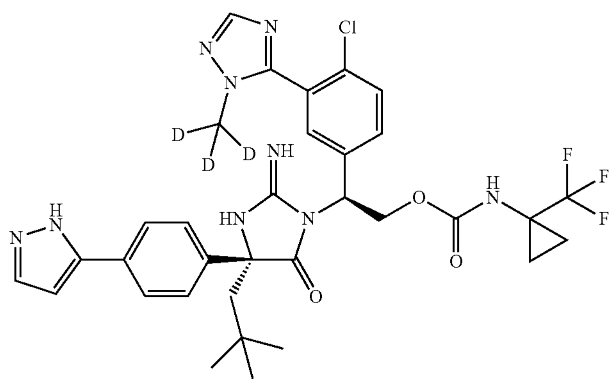 [SMILES: [2H]C([2H])([2H])n1ncnc1-c1cc([C@@H](COC(=O)NC2(C(F)(F)F)CC2)N2C(=N)N[C@](CC(C)(C)C)(c3ccc(-c4ccn[nH]4)cc3)C2=O)ccc1Cl] | calc'd for C$_{33}$H$_{32}$D$_3$ClF$_3$N$_9$O$_3$: 701.3 (M + H+); Found: 701.1 (M + H+). | $^1$H NMR (400 MHz, Methanol-d$_4$) δ 8.16 (s, 1H), 7.85 (s, 1H), 7.81-7.69 (m, 4H), 7.63-7.38 (m, 5H), 7.18 (d, J = 2.2 Hz, 1H), 6.72 (d, J = 2.3 Hz, 1H), 5.65 (dd, J = 9.6, 5.0 Hz, 1H), 5.09 (t, J = 10.6 Hz, 1H), 4.71 (dd, J = 11.5, 5.0 Hz, 1H), 2.49 (d, J = 15.1 Hz, 1H), 2.16 (d, J = 15.1 Hz, 1H), 1.38-1.22 (m, 2H), 1.09 (s, 2H), 1.00 (s, 9H). |
| Compd 63 | 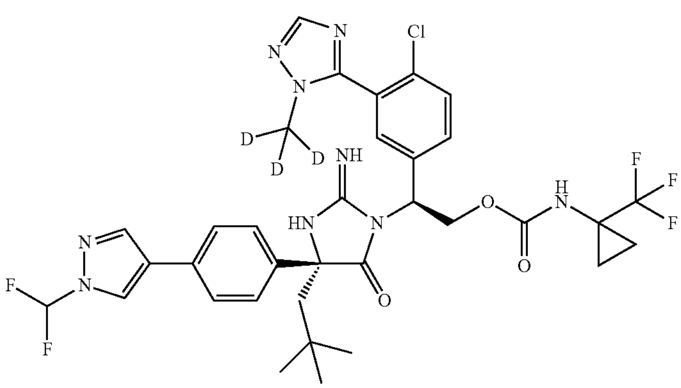 [SMILES: [2H]C([2H])([2H])n1ncnc1-c1cc([C@@H](COC(=O)NC2(C(F)(F)F)CC2)N2C(=N)N[C@](CC(C)(C)C)(c3ccc(-c4cnn(C(F)F)c4)cc3)C2=O)ccc1Cl] | LCMS-ESI+: calc'd for C$_{34}$H$_{32}$D3ClF$_5$N$_9$O$_3$: 751.3 (M + H+); Found: 751.0 (M + H+). | $^1$H NMR (400 MHz, Methanol-d$_4$) δ 8.47 (s, 1H), 8.11 (s, 1H), 7.86 (s, 1H), 7.71-7.31 (m, 7H), 7.14 (d, J = 2.3 Hz, 1H), 5.66 (dd, J = 9.7, 4.9 Hz, 1H), 5.08 (dd, J = 11.4, 9.7 Hz, 1H), 4.71 (dd, J = 11.4, 4.9 Hz, 1H), 2.46 (d, J = 15.1 Hz, 1H), 2.15 (d, J = 15.1 Hz, 1H), 1.34-1.20 (m, 2H), 1.15-1.02 (m, 2H), 0.99 (s, 9H). |

-continued

| Compound # | Structures | Mass data | NMR data |
|---|---|---|---|
| Compd 64 | 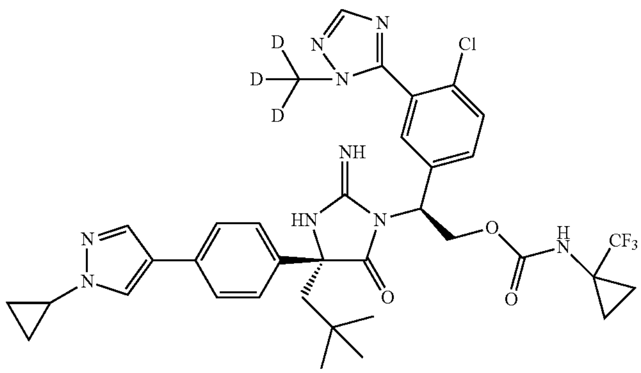 [SMILES: [2H]C([2H])([2H])n1ncnc1-c1cc([C@@H](COC(=O)NC2(C(F)(F)F)CC2)N2C(=N)N[C@](CC(C)(C)C)(c3ccc(-c4cnn(C5CC5)c4)cc3)C2=O)ccc1Cl] | LCMS-ESI+: calc'd for $C_{36}H_{36}D_3ClF_3N_9O_3$: 741.3 (M + H+); Found: 741.0 (M + H+). | $^1$H NMR (400 MHz, Methanol-$d_4$) δ 8.48 (s, 1H), 8.12 (s, 1H), 7.86 (s, 1H), 7.75-7.31 (m, 7H), 7.12 (d, J = 2.2 Hz, 1H), 5.62 (dd, J = 9.6, 5.0 Hz, 1H), 5.13-4.93 (m, 1H), 4.68 (dd, J = 11.5, 5.0 Hz, 1H), 2.49 (d, J = 15.1 Hz, 1H), 2.14 (d, J = 15.2 Hz, 1H), 1.32 (s, 3H), 1.00 (s, 9H), 0.77-0.63 (m, 2H), 0.58 (d, J = 6.4 Hz, 2H). |
| Compd 65 | 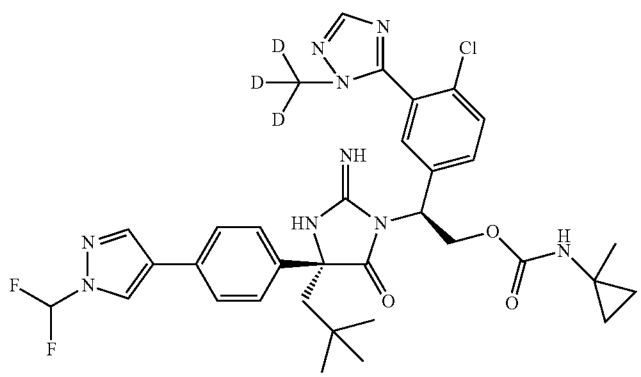 [SMILES: [2H]C([2H])([2H])n1ncnc1-c1cc([C@@H](COC(=O)NC2(C)CC2)N2C(=N)N[C@](CC(C)(C)C)(c3ccc(-c4cnn(C(F)F)c4)cc3)C2=O)ccc1Cl] | LCMS-ESI+: calc'd for $C_{34}H_{35}D_3ClF_2N_9O_3$: 697.3 (M + H+); Found: 697.0 (M + H+). | $^1$H NMR (400 MHz, Methanol-$d_4$) δ 8.48 (s, 1H), 8.12 (s, 1H), 7.86 (s, 1H), 7.75-7.31 (m, 7H), 7.12 (d, J = 2.2 Hz, 1H), 5.62 (dd, J = 9.6, 5.0 Hz, 1H), 5.13-4.93 (m, 1H), 4.68 (dd, J = 11.5, 5.0 Hz, 1H), 2.49 (d, J = 15.1 Hz, 1H), 2.14 (d, J = 15.2 Hz, 1H), 1.32 (s, 3H), 1.00 (s, 9H), 0.77-0.63 (m, 2H), 0.58 (d, J = 6.4 Hz, 2H). |
| Compd 66 | 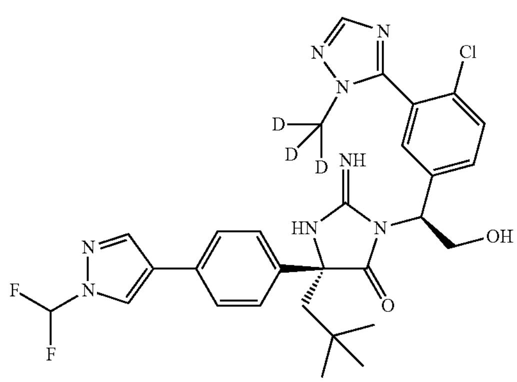 [SMILES: [2H]C([2H])([2H])n1ncnc1-c1cc([C@@H](CO)N2C(=N)N[C@](CC(C)(C)C)(c3ccc(-c4cnn(C(F)F)c4)cc3)C2=O)ccc1Cl] | LCMS-ESI+: calc'd for $C_{29}H_{28}D_3ClF_2N_8O_2$: 600.2 (M + H+); Found: 600.4 (M + H+). | $^1$H NMR (400 MHz, CD3CN) δ 8.33 (s, 1H), 8.07 (s, 1H), 7.91 (s, 1H), 7.66-7.22 (m, 8H), 5.40 (dd, J = 6.0, 3.0 Hz, 1H), 4.28 (dd, J = 12.4, 6.0 Hz, 1H), 4.15 (dd, J = 12.3, 3.1 Hz, 1H), 2.27-2.13 (m, 2H), 0.84 (s, 9H). |
| Compd 67 | 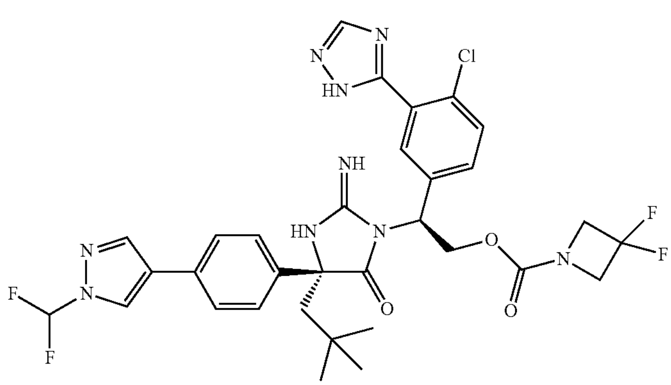 [SMILES: CC(C)(C)C[C@]1(c2ccc(-c3cnn(C(F)F)c3)cc2)NC(=N)N([C@H](COC(=O)N2CC(F)(F)C2)c2ccc(Cl)c(-c3ncn[nH]3)c2)C1=O] | LCMS-ESI+: calc'd for $C_{32}H_{33}ClF_4N_9O_3$: 702.2 (M + H+); Found: 702.5 (M + H+). | $^1$H NMR (400 MHz, Methanol-$d_4$) δ 8.43 (s, 1H), 8.32 (s, 1H), 8.08 (s, 1H), 7.62-7.58 (m, 2H), 7.55 (d, J = 2.4 Hz, 1H), 7.51 (d, J = 8.4 Hz, 1H), 7.50 (t, J = 59.8 Hz, 1H), 7.46-7.42 (m, 2H), 7.40-7.33 (m, 1H), 5.65 (dd, J = 9.9, 4.5 Hz, 1H), 5.08 (dd, J = 11.6, 9.9 Hz, 1H), 4.87 (dd, J = 11.6, 4.6 Hz, 1H), 4.25 (t, J = 11.7 Hz, 4H), 2.48 (d, J = 15.2 Hz, 1H), 2.14 (d, J = 15.2 Hz, 1H), 1.02 (s, 9H). |

-continued

| Compound # | Structures | Mass data | NMR data |
|---|---|---|---|
| Compd 68 | 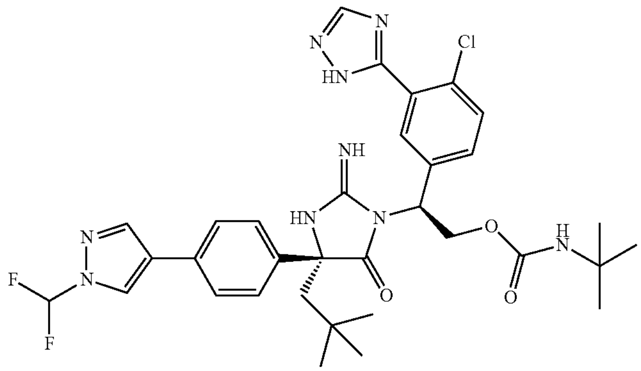 [SMILES: CC(C)(C)C[C@]1(c2ccc(-c3cnn(C(F)F)c3)cc2)NC(=N)N([C@H](COC(=O)NC(C)(C)C)c2ccc(Cl)c(-c3ncn[nH]3)c2)C1=O] | LCMS-ESI+: calc'd for C₃₃H₃₈ClF₂N₉O₃: 682.3 (M + H+); Found: 862.4 (M + H+). | ¹H NMR (400 MHz, Methanol-d₄) δ 8.45 (s, 1H), 8.30 (s, 1H), 8.09 (s, 1H), 7.59 (d, J = 8.5 Hz, 2H), 7.51 (t, J = 59.6 Hz, 1H), 7.50 (s, 1H), 7.48 (d, J = 8.4 Hz, 1H), 7.44 (d, J = 8.5 Hz, 2H), 7.40- 7.32 (m, 1H), 5.62 (dd, J = 9.4, 5.1 Hz, 1H), 5.03 (dd, J = 11.5, 9.5 Hz, 1H), 4.62 (dd, J = 11.5, 5.1 Hz, 1H), 2.46 (d, J = 15.1 Hz, 1H), 2.17 (d, J = 15.1 Hz, 1H), 1.28 (s, 9H), 1.00 (s, 9H). |
| Compd 69 | 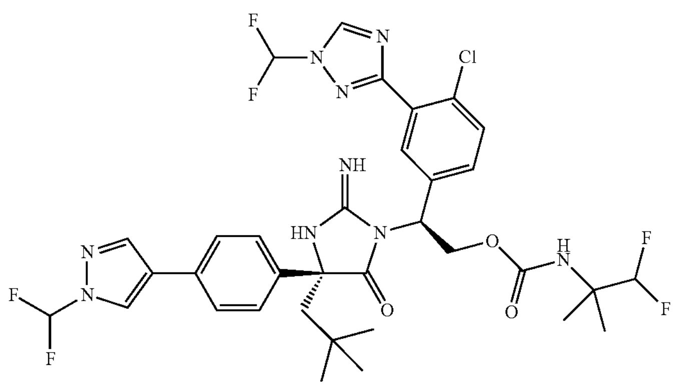 [SMILES: CC(C)(C)C[C@]1(c2ccc(-c3cnn(C(F)F)c3)cc2)NC(=N)N([C@H](COC(=O)NC(C)(C)C(F)F)c2ccc(Cl)c(-c3ncn(C(F)F)n3)c2)C1=O] | LCMS-ESI+: calc'd for C₃₄H₃₆ClF₆N₉O₃: 768.2 (M + H+); Found: 768.0 (M + H+). | ¹H NMR (400 MHz, Methanol-d₄) δ 8.88 (s, 1H), 8.45 (s, 1H), 8.10 (s, 1H), 7.68-7.41 (m, 7H), 7.32-7.12 (m, 2H), 6.13 (s, 1H), 5.66 (dd, J = 9.4, 5.1 Hz, 1H), 5.06 (t, J = 10.5 Hz, 1H), 4.66 (dd, J = 11.5, 5.1 Hz, 1H), 2.44 (d, J = 15.1 Hz, 1H), 2.19 (d, J = 15.1 Hz, 1H), 1.32 (s, 6H), 1.00 (s, 9H). |
| Compd 70 | 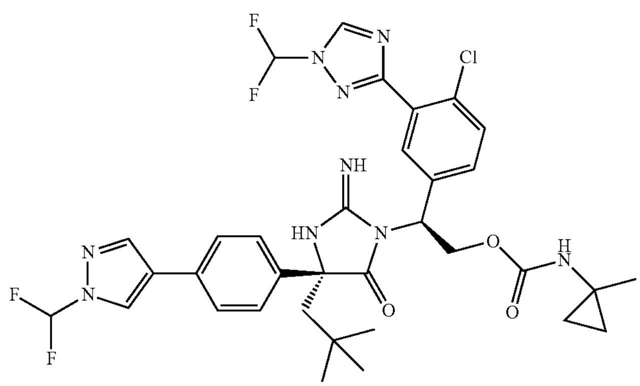 [SMILES: CC(C)(C)C[C@]1(c2ccc(-c3cnn(C(F)F)c3)cc2)NC(=N)N([C@H](COC(=O)NC2(C)CC2)c2ccc(Cl)c(-c3ncn(C(F)F)n3)c2)C1=O] | LCMS-ESI+: calc'd for C₃₄H₃₆ClF₄N₉O₃: 730.3 (M + H+); Found: 730.2 (M + H+). | 1H NMR (400 MHz, Methanol-d4) δ 8.88 (s, 1H), 8.45 (s, 1H), 8.10 (s, 1H), 7.74-7.21 (m, 9H), 5.63 (dd, J = 9.7, 4.9 Hz, 1H), 5.05 (t, J = 10.5 Hz, 1H), 4.66 (dd, J = 11.5, 5.0 Hz, 1H), 2.46 (d, J = 15.1 Hz, 1H), 2.15 (d, J = 15.2 Hz, 1H), 1.31 (s, 3H), 0.99 (s, 9H), 0.78-0.47 (m, 4H). |
| Compd 71 | 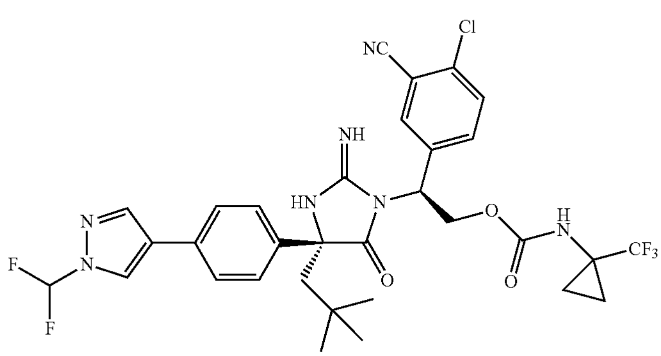 [SMILES: CC(C)(C)C[C@]1(c2ccc(-c3cnn(C(F)F)c3)cc2)NC(=N)N([C@H](COC(=O)NC2(C(F)(F)F)CC2)c2ccc(Cl)c(C#N)c2)C1=O] | LCMS-ESI+: calc'd for C₃₂H₃₁ClF₅N₇O₃: 692.2 (M + H+); Found: 792.3 (M + H+). | ¹H NMR (400 MHz, Methanol-d₄) δ 8.44 (s, 1H), 8.20 (s, 1H), 8.09 (s, 1H), 7.72-7.66 (m, 2H), 7.57-7.18 (m, 5H), 5.59 (dd, J = 9.6, 5.0 Hz, 1H), 5.05 (dd, J = 11.4, 9.6 Hz, 1H), 4.69 (dd, J = 11.5, 5.0 Hz, 1H), 2.47 (d, J = 15.1 Hz, 1H), 2.17 (d, J = 15.2 Hz, 1H), 1.32-1.19 (m, 2H), 1.08 (s, 2H), 1.00 (s, 9H). |

-continued

| Compound # | Structures | Mass data | NMR data |
|---|---|---|---|
| Compd 72 | 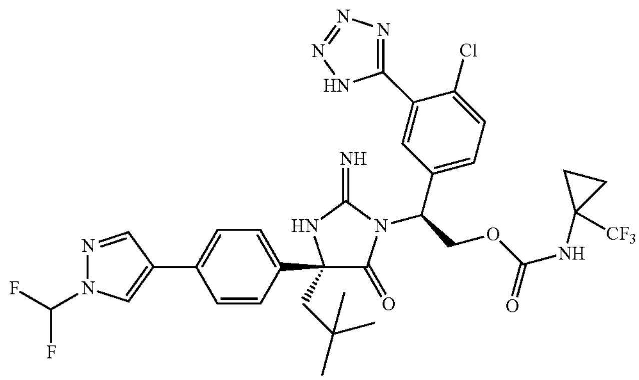 [SMILES: CC(C)(C)C[C@]1(c2ccc(-c3cnn(C(F)F)c3)cc2)NC(=N)N([C@H](COC(=O)NC2(C(F)(F)F)CC2)c2ccc(Cl)c(-c3nnn[nH]3)c2)C1=O] | LCMS-ESI+: calc'd for C₃₂H₃₂ClF₅N₁₀O₃: 735.2 (M + H+); Found: 735.2 (M + H+). | ¹H NMR (400 MHz, Methanol-d₄) δ 8.42 (d, J = 0.7 Hz, 1H), 8.19 (s, 1H), 8.07 (s, 1H), 7.68-7.42 (m, 6H), 7.39 (d, J = 20.0 Hz, 1H), 5.67 (dd, J = 9.6, 4.9 Hz, 1H), 5.15-5.05 (m, 1H), 4.74 (dd, J = 11.5, 4.9 Hz, 1H), 2.48 (d, J = 15.1 Hz, 1H), 2.15 (d, J = 15.1 Hz, 1H), 1.31-1.24 (m, 2H), 1.08 (s, 2H), 1.00 (s, 9H). |
| Compd 73 | 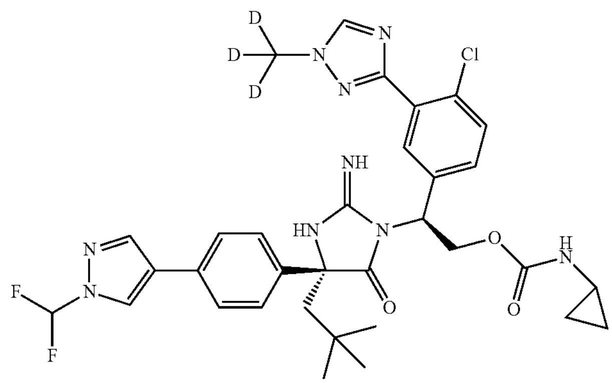 [SMILES: [2H]C([2H])([2H])n1cnc(-c2cc([C@@H](COC(=O)NC3CC3)N3C(=N)N[C@](CC(C)(C)C)(c4ccc(-c5cnn(C(F)F)c5)cc4)C3=O)ccc2Cl)n1] | LCMS-ESI+: calc'd for C₃₃H₃₃ClD₃F₂N₉O₃: 683.2 (M + H+); Found: 683.0 (M + H+). | ¹H NMR (400 MHz, Methanol-d₄) δ 8.47 (s, 1H), 8.31 (s, 1H), 8.10 (s, 1H), 7.77-7.17 (m, 8H), 5.60 (dd, J = 9.6, 5.0 Hz, 1H), 5.09 (dd, J = 11.5, 9.7 Hz, 1H), 4.68 (dd, J = 11.7, 4.8 Hz, 1H), 2.45 (d, J = 15.2 Hz, 1H), 2.47-2.44 (m, 1H), 2.14 (d, J = 15.1 Hz, 1H), 1.00 (s, 9H), 0.65 (d, J = 6.5 Hz, 2H), 0.52-0.29 (m, 2H). |
| Compd 74 | 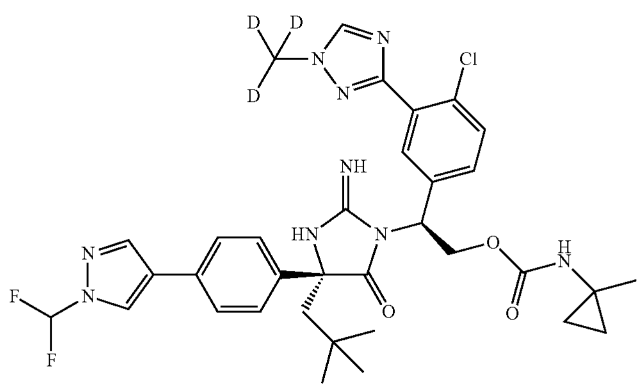 [SMILES: [2H]C([2H])([2H])n1cnc(-c2cc([C@@H](COC(=O)NC3(C)CC3)N3C(=N)N[C@](CC(C)(C)C)(c4ccc(-c5cnn(C(F)F)c5)cc4)C3=O)ccc2Cl)n1] | LCMS-ESI+: calc'd for C₃₄H₃₅ClD₃F₂N₉O₃: 697.2 (M + H+); Found: 697.0 (M + H+). | ¹H NMR (400 MHz, Methanol-d₄) δ 8.47 (s, 1H), 8.30 (s, 1H), 8.10 (s, 1H), 7.62-7.49 (m, 3H), 7.49-7.38 (m, 4H), 7.39-7.28 (m, 1H), 5.59 (dd, J = 9.6, 4.9 Hz, 1H), 5.10-4.99 (m, 1H), 4.67 (dd, J = 11.5, 5.0 Hz, 1H), 2.46 (d, J = 15.1 Hz, 1H), 2.14 (d, J = 15.2 Hz, 1H), 1.31 (s, 3H), 1.00 (s, 9H), 0.73-0.48 (m, 4H). |
| Compd 75 | 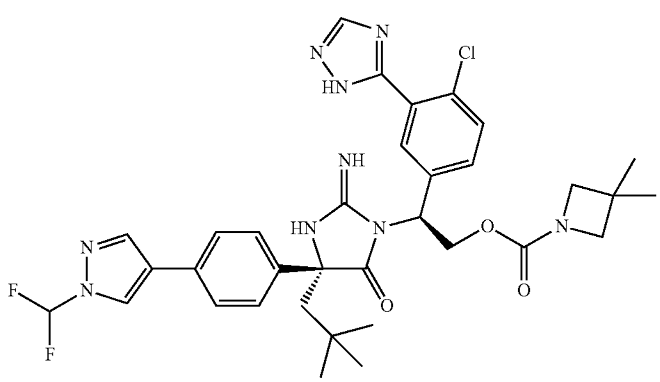 [SMILES: CC(C)(C)C[C@]1(c2ccc(-c3cnn(C(F)F)c3)cc2)NC(=N)N([C@H](COC(=O)N2CC(C)(C)C2)c2ccc(Cl)c(-c3ncn[nH]3)c2)C1=O] | LCMS-ESI+: calc'd for C₃₄H₃₈ClF₂N₉O₃: 694.3 (M + H+); Found: 694.4 (M + H+). | ¹H NMR (400 MHz, CD3CN) δ 8.31 (d, J = 0.7 Hz, 1H), 8.23 (s, 1H), 8.05 (s, 1H), 7.78 (d, J = 2.4 Hz, 1H), 7.61-7.22 (m, 7H), 5.45 (dd, J = 9.8, 4.5 Hz, 1H), 4.83 (dd, J = 11.6, 9.8 Hz, 1H), 4.73 (dd, J = 11.6, 4.6 Hz, 1H), 3.61-3.31 (m, broad, 4H), 2.35-2.10 (m, 2H), 1.19-1.08 (m, broad, 6H), 0.93 (s, 9H). |

| Compound # | Structures | Mass data | NMR data |
|---|---|---|---|
| Compd 76 | 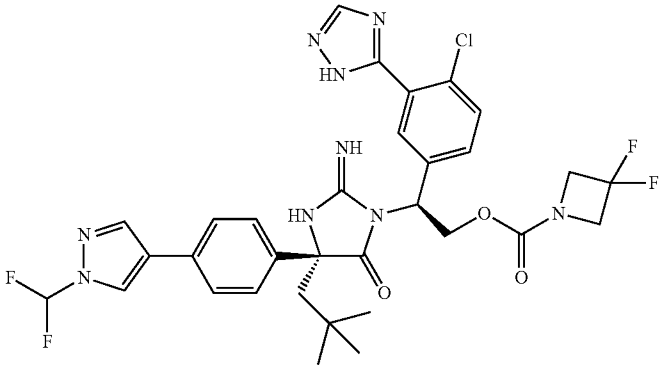 | LCMS-ESI+: calc'd for C33H35ClF3N9O3: 698.2 (M + H+); Found: 698.4 (M + H+). | 1H NMR (400 MHz, CD3CN) δ 8.30 (d, J = 0.7 Hz, 1H), 8.22 (s, 1H), 8.05 (s, 1H), 7.79 (d, J = 2.4 Hz, 1H), 7.61-7.22 (m, 7H), 5.47 (dd, J = 9.7, 4.6 Hz, 1H), 4.86 (t, J = 10.7 Hz, 1H), 4.76 (dd, J = 11.5, 4.6 Hz, 1H), 4.10-3.55 (m, broad, 4H), 2.36-2.14 (m, 2H), 1.47 (d, broad, JHF = 21.9 Hz, 3H), 0.93 (s, 9H). |
| Compd 77 | 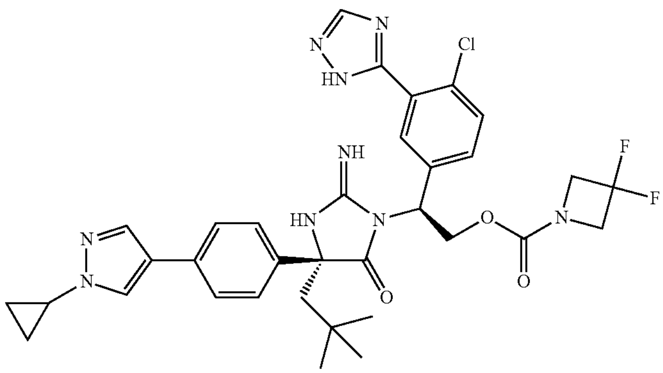 [SMILES: CC(C)(C)C[C@]1(c2ccc(-c3cnn(C4CC4)c3)cc2)NC(=N)N([C@H](COC(=O)N2CC(F)(F)C2)c2ccc(Cl)c(-c3ncn[nH]3)c2)C1=O] | LCMS-ESI+: calc'd for C34H36ClF2N9O3: 692.3 (M + H+); Found: 692.3 (M + H+). | 1H NMR (400 MHz, Methanol-d4) δ 8.32 (br s, 1H), 8.05 (s, 1H), 7.80 (s, 1H), 7.56-7.47 (m, 4H), 7.41-7.33 (m, 3H), 5.64 (dd, J = 9.8, 4.5 Hz, 1H), 5.07 (dd, J = 11.5, 10.0 Hz, 1H), 4.38-4.16 (m, 4H), 3.75-3.66 (m, 1H), 2.49 (d, J = 15.2 Hz, 1H), 2.12 (d, J = 15.2 Hz, 1H), 1.17-1.05 (m, 4H), 1.01 (s, 9H). |
| Compd 78 | 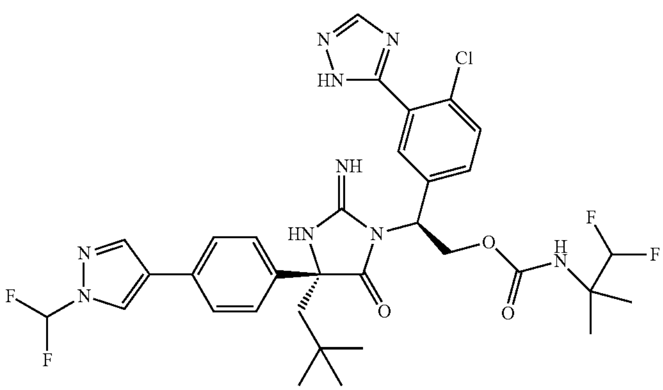 [SMILES: CC(C)(C)C[C@]1(c2ccc(-c3cnn(C(F)F)c3)cc2)NC(=N)N([C@H](COC(=O)NC(C)(C)C(F)F)c2ccc(Cl)c(-c3ncn[nH]3)c2)C1=O] | LCMS-ESI+: calc'd for C33H36ClF4N9O3: 718.2 (M + H+); Found: 719.0 (M + H+). | 1H NMR (400 MHz, Methanol-d4) δ 8.43 (s, 1H), 8.30 (s, 1H), 8.08 (s, 1H), 7.70-7.27 (m, 9H), 6.13 (t, J = 57.3 Hz, 1H), 5.64 (dd, J = 9.4, 5.0 Hz, 1H), 5.20-4.98 (m, 1H), 4.67 (dd, J = 11.6, 5.1 Hz, 1H), 2.43 (d, J = 15.1 Hz, 1H), 2.18 (d, J = 15.1 Hz, 1H), 1.31 (s, 6H), 1.00 (s, 9H). |
| Compd 79 | 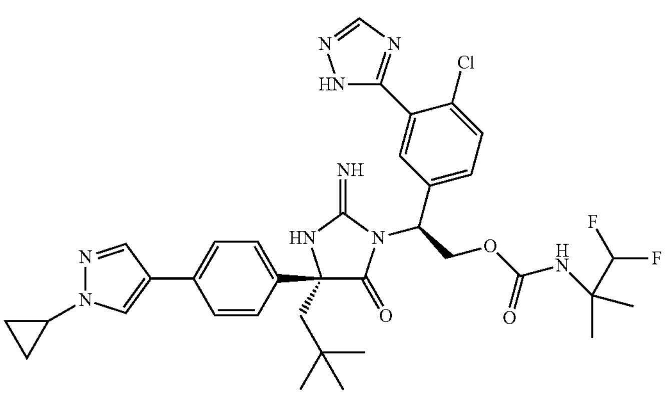 [SMILES: CC(C)(C)C[C@]1(c2ccc(-c3cnn(C4CC4)c3)cc2)NC(=N)N([C@H](COC(=O)NC(C)(C)C(F)F)c2ccc(Cl)c(-c3ncn[nH]3)c2)C1=O] | LCMS-ESI+: calc'd for C35H40ClF2N9O3: 708.3 (M + H+); Found: 709.0 (M + H+). | 1H NMR (400 MHz, Methanol-d4) δ 8.29 (s, 1H), 8.05 (s, 1H), 7.80 (s, 1H), 7.58-7.41 (m, 4H), 7.41-7.21 (m, 3H), 6.13 (t, J = 57.3 Hz, 1H), 5.63 (dd, J = 9.3, 5.1 Hz, 1H), 5.15-4.99 (m, 1H), 4.67 (dd, J = 11.5, 5.1 Hz, 1H), 3.69 (tt, J = 7.3, 3.8 Hz, 1H), 2.43 (d, J = 15.3 Hz, 1H), 2.17 (d, J = 15.1 Hz, 1H), 1.31 (s, 6H), 1.14 (dt, J = 7.6, 2.5 Hz, 2H), 1.10-1.03 (m, 2H), 1.00 (s, 9H). |

-continued

| Compound # | Structures | Mass data | NMR data |
|---|---|---|---|
| Compd 80 | 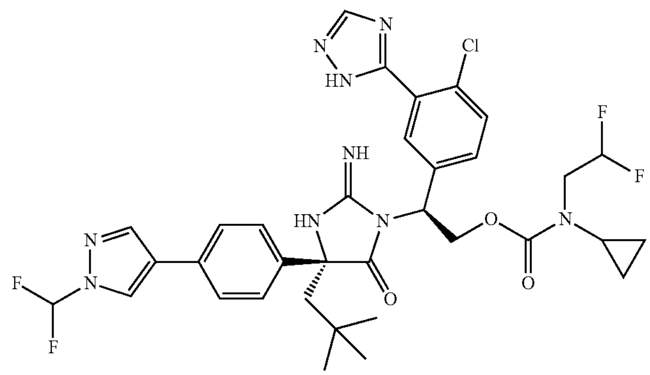 [SMILES: CC(C)(C)C[C@]1(c2ccc(-c3cnn(C(F)F)c3)cc2)NC(=N)N([C@H](COC(=O)N(CC(F)F)C2CC2)c2ccc(Cl)c(-c3ncn[nH]3)c2)C1=O] | LCMS-ESI+: calc'd for $C_{34}H_{36}ClF_4N_9O_3$: 730.3 (M + H+); Found: 730.5 (M + H+). | $^1$H NMR (400 MHz, CD3CN) δ 8.30 (s, 1H), 8.27-8.16 (m, 2H), 8.04 (s, 1H), 7.88-7.81 (m, 1H), 7.66-7.18 (m, 8H), 5.60-5.53 (m, 1H), 5.05-4.94 (m, 1H), 4.76 (dd, J = 11.6, 4.8 Hz, 1H), 3.40-3.57 (m, 1H), 3.02 (app. d, JHF = 46.4 Hz, 2H), 2.33-2.17 (m, 2H), 0.91 (s, 9H), 0.73-0.60 (m, 2H), 0.60-0.48 (m, 2H). |
| Compd 81 | 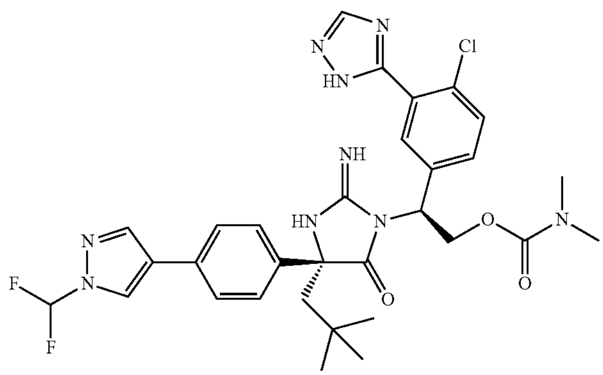 [SMILES: CN(C)C(=O)OC[C@H](c1ccc(Cl)c(-c2ncn[nH]2)c1)N1C(=N)N[C@](CC(C)(C)C)(c2ccc(-c3cnn(C(F)F)c3)cc2)C1=O] | LCMS-ESI+: calc'd for $C_{31}H_{34}ClF_2N_9O_3$: 654.2 (M + H+); Found: 654.4 (M + H+). | $^1$H NMR (400 MHz, CD3CN) δ 8.30 (d, J = 0.7 Hz, 1H), 8.23 (s, 1H), 8.04 (s, 1H), 7.78 (d, J = 2.4 Hz, 1H), 7.61-7.22 (m, 8H), 5.48 (dd, J = 9.8, 4.5 Hz, 1H), 4.94 (dd, J = 11.6, 9.8 Hz, 1H), 4.72 (dd, J = 11.6, 4.5 Hz, 1H), 2.78 (s, 3H), 2.69 (s, 3H), 2.37-2.14 (m, 2H), 0.92 (s, 9H). |
| Compd 82 | 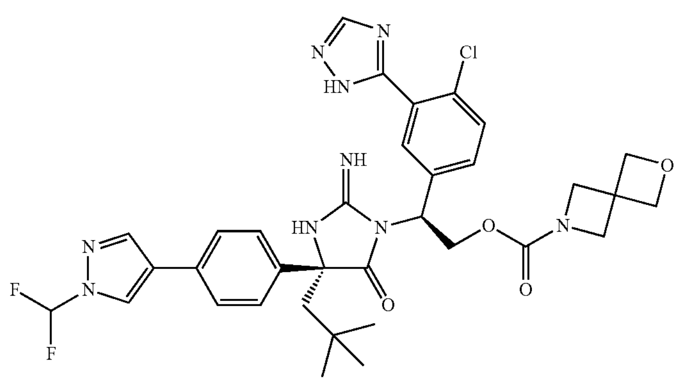 [SMILES: CC(C)(C)C[C@]1(c2ccc(-c3cnn(C(F)F)c3)cc2)NC(=N)N([C@H](COC(=O)N2CC3(COC3)C2)c2ccc(Cl)c(-c3ncn[nH]3)c2)C1=O] | LCMS-ESI+: calc'd for $C_{34}H_{36}ClF_2N_9O_4$: 708.2 (M + H+); Found: 708.6 (M + H+). | $^1$H NMR (400 MHz, Methanol-d$_4$) δ 8.46 (s, 1H), 8.33 (s, 1H), 8.10 (s, 1H), 7.64-7.59 (m, 2H), 7.60-7.46 (m, 3H), 7.51 (t, J = 59.9 Hz, 2H), 7.45 (d, J = 8.7 Hz, 2H), 7.40-7.32 (m, 1H), 5.66-5.57 (m, 1H), 4.99 (dd, J = 11.5, 9.9 Hz, 1H), 4.80 (d, J = 4.6 Hz, 1H), 4.69 (d, J = 5.5 Hz, 3H), 4.52 (s, 1H), 4.05 (d, J = 7.9 Hz, 3H), 3.79 (s, 1H), 2.48 (d, J = 15.1 Hz, 1H), 2.14 (d, J = 15.2 Hz, 1H), 1.01 (s, 9H). |
| Compd 83 | 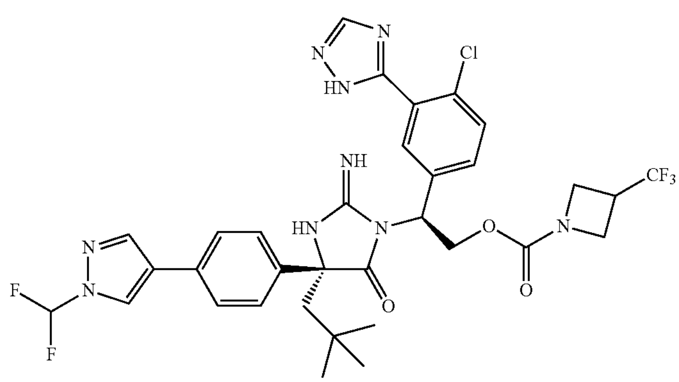 [SMILES: CC(C)(C)C[C@]1(c2ccc(-c3cnn(C(F)F)c3)cc2)NC(=N)N([C@H](COC(=O)N2CC(C(F)(F)F)C2)c2ccc(Cl)c(-c3ncn[nH]3)c2)C1=O] | LCMS-ESI+: calc'd for $C_{33}H_{33}ClF_5N_9O_3$: 734.2 (M + H+); Found: 734.5 (M + H+). | $^1$H NMR (400 MHz, CD3CN) δ 8.30 (s, 1H), 8.23 (s, 1H), 8.04 (s, 1H), 7.78 (d, J = 2.4 Hz, 1H), 7.61-7.21 (m, 8H), 5.52-5.33 (m, broad, 1H), 4.88 (t, J = 10.7 Hz, 1H), 4.76 (dd, J = 11.6, 4.5 Hz, 1H), 4.09 (t, J = 8.9 Hz, 1H), 4.01 (t, J = 9.1 Hz, 1H), 3.94-3.80 (m, 3H), 2.38-2.13 (m, 2H), 0.94 (s, 9H). |

-continued

| Compound # | Structures | Mass data | NMR data |
|---|---|---|---|
| Compd 84 | 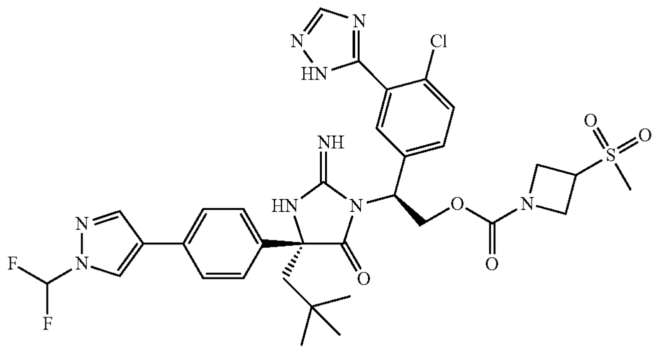 [SMILES: CC(C)(C)C[C@]1(c2ccc(-c3cnn(C(F)F)c3)cc2)NC(=N)N([C@H](COC(=O)N2CC(S(C)(=O)=O)C2)c2ccc(Cl)c(-c3ncn[nH]3)c2)C1=O] | LCMS-ESI+: calc'd for C₃₃H₃₆ClF₂N₉O₅S: 734.2 (M + H+); Found: 744.5 (M + H+). | 1H NMR (400 MHz, CD₃CN) δ 8.31 (s, 1H), 8.23 (s, 1H), 8.05 (s, 1H), 7.76 (d, J = 2.4 Hz, 1H), 7.67-7.21 (m, 8H), 5.50-5.37 (m, 1H), 4.90 (dd, J = 11.5, 9.6 Hz, 1H), 4.76 (dd, J = 11.5, 4.6 Hz, 1H), 4.16-3.87 (m, 5H), 2.82 (s, 3H), 2.38-2.13 (m, 2H), 0.94 (s, 9H). |
| Compd 85 | 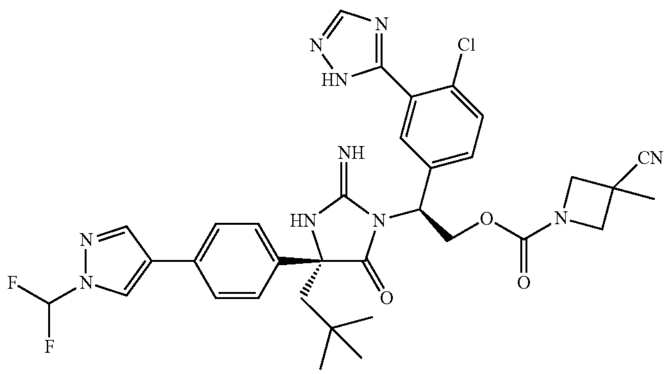 [SMILES: CC(C)(C)C[C@]1(c2ccc(-c3cnn(C(F)F)c3)cc2)NC(=N)N([C@H](COC(=O)N2CC(C)(C#N)C2)c2ccc(Cl)c(-c3ncn[nH]3)c2)C1=O] | LCMS-ESI+: calc'd for C₃₄H₃₅ClF₂N₁₀O₃: 705.3 (M + H+); Found: 705.5 (M + H+). | ¹H NMR (400 MHz, CD₃CN) δ 8.31 (s, 1H), 8.21 (s, 1H), 8.06 (s, 1H), 7.80 (d, J = 2.4 Hz, 1H), 7.65-7.21 (m, 8H), 5.47 (dt, J = 8.9, 4.4 Hz, 1H), 4.89-4.80 (m, 1H), 4.76 (dd, J = 11.6, 4.8 Hz, 1H), 4.14-3.97 (m, broad, 2H), 3.72-3.51 (m, broad, 2H), 2.38-2.14 (m, 2H), 1.51 (s, 3H), 0.94 (s, 9H). |
| Compd 86 | 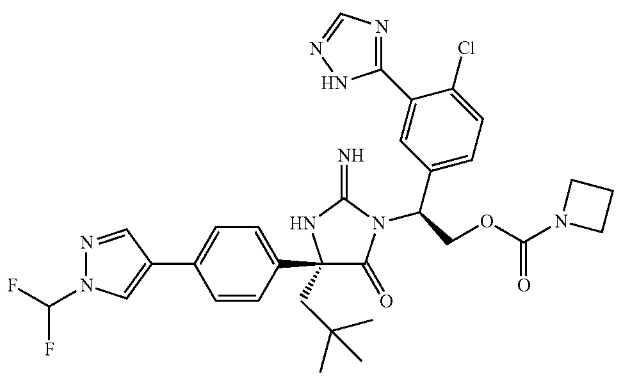 [SMILES: CC(C)(C)C[C@]1(c2ccc(-c3cnn(C(F)F)c3)cc2)NC(=N)N([C@H](COC(=O)N2CCC2)c2ccc(Cl)c(-c3ncn[nH]3)c2)C1=O] | LCMS-ESI+: calc'd for C₃₂H₃₄ClF₂N₉O₃: 666.2 (M + H+); Found: 666.4 (M + H+). | ¹H NMR (400 MHz, CD₃CN) δ 8.30 (s, 1H), 8.24 (s, 1H), 8.05 (s, 1H), 7.78 (d, J = 2.4 Hz, 1H), 7.62-7.21 (m, 8H), 5.46 (dd, J = 9.8, 4.5 Hz, 1H), 4.87 (dd, J = 11.6, 9.9 Hz, 1H), 4.71 (dd, J = 11.6, 4.5 Hz, 1H), 3.97-3.63 (m, 4H), 2.38-2.02 (m, 4H), 0.94 (s, 9H). |
| Compd 87 | 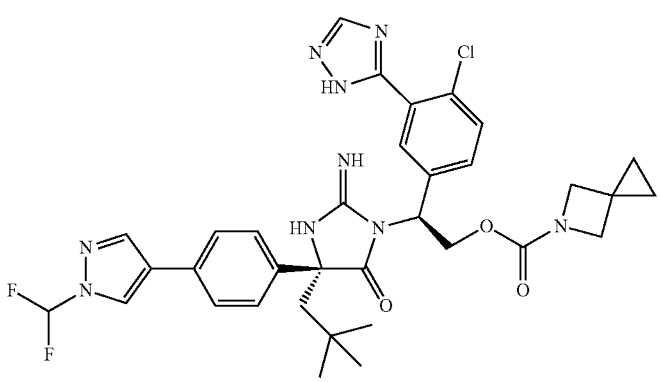 [SMILES: CC(C)(C)C[C@]1(c2ccc(-c3cnn(C(F)F)c3)cc2)NC(=N)N([C@H](COC(=O)N2CC3(CC3)C2)c2ccc(Cl)c(-c3ncn[nH]3)c2)C1=O] | LCMS-ESI+: calc'd for C₃₄H₃₆ClF₂N₉O₃: 692.3 (M + H+); Found: 692.4 (M + H+). | ¹H NMR (400 MHz, CD₃CN) δ 8.31 (s, 1H), 8.22 (s, 1H), 8.05 (s, 1H), 7.80 (d, J = 2.4 Hz, 1H), 7.65-7.19 (m, 8H), 5.50 (dd, J = 10.0, 4.6 Hz, 1H), 4.88 (dd, J = 11.6, 9.9 Hz, 1H), 4.74 (dd, J = 11.6, 4.6 Hz, 1H), 3.95-3.67 (m, 4H), 2.36-2.15 (m, 2H), 0.93 (s, 9H), 0.60-0.44 (m, 4H). |

| Compound # | Structures | Mass data | NMR data |
| --- | --- | --- | --- |
| Compd 88 | 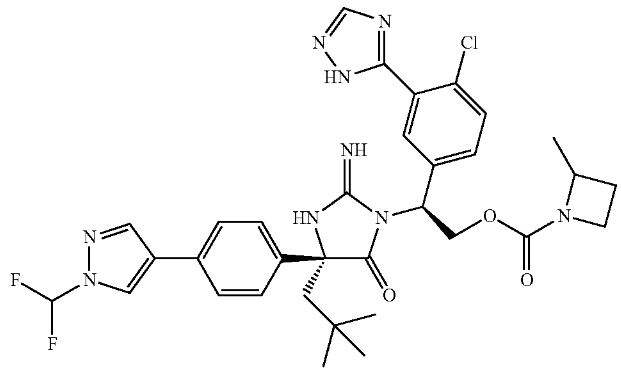 [SMILES: CC1CCN1C(=O)OC[C@H](c1ccc(Cl)c(-c2ncn[nH]2)c1)N1C(=N)N[C@](CC(C)(C)C)(c2ccc(-c3cnn(C(F)F)c3)cc2)C1=O] | LCMS-ESI+: calc'd for C₃₃H₃₆ClF₂N₉O₃: 680.3 (M + H+); Found: 680.4 (M + H+). | ¹H NMR (400 MHz, CD₃CN) δ 8.30 (s, 1H), 8.24 (s, 1H), 8.04 (s, 1H), 7.79 (d, J = 2.5 Hz, 1H), 7.67-7.19 (m, 8H), 5.56-5.31 (m, broad, 1H), 4.98-4.78 (m, broad, 1H), 4.76-4.63 (m, broad, 1H), 4.53-3.82 (m, 2H), 3.81-3.53 (m, 1H), 2.40-2.13 (m, 2H), 1.81-1.13 (m, broad, 5H), 0.93 (s, 9H). |
| Compd 89 | 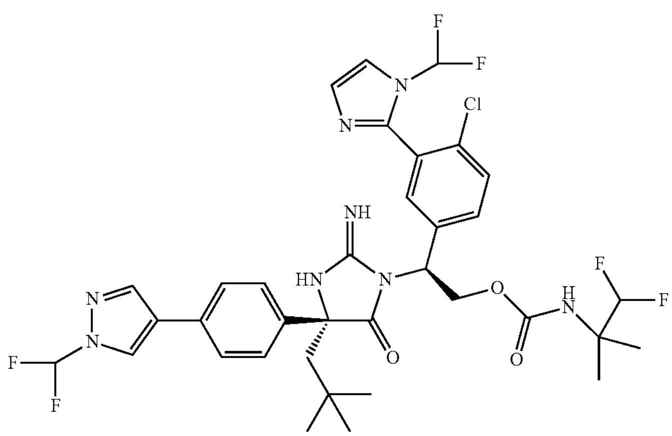 [SMILES: CC(C)(C)C[C@]1(c2ccc(-c3cnn(C(F)F)c3)cc2)NC(=N)N([C@H](COC(=O)NC(C)(C)C(F)F)c2ccc(Cl)c(-c3nccn3C(F)F)c2)C1=O] | LCMS-ESI+: calc'd for C₃₅H₃₇ClF₆N₈O₃: 767.3 (M + H+); Found: 766.9 (M + H+). | ¹H NMR (400 MHz, Methanol-d₄) δ 8.41 (d, J = 0.7 Hz, 1H), 8.08 (d, J = 0.6 Hz, 1H), 7.74-6.69 (m, 11H), 6.10 (t, J = 57.5 Hz, 1H), 5.51 (t, J = 7.2 Hz, 1H), 5.00 (t, J = 10.1 Hz, 1H), 4.67-4.59 (m, 1H), 2.32 (d, J = 14.8 Hz, 1H), 2.11-1.96 (m, 1H), 1.28 (s, 6H), 0.96 (s, 9H). |
| Compd 90 | 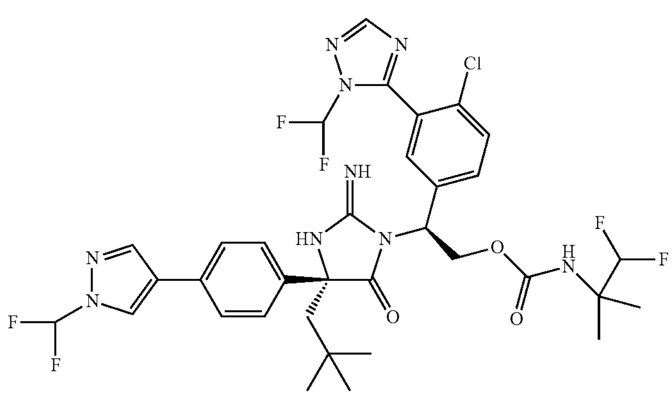 [SMILES: CC(C)(C)C[C@]1(c2ccc(-c3cnn(C(F)F)c3)cc2)NC(=N)N([C@H](COC(=O)NC(C)(C)C(F)F)c2ccc(Cl)c(-c3ncnn3C(F)F)c2)C1=O] | LCMS-ESI+: calc'd for C₃₄H₃₆ClF₆N₉O₃: 768.2 (M + H+); Found: 768.0 (M + H+). | ¹H NMR (400 MHz, Methanol-d₄) δ 8.40 (d, J = 0.7 Hz, 1H), 8.08 (s, 1H), 8.01 (s, 1H), 7.73-7.00 (m, 9H), 6.09 (t, J = 57.4 Hz, 1H), 5.48 (s, 1H), 4.98 (t, J = 9.9 Hz, 1H), 4.61 (dd, J = 11.1, 5.7 Hz, 1H), 2.29 (d, J = 14.6 Hz, 1H), 1.96 (d, J = 14.6 Hz, 1H), 1.27 (s, 6H), 0.96 (s, 9H). |

-continued

| Compound # | Structures | Mass data | NMR data |
|---|---|---|---|
| Compd 91 | 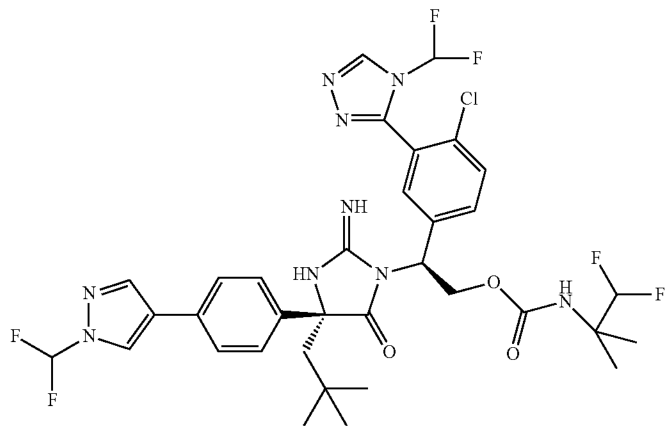 [SMILES: CC(C)(C)C[C@]1(c2ccc(-c3cnn(C(F)F)c3)cc2)NC(=N)N([C@H](COC(=O)NC(C)(C)C(F)F)c2ccc(Cl)c(-c3nncn3C(F)F)c2)C1=O] | LCMS-ESI+: calc'd for C$_{34}$H$_{36}$ClF$_6$N$_9$O$_3$: 768.2 (M + H+); Found: 768.1 (M + H+). | 1H NMR (400 MHz, Methanol-d4) δ 8.86 (s, 1H), 8.40 (d, J = 0.7 Hz, 1H), 8.06 (d, J = 0.7 Hz, 1H), 7.87-7.26 (m, 9H), 6.11 (t, J = 57.4 Hz, 1H), 5.53 (dd, J = 9.0, 5.6 Hz, 1H), 5.02 (t, J = 10.2 Hz, 1H), 4.64 (dd, J = 11.3, 5.6 Hz, 1H), 2.34 (d, J = 14.8 Hz, 1H), 2.05 (d, J = 14.8 Hz, 1H), 1.28 (s, 6H), 0.97 (s, 9H). |
| Compd 92 | 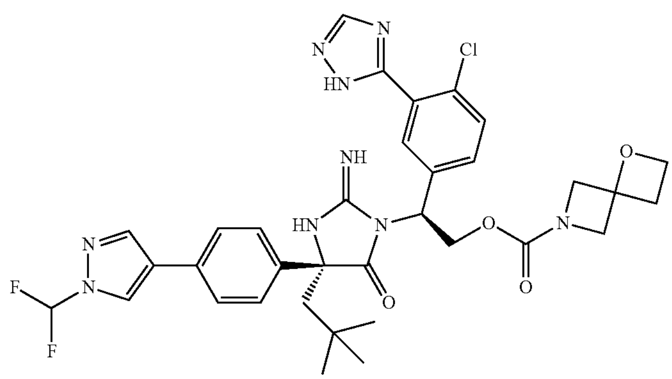 [SMILES: CC(C)(C)C[C@]1(c2ccc(-c3cnn(C(F)F)c3)cc2)NC(=N)N([C@H](COC(=O)N2CC3(CCO3)C2)c2ccc(Cl)c(-c3ncn[nH]3)c2)C1=O] | LCMS-ESI+: calc'd for C$_{34}$H$_{36}$ClF$_2$N$_9$O$_4$: 708.2 (M + H+); Found: 708.5 (M + H+). | $^1$H NMR (400 MHz, Methanol-d$_4$) δ 8.45 (s, 1H), 8.32 (s, 1H), 8.09 (s, 1H), 7.60 (d, J = 8.3 Hz, 2H), 7.54 (d, J = 2.3 Hz, 1H), 7.51 (t, J = 59.8 Hz, 1H), 7.50 (d, J = 8.4 Hz, 1H), 7.44 (d, J = 8.3 Hz, 2H), 7.40-7.33 (m, 1H), 5.63 (dd, J = 10.1, 4.5 Hz, 1H), 5.12-4.93 (m, 1H), 4.44 (d, J = 7.8 Hz, 2H), 4.20-3.92 (m, 4H), 2.81 (t, J = 7.8 Hz, 2H), 2.48 (d, J = 15.1 Hz, 1H), 2.13 (d, J = 15.1 Hz, 1H), 1.01 (s, 9H). |
| Compd 93 | 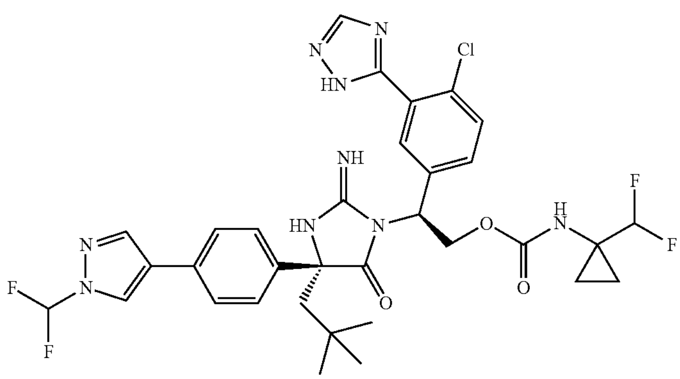 [SMILES: CC(C)(C)C[C@]1(c2ccc(-c3cnn(C(F)F)c3)cc2)NC(=N)N([C@H](COC(=O)NC2(C(F)F)CC2)c2ccc(Cl)c(-c3ncn[nH]3)c2)C1=O] | LCMS-ESI+: calc'd for C$_{33}$H$_{34}$ClF$_4$N$_9$O$_3$: 716.2 (M + H+); Found: 716.5 (M + H+). | $^1$H NMR (400 MHz, CD$_3$CN) δ 8.30 (d, J = 0.7 Hz, 1H), 8.21 (s, 1H), 8.04 (s, 1H), 7.76 (s, 1H), 7.60-7.21 (m, 8H), 6.30 (s, broad, 1H), 5.72 (t, JHF = 56.7 Hz, 1H), 5.43 (dd, J = 9.3, 4.4 Hz, 1H), 4.93 (t, J = 10.5 Hz, 1H), 4.65 (dd, J = 11.6, 4.4 Hz, 1H), 2.36-2.12 (m, 2H), 1.07-0.99 (m, 2H), 0.92 (s, 9H), 0.90-0.83 (m, 2H). |
| Compd 94 | 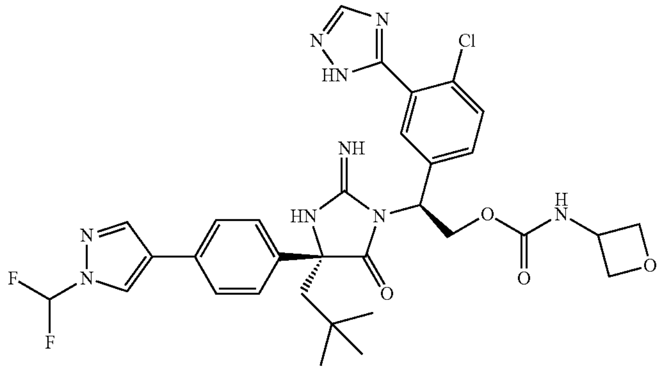 [SMILES: CC(C)(C)C[C@]1(c2ccc(-c3cnn(C(F)F)c3)cc2)NC(=N)N([C@H](COC(=O)NC2COC2)c2ccc(Cl)c(-c3ncn[nH]3)c2)C1=O] | LCMS-ESI+: calc'd for C$_{32}$H$_{34}$ClF$_2$N$_9$O$_4$: 682.2 (M + H+); Found: 682.5 (M + H+). | $^1$H NMR (400 MHz, Methanol-d$_4$) δ 8.44 (s, 1H), 8.31 (s, 1H), 8.09 (s, 1H), 7.59 (d, J = 8.2 Hz, 2H), 7.58 (t, J = 59.8 Hz, 1H), 7.53 (d, J = 2.4 Hz, 1H), 7.48 (d, J = 8.4 Hz, 1H), 7.43 (d, J = 8.3 Hz, 2H), 7.38-7.33 (m, 1H), 5.63 (dd, J = 9.4, 5.0 Hz, 1H), 5.11 (dd, J = 11.6, 9.4 Hz, 1H), 4.82-4.76 (m, 2H), 4.72 (dd, J = 11.8, 5.4 Hz, 2H), 4.53 (q, J = 5.6 Hz, 2H), 2.47 (d, J = 15.1 Hz, 1H), 2.15 (d, J = 15.1 Hz, 1H), 1.01 (s, 9H). |

-continued

| Compound # | Structures | Mass data | NMR data |
|---|---|---|---|
| Compd 95 | 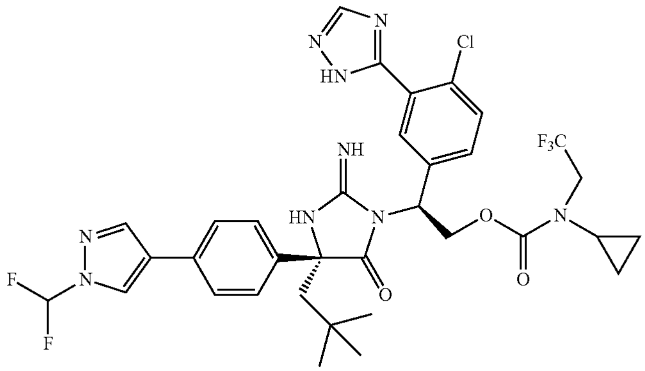 [SMILES: CC(C)(C)C[C@]1(c2ccc(-c3cnn(C(F)F)c3)cc2)NC(=N)N([C@H](COC(=O)N(CC(F)(F)F)C2CC2)c2ccc(Cl)c(-c3ncn[nH]3)c2)C1=O] | LCMS-ESI+: calc'd for C₃₄H₃₅ClF₅N₉O₃: 748.2 (M + H+); Found: 748.5 (M + H+). | ¹H NMR (400 MHz, CD₃CN) δ 8.30 (d, J = 0.7 Hz, 1H), 8.25 (s, 1H), 8.04 (s, 1H), 7.82 (s, broad, 1H), 7.60-7.18 (m, 8H), 5.59-5.46 (m, broad, 1H), 5.02 (dd, J = 11.7, 9.4 Hz, 1H), 4.79 (dd, J = 11.7, 4.6 Hz, 1H), 3.86-3.71 (m, broad, 1H), 2.34-2.15 (m, 2H), 0.91 (s, 9H), 0.73-0.61 (m, broad, 2H), 0.61-0.52 (m, 2H). |
| Compd 96 | 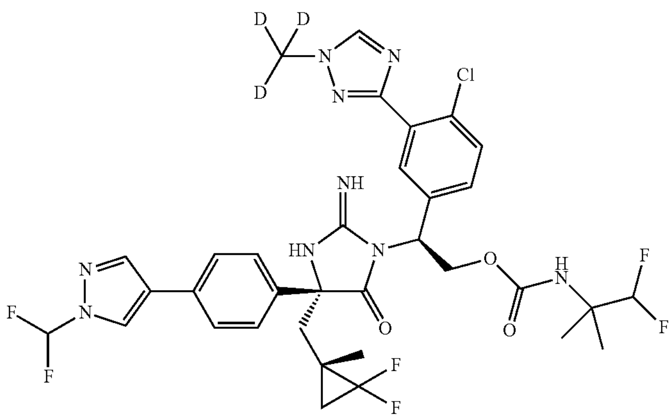 [SMILES: [2H]C([2H])([2H])n1cnc(-c2cc([C@@H](COC(=O)NC(C)(C)C(F)F)N3C(=N)N[C@](C[C@@]4(C)CC4(F)F)(c4ccc(-c5cnn(C(F)F)c5)cc4)C3=O)ccc2Cl)n1] | LCMS-ESI+: calc'd for C₃₄H₃₁D₃ClF₆N₉O₃: 769.3 (M + H+); Found: 767.0 (M + H+). | ¹H NMR (400 MHz, Methanol-d₄) δ 8.49 (d, J = 0.8 Hz, 1H), 8.12 (s, 1H), 7.90 (s, 1H), 7.69-7.31 (m, 6H), 7.21 (d, J = 2.1 Hz, 1H), 6.12 (t, J = 57.3 Hz, 1H), 5.70 (dd, J = 9.4, 4.9 Hz, 1H), 5.05 (dd, J = 11.8, 9.4 Hz, 1H), 4.73-4.62 (m, 1H), 2.73 (d, J = 15.4 Hz, 1H), 2.42 (d, J = 15.4 Hz, 1H), 1.98 (dd, J = 38.9, 0.8 Hz, 0H), 1.31 (d, J = 5.6 Hz, 6H), 1.16 (d, J = 7.2 Hz, 3H), 0.99-0.81 (m, 2H). |
| Compd 97 | 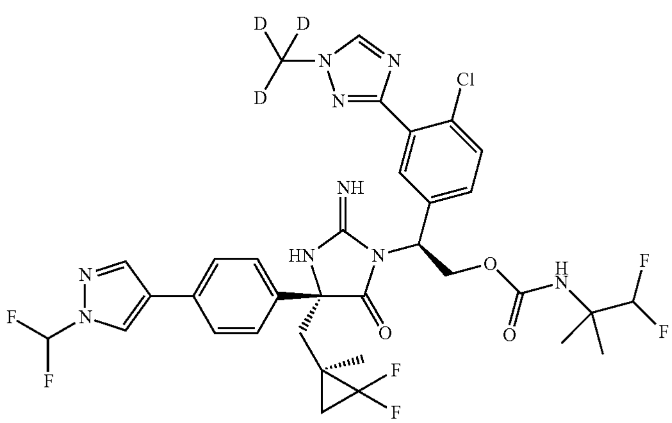 [SMILES: [2H]C([2H])([2H])n1cnc(-c2cc([C@@H](COC(=O)NC(C)(C)C(F)F)N3C(=N)N[C@](C[C@]4(C)CC4(F)F)(c4ccc(-c5cnn(C(F)F)c5)cc4)C3=O)ccc2Cl)n1] | LCMS-ESI+: calc'd for C₃₄H₃₁D₃ClF₆N₉O₃: 769.3 (M + H+); Found: 767.0 (M + H+). | ¹H NMR (400 MHz, Methanol-d₄) δ 8.49 (d, J = 0.8 Hz, 1H), 8.12 (s, 1H), 7.92 (s, 1H), 7.80-7.33 (m, 8H), 7.23 (d, J = 2.2 Hz, 1H), 6.11 (t, J = 57.3 Hz, 1H), 5.68 (dd, J = 9.5, 5.0 Hz, 1H), 5.16-4.96 (m, 1H), 4.71 (dd, J = 11.8, 5.0 Hz, 1H), 2.58 (s, 2H), 1.31 (d, J = 5.6 Hz, 6H), 1.21-1.12 (m, 1H), 1.07 (d, J = 2.5 Hz, 3H), 0.96-0.81 (m, 1H). |

| Compound # | Structures | Mass data | NMR data |
|---|---|---|---|
| Compd 98 | 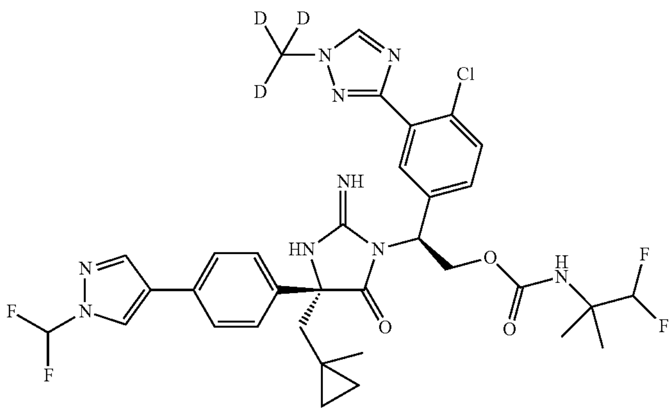 [SMILES: [2H]C([2H])([2H])n1cnc(-c2cc([C@@H](COC(=O)NC(C)(C)C(F)F)N3C(=N)N[C@](CC4(C)CC4)(c4ccc(-c5cnn(C(F)F)c5)cc4)C3=O)ccc2Cl)n1] | LCMS-ESI+: calc'd for C₃₄H₃₃D₃ClF₄N₉O₃: 733.3 (M + H+); Found: 733.1 (M + H+). | ¹H NMR (400 MHz, Methanol-d₄) δ 8.47 (s, 1H), 8.11 (s, 1H), 7.92 (s, 1H), 7.77-7.33 (m, 7H), 7.25 (d, J = 2.4 Hz, 1H), 6.11 (t, J = 57.3 Hz, 1H), 5.69 (dd, J = 9.2, 5.1 Hz, 1H), 5.03 (dd, J = 11.6, 9.2 Hz, 1H), 4.71 (dd, J = 11.7, 5.1 Hz, 1H), 2.45-2.15 (m, 2H), 1.29 (s, 6H), 1.00 (s, 3H), 0.61-0.23 (m, 4H). |
| Compd 99 | 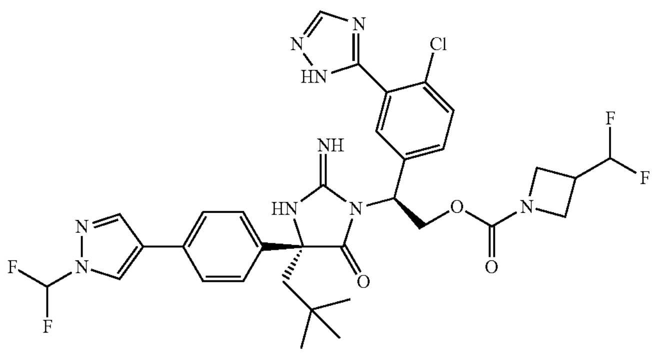 [SMILES: CC(C)(C)C[C@]1(c2ccc(-c3cnn(C(F)F)c3)cc2)NC(=N)N([C@H](COC(=O)N2CC(C(F)F)C2)c2ccc(Cl)c(-c3ncn[nH]3)c2)C1=O] | LCMS-ESI+: calc'd for C₃₃H₃₄ClF₄N₉O₃: 716.2 (M + H+); Found: 716.6 (M + H+). | 1H NMR (400 MHz, Methanol-d₄) δ 8.44 (s, 1H), 8.32 (s, 1H), 8.09 (s, 1H), 7.60 (d, J = 8.2 Hz, 2H), 7.56-7.47 (m, 2H), 7.51 (t, J = 59.8 Hz, 1H), 7.44 (d, J = 8.2 Hz, 2H), 7.41-7.33 (m, 1H), 6.06 (td, J = 56.2, 3.4 Hz, 1H), 5.62 (dd, J = 10.2, 4.5 Hz, 1H), 5.05 (t, J = 10.8 Hz, 1H), 4.17-3.83 (m, 4H), 3.06 (s, 1H), 2.49 (d, J = 15.1 Hz, 1H), 2.14 (d, J = 15.1 Hz, 1H), 1.03 (s, 9H). |
| Compd 100 | 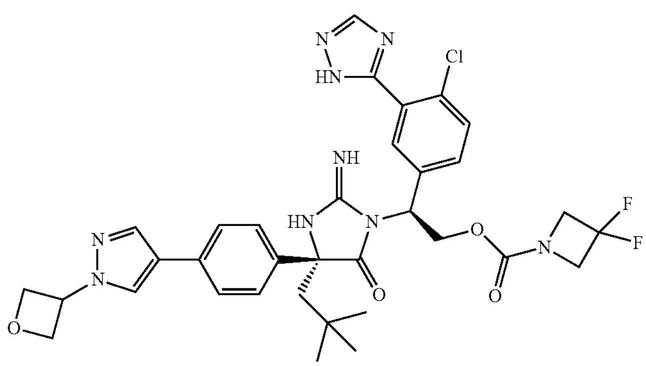 [SMILES: CC(C)(C)C[C@]1(c2ccc(-c3cnn(C4COC4)c3)cc2)NC(=N)N([C@H](COC(=O)N2CC(F)(F)C2)c2ccc(Cl)c(-c3ncn[nH]3)c2)C1=O] | LCMS-ESI+: calc'd for C₃₄H₃₆ClF₂N₉O₄: 708.2 (M + H+); Found: 708.6 (M + H+). | ¹H NMR (400 MHz, Methanol-d₄) δ 8.32 (s, 1H), 8.16 (s, 1H), 7.95 (s, 1H), 7.60-7.44 (m, 4H), 7.41-7.29 (m, 3H), 5.68-5.62 (m, 1H), 5.58 (q, J = 6.9 Hz, 1H), 5.21-4.99 (m, 5H), 4.91-4.86 (m, 1H), 4.25 (t, J = 11.7 Hz, 4H), 2.49 (d, J = 15.2 Hz, 1H), 2.13 (d, J = 15.2 Hz, 1H), 1.02 (s, 9H). |
| Compd 101 | 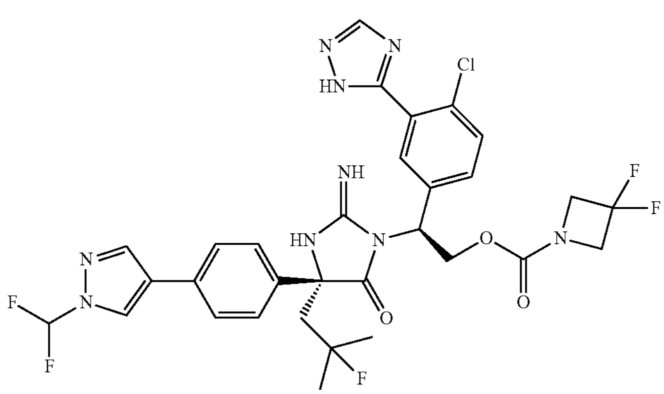 [SMILES: CC(C)(F)C[C@]1(c2ccc(-c3cnn(C(F)F)c3)cc2)NC(=N)N([C@H](COC(=O)N2CC(F)(F)C2)c2ccc(Cl)c(-c3ncn[nH]3)c2)C1=O] | LCMS-ESI+: calc'd for C₃₁H₂₉ClF₅N₉O₃: 706.2 (M + H+); Found: 706.4 (M + H+). | ¹H NMR (400 MHz, CD₃CN) δ 8.31 (s, 1H), 8.24 (s, 1H), 8.05 (s, 1H), 7.84 (d, J = 2.4 Hz, 1H), 7.67-7.22 (m, 8H), 5.61-5.50 (m, 1H), 4.89-4.81 (m, 1H), 4.74 (dd, J = 11.5, 4.8 Hz, 1H), 4.16-3.94 (m, 4H), 2.89 (dd, JHH = 15.4, JHF = 5.9 Hz, 1H), 2.47 (dd, JHF = 28.0, JHH = 15.4 Hz, 1H), 1.44 (d, JHF = 3.5 Hz, 3H), 1.39 (d, JHF = 2.6 Hz, 3H). |

-continued

| Compound # | Structures | Mass data | NMR data |
|---|---|---|---|
| Compd 102 | 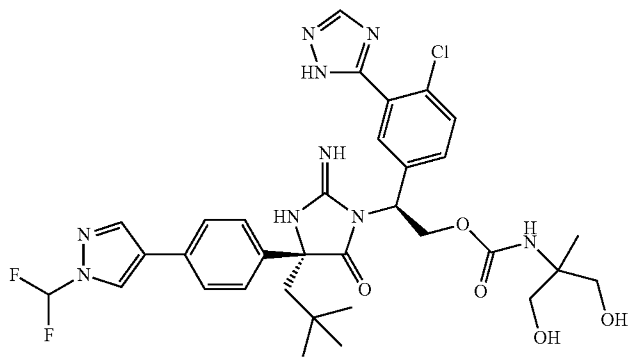 [SMILES: CC(C)(C)C[C@]1(c2ccc(-c3cnn(C(F)F)c3)cc2)NC(=N)N([C@H](COC(=O)NC(C)(CO)CO)c2ccc(Cl)c(-c3ncn[nH]3)c2)C1=O] | LCMS-ESI+: calc'd for C₃₃H₃₈ClF₂N₉O₅: 714.3 (M + H+); Found: 714.2 (M + H+). | ¹H NMR (400 MHz, Methanol-d₄) δ 8.44 (s, 1H), 8.32 (s, 1H), 8.08 (s, 1H), 7.59 (d, J = 8.3 Hz, 2H), 7.51 (t, J = 59.8 Hz, 1H), 7.54 (t, J = 2.7 Hz, 1H), 7.49 (dd, J = 8.5, 1.5 Hz, 1H), 7.42 (d, J = 8.4 Hz, 2H), 7.37-7.32 (m, 1H), 5.65 (dd, J = 9.2, 5.4 Hz, 1H), 5.23 (ddd, J = 11.3, 9.3, 5.9 Hz, 1H), 4.96 (ddd, J = 11.9, 7.4, 5.5 Hz, 1H), 4.40-4.15 (m, 2H), 3.63 (dd, J = 11.5, 8.1 Hz, 1H), 3.55 (dd, J = 11.5, 3.0 Hz, 1H), 2.49 (d, J = 15.1 Hz, 1H), 2.14 (d, J = 15.1 Hz, 1H), 1.29 (d, J = 1.7 Hz, 3H), 1.02 (s, 9H). |
| Compd 103 | 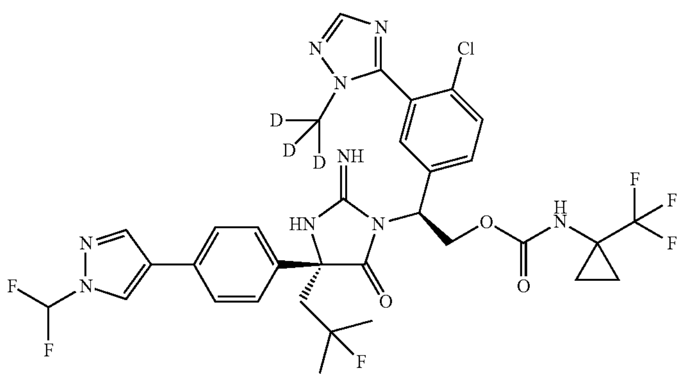 [SMILES: [2H]C([2H])([2H])n1ncnc1-c1cc([C@@H](COC(=O)NC2(C(F)(F)F)CC2)N2C(=N)N[C@](CC(C)(C)F)(c3ccc(-c4cnn(C(F)F)c4)cc3)C2=O)ccc1Cl] | LCMS-ESI+: calc'd for C₃₃H₂₉D₃ClF₆N₉O₃: 755.2 (M + H+); Found: 755.5 (M + H+). | ¹H NMR (400 MHz, CD₃CN) δ 8.33 (s, 1H), 8.07 (s, 1H), 7.88 (s, 1H), 7.68-7.19 (m, 8H), 5.46 (dd, J = 8.9, 4.4 Hz, 1H), 4.89 (t, J = 10.3 Hz, 1H), 4.62 (dd, J = 11.6, 4.4 Hz, 1H), 2.82 (dd, JHH = 15.4 Hz, JHF = 6.9 Hz, 1H), 2.47 (dd, JHF = 27.9 Hz, JHH = 15.4 Hz, 1H), 1.40 (d, JHF = 10.3 Hz, 3H), 1.34 (d, JHF = 9.5 Hz, 3H), 1.28-1.20 (m, 2H), 1.05 (d, J = 12.5 Hz, 2H). |
| Compd 104 | 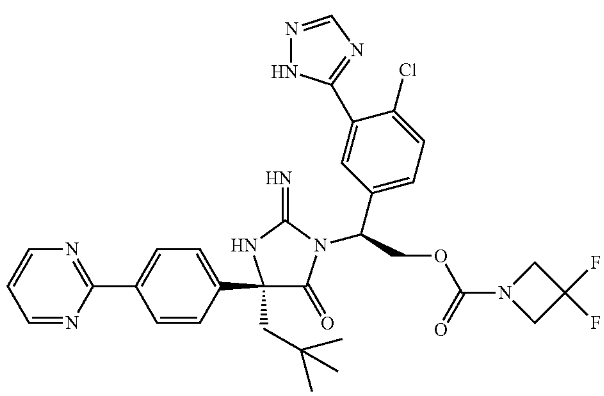 [SMILES: CC(C)(C)C[C@]1(c2ccc(-c3ncccn3)cc2)NC(=N)N([C@H](COC(=O)N2CC(F)(F)C2)c2ccc(Cl)c(-c3ncn[nH]3)c2)C1=O] | LCMS-ESI+: calc'd for C₃₂H₃₃ClF₂N₉O₃: 664.2 (M + H+); Found: 664.1 (M + H+). | ¹H NMR (400 MHz, Methanol-d₄) δ 8.87 (d, J = 4.9 Hz, 2H), 8.40-8.33 (m, 2H), 8.28 (s, 1H), 7.61-7.53 (m, 2H), 7.54-7.47 (m, 2H), 7.43-7.33 (m, 2H), 5.67 (dd, J = 9.9, 4.5 Hz, 1H), 5.08 (dd, J = 11.5, 9.9 Hz, 1H), 4.26 (t, J = 11.8 Hz, 1H), 2.53 (d, J = 15.1 Hz, 1H), 2.17 (d, J = 15.2 Hz, 1H), 1.03 (s, 9H). |

-continued

| Compound # | Structures | Mass data | NMR data |
|---|---|---|---|
| Compd 105 | 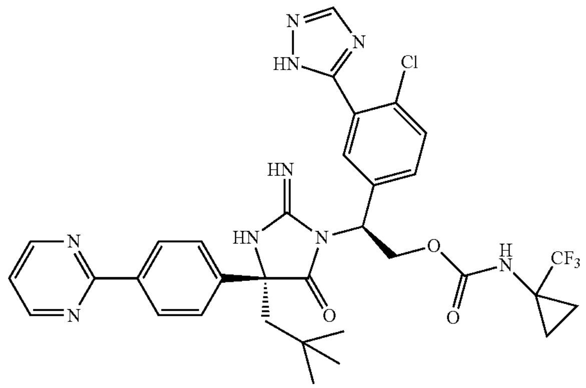 [SMILES: CC(C)(C)C[C@]1(c2ccc(-c3ncccn3)cc2)NC(=N)N([C@H](COC(=O)NC2(C(F)(F)F)CC2)c2ccc(Cl)c(-c3ncn[nH]3)c2)C1=O] | LCMS-ESI+: calc'd for C$_{33}$H$_{34}$ClF$_3$N$_9$O$_3$: 696.2 (M + H+); Found: 696.1 (M + H+). | $^1$H NMR (400 MHz, Methanol-d$_4$) δ 8.87 (d, J = 4.9 Hz, 2H), 8.41-8.28 (m, 2H), 8.20 (d, J = 40.8 Hz, 2H), 7.68-7.19 (m, 6H), 5.66 (dd, J = 9.6, 4.8 Hz, 1H), 5.11 (dd, J = 11.4, 9.8 Hz, 1H), 4.72 (dd, J = 11.5, 4.9 Hz, 1H), 2.50 (d, J = 15.1 Hz, 1H), 2.20 (d, J = 15.1 Hz, 1H), 1.33-1.21 (m, 2H), 1.08 (s, 2H), 1.01 (s, 9H). |
| Compd 106 | 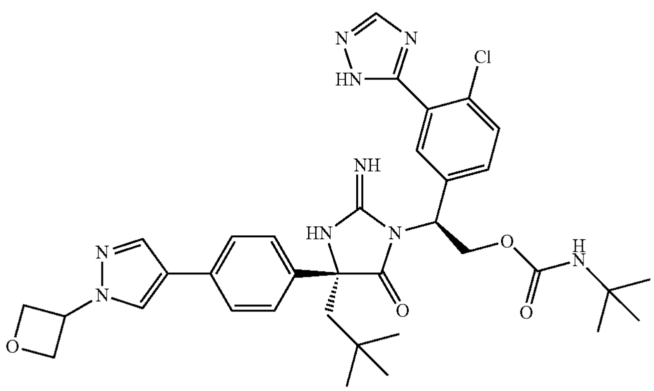 [SMILES: CC(C)(C)C[C@]1(c2ccc(-c3cnn(C4COC4)c3)cc2)NC(=N)N([C@H](COC(=O)NC(C)(C)C)c2ccc(Cl)c(-c3ncn[nH]3)c2)C1=O] | LCMS-ESI+: calc'd for C$_{35}$H$_{42}$ClN$_9$O$_4$: 688.3 (M + H+); Found: 688.6 (M + H+). | $^1$H NMR (400 MHz, Methanol-d$_4$) δ 8.30 (s, 1H), 8.16 (s, 1H), 7.95 (s, 1H), 7.56-7.50 (m, 3H), 7.47 (d, J = 8.5 Hz, 1H), 7.42-7.37 (m, 2H), 7.35 (dd, J = 8.8, 2.2 Hz, 1H), 5.69-5.53 (m, 2H), 5.11-4.97 (m, 5H), 4.69-4.58 (m, 1H), 2.47 (d, J = 15.1 Hz, 1H), 2.17 (d, J = 15.1 Hz, 1H), 1.28 (s, 9H), 1.01 (s, 9H). |
| Compd 107 | 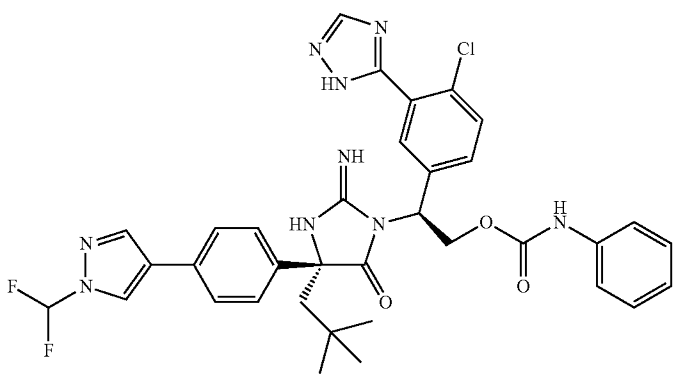 [SMILES: CC(C)(C)C[C@]1(c2ccc(-c3cnn(C(F)F)c3)cc2)NC(=N)N([C@H](COC(=O)Nc2ccccc2)c2ccc(Cl)c(-c3ncn[nH]3)c2)C1=O] | LCMS-ESI+: calc'd for C$_{35}$H$_{34}$ClF$_2$N$_9$O$_3$: 702.2 (M + H+); Found: 702.6 (M + H+). | $^1$H NMR (400 MHz, CD$_3$CN) δ 8.24 (s, 1H), 8.21 (s, 1H), 8.00 (s, 1H), 7.83 (d, J = 2.4 Hz, 2H), 7.57-6.97 (m, 13H), 5.53 (dd, J = 9.5, 4.5 Hz, 1H), 5.13 (dd, J = 11.6, 9.6 Hz, 1H), 4.72 (dd, J = 11.6, 4.5 Hz, 1H), 2.33-2.13 (m, 2H), 0.89 (s, 9H). |
| Compd 108 | 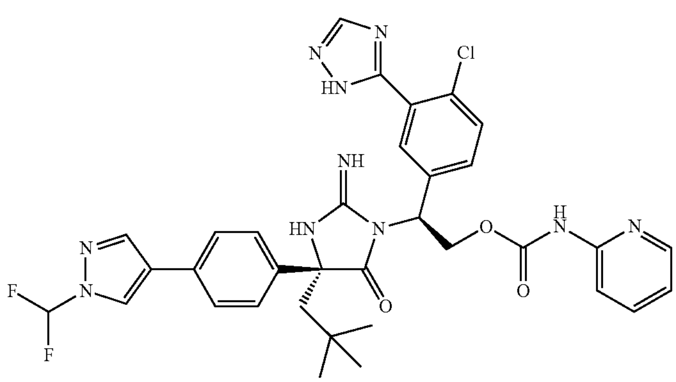 | LCMS-ESI+: calc'd for C$_{34}$H$_{33}$ClF$_2$N$_{10}$O$_3$: 703.2 (M + H+); Found: 703.4 (M + H+). | $^1$H NMR (400 MHz, CD$_3$CN) δ 8.25 (s, 1H), 8.21 (s, 1H), 8.14 (d, J = 5.4 Hz, 1H), 8.00 (s, 1H), 7.96-7.80 (m, 3H), 7.58-7.08 (m, 10H), 5.63 (dd, J = 9.2, 4.5 Hz, 1H), 5.20 (dd, J = 11.6, 9.3 Hz, 1H), 4.79 (dd, J = 11.7, 4.6 Hz, 1H), 2.35-2.14 (m, 2H), 0.90 (s, 9H). |

| Compound # | Structures | Mass data | NMR data |
|---|---|---|---|
| Compd 109 | 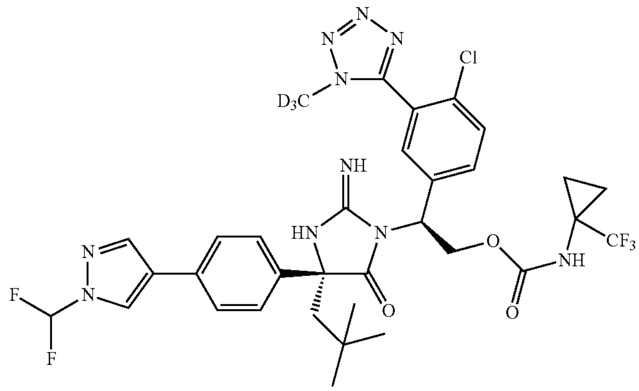 [SMILES: [2H]C([2H])([2H])n1nnnc1-c1cc([C@@H](COC(=O)NC2(C(F)(F)F)CC2)N2C(=N)N[C@](CC(C)(C)C)(c3ccc(-c4cnn(C(F)F)c4)cc3)C2=O)ccc1Cl] | LCMS-ESI+: calc'd for C$_{33}$H$_{31}$ClD$_3$F$_5$N$_{10}$O$_3$: 752.2 (M + H+); Found: 752.6 (M + H+). | 1H NMR (400 MHz, Methanol-d$_4$) δ 8.46 (s, 1H), 8.18 (s, 1H), 8.09 (s, 1H), 7.64-7.48 (m, 4H), 7.45-7.36 (m, 3H), 5.65 (dd, J = 9.8, 4.9 Hz, 1H), 5.10 (t, J = 10.6 Hz, 1H), 4.72 (dd, J = 11.4, 5.0 Hz, 1H), 2.47 (d, J = 15.1 Hz, 1H), 2.14 (d, J = 15.1 Hz, 1H), 1.27 (s, 2H), 1.08 (s, 2H), 1.00 (s, 9H). |
| Compd 110 | 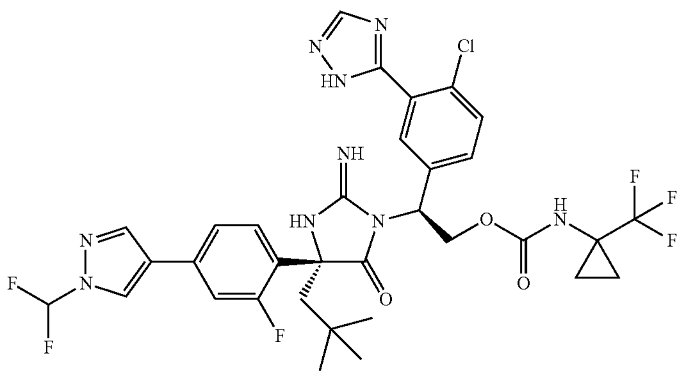 [SMILES: CC(C)(C)C[C@]1(c2ccc(-c3cnn(C(F)F)c3)cc2F)NC(=N)N([C@H](COC(=O)NC2(C(F)(F)F)CC2)c2ccc(Cl)c(-c3ncn[nH]3)c2)C1=O] | LCMS-ESI+: calc'd for C$_{33}$H$_{32}$ClF$_6$N$_9$O$_3$: 752.2 (M + H+); Found: 752.6 (M + H+). | $^1$H NMR (400 MHz, CD$_3$CN) δ 8.32 (d, J = 0.7 Hz, 1H), 8.26 (s, 1H), 8.03 (s, 1H), 7.89 (d, J = 2.4 Hz, 1H), 7.60-7.18 (m, 8H), 6.62 (s, 1H), 5.45 (dd, J = 9.3, 4.5 Hz, 1H), 5.04-4.94 (m, 1H), 4.69 (dd, J = 11.6, 4.4 Hz, 1H), 2.41-2.21 (m, 2H), 1.31-1.20 (m, 2H), 1.11-1.03 (m, 2H), 0.96 (s, 9H). |
| Compd 111 | 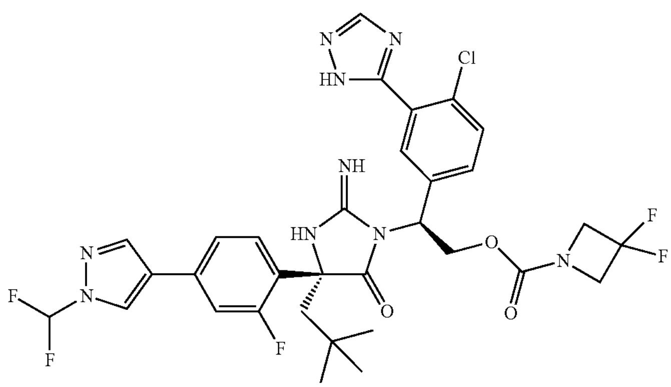 [SMILES: CC(C)(C)C[C@]1(c2ccc(-c3cnn(C(F)F)c3)cc2F)NC(=N)N([C@H](COC(=O)N2CC(F)(F)C2)c2ccc(Cl)c(-c3ncn[nH]3)c2)C1=O] | LCMS-ESI+: calc'd for C$_{32}$H$_{31}$ClF$_5$N$_9$O$_3$: 720.2 (M + H+); Found: 720.6 (M + H+). | $^1$H NMR (400 MHz, Methanol-d$_4$) δ 8.51 (s, 1H), 8.42 (s, 1H), 8.11 (s, 1H), 7.74 (d, J = 2.3 Hz, 1H), 7.62 (d, J = 8.4 Hz, 1H), 7.54 (dd, J = 8.5, 2.3 Hz, 1H), 7.51 (t, J = 59.6 Hz, 1H), 7.45 (d, J = 13.8 Hz, 1H), 7.36 (d, J = 8.5 Hz, 1H), 7.27 (t, J = 8.4 Hz, 1H), 5.66 (dd, J = 9.8, 4.4 Hz, 1H), 5.36-5.04 (m, 1H), 4.34 (t, J = 12.4 Hz, 4H), 2.39 (d, J = 15.0 Hz, 1H), 2.33 (d, J = 15.0 Hz, 1H), 1.04 (s, 9H). |
| Compd 112 | 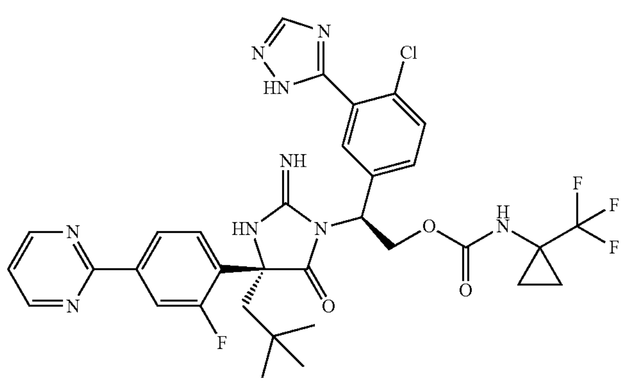 [SMILES: CC(C)(C)C[C@]1(c2ccc(-c3ncccn3)cc2F)NC(=N)N([C@H](COC(=O)NC2(C(F)(F)F)CC2)c2ccc(Cl)c(-c3ncn[nH]3)c2)C1=O] | LCMS-ESI+: calc'd for C$_{33}$H$_{32}$ClF$_4$N$_9$O$_3$: 714.2 (M + H+); Found: 714.6 (M + H+). | $^1$H NMR (400 MHz, CD$_3$CN) δ 8.85 (dd, J = 4.9, 1.0 Hz, 2H), 8.25 (d, J = 1.0 Hz, 1H), 8.15-7.99 (m, 3H), 7.85 (d, J = 2.3 Hz, 1H), 7.59-7.31 (m, 4H), 6.66 (s, 1H), 5.45 (dd, J = 9.6, 4.4 Hz, 1H), 5.09-4.85 (m, 1H), 4.70 (dd, J = 11.5, 4.4 Hz, 1H), 2.42-2.25 (m, 2H), 1.30-1.23 (m, 2H), 1.10-1.03 (m, 2H), 0.97 (s, 9H). |

-continued

| Compound # | Structures | Mass data | NMR data |
|---|---|---|---|
| Compd 113 | 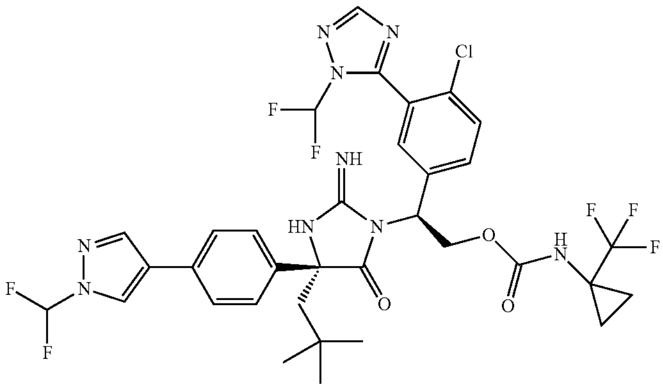 [SMILES: CC(C)(C)C[C@]1(c2ccc(-c3cnn(C(F)F)c3)cc2)NC(=N)N([C@H](COC(=O)NC2(C(F)(F)F)CC2)c2ccc(Cl)c(-c3ncnn3C(F)F)c2)C1=O] | LCMS-ESI+: calc'd for $C_{34}H_{33}ClF_7N_9O_3$: 784.2 (M + H+); Found: 784.1 (M + H+). | $^1$H NMR (400 MHz, Methanol-$d_4$) δ 8.47 (s, 1H), 8.20 (s, 1H), 8.11 (s, 1H), 8.02 (s, 1H), 7.75-7.01 (m, 9H), 5.67 (dd, J = 9.8, 4.9 Hz, 1H), 5.10 (t, J = 10.6 Hz, 1H), 4.69 (dd, J = 11.5, 5.0 Hz, 1H), 2.47 (d, J = 15.2 Hz, 1H), 2.15 (d, J = 15.1 Hz, 1H), 1.37-1.16 (m, 2H), 1.16-1.03 (m, 2H), 1.00 (s, 9H). |
| Compd 114 | 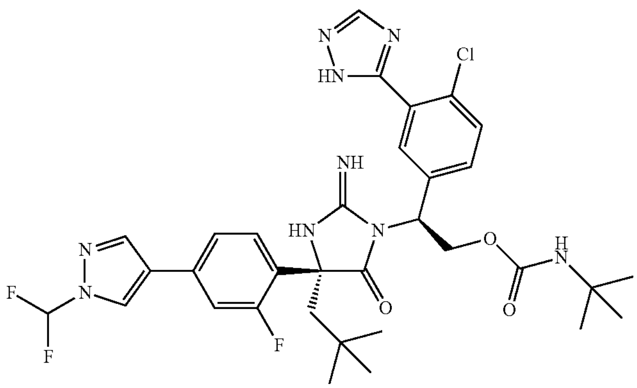 [SMILES: CC(C)(C)C[C@]1(c2ccc(-c3cnn(C(F)F)c3)cc2F)NC(=N)N([C@H](COC(=O)NC(C)(C)C)c2ccc(Cl)c(-c3ncn[nH]3)c2)C1=O] | LCMS-ESI+: calc'd for $C_{33}H_{37}ClF_3N_9O_3$: 700.3 (M + H+); Found: 700.5 (M + H+). | $^1$H NMR (400 MHz, Methanol-$d_4$) δ 8.51 (s, 1H), 8.40 (s, 1H), 8.11 (s, 1H), 7.74 (s, 1H), 7.60 (d, J = 8.4 Hz, 1H), 7.54 (d, J = 8.7 Hz, 1H), 7.51 (t, J = 59.6 Hz, 1H), 7.43 (d, J = 13.9 Hz, 1H), 7.40-7.31 (m, 2H), 5.65 (dd, J = 9.3, 5.1 Hz, 1H), 5.09 (t, J = 10.4 Hz, 1H), 4.67 (dd, J = 11.6, 5.1 Hz, 1H), 2.37 (s, 2H), 1.29 (s, 9H), 1.04 (s, 9H). |
| Compd 115 | 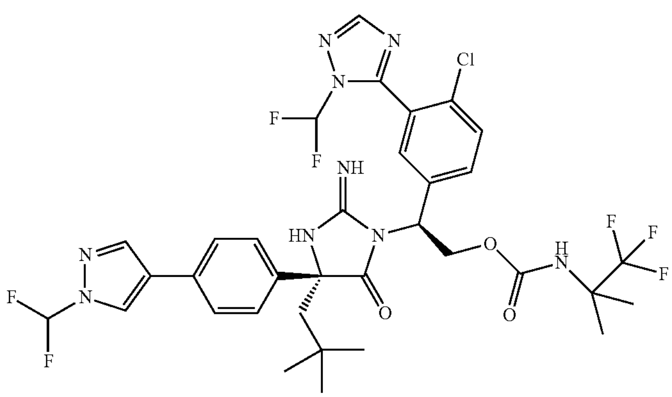 [SMILES: CC(C)(C)C[C@]1(c2ccc(-c3cnn(C(F)F)c3)cc2)NC(=N)N([C@H](COC(=O)NC(C)(C)C(F)(F)F)c2ccc(Cl)c(-c3ncnn3C(F)F)c2)C1=O] | LCMS-ESI+: calc'd for $C_{34}H_{35}ClF_7N_9O_3$: 786.2 (M + H+); Found: 786.0 (M + H+). | $^1$H NMR (400 MHz, Methanol-$d_4$) δ 8.43 (s, 1H), 8.05 (d, J = 31.0 Hz, 2H), 7.70-7.07 (m, 9H), 5.58 (s, 1H), 5.15-4.98 (m, 1H), 4.64 (dd, J = 11.4, 5.5 Hz, 1H), 2.39 (d, J = 14.9 Hz, 1H), 2.08 (d, J = 15.4 Hz, 1H), 1.49 (s, 6H), 0.98 (s, 9H). |
| Compd 116 | 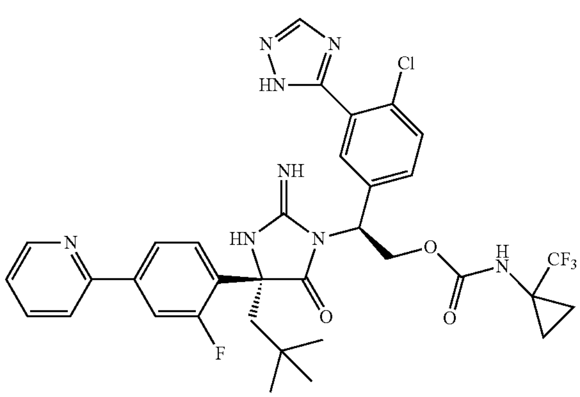 [SMILES: CC(C)(C)C[C@]1(c2ccc(-c3ccccn3)cc2F)NC(=N)N([C@H](COC(=O)NC2(C(F)(F)F)CC2)c2ccc(Cl)c(-c3ncn[nH]3)c2)C1=O] | LCMS-ESI+: calc'd for $C_{34}H_{33}ClF_4N_8O_3$: 713.2 (M + H+); Found: 713.4 (M + H+). | $^1$H NMR (400 MHz, Methanol-$d_4$) δ 8.67 (d, J = 5.0 Hz, 1H), 8.39 (s, 1H), 8.20 (s, 1H), 7.99 (t, J = 7.7 Hz, 1H), 7.91 (d, J = 8.0 Hz, 1H), 7.80-7.68 (m, 3H), 7.62-7.52 (m, 2H), 7.52-7.41 (m, 2H), 5.69 (dd, J = 9.8, 4.8 Hz, 1H), 5.18 (t, J = 10.6 Hz, 1H), 4.75 (dd, J = 11.5, 4.9 Hz, 1H), 2.42 (d, J = 16 Hz, 1H), 2.89 (d, J = 12 Hz, 1H), 1.27 (d, J = 6.1 Hz, 2H), 1.09 (s, 2H), 1.05 (s, 9H). |

-continued

| Compound # | Structures | Mass data | NMR data |
|---|---|---|---|
| Compd 117 | 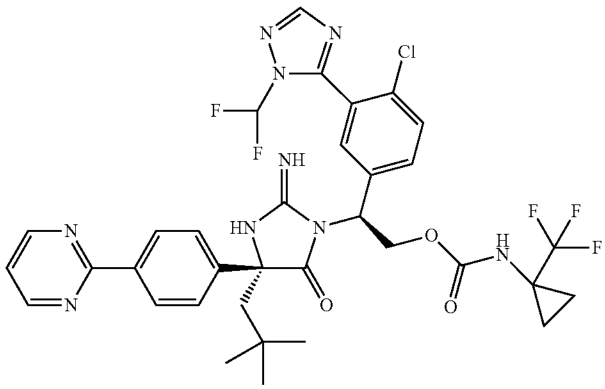 [SMILES: CC(C)(C)C[C@]1(c2ccc(-c3ncccn3)cc2)NC(=N)N([C@H](COC(=O)NC2(C(F)(F)F)CC2)c2ccc(Cl)c(-c3ncnn3C(F)F)c2)C1=O] | LCMS-ESI+: calc'd for C$_{34}$H$_{33}$ClF$_5$N$_9$O$_3$: 746.2 (M + H+); Found: 746.0 (M + H+). | $^1$H NMR (400 MHz, Methanol-d$_4$) δ 9.00-8.80 (m, 2H), 8.37 (d, J = 8.5 Hz, 2H), 8.16 (s, 1H), 7.99 (s, 1H), 7.55 (dd, J = 5.9, 2.8 Hz, 4H), 7.47-7.03 (m, 3H), 5.68 (dd, J = 9.7, 4.9 Hz, 1H), 5.09 (t, J = 10.6 Hz, 1H), 4.69 (dd, J = 11.5, 4.9 Hz, 1H), 2.52 (d, J = 15.2 Hz, 1H), 2.19 (d, J = 15.1 Hz, 1H), 1.27 (s, 2H), 1.08 (s, 3H), 1.01 (s, 9H). |
| Compd 118 | 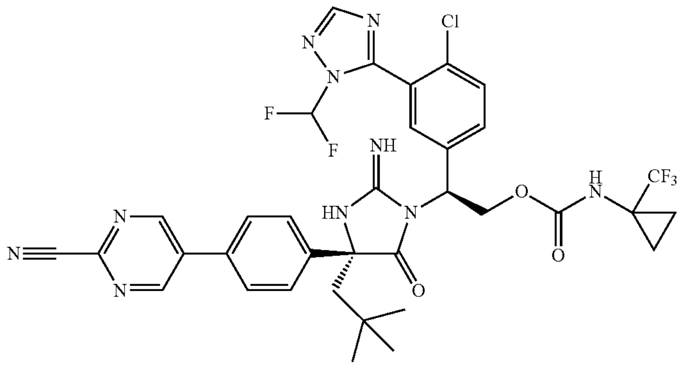 [SMILES: CC(C)(C)C[C@]1(c2ccc(-c3cnc(C#N)nc3)cc2)NC(=N)N([C@H](COC(=O)NC2(C(F)(F)F)CC2)c2ccc(Cl)c(-c3ncnn3C(F)F)c2)C1=O] | LCMS-ESI+: calc'd for C$_{35}$H$_{32}$ClF$_5$N$_{10}$O$_3$: 771.2 (M + H+); Found: 771.2 (M + H+). | $^1$H NMR (400 MHz, Methanol-d$_4$) δ 9.21 (s, 2H), 8.10 (s, 1H), 7.85-7.02 (m, 9H), 5.67 (dd, J = 9.5, 4.8 Hz, 1H), 5.11 (t, J = 10.7 Hz, 1H), 4.70 (dd, J = 11.5, 5.1 Hz, 1H), 2.50 (d, J = 15.1 Hz, 1H), 2.18 (d, J = 15.2 Hz, 1H), 1.18 (d, J = 75.4 Hz, 4H), 1.01 (s, 9H). |
| Compd 119 | 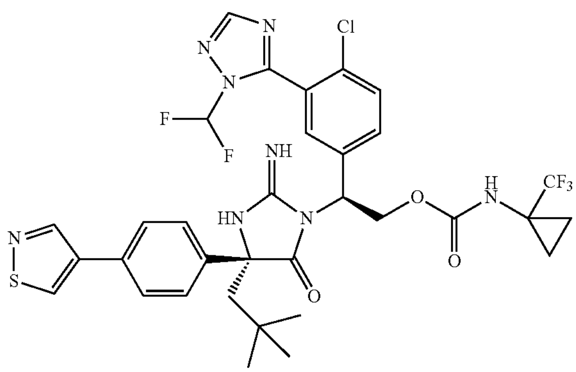 [SMILES: CC(C)(C)C[C@]1(c2ccc(-c3cnsc3)cc2)NC(=N)N([C@H](COC(=O)NC2(C(F)(F)F)CC2)c2ccc(Cl)c(-c3ncnn3C(F)F)c2)C1=O] | LCMS-ESI+: calc'd for C$_{33}$H$_{32}$ClF$_5$N$_8$O$_3$S: 751.2 (M + H+); Found: 751.3 (M + H+). | $^1$H NMR (400 MHz, Methanol-d$_4$) δ 9.14 (s, 1H), 8.89 (s, 1H), 7.98 (s, 1H), 7.76-7.02 (m, 8H), 5.73-5.58 (m, 1H), 5.10 (t, J = 10.5 Hz, 1H), 4.79-4.61 (m, 6H), 2.50 (d, J = 15.2 Hz, 1H), 2.17 (d, J = 15.2 Hz, 1H), 1.18 (d, J = 75.3 Hz, 4H), 1.01 (s, 9H). |
| Compd 120 | 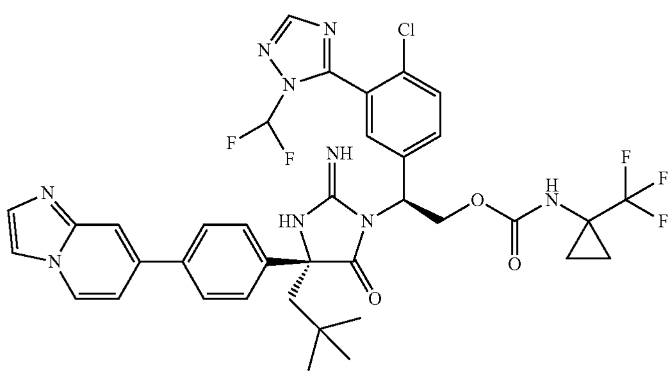 [SMILES: CC(C)(C)C[C@]1(c2ccc(-c3ccn4ccnc4c3)cc2)NC(=N)N([C@H](COC(=O)NC2(C(F)(F)F)CC2)c2ccc(Cl)c(-c3ncnn3C(F)F)c2)C1=O] | LCMS-ESI+: calc'd for C$_{37}$H$_{35}$ClF$_5$N$_9$O$_3$: 784.2 (M + H+); Found: 784.3 (M + H+). | $^1$H NMR (400 MHz, Methanol-d$_4$) δ 8.87 (d, J = 7.1 Hz, 1H), 8.28-8.01 (m, 5H), 7.91-7.77 (m, 4H), 7.69-7.11 (m, 6H), 5.69 (dd, J = 10.0, 4.8 Hz, 1H), 5.13 (t, J = 10.6 Hz, 1H), 4.69 (dd, J = 11.4, 4.8 Hz, 1H), 2.47 (d, J = 15.2 Hz, 1H), 2.19 (d, J = 15.1 Hz, 1H), 1.18 (d, J = 74.9 Hz, 4H), 1.00 (s, 9H). |

-continued

| Compound # | Structures | Mass data | NMR data |
|---|---|---|---|
| Compd 121 | 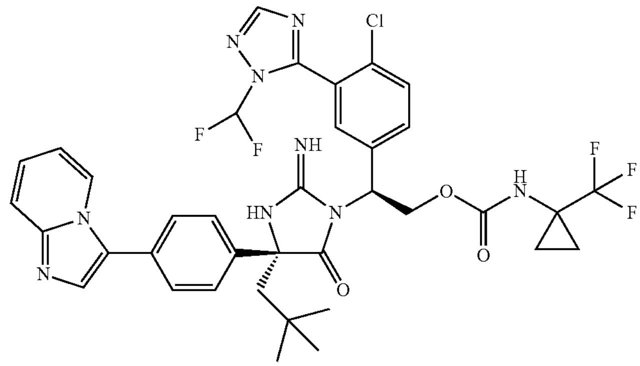 [SMILES: CC(C)(C)C[C@]1(c2ccc(-c3cnc4ccccn34)cc2)NC(=N)N([C@H](COC(=O)NC2(C(F)(F)F)CC2)c2ccc(Cl)c(-c3ncnn3C(F)F)c2)C1=O] | LCMS-ESI+: calc'd for C₃₇H₃₅ClF₅N₉O₃: 784.2 (M + H+); Found: 784.3 (M + H+). | ¹H NMR (400 MHz, Methanol-d₄) δ 8.69 (d, J = 7.0 Hz, 1H), 8.31-7.94 (m, 4H), 7.81-7.13 (m, 8H), 5.67 (dd, J = 9.6, 4.7 Hz, 1H), 5.22-4.99 (m, 1H), 4.71 (dd, J = 11.3, 4.9 Hz, 1H), 2.50 (d, J = 15.2 Hz, 1H), 2.22 (d, J = 15.1 Hz, 1H), 1.19 (d, J = 74.6 Hz, 4H), 1.02 (s, 8H). |
| Compd 122 | 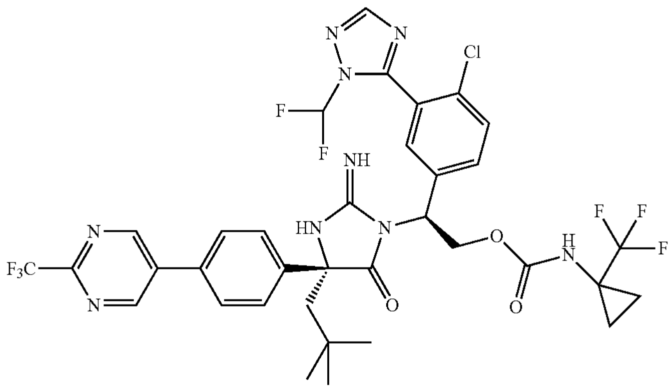 [SMILES: CC(C)(C)C[C@]1(c2ccc(-c3cnc(C(F)(F)F)nc3)cc2)NC(=N)N([C@H](COC(=O)NC2(C(F)(F)F)CC2)c2ccc(Cl)c(-c3ncnn3C(F)F)c2)C1=O] | LCMS-ESI+: calc'd for C₃₅H₃₂ClF₈N₉O₃: 814.2 (M + H+); Found: 814.3 (M + H+). | ¹H NMR (400 MHz, Methanol-d₄) δ 9.24 (s, 2H), 8.10 (s, 1H), 7.85-7.07 (m, 9H), 5.67 (dd, J = 9.7, 4.9 Hz, 1H), 5.11 (t, J = 10.6 Hz, 1H), 4.70 (dd, J = 11.6, 4.9 Hz, 1H), 2.49 (d, J = 15.1 Hz, 1H), 2.19 (d, J = 15.2 Hz, 1H), 1.37-1.03 (m, 5H), 1.00 (s, 9H). |
| Compd 123 | 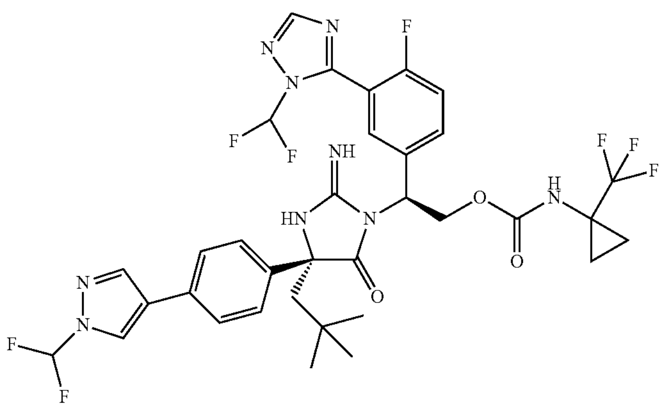 [SMILES: CC(C)(C)C[C@]1(c2ccc(-c3cnn(C(F)F)c3)cc2)NC(=N)N([C@H](COC(=O)NC2(C(F)(F)F)CC2)c2ccc(F)c(-c3ncnn3C(F)F)c2)C1=O] | LCMS-ESI+: calc'd for C₃₄H₃₃F₈N₉O₃: 768.3 (M + H+); Found: 768.2 (M + H+). | ¹H NMR (400 MHz, Methanol-d₄) δ 8.43 (s, 1H), 8.12 (d, J = 35.6 Hz, 3H), 7.74-7.19 (m, 9H), 5.65 (dd, J = 9.6, 4.9 Hz, 1H), 5.12 (t, J = 10.6 Hz, 1H), 4.69 (dd, J = 11.5, 4.9 Hz, 1H), 2.45 (d, J = 15.2 Hz, 1H), 2.15 (d, J = 15.1 Hz, 1H), 1.39-1.20 (m, 2H), 1.08 (s, 2H), 0.99 (s, 9H). 9 (s, 9H). |
| Compd 124 | 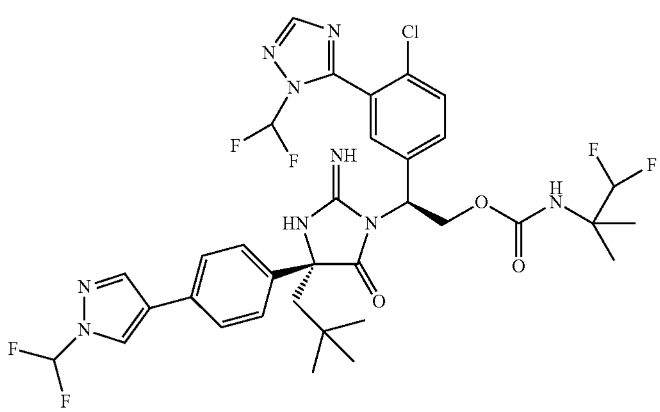 | LCMS-ESI+: calc'd for C₃₄H₃₆ClF₇N₉O₃: 752.3 (M + H+); Found: 752.3 (M + H+). | ¹H NMR (400 MHz, Methanol-d₄) δ 8.43 (s, 1H), 8.08 (s, 2H), 7.70-7.20 (m, 9H), 6.13 (t, J = 57.4 Hz, 1H), 5.65 (dd, J = 9.4, 5.2 Hz, 1H), 5.12-4.97 (m, 1H), 4.66 (dd, J = 11.5, 5.2 Hz, 1H), 2.44 (d, J = 15.2 Hz, 1H), 2.18 (d, J = 15.1 Hz, 1H), 1.32 (s, 6H), 1.00 (s, 9H). |

-continued

| Compound # | Structures | Mass data | NMR data |
|---|---|---|---|
| Compd 125 | 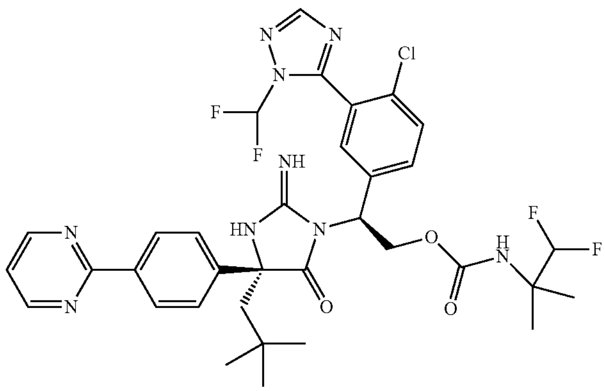 [SMILES: CC(C)(C)C[C@]1(c2ccc(-c3ncccn3)cc2)NC(=N)N([C@H](COC(=O)NC(C)(C)C(F)F)c2ccc(Cl)c(-c3ncnn3C(F)F)c2)C1=O] | LCMS-ESI+: calc'd for C$_{34}$H$_{36}$ClF$_4$N$_9$O$_3$: 730.3 (M + H+); Found: 730.0 (M + H+). | $^1$H NMR (400 MHz, Methanol-d$_4$) δ 8.88 (dd, J = 4.9, 0.5 Hz, 2H), 8.42-8.33 (m, 2H), 8.01 (s, 1H), 7.60-7.57 (m, 1H), 7.56 (d, J = 1.9 Hz, 3H), 7.44-7.16 (t, J = 57 Hz, 1H), 7.41 (td, J = 4.9, 0.8 Hz, 1H), 7.13 (s, 1H), 6.14 (t, J = 57.3 Hz, 1H), 5.68 (dd, J = 9.4, 5.1 Hz, 1H), 5.12-4.97 (m, 1H), 4.66 (dd, J = 11.6, 5.2 Hz, 1H), 2.50 (d, J = 15.0 Hz, 1H), 2.23 (d, J = 15.1 Hz, 1H), 1.37-1.27 (m, 6H), 1.01 (d, J = 0.9 Hz, 9H). |
| Compd 126 | 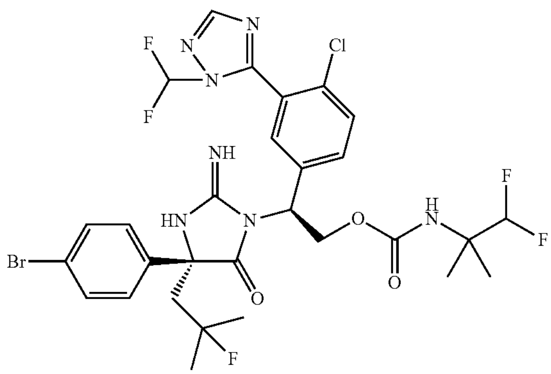 [SMILES: CC(C)(F)C[C@]1(c2ccc(Br)cc2)NC(=N)N([C@H](COC(=O)NC(C)(C)C(F)F)c2ccc(Cl)c(-c3ncnn3C(F)F)c2)C1=O] | LCMS-ESI+: calc'd for C$_{29}$H$_{30}$BrClF$_5$N$_7$O$_3$: 734.1 (M + H)/ 736.1 (M + H + 2); Found: 734.1 (M + H)/ 735.9 (M + H + 2). | $^1$H NMR (400 MHz, Methanol-d$_4$) δ 8.27 (d, J = 0.5 Hz, 1H), 7.64-7.60 (m, 1H), 7.60-7.56 (m, 1H), 7.54 (d, J = 2.2 Hz, 1H), 7.52 (d, J = 2.1 Hz, 1H), 7.41-7.36 (m, 2H), 7.54-7.25 (t, J = 57 Hz, 1H), 7.30 (d, J = 2.1 Hz, 1H), 6.09 (t, J = 57.3 Hz, 1H), 5.63 (dd, J = 8.8, 5.4 Hz, 1H), 5.01-4.90 (m, 1H), 4.68 (dd, J = 11.6, 5.5 Hz, 1H), 2.86 (dd, J = 15.3, 8.8 Hz, 1H), 2.51 (dd, J = 26.2, 15.3 Hz, 1H), 1.43 (d, J = 22.2 Hz, 3H), 1.32 (d, J = 21.9 Hz, 3H), 1.28 (s, 6H). |
| Compd 127 | 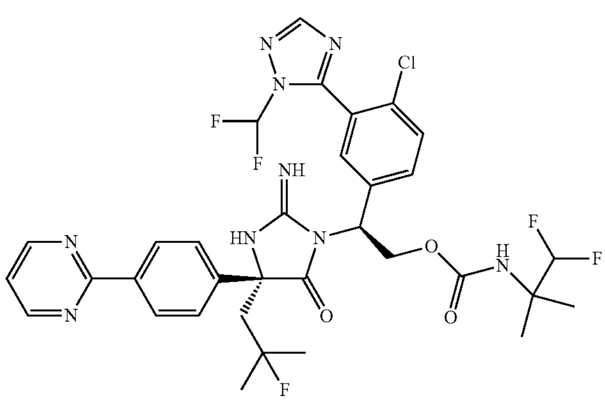 [SMILES: CC(C)(F)C[C@]1(c2ccc(-c3ncccn3)cc2)NC(=N)N([C@H](COC(=O)NC(C)(C)C(F)F)c2ccc(Cl)c(-c3ncnn3C(F)F)c2)C1=O] | LCMS-ESI+: calc'd for C$_{33}$H$_{33}$ClF$_5$N$_9$O$_3$: 734.2 (M + H+); Found: 734.0 (M + H+). | $^1$H NMR (400 MHz, Methanol-d$_4$) δ 8.88 (d, J = 4.9 Hz, 2H), 8.47-8.38 (m, 2H), 8.09 (s, 1H), 7.62 (d, J = 2.0 Hz, 1H), 7.60 (q, J = 1.0, 0.6 Hz, 3H), 7.48-7.19 (t, J = 57 Hz, 1 H), 7.40 (t, J = 4.9 Hz, 1H), 7.27 (s, 1H), 6.10 (t, J = 57.3 Hz, 1H), 5.68 (dd, J = 8.9, 5.3 Hz, 1H), 5.05-4.94 (m, 1H), 4.70 (dd, J = 11.6, 5.3 Hz, 1H), 2.97 (dd, J = 15.4, 8.9 Hz, 1H), 2.63 (dd, J = 26.2, 15.4 Hz, 1H), 1.47 (d, J = 22.2 Hz, 3H), 1.35 (d, J = 21.7 Hz, 3H), 1.29 (s, 6H). |

-continued

| Compound # | Structures | Mass data | NMR data |
|---|---|---|---|
| Compd 128 | 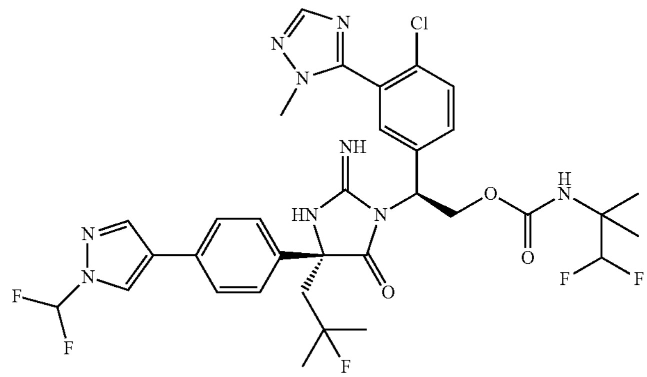 [SMILES: Cn1ncnc1-c1cc([C@@H](COC(=O)NC(C)(C)C(F)F)N2C(=N)N[C@](CC(C)(C)F)(c3ccc(-c4cnn(C(F)F)c4)cc3)C2=O)ccc1Cl] | LCMS-ESI+: calc'd for C$_{33}$H$_{35}$ClF$_5$N$_9$O$_3$: 736.2 (M + H+); Found: 736.0 (M + H+). | $^1$H NMR (400 MHz, Methanol-d$_4$) δ 8.48 (d, J = 7.4 Hz, 1H), 8.11 (d, J = 7.3 Hz, 1H), 7.85 (s, 1H), 7.74-6.96 (m, 8H), 5.66 (dd, J = 9.3, 5.0 Hz, 1H), 5.16-4.96 (m, 1H), 4.77-4.62 (m, 0H), 3.49 (s, 3H), 2.74 (d, J = 15.4 Hz, 1H), 2.49 (d, J = 15.5 Hz, 1H), 1.33 (s, 6H), 1.18 (d, J = 9.0 Hz, 6H). |
| Compd 129 | 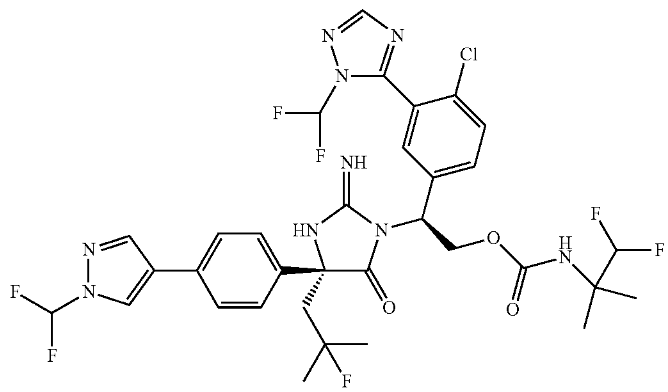 [SMILES: CC(C)(F)C[C@]1(c2ccc(-c3cnn(C(F)F)c3)cc2)NC(=N)N([C@H](COC(=O)NC(C)(C)C(F)F)c2ccc(Cl)c(-c3ncnn3C(F)F)c2)C1=O] | LCMS-ESI+: calc'd for C$_{33}$H$_{33}$ClF$_7$N$_9$O$_3$: 772.2 (M + H); Found 772.0 (M + H). | $^1$H NMR (400 MHz, Methanol-d$_4$) δ 8.46 (s, 1H), 8.10 (s, 2H), 7.69-7.58 (m, 4H), 7.54-7.45 (m, 2H), 7.51-7.22 (t, J = 57.0 Hz, 1H), 7.28 (s, 1H), 6.09 (t, J = 57.3 Hz, 1H), 5.66 (dd, J = 8.9, 5.3 Hz, 1H), 5.08-4.91 (m, 1H), 4.69 (dd, J = 11.7, 5.3 Hz, 1H), 2.92 (dd, J = 15.4, 8.9 Hz, 1H), 2.58 (dd, J = 26.2, 15.4 Hz, 1H), 1.50-1.42 (d, J = 22.2 Hz, 3H), 1.37-1.32 (d, J = 21.7 Hz, 3H), 1.31-1.25 (S, 6H). |
| Compd 130 | 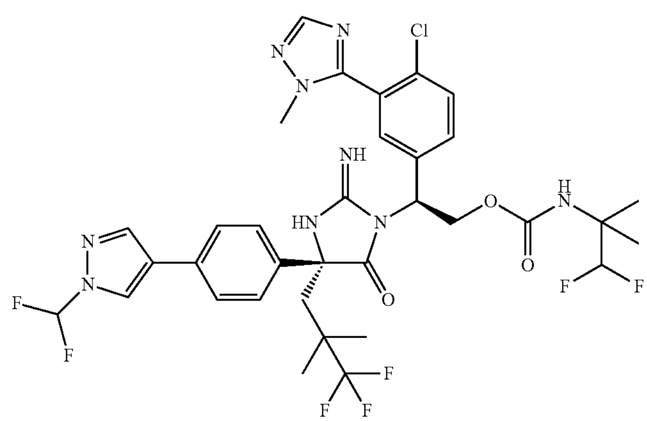 [SMILES: Cn1ncnc1-c1cc([C@@H](COC(=O)NC(C)(C)C(F)F)N2C(=N)N[C@](CC(C)(C)C(F)(F)F)(c3ccc(-c4cnn(C(F)F)c4)cc3)C2=O)ccc1Cl] | LCMS-ESI+: calc'd for C$_{34}$H$_{35}$ClF$_7$N$_9$O$_3$: 786.2 (M + H+); Found: 786.0 (M + H+). | $^1$H NMR (400 MHz, Methanol-d$_4$) δ 8.42 (s, 1H), 8.24 (s, 1H), 8.09 (s, 1H), 7.89 (d, J = 3.9 Hz, 1H), 7.57-7.47 (m, 5H), 7.35-7.18 (m, 5H), 5.48 (s, 1H), 4.69 (s, 1H), 4.29 (s, 2H), 3.51 (s, 2H), 2.76 (d, J = 15.2 Hz, 2H), 1.51-1.13 (m, 12H). |
| Compd 131 | 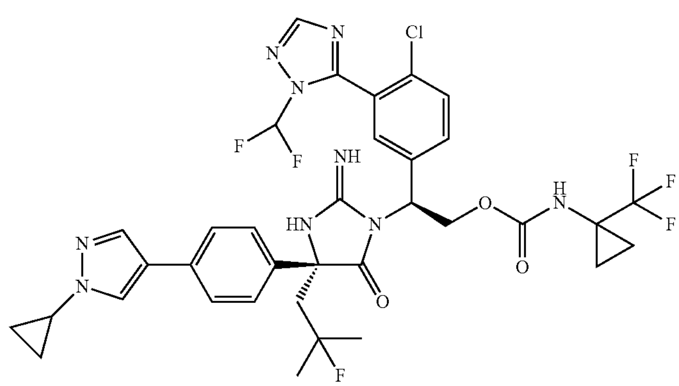 [SMILES: CC(C)(F)C[C@]1(c2ccc(-c3cnn(C4CC4)c3)cc2)NC(=N)N([C@H](COC(=O)NC2(C(F)(F)F)CC2)c2ccc(Cl)c(-c3ncnn3C(F)F)c2)C1=O] | LCMS-ESI+: calc'd for C$_{35}$H$_{34}$ClF$_6$N$_9$O$_3$: 778.2 (M + H+); Found: 778.1 (M + H+). | $^1$H NMR (400 MHz, Methanol-d$_4$) δ 8.15-7.95 (m, 2H), 7.82 (s, 1H), 7.63-7.13 (m, 8H), 5.65 (dd, J = 9.2, 5.1 Hz, 1H), 5.05 (t, J = 10.4 Hz, 1H), 4.69 (dd, J = 11.5, 5.2 Hz, 1H), 3.70 (tt, J = 7.4, 3.8 Hz, 1H), 2.90 (dd, J = 15.4, 8.7 Hz, 1H), 2.54 (dd, J = 25.8, 15.4 Hz, 1H), 1.43 (d, J = 22.2 Hz, 3H), 1.35 (d, J = 21.6 Hz, 3H), 1.28-0.99 (m, 7H). |

-continued

| Compound # | Structures | Mass data | NMR data |
|---|---|---|---|
| Compd 132 | 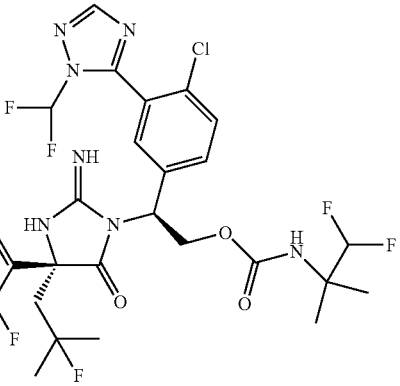 | LCMS-ESI+: calc'd for C$_{33}$H$_{32}$ClF$_6$N$_9$O$_3$: 752.2 (M + H+); Found: 752.1 (M + H+). | $^1$H NMR (400 MHz, Methanol-d$_4$) δ 8.88 (d, J = 4.9 Hz, 2H), 8.28 (dd, J = 8.4, 1.7 Hz, 1H), 8.23 (d, J = 0.4 Hz, 1H), 8.14 (dd, J = 14.0, 1.7 Hz, 1H), 7.78-7.67 (m, 2H), 7.62 (t, J = 8.3 Hz, 1H), 7.58-7.30 (t, J = 57 Hz, 1H), 7.56 (d, J = 2.2 Hz, 1H), 7.42 (t, J = 4.9 Hz, 1H), 6.10 (t, J = 57.3 Hz, 1H), 5.69 (dd, J = 8.2, 5.8 Hz, 1H), 4.97 (dd, J = 11.6, 8.3 Hz, 1H), 4.76 (dd, J = 11.5, 5.7 Hz, 1H), 2.96-2.79 (m, 2H), 1.53 (d, J = 2.0 Hz, 3H), 1.47 (d, J = 2.9 Hz, 3H), 1.30 (dd, J = 3.2, 1.6 Hz, 6H). |
| Compd 133 | 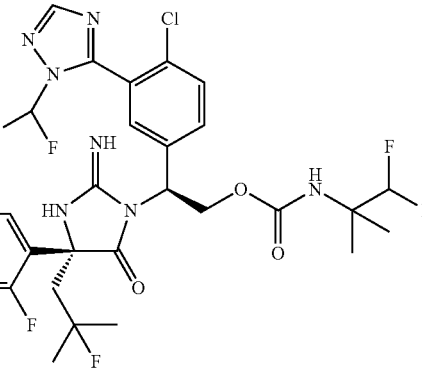 | LCMS-ESI+: calc'd for C$_{35}$H$_{36}$ClF$_6$N$_9$O$_3$: 780.2 (M + H+); Found: 780.1 (M + H+). | |
| Compd 134 | 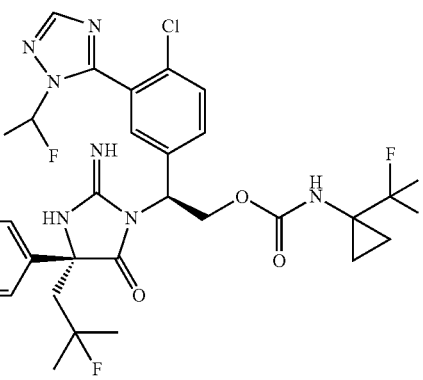 | LCMS-ESI+: calc'd for C$_{33}$H$_{30}$ClF$_8$N$_9$O$_3$: 788.2 (M + H+); Found: 788.0 (M + H+). | $^1$H NMR (400 MHz, Methanol-d$_4$) δ 8.45 (s, 1H), 8.23-7.96 (m, 2H), 7.72-7.10 (m, 9H), 5.66 (dd, J = 9.2, 5.2 Hz, 1H), 5.05 (t, J = 10.4 Hz, 1H), 4.69 (dd, J = 11.5, 5.1 Hz, 1H), 2.91 (dd, J = 15.4, 8.6 Hz, 1H), 2.55 (dd, J = 25.7, 15.4 Hz, 1H), 1.44 (d, J = 22.2 Hz, 3H), 1.35 (d, J = 21.6 Hz, 3H), 1.24 (q, J = 5.8, 5.2 Hz, 2H), 1.05 (s, 2H). |

-continued

| Compound # | Structures | Mass data | NMR data |
|---|---|---|---|
| Compd 135 | 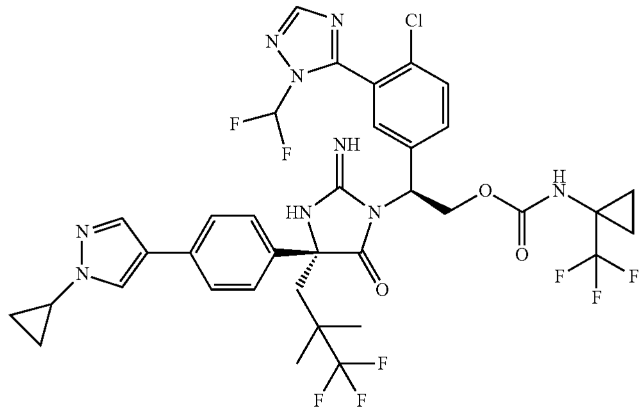 [SMILES: CC(C)(C[C@]1(c2ccc(-c3cnn(C4CC4)c3)cc2)NC(=N)N([C@H](COC(=O)NC2(C(F)(F)F)CC2)c2ccc(Cl)c(-c3ncnn3C(F)F)c2)C1=O)C(F)(F)F] | LCMS-ESI+: calc'd for C$_{36}$H$_{34}$ClF$_8$N$_9$O$_3$: 828.2 (M + H+); Found: 828.0 (M + H+). | $^1$H NMR (400 MHz, Methanol-d$_4$) δ 8.03 (d, J = 39.0 Hz, 2H), 7.83 (d, J = 0.9 Hz, 1H), 7.61-7.21 (m, 8H), 5.67 (dd, J = 9.6, 4.8 Hz, 1H), 5.23-4.99 (m, 1H), 4.69 (dd, J = 11.7, 4.9 Hz, 1H), 3.71 (tt, J = 7.4, 3.9 Hz, 1H), 2.74 (d, J = 15.5 Hz, 1H), 2.45 (d, J = 15.5 Hz, 1H), 1.24-0.99 (m, 10H). |
| Compd 136 | 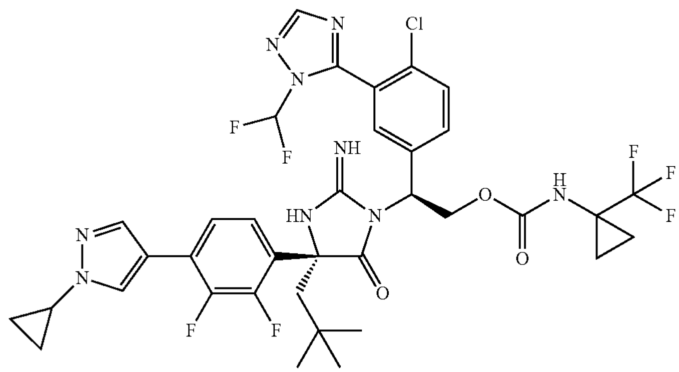 [SMILES: CC(C)(C)C[C@]1(c2ccc(-c3cnn(C4CC4)c3)c(F)c2F)NC(=N)N([C@H](COC(=O)NC2(C(F)(F)F)CC2)c2ccc(Cl)c(-c3ncnn3C(F)F)c2)C1=O] | LCMS-ESI+: calc'd for C$_{36}$H$_{35}$ClF$_7$N$_9$O$_3$: 810.2 (M + H+); Found: 810.0 (M + H+). | $^1$H NMR (400 MHz, Methanol-d$_4$) δ 8.20-8.05 (m, 3H), 7.88 (t, J = 1.1 Hz, 1H), 7.76-7.35 (m, 5H), 7.12 (t, J = 8.0 Hz, 1H), 5.69 (dd, J = 9.6, 4.8 Hz, 1H), 5.13 (dd, J = 11.5, 9.8 Hz, 1H), 4.73 (dd, J = 11.6, 4.8 Hz, 1H), 3.73 (tt, J = 7.4, 3.9 Hz, 1H), 2.38 (q, J = 15.2 Hz, 2H), 1.30-1.23 (m, 2H), 1.17-1.04 (m, 6H), 1.02 (s, 9H). |
| Compd 137 | 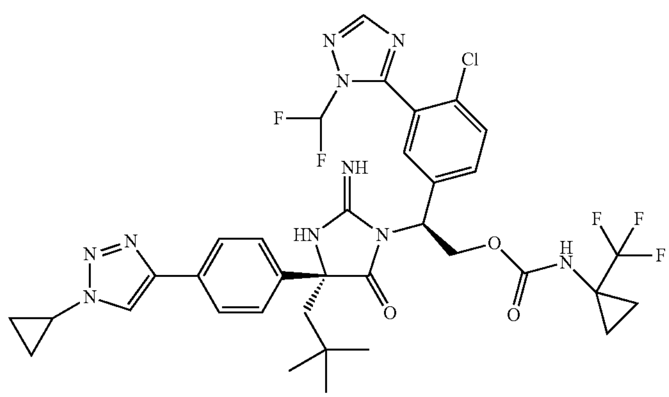 [SMILES: CC(C)(C)C[C@]1(c2ccc(-c3cn(C4CC4)nn3)cc2)NC(=N)N([C@H](COC(=O)NC2(C(F)(F)F)CC2)c2ccc(Cl)c(-c3ncnn3C(F)F)c2)C1=O] | LCMS-ESI+: calc'd for C$_{35}$H$_{36}$ClF$_5$N$_{10}$O$_3$: 775.2 (M + H+); Found: 775.0 (M + H+). | |
| Compd 138 | 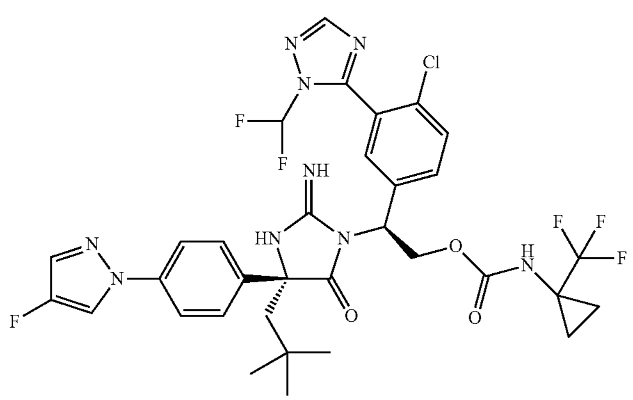 [SMILES: CC(C)(C)C[C@]1(c2ccc(-n3cc(F)cn3)cc2)NC(=N)N([C@H](COC(=O)NC2(C(F)(F)F)CC2)c2ccc(Cl)c(-c3ncnn3C(F)F)c2)C1=O] | LCMS-ESI+: calc'd for C$_{33}$H$_{32}$ClF$_5$N$_{10}$O$_3$: 752.2 (M + H+); Found: 752.0 (M + H+). | $^1$H NMR (400 MHz, Methanol-d$_4$) δ 8.33-8.27 (m, 1H), 7.98 (s, 1H), 7.71 (s, 1H), 7.70-7.68 (m, 2H), 7.62-7.50 (m, 4H), 7.48-7.19 (t, J = 57.2 Hz, 1H), 7.08 (s, 1H), 5.67 (dd, J = 9.7, 4.9 Hz, 1H), 5.13-5.03 (m, 1H), 4.69 (dd, J = 11.5, 5.0 Hz, 1H), 2.48 (d, J = 15.1 Hz, 1H), 2.15 (d, J = 15.2 Hz, 1H), 1.36-1.18 (m, 2H), 1.08 (s, 2H), 1.00 (s, 9H). |

-continued

| Compound # | Structures | Mass data | NMR data |
|---|---|---|---|
| Compd 139 | 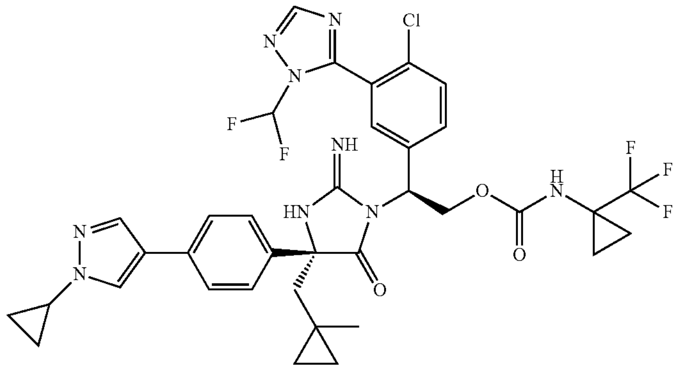 [SMILES: CC1(C[C@]2(c3ccc(-c4cnn(C5CC5)c4)cc3)NC(=N)N([C@H](COC(=O)NC3(C(F)(F)F)CC3)c3ccc(Cl)c(-c4ncnn4C(F)F)c3)C2=O)CC1] | LCMS-ESI+: calc'd for C₃₆H₃₅ClF₅N₉O₃: 776.2 (M + H+); Found: 772.1 (M + H+). | ¹H NMR (400 MHz, Methanol-d₄) δ 8.20-7.99 (m, 2H), 7.87-7.18 (m, 9H), 5.69 (dd, J = 9.4, 4.9 Hz, 1H), 5.22-4.99 (m, 1H), 4.73 (dd, J = 11.7, 4.9 Hz, 1H), 3.70 (tt, J = 7.3, 3.8 Hz, 1H), 2.30 (d, J = 3.7 Hz, 2H), 1.24 (d, J = 6.3 Hz, 1H), 1.17-1.03 (m, 4H), 1.01 (s, 3H), 0.42 (dd, J = 57.5, 20.9 Hz, 4H). |
| Compd 140 | 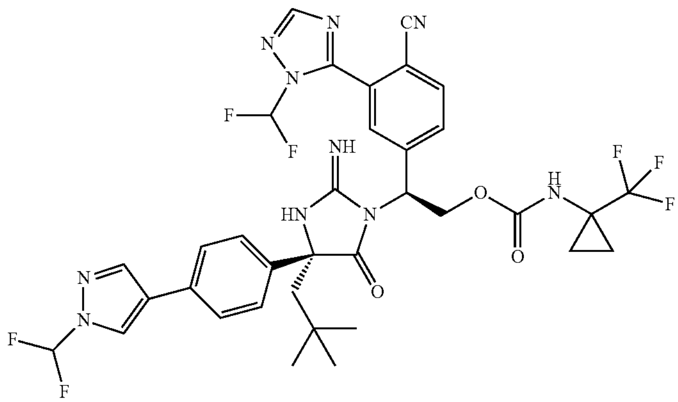 [SMILES: CC(C)(C)C[C@]1(c2ccc(-c3cnn(C(F)F)c3)cc2)NC(=N)N([C@H](COC(=O)NC2(C(F)(F)F)CC2)c2ccc(C#N)c(-c3ncnn3C(F)F)c2)C1=O] | LCMS-ESI+: calc'd for C₃₅H₃₃F₇N₁₀O₃: 775.3 (M + H+); Found: 775.0 (M + H+). | ¹H NMR (400 MHz, Methanol-d₄) δ 8.44 (s, 1H), 8.20-7.88 (m, 3H), 7.75-7.17 (m, 8H), 5.75 (dd, J = 9.4, 5.2 Hz, 1H), 5.08 (t, J = 10.5 Hz, 1H), 2.48 (d, J = 15.2 Hz, 1H), 2.16 (d, J = 15.2 Hz, 1H), 1.42-1.04 (m, 4H), 1.00 (s, 9H). |
| Compd 141 | 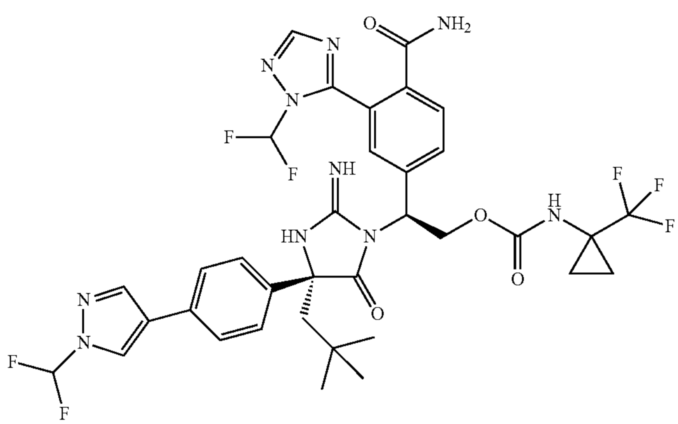 [SMILES: CC(C)(C)C[C@]1(c2ccc(-c3cnn(C(F)F)c3)cc2)NC(=N)N([C@H](COC(=O)NC2(C(F)(F)F)CC2)c2ccc(C(N)=O)c(-c3ncnn3C(F)F)c2)C1=O] | LCMS-ESI+: calc'd for C₃₅H₃₅F₇N₁₀O₄: 793.3 (M + H+); Found: 793.0 (M + H+). | 1H NMR (400 MHz, Methanol-d₄) δ 8.45 (s, 1H), 8.10 (s, 1H), 7.95-6.88 (m, 10H), 5.72 (dd, J = 9.8, 4.9 Hz, 1H), 5.11 (t, J = 10.7 Hz, 1H), 4.78-4.64 (m, 1H), 2.48 (d, J = 15.2 Hz, 1H), 2.16 (d, J = 15.2 Hz, 1H), 1.34-1.08 (m, 4H), 1.00 (s, 9H). |
| Compd 142 | 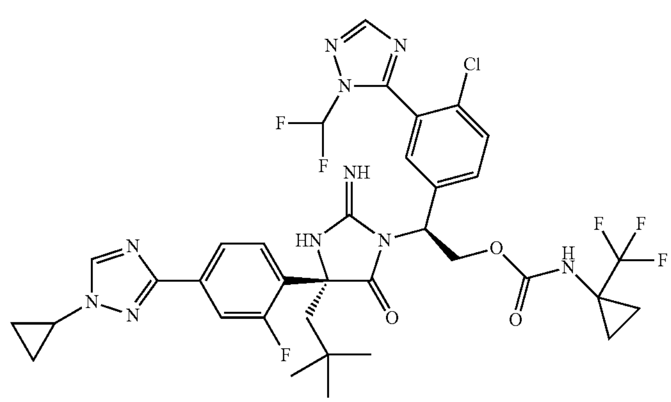 [SMILES: CC(C)(C)C[C@]1(c2ccc(-c3ncn(C4CC4)n3)cc2F)NC(=N)N([C@H](COC(=O)NC2(C(F)(F)F)CC2)c2ccc(Cl)c(-c3ncnn3C(F)F)c2)C1=O] | LCMS-ESI+: calc'd for C₃₅H₃₅ClF₆N₁₀O₃: 793.2 (M + H+); Found: 793.1 (M + H+). | ¹H NMR (400 MHz, Methanol-d₄) δ 8.56 (d, J = 0.6 Hz, 1H), 8.19 (s, 1H), 7.79 (dd, J = 8.3, 1.7 Hz, 1H), 7.74-7.65 (m, 3H), 7.57-7.28 (t, J = 57.2 Hz, 1H), 7.52-7.43 (m, 2H), 5.68 (dd, J = 9.6, 4.8 Hz, 1H), 5.20-5.09 (m, 1H), 4.73 (dd, J = 11.6, 4.9 Hz, 1H), 3.81 (tt, J = 7.3, 3.8 Hz, 1H), 2.48-2.30 (m, 2H), 1.31-1.25 (m, 2H), 1.25-1.18 (m, 2H), 1.18-1.11 (m, 2H), 1.08 (m, 2H), 1.03 (s, 9H). |

| Compound # | Structures | Mass data | NMR data |
|---|---|---|---|
| Compd 143 | 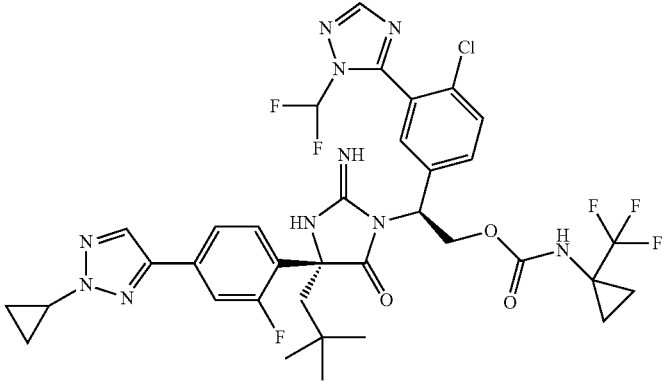 [SMILES: CC(C)(C)C[C@]1(c2ccc(-c3cnn(C4CC4)n3)cc2F)NC(=N)N([C@H](COC(=O)NC2(C(F)(F)F)CC2)c2ccc(Cl)c(-c3ncnn3C(F)F)c2)C1=O] | LCMS-ESI+: calc'd for $C_{35}H_{35}ClF_6N_{10}O_3$: 793.2 (M + H+); Found: 793.1 (M + H+). | $^1$H NMR (400 MHz, Methanol-$d_4$) δ 8.18 (s, 1H), 8.02 (s, 1H), 7.72 (dd, J = 8.5, 2.2 Hz, 1H), 7.67 (d, J = 8.5 Hz, 1H), 7.59-7.52 (m, 2H), 7.56-7.28 (t, J = 57 Hz, 1H), 7.48 (d, J = 2.1 Hz, 1H), 7.44-7.36 (m, 1H), 5.67 (dd, J = 9.5, 4.9 Hz, 1H), 5.14 (dd, J = 11.5, 9.5 Hz, 1H), 4.11 (tt, J = 7.5, 3.8 Hz, 1H), 2.43-2.28 (m, 2H), 1.37-1.31 (m, 2H), 1.27 (dt, J = 7.7, 3.8 Hz, 2H), 1.15 (td, J = 7.7, 5.4 Hz, 2H), 1.11-1.06 (m, 2H), 1.03 (s, 9H). |
| Compd 144 | 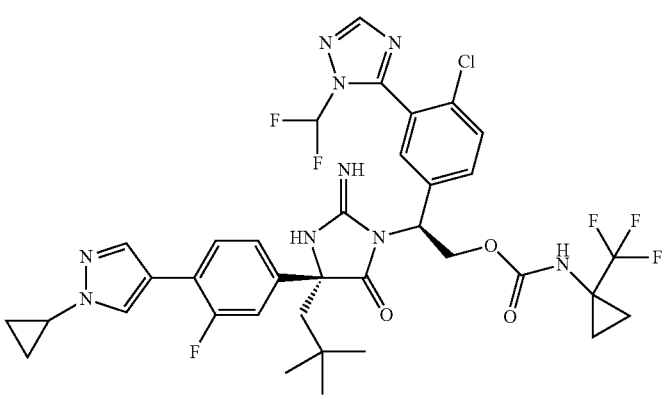 [SMILES: CC(C)(C)C[C@]1(c2ccc(-c3cnn(C4CC4)c3)c(F)c2)NC(=N)N([C@H](COC(=O)NC2(C(F)(F)F)CC2)c2ccc(Cl)c(-c3ncnn3C(F)F)c2)C1=O] | LCMS-ESI+: calc'd for $C_{36}H_{36}ClF_6N_9O_3$: 792.2 (M + H+); Found: 792.3 (M + H+). | $^1$H NMR (400 MHz, Methanol-$d_4$) δ 8.10 (d, J = 1.7 Hz, 1H), 8.02 (s, 1H), 7.88 (dd, J = 1.6, 0.8 Hz, 1H), 7.65-7.55 (m, 3H), 7.49-7.20 (t, J = 57 Hz, 1H), 7.27-7.20 (m, 2H), 7.15 (s, 1H), 5.67 (dd, J = 9.7, 4.9 Hz, 1H), 5.15-5.04 (m, 1H), 4.69 (dd, J = 11.6, 4.9 Hz, 1H), 3.73 (tt, J = 7.3, 3.9 Hz, 1H), 2.43 (d, J = 15.2 Hz, 1H), 2.14 (d, J = 15.1 Hz, 1H), 1.30-1.25 (m, 2H), 1.20-1.13 (m, 2H), 1.13-1.09 (m, 2H), 1.09-1.05 (m, 2H), 0.99 (s, 9H). |
| Compd 145 | 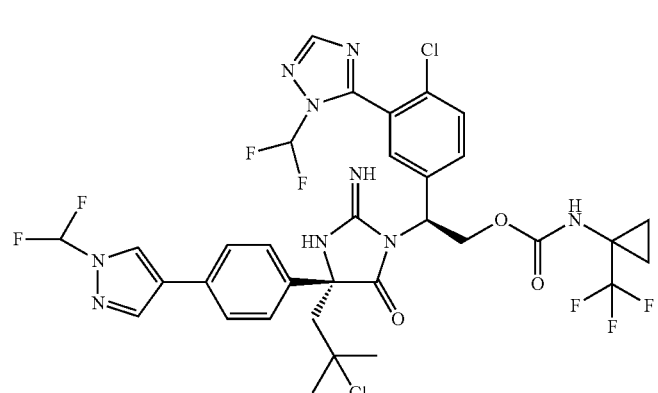 | LCMS-ESI+: calc'd for $C_{33}H_{30}Cl_2F_7N_9O_3$: 804.2 (M + H+); Found: 804.2 (M + H+). | 1H NMR (400 MHz, Methanol-$d_4$) δ 8.40 (s, 1H), 8.05 (m, 2H), 7.60-7.03 (m, 9H), 5.47 (s, 1H), 5.00 (d, J = 10.1 Hz, 1H), 4.76-4.61 (m, 1H), 3.13 (d, J = 7.5 Hz, 1H), 2.93 (d, J = 14.8 Hz, 1H), 1.61 (d, J = 6.3 Hz, 6H), 1.13 (d, J = 69.0 Hz, 4H). |

| Compound # | Structures | Mass data | NMR data |
|---|---|---|---|
| Compd 146 | 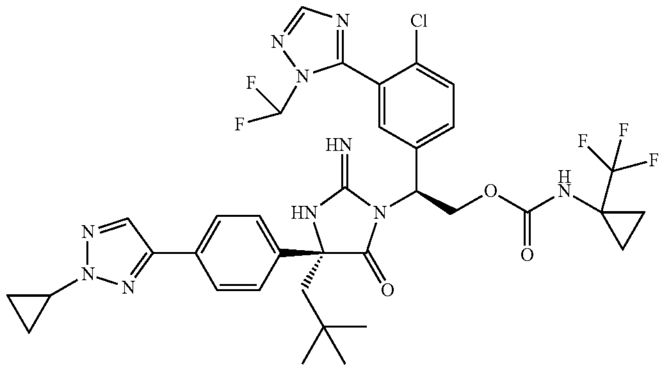 [SMILES: CC(C)(C)C[C@]1(c2ccc(-c3cnn(C4CC4)n3)cc2)NC(=N)N([C@H](COC(=O)NC2(C(F)(F)F)CC2)c2ccc(Cl)c(-c3ncnn3C(F)F)c2)C1=O] | LCMS-ESI+: calc'd for C$_{35}$H$_{36}$ClF$_5$N$_{10}$O$_3$: 775.3 (M + H+); Found: 775.4 (M + H+). | $^1$H NMR (400 MHz, Methanol-d$_4$) δ 8.00 (m, 2H), 7.77 (d, J = 8.5 Hz, 2H), 7.62-7.42 (m, 4H), 7.32 (t, J = 57.2 Hz, 1H), 7.12 (s, 1H), 5.66 (dd, J = 9.5, 5.0 Hz, 1H), 5.15-4.99 (m, 1H), 4.69 (dd, J = 11.5, 5.0 Hz, 1H), 4.12 (tt, J = 7.5, 3.8 Hz, 1H), 2.48 (d, J = 15.1 Hz, 1H), 2.15 (d, J = 15.1 Hz, 1H), 1.36 (tdd, J = 5.2, 4.4, 2.1 Hz, 2H), 1.28 (d, J = 7.0 Hz, 2H), 1.19-1.12 (m, 2H), 1.08 (s, 2H), 1.00 (s, 9H). |
| Compd 147 | 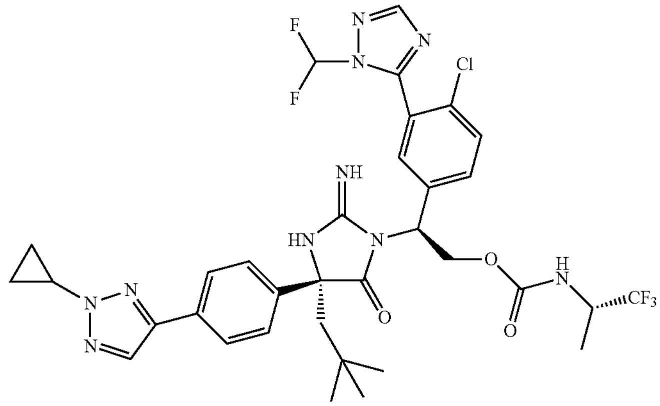 [SMILES: C[C@H](NC(=O)OC[C@H](c1ccc(Cl)c(-c2ncnn2C(F)F)c1)N1C(=N)N[C@](CC(C)(C)C)(c2ccc(-c3cnn(C4CC4)n3)cc2)C1=O)C(F)(F)F] | LCMS-ESI+: calc'd for C$_{34}$H$_{37}$ClF$_5$N$_{10}$O$_3$: 763.3 (M + H+); Found: 763.4 (M + H+). | $^1$H NMR (400 MHz, Methanol-d$_4$) δ 8.01 (m, 2H), 7.88 (d, J = 9.1 Hz, 1H), 7.83-7.70 (m, 2H), 7.63-7.51 (m, 2H), 7.53-7.44 (m, 2H), 7.27 (d, J = 57.2 Hz, 1H), 7.13 (d, J = 1.9 Hz, 1H), 5.74 (dd, J = 9.7, 4.9 Hz, 1H), 5.11 (dd, J = 11.6, 9.7 Hz, 1H), 4.73 (dd, J = 11.6, 5.0 Hz, 1H), 4.31 (q, J = 7.5 Hz, 1H), 4.12 (dt, J = 7.5, 3.7 Hz, 1H), 2.48 (d, J = 15.1 Hz, 1H), 2.17 (d, J = 15.2 Hz, 1H), 1.39-1.31 (m, 2H), 1.29 (d, J = 7.0 Hz, 2H), 1.16 (tdd, J = 8.1, 5.1, 0.8 Hz, 2H), 1.01 (s, 9H). |
| Compd 148 | 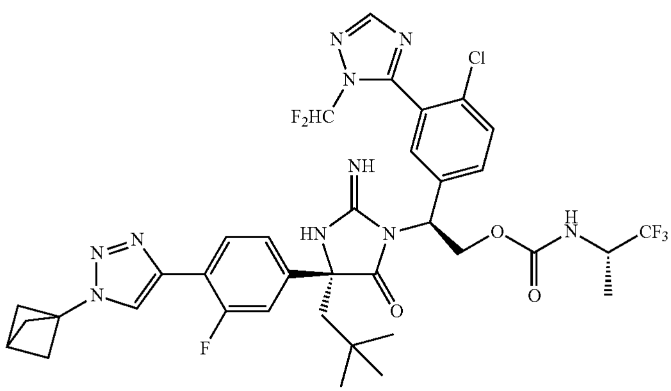 [SMILES: C[C@H](NC(=O)OC[C@H](c1ccc(Cl)c(-c2ncnn2C(F)F)c1)N1C(=N)N[C@](CC(C)(C)C)(c2ccc(-c3cn(C45CC(C4)C5)nn3)c(F)c2)C1=O)C(F)(F)F] | LCMS-ESI+: calc'd for C$_{36}$H$_{37}$ClF$_6$N$_{10}$O$_3$: 807.3 (M + H+); Found: 807.4 (M + H+). | $^1$H NMR (400 MHz, Methanol-d$_4$) δ 8.29 (d, J = 3.4 Hz, 1H), 8.09 (dd, J = 8.6, 7.8 Hz, 1H), 8.04 (s, 1H), 7.65-7.54 (m, 2H), 7.50-7.20 (t, J = 57 Hz, 1H), 7.37-7.32 (m, 2H), 7.17 (t, J = 1.2 Hz, 1H), 5.75 (dd, J = 9.6, 5.0 Hz, 1H), 5.15-5.05 (m, 1H), 4.78-4.71 (m, 1H), 4.38-4.25 (m, 1H), 2.76 (s, 1H), 2.49 (s, 6H), 2.47 (d, J = 15.2 Hz, 1H), 2.17 (d, J = 15.2 Hz, 1H), 1.29 (d, J = 7.1 Hz, 3H), 1.01 (s, 9H). |
| Compd 149 | 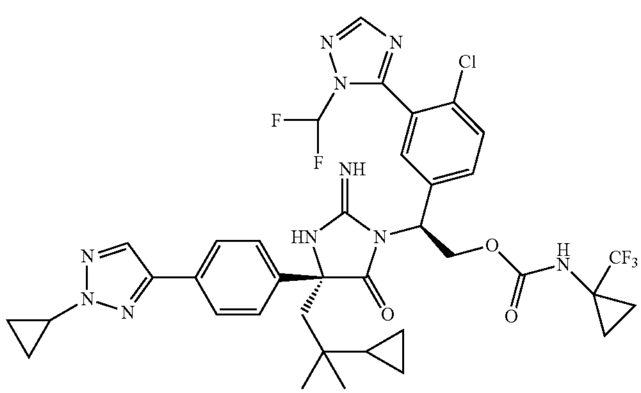 [SMILES: CC(C)(C[C@]1(c2ccc(-c3cnn(C4CC4)n3)cc2)NC(=N)N([C@H](COC(=O)NC2(C(F)(F)F)CC2)c2ccc(Cl)c(-c3ncnn3C(F)F)c2)C1=O)C1CC1] | LCMS-ESI+: calc'd for C$_{37}$H$_{38}$ClF$_5$N$_{10}$O$_3$: 801.3 (M + H+); Found: 801.4 (M + H+). | $^1$H NMR (400 MHz, Methanol-d$_4$) δ 8.00 (s, 1H), 7.96 (s, 1H), 7.68 (s, 1H), 7.66 (s, 1H), 7.56-7.49 (m, 4H), 7.26 (t, J = 57 Hz, 1H), 7.17 (s, 1H), 5.49 (s, 1H), 5.02 (dd, J = 11.2, 8.8 Hz, 1H), 4.66 (dd, J = 11.1, 5.8 Hz, 1H), 4.10 (tt, J = 7.5, 3.8 Hz, 1H), 2.37 (d, J = 14.7 Hz, 1H), 2.06 (d, J = 14.7 Hz, 1H), 1.39-1.32 (m, 2H), 1.21 (d, J = 5.9 Hz, 2H), 1.18-1.10 (m, 2H), 1.03 (d, J = 2.5 Hz, 2H), 0.80 (s, 3H), 0.77 (s, |

| Compound # | Structures | Mass data | NMR data |
|---|---|---|---|
| | | | 3H), 0.76-0.69 (m, 1H), 0.30-0.13 (m, 4H). |
| Compd 150 | 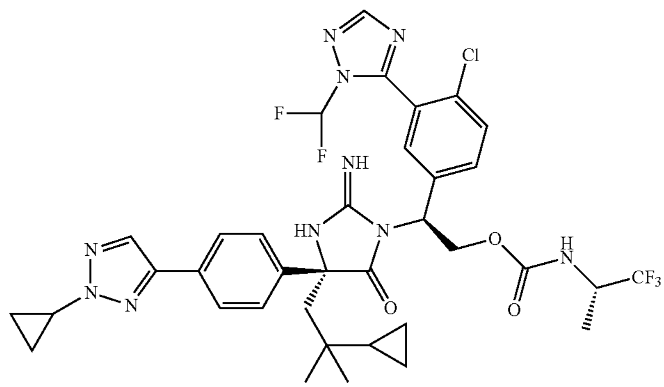 [SMILES: C[C@H](NC(=O)OC[C@H](c1ccc(Cl)c(-c2ncnn2C(F)F)c1)N1C(=N)N[C@](CC(C)(C)C2CC2)(c2ccc(-c3cnn(C4CC4)n3)cc2)C1=O)C(F)(F)F] | LCMS-ESI+: calc'd for C₃₆H₃₈ClF₅N₁₀O₃: 789.3 (M + H+); Found: 789.5 (M + H+). | ¹H NMR (400 MHz, Methanol-d₄) δ 8.00 (s, 1H), 7.97 (s, 1H), 7.72 (d, J = 1.9 Hz, 1H), 7.70 (d, J = 2.0 Hz, 1H), 7.56-7.48 (m, 4H), 7.42-7.14 (t, J = 57 Hz, 1H), 7.15 (s, 1H), 5.57 (t, J = 7.4 Hz, 1H), 5.08 (dd, J = 11.3, 8.9 Hz, 1H), 4.70 (dd, J = 11.4, 5.6 Hz, 1H), 4.28 (p, J = 7.3 Hz, 1H), 4.10 (tt, J = 7.5, 3.8 Hz, 1H), 2.45 (d, J = 14.8 Hz, 1H), 2.14 (d, J = 14.8 Hz, 1H), 1.40-1.32 (m, 2H), 1.27 (d, J = 1.2 Hz, 3H), 1.19-1.11 (m, 2H), 0.82 (s, 3H), 0.81 (s, 3H), 0.76-0.69 (m, 1H), 0.37-0.16 (m, 4H). |
| Compd 151 | 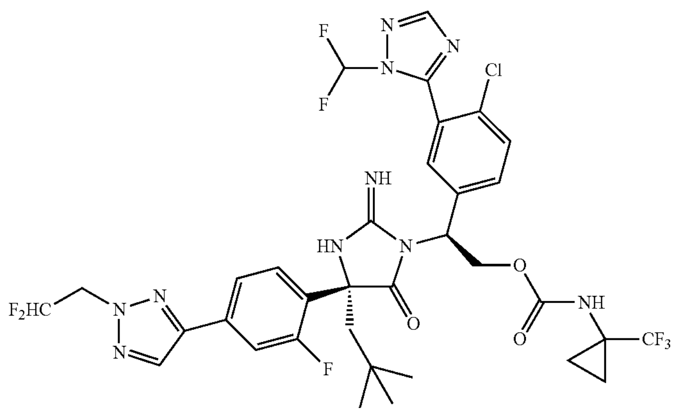 [SMILES: CC(C)(C)C[C@]1(c2ccc(-c3cnn(CC(F)F)n3)cc2F)NC(=N)N([C@H](COC(=O)NC2(C(F)(F)F)CC2)c2ccc(Cl)c(-c3ncnn3C(F)F)c2)C1=O] | LCMS-ESI+: calc'd for C₃₄H₃₄ClF₈N₁₀O₃: 817.2 (M + H+); Found: 817.9 (M + H+). | 1H NMR (400 MHz, Methanol-d₄) δ 8.16 (d, J = 2.1 Hz, 3H), 7.81-7.52 (m, 5H), 7.51-7.22 (m, 3H), 6.36 (tt, J = 54.8, 4.0 Hz, 1H), 5.69 (dd, J = 9.6, 4.8 Hz, 1H), 5.23-5.07 (m, 1H), 4.91 (td, J = 13.8, 4.0 Hz, 2H), 4.74 (dd8, J = 11.5, 4.9 Hz, 1H), 2.53-2.21 (m, 2H), 1.26 (d, J = 6.1 Hz, 2H), 1.03 (s, 11H). |
| Compd 152 | 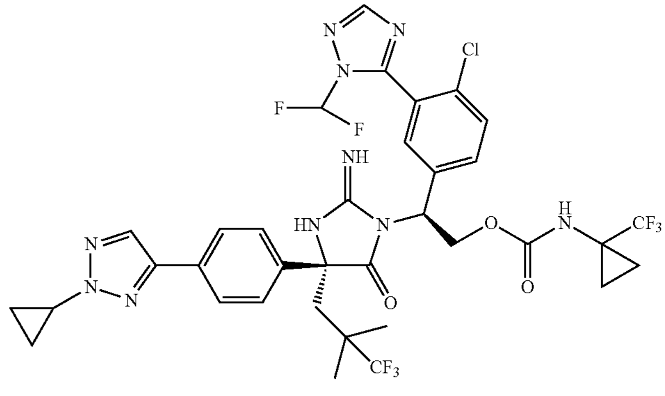 [SMILES: CC(C)(C[C@]1(c2ccc(-c3cnn(C4CC4)n3)cc2)NC(=N)N([C@H](COC(=O)NC2(C(F)(F)F)CC2)c2ccc(Cl)c(-c3ncnn3C(F)F)c2)C1=O)C(F)(F)F] | LCMS-ESI+: calc'd for C₃₅H₃₃ClF₈N₁₀O₃: 829.2 (M + H+); Found: 829.2 (M + H+). | ¹H NMR (400 MHz, Methanol-d₄) δ 8.00 (m, 2H), 7.92-6.96 (m, 9H), 5.68 (dd, J = 9.6, 4.8 Hz, 1H), 5.23-5.04 (m, 1H), 4.69 (dd, J = 11.8, 4.8 Hz, 1H), 4.12 (tt, J = 7.5, 3.8 Hz, 1H), 2.77 (d, J = 15.5 Hz, 1H), 2.47 (d, J = 15.5 Hz, 1H), 1.46-1.00 (m, 14H). |

| Compound # | Structures | Mass data | NMR data |
|---|---|---|---|
| Compd 153 | 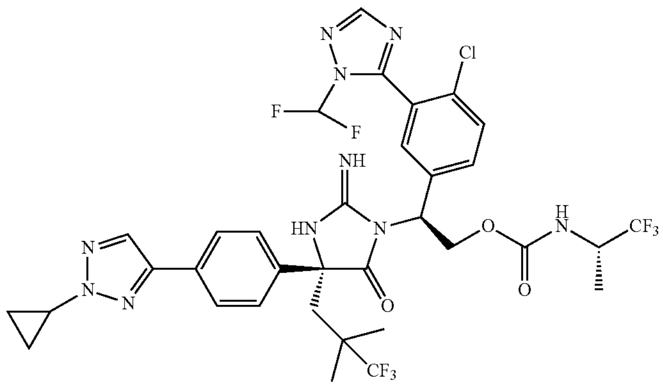 [SMILES: C[C@H](NC(=O)OC[C@H](c1ccc(Cl)c(-c2ncnn2C(F)F)c1)N1C(=N)N[C@](CC(C)(C)C(F)(F)F)(c2ccc(-c3cnn(C4CC4)n3)cc2)C1=O)C(F)(F)F] | LCMS-ESI+: calc'd for C$_{34}$H$_{33}$ClF$_8$N$_{10}$O$_3$, 817.2 (M + H); Found, 817.2 (M + H). | 1H NMR (400 MHz, Methanol-d4) δ 8.00 (d, J = 6.1 Hz, 2H), 7.87-7.78 (m, 2H), 7.63-7.42 (m, 5H), 7.34-7.04 (m, 2H), 5.75 (dd, J = 9.6, 5.0 Hz, 1H), 5.10 (dd, J = 11.7, 9.7 Hz, 1H), 4.75 (dd, J = 11.8, 5.1 Hz, 1H), 4.31 (hept, J = 7.7, 7.1 Hz, 1H), 4.12 (tt, J = 7.5, 3.8 Hz, 1H), 2.75 (d, J = 15.5 Hz, 1H), 2.47 (d, J = 15.5 Hz, 1H), 1.42-1.08 (m, 14H). |
| Compd 154 | 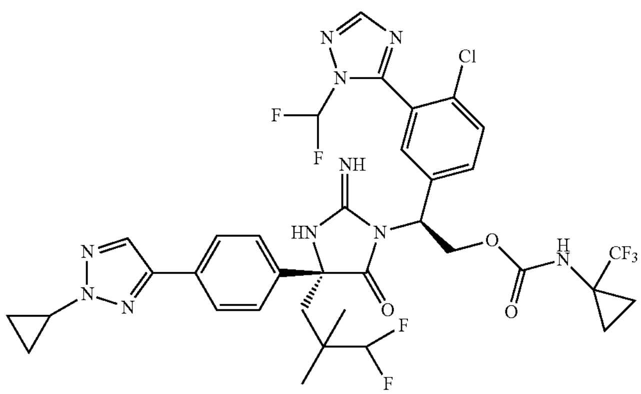 [SMILES: CC(C)(C[C@]1(c2ccc(-c3cnn(C4CC4)n3)cc2)NC(=N)N([C@H](COC(=O)NC2(C(F)(F)F)CC2)c2ccc(Cl)c(-c3ncnn3C(F)F)c2)C1=O)C(F)F] | LCMS-ESI+: calc'd for C$_{35}$H$_{34}$ClF$_7$N$_{10}$O$_3$, 811.2 (M + H); Found 811.4 (M + H). | $^1$H NMR (400 MHz, Methanol-d$_4$) δ 7.99 (s, 1H), 7.98 (s, 1H), 7.72 (s, 1H), 7.70 (s, 1H), 7.55-7.51 (m, 2H), 7.51 (s, 1H), 7.49 (s, 1H), 7.29 (t, J = 57 Hz, 1H), 7.12 (s, 1H), 5.86-5.58 (m, 1H), 5.53 (s, 1H), 5.13-4.99 (m, 1H), 4.65 (dd, J = 11.3, 5.2 Hz, 1H), 4.18 -4.02 (m, 1H), 2.50-2.20 (m, 2H), 1.37-1.32 (m, 2H), 1.26-1.22 (m, 2H), 1.19-1.03 (m, 4H), 1.01 (s, 3H), 0.98 (s, 3H). |
| Compd 155 | 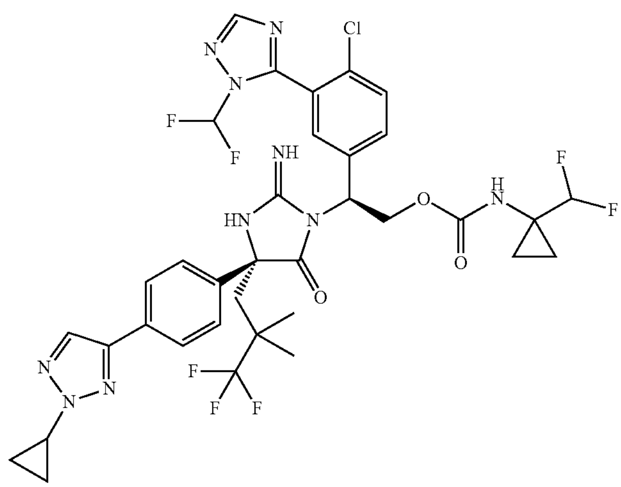 [SMILES: CC(C)(C[C@]1(c2ccc(-c3cnn(C4CC4)n3)cc2)NC(=N)N([C@H](COC(=O)NC2(C(F)F)CC2)c2ccc(Cl)c(-c3ncnn3C(F)F)c2)C1=O)C(F)(F)F] | LCMS-ESI+: calc'd for C$_{35}$H$_{34}$ClF$_7$N$_{10}$O$_3$: 811.2 (M + H+); Found: 811.4 (M + H+). | $^1$H NMR (400 MHz, Methanol-d$_4$) δ 8.00 (m, 2H), 7.84-7.75 (m, 2H), 7.61-7.47 (m, 4H), 7.32 (t, J = 57.2 Hz, 1H), 7.12 (d, J = 2.0 Hz, 1H), 5.77 (t, J = 56.7 Hz, 1H) 5.68-5.60 (m, 1H), 5.09 (dd, J = 11.6, 9.6 Hz, 1H), 4.69 (dd, J = 11.6, 4.9 Hz, 1H), 4.12 (tt, J = 7.5, 3.8 Hz, 1H), 2.74 (d, J = 15.5 Hz, 1H), 2.45 (d, J = 15.5 Hz, 1H), 1.39-1.32 (m, 2H), 1.19 (s, 3H), 1.17 (s, 3H), 1.18-1.13 (m, 2H), 1.09-1.04 (m, 2H), 0.95-0.85 (m, 2H). |

| Compound # | Structures | Mass data | NMR data |
|---|---|---|---|
| Compd 156 | 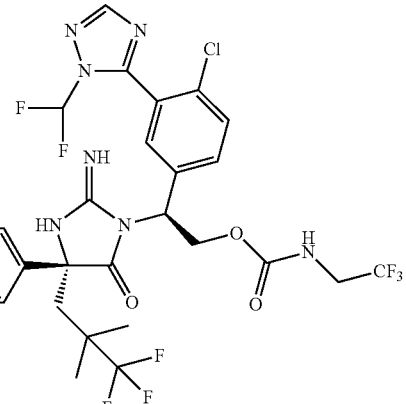 | LCMS-ESI+: calc'd for $C_{33}H_{31}ClF_8N_{10}O_3$, 803.2 (M + H); Found 803.3 (M + H). | $^1$H NMR (400 MHz, Methanol-$d_4$) δ 8.00 (m, 2H), 7.81 (d, J = 2.0 Hz, 1H), 7.79 (d, J = 2.0 Hz, 1H), 7.60-7.52 (m, 2H), 7.50 (d, J = 2.0 Hz, 1H), 7.48 (d, J = 1.9 Hz, 1H), 7.32 (t, J = 57.2 Hz, 1H), 7.12 (d, J = 2.0 Hz, 1H), 5.69 (dd, J = 9.6, 4.8 Hz, 1H), 5.15 (dd, J = 11.7, 9.7 Hz, 1H), 4.75 (dd, J = 11.7, 4.9 Hz, 1H), 4.12 (tt, J = 7.5, 3.8 Hz, 1H), 3.88-3.71 (m, 2H), 2.75 (d, J = 15.5 Hz, 1H), 2.45 (d, J = 15.5 Hz, 1H), 1.39-1.33 (m, 2H), 1.19 (s, 6H), 1.16 (ddd, J = 7.3, 2.6, 0.9 Hz, 2H). |
| Compd 157 | 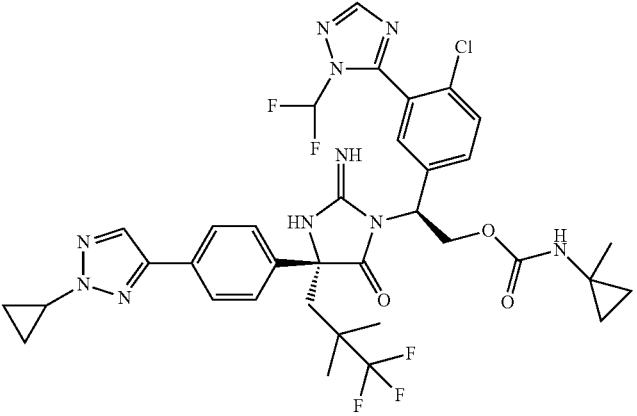 [SMILES: CC1(NC(=O)OC[C@H](c2ccc(Cl)c(-c3ncnn3C(F)F)c2)N2C(=N)N[C@](CC(C)(C)C(F)(F)F)(c3ccc(-c4cnn(C5CC5)n4)cc3)C2=O)CC1] | LCMS-ESI+: calc'd for $C_{35}H_{36}ClF_5N_{10}O_3$, 775.3 (M + H); Found 775.6 (M + H). | $^1$H NMR (400 MHz, Methanol-$d_4$) δ 8.005 (s, 1H), 7.995 (s, 1H), 7.79 (s, 1H), 7.77 (s, 1H), 7.61-7.37 (m, 4H), 7.46-7.17 (t-, J = 57 Hz, 1H), 7.12 (d, J = 2.0 Hz, 1H), 5.59 (dd, J = 9.4, 5.0 Hz, 1H), 5.09-4.98 (m, 1H), 4.64 (dd, J = 11.6, 5.0 Hz, 1H), 4.11 (tt, J = 7.6, 3.8 Hz, 1H), 2.71 (d, J = 15.4 Hz, 1H), 2.41 (d, J = 15.4 Hz, 1H), 1.40-1.32 (m, 2H), 1.31 (s, 3H), 1.21-1.09 (m, 8H), 0.68 (s, 2H), 0.58 (d, J = 5.3 Hz, 2H). |
| Compd 158 | 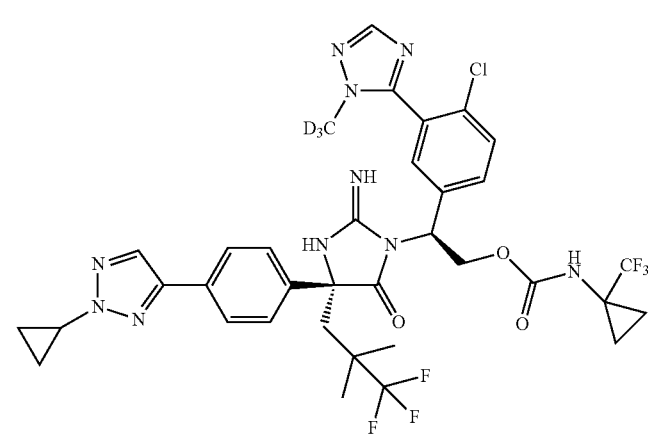 [SMILES: [2H]C([2H])([2H])n1ncnc1-c1cc([C@@H](COC(=O)NC2(C(F)(F)F)CC2)N2C(=N)N[C@](CC(C)(C)C(F)(F)F)(c3ccc(-c4cnn(C5CC5)n4)cc3)C2=O)ccc1Cl] | LCMS-ESI+: calc'd for $C_{35}H_{32}D_3ClF_6N_{10}O_3$, 796.3 (M + H); Found 796.3 (M + H). | 1H NMR (400 MHz, Methanol-d4) δ 8.01 (s, 1H), 7.92-7.71 (m, 3H), 7.65-7.42 (m, 4H), 7.07 (d, J = 2.2 Hz, 1H), 5.67 (dd, J = 9.6, 4.7 Hz, 1H), 5.12 (t, J = 10.6 Hz, 1H), 4.71 (dd, J = 11.7, 4.7 Hz, 1H), 4.12 (tt, J = 7.5, 3.8 Hz, 1H), 2.78 (d, J = 15.5 Hz, 1H), 2.47 (d, J = 15.5 Hz, 1H), 1.45-1.00 (m, 15H). |

-continued

| Compound # | Structures | Mass data | NMR data |
|---|---|---|---|
| Compd 159 | 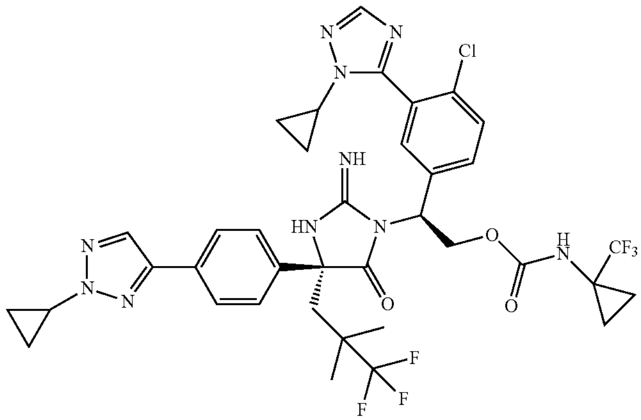 [SMILES: CC(C)(C[C@]1(c2ccc(-c3cnn(C4CC4)n3)cc2)NC(=N)N([C@H](COC(=O)NC2(C(F)(F)F)CC2)c2ccc(Cl)c(-c3ncnn3C3CC3)c2)C1=O)C(F)(F)F] | LCMS-ESI+: calc'd for $C_{37}H_{37}ClF_6N_{10}O_3$, 819.3 (M + H); Found 819.4 (M + H). | 1H NMR (400 MHz, Methanol-d4) δ 8.02 (s, 1H), 7.88-7.74 (m, 3H), 7.62-7.43 (m, 4H), 5.66 (dd, J = 9.5, 4.8 Hz, 1H), 5.18-5.05 (m, 1H), 4.71 (dd, J = 11.6, 4.8 Hz, 1H), 4.12 (tt, J = 7.6, 3.9 Hz, 1H), 2.79 (d, J = 15.5 Hz, 1H), 2.47 (d, J = 15.5 Hz, 1H), 1.40-1.00 (m, 18H). |
| Compd 160 | 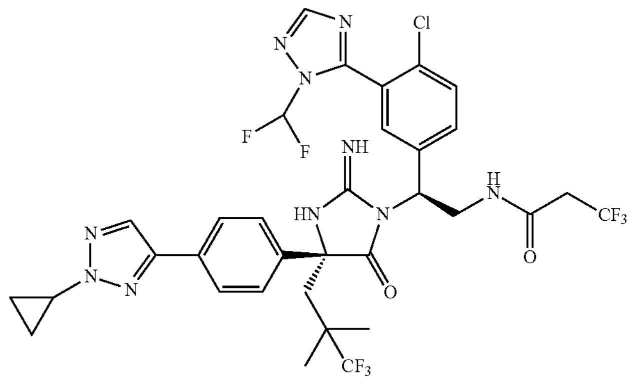 | LCMS-ESI+: calc'd for $C_{33}H_{31}ClF_8N_{10}O_2$, 787.2 (M + H); Found 787.3 (M + H). | $^1$H NMR (400 MHz, Methanol-$d_4$) δ 8.04 (s, 1H), 8.00 (s, 1H), 7.80 (d, J = 8.1 Hz, 2H), 7.60-7.50 (m, 4H), 7.32 (t, J = 51.2 Hz, 1H), 7.16 (d, J = 2.0 Hz, 1H), 5.55 (s, 1H), 4.30 (dd, J = 14.1, 9.1 Hz, 1H), 4.18-4.06 (m, 1H), 3.98 (dd, J = 14.0, 6.0 Hz, 1H), 3.17-2.91 (m, 2H), 2.76-2.47 (m, 2H), 1.39-1.32 (m, 2H), 1.17 (s, 3H), 1.16-1.11 (m, 2H), 1.08 (s, 3H). |
| Compd 161 | 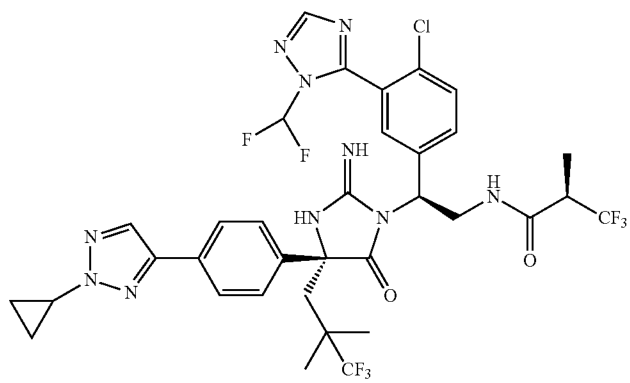 [SMILES: C[C@H](C(=O)NC[C@H](c1ccc(Cl)c(-c2ncnn2C(F)F)c1)N1C(=N)N[C@](CC(C)(C)C(F)(F)F)(c2ccc(-c3cnn(C4CC4)n3)cc2)C1=O)C(F)(F)F] | LCMS-ESI+: calc'd for $C_{34}H_{33}ClF_8N_{10}O_2$, 801.2 (M + H); Found 801.5 (M + H). | $^1$H NMR (400 MHz, Methanol-$d_4$) δ 8.01 (m, 2H), 7.82 (d, J = 1.9 Hz, 1H), 7.81 (d, J = 2.0 Hz, 1H), 7.57-7.52 (m, 4H), 7.32 (t, J = 57.2 Hz, 1H), 7.13 (d, J = 2.0 Hz, 1H), 5.62 (dd, J = 9.2, 5.6 Hz, 1H), 4.29 (dd, J = 14.0, 9.4 Hz, 1H), 4.12 (tt, J = 7.5, 3.8 Hz, 1H), 4.01 (dd, J = 14.0, 5.7 Hz, 1H), 3.26-3.08 (m, 1H), 2.66 (s, 2H), 1.39-1.32 (m, 2H), 1.29 (d, J = 7.1 Hz, 3H), 1.18 (s, 3H), 1.17-1.11 (m, 2H), 1.03 (s, 3H). |
| Compd 162 | 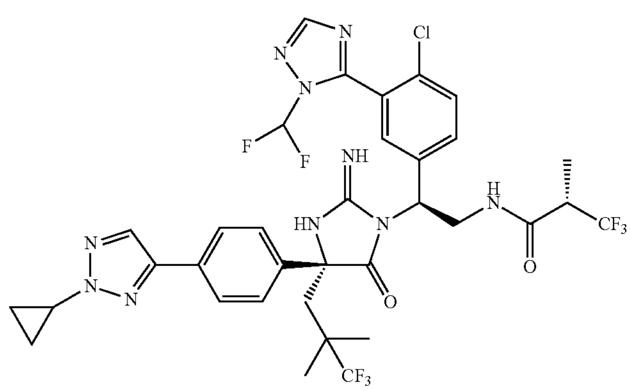 [SMILES: C[C@@H](C(=O)NC[C@H](c1ccc(Cl)c(-c2ncnn2C(F)F)c1)N1C(=N)N[C@](CC(C)(C)C(F)(F)F)(c2ccc(-c3cnn(C4CC4)n3)cc2)C1=O)C(F)(F)F] | LCMS-ESI+: calc'd for $C_{34}H_{33}ClF_8N_{10}O_2$, 801.2 (M + H); Found 801.6 (M + H). | $^1$H NMR (400 MHz, Methanol-$d_4$) δ 8.04 (d, J = 0.4 Hz, 1H), 8.00 (s, 1H), 7.81 (d, J = 2.0 Hz, 1H), 7.79 (d, J = 2.0 Hz, 1H), 7.54 (m, 2H), 7.53 (d, J = 2.0 Hz, 1H), 7.51 (d, J = 1.9 Hz, 1H), 7.45-7.16 (t, J = 57 Hz, 1H) 7.19 (d, J = 1.8 Hz, 1H), 5.49 (dd, J = 8.6, 5.8 Hz, 1H), 4.39 (dd, J = 14.1, 8.6 Hz, 1H), 4.11 (tt, J = 7.5, 3.8 Hz, 1H), 3.96 (dd, J = 14.0, 5.8 Hz, 1H), 3.21-3.06 (m, 1H), 2.77-2.54 (m, 2H), 1.39-1.31 (m, 2H), 1.27 (d, J = |

-continued

| Compound # | Structures | Mass data | NMR data |
|---|---|---|---|
| | | | 7.1 Hz, 3H), 1.16 (s, 3H), 1.21-1.10 (m, 2H), 1.04 (s, 3H). |
| Compd 163 | 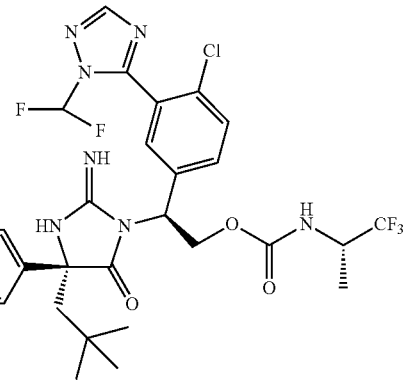 | LCMS-ESI+: calc'd for C₃₂H₃₂ClF₇N₁₀O₃, 773.2 (M + H); Found 772.2 (M). | 1H NMR (400 MHz, Methanol-d4) δ 8.45 (s, 1H), 8.06 (d, J = 36.3 Hz, 2H), 7.75-7.05 (m, 10H), 5.73 (dd, J = 9.6, 5.0 Hz, 1H), 5.10 (dd, J = 11.6, 9.7 Hz, 1H), 4.74 (dd, J = 11.6, 5.1 Hz, 1H), 4.30 (p, J = 7.2 Hz, 1H), 2.46 (d, J = 15.1 Hz, 1H), 2.16 (d, J = 15.1 Hz, 1H), 1.29 (d, J = 7.1 Hz, 3H), 1.01 (s, 9H). |
| Compd 164 | 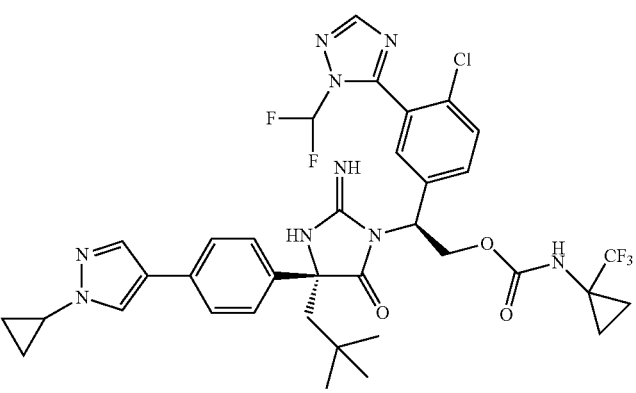 [SMILES: CC(C)(C)C[C@]1(c2ccc(-c3cnn(C4CC4)c3)cc2)NC(=N)N([C@H](COC(=O)NC2(C(F)(F)F)CC2)c2ccc(Cl)c(-c3ncnn3C(F)F)c2)C1=O] | LCMS-ESI+: calc'd for C₃₆H₃₇ClF₅N₉O₃, 774.3 (M + H); Found 774.3 (M + H). | ¹H NMR (400 MHz, Methanol-d₄) δ 8.06 (s, 1H), 7.99 (s, 1H), 7.82 (d, J = 0.8 Hz, 1H), 7.61-7.48 (m, 4H), 7.47-7.19 (t, J = 57 Hz, 1H), 7.39-7.35 (m, 2H), 7.12 (s, 1H), 5.66 (dd, J = 9.6, 5.0 Hz, 1H), 5.09 (t, J = 10.6 Hz, 1H), 4.69 (dd, J = 11.5, 5.0 Hz, 1H), 3.76-3.66 (m, 1H), 2.47 (d, J = 15.1 Hz, 1H), 2.14 (d, J = 15.2 Hz, 1H), 1.30-1.25 (m, 2H), 1.18-1.12 (m, 2H), 1.11-1.05 (m, 4H), 1.00 (s, 9H). |

Example 48: Preparation of Compound 165

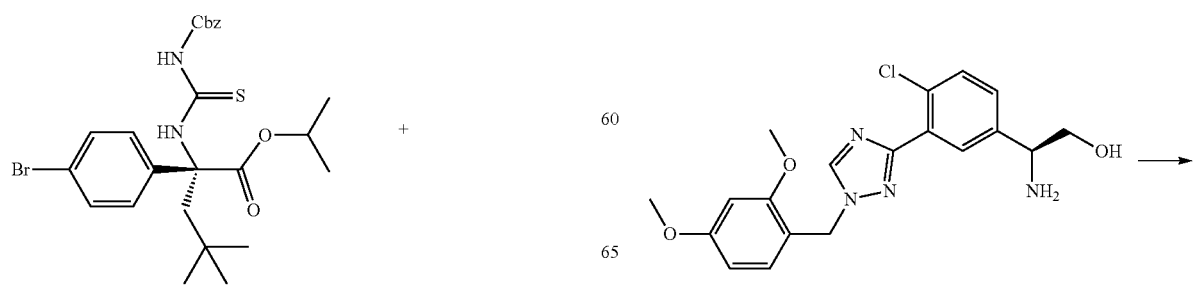

-continued

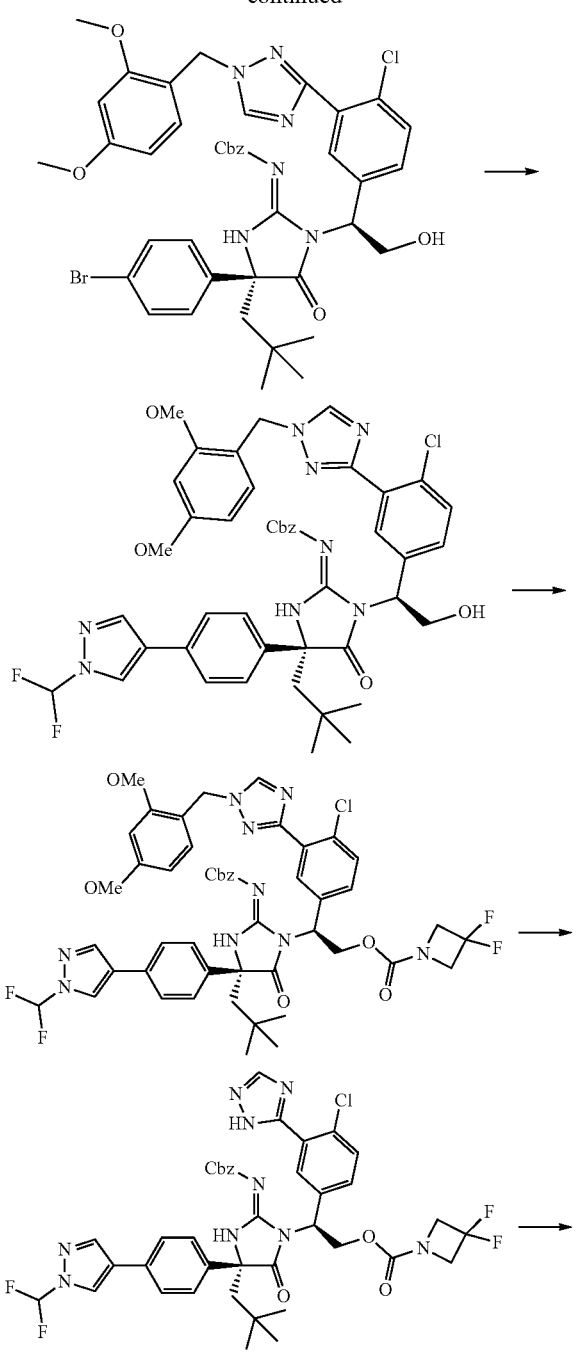

Preparation of (S)-2-((R)-2-(((benzyloxy)carbonyl)imino)-4-(4-(1-(difluoromethyl)-1H-pyrazol-4-yl)phenyl)-4-neopentyl-5-oxoimidazolidin-1-yl)-2-(4-chloro-3-(1-(2,4-dimethoxybenzyl)-1H-1,2,4-triazol-3-yl)phenyl)ethyl 3,3-difluoroazetidine-1-carboxylate: (S)-2-((R)-2-(((benzyloxy)carbonyl)imino)-4-(4-(1-(difluoromethyl)-1H-pyrazol-4-yl)phenyl)-4-neopentyl-5-oxoimidazolidin-1-yl)-2-(4-chloro-3-(1-(2,4-dimethoxybenzyl)-1H-1,2,4-triazol-3-yl)phenyl)ethyl 3,3-difluoroazetidine-1-carboxylate was prepared following the procedure to prepare benzyl ((R)-1-((S)-1-(4-chloro-3-(3-methylpyridin-2-yl)phenyl)-2-((cyclopropylcarbamoyl)oxy)ethyl)-4-(4-(1-(difluoromethyl)-1H-pyrazol-4-yl)-2-fluorophenyl)-4-neopentyl-5-oxoimidazolidin-2-ylidene)carbamate described in Example 12, except that (S)-2-amino-2-(4-chloro-3-(1-(2,4-dimethoxybenzyl)-1H-1,2,4-triazol-3-yl)phenyl)ethan-1-ol was used instead of (S)-2-amino-2-(4-chloro-3-(3-methylpyridin-2-yl)phenyl)ethan-1-ol hydrochloride and 3,3-difluoroazetidine was used instead of cyclopropylamine.

Preparation of (S)-2-((R)-2-(((benzyloxy)carbonyl)imino)-4-(4-(1-(difluoromethyl)-1H-pyrazol-4-yl)phenyl)-4-neopentyl-5-oxoimidazolidin-1-yl)-2-(4-chloro-3-(1H-1,2,4-triazol-5-yl)phenyl)ethyl 3,3-difluoroazetidine-1-carboxylate: A mixture of (S)-2-((R)-2-(((benzyloxy)carbonyl)imino)-4-(4-(1-(difluoromethyl)-1H-pyrazol-4-yl)phenyl)-4-neopentyl-5-oxoimidazolidin-1-yl)-2-(4-chloro-3-(1-(2,4-dimethoxybenzyl)-1H-1,2,4-triazol-3-yl)phenyl)ethyl 3,3-difluoroazetidine-1-carboxylate (129 mg, 0.13 mmol) and ammonium cerium(IV) sulfate dihydrate (1650 mg, 2.62 mmol) in water (5 mL) and acetonitrile (5 mL) was heated at 60° C. for 3 h. The reaction mixture was cooled down to rt and filtered. The filtrate was extracted with EtOAc. The organic phase was dried over sodium sulfate, filtered, and concentrated down. The residue was purified by silica gel column chromatography (0-100% gradient EtOAc/hexanes) to give the product.

Preparation of Compound 165: A mixture of (S)-2-((R)-2-(((benzyloxy)carbonyl)imino)-4-(4-(1-(difluoromethyl)-1H-pyrazol-4-yl)phenyl)-4-neopentyl-5-oxoimidazolidin-1-yl)-2-(4-chloro-3-(1H-1,2,4-triazol-5-yl)phenyl)ethyl 3,3-difluoroazetidine-1-carboxylate in DCM (0.5 mL) and TFA (1 mL) was heated at 40° C. for 16 h. The reaction mixture was concentrated down. The residue was purified by reverse phase HPLC (acetonitrile/water, both containing 0.1% TFA) to give the product.

Example 49: Preparation of Compound 166

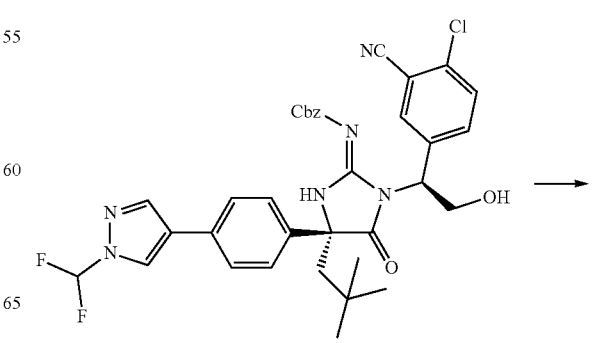

-continued

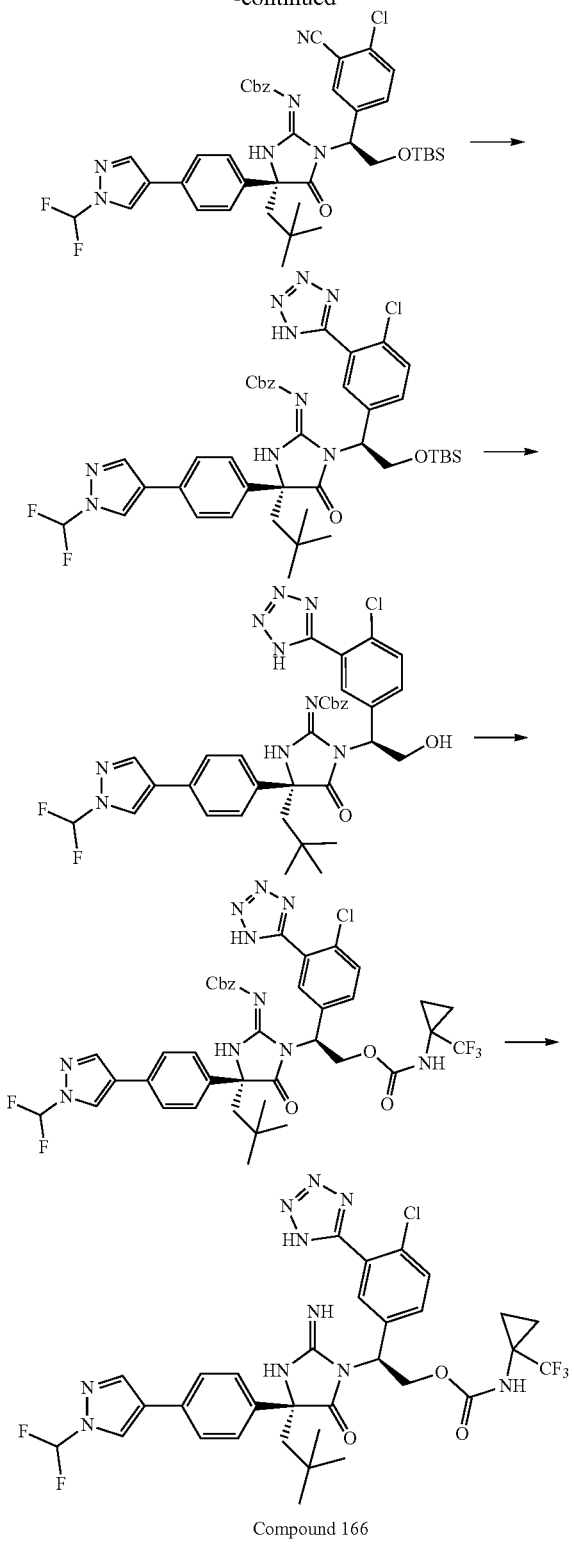

Compound 166

Preparation of benzyl ((R)-1-((S)-2-((tert-butyldimethylsilyl)oxy)-1-(4-chloro-3-cyanophenyl)ethyl)-4-(4-(1-(difluoromethyl)-1H-pyrazol-4-yl)phenyl)-4-neopentyl-5-oxoimidazolidin-2-ylidene)carbamate: To a solution of benzyl ((R)-1-((S)-1-(4-chloro-3-cyanophenyl)-2-hydroxyethyl)-4-(4-(1-(difluoromethyl)-1H-pyrazol-4-yl)phenyl)-4-neopentyl-5-oxoimidazolidin-2-ylidene)carbamate (110 mg, 0.16 mmol) in DCM (3.0 mL) were added imidazole (33 mg, 0.49 mmol) and tert-butyldimethylsilyl chloride (49 mg, 0.33 mmol). The reaction mixture was stirred at rt overnight. The reaction mixture was treated with saturated ammonium chloride solution and extracted with DCM. The organic phase was dried over MgSO₄, filtered and concentrated down. The residue was purified by silica gel column chromatography (0-100% gradient EtOAc/hexanes) to give the product.

Preparation of benzyl ((R)-1-((S)-2-((tert-butyldimethylsilyl)oxy)-1-(4-chloro-3-(1H-tetrazol-5-yl)phenyl)ethyl)-4-(4-(1-(difluoromethyl)-1H-pyrazol-4-yl)phenyl)-4-neopentyl-5-oxoimidazolidin-2-ylidene)carbamate: A mixture of benzyl ((R)-1-((S)-2-((tert-butyldimethylsilyl)oxy)-1-(4-chloro-3-cyanophenyl)ethyl)-4-(4-(1-(difluoromethyl)-1H-pyrazol-4-yl)phenyl)-4-neopentyl-5-oxoimidazolidin-2-ylidene)carbamate (30 mg, 0.038 mmol), azidotrimethylsilane (0.05 mL, 0.38 mmol) and di-n-butyltin oxide (3.8 mg, 0.015 mmol) in toluene (1.0 mL) was heated at 90° C. for 1 h. Then to the mixture were added another batch of azidotrimethylsilane (0.05 mL, 0.38 mmol) and di-n-butyltin oxide (3.8 mg, 0.015 mmol) and the reaction was stirred at 90° C. for 4 h. The reaction mixture was concentrated down. The residue was purified by silica gel column chromatography (0-100% gradient EtOAc/hexanes) to give the product.

Preparation of benzyl ((R)-1-((S)-1-(4-chloro-3-(1H-tetrazol-5-yl)phenyl)-2-hydroxyethyl)-4-(4-(1-(difluoromethyl)-1H-pyrazol-4-yl)phenyl)-4-neopentyl-5-oxoimidazolidin-2-ylidene)carbamate: A mixture of benzyl ((R)-1-((S)-2-((tert-butyldimethylsilyl)oxy)-1-(4-chloro-3-(1H-tetrazol-5-yl)phenyl)ethyl)-4-(4-(1-(difluoromethyl)-1H-pyrazol-4-yl)phenyl)-4-neopentyl-5-oxoimidazolidin-2-ylidene) carbamate (18 mg, 0.022 mmol), tetrabutylammonium fluoride in THF (1.0M, 0.04 mL) and acetic acid (0.007 mL, 0.13 mmol) in THF (1.0 mL) was stirred at rt for 20 h. The reaction mixture was concentrated down. The residue was purified by reverse phase HPLC (acetonitrile/water, both containing 0.1% TFA) to give the product.

Preparation of benzyl ((R)-1-((S)-1-(4-chloro-3-(1H-tetrazol-5-yl)phenyl)-2-(((1-(trifluoromethyl)cyclopropyl)carbamoyl)oxy)ethyl)-4-(4-(1-(difluoromethyl)-1H-pyrazol-4-yl)phenyl)-4-neopentyl-5-oxoimidazolidin-2-ylidene) carbamate: A mixture of benzyl ((R)-1-((S)-1-(4-chloro-3-(1H-tetrazol-5-yl)phenyl)-2-hydroxyethyl)-4-(4-(1-(difluoromethyl)-1H-pyrazol-4-yl)phenyl)-4-neopentyl-5-oxoimidazolidin-2-ylidene)carbamate (7 mg, 0.0097 mmol), 1-isocyanato-1-(trifluoromethyl)cyclopropane in toluene (1.13 M, 0.086 mL) and CuCl (0.96 mg, 0.0097 mmol) in DCM (0.5 mL) was stirred at rt overnight. The reaction mixture was concentrated down and purified by silica gel column chromatography (0-100% gradient EtOAc/hexanes) to give the product.

Preparation of Compound 166: A solution of benzyl ((R)-1-((S)-1-(4-chloro-3-(1H-tetrazol-5-yl)phenyl)-2-(((1-(trifluoromethyl)cyclopropyl)carbamoyl)oxy)ethyl)-4-(4-(1-(difluoromethyl)-1H-pyrazol-4-yl)phenyl)-4-neopentyl-5-oxoimidazolidin-2-ylidene)carbamate (8 mg, 0.0092 mmol) in TFA (1.0 mL) was stirred at 60° C. for 2 h. The reaction mixture was concentrated down and the residue was purified by reverse phase HPLC (acetonitrile/water, both containing 0.1% TFA) to give the product.

Example 50: Preparation of Compound 167

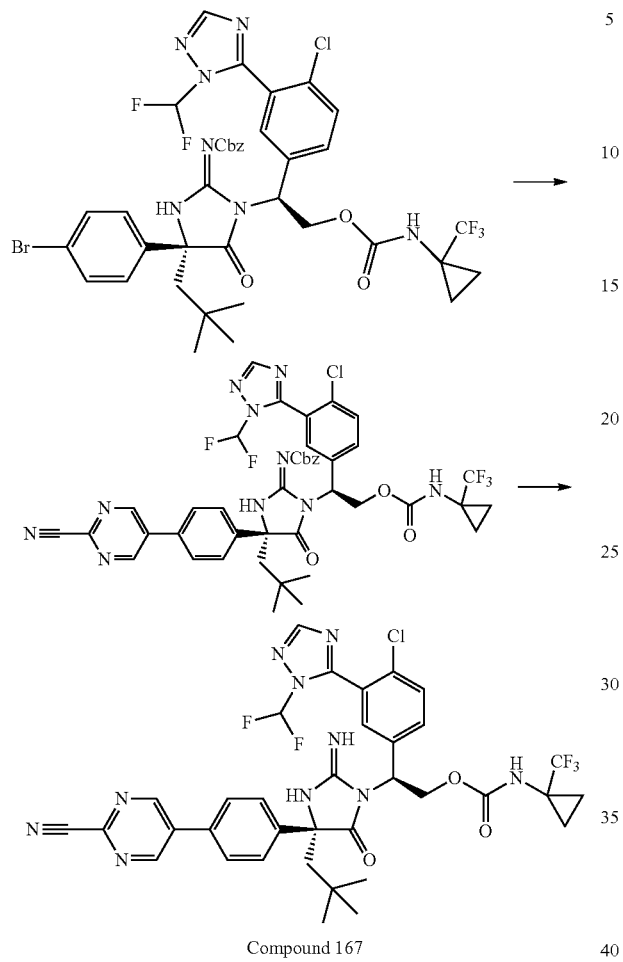

Compound 167

Preparation of Compound 167: To a solution of benzyl ((R)-4-(4-bromophenyl)-1-((S)-1-(4-chloro-3-(1-(difluoromethyl)-1H-1,2,4-triazol-5-yl)phenyl)-2-((1-(trifluoromethyl)cyclopropyl)carbamoyl)oxy)ethyl)-4-neopentyl-5-oxoimidazolidin-2-ylidene)carbamate (0.03 g, 0.034 mmol) in dioxane (4 mL) and water (0.6 mL) were added 2-cyanopyrimidine-5-boronic acid pinacol ester (0.04 g, 0.017 mol), tetrakis(triphenylphosphine)palladium(O) (6 mg, 0.0017 mol) and potassium carbonate (11 mg, 0.017 mmol) was stirred at 85° C. for 1 h. The reaction mixture was treated with saturated ammonium chloride solution and extracted with DCM. The organic phase was dried over MgSO₄, filtered and concentrated in vacuo. The crude mixture was purified by silica gel column chromatography (EtOAc/hexanes) to give the product (S)-2-((R)-2-(((benzyloxy)carbonyl)imino)-4-(4-(2-cyanopyrimidine-5-yl)phenyl)-4-neopentyl-5-oxoimidazolidin-1-yl)-2-(4-chloro-3-(1-(difluoromethyl)-1H-1,2,4-triazol-5-yl)phenyl)ethyl (1-(trifluoromethyl)cyclopropyl)carbamate. Then, this compound was dissolved in dichloromethane (1 mL) and trifluoroacetic acid (3 mL). The mixture was heated at 60° C. for 2 h. The mixture was concentrated down and purified by reverse phase HPLC (acetonitrile/water, both containing 0.1% TFA) to give the product.

Example 51: Preparation of Compound 168

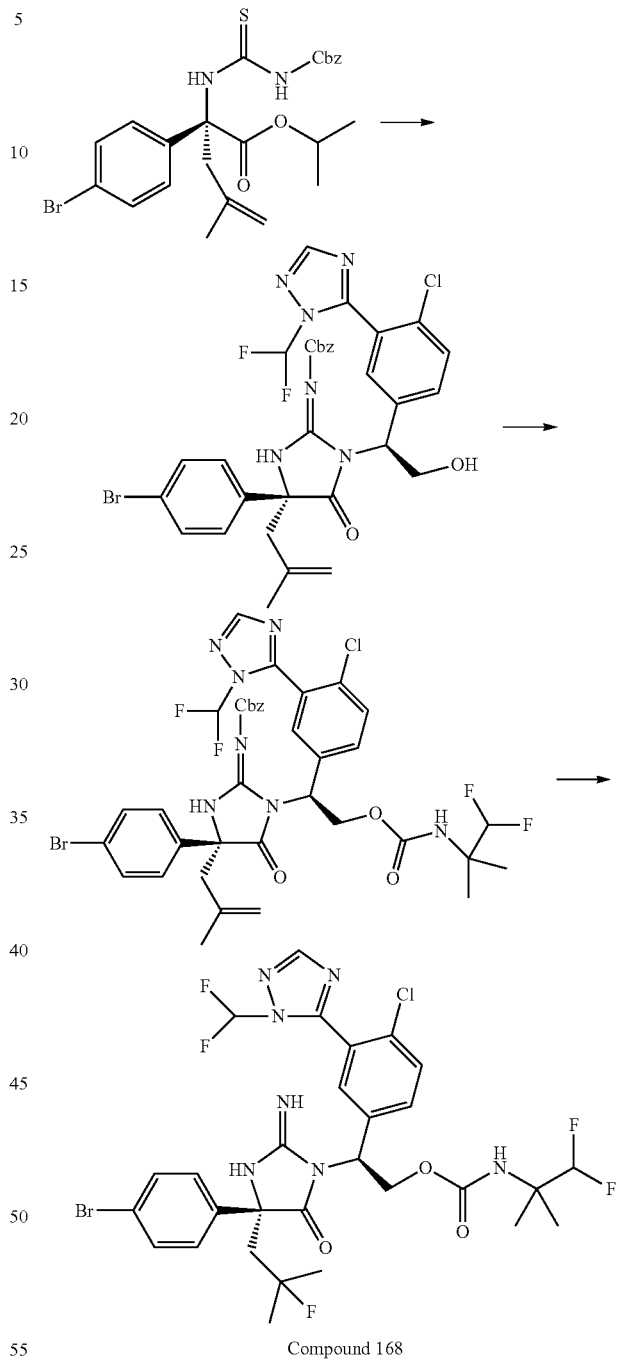

Compound 168

Preparation of (S)-2-((R)-2-(((benzyloxy)carbonyl)imino)-4-(4-bromophenyl)-4-(2-methylallyl)-5-oxoimidazolidin-1-yl)-2-(4-chloro-3-(1-(difluoromethyl)-1H-1,2,4-triazol-5-yl)phenyl)ethyl (1,1-difluoro-2-methylpropan-2-yl)carbamate: (S)-2-((R)-2-(((benzyloxy)carbonyl)imino)-4-(4-bromophenyl)-4-(2-methylallyl)-5-oxoimidazolidin-1-yl)-2-(4-chloro-3-(1-(difluoromethyl)-1H-1,2,4-triazol-5-yl)phenyl)ethyl (1,1-difluoro-2-methylpropan-2-yl) carbamate was prepared following the procedure to prepare benzyl ((R)-1-((S)-1-(4-chloro-3-(pyridin-2-yl)phenyl)-2-

(((1-(trifluoromethyl)cyclopropyl)carbamoyl)oxy)ethyl)-4-(4-(1-(difluoromethyl)-1H-pyrazol-4-yl)phenyl)-4-neopentyl-5-oxoimidazolidin-2-ylidene)carbamate described in Example 20, except that (S)-2-amino-2-(3-(1-(difluoromethyl)-1H-1,2,4-triazol-5-yl)-4-fluorophenyl)ethan-1-ol was used instead of (S)-2-amino-2-(4-chloro-3-(pyridin-2-yl)phenyl)ethan-1-ol and 1,1-difluoro-2-isocyanato-2-methylpropane was used instead of 1-isocyanato-1-(trifluoromethyl)cyclopropane.

Preparation of Compound 168: (S)-2-((R)-2-(((benzyloxy)carbonyl)imino)-4-(4-bromophenyl)-4-(2-methylallyl)-5-oxoimidazolidin-1-yl)-2-(4-chloro-3-(1-(difluoromethyl)-1H-1,2,4-triazol-5-yl)phenyl)ethyl (1,1-difluoro-2-methylpropan-2-yl)carbamate (200 mg, 0.23 mol) was treated with HF-urea (70%, 8 mL) and stirred at rt for 1.5 h. The reaction mixture was added to a bottle with saturated NaHCO$_3$ solution and DCM in an ice bath. The two layers were separated and the aqueous phase was extracted the DCM. The combined organic phases were dried (over Na$_2$SO$_4$), filtered, and concentrated down. The residue was purified by silica gel column chromatography (0-10% MeOH in (3/1) DCM/hexanes) to give the product.

Example 52: Preparation of Compound 169

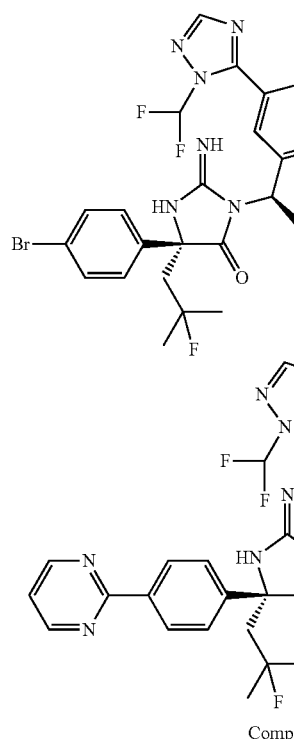

Compound 169

Preparation of Compound 169: To an argon purged solution of (S)-2-((R)-4-(4-bromophenyl)-4-(2-fluoro-2-methylpropyl)-2-imino-5-oxoimidazolidin-1-yl)-2-(4-chloro-3-(1-(difluoromethyl)-1H-1,2,4-triazol-5-yl)phenyl)ethyl (1,1-difluoro-2-methylpropan-2-yl)carbamate (95 mg, 0.13 mmol) in dioxane (3.0 mL) were added 2-(tributylstannyl)pyrimidine (75 mg, 0.19 mmol) and Pd(t-Bu$_3$P)$_2$ (17 mg, 0.033 mmol). The reaction mixture was bubbled with argon for 2 min, and stirred at 90° C. for 20 min. The reaction mixture was treated with aqueous KF solution and EtOAc.

The organic layer was separated and concentrated. The residue was purified by reverse phase HPLC (acetonitrile/H$_2$O, both containing 0.1% TFA) to give the product.

Example 53: Preparation of Compound 170 and Compound 171

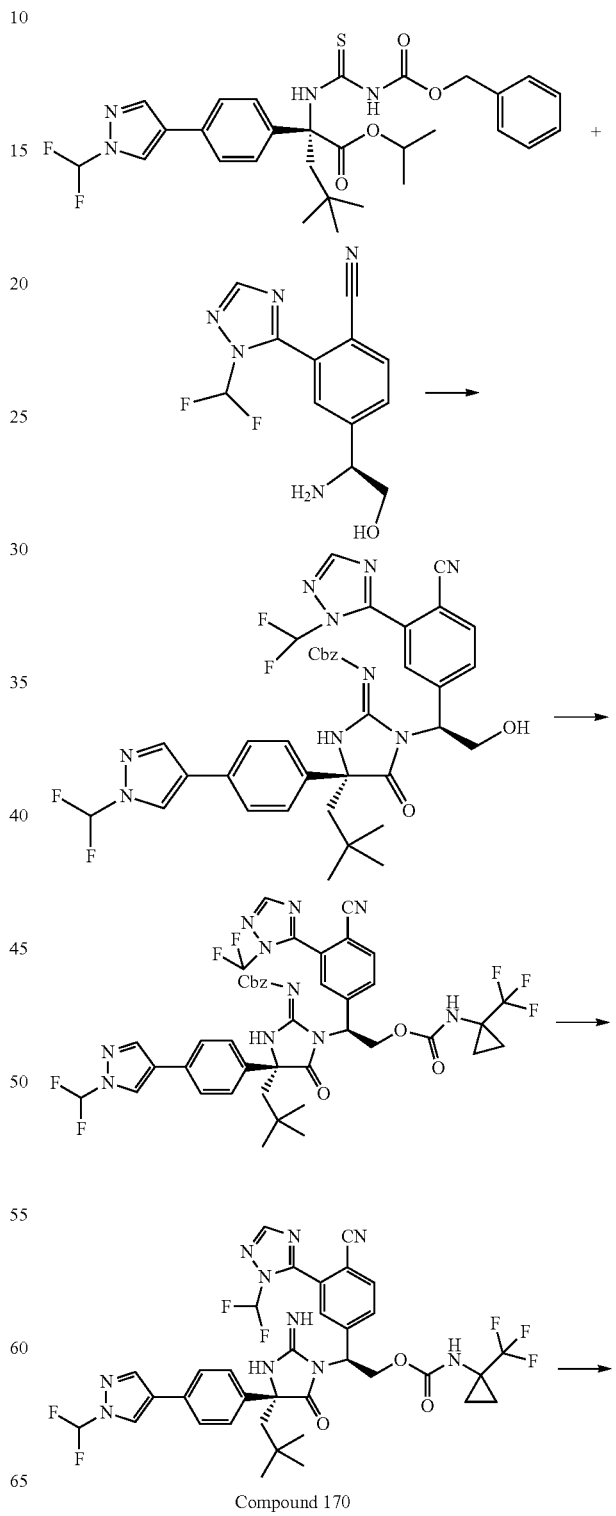

Compound 170

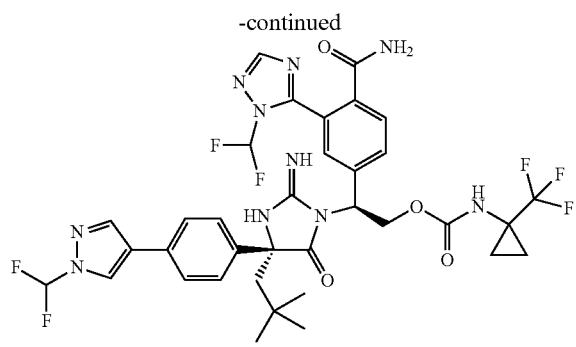

Compound 171

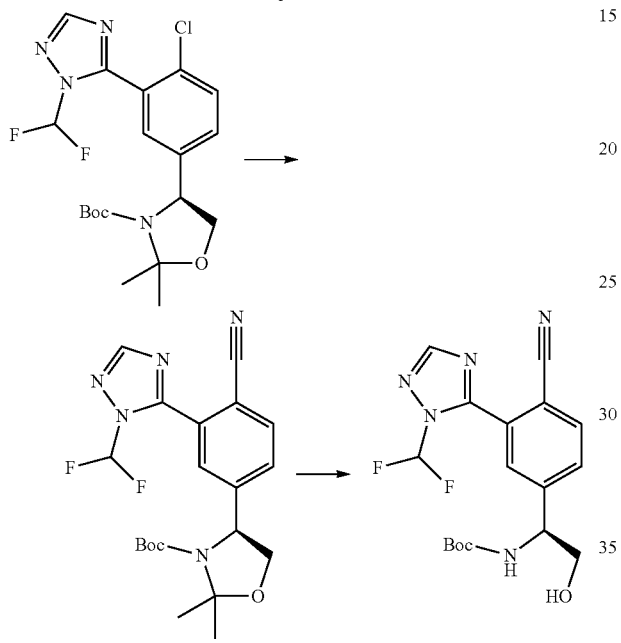

Compound 170 and Compound 171 were prepared following the procedure to prepare Compound 20, except that (S)-4-(1-amino-2-hydroxyethyl)-2-(1-(difluoromethyl)-1H-1,2,4-triazol-5-yl)benzonitrile was used instead of (S)-2-amino-2-(4-chloro-3-(pyridin-2-yl)phenyl)ethan-1-ol hydrochloride. For the final Cbz deprotection, neat TFA was used instead of boron tribromide and the reaction mixture was heated at 60° C. for 2 h. The two products were separated by HPLC.

Preparation of tert-butyl (S)-4-(4-cyano-3-(1-(difluoromethyl)-1H-1,2,4-triazol-5-yl)phenyl)-2,2-dimethyloxazolidine-3-carboxylate: A mixture of tert-butyl (S)-4-(4-chloro-3-(1-(difluoromethyl)-1H-1,2,4-triazol-5-yl)phenyl)-2,2-dimethyloxazolidine-3-carboxylate (0.3 g, 0.7 mmol), 2-dicyclohexylphosphino-2',6'-dimethoxybiphenyl (61 mg, 0.14 mmol), tris(dibenzylideneacetone) dipalladium (0) (256 mg, 0.28 mmol), zinc cyanide (493 mg, 4.21 mmol) and potassium carbonate (290 mg, 2.1 mmol) in DMF (1 mL) was flushed with argon for 15 min and then heated at 120° C. for 4 h. The reaction mixture was cooled and filtered through Celite. The filter cake was washed with ethyl acetate. The filtrate and the washing were combined, concentrated down, and the residue was purified by silica gel column chromatography (0-100% gradient EtOAc/hexanes) to give the product.

Preparation of tert-butyl (S)-(1-(4-cyano-3-(1-(difluoromethyl)-1H-1,2,4-triazol-5-yl)phenyl)-2-hydroxyethyl) carbamate: A solution of tert-butyl (S)-4-(4-cyano-3-(1-(difluoromethyl)-1H-1,2,4-triazol-5-yl)phenyl)-2,2-dimethyloxazolidine-3-carboxylate (41.3 mg, 0.098 mmol) in trifluoroacetic acid/water (3:1, 4 mL) stirred at rt for 3 h. The mixture was then concentrated to dryness. The crude material was directly used in the next reaction without further purification.

Example 54: Preparation of Compound 172

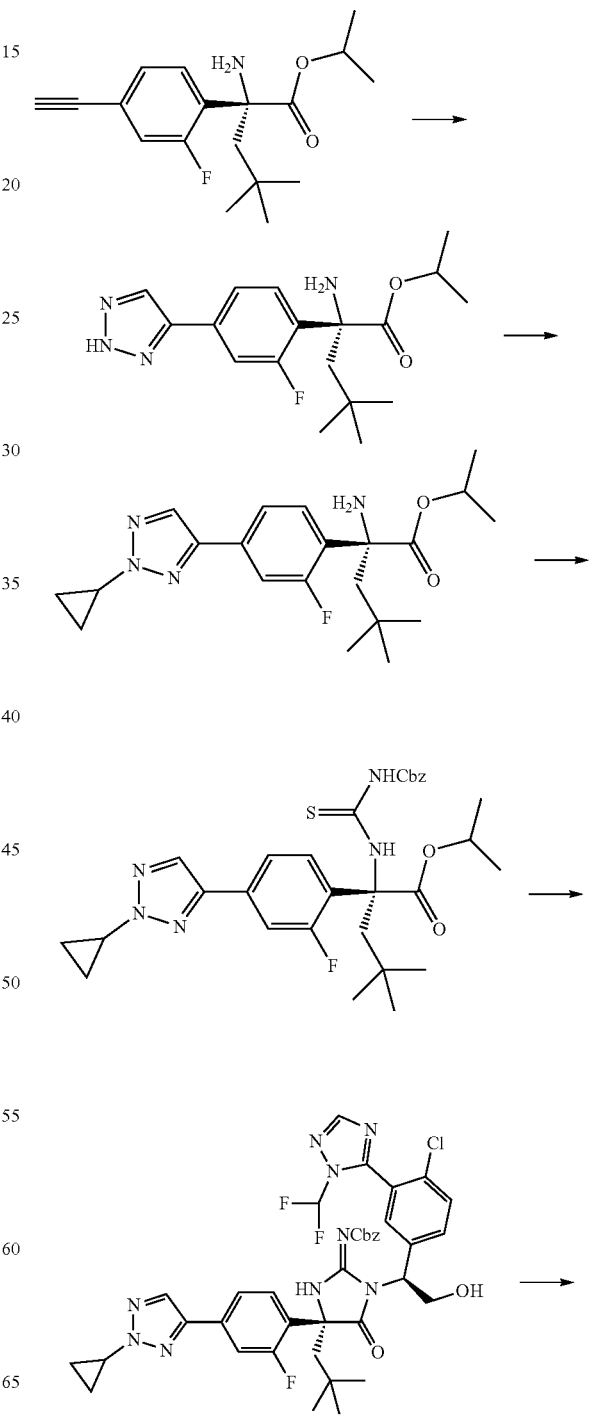

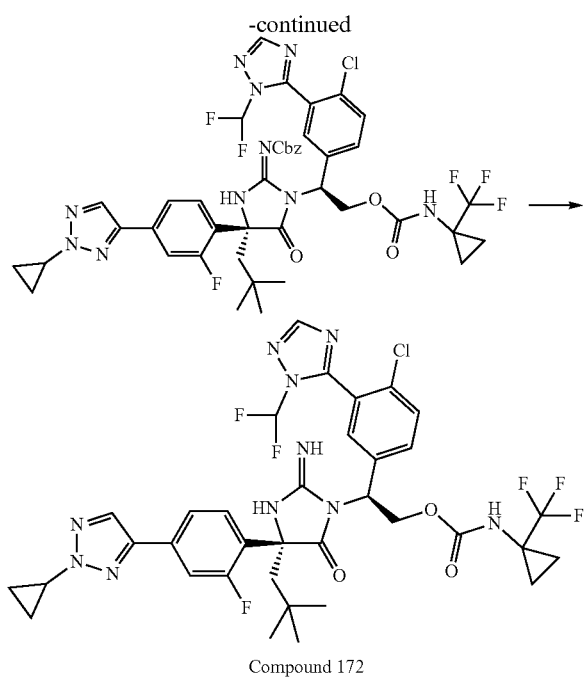

Compound 172

Preparation of isopropyl (R)-2-amino-2-(2-fluoro-4-(1H-1,2,3-triazol-4-yl)phenyl)-4,4-dimethylpentanoate: To a solution of isopropyl (R)-2-amino-2-(4-ethynyl-2-fluorophenyl)-4,4-dimethylpentanoate (320 mg, 1.05 mmol) in THF (4 mL) were added azidotrimethylsilane (0.2 mL, 1.45 mmol) and copper(I)-thiophene-2-carboxylate (41 mg, 0.16 mmol). The reaction was stirred at rt for 30 min. Additional azidotrimethylsilane (0.2 mL, 1.45 mmol) and copper(I)-thiophene-2-carboxylate (41 mg, 0.16 mmol) were added and the reaction mixture was stirred at rt for another 30 min. Additional azidotrimethylsilane (0.8 mL, 5.8 mmol) and copper(I)-thiophene-2-carboxylate (41 mg, 0.16 mmol) were added and the reaction mixture was stirred at rt for 3 h. The reaction mixture was then diluted with EtOAc and saturated aqueous NaHCO₃. The two layers were separated and the aqueous phase was further extracted with EtOAc. The combined organic phase was washed with brine and concentrated down. The residue was purified by silica gel column chromatography (0-100% gradient EtOAc/hexanes) to give the product.

Preparation of isopropyl (R)-2-amino-2-(4-(1-cyclopropyl-1H-1,2,3-triazol-4-yl)-2-fluorophenyl)-4,4-dimethylpentanoate: A mixture of isopropyl (R)-2-amino-2-(2-fluoro-4-(1H-1,2,3-triazol-4-yl)phenyl)-4,4-dimethylpentanoate (116 mg, 0.33 mmol), cyclopropylboronic acid (85%, 376 mg, 3.72 mmol), cupric acetate (181 mg, 1.0 mmol), N,N-diisopropylethylamine (0.70 mL, 4.0 mmol) and pyridine (0.32 mL, 4.0 mmol) was heated at 100° C. for 6 h. The reaction mixture was cooled to rt, and filtered through a pad of Celite. The filtrate was diluted with EtOAc, washed with 3% lithium chloride solution and then with saturated aqueous ammonium chloride. The organic layer was dried over MgSO₄, filtered, and concentrated. The residue was purified by silica gel column chromatography (EtOAc/hexanes) to give the product (20 mg, 15%).

Compound 172 was then prepared following the procedure to prepare Example 20, except that isopropyl (R)-2-amino-2-(4-(1-cyclopropyl-1H-1,2,3-triazol-4-yl)-2-fluorophenyl)-4,4-dimethylpentanoate was used instead of isopropyl (R)-2-(3-((benzyloxy)carbonyl)thioureido)-2-(4-(1-(difluoromethyl)-1H-pyrazol-4-yl)phenyl)-4,4-dimethylpentanoate and (S)-2-amino-2-(3-(1-(difluoromethyl)-1H-1,2,4-triazol-5-yl)-4-fluorophenyl)ethan-1-ol was used instead of (S)-2-amino-2-(4-chloro-3-(pyridin-2-yl)phenyl)ethan-1-ol.

Example 55: Preparation of Compound 173

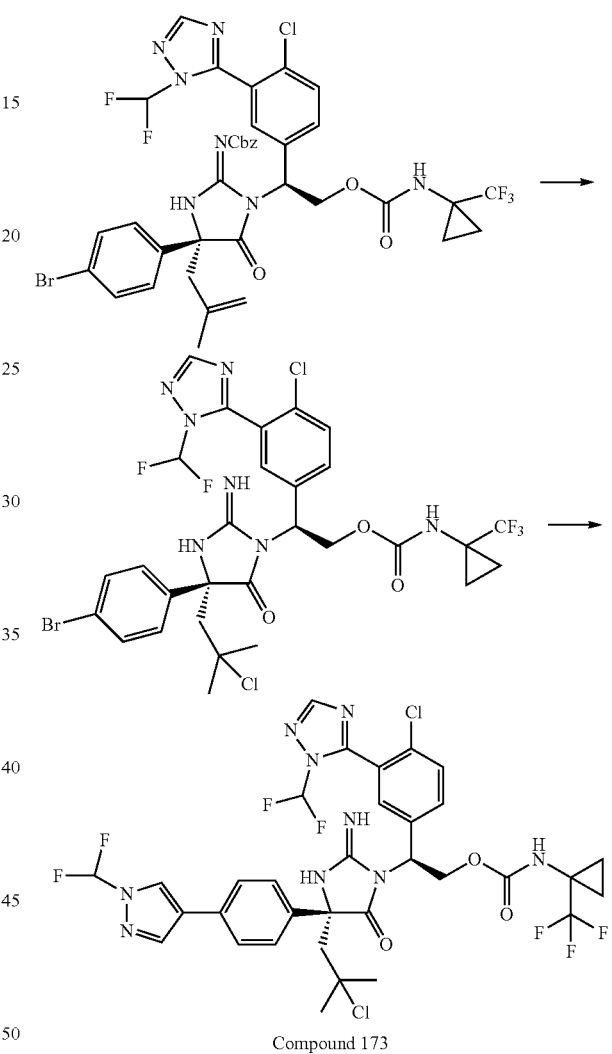

Compound 173

Preparation of (S)-2-((R)-4-(4-bromophenyl)-4-(2-chloro-2-methylpropyl)-2-imino-5-oxoimidazolidin-1-yl)-2-(4-chloro-3-(1-(difluoromethyl)-1H-1,2,4-triazol-5-yl)phenyl)ethyl (1-(trifluoromethyl)cyclopropyl)carbamate: To a solution of benzyl ((R)-4-(4-bromophenyl)-1-((S)-1-(4-chloro-3-(1-(difluoromethyl)-1H-1,2,4-triazol-5-yl)phenyl)-2-(((1-(trifluoromethyl)cyclopropyl)carbamoyl)oxy)ethyl)-4-(2-methylallyl)-5-oxoimidazolidin-2-ylidene)carbamate (100 mg, 0.12 mmol) and methanol (0.047 mL, 0.15 mol) in DCM (2 mL) was cooled under nitrogen in an ice bath. Titanium tetrachloride in DCM (1.0M, 0.063 mL) was added drop wise to the cooled olefinic solution and the reaction was stirred for 1 h. The reaction mixture was passed down a 2 cm×3 cm column of alumina, eluting with dichloromethane, and the solvent was removed to give the product.

Preparation of Compound 173: To a solution of (S)-2-((R)-4-(4-bromophenyl)-4-(2-chloro-2-methylpropyl)-2-imino-5-oxoimidazolidin-1-yl)-2-(4-chloro-3-(1-(difluoromethyl)-1H-1,2,4-triazol-5-yl)phenyl)ethyl (1-(trifluoromethyl)cyclopropyl)carbamate (10 mg, 0.013 mmol) in dioxane (1 mL) and water (0.15 mL) were added 1-(difluoromethyl)-4-(4,4,5,5-tetramethyl-1,3,2-dioxaborolan-2-yl)-1H-pyrazole (16 mg, 0.065 mmol), tetrakis(triphenylphosphine)palladium(0) (3.7 mg, 0.0033 mmol) and potassium carbonate (9 mg, 0.065 mol). The reaction mixture was stirred at 85° C. for 1 h. The reaction mixture was treated with saturated ammonium chloride solution and extracted with DCM. The organic phase was dried over MgSO$_4$, filtered and concentrated in vacuo. The crude mixture was purified by silica gel column chromatography (0-10% gradient of DCM/hexanes (2:1) and methanol) to give the product.

Example 56: Preparation of Compound 146

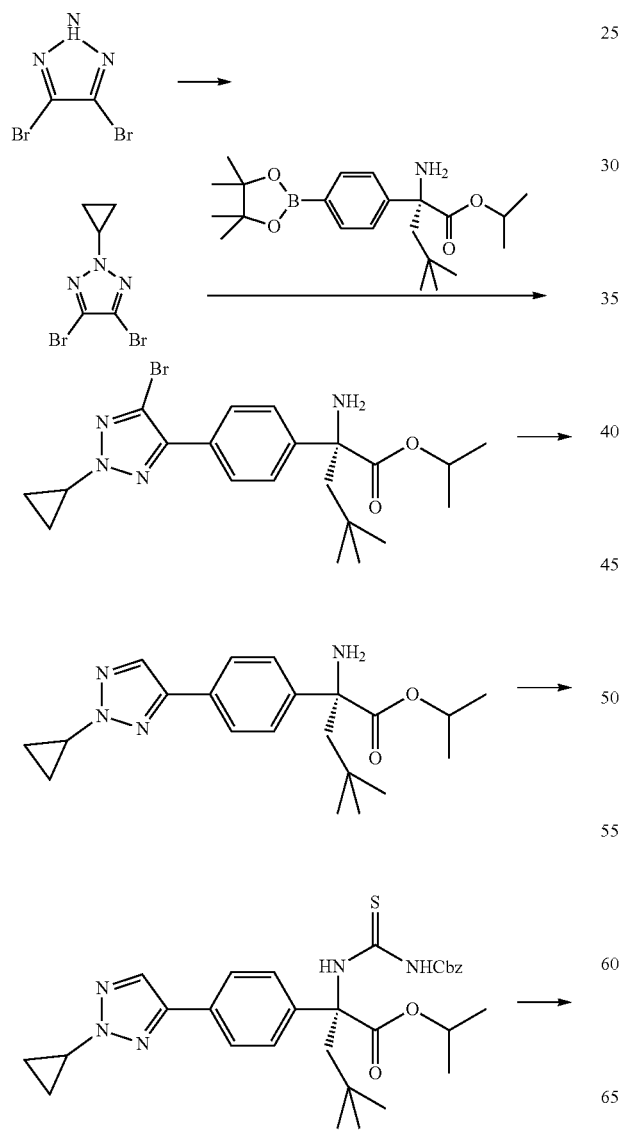

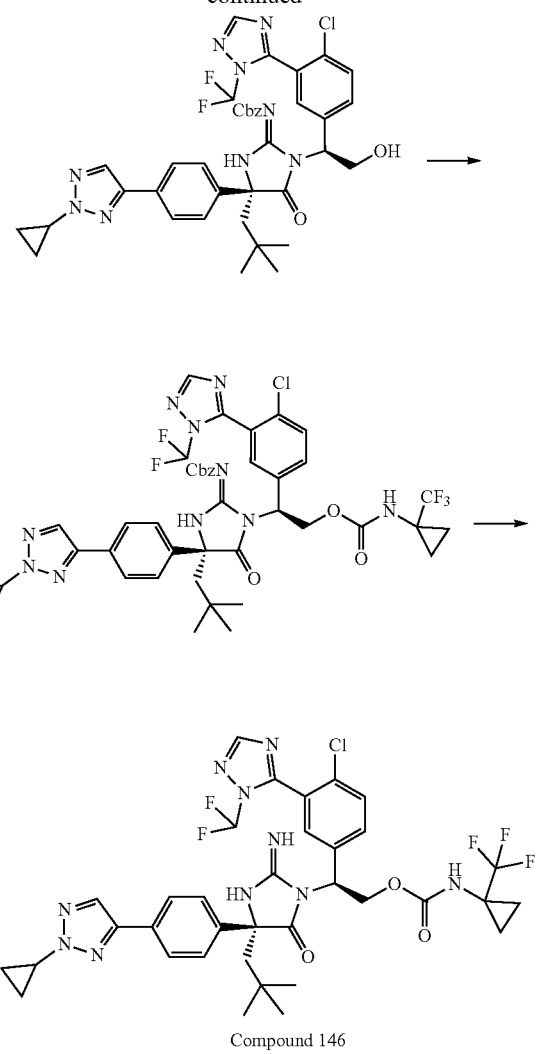

Compound 146

Preparation of 4,5-dibromo-2-cyclopropyl-2H-1,2,3-triazole: A mixture of 4,5-dibromo-2H-1,2,3-triazole (95%, 10 g, 42 mmol), cyclopropylboronic acid (7.2 g, 84 mmol), cupric acetate (anhydrous, 7.6 g, 42 mmol), 2,2'-bipyridyl (6.6 g, 42 mmol), sodium carbonate (8.9 g, 84 mmol) in DCE (15 mL) was stirred at 75° C. overnight. Then the reaction mixture was stirred at rt for 3 days. The reaction mixture was diluted with isopropyl acetate and sequentially washed with saturated ammonium chloride solution, 1M HCl solution and saturated NaHCO$_3$ solution. The organic phase was dried over MgSO$_4$, filtered, concentrated down and purified by silica gel column chromatography, eluting by 0-100% gradient EtOAc/hexanes, to give the product.

Preparation of isopropyl (R)-2-amino-2-(4-(5-bromo-2-cyclopropyl-2H-1,2,3-triazol-4-yl)phenyl)-4,4-dimethylpentanoate: To a solution of 4,5-dibromo-2-cyclopropyl-2H-1,2,3-triazole (433 mg, 1.63 mmol) and isopropyl (R)-2-amino-2-(3-fluoro-4-(4,4,5,5-tetramethyl-1,3,2-dioxaborolan-2-yl)phenyl)-4,4-dimethylpentanoate (300 mg, 0.77 mmol) in dioxane (2 mL) and water (0.35 mL) were added Pd(PPh$_3$)$_4$ (178 mg, 0.15 mmol), K$_2$CO$_3$ (200 mg, 1.45 mmol). The reaction mixture was stirred at 90° C. for 1 h. The reaction mixture was treated with saturated ammonium chloride solution and extracted with DCM. The organic phase was dried over MgSO₄, filtered and concentrated in vacuo. The reaction mixture was purified by silica gel column chromatography (0-100% gradient EtOAc/hexanes) to give the product.

Preparation of isopropyl (R)-2-amino-2-(4-(2-cyclopropyl-2H-1,2,3-triazol-4-yl)phenyl)-4,4-dimethylpentanoate: The reaction mixture of isopropyl (R)-2-amino-2-(4-(5-bromo-2-cyclopropyl-2H-1,2,3-triazol-4-yl)phenyl)-4,4-dimethylpentanoate (70%, 450 mg, 0.7 mmol) and Pd/C (5%, 275 mg) in ethanol (5 mL) and isopropyl alcohol (5 mL) was stirred at rt with hydrogen balloon for 1 h. The reaction mixture was filtered through Celite. The filtrated was concentrated down and directly used in the next reaction.

Compound 146 was prepared following the procedure to prepare Example 44, except that (S)-2-amino-2-(4-chloro-3-(1-(difluoromethyl)-1H-1,2,4-triazol-5-yl)phenyl)ethan-1-ol was used instead of (S)-2-amino-2-(4-chloro-3-(pyridin-2-yl)phenyl)ethan-1-ol hydrochloride and isocyanato-1-(trifluoromethyl)cyclopropane was used instead of 1-isocyanato-1-methylcyclopropane.

Example 57: Preparation of Compound 175

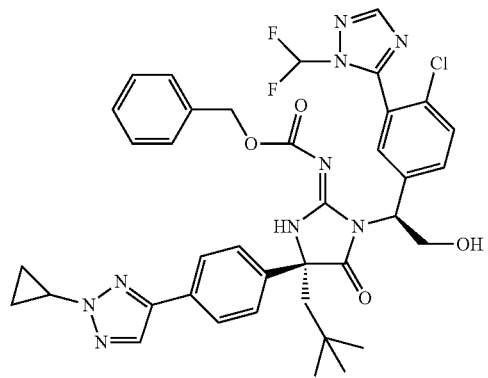

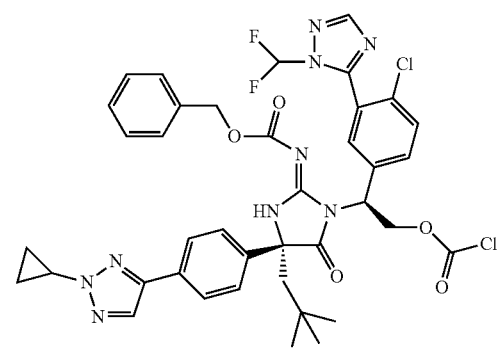

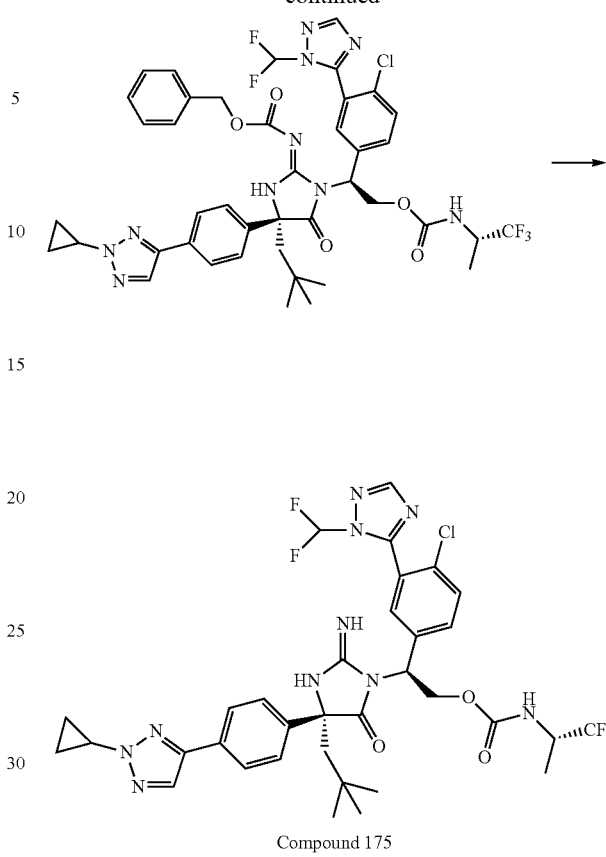

Compound 175

Preparation of benzyl ((R)-1-((S)-1-(4-chloro-3-(1-(difluoromethyl)-1H-1,2,4-triazol-5-yl)phenyl)-2-((((S)-1,1,1-trifluoropropan-2-yl)carbamoyl)oxy)ethyl)-4-(4-(2-cyclopropyl-2H-1,2,3-triazol-4-yl)phenyl)-4-neopentyl-5-oxoimidazolidin-2-ylidene)carbamate: To a solution of benzyl ((R)-1-((S)-1-(4-chloro-3-(1-(difluoromethyl)-1H-1,2,4-triazol-5-yl)phenyl)-2-hydroxyethyl)-4-(4-(2-cyclopropyl-2H-1,2,3-triazol-4-yl)phenyl)-4-neopentyl-5-oxoimidazolidin-2-ylidene)carbamate (54 mg, 0.071 mmol) in DCM (3 mL) was added 2,6-di-tert-butyl-4-methylpyridine (0.06 mL, 0.43 mmol) and triphosgene (12.7 mg, 0.043 mmol). The reaction mixture was stirred at rt for 1 h. Then to the mixture were added N,N-diisopropylethylamine (0.04 mL, 0.21 mmol) and (S)-1,1,1-trifluoro-2-propylamine (0.04 g, 0.35 mmol). The reaction mixture was stirred at rt for 1 h. The reaction mixture was diluted with EtOAc and washed with saturated ammonium chloride solution. The organic phase was concentrated down. The residue was purified by silica gel column chromatography (0-100% gradient EtOAc/hexanes) to give the product.

Preparation of Compound 175: A solution of benzyl ((R)-1-((S)-1-(4-chloro-3-(1-(difluoromethyl)-1H-1,2,4-triazol-5-yl)phenyl)-2-((((S)-1,1,1-trifluoropropan-2-yl)carbamoyl)oxy)ethyl)-4-(4-(2-cyclopropyl-2H-1,2,3-triazol-4-yl)phenyl)-4-neopentyl-5-oxoimidazolidin-2-ylidene) carbamate (58 mg, 0.064 mmol) in TFA (2 mL) was stirred at 45° C. overnight. The reaction mixture was then concentrated down and the residue was purified by reverse phase HPLC (acetonitrile/water, both containing 0.1% TFA) to give the product.

Example 58: Preparation of Compound 176
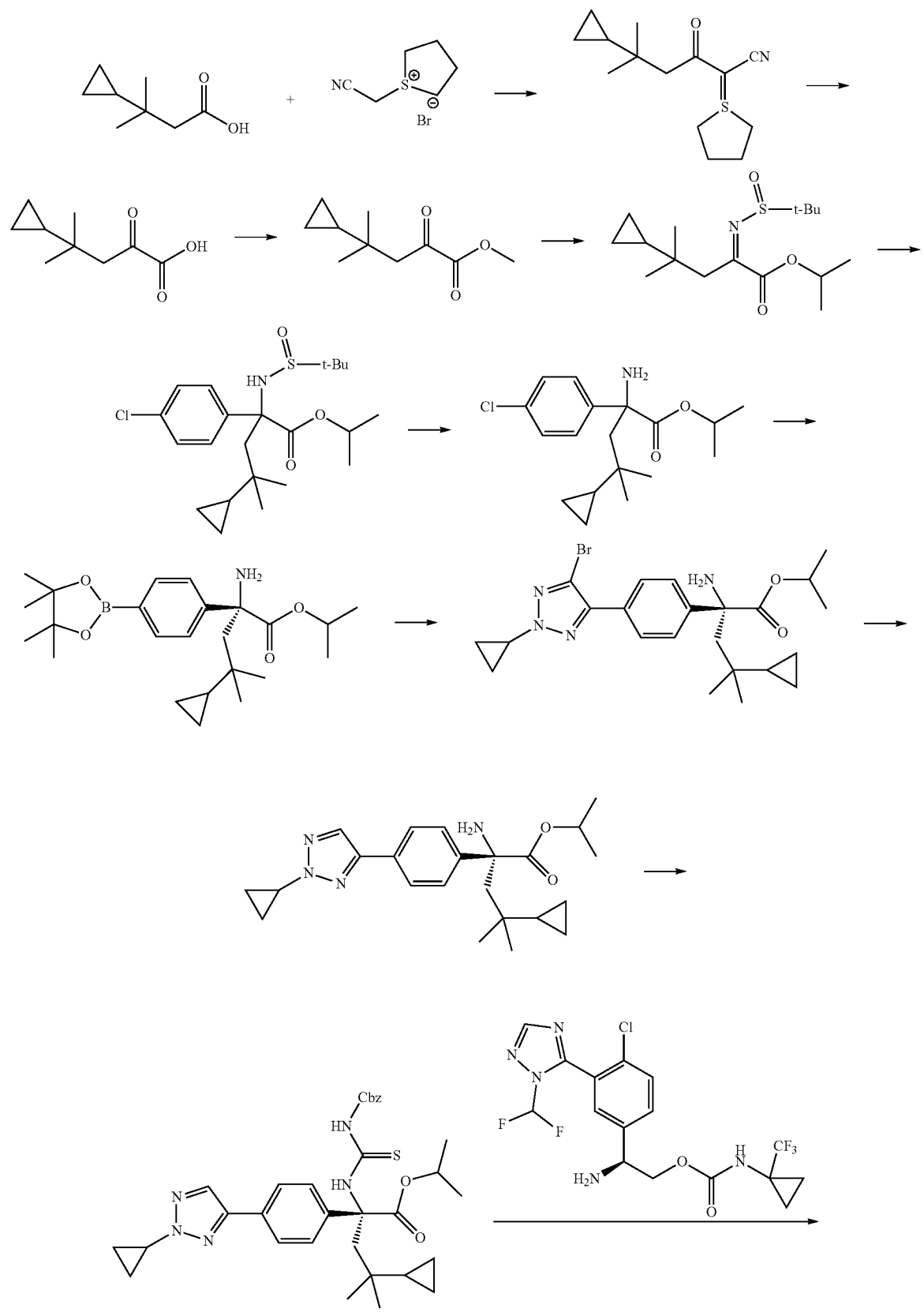

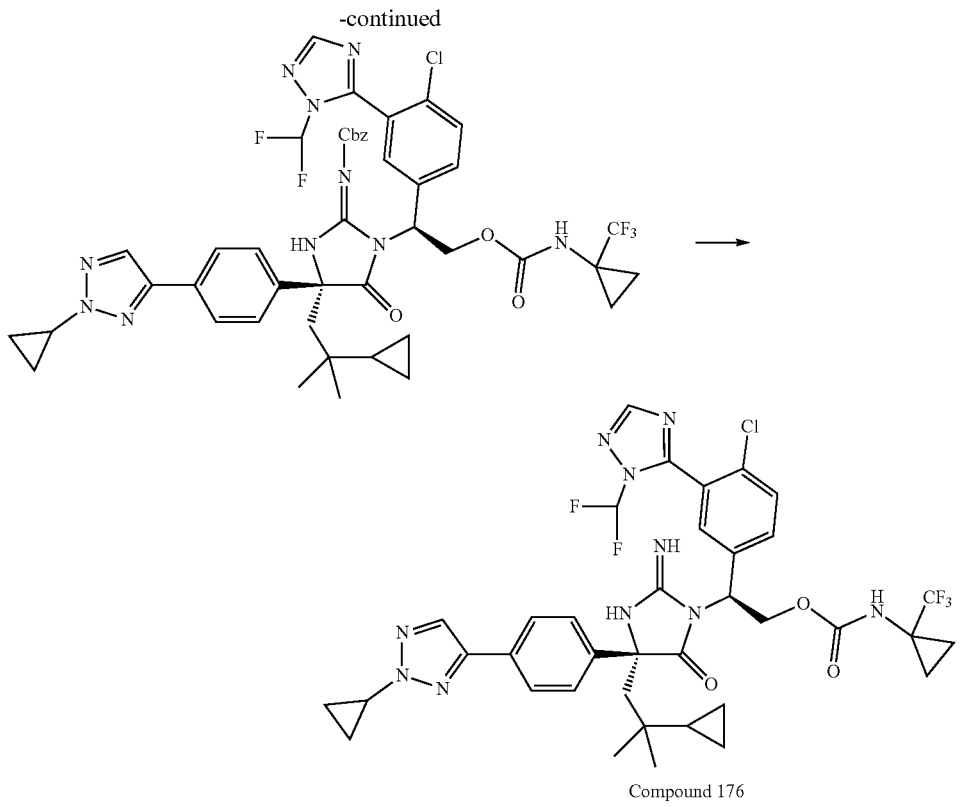

Compound 176

Preparation of 5-cyclopropyl-5-methyl-3-oxo-2-(tetrahydro-1-thiophen-1-ylidene)hexanenitrile: 3-Cyclopropyl-3-methylbutanoic acid (3.0 g, 0.021 mol) and 2-(7-aza-1H-benzotriazole-1-yl)-1,1,3,3-tetramethyluronium hexafluorophosphate (HATU) (10.3 g, 0.032 mol) were suspended in $CH_2Cl_2$ (3 mL). Then N,N-diisopropylethylamine (11 mL, 0.063 mol) and cyanosulfonium bromide (6.59 g, 0.032 mol) were added to give a yellow suspension. The reaction mixture was stirred for 1 h at rt and then poured into saturated aqueous $NH_4Cl$. After separating the layers, the aqueous layer was extracted with $CH_2Cl_2$. The combined organic layers were washed with brine, dried over $Na_2SO_4$, filtered, and concentrated. The residue was purified by silica gel column chromatography (EtOAc/hexanes) to give the product.

Preparation of 4-cyclopropyl-4-methyl-2-oxopentanoic acid: 5-cyclopropyl-5-methyl-3-oxo-2-(tetrahydro-1-thiophen-1-ylidene)hexanenitrile (5.3 g, 21 mmol) was dissolved in THF (80 mL) and $H_2O$ (40 mL). Oxone (26 g, 42 mmol) was added and the white suspension was stirred vigorously for 30 min. The reaction mixture was then poured into water and diethyl ether. After the layers were separated, the aqueous phase was extracted with 2×180 mL diethyl ether. The combined organic layers were dried over $Na_2SO_4$, filtered, and concentrated. Not all solvent was removed. This material was taken into the next step without further purification.

Preparation of methyl 4-cyclopropyl-4-methyl-2-oxopentanoate: To a solution of the 4-cyclopropyl-4-methyl-2-oxopentanoic acid (2.0 g, 12 mmol) in DCM (3.0 mL) was added triethylamine (1.64 mL, 12 mmol) and the solution was cooled at 0° C. To this solution was then added ethylchloroformate (0.91 mL, 12 mmol) and stirred for 30 min. After this period, the reaction mixture was partitioned between water and diethyl ether. The diethyl ether layer was taken and the aqueous layer was extracted with diethyl ether. The combined organic layers was dried over magnesium sulfate, filtered, and concentrated. The residue was purified by silica gel column chromatography (pentanes/diethyl ether) to give the product.

Preparation of isopropyl 2-((tert-butylsulfinyl)imino)-4-cyclopropyl-4-methylpentanoate: To a solution of methyl 4-cyclopropyl-4-methyl-2-oxopentanoate (1.95 g, 11 mmol) in hexanes (70 mL) were added (R)-2-methylpropane-2-sulfinamide (1.92 g, 16 mmol) and Ti(O-iPr)$_4$ (4.51 g, 16 mmol). The reaction mixture was stirred at rt overnight. The reaction mixture was solid loaded and purified by silica gel column chromatography (0-100% EtOAc/hexanes) to give the product (1.1 g, 33%).

Preparation of isopropyl 2-((tert-butylsulfinyl)amino)-2-(4-chlorophenyl)-4-cyclopropyl-4-methylpentanoate: A solution of isopropyl 2-((tert-butylsulfinyl)imino)-4-cyclopropyl-4-methylpentanoate (1.1 g, 3.49 mmol) in THF (20 mL) and DCM (10 mL) was cooled down to −78° C. under argon. Then, (4-chlorophenyl)magnesium bromide (1M, 5.23 mL) was added dropwise. The reaction mixture was then stirred at the same temperature for 1 h. At −78° C., saturated aqeuous $NH_4Cl$ was added to quench the reaction. The mixture was warmed up to rt and extracted with EtOAc. The organic phase was washed with brine, filtered, and concentrated. The residue was purified by silica gel column chromatography (0-100% gradient EtOAc/hexanes) to give the product.

Preparation of isopropyl 2-amino-2-(4-chlorophenyl)-4-cyclopropyl-4-methylpentanoate: The solution of isopropyl 2-((tert-butylsulfinyl)amino)-2-(4-chlorophenyl)-4-cyclopropyl-4-methylpentanoate (0.73 g, 1.73 mmol) in HCl in dioxane (4M, 10 mL) was stirred at rt for 20 min. Then the reaction mixture was concentrated to dryness. The residue was partitioned between EtOAc and saturated aqueous NaHCO₃. The organic phase was washed with brine, dried over MgSO₄, filtered, and concentrated. The residue was processed immediately in the next step.

Preparation of isopropyl (R)-2-amino-4-cyclopropyl-4-methyl-2-(4-(4,4,5,5-tetramethyl-1,3,2-dioxaborolan-2-yl)phenyl)pentanoate: A mixture of isopropyl 2-amino-2-(4-chlorophenyl)-4-cyclopropyl-4-methylpentanoate (280 mg, 0.86 mmol), bis(pinacolato) diboron (439 mg, 1.73 mmol), potassium acetate (255 mg, 2.59 mmol) and SPhos palladacycle pre-cat (125 mg, 0.17 mmol) in dioxane (3.0 mL) was sparged with argon for 5 min, and heated at 100° C. for 2 h. The reaction mixture was treated with saturated aqueous ammonium chloride and extracted with DCM. The organic phase was dried over MgSO₄, filtered and concentrated in vacuo. Then the reaction mixture was purified by silica gel column chromatography (0-70% EtOAc/hexanes) to give the product.

Compound 176 was then prepared following the procedure to prepare Compound 175, except that (S)-2-amino-2-(4-chloro-3-(1-(difluoromethyl)-1H-1,2,4-triazol-5-yl)phenyl)ethyl (1-(trifluoromethyl)cyclopropyl)carbamate was used instead of (S)-2-amino-2-(4-chloro-3-(1-(difluoromethyl)-1H-1,2,4-triazol-5-yl)phenyl)ethan-1-ol.

Example 59: Preparation of Compound 152

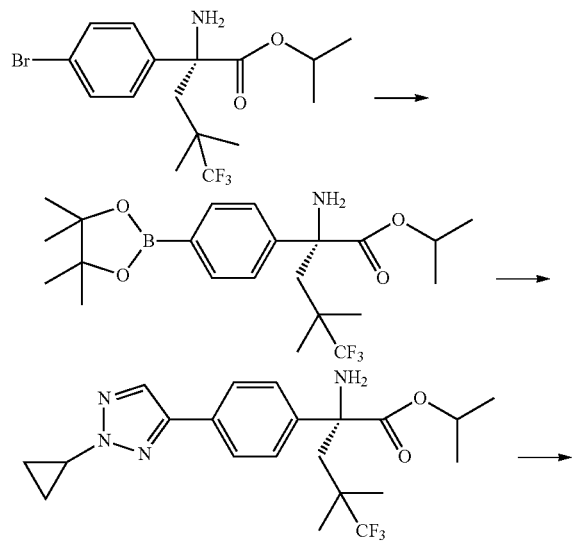

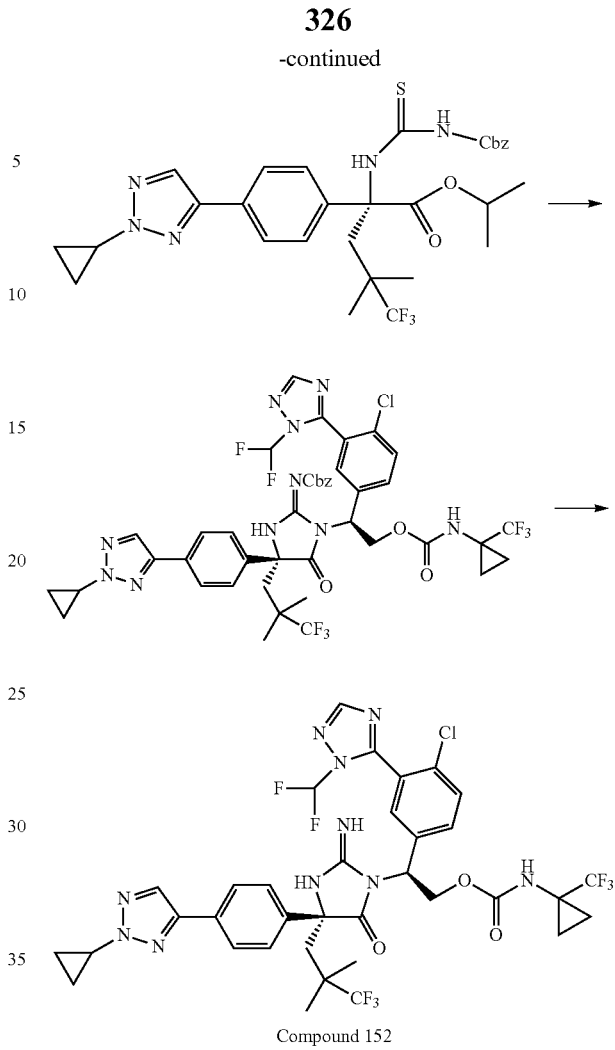

Compound 152

Compound 152 was prepared by following the procedure similar to that for preparation of isopropyl (R)-2-amino-2-(4-(2-cyclopropyl-2H-1,2,3-triazol-4-yl)phenyl)-4,4-dimethylpentanoate (Compound 147), except isopropyl (R)-2-amino-2-(4-bromophenyl)-5,5,5-trifluoro-4,4-dimethylpentanoate was used instead of isopropyl (R)-2-amino-2-(4-bromophenyl)-4,4-dimethylpentanoate.

Example 60: Preparation of Compound 154

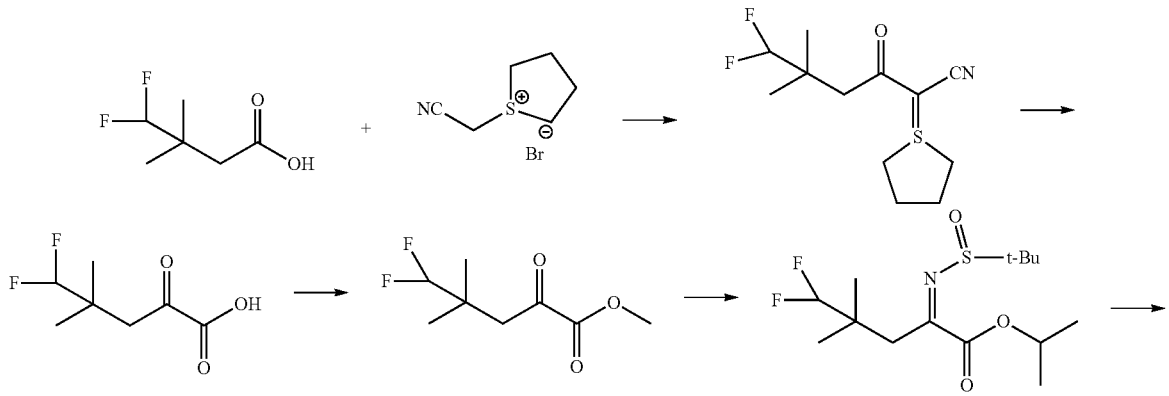

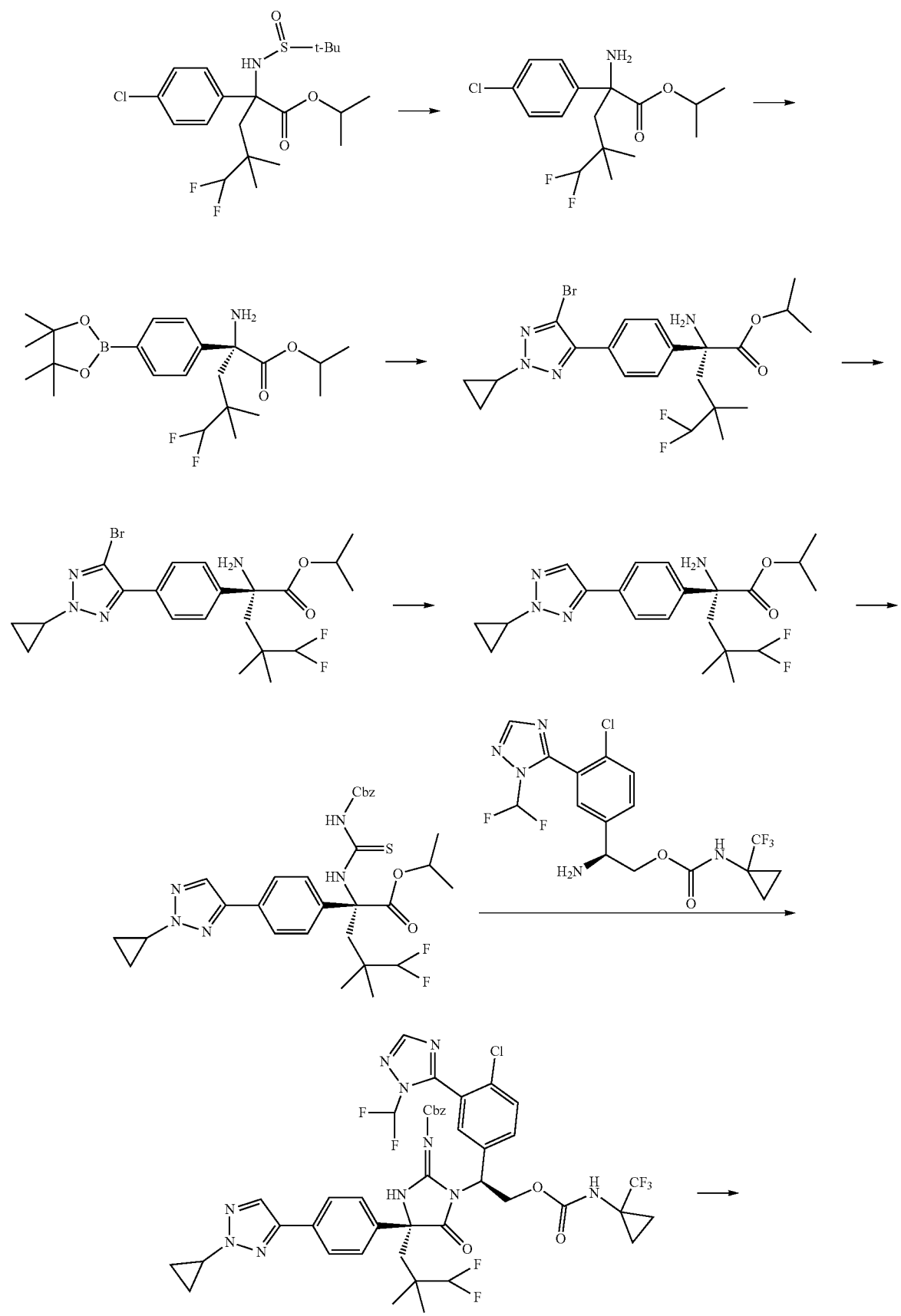

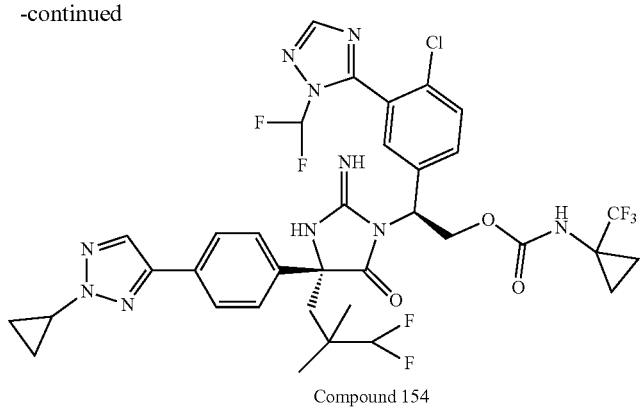
Compound 154
Compound 154 was prepared in a manner similar to that for preparation of Compound 149, except that 4,4-difluoro-3,3-dimethylbutoic acid was used as a starting material instead of 3-cyclopropyl-3-methylbutoic acid.
Example 61: Preparation of Compound 155
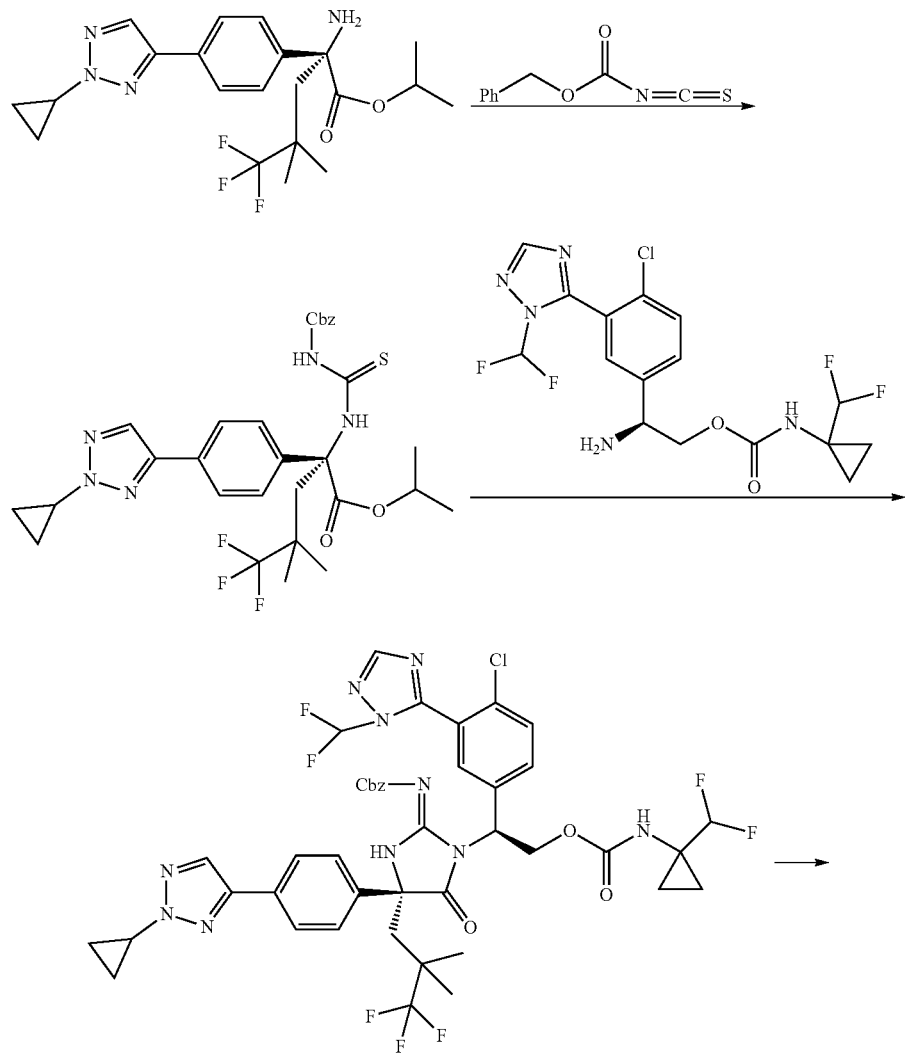

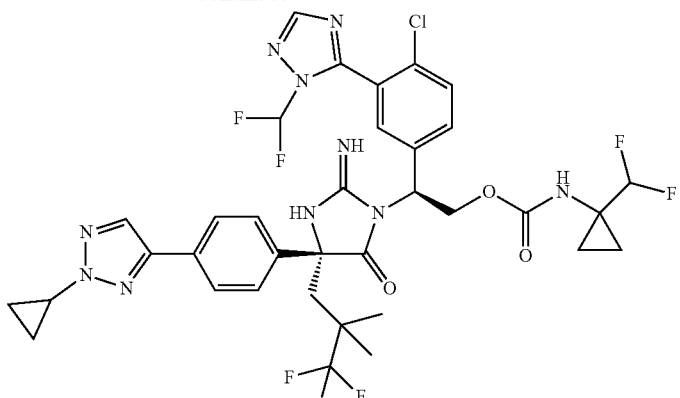

Compound 155

Preparation of isopropyl (R)-2-(3-((benzyloxy)carbonyl) thioureido)-2-(4-(2-cyclopropyl-2H-1,2,3-triazol-4-yl)phenyl)-5,5,5-trifluoro-4,4-dimethylpentanoate: To a gently stirred biphasic solution of isopropyl (R)-2-amino-2-(4-(2-cyclopropyl-2H-1,2,3-triazol-4-yl)phenyl)-5,5,5-trifluoro-4,4-dimethylpentanoate (1600 mg, 3.8 mmol) in EtOAc (10 mL) and aq. saturated NaHCO₃ (15 mL) was added O-benzyl carbonisothiocyanatidate (1240 mg, 6.4 mmol). The reaction mixture was maintained at rt for 90 min. The layers were separated and the aqueous layer was further extracted with EtOAc. The combined organic layers were washed with brine. The crude mixture was purified by SiO2 column chromatography (ISCO gold, column; 0-100% EtOAc/hexanes) to afford the product (98%).

Preparation of (S)-2-((R)-2-(((benzyloxy)carbonyl)imino)-4-(4-(2-cyclopropyl-2H-1,2,3-triazol-4-yl)phenyl)-5-oxo-4-(3,3,3-trifluoro-2,2-dimethylpropyl)imidazolidin-1-yl)-2-(4-chloro-3-(1-(difluoromethyl)-1H-1,2,4-triazol-5-yl)phenyl)ethyl (1-(difluoromethyl)cyclopropyl)carbamate: To a solution of (S)-2-amino-2-(4-chloro-3-(1-(difluoromethyl)-1H-1,2,4-triazol-5-yl)phenyl)ethyl (1-(difluoromethyl)cyclopropyl)carbamate (460 mg, 1.1 mmol) and isopropyl (R)-2-amino-2-(4-(2-cyclopropyl-2H-1,2,3-triazol-4-yl)phenyl)-5,5,5-trifluoro-4,4-dimethylpentanoate (566 mg, 0.89 mmol) in dry DMF (5 mL) were added DIEA (1 mL, 5.5 mmol) and EDCI (513 mg, 2.7 mmol) sequentially at rt under argon atmosphere. The reaction mixture was then stirred at rt for 2 h and then was heated at 50° C. over 17 h. After cooling to rt, the mixture was diluted with EtOAc, washed with aq. NaHCO₃ and then with brine, and concentrated. The residue was purified on silica gel column with 0-100% EtOAc/hexanes to give the product (95%).

Preparation of Compound 155: (S)-2-((R)-2-(((benzyloxy)carbonyl)imino)-4-(4-(2-cyclopropyl-2H-1,2,3-triazol-4-yl)phenyl)-5-oxo-4-(3,3,3-trifluoro-2,2-dimethylpropyl)imidazolidin-1-yl)-2-(4-chloro-3-(1-(difluoromethyl)-1H-1,2,4-triazol-5-yl)phenyl)ethyl (1-(difluoromethyl)cyclopropyl)carbamate (809 mg, 0.86 mmol) was dissolved in TFA (36 mL) and heated at 80° C. for 1 hr. After cooling to rt, the mixture was concentrated to dryness. The residue was purified on silica gel column eluted with 0-100% EtOAc/hexanes to afford the product (76%).

Example 62: Preparation of Compound 156

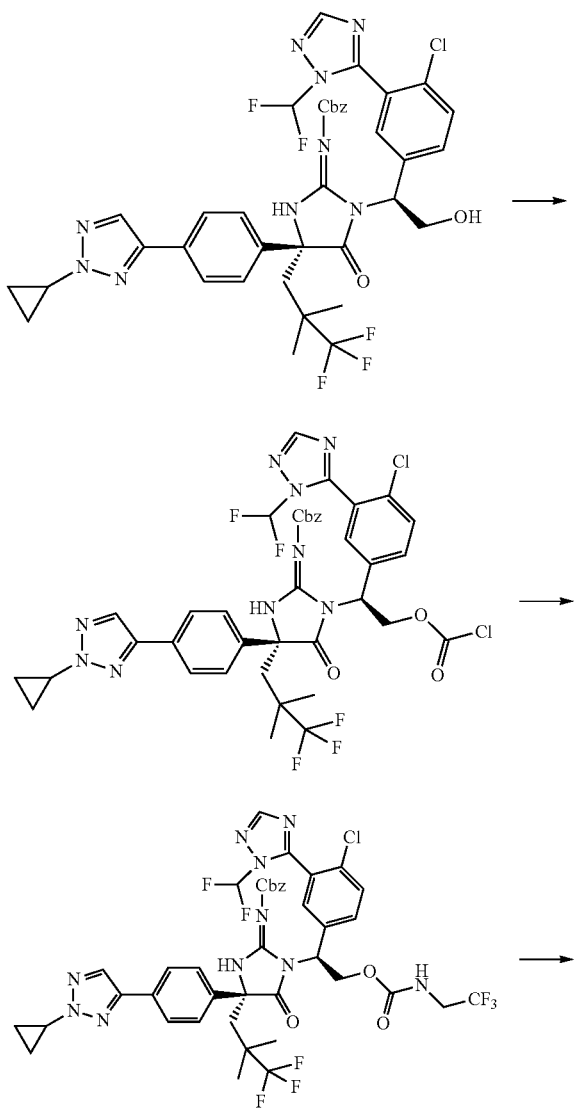

-continued

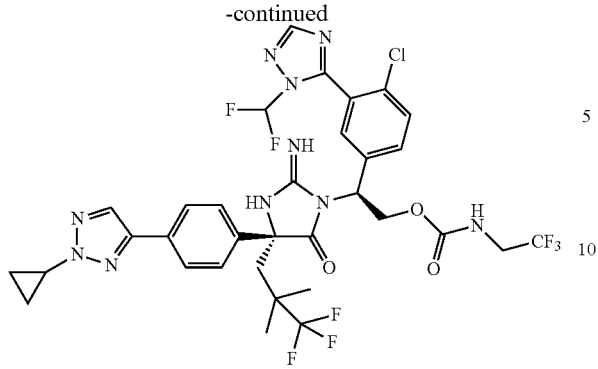

Compound 156 was prepared starting from benzyl ((R)-1-((S)-1-(4-chloro-3-(1-(difluoromethyl)-1H-1,2,4-triazol-5-yl)phenyl)-2-hydroxyethyl)-4-(4-(2-cyclopropyl-2H-1,2,3-triazol-4-yl)phenyl)-5-oxo-4-(3,3,3-trifluoro-2,2-dimethylpropyl)imidazolidin-2-ylidene)carbamate, following the procedure to prepare Compound 147, except that trifluoroethylamine was used to form carbamate instead of (S)-1,1,1-trifluoropropan-2-amine.

Example 63: Preparation of Compound 160

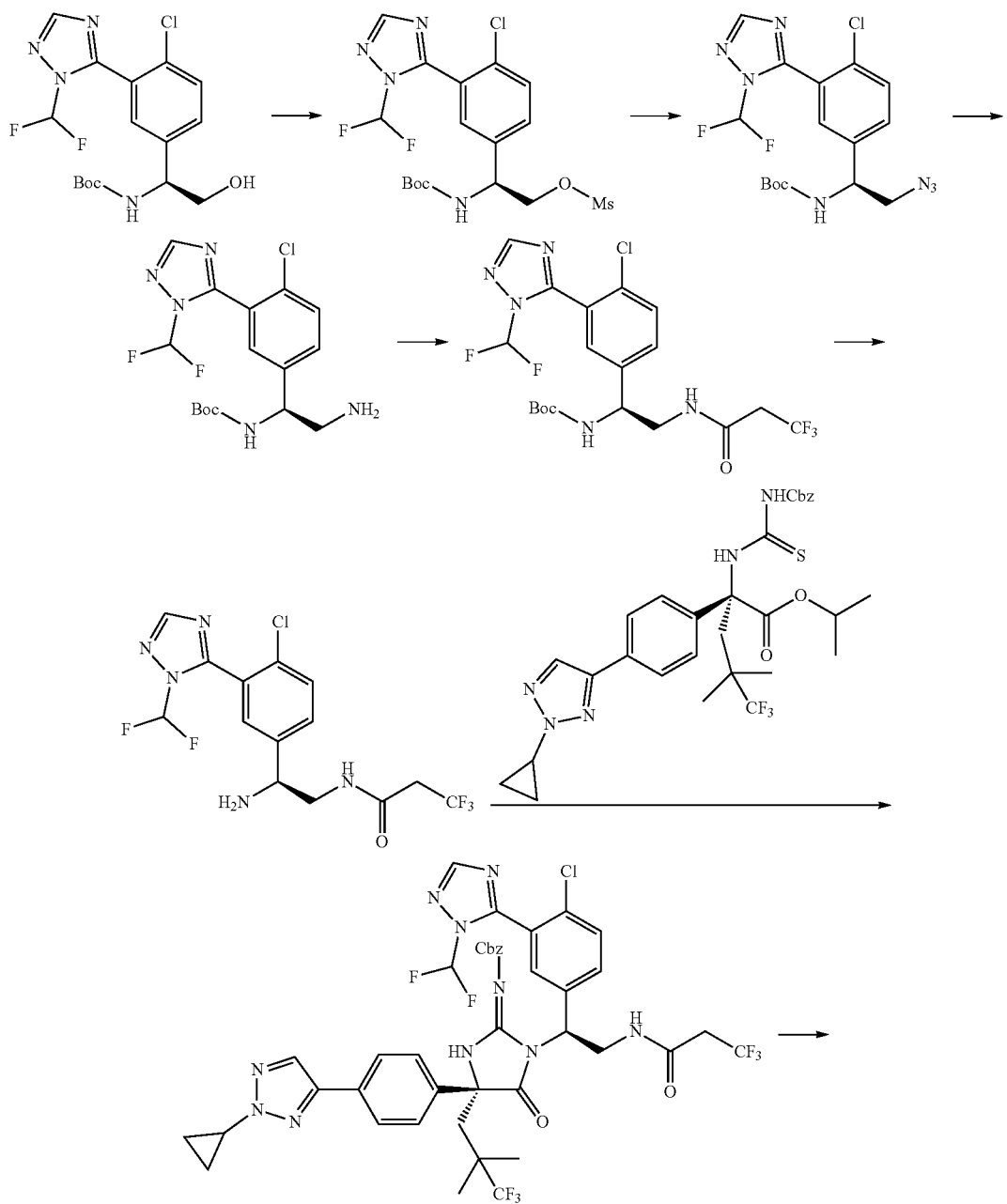

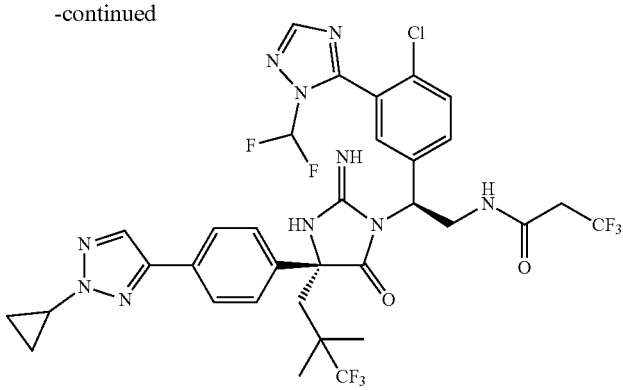

Compound 160

Compound 160 was prepared following the procedure to prepare Compound 383, except that tert-butyl (S)-(1-(4-chloro-3-(1-(difluoromethyl)-1H-1,2,4-triazol-5-yl)phenyl)-2-hydroxyethyl)carbamate was used as starting material instead of tert-butyl (S)-(2-amino-1-(4-chloro-3-(5-(difluoromethyl)-1H-1,2,4-triazol-1-yl)phenyl)ethyl)carbamate.

Example 64: Preparation of Compound 161 and Compound 162

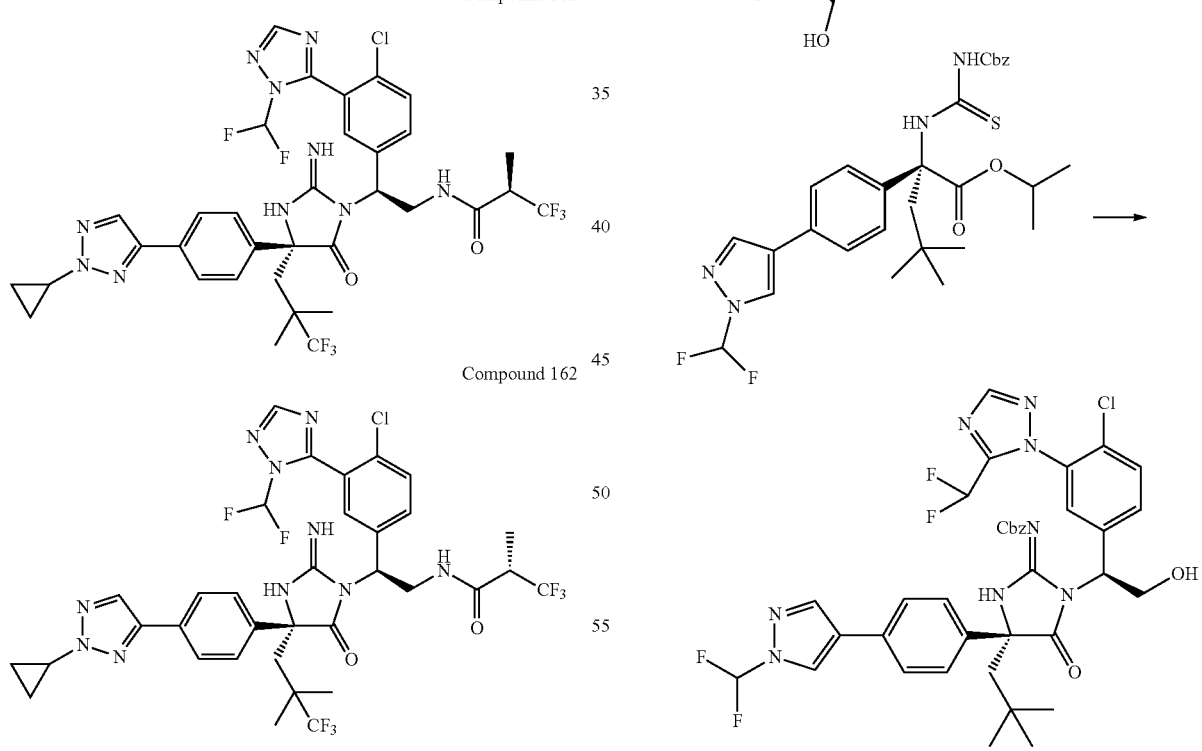

Compound 161 and Compound 162 were prepared following the procedure to prepare Compound 160 except that 3,3,3-trifluoro-2-methylpropanoic acid was used to form the amide instead of 3,3,3-trifluoropropanoic acid. The two stereoisomers were separated by chiral HPLC.

Preparation of benzyl ((R)-1-((S)-1-(4-chloro-3-(5-(difluoromethyl)-1H-1,2,4-triazol-1-yl)phenyl)-2-hydroxyethyl)-4-(4-(1-(difluoromethyl)-1H-pyrazol-4-yl)phenyl)-4-neopentyl-5-oxoimidazolidin-2-ylidene)carbamate: To a solution of (S)-2-amino-2-(4-chloro-3-(5-(difluoromethyl)-1H-1,2,4-triazol-1-yl)phenyl)ethan-1-ol TFA salt (50 mg, 0.17 mmol), isopropyl (R)-2-(3-((benzyloxy)carbonyl) thioureido)-2-(4-(1-(difluoromethyl)-1H-pyrazol-4-yl)phenyl)-4,4-dimethylpentanoate (99 mg, 0.17 mmol) and 1-(3-dimethylaminopropyl)-3-ethylcarbodiimide hydrochloride (100 mg, 0.52 mmol) in DMF (1.7 mL) was added N,N-diisopropylethylamine (0.15 mL, 0.87 mmol). The reaction mixture was stirred at 65° C. overnight. The reaction mixture was cooled to rt, treated with saturated aqueous NH$_4$Cl, and extracted with EtOAc. The layers were separated and the aqueous layer was further extracted with EtOAc. The combined organic layers were washed with 10% aqueous LiCl and then with brine, dried (over Na$_2$SO$_4$), filtered and concentrated in vacuo. The crude mixture was purified by silica gel column chromatography (eluting with 0-100% EtOAc/hexanes) to afford the product. LCMS-ESI+ (m/z): [M+H]+ calc'd for C$_{37}$H$_{35}$ClF$_4$N$_8$O$_4$: 767.2. found: 767.3. 1H NMR (400 MHz, Chloroform-d) δ 9.52 (s, 1H), 8.04 (m, 2H), 7.92 (s, 1H), 7.66-6.97 (m, 12H), 6.62 (t, J=52.6 Hz, 1H), 5.44 (d, J=5.8 Hz, 1H), 5.38-5.11 (m, 2H), 4.35-4.05 (m, 3H), 2.29-2.09 (m, 2H), 0.86 (s, 9H).

Example 65: Preparation of Compound 177

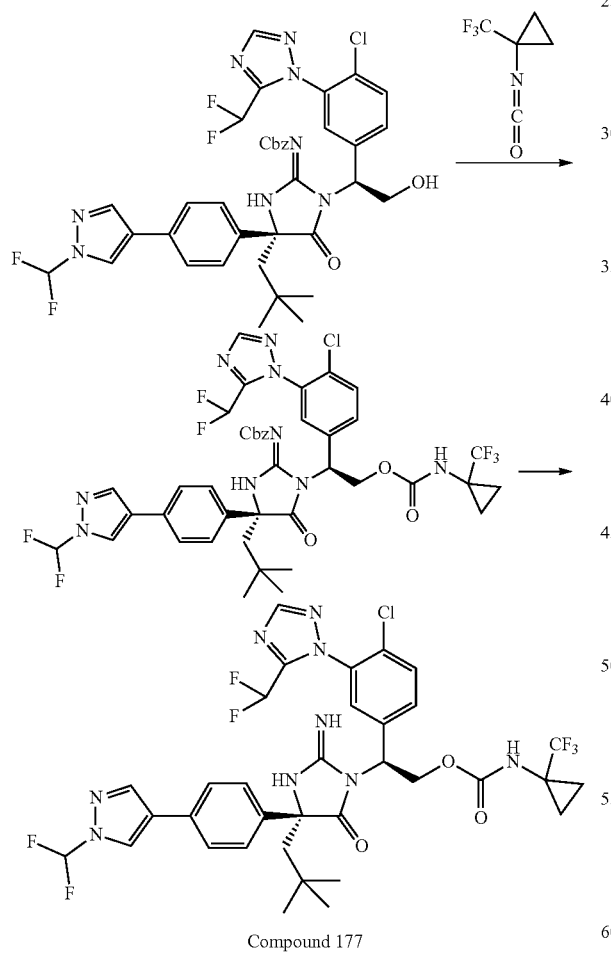

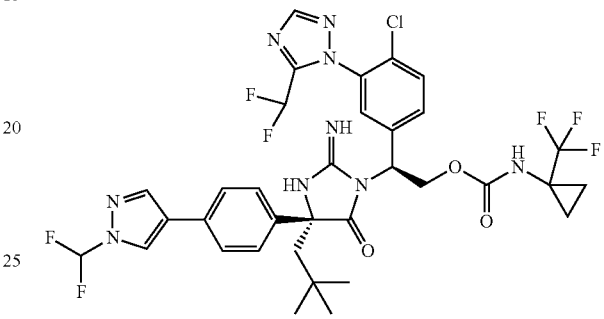

Compound 177

Preparation of benzyl ((R)-1-((S)-1-(4-chloro-3-(5-(difluoromethyl)-1H-1,2,4-triazol-1-yl)phenyl)-2-(((1-(trifluoromethyl)cyclopropyl)carbamoyl)oxy)ethyl)-4-(4-(1-(difluoromethyl)-1H-pyrazol-4-yl)phenyl)-4-neopentyl-5-oxoimidazolidin-2-ylidene)carbamate: To a solution of benzyl ((R)-1-((S)-1-(4-chloro-3-(5-(difluoromethyl)-1H-1,2,4-triazol-1-yl)phenyl)-2-hydroxyethyl)-4-(4-(1-(difluoromethyl)-1H-pyrazol-4-yl)phenyl)-4-neopentyl-5-oxoimidazolidin-2-ylidene)carbamate (13 mg, 0.02 mmol) in CH$_2$Cl$_2$ (0.20 mL) were added 1-isocyanato-1-(trifluoromethyl)cyclopropane (0.63 M, 0.16 mL in toluene) and titanium (IV) tert-butoxide (5.8 mg, 0.02 mmol). The reaction mixture was maintained at rt for 2 h. The reaction mixture was then directly purified by silica gel column chromatography (eluting with 0-100% EtOAc/hexanes) to afford the product (15 mg, 96%).

Compound 177

Preparation of Compound 177: A solution of benzyl ((R)-1-((S)-1-(4-chloro-3-(5-difluoromethyl)-1H-1,2,4-triazol-1-yl)phenyl)-2-(((1-(trifluoromethyl)cyclopropyl)carbamoyl)oxy)ethyl)-4-(4-(1-(difluoromethyl)-1H-pyrazol-4-yl)phenyl)-4-neopentyl-5-oxoimidazolidin-2-ylidene) carbamate (15 mg, 0.016 mmol) in TFA (0.2 mL) was heated at 60° C. for 1.5 h. The reaction mixture was diluted with toluene and concentrated in vacuo. This sequence was repeated twice, then the crude mixture was purified by silica gel column chromatography (0-10% MeOH in 3:1,CH$_2$Cl$_2$/hexanes) to afford the product. LCMS-ESI+ (m/z): [M+H]+ calc'd for C$_{34}$H$_{33}$ClF$_7$N$_9$O$_3$: 784.2. found: 784.3. 1H NMR (400 MHz, Methanol-d$_4$) δ 8.39 (d, J=0.7 Hz, 1H), 8.07 (s, 1H), 8.01 (s, 1H), 7.69-7.16 (m, 8H), 6.73 (t, J=52.2 Hz, 1H), 5.51 (dd, J=8.8, 5.7 Hz, 1H), 5.04 (dd, J=11.1, 9.0 Hz, 1H), 4.66 (dd, J=11.1, 5.7 Hz, 1H), 2.30 (d, J=14.7 Hz, 1H), 1.94 (d, J=14.6 Hz, 1H), 1.22 (m, 2H), 1.04 (m, 2H), 0.95 (s 9H).

Example 66: Preparation of Compound 178

Compound 178

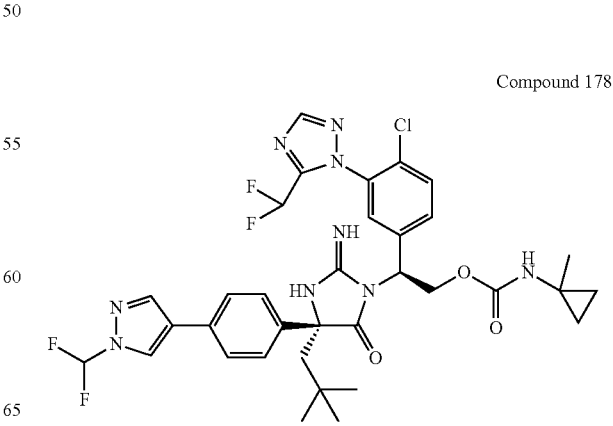

Compound 178 was prepared by a method similar to prepare Compound 177, except that 1-methylcyclopropane-1-carboxylic acid was used to prepare 1-isocyanato-1-methylcyclopropane. LCMS-ESI+ (m/z): [M+H]+ calc'd for $C_{34}H_{36}ClF_4N_9O_3$: 730.3. found: 730.3. $^1$H NMR (400 MHz, Methanol-$d_4$) δ 8.40 (s, 1H), 8.08 (s, 1H), 8.02 (s, 1H), 7.70-7.31 (m, 7H), 7.24 (s, 1H), 6.75 (t, J=52.2 Hz, 1H), 5.49 (t, J=7.4 Hz, 1H), 4.97 (t, J=10.0 Hz, 1H), 4.63 (dd, J=11.1, 5.7 Hz, 1H), 2.30 (d, J=14.7 Hz, 1H), 1.94 (d, J=14.7 Hz, 1H), 1.28 (s, 3H), 0.95 (s, 9H), 0.70-0.60 (m, 2H), 0.58-0.48 (m, 2H).

Example 67: Preparation of Compound 179

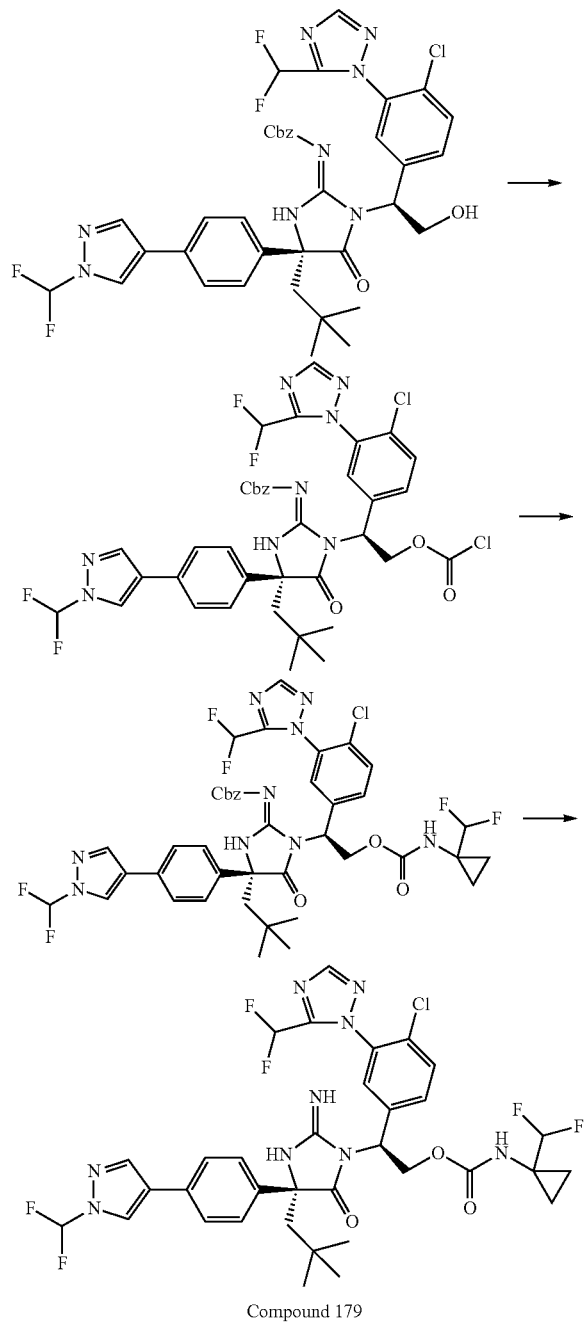

Compound 179

Preparation of (S)-2-((R)-2-(((benzyloxy)carbonyl)imino)-4-(4-(1-(difluoromethyl)-1H-pyrazol-4-yl)phenyl)-4-neopentyl-5-oxoimidazolidin-1-yl)-2-(4-chloro-3-(5-(difluoromethyl)-1H-1,2,4-triazol-1-yl)phenyl)ethyl carbonochloridate: To a solution of benzyl ((R)-1-((S)-1-(4-chloro-3-(5-(difluoromethyl)-1H-1,2,4-triazol-1-yl)phenyl)-2-hydroxyethyl)-4-(4-(1-(difluoromethyl)-1H-pyrazol-4-yl)phenyl)-4-neopentyl-5-oxoimidazolidin-2-ylidene)carbamate (50 mg, 0.065 mmol) in DCM (2 mL) were added 2,6-di-tert-butyl-4-methylpyridine (81 mg, 0.39 mmol) and triphosgene (9.7 mg, 0.33 mmol). The reaction mixture was stirred at rt for 4 h and used for the next reaction immediately without further purification.

Preparation of (S)-2-((R)-2-(((benzyloxy)carbonyl)imino)-4-(4-(1-(difluoromethyl)-1H-pyrazol-4-yl)phenyl)-4-neopentyl-5-oxoimidazolidin-1-yl)-2-(4-chloro-3-(5-(difluoromethyl)-1H-1,2,4-triazol-1-yl)phenyl)ethyl (1-(difluoromethyl)cyclopropyl)carbamate: To a solution of (S)-2-((R)-2-(((benzyloxy)carbonyl)imino)-4-(4-(1-(difluoromethyl)-1H-pyrazol-4-yl)phenyl)-4-neopentyl-5-oxoimidazolidin-1-yl)-2-(4-chloro-3-(5-(difluoromethyl)-1H-1,2,4-triazol-1-yl)phenyl)ethyl carbonochloridate in DCM (2 mL) was added difluoromethylcyclopropyl amine HCl (47 mg, 0.33 mmol) and diisopropylethylamine (34 mg, 0.26 mmol). The reaction mixture was stirred at rt for 1 h. The reaction mixture was treated with 1N HCl solution, extracted with EtOAc, dried over MgSO$_4$, filtered, concentrated down, and purified by silica gel column chromatography, eluting by 0-100% gradient EtOAc/hexanes to give the product.

Preparation of Compound 182: A solution of (S)-2-((R)-2-(((benzyloxy)carbonyl)imino)-4-(4-(1-(difluoromethyl)-1H-pyrazol-4-yl)phenyl)-4-neopentyl-5-oxoimidazolidin-1-yl)-2-(4-chloro-3-(5-(difluoromethyl)-1H-1,2,4-triazol-1-yl)phenyl)ethyl (1-(difluoromethyl)cyclopropyl)carbamate (50 mg, 0.056 mmol) in TFA (2 mL) was heated at 60° C. for 2 h. The reaction mixture was concentrated, dissolved in MeOH, and purified by reverse phase HPLC, eluting with 5-100% acetonitrile in water containing 0.1% TFA, to afford the product (40 mg, 83%). LCMS-ESI+: calc'd for $C_{34}H_{34}ClF_6N_9O_3$: 766.2 (M+H+). found: 766.2 (M+H+). 1H NMR (400 MHz, Methanol-$d_4$) δ 8.45 (s, 1H), 8.07 (m, 2H), 7.71-7.17 (m, 8H), 6.78 (t, J=52 Hz, 1H), 5.95-5.46 (m, 2H), 5.09 (t, J=10.6 Hz, 1H), 4.70 (dd, J=11.4, 4.9 Hz, 1H), 2.44 (d, J=15.1 Hz, 1H), 2.15 (d, J=15.1 Hz, 1H), 1.07 (m, 2H), 0.99 (s, 9H), 0.91 (m, 2H).

Example 68: Preparation of Compound 180

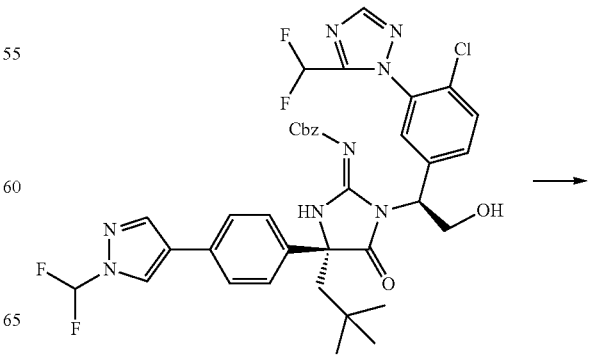

-continued

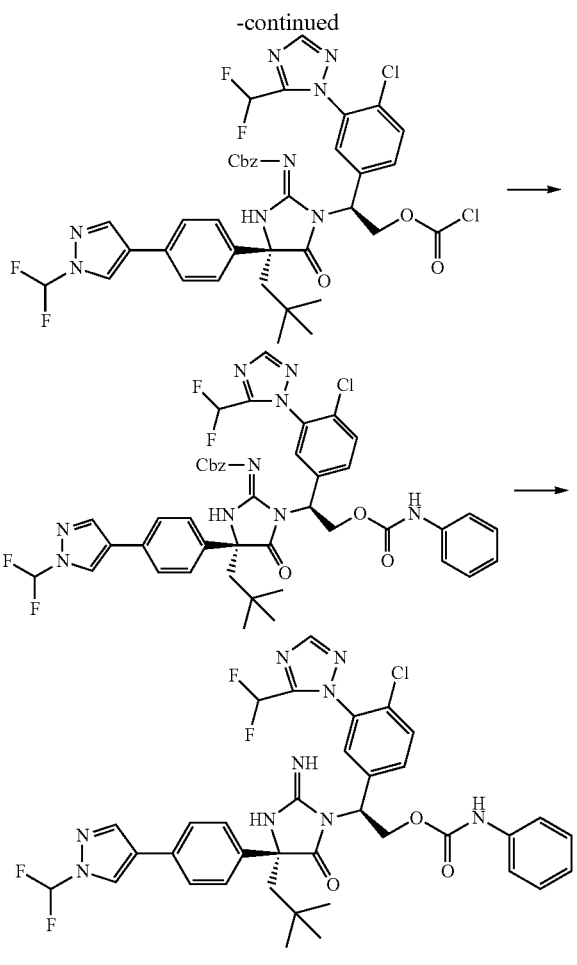

Compound 180

Compound 180 was prepared by a method similar to that for preparation of Compound 179, except that aniline was used instead of difluomethylcyclopropyl amine. LCMS-ESI+m/z Calc'd for $C_{36}H_{34}ClF_4N_9O_3$ [M+H+]: 752.2. found: 752.6 [M+H+]. 1H NMR (400 MHz, CD3CN) δ 8.28 (s, 1H), 8.08 (s, 1H), 8.03 (s, 1H), 7.87 (s, 1H), 7.67-7.02 (m, 13H), 6.71 (t, JHF=52.3 Hz, 1H), 5.52 (dd, J=9.5, 4.4 Hz, 1H), 5.09 (dd, J=11.6, 9.6 Hz, 1H), 4.73 (dd, J=11.6, 4.5 Hz, 1H), 2.32-2.12 (m, 2H), 0.88 (s, 9H).

Example 69: Preparation of Compound 181

Compound 181

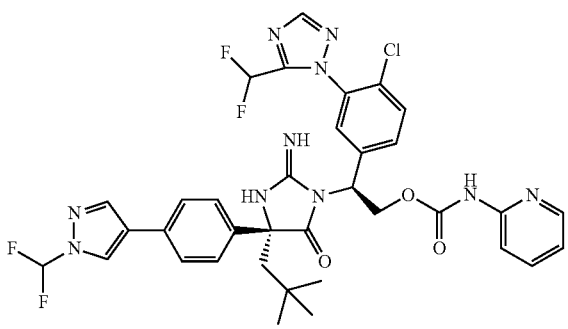

Compound 181 was prepared by a method similar to prepare Compound 180, except that pyridin-2-amine was used instead of difluomethylcyclopropyl amine. LCMS-ESI+m/z Calc'd for $C_{35}H_{33}ClF_4N_{10}O_3$ [M+H+]: 753.2 [M+H+]. found: 753.2. 1H NMR (400 MHz, CD3CN) δ 8.56 (s, 1H), 8.28 (s, 1H), 8.18 (d, J=5.1 Hz, 1H), 8.12-8.04 (m, 1H), 8.03 (s, 1H), 7.86-7.00 (m, 11H), 6.79 (t, $J_{HF}$=52.5 Hz, 1H), 5.65-5.50 (m, 1H), 5.22-5.05 (m, 1H), 4.76 (dd, J=11.7, 4.6 Hz, 1H), 2.31-2.14 (m, 2H), 0.87 (s, 9H).

Example 70: Preparation of Compound 182

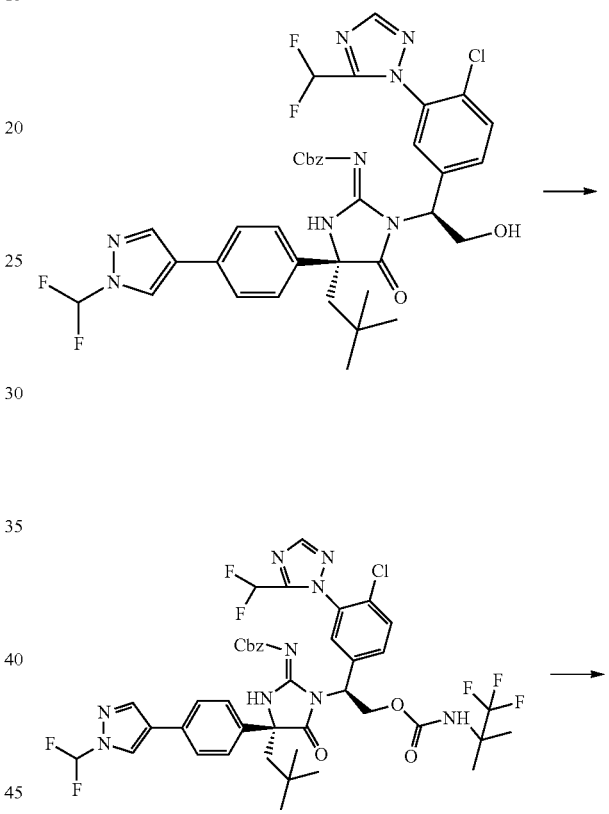

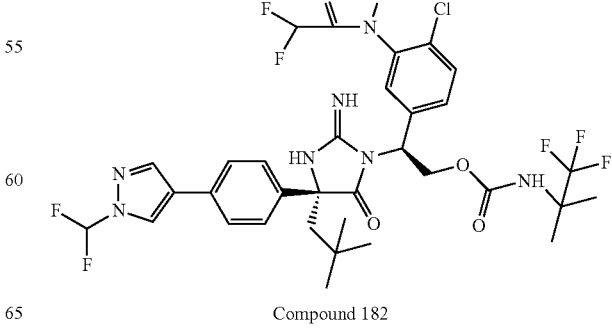

Compound 182

Compound 182 was prepared following the procedure used to prepare compound 177, except that 3,3,3-trifluoro-2,2-dimethylpropanoic acid was used instead of 1-(trifluoromethyl)cyclopropane-1-carboxylic acid and copper chloride was used instead of titanium (IV) tert-butoxide. LCMS-ESI+: calc'd for $C_{34}H_{35}ClF_7N_9O_3$: 786.2 (M+H+). found: 786.4 (M+H+). 1H NMR (400 MHz, Methanol-$d_4$) δ 8.46 (s, 1H), 8.11 (s, 1H), 8.03 (s, 1H), 7.70-7.50 (m, 5H), 7.49-7.17 (m, 3H), 6.78 (t, J=52 Hz, 1H), 5.68 (dd, J=9.3, 5.0 Hz, 1H), 5.09 (dd, J=11.5, 9.4 Hz, 1H), 4.65 (dd, J=11.5, 5.0 Hz, 1H), 2.45 (d, J=15.1 Hz, 1H), 2.18 (d, J=15.1 Hz, 1H), 1.51 (s, 6H), 0.99 (s, 9H).

Example 71: Preparation of Compound 183

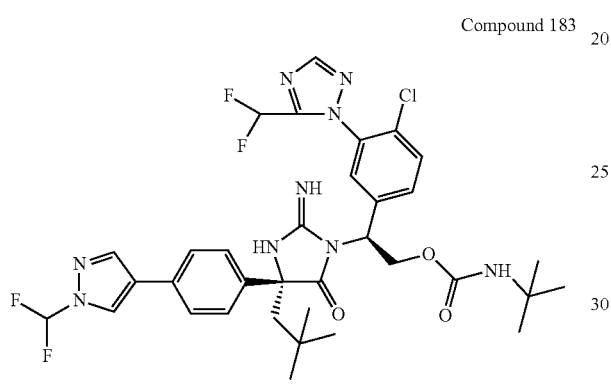

Compound 183

Compound 183 was prepared following the procedure used to prepare compound 177, except that 2-isocyanato-2-methylpropane was used instead of 1-isocyanato-1-(trifluoromethyl)cyclopropane and $MoO_2Cl_2(DMF)_2$ was used instead of titanium (IV) tert-butoxide. LCMS-ESI+: calc'd for $C_{34}H_{38}ClF_4N_9O_3$: 732.3 (M+H+). found: 732.4 (M+H+). 1H NMR (400 MHz, Methanol-$d_4$) δ 8.47 (s, 1H), 8.11 (s, 1H), 8.04 (s, 1H), 7.70-7.50 (m, 5H), 7.46-7.18 (m, 3H), 6.8 (t, J=52 Hz, 1H), 5.65 (dd, J=9.4, 5.1 Hz, 1H), 5.02 (t, J=10.6 Hz, 1H), 4.63 (dd, J=11.5, 5.1 Hz, 1H), 2.48 (d, J=15.1 Hz, 1H), 2.17 (d, J=15.2 Hz, 1H), 1.29 (s, 9H), 1.00 (s, 9H).

Example 72: Preparation of Compound 184

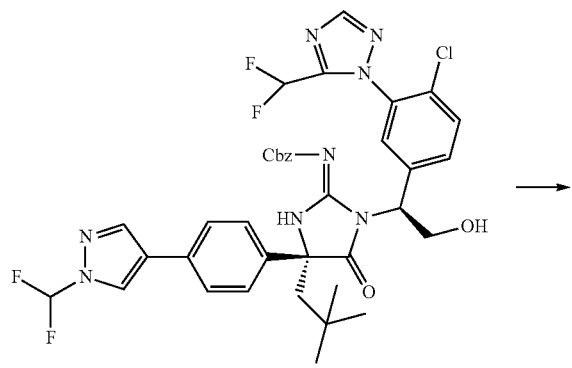

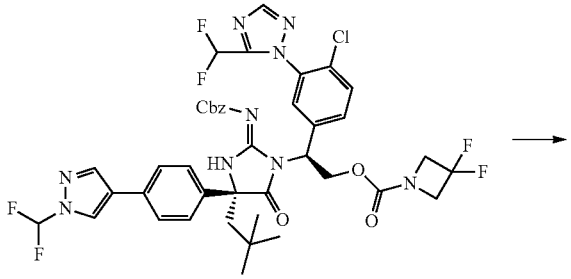

Compound 184

Preparation of (S)-2-((R)-2-(((benzyloxy)carbonyl)imino)-4-(4-(1-(difluoromethyl)-1H-pyrazol-4-yl)phenyl)-4-neopentyl-5-oxoimidazolidin-1-yl)-2-(4-chloro-3-(5-(difluoromethyl)-1H-1,2,4-triazol-1-yl)phenyl)ethyl 3,3-difluoroazetidine-1-carboxylate: To a solution of benzyl ((R)-1-((S)-1-(4-chloro-3-(5-(difluoromethyl)-1H-1,2,4-triazol-1-yl)phenyl)-2-hydroxyethyl)-4-(4-(1-(difluoromethyl)-1H-pyrazol-4-yl)phenyl)-4-neopentyl-5-oxoimidazolidin-2-ylidene)carbamate (20 mg, 0.026 mmol) in DCM (2 mL) were added diisopropylethylamine (33.6 mg, 0.26 mmol) and 1,1'-carbonyldiimidazole (10.6 mg, 0.065 mmol). The reaction mixture was stirred at rt for 30 min, then 3,3-difluoroazetidine hydrochloride (16.9 mg, 0.13 mmol) was added. The reaction mixture was stirred at rt overnight. The reaction mixture was treated with saturated aqueous $NaHCO_3$ and extracted with EtOAc. The organic phase was separated, dried over $MgSO_4$, filtered, concentrated down, and purified by silica gel chromatography (0-100% gradient EtOAc/hexanes) to give the product.

Preparation of Compound 187: A solution of (S)-2-((R)-2-((((benzyloxy)carbonyl)imino)-4-(4-(1-(difluoromethyl)-1H-pyrazol-4-yl)phenyl)-4-neopentyl-5-oxoimidazolidin-1-yl)-2-(4-chloro-3-(5-(difluoromethyl)-1H-1,2,4-triazol-1-yl)phenyl)ethyl 3,3-difluoroazetidine-1-carboxylate (17 mg, 0.019 mmol) in TFA (1 mL) was heated at 60° C. for 2 h. The reaction mixture was concentrated down, dissolved in MeOH, and purified by reversed phase HPLC, eluting by 5-100% acetonitrile in water with 0.1% TFA, to afford the product (12.2 mg, 87%). LCMS-ESI+: calc'd for $C_{33}H_{32}ClF_6N_9O_3$: 752.2 [M+H]+. found: 752.4 [M+H]+. 1H NMR (400 MHz, Methanol-$d_4$) δ 8.46 (d, J=0.7 Hz, 1H), 8.14-7.96 (m, 2H), 7.71-7.25 (m, 8H), 6.82 (t, J=52 Hz, 1H), 5.67 (dd, J=9.6, 4.6 Hz, 1H), 5.06 (dd, J=11.5, 9.7 Hz, 1H), 4.88-4.79 (m, 1H), 4.29 (t, J=11.8 Hz, 4H), 2.48 (d, J=15.2 Hz, 1H), 2.13 (d, J=15.2 Hz, 1H), 1.01 (s, 9H).

Example 73: Preparation of Compound 185

Example 74: Preparation of Compound 186

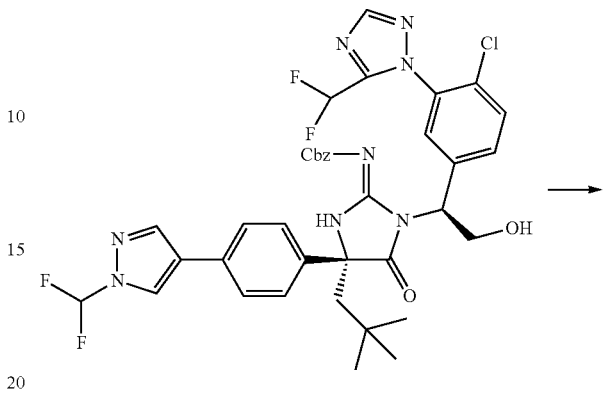

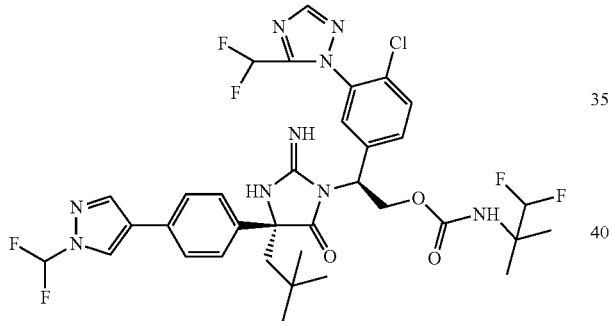

Compound 185

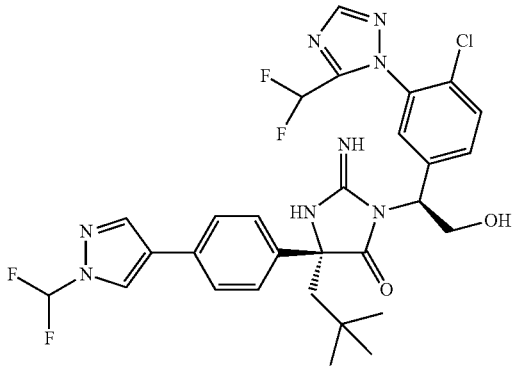

Compound 186

Compound 185 was prepared following the procedure used to prepare Compound 177, except that 3,3-difluoro-2,2-dimethylpropanoic acid was used instead of trifluoromethylcyclopropane-1-carboxylic acid and copper chloride was used instead of titanium (IV) tert-butoxide. LCMS-ESI+: calc'd for $C_{34}H_{36}ClF_6N_9O_3$: 768.3 (M+H+). Found: 768.4 (M+H+). 1H NMR (400 MHz, Methanol-$d_4$) δ 8.46 (d, J=0.8 Hz, 1H), 8.11 (s, 1H), 8.03 (s, 1H), 7.73-7.13 (m, 9H), 6.80 (t, J=52 Hz, 1H), 6.14 (t, J=60 Hz, 1H), 5.68 (dd, J=9.4, 5.1 Hz, 1H), 5.10-5.00 (m, 1H), 4.67 (dd, J=11.6, 5.1 Hz, 1H), 2.45 (d, J=15.1 Hz, 1H), 2.18 (d, J=15.1 Hz, 1H), 1.32 (s, 6H), 1.00 (s, 9H).

Preparation of Compound 186: A solution of benzyl ((R)-1-((S)-1-(4-chloro-3-(5-(difluoromethyl)-1H-1,2,4-triazol-1-yl)phenyl)-2-hydroxyethyl)-4-(4-(1-(difluoromethyl)-1H-pyrazol-4-yl)phenyl)-4-neopentyl-5-oxoimidazolidin-2-ylidene)carbamate (10 mg, 0.013 mmol) in TFA (1 mL) was heated at 60° C. for 2 h. The reaction mixture was concentrated down, dissolved in MeOH, and purified by reversed phase HPLC, eluting by 5-100% acetonitrile in water with 0.1% TFA, to afford the product (4.3 mg, 44%). LCMS-ESI+m/z Calc'd for $C_{29}H_{29}ClF_4N_8O_2$ [M+H+]: 633.2. Found: 633.5 [M+H+]. 1H NMR (400 MHz, $CD_3CN$) δ 8.35 (d, J=0.7 Hz, 1H), 8.18 (s, 1H), 8.09 (s, 1H), 7.74-7.23 (m, 9H), 6.84 (t, $J_{HF}$=52.3 Hz, 1H), 5.44 (dd, J=5.9, 3.0 Hz, 1H), 4.28 (dd, J=12.4, 5.9 Hz, 1H), 4.17 (dd, J=12.4, 3.1 Hz, 1H), 2.27-2.14 (m, 2H), 0.85 (s, 9H).

Unless otherwise stated, the following examples were prepared in a similar manner.

| Compound # | Structures | Mass data | NMR data |
|---|---|---|---|
| 187 | 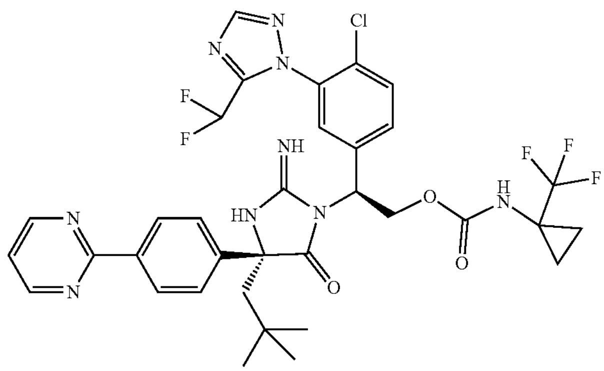 [SMILES: CC(C)(C)C[C@]1(c2ccc(-c3ncccn3)cc2)NC(=N)N([C@H](COC(=O)NC2(C(F)(F)F)CC2)c2ccc(Cl)c(-n3ncnc3C(F)F)c2)C1=O] | LCMS-ESI+ m/z Calc'd for C$_{34}$H$_{34}$ClF$_5$N$_9$O$_3$ [M + H+]: 746.2; Found: 746.3 [M + H+]. | 1H NMR (400 MHz, Methanol-d$_4$) δ 8.88 (d, J = 4.9 Hz, 2H), 8.37 (d, J = 8.7 Hz, 2H), 8.17 (s, 1H), 8.00 (s, 1H), 7.71-7.48 (m, 4H), 7.41 (t, J = 4.9 Hz, 1H), 7.19 (s, 1H), 6.75 (t, J = 52.2 Hz, 1H), 5.70 (dd, J = 9.7, 4.8 Hz, 1H), 5.20-5.02 (m, 1H), 4.72 (dd, J = 11.5, 4.9 Hz, 1H), 2.52 (d, J = 15.2 Hz, 1H), 2.20 (d, J = 15.2 Hz, 1H), 1.27 (m, 2H), 1.09 (m, 2H), 1.01 (s, 9H). |
| 188 | 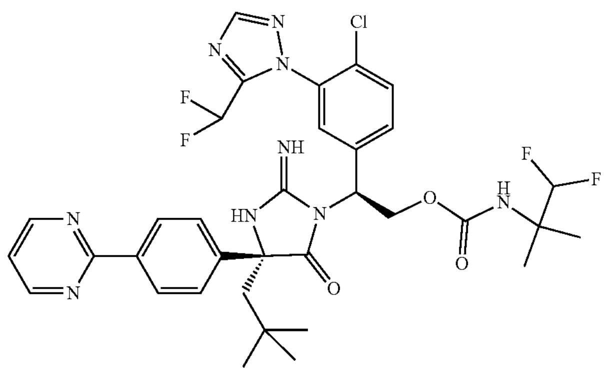 [SMILES: CC(C)(C)C[C@]1(c2ccc(-c3ncccn3)cc2)NC(=N)N([C@H](COC(=O)NC(C)(C)C(F)F)c2ccc(Cl)c(-n3ncnc3C(F)F)c2)C1=O] | LCMS-ESI+ m/z Calc'd for C$_{34}$H$_{37}$ClF$_4$N$_9$O$_3$ [M + H+]: 730.3; Found: 730.9 [M + H+]. | 1H NMR (400 MHz, Methanol-d$_4$) δ 8.88 (dd, J = 4.9, 1.1 Hz, 2H), 8.27-8.15 (m, 2H), 8.12 (dd, J = 14.1, 1.6 Hz, 1H), 7.73 (s, 2H), 7.60 (s, 1H), 7.56-7.34 (m, 3H), 6.90 (t, J = 52.2 Hz, 1H), 5.71 (dd, J = 9.2, 5.2 Hz, 1H), 5.14 (dd, J = 11.6, 9.3 Hz, 1H), 4.72 (dd, J = 11.7, 5.2 Hz, 1H), 2.43 (s, 2H), 1.52 (s, 6H), 1.05 (s, 9H). |
| 189 | 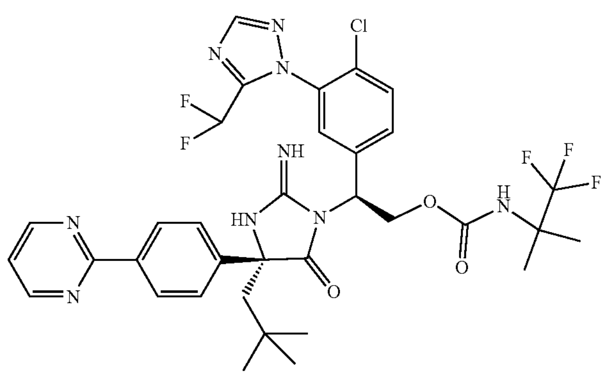 | LCMS-ESI+ m/z Calc'd for C$_{34}$H$_{36}$ClF$_5$N$_9$O$_3$ [M + H+]: 748.2; Found: 748.9 [M + H+]. | 1H NMR (400 MHz, Methanol-d$_4$) δ 8.89 (dd, J = 4.9, 1.0 Hz, 2H), 8.38 (d, J = 8.4 Hz, 2H), 7.68-7.33 (m, 6H), 7.18 (s, 1H), 6.76 (t, J = 52.2 Hz, 1H), 5.69 (dd, J = 9.4, 5.1 Hz, 1H), 5.18-5.00 (m, 1H), 4.66 (dd, J = 11.6, 5.1 Hz, 1H), 2.52 (d, J = 15.1 Hz, 1H), 2.23 (d, J = 15.1 Hz, 1H), 1.52 (m, 6H), 1.01 (s, 9H). |
| 190 | 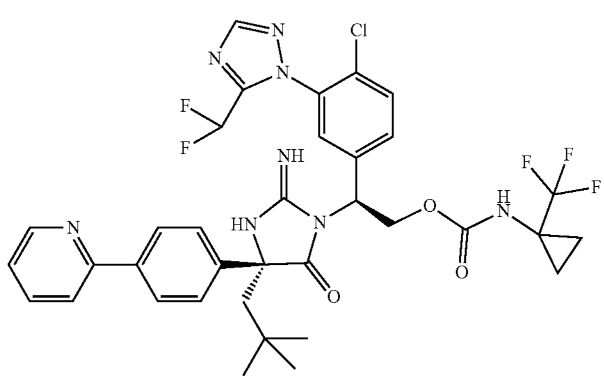 [SMILES: CC(C)(C)C[C@]1(c2ccc(-c3ccccn3)cc2)NC(=N)N([C@H](COC(=O)NC2(C(F)(F)F)CC2)c2ccc(Cl)c(-n3ncnc3C(F)F)c2)C1=O] | LCMS-ESI+ m/z Calc'd for C$_{35}$H$_{35}$ClF$_5$N$_8$O$_3$ [M + H+]: 745.2; Found: 745.1 [M + H+]. | 1H NMR (400 MHz, Methanol-d$_4$) δ 8.74-8.60 (m, 1H), 8.17 (s, 1H), 8.10-7.87 (m, 5H), 7.67-7.43 (m, 5H), 7.29 (s, 1H), 6.79 (t, J = 52.2 Hz, 1H), 5.68 (dd, J = 9.7, 5.1 Hz, 1H), 5.19-5.05 (m, 1H), 4.72 (dd, J = 11.5, 5.0 Hz, 1H), 2.52 (d, J = 15.2 Hz, 1H), 2.20 (d, J = 15.2 Hz, 1H), 1.32-1.17 (m, 2H), 1.14-1.02 (m, 2H), 1.01 (s, 9H). |

| Compound # | Structures | Mass data | NMR data |
|---|---|---|---|
| 191 | 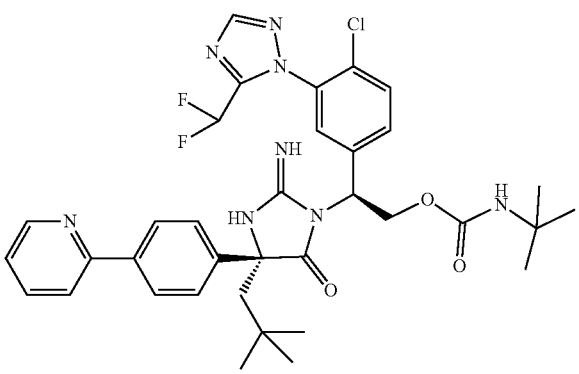 [SMILES: CC(C)(C)C[C@]1(c2ccc(-c3ccccn3)cc2)NC(=N)N([C@H](COC(=O)NC(C)(C)C)c2ccc(Cl)c(-n3ncnc3C(F)F)c2)C1=O] | LCMS-ESI+ m/z Calc'd for C₃₅H₄₀ClF₂N₈O₃ [M + H+]: 693.3; Found: 693.1 [M + H+]. | 1H NMR (400 MHz, Methanol-d₄) δ 8.69 (ddd, J = 5.2, 1.7, 0.9 Hz, 1H), 8.17-7.85 (m, 5H), 7.73-7.40 (m, 5H), 7.41-7.22 (m, 1H), 6.80 (t, J = 52.2 Hz, 1H), 5.65 (dt, J = 8.7, 4.4 Hz, 1H), 5.04 (t, J = 10.5 Hz, 1H), 4.63 (dd, J = 11.8, 5.1 Hz, 1H), 2.49 (d, J = 15.1 Hz, 1H), 2.23 (d, J = 15.1 Hz, 1H), 1.29 (s, 9H), 1.01 (s, 9H). |
| 192 | 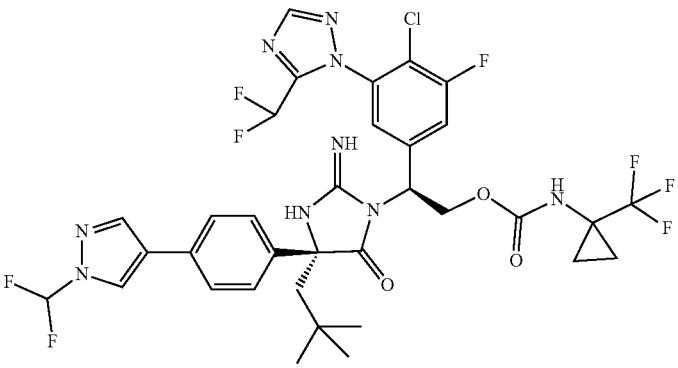 [SMILES: CC(C)(C)C[C@]1(c2ccc(-c3cnn(C(F)F)c3)cc2)NC(=N)N([C@H](COC(=O)NC2(C(F)(F)F)CC2)c2cc(F)c(Cl)c(-n3ncnc3C(F)F)c2)C1=O] | LCMS-ESI+ m/z Calc'd for C₃₄H₃₂ClF₈N₉O₃ [M + H+]: 801.2; Found: 801.8 [M + H+]. | 1H NMR (400 MHz, DMSO-d₆) δ 7.64 (s, 1H), 7.44-7.15 (m, 3H), 6.93-6.50 (m, 6H), 6.24 (s, 1H), 6.01 (t, J = 52.1 Hz, 1H), 4.87 (dd, J = 9.3, 5.0 Hz, 1H), 4.35-4.16 (m, 1H), 3.93 (dd, J = 11.6, 5.1 Hz, 1H), 1.68 (d, J = 15.1 Hz, 1H), 1.35 (d, J = 15.2 Hz, 1H), 0.59-0.22 (m, 4H), 0.19 (s, 9H). |
| 193 | 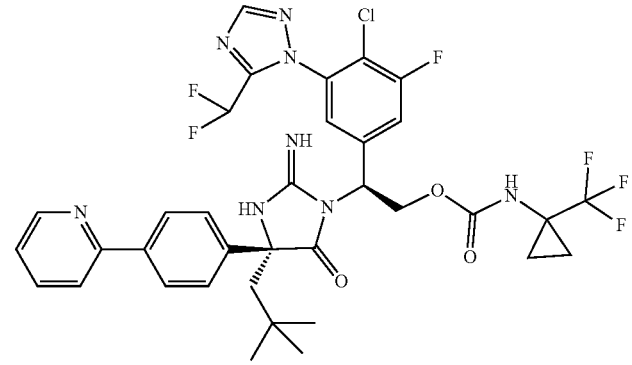 [SMILES: CC(C)(C)C[C@]1(c2ccc(-c3ccccn3)cc2)NC(=N)N([C@H](COC(=O)NC2(C(F)(F)F)CC2)c2cc(F)c(Cl)c(-n3ncnc3C(F)F)c2)C1=O] | LCMS-ESI+ m/z Calc'd for C₃₅H₃₃ClF₆N₉O₃ [M + H+]: 763.2; Found: 763.0 [M + H+]. | 1H NMR (400 MHz, DMSO-d₆) δ 7.94 (dt, J = 5.1, 1.4 Hz, 1H), 7.63-6.63 (m, 9H), 6.38 (s, 1H), 6.01 (t, J = 52.1 Hz, 1H), 4.87 (dd, J = 9.5, 4.9 Hz, 1H), 4.48-4.16 (m, 1H), 3.92 (dd, J = 11.5, 4.9 Hz, 1H), 1.68 (d, J = 15.2 Hz, 1H), 1.40 (d, J = 15.2 Hz, 1H), 0.54-0.22 (m, 4H), 0.19 (s, 9H). |
| 194 | 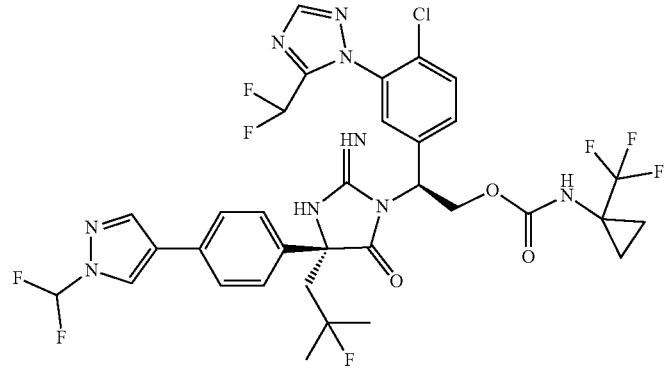 [SMILES: CC(C)(F)C[C@]1(c2ccc(-c3cnn(C(F)F)c3)cc2)NC(=N)N([C@H](COC(=O)NC2(C(F)(F)F)CC2)c2ccc(Cl)c(-n3ncnc3C(F)F)c2)C1=O] | LCMS-ESI+ m/z Calc'd for C₃₃H₃₀ClF₈N₉O₃ [M + H+]: 788.2; Found: 788.5 [M + H+]. | 1H NMR (400 MHz, Methanol-d₄) δ 8.40 (d, J = 0.7 Hz, 1H), 8.08 (m, 2H), 7.71-7.46 (m, 7H), 7.34 (d, J = 4.0 Hz, 1H), 6.77 (t, J = 52.2 Hz, 1H), 5.51 (t, J = 7.2 Hz, 1H), 5.01-4.90 (m, 1H), 4.70 (dd, J = 11.2, 6.0 Hz, 1H), 2.74 (dd, J = 14.9, 9.3 Hz, 1H), 2.30 (dd, J = 26.5, 15.1 Hz, 1H), 1.39 (d, J = 5.9 Hz, 3H), 1.34 (d, J = 5.6 Hz, 3H), 1.21-1.17 (m, 2H), 1.06-0.98 (m, 2H). |

| Compound # | Structures | Mass data | NMR data |
|---|---|---|---|
| 195 | 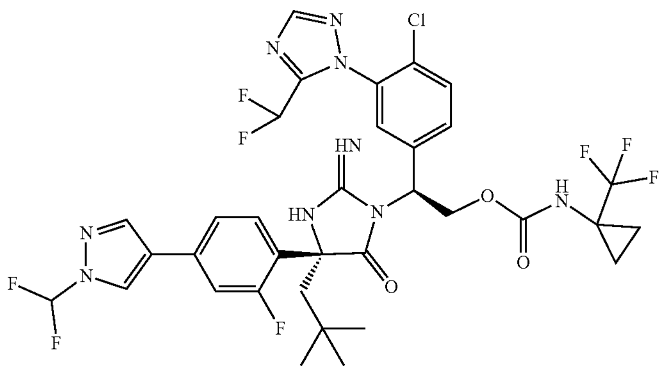 [SMILES: CC(C)(C)C[C@]1(c2ccc(-c3cnn(C(F)F)c3)cc2F)NC(=N)N([C@H](COC(=O)NC2(C(F)(F)F)CC2)c2ccc(Cl)c(-n3ncnc3C(F)F)c2)C1=O] | LCMS-ESI+ m/z Calc'd for C$_{34}$H$_{32}$ClF$_8$N$_9$O$_3$ [M + H+]: 802.2; Found: 802.6 [M + H+]. | 1H NMR (400 MHz, CD$_3$CN) δ 8.35 (s, 1H), 8.14 (s, 1H), 8.06 (s, 1H), 7.69-7.11 (m, 7H), 6.93-6.61 (m, 2H), 5.42 (dd, J = 9.8, 4.3 Hz, 1H), 4.96 (t, J = 10.6 Hz, 1H), 4.69 (dd, J = 11.4, 4.3 Hz, 1H), 2.42-2.18 (m, 2H), 1.34-1.21 (m, 2H), 1.12-1.01 (m, 2H), 0.95 (s, 9H). |
| 196 | 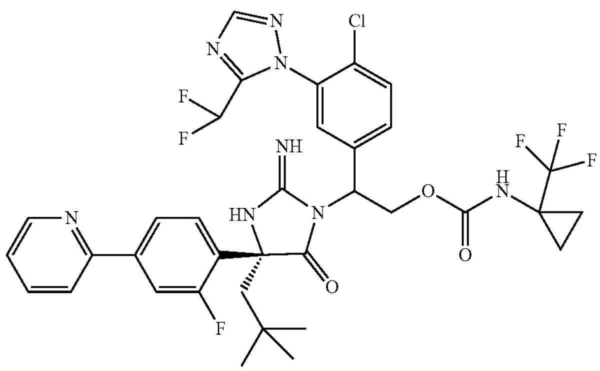 [SMILES: CC(C)(C)C[C@]1(c2ccc(-c3ccccn3)cc2F)NC(=N)N(C(COC(=O)NC2(C(F)(F)F)CC2)c2ccc(Cl)c(-n3ncnc3C(F)F)c2)C1=O] | LCMS-ESI+ m/z Calc'd for C$_{35}$H$_{33}$ClF$_6$N$_8$O$_3$ [M + H+]: 763.2; Found: 763.6 [M + H+]. | 1H NMR (400 MHz, Methanol-d$_4$) δ 8.67 (d, J = 5.0 Hz, 1H), 8.20 (d, J = 14.9 Hz, 2H), 7.99 (t, J = 7.7 Hz, 1H), 7.93 (d, J = 8.0 Hz, 1H), 7.78 (d, J = 11.0 Hz, 2H), 7.73 (m, 2H), 7.64 (s, 1H), 7.48 (t, J = 6.5 Hz, 2H), 6.92 (t, J = 52.2 Hz, 1H), 5.70 (dd, J = 9.7, 4.8 Hz, 1H), 5.16 (t, J = 10.6 Hz, 1H), 4.75 (dd, J = 11.5, 4.9 Hz, 1H), 2.41 (m, 2H), 1.28 (d, J = 2.3 Hz, 2H), 1.09 (s, 2H), 1.05 (s, 9H). |
| 197 | 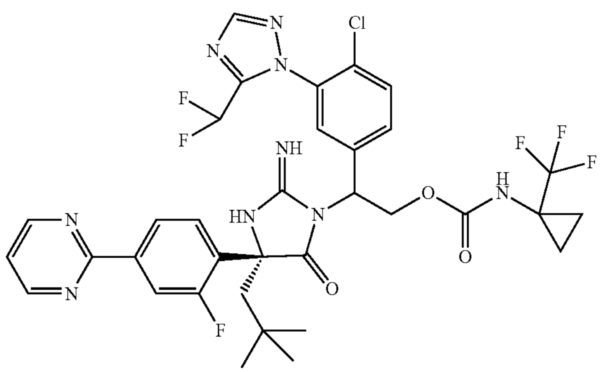 [SMILES: CC(C)(C)C[C@]1(c2ccc(-c3ncccn3)cc2F)NC(=N)N(C(COC(=O)NC2(C(F)(F)F)CC2)c2ccc(Cl)c(-n3ncnc3C(F)F)c2)C1=O] | LCMS-ESI+ m/z Calc'd for C$_{34}$H$_{33}$ClF$_6$N$_9$O$_3$ [M + H+]: 764.2; Found: 764.9 [M + H+]. | 1H NMR (400 MHz, Methanol-d$_4$) δ 8.88 (d, J = 4.9 Hz, 2H), 8.29-8.01 (m, 3H), 7.73 (m, 2H), 7.61 (s, 1H), 7.52-7.36 (m, 2H), 6.90 (t, J = 52.2 Hz, 1H), 5.71 (dd, J = 9.7, 4.8 Hz, 1H), 5.16 (dd, J = 11.4, 9.9 Hz, 1H), 4.76 (dd, J = 11.5, 4.9 Hz, 1H), 2.50-2.31 (m, 2H), 1.33-1.24 (m, 2H), 1.05 (s, 11H). |
| 198 | 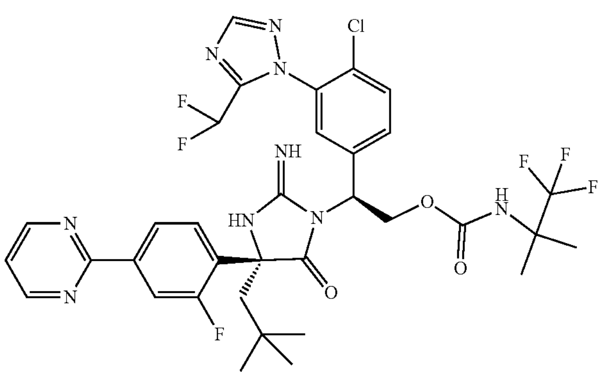 [SMILES: CC(C)(C)C[C@]1(c2ccc(-c3ncccn3)cc2F)NC(=N)N([C@H](COC(=O)NC(C)(C)C(F)(F)F)c2ccc(Cl)c(-n3ncnc3C(F)F)c2)C1=O] | LCMS-ESI+ m/z Calc'd for C$_{34}$H$_{35}$ClF$_6$N$_9$O$_3$ [M + H+]: 766.2; Found: 766.9 [M + H+]. | 1H NMR (400 MHz, Methanol-d$_4$) δ 8.88 (d, J = 4.9 Hz, 2H), 8.25-8.01 (m, 3H), 7.72 (m, 2H), 7.58 (s, 1H), 7.49 (t, J = 8.3 Hz, 1H), 7.42 (t, J = 4.9 Hz, 1H), 6.88 (t, J = 52.2 Hz, 1H), 5.70 (dd, J = 9.1, 5.2 Hz, 1H), 5.13 (dd, J = 11.6, 9.2 Hz, 1H), 4.73 (dd, J = 11.7, 5.2 Hz, 1H), 2.42 (s, 2H), 1.51 (s, 6H), 1.05 (s, 9H). |

| Compound # | Structures | Mass data | NMR data |
|---|---|---|---|
| 199 | 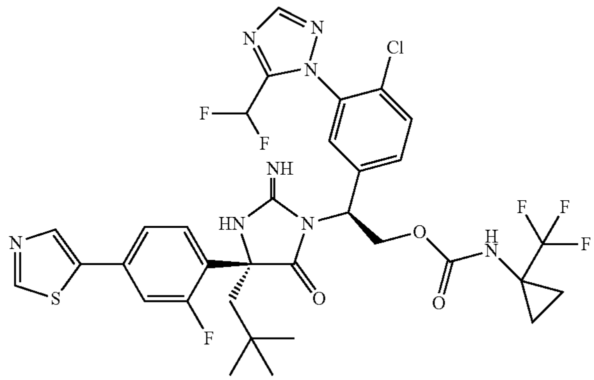 [SMILES: CC(C)(C)C[C@]1(c2ccc(-c3cncs3)cc2F)NC(=N)N([C@H](COC(=O)NC2(C(F)(F)F)CC2)c2ccc(Cl)c(-n3ncnc3C(F)F)c2)C1=O] | LCMS-ESI+: calc'd for C₃₃H₃₁ClF₆N₈O₃S: 769.2 (M + H+); Found: 769.6 (M + H+). | 1H NMR (400 MHz, Methanol-d₄) δ 9.05 (s, 1H), 8.27 (s, 1H), 8.22 (m, 2H), 7.74 (m, 2H), 7.62 (s, 1H), 7.52-7.38 (m, 3H), 6.92 (t, J = 52.2 Hz, 1H), 5.70 (dd, J = 9.7, 4.9 Hz, 1H), 5.21-5.10 (m, 1H), 4.75 (dd, J = 11.5, 4.9 Hz, 1H), 2.41 (d, J = 15.1 Hz, 1H), 2.36 (d, J = 15.0 Hz, 1H), 1.32-1.25 (m, 2H), 1.09 (s, 2H), 1.04 (s, 9H). |
| 200 | 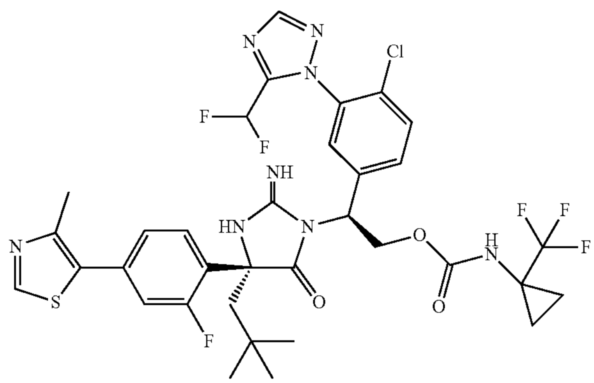 [SMILES: Cc1ncsc1-c1ccc([C@@]2(CC(C)(C)C)NC(=N)N([C@H](COC(=O)NC3(C(F)(F)F)CC3)c3ccc(Cl)c(-n4ncnc4C(F)F)c3)C2=O)c(F)c1] | LCMS-ESI+: calc'd for C₃₄H₃₃ClF₆N₈O₃S: 783.2 (M + H+); Found: 783.6 (M + H+). | 1H NMR (400 MHz, Methanol-d₄) δ 8.96 (s, 1H), 8.23 (m, 2H), 7.74 (m, 2H), 7.67 (s, 1H), 7.45 (t, J = 8.5 Hz, 1H), 7.35-7.25 (m, 2H), 6.94 (t, J = 52.2 Hz, 1H), 5.69 (dd, J = 9.6, 4.9 Hz, 1H), 5.17 (t, J = 10.6 Hz, 1H), 4.75 (dd, J = 11.6, 5.0 Hz, 1H), 2.49 (s, 3H), 2.43 (d, J = 14.9 Hz, 1H), 2.38 (d, J = 14.8 Hz, 1H), 1.27 (d, J = 6.2 Hz, 2H), 1.09 (s, 2H), 1.05 (s, 9H). |
| 201 | 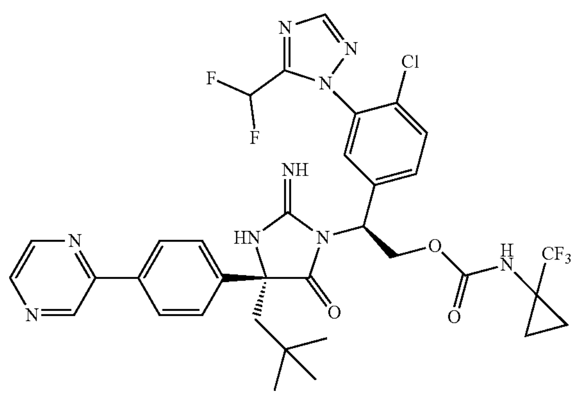 [SMILES: CC(C)(C)C[C@]1(c2ccc(-c3cnccn3)cc2)NC(=N)N([C@H](COC(=O)NC2(C(F)(F)F)CC2)c2ccc(Cl)c(-n3ncnc3C(F)F)c2)C1=O] | LCMS-ESI+: calc'd for C₃₄H₃₃ClF₅N₉O₃: 746.2 (M + H+); Found: 746.1 (M + H+). | 1H NMR (400 MHz, Chloroform-d) δ 12.20 (s, 1H), 9.05 (s, 1H), 8.83 (s, 1H), 8.58 (s, 1H), 8.15 (s, 1H), 8.06 (d, J = 8.1 Hz, 2H), 7.65 (m, 3H), 7.53-7.29 (m, 3H), 6.77 (t, J = 52.4 Hz, 1H), 6.17 (s, 1H), 5.13 (dd, J = 12.6, 6.7 Hz, 1H), 4.47 (d, J = 12.7 Hz, 1H), 2.24 (dd, J = 15.7, 5.5 Hz, 2H), 1.26 (m, 2H), 1.04 (m, 2H), 0.89 (d, J = 9.3 Hz, 9H). |
| 202 | 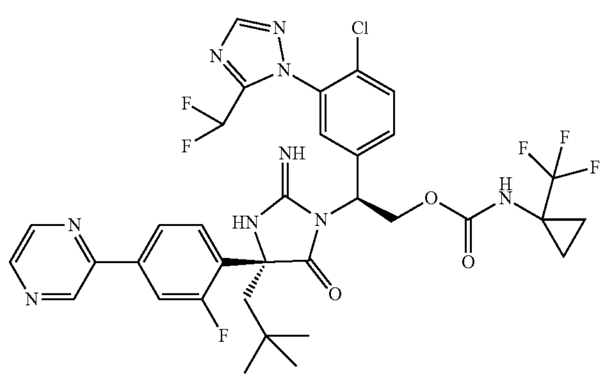 [SMILES: CC(C)(C)C[C@]1(c2ccc(-c3cnccn3)cc2F)NC(=N)N([C@H](COC(=O)NC2(C(F)(F)F)CC2)c2ccc(Cl)c(-n3ncnc3C(F)F)c2)C1=O] | LCMS-ESI+: calc'd for C₃₄H₃₂ClF₆N₉O₃ [M + H+]: 764.2; Found: 764.6 [M + H+]. | 1H NMR (400 MHz, CD₃CN) δ 9.09 (d, J = 1.5 Hz, 1H), 8.66 (t, J = 2.0 Hz, 1H), 8.58 (d, J = 2.5 Hz, 1H), 8.13 (s, 1H), 7.93-7.76 (m, 2H), 7.71-7.53 (m, 3H), 7.36 (t, J = 8.3 Hz, 1H), 6.95-6.56 (m, 2H), 5.44 (dd, J = 9.7, 4.3 Hz, 1H), 4.97 (t, J = 10.6 Hz, 1H), 4.70 (dd, J = 11.4, 4.3 Hz, 1H), 2.43-2.22 (m, 2H), 1.32-1.22 (m, 2H), 1.11-1.04 (m, 2H), 0.96 (s, 9H). |

-continued

| Compound # | Structures | Mass data | NMR data |
|---|---|---|---|
| 203 | 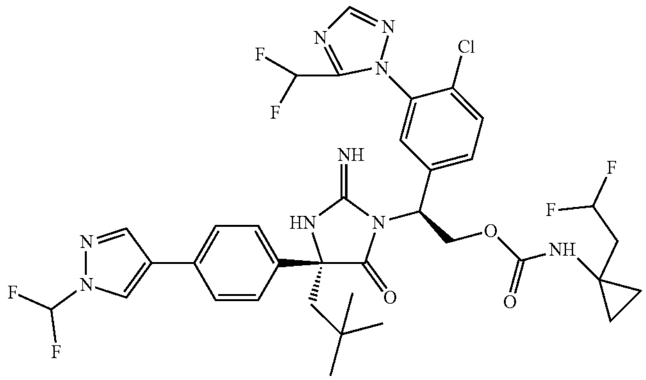 [SMILES: CC(C)(C)C[C@]1(c2ccc(-c3cnn(C(F)F)c3)cc2)NC(=N)N([C@H](COC(=O)NC2(CC(F)F)CC2)c2ccc(Cl)c(-n3ncnc3C(F)F)c2)C1=O] | LCMS-ESI+ (m/z): [M + H]+ calc'd for C₃₅H₃₆ClF₆N₉O₃: 780.2; found: 780.3. | 1H NMR (400 MHz, Methanol-d₄) δ 8.44 (s, 1H), 8.06 (m, 2H), 7.75-7.19 (m, 8H), 6.78 (t, J = 52 Hz, 1H), 6.02 (m, 1H), 5.65 (dd, J = 9.5, 4.9 Hz, 1H), 5.04 (dd, J = 11.5, 9.6 Hz, 1H), 4.70 (dd, J = 11.5, 5.0 Hz, 1H), 2.43 (d, J = 15.1 Hz, 1H), 2.25-1.85 (m, 3H), 0.98 (s, 9H), 0.77 (s, 4H). |
| 204 | 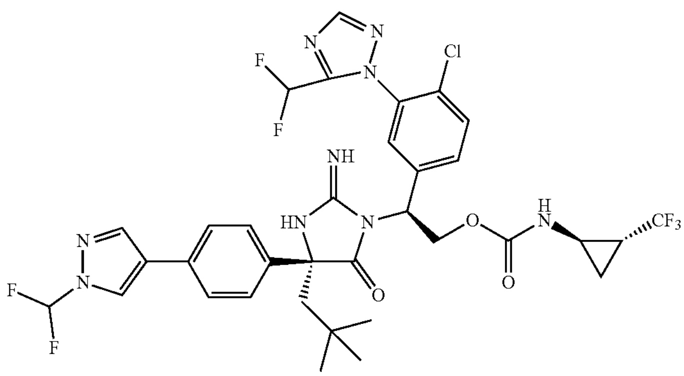 [SMILES: CC(C)(C)C[C@]1(c2ccc(-c3cnn(C(F)F)c3)cc2)NC(=N)N([C@H](COC(=O)N[C@@H]2C[C@H]2C(F)(F)F)c2ccc(Cl)c(-n3ncnc3C(F)F)c2)C1=O] | LCMS-ESI+ (m/z): [M + H]+ calc'd for C₃₄H₃₃ClF₇N₉O₃: 784.2; found: 784.3. | 1H NMR (400 MHz, Methanol-d₄) δ 8.46 (d, J = 0.7 Hz, 1H), 8.07 (m, 2H), 7.69-7.18 (m, 8H), 6.80 (t, J = 52 Hz, 1H), 5.66 (dd, J = 9.2, 5.0 Hz, 1H), 5.20-5.03 (m, 1H), 4.74 (dt, J = 10.8, 5.0 Hz, 1H), 2.87 (d, J = 10.0 Hz, 1H), 2.45 (d, J = 15.2 Hz, 1H), 2.15 (d, J = 15.1 Hz, 1H), 1.76-1.75 (m, 1H), 1.15 (t, J = 7.2 Hz, 1H), 1.13-1.04 (m, 1H), 0.99 (d, J = 1.1 Hz, 9H). |
| 205 | 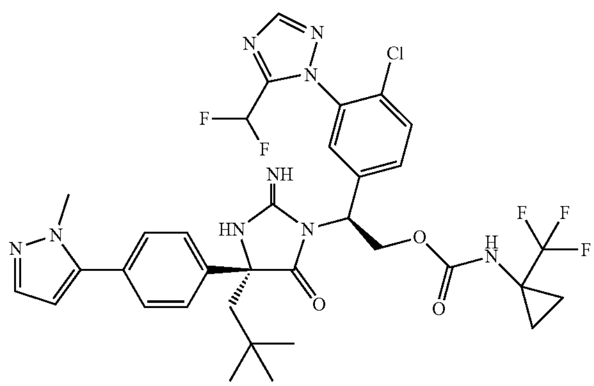 [SMILES: Cn1nccc1-c1ccc([C@@]2(CC(C)(C)C)NC(=N)N([C@H](COC(=O)NC3(C(F)(F)F)CC3)c3ccc(Cl)c(-n4ncnc4C(F)F)c3)C2=O)cc1] | LCMS-ESI+: calc'd for C₃₄H₃₅ClF₅N₉O₃: 748.2 (M + H+); Found: 748.3 (M + H+). | 1H NMR (400 MHz, Methanol-d₄) δ 8.19 (s, 1H), 8.08 (s, 1H), 7.66-7.31 (m, 7H), 6.87 (t, J = 52 Hz, 1H), 6.41 (d, J = 1.9 Hz, 1H), 5.67 (dd, J = 9.7, 4.9 Hz, 1H), 5.13 (t, J = 10.6 Hz, 1H), 4.71 (dd, J = 11.5, 5.0 Hz, 1H), 3.84 (s, 3H), 2.47 (d, J = 15.1 Hz, 1H), 2.18 (d, J = 15.2 Hz, 1H), 1.27 (m, 2H), 1.09 (m, 2H), 1.00 (s, 9H). |
| 206 | 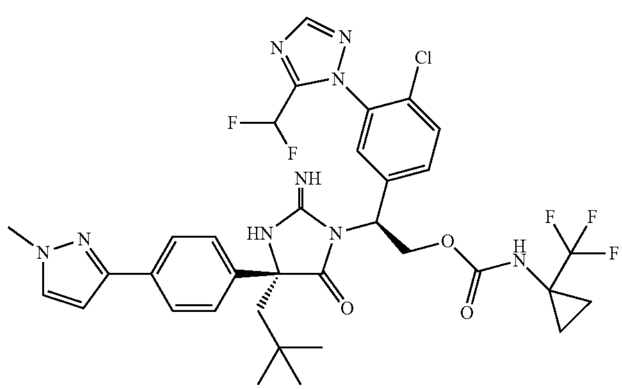 [SMILES: Cn1ccc(-c2ccc([C@@]3(CC(C)(C)C)NC(=N)N([C@H](COC(=O)NC4(C(F)(F)F)CC4)c4ccc(Cl)c(-n5ncnc5C(F)F)c4)C3=O)cc2)n1] | LCMS-ESI+: calc'd for C₃₄H₃₅ClF₅N₉O₃: 748.2 (M + H+); Found: 748.3 (M + H+). | 1H NMR (400 MHz, Methanol-d₄) δ 8.16 (s, 1H), 8.02 (s, 1H), 7.73 (d, J = 8.3 Hz, 2H), 7.67-7.58 (m, 2H), 7.58-7.48 (m, 1H), 7.42 (d, J = 8.3 Hz, 2H), 7.25 (d, J = 2.1 Hz, 1H), 6.92-6.63 (m, 2H), 5.67 (dd, J = 9.7, 4.9 Hz, 1H), 5.09 (t, J = 10.6 Hz, 1H), 4.70 (dd, J = 11.5, 4.9 Hz, 1H), 3.95 (s, 3H), 2.46 (d, J = 15.2 Hz, 1H), 2.16 (d, J = 15.2 Hz, 1H), 1.27 (m, 2H), 1.08 (m, 2H), 0.99 (s, 9H). |

| Compound # | Structures | Mass data | NMR data |
|---|---|---|---|
| 207 | 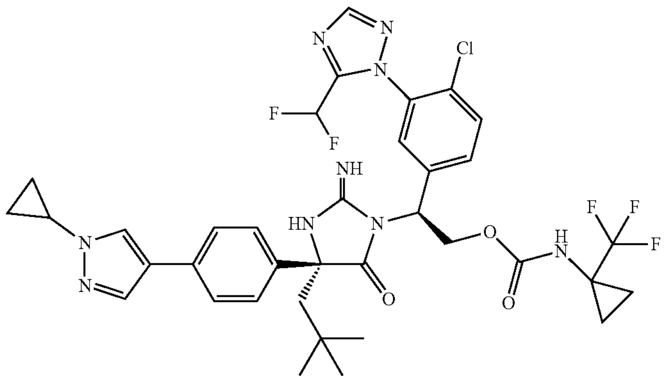 [SMILES: CC(C)(C)C[C@]1(c2ccc(-c3cnn(C4CC4)c3)cc2)NC(=N)N([C@H](COC(=O)NC2(C(F)(F)F)CC2)c2ccc(Cl)c(-n3ncnc3C(F)F)c2)C1=O] | LCMS-ESI+: calc'd for C₃₆H₃₇ClF₅N₉O₃: 774.2 (M + H+); Found: 774.3 (M + H+). | 1H NMR (400 MHz, Chloroform-d) δ 8.07 (s, 1H), 7.70 (d, J = 13.2 Hz, 2H), 7.57-7.31 (m, 7H), 6.67 (t, J = 52.6 Hz, 1H), 5.51 (t, J = 7.7 Hz, 1H), 4.78 (d, J = 6.0 Hz, 2H), 4.61 (s, 1H), 3.62 (tt, J = 7.4, 3.8 Hz, 1H), 2.38-1.91 (m, 2H), 1.19-0.80 (m, 17H). |
| 208 | 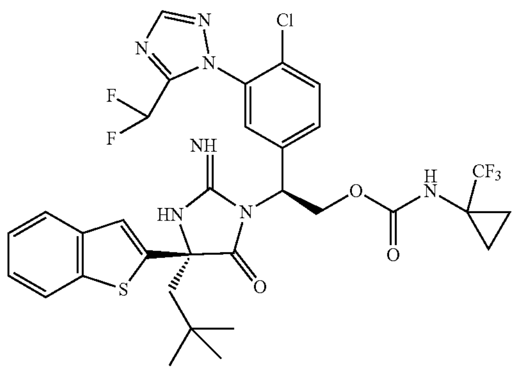 [SMILES: CC(C)(C)C[C@]1(c2cc3ccccc3s2)NC(=N)N([C@H](COC(=O)NC2(C(F)(F)F)CC2)c2ccc(Cl)c(-n3ncnc3C(F)F)c2)C1=O] | LCMS-ESI+: calc'd for C₃₂H₃₁ClF₅N₇O₃S: 724.2 (M + H+); Found: 724.6 (M + H+). | 1H NMR (400 MHz, Chloroform-d) δ 8.04 (s, 1H), 7.75 (d, J = 7.7 Hz, 1H), 7.68 (d, J = 7.6 Hz, 1H), 7.57-7.39 (m, 3H), 7.39-7.27 (m, 3H), 6.63 (t, J = 52.6 Hz, 1H), 5.53 (t, J = 7.6 Hz, 1H), 4.88-4.58 (m, 3H), 2.36 (d, J = 14.6 Hz, 1H), 2.15 (d, J = 14.7 Hz, 1H), 1.09 (m, 2H), 0.94 (s, 9H), 0.75 (m, 2H). |
| 209 | 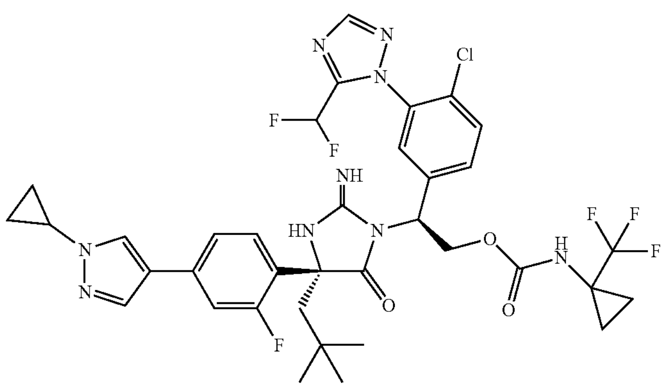 [SMILES: CC(C)(C)C[C@]1(c2ccc(-c3cnn(C4CC4)c3)cc2F)NC(=N)N([C@H](COC(=O)NC2(C(F)(F)F)CC2)c2ccc(Cl)c(-n3ncnc3C(F)F)c2)C1=O] | LCMS-ESI+: calc'd for C₃₆H₃₆ClF₆N₉O₃: 792.2 (M + H+); Found: 792.4 (M + H+). | 1H NMR (400 MHz, Methanol-d₄) δ 8.25-8.11 (m, 3H), 7.86-7.56 (m, 4H), 7.33-7.26 (m, 2H), 6.91 (t, J = 52 Hz, 1H), 5.70 (dd, J = 9.7, 4.8 Hz, 1H), 5.15 (dd, J = 11.4, 9.8 Hz, 1H), 4.73 (dd, J = 11.4, 4.8 Hz, 1H), 3.68 (tt, J = 7.3, 3.6 Hz, 1H), 2.44-2.20 (m, 2H), 1.27 (d, J = 2.4 Hz, 2H), 1.20-1.04 (m, 6H), 1.02 (s, 9H). |
| 210 | 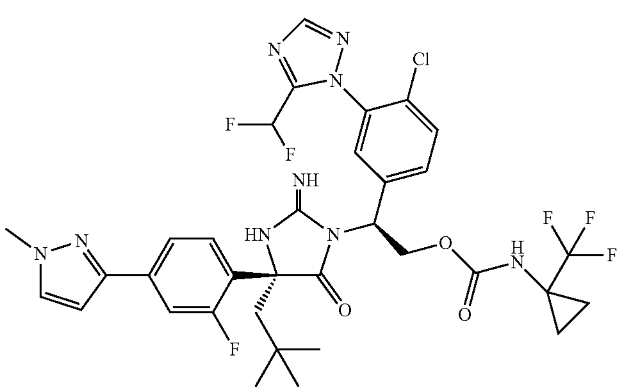 [SMILES: Cn1ccc(-c2ccc([C@@]3(CC(C)(C)C)NC(=N)N([C@H](COC(=O)NC4(C(F)(F)F)CC4)c4ccc(Cl)c(-n5ncnc5C(F)F)c4)C3=O)c(F)c2)n1] | LCMS-ESI+: calc'd for C₃₄H₃₄ClF₆N₉O₃: 766.2 (M + H+); Found: 766.3 (M + H+). | 1H NMR (400 MHz, Methanol-d₄) δ 8.18 (s, 1H), 7.71 (m, 2H), 7.62 (m, 2H), 7.56-7.44 (m, 2H), 7.32 (t, J = 8.4 Hz, 1H), 6.90 (t, J = 52.3 Hz, 1H), 6.65 (d, J = 2.3 Hz, 1H), 5.69 (dd, J = 9.6, 4.8 Hz, 1H), 5.15 (dd, J = 11.4, 9.7 Hz, 1H), 4.74 (dd, J = 11.5, 4.9 Hz, 1H), 3.93 (s, 3H), 2.37 (d, J = 1.9 Hz, 2H), 1.26 (t, J = 3.8 Hz, 2H), 1.08 (s, 2H), 1.03 (s, 9H). |

-continued

| Compound # | Structures | Mass data | NMR data |
|---|---|---|---|
| 211 | 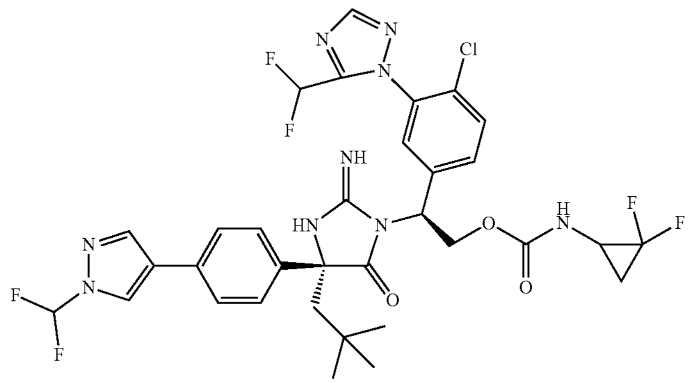 [SMILES: CC(C)(C)C[C@]1(c2ccc(-c3cnn(C(F)F)c3)cc2)NC(=N)N([C@H](COC(=O)NC2CC2(F)F)c2ccc(Cl)c(-n3ncnc3C(F)F)c2)C1=O] | LCMS-ESI+: calc'd for C₃₃H₃₂ClF₆N₉O₃: 752.2 (M + H+); Found: 752.6 (M + H+). | 1H NMR (400 MHz, Methanol-d₄) δ 8.44 (s, 1H), 8.09 (s, 1H), 8.03 (m, 1H), 7.74-7.16 (m, 8H), 6.78 (t, J = 52 Hz 1H), 5.68 (m, 4.8 Hz, 1H), 5.13 (q, J = 10.0 Hz, 1H), 4.80-4.65 (m, 1H), 3.12 (m, 1H), 2.44 (dd, J = 15.1, 3.4 Hz, 1H), 2.15 (dd, J = 15.2, 4.8 Hz, 1H), 1.75 (br s, 1H), 1.41 (br s, 1H), 0.99 (m, 9H). |
| 212 | or | LCMS-ESI+: calc'd for C₃₄H₃₃ClF₇N₉O₃: 784.2 (M + H+); Found: 784.7 (M + H+). | 1H NMR (400 MHz, Methanol-d₄) δ 8.17 (s, 1H), 8.11 (s, 1H), 8.01 (s, 1H), 7.88-7.73 (m, 2H), 7.70-7.19 (m, 6H), 6.92-6.56 (m, 2H), 5.68 (dd, J = 9.7, 4.8 Hz, 1H), 5.09 (dd, J = 11.5, 9.7 Hz, 1H), 4.70 (dd, J = 11.5, 4.9 Hz, 1H), 2.46 (d, J = 15.2 Hz, 1H), 2.17 (d, J = 15.1 Hz, 1H), 1.31-1.21 (m, 2H), 1.08 (m, 2H), 0.99 (s, 9H). |
| 213 | or | LCMS-ESI+: calc'd for C₃₄H₃₃ClF₇N₉O₃: 784.2 (M + H+); Found: 784.2 (M + H+). | 1H NMR (400 MHz, Methanol-d₄) δ 8.19 (s, 1H), 8.17 (s, 1H), 7.77 (d, J = 1.7 Hz, 1H), 7.68-7.22 (m, 7H), 6.84 (t, J = 52 Hz, 1H), 6.59 (d, J = 1.7 Hz, 1H), 5.67 (dd, J = 9.8, 4.9 Hz, 1H), 5.19-5.02 (m, 1H), 4.71 (dd, J = 11.5, 4.9 Hz, 1H), 2.50 (d, J = 15.2 Hz, 1H), 2.19 (d, J = 15.1 Hz, 1H), 1.27 (m, 2H), 1.09 (m, 2H), 1.01 (s, 9H). |

| Compound # | Structures | Mass data | NMR data |
|---|---|---|---|
| | 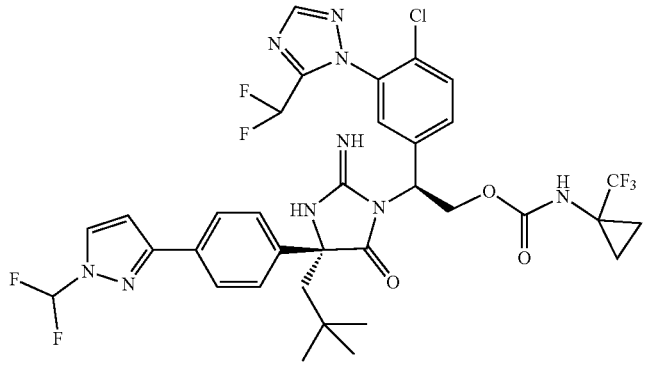 [SMILES: CC(C)(C)C[C@]1(c2ccc(-c3ccn(C(F)F)n3)cc2)NC(=N)N([C@H](COC(=O)NC2(C(F)(F)F)CC2)c2ccc(Cl)c(-n3ncnc3C(F)F)c2)C1=O] | | |
| 214 | 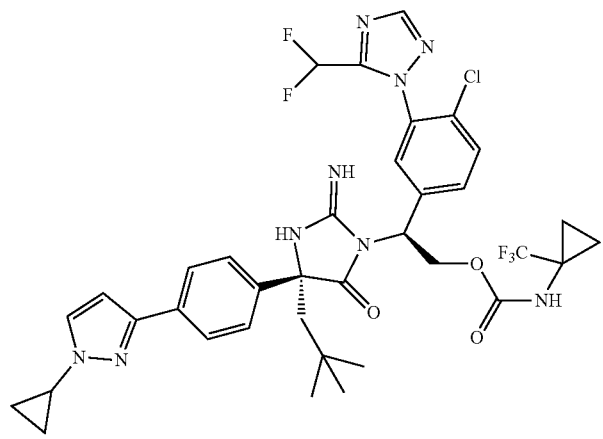 [SMILES: CC(C)(C)C[C@]1(c2ccc(-c3ccn(C4CC4)n3)cc2)NC(=N)N([C@H](COC(=O)NC2(C(F)(F)F)CC2)c2ccc(Cl)c(-n3ncnc3C(F)F)c2)C1=O] | LCMS-ESI+: calc'd for $C_{36}H_{37}ClF_5N_9O_3$: 774.2 (M + H+); Found: 774.2 (M + H+). | 1H NMR (400 MHz, Chloroform-d) δ 8.07 (s, 1H), 7.76 (d, J = 8.2 Hz, 2H), 7.63-7.33 (m, 6H), 6.69 (t, J = 52.6 Hz, 1H), 6.50 (d, J = 2.3 Hz, 1H), 5.52 (t, J = 7.7 Hz, 1H), 4.77 (m, 2H), 4.66 (s, 1H), 3.63 (tt, J = 7.5, 3.9 Hz, 1H), 2.27 (d, 15.2 Hz, 1H), 2.06 (d, J = 15.2 Hz, 1H), 1.24-0.98 (m, 8H), 0.90 (s, 9H). |
| 215 | 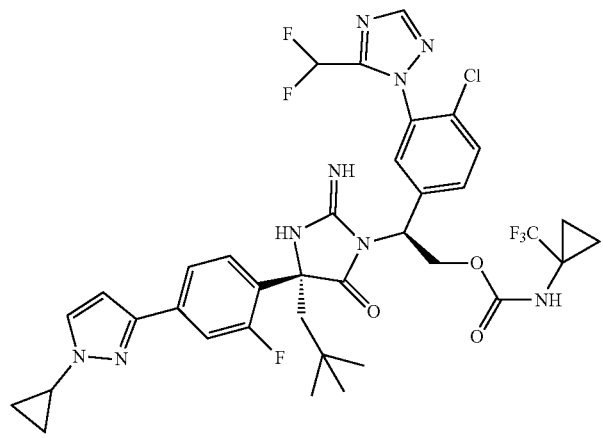 [SMILES: CC(C)(C)C[C@]1(c2ccc(-c3ccn(C4CC4)n3)cc2F)NC(=N)N([C@H](COC(=O)NC2(C(F)(F)F)CC2)c2ccc(Cl)c(-n3ncnc3C(F)F)c2)C1=O] | LCMS-ESI+: calc'd for $C_{36}H_{36}ClF_6N_9O_3$: 792.2 (M + H+); Found: 792.3 (M + H+). | 1H NMR (400 MHz, Methanol-d4) δ 8.18 (d, J = 3.0 Hz, 1H), 7.74-7.44 (m, 6H), 7.33 (t, J = 8.4 Hz, 1H), 6.90 (t, J = 52 Hz, 1H), 6.63 (d, J = 2.4 Hz, 1H), 5.69 (dd, J = 9.6, 4.9 Hz, 1H), 5.21-5.06 (m, 1H), 4.75 (dd, J = 11.5, 4.9 Hz, 1H), 3.70 (tt, J = 7.4, 3.9 Hz, 1H), 2.65 (s, 2H), 2.38 (m, 2H), 1.25 (m, 2H), 1.14 (m, 2H), 1.11-1.06 (m, 2H), 1.03 (s, 9H). |

-continued

| Compound # | Structures | Mass data | NMR data |
|---|---|---|---|
| 216 | 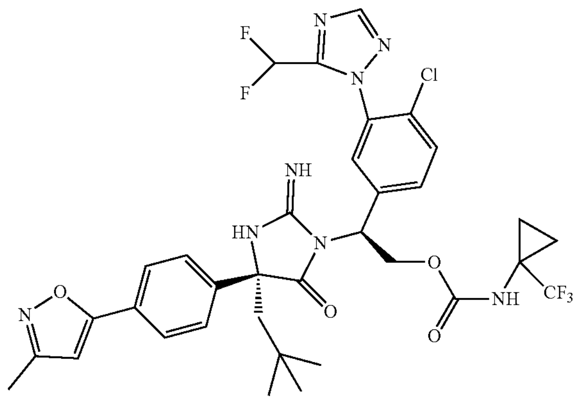 [SMILES: Cc1cc(-c2ccc([C@@]3(CC(C)(C)C)NC(=N)N([C@H](COC(=O)NC4(C(F)(F)F)CC4)c4ccc(Cl)c(-n5ncnc5C(F)F)c4)C3=O)cc2)on1] | LCMS-ESI+: calc'd for C₃₄H₃₃ClF₅N₈O₄: 749.2 (M + H+); Found: 749.6 (M + H+). | 1H NMR (400 MHz, Methanol-d₄) δ 8.82 (s, 1H), 8.18 (s, 1H), 8.14 (s, 1H), 7.68-7.52 (m, 2H), 7.47 (m, 3H), 7.30 (s, 1H), 6.80 (t, J = 52.2 Hz, 1H), 5.67 (dd, J = 9.7, 4.9 Hz, 1H), 5.11 (t, J = 10.6 Hz, 1H), 4.70 (dd, J = 11.6, 4.9 Hz, 1H), 2.65 (s, 2H), 2.45 (d, J = 15.1 Hz, 1H), 2.40 (s, 3H), 2.16 (d, J = 15.2 Hz, 1H), 1.35-1.20 (m, 2H), 1.08 (m, 2H), 0.99 (s, 9H). |
| 217 | 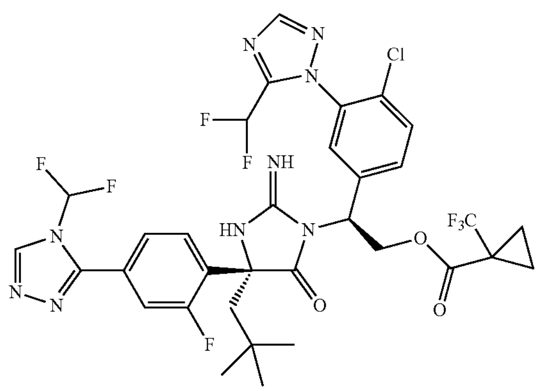 | LCMS-ESI+: calc'd for C₃₃H₃₁ClF₈N₁₀O₃: 803.2 (M + H+); Found: 803.0 (M + H+). | ¹H NMR (400 MHz, Methanol-d₄) δ 9.04 (d, J = 1.6 Hz, 1H), 8.22 (s, 1H), 7.81-7.34 (m, 7H), 6.91 (t, J = 52 Hz, 1H), 5.59 (s, 1H), 5.13-5.08 (m, 1H), 4.76 (dd, J = 11.2, 5.7 Hz, 1H), 2.26 (m, 2H), 1.32-1.15 (m, 2H), 1.07 (m, 2H), 1.00 (s, 9H). |
| 218 | 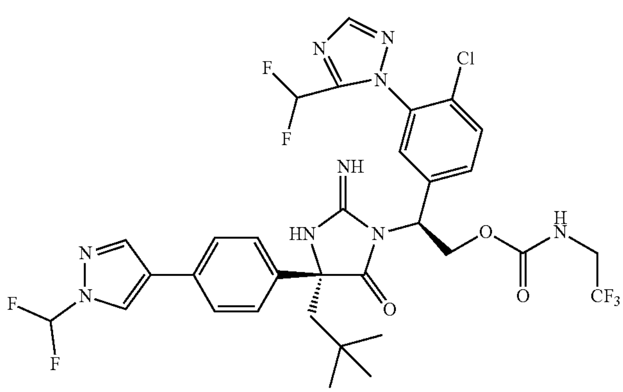 [SMILES: CC(C)(C)C[C@]1(c2ccc(-c3cnn(C(F)F)c3)cc2)NC(=N)N([C@H](COC(=O)NCC(F)(F)F)c2ccc(Cl)c(-n3ncnc3C(F)F)c2)C1=O] | LCMS-ESI+: calc'd for C₃₂H₃₁ClF₇N₉O₃: 758.2 (M + H+); Found: 758.2 (M + H+). | 1H NMR (400 MHz, Methanol-d₄) δ 8.45 (s, 1H), 8.10 (s, 1H), 8.03 (s, 1H), 7.85 (t, J = 6.5 Hz, 1H), 7.73-7.14 (m, 7H), 6.78 (t, J = 52 Hz, 1H), 5.70 (dd, J = 9.7, 4.9 Hz, 1H), 5.14 (dd, J = 11.5, 9.7 Hz, 1H), 4.76 (dd, J = 11.5, 4.9 Hz, 1H), 3.87-3.66 (m, 2H), 2.45 (d, J = 15.2 Hz, 1H), 2.14 (d, J = 15.0 Hz, 1H), 1.00 (s, 9H). |
| 219 | 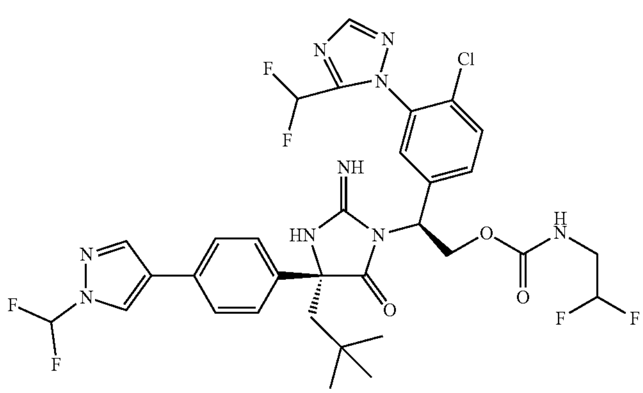 [SMILES: CC(C)(C)C[C@]1(c2ccc(-c3cnn(C(F)F)c3)cc2)NC(=N)N([C@H](COC(=O)NCC(F)F)c2ccc(Cl)c(-n3ncnc3C(F)F)c2)C1=O] | LCMS-ESI+: calc'd for C₃₂H₃₂ClF₆N₉O₃: 740.2 (M + H+); Found: 740.3 (M + H+). | 1H NMR (400 MHz, Methanol-d₄) δ 8.45 (s, 1H), 8.06 (m, 2H), 7.72-7.13 (m, 8H), 6.79 (t, J = 52 Hz, 1H), 6.01-5.71 (m, 1H), 5.67 (dd, J = 9.5, 4.9 Hz, 1H), 5.11 (dd, J = 11.5, 9.6 Hz, 1H), 4.75 (dd, J = 11.5, 4.9 Hz, 1H), 3.45 (t, J = 14.9 Hz, 2H), 2.46 (d, J = 15.2 Hz, 1H), 2.14 (d, J = 15.1 Hz, 1H), 1.00 (s, 9H). |

-continued

| Compound # | Structures | Mass data | NMR data |
|---|---|---|---|
| 220 | 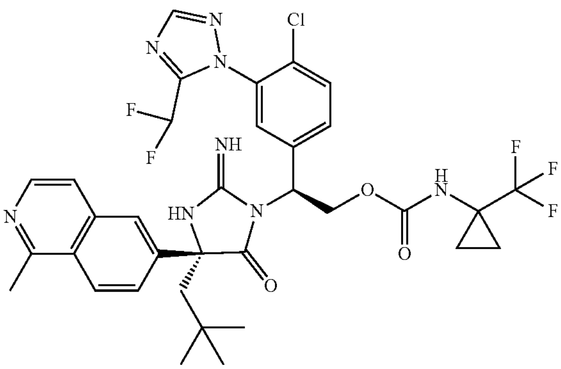 [SMILES: Cc1nccc2cc([C@@]3(CC(C)(C)C)NC(=N)N([C@H](COC(=O)NC4(C(F)(F)F)CC4)c4ccc(Cl)c(-n5ncnc5C(F)F)c4)C3=O)ccc12] | LCMS-ESI+: calc'd for C₃₃H₃₃ClF₅N₈O₃: 733.2 (M + H+); Found: 733.8 (M + H+). | 1H NMR (400 MHz, Methanol-d₄) δ 8.56 (d, J = 9.1 Hz, 1H), 8.44 (d, J = 6.6 Hz, 1H), 8.29 (d, J = 2.0 Hz, 1H), 8.25-8.18 (m, 2H), 8.14 (dd, J = 9.1, 2.0 Hz, 1H), 8.04 (s, 1H), 7.67-7.50 (m, 2H), 7.28-7.10 (m, 1H), 6.67 (t, J = 52.2 Hz, 1H), 5.70 (dd, J = 9.8, 4.7 Hz, 1H), 5.13 (t, J = 10.6 Hz, 1H), 4.71 (dd, J = 11.5, 4.7 Hz, 1H), 3.22 (s, 3H), 2.56 (d, J = 15.1 Hz, 1H), 2.29 (d, J = 15.2 Hz, 1H), 1.36-1.21 (m, 2H), 1.09 (m, 2H), 1.00 (s, 9H). |
| 221 | 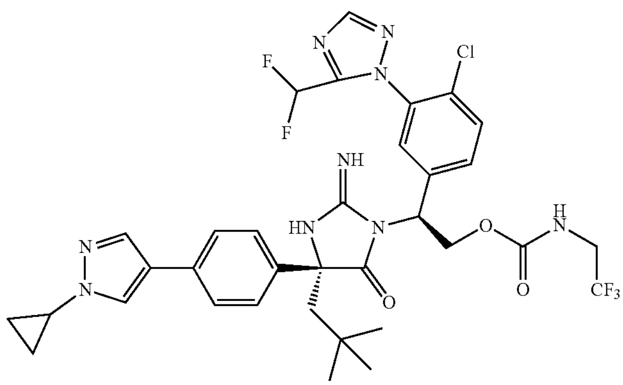 [SMILES: CC(C)(C)C[C@]1(c2ccc(-c3cnn(C4CC4)c3)cc2)NC(=N)N([C@H](COC(=O)NCC(F)(F)F)c2ccc(Cl)c(-n3ncnc3C(F)F)c2)C1=O] | LCMS-ESI+: calc'd for C₃₄H₃₅ClF₅N₉O₃: 748.2 (M + H+); Found: 748.3 (M + H+). | 1H NMR (400 MHz, Methanol-d₄) δ 8.06 (s, 1H), 8.01 (s, 1H), 7.89-7.78 (m, 2H), 7.68-7.11 (m, 7H), 6.78 (t, J = 52 Hz, 1H), 5.70 (dd, J = 9.6, 4.9 Hz, 1H), 5.19-5.03 (m, 1H), 4.76 (dd, J = 11.5, 5.0 Hz, 1H), 3.90-3.74 (m, 2H), 3.70 (tt, J = 7.4, 3.9 Hz, 1H), 2.46 (d, J = 15.2 Hz, 1H), 2.13 (d, J = 15.1 Hz, 1H), 1.20-1.10 (m, 2H), 1.10-1.04 (m, 2H), 1.00 (s, 9H). |
| 222 | 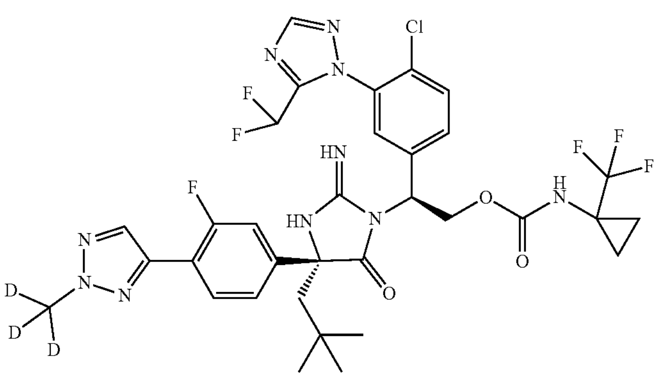 [SMILES: [2H]C([2H])([2H])n1ncc(-c2ccc([C@@]3(CC(C)(C)C)NC(=N)N([C@H](COC(=O)NC4(C(F)(F)F)CC4)c4ccc(Cl)c(-n5ncnc5C(F)F)c4)C3=O)cc2F)n1] | LCMS-ESI+: calc'd for C₃₃H₃₀ClD₃F₆N₁₀O₃: 770.2 (M + H+); Found: 770.4 (M + H+). | 1H NMR (400 MHz, Methanol-d₄) δ 8.19 (s, 1H), 8.04 (s, 1H), 8.02-7.86 (m, 2H), 7.69-7.51 (m, 2H), 7.34-7.21 (m, 3H), 6.78 (t, J = 52.2 Hz, 1H), 5.69 (dd, J = 9.8, 4.8 Hz, 1H), 5.10 (dd, J = 11.5, 9.8 Hz, 1H), 4.70 (dd, J = 11.5, 4.8 Hz, 1H), 2.42 (d, J = 15.2 Hz, 1H), 2.15 (d, J = 15.1 Hz, 1H), 1.30-1.22 (m, 2H), 1.08 (m, 2H), 0.98 (s, 9H). |
| 223 | 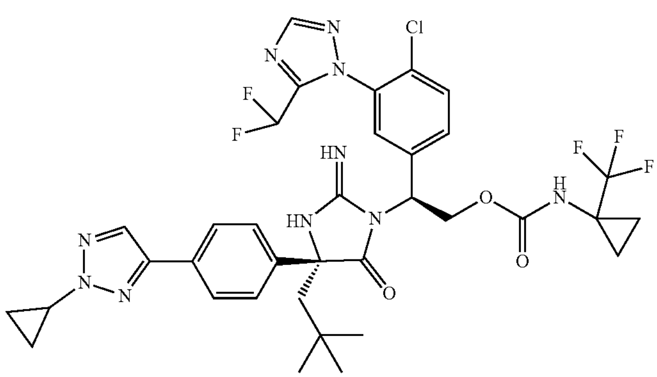 [SMILES: CC(C)(C)C[C@]1(c2ccc(-c3cnn(C4CC4)n3)cc2)NC(=N)N([C@H](COC(=O)NC2(C(F)(F)F)CC2)c2ccc(Cl)c(-n3ncnc3C(F)F)c2)C1=O] | LCMS-ESI+: calc'd for C₃₅H₃₆ClF₅N₁₀O₃: 775.2 (M + H+); Found: 775.4 (M + H+). | 1H NMR (400 MHz, Methanol-d₄) δ 8.02 (s, 1H), 7.99 (s, 1H), 7.82-7.74 (m, 2H), 7.61 (d, J = 8.5 Hz, 1H), 7.55 (dd, J = 8.5, 2.2 Hz, 1H), 7.50-7.43 (m, 2H), 7.19 (s, 1H), 6.78 (t, J = 52.2 Hz, 1H), 5.68 (dd, J = 9.6, 5.0 Hz, 1H), 5.16-5.02 (m, 1H), 4.71 (dd, J = 11.6, 5.0 Hz, 1H), 4.11 (tt, J = 7.5, 3.8 Hz, 1H), 2.49 (d, J = 15.1 Hz, 1H), 2.16 (d, J = 15.2 Hz, 1H), 1.36 (tdd, J = 5.1, 4.3, 2.0 Hz, 2H), 1.28 |

| Compound # | Structures | Mass data | NMR data |
|---|---|---|---|
| | | | (dt, J = 7.7, 3.2 Hz, 2H), 1.19-1.12 (m, 2H), 1.09 (m, 2H), 1.00 (s, 9H). |
| 224 | 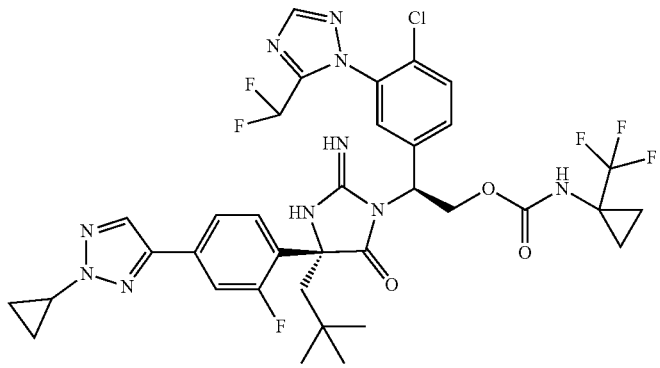 [SMILES: CC(C)(C)C[C@]1(c2ccc(-c3cnn(C4CC4)n3)cc2F)NC(=N)N([C@H](COC(=O)NC2(C(F)(F)F)CC2)c2ccc(Cl)c(-n3ncnc3C(F)F)c2)C1=O] | LCMS-ESI+: calc'd for C$_{35}$H$_{35}$ClF$_6$N$_{10}$O$_3$: 793.2 (M + H+); Found: 793.4 (M + H+). $^1$H | NMR (400 MHz, Methanol-d$_4$) δ 8.19 (s, 1H), 8.02 (s, 1H), 7.72 (m, 2H), 7.62-7.53 (m, 3H), 7.39 (t, J = 8.4 Hz, 1H), 6.90 (t, J = 52.2 Hz, 1H), 5.68 (dd, J = 9.4, 5.0 Hz, 1H), 5.14 (dd, J = 11.4, 9.5 Hz, 1H), 4.76 (dd, J = 11.5, 5.1 Hz, 1H), 4.11 (tt, J = 7.5, 3.8 Hz, 1H), 2.46-2.28 (m, 2H), 1.37-1.31 (m, 2H), 1.30-1.25 (m, 2H), 1.18-1.11 (m, 2H), 1.09 (d, J = 3.0 Hz, 2H), 1.03 (s, 9H). |
| 225 | 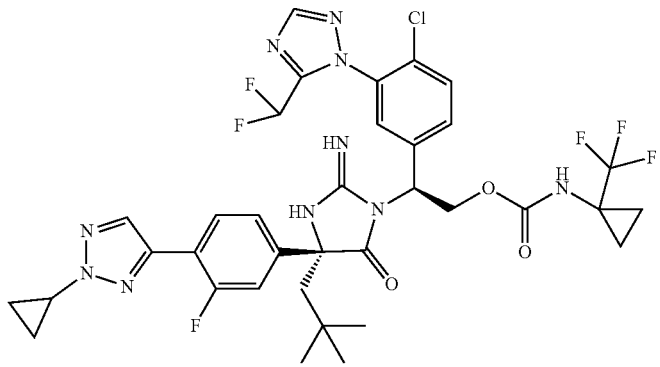 [SMILES: CC(C)(C)C[C@]1(c2ccc(-c3cnn(C4CC4)n3)c(F)c2)NC(=N)N([C@H](COC(=O)NC2(C(F)(F)F)CC2)c2ccc(Cl)c(-n3ncnc3C(F)F)c2)C1=O] | LCMS-ESI+: calc'd for C$_{35}$H$_{35}$ClF$_6$N$_{10}$O$_3$: 793.2 (M + H+); Found: 793.4 (M + H+). | 1H NMR (400 MHz, Methanol-d$_4$) δ 8.02 (s, 1H), 7.93 (d, J = 3.9 Hz, 1H), 7.89 (t, J = 8.2 Hz, 1H), 7.58 (m, 2H), 7.40-7.15 (m, 4H), 6.76 (t, J = 52.2 Hz, 1H), 5.61 (dd, J = 9.4, 5.1 Hz, 1H), 5.08 (dd, J = 11.4, 9.5 Hz, 1H), 4.68 (dd, J = 11.3, 5.1 Hz, 1H), 4.14 (dt, J = 7.5, 3.8 Hz, 1H), 2.35 (d, J = 14.9 Hz, 1H), 2.06 (d, J = 15.0 Hz, 1H), 1.35 (m, 2H), 1.29-1.22 (m, 2H), 1.15 (td, J = 7.6, 5.4 Hz, 2H), 1.07 (m, 2H), 0.97 (s, 9H). |
| 226 | 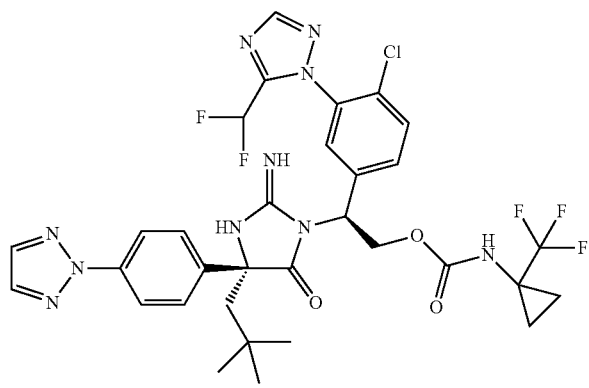 [SMILES: CC(C)(C)C[C@]1(c2ccc(-n3nccn3)cc2)NC(=N)N([C@H](COC(=O)NC2(C(F)(F)F)CC2)c2ccc(Cl)c(-n3ncnc3C(F)F)c2)C1=O] | LCMS-ESI+: calc'd for C$_{32}$H$_{32}$ClF$_5$N$_{10}$O$_3$, 735.2 (M + H); Found, 735.4. | $^1$H NMR (400 MHz, Methanol-d$_4$) δ 8.10-8.01 (m, 2H), 7.99-7.95 (m, 3H), 7.62 (d, J = 8.4 Hz, 1H), 7.57 (dd, J = 9.2, 2.3 Hz, 3H), 7.18 (s, 1H), 6.77 (t, J = 52.2 Hz, 1H), 5.69 (dd, J = 9.7, 5.0 Hz, 1H), 5.15-5.05 (m, 1H), 4.72 (dd, J = 11.6, 5.0 Hz, 1H), 2.50 (d, J = 15.1 Hz, 1H), 2.18 (d, J = 15.1 Hz, 1H), 1.32-1.23 (m, 2H), 1.11-1.07 (m, 2H), 1.01 (s, 9H). |

| Compound # | Structures | Mass data | NMR data |
|---|---|---|---|
| 227 | 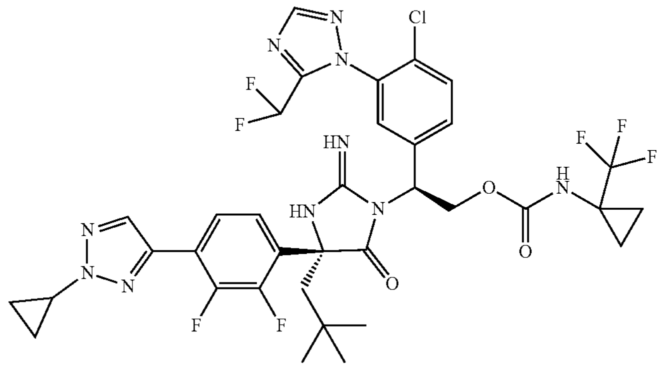 [SMILES: CC(C)(C)C[C@]1(c2ccc(-c3cnn(C4CC4)n3)c(F)c2F)NC(=N)N([C@H](COC(=O)NC2(C(F)(F)F)CC2)c2ccc(Cl)c(-n3ncnc3C(F)F)c2)C1=O] | LCMS-ESI+: calc'd for C₃₅H₃₄ClF₇N₁₀O₃: 811.2 (M + H+); Found: 811.4 (M + H+). | 1H NMR (400 MHz, Methanol-d₄) δ 8.31-7.88 (m, 3H), 7.86-7.45 (m, 4H), 7.19 (t, J = 7.9 Hz, 1H), 6.87 (t, J = 52.3 Hz, 1H), 5.71 (dd, J = 9.7, 4.8 Hz, 1H), 5.14 (t, J = 10.6 Hz, 1H), 4.74 (dd, J = 11.4, 4.8 Hz, 1H), 2.39 (q, J = 15.1 Hz, 2H), 1.38-1.07 (m, 8H), 1.03 (s, 9H). |
| 228 | 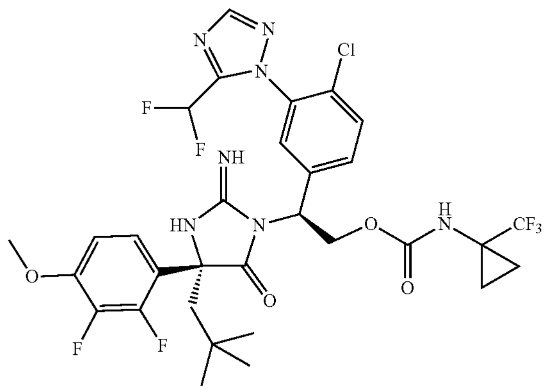 [SMILES: COc1ccc([C@@]2(CC(C)(C)C)NC(=N)N([C@H](COC(=O)NC3(C(F)(F)F)CC3)c3ccc(Cl)c(-n4ncnc4C(F)F)c3)C2=O)c(F)c1F] | LCMS-ESI+: calc'd for C₃₁H₃₁ClF₇N₇O₄: 734.2 (M + H+); Found: 734.2 (M + H+). | 1H NMR (400 MHz, Methanol-d₄) δ 8.27 (m, 1H), 7.71 (d, J = 4.6 Hz, 2H), 7.51 (s, 1H), 7.02-6.75 (m, 3H), 5.67 (dd, J = 9.1, 5.0 Hz, 1H), 5.25-5.06 (m, 1H), 4.74 (dd, J = 11.6, 5.1 Hz, 1H), 3.89 (s, 3H), 2.45-2.26 (m, 2H), 1.40-1.26 (m, 4H), 1.01 (s, 9H). |
| 229 | 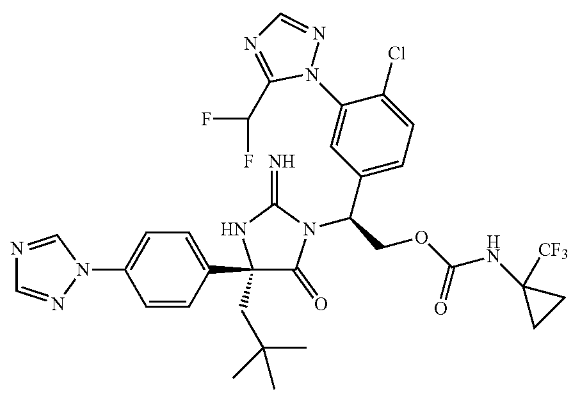 [SMILES: CC(C)(C)C[C@]1(c2ccc(-n3cncn3)cc2)NC(=N)N([C@H](COC(=O)NC2(C(F)(F)F)CC2)c2ccc(Cl)c(-n3ncnc3C(F)F)c2)C1=O] | LCMS-ESI+: calc'd for for C₃₂H₃₂ClF₅N₁₀O₃: 735.2 (M + H+); Found: 732.5 (M + H+). | ¹H NMR (400 MHz, Methanol-d₄) δ 9.12 (s, 1H), 8.20 (s, 1H), 8.02 (s, 1H), 7.82 (d, J = 8.8 Hz, 2H), 7.68-7.53 (m, 4H), 7.18 (s, 1H), 6.79 (t, J = 52.2 Hz, 1H), 5.68 (dd, J = 9.6, 5.0 Hz, 1H), 5.15-5.04 (m, 1H), 4.72 (dd, J = 11.5, 5.0 Hz, 1H), 2.50 (d, J = 15.1 Hz, 1H), 2.17 (d, J = 15.2 Hz, 1H), 1.32-1.24 (m, 2H), 1.11-1.07 (m, 2H), 1.01 (s, 9H). |
| 230 | 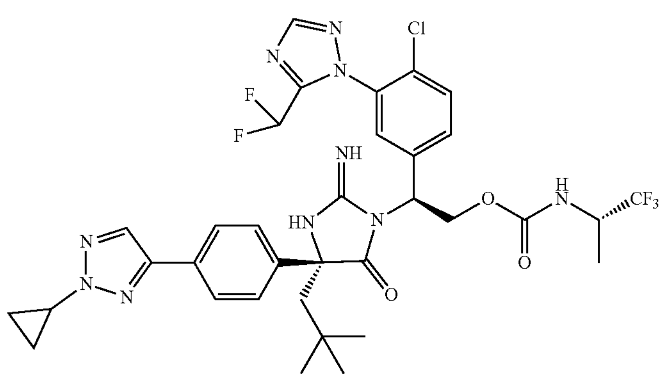 [SMILES: C[C@H](NC(=O)OC[C@H](c1ccc(Cl)c(-n2ncnc2C(F)F)c1)N1C(=N)N[C@](CC(C)(C)C)(c2ccc(-c3cnn(C4CC4)n3)cc2)C1=O)C(F)(F)F] | LCMS-ESI+: calc'd C₃₄H₃₆ClF₅N₁₀O₃: 763.3 (M + H+); Found: 763.9 (M + H+). | 1H NMR (400 MHz, Methanol-d₄) δ 8.01 (m, 2H), 7.89 (d, J = 9.1 Hz, 1H), 7.78 (d, J = 8.6 Hz, 2H), 7.70-7.53 (m, 2H), 7.48 (d, J = 8.6 Hz, 2H), 7.20 (d, J = 2.2 Hz, 1H), 6.79 (t, J = 52.2 Hz, 1H), 5.76 (dd, J = 9.6, 5.0 Hz, 1H), 5.11 (dd, J = 11.6, 9.7 Hz, 1H), 4.75 (dd, J = 11.6, 5.1 Hz, 1H), 4.39-4.23 (m, 1H), 4.12 (dt, J = 7.5, 3.7 Hz, 1H), 2.48 (d, J = 15.1 Hz, 1H), 2.17 (d, J = 15.2 Hz, 1H), 1.36 (ddd, J = 3.7, 2.7, 0.9 Hz, 2H), 1.29 |

-continued

| Compound # | Structures | Mass data | NMR data |
|---|---|---|---|
| | | | (d, J = 7.1 Hz, 3H), 1.15 (tdd, J = 8.0, 5.1, 0.8 Hz, 2H), 1.01 (s, 9H). |
| 231 | 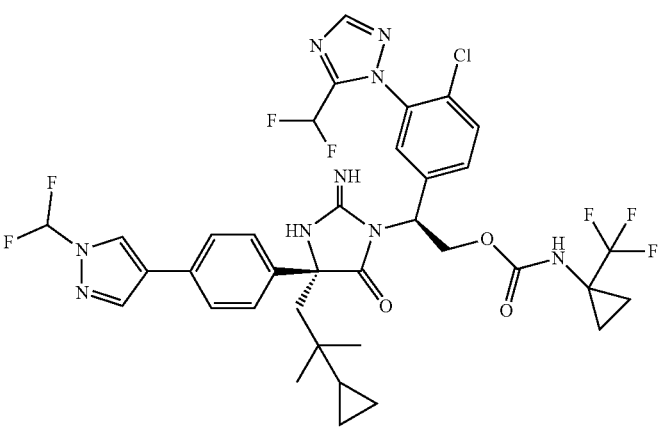 [SMILES: CC(C)(C[C@]1(c2ccc(-c3cnn(C(F)F)c3)cc2)NC(=N)N([C@H](COC(=O)NC2(C(F)(F)F)CC2)c2ccc(Cl)c(-n3ncnc3C(F)F)c2)C1=O)C1CC1] | LCMS-ESI+: calc'd for C₃₆H₃₅ClF₇N₉O₃: 810.2; Found 810.4. | 1H NMR (400 MHz, Methanol-d₄) δ 8.41 (s, 1H), 8.04 (m, 2H), 7.84-7.09 (m, 8H), 6.75 (t, J = 52.2 Hz, 1H), 5.54 (t, J = 7.4 Hz, 1H), 5.13-4.97 (m, 1H), 4.68 (dd, J = 11.3, 5.6 Hz, 1H), 2.43 (d, J = 14.8 Hz, 1H), 2.10 (d, J = 14.8 Hz, 1H), 1.23 (m, 2H), 1.05 (m, 2H), 0.79 (s, 6H), 0.25 (dd, J = 19.8, 7.5 Hz, 5H). |
| 232 | 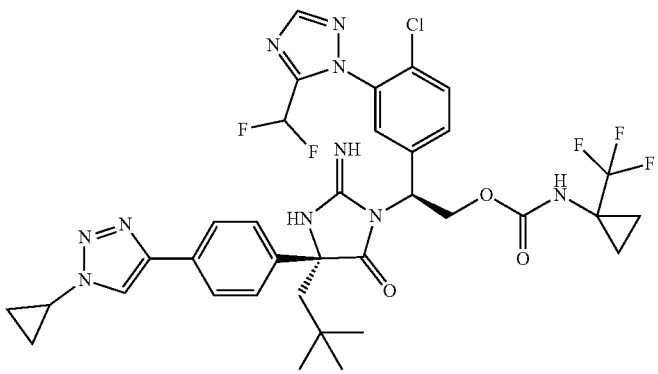 [SMILES: CC(C)(C)C[C@]1(c2ccc(-c3cn(C4CC4)nn3)cc2)NC(=N)N([C@H](COC(=O)NC2(C(F)(F)F)CC2)c2ccc(Cl)c(-n3ncnc3C(F)F)c2)C1=O] | LCMS-ESI+: calc'd C₃₅H₃₆ClF₅N₁₀O₃: 775.3 (M + H+); Found: 775.8 (M + H+). | 1H NMR (400 MHz, Methanol-d₄) δ 8.38 (s, 1H), 8.18 (s, 1H), 8.02 (s, 1H), 7.77 (d, J = 8.5 Hz, 2H), 7.63-7.53 (m, 2H), 7.48 (d, J = 8.3 Hz, 2H), 7.22 (d, J = 2.1 Hz, 1H), 6.76 (t, J = 52.2 Hz, 1H), 5.68 (dd, J = 9.8, 4.8 Hz, 1H), 5.09 (t, J = 10.6 Hz, 1H), 4.69 (dd, J = 11.5, 4.8 Hz, 1H), 3.98 (tt, J = 7.5, 3.9 Hz, 1H), 2.44 (d, J = 15.2 Hz, 1H), 2.16 (d, J = 15.1 Hz, 1H), 1.34-1.17 (m, 6H), 1.08 (s, 2H), 0.98 (s, 9H). |
| 233 | 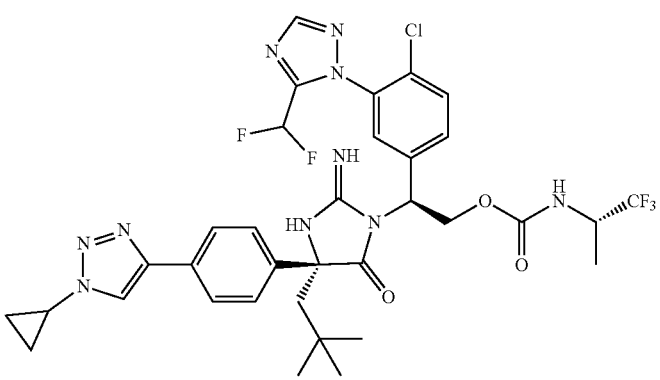 [SMILES: C[C@H](NC(=O)OC[C@H](c1ccc(Cl)c(-n2ncnc2C(F)F)c1)N1C(=N)N[C@](CC(C)(C)C)(c2ccc(-c3cn(C4CC4)nn3)cc2)C1=O)C(F)(F)F] | LCMS-ESI+: calc'd C₃₄H₃₆ClF₅N₁₀O₃: 763.3 (M + H+); Found: 763.8 (M + H+). | 1H NMR (400 MHz, Methanol-d₄) δ 8.38 (s, 1H), 8.02 (s, 1H), 7.83-7.72 (m, 2H), 7.63-7.52 (m, 2H), 7.49 (d, J = 8.5 Hz, 2H), 7.20 (d, J = 2.1 Hz, 1H), 6.77 (t, J = 52.2 Hz, 1H), 5.74 (dd, J = 9.6, 5.0 Hz, 1H), 5.12 (dd, J = 11.5, 9.7 Hz, 1H), 4.74 (dd, J = 11.6, 5.0 Hz, 1H), 4.30 (p, J = 7.2 Hz, 1H), 3.99 (tt, J = 7.5, 3.9 Hz, 1H), 2.44 (d, J = 15.1 Hz, 1H), 2.17 (d, J = 15.2 Hz, 1H), 1.35-1.17 (m, 7H), 0.99 (s, 9H). |

| Compound # | Structures | Mass data | NMR data |
|---|---|---|---|
| 234 | 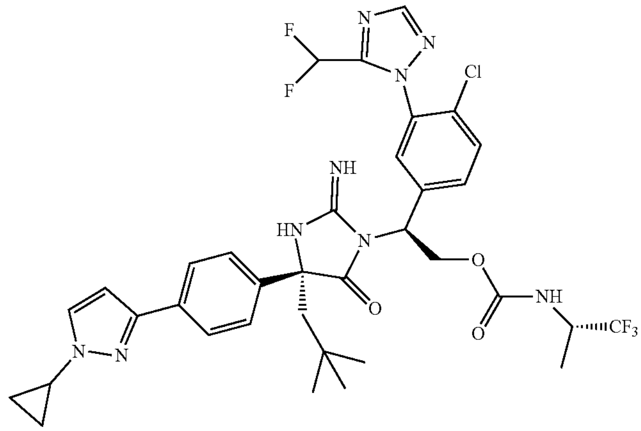 [SMILES: C[C@H](NC(=O)OC[C@H](c1ccc(Cl)c(-n2ncnc2C(F)F)c1)N1C(=N)N[C@](CC(C)(C)C)(c2ccc(-c3ccn(C4CC4)n3)cc2)C1=O)C(F)(F)F] | LCMS-ESI+: calc'd C₃₅H₃₈ClF₅N₉O₃: 762.3 (M + H+); Found: 763.0 (M + H+). | 1H NMR (400 MHz, Methanol-d₄) δ 8.06 (s, 1H), 8.00 (s, 1H), 7.88-7.73 (m, 2H), 7.67-7.52 (m, 2H), 7.50 (d, J = 8.5 Hz, 2H), 7.37 (d, J = 8.4 Hz, 2H), 7.18 (s, 1H), 6.79 (t, J = 52.2 Hz, 1H), 5.74 (dd, J = 9.6, 5.0 Hz, 1H), 5.10 (dd, J = 11.6, 9.6 Hz, 1H), 4.74 (dd, J = 11.7, 5.1 Hz, 1H), 4.39-4.14 (m, 1H), 3.74-3.63 (m, 1H), 2.45 (d, J = 15.1 Hz, 1H), 2.15 (d, J = 15.1 Hz, 1H), 1.29 (d, J = 7.1 Hz, 3H), 1.15 (m, 2H), 1.13-1.03 (m, 2H), 1.00 (s, 9H). |
| 235 | 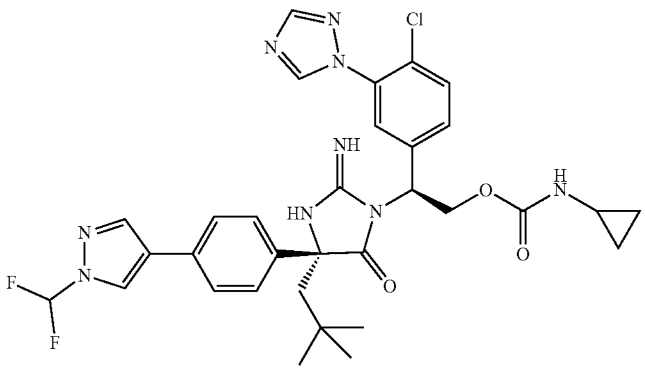 [SMILES: CC(C)(C)C[C@]1(c2ccc(-c3cnn(C(F)F)c3)cc2)NC(=N)N([C@H](COC(=O)NC2CC2)c2ccc(Cl)c(-n3cncn3)c2)C1=O] | LCMS-ESI+: calc'd for C₃₂H₃₄ClF₂N₉O₃: 666.2 (M + H+); Found: 662.4 (M + H+). | 1H NMR (400 MHz, Methanol-d₄) δ 8.61 (s, 1H), 8.40 (s, 1H), 8.07 (s, 1H), 8.01 (s, 1H), 7.71-7.32 (m, 9H), 5.61-5.36 (m, 1H), 5.02 (dd, J = 11.1, 8.9 Hz, 1H), 4.72-4.58 (m, 1H), 2.45 (s, 1H), 2.30 (d, J = 14.7 Hz, 1H), 1.96 (d, J = 14.6 Hz, 1H), 0.96 (s, 9H), 0.62 (d, J = 6.7 Hz, 2H), 0.41 (m, 2H). |
| 236 | 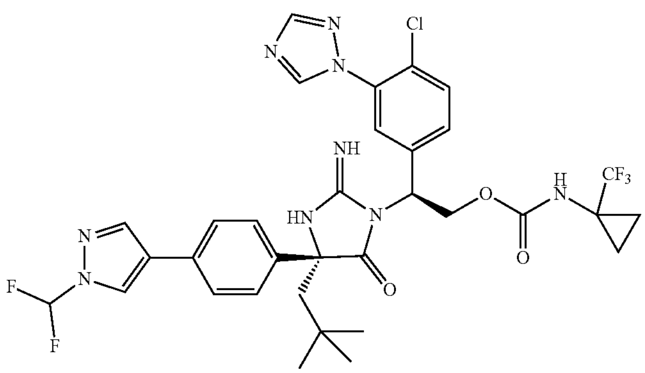 [SMILES: CC(C)(C)C[C@]1(c2ccc(-c3cnn(C(F)F)c3)cc2)NC(=N)N([C@H](COC(=O)NC2(C(F)(F)F)CC2)c2ccc(Cl)c(-n3cncn3)c2)C1=O] | LCMS-ESI+: calc'd for C₃₃H₃₃ClF₅N₉O₃: 734.1 (M + H+); Found: 734.2 (M + H+). | 1H NMR (400 MHz, Methanol-d₄) δ 8.60 (s, 1H), 8.41 (s, 1H), 8.04 (m, 2H), 7.72-7.23 (m, 8H), 5.49 (t, J = 7.1 Hz, 1H), 5.12-4.97 (m, 1H), 4.67 (dd, J = 11.1, 5.8 Hz, 1H), 2.30 (d, J = 14.7 Hz, 1H), 1.96 (d, J = 14.6 Hz, 1H), 1.23 (s, 2H), 1.04 (s, 2H), 0.96 (s, 9H). |
| 237 | 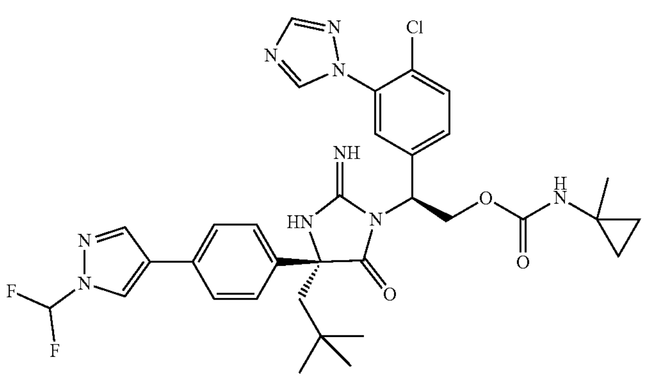 [SMILES: CC(C)(C)C[C@]1(c2ccc(-c3cnn(C(F)F)c3)cc2)NC(=N)N([C@H](COC(=O)NC2(C)CC2)c2ccc(Cl)c(-n3cncn3)c2)C1=O] | LCMS-ESI+: calc'd for C₃₃H₃₆ClF₂N₉O₃: 680.2 (M + H+); Found: 680.3 (M + H+). | 1H NMR (400 MHz, Methanol-d₄) δ 8.61 (s, 1H), 8.41 (s, 1H), 8.05 (m, 2H), 7.72-7.14 (m, 8H), 5.46-5.47 (m, 1H), 4.96-4.97 (m, 1H), 4.62-4.63 (m, 1H), 2.30 (d, J = 14.6 Hz, 1H), 1.94 (d, J = 14.6 Hz, 1H), 1.30 (d, J = 24.5 Hz, 3H), 0.96 (s, 9H), 0.65 (m, 2H), 0.53 (m, 2H). |

-continued

| Compound # | Structures | Mass data | NMR data |
|---|---|---|---|
| 238 | 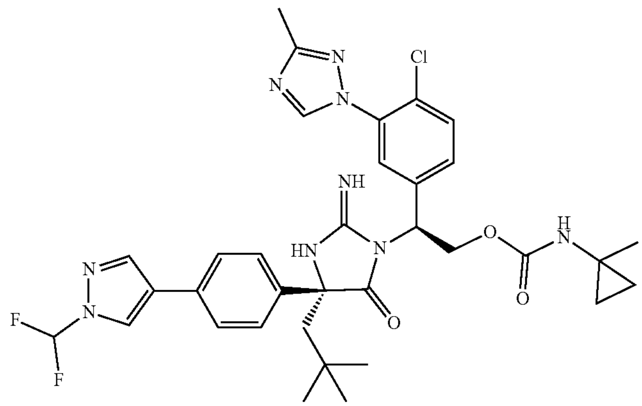 [SMILES: Cc1ncn(-c2cc([C@@H](COC(=O)NC3(C)CC3)N3C(=N)N[C@](CC(C)(C)C)(c4ccc(-c5cnn(C(F)F)c5)cc4)C3=O)ccc2Cl)n1] | LCMS-ESI+: calc'd for C₃₄H₃₈ClF₂N₉O₃: 694.2 (M + H+); Found: 694.4 (M + H+). | 1H NMR (400 MHz, Methanol-d₄) δ 8.54 (s, 1H), 8.46 (d, J = 0.8 Hz, 1H), 8.10 (s, 1H), 7.75-7.22 (m, 8H), 5.62 (dd, J = 9.4, 5.0 Hz, 1H), 5.02 (t, J = 10.5 Hz, 1H), 4.68 (dd, J = 11.5, 5.0 Hz, 1H), 2.46 (d, J = 15.0 Hz, 1H), 2.28 (s, 3H), 2.15 (d, J = 15.1 Hz, 1H), 1.31 (s, 3H), 1.00 (s, 9H), 0.69 (m, 2H), 0.59 (m, 2H). |
| 239 | 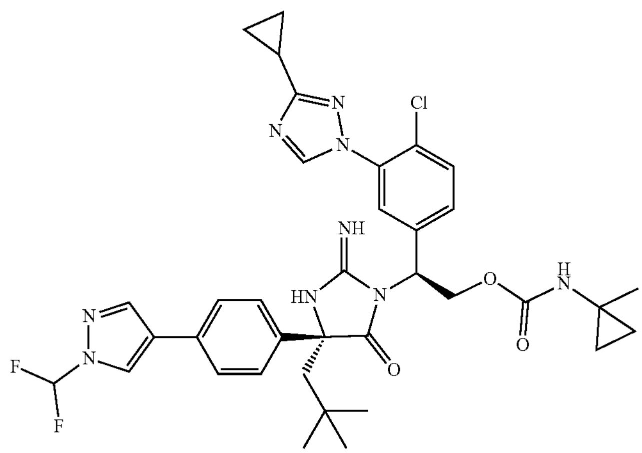 [SMILES: CC(C)(C)C[C@]1(c2ccc(-c3cnn(C(F)F)c3)cc2)NC(=N)N([C@H](COC(=O)NC2(C)CC2)c2ccc(Cl)c(-n3cnc(C4CC4)n3)c2)C1=O] | LCMS-ESI+: calc'd for C₃₆H₄₀ClF₂N₉O₃: 720.2 (M + H+); Found: 720.3 (M + H+). | 1H NMR (400 MHz, Methanol-d₄) δ 8.46 (m, 2H), 8.09 (s, 1H), 7.73-7.29 (m, 8H), 5.61 (dd, J = 9.5, 4.9 Hz, 1H), 5.02 (dd, J = 11.4, 9.7 Hz, 1H), 4.67 (dd, J = 11.4, 4.9 Hz, 1H), 2.43 (d, J = 15.1 Hz, 1H), 2.16 (d, J = 15.1 Hz, 1H), 1.96 (tt, J = 8.4, 4.9 Hz, 1H), 1.31 (s, 3H), 0.99 (s, 9H), 0.97-0.88 (m, 2H), 0.87 (m, 2H), 0.68 (m, 2H), 0.58 (m, 2H). |
| 240 | 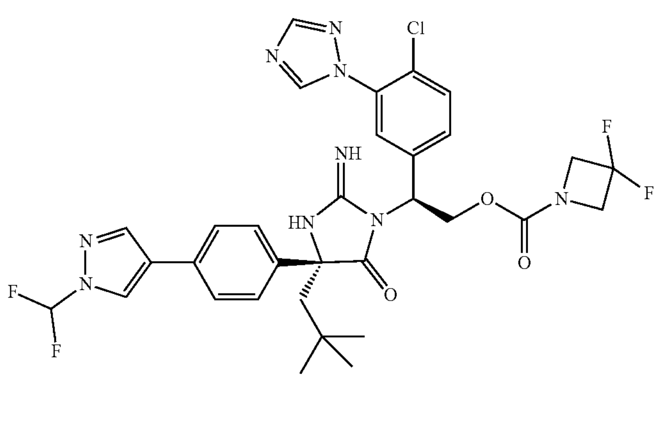 [SMILES: CC(C)(C)C[C@]1(c2ccc(-c3cnn(C(F)F)c3)cc2)NC(=N)N([C@H](COC(=O)N2CC(F)(F)C2)c2ccc(Cl)c(-n3cncn3)c2)C1=O] | LCMS-ESI+: calc'd for C₃₂H₃₂ClF₄N₉O₃: 702.1 (M + H+); Found: 702.3 (M + H+). | 1H NMR (400 MHz, Methanol-d₄) δ 8.69 (s, 1H), 8.47 (d, J = 0.7 Hz, 1H), 8.11 (d, J = 0.7 Hz, 1H), 8.04 (s, 1H), 7.73-7.53 (m, 3H), 7.53-7.42 (m, 4H), 7.42-7.29 (m, 1H), 5.67 (dd, J = 9.8, 4.6 Hz, 1H), 5.04 (dd, J = 11.5, 9.8 Hz, 1H), 4.85-4.86 (m, 1H), 4.27 (m, 4H), 2.47 (d, J = 15.1 Hz, 1H), 2.14 (d, J = 15.1 Hz, 1H), 1.01 (s, 9H). |

| Compound # | Structures | Mass data | NMR data |
|---|---|---|---|
| 241 | 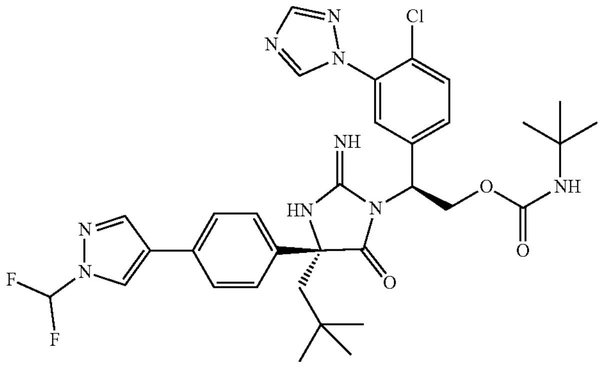 [SMILES: CC(C)(C)C[C@]1(c2ccc(-c3cnn(C(F)F)c3)cc2)NC(=N)N([C@H](COC(=O)NC(C)(C)C)c2ccc(Cl)c(-n3cncn3)c2)C1=O] | LCMS-ESI+: calc'd for C$_{33}$H$_{38}$ClF$_2$N$_9$O$_3$: 682.3 (M + H+); Found: 682.4 (M + H+). | 1H NMR (400 MHz, Methanol-d$_4$) δ 8.68 (s, 1H), 8.46 (d, J = 0.7 Hz, 1H), 8.10 (d, J = 0.7 Hz, 1H), 8.02 (s, 1H), 7.74-7.25 (m, 8H), 5.64 (dd, J = 9.4, 5.0 Hz, 1H), 5.02 (dd, J = 11.5, 9.5 Hz, 1H), 4.62 (dd, J = 11.5, 5.1 Hz, 1H), 2.44 (d, J = 15.1 Hz, 1H), 2.18 (d, J = 15.1 Hz, 1H), 1.29 (s, 9H), 0.99 (s, 9H). |
| 242 | 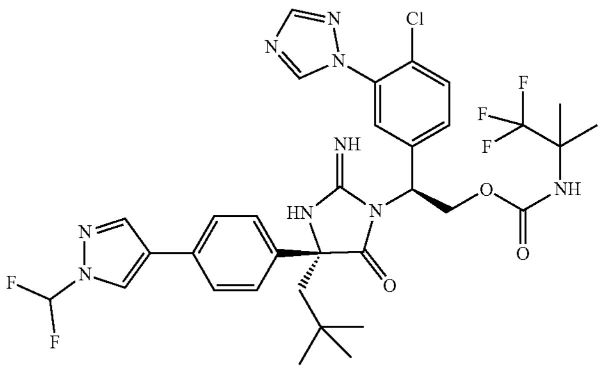 [SMILES: CC(C)(C)C[C@]1(c2ccc(-c3cnn(C(F)F)c3)cc2)NC(=N)N([C@H](COC(=O)NC(C)(C)C(F)(F)F)c2ccc(Cl)c(-n3cncn3)c2)C1=O] | LCMS-ESI+: calc'd for C$_{33}$H$_{35}$ClF$_5$N$_9$O$_3$: 736.2 (M + H+); Found: 736.3 (M + H+). | 1H NMR (400 MHz, Methanol-d$_4$) δ 8.67 (s, 1H), 8.46 (d, J = 0.7 Hz, 1H), 8.10 (d, J = 0.7 Hz, 1H), 8.01 (s, 1H), 7.68-7.29 (m, 8H), 5.66 (dd, J = 9.4, 5.0 Hz, 1H), 5.09 (dd, J = 11.5, 9.4 Hz, 1H), 4.64 (dd, J = 11.5, 5.0 Hz, 1H), 2.42 (d, J = 15.1 Hz, 1H), 2.19 (d, J = 15.1 Hz, 1H), 1.51 (s, 6H), 0.98 (s, 9H). |
| 243 | 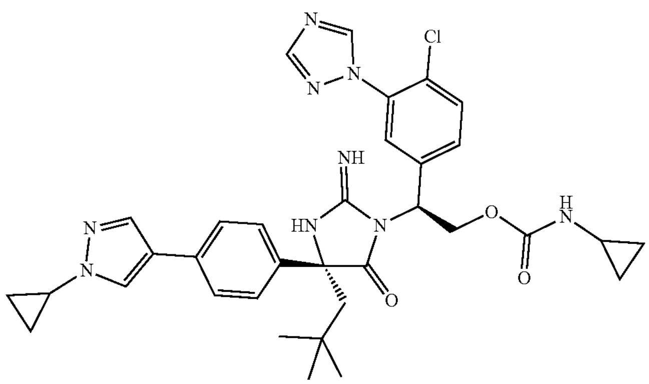 [SMILES: CC(C)(C)C[C@]1(c2ccc(-c3cnn(C4CC4)c3)cc2)NC(=N)N([C@H](COC(=O)NC2CC2)c2ccc(Cl)c(-n3cncn3)c2)C1=O] | LCMS-ESI+: calc'd for C$_{34}$H$_{38}$ClN$_9$O$_3$: 656.2 (M + H+); Found: 656.1 (M + H+). | 1H NMR (400 MHz, Methanol-d$_4$) δ 8.66 (s, 1H), 8.05 (m, 2H), 7.83 (s, 1H), 7.67-7.23 (m, 7H), 5.63 (m, 1H), 5.06 (t, J = 10.5 Hz, 1H), 4.76-4.63 (m, 1H), 3.70 (tt, J = 7.3, 3.8 Hz, 1H), 2.45 (m, 2H), 2.14 (d, J = 15.1 Hz, 1H), 1.21-1.03 (m, 4H), 0.99 (s, 9H), 0.72-0.34 (m, 4H). |
| 244 | 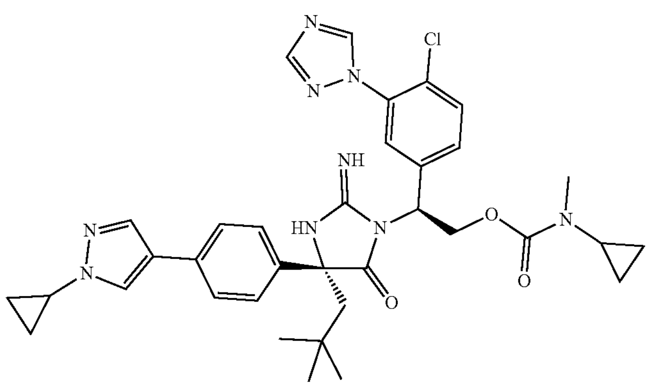 [SMILES: CN(C(=O)OC[C@H](c1ccc(Cl)c(-n2cncn2)c1)N1C(=N)N[C@](CC(C)(C)C)(c2ccc(-c3cnn(C4CC4)c3)cc2)C1=O)C1CC1] | LCMS-ESI+: calc'd for C$_{35}$H$_{40}$ClN$_9$O$_3$: 670.3 (M + H+); Found: 670.1 (M + H+). | 1H NMR (400 MHz, Methanol-d$_4$) δ 8.69 (s, 1H), 8.06 (m, 2H), 7.83 (s, 1H), 7.67-7.27 (m, 7H), 5.69 (m, 1H), 5.06 (m, 1H), 4.84 (m, 1H), 3.70 (dt, J = 7.5, 3.6 Hz, 1H), 2.83 (s, 3H), 2.45 (m, 2H), 2.14 (d, J = 15.1 Hz, 1H), 1.24-1.03 (m, 4H), 0.99 (s, 9H), 0.80-0.48 (m, 4H). |

-continued

| Compound # | Structures | Mass data | NMR data |
|---|---|---|---|
| 245 | 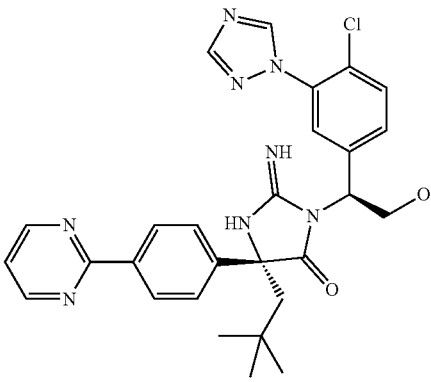 | LCMS-ESI+: calc'd for C₂₈H₂₉ClN₈O₂: 545.2 (M + H+); Found: 545.2 (M + H+). | 1H NMR (400 MHz, Methanol-d₄) δ 8.87 (d, J = 4.9 Hz, 2H), 8.73 (m, 1H), 8.47-8.33 (m, 2H), 8.05 (s, 1H), 7.61 (dd, J = 8.6, 1.6 Hz, 3H), 7.46 (ddd, J = 8.5, 2.4, 0.6 Hz, 1H), 7.42-7.32 (m, 2H), 5.45 (dd, J = 8.3, 4.4 Hz, 1H), 4.46 (dd, J = 11.2, 8.4 Hz, 1H), 4.22 (dd, J = 11.3, 4.4 Hz, 1H), 2.48 (d, J = 15.1 Hz, 1H), 2.19 (d, J = 15.1 Hz, 1H), 0.99 (s, 9H). |
| 246 | 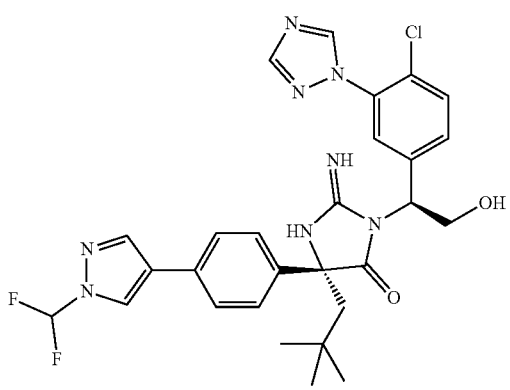 [SMILES: CC(C)(C)C[C@]1(c2ccc(-c3cnn(C(F)F)c3)cc2)NC(=N)N([C@H](CO)c2ccc(Cl)c(-n3cncn3)c2)C1=O] | LCMS-ESI+: Calc'd for C₂₈H₂₉ClF₂N₈O₂: 583.2 [M + H+]; Found: 583.3 [M + H+]. | 1H NMR (400 MHz, CD₃CN) δ 8.52 (s, 1H), 8.33 (s, 1H), 8.07 (s, 1H), 8.06 (s, 1H), 7.68-7.20 (m, 8H), 5.49-5.39 (m, 1H), 4.32-4.23 (m, 1H), 4.16 (dd, J = 12.3, 3.1 Hz, 1H), 2.25-2.01 (m, 2H), 0.85 (s, 9H). |
| 247 | 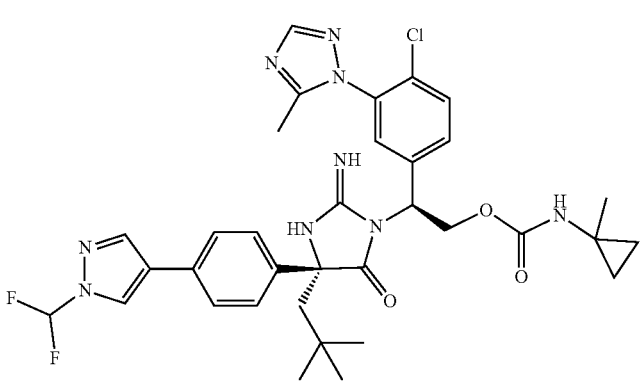 [SMILES: Cc1ncnn1-c1cc([C@@H](COC(=O)NC2(C)CC2)N2C(=N)N[C@](CC(C)(C)C)(c3ccc(-c4cnn(C(F)F)c4)cc3)C2=O)ccc1Cl] | LCMS-ESI+: Calc'd for C₃₄H₃₈ClF₂N₉O₃: 694.2 [M + H+]; Found: 694.3 [M + H+]. | 1H NMR (400 MHz, Methanol-d₄) δ 8.47 (s, 1H), 8.11 (s, 1H), 7.87 (s, 1H), 7.70-7.14 (m, 8H), 5.63 (dd, J = 9.6, 4.9 Hz, 1H), 5.03 (t, J = 10.5 Hz, 1H), 4.68 (dd, J = 11.5, 4.9 Hz, 1H), 2.45 (d, J = 15.1 Hz, 1H), 2.14 (d, J = 15.1 Hz, 1H), 2.03 (s, 3H), 1.32 (s, 3H), 0.99 (s, 9H), 0.75-0.65 (m, 2H), 0.63-0.51 (m, 2H). |
| 248 | 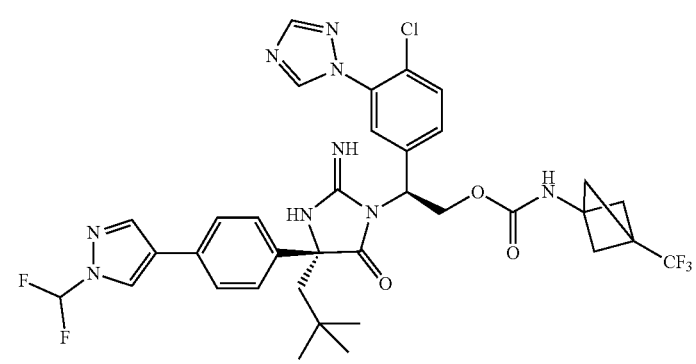 [SMILES: CC(C)(C)C[C@]1(c2ccc(-c3cnn(C(F)F)c3)cc2)NC(=N)N([C@H](COC(=O)NC23CC(C(F)(F)F)(C2)C3)c2ccc(Cl)c(-n3cncn3)c2)C1=O] | LCMS-ESI+: calc'd for C₃₅H₃₅ClF₅N₉O₃: 760.2 (M + H+); Found: 760.2 (M + H+). | 1H NMR (400 MHz, Methanol-d₄) δ 8.67 (s, 1H), 8.46 (d, J = 0.8 Hz, 1H), 8.06 (m, 2H), 7.72-7.25 (m, 8H), 5.63 (dd, J = 9.4, 4.9 Hz, 1H), 5.08 (t, J = 10.6 Hz, 1H), 4.70 (dd, J = 11.6, 5.0 Hz, 1H), 2.46 (d, J = 15.1 Hz, 1H), 2.35-1.96 (m, 7H), 1.00 (s, 9H). |

-continued

| Compound # | Structures | Mass data | NMR data |
|---|---|---|---|
| 249 | 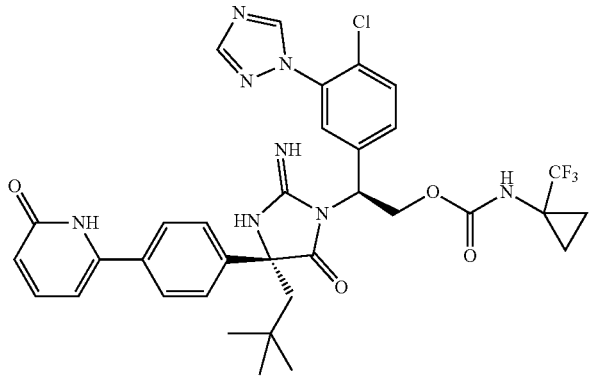 [SMILES: CC(C)(C)C[C@]1(c2ccc(-c3cccc(=O)[nH]3)cc2)NC(=N)N([C@H](COC(=O)NC2(C(F)(F)F)CC2)c2ccc(Cl)c(-n3cncn3)c2)C1=O] | LCMS-ESI+: calc'd for C$_{34}$H$_{34}$ClF$_3$N$_8$O$_4$: 711.3 (M + H+); Found: 711.2 (M + H+). | 1H NMR (400 MHz, Methanol-d$_4$) δ 8.64 (s, 1H), 8.20 (s, 1H), 8.09 (s, 1H), 7.76-7.62 (m, 3H), 7.60-7.55 (m, 2H), 7.49-7.38 (m, 1H), 7.34 (d, J = 2.2 Hz, 1H), 6.69 (d, 1H), 6.57 (d, 1H), 5.66 (dd, J = 9.7, 4.9 Hz, 1H), 5.16-5.01 (m, 1H), 4.71 (dd, J = 11.5, 4.9 Hz, 1H), 2.47 (d, J = 15.1 Hz, 1H), 2.18 (d, 15.1 Hz, 1H), 1.36-1.19 (m, 2H), 1.09 (m, 2H), 1.00 (s, 9H). |
| 250 | 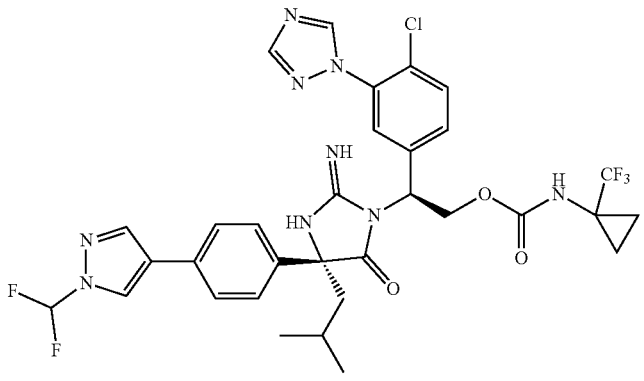 [SMILES: CC(C)C[C@]1(c2ccc(-c3cnn(C(F)F)c3)cc2)NC(=N)N([C@H](COC(=O)NC2(C(F)(F)F)CC2)c2ccc(Cl)c(-n3cncn3)c2)C1=O] | LCMS-ESI+: calc'd for C$_{32}$H$_{31}$ClF$_5$N$_9$O$_3$: 720.2 (M + H+); Found: 720.0 (M + H+). | 1H NMR (400 MHz, Methanol-d$_4$) δ 8.71 (s, 1H), 8.46 (s, 1H), 8.08 (m, 2H), 7.69-7.59 (m, 3H), 7.55-7.30 (m, 5H), 5.67 (dd, J = 9.7, 4.8 Hz, 1H), 5.11 (dd, J = 11.5, 9.8 Hz, 1H), 4.71 (dd, J = 11.5, 4.9 Hz, 1H), 2.29 (dd, J = 14.7, 6.3 Hz, 1H), 2.15 (dd, J = 14.7, 6.1 Hz, 1H), 1.76 (hept, J = 6.6 Hz, 1H), 1.32-1.24 (m, 2H), 1.08 (m, 2H), 0.96 (d, J = 6.7 Hz, 3H), 0.91 (d, J = 6.7 Hz, 3H). |
| 251 | 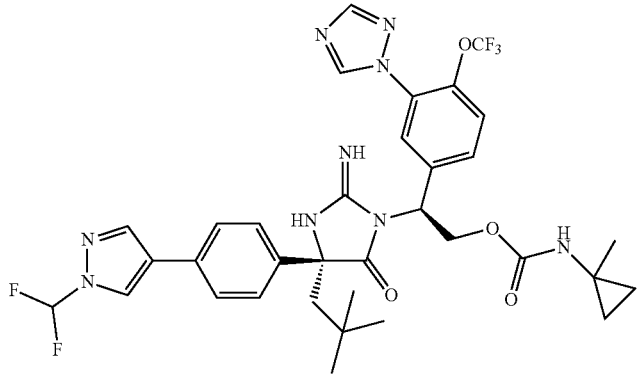 [SMILES: CC(C)(C)C[C@]1(c2ccc(-c3cnn(C(F)F)c3)cc2)NC(=N)N([C@H](COC(=O)NC2(C)CC2)c2ccc(OC(F)(F)F)c(-n3cncn3)c2)C1=O] | LCMS-ESI+: calc'd for C$_{34}$H$_{36}$F$_5$N$_9$O$_4$: 730.3 (M + H+); Found: 730.2 (M + H+). | 1H NMR (400 MHz, Methanol-d$_4$) δ 8.70 (s, 1H), 8.45 (d, J = 0.7 Hz, 1H), 8.07 (m, 2H), 7.69-7.58 (m, 3H), 7.58-7.44 (m, 5H), 5.67 (dd, J = 9.6, 5.0 Hz, 1H), 5.06 (dd, J = 11.4, 9.6 Hz, 1H), 4.71 (dd, J = 11.4, 5.0 Hz, 1H), 2.46 (d, J = 15.2 Hz, 1H), 2.17 (d, J = 15.2 Hz, 1H), 1.32 (s, 3H), 1.01 (s, 9H), 0.79-0.65 (m, 2H), 0.60 (m, 2H). |
| 252 | 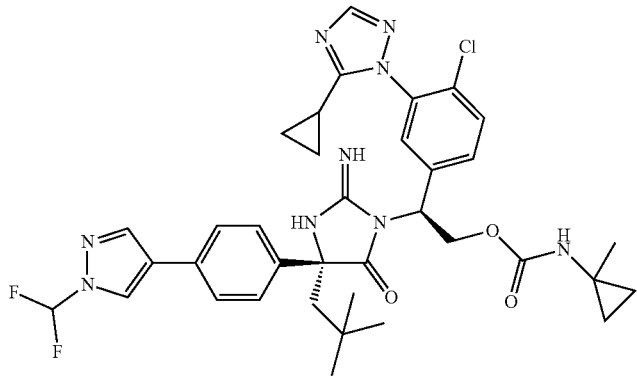 [SMILES: CC(C)(C)C[C@]1(c2ccc(-c3cnn(C(F)F)c3)cc2)NC(=N)N([C@H](COC(=O)NC2(C)CC2)c2ccc(Cl)c(-n3ncnc3C3CC3)c2)C1=O] | LCMS-ESI+: calc'd for C$_{36}$H$_{40}$ClF$_2$N$_9$O$_3$: 720.3 (M + H+); Found: 720.2 (M + H+). | 1H NMR (400 MHz, Methanol-d$_4$) δ 8.40 (s, 1H), 8.07 (s, 1H), 7.77 (s, 1H), 7.68-7.31 (m, 7H), 7.26 (s, 1H), 5.56-5.36 (m, 1H), 4.98 (t, J = 10.0 Hz, 1H), 4.65 (dd, J = 11.3, 5.8 Hz, 1H), 2.30 (d, J = 14.7 Hz, 1H), 1.95 (d, J = 14.7 Hz, 1H), 1.40 (p, J = 6.9 Hz, 1H), 1.28 (s, 3H), 0.96 (s, 9H), 0.94-0.80 (m, 4H), 0.70-0.62 (m, 2H), 0.61-0.50 (m, 2H). |

-continued

| Compound # | Structures | Mass data | NMR data |
|---|---|---|---|
| 253 | 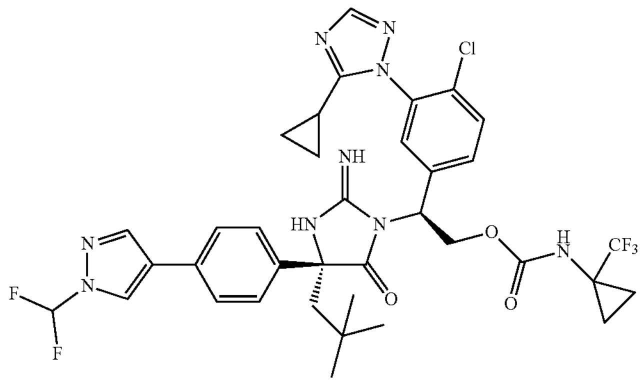 [SMILES: CC(C)(C)C[C@]1(c2ccc(-c3cnn(C(F)F)c3)cc2)NC(=N)N([C@H](COC(=O)NC2(C(F)(F)F)CC2)c2ccc(Cl)c(-n3ncnc3C3CC3)c2)C1=O] | LCMS-ESI+: calc'd for C₃₆H₃₇F₅N₉O₃: 774.3 (M + H+); Found: 774.2 (M + H+). | 1H NMR (400 MHz, Methanol-d₄) δ 8.40 (s, 1H), 8.07 (s, 1H), 7.75 (s, 1H), 7.70-7.31 (m, 7H), 7.25 (s, 1H), 5.63-5.39 (m, 1H), 5.14-4.96 (m, 1H), 4.68 (dd, J = 11.1, 5.8 Hz, 1H), 2.29 (d, J = 14.7 Hz, 1H), 1.94 (d, J = 14.6 Hz, 1H), 1.39 (dt, J = 13.6, 6.9 Hz, 1H), 1.26-1.19 (m, 2H), 1.10-1.00 (m, 2H), 0.95 (s, 9H), 0.93-0.84 (m, 4H). |
| 254 | 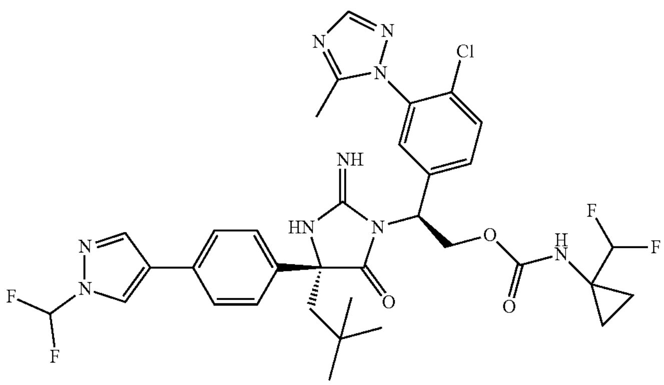 [SMILES: Cc1ncnn1-c1cc([C@@H](COC(=O)NC2(C(F)F)CC2)N2C(=N)N[C@](CC(C)(C)C)(c3ccc(-c4cnn(C(F)F)c4)cc3)C2=O)ccc1Cl] | LCMS-ESI+: calc'd for C₃₄H₃₆ClF₄N₉O₃: 730.3 (M + H+); Found: 730.3 (M + H+). | 1H NMR (400 MHz, Methanol-d₄) δ 8.48 (s, 1H), 8.11 (s, 1H), 7.97 (s, 1H), 7.88 (s, 1H), 7.72-7.19 (m, 8H), 5.67 (t, J = 56 Hz, 1H), 5.65 (m, 1H), 5.08 (d, J = 10.8 Hz, 1H), 4.71 (m, 1H), 2.45 (d, J = 15.1 Hz, 1H), 2.14 (d, J = 15.1 Hz, 1H)-2.02 (s, 3H), 1.07 (m, 2H), 0.99 (s, 9H), 0.91 (m, 2H). |
| 255 | 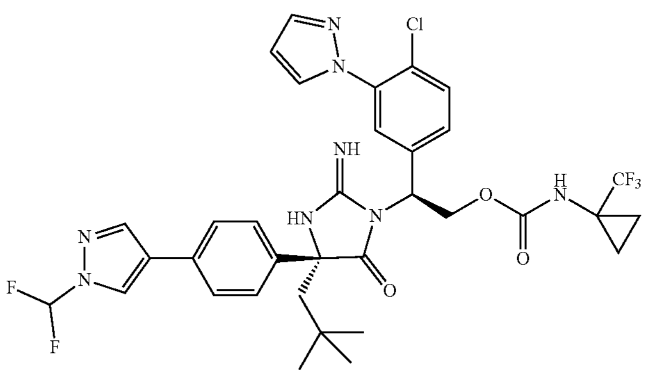 [SMILES: CC(C)(C)C[C@]1(c2ccc(-c3cnn(C(F)F)c3)cc2)NC(=N)N([C@H](COC(=O)NC2(C(F)(F)F)CC2)c2ccc(Cl)c(-n3cccn3)c2)C1=O] | LCMS-ESI+: calc'd for C₃₃H₃₄ClF₅N₈O₃: 733.2 (M + H+); Found: 733.2 (M + H+). | 1H NMR (400 MHz, Methanol-d₄) δ 8.46 (s, 1H), 8.16 (s, 1H), 8.10 (s, 1H), 7.70 (d, J = 2.5 Hz, 1H), 7.68-7.32 (m, 8H), 7.19 (d, J = 2.3 Hz, 1H), 6.30 (t, J = 2.2 Hz, 1H), 5.64 (dd, J = 9.6, 4.9 Hz, 1H), 5.08 (t, J = 10.6 Hz, 1H), 4.70 (dd, J = 11.5, 4.9 Hz, 1H), 2.45 (d, J = 15.1 Hz, 1H), 2.15 (d, J = 15.1 Hz, 1H), 1.31-1.23 (m, 2H), 1.12-1.05 (m, 2H), 0.99 (s, 9H). |
| 256 | 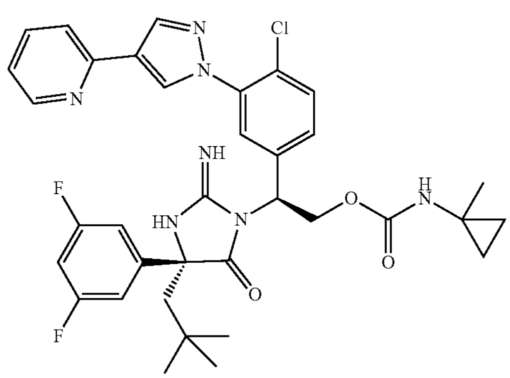 [SMILES: CC(C)(C)C[C@]1(c2cc(F)cc(F)c2)NC(=N)N([C@H](COC(=O)NC2(C)CC2)c2ccc(Cl)c(-n3cc(-c4ccccn4)cn3)c2)C1=O] | LCMS-ESI+: calc'd for C₃₅H₃₆ClF₂N₇O₃: 676.2 (M + H+); Found: 676.2 (M + H+). | 1H NMR (400 MHz, Methanol-d₄) δ 8.68-8.50 (m, 2H), 8.30 (s, 1H), 8.14-8.00 (m, 1H), 7.94 (dd, J = 7.6, 1.2 Hz, 1H), 7.64 (d, J = 8.4 Hz, 1H), 7.46 (q, J = 6.7 Hz, 2H), 7.31 (d, J = 2.1 Hz, 1H), 7.17-7.01 (m, 2H), 6.89 (s, 1H), 5.64 (dd, J = 9.5, 5.0 Hz, 1H), 5.05 (q, J = 12.9, 10.3 Hz, 1H), 4.69 (dd, J = 11.6, 5.0 Hz, 1H), 2.41 (d, J = 15.1 Hz, 1H), 2.12 (d, J = 15.2 Hz, 1H), 1.32 (s, 3H), 0.99 (s, 9H), 0.77-0.50 (m, 4H). |

-continued

| Compound # | Structures | Mass data | NMR data |
|---|---|---|---|
| 257 | 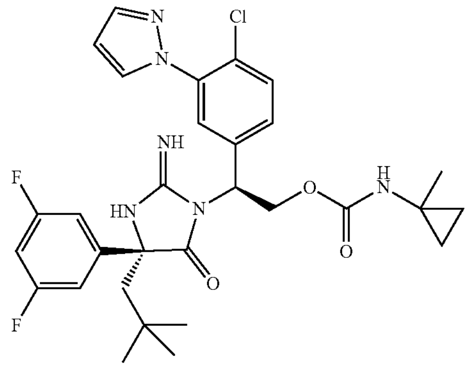 [SMILES: CC(C)(C)C[C@]1(c2cc(F)cc(F)c2)NC(=N)N([C@H](COC(=O)NC2(C)CC2)c2ccc(Cl)c(-n3cccn3)c2)C1=O] | LCMS-ESI+: calc'd for C$_{30}$H$_{33}$ClF$_2$N$_6$O$_3$: 599.2 (M + H+); Found: 599.1 (M + H+). | 1H NMR (400 MHz, Methanol-d$_4$) δ 7.79 (d, J = 2.5 Hz, 1H), 7.68 (d, J = 1.9 Hz, 1H), 7.51 (d, J = 8.4 Hz, 1H), 7.40-7.31 (m, 1H), 7.24 (s, 1H), 7.08 (d, J = 8.4 Hz, 2H), 6.86-6.76 (m, 1H), 6.49 (t, J = 2.2 Hz, 1H), 5.44 (t, J = 7.4 Hz, 1H), 5.04-4.93 (m, 1H), 4.61 (dd, J = 11.2, 5.5 Hz, 1H), 2.18 (d, J = 14.6 Hz, 1H), 1.92 (d, J = 14.6 Hz, 1H), 1.29 (s, 3H), 0.93 (s, 9H), 0.67 (s, 2H), 0.55 (s, 2H). |
| 258 | 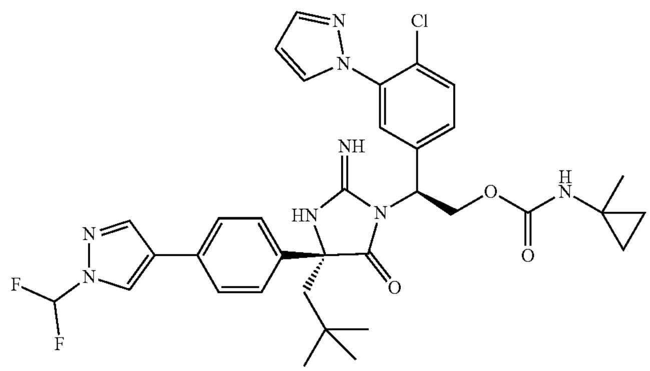 [SMILES: CC(C)(C)C[C@]1(c2ccc(-c3cnn(C(F)F)c3)cc2)NC(=N)N([C@H](COC(=O)NC2(C)CC2)c2ccc(Cl)c(-n3cccn3)c2)C1=O] | LCMS-ESI+: calc'd for C$_{34}$H$_{37}$ClF$_2$N$_8$O$_3$: 679.2 (M + H+); Found: 679.3 (M + H+). | 1H NMR (400 MHz, Methanol-d$_4$) δ 8.42 (s, 1H), 8.08 (s, 1H), 7.67-7.45 (m, 9H), 7.36 (d, J = 4.7 Hz, 1H), 7.22 (s, 1H), 6.37-6.21 (m, 1H), 5.59-5.40 (m, 1H), 4.97 (t, J = 10.1 Hz, 1H), 4.64 (dd, J = 11.2, 5.6 Hz, 1H), 2.34 (d, J = 14.8 Hz, 1H), 1.97 (d, 1H), 1.28 (s, 3H), 0.97 (s, 9H), 0.71-0.60 (m, 2H), 0.58-0.47 (m, 2H). |
| 259 | 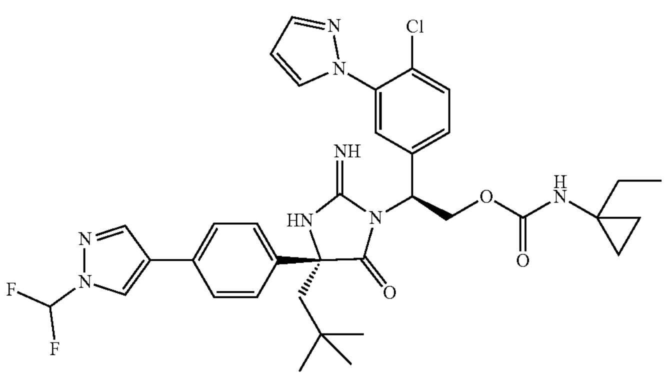 [SMILES: CCC1(NC(=O)OC[C@H](c2ccc(Cl)c(-n3cccn3)c2)N2C(=N)N[C@](CC(C)(C)C)(c3ccc(-c4cnn(C(F)F)c4)cc3)C2=O)CC1] | LCMS-ESI+: calc'd for C$_{35}$H$_{39}$ClF$_2$N$_8$O$_3$: 693.3 (M + H+); Found: 693.3 (M + H+). | 1H NMR (400 MHz, Methanol-d$_4$) δ 8.42 (s, 1H), 8.08 (s, 1H), 7.68-7.45 (m, 9H), 7.39-7.33 (m, 1H), 7.23 (d, J = 2.2 Hz, 1H), 6.30 (t, J = 2.2 Hz, 1H), 5.47 (dd, J = 8.6, 5.9 Hz, 1H), 4.96 (dd, J = 11.2, 8.9 Hz, 1H), 4.64 (dd, J = 11.2, 5.7 Hz, 1H), 2.33 (d, J = 14.8 Hz, 1H), 1.99 (d, J = 14.9 Hz, 1H), 1.51 (dt, J = 9.0, 6.5 Hz, 2H), 0.96 (s, 9H), 0.91 (t, J = 7.5 Hz, 3H), 0.69-0.61 (m, 2H), 0.61-0.52 (m, 2H). |
| 260 | 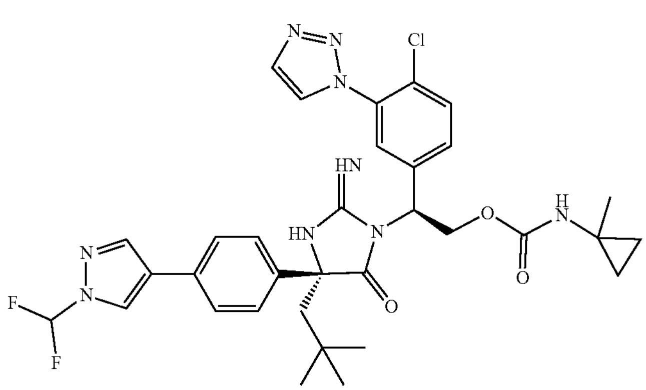 [SMILES: CC(C)(C)C[C@]1(c2ccc(-c3cnn(C(F)F)c3)cc2)NC(=N)N([C@H](COC(=O)NC2(C)CC2)c2ccc(Cl)c(-n3ccnn3)c2)C1=O] | LCMS-ESI+: calc'd for C$_{33}$H$_{36}$ClF$_2$N$_9$O$_3$: 680.3 (M + H+); Found: 680.3 (M + H+). | 1H NMR (400 MHz, Methanol-d$_4$) δ 8.44 (s, 1H), 8.16-8.02 (m, 2H), 7.66 (d, J = 2.3 Hz, 1H), 7.63-7.35 (m, 7H), 7.27 (s, 1H), 5.57 (dd, J = 9.1, 5.5 Hz, 1H), 4.99 (t, J = 10.2 Hz, 1H), 4.68 (dd, J = 11.3, 5.4 Hz, 1H), 2.40 (d, J = 14.9 Hz, 1H), 2.05 (d, J = 14.9 Hz, 1H), 1.29 (s, 3H), 0.98 (s, 9H), 0.71-0.62 (m, 2H), 0.59-0.52 (m, 2H). |

| Compound # | Structures | Mass data | NMR data |
|---|---|---|---|
| 261 | 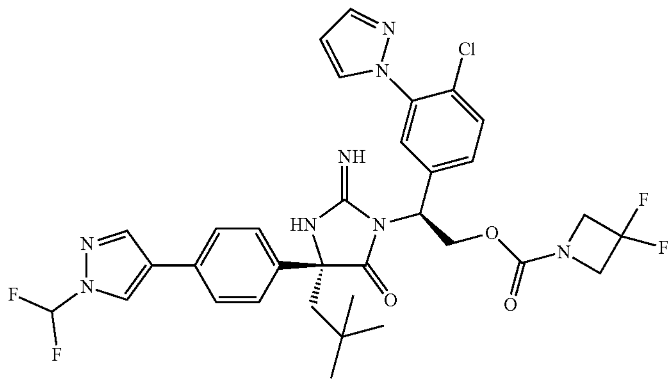 [SMILES: CC(C)(C)C[C@]1(c2ccc(-c3cnn(C(F)F)c3)cc2)NC(=N)N([C@H](COC(=O)N2CC(F)(F)C2)c2ccc(Cl)c(-n3cccn3)c2)C1=O] | LCMS-ESI+: calc'd for C₃₃H₃₃ClF₄N₈O₃: 701.2 (M + H+); Found: 701.3 (M + H+). | 1H NMR (400 MHz, Methanol-d₄) δ 8.46 (d, J = 0.8 Hz, 1H), 8.10 (s, 1H), 7.74 (d, J = 2.5 Hz, 1H), 7.69-7.57 (m, 4H), 7.54 (d, J = 14.3 Hz, 1H), 7.50-7.43 (m, 2H), 7.40-7.34 (m, 1H), 7.24 (d, J = 2.3 Hz, 1H), 6.32 (t, J = 2.2 Hz, 1H), 5.65 (dd, J = 9.7, 4.6 Hz, 1H), 5.04 (dd, J = 11.5, 9.8 Hz, 1H), 4.90-4.83 (m, 1H), 4.27 (t, J = 11.8 Hz, 4H), 2.48 (d, J = 15.2 Hz, 1H), 2.14 (d, J = 15.2 Hz, 1H), 1.01 (s, 9H). |
| 262 | 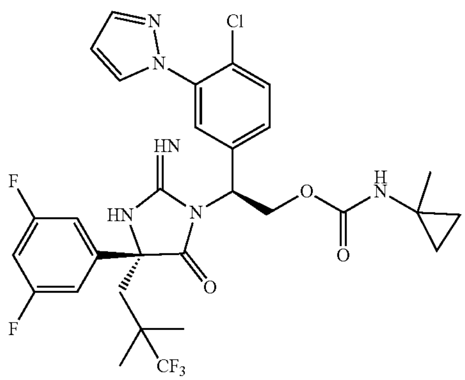 [SMILES: CC1(NC(=O)OC[C@H](c2ccc(Cl)c(-n3cccn3)c2)N2C(=N)N[C@](CC(C)(C)C(F)(F)F)(c3cc(F)cc(F)c3)C2=O)CC1] | LCMS-ESI+: calc'd for C₃₀H₃₀ClF₅N₆O₃: 653.2 (M + H+); Found: 653.0 (M + H+). | 1H NMR (400 MHz, Methanol-d₄) δ 7.77 (d, J = 2.5 Hz, 1H), 7.68 (d, J = 1.9 Hz, 1H), 7.50 (d, J = 8.4 Hz, 1H), 7.33 (dd, J = 8.3, 2.2 Hz, 1H), 7.25-7.08 (m, 3H), 6.80 (tt, J = 8.8, 2.4 Hz, 1H), 6.49 (t, J = 2.2 Hz, 1H), 5.40 (d, J = 7.8 Hz, 1H), 5.00 (dd, J = 11.2, 9.1 Hz, 1H), 4.58 (dd, J = 11.2, 5.4 Hz, 1H), 2.35 (d, J = 14.7 Hz, 1H), 2.14 (d, J = 14.6 Hz, 1H), 1.29 (s, 3H), 1.13 (d, J = 8.0 Hz, 6H), 0.67 (t, J = 3.3 Hz, 2H), 0.56 (q, J = 4.7 Hz, 2H). |
| 263 | 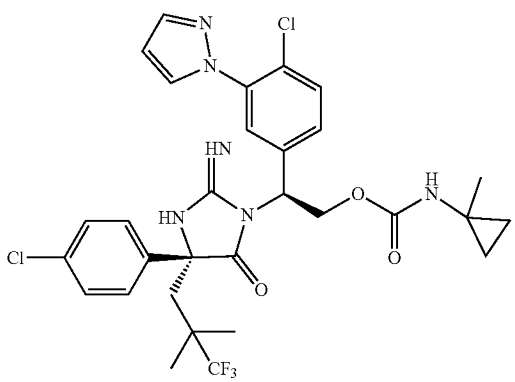 [SMILES: CC1(NC(=O)OC[C@H](c2ccc(Cl)c(-n3cccn3)c2)N2C(=N)N[C@](CC(C)(C)C(F)(F)F)(c3ccc(Cl)cc3)C2=O)CC1] | LCMS-ESI+: calc'd for C₃₀H₃₁Cl₂F₃N₆O₃: 651.2 (M + H+); Found: 651.0 (M + H+). | 1H NMR (400 MHz, Methanol-d₄) δ 7.68 (m, 2H), 7.47 (m, 3H), 7.37-7.13 (m, 4H), 6.50 (t, J = 2.2 Hz, 1H), 5.38 (d, J = 9.4 Hz, 1H), 4.99 (dd, J = 11.1, 9.2 Hz, 1H), 4.58 (dd, J = 11.2, 5.4 Hz, 1H), 2.44 (d, J = 14.6 Hz, 1H), 2.15 (d, J = 14.6 Hz, 1H), 1.29 (s, 3H), 1.13 (s, 6H), 0.67 (dd, J = 4.8, 4.3 Hz, 2H), 0.56 (t, J = 3.4 Hz, 2H). |

| Compound # | Structures | Mass data | NMR data |
|---|---|---|---|
| 264 | 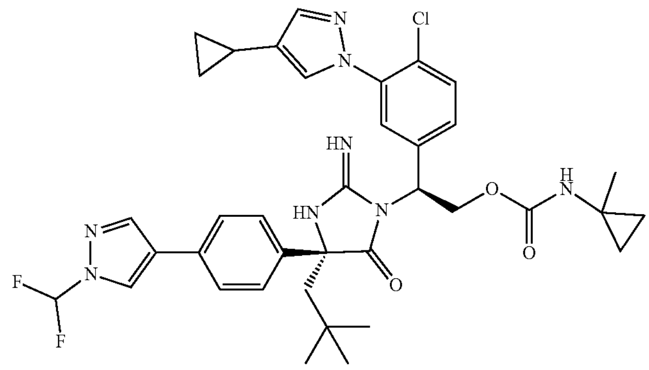 [SMILES: CC(C)(C)C[C@]1(c2ccc(-c3cnn(C(F)F)c3)cc2)NC(=N)N([C@H](COC(=O)NC2(C)CC2)c2ccc(Cl)c(-n3cc(C4CC4)cn3)c2)C1=O] | LCMS-ESI+: calc'd for C₃₇H₄₁ClF₂N₈O₃: 719.3 (M + H+); Found: 719.3 (M + H+). | ¹H NMR (400 MHz, Methanol-d₄) δ 8.41 (s, 1H), 8.08 (s, 1H), 7.66-7.38 (m, 7H), 7.38-7.30 (m, 2H), 7.22 (s, 1H), 5.42 (t, J = 7.4 Hz, 1H), 4.96 (t, J = 10.0 Hz, 1H), 4.61 (dd, J = 11.2, 5.8 Hz, 1H), 2.30 (d, J = 14.6 Hz, 1H), 1.95 (d, J = 14.4 Hz, 1H), 1.60 (tt, J = 8.7, 5.0 Hz, 1H), 1.27 (s, 3H), 0.96 (s, 9H), 0.84-0.75 (m, 2H), 0.68-0.62 (m, 2H), 0.58-0.50 (m, 2H), 0.46 (dt, J = 6.4, 4.5 Hz, 2H). |
| 265 | 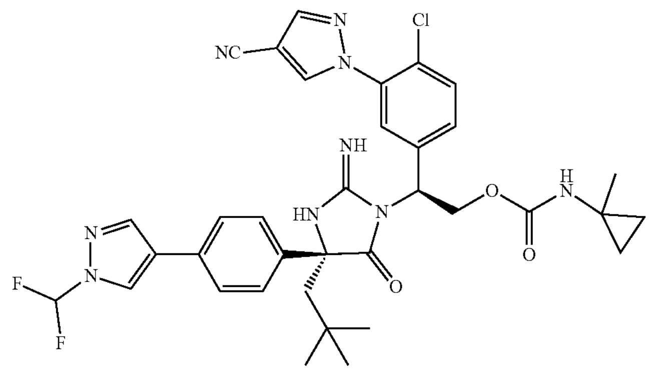 [SMILES: CC(C)(C)C[C@]1(c2ccc(-c3cnn(C(F)F)c3)cc2)NC(=N)N([C@H](COC(=O)NC2(C)CC2)c2ccc(Cl)c(-n3cc(C#N)cn3)c2)C1=O] | LCMS-ESI+: calc'd for C₃₅H₃₆ClF₂N₉O₃: 704.3 (M + H+); Found: 704.3 (M + H+). | 1H NMR (400 MHz, Methanol-d₄) δ 8.42 (m, 2H), 8.09 (s, 1H), 7.94 (s, 1H), 7.72-7.20 (m, 8H), 5.45 (t, J = 7.5 Hz, 1H), 5.03-4.89 (m, 1H), 4.63 (dd, J = 11.0, 5.8 Hz, 1H), 2.30 (d, J = 14.7 Hz, 1H), 1.94 (d, J = 14.6 Hz, 1H), 1.28 (d, J = 2.3 Hz, 3H), 0.96 (s, 9H), 0.65 (m, 2H), 0.53 (m, 2H). |
| 266 | 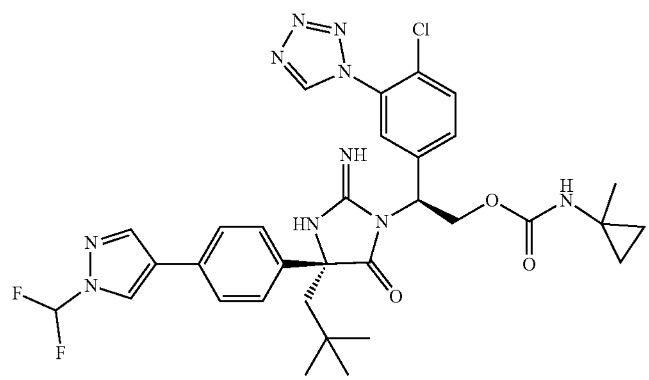 [SMILES: CC(C)(C)C[C@]1(c2ccc(-c3cnn(C(F)F)c3)cc2)NC(=N)N([C@H](COC(=O)NC2(C)CC2)c2ccc(Cl)c(-n3cnnn3)c2)C1=O] | LCMS-ESI+: calc'd for C₃₂H₃₅ClF₂N₁₀O₃: 681.3 (M + H+); Found: 681.2 (M + H+). | 1H NMR (400 MHz, Methanol-d₄) δ 9.37 (s, 1H), 8.40 (s, 1H), 8.08 (s, 1H), 7.70-7.08 (m, 8H), 5.50 (t, J = 7.3 Hz, 1H), 4.99-4.89 (m, 1H), 4.66 (dd, J = 11.2, 5.8 Hz, 1H), 2.31 (d, J = 14.7 Hz, 1H), 1.96 (d, J = 14.7 Hz, 1H), 1.27 (s, 3H), 0.96 (s, 9H), 0.69-0.60 (m, 2H), 0.58-0.49 (m, 2H). |
| 267 | 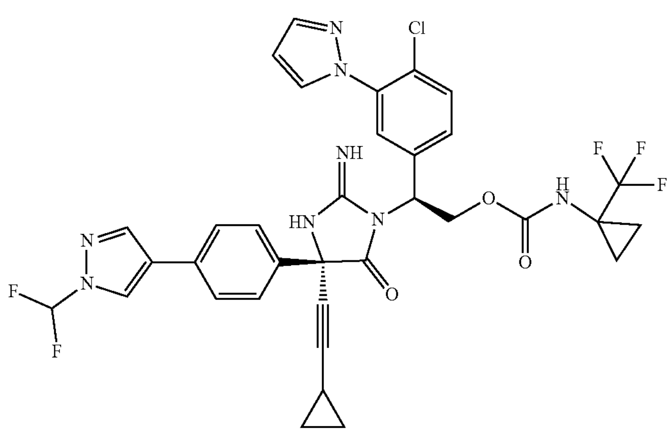 [SMILES: N=C1N[C@](C#CC2CC2)(c2ccc(-c3cnn(C(F)F)c3)cc2)C(=O)N1[C@H](COC(=O)NC1(C(F)(F)F)CC1)c1ccc(Cl)c(-n2cccn2)c1] | LCMS-ESI+: calc'd for C₃₄H₂₈ClF₅N₈O₃: 727.2 (M + H+); Found: 727.2 (M + H+). | 1H NMR (400 MHz, Methanol-d₄) δ 8.41 (s, 1H), 8.07 (s, 1H), 7.82 (d, J = 2.5 Hz, 1H), 7.73-7.28 (m, 10H), 6.42 (d, J = 2.4 Hz, 1H), 5.46 (t, J = 7.4 Hz, 1H), 5.08-4.90 (m, 1H), 4.75 (dd, J = 11.3, 5.6 Hz, 1H), 1.43-1.35 (m, 1H), 1.28-1.20 (m, 2H), 1.13-1.02 (m, 2H), 0.86-0.80 (m, 2H), 0.74-0.61 (m, 2H). |

-continued

| Compound # | Structures | Mass data | NMR data |
|---|---|---|---|
| 268 | 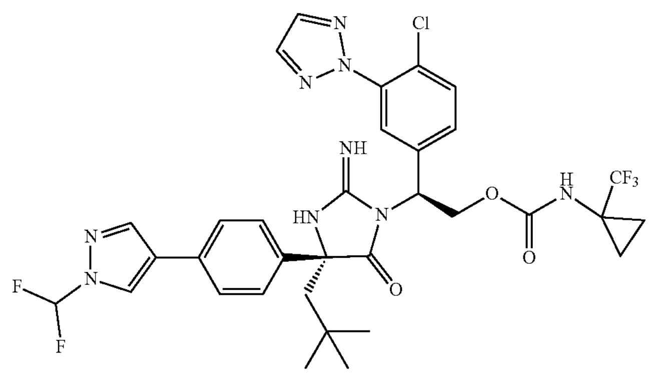 [SMILES: CC(C)(C)C[C@]1(c2ccc(-c3cnn(C(F)F)c3)cc2)NC(=N)N([C@H](COC(=O)NC2(C(F)(F)F)CC2)c2ccc(Cl)c(-n3nccn3)c2)C1=O] | LCMS-ESI+: calc'd for $C_{33}H_{33}ClF_5N_9O_3$: 734.2 (M + H+); Found: 734.0 (M + H+). | 1H NMR (400 MHz, Methanol-$d_4$) δ 8.46 (s, 1H), 8.10 (s, 2H), 7.89-7.08 (m, 9H), 5.6 (m, 1H), 5.1 (m, 1H), 4.8 (m, 1H), 2.47 (m, 1H), 2.24 (m, 1H), 1.30-1.05 (m, 4H), 1.01 (s, 9H). |
| 269 | 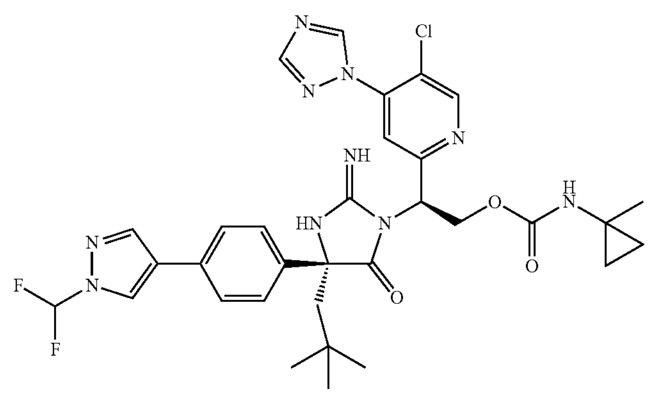 [SMILES: CC(C)(C)C[C@]1(c2ccc(-c3cnn(C(F)F)c3)cc2)NC(=N)N([C@H](COC(=O)NC2(C)CC2)c2cc(-n3cncn3)c(Cl)cn2)C1=O] | LCMS-ESI+: calc'd for $C_{32}H_{35}ClF_2N_{10}O_3$: 681.3 (M + H+); Found: 681.3 (M + H+). | 1H NMR (400 MHz, Methanol-$d_4$) δ 8.67 (s, 1H), 8.49 (s, 1H), 8.16 (m, , 2H), 7.84-7.31 (m, 7H), 5.89 (m, 1H), 4.92 (t, J = 10.9 Hz, 1H), 2.50 (d, J = 15.2 Hz, 1H), 2.16 (d, J = 15.2 Hz, 1H), 1.31 (m, 3H), 0.99 (s, 9H), 0.52 (m, 4H). |
| 270 | 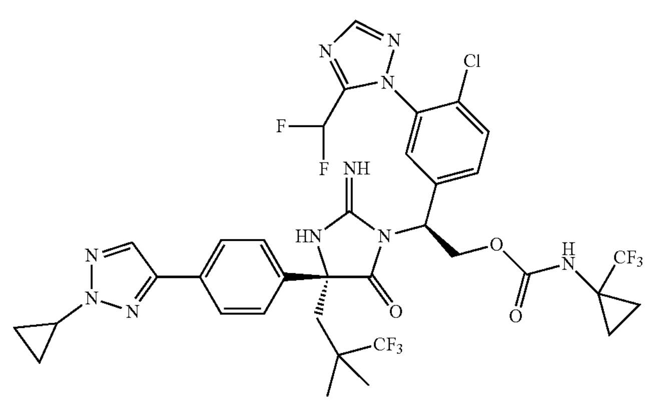 [SMILES: CC(C)(C[C@]1(c2ccc(-c3cnn(C4CC4)n3)cc2)NC(=N)N([C@H](COC(=O)NC2(C(F)(F)F)CC2)c2ccc(Cl)c(-n3ncnc3C(F)F)c2)C1=O)C(F)(F)F] | LCMS-ESI+: calc'd for $C_{35}H_{33}ClF_8N_{10}O_3$, 829.2(M + H); Found 829.3 (M + H). | $^1$H NMR (400 MHz, Methanol-$d_4$) δ 8.00 (m, 2H), 7.85-7.75 (m, 2H), 7.60 (d, J = 8.5 Hz, 1H), 7.54 (dd, J = 8.6, 2.2 Hz, 1H), 7.51-7.45 (m, 2H), 7.18 (s, 1H), 6.77 (t, J = 52.2 Hz, 1H), 5.68 (dd, J = 9.5, 4.8 Hz, 1H), 5.17-5.07 (m, 1H), 4.70 (dd, J = 11.7, 4.9 Hz, 1H), 4.12 (tt, J = 7.5, 3.8 Hz, 1H), 2.76 (d, J = 15.5 Hz, 1H), 2.46 (d, J = 15.5 Hz, 1H), 1.39-1.33 (m, 2H), 1.30-1.25 (m, 2H), 1.21-1.13 (m, 8H), 1.12-1.07 (m, 2H). |

| Compound # | Structures | Mass data | NMR data |
|---|---|---|---|
| 271 | 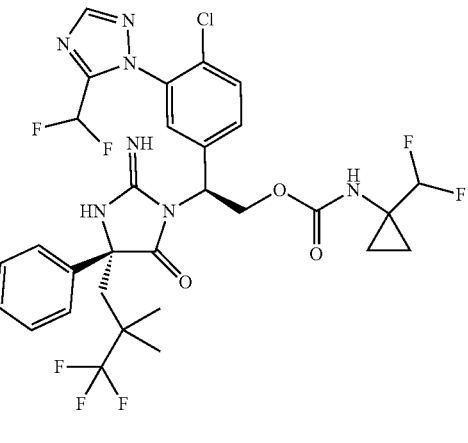 | LCMS-ESI+: calc'd for $C_{35}H_{34}ClF_7N_{10}O_3$, 811.2(M + H); Found 811.5(M + H). | $^1$H NMR (400 MHz, Methanol-$d_4$) δ 8.01 (m, 2H), 7.80 (m, 2H), 7.66-7.43 (m, 5H), 7.19 (d, J = 2.2 Hz, 1H), 6.78 (t, J = 52.2 Hz, 1H), 5.91-5.63(t, J = 56.8 Hz, 1H), 5.69-5.58 (m, 1H), 5.10 (dd, J = 11.6, 9.6 Hz, 1H), 4.71 (dd, J = 11.6, 4.9 Hz, 1H), 4.12 (tt, J = 7.5, 3.8 Hz, 1H), 2.75 (d, J = 15.4 Hz, 1H), 2.45 (d, J = 15.5 Hz, 1H), 1.40-1.31 (m, 2H), 1.21-1.17 (m, 6H), 1.15 (m, 2H), 1.07 (m, 2H), 0.91 (m, 2H). |

Example 75: Preparation of Compound 272

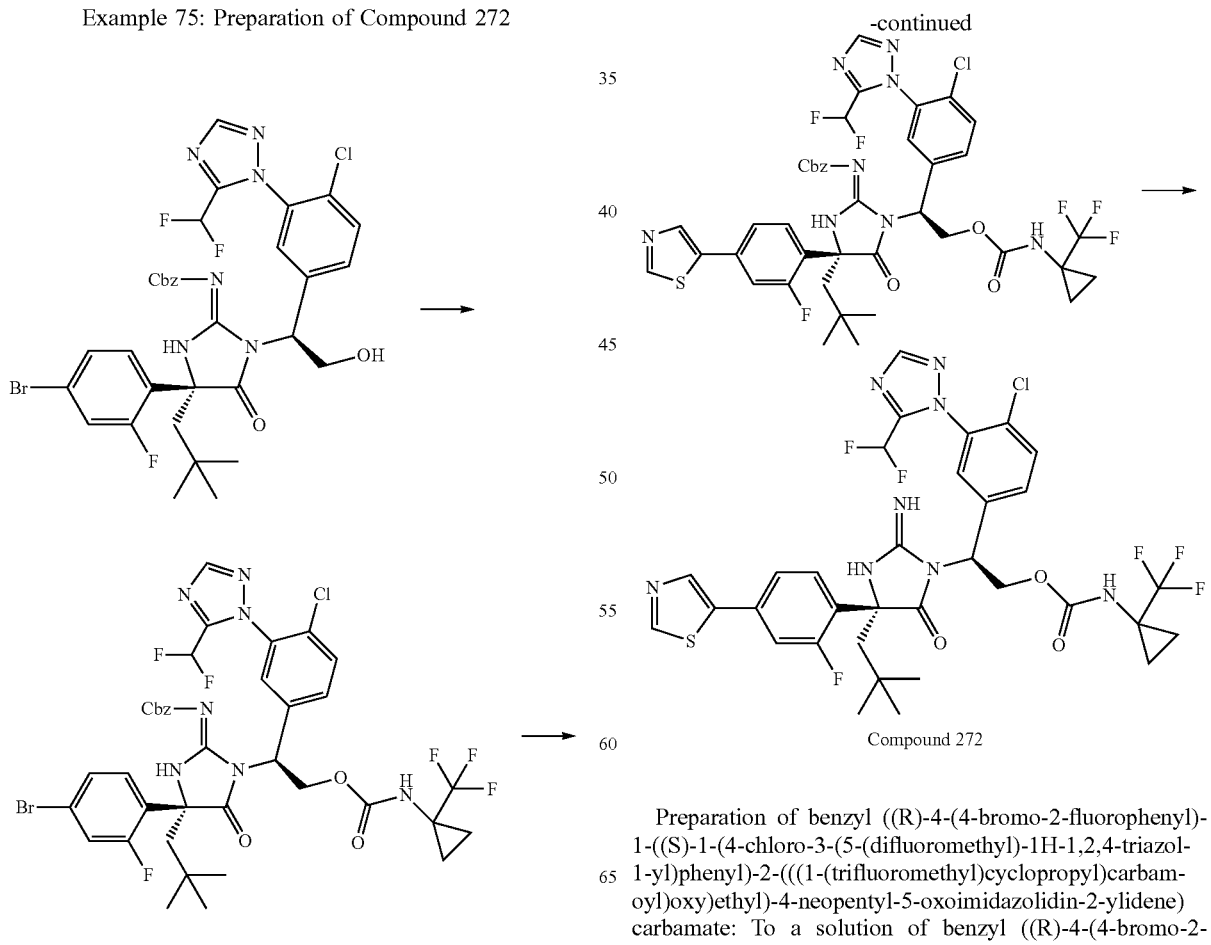

Compound 272

Preparation of benzyl ((R)-4-(4-bromo-2-fluorophenyl)-1-((S)-1-(4-chloro-3-(5-(difluoromethyl)-1H-1,2,4-triazol-1-yl)phenyl)-2-(((1-(trifluoromethyl)cyclopropyl)carbamoyl)oxy)ethyl)-4-neopentyl-5-oxoimidazolidin-2-ylidene) carbamate: To a solution of benzyl ((R)-4-(4-bromo-2- fluorophenyl)-1-((S)-1-(4-chloro-3-(5-(difluoromethyl)-1H-1,2,4-triazol-1-yl)phenyl)-2-hydroxyethyl)-4-neopentyl-5-oxoimidazolidin-2-ylidene)carbamate (120 mg, 0.16 mmol) in CH$_2$Cl$_2$ (1.0 mL) was added 1-isocyanato-1-(trifluoromethyl)cyclopropane in toluene (1.13 M, 1.0 mL), followed by titanium (IV) tert-butoxide (55 mg, 0.16 mmol). The reaction mixture was maintained at rt for 1 h. The reaction mixture was directly purified by silica gel column chromatography (eluting with 0-100% EtOAc/hexanes) to afford the product.

Preparation of benzyl ((R)-1-((S)-1-(4-chloro-3-(5-(difluoromethyl)-1H-1,2,4-triazol-1-yl)phenyl)-2-(((1-(trifluoromethyl)cyclopropyl)carbamoyl)oxy)ethyl)-4-(2-fluoro-4-(thiazol-5-yl)phenyl)-4-neopentyl-5-oxoimidazolidin-2-ylidene)carbamate: A degassed mixture of a solution of benzyl ((R)-4-(4-bromo-2-fluorophenyl)-1-((S)-1-(4-chloro-3-(5-(difluoromethyl)-1H-1,2,4-triazol-1-yl)phenyl)-2-(((1-(trifluoromethyl)cyclopropyl)carbamoyl)oxy)ethyl)-4-neopentyl-5-oxoimidazolidin-2-ylidene)carbamate (30 mg, 0.033 mmol) in dioxane (1 mL), 5-(4,4,5,5-tetramethyl-1,3,2-dioxaborolan-2-yl)thiazole (14 mg, 0.067 mmol), tetrakis(triphenylphosphine)palladium(0) (7.7 mg, 7.0 umol) and potassium carbonate (23 mg, 0.17 mmol) and water (0.20 mL) was stirred at 100° C. for 0.5 h. The reaction mixture was cooled to rt and treated with saturated aqueous NH$_4$Cl and EtOAc. After stirring for 10 min, the layers were separated and the aqueous layer was further extracted with EtOAc. The combined organic layers were washed with saturated aqueous NH$_4$Cl and then with brine, dried (over Na$_2$SO$_4$), filtered, and concentrated in vacuo. The residue was purified by silica gel column chromatography (0-100% EtOAc/hexanes) to afford the desired product.

Preparation of Compound 272: A solution of benzyl ((R)-1-((S)-1-(4-chloro-3-(5-(difluoromethyl)-1H-1,2,4-triazol-1-yl)phenyl)-2-(((1-(trifluoromethyl)cyclopropyl)carbamoyl)oxy)ethyl)-4-(2-fluoro-4-(thiazol-5-yl)phenyl)-4-neopentyl-5-oxoimidazolidin-2-ylidene)carbamate (21 mg, 0.023 mmol) in TFA (1.0 mL) was heated at 60° C. for 2 h. The reaction mixture was concentrated, dissolved in MeOH, and purified by reverse phase HPLC, eluting with 5-100% acetonitrile in water containing 0.1% TFA to afford the product.

Example 76: Preparation of Compound 273

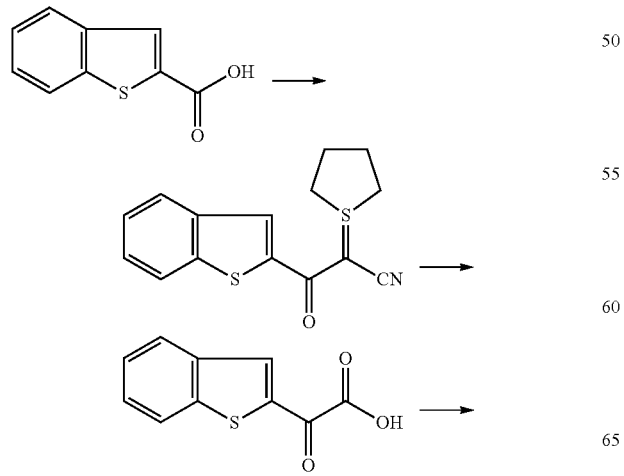

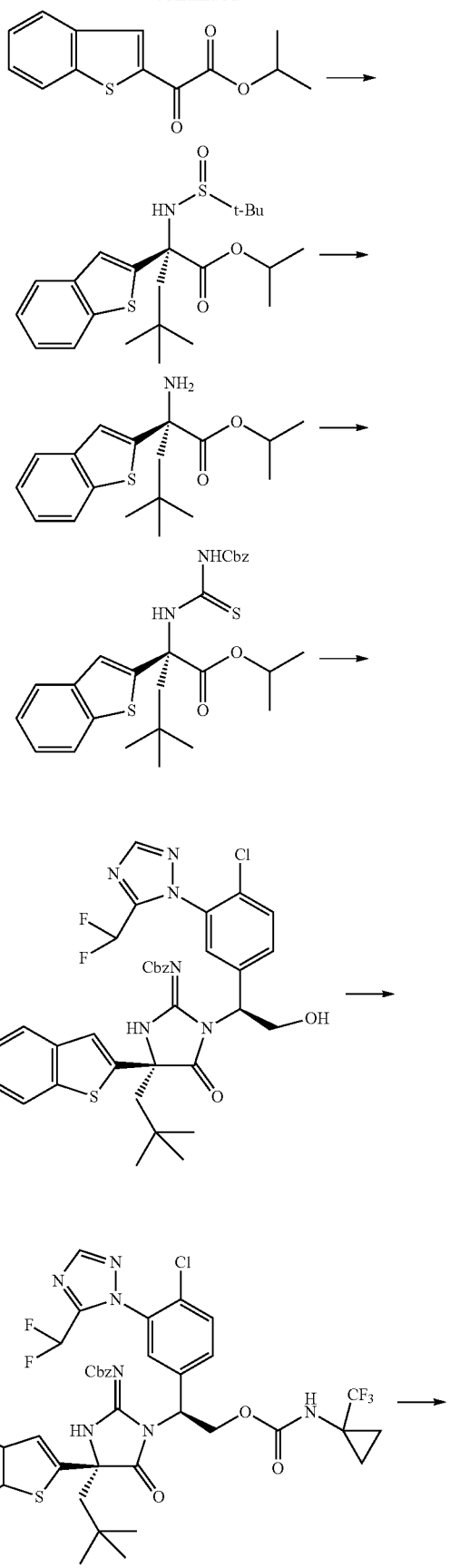

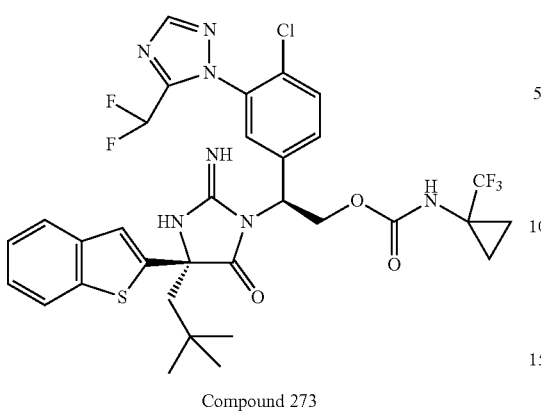

Compound 273

Preparation of 3-(benzo[b]thiophen-2-yl)-3-oxo-2-(tetrahydro-1l4-thiophen-1-ylidene)propanenitrile: To a solution of benzo[b]thiophene-2-carboxylic acid (3.0 g, 17 mmol), 1-(cyanomethyl)tetrahydro-1H-thiophen-1-ium, bromide salt sulfur ylide (4.6 g, 22 mmol) and HATU (7.0 g, 18.5 mmol) in dichloromethane (100 mL) was added N,N-diisopropylethylamine (8.8 mL, 50.5 mmol). The reaction mixture was stirred at rt for 2 h. The reaction mixture was quenched by the addition of saturated aqueous NH$_4$Cl and EtOAc. The layers were separated and the aqueous layer was further extracted with EtOAc. The combined organic layers were washed with brine, dried (over Na$_2$SO$_4$), filtered and concentrated in vacuo. The residue was purified by silica gel column chromatography (0-100% gradient EtOAc/hexanes) to give the product, which was used for the next reaction immediately.

Preparation of 2-(benzo[b]thiophen-2-yl)-2-oxoacetic acid: To a solution of 3-(benzo[b]thiophen-2-yl)-3-oxo-2-(tetrahydro-1l4-thiophen-1-ylidene)propanenitrile (4.8 g, 17 mmol) in DMF (100 mL) was added Oxone® (potassium peroxomonosulfate, 10 g, 33 mmol) as a solution in water (100 mL) in a water bath. The reaction mixture was stirred at rt for 1 h, then quenched by the addition of saturated aqueous sodium thiosulfate and EtOAc. The layers were separated and the aqueous layer was further extracted with EtOAc. The combined organic layers were washed with brine, dried (over Na$_2$SO$_4$), filtered and concentrated in vacuo. The crude mixture was carried forward immediately.

Preparation of isopropyl 2-(benzo[b]thiophen-2-yl)-2-oxoacetate: To a solution of the crude 2-(benzo[b]thiophen-2-yl)-2-oxoacetic acid (3.4 g, 0.020 mol) in dichloromethane (100 mL) were added N,N-diisopropylethylamine (7.3 mL, 0.042 mol), 1-(3-dimethylaminopropyl)-3-ethylcarbodiimide hydrochloride (4.8 g, 0.025 mol), 4-(dimethylamino) pyridine (0.10 g, 0.083 mol) and 2-propanol (2.6 mL, 0.033 mol). The reaction mixture was maintained at rt for 2 h. The reaction mixture was treated with saturated NH$_4$Cl and EtOAc. The layers were separated and the aqueous layer was further extracted with EtOAc. The combined organic layers were washed with brine, dried (over Na$_2$SO$_4$), filtered and concentrated in vacuo. The residue was purified by silica gel column chromatography (0-100% EtOAc/hexanes) to give the product.

Compound 275 was then prepared by following the procedure to prepare Compound 177.

Example 77: Preparation of Compound 274

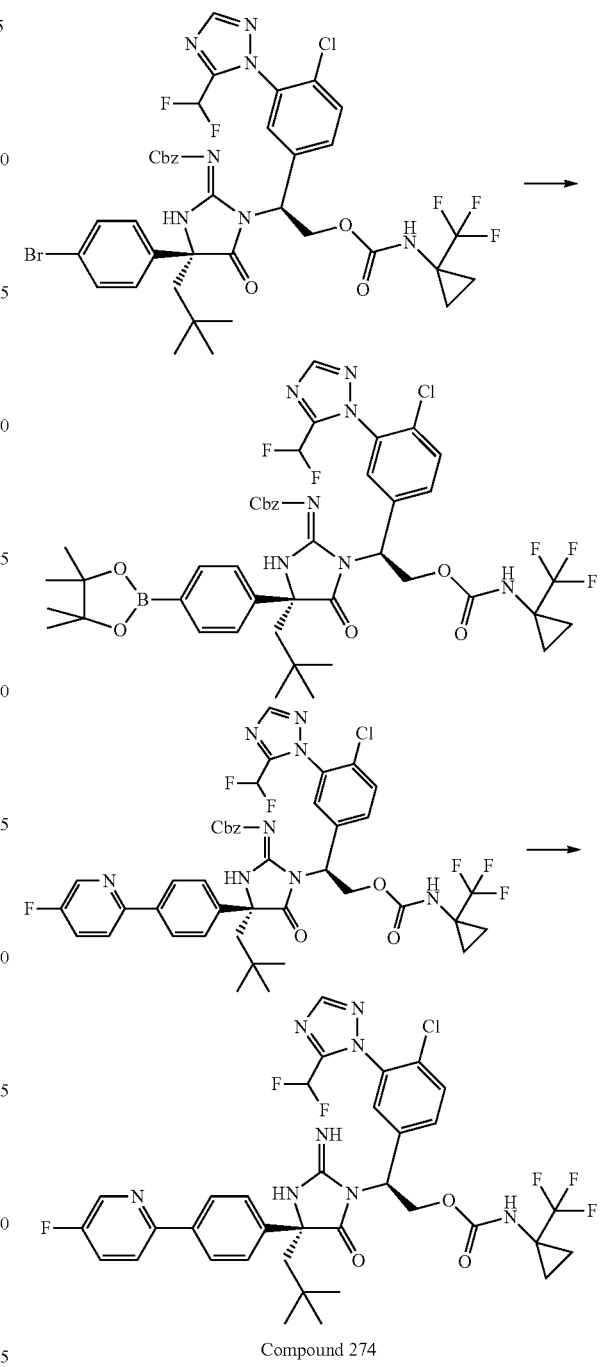

Compound 274

Preparation of benzyl ((R)-1-((S)-1-(4-chloro-3-(5-(difluoromethyl)-1H-1,2,4-triazol-1-yl)phenyl)-2-(((1-(trifluoromethyl)cyclopropyl)carbamoyl)oxy)ethyl)-4-neopentyl-5-oxo-4-(4-(4,4,5,5-tetramethyl-1,3,2-dioxaborolan-2-yl) phenyl)imidazolidin-2-ylidene)carbamate: A degassed mixture of a solution of benzyl ((R)-4-(4-bromophenyl)-1-((S)-1-(4-chloro-3-(5-(difluoromethyl)-1H-1,2,4-triazol-1-yl)phenyl)-2-((1-(trifluoromethyl)cyclopropyl)carbamoyl) oxy)ethyl)-4-neopentyl-5-oxoimidazolidin-2-ylidene) carbamate (30 mg, 0.033 mmol) in dioxane (1 mL), bis (pinacolato)diboron (17.3 mg, 0.070 mmol), palladium acetate (1.2 mg, 0.010 mmol), 2-(dicyclohexylphosphino)-2',4',6'-triisopropylbiphenyl (3.3 mg, 0.01 mmol) and potassium acetate (10 mg, 0.10 mmol) was stirred at 100° C. for 0.5 h. The reaction mixture was cooled to rt, treated with saturated aqueous sodium bicarbonate and EtOAc. The layers were separated and the aqueous layer was further extracted with EtOAc. The combined organic layers were dried (over $Na_2SO_4$), filtered, and concentrated in vacuo. The crude mixture was purified by silica gel column chromatography 0-100% EtOAc/hexanes) to afford the desired product.

Preparation of benzyl ((R)-1-((S)-1-(4-chloro-3-(5-(difluoromethyl)-1H-1,2,4-triazol-1-yl)phenyl)-2-(((1-(trifluoromethyl)cyclopropyl)carbamoyl)oxy)ethyl)-4-(2-fluoro-4-(5-fluoropyridin-2-yl)phenyl)-4-neopentyl-5-oxoimidazolidin-2-ylidene)carbamate: A degassed mixture of benzyl ((R)-1-((S)-1-(4-chloro-3-(5-(difluoromethyl)-1H-1,2,4-triazol-1-yl)phenyl)-2-(((1-(trifluoromethyl)cyclopropyl)carbamoyl)oxy)ethyl)-4-neopentyl-5-oxo-4-(4-(4,4,5,5-tetramethyl-1,3,2-dioxaborolan-2-yl)phenyl)imidazolidin-2-ylidene)carbamate (15 mg, 0.016 mmol) in dioxane (1.0 mL), 2-bromo-5-fluoropyridine (14 mg, 0.080 mmol), tetrakis(triphenylphosphine)palladium (2.8 mg, 1.0 umol), potassium carbonate (18 mg, 0.029 mmol) and water (0.20 mL) was stirred at 100° C. for 45 min. The reaction was cooled to rt and quenched by addition of saturated aqeuous sodium bicarbonate, and the mixture was extracted with EtOAc. The aqueous layer was further extracted with EtOAc. The combined organic layers were dried (over $Na_2SO_4$), filtered and concentrated in vacuo. The crude mixture was purified by silica gel column chromatography (0-100% EtOAc/hexanes) to afford the desired product.

Preparation of Compound 274: A solution of benzyl ((R)-1-((S)-1-(4-chloro-3-(5-(difluoromethyl)-1H-1,2,4-triazol-1-yl)phenyl)-2-(((1-(trifluoromethyl)cyclopropyl)carbamoyl)oxy)ethyl)-4-(2-fluoro-4-(5-fluoropyridin-2-yl)phenyl)-4-neopentyl-5-oxoimidazolidin-2-ylidene)carbamate (5.0 mg, 0.0056 mmol) in TFA (1 mL) was heated at 60° C. for 2 h. The reaction mixture was concentrated down, dissolved in MeOH, and purified by reversed phase HPLC, eluting by 5-100% acetonitrile in water containing 0.1% TFA to afford Compound 274 (3.0 mg, 65%). LCMS-ESI+ m/z Calc'd for $C_{35}H_{33}ClF_6N_8O_3$ [M+H+]: 763.2 (M+H+). found: 763.4 (M+H+). 1H NMR (400 MHz, Methanol-$d_4$) δ 8.56 (dt, J=3.0, 0.6 Hz, 1H), 8.21 (s, 1H), 8.09-7.82 (m, 4H), 7.71 (ddd, J=8.9, 8.2, 3.0 Hz, 1H), 7.67-7.46 (m, 4H), 7.24 (s, 1H), 6.78 (t, J=52 Hz, 1H), 5.69 (dd, J=9.7, 4.9 Hz, 1H), 5.11 (dd, J=11.5, 9.8 Hz, 1H), 4.71 (dd, J=11.5, 4.9 Hz, 1H), 2.51 (d, J=15.1 Hz, 1H), 2.18 (d, J=15.2 Hz, 1H), 1.30-1.25 (m, 2H), 1.09 (m, 2H), 1.01 (s, 9H).

Similarly, the following examples were prepared.

| Compound # | Structures | Mass data | NMR data |
|---|---|---|---|
| 275 | 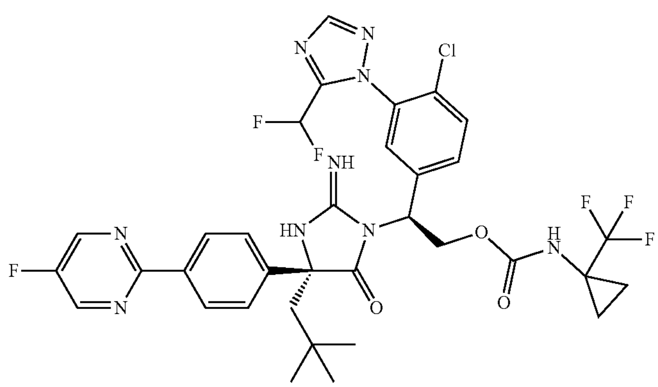 [SMILES: CC(C)(C)C[C@]1(c2ccc(-c3ncc(F)cn3)cc2)NC(=N)N([C@H](COC(=O)NC2(C(F)(F)F)CC2)c2ccc(Cl)c(-n3ncnc3C(F)F)c2)C1=O] | LCMS-ESI+: calc'd for $C_{34}H_{32}ClF_6N_9O_3$: 764.2 (M + H+); Found: 764.4 (M + H+). | 1H NMR (400 MHz, Methanol-d4) δ 8.82 (s, 2H), 8.34 (d, J = 8.6 Hz, 2H), 8.17 (s, 1H), 8.01 (s, 1H), 7.69-7.45 (m, 3H), 7.13 (s, 1H), 6.73 (t, J = 52.5 Hz, 1H), 5.74-5.62 (m, 1H), 5.15-4.98 (m, 1H), 4.76-4.65 (m, 1H), 2.51 (d, J = 15.1 Hz, 1H), 2.19 (d, J = 15.0 Hz, 1H), 1.35-1.18 (m, 2H), 1.09 (m, 2H), 1.01 (s, 9H). |
| 276 | 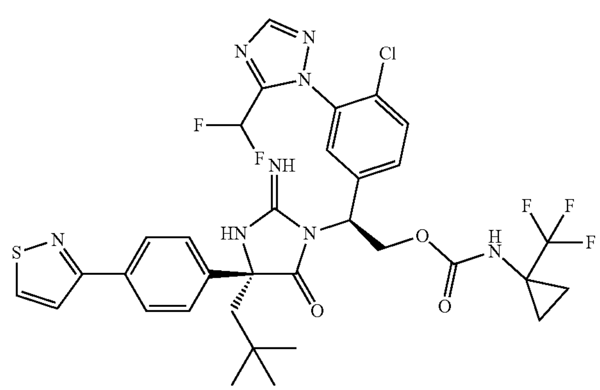 [SMILES: CC(C)(C)C[C@]1(c2ccc(-c3ccsn3)cc2)NC(=N)N([C@H](COC(=O)NC2(C(F)(F)F)CC2)c2ccc(Cl)c(-n3ncnc3C(F)F)c2)C1=O] | LCMS-ESI+: calc'd for $C_{33}H_{32}ClF_5N_8O_3S$: 751.2 (M + H+); Found: 751.4 (M + H+). | 1H NMR (400 MHz, Methanol-d4) δ 9.01 (d, J = 4.8 Hz, 1H), 8.16 (s, 1H), 8.02-7.90 (m, 3H), 7.80 (d, J = 4.7 Hz, 1H), 7.66-7.40 (m, 4H), 7.20 (s, 1H), 6.78 (t, J = 52.2 Hz, 1H), 5.67 (d, J = 6.7 Hz, 1H), 5.09 (t, J = 10.5 Hz, 1H), 4.71 (dd, J = 11.6, 5.0 Hz, 1H), 2.5 (d, J = 15.2 Hz, 1H), 2.18 (d, J = 15.2 Hz, 1H), 1.30-1.05 (m, 4H), 1.01 (s, 9H). |

-continued

| Compound # | Structures | Mass data | NMR data |
|---|---|---|---|
| 277 | 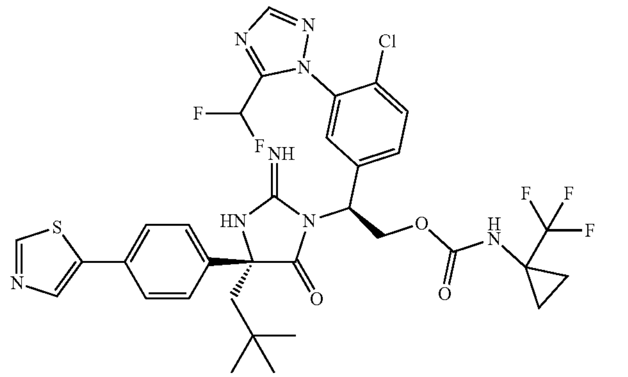 [SMILES: CC(C)(C)C[C@]1(c2ccc(-c3cncs3)cc2)NC(=N)N([C@H](COC(=O)NC2(C(F)(F)F)CC2)c2ccc(Cl)c(-n3ncnc3C(F)F)c2)C1=O] | LCMS-ESI+: calc'd for C₃₃H₃₂ClF₅N₈O₃S: 751.2 (M + H+); Found: 751.1 (M + H+). | 1H NMR (400 MHz, Methanol-d4) δ 8.34-7.90 (m, 3H), 7.71-7.52 (m, 4H), 7.48 (d, J = 8.5 Hz, 2H), 6.79 (t, J = 52.3 Hz, 1H), 5.68 (dd, J = 9.4, 4.8 Hz, 1H), 5.11 (t, J = 10.7 Hz, 1H), 2.48 (d, J = 15.1 Hz, 1H), 2.16 (d, J = 15.1 Hz, 1H), 1.30-1.05 (m, 4H), 1.00 (s, 9H). |
| 278 | 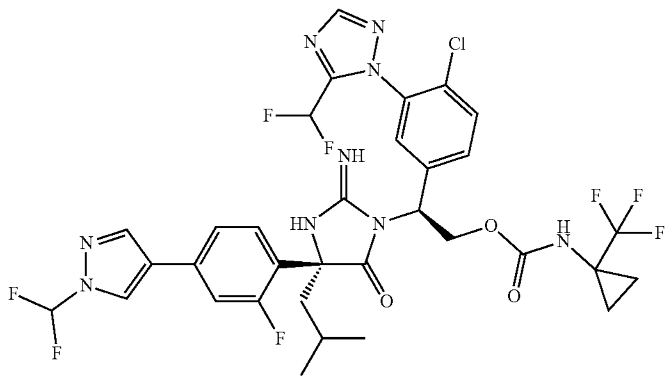 [SMILES: CC(C)C[C@]1(c2ccc(-c3cnn(C(F)F)c3)cc2F)NC(=N)N([C@H](COC(=O)NC2(C(F)(F)F)CC2)c2ccc(Cl)c(-n3ncnc3C(F)F)c2)C1=O] | LCMS-ESI+: calc'd for C₃₃H₃₀ClF₈N₉O₃: 788.2 (M + H+); Found: 788.6 (M + H+). | 1H NMR (400 MHz, Methanol-d4) δ 8.51 (d, J = 0.7 Hz, 1H), 8.26-7.28 (m, 10H), 6.93 (t, J = 52.2 Hz, 1H), 5.69 (dd, J = 9.7, 4.9 Hz, 1H), 5.16 (t, J = 10.7 Hz, 1H), 4.72 (dd, J = 11.7, 4.9 Hz, 1H), 2.31 (t, J = 5.7 Hz, 2H), 1.80-1.68 (m, 1H), 1.27 (m, 2H), 1.09 (m, 2H), 1.05 (d, J = 6.6 Hz, 3H), 0.99 (d, J = 6.7 Hz, 3H). |
| 279 | 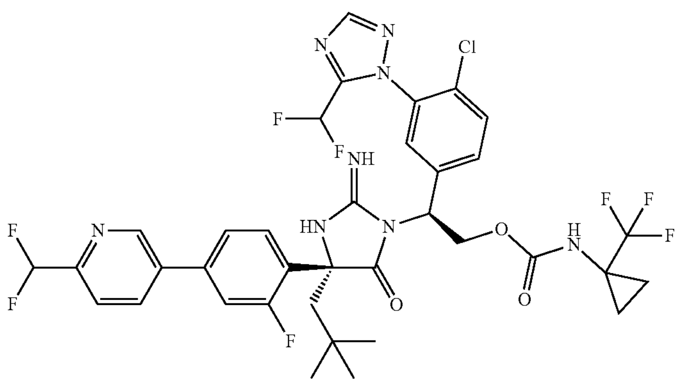 [SMILES: CC(C)(C)C[C@]1(c2ccc(-c3ccc(C(F)F)nc3)cc2F)NC(=N)N([C@H](COC(=O)NC2(C(F)(F)F)CC2)c2ccc(Cl)c(-n3ncnc3C(F)F)c2)C1=O] | LCMS-ESI+: calc'd for C₃₆H₃₃ClF₈N₈O₃: 813.2 (M + H+); Found: 813.6 (M + H+). | 1HNMR (400 MHz, Methanol-d4) δ 8.89 (d, J = 2.2 Hz, 1H), 8.26-8.15 (m, 3H), 7.80 (d, J = 8.2 Hz, 1H), 7.73 (m, 2H), 7.61 (s, 1H), 7.58-7.46 (m, 3H), 6.91 (t, J = 52.2 Hz, 1H), 6.78 (t, J = 55.3 Hz, 1H), 5.70 (dd, J = 9.6, 4.9 Hz, 1H), 5.16 (t, J = 10.6 Hz, 1H), 4.76 (dd, J = 11.6, 5.0 Hz, 1H), 2.44 (d, J = 15.2 Hz, 1H), 2.39 (d, J = 14.8 Hz, 1H), 1.27 (t, J = 3.8 Hz, 2H), 1.09 (s, 2H), 1.05 (s, 9H). |
| 280 | 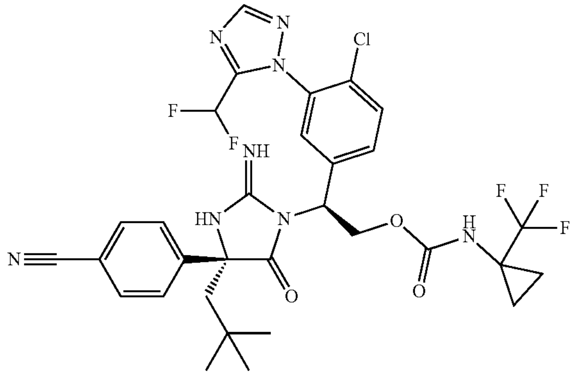 [SMILES: CC(C)(C)C[C@]1(c2ccc(C#N)cc2)NC(=N)N([C@H](COC(=O)NC2(C(F)(F)F)CC2)c2ccc(Cl)c(-n3ncnc3C(F)F)c2)C1=O] | LCMS-ESI+: calc'd for C₃₁H₃₀ClF₅N₈O₃: 692.2 (M + H+); Found: 693.6 (M + H+). | 1H NMR (400 MHz, Methanol-d4) δ 8.24 (s, 1H), 8.17 (s, 1H), 7.71 (d, J = 8.3 Hz, 2H), 7.66-7.49 (m, 4H), 7.24 (s, 1H), 6.85 (t, J = 52.2 Hz, 1H), 5.66 (dd, J = 9.7, 5.0 Hz, 1H), 5.09 (t, J = 10.6 Hz, 1H), 4.70 (dd, J = 11.6, 4.9 Hz, 1H), 2.46 (d, J = 15.1 Hz, 1H), 2.14 (d, J = 15.1 Hz, 1H), 1.28 (q, J = 5.4 Hz, 2H), 1.08 (m, 2H), 0.98 (s, 9H). |

| Compound # | Structures | Mass data | NMR data |
|---|---|---|---|
| 281 | 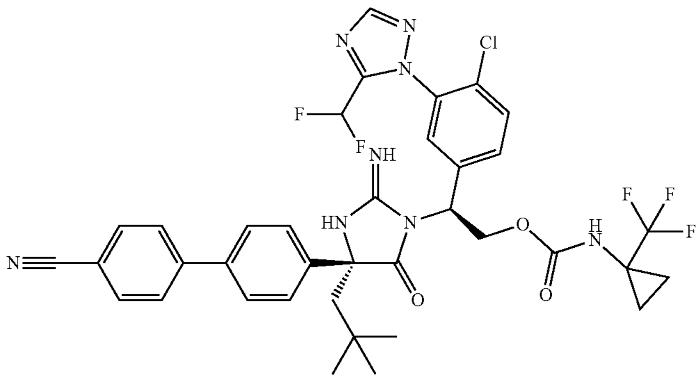 [SMILES: CC(C)(C)C[C@]1(c2ccc(-c3ccc(C#N)cc3)cc2)NC(=N)N([C@H](COC(=O)NC2(C(F)(F)F)CC2)c2ccc(Cl)c(-n3ncnc3C(F)F)c2)C1=O] | LCMS-ESI+: calc'd for C₃₇H₃₄ClF₅N₈O₃: 769.2 (M + H+); Found: 769.6 (M + H+). | 1H NMR (400 MHz, Methanol-d4) δ 8.16 (s, 1H), 8.03 (s, 1H), 7.87-7.77 (m, 4H), 7.68 (d, J = 8.4 Hz, 2H), 7.65-7.54 (m, 2H), 7.54-7.50 (m, 2H), 7.26 (s, 1H), 6.79 (t, J = 52.2 Hz, 1H), 5.74-5.62 (m, 1H), 5.11 (t, J = 10.7 Hz, 1H), 4.71 (dd, J = 11.6, 5.0 Hz, 1H), 2.50 (d, J = 15.2 Hz, 1H), 2.18 (d, J = 15.2 Hz, 1H), 1.28 (q, J = 5.2 Hz, 2H), 1.09 (m, 2H), 1.01 (s, 9H). |
| 282 | 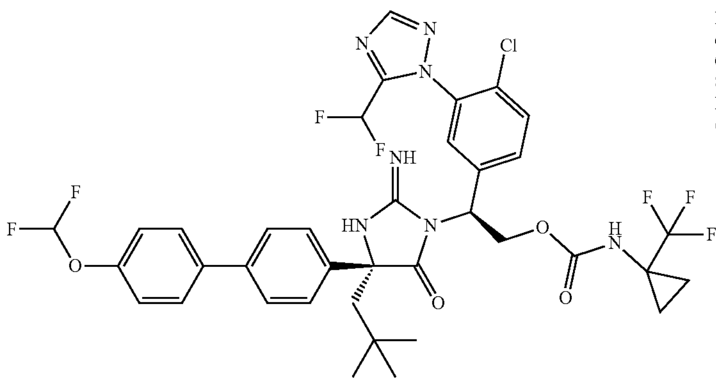 [SMILES: CC(C)(C)C[C@]1(c2ccc(-c3ccc(OC(F)F)cc3)cc2)NC(=N)N([C@H](COC(=O)NC2(C(F)(F)F)CC2)c2ccc(Cl)c(-n3ncnc3C(F)F)c2)C1=O] | LCMS-ESI+: calc'd for C₃₇H₃₅ClF₇N₇O₄: 810.2 (M + H+); Found: 810.6 (M + H+). | 1H NMR (400 MHz, Methanol-d4) δ 8.01 (s, 1H), 7.71-7.52 (m, 6H), 7.49-7.43 (m, 2H), 7.30-7.21 (m, 3H), 6.87 (t, J = 74.0 Hz, 1H), 6.79 (t, J = 52.2 Hz, 1H), 5.68 (dd, J = 9.6, 5.0 Hz, 1H), 5.11 (t, J = 10.6 Hz, 1H), 4.71 (dd, J = 11.5, 5.0 Hz, 1H), 2.50 (d, J = 15.2 Hz, 1H), 2.18 (d, J = 15.2 Hz, 1H), 1.28 (d, J = 6.2 Hz, 2H), 1.08 (m, 2H), 1.01 (s, 9H). |
| 283 | 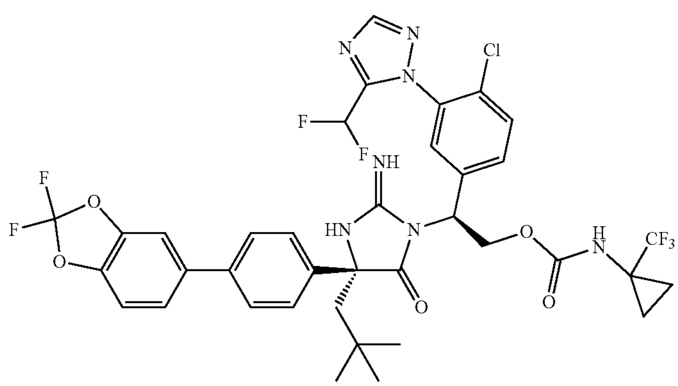 [SMILES: CC(C)(C)C[C@]1(c2ccc(-c3ccc4c(c3)OC(F)(F)O4)cc2)NC(=N)N([C@H](COC(=O)NC2(C(F)(F)F)CC2)c2ccc(Cl)c(-n3ncnc3C(F)F)c2)C1=O] | LCMS-ESI+: calc'd for C₃₇H₃₃ClF₇N₇O₅: 824.2 (M + H+); Found: 824.6 (M + H+). | 1H NMR (400 MHz, Methanol-d4) δ 8.17 (s, 1H), 8.05 (s, 1H), 7.59 (m, 4H), 7.52-7.45 (m, 3H), 7.42 (dd, J = 8.4, 1.8 Hz, 1H), 7.29 (d, J = 8.4 Hz, 2H), 6.79 (t, J = 52.2 Hz, 1H), 5.68 (dd, J = 9.7, 4.9 Hz, 1H), 5.11 (t, J = 10.6 Hz, 1H), 4.71 (dd, J = 11.5, 5.0 Hz, 1H), 2.48 (d, J = 15.1 Hz, 1H), 2.17 (d, J = 15.1 Hz, 1H), 1.30-1.24 (m, 2H), 1.09 (m, 2H), 1.00 (s, 9H). |
| 284 | 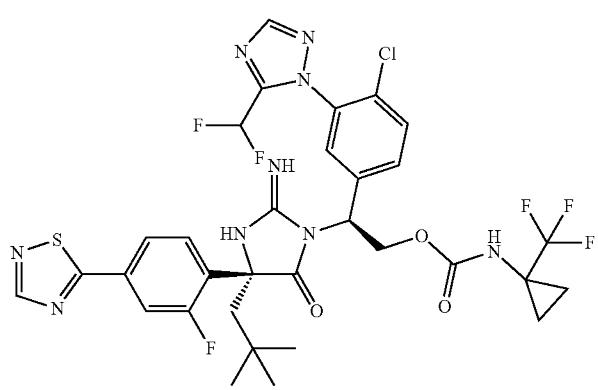 [SMILES: CC(C)(C)C[C@]1(c2ccc(-c3ncns3)cc2F)NC(=N)N([C@H](COC(=O)NC2(C(F)(F)F)CC2)c2ccc(Cl)c(-n3ncnc3C(F)F)c2)C1=O] | LCMS-ESI+: calc'd for C₃₂H₃₀ClF₆N₉O₃S: 770.2 (M + H+); Found: 770.2 (M + H+). | 1H NMR (400 MHz, Methanol-d4) δ 8.82 (s, 1H), 8.19 (m, 2H), 7.90-7.83 (m, 1H), 7.82 (s, 1H), 7.73 (m, 2H), 7.60 (s, 1H), 7.54 (t, J = 8.2 Hz, 1H), 6.90 (t, J = 52.2 Hz, 1H), 5.70 (dd, J = 9.6, 4.9 Hz, 1H), 5.15 (t, J = 10.6 Hz, 1H), 4.76 (dd, J = 11.6, 4.9 Hz, 1H), 2.48-2.35 (m, 2H), 1.27 (m, 2H), 1.09 (m, 2H), 1.04 (s, 9H). |

-continued

| Compound # | Structures | Mass data | NMR data |
|---|---|---|---|
| 285 | 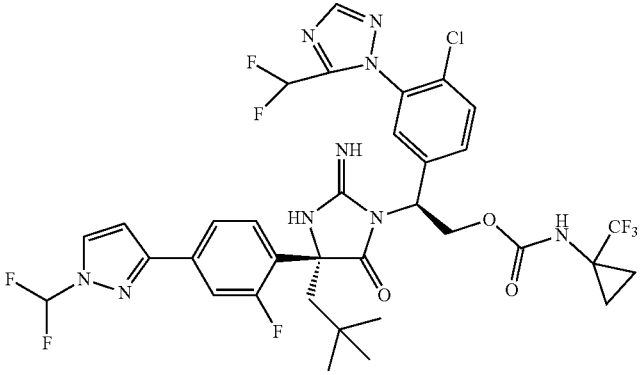 [SMILES: CC(C)(C)C[C@]1(c2ccc(-c3ccn(C(F)F)n3)cc2F)NC(=N)N([C@H](COC(=O)NC2(C(F)(F)F)CC2)c2ccc(Cl)c(-n3ncnc3C(F)F)c2)C1=O] | LCMS-ESI+: calc'd for $C_{34}H_{32}ClF_8N_9O_3$: 802.2 (M + H+); Found: 802.8 (M + H+). | 1H NMR (400 MHz, Methanol-d4) δ 8.18 (d, J = 6.6 Hz, 1H), 8.11 (d, J = 2.7 Hz, 1H), 7.79-7.46 (m, 6H), 7.45-7.34 (m, 1H), 7.05-6.71 (m, 2H), 5.69 (dd, J = 9.5, 4.9 Hz, 1H), 5.15 (t, J = 10.6 Hz, 1H), 4.76 (dd, J = 11.5, 5.0 Hz, 1H), 2.48-2.29 (m, 2H), 1.27 (m, 2H), 1.09 (m, 2H), 1.04 (s, 9H). |
| 286 | 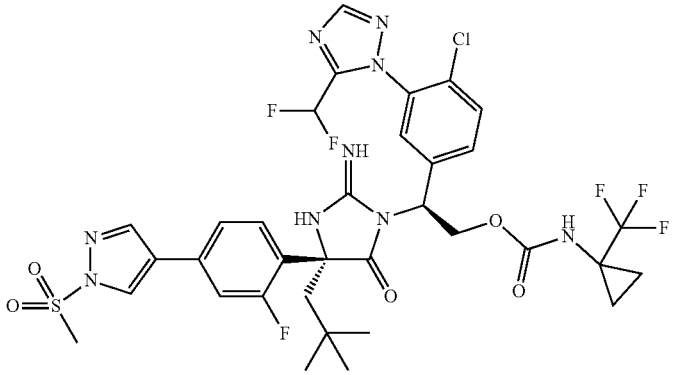 [SMILES: CC(C)(C)C[C@]1(c2ccc(-c3cnn(S(C)(=O)=O)c3)cc2F)NC(=N)N([C@H](COC(=O)NC2(C(F)(F)F)CC2)c2ccc(Cl)c(-n3ncnc3C(F)F)c2)C1=O] | LCMS-ESI+: calc'd for $C_{34}H_{34}ClF_6N_9O_5S$: 830.3 (M + H+); Found: 830.2 (M + H+). | 1H NMR (400 MHz, Methanol-d4) δ 8.58 (d, J = 0.8 Hz, 1H), 8.26 (d, J = 0.7 Hz, 1H), 8.18 (s, 1H), 7.79-7.58 (m, 2H), 7.53 (d, J = 2.0 Hz, 1H), 7.48-7.37 (m, 1H), 7.35-7.23 (m, 2H), 6.93 (d, J = 52.1 Hz, 1H), 5.57 (dd, J = 8.7, 5.9 Hz, 1H), 5.07 (dd, J = 11.1, 8.8 Hz, 1H), 4.74 (dd, J = 11.1, 5.9 Hz, 1H), 3.45 (s, 3H), 2.30-2.08 (m, 2H), 1.26-1.19 (m, 2H), 1.06 (m, 2H), 0.98 (s, 9H). |
| 287 | 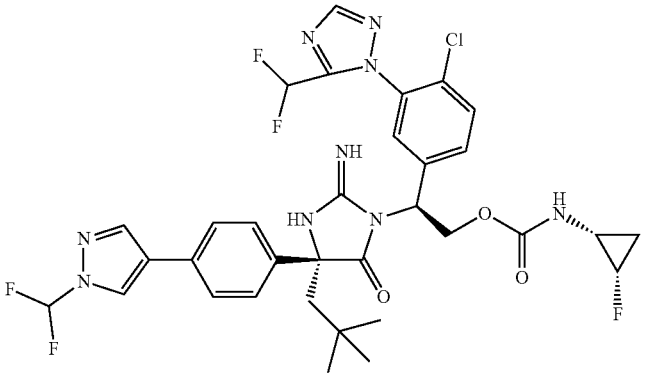 [SMILES: CC(C)(C)C[C@]1(c2ccc(-c3cnn(C(F)F)c3)cc2)NC(=N)N([C@H](COC(=O)N[C@@H]2C[C@@H]2F)c2ccc(Cl)c(-n3ncnc3C(F)F)c2)C1=O] | LCMS-ESI+: calc'd for $C_{33}H_{33}ClF_5N_9O_3$: 734.2 (M + H+); Found: 734.3 (M + H+). | 1H NMR (400 MHz, Methanol-d4) δ 8.46 (s, 1H), 8.07 (m, 2H), 7.76-7.17 (m, 8H), 6.79 (t, J = 52 Hz 1H), 5.66 (dd, J = 9.5, 4.9 Hz, 1H), 5.13 (dd, J = 11.5, 9.5 Hz, 1H), 4.73 (dd, J = 11.5, 5.0 Hz, 1H), 4.69-4.44 (m, 1H), 2.54 (dt, J = 9.9, 5.2 Hz, 1H), 2.45 (d, J = 15.1 Hz, 1H), 2.15 (d, J = 15.1 Hz, 1H), 1.18-1.01 (m, 1H), 1.0-0.80 (m, 10H). |

| Compound # | Structures | Mass data | NMR data |
|---|---|---|---|
| 288 | 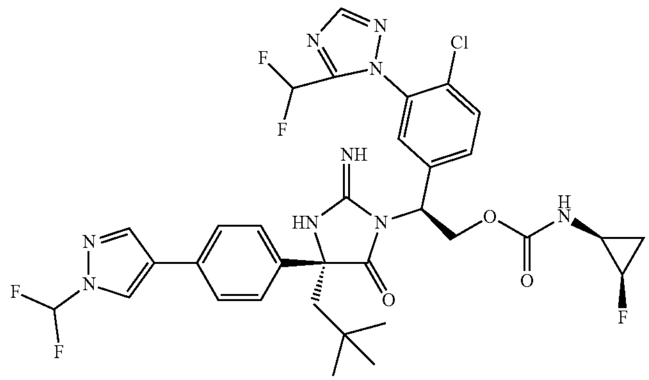 [SMILES: CC(C)(C)C[C@]1(c2ccc(-c3cnn(C(F)F)c3)cc2)NC(=N)N([C@H](COC(=O)N[C@H]2C[C@H]2F)c2ccc(Cl)c(-n3ncnc3C(F)F)c2)C1=O] | LCMS-ESI+: calc'd for C₃₃H₃₃ClF₅N₉O₃: 734.2 (M + H+); Found: 734.3 (M + H+). | 1H NMR (400 MHz, Methanol-d4) δ 8.46 (s, 1H), 8.07 (m, 2H), 7.73-7.19 (m, 8H), 6.79 (t, J = 52 Hz 1H), 5.69 (dd, J = 9.6, 4.8 Hz, 1H), 5.12 (dd, J = 11.5, 9.8 Hz, 1H), 4.76-4.66 (m, 1H), 4.66-4.50 (m, 1H), 2.52 (dt, J = 9.4, 5.3 Hz, 1H), 2.45 (d, J = 15.2 Hz, 1H), 2.15 (d, J = 15.2 Hz, 1H), 1.17-1.02 (m, 1H), 0.98 (s, 9H), 0.95-0.78 (m, 1H). |
| 289 | 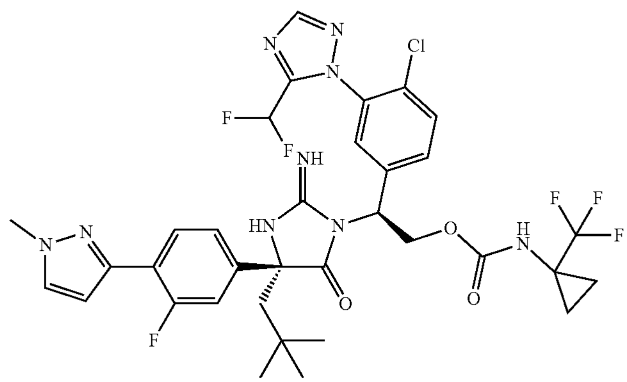 [SMILES: Cn1ccc(-c2ccc([C@@]3(CC(C)(C)C)NC(=N)N([C@H](COC(=O)NC4(C(F)(F)F)CC4)c4ccc(Cl)c(-n5ncnc5C(F)F)c4)C3=O)cc2F)n1] | LCMS-ESI+: calc'd for C₃₄H₃₄ClF₆N₉O₃: 766.2 (M + H+); Found: 766.3 (M + H+). | ¹H NMR (400 MHz, Methanol-d₄) δ 8.03 (s, 1H), 7.77 (t, J = 7.8 Hz, 1H), 7.64 (d, J = 2.3 Hz, 1H), 7.56 (m, 2H), 7.39-7.15 (m, 3H), 6.92-6.61 (m, 2H), 5.49 (br s, 1H), 5.05 (dd, J = 11.1, 9.0 Hz, 1H), 4.70-4.58 (m, 1H), 3.96 (s, 3H), 2.25 (d, J = 14.6 Hz, 1H), 1.93 (d, J = 14.7 Hz, 1H), 1.23 (m, 2H), 1.04 (m, 2H), 0.95 (s, 9H). |
| 290 | 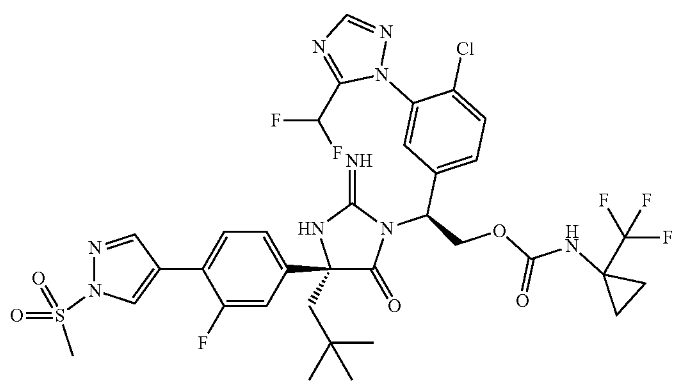 [SMILES: CC(C)(C)C[C@]1(c2ccc(-c3cnn(S(C)(=O)=O)c3)c(F)c2)NC(=N)N([C@H](COC(=O)NC2(C(F)(F)F)CC2)c2ccc(Cl)c(-n3ncnc3C(F)F)c2)C1=O] | LCMS-ESI+: calc'd for C₃₄H₃₄ClF₆N₉O₅S: 830.3 (M + H+); Found: 830.2 (M + H+). | 1H NMR (400 MHz, Methanol-d4) δ 8.51 (d, J = 1.6 Hz, 1H), 8.29 (s, 1H), 8.04 (s, 1H), 7.59 (m, 3H), 7.47-7.23 (m, 2H), 7.17 (s, 1H), 6.74 (t, J = 52.2 Hz, 1H), 5.49 (dd, J = 8.9, 5.5 Hz, 1H), 5.15-4.98 (m, 1H), 4.65 (dd, J = 11.1, 5.6 Hz, 1H), 3.47 (s, 3H), 2.29-2.17 (m, 1H), 1.98-1.88 (m, 1H), 1.32-1.26 (m, 4H), 0.94 (s, 9H). |
| 291 | 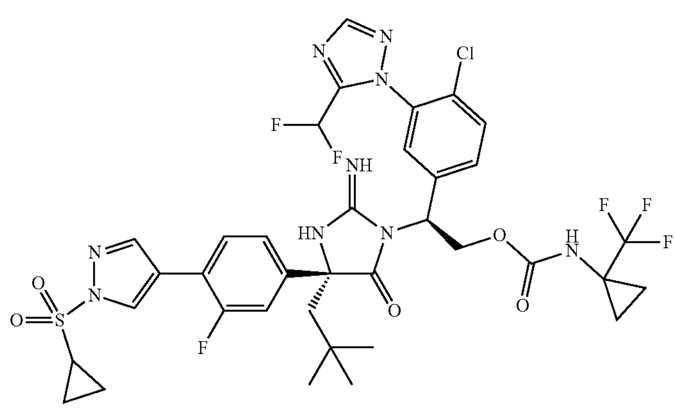 [SMILES: CC(C)(C)C[C@]1(c2ccc(-c3cnn(S(=O)(=O)C4CC4)c3)c(F)c2)NC(=N)N([C@H](COC(=O)NC2(C(F)(F)F)CC2)c2ccc(Cl)c(-n3ncnc3C(F)F)c2)C1=O] | LCMS-ESI+: calc'd for C₃₆H₃₆ClF₆N₉O₅S: 856.2 (M + H+); Found: 856.4 (M + H+). | ¹H NMR (400 MHz, Methanol-d₄) δ 8.49 (d, J = 1.6 Hz, 1H), 8.27 (s, 1H), 8.02 (s, 1H), 7.59 (m, 3H), 7.39-7.16 (m, 3H), 6.74 (t, J = 52 Hz, 1H), 5.49 (dd, J = 8.8, 5.6 Hz, 1H), 5.13-5.01 (m, 1H), 4.65 (dd, J = 11.1, 5.6 Hz, 1H), 3.01 (ddd, J = 12.5, 8.1, 4.6 Hz, 1H), 2.32-2.14 (m, 1H), 1.99-1.86 (m, 1H), 1.46-1.15 (m, 8H), 0.95 (s, 9H). |

-continued

| Compound # | Structures | Mass data | NMR data |
|---|---|---|---|
| 292 | 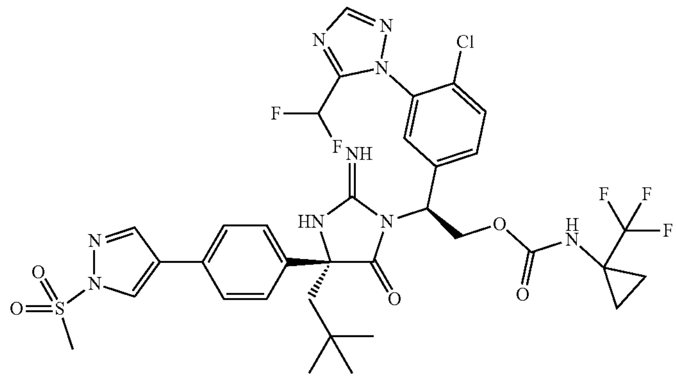 [SMILES: CC(C)(C)C[C@]1(c2ccc(-c3cnn(S(C)(=O)=O)c3)cc2)NC(=N)N([C@H](COC(=O)NC2(C(F)(F)F)CC2)c2ccc(Cl)c(-n3ncnc3C(F)F)c2)C1=O] | LCMS-ESI+: calc'd for C$_{34}$H$_{35}$ClF$_5$N$_9$O$_5$S: 812.2 (M + H+); Found: 812.2 (M + H+). | 1H NMR (400 MHz, Methanol-d4) δ 8.52 (d, J = 0.8 Hz, 1H), 8.25 (d, J = 0.8 Hz, 1H), 8.03 (s, 1H), 7.68-7.39 (m, 6H), 7.16 (s, 1H), 6.72 (t, J = 52.2 Hz, 1H), 5.52 (dd, J = 8.9, 5.5 Hz, 1H), 5.16-4.99 (m, 1H), 4.65 (dd, J = 11.1, 5.6 Hz, 1H), 3.45 (s, 3H), 2.31 (d, J = 14.7 Hz, 1H), 2.00-1.90 (m, 1H), 1.23-1.05 (m, 4H), 0.95 (s, 9H). |
| 293 | 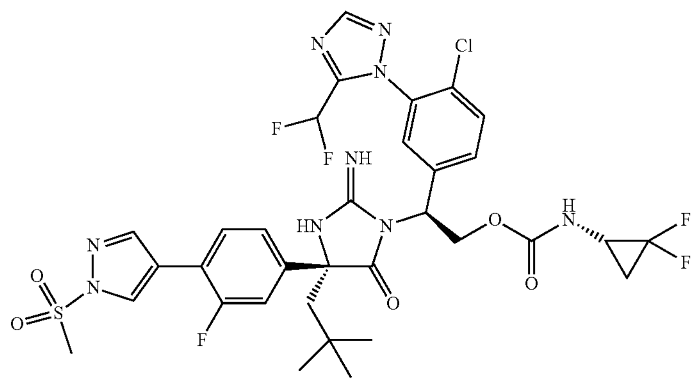 | LCMS-ESI+: calc'd for C$_{33}$H$_{33}$ClF$_5$N$_9$O$_5$S: 798.2 (M + H+); Found: 798.2 (M + H+). | 1H NMR (400 MHz, Methanol-d4) δ 8.52 (d, J = 1.6 Hz, 1H), 8.30 (d, J = 1.2 Hz, 1H), 8.05 (s, 1H), 7.60 (m, 3H), 7.48-7.24 (m, 2H), 7.19 (s, 1H), 6.76 (t, J = 52.2 Hz, 1H), 5.51 (s, 1H), 5.11 (t, J = 10.1 Hz, 1H), 4.75-4.56 (m, 1H), 3.47 (s, 3H), 3.12-3.09 (m, 1H), 2.33-2.19 (m, 1H), 2.02-1.89 (m, 1H), 1.70-1.64 (m, 1H), 1.45-1.31 (m, 1H), 0.95 (s, 9H). |
| 294 | 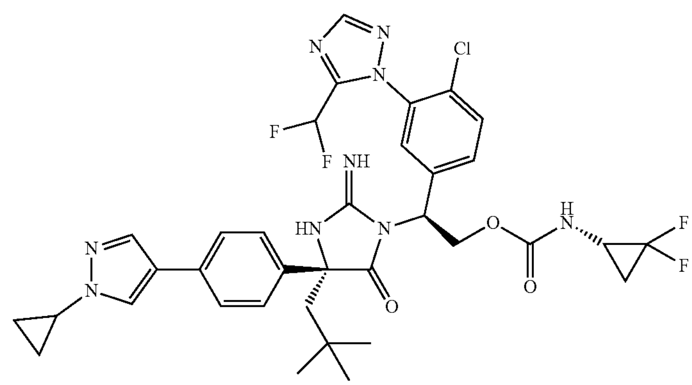 | LCMS-ESI+: calc'd for C$_{35}$H$_{36}$ClF$_4$N$_9$O$_3$: 742.3 (M + H+); Found: 742.4 (M + H+). | 1H NMR (400 MHz, Methanol-d4) δ 8.04 (m, 2H), 7.82 (s, 1H), 7.73-7.11 (m, 7H), 6.79 (t, J = 52 HZ, 1H), 5.69 (dd, J = 9.7, 4.9 Hz, 1H), 5.19-5.03 (m, 1H), 4.74 (dd, J = 11.4, 5.0 Hz, 1H), 3.70 (tt, J = 7.3, 3.9 Hz, 1H), 3.10 (s, 1H), 2.45 (d, J = 15.2 Hz, 1H), 2.13 (d, J = 15.1 Hz, 1H), 1.78 (m, 1H), 1.40 (m, 2H), 1.25-1.10 (m, 2H), 1.07 (m, 2H), 0.99 (s, 9H). |
| 295 | 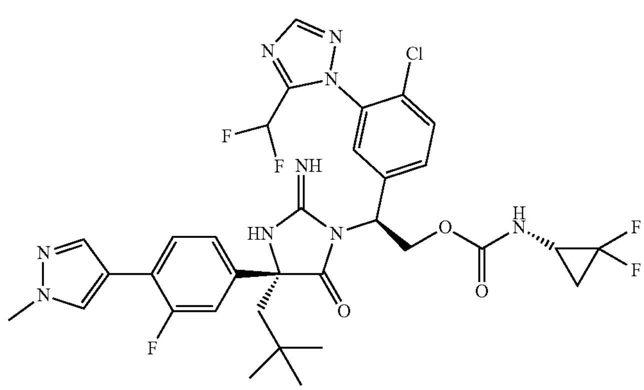 | LCMS-ESI+: calc'd for C$_{33}$H$_{33}$ClF$_5$N$_9$O$_3$: 734.2 (M + H+); Found: 734.2 (M + H+). | 1H NMR (400 MHz, Methanol-d4) δ 8.03 (s, 1H), 7.78 (t, J = 8.1 Hz, 1H), 7.64 (d, J = 2.2 Hz, 1H), 7.57 (m, 2H), 7.45-7.17 (m, 3H), 6.78 (t, J = 52 HZ, 1H), 6.65 (m, 1H), 5.50 (t, J = 7.5 Hz, 1H), 5.11 (t, J = 10.1 Hz, 1H), 4.73-4.55 (m, 1H), 3.96 (s, 3H), 3.20-3.15 (m, 1H), 2.26 (d, J = 14.6 Hz, 1H), 1.93 (d, J = 14.6 Hz, 1H), 1.80-1.55 (m, 1H), 1.45-1.25 (m, 1H), |

-continued

| Compound # | Structures | Mass data | NMR data |
|---|---|---|---|
| | | | 0.95 (s, 9H). |
| 296 | 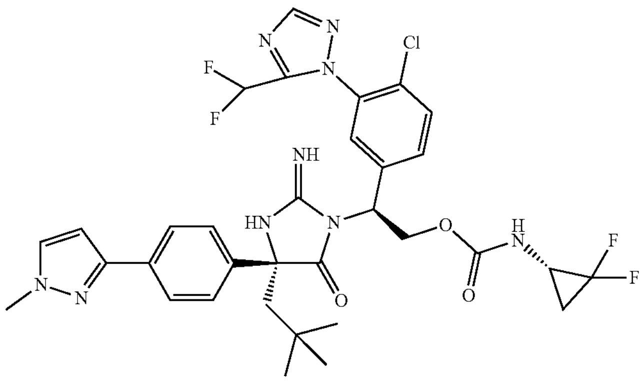 [SMILES: Cn1ccc(-c2ccc([C@@]3(CC(C)(C)C)NC(=N)N([C@H](COC(=O)N[C@H]4CC4(F)F)c4ccc(Cl)c(-n5ncnc5C(F)F)c4)C3=O)cc2)n1] | LCMS-ESI+: calc'd for C₃₃H₃₄ClF₄N₉O₃: 716.2 (M + H+); Found: 716.4 (M + H+). | 1H NMR (400 MHz, Methanol-d4) δ 8.03 (s, 1H), 7.78-7.12 (m, 8H), 6.80 (t, J = 52 Hz, 1H), 6.64 (m, 1H), 5.69 (dd, J = 9.8, 4.9 Hz, 1H), 5.11 (t, J = 10.6 Hz, 1H), 4.74 (dd, J = 11.6, 5.0 Hz, 1H), 3.95 (s, 3H), 3.10 (m, 1H), 2.46 (d, J = 15.2 Hz, 1H), 2.15 (d, J = 15.1 Hz, 1H), 1.77-1.70 (m, 1H), 1.42-1.38 (m, 1H), 0.99 (s, 9H). |
| 297 | 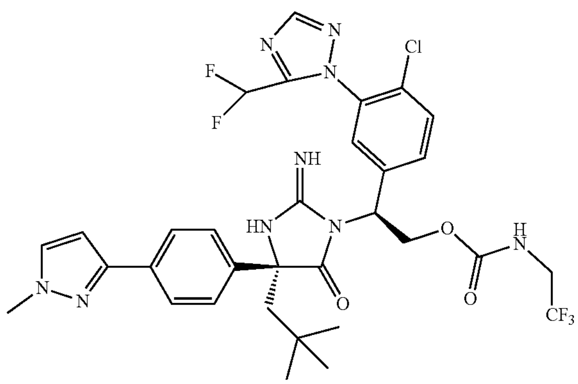 [SMILES: Cn1ccc(-c2ccc([C@@]3(CC(C)(C)C)NC(=N)N([C@H](COC(=O)NCC(F)(F)F)c4ccc(Cl)c(-n5ncnc5C(F)F)c4)C3=O)cc2)n1] | LCMS-ESI+: calc'd for C₃₂H₃₃ClF₅N₉O₃: 722.2 (M + H+); Found: 722.4 (M + H+). | 1H NMR (400 MHz, Methanol-d4) δ 8.03 (s, 1H), 7.88 (t, J = 6.5 Hz, 1H), 7.80-7.68 (m, 2H), 7.68-7.58 (m, 2H), 7.58-7.17 (m, 3H), 6.80 (t, J = 52 Hz, 1H), 6.65 (s, 1H), 5.70 (dd, J = 9.7, 4.9 Hz, 1H), 5.14 (dd, J = 11.5, 9.8 Hz, 1H), 4.76 (dd, J = 11.5, 4.9 Hz, 1H), 3.96 (s, 3H), 3.88-3.65 (m, 2H), 2.48 (d, J = 15.2 Hz, 1H), 2.15 (d, J = 15.2 Hz, 1H), 1.00 (s, 9H). |
| 298 | 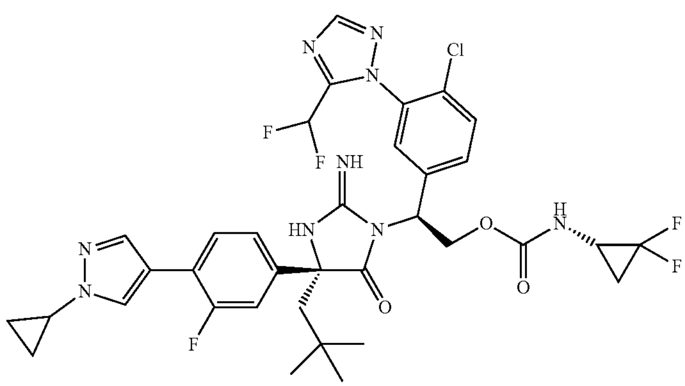 | LCMS-ESI+: calc'd for C₃₅H₃₅ClF₅N₉O₃: 760.2 (M + H+); Found: 760.3 (M + H+). | ¹H NMR (400 MHz, Methanol-d₄) δ 8.11 (d, J = 1.8 Hz, 1H), 8.03 (s, 1H), 7.89 (d, J = 1.4 Hz, 1H), 7.71-7.52 (m, 3H), 7.28-7.15 (m, 3H), 6.81 (t, J = 52.2 Hz, 1H), 5.71 (dd, J = 9.6, 5.0 Hz, 1H), 5.12 (dd, J = 11.6, 9.7 Hz, 1H), 4.74 (dd, J = 11.6, 5.0 Hz, 1H), 3.73 (tt, J = 7.3, 3.6 Hz, 1H), 3.11 (tdd, J = 10.2, 5.6, 2.8 Hz, 1H), 2.44 (d, J = 15.2 Hz, 1H), 2.20-2.05 (m, 1H), 1.85-1.67 (m, 1H), 1.46-1.43 (m, 1H), 1.20-1.05 (m, 4H), 0.98 (s, 9H). |

| Compound # | Structures | Mass data | NMR data |
|---|---|---|---|
| 299 | 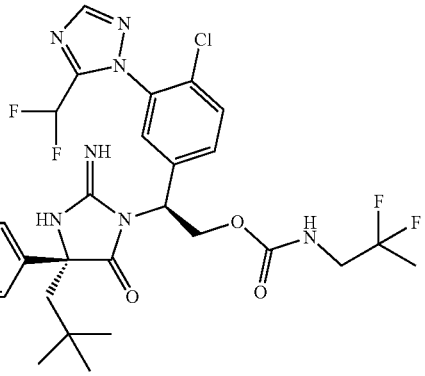 | LCMS-ESI+: calc'd for $C_{33}H_{33}ClF_7N_9O_3$: 772.2 (M + H+); Found: 772.4 (M + H+). | 1H NMR (400 MHz, Methanol-d4) δ 8.47 (d, J = 1.7 Hz, 1H), 8.16 (d, J = 1.2 Hz, 1H), 8.05 (s, 1H), 7.77-7.17 (m, 8H), 6.82 (t, J = 52.2 Hz, 1H), 5.69 (dd, J = 9.5, 4.9 Hz, 1H), 5.12 (dd, J = 11.5, 9.6 Hz, 1H), 4.75 (dd, J = 11.6, 5.0 Hz, 1H), 3.59-3.37 (m, 2H), 2.45 (d, J = 15.1 Hz, 1H), 2.14 (d, J = 15.1 Hz, 1H), 1.57 (t, J = 18.6 Hz, 3H), 1.00 (s, 9H). |
| 300 | 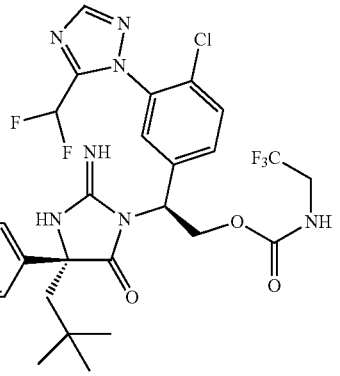 | LCMS-ESI+: calc'd for $C_{32}H_{32}ClF_6N_9O_5S$: 804.2 (M + H+); Found: 804.2 (M + H+). | 1H NMR (400 MHz, Methanol-d4) δ 8.51 (dd, J = 1.7, 0.7 Hz, 1H), 8.29 (t, J = 1.0 Hz, 1H), 8.04 (s, 1H), 7.65-7.55 (m, 3H), 7.38-7.26 (m, 2H), 7.19 (s, 1H), 6.75 (t, J = 52.2 Hz, 1H), 5.51 (dd, J = 8.9, 5.4 Hz, 1H), 5.11 (dd, J = 11.1, 9.0 Hz, 1H), 4.70 (dd, J = 11.2, 5.6 Hz, 1H), 3.75 (q, J = 8.9 Hz, 2H), 3.47 (s, 3H), 2.26 (d, J = 14.6 Hz, 1H), 1.94 (m, 1H), 0.96 (s, 9H). |
| 301 | 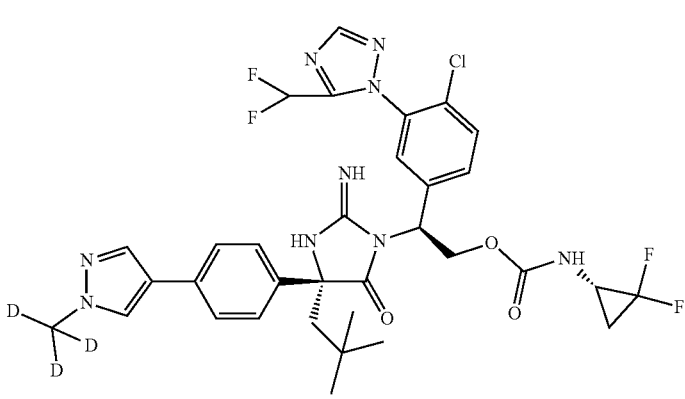 [SMILES: [2H]C([2H])([2H])n1cc(-c2ccc([C@@]3(CC(C)(C)C)NC(=N)N([C@H](COC(=O)N[C@H]4CC4(F)F)c4ccc(Cl)c(-n5ncnc5C(F)F)c4)C3=O)cc2)cn1] | LCMS-ESI+: calc'd for $C_{33}H_{31}D_3ClF_4N_9O_3$: 719.2 (M + H+); Found: 719.4 (M + H+). | 1H NMR (400 MHz, Methanol-d4) δ 8.03 (s, 1H), 7.97 (d, J = 0.8 Hz, 1H), 7.82 (d, J = 0.9 Hz, 1H), 7.76-7.19 (m, 7H), 6.79 (t, J = 52.2 Hz, 1H), 5.77-5.63 (m, 1H), 5.11 (t, J = 10.5 Hz, 1H), 4.74 (dd, J = 11.5, 5.0 Hz, 1H), 3.11 (d, J = 8.6 Hz, 1H), 2.45 (d, J = 15.2 Hz, 1H), 2.13 (d, J = 15.1 Hz, 1H), 1.75 (m, 1H), 1.38 (m, 1H), 0.99 (s, 9H). |

-continued

| Compound # | Structures | Mass data | NMR data |
|---|---|---|---|
| 302 | 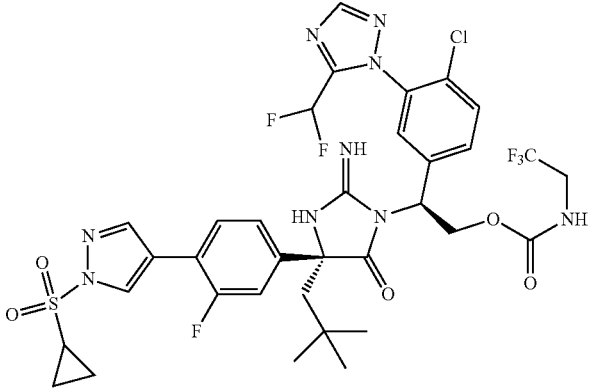 [SMILES: CC(C)(C)C[C@]1(c2ccc(-c3cnn(S(=O)(=O)C4CC4)c3)c(F)c2)NC(=N)N([C@H](COC(=O)NCC(F)(F)F)c2ccc(Cl)c(-n3ncnc3C(F)F)c2)C1=O] | LCMS-ESI+: calc'd for $C_{34}H_{34}ClF_6N_9O_5S$: 830.2 (M + H+); Found: 830.3 (M + H+). | 1H NMR (400 MHz, Methanol-d4) δ 8.49 (dd, J = 1.8, 0.7 Hz, 1H), 8.28 (t, J = 1.0 Hz, 1H), 8.02 (s, 1H), 7.69-7.52 (m, 3H), 7.39-7.25 (m, 2H), 7.20 (s, 1H), 6.74 (t, J = 52.2 Hz, 1H), 5.53 (d, J = 16.7 Hz, 1H), 5.11 (dd, J = 11.1, 9.0 Hz, 1H), 4.70 (dd, J = 11.1, 5.6 Hz, 1H), 3.75 (q, J = 9.2 Hz, 2H), 3.01 (tt, J = 7.9, 4.7 Hz, 1H), 2.26 (d, J = 14.6 Hz, 1H), 1.93 (d, J = 14.6 Hz, 1H), 1.47-1.37 (m, 2H), 1.27-1.20 (m, 2H), 0.96 (s, 9H). |
| 303 | 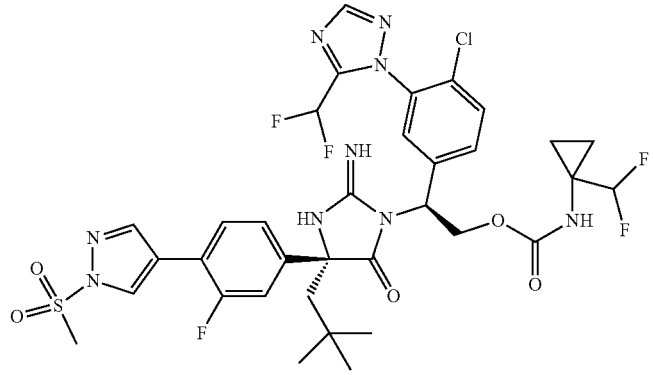 [SMILES: CC(C)(C)C[C@]1(c2ccc(-c3cnn(S(C)(=O)=O)c3)c(F)c2)NC(=N)N([C@H](COC(=O)NC2(C(F)F)CC2)c2ccc(Cl)c(-n3ncnc3C(F)F)c2)C1=O] | LCMS-ESI+: calc'd for $C_{34}H_{35}ClF_5N_9O_5S$: 812.2 (M + H+); Found: 812.5 (M + H+). | 1H NMR (400 MHz, Methanol-d4) δ 8.59-8.44 (m, 1H), 8.29 (t, J = 1.0 Hz, 1H), 8.04 (s, 1H), 7.65-7.51 (m, 3H), 7.32 (t, J = 11.7 Hz, 2H), 7.19 (s, 1H), 6.75 (t, J = 52.2 Hz, 1H), 5.81 (t, J = 57.3 Hz, 1H), 5.49 (s, 1H), 5.11-4.93 (m, 1H), 4.66 (dd, J = 11.1, 5.6 Hz, 1H), 3.47 (s, 3H), 2.24 (d, J = 14.6 Hz, 1H), 1.97-1.88 (m, 1H), 1.08-1.02 (m, 2H), 0.95 (s, 9H), 0.90-0.84 (m, 2H). |
| 304 | 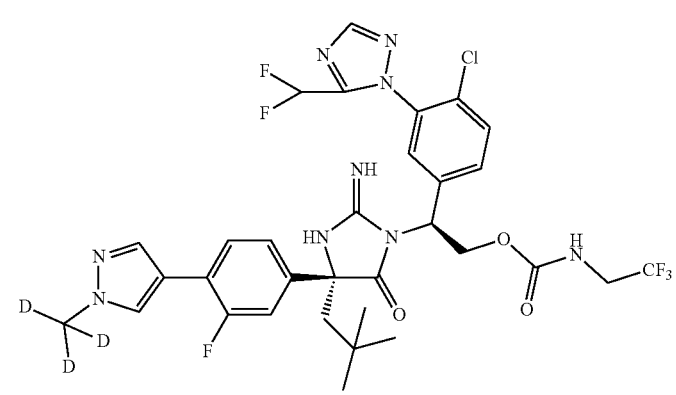 [SMILES: [2H]C([2H])([2H])n1cc(-c2ccc([C@@]3(CC(C)(C)C)NC(=N)N([C@H](COC(=O)NCC(F)(F)F)c4ccc(Cl)c(-n5ncnc5C(F)F)c4)C3=O)cc2F)cn1] | LCMS-ESI+: calc'd for $C_{32}H_{29}ClD_3F_6N_9O_3$: 743.2 (M + H+); Found: 743.4 (M + H+). | 1H NMR (400 MHz, Methanol-d4) δ 8.03 (m, 2H), 7.95-7.81 (m, 1H), 7.67-7.51 (m, 3H), 7.29-7.15 (m, 3H), 6.79 (t, J = 52 Hz, 1H), 5.70 (dd, J = 9.7, 4.8 Hz, 1H), 5.14 (dd, J = 11.5, 9.8 Hz, 1H), 4.76 (dd, J = 11.5, 4.8 Hz, 1H), 3.78 (m, 2H), 2.41 (d, J = 15.1 Hz, 1H), 2.13 (d, J = 15.1 Hz, 1H), 0.99 (s, 9H). |

-continued

| Compound # | Structures | Mass data | NMR data |
|---|---|---|---|
| 305 | 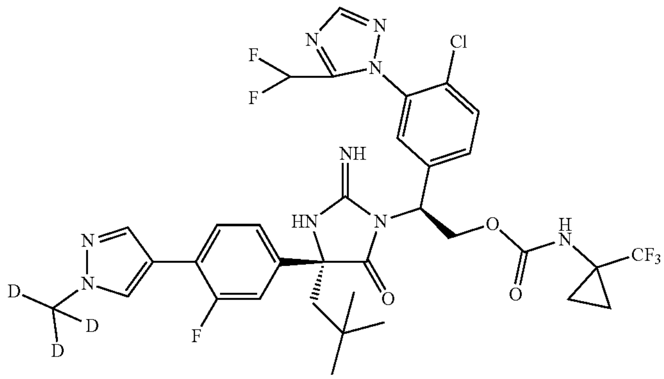 [SMILES: [2H]C([2H])([2H])n1cc(-c2ccc([C@@]3(CC(C)(C)C)NC(=N)N([C@H](COC(=O)NC4(C(F)(F)F)CC4)c4ccc(Cl)c(-n5ncnc5C(F)F)c4)C3=O)cc2F)cn1] | LCMS-ESI+: calc'd for C₃₄H₃₁ClD₃F₆N₉O₃: 769.2 (M + H+); Found: 769.4 (M + H+). | 1H NMR (400 MHz, Methanol-d4) δ 8.18 (s, 1H), 8.03 (m, 2H), 7.89 (d, J = 1.3 Hz, 1H), 7.70-7.49 (m, 3H), 7.30-7.11 (m, 2H), 6.78 (t, J = 52 Hz, 1H), 5.68 (dd, J = 9.8, 4.8 Hz, 1H), 5.10 (dd, J = 11.5, 9.8 Hz, 1H), 4.70 (dd, J = 11.5, 4.8 Hz, 1H), 2.40 (d, J = 15.2 Hz, 1H), 2.13 (d, J = 15.2 Hz, 1H), 1.36-1.21 (m, 2H), 1.08 (m, 2H), 0.98 (s, 9H). |
| 306 | 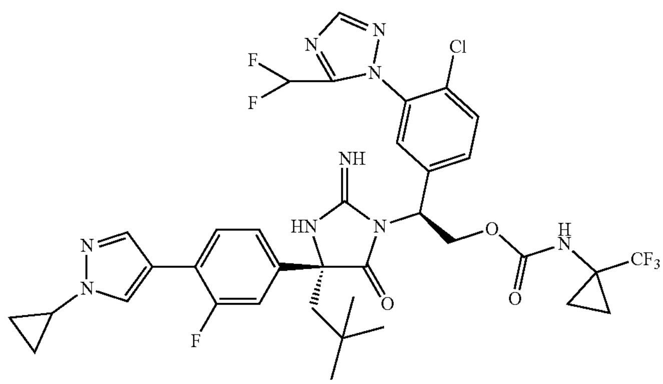 [SMILES: CC(C)(C)C[C@]1(c2ccc(-c3cnn(C4CC4)c3)c(F)c2)NC(=N)N([C@H](COC(=O)NC2(C(F)(F)F)CC2)c2ccc(Cl)c(-n3ncnc3C(F)F)c2)C1=O] | LCMS-ESI+: calc'd for C₃₆H₃₆ClF₆N₉O₃: 792.2 (M + H+); Found: 792.4 (M + H+). | 1H NMR (400 MHz, Methanol-d4) δ 8.18 (s, 1H), 8.09 (d, J = 1.8 Hz, 1H), 8.02 (s, 1H), 7.88 (d, J = 1.4 Hz, 1H), 7.62-7.51 (m, 2H), 7.26-7.14 (m, 3H), 6.78 (t, J = 52 Hz, 1H), 5.68 (dd, J = 9.8, 4.8 Hz, 1H), 5.10 (dd, J = 11.5, 9.8 Hz, 1H), 4.70 (dd, J = 11.5, 4.8 Hz, 1H), 3.72 (tt, J = 7.4, 3.9 Hz, 1H), 2.40 (d, J = 15.1 Hz, 1H), 2.13 (d, J = 15.1 Hz, 1H), 1.27 (m, 2H), 1.15 (m, 2H), 1.08 (m, 4H), 0.98 (s, 9H). |
| 307 | 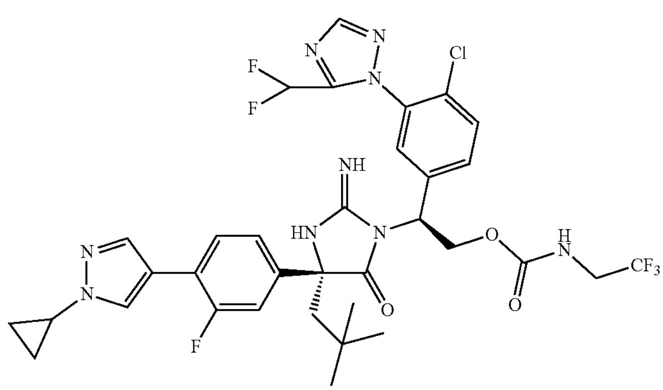 [SMILES: CC(C)(C)C[C@]1(c2ccc(-c3cnn(C4CC4)c3)c(F)c2)NC(=N)N([C@H](COC(=O)NCC(F)(F)F)c2ccc(Cl)c(-n3ncnc3C(F)F)c2)C1=O] | LCMS-ESI+: calc'd for C₃₄H₃₄ClF₆N₉O₃: 766.2 (M + H+); Found: 766.4 (M + H+). | 1H NMR (400 MHz, Methanol-d4) δ 8.09 (m, 1H), 8.02 (s, 1H), 7.91-7.81 (m, 2H), 7.71-7.53 (m, 3H), 7.26-7.19 (m, 2H), 6.79 (t, J = 52 Hz, 1H), 5.70 (dd, J = 9.7, 4.8 Hz, 1H), 5.14 (dd, J = 11.5, 9.8 Hz, 1H), 4.76 (dd, J = 11.5, 4.9 Hz, 1H), 3.88-3.65 (m, 3H), 2.42 (d, J = 15.2 Hz, 1H), 2.13 (d, J = 15.1 Hz, 1H), 1.18-1.10 (m, 2H), 1.11-1.04 (m, 2H), 0.99 (s, 9H). |

-continued

| Compound # | Structures | Mass data | NMR data |
|---|---|---|---|
| 308 | 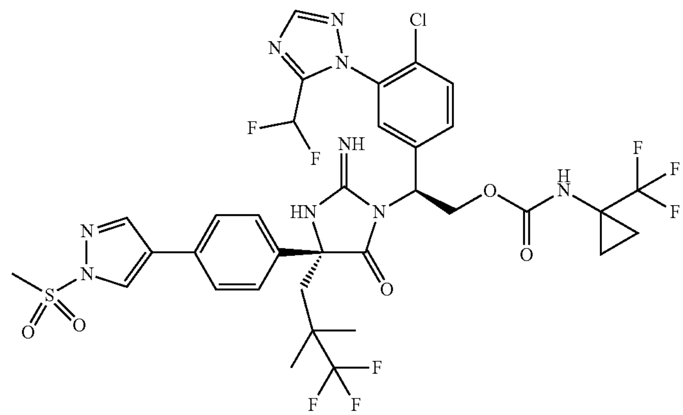 [SMILES: CC(C)(C[C@]1(c2ccc(-c3cnn(S(C)(=O)=O)c3)cc2)NC(=N)N([C@H](COC(=O)NC2(C(F)(F)F)CC2)c2ccc(Cl)c(-n3ncnc3C(F)F)c2)C1=O)C(F)(F)F] | LCMS-ESI+: calc'd for $C_{34}H_{32}ClF_8N_9O_5S$: 866.2 (M + H+); Found: 866.4 (M + H+). | 1H NMR (400 MHz, Methanol-d4) δ 8.52 (s, 1H), 8.33 (s, 1H), 8.25 (s, 1H), 7.64-7.41 (m, 6H), 7.11 (s, 1H), 6.73 (t, J = 52.2 Hz, 1H), 5.48 (d, J = 7.7 Hz, 1H), 5.08 (t, J = 10.3 Hz, 1H), 4.62 (dd, J = 11.2, 5.3 Hz, 1H), 3.46 (s, 3H), 2.53 (d, J = 14.7 Hz, 1H), 2.19 (d, J = 14.7 Hz, 1H), 1.24 (m, 2H), 1.16 (d, J = 7.1 Hz, 6H), 1.07 (m, 2H). |
| 309 | 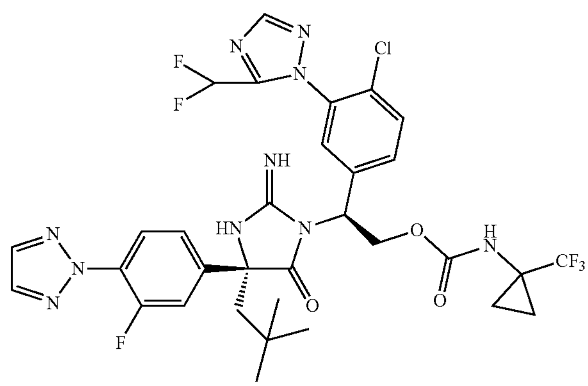 [SMILES: CC(C)(C)C[C@]1(c2ccc(-n3nccn3)c(F)c2)NC(=N)N([C@H](COC(=O)NC2(C(F)(F)F)CC2)c2ccc(Cl)c(-n3ncnc3C(F)F)c2)C1=O] | LCMS-ESI+: calc'd for $C_{32}H_{31}ClF_6N_{10}O_3$: 753.2 (M + H+); Found: 753.4 (M + H+). | 1H NMR (400 MHz, Methanol-d4) δ 8.18 (s, 1H), 8.10 (s, 1H), 8.02 (s, 2H), 7.85 (t, J = 8.2 Hz, 1H), 7.70-7.56 (m, 2H), 7.48 (dd, J = 12.2, 2.1 Hz, 1H), 7.45-7.37 (m, 1H), 7.37-7.26 (m, 1H), 6.83 (t, J = 52.2 Hz, 1H), 5.68 (dd, J = 9.7, 4.8 Hz, 1H), 5.10 (t, J = 10.6 Hz, 1H), 4.72 (dd, J = 11.6, 4.9 Hz, 1H), 2.46 (d, J = 15.2 Hz, 1H), 2.18 (d, J = 15.1 Hz, 1H), 1.33-1.22 (m, 2H), 1.14-1.03 (m, 2H), 1.00 (s, 9H). |
| 310 | 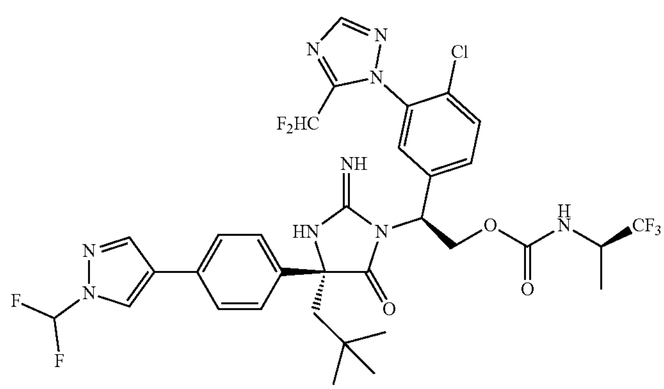 [SMILES: C[C@@H](NC(=O)OC[C@H](c1ccc(Cl)c(-n2ncnc2C(F)F)c1)N1C(=N)N[C@](CC(C)(C)C)(c2ccc(-c3cnn(C(F)F)c3)cc2)C1=O)C(F)(F)F] | LCMS-ESI+: calc'd for $C_{33}H_{33}ClF_7N_9O_3$: 772.2 (M + H+); Found: 772.2 (M + H+). | 1H NMR (400 MHz, Methanol-d4) δ 8.44 (s, 1H), 8.09 (s, 1H), 8.03 (s, 1H), 7.69-7.15 (m, 8H), 6.77 (t, J = 52.2 Hz, 1H), 5.66 (dd, J = 9.5, 4.8 Hz, 1H), 5.16 (dd, J = 11.4, 9.6 Hz, 1H), 4.71 (dd, J = 11.4, 4.9 Hz, 1H), 4.32 (m, 1H), 2.42 (d, J = 15.1 Hz, 1H), 2.15 (d, J = 15.1 Hz, 1H), 1.31 (d, J = 7.1 Hz, 3H), 0.98 (s, 9H). |

-continued

| Compound # | Structures | Mass data | NMR data |
|---|---|---|---|
| 311 | 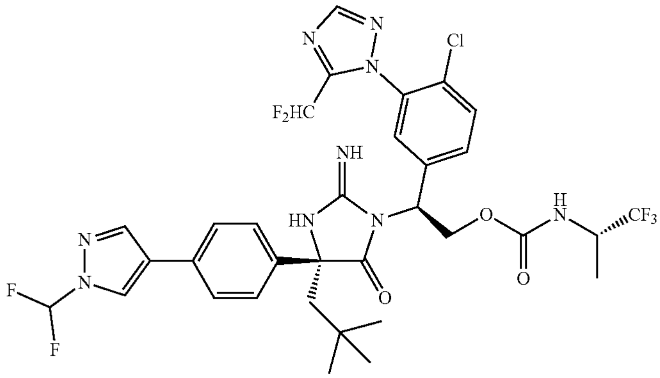 [SMILES: C[C@H](NC(=O)OC[C@H](c1ccc(Cl)c(-n2ncnc2C(F)F)c1)N1C(=N)N[C@](CC(C)(C)C)(c2ccc(-c3cnn(C(F)F)c3)cc2)C1=O)C(F)(F)F] | LCMS-ESI+: calc'd for C₃₃H₃₃ClF₇N₉O₃: 772.2 (M + H+); Found: 772.3 (M + H+). | 1H NMR (400 MHz, Methanol-d4) δ 8.45 (s, 1H), 8.10 (s, 1H), 8.02 (s, 1H), 7.73-7.13 (m, 8H), 6.79 (t, J = 52.2 Hz, 1H), 5.74 (dd, J = 9.6, 5.0 Hz, 1H), 5.12 (dd, J = 11.6, 9.7 Hz, 1H), 4.74 (dd, J = 11.6, 5.0 Hz, 1H), 4.31 (m, 1H), 2.44 (d, J = 15.1 Hz, 1H), 2.16 (d, J = 15.1 Hz, 1H), 1.29 (d, J = 7.1 Hz, 3H), 1.00 (s, 9H). |
| 312 | 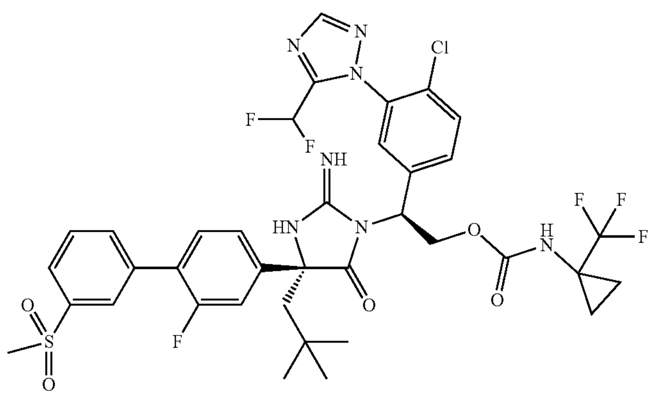 [SMILES: CC(C)(C)C[C@]1(c2ccc(-c3cccc(S(C)(=O)=O)c3)c(F)c2)NC(=N)N([C@H](COC(=O)NC2(C(F)(F)F)CC2)c2ccc(Cl)c(-n3ncnc3C(F)F)c2)C1=O] | LCMS-ESI+: calc'd C₃₇H₃₆ClF₆N₇O₅S: 840.2 (M + H+); Found: 840.5 (M + H+). | 1H NMR (400 MHz, Methanol-d4) δ 8.20 (s, 1H), 8.13-8.08 (m, 2H), 8.01 (ddd, J = 7.9, 1.9, 1.1 Hz, 1H), 7.89 (dd, J = 7.8, 1.6 Hz, 1H), 7.75 (t, J = 7.8 Hz, 1H), 7.69-7.60 (m, 2H), 7.55 (t, J = 8.3 Hz, 1H), 7.42-7.26 (m, 3H), 6.82 (t, J = 52.2 Hz, 1H), 5.69 (dd, J = 9.7, 4.8 Hz, 1H), 5.12 (t, J = 10.6 Hz, 1H), 4.72 (dd, J = 11.5, 4.9 Hz, 1H), 3.19 (s, 3H), 2.46 (d, J = 15.2 Hz, 1H), 2.18 (d, J = 15.1 Hz, 1H), 1.33-1.23 (m, 2H), 1.09 (m, 2H), 1.00 (s, 9H). |
| 313 | 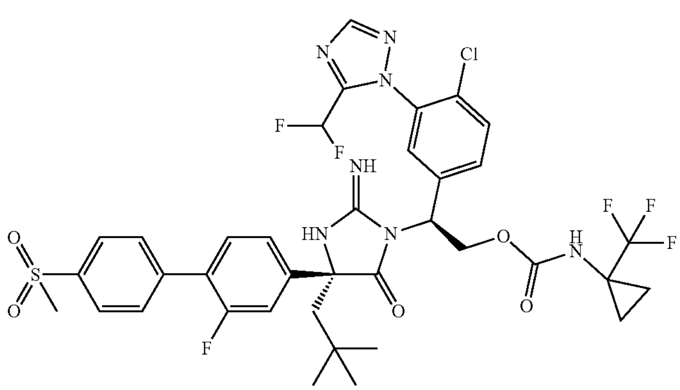 [SMILES: CC(C)(C)C[C@]1(c2ccc(-c3ccc(S(C)(=O)=O)cc3)c(F)c2)NC(=N)N([C@H](COC(=O)NC2(C(F)(F)F)CC2)c2ccc(Cl)c(-n3ncnc3C(F)F)c2)C1=O] | LCMS-ESI+: calc'd C₃₇H₃₆ClF₆N₇O₅S: 840.2 (M + H+); Found: 840.3 (M + H+). | 1H NMR (400 MHz, Methanol-d4) δ 8.19 (s, 1H), 8.10 (s, 1H), 8.06 (m, 2H), 7.80 (dd, J = 8.5, 1.5 Hz, 2H), 7.60 (m, 3H), 7.35 (m, 3H), 6.82 (t, J = 52.2 Hz, 1H), 5.68 (dd, J = 9.8, 4.8 Hz, 1H), 5.20-5.05 (m, 1H), 4.72 (dd, J = 11.5, 4.9 Hz, 1H), 3.17 (s, 3H), 2.46 (d, J = 15.2 Hz, 1H), 2.18 (d, J = 15.1 Hz, 1H), 1.35-1.20 (m, 2H), 1.09 (m, 2H), 1.00 (s, 9H). |

| Compound # | Structures | Mass data | NMR data |
|---|---|---|---|
| 314 | 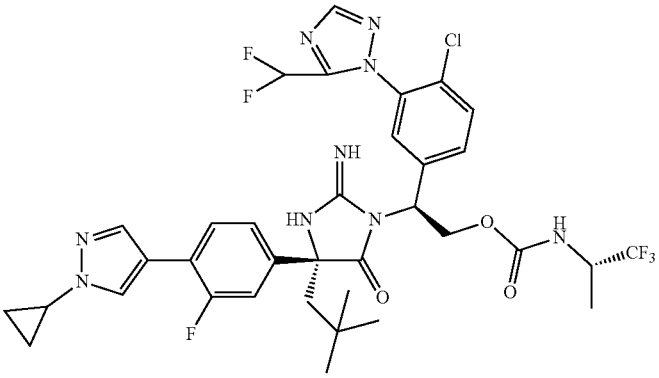 [SMILES: C[C@H](NC(=O)OC[C@H](c1ccc(Cl)c(-n2ncnc2C(F)F)c1)N1C(=N)N[C@](CC(C)(C)C)(c2ccc(-c3cnn(C4CC4)c3)c(F)c2)C1=O)C(F)(F)F] | LCMS-ESI+: calc'd $C_{35}H_{37}ClF_6N_9O_3$: 780.3 (M + H+); Found: 780.6 (M + H+). | 1H NMR (400 MHz, Methanol-d4) δ 8.10 (d, J = 1.8 Hz, 1H), 8.02 (s, 1H), 7.86 (m, 2H), 7.70-7.50 (m, 3H), 7.32-7.13 (m, 3H), 6.80 (t, J = 52.2 Hz, 1H), 5.75 (dd, J = 9.6, 5.0 Hz, 1H), 5.11 (dd, J = 11.6, 9.7 Hz, 1H), 4.75 (dd, J = 11.6, 5.0 Hz, 1H), 4.40-4.14 (m, 1H), 3.73 (dt, J = 7.4, 3.5 Hz, 1H), 2.42 (d, J = 15.1 Hz, 1H), 2.14 (d, J = 15.1 Hz, 1H), 1.29 (d, J = 7.1 Hz, 3H), 1.15 (m, 2H), 1.12-1.04 (m, 2H), 1.00 (s, 9H). |
| 315 | 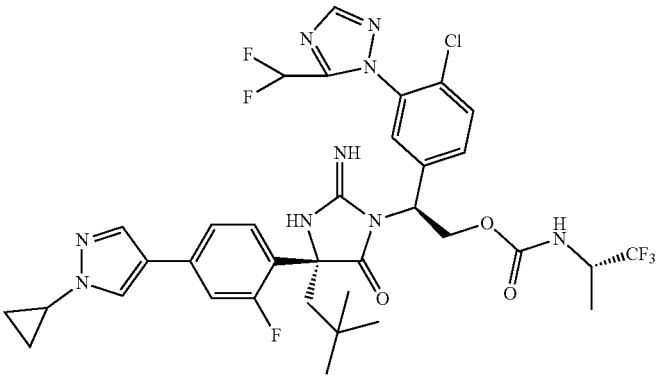 [SMILES: C[C@H](NC(=O)OC[C@H](c1ccc(Cl)c(-n2ncnc2C(F)F)c1)N1C(=N)N[C@](CC(C)(C)C)(c2ccc(-c3cnn(C4CC4)c3)cc2F)C1=O)C(F)(F)F] | LCMS-ESI+: calc'd $C_{35}H_{36}ClF_6N_9O_3$: 780.3 (M + H+); Found: 781.0 (M + H+). | 1H NMR (400 MHz, Methanol-d4) δ 8.18 (s, 1H), 8.11 (s, 1H), 7.83 (s, 1H), 7.72 (m, 2H), 7.57 (s, 1H), 7.36-7.24 (m, 3H), 6.90 (t, J = 52.2 Hz, 1H), 5.74 (dd, J = 9.5, 5.0 Hz, 1H), 5.16 (dd, J = 11.6, 9.5 Hz, 1H), 4.83-4.74 (m, 1H), 4.33 (p, J = 7.1 Hz, 1H), 3.69 (tt, J = 7.4, 3.6 Hz, 1H), 2.36 (m, 2H), 1.31 (d, J = 7.1 Hz, 3H), 1.19-1.10 (m, 2H), 1.08-1.04 (m, 11H). |
| 316 | 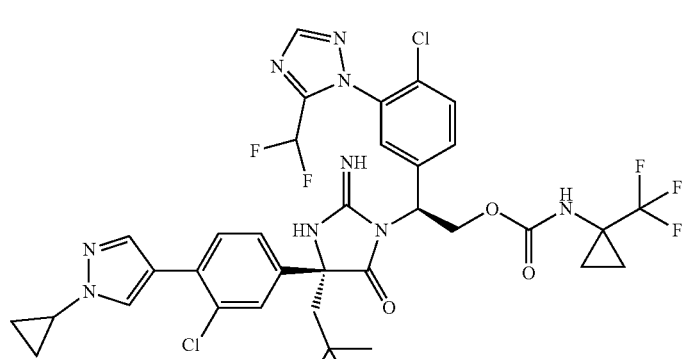 | LCMS-ESI+: calc'd $C_{36}H_{36}Cl_2F_5N_9O_3$: 808.2 (M + H+); Found: 808.3 (M + H+). | 1H NMR (400 MHz, Methanol-d4) δ 8.17 (s, 1H), 8.12 (s, 1H), 8.08 (s, 1H), 7.86-7.82 (m, 1H), 7.68-7.49 (m, 3H), 7.47 (d, J = 2.1 Hz, 1H), 7.34 (dd, J = 8.3, 2.2 Hz, 1H), 7.27 (s, 1H), 6.80 (t, J = 52.2 Hz, 1H), 5.68 (dd, J = 9.6, 4.9 Hz, 1H), 5.21-5.01 (m, 1H), 4.71 (dd, J = 11.6, 5.0 Hz, 1H), 3.79-3.68 (m, 1H), 2.43 (d, J = 15.2 Hz, 1H), 2.13 (d, J = 15.1 Hz, 1H), 1.35-1.04 (m, 8H), 0.99 (s, 9H). |

-continued

| Compound # | Structures | Mass data | NMR data |
|---|---|---|---|
| 317 | 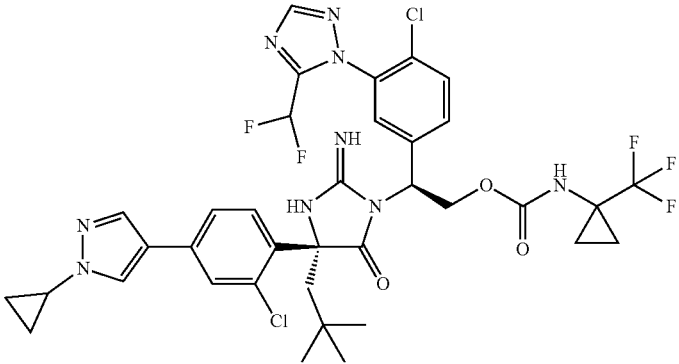 [SMILES: CC(C)(C)C[C@]1(c2ccc(-c3cnn(C4CC4)c3)cc2Cl)NC(=N)N([C@H](COC(=O)NC2(C(F)(F)F)CC2)c2ccc(Cl)c(-n3ncnc3C(F)F)c2)C1=O] | LCMS-ESI+: calc'd $C_{36}H_{36}Cl_2F_5N_9O_3$: 808.2 (M + H+); Found: 808.4 (M + H+). | 1H NMR (400 MHz, Methanol-d4) δ 8.33-8.05 (m, 2H), 7.92-7.62 (m, 5H), 7.38 (dd, J = 8.4, 1.9 Hz, 1H), 7.14 (d, J = 8.4 Hz, 1H), 6.94 (t, J = 52.2 Hz, 1H), 5.71 (dd, J = 9.7, 4.8 Hz, 1H), 5.15 (t, J = 10.6 Hz, 1H), 4.78 (dd, J = 11.5, 4.9 Hz, 1H), 3.68 (tt, J = 7.3, 3.6 Hz, 1H), 2.49 (d, J = 15.1 Hz, 1H), 2.27 (d, J = 15.1 Hz, 1H), 1.27 (m, J = 2.3 Hz, 2H), 1.14-1.05 (m, 6H), 1.04 (s, 9H). |
| 318 | 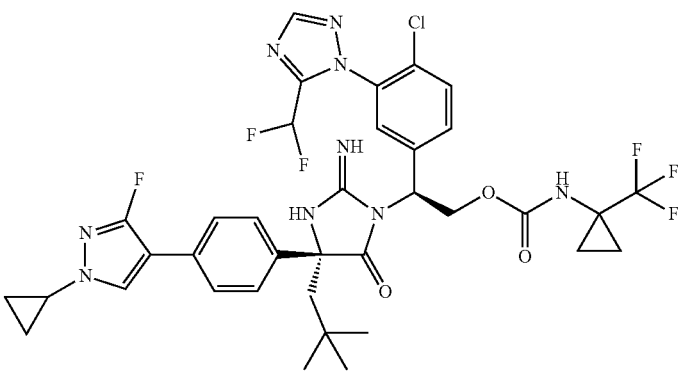 [SMILES: CC(C)(C)C[C@]1(c2ccc(-c3cn(C4CC4)nc3F)cc2)NC(=N)N([C@H](COC(=O)NC2(C(F)(F)F)CC2)c2ccc(Cl)c(-n3ncnc3C(F)F)c2)C1=O] | LCMS-ESI+: calc'd for C36H36ClF6N9O3: 792.2 (M + H+); Found: 792.2 (M + H+). | 1H NMR (400 MHz, Methanol-d4) δ 8.17 (s, 1H), 8.05 (s, 1H), 7.98 (d, J = 2.4 Hz, 1H), 7.61 (d, J = 8.4 Hz, 1H), 7.55 (dd, J = 8.7, 2.1 Hz, 1H), 7.50 (d, J = 8.3 Hz, 2H), 7.40 (d, J = 8.6 Hz, 2H), 7.21 (d, J = 2.1 Hz, 1H), 6.76 (t, J = 52.2 Hz, 1H), 5.67 (dd, J = 9.7, 4.8 Hz, 1H), 5.09 (t, J = 10.6 Hz, 1H), 4.69 (dd, J = 11.5, 4.9 Hz, 1H), 3.60 (tt, J = 7.3, 3.8 Hz, 1H), 2.43 (d, J = 15.2 Hz, 1H), 2.14 (d, J = 15.2 Hz, 1H), 1.27 (d, J = 2.3 Hz, 2H), 1.14-1.05 (m, 4H), 1.05-0.99 (m, 2H), 0.98 (s, 9H). |
| 319 | 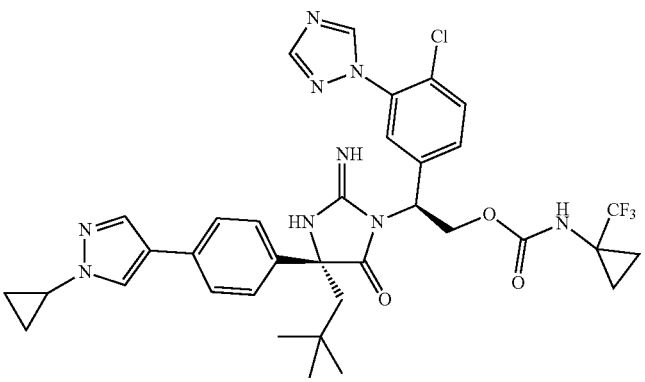 [SMILES: CC(C)(C)C[C@]1(c2ccc(-c3cnn(C4CC4)c3)cc2)NC(=N)N([C@H](COC(=O)NC2(C(F)(F)F)CC2)c2ccc(Cl)c(-n3cncn3)c2)C1=O] | LCMS-ESI+: calc'd for $C_{35}H_{37}ClF_3N_9O_3$: 724.3 (M + H+); Found: 724.2 (M + H+). | 1H NMR (400 MHz, Chloroform-d) δ 8.47 (s, 1H), 8.05 (s, 1H), 7.71 (d, J = 10.9 Hz, 2H), 7.52 (m, 4H), 7.41 (d, J = 8.1 Hz, 2H), 7.33 (d, J = 8.4 Hz, 1H), 5.51 (dd, J = 9.1, 6.0 Hz, 1H), 4.87-4.60 (m, 3H), 3.63 (tt, J = 7.3, 3.8 Hz, 1H), 2.29 (d, J = 14.7 Hz, 1H), 2.11-1.97 (m, 1H), 1.20-0.99 (m, 6H), 0.95-0.80 (m, 11H). |

| Compound # | Structures | Mass data | NMR data |
|---|---|---|---|
| 320 | 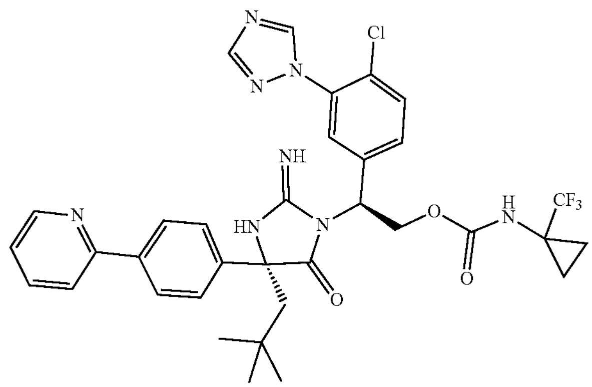 [SMILES: CC(C)(C)C[C@]1(c2ccc(-c3ccccn3)cc2)NC(=N)N([C@H](COC(=O)NC2(C(F)(F)F)CC2)c2ccc(Cl)c(-n3cncn3)c2)C1=O] | LCMS-ESI+: calc'd for $C_{34}H_{34}ClF_3N_8O_3$: 695.2 (M + H+); Found: 695.2 (M + H+). | 1H NMR (400 MHz, Methanol-d4) δ 8.75-8.65 (m, 2H), 8.18 (m, 2H), 8.08-7.99 (m, 2H), 7.96 (d, J = 8.3 Hz, 2H), 7.61 (m, 4H), 7.45 (d, J = 8.3 Hz, 1H), 7.33 (s, 1H), 5.68 (dt, J = 9.8, 4.8 Hz, 1H), 5.10 (t, J = 10.6 Hz, 1H), 4.72 (dd, J = 11.5, 4.9 Hz, 1H), 2.50 (d, J = 15.1 Hz, 1H), 2.33-2.12 (m, 1H), 1.15 (d, J = 6.1 Hz, 2H), 1.09 (m, 1H), 1.01 (s, 9H). |
| 321 | 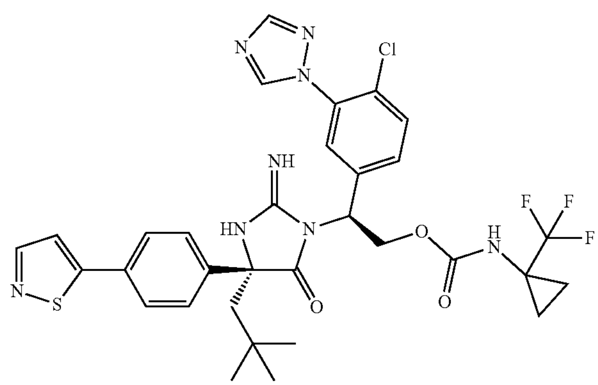 [SMILES: CC(C)(C)C[C@]1(c2ccc(-c3ccns3)cc2)NC(=N)N([C@H](COC(=O)NC2(C(F)(F)F)CC2)c2ccc(Cl)c(-n3cncn3)c2)C1=O] | LCMS-ESI+: calc'd for $C_{32}H_{32}ClF_3N_8O_3S$: 701.2 (M + H+); Found: 701.3 (M + H+). | 1H NMR (400 MHz, Methanol-d4) δ 8.57 (s, 1H), 8.18 (s, 1H), 7.69 (m, 2H), 7.58 (m, 2H), 7.45 (d, J = 8.4 Hz, 1H), 7.34 (s, 1H), 7.22 (dd, J = 24.3, 7.7 Hz, 2H), 7.05 (t, J = 7.2 Hz, 1H), 5.67 (dd, J = 9.5, 4.8 Hz, 1H), 5.09 (t, J = 10.5 Hz, 1H), 4.70 (d, J = 10.0 Hz, 1H), 2.44 (d, J = 15.4 Hz, 1H), 2.17 (d, J = 15.1 Hz, 1H), 1.28 (m, 2H), 1.08 (m, 2H), 0.99 (s, 9H). |
| 322 | 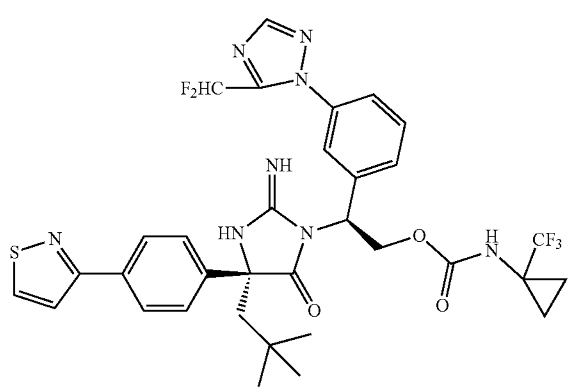 [SMILES: CC(C)(C)C[C@]1(c2ccc(-c3ccsn3)cc2)NC(=N)N([C@H](COC(=O)NC2(C(F)(F)F)CC2)c2cccc(-n3ncnc3C(F)F)c2)C1=O] | LCMS-ESI+: calc'd for $C_{33}H_{33}F_5N_8O_3S$: 717.2 (M + H+); Found: 717.3 (M + H+). | 1H NMR (400 MHz, Chloroform-d) δ 8.74 (d, J = 4.7 Hz, 1H), 8.14-7.84 (m, 2H), 7.70-7.55 (m, 4H), 7.53-7.33 (m, 2H), 6.83 (t, J = 52.3 Hz, 1H), 5.76 (m, 2H), 5.03 (dd, J = 12.3, 7.4 Hz, 1H), 4.58 (d, J = 12.1 Hz, 1H), 2.27 (q, J = 15.2 Hz, 2H), 1.23 m, 2H), 0.99 (m, 2H), 0.92 (s, 9H). |

-continued

| Compound # | Structures | Mass data | NMR data |
|---|---|---|---|
| 323 | 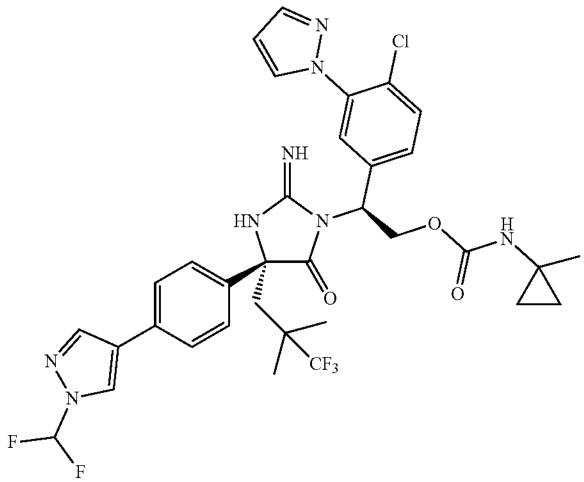 [SMILES: CC1(NC(=O)OC[C@H](c2ccc(Cl)c(-n3cccn3)c2)N2C(=N)N[C@](CC(C)(C)C(F)(F)F)(c3ccc(-c4cnn(C(F)F)c4)cc3)C2=O)CC1] | LCMS-ESI+: calc'd for C$_{34}$H$_{34}$Cl$_1$F$_5$N$_8$O$_3$: 733.2 (M + H+); Found: 733.0 (M + H+). | 1H NMR (400 MHz, Methanol-d4) δ 8.41 (s, 1H), 8.08 (s, 1H), 7.62-7.35 (m, 9H), 7.33 (dd, J = 8.8, 2.3 Hz, 1H), 7.19 (d, J = 2.2 Hz, 1H), 6.28 (t, J = 2.2 Hz, 1H), 5.44 (td, J = 11.2, 9.1, 4.8 Hz, 1H), 5.00 (dd, J = 11.1, 9.3 Hz, 1H), 4.60 (dd, J = 11.2, 5.5 Hz, 1H), 2.53 (d, J = 14.7 Hz, 1H), 2.21 (d, J = 14.7 Hz, 1H), 1.28 (s, 3H), 1.16 (s, 3H), 1.15 (s, 3H), 0.66 (q, J = 4.8, 4.3 Hz, 2H), 0.54 (q, J = 4.8 Hz, 2H). |
| 324 | 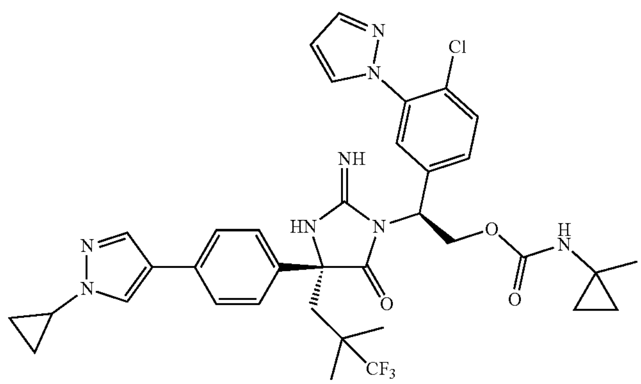 [SMILES: CC1(NC(=O)OC[C@H](c2ccc(Cl)c(-n3cccn3)c2)N2C(=N)N[C@](CC(C)(C)C(F)(F)F)(c3ccc(-c4cnn(C5CC5)c4)cc3)C2=O)CC1] | LCMS-ESI+: calc'd for C$_{36}$H$_{38}$ClF$_3$N$_8$O$_3$: 723.2 (M + H+); Found: 723.1 (M + H+). | 1H NMR (400 MHz, Methanol-d4) δ 8.03 (s, 1H), 7.80 (d, J = 0.8 Hz, 1H), 7.58 (dd, J = 4.9, 2.2 Hz, 2H), 7.48-7.43 (m, 6H), 7.32 (d, J = 8.6 Hz, 1H), 7.22 (s, 1H), 6.29 (t, J = 2.2 Hz, 1H), 5.44 (br s, 1H), 4.99 (t, J = 10.2 Hz, 1H), 4.59 (dd, J = 11.1, 5.5 Hz, 1H), 3.68 (tt, J = 7.3, 3.6 Hz, 1H), 2.51 (d, J = 14.7 Hz, 1H), 2.18 (d, J = 14.7 Hz, 1H), 1.28 (s, 3H), 1.16 (s, 3H), 1.14 (s, 3H), 0.65 (t, J = 3.3 Hz, 2H), 0.54 (t, J = 3.2 Hz, 2H). |

Example 78: Preparation of Compound 325

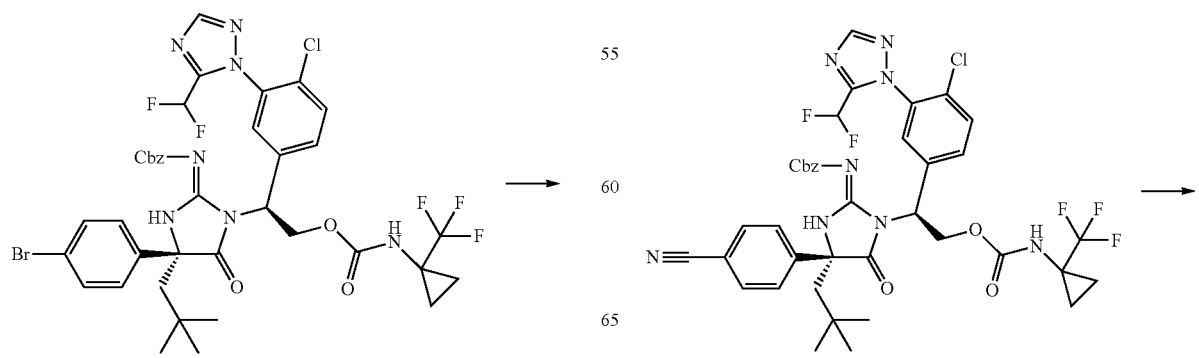

-continued

431

-continued

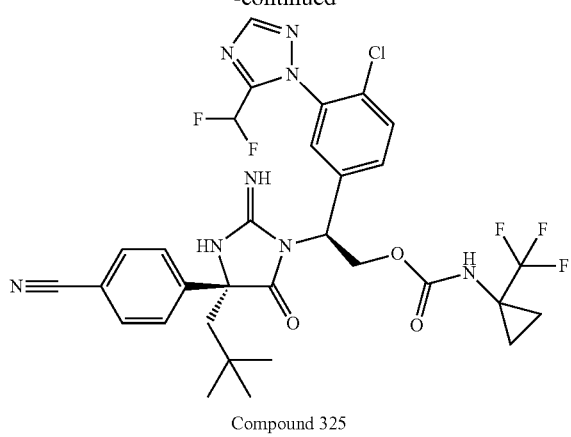

Compound 325

Preparation of benzyl ((R)-1-((S)-1-(4-chloro-3-(5-(difluoromethyl)-1H-1,2,4-triazol-1-yl)phenyl)-2-(((1-(trifluoromethyl)cyclopropyl)carbamoyl)oxy)ethyl)-4-(4-cyanophenyl)-4-neopentyl-5-oxoimidazolidin-2-ylidene)carbamate: A degassed solution of benzyl ((R)-4-(4-bromophenyl)-1-((S)-1-(4-chloro-3-(5-(difluoromethyl)-1H-1,2,4-triazol-1-yl)phenyl)-2-(((1-(trifluoromethyl)cyclopropyl)carbamoyl)oxy)ethyl)-4-neopentyl-5-oxoimidazolidin-2-ylidene)carbamate (30 mg, 0.034 mmol), tetrakis(triphenylphosphine)palladium (5.9 mg, 10 umol), zinc cyanide (12 mg, 0.10 mmol) in DMF (1.0 mL) was heated at 100° C. for 1 h. The reaction mixture was cooled to rt, diluted with water, and extracted with EtOAC. The organic phase was washed with 5% aqueous lithium chloride then brine, dried over sodium sulfate, concentrated down and purified by silica gel column chromatography (eluting with 0-100% gradient EtOAc/hexanes) to give the product.

Preparation of Compound 325: A solution of benzyl ((R)-1-((S)-1-(4-chloro-3-(5-(difluoromethyl)-1H-1,2,4-triazol-1-yl)phenyl)-2-(((1-(trifluoromethyl)cyclopropyl)carbamoyl)oxy)ethyl)-4-(4-cyanophenyl)-4-neopentyl-5-oxoimidazolidin-2-ylidene)carbamate (15 mg, 0.018 mmol) in TFA (1.0 mL) was heated at 60° C. for 2 h. The reaction mixture was concentrated, dissolved in MeOH, and purified by reversed phase HPLC, eluting with 5-100% acetonitrile in water containing 0.1% TFA, to afford the product.

Example 79: Preparation of Compound 326

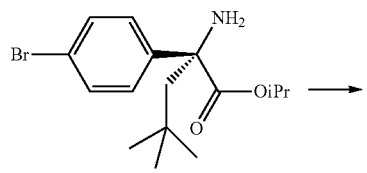

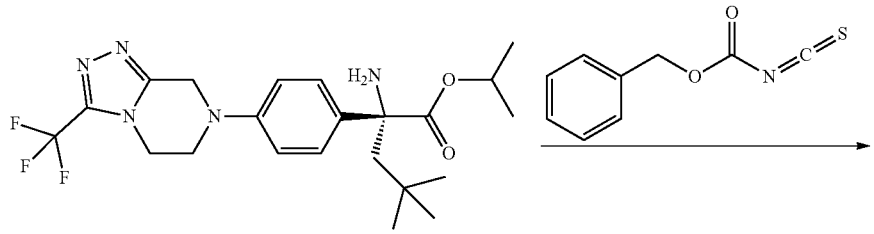

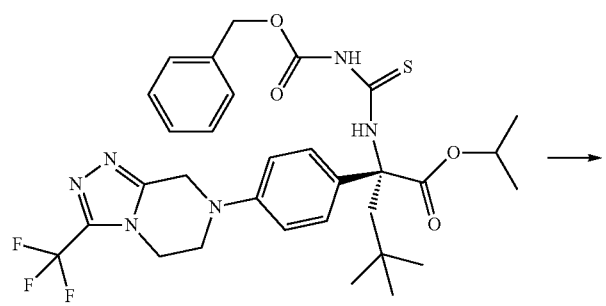

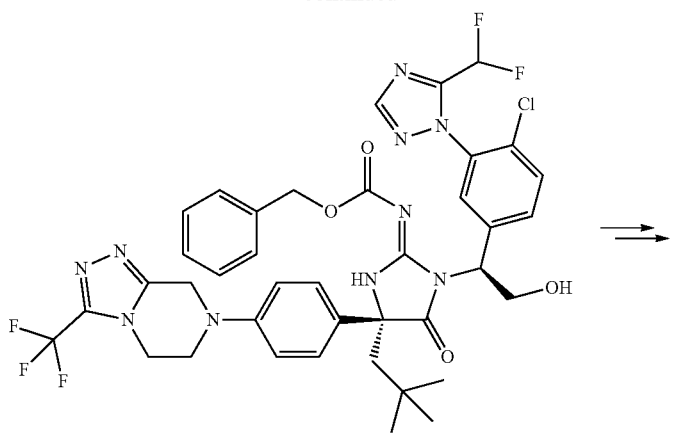

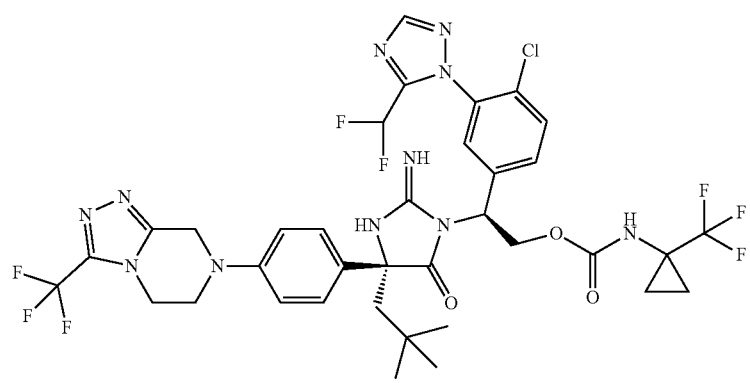

Compound 326

Preparation of isopropyl (R)-2-amino-4,4-dimethyl-2-(4-(3-(trifluoromethyl)-5,6-dihydro-[1,2,4]triazolo[4,3-a]pyrazin-7(8H)-yl)phenyl)pentanoate: To a degassed solution of isopropyl (R)-2-amino-2-(4-bromophenyl)-4,4-dimethyl-pentanoate (57 mg, 0.017 mmol), 3-(trifluoromethyl)-5,6,7,8-tetrahydro-[1,2,4]triazolo[4,3-a]pyrazine (57 mg, 0.030 mmol), S-Phos phenethylamine chloride precatalyst (12 mg, 0.015 mol) in 1,4-dioxane (2 mL) was added potassium t-butoxide (57 g, 0.51 mmol). The reaction was stirred at 100° C. for 15 min. The reaction mixture was cooled to rt, treated with saturated aq. ammonium chloride solution and EtOAc. The organic phase was dried over $Na_2SO_4$, filtered, concentrated down, and the residue was directly used in the next step.

Compound 326 was then prepared by following the procedure to prepare Compound 177. LCMS-ESI+: calc'd for $C_{36}H_{36}ClF_8N_{11}O_3$ [M+H+]: 858.3. Found: 858.8 [M+H+]. 1H NMR (400 MHz, $CD_3CN$) δ 8.13 (s, 1H), 7.59 (d, J 8.5 Hz, 1H), 7.50 (d, J=8.5 Hz, 1H), 7.39-7.28 (m, 3H), 7.04-6.93 (m, 2H), 6.85-6.53 (m, 2H), 5.39 (dd, J=9.6, 4.5 Hz, 1H), 4.91 (t, J=10.6 Hz, 1H), 4.63 (s, 3H), 4.25 (t, J=5.4 Hz, 2H), 3.77 (t, J=5.5 Hz, 2H), 2.30-2.05 (m, 2H), 1.31-1.22 (m, 2H), 1.07 (s, 2H), 0.90 (s, 9H).

Example 80: Preparation of Compound 327

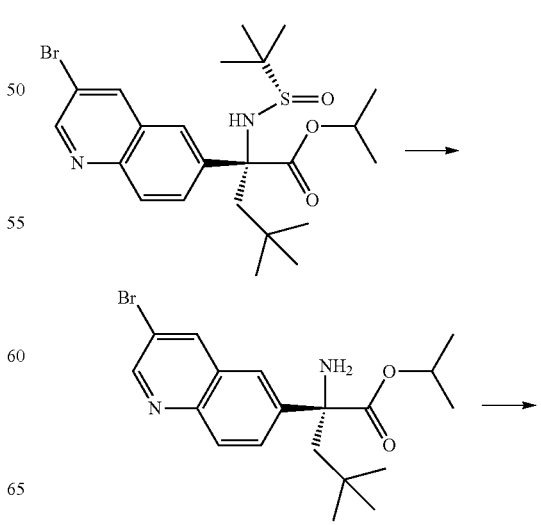

-continued

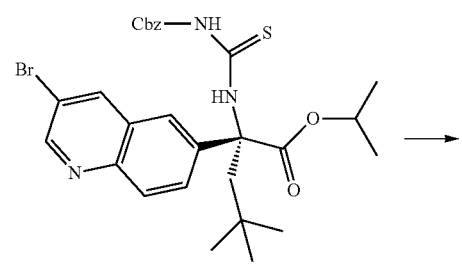

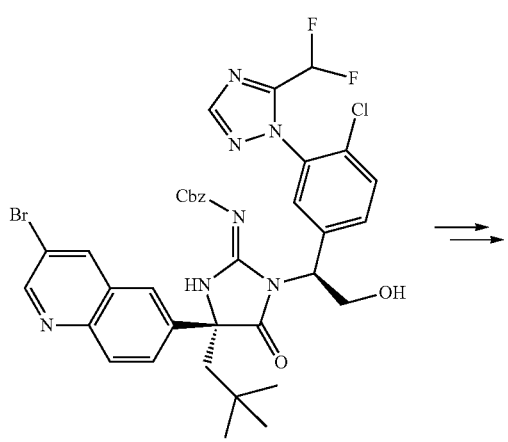

Compound 327

Compound 327 was prepared by following the procedure to prepare Compound 179, starting with isopropyl (R)-2-(3-bromoquinolin-6-yl)-2-(((S)-tert-butylsulfinyl)amino)-4,4-dimethylpentanoate. LCMS-ESI+: calc'd for $C_{33}H_{32}BrClF_4N_8O_3$: 779.1 (M+H+). Found: 779.4 (M+H+). 1H NMR (400 MHz, Methanol-$d_4$) δ 8.97 (d, J=2.3 Hz, 1H), 8.54 (d, J=2.2 Hz, 1H), 8.10-7.96 (m, 2H), 7.94-7.79 (m, 2H), 7.57 (d, J=1.2 Hz, 2H), 7.22 (d, J=25.0 Hz, 1H), 6.69 (s, 1H), 6.14 (s, 1H), 5.69 (dd, J=9.4, 5.1 Hz, 1H), 5.17-4.98 (m, 1H), 4.69 (dd, J=11.6, 5.2 Hz, 1H), 2.55 (d, J=15.1 Hz, 1H), 2.28 (d, J=15.1 Hz, 1H), 1.32 (s, 6H), 1.02 (s, 9H).

Example 81: Preparation of Compound 328

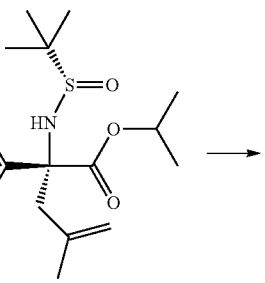

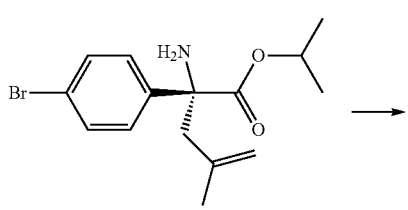

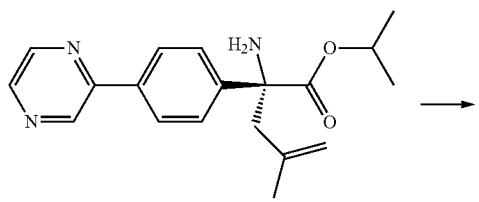

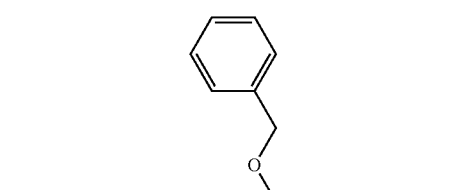

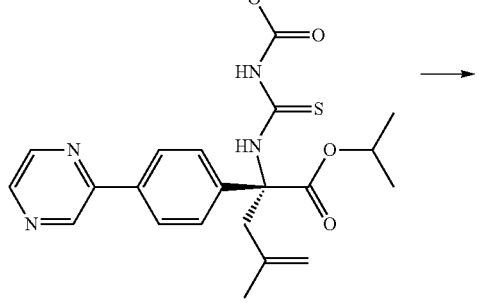

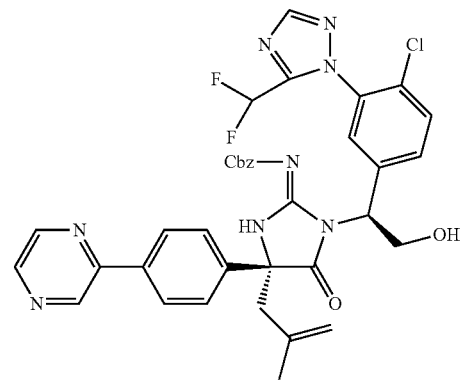

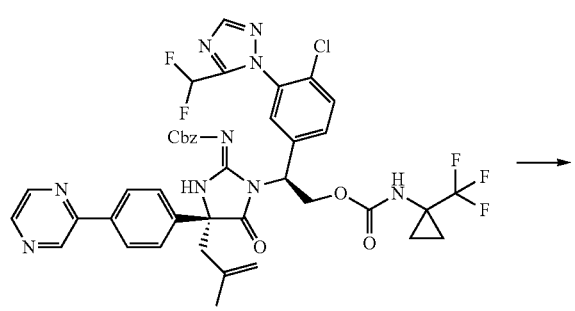

Preparation of (S)-2-((R)-2-(((benzyloxy)carbonyl)imino)-4-(2-methylallyl)-5-oxo-4-(4-(pyrazin-2-yl)phenyl)imidazolidin-1-yl)-2-(4-chloro-3-(5-(difluoromethyl)-1H-1,2,4-triazol-1-yl)phenyl)ethyl (1-(trifluoromethyl)cyclopropyl)carbamate: (S)-2-((R)-2-(((benzyloxy)carbonyl)imino)-4-(2-methylallyl)-5-oxo-4-(4-(pyrazin-2-yl)phenyl)imidazolidin-1-yl)-2-(4-chloro-3-(5-(difluoromethyl)-1H-1,2,4-triazol-1-yl)phenyl)ethyl (1-(trifluoromethyl)cyclopropyl)carbamate was prepared following the procedure to prepare benzyl ((R)-1-((S)-1-(4-chloro-3-(5-(difluoromethyl)-1H-1,2,4-triazol-1-yl)phenyl)-2-hydroxyethyl)-4-(2-fluoro-4-(pyrazin-2-yl)phenyl)-4-neopentyl-5-oxoimidazolidin-2-ylidene)carbamate described in Example 75, starting with isopropyl (R)-2-(4-bromophenyl)-2-((S)-tert-butylsulfinyl)amino)-4-methylpent-4-enoate.

Preparation of Compound 328: A solution of (S)-2-((R)-2-(((benzyloxy)carbonyl)imino)-4-(2-methylallyl)-5-oxo-4-(4-(pyrazin-2-yl)phenyl)imidazolidin-1-yl)-2-(4-chloro-3-(5-(difluoromethyl)-1H-1,2,4-triazol-1-yl)phenyl)ethyl (1-(trifluoromethyl)cyclopropyl)carbamate (126 mg, 0.146 mmol) in DCM (0.6 mL), was added into a polypropylene bottle containing 70% HF-urea (3 mL). The reaction mixture was stirred at rt for 4 h. The mixture was then slowly added to a stirred mixture of DCM (100 mL), aqueous NaOH (1M, 100 mL) and NaOH pellets (10 g) at 0° C. The neutralized mixture was extracted with DCM. The organic phase was washed with water and then with brine, dried over $Na_2SO_4$, filtered, and concentrated down. The residue was purified by reverse phase HPLC, eluting by 5-100% acetonitrile in water containing 0.1% TFA, to give the product. LCMS-ESI+m/z Calc'd for $C_{33}H_{30}ClF_6N_9O_3$ [M+H+]: 750.2. Found: 750.6 [M+H+]. 1H NMR (400 MHz, $CD_3CN$) δ 9.11 (s, 1H), 8.66 (t, J=1.9 Hz, 1H), 8.56 (s, 1H), 8.16-8.01 (m, 3H), 7.70-7.37 (m, 5H), 6.72 (t, J=52.3 Hz, 1H), 6.50 (s, 1H), 5.48 (dd, J=9.0, 4.3 Hz, 1H), 4.97-4.82 (m, 1H), 4.62 (dd, J=11.5, 4.3 Hz, 1H), 2.90-2.43 (m, 2H), 1.44-1.32 (m, 6H), 1.29-1.20 (m, 2H), 1.09-0.99 (m, 2H).

Example 82: Preparation of Compound 329

Compound 329

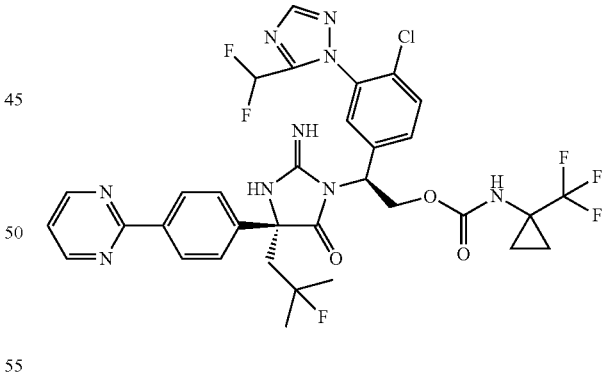

Compound 329 was then prepared by following the procedure to prepare Compound 278, except that 2-(tributylstannyl)pyrimidine was used instead of 2-(tributylstannyl)pyrazine. LCMS-ESI+m/z Calc'd for $C_{33}H_{30}ClF_6N_9O_3$ [M+H+]: 750.2. Found: 750.6 [M+H+]. 1H NMR (400 MHz, Methanol-$d_4$) δ 8.88 (d, J=4.9 Hz, 2H), 8.41 (d, J=8.6 Hz, 2H), 8.07 (s, 1H), 7.67-7.55 (m, 4H), 7.40 (t, J=4.9 Hz, 1H), 7.32 (d, J=2.1 Hz, 1H), 6.78 (t, J=52.2 Hz, 1H), 5.68 (dd, J=9.2, 5.2 Hz, 1H), 5.06 (dd, J=11.5, 9.3 Hz, 1H), 4.71 (dd, J=11.6, 5.1 Hz, 1H), 2.97 (dd, J=15.4, 8.9 Hz, 1H), 2.61 (dd, J=25.7, 15.4 Hz, 1H), 1.46 (d, J=22.2 Hz, 3H), 1.35 (d, J=21.6 Hz, 3H), 1.28-1.20 (m, 2H), 1.05 (s, 2H).

Example 83: Preparation of Compound 330 and Compound 331

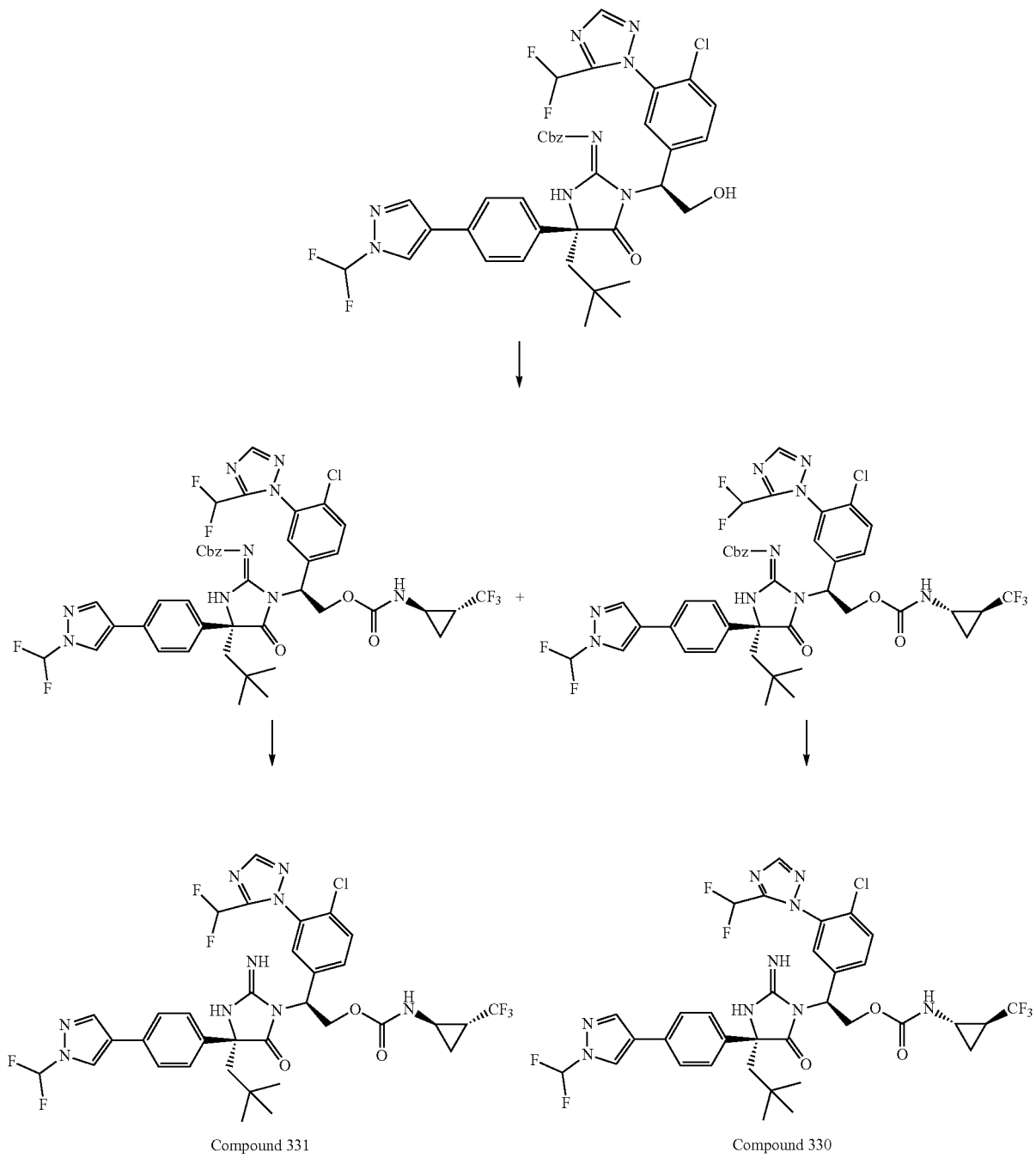

Compound 331                    Compound 330

Both Compound 330 and Compound 331 were prepared following the procedure to prepare Compound 204, except that the two single diastereoisomers are obtained by chiral separation at the Cbz-protected stage (Chiralpak IC, 150×4.6 nm, 5 micron, 15 mL/min, 200 bar, heptane:isopropanol, 70:30) and went to the final deprotection step individually. The stereochemistry of the two diastereomers at the cyclopropyl group is arbitrarily assigned. For the fast eluting isomer Compound 330: LCMS-ESI+: calc'd for $C_{34}H_{33}ClF_4N_9O_3$: 784.2 (M+H+). Found: 784.3 (M+H+). 1H NMR (400 MHz, Methanol-$d_4$) δ 8.60 (s, 1H), 8.21 (d, J=24.3 Hz, 2H), 7.85-7.30 (m, 8H), 6.94 (s, 1H), 5.79 (s, 1H), 5.22 (t, J=10.5 Hz, 1H), 4.88 (dd, J=11.4, 5.2 Hz, 1H), 3.03 (s, 1H), 2.59 (dd, J=15.0, 4.2 Hz, 1H), 2.28 (d, J=15.3 Hz, 1H), 1.88 (s, 1H), 1.24 (d, J=37.4 Hz, 2H), 1.12 (s, 9H). For the slow eluting isomer Compound 331: LCMS-ESI+: calc'd for $C_{34}H_{33}ClF_7N_9O_3$: 784.2 (M+H+). Found: 784.3 (M+H+). 1H NMR (400 MHz, Methanol-$d_4$) δ 8.45 (s, 1H), 8.10 (s, 1H), 8.04 (s, 1H), 7.71-7.16 (m, 8H), 6.80 (s, 1H), 5.65 (dd, J=9.4, 5.0 Hz, 1H), 5.10 (t, J=10.4 Hz, 1H), 4.73 (dd, J=11.6, 5.0 Hz, 1H), 2.87 (s, 1H), 2.46 (d, J=15.2 Hz, 1H), 2.15 (d, J=15.2 Hz, 1H), 1.74 (s, 1H), 1.18-1.10 (m, 1H), 1.05 (s, 1H), 0.99 (s, 9H).

Example 84: Preparation of Compound 332 and Compound 333

Example 85: Preparation of Compound 334 and Compound 335

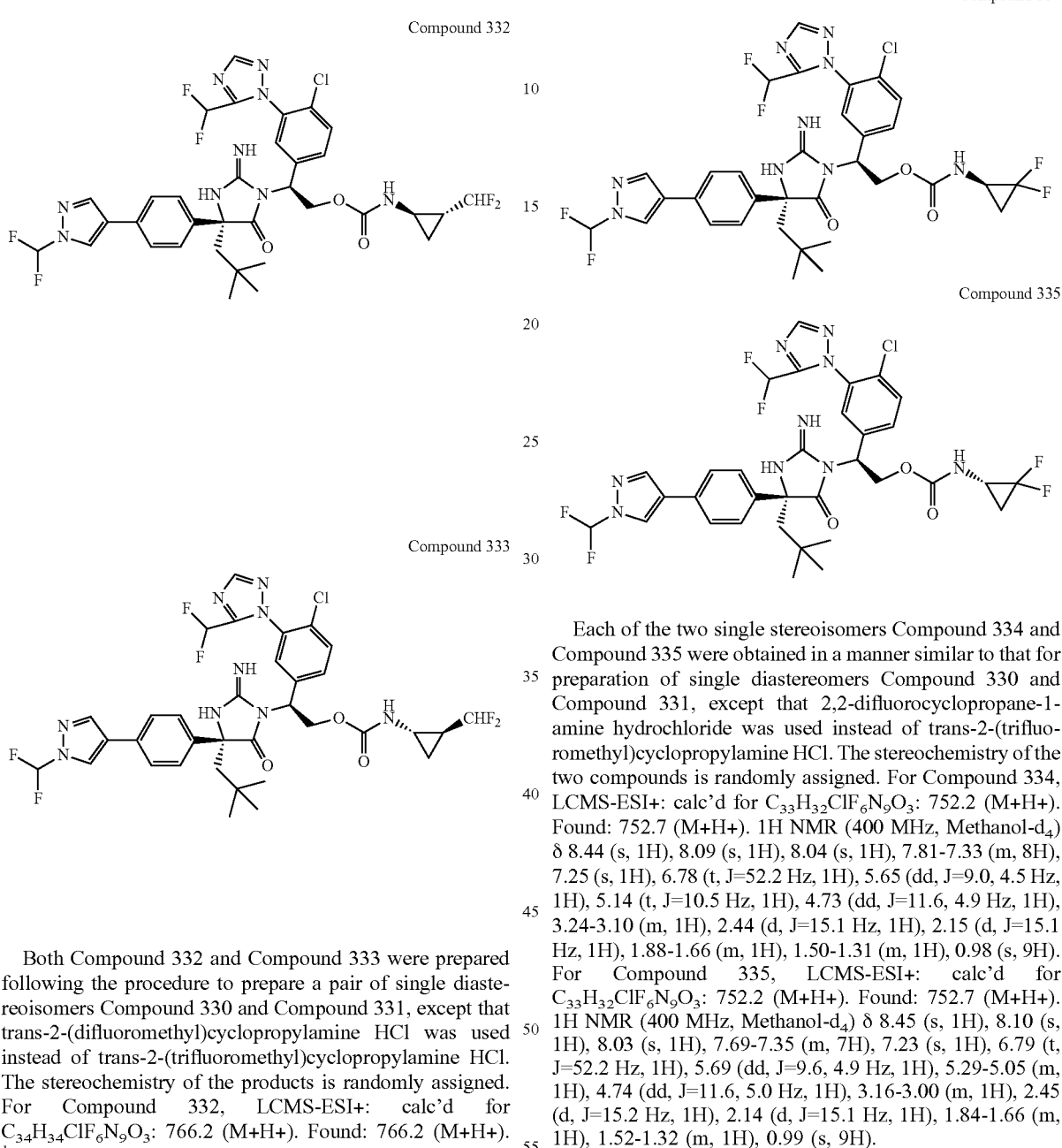

Both Compound 332 and Compound 333 were prepared following the procedure to prepare a pair of single diastereoisomers Compound 330 and Compound 331, except that trans-2-(difluoromethyl)cyclopropylamine HCl was used instead of trans-2-(trifluoromethyl)cyclopropylamine HCl. The stereochemistry of the products is randomly assigned. For Compound 332, LCMS-ESI+: calc'd for $C_{34}H_{34}ClF_6N_9O_3$: 766.2 (M+H+). Found: 766.2 (M+H+). $^1$H NMR (400 MHz, Methanol-$d_4$) δ 8.45 (s, 1H), 8.10 (s, 1H), 8.04 (s, 1H), 7.71-7.17 (m, 8H), 6.80 (s, 1H), 5.92-5.53 (m, 2H), 5.08 (t, J=10.5 Hz, 1H), 4.73 (dd, J=11.4, 5.2 Hz, 1H), 2.72 (s, 1H), 2.47 (d, J=15.2 Hz, 1H), 2.24-2.08 (m, 1H), 1.43 (s, 1H), 1.00 (s, 9H), 0.86 (d, J=14.2 Hz, 2H). For Compound 333, LCMS-ESI+: calc'd for $C_{34}H_{34}ClF_6N_9O_3$: 766.2 (M+H+). Found: 766.3 (M+H+). 1H NMR (400 MHz, Methanol-$d_4$) δ 8.49-8.37 (m, 1H), 8.07 (d, J=22.4 Hz, 2H), 7.72-7.20 (m, 8H), 6.80 (s, 1H), 5.91-5.53 (m, 2H), 5.09 (t, J=10.5 Hz, 1H), 4.74-4.60 (m, 1H), 2.71 (s, 1H), 2.46 (d, J=15.1 Hz, 1H), 2.15 (d, J=15.1 Hz, 1H), 1.42 (s, 1H), 1.00 (s, 9H), 0.87 (s, 1H).

Each of the two single stereoisomers Compound 334 and Compound 335 were obtained in a manner similar to that for preparation of single diastereomers Compound 330 and Compound 331, except that 2,2-difluorocyclopropane-1-amine hydrochloride was used instead of trans-2-(trifluoromethyl)cyclopropylamine HCl. The stereochemistry of the two compounds is randomly assigned. For Compound 334, LCMS-ESI+: calc'd for $C_{33}H_{32}ClF_6N_9O_3$: 752.2 (M+H+). Found: 752.7 (M+H+). 1H NMR (400 MHz, Methanol-$d_4$) δ 8.44 (s, 1H), 8.09 (s, 1H), 8.04 (s, 1H), 7.81-7.33 (m, 8H), 7.25 (s, 1H), 6.78 (t, J=52.2 Hz, 1H), 5.65 (dd, J=9.0, 4.5 Hz, 1H), 5.14 (t, J=10.5 Hz, 1H), 4.73 (dd, J=11.6, 4.9 Hz, 1H), 3.24-3.10 (m, 1H), 2.44 (d, J=15.1 Hz, 1H), 2.15 (d, J=15.1 Hz, 1H), 1.88-1.66 (m, 1H), 1.50-1.31 (m, 1H), 0.98 (s, 9H). For Compound 335, LCMS-ESI+: calc'd for $C_{33}H_{32}ClF_6N_9O_3$: 752.2 (M+H+). Found: 752.7 (M+H+). 1H NMR (400 MHz, Methanol-$d_4$) δ 8.45 (s, 1H), 8.10 (s, 1H), 8.03 (s, 1H), 7.69-7.35 (m, 7H), 7.23 (s, 1H), 6.79 (t, J=52.2 Hz, 1H), 5.69 (dd, J=9.6, 4.9 Hz, 1H), 5.29-5.05 (m, 1H), 4.74 (dd, J=11.6, 5.0 Hz, 1H), 3.16-3.00 (m, 1H), 2.45 (d, J=15.2 Hz, 1H), 2.14 (d, J=15.1 Hz, 1H), 1.84-1.66 (m, 1H), 1.52-1.32 (m, 1H), 0.99 (s, 9H).

Example 86: Preparation of Compound 336

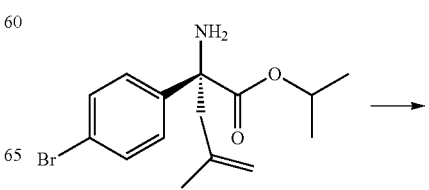

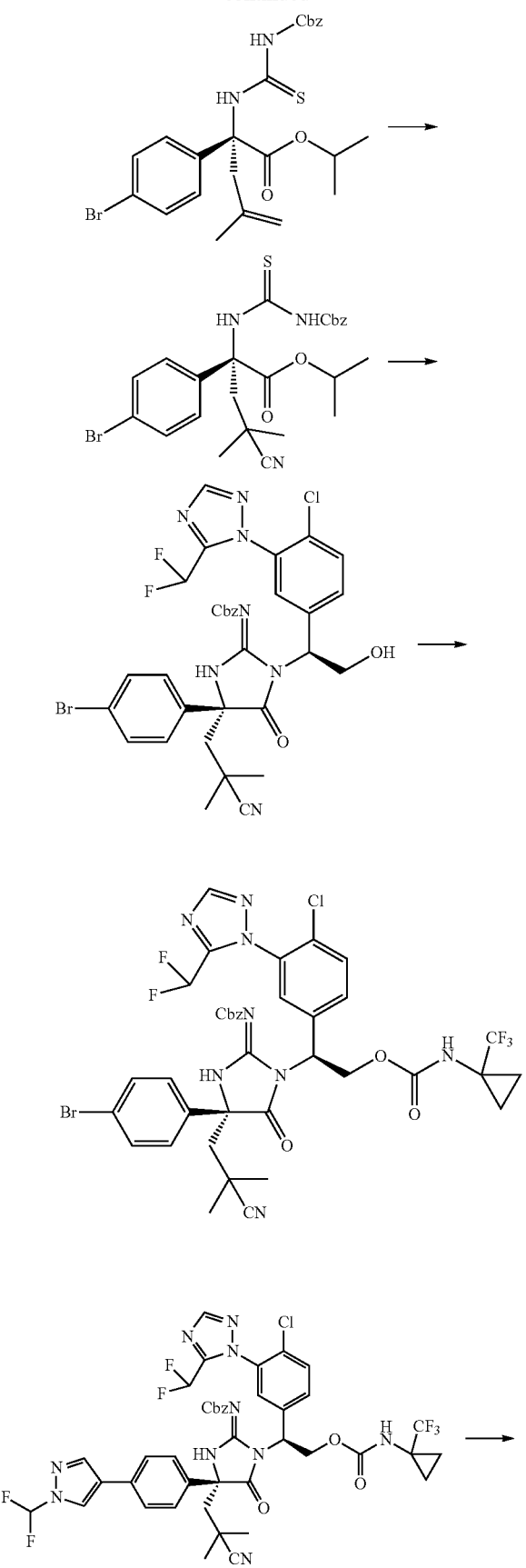

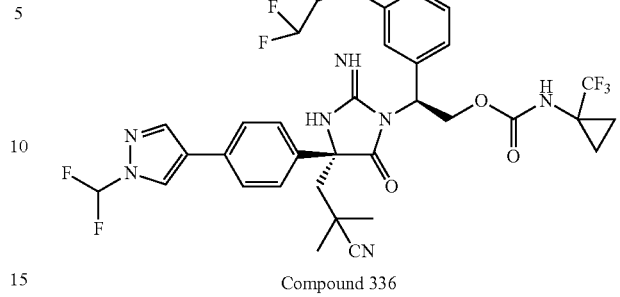

Compound 336

Preparation of isopropyl (R)-2-(3-((benzyloxy)carbonyl)thioureido)-2-(4-bromophenyl)-4-methylpent-4-enoate: isopropyl (R)-2-(3-((benzyloxy)carbonyl)thioureido)-2-(4-bromophenyl)-4-methylpent-4-enoate was prepared following the procedure to prepare isopropyl (R)-2-(3-((benzyloxy)carbonyl)thioureido)-2-(4-(1-(difluoromethyl)-1H-pyrazol-4-yl)phenyl)-4,4-dimethylpentanoate described in Example 65.

Preparation of isopropyl (R)-2-(3-((benzyloxy)carbonyl)thioureido)-2-(4-bromophenyl)-4-cyano-4-methylpentanoate: Catalyst Co salen catalyst (7 mg, 0.01 mmol) was dissolved in EtOH (5.0 mL; absolute) at rt under argon. After 2 min, isopropyl (R)-2-(3-((benzyloxy)carbonyl)thioureido)-2-(4-bromophenyl)-4-methylpent-4-enoate (300 mg, 0.58 mmol) was added to the red solution followed by TsCN (136 mg, 0.75 mmol). Then phenylsilane (0.08 mL, 0.58 mmol) and another portion of EtOH (0.5 mL) were added. The resulting solution was stirred at rt for 3 h. The solvent was removed by evaporation and the crude residue was purified by silica gel chromatography (0-100% gradient EtOAc/hexanes) to afford the product.

Preparation of benzyl ((R)-4-(4-bromophenyl)-1-((S)-1-(4-chloro-3-(5-(difluoromethyl)-1H-1,2,4-triazol-1-yl)phenyl)-2-hydroxyethyl)-4-(2-cyano-2-methylpropyl)-5-oxoimidazolidin-2-ylidene)carbamate: benzyl ((R)-4-(4-bromophenyl)-1-((S)-1-(4-chloro-3-(5-(difluoromethyl)-1H-1,2,4-triazol-1-yl)phenyl)-2-hydroxyethyl)-4-(2-cyano-2-methylpropyl)-5-oxoimidazolidin-2-ylidene)carbamate was prepared following the procedure to prepare ((R)-1-((S)-1-(4-chloro-3-(5-(difluoromethyl)-1H-1,2,4-triazol-1-yl)phenyl)-2-hydroxyethyl)-4-(4-(1-(difluoromethyl)-1H-pyrazol-4-yl)phenyl)-4-neopentyl-5-oxoimidazolidin-2-ylidene)carbamate described in Example 65.

Compound 336 was then prepared by following the procedure to prepare Compound 272, starting with benzyl ((R)-4-(4-bromophenyl)-1-((S)-1-(4-chloro-3-(5-(difluoromethyl)-1H-1,2,4-triazol-1-yl)phenyl)-2-hydroxyethyl)-4-(2-cyano-2-methylpropyl)-5-oxoimidazolidin-2-ylidene)carbamate. LCMS-ESI+: calc'd for $C_{34}H_{30}ClF_7N_{10}O_3$: 795.2 (M+H+). Found: 795.2 (M+H+). 1H NMR (400 MHz, Methanol-$d_4$) δ 8.46 (s, 1H), 8.10 (s, 1H), 8.05 (s, 1H), 8.02 (s, 1H), 7.70-7.33 (m, 7H), 7.28 (s, 1H), 6.79 (t, J=52.2 Hz, 1H), 5.69 (dd, J=9.2, 5.3 Hz, 1H), 5.06 (dd, J=11.6, 9.3 Hz, 1H), 4.79 (dd, J=11.6, 5.3 Hz, 1H), 2.80 (d, J=15.3 Hz, 1H), 2.52 (d, J=15.3 Hz, 1H), 1.48-1.39 (m, 6H), 1.29-1.23 (m, 2H), 1.16-1.04 (m, 2H).

Example 87: Preparation of Compound 337 and Compound 338

Compound 337

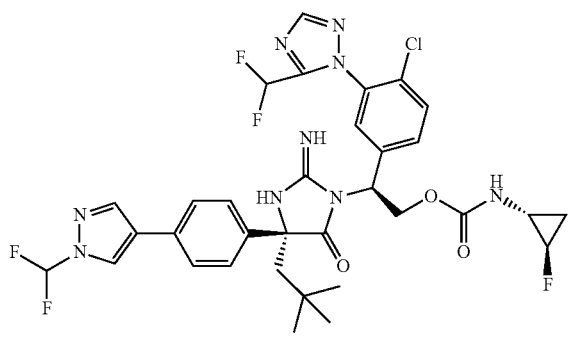

Compound 338

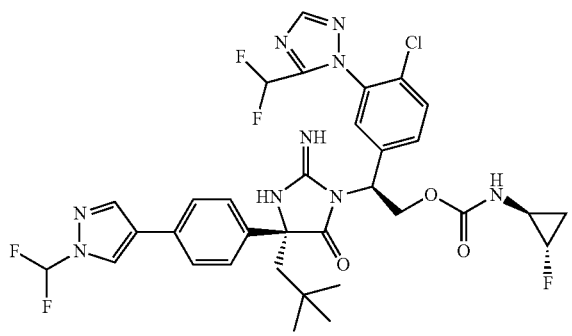

Each of the two single diastereoisomers Compound 337 and Compound 338 were obtained in a manner similar to obtain Compound 331 and Compound 332, except starting with trans-2-fluorocyclopraoanecarboxylic acid instead of trans-2-(trifluoromethyl)cyclopropylamine HCl. The final stereochemistries were randomly assigned. For Compound 337: LCMS-ESI+: calc'd for $C_{33}H_{33}ClF_5N_9O_3$: 734.2 (M+H+). Found: 734.2 (M+H+). 1H NMR (400 MHz, Methanol-$d_4$) δ 8.45 (s, 1H), 8.10 (s, 1H), 8.04 (s, 1H), 7.73-7.19 (m, 8H), 6.79 (s, 1H), 5.64 (s, 1H), 5.08 (t, J=10.5 Hz, 1H), 4.72 (dd, J=11.7, 4.9 Hz, 1H), 4.59 (s, 1H), 2.84 (s, 1H), 2.45 (d, J=15.1 Hz, 1H), 2.15 (d, J=15.2 Hz, 1H), 1.36-1.14 (m, 1H), 0.99 (s, 9H), 0.90 (dt, J=12.6, 6.5 Hz, 1H). For Compound 338: LCMS-ESI+: calc'd for $C_{33}H_{33}ClF_5N_9O_3$: 734.2 (M+H+). Found: 734.2 (M+H+). 1H NMR (400 MHz, Methanol-$d_4$) δ 8.45 (s, 1H), 8.07 (d, J=20.8 Hz, 2H), 7.73-7.20 (m, 8H), 6.79 (t, J=50 Hz, 1H), 5.66-5.64 (m, 1H), 5.18-5.01 (m, 1H), 4.72 (dd, J=10.8, 4.7 Hz, 1H), 4.51 (d, J=60.6 Hz, 1H), 2.86-2.81 (m, 1H), 2.45 (d, J=15.1 Hz, 1H), 2.14 (d, J=15.1 Hz, 1H), 1.24 (dd, J=21.3, 10.0 Hz, 1H), 0.99 (s, 9H), 0.89 (dq, J=12.9, 7.0 Hz, 1H).

Example 88: Preparation of Compound 339 and Compound 340

Compound 339

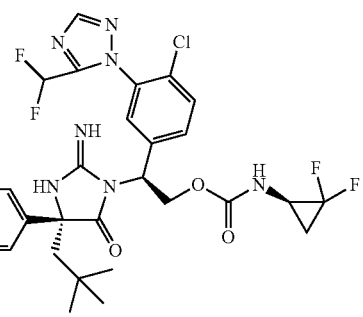

Compound 340

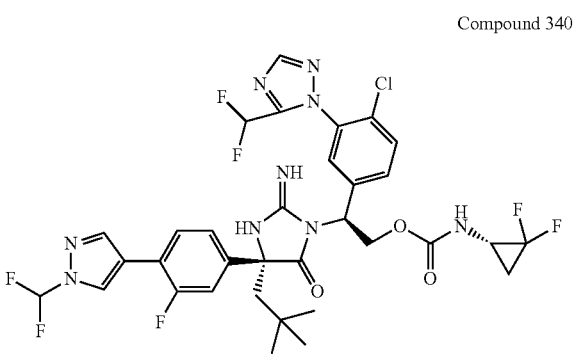

Each of the two single diastereoisomers Compound 339 and Compound 340 were obtained following the procedure to prepare Compound 330 and Compound 331, except that 2,2-difluorocyclopropane-1-carboxylic acid was used instead of trans-2-(trifluoromethyl)cyclopropylamine HCl. For Compound 339: LCMS-ESI+: calc'd for $C_{33}H_{31}ClF_7N_9O_3$: 770.2 (M+H+). Found: 770.0 (M+H+). $^1$H NMR (400 MHz, Methanol-$d_4$) δ 8.42 (d, J=1.6 Hz, 1H), 8.13 (s, 1H), 8.03 (s, 1H), 7.75-7.16 (m, 6H), 6.76 (t, J=52.2 Hz, 1H), 5.44 (s, 1H), 5.07 (t, J=10.0 Hz, 1H), 4.70 (dd, J=11.1, 5.8 Hz, 1H), 3.10 (s, 1H), 2.25 (d, J=14.6 Hz, 1H), 1.92 (d, J=14.6 Hz, 1H), 1.80-1.67 (m, 1H), 1.43-1.30 (m, 1H), 0.95 (s, 9H). For Compound 340: LCMS-ESI+: calc'd for $C_{33}H_{31}ClF_7N_9O_3$: 770.2 (M+H+). Found: 770.0 (M+H+). $^1$H NMR (400 MHz, Methanol-$d_4$) δ 8.50-8.26 (m, 1H), 8.14 (d, J=1.2 Hz, 1H), 8.02 (s, 1H), 7.78-7.15 (m, 7H), 6.76 (t, J=52.2 Hz, 1H), 5.60-5.40 (m, 1H), 5.22-5.03 (m, 1H), 4.66 (dd, J=11.1, 5.6 Hz, 1H), 3.20-2.99 (m, 1H), 2.25 (d, J=14.6 Hz, 1H), 1.99-1.83 (m, 1H), 1.78-1.67 (m, 1H), 1.46-1.27 (m, 1H), 0.95 (s, 9H).

Example 89: Preparation of Compound 341 and Compound 342

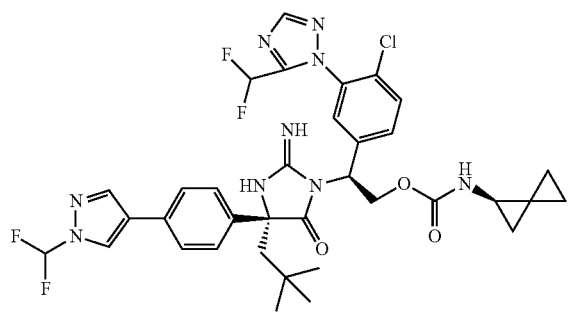

Compound 341

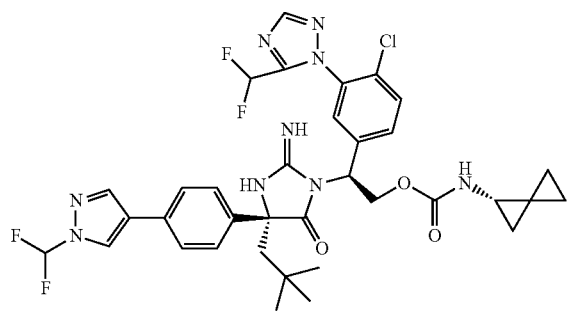

Compound 342

Each of the two diastereoisomers Compound 341 and Compound 342 were obtained following the procedure to prepare Compound 330 and Compound 331, except that spiro[2.2]pentane-1-carboxylic acid was used instead of trans-2-(trifluoromethyl)cyclopropylamine HCl. The final stereochemistries were randomly assigned. For Compound 341: LCMS-ESI+: calc'd for $C_{35}H_{36}ClF_4N_9O_3$: 742.3 (M+H+). Found: 742.4 (M+H+). 1H NMR (400 MHz, Methanol-$d_4$) δ 8.45 (s, 1H), 8.10 (s, 1H), 8.03 (s, 1H), 7.72-7.10 (m, 8H), 6.80 (t, J=52 Hz, 1H), 5.65 (dd, J=9.3, 5.1 Hz, 1H), 5.17-4.95 (m, 1H), 4.70 (dd, J=11.5, 5.0 Hz, 1H), 2.80 (d, J=5.8 Hz, 1H), 2.46 (d, J=15.2 Hz, 1H), 2.15 (d, J=15.1 Hz, 1H), 1.18 (q, J=7.0, 6.5 Hz, 2H), 1.00 (s, 9H), 0.95-0.84 (m, 2H), 0.78 (q, J=9.0 Hz, 2H). For Compound 342: LCMS-ESI+: calc'd for $C_{35}H_{36}ClF_4N_9O_3$: 742.3 (M+H+). Found: 742.4 (M+H+). 1H NMR (400 MHz, Methanol-$d_4$) δ 8.45 (s, 1H), 8.10 (s, 1H), 8.03 (s, 1H), 7.77-7.14 (m, 8H), 6.80 (t, J=52 Hz, 1H), 5.66 (dd, J=9.4, 5.1 Hz, 1H), 5.06 (q, J=16.3, 13.5 Hz, 1H), 4.67 (dd, J=11.6, 5.2 Hz, 1H), 2.80 (d, J=4.1 Hz, 1H), 2.47 (d, J=15.2 Hz, 1H), 2.15 (d, J=15.1 Hz, 1H), 1.17 (t, J=6.1 Hz, 2H), 1.00 (s, 9H), 0.90 (d, J=14.6 Hz, 2H), 0.78 (d, J=17.1 Hz, 2H).

Example 90: Preparation of Compound 343 and Compound 344

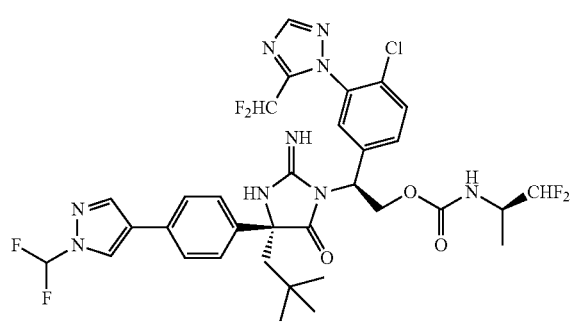

Compound 343

Compound 344

Each of the two stereoisomers Compound 343 and Compound 344 were obtained in a manner similar to that for Compound 312, except 1,1-difluoropropan-2-amine was used instead of that (R)-1,1,1-Trifluoro-2-propylamine. The two isomeric intermediates (S)-2-((R)-2-(((benzyloxy)carbonyl)imino)-4-(4-(1-(difluoromethyl)-1H-pyrazol-4-yl)phenyl)-4-neopentyl-5-oxoimidazolidin-1-yl)-2-(4-chloro-3-(5-(difluoromethyl)-1H-1,2,4-triazol-1-yl)phenyl)ethyl (1,1-difluoropropan-2-yl)carbamate were separated by chiral HPLC and the stereochemistry was randomly assigned. For Compound 343, LCMS-ESI+: calc'd for $C_{33}H_{34}ClF_6N_9O_3$: 754.2 (M+H). Found: 754.3 (M+H). 1H NMR (400 MHz, Methanol-$d_4$) δ 8.60-7.90 (m, 3H), 7.73-7.15 (m, 9H), 6.79 (t, J=52.2 Hz, 1H), 5.77 (d, J=3.1 Hz, 1H), 5.64 (t, J=7.2 Hz, 1H), 5.29-5.00 (m, 1H), 4.71 (dd, J=11.6, 5.1 Hz, 1H), 2.46 (d, J=15.2 Hz, 1H), 2.15 (d, J=15.1 Hz, 1H), 1.17 (d, J=7.0 Hz, 3H), 1.00 (s, 9H). For Compound 344, LCMS-ESI+: calc'd for $C_{33}H_{34}ClF_6N_9O_3$: 754.2 (M+H). Found: 754.3 (M+H). 1H NMR (400 MHz, Methanol-$d_4$) δ 8.60-7.92 (m, 3H), 7.83-7.14 (m, 8H), 6.79 (t, J=52.2 Hz, 1H), 5.85-5.58 (m, 2H), 5.09 (dd, J=11.6, 9.5 Hz, 1H), 4.73 (dd, J=11.7, 5.1 Hz, 1H), 3.93 (s, 1H), 2.46 (d, J=15.2 Hz, 1H), 2.16 (d, J=15.1 Hz, 1H), 1.18 (d, J=6.9 Hz, 3H), 1.00 (s, 9H).

Example 91: Preparation of Compound 345

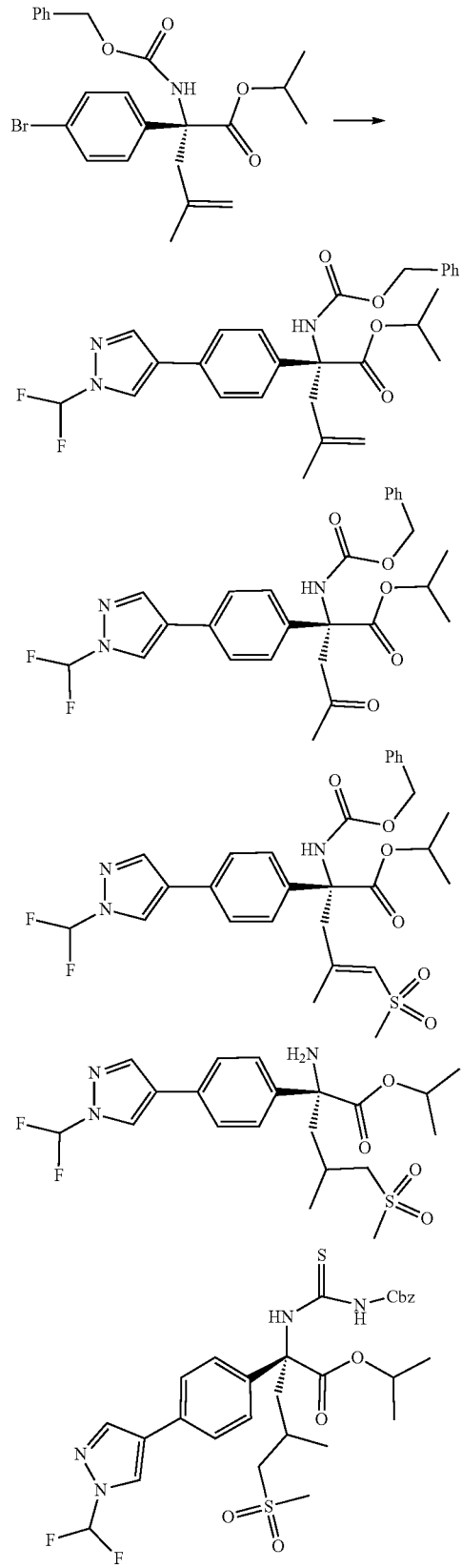

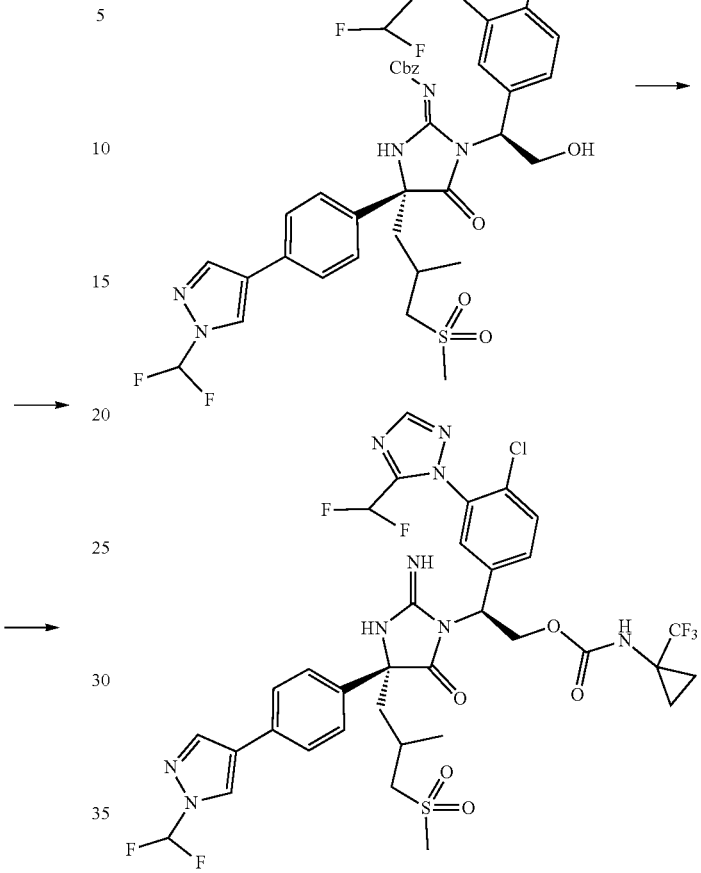

Compound 345

Preparation of isopropyl (R)-2-(((benzyloxy)carbonyl)amino)-2-(4-(1-(difluoromethyl)-1H-pyrazol-4-yl)phenyl)-4-methylpent-4-enoate: isopropyl (R)-2-(((benzyloxy)carbonyl)amino)-2-(4-(1-(difluoromethyl)-1H-pyrazol-4-yl)phenyl)-4-methylpent-4-enoate was prepared following the procedure to prepare isopropyl (R)-2-amino-2-(4-(1-(difluoromethyl)-1H-pyrazol-4-yl)phenyl)-4-methylpentanoate described in Example 65.

Preparation of isopropyl (R)-2-(((benzyloxy)carbonyl)amino)-2-(4-(1-(difluoromethyl)-1H-pyrazol-4-yl)phenyl)-4-oxopentanoate: To a solution of isopropyl (R)-2-(((benzyloxy)carbonyl)amino)-2-(4-(1-(difluoromethyl)-1H-pyrazol-4-yl)phenyl)-4-methylpent-4-enoate (0.50 g, 1 mmol) in THF (18 mL) and water (0.5 mL) were added osmium tetraoxide (3.15 mL, 0.25 mmol) and sodium periodate (2.15 g, 0.01 mol) sequentially. The reaction mixture was allowed to stir at rt overnight. Then the mixture was poured over ammonium chloride solution and ethyl acetate, and the aqueous layer was further extracted with ethyl acetate. The combined organic layers were dried over magnesium sulfate, filtered, and concentrated. The residue was purified via silica gel column chromatography, eluting with a 0-100% gradient with ethyl acetate/hexanes to provide the desired product.

Preparation of isopropyl (R)-2-(((benzyloxy)carbonyl)amino)-2-(4-(1-(difluoromethyl)-1H-pyrazol-4-yl)phenyl)-4-methyl-5-(methylsulfonyl)pent-4-enoate: To a solution of diethyl(methylsulfonylmethyl)phosphonate (0.14 g, 0.60 mmol) in THF (2 mL) at 0° C. was added n-butyllithium solution in hexanes (2.5 M, 0.23 mL). The reaction was stirred at 0° C. for 30 minutes. Then a solution of isopropyl (R)-2-(((benzyloxy)carbonyl)amino)-2-(4-(1-(difluoromethyl)-1H-pyrazol-4-yl)phenyl)-4-oxopentanoate (0.1 g, 0.2 mmol) in THF (1 mL) was added. The reaction was allowed to stir at rt overnight. The crude mixture was concentrated, and partitioned between water and EtOAc. The organic layer was dried over magnesium sulfate, filtered, and concentrated. The residue was purified via silica gel column chromatography, eluting with a 0-100% gradient with ethyl acetate/hexanes to provide the desired product.

Preparation of isopropyl (2R)-2-amino-2-(4-(1-(difluoromethyl)-1H-pyrazol-4-yl)phenyl)-4-methyl-5-(methylsulfonyl)pentanoate: To a solution of isopropyl (R)-2-(((benzyloxy)carbonyl)amino)-2-(4-(1-(difluoromethyl)-1H-pyrazol-4-yl)phenyl)-4-methyl-5-(methylsulfonyl)pent-4-enoate (0.05 g, 0.087 mmol) in EtOH (1.5 mL) was added palladium on carbon (10%, 0.046 g, 0.043 mmol) and a hydrogen balloon was attached. The reaction mixture was stirred at rt for 2 h. Then the reaction mixture was filtered through Celite. The filterate was concentrated. The residue was diluted in methanol and purified via reverse phase HPLC eluting with a gradient of 30-100% acetonitrile/water, both solvents containing 0.1% TFA, to give the product.

Compound 345 was then prepared by following the procedure to prepare Compound 178 and Compound 179. LCMS-ESI+: calc'd for $C_{34}H_{33}ClF_7N_9O_5S$: 848.2 (M+H+). Found: 848.2 (M+H+). $^1$H NMR (400 MHz, Methanol-$d_4$) δ 8.46 (s, 1H), 8.11 (d, J=6.7 Hz, 2H), 7.85-7.37 (m, 8H), 6.83 (t, J=52.0 Hz 1H), 5.66 (s, 1H), 5.10-4.97 (m, 1H), 4.80-4.78 (m, 1H), 3.15 (s, 1H), 2.97 (d, J=11.0 Hz, 3H), 2.89 (s, 1H), 2.30 (dd, J=14.3, 8.0 Hz, 2H), 1.27 (d, J=10.9 Hz, 2H), 1.21-1.01 (m, 4H), 0.88 (d, J=15.8 Hz, 2H).

Example 92: Preparation of Compound 346 and Compound 347

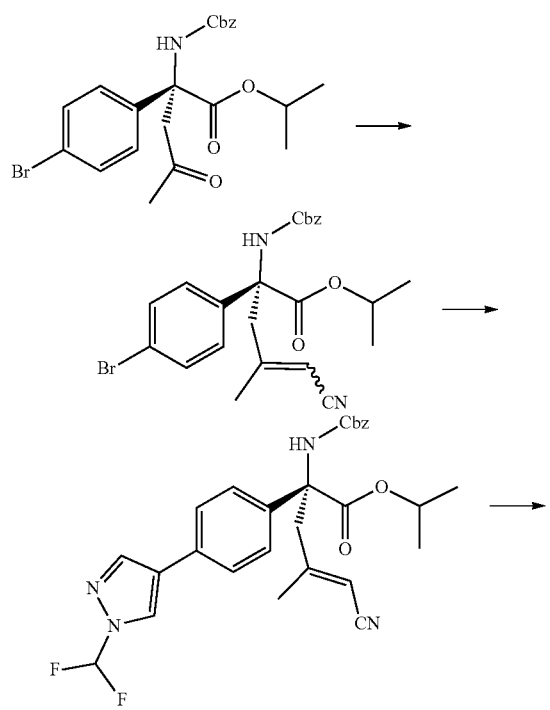

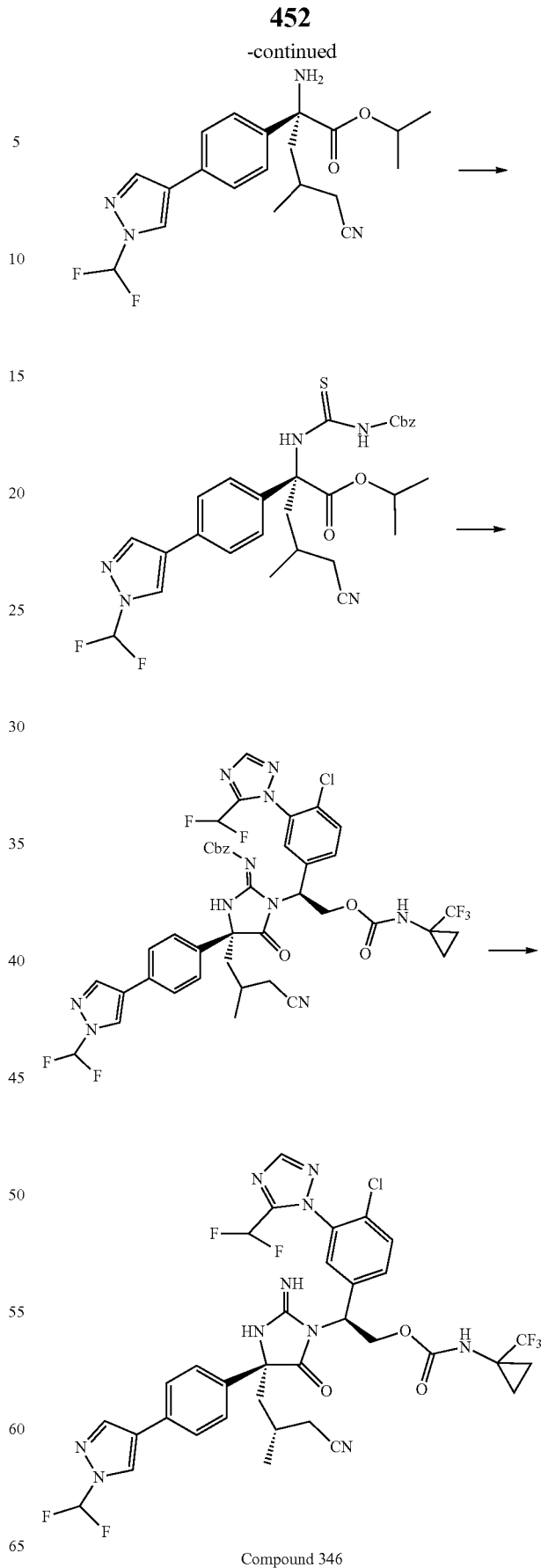

Compound 346

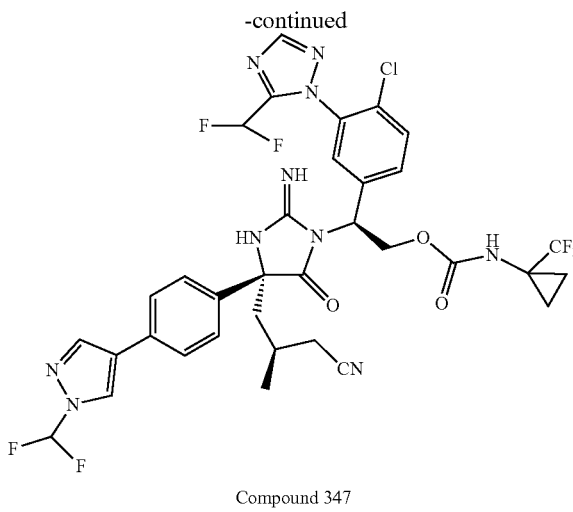

Compound 347

Preparation of isopropyl (R)-2-(((benzyloxy)carbonyl)amino)-2-(4-bromophenyl)-5-cyano-4-methylpent-4-enoate: To a solution of isopropyl (R)-2-(((benzyloxy)carbonyl)amino)-2-(4-bromophenyl)-4-oxopentanoate (172 mg, 0.37 mmol) in THF (3.8 mL) was added cyanomethylphosphonic acid diethyl ester (0.24 mL, 1.49 mmol) at −20° C. The reaction was allowed to slowly warm up to rt over 2 h. The reaction was quenched by adding saturated ammonium chloride and the mixture was extracted with EtOAc. The ethyl acetate extract was dried over $MgSO_4$, filtered, concentrated, and purified by silica gel column, eluting by 0-100% gradient EtOAc/hexanes to give the desired product.

Preparation of isopropyl (R)-2-(((benzyloxy)carbonyl)amino)-5-cyano-2-(4-(1-(difluoromethyl)-1H-pyrazol-4-yl)phenyl)-4-methylpent-4-enoate: isopropyl (R)-2-(((benzyloxy)carbonyl)amino)-5-cyano-2-(4-(1-(difluoromethyl)-1H-pyrazol-4-yl)phenyl)-4-methylpent-4-enoate was prepared following the procedure to prepare isopropyl (R)-2-amino-2-(4-(1-(difluoromethyl)-1H-pyrazol-4-yl)phenyl)-4-methylpentanoate described in Example 65.

Preparation of isopropyl (2R)-2-(3-((benzyloxy)carbonyl)thioureido)-5-cyano-2-(4-(1-(difluoromethyl)-1H-pyrazol-4-yl)phenyl)-4-methylpentanoate: isopropyl (2R)-2-(3-((benzyloxy)carbonyl)thioureido)-5-cyano-2-(4-(1-(difluoromethyl)-1H-pyrazol-4-yl)phenyl)-4-methylpentanoate was prepared following the procedure to prepare isopropyl (2R)-2-(3-((benzyloxy)carbonyl)thioureido)-2-(4-(1-(difluoromethyl)-1H-pyrazol-4-yl)phenyl)-4-methyl-5-(methylsulfonyl)pentanoate described in Example 91. The two isomers were separated by silica gel column chromatography and went forward respectively.

Preparation of benzyl ((4R)-1-((S)-1-(4-chloro-3-(5-(difluoromethyl)-1H-1,2,4-triazol-1-yl)phenyl)-2-(((1-(trifluoromethyl)cyclopropyl)carbamoyl)oxy)ethyl)-4-(3-cyano-2-methylpropyl)-4-(4-(1-(difluoromethyl)-1H-pyrazol-4-yl)phenyl)-5-oxoimidazolidin-2-ylidene)carbamate: To a solution of isopropyl (2R)-2-(3-((benzyloxy)carbonyl)thioureido)-5-cyano-2-(4-(1-(difluoromethyl)-1H-pyrazol-4-yl)phenyl)-4-methylpentanoate (30 mg, 0.05 mmol) in DMF (0.5 mL) were added (S)-2-amino-2-(4-chloro-3-(5-(difluoromethyl)-1H-1,2,4-triazol-1-yl)phenyl)ethyl (1-(trifluoromethyl)cyclopropyl)carbamate (34 mg, 0.08 mmol), 1-(3-dimethylaminopropyl)-3-ethylcarbodiimide hydrochloride (30 mg, 0.15 mmol) and N,N-diisopropylethylamine (0.04 mL, 0.26 mmol). The reaction mixture was stirred at 65° C. overnight. The reaction mixture was cooled to rt, treated with saturated ammonium chloride solution and extracted by EtOAc. The organic phase was washed by brine, dried (over sodium sulfate), filtered, and concentrated down. The residue was purified by silica gel column chromatography (0-100% gradient EtOAc/hexanes) to give the product.

Each of the two isomers Compound 346 and Compound 347 were then obtained in a manner similar to the preparation of Compound 177, starting with benzyl ((4R)-1-((S)-1-(4-chloro-3-(5-(difluoromethyl)-1H-1,2,4-triazol-1-yl)phenyl)-2-(((1-(trifluoromethyl)cyclopropyl)carbamoyl)oxy)ethyl)-4-(3-cyano-2-methylpropyl)-4-(4-(1-(difluoromethyl)-1H-pyrazol-4-yl)phenyl)-5-oxoimidazolidin-2-ylidene)carbamate. The stereochemistry of the two compounds was arbitrarily assigned. For Compound 346: LCMS-ESI+: calc'd for $C_{34}H_{30}ClF_7N_{10}O_3$: 795.2 (M+H+). Found: 795.3 (M+H+). $^1H$ NMR (400 MHz, Methanol-$d_4$) δ 8.47 (d, J=4.6 Hz, 1H), 8.30 (s, 0.2H), 8.17 (s, 0.8H), 8.11 (d, J=2.3 Hz, 1.6H), 8.01 (s, 0.4H), 7.98-7.33 (m, 9H), 7.20-6.61 (m, 1H), 5.70-5.59 (m, 1H), 5.22-5.11 (m, 0.8H), 4.99 (t, J=10.6 Hz, 0.2H), 4.74 (dd, J=11.8, 4.7 Hz, 0.8H), 4.69 (dd, J=11.6, 5.1 Hz, 0.2H), 2.57-2.12 (m, 4H), 2.12-1.97 (m, 0.8H), 1.85-1.66 (m, 0.2H), 1.35-1.21 (m, 2H), 1.12 (m, 2H), 1.00 (d, J=6.7 Hz, 2.4H), 0.93 (d, J=6.8 Hz, 0.6H). For Compound 347: LCMS-ESI+: calc'd for $C_{34}H_{30}ClF_7N_{10}O_3$: 795.2 (M+H+). Found: 795.3 (M+H+). $^1H$ NMR (400 MHz, Methanol-$d_4$) δ 8.47 (d, J=4.5 Hz, 1H), 8.28 (s, 0.2H), 8.24 (s, 0.8H), 8.15-7.96 (m, 2H), 7.89-7.30 (m, 9H), 7.24-6.40 (m, 1H), 5.65 (dd, J=9.7, 4.6 Hz, 1H), 5.18 (t, J=10.7 Hz, 0.8H), 5.00 (t, J=10.7 Hz, 0.2H), 4.71 (dd, J=11.7, 4.7 Hz, 0.8H), 4.65 (dd, J=11.5, 5.0 Hz, 0.2H), 2.53-2.18 (m, 4H), 2.06 (m, 0.8H), 1.86 (m, 0.2H), 1.35-1.20 (m, 2H), 1.14 (m, 2H), 1.08 (d, J=6.7 Hz, 2.4H), 0.81 (d, J=6.7 Hz, 0.6H).

Example 93: Preparation of Compound 348

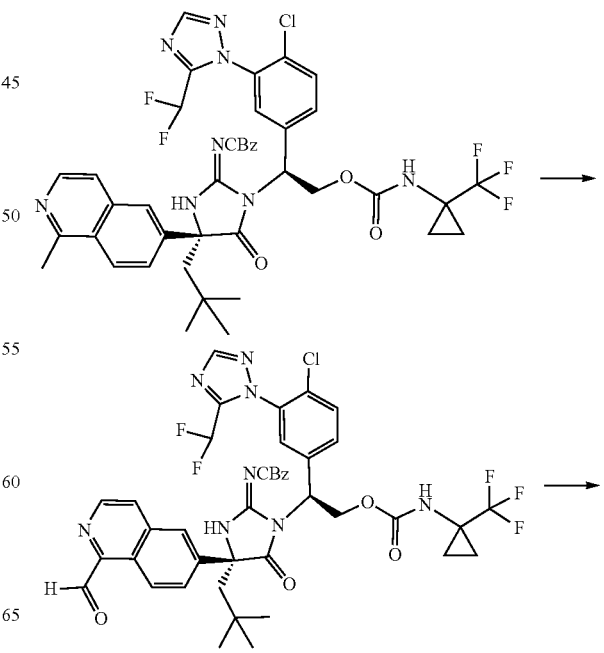

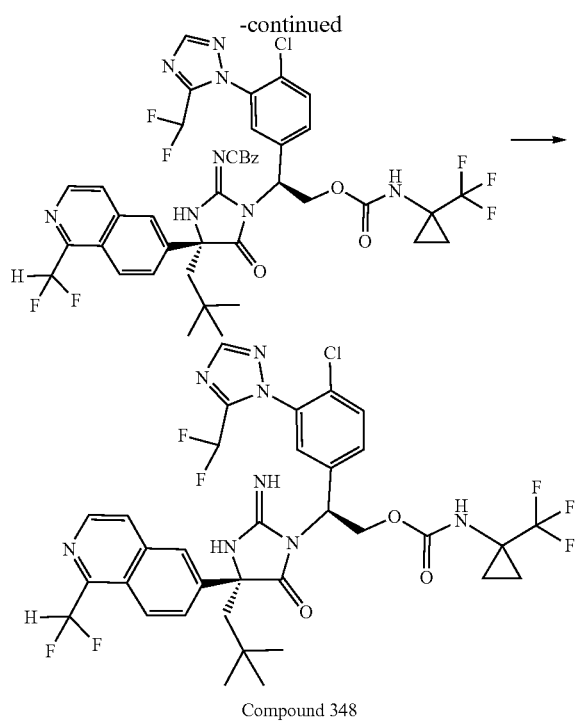

Compound 348

Found: 769.7 (M+H+). ¹H NMR (400 MHz, Methanol-d₄) δ 8.56 (d, J=5.7 Hz, 1H), 8.45 (d, J=9.1 Hz, 1H), 8.19 (s, 1H, D₂O exchangeable), 8.02 (d, J=2.0 Hz, 1H), 7.98-7.89 (m, 2H), 7.86 (dd, J=9.1, 2.1 Hz, 1H), 7.64-7.50 (m, 2H), 7.23 (d, J=18.3 Hz, 1H), 7.05 (d, J=54.0 Hz, 1H), 6.64 (t, J=52.3 Hz, 1H), 5.70 (dd, J=9.7, 4.8 Hz, 1H), 5.13 (t, J=10.6 Hz, 1H), 4.72 (dd, J=11.6, 4.9 Hz, 1H), 2.57 (d, J=15.2 Hz, 1H), 2.26 (d, J=15.2 Hz, 1H), 1.29 (dt, J=12.8, 6.7 Hz, 2H), 1.08 (s, 2H), 1.01 (s, 9H).

Example 94: Preparation of Compound 349

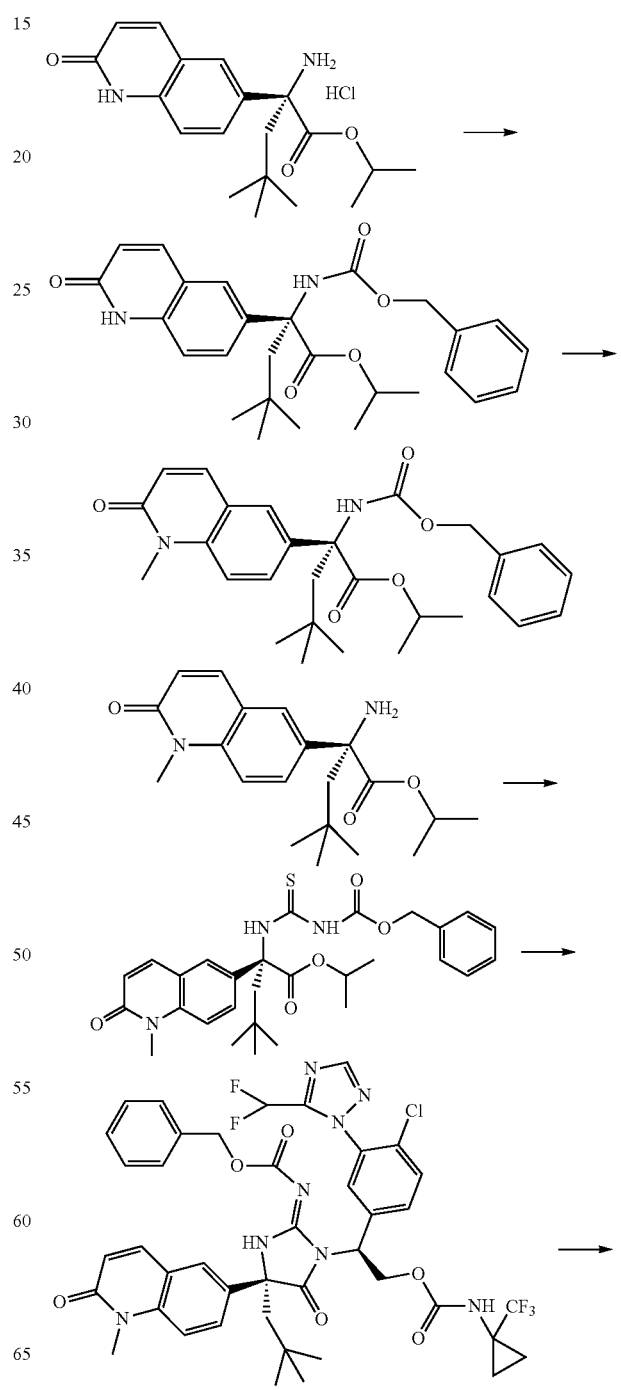

Preparation of (S)-2-((R)-2-(((benzyloxy)carbonyl)imino)-4-(1-formylisoquinolin-6-yl)-4-neopentyl-5-oxoimidazolidin-1-yl)-2-(4-chloro-3-(5-(difluoromethyl)-1H-1,2,4-triazol-1-yl)phenyl)ethyl (1-(trifluoromethyl)cyclopropyl)carbamate: To a solution of (S)-2-((R)-2-(((benzyloxy)carbonyl)imino)-4-(1-methylisoquinolin-6-yl)-4-neopentyl-5-oxoimidazolidin-1-yl)-2-(4-chloro-3-(5-(difluoromethyl)-1H-1,2,4-triazol-1-yl)phenyl)ethyl (1-(trifluoromethyl)cyclopropyl)carbamate (100 mg, 0.12 mmol) in dioxane (2 mL) was added selenium(IV) oxide (13 mg, 0.12 mmol). The reaction was heated at 60° C. for 2 h. The reaction mixture was concentrated down and the residue was purified by silica gel column chromatography (0-100% gradient EtOAc/hexanes) to give the product.

Preparation of (S)-2-((R)-2-(((benzyloxy)carbonyl)imino)-4-(1-(difluoromethyl)isoquinolin-6-yl)-4-neopentyl-5-oxoimidazolidin-1-yl)-2-(4-chloro-3-(5-(difluoromethyl)-1H-1,2,4-triazol-1-yl)phenyl)ethyl (1-(trifluoromethyl)cyclopropyl)carbamate: To a solution of (S)-2-((R)-2-(((benzyloxy)carbonyl)imino)-4-(1-formylisoquinolin-6-yl)-4-neopentyl-5-oxoimidazolidin-1-yl)-2-(4-chloro-3-(5-(difluoromethyl)-1H-1,2,4-triazol-1-yl)phenyl)ethyl (1-(trifluoromethyl)cyclopropyl)carbamate (80 mg, 0.09 mmol) in DCM (2 mL, containing 2 drops of ethanol) was added deoxo-Fluor (30 mg, 0.014 mol). The reaction mixture was stirred at rt for 16 h. The mixture was poured into icy cold aqueous sodium bicarbonate solution and extracted with dichloromethane. The organic phase was dried over MgSO₄, filtered, concentrated down, and purified by silica gel column chromatography (0-100% gradient EtOAc/hexanes) to give the product.

Compound 348 was then prepared by following the procedure to prepared Compound 177, starting with (S)-2-((R)-2-(((benzyloxy)carbonyl)imino)-4-(1-(difluoromethyl)isoquinolin-6-yl)-4-neopentyl-5-oxoimidazolidin-1-yl)-2-(4-chloro-3-(5-(difluoromethyl)-1H-1,2,4-triazol-1-yl)phenyl)ethyl (1-(trifluoromethyl)cyclopropyl)carbamate. LCMS-ESI+: calc'd for $C_{34}H_{32}ClF_7N_8O_3$: 769.2 (M+H+).

Example 95: Preparation of Compound 350

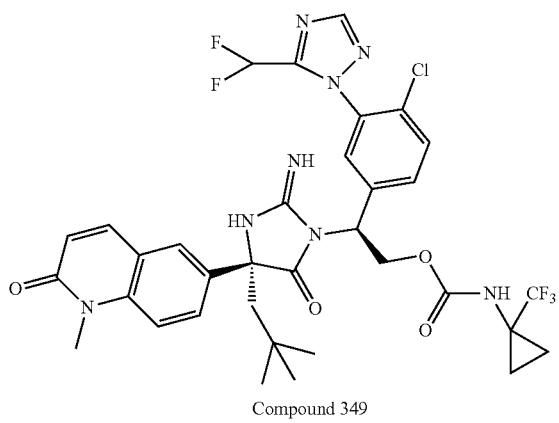

Compound 349

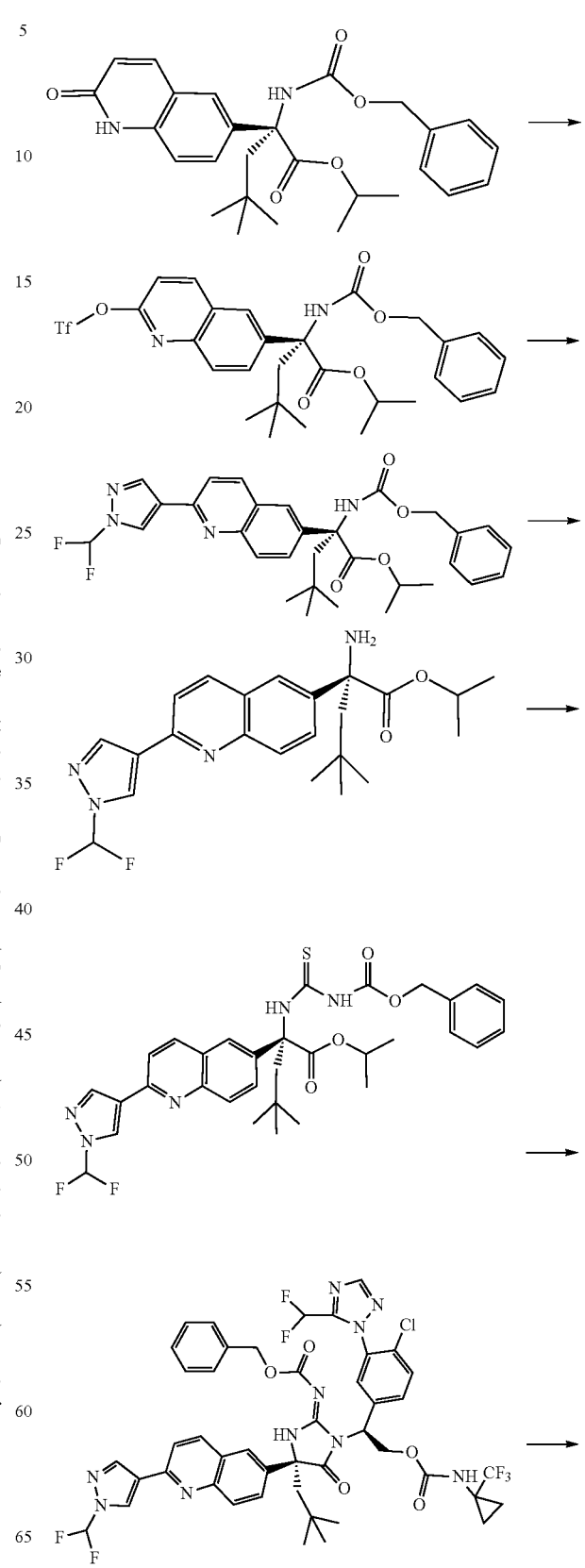

Preparation of isopropyl (R)-2-(((benzyloxy)carbonyl) amino)-4,4-dimethyl-2-(2-oxo-1,2-dihydroquinolin-6-yl) pentanoate: To a suspension of isopropyl (R)-2-amino-4,4-dimethyl-2-(2-oxo-1,2-dihydroquinolin-6-yl)pentanoate hydrochloride (1.0 g, 2.72 mmol) in EtOAc (50 mL) was added saturated NaHCO₃ solution (50 mL). After all the solid was dissolved, benzyl chloroformate (0.97 mL, 6.81 mmol) was added and the reaction mixture was stirred at rt overnight. The organic phase was separated and concentrated. The residue was purified by silica gel column chromatography to give the product.

Preparation of isopropyl (R)-2-(((benzyloxy)carbonyl) amino)-4,4-dimethyl-2-(1-methyl-2-oxo-1,2-dihydroquinolin-6-yl)pentanoate: To a solution of isopropyl (R)-2-(((benzyloxy)carbonyl)amino)-4,4-dimethyl-2-(2-oxo-1,2-dihydroquinolin-6-yl)pentanoate (60 mg, 0.129 mmol) in DMF (1.5 mL) was added cesium carbonate (126 mg, 0.39 mmol) and iodomethane (16 μL, 0.26 mmol). The reaction mixture was stirred at 55° C. for 90 min. The mixture was cooled to rt. The reaction was quenched by adding water, and extracted with EtOAc. The organic phase was separated and concentrated. The residue was purified by silica gel column chromatography t give the product.

Preparation of isopropyl (R)-2-amino-4,4-dimethyl-2-(1-methyl-2-oxo-1,2-dihydroquinolin-6-yl)pentanoate: A solution of isopropyl (R)-2-(((benzyloxy)carbonyl)amino)-4,4-dimethyl-2-(1-methyl-2-oxo-1,2-dihydroquinolin-6-yl) pentanoate (55 mg, 0.11 mmol) in TFA (1 mL) was heated at 60° C. for 6 h. Then the reaction mixture was stirred at 50° C. overnight. The crude mixture was concentrated down and used for the next reaction without further purification.

Compound 351 was then prepared following the procedure to prepare Compound 349. LCMS-ESI+: calc'd for $C_{34}H_{35}ClF_5N_8O_3$: 749.2 (M+H+). Found: 749.2 (M+H+). 1H NMR (400 MHz, Methanol-$d_4$) δ 8.19 (s, 1H), 8.02 (s, 1H), 7.83 (d, J=9.5 Hz, 1H), 7.75-7.45 (m, 5H), 7.04 (s, 1H), 6.89-6.44 (m, 1H), 5.69 (dd, J=9.7, 4.9 Hz, 1H), 5.10 (dd, J=11.5, 9.8 Hz, 1H), 4.71 (dd, J=11.5, 4.9 Hz, 1H), 3.72 (d, J=1.0 Hz, 3H), 2.51 (d, J=15.2 Hz, 1H), 2.17 (d, J=15.1 Hz, 1H), 1.35-1.16 (m, 2H), 1.09 (s, 2H), 1.00 (s, 9H).

-continued

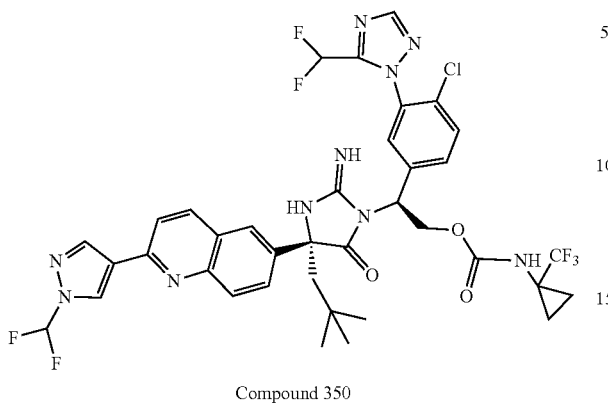

Compound 350

Preparation of isopropyl (R)-2-(((benzyloxy)carbonyl)amino)-4,4-dimethyl-2-(2-(((trifluoromethyl)sulfonyl)oxy)quinolin-6-yl)pentanoate: To a solution of isopropyl (R)-2-(((benzyloxy)carbonyl)amino)-4,4-dimethyl-2-(2-oxo-1,2-dihydroquinolin-6-yl)pentanoate in pyride (1.5 mL) was added trifluoromethanesulfonic anhydride (0.12 mL, 0.71 mmol) dropwise at 0° C. The reaction mixture was then allowed to slowly warm up to rt and stirred at rt for 1 h. The reaction was quenched by adding water and extracted with EtOAc. The organic phase was separated and concentrated down. The residue was purified by silica gel column chromatography to give the product.

Preparation of isopropyl (R)-2-(((benzyloxy)carbonyl)amino)-2-(2-(1-(difluoromethyl)-1H-pyrazol-4-yl)quinolin-6-yl)-4,4-dimethylpentanoate: A solution of isopropyl (R)-2-(((benzyloxy)carbonyl)amino)-4,4-dimethyl-2-(2-(((trifluoromethyl)sulfonyl)oxy)quinolin-6-yl)pentanoate (50 mg, 0.08 mmol), 1-(difluoromethyl)-4-(4,4,5,5-tetramethyl-1,3,2-dioxaborolan-2-yl)-1H-pyrazole (102 mg, 0.42 mmol), tetrakis(triphenylphosphine)palladium (0) (9.7 mg, 0.01 mmol) and potassium carbonate (116 mg, 0.84 mmol) in dioxane (2 mL) and water (0.5 mL) was stirred at 80° C. for 30 min. The reaction mixture was cooled to rt. The reaction was quenched by adding saturated ammonium chloride solution and the mixture was extracted with EtOAc. The organic phase was separated and concentrated. The residue was purified by silica gel column chromatography to give the product.

Compound 350 was then prepared by following the procedure to prepare Compound 349, starting with isopropyl (R)-2-(((benzyloxy)carbonyl)amino)-2-(2-(1-(difluoromethyl)-1H-pyrazol-4-yl)quinolin-6-yl)-4,4-dimethylpentanoate. LCMS-ESI+: calc'd for $C_{39}H_{36}ClF_{10}N_{10}O_4$: 835.2 (M+H+). Found: 835.6 (M+H+). 1H NMR (400 MHz, Methanol-$d_4$) δ 8.89 (s, 1H), 8.49 (s, 1H), 8.35 (d, J=8.6 Hz, 1H), 8.18 (s, 1H), 8.11-7.41 (m, 7H), 7.17 (s, 1H), 6.68 (t, J=52.2 Hz, 1H), 5.70 (dd, J=9.7, 4.9 Hz, 1H), 5.12 (t, J=10.6 Hz, 1H), 4.72 (dd, J=11.6, 4.9 Hz, 1H), 2.58 (d, J=15.2 Hz, 1H), 2.26 (d, J=15.2 Hz, 1H), 1.28 (s, 2H), 1.09 (s, 2H), 1.02 (s, 9H).

Example 96: Preparation of Compound 351

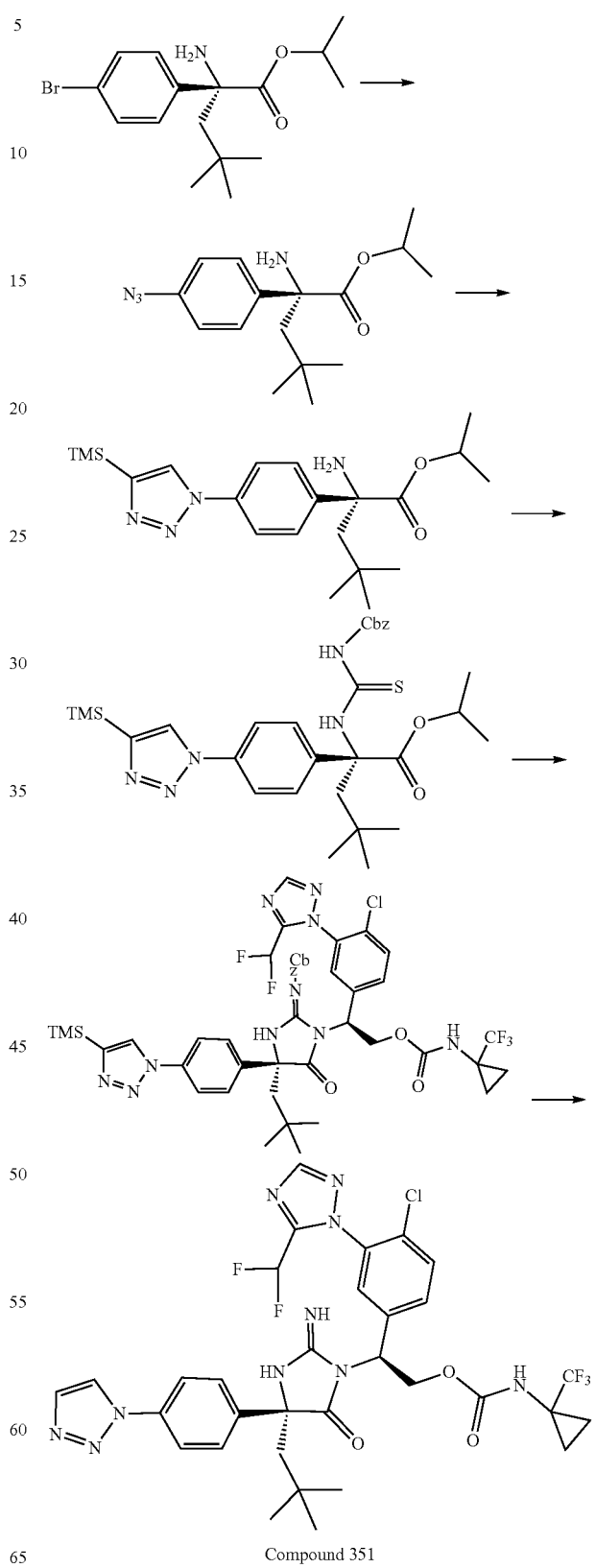

Compound 351

Preparation of isopropyl (R)-2-amino-2-(4-azidophenyl)-4,4-dimethylpentanoate: The solution of isopropyl (R)-2-amino-2-(4-bromophenyl)-4,4-dimethylpentanoate (1000 mg, 2.92 mmol), sodium azide (380 mg, 5.84 mmol) and sodium ascorbate (+) (29 mg, 0.15 mmol) in isopropyl alcohol (3.5 mL) and water (1.5 mL) was sparged with argon for 5 min. Then copper iodide was added and again sparged with argon for 3 min. The reaction mixture was heated at 80° C. in a sealed tube. After 4.5 h, sodium azide (596 mg, 9.17 mmol) and sodium ascorbate (+) (44 mg, 0.23 mmol) was added and the reaction mixture was stirred at 80° C. The resulting mixture was treated with saturated ammonium chloride solution and extracted with EtOAc. The organic phase was separated and concentrated down and purified by silica gel column chromatography (0-100% gradient EtOAc/hexanes) to give the product.

Preparation of isopropyl (R)-2-amino-4,4-dimethyl-2-(4-(4-(trimethylsilyl)-1H-1,2,3-triazol-1-yl)phenyl)pentanoate: To a solution of isopropyl (R)-2-amino-2-(4-azidophenyl)-4,4-dimethylpentanoate (150 mg, 0.49 mmol) in THF (1 mL) were added ethynyltrimethylsilane (95%, 66 mg, 0.64 mmol) and copper(I) thiophene-2-carboxylate in THF (0.1 M, 0.74 mL). The slurry was sonicated for 30 sec and then stirred at rt for 30 min. The reaction mixture was treated with brine and extracted with EtOAc. The organic phase was separated, concentrated and purified by silica gel column chromatography to give the product.

Preparation of benzyl ((R)-1-((S)-1-(4-chloro-3-(5-(difluoromethyl)-1H-1,2,4-triazol-1-yl)phenyl)-2-(((1-(trifluoromethyl)cyclopropyl)carbamoyl)oxy)ethyl)-4-neopentyl-5-oxo-4-(4-(4-(trimethylsilyl)-1H-1,2,3-triazol-1-yl)phenyl)imidazolidin-2-ylidene)carbamate: benzyl ((R)-1-((S)-1-(4-chloro-3-(5-(difluoromethyl)-1H-1,2,4-triazol-1-yl)phenyl)-2-(((1-(trifluoromethyl)cyclopropyl)carbamoyl)oxy)ethyl)-4-neopentyl-5-oxo-4-(4-(4-(trimethylsilyl)-1H-1,2,3-triazol-1-yl)phenyl)imidazolidin-2-ylidene)carbamate was prepared following the procedure to prepare benzyl ((R)-1-((S)-1-(4-chloro-3-(5-(difluoromethyl)-1H-1,2,4-triazol-1-yl)phenyl)-2-(((1-(trifluoromethyl)cyclopropyl)carbamoyl)oxy)ethyl)-4-(1-methyl-2-oxo-1,2-dihydroquinolin-6-yl)-4-neopentyl-5-oxoimidazolidin-2-ylidene)carbamate described in Example 94, starting with isopropyl (R)-2-amino-4,4-dimethyl-2-(4-(4-(trimethylsilyl)-1H-1,2,3-triazol-1-yl)phenyl)pentanoate.

Preparation of Compound 351: The solution of benzyl ((R)-1-((S)-1-(4-chloro-3-(5-(difluoromethyl)-1H-1,2,4-triazol-1-yl)phenyl)-2-(((1-(trifluoromethyl)cyclopropyl)carbamoyl)oxy)ethyl)-4-neopentyl-5-oxo-4-(4-(4-(trimethylsilyl)-1H-1,2,3-triazol-1-yl)phenyl)imidazolidin-2-ylidene)carbamate (38 mg, 0.04 mmol) in hydrogen fluoride-urea (1 mL) in a falcon vial was stirred at rt for 3 h. The reaction mixture was then neutralized to pH=8 and extracted with EtOAc. The organic phase was concentrated down and the residue was purified by reserve phase HPLC, eluting with 5-100% acetonitrile in water containing 0.1% TFA, to give the product (4 mg, 13%). LCMS-ESI+: calc'd for $C_{32}H_{32}ClF_5N_{10}O_3$, 735.2 (M+H). Found 735.3 (M+H). $^1$H NMR (400 MHz, Methanol-$d_4$) δ 8.56 (d, J=1.2 Hz, 1H), 8.01 (s, 1H), 7.94 (d, J=1.2 Hz, 1H), 7.92-7.84 (m, 2H), 7.63 (d, J=8.2 Hz, 3H), 7.58 (dd, J=8.5, 2.2 Hz, 1H), 7.21 (d, J=3.5 Hz, 1H), 6.80 (t, J=52.2 Hz, 1H), 5.69 (dd, J=9.6, 5.0 Hz, 1H), 5.16-5.06 (m, 1H), 4.72 (dd, J=11.6, 5.0 Hz, 1H), 2.52 (d, J=15.1 Hz, 1H), 2.19 (d, J=15.2 Hz, 1H), 1.30-1.26 (m, 2H), 1.12-1.08 (m, 2H), 1.02 (s, 9H).

Example 97: Preparation of Compound 352

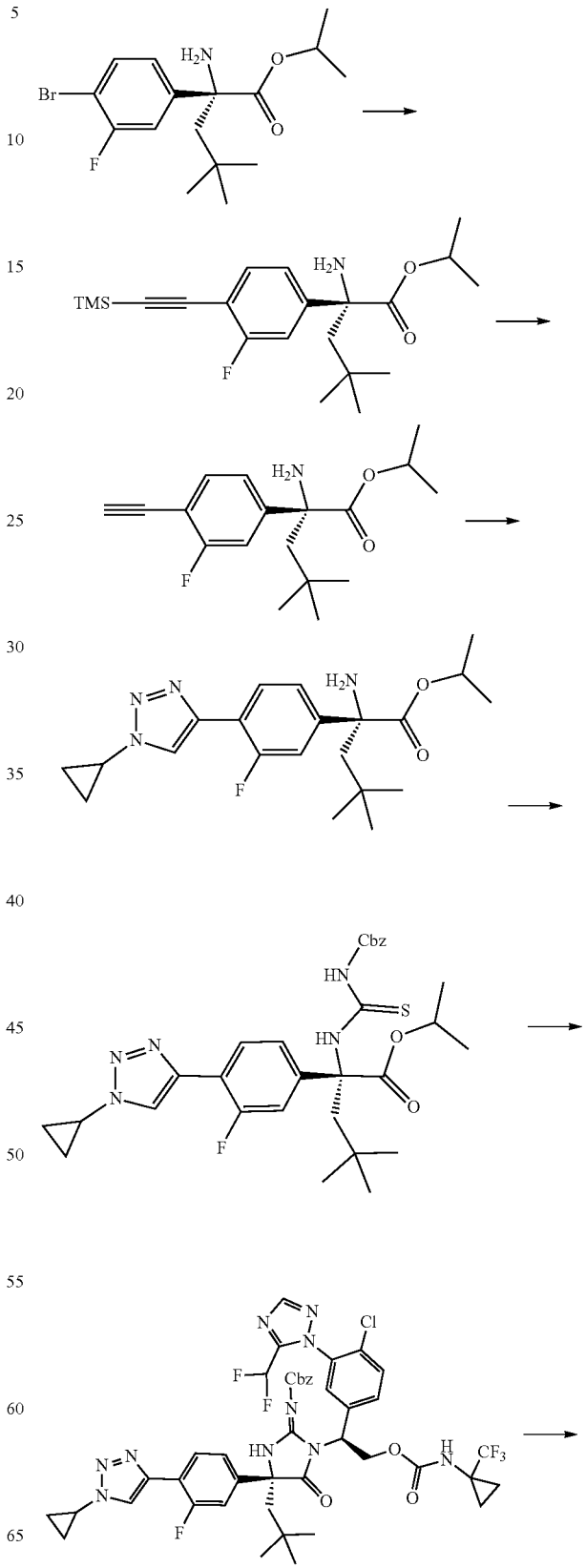

-continued

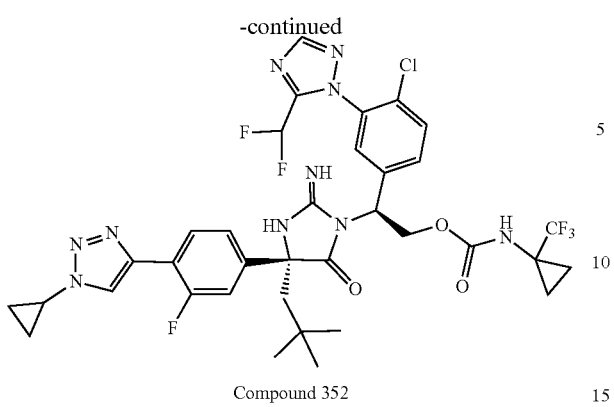

Compound 352

Preparation of isopropyl (R)-2-amino-2-(3-fluoro-4-((trimethylsilyl)ethynyl)phenyl)-4,4-dimethylpentanoate: To a solution of isopropyl (R)-2-amino-2-(4-bromophenyl)-4,4-dimethylpentanoate (1000 mg, 2.78 mmol) in triethylamine (7 mL) was added TMS acetylene (1.78 mL, 12.5 mmol) and CuI (264 mg, 1.39 mmol) under argon. The mixture was sparged with argon. Then tetrakis(triphenylphosphine)palladium(O) (1058 mg, 0.92 mmol) was added and sparged with argon. The reaction mixture was then heated at 90° C. for 1.5 h. The reaction mixture was diluted with EtOAc and water. The resulting mixture was filtered through Celite. The two layers were separated and the aqueous phase was extracted with EtOAc. The combined organic phases were washed with brine and concentrated down. The residue was purified by silica gel column chromatography to give the product.

Preparation of isopropyl (R)-2-amino-2-(4-ethynyl-3-fluorophenyl)-4,4-dimethylpentanoate: To a solution of isopropyl (R)-2-amino-2-(3-fluoro-4-((trimethylsilyl)ethynyl)phenyl)-4,4-dimethylpentanoate (417 mg, 1.1 mmol) in THF (8 mL) was added tetra-n-butylammonium fluoride in THF (1.5 M, 0.74 ml) dropwise at rt. The mixture was stirred at rt under argon for 10 min. The reaction mixture was partitioned between water and EtOAc. The organic phase was washed with saturated ammonium chloride solution and then with water, and concentrated. The residue was purified by silica gel column chromatography to give the product.

Preparation of isopropyl (R)-2-amino-2-(4-(1-cyclopropyl-1H-1,2,3-triazol-4-yl)-3-fluorophenyl)-4,4-dimethylpentanoate: To a solution of isopropyl (R)-2-amino-2-(4-ethynyl-3-fluorophenyl)-4,4-dimethylpentanoate (400 mg, 1.39 mmol) in THF (4 mL) under argon were added cyclopropyl azide (95%, 158 mg, 1.81 mmol) and copper(I)-thiophene-2-carboxylate in THF (0.1M, 2.09 mL). The reaction mixture was stirred at rt for 30 min. The reaction mixture was partitioned between saturated NaHCO₃ solution and EtOAc. The organic phase was washed with brine, concentrated down, and purified by silica gel column chromatography to give the product.

Compound 352 was then prepared by following the procedure to prepare Compound 350, starting with isopropyl (R)-2-amino-2-(4-(1-cyclopropyl-1H-1,2,3-triazol-4-yl)-3-fluorophenyl)-4,4-dimethylpentanoate. LCMS-ESI+: calc'd for $C_{35}H_{35}ClF_6N_{10}O_3$: 793.2 (M+H+). Found: 793.5 (M+H+). ¹H NMR (400 MHz, Methanol-d₄) δ 8.32 (d, J=3.5 Hz, 1H), 8.11-8.00 (m, 2H), 7.68-7.55 (m, 2H), 7.37-7.28 (m, 2H), 7.21 (s, 1H), 6.78 (t, J=52.2 Hz, 1H), 5.68 (dd, J=9.6, 4.9 Hz, 1H), 5.10 (dd, J=11.5, 9.7 Hz, 1H), 4.71 (dd, J=11.6, 5.0 Hz, 1H), 4.01 (tt, J=7.5, 3.9 Hz, 1H), 2.47 (d, J=15.1 Hz, 1H), 2.15 (d, J=15.2 Hz, 1H), 1.35-1.31 (m, 2H), 1.31-1.20 (m, 4H), 1.11-1.07 (m, 2H), 1.00 (s, 9H).

Example 98: Preparation of Compound 353

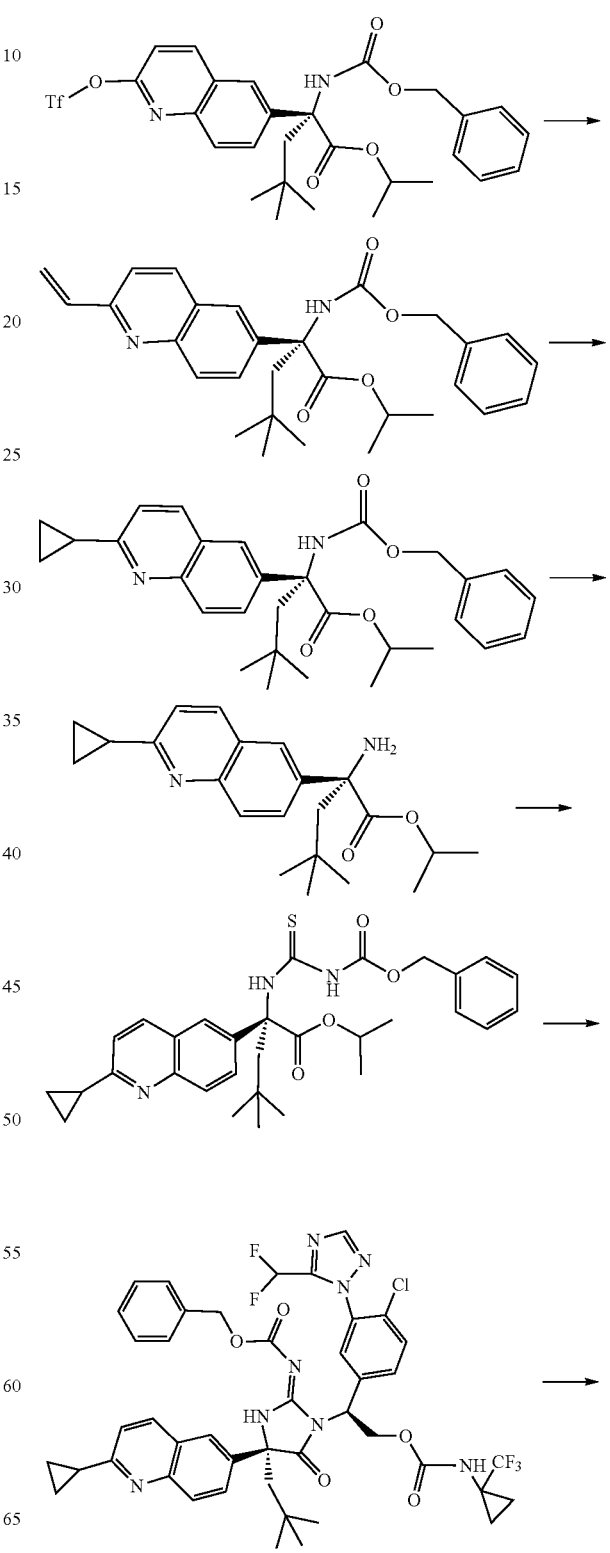

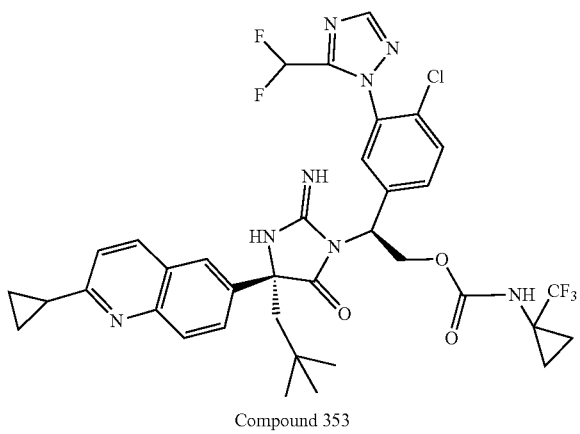

Compound 353

Preparation of isopropyl (R)-2-(((benzyloxy)carbonyl)amino)-4,4-dimethyl-2-(2-vinylquinolin-6-yl)pentanoate: A mixture of isopropyl (R)-2-(((benzyloxy)carbonyl)amino)-4,4-dimethyl-2-(2-(((trifluoromethyl)sulfonyl)oxy)quinolin-6-yl)pentanoate (100 mg, 0.17 mmol), 4,4,5, 5-tetramethyl-2-vinyl-1,3,2-dioxaborolane (0.14 mL, 0.84 mmol), tetrakis(triphenylphosphine)palladium(O) (19 mg, 0.02 mmol), potassium carbonate (232 mg, 1.68 mmol) and palladium (II) trimethylacetate (10 mg, 0.03 mmol) in THF (2 mL) and water (0.3 mL) was stirred at 80° C. for 1 h. The reaction mixture was cooled to rt, diluted with saturated NaHCO₃, and extracted with EtOAc. The organic phase was washed with brine, concentrated down and the residue was purified by silica gel column chromatography to give the product.

Preparation of isopropyl (R)-2-(((benzyloxy)carbonyl)amino)-2-(2-cyclopropylquinolin-6-yl)-4,4-dimethylpentanoate: Diazomethane was prepared by the following procedure: To a suspension of 1-methyl-3-nitro-1-nitrosoguanidine in ethyl ester (1 mL) at 0° C. was added 50% potassium hydroxide (1 mL). Then, the resulting organic layer was used for the next reaction. To a solution of isopropyl (R)-2-(((benzyloxy)carbonyl)amino)-4,4-dimethyl-2-(2-vinylquinolin-6-yl)pentanoate (28 mg, 0.06 mmol) was added palladium (II) trimethylacetate (3.6 mg, 0.01 mmol). Then to the mixture was added the freshly made diazomethane solution in ethyl ester dropwise. The reaction mixture was stirred at 0° C. for 5 min. The mixture was concentrated and the residue was purified by silica gel column chromatography to give the product.

Compound 353 was then prepared following the procedure to prepare Compound 349, starting with isopropyl (R)-2-(((benzyloxy)carbonyl)amino)-2-(2-cyclopropyl quinolin-6-yl)-4,4-dimethylpentanoate. LCMS-ESI+: calc'd for $C_{36}H_{37}ClF_5N_8O_3$: 759.3 (M+H+). Found: 759.6 (M+H+). ¹H NMR (400 MHz, Methanol-$d_4$) δ 8.50 (d, J=8.8 Hz, 1H), 8.19 (s, 1H), 8.04 (s, 1H), 7.99 (d, J=4.0 Hz, 3H), 7.57 (d, J=1.3 Hz, 2H), 7.47 (d, J=8.8 Hz, 1H), 7.15 (s, 1H), 6.67 (t, J=52.2 Hz, 1H), 5.69 (dd, J=9.7, 4.9 Hz, 1H), 5.12 (t, J=10.6 Hz, 1H), 4.71 (dd, J=11.5, 4.9 Hz, 1H), 2.57 (d, J=15.1 Hz, 1H), 2.46 (dt, J=8.1, 3.7 Hz, 1H), 2.24 (d, J=15.2 Hz, 1H), 1.53-1.41 (m, 2H), 1.42-1.32 (m, 2H), 1.27 (d, J=6.5 Hz, 2H), 1.09 (s, 2H), 1.01 (s, 9H).

Example 99: Preparation of Compound 354

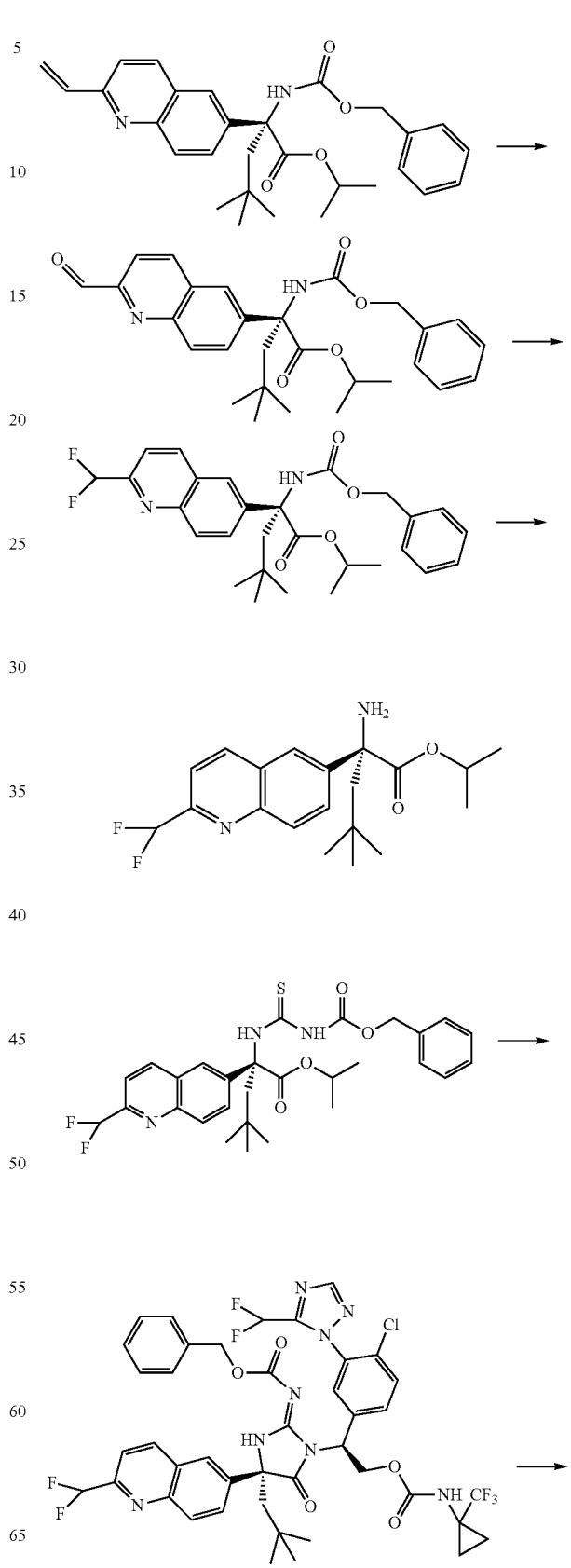

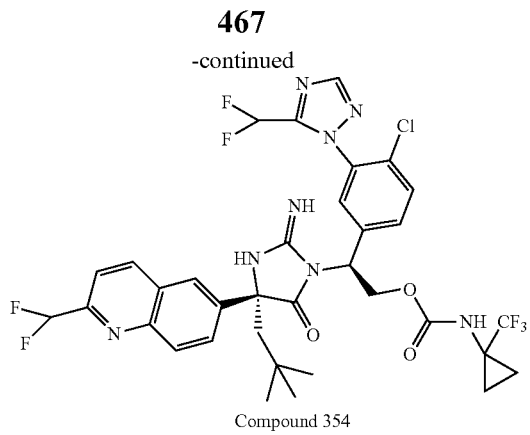

Compound 354

Preparation of isopropyl (R)-2-(((benzyloxy)carbonyl)amino)-2-(2-formylquinolin-6-yl)-4,4-dimethylpentanoate: To a solution of isopropyl (R)-2-(((benzyloxy)carbonyl)amino)-4,4-dimethyl-2-(2-vinylquinolin-6-yl)pentanoate (30 mg, 0.063 mmol) in THF (1.5 mL) and water (1.2 mL) was added osmium tetraoxide in t-BuOH (2.5 wt. %, 12.86 µL, 0.001 mmol). The reaction mixture was stirred at rt for 30 min. Then sodium periodate (41 mg, 0.19 mmol) was added. The reaction mixture was stirred at rt for 3 h. The reaction mixture was diluted with EtOAc and washed with $H_2O$ and then with brine. The organic extract was concentrated down and the residue was purified by silica gel column chromatography to give the product.

Preparation of isopropyl (R)-2-(((benzyloxy)carbonyl)amino)-2-(2-(difluoromethyl)quinolin-6-yl)-4,4-dimethylpentanoate: To a solution of isopropyl (R)-2-(((benzyloxy)carbonyl)amino)-2-(2-formylquinolin-6-yl)-4,4-dimethylpentanoate (15 mg, 31 µmol) in DCM (2 mL) was added deoxo-fluor (209 mg, 0.094 mmol). The reaction was stirred at rt. The crude mixture was added dropwise to an ice-cold saturated sodium carbonate solution. This aqueous mixture was extracted with EtOAc. The organic phase was concentrated down and the residue was purified by silica gel column chromatography to give the product. Compound 354 was then prepared following the procedure to prepare Compound 349, starting with isopropyl (R)-2-(((benzyloxy)carbonyl)amino)-2-(2-(difluoromethyl)quinolin-6-yl)-4,4-dimethylpentanoate. LCMS-ESI+: calc'd for $C_{34}H_{33}ClF_7N_8O_3$: 769.2 (M+H+). Found: 769.5 (M+H+). $^1$H NMR (400 MHz, Methanol-$d_4$) δ 8.47 (d, J=8.6 Hz, 1H), 8.19 (s, 1H), 8.09 (d, J=9.0 Hz, 1H), 8.03-7.87 (m, 2H), 7.83 (d, J=8.5 Hz, 1H), 7.56 (d, J=1.3 Hz, 2H), 7.15 (s, 1H), 7.06-6.45 (m, 2H), 5.70 (dd, J=9.6, 4.9 Hz, 1H), 5.12 (dd, J=11.5, 9.7 Hz, 1H), 4.72 (dd, J=11.6, 4.9 Hz, 1H), 2.59 (d, J=15.2 Hz, 1H), 2.26 (d, J=15.2 Hz, 1H), 1.36-1.22 (m, 2H), 1.08 (s, 2H), 1.02 (s, 9H).

Example 100: Preparation of Compound 355

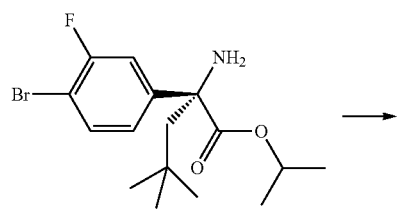

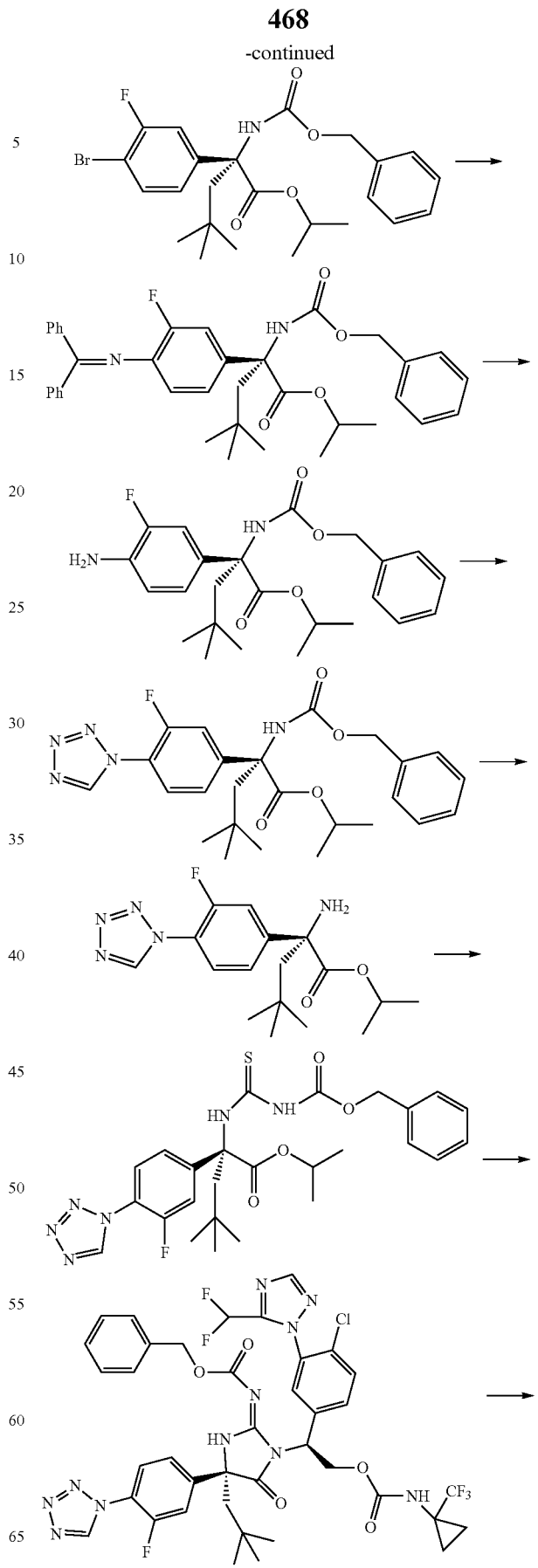

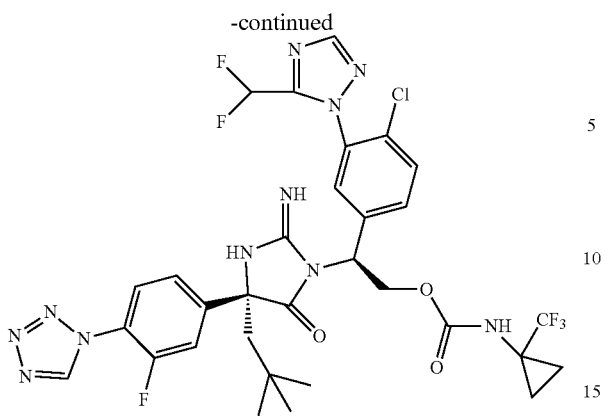

Preparation of isopropyl (R)-2-(((benzyloxy)carbonyl)amino)-2-(4-bromo-3-fluorophenyl)-4,4-dimethylpentanoate: To a biphasic solution of isopropyl (R)-2-amino-2-(4-bromo-3-fluorophenyl)-4,4-dimethylpentanoate (1.0 g, 2.78 mmol) in EtOAc (50 mL) and saturated aqueous NaHCO₃ (50 mL) was added benzyl chloroformate (0.99 mL, 6.94 mmol). The reaction mixture was stirred at rt overnight. The organic phase was concentrated down and the residue was purified by silica gel column chromatography to give the product.

Preparation of isopropyl (R)-2-(((benzyloxy)carbonyl)amino)-2-(4-((diphenylmethylene)amino)-3-fluorophenyl)-4,4-dimethylpentanoate: To a solution of isopropyl (R)-2-(((benzyloxy)carbonyl)amino)-2-(4-bromo-3-fluorophenyl)-4,4-dimethylpentanoate (400 mg, 0.81 mmol) in toluene (6 mL) were added 2-(di-t-butylphosphino)biphenyl (56 mg, 0.19 mmol), tris(dibenzylideneacetone) dipalladium (0) (89 mg, 0.1 mmol) and sodium t-butoxide (194 mg, 2.02 mmol). The mixture was purged with argon and then heated at 63° C. for 2 h. The mixture was cooled to rt and filtered through Celite. The filtrate was concentrated and the residue was purified by silica gel column chromatography to give the product.

Preparation of isopropyl (R)-2-(4-amino-3-fluorophenyl)-2-(((benzyloxy)carbonyl)amino)-4,4-dimethylpentanoate: To a solution of isopropyl (R)-2-(((benzyloxy)carbonyl)amino)-2-(4-((diphenylmethylene)amino)-3-fluorophenyl)-4,4-dimethylpentanoate (481 mg, 0.81 mmol) in THF (5 mL) was added concentrated HCl (2 mL) dropwise. The reaction mixture was stirred at rt for 5 min. The mixture was diluted with brine and extracted with EtOAc. The organic phase was washed with saturated aqueous NaHCO₃, and concentrated. The residue was purified by silica gel column chromatography to give the product.

Preparation of isopropyl (R)-2-(((benzyloxy)carbonyl)amino)-2-(3-fluoro-4-(1H-tetrazol-1-yl)phenyl)-4,4-dimethylpentanoate: To a solution of isopropyl (R)-2-(4-amino-3-fluorophenyl)-2-(((benzyloxy)carbonyl)amino)-4,4-dimethylpentanoate (169 mg, 392 μmol) in AcOH (4 mL) was added sodium azide (0.08 g, 1.18 mmol). Then trimethyl orthoformate (0.13 mL, 1.21 mmol) was added. The reaction mixture was stirred at rt overnight. The mixture was diluted with toluene and then concentrated down to remove AcOH. The residue was diluted with saturated NaHCO₃ and extracted with EtOAc. The organic phase was concentrated down and the residue was purified by silica gel column chromatography (0-100% gradient EtOAc/hexanes) to give the product. Compound 355 was then prepared by following the procedure to prepare Compound 349, starting with isopropyl (R)-2-(((benzyloxy)carbonyl)amino)-2-(3-fluoro-4-(1H-tetrazol-1-yl)phenyl)-4,4-dimethylpentanoate.

LCMS-ESI+: calc'd for $C_{31}H_{31}ClF_6N_{11}O_3$: 754.2 (M+H+). Found: 754.3 (M+H+). 1H NMR (400 MHz, Methanol-d₄) δ 9.63 (d, J=2.1 Hz, 1H), 8.20 (s, 1H), 8.13 (s, 1H), 7.91 (t, J=8.1 Hz, 1H), 7.63 (dt, J=12.0, 5.2 Hz, 2H), 7.53 (dd, J=8.8, 2.1 Hz, 1H), 7.36 (d, J=2.0 Hz, 1H), 6.84 (t, J=52.2 Hz, 1H), 5.69 (dd, J=9.7, 4.7 Hz, 1H), 5.12 (dd, J=11.5, 9.8 Hz, 1H), 4.71 (dd, J=11.6, 4.8 Hz, 1H), 2.46 (d, J=15.1 Hz, 1H), 2.19 (d, J=15.1 Hz, 1H), 1.28 (d, J=2.3 Hz, 2H), 1.09 (s, 2H), 1.00 (s, 9H).

Example 101: Preparation of Compound 356

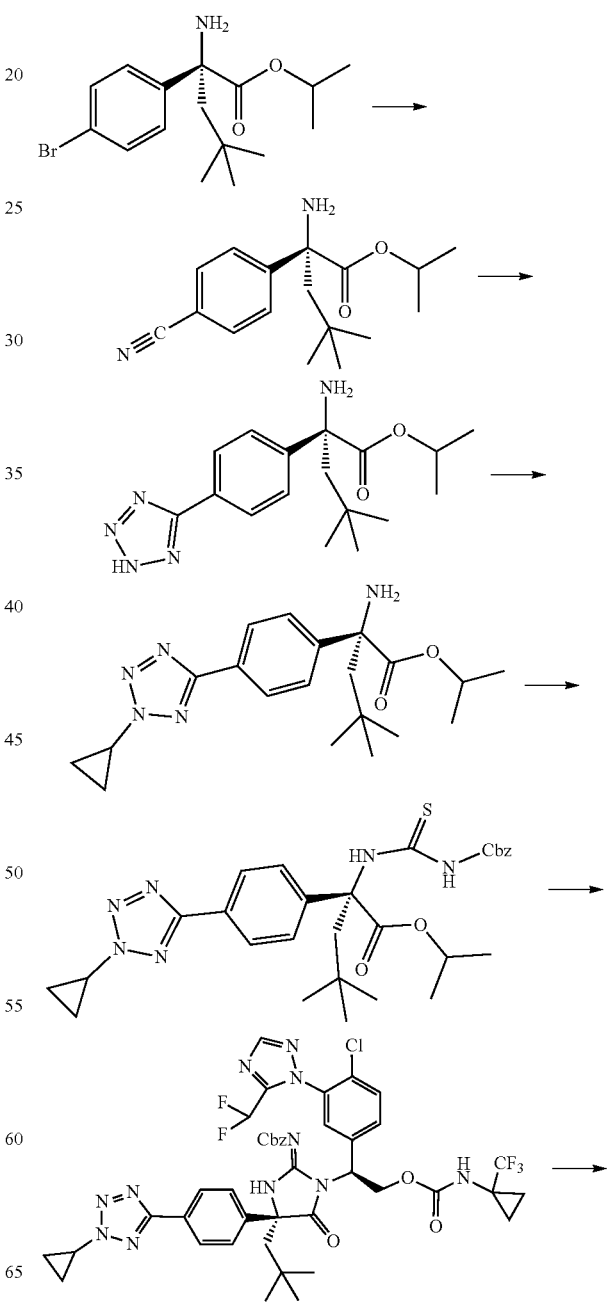

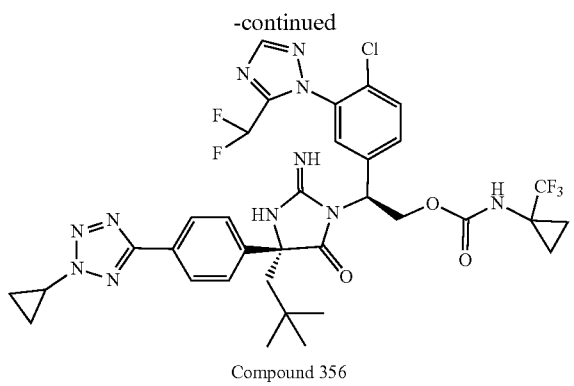

Compound 356

Preparation of isopropyl (R)-2-amino-2-(4-cyanophenyl)-4,4-dimethylpentanoate: To a solution of isopropyl (R)-2-amino-2-(4-bromophenyl)-4,4-dimethylpentanoate (100 mg, 0.29 mmol) in DMF (1.0 mL) and water (0.01 mL) were added zinc cyanide (34 mg, 0.29 mmol), chloro(2-dicyclohexylphosphino-2',6'-dimethoxy-1,1'-biphenyl)(2'-amino-1,1'-biphenyl-2-yl) palladium(II) min. 98% [SPhos Palladacycle] (40.1 mg, 0.06 mmol), tris(dibenzylideneacetone) dipalladium (0) (27 mg, 0.03 mmol) and 1,1'-bis(diphenylphosphino)ferrocene (32 mg, 0.06 mmol). The reaction mixture was stirred at 95° C. for 16 h. The reaction mixture was treated with saturated ammonium chloride solution, and extracted with EtOAc. The organic phase was dried over sodium sulfate, filtered, concentrated down. The residue was purified by silica gel column chromatography (0-100% gradient EtOAc/hexanes) to give the product.

Preparation of isopropyl (R)-2-(4-(2H-tetrazol-5-yl)phenyl)-2-amino-4,4-dimethylpentanoate: A mixture of isopropyl (R)-2-amino-2-(4-cyanophenyl)-4,4-dimethylpentanoate (450 mg, 1.56 mmol) and sodium azide (182 mg, 2.81 mmol) in DMF (1.5 mL) was heated at 110° C. for 10 h. After cooling, the mixture was partitioned between ethyl acetate and water. The ethyl acetate layer was washed with 10% LiCl and then with brine, and concentrated. The crude was treated with dichloromethane. The resulting precipitate was collected by filtration to afford the product (180 mg). The filtrate was purified by silica gel column chromatography (0-100% gradient EtOAc/hexanes) to obtain the product.

Preparation of isopropyl (R)-2-amino-2-(4-(2-cyclopropyl-2H-tetrazol-5-yl)phenyl)-4,4-dimethylpentanoate: A mixture of cupric acetate (anhydrous, 164 mg, 0.91 mmol) and 2,2'-bipyridyl (141 mg, 0.91 mmol) in DCE (1 mL) was stirred at 70° C. for 30 min. Then to the mixture were added cyclopropylboronic acid (97 mg, 1.13 mmol), sodium carbonate (120 mg, 1.13 mmol), and a solution of isopropyl (R)-2-(4-(2H-tetrazol-5-yl)phenyl)-2-amino-4,4-dimethylpentanoate (150 mg, 0.45 mmol) in DCE and 2-Me THF (1 mL, 1:1). The reaction mixture was stirred at 70° C. for 3 h. The reaction was quenched by adding saturated ammonium chloride solution, and the mixture was extracted with EtOAc. The organic phase was dried over $Na_2SO_4$, filtered, and concentrated down. The residue was purified by silica gel column chromatography to give the product. Compound 356 was then prepared in a manner similar to that for preparation of Compound 349, starting with isopropyl (R)-2-amino-2-(4-(2-cyclopropyl-2H-tetrazol-5-yl)phenyl)-4,4-dimethylpentanoate. LCMS-ESI+: calc'd for $C_{34}H_{35}ClF_5N_{11}O_3$: 776.2 (M+H+). Found: 776.6 (M+H+). 1H NMR (400 MHz, Methanol-$d_4$) δ 8.21 (s, 1H), 8.11-7.94 (m, 3H), 7.66-7.51 (m, 4H), 7.31-7.18 (m, 1H), 6.75 (t, J=52.2 Hz, 1H), 5.70 (dd, J=9.8, 4.8 Hz, 1H), 5.11 (dd, J=11.4, 9.8 Hz, 1H), 4.70 (dd, J=11.4, 4.8 Hz, 1H), 4.40 (tt, J=7.5, 3.8 Hz, 1H), 2.46 (d, J=15.1 Hz, 1H), 2.18 (d, J=15.1 Hz, 1H), 1.49 (ddt, J=5.7, 4.4, 2.9 Hz, 2H), 1.35-1.24 (m, 4H), 1.09 (s, 2H), 1.03-0.92 (m, 9H).

Example 102: Preparation of Compound 357 and Compound 358

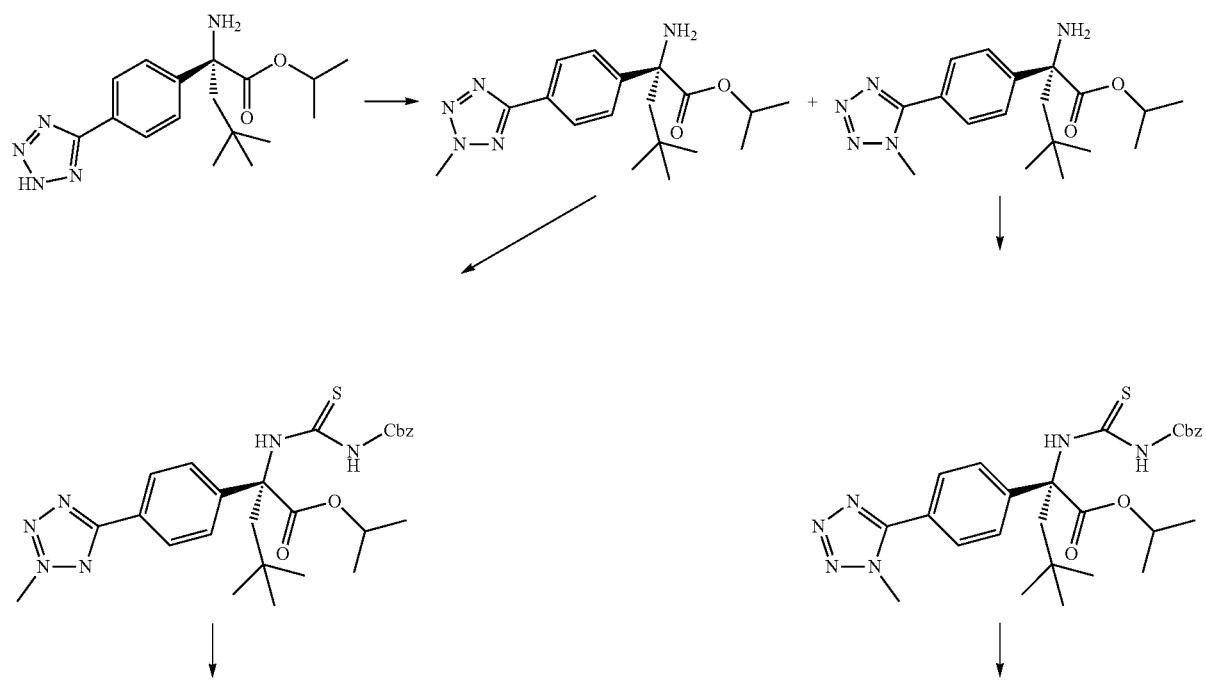

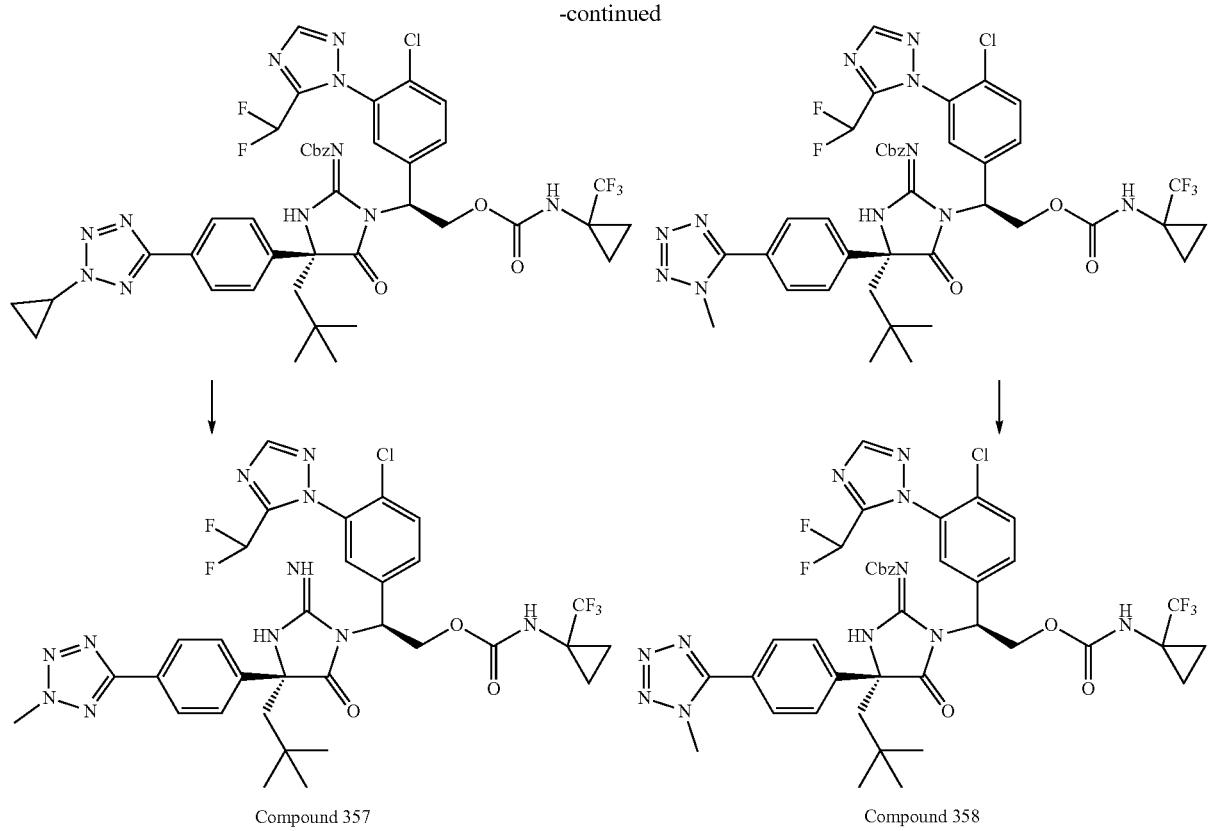

Compound 357

Compound 358

Preparation of isopropyl (R)-2-amino-4,4-dimethyl-2-(4-(2-methyl-2H-tetrazol-5-yl)phenyl)pentanoate and isopropyl (R)-2-amino-4,4-dimethyl-2-(4-(1-methyl-1H-tetrazol-5-yl)phenyl)pentanoate: To a solution of isopropyl (R)-2-(4-(2H-tetrazol-5-yl)phenyl)-2-amino-4,4-dimethylpentanoate (100 mg, 0.30 mmol) in toluene (3.0 mL) and methanol (1.5 mL) was added (trimethylsilyl)diazomethane solution in hexanes (2M, 0.18 mL). The reaction mixture was maintained at rt for 0.5 h. The reaction mixture was concentrated in vacuo and purified by silica gel column chromatography (0-100% EtOAc/hexane) to afford the products. The first eluting isomer was the major and tentatively designated as the N2-isomer. The minor isomer was also collected.

Both Compound 357 and Compound 358 were then prepared by following the procedure to prepare Compound 356, starting with isopropyl (R)-2-amino-4,4-dimethyl-2-(4-(2-methyl-2H-tetrazol-5-yl)phenyl)pentanoate. For Compound 357: LCMS-ESI+: calc'd for $C_{32}H_{33}ClF_5N_{11}O_3$: 750.2 (M+H+). Found: 750.6 (M+H+). 1H NMR (400 MHz, Methanol-$d_4$) δ 8.22 (s, 1H), 8.10-8.02 (m, 3H), 7.65-7.52 (m, 4H), 7.20 (d, J=2.1 Hz, 1H), 6.76 (t, J=52.2 Hz, 1H), 5.70 (dd, J=9.8, 4.8 Hz, 1H), 5.10 (dd, J=11.4, 9.8 Hz, 1H), 4.71 (dd, J=11.5, 4.8 Hz, 1H), 4.44 (s, 3H), 2.48 (d, J=15.1 Hz, 1H), 2.18 (d, J=15.1 Hz, 1H), 1.34-1.24 (m, 2H), 1.11-1.01 (m, 2H), 1.00 (s, 9H). For Compound 358: LCMS-ESI+: calc'd for $C_{32}H_{33}ClF_5N_{11}O_3$: 750.2 (M+H+). Found: 750.6 (M+H+). 1H NMR (400 MHz, Methanol-$d_4$) δ 8.24 (s, 1H), 8.11 (s, 1H), 7.90-7.81 (m, 2H), 7.69 (d, J=8.6 Hz, 2H), 7.67-7.52 (m, 2H), 7.38 (s, 1H), 6.84 (t, J=52.1 Hz, 1H), 5.68 (dd, J=9.8, 4.8 Hz, 1H), 5.13 (t, J=10.6 Hz, 1H), 4.71 (dd, J=11.5, 4.8 Hz, 1H), 4.19 (s, 3H), 2.48 (d, J=15.2 Hz, 1H), 2.20 (d, J=15.2 Hz, 1H), 1.33-1.22 (m, 2H), 1.14-1.05 (m, 2H), 1.00 (s, 9H).

Example 103: Preparation of Compound 359

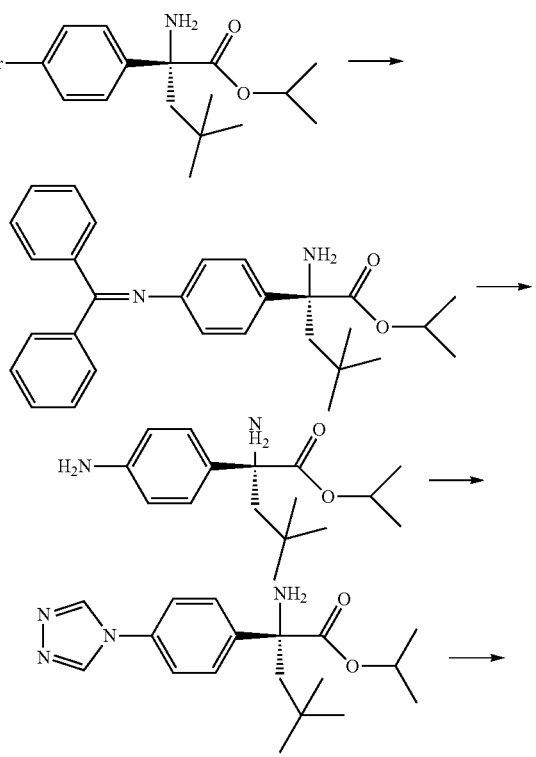

1H), 5.11 (dd, J=11.5, 9.7 Hz, 1H), 4.71 (dd, J=11.5, 4.9 Hz, 1H), 2.48 (d, J=15.2 Hz, 1H), 2.17 (d, J=15.1 Hz, 1H), 1.34-1.23 (m, 2H), 1.11-1.08 (m, 2H), 1.00 (s, 9H).

Example 104: Preparation of Compound 360

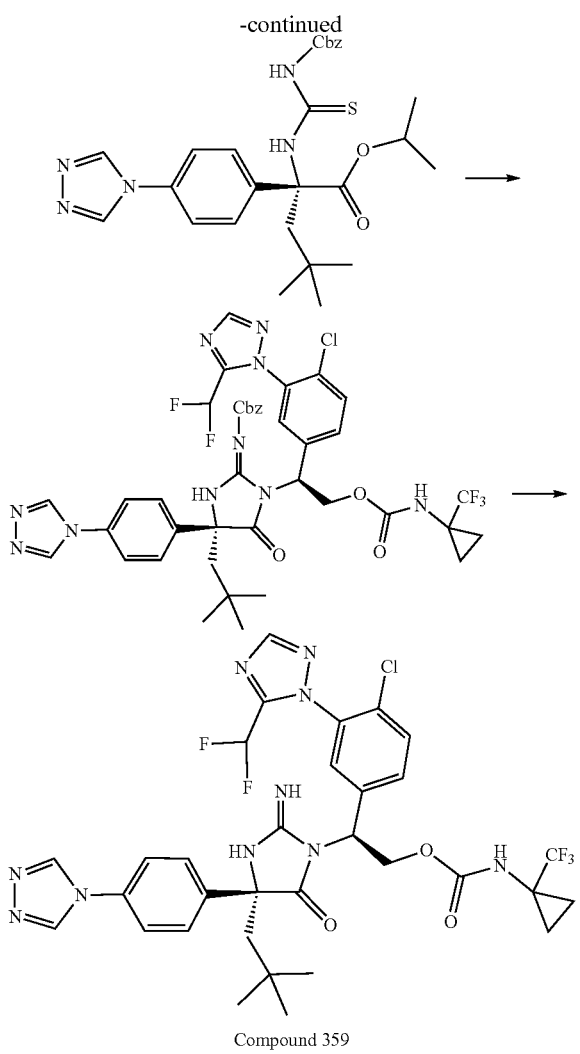

Compound 359

Preparation of isopropyl (R)-2-amino-2-(4-aminophenyl)-4,4-dimethylpentanoate: isopropyl (R)-2-amino-2-(4-aminophenyl)-4,4-dimethylpentanoate was prepared following the procedure to prepare isopropyl (R)-2-(4-amino-3-fluorophenyl)-2-(((benzyloxy)carbonyl)amino)-4,4-dimethylpentanoate described in Example 100, starting with isopropyl (R)-2-amino-2-(4-bromophenyl)-4,4-dimethylpentanoate.

Preparation of isopropyl (R)-2-(4-(4H-1,2,4-triazol-4-yl)phenyl)-2-amino-4,4-dimethylpentanoate: To a solution of isopropyl (R)-2-amino-2-(4-((diphenylmethylene)amino)phenyl)-4,4-dimethylpentanoate (100 mg, 0.23 mmol) in THF (2 ml) was added concentrated HCl (0.35 mL) dropwise. The reaction mixture was stirred for 5 min at rt. The mixture was partitioned between EtOAc and brine. The organic layer was further washed with saturated aqueous NaHCO$_3$, filtered, and concentrated in vacuo. The residue was purified by silica gel column chromatography (0-100% gradient EtOAc/hexanes) to give the product.

Compound 359 was then prepared following the procedure to prepare Compound 349, starting with isopropyl (R)-2-(4-(4H-1,2,4-triazol-4-yl)phenyl)-2-amino-4,4-dimethylpentanoate. LCMS-ESI+: calc'd C$_{32}$H$_{32}$ClF$_5$N$_{10}$O$_3$, 735.2 (M+H+). Found: 735.3 (M+H+). $^1$H NMR (400 MHz, Methanol-d$_4$) δ 9.05 (s, 1H), 8.09 (s, 1H), 7.65-7.55 (m, 7H), 7.25 (s, 1H), 6.82 (t, J=52.2 Hz, 1H), 5.68 (dd, J=9.7, 4.8 Hz,

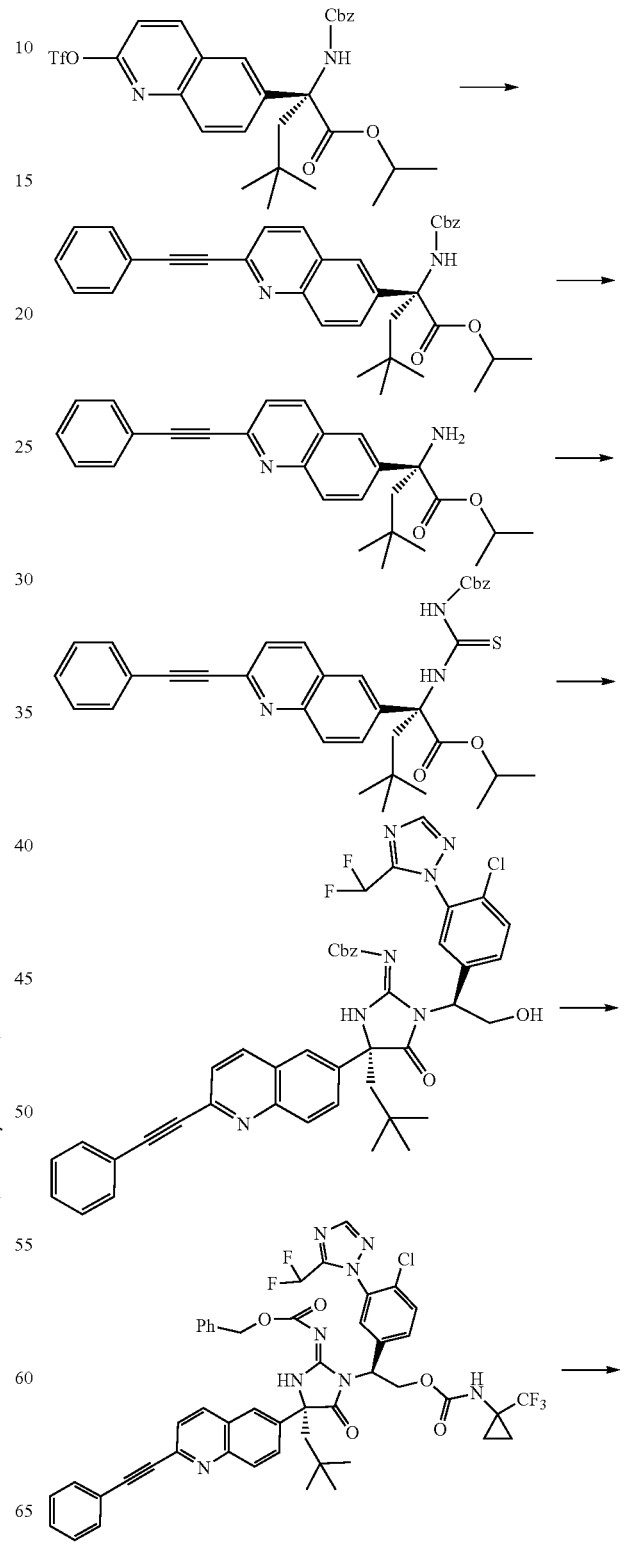

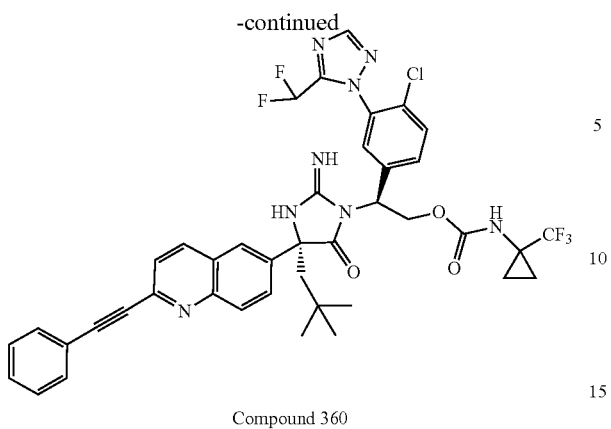

Compound 360

Preparation of isopropyl (R)-2-(((benzyloxy)carbonyl)amino)-4,4-dimethyl-2-(2-(phenylethynyl)quinolin-6-yl)pentanoate: To a mixture of isopropyl (R)-2-(((benzyloxy)carbonyl)amino)-4,4-dimethyl-2-(2-(((trifluoromethyl)sulfonyl)oxy)quinolin-6-yl)pentanoate (140 mg, 0.23 mmol), phenyl acetylene (36 mg, 0.35 mmol), triethylamine (1 mL) and ethyl acetate (1 mL) purged with argon were added copper(i) iodide (3 mg, 0.016 mmol) and bis(triphenylphosphine)palladium(II) dichloride (21 mg, 0.03 mmol). The reaction mixture was stirred at rt for 16 h. Then the mixture was partitioned between water and EtOAc. The organic phase was concentrated down and the residue was purified by silica gel column chromatography to give the product.

Preparation of isopropyl (R)-2-amino-4,4-dimethyl-2-(2-(phenylethynyl)quinolin-6-yl)pentanoate: The mixture of isopropyl (R)-2-(((benzyloxy)carbonyl)amino)-4,4-dimethyl-2-(2-(phenyl ethynyl)quinolin-6-yl)pentanoate (120 mg, 0.219 mmol) in TFA (2.0 mL) was heated at 60° C. for 16 h. The reaction mixture was then cooled down, concentrated down and used for the next reaction without further purification.

Compound 362 was then prepared following the procedure to prepare Compound 178 and Compound 179, starting with isopropyl (R)-2-amino-4,4-dimethyl-2-(2-(phenylethynyl)quinolin-6-yl)pentanoate. LCMS-ESI+: calc'd $C_{41}H_{36}ClF_5N_8O_3$: 819.2 (M+H+). Found: 820.2 (M+H+). 1H NMR (400 MHz, Methanol-$d_4$) δ 8.36 (d, J=8.5 Hz, 1H), 8.19 (s, 1H), 8.04-7.94 (m, 3H), 7.90 (dd, J=9.0, 2.3 Hz, 1H), 7.78 (d, J=8.5 Hz, 1H), 7.73-7.65 (m, 2H), 7.57 (d, J=1.3 Hz, 2H), 7.51-7.41 (m, 3H), 7.21 (s, 1H), 6.69 (t, J=52.1 Hz, 1H), 5.70 (dd, J=9.7, 4.8 Hz, 1H), 5.12 (t, J=10.6 Hz, 1H), 4.72 (dd, J=11.5, 4.9 Hz, 1H), 2.57 (d, J=15.2 Hz, 1H), 2.26 (d, J=15.2 Hz, 1H), 1.28 (dt, J=7.6, 3.5 Hz, 2H), 1.09 (s, 2H), 1.01 (s, 9H).

Example 105: Preparation of Compound 361

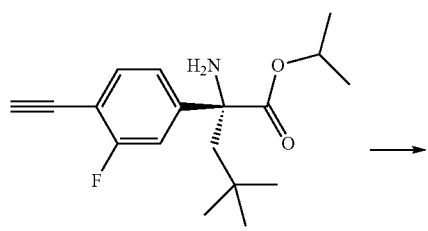

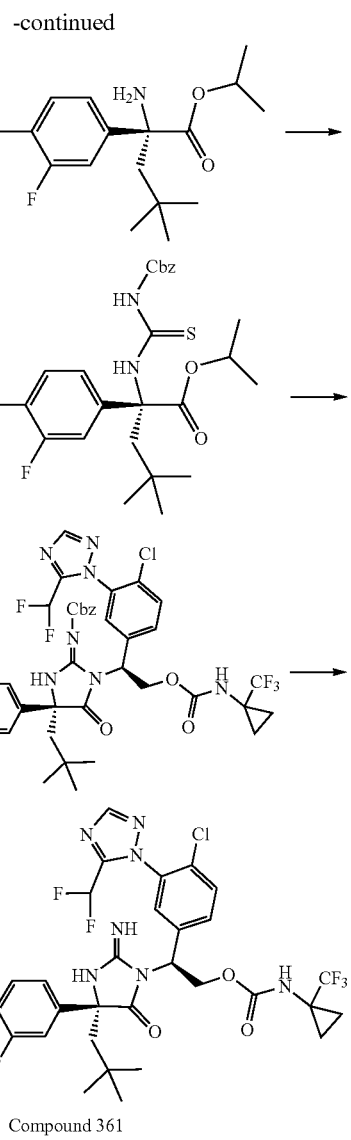

Compound 361

Preparation of isopropyl (R)-2-amino-2-(4-((1-(difluoromethyl)-1H-pyrazol-4-yl)ethynyl)-3-fluorophenyl)-4,4-dimethylpentanoate: To a solution of isopropyl (R)-2-amino-2-(4-ethynyl-3-fluorophenyl)-4,4-dimethylpentanoate (200 mg, 0.65 mmol) in triethylamine (14 mL) were added 1-(difluoromethyl)-4-iodo-1H-pyrazole (1.04 mL, 2.95 mmol), CuI (62 mg, 0.33 mmol) and Pd(PPh$_3$)$_4$ (250 mg, 0.22 mmol). The mixture was sparged with argon for 3 min and then heated at 85° C. for 2 h. The reaction mixture was concentrated down and purified by silica gel column chromatography to give the product.

Compound 361 was then prepared following the procedure to prepare Compound 352. LCMS-ESI+: calc'd for $C_{36}H_{32}ClF_8N_9O_3$, 826.2 (M+H). Found, 826.3 (M+H). 1H NMR (400 MHz, Methanol-$d_4$) δ 8.40 (d, J=0.6 Hz, 1H), 8.22 (s, 1H), 7.92 (s, 1H), 7.66-7.37 (t, J=60 Hz, 1H), 7.64-7.56 (m, 2H), 7.50-7.46 (m, 1H), 7.33-7.23 (m, 3H), 6.98-6.72 (t, J=52 Hz, 1H), 5.67 (dd, J=9.7, 4.8 Hz, 1H), 5.09 (dd, J=11.5, 9.8 Hz, 1H), 4.70 (dd, J=11.5, 4.8 Hz, 1H), 2.40 (d, J=15.1 Hz, 1H), 2.13 (d, J=15.2 Hz, 1H), 1.33-1.24 (m, 2H), 1.11-1.07 (m, 2H), 0.99 (s, 9H).

Example 106: Preparation of Compound 362
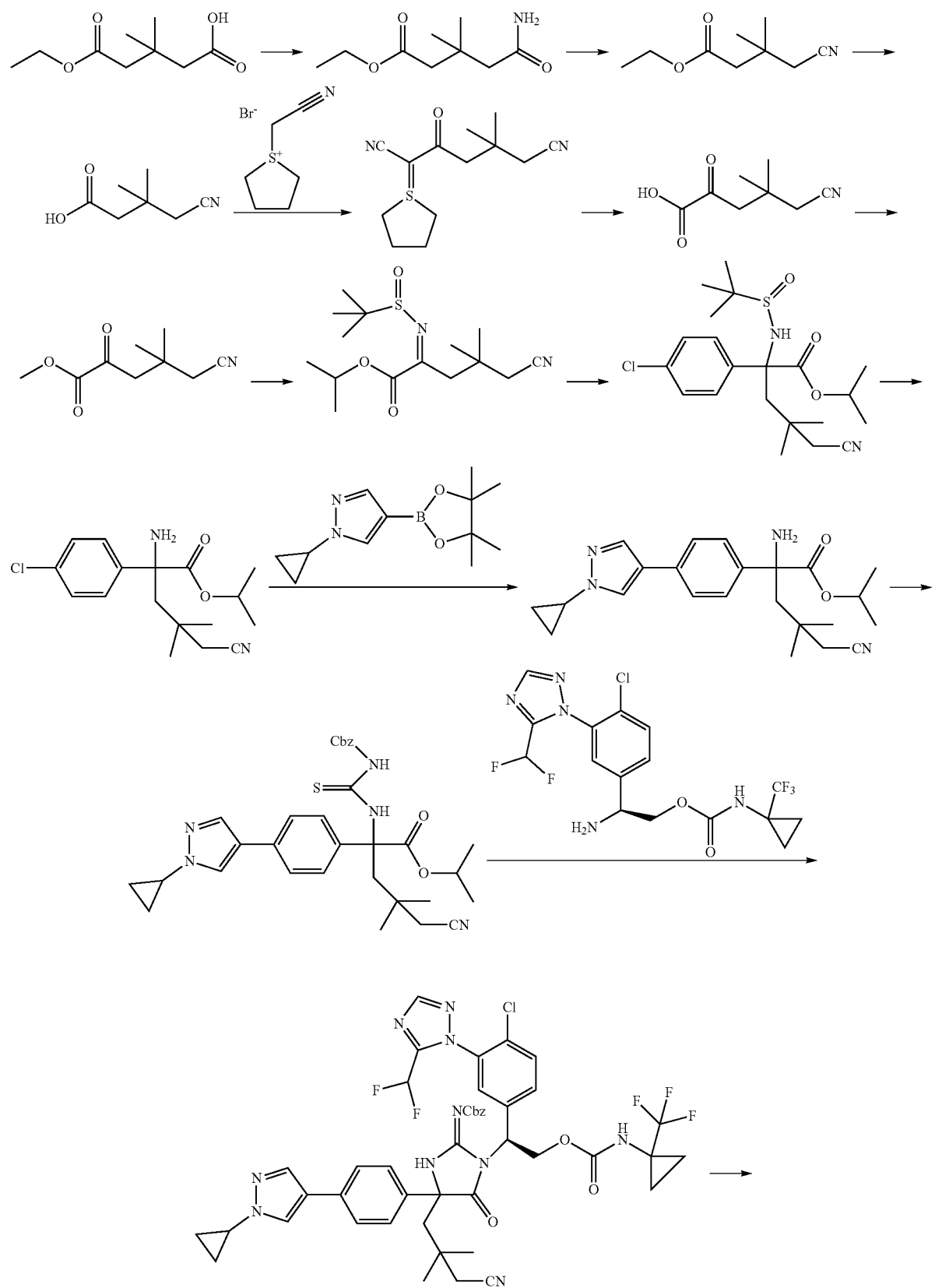

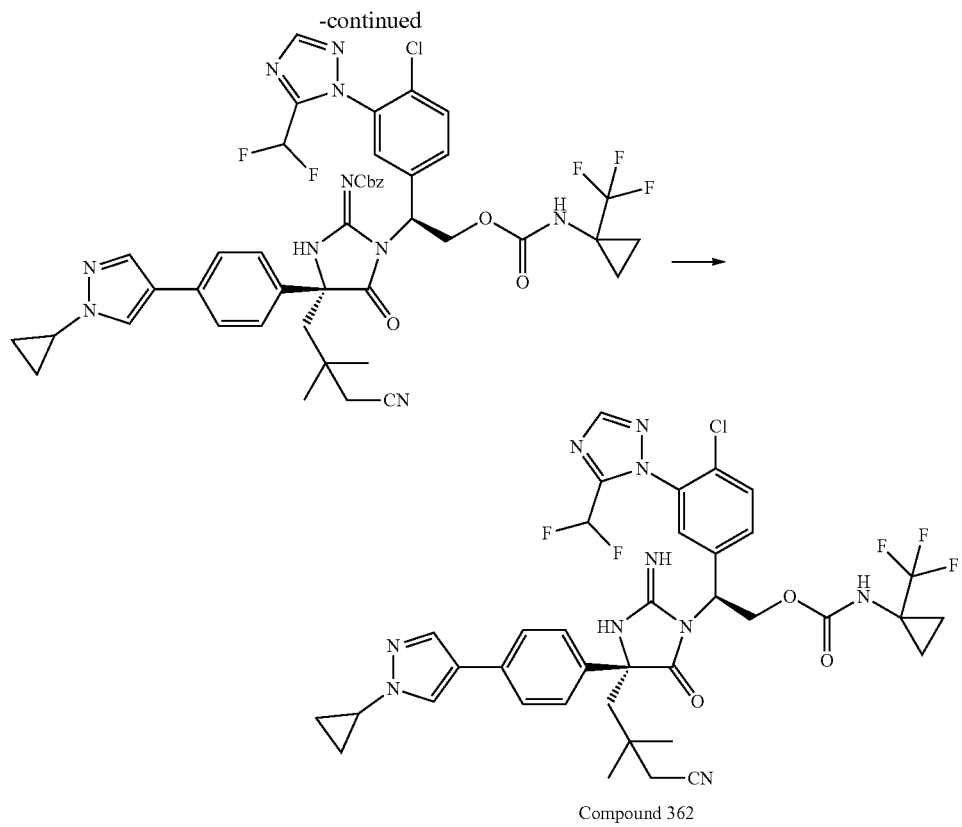

Compound 362

Preparation of ethyl 5-amino-3,3-dimethyl-5-oxopentanoate: To a solution of 5-ethoxy-3,3-dimethyl-5-oxopentanoic acid (4.0 g, 21.3 mmol), ammonium chloride (3.13 g, 58.4 mmol), HATU (12.1 g, 31.9 mmol) in DMF (30 mL) was added N,N-diisopropylethylamine (14.8 mL, 85 mmol). The reaction mixture was maintained at rt for 3 h. The reaction mixture was then quenched by the addition of sat NH$_4$Cl and EtOAc. The layers were separated and the aqueous layer was further extracted with EtOAc. The combined organic extracts were washed with 10% LiCl (as) and then with brine, dried (over sodium sulfate), filtered and concentrated in vacuo. The residue was purified by silica gel column chromatography (ISCO gold, 120 g column; 0-100% gradient EtOAc/hexanes) to afford the product.

Preparation of ethyl 4-cyano-3,3-dimethylbutanoate: To an ice bath (0° C.) solution of ethyl 5-amino-3,3-dimethyl-5-oxopentanoate (4.0 g, 21.4 mmol) and triethylamine (6.0 mL, 42.7 mmol) in CH$_2$Cl$_2$ (200 mL) was added trifluoromethanesulfonic anhydride (4.03 mL, 24.6 mmol) slowly as a steady stream down the side of the reaction vessel. The mixture was maintained at 0° C. for 30 min, and then quenched by the addition of water and EtOAc. The layers were separated and the aqueous layer was further extracted with EtOAc. The combined organic layers were washed with brine, dried (over sodium sulfate), filtered and concentrated in vacuo. The crude mixture was purified by silica gel column chromatography (ISCO gold, 120 g column; 0-100% gradient EtOAc/hexanes) to afford the product.

Preparation of 4-cyano-3,3-dimethylbutanoic acid: To a solution of ethyl 4-cyano-3,3-dimethylbutanoate (2.6 g, 15.4 mmol) in THF/methanol (50 mL and 15 mL) was added 2M sodium hydroxide solution (9.6 mL). The reaction mixture was stirred at rt until the starting material was consumed (~7 h). The reaction mixture was neutralized by the addition of 2N HCl and extracted with EtOAc. The organic layer was separated and the aqueous layer was further extracted with EtOAc. The combined organic layers were washed with brine, dried (over sodium sulfate), filtered, and concentrated in vacuo. The crude product was processed in the next step immediately (2.23 g).

Preparation of 1-(cyanomethyl)tetrahydro-1H-thiophen-1-ium bromide: To tetrahydrothiophene (2.0 g, 23 mmol) was added bromoacetonitrile (2.72 g, 23 mmol) at rt. The mixture was stirred over 24 h at rt. The resulting solid was washed with diethyl ether (3×20 mL), and dried under vacuum to afford the product, which was stored under nitrogen in the refrigerator before use.

Preparation of 5,5-dimethyl-3-oxo-2-(tetrahydro-1-λ$^4$-thiophen-1-ylidene)heptanedinitrile:

To a solution of 4-cyano-3,3-dimethylbutanoic acid (2.2 g, 15.6 mmol) and 1-(cyanomethyl)tetrahydro-1H-thiophen-1-ium bromide (4.87 g, 23.4 mmol) in DCM (40 mL) and DMF (4 mL) was added HATU (8.89 g, 23.4 mmol) and DIEA (8.1 mL, 46.8 mmol). The reaction mixture was stirred at rt for 17 h. After this period, the reaction mixture was concentrated and the residue was loaded into a 80 g silica gel cartridge and purified via column chromatography eluting with a 0-50% gradient of DCM/(20% MeOH in DCM). The product eluted about 25% of 20% MeOH in DCM (3.9 g, 99%).

Preparation of 5-cyano-4,4-dimethyl-2-oxopentanoic acid: The product from the previous step 5,5-dimethyl-3-oxo-2-(tetrahydro-1-λ$^4$-thiophen-1-ylidene)heptanedinitrile was dissolved in THF (100 mL). To this mixture was added OXONE® monopersulfate compound (10.3 g, 33.4 mmol) as a solution in water (100 mL), while cooling in a water bath. The reaction mixture was stirred at rt for 1 h, and then quenched by the addition of saturated aqueous sodium thiosulfate and EtOAc. The layers were separated and the aqueous layer was further extracted with EtOAc. The combined organic layers were washed with brine, dried over sodium sulfate, filtered, and concentrated in vacuo. The crude product was carried forward immediately.

Preparation of methyl 5-cyano-4,4-dimethyl-2-oxopentanoate: To a solution of 5-cyano-4,4-dimethyl-2-oxopentanoic acid (2.6 g, 15.6 mmol) in DCM (45 mL) was added TEA (2.17 mL, 15.6 mmol) and the solution was cooled to 0° C. This solution was then added methylchloroformate (1.2 mL, 15.6 mmol) and stirred for 30 min. After this period the reaction mixture was treated with water and diethyl ether. The organic layer was taken and the aqueous layer was further extracted with diethyl ether. The organic layers were combined, dried over magnesium sulfate, filtered, and concentrated. The crude mixture was loaded into a silica gel column, and purified by silica gel column chromatography (0-100% gradient EtOAc/hexanes) to afford the product.

Preparation of isopropyl (S)-2-((tert-butylsulfinyl)imino)-5-cyano-4,4-dimethylpentanoate: To a solution of methyl 5-cyano-4,4-dimethyl-2-oxopentanoate (0.37 g, 2.0 mmol) and (S)-(−)-2-methyl-2-propanesulfinamide (0.27 g, 2.2 mmol) was added titanium (IV) isopropoxide (0.66 mL, 2.24 mmol) dropwise at rt. After stirring for 2 h, saturated aq NH₄Cl was added. The resulting mixture was diluted with EtOAc, filtered through Celite, the filter cakes were washed with EtOAc. The layers were separated and the organic layer was concentrated in vacuo. The residue was purified by combiflash chromatography (24 g gold column, (0-100% gradient EtOAc/hexanes)) to give the product.

Preparation of isopropyl 2-((tert-butylsulfinyl)amino)-2-(4-chlorophenyl)-5-cyano-4,4-dimethylpentanoate: Isopropyl (S)-2-((tert-butylsulfinyl)imino)-5-cyano-4,4-dimethylpentanoate (240 mg, 0.76 mmol) was dissolved in THF (2 mL) and cooled to 0° C., 4-Chlorophenylmagnesium bromide (1M in THF, 0.99 mL, 0.99 mmol) was added dropwise at the same temperature. The reaction mixture was kept stirring at 0° C. for 1 h and then treated with NH₄Cl/water at 0° C. The mixture was extracted with ethyl acetate, and the organic layer was washed with brine, concentrated, and purified on silica gel column, eluted with 0-100% EtOAc/hexanes, to give the product.

Compound 362 was then prepared according to the similar procedure to prepare Compound 234, except that (S)-2-amino-2-(4-chloro-3-(5-(difluoromethyl)-1H-1,2,4-triazol-1-yl)phenyl)ethyl (1-(trifluoromethyl)cyclopropyl) carbamate 2,2,2-trifluoroacetate was used for cyclization to prepare (2S)-2-((E)-2-(((benzyloxy)carbonyl)imino)-4-(3-cyano-2,2-dimethylpropyl)-4-(4-(1-cyclopropyl-1H-pyrazol-4-yl)phenyl)-5-oxoimidazolidin-1-yl)-2-(4-chloro-3-(5-(difluoromethyl)-1H-1,2,4-triazol-1-yl)phenyl)ethyl (1-(trifluoromethyl)cyclopropyl)carbamate. This cyclization product was a mixture of the two diastereomers and it was further subject to a chiral SFC condition to afford the desired diastereomer (S)-2-((R)-2-(((benzyloxy)carbonyl)imino)-4-(3-cyano-2,2-dimethylpropyl)-4-(4-(1-cyclopropyl-1H-pyrazol-4-yl)phenyl)-5-oxoimidazolidin-1-yl)-2-(4-chloro-3-(5-(difluoromethyl)-1H-1,2,4-triazol-1-yl)phenyl)ethyl (1-(trifluoromethyl)cyclopropyl)carbamate, which is the isomer with longer retention time (IF SFC 5 µM 21×250 mm with 30% IPA as co-solvent). For Compound 362: LCMS-ESI+: calc'd for $C_{37}H_{36}ClF_5N_{10}O_3$: 799.3 (M+H). Found: 799.7 (M+H). 1H NMR (400 MHz, Methanol-$d_4$) δ 8.18 (s, 1H), 8.09 (s, 1H), 8.02 (s, 1H), 7.84 (d, J=0.8 Hz, 1H), 7.62 (d, J=8.5 Hz, 1H), 7.59-7.50 (m, 3H), 7.45-7.37 (m, 2H), 7.23 (s, 1H), 6.79 (t, J=52.2 Hz, 1H), 5.68 (dd, J 9.8, 4.8 Hz, 1H), 5.11 (q, J=10.9 Hz, 1H), 4.74 (dd, J=11.6, 4.8 Hz, 1H), 3.71 (tt, J=7.3, 3.9 Hz, 1H), 2.55 (d, J=15.4 Hz, 1H), 2.50-2.27 (m, 3H), 1.34-1.25 (m, 2H), 1.19-1.06 (m, 12H).

Example 107: Preparation of Compound 363

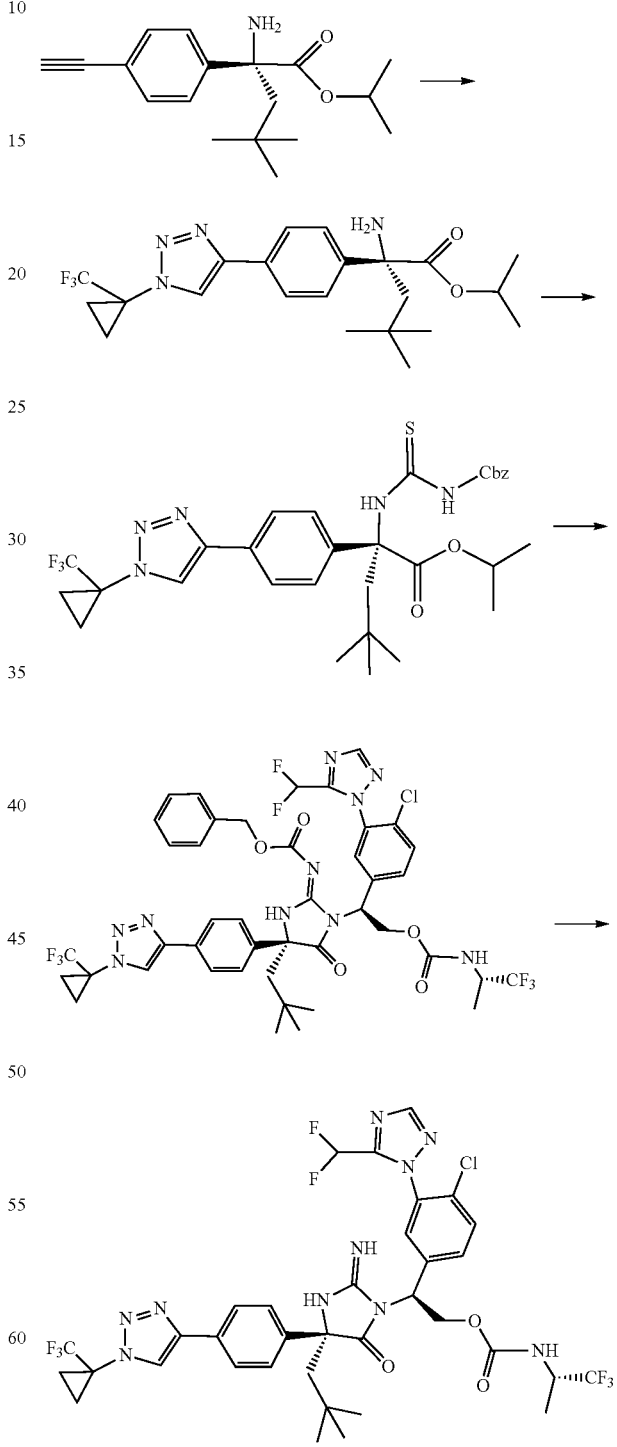

Compound 363

Preparation of isopropyl (R)-2-amino-4,4-dimethyl-2-(4-(1-(1-(trifluoromethyl)cyclopropyl)-1H-1,2,3-triazol-4-yl)phenyl)pentanoate:

Isopropyl (R)-2-amino-2-(4-ethynylphenyl)-4,4-dimethylpentanoate was prepared following the procedure to prepare isopropyl (R)-2-amino-2-(4-ethynyl-3-fluorophenyl)-4,4-dimethylpentanoate described in Example 97. To a solution of isopropyl (R)-2-amino-2-(4-ethynylphenyl)-4,4-dimethylpentanoate (93 mg, 0.32 mmol) in benzene (1.5 mL) were added copper(I) thiophene-2-carboxylate (12 mg, 0.06 mmol) and 1-azido-1-(trifluoromethyl)cyclopropane (51 mg, 0.34 mmol). The reaction mixture was stirred at rt for 2 h. Then the reaction mixture was treated with brine, and extracted by EtOAc. The organic phase was concentrated down and the residue was purified by silica gel column chromatography to give the product.

Compound 363 was then prepared by following the procedure to prepare Compound 236. LCMS-ESI+: calc'd $C_{35}H_{36}ClF_8N_{10}O_3$: 831.2 (M+H+). Found: 831.7 (M+H+). 1H NMR (400 MHz, Methanol-$d_4$) δ 8.68 (s, 1H), 7.98 (s, 1H), 7.90-7.76 (m, 2H), 7.70-7.41 (m, 4H), 7.14 (d, J=2.1 Hz, 1H), 6.77 (t, J=52.2 Hz, 1H), 5.76 (dd, J=9.6, 5.0 Hz, 1H), 5.10 (dd, J=11.6, 9.7 Hz, 1H), 4.75 (dd, J=11.7, 5.1 Hz, 1H), 4.42-4.19 (m, 1H), 2.49 (d, J=15.1 Hz, 1H), 2.17 (d, J=15.2 Hz, 1H), 1.81 (s, 4H), 1.29 (d, J=7.1 Hz, 3H), 1.01 (s, 9H).

Example 108: Preparation of Compound 364

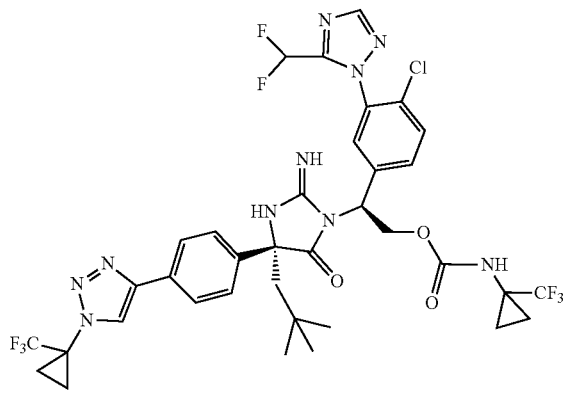

Compound 364

Compound 364 was prepared by following the procedure to prepare Compound 220. LCMS-ESI+: calc'd $C_{36}H_{36}ClF_8N_{10}O_3$: 843.2 (M+H+). Found: 843.3 (M+H+). $^1$H NMR (400 MHz, Methanol-$d_4$) δ 8.68 (s, 1H), 8.16 (s, 1H), 7.99 (s, 1H), 7.88-7.73 (m, 2H), 7.69-7.38 (m, 4H), 7.15 (s, 1H), 6.76 (t, J=52.2 Hz, 1H), 5.69 (dd, J=9.7, 4.9 Hz, 1H), 5.09 (t, J=10.6 Hz, 1H), 4.70 (dd, J=11.6, 4.9 Hz, 1H), 2.48 (d, J=15.2 Hz, 1H), 2.17 (d, J=15.1 Hz, 1H), 1.81 (s, 4H), 1.32-1.21 (m, 2H), 1.08 (s, 2H), 1.00 (s, 9H).

Example 109: Preparation of Compound 365

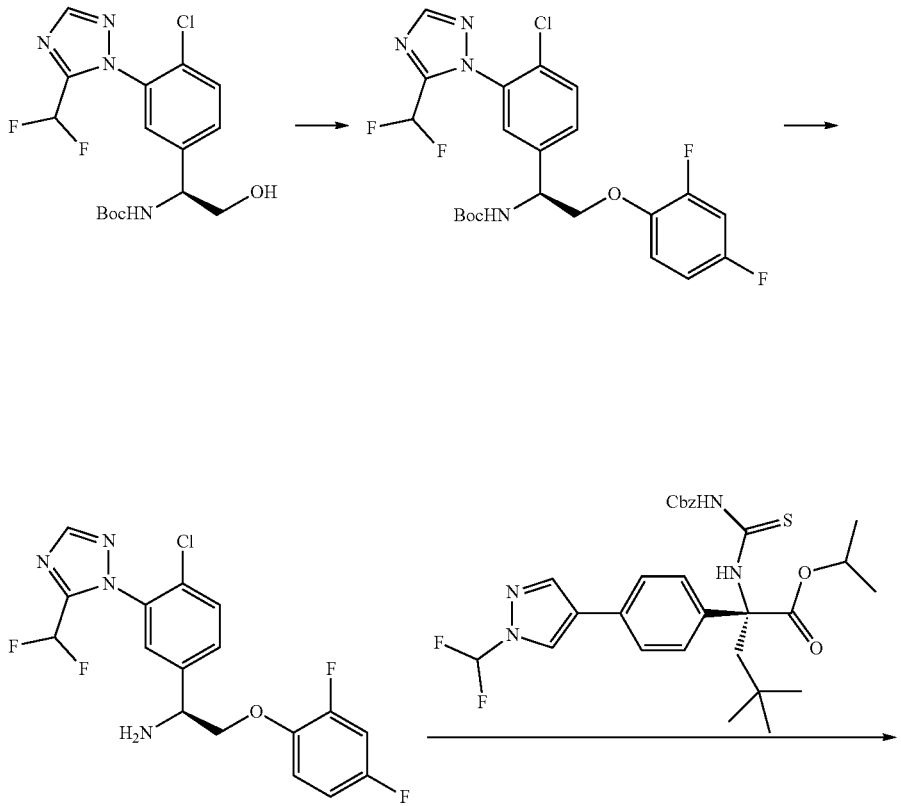

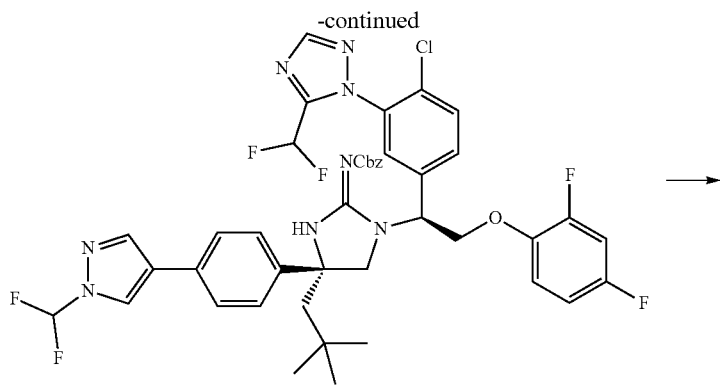

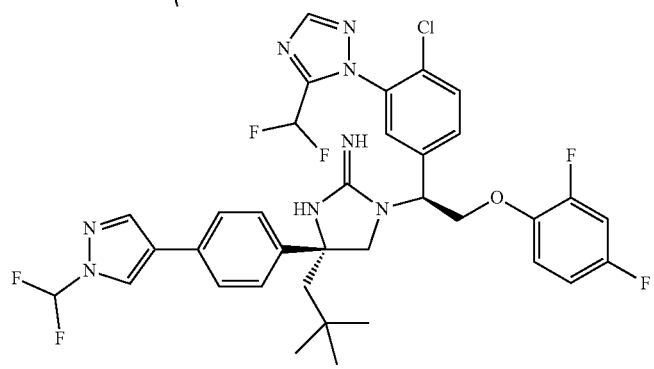

Compound 365

Preparation of tert-butyl (S)-(1-(4-chloro-3-(5-(difluoromethyl)-1H-1,2,4-triazol-1-yl)phenyl)-2-(2,4-difluorophenoxy)ethyl)carbamate: A mixture of tert-butyl (S)-(1-(4-chloro-3-(5-(difluoromethyl)-1H-1,2,4-triazol-1-yl)phenyl)-2-hydroxyethyl)carbamate (50 mg, 0.13 mmol), 2,4-difluorophenol (33 mg, 0.26 mmol), triphenylphosphine (38 mg, 0.15 mmol) in THF (1.3 mL) was cooled to 0° C. and to the mixture was added diisopropyl azodicarboxylate (0.03 mL, 0.15 mmol). The reaction mixture was then allowed to warm up to and stirred at rt overnight. The reaction mixture was concentrated, and the residue was purified by silica gel column chromatography (0-100% gradient EtOAc/hexanes) to give the product.

Preparation of (S)-1-(4-chloro-3-(5-(difluoromethyl)-1H-1,2,4-triazol-1-yl)phenyl)-2-(2,4-difluorophenoxy)ethan-1-amine: A mixture of tert-butyl (S)-(1-(4-chloro-3-(5-(difluoromethyl)-1H-1,2,4-triazol-1-yl)phenyl)-2-(2,4-difluorophenoxy)ethyl)carbamate (50 mg, 0.1 mmol) and TFA (0.5 mL) was stirred at rt for 30 min. Then, the reaction mixture was concentrated and directly used for the next reaction without purification.

Compound 365 was then prepared by following the procedure to prepare Compound 220, except that (S)-1-(4-chloro-3-(5-(difluoromethyl)-1H-1,2,4-triazol-1-yl)phenyl)-2-(2,4-difluorophenoxy)ethan-1-amine was used instead of (S)-2-amino-2-(4-chloro-3-(5-(difluoromethyl)-1H-1,2,4-triazol-1-yl)phenyl)ethyl (1-(trifluoromethyl)cyclopropyl)carbamate. LCMS-ESI+: calc'd $C_{35}H_{31}ClF_6N_8O_2$: 745.2 (M+H+). Found: 745.3 (M+H+). $^1$H NMR (400 MHz, Methanol-$d_4$) δ 8.44 (s, 1H), 8.07 (d, J=13.5 Hz, 2H), 7.71-7.32 (m, 8H), 7.22 (td, J=9.3, 5.1 Hz, 1H), 7.04 (ddd, J=11.3, 8.5, 3.0 Hz, 1H), 7.00-6.58 (m, 2H), 5.84 (dd, J=10.3, 4.2 Hz, 1H), 5.10 (t, J=10.1 Hz, 1H), 4.76 (dd, J=9.8, 4.3 Hz, 1H), 2.39 (d, J=15.2 Hz, 1H), 2.07 (d, J=15.2 Hz, 1H), 0.89 (s, 9H).

Example 110: Preparation of Compound 366

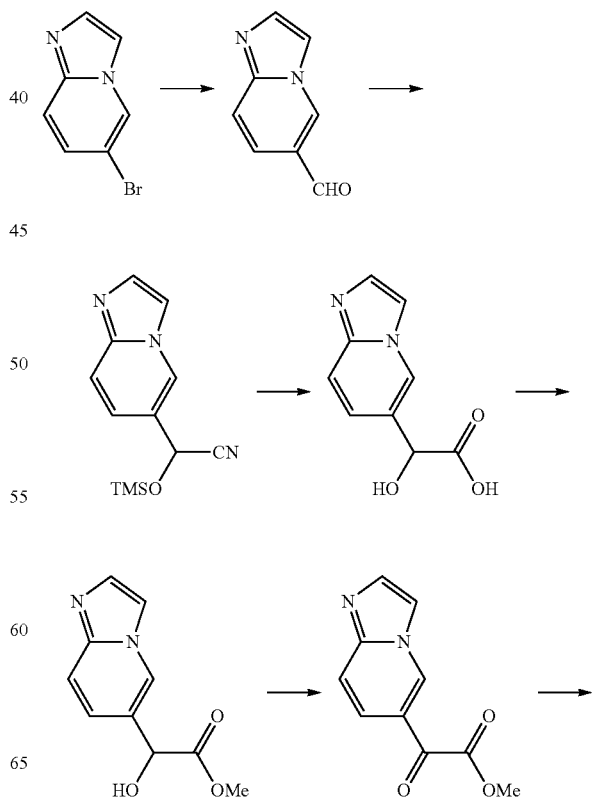

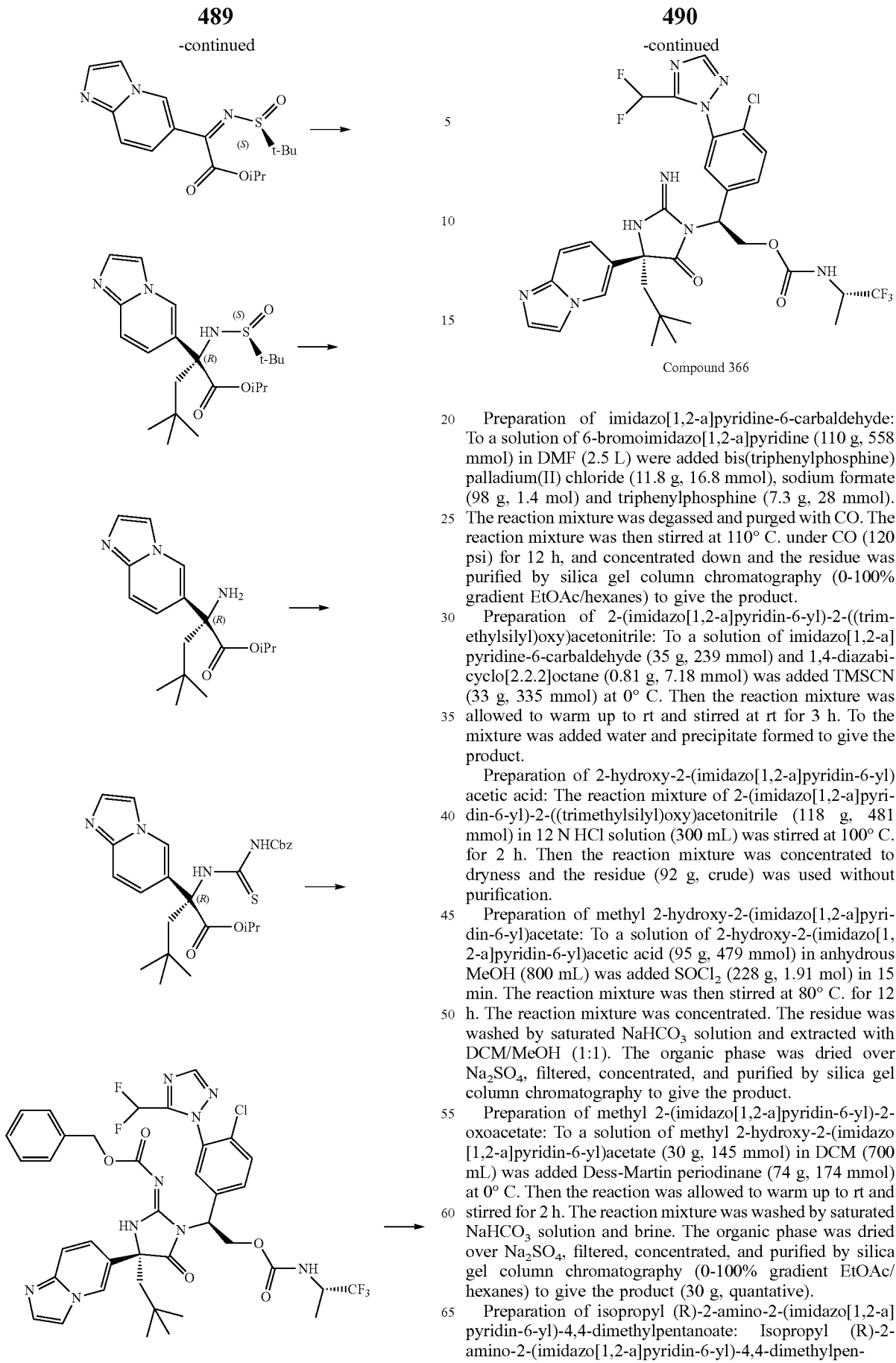

Preparation of imidazo[1,2-a]pyridine-6-carbaldehyde: To a solution of 6-bromoimidazo[1,2-a]pyridine (110 g, 558 mmol) in DMF (2.5 L) were added bis(triphenylphosphine)palladium(II) chloride (11.8 g, 16.8 mmol), sodium formate (98 g, 1.4 mol) and triphenylphosphine (7.3 g, 28 mmol). The reaction mixture was degassed and purged with CO. The reaction mixture was then stirred at 110° C. under CO (120 psi) for 12 h, and concentrated down and the residue was purified by silica gel column chromatography (0-100% gradient EtOAc/hexanes) to give the product.

Preparation of 2-(imidazo[1,2-a]pyridin-6-yl)-2-((trimethylsilyl)oxy)acetonitrile: To a solution of imidazo[1,2-a]pyridine-6-carbaldehyde (35 g, 239 mmol) and 1,4-diazabicyclo[2.2.2]octane (0.81 g, 7.18 mmol) was added TMSCN (33 g, 335 mmol) at 0° C. Then the reaction mixture was allowed to warm up to rt and stirred at rt for 3 h. To the mixture was added water and precipitate formed to give the product.

Preparation of 2-hydroxy-2-(imidazo[1,2-a]pyridin-6-yl)acetic acid: The reaction mixture of 2-(imidazo[1,2-a]pyridin-6-yl)-2-((trimethylsilyl)oxy)acetonitrile (118 g, 481 mmol) in 12 N HCl solution (300 mL) was stirred at 100° C. for 2 h. Then the reaction mixture was concentrated to dryness and the residue (92 g, crude) was used without purification.

Preparation of methyl 2-hydroxy-2-(imidazo[1,2-a]pyridin-6-yl)acetate: To a solution of 2-hydroxy-2-(imidazo[1,2-a]pyridin-6-yl)acetic acid (95 g, 479 mmol) in anhydrous MeOH (800 mL) was added SOCl$_2$ (228 g, 1.91 mol) in 15 min. The reaction mixture was then stirred at 80° C. for 12 h. The reaction mixture was concentrated. The residue was washed by saturated NaHCO$_3$ solution and extracted with DCM/MeOH (1:1). The organic phase was dried over Na$_2$SO$_4$, filtered, concentrated, and purified by silica gel column chromatography to give the product.

Preparation of methyl 2-(imidazo[1,2-a]pyridin-6-yl)-2-oxoacetate: To a solution of methyl 2-hydroxy-2-(imidazo[1,2-a]pyridin-6-yl)acetate (30 g, 145 mmol) in DCM (700 mL) was added Dess-Martin periodinane (74 g, 174 mmol) at 0° C. Then the reaction was allowed to warm up to rt and stirred for 2 h. The reaction mixture was washed by saturated NaHCO$_3$ solution and brine. The organic phase was dried over Na$_2$SO$_4$, filtered, concentrated, and purified by silica gel column chromatography (0-100% gradient EtOAc/hexanes) to give the product (30 g, quantative).

Preparation of isopropyl (R)-2-amino-2-(imidazo[1,2-a]pyridin-6-yl)-4,4-dimethylpentanoate: Isopropyl (R)-2-amino-2-(imidazo[1,2-a]pyridin-6-yl)-4,4-dimethylpentanoate was prepared following the procedure to prepare isopropyl (R)-2-amino-2-(4-bromophenyl)-4,4-dimethylpentanoate, starting with methyl 2-(imidazo[1,2-a]pyridin-6-yl)-2-oxoacetate.

Preparation of isopropyl (R)-2-(3-((benzyloxy)carbonyl)thioureido)-2-(imidazo[1,2-a]pyridin-6-yl)-4,4-dimethylpentanoate: Isopropyl (R)-2-(3-((benzyloxy)carbonyl)thioureido)-2-(imidazo[1,2-a]pyridin-6-yl)-4,4-dimethylpentanoate was prepared following the procedure to prepare isopropyl (R)-2-(3-((benzyloxy)carbonyl)thioureido)-2-(4-(1-(difluoromethyl)-1H-pyrazol-4-yl)phenyl)-4,4-dimethylpentanoate, starting with isopropyl (R)-2-amino-2-(imidazo[1,2-a]pyridin-6-yl)-4,4-dimethylpentanoate.

Compound 366 was then prepared by following the procedure to prepare Compound 220, except that (S)-2-amino-2-(4-chloro-3-(5-(difluoromethyl)-1H-1,2,4-triazol-1-yl)phenyl)ethyl ((S)-1,1,1-trifluoropropan-2-yl)carbamate was used instead of (S)-2-amino-2-(4-chloro-3-(5-(difluoromethyl)-1H-1,2,4-triazol-1-yl)phenyl)ethyl (1-(trifluoromethyl)cyclopropyl)carbamate, starting with isopropyl (R)-2-(3-((benzyloxy)carbonyl)thioureido)-2-(imidazo[1,2-a]pyridin-6-yl)-4,4-dimethylpentanoate. LCMS-ESI+: calc'd $C_{30}H_{32}ClF_5N_9O_3$: 696.2 (M+H+). Found: 696.9 (M+H+). $^1$H NMR (400 MHz, Methanol-$d_4$) δ 8.88 (s, 1H), 8.21-7.94 (m, 4H), 7.88 (d, J=9.6 Hz, 1H), 7.70-7.51 (m, 2H), 7.39 (s, 1H), 6.77 (t, J=52.2 Hz, 1H), 5.71 (dd, J=9.6, 5.0 Hz, 1H), 5.20-5.03 (m, 1H), 4.79-4.75 (m, 1H), 4.39-4.19 (m, 1H), 2.47 (d, J=15.0 Hz, 1H), 2.21 (d, J 15.0 Hz, 1H), 1.30 (d, J=7.1 Hz, 3H), 1.02 (s, 9H).

Example 111: Preparation of Compound 367

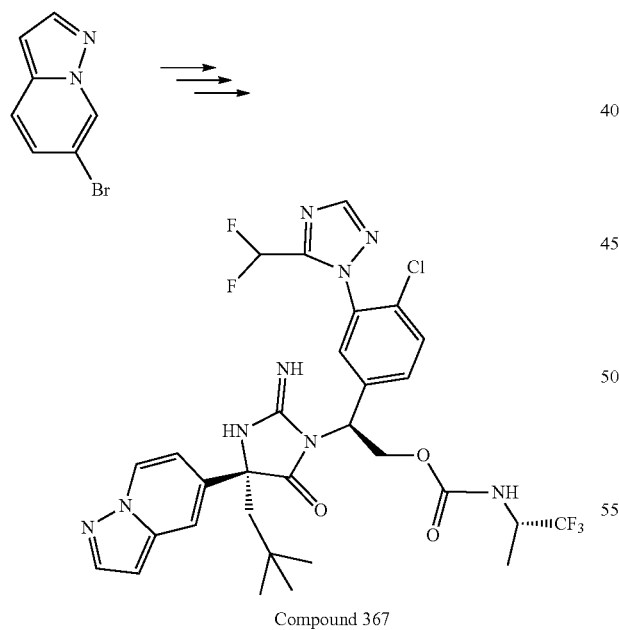

Compound 367

Compound 367 was prepared following the procedure to prepare Compound 366. LCMS-ESI+: calc'd $C_{30}H_{32}ClF_5N_9O_3$: 696.2 (M+H+). Found: 696.9 (M+H+). $^1$H NMR (400 MHz, Methanol-$d_4$) δ 8.49 (d, J=7.5 Hz, 1H), 8.10-7.97 (m, 2H), 7.68-7.52 (m, 3H), 7.28 (s, 1H), 7.04-6.49 (m, 3H), 5.76 (dd, J=9.6, 5.0 Hz, 1H), 5.19-5.04 (m, 1H), 4.80-4.68 (m, 1H), 4.36-4.12 (m, 1H), 2.49 (d, J=15.1 Hz, 1H), 2.18 (d, J=15.2 Hz, 1H), 1.25 (d, J=7.1 Hz, 3H), 1.02 (s, 9H).

Example 112: Preparation of Compound 368

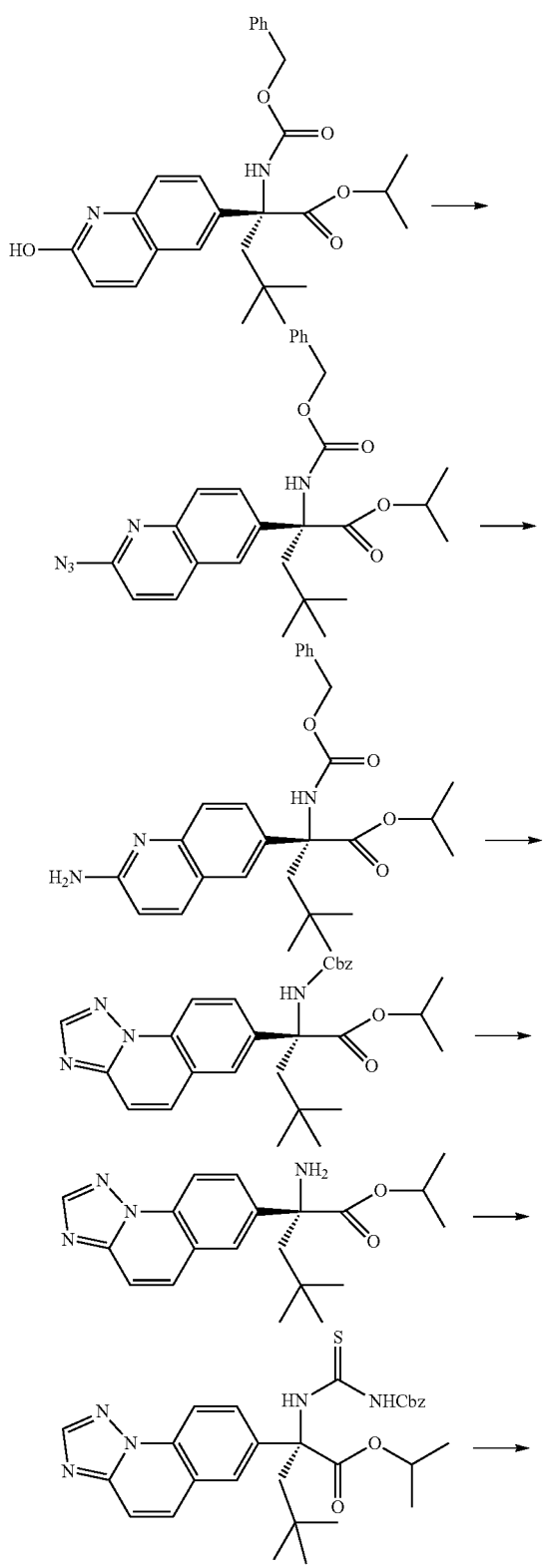

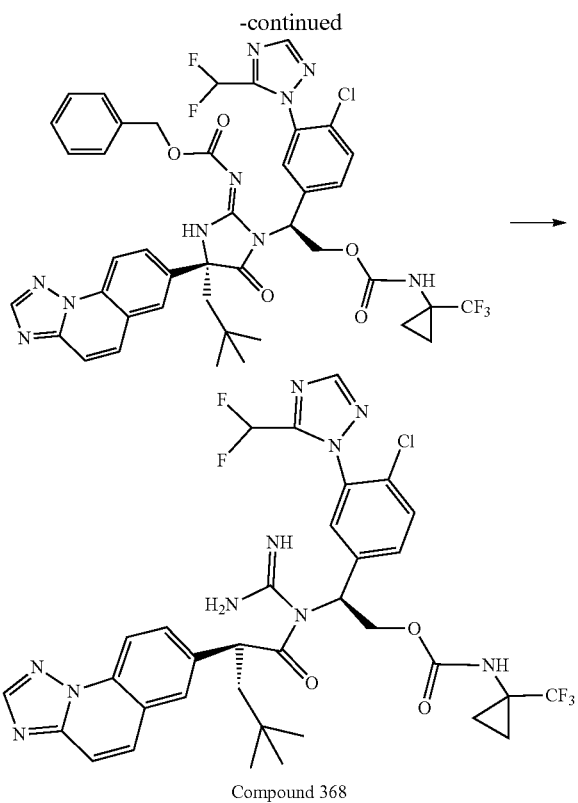

Compound 368

Preparation of isopropyl (R)-2-(2-azidoquinoline-6-yl)-2-(((benzyloxy)carbonyl)amino)-4,4-dimethylpentanoate: A mixture of isopropyl (R)-2-(((benzyloxy)carbonyl)amino)-2-(2-hydroxyquinolin-6-yl)-4,4-dimethylpentanoate (0.52 g, 1.12 mmol) and diphenyl phosphorazidate (0.37 g, 1.34 mmol) in pyridine (3.0 mL) was stirred at 120° C. for 16 h. The reaction mixture partitioned between ethyl acetated and saturated NaHCO₃ solution. The organic layer was concentrated down and used directly for the next reaction without further purification.

Preparation of isopropyl (R)-2-(2-aminoquinolin-6-yl)-2-(((benzyloxy)carbonyl)amino)-4,4-dimethylpentanoate: A mixture of isopropyl (R)-2-(2-azidoquinoline-6-yl)-2-(((benzyloxy)carbonyl)amino)-4,4-dimethylpentanoate (0.55 g, 1.12 mmol) and triethylphosphine (0.4 g, 3.39 mmol) in THF (20 mL) and water (2 mL) was stirred at 80° C. for 16 h. The reaction mixture was partitioned between ethyl acetate and saturated NaHCO₃ solution. The organic layer was concentrated and the residue was purified by silica gel column chromatography (0-100% gradient EtOAc/hexanes) to give the product.

Preparation of isopropyl (R)-2-([1,2,4]triazolo[1,5-a]quinolin-7-yl)-2-(((benzyloxy)carbonyl)amino)-4,4-dimethylpentanoate: A mixture of isopropyl (R)-2-(2-aminoquinolin-6-yl)-2-(((benzyloxy)carbonyl)amino)-4,4-dimethylpentanoate (0.46 g, 0.99 mmol), dimethoxymethyldimethylamine (1.18 g, 9.92 mmol) in DMF (2 mL) was heated at 130° C. for 1 h. Then the reaction mixture was concentrated. The residue was dissolved in methanol (3 mL) and pyridine (1 mL). To the solution was added hydroxylamine-O-sulfonate (0.22 g, 1.98 mmol). The mixture was stirred at 45° C. for 16 h. The reaction mixture was concentrated. The residue was partitioned between ethyl acetate and water. The organic phase was concentrated down and purified by silica gel column chromatography (0-100% gradient EtOAc/hexanes) to give the product.

Preparation of isopropyl (R)-2-([1,2,4]triazolo[1,5-a]quinolin-7-yl)-2-amino-4,4-dimethylpentanoate: A solution of isopropyl (R)-2-([1,2,4]triazolo[1,5-a]quinolin-7-yl)-2-(((benzyloxy)carbonyl)amino)-4,4-dimethylpentanoate (0.24 g, 0.49 mmol) in TFA (2.0 mL) was heated at 60° C. for 8 h. The mixture was concentrated and used directly in the next reaction.

Compound 368 was then prepared by following the procedure to prepare Compound 220. LCMS-ESI+: calc'd $C_{34}H_{33}ClF_5N_{10}O_3$: 759.2 (M+H+). Found: 759.8 (M+H+). ¹H NMR (400 MHz, Methanol-$d_4$) δ 8.55 (s, 1H), 8.48 (d, J=8.9 Hz, 1H), 8.19 (s, 1H), 8.09 (d, J=2.1 Hz, 1H), 8.02 (d, J=9.4 Hz, 1H), 7.93 (dd, J=8.9, 2.2 Hz, 1H), 7.85-7.66 (m, 2H), 7.58 (d, J=1.3 Hz, 2H), 7.03 (s, 1H), 6.63 (t, J=52.1 Hz, 1H), 5.71 (dd, J=9.7, 4.9 Hz, 1H), 5.11 (t, J=10.6 Hz, 1H), 4.72 (dd, J=11.5, 4.9 Hz, 1H), 2.61 (d, J=15.2 Hz, 1H), 2.26 (d, J=15.2 Hz, 1H), 1.27 (d, J=6.4 Hz, 2H), 1.09 (s, 2H), 1.03 (s, 9H).

Example 113: Preparation of Compound 369

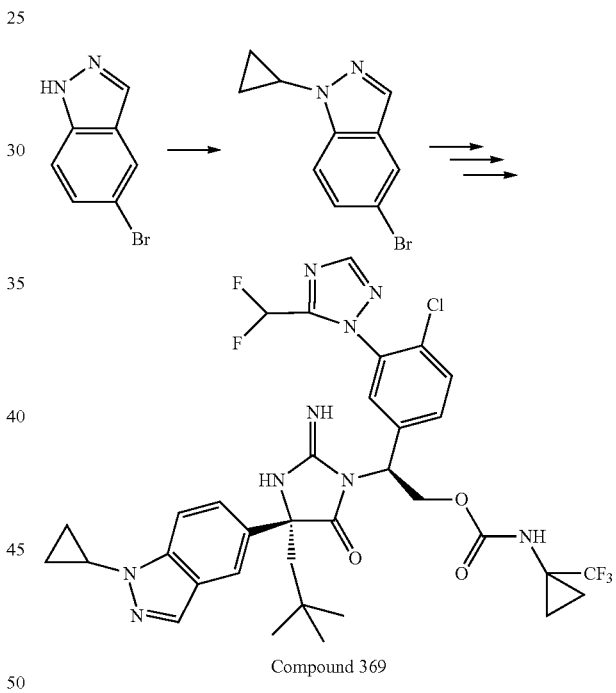

Compound 369

Preparation of 5-bromo-1-cyclopropyl-1H-indazole: To a mixture of 5-bromo-1H-indazole (150 g, 761 mmol) in DCM (4.0 L) were added cyclopropylboronic acid (131 g, 1.52 mol), bipyridinyl (119 g, 761 mmol), Cu(OAc)₂ (138 g, 761 mmol) and Na₂CO₃ (161 g, 1.52 mol). The reaction mixture was stirred at 60° C. for 12 h. The reaction mixture was filtered through Celite and the filter cake was washed with DCM. The filtrate and the washings were washed with 1 N HCl, and then with brine, dried over Na₂SO₄, filtered, and concentrated. The residue was purified by silica gel column chromatography (0-100% gradient EtOAc/hexanes) to give the product.

Compound 369 was then prepared by following the procedure to prepare Compound 366, except that (S)-2-amino-2-(4-chloro-3-(5-(difluoromethyl)-1H-1,2,4-triazol-1-yl)phenyl)ethyl ((S)-1,1,1-trifluoropropan-2-yl)carbamate was used instead of (S)-2-amino-2-(4-chloro-3-(5-(difluoromethyl)-1H-1,2,4-triazol-1-yl)phenyl)ethyl ((S)-1,1,1-trifluoropropan-2-yl)carbamate. LCMS-ESI+: calc'd $C_{34}H_{36}ClF_5N_9O_3$: 748.2 (M+H+). Found: 748.4 (M+H+). 1H NMR (400 MHz, Methanol-$d_4$) δ 8.17 (s, 1H), 7.98 (s, 1H), 7.94 (d, J=0.9 Hz, 1H), 7.73 (dd, J=1.9, 0.8 Hz, 1H), 7.69-7.43 (m, 4H), 7.02 (s, 1H), 6.64 (t, J=52.2 Hz, 1H), 5.69 (dd, J=9.6, 4.9 Hz, 1H), 5.10 (t, J=10.6 Hz, 1H), 4.70 (dd, J=11.5, 5.0 Hz, 1H), 3.69 (p, J=5.4 Hz, 1H), 2.53 (d, J=15.2 Hz, 1H), 2.18 (d, J=15.1 Hz, 1H), 1.32-1.23 (m, 2H), 1.24-1.15 (m, 4H), 1.08 (s, 2H), 1.00 (s, 9H).

Example 114: Preparation of Compound 370

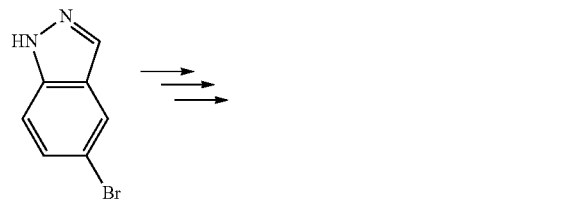

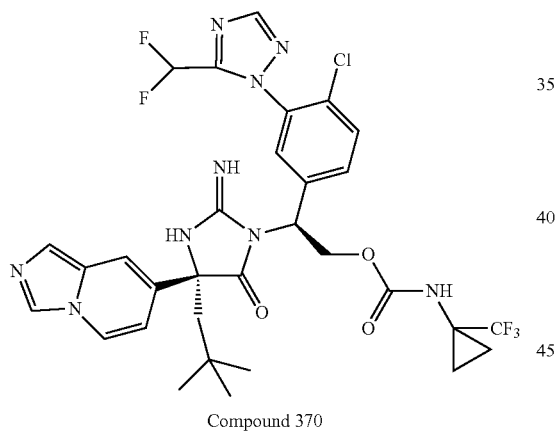

Compound 370

Compound 370 was prepared by following the procedure to prepare Compound 366, except that (S)-2-amino-2-(4-chloro-3-(5-(difluoromethyl)-1H-1,2,4-triazol-1-yl)phenyl)ethyl ((S)-1,1,1-trifluoropropan-2-yl)carbamate was used instead of (S)-2-amino-2-(4-chloro-3-(5-(difluoromethyl)-1H-1,2,4-triazol-1-yl)phenyl)ethyl ((S)-1,1,1-trifluoropropan-2-yl)carbamate. LCMS-ESI+: calc'd $C_{31}H_{32}ClF_5N_9O_3$: 708.2 (M+H+). Found: 708.2 (M+H+). $^1$H NMR (400 MHz, Methanol-$d_4$) δ 9.04 (s, 1H), 8.36 (dd, J=7.7, 1.2 Hz, 1H), 8.19 (s, 1H), 8.06 (s, 1H), 7.77 (s, 1H), 7.68 (s, 1H), 7.63 (d, J=1.3 Hz, 2H), 7.32 (s, 1H), 7.08 (dd, J=7.6, 2.0 Hz, 1H), 6.77 (t, J=52.2 Hz, 1H), 5.67 (dd, J=9.7, 4.8 Hz, 1H), 5.11 (t, J=10.7 Hz, 1H), 4.72 (dd, J=11.5, 4.9 Hz, 1H), 2.44 (d, J=15.2 Hz, 1H), 2.15 (d, J=15.2 Hz, 1H), 1.36-1.20 (m, 2H), 1.09 (s, 2H), 1.01 (s, 9H).

Example 115: Preparation of Compound 371 and Compound 372

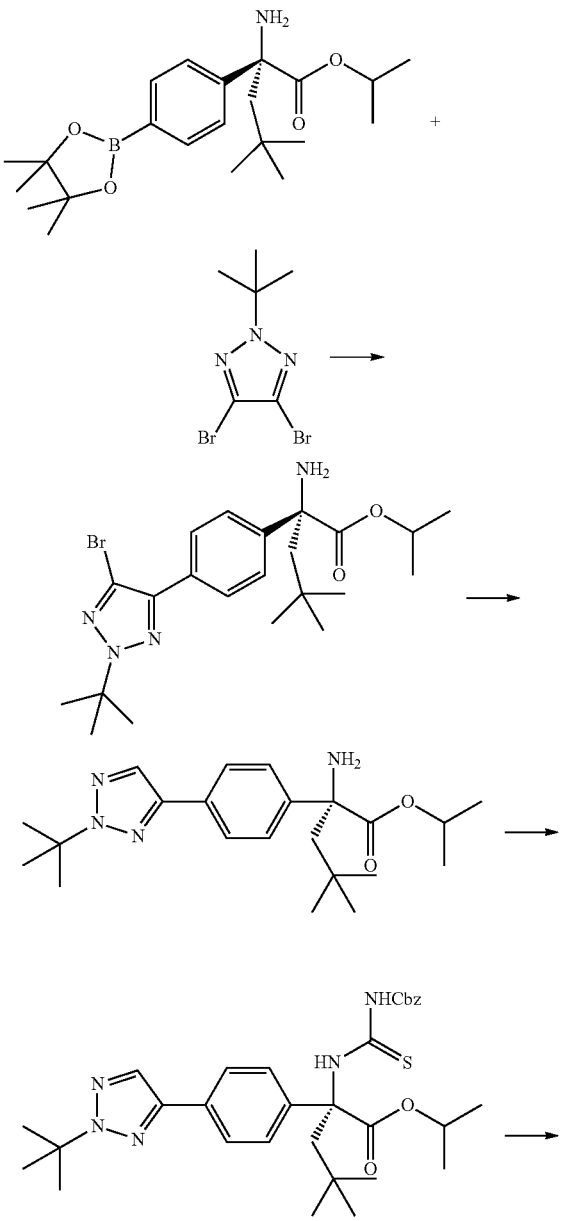

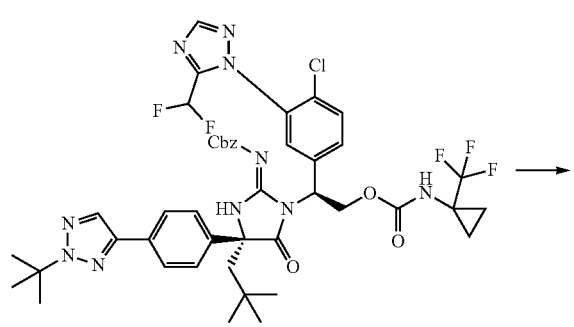

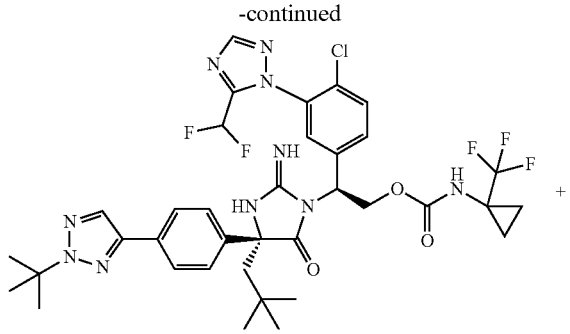

Compound 371

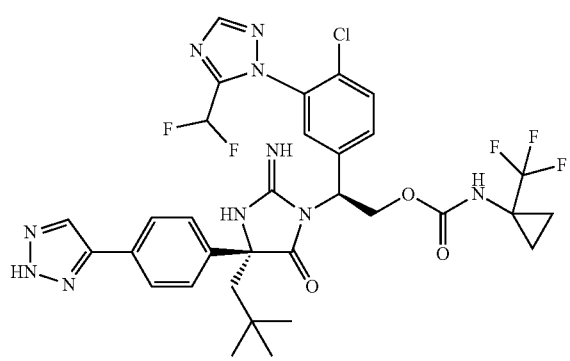

Compound 372

Preparation of 4,5-dibromo-2-(tert-butyl)-2H-1,2,3-triazole: The reaction mixture of 4,5-dibromo-2H-1,2,3-triazole (100 mg, 0.44 mmol) and sulfuric acid (17.8 M, 0.025 mL) in tert-butanol (2.5 mL) was heated to 80° C. overnight. The reaction mixture was dilute with EtOAc and was carefully quenched with saturated aqueous $NaHCO_3$. The two layers were separated and the aqueous layer was further extracted with EtOAc. The combined organic layers were washed with brine, dried (over $Na_2SO_4$), filtered and concentrated in vacuo. The residue was purified by silica gel column chromatography (0-100% EtOAc/hexanes) to give the product.

Compound 371 and Compound 372 were prepared following the procedure to prepare Compound 222, except that 4 4,5-dibromo-2-(tert-butyl)-2H-1,2,3-triazole was used instead of 4,5-dibromo-2-(methyl-$d_3$)-2H-1,2,3-triazole. For Compound 371: LCMS-ESI+: calc'd $C_{36}H_{40}ClF_5N_{10}O_3$: 791.3 (M+H+). Found: 791.2 (M+H+). $^1$H NMR (400 MHz, Methanol-$d_4$) δ 8.16 (s, 1H), 7.99 (d, J=3.7 Hz, 2H), 7.79 (d, J=8.4 Hz, 2H), 7.61 (d, J=8.4 Hz, 1H), 7.55 (dd, J=8.6, 2.2 Hz, 1H), 7.47 (d, J=8.5 Hz, 2H), 7.23 (s, 1H), 6.77 (t, J=52.2 Hz, 1H), 5.68 (dd, J=9.7, 4.9 Hz, 1H), 5.10 (t, J=10.6 Hz, 1H), 4.70 (dd, J=11.5, 4.9 Hz, 1H), 2.46 (d, J=15.2 Hz, 1H), 2.16 (d, J=15.1 Hz, 1H), 1.72 (s, 9H), 1.26 (t, J=3.9 Hz, 2H), 1.08 (m, 2H), 0.99 (s, 9H). For Compound 372: LCMS-ESI+: calc'd $C_{32}H_{32}ClF_5N_{10}O_3$: 735.2 (M+H+). Found: 735.2 (M+H+). $^1$H NMR (400 MHz, Methanol-$d_4$) δ 8.19 (d, J=7.1 Hz, 2H), 8.01 (s, 1H), 7.88-7.78 (m, 2H), 7.61 (d, J=8.4 Hz, 1H), 7.55 (dd, J=8.6, 2.2 Hz, 1H), 7.52-7.43 (m, 2H), 7.22 (s, 1H), 6.78 (t, J=52.2 Hz, 1H), 5.69 (dd, J=9.8, 4.8 Hz, 1H), 5.10 (t, J=10.6 Hz, 1H), 4.71 (dd, J=11.5, 4.9 Hz, 1H), 2.48 (d, J=15.1 Hz, 1H), 2.17 (d, J=15.0 Hz, 1H), 1.32-1.25 (m, 2H), 1.13-1.05 (m, 2H), 1.00 (s, 9H). 1.13-1.05 (m, 2H), 1.00 (s, 9H).

Example 116: Preparation of Compound 373

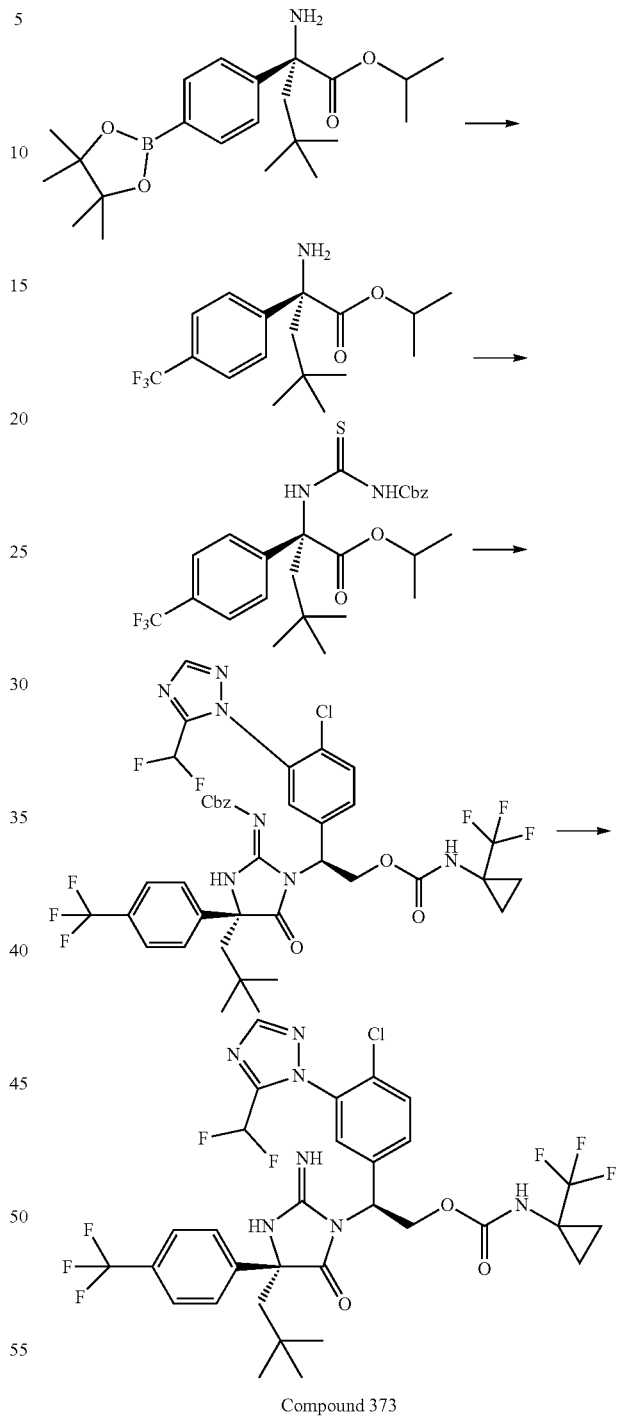

Compound 373

Preparation of isopropyl (R)-2-amino-4,4-dimethyl-2-(4-(trifluoromethyl)phenyl)pentanoate: A mixture of isopropyl (R)-2-amino-4,4-dimethyl-2-(4-(4,4,5,5-tetramethyl-1,3,2-dioxaborolan-2-yl)phenyl)pentanoate (150 mg, 0.39 mmol), Hartwig reagent (144 mg, 0.46 mmol) and potassium fluoride (22 mg, 0.39 mmol) in DMF (3.5 mL) was stirred at 50° C. overnight. The reaction mixture was cooled and filtered through a pad of celite. The filtrate was washed with 10% lithium chloride, and extracted with ethyl acetate. The organic phase was dried over MgSO$_4$, filtered, concentrated. The residue was purified by silica gel column chromatography (0-100% gradient EtOAc/hexanes) to give the product.

Compound 373 was then prepared by following the procedure to prepare Compound 220. LCMS-ESI+: calc'd for C$_{31}$H$_{30}$ClF$_8$N$_7$O$_3$: 736.20 (M+H). Found: 736.71 (M+H). $^1$H NMR (400 MHz, Methanol-d$_4$) δ 8.22-8.17 (m, 2H), 7.71-7.53 (m, 6H), 7.43-7.33 (m, 1H), 6.80 (t, J=52.2 Hz, 1H), 5.66 (dd, J=9.8, 4.8 Hz, 1H), 5.11 (dd, J=11.5, 9.9 Hz, 1H), 4.69 (dd, J=11.5, 4.8 Hz, 1H), 2.43 (d, J=15.1 Hz, 1H), 2.16 (d, J=15.1 Hz, 1H), 1.29-1.24 (m, 2H), 1.11-1.03 (m, 2H), 0.97 (s, 9H).

Example 117: Preparation of Compound 374

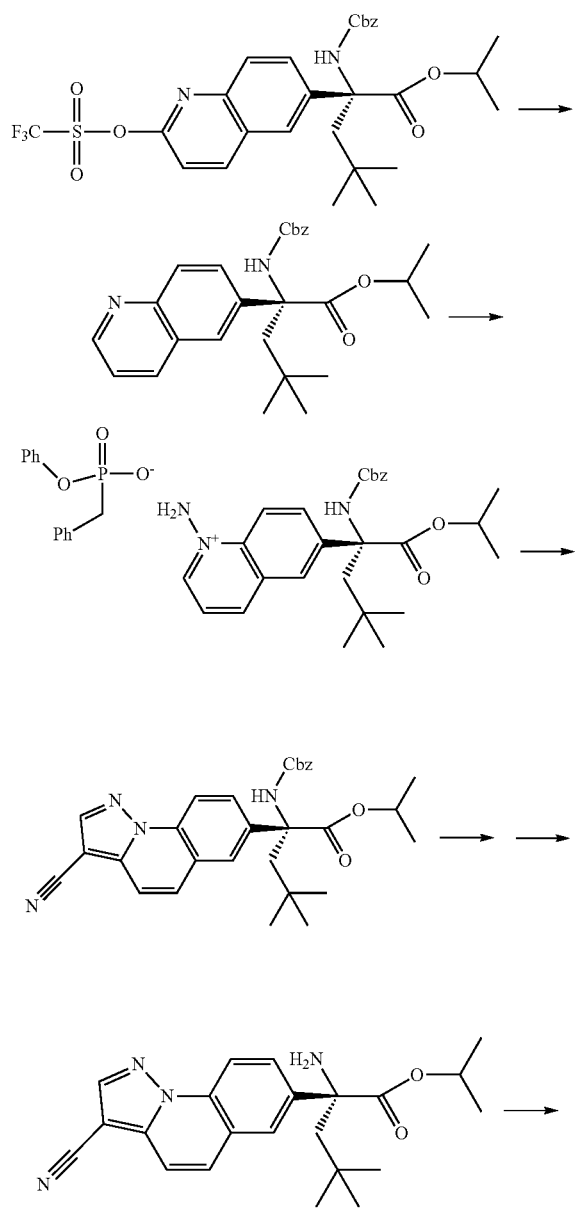

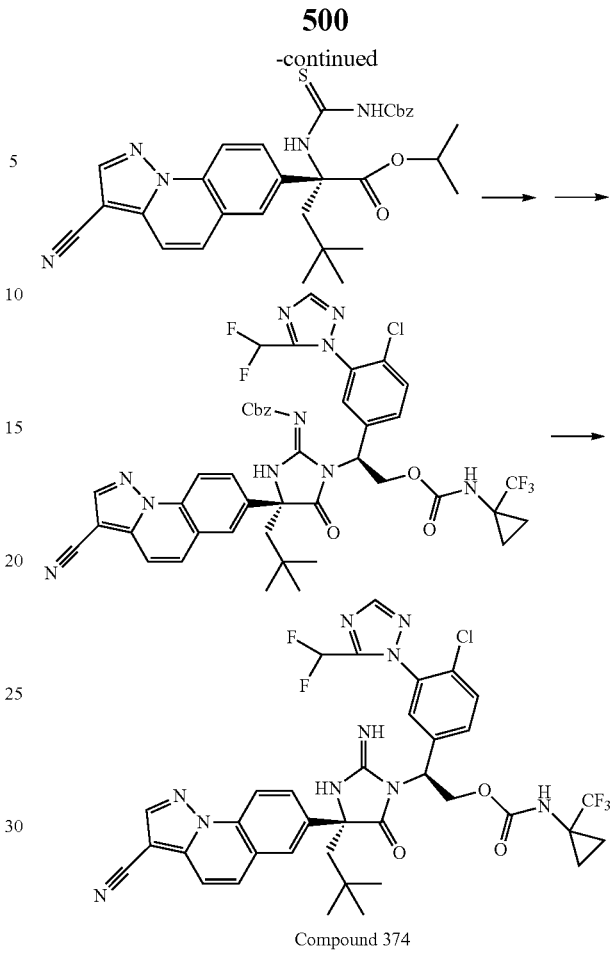

Compound 374

Preparation of isopropyl (R)-2-(((benzyloxy)carbonyl) amino)-4,4-dimethyl-2-(quinolin-6-yl)pentanoate: A mixture of isopropyl (R)-2-(((benzyloxy)carbonyl)amino)-4,4-dimethyl-2-(2-(((trifluoromethyl)sulfonyl)oxy)quinolin-6-yl)pentanoate (0.35 g, 0.59 mmol), Pd(PPh$_3$)$_4$ (100 mg, 0.086 mmol), triethylsilane (2 mL, 12.5 mmol), TEA (0.5 mL, 3.58 mmol) in THF (20 mL) was heated at 80° C. for 16 h. The reaction mixture was concentrated and purified by silica gel column chromatography (0-100% gradient EtOAc/hexanes) to give the product.

Preparation of diphenyl hydrogen phosphate, (R)-1-amino-6-(2-(((benzyloxy)carbonyl)amino)-1-isopropoxy-4,4-dimethyl-1-oxopentan-2-yl)quinolin-1-ium salt: A mixture of isopropyl (R)-2-(((benzyloxy)carbonyl)amino)-4,4-dimethyl-2-(quinolin-6-yl)pentanoate (0.22 g, 0.49 mmol), diphenyl (aminooxy)phosphonate (0.17 g, 0.64 mmol) in 1,2-dichloroethane (5 mL) was heated at 60° C. for 16 h. The reaction mixture was concentrated and directly used for the next reaction.

Preparation of isopropyl (R)-2-(((benzyloxy)carbonyl) amino)-2-(3-cyanopyrazolo[1,5-a]quinolin-7-yl)-4,4-dimethylpentanoate: A mixture of diphenyl hydrogen phosphate, (R)-1-amino-6-(2-(((benzyloxy)carbonyl)amino)-1-isopropoxy-4,4-dimethyl-1-oxopentan-2-yl)quinolin-1-ium salt (0.18 g, 0.245 mmol) was dissolved in ethanol (5 mL). To this mixture triethylamine (0.07 g, 0.73 mmol) and 3-methoxyacrylonitrile (0.06 g, 0.73 mmol) was added. The mixture was stirred at 60° C. for 16 h. The mixture was concentrated and purified by silica gel column chromatography (0-100% gradient EtOAc/hexanes) to give the product.

Preparation of isopropyl (R)-2-amino-2-(3-cyanopyrazolo[1,5-a]quinolin-7-yl)-4,4-dimethylpentanoate: A mixture of isopropyl (R)-2-(((benzyloxy)carbonyl)amino)-2-(3-cyanopyrazolo[1,5-a]quinolin-7-yl)-4,4-dimethylpentanoate (0.096 g, 0.19 mmol) and TFA (1 mL) was heated at 60° C. for 4 h. The reaction mixture was concentrated and directly used in the next step. Compound 374 was then prepared by following the procedure to prepare Compound 220. LCMS-ESI+: calc'd $C_{36}H_{32}ClF_5N_{10}O_3$: 783. (M+H+). Found: 783.3 (M+H+). $^1$H NMR (400 MHz, Methanol-$d_4$) δ 8.55 (d, J=9.0 Hz, 1H), 8.50 (s, 1H), 8.22 (s, 1H), 8.04 (d, J=2.2 Hz, 1H), 7.94-7.83 (m, 2H), 7.79 (d, J=9.2 Hz, 2H), 7.58 (d, J=1.3 Hz, 2H), 7.01 (s, 1H), 6.64 (t, J=52.3 Hz, 1H), 5.72 (dd, J=9.7, 4.8 Hz, 1H), 5.16-5.04 (m, 1H), 4.72 (dd, J=11.5, 4.9 Hz, 1H), 2.61 (d, J=15.2 Hz, 1H), 2.24 (d, J=15.2 Hz, 1H), 1.27 (d, J=6.1 Hz, 2H), 1.09 (s, 2H), 1.03 (s, 9H).

Example 118: Preparation of Compound 375

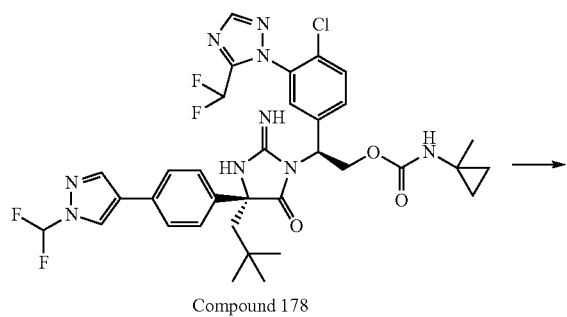

Compound 178

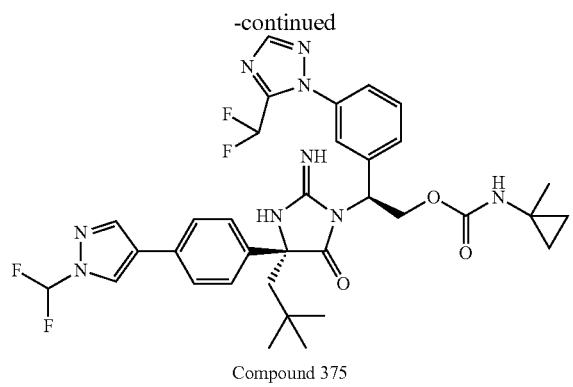

Compound 375

Preparation of Compound 375: To a solution of Compound 178 (9 mg, 0.01 mmol) in ethanol (1.0 mL) under an atmosphere of argon was added platinum(IV) oxide (4.9 mg, 0.02 mmol). Argon was replaced by hydrogen (balloon of hydrogen gas) via several purge-pump cycles, and the reaction mixture was stirred at rt overnight. The reaction mixture was filtered through a pad of Celite, and purified by reverse phase HPLC (MeCN/H$_2$O+0.1% TFA), which was re-purified by silica gel column chromatography (MeOH/(CH$_2$Cl$_2$/hexanes, 3:1) to give the product. LCMS-ESI+: calc'd for $C_{34}H_{37}F_4N_9O_3$: 696.3 (M+H+). Found: 696.4 (M+H+). 1H NMR (400 MHz, Methanol-$d_4$) δ 8.38 (s, 1H), 8.05 (s, 1H), 8.00 (s, 1H), 7.71-7.23 (m, 9H), 6.81 (t, J=52.1 Hz, 1H), 5.60-5.41 (m, 1H), 5.01 (t, J=10.1 Hz, 1H), 4.65 (dd, J=11.1, 5.7 Hz, 1H), 2.31 (d, J=14.6 Hz, 1H), 1.96 (d, J=14.6 Hz, 1H), 1.28 (s, 3H), 0.96 (s, 9H), 0.65 (s, 2H), 0.53 (s, 2H).

Example 119: Preparation of Compound 376

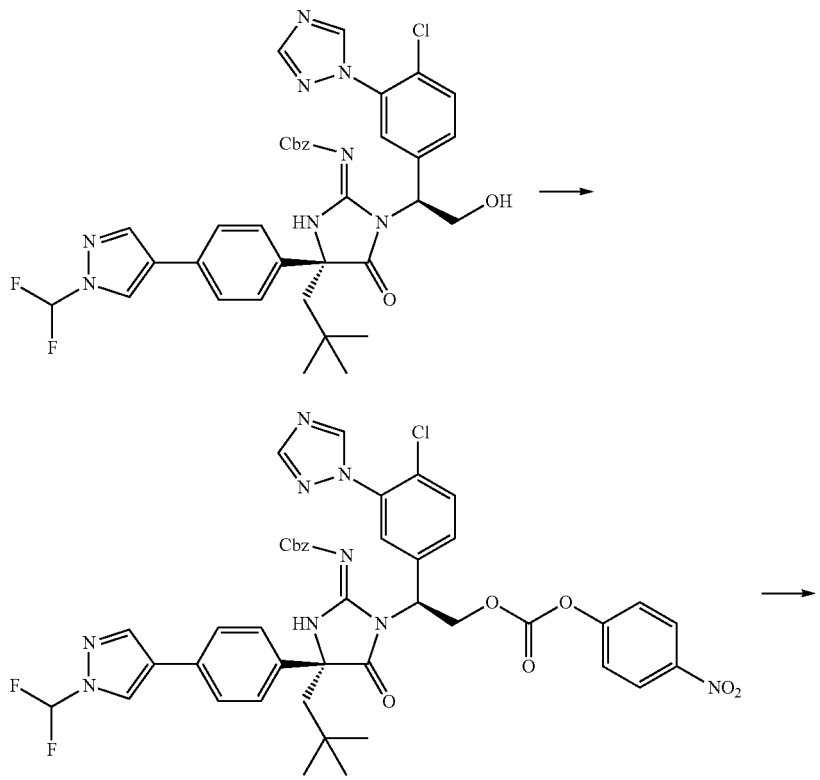

-continued

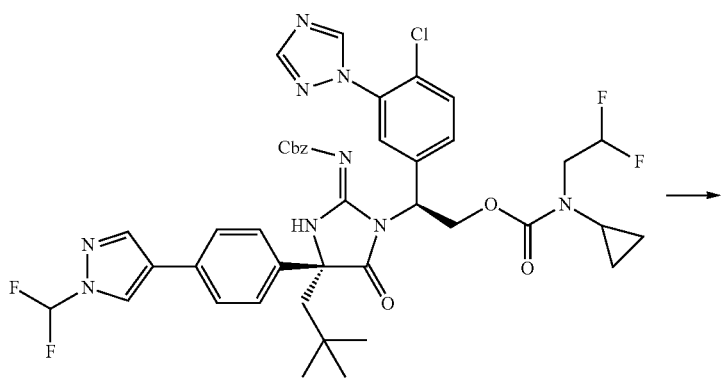

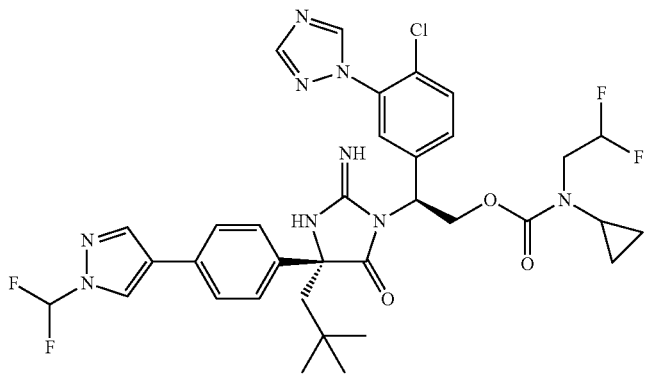

Compound 376

Preparation of benzyl ((R)-1-((S)-1-(4-chloro-3-(1H-1,2,4-triazol-1-yl)phenyl)-2-0(4-nitrophenoxy)carbonyl)oxy)ethyl)-4-(4-(1-(difluoromethyl)-1H-pyrazol-4-yl)phenyl)-4-neopentyl-5-oxoimidazolidin-2-ylidene)carbamate: To a solution of benzyl ((R)-1-((S)-1-(4-chloro-3-(1H-1,2,4-triazol-1-yl)phenyl)-2-hydroxyethyl)-4-(4-(1-(difluoromethyl)-1H-pyrazol-4-yl)phenyl)-4-neopentyl-5-oxoimidazolidin-2-ylidene)carbamate (130 mg, 0.18 mmol) in DCM (2 mL) was added 4-nitrophenyl carbonochloridate (54.8 mg, 0.27 mmol) followed by N,N-diisopropylethylamine (0.22 mL, 1.27 mmol). The reaction mixture was stirred at rt for 24 h. The mixture was concentrated down an purified by silica gel column chromatography (0-100% gradient EtOAc/hexanes) to give the product.

Preparation of (S)-2-((R)-2-(((benzyloxy)carbonyl)imino)-4-(4-(1-(difluoromethyl)-1H-pyrazol-4-yl)phenyl)-4-neopentyl-5-oxoimidazolidin-1-yl)-2-(4-chloro-3-(1H-1,2,4-triazol-1-yl)phenyl)ethyl cyclopropyl(2,2-difluoroethyl)carbamate: To a solution of benzyl ((R)-1-((S)-1-(4-chloro-3-(1H-1,2,4-triazol-1-yl)phenyl)-2-(((4-nitrophenoxy)carbonyl)oxy)ethyl)-4-(4-(1-(difluoromethyl)-1H-pyrazol-4-yl)phenyl)-4-neopentyl-5-oxoimidazolidin-2-ylidene)carbamate (22 mg, 0.02 mmol) in DCM (1 mL) were added N-(2,2-difluoroethyl)cyclopropanamine hydrochloride (39.3 mg, 0.25 mmol) and N-ethyldiisopropylamine (0.22 mL, 1.25 mmol). The reaction mixture was stirred at 40° C. for 24 h. The reaction mixture was concentrated and purified by silica gel column chromatography to give the product.

Compound 376 was then prepared following the procedure to prepare Compound 244, staring with (S)-2-((R)-2-(((benzyloxy)carbonyl)imino)-4-(4-(1-(difluoromethyl)-1H-pyrazol-4-yl)phenyl)-4-neopentyl-5-oxoimidazolidin-1-yl)-2-(4-chloro-3-(1H-1,2,4-triazol-1-yl)phenyl)ethyl cyclopropyl(2,2-difluoroethyl)carbamate. LCMS-ESI+: calc'd for $C_{34}H_{36}ClF_4N_9O_3$: 730.3 (M+H+). Found: 730.0 (M+H+). $^1$H NMR (400 MHz, Methanol-$d_4$) δ 8.70 (s, 1H), 8.47 (s, 1H), 8.08 (d, J=22.2 Hz, 2H), 7.80-7.23 (m, 7H), 7.37-7.32 (m, 1H), 5.99 (s, 1H), 5.28-5.05 (m, 1H), 4.84 (s, 1H), 3.84-3.37 (m, 2H), 3.17-2.77 (m, 2H), 2.99 (t, J=56 Hz, 1H), 2.47 (d, J=15.3 Hz, 1H), J=1.00 (s, 9H), 0.71 (d, J=40.3 Hz, 4H).

Example 120: Preparation of Compound 377

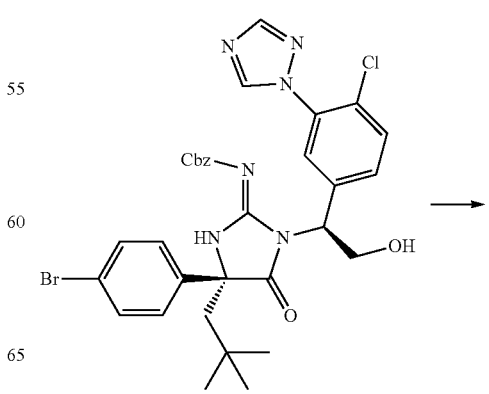

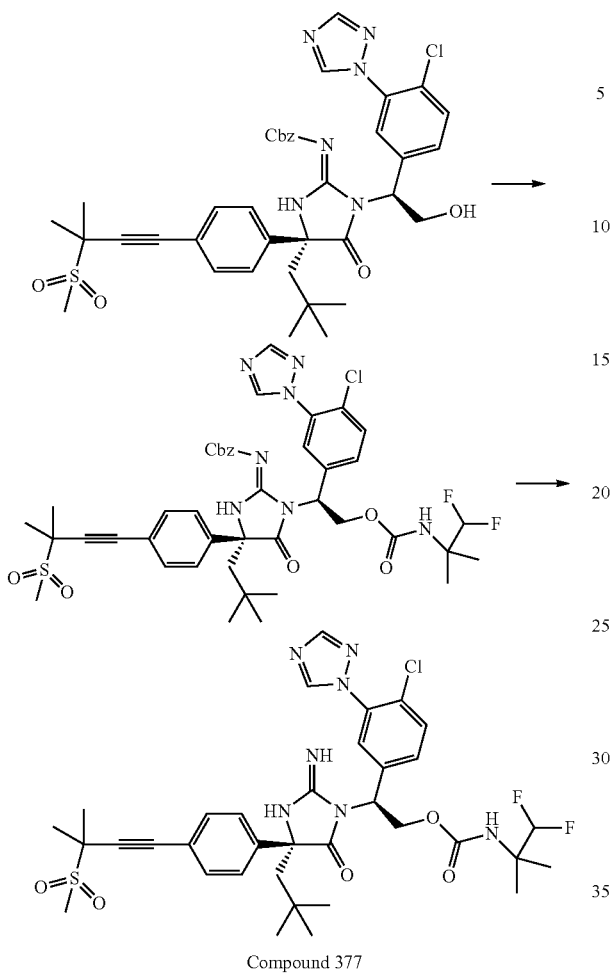

Compound 377

Preparation of benzyl ((R)-1-((S)-1-(4-chloro-3-(1H-1,2,4-triazol-1-yl)phenyl)-2-hydroxyethyl)-4-(4-(3-methyl-3-(methylsulfonyl)but-1-yn-1-yl)phenyl)-4-neopentyl-5-oxo-imidazolidin-2-ylidene)carbamate: A mixture of benzyl ((R)-4-(4-bromophenyl)-1-((S)-1-(4-chloro-3-(1H-1,2,4-triazol-1-yl)phenyl)-2-hydroxyethyl)-4-neopentyl-5-oxoimidazolidin-2-ylidene)carbamate (30 mg, 0.04 mmol), 3-methyl-3-(methylsulfonyl)but-1-yne (45 mg, 0.31 mmol), cuprous iodide (8.4 mg, 0.04 mmol), trakis(triphenylphosphine)palladium (13 mg, 0.088 mmol) and triethylamine (1.5 mL) was stirred at 80° C. for 17 h. The reaction mixture was treated with water, and extracted with EtOAc. The organic phase was washed with water and brine, and concentrated. The residue was purified by silica gel column chromatography (0-100% gradient EtOAc/hexanes) to give the product.

Compound 377 was then prepared following the procedure to prepare Compound 177, except that 3,3-difluoro-2,2-dimethylpropanoic acid was used instead of 1-(trifluoromethyl)cyclopropane-1-carboxylic acid. LCMS-ESI+: calc'd for $C_{35}H_{42}ClF_2N_7O_5S$: 746.3 (M+H+). Found: 747.9 (M+H+). $^1$H NMR (400 MHz, Methanol-$d_4$) δ 8.71 (s, 1H), 8.18 (s, 1H), 7.62 (d, J=8.5 Hz, 1H), 7.45 (s, 5H), 7.21 (d, J=2.3 Hz, 1H), 6.13 (t, J=57.3 Hz, 1H), 5.65 (dd, J=9.4, 5.1 Hz, 1H), 5.02 (dd, J=11.5, 9.4 Hz, 1H), 4.67 (dd, J=11.6, 5.2 Hz, 1H), 3.15 (s, 3H), 2.43 (d, J=15.1 Hz, 1H), 2.16 (d, J=15.1 Hz, 1H), 1.74 (s, 6H), 1.42-1.21 (m, 6H), 0.98 (s, 9H).

Example 121: Preparation of Compound 378

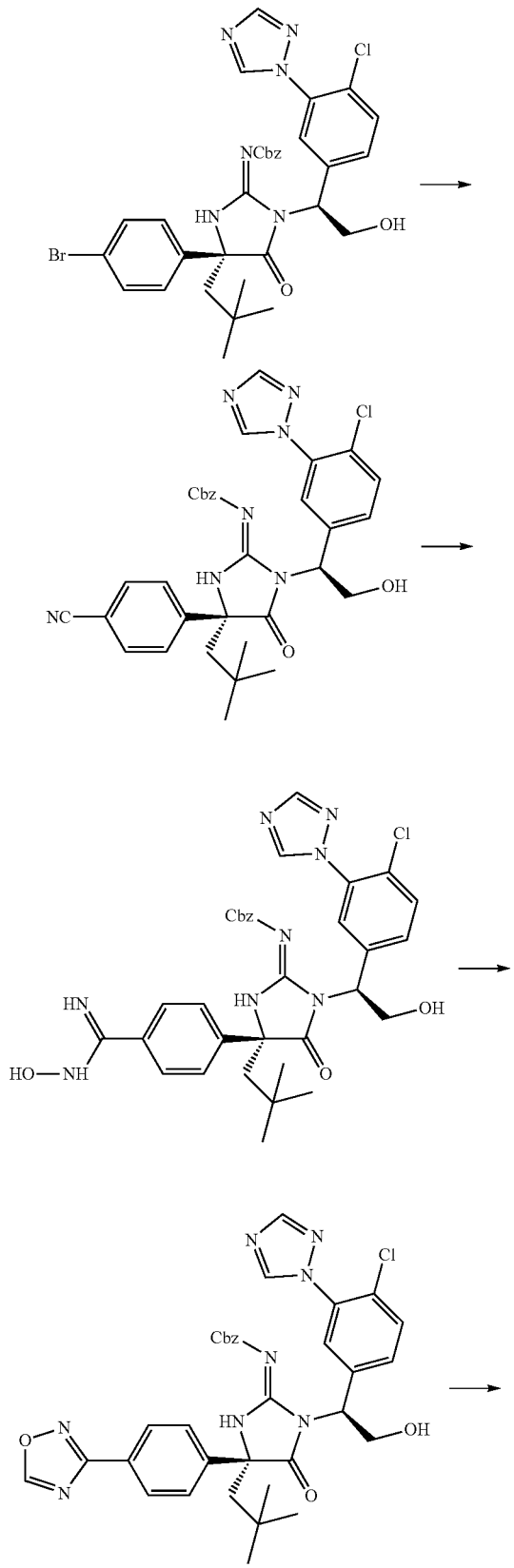

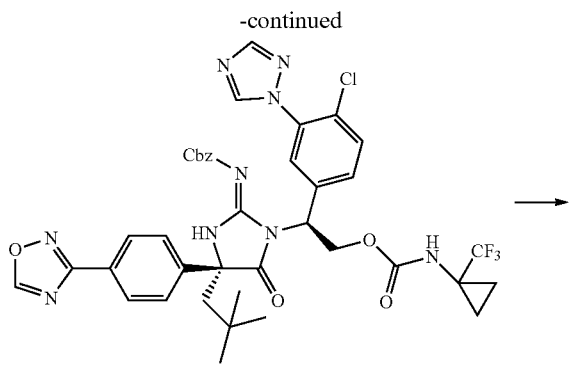

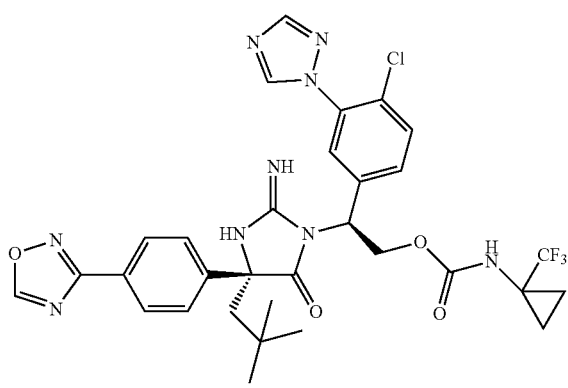

Compound 378

Preparation of benzyl ((R)-1-((S)-1-(4-chloro-3-(1H-1,2,4-triazol-1-yl)phenyl)-2-hydroxyethyl)-4-(4-cyanophenyl)-4-neopentyl-5-oxoimidazolidin-2-ylidene)carbamate: A mixture of benzyl ((R)-4-(4-bromophenyl)-1-((S)-1-(4-chloro-3-(1H-1,2,4-triazol-1-yl)phenyl)-2-hydroxyethyl)-4-neopentyl-5-oxoimidazolidin-2-ylidene)carbamate (200 mg, 0.32 mmol), zinc cyanide (152 mg, 1.29 mmol) and tetrakis(triphenylphosphine)palladium (56 mg, 0.05 mmol) in DMF (1.6 mL) was sparged with $N_2$ for 5 min, then the mixture was heated at 100° C. for 2 h. The reaction mixture was cooled and concentrated. The residue was purified by silica gel column chromatography (EtOAc/hexanes) to give the product (200 mg, 98%).

Preparation of benzyl ((R)-1-((S)-1-(4-chloro-3-(1H-1,2,4-triazol-1-yl)phenyl)-2-hydroxyethyl)-4-(4-(N-hydroxycarbamimidoyl)phenyl)-4-neopentyl-5-oxoimidazolidin-2-ylidene)carbamate: A mixture of benzyl ((R)-1-((S)-1-(4-chloro-3-(1H-1,2,4-triazol-1-yl)phenyl)-2-hydroxyethyl)-4-(4-cyanophenyl)-4-neopentyl-5-oxoimidazolidin-2-ylidene)carbamate (200 mg, 0.32 mmol), hydroxylamine hydrochloride (67 mg, 0.96 mmol) and triethylamine (0.45 mL, 3 mmol) in EtOH (4.0 mL) was heated at 100° C. for 4 h. The reaction mixture was cooled down to rt and concentrated down. The residue was washed with brine, and extracted with EtOAc. The organic phase was dried over $Na_2SO_4$, filtered, concentrated and purified by silica gel column chromatography (0-100% gradient EtOAc/hexanes) to give the product.

Preparation of ethyl ((R)-4-(4-(1,2,4-oxadiazol-3-yl)phenyl)-1-((S)-1-(4-chloro-3-(1H-1,2,4-triazol-1-yl)phenyl)-2-hydroxyethyl)-4-neopentyl-5-oxoimidazolidin-2-ylidene)carbamate: A mixture of benzyl ((R)-1-((S)-1-(4-chloro-3-(1H-1,2,4-triazol-1-yl)phenyl)-2-hydroxyethyl)-4-(4-(N-hydroxycarbamimidoyl)phenyl)-4-neopentyl-5-oxoimidazolidin-2-ylidene)carbamate (200 mg, 0.3 mmol) and triethyl orthoformate (45 mg, 0.30 mmol) was heated at 150° C. for 20 h. The reaction mixture was then cooled and concentrated. The residue was purified by silica gel column chromatography (0-100% gradient EtOAc/hexanes) to give the product.

Preparation of ethyl ((R)-4-(4-(1,2,4-oxadiazol-3-yl)phenyl)-1-((S)-1-(4-chloro-3-(1H-1,2,4-triazol-1-yl)phenyl)-2-(((1-(trifluoromethyl)cyclopropyl)carbamoyl)oxy)ethyl)-4-neopentyl-5-oxoimidazolidin-2-ylidene)carbamate: Ethyl ((R)-4-(4-(1,2,4-oxadiazol-3-yl)phenyl)-1-((S)-1-(4-chloro-3-(1H-1,2,4-triazol-1-yl)phenyl)-2-(((1-(trifluoromethyl)cyclopropyl)carbamoyl)oxy)ethyl)-4-neopentyl-5-oxoimidazolidin-2-ylidene)carbamate was prepared following the procedure to prepare ((R)-1-((S)-1-(4-chloro-3-(5-(difluoromethyl)-1H-1,2,4-triazol-1-yl)phenyl)-2-(((1-(trifluoromethyl)cyclopropyl)carbamoyl)oxy)ethyl)-4-(4-(1-(difluoromethyl)-1H-pyrazol-4-yl)phenyl)-4-neopentyl-5-oxoimidazolidin-2-ylidene)carbamate described in Example 65, starting with benzyl ((R)-1-((S)-1-(4-chloro-3-(1H-1,2,4-triazol-1-yl)phenyl)-2-hydroxyethyl)-4-(4-(N-hydroxycarbamimidoyl)phenyl)-4-neopentyl-5-oxoimidazolidin-2-ylidene)carbamate.

Preparation of Compound 378: A mixture of ethyl ((R)-4-(4-(1,2,4-oxadiazol-3-yl)phenyl)-1-((S)-1-(4-chloro-3-(1H-1,2,4-triazol-1-yl)phenyl)-2-(((1-(trifluoromethyl)cyclopropyl)carbamoyl)oxy)ethyl)-4-neopentyl-5-oxoimidazolidin-2-ylidene)carbamate (120 mg, 0.16 mmol) and bromotrimethylsilane (300 μL, 2.25 mmol) in 1-methyl-2-pyrrolidinone (2 mL) was heated at 120° C. for 30 min using a microwave reactor. The reaction mixture was cooled to rt, diluted with EtOAc, washed with 3% lithium chloride solution and then with brine. The organic phase was dried over $Na_2SO_4$, filtered, concentrated and purified by reverse phase HPLC with 10-90% MeCN/water containing 0.1% TFA to give the product. LCMS-ESI+: calc'd for $C_{31}H_{31}ClF_3N_9O_4$: 686.2 (M+H+). Found: 686.2 (M+H+). $^1$H NMR (400 MHz, Chloroform-d) δ 8.96 (s, 1H), 8.81 (s, 1H), 8.30 (d, J=19.3 Hz, 1H), 8.12 (d, J=8.1 Hz, 2H), 7.60 (dd, J=27.6, 15.2 Hz, 4H), 7.40 (d, J=8.6 Hz, 1H), 6.13 (d, J=41.1 Hz, 1H), 5.65 (s, 1H), 5.13 (t, J=10.2 Hz, 1H), 4.55 (d, J=12.7 Hz, 1H), 2.37 (t, J=7.5 Hz, 1H), 2.33-2.13 (m, 1H), 1.68-1.57 (m, 2H), 1.07 (t, J=13.6 Hz, 2H), 0.91 (s, 9H).

Preparation of a mixture of tert-butyl (S)-4-(3-(5-(difluoromethyl)-1H-1,2,4-triazol-1-yl)-4-fluorophenyl)-2,2-dimethyloxazolidine-3-carboxylate and tert-butyl (S)-4-(4-(5-(difluoromethyl)-1H-1,2,4-triazol-1-yl)-3-fluorophenyl)-2,2-dimethyloxazolidine-3-carboxylate

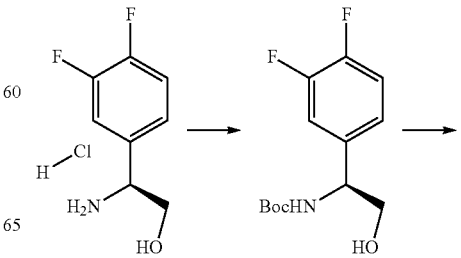

509
-continued

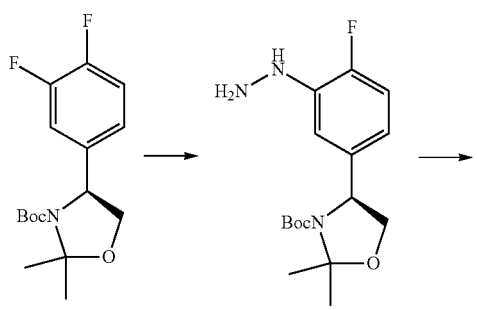

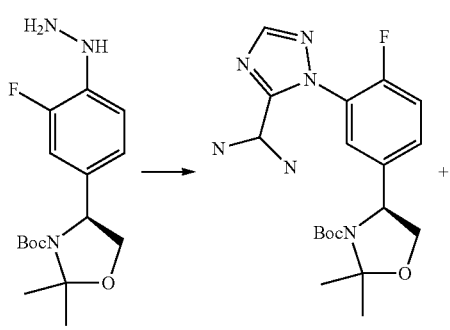

510
-continued

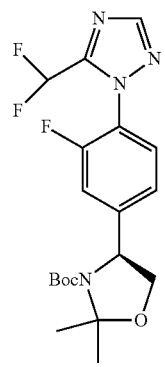

Preparation of a mixture of tert-butyl (S)-4-(3-(5-(difluoromethyl)-1H-1,2,4-triazol-1-yl)-4-fluorophenyl)-2,2-dimethyloxazolidine-3-carboxylate and tert-butyl (S)-4-(4-(5-(difluoromethyl)-1H-1,2,4-triazol-1-yl)-3-fluorophenyl)-2,2-dimethyloxazolidine-3-carboxylate: A mixture of tert-butyl (S)-4-(3-(5-(difluoromethyl)-1H-1,2,4-triazol-1-yl)-4-fluorophenyl)-2,2-dimethyloxazolidine-3-carboxylate and tert-butyl (S)-4-(4-(5-(difluoromethyl)-1H-1,2,4-triazol-1-yl)-3-fluorophenyl)-2,2-dimethyloxazolidine-3-carboxylate was prepared following the procedure described in the preparation of (S)-2-amino-2-(4-chloro-3-(5-(difluoromethyl)-1H-1,2,4-triazol-1-yl)phenyl)ethan-1-ol.

Example 122: Preparation of Compound 379 and Compound 380

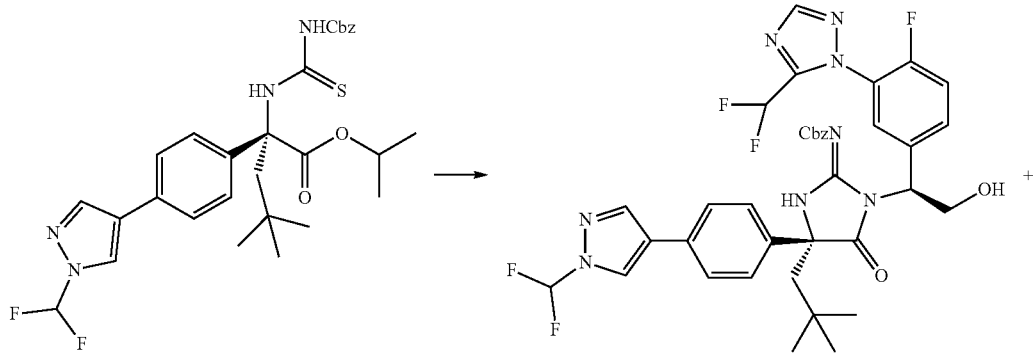

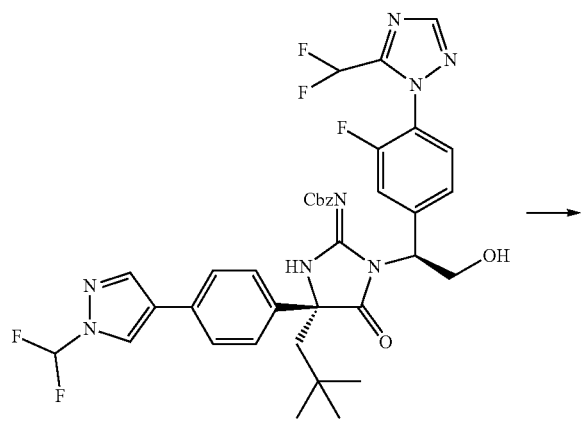

-continued

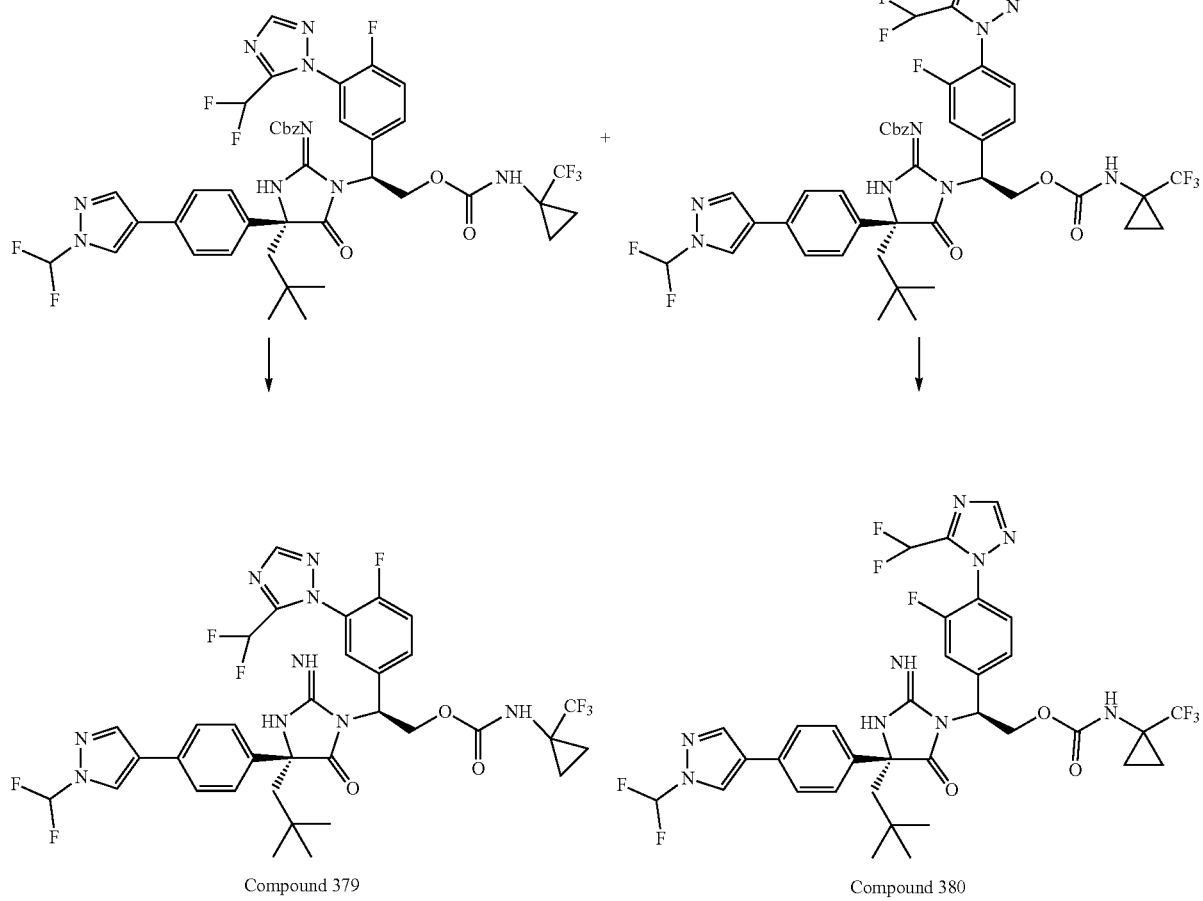

Compound 379

Compound 380

Compound 379 and Compound 380 were prepared in a manner similar to that for preparation of Compound 177, starting with isopropyl (R)-2-(3-((benzyloxy)carbonyl)thioureido)-2-(4-(1-(difluoromethyl)-1H-pyrazol-4-yl)phenyl)-4,4-dimethylpentanoate, except that a mixture of tert-butyl (S)-4-(3-(5-(difluoromethyl)-1H-1,2,4-triazol-1-yl)-4-fluorophenyl)-2,2-dimethyloxazolidine-3-carboxylate and tert-butyl (S)-4-(4-(5-(difluoromethyl)-1H-1,2,4-triazol-1-yl)-3-fluorophenyl)-2,2-dimethyloxazolidine-3-carboxylate was used instead of (S)-2-amino-2-(4-chloro-3-(5-(difluoromethyl)-1H-1,2,4-triazol-1-yl)phenyl)ethan-1-ol. The two isomers were separated before the Cbz-group de-protection. For Compound 379: LCMS-ESI+: calc'd for $C_{34}H_{33}F_8N_9O_3$: 768.3 (M+H+). Found: 768.4 (M+H+). $^1$H NMR (400 MHz, Methanol-$d_4$) δ 8.37 (s, 1H), 8.20 (s, 1H), 8.04 (s, 1H), 7.63-7.39 (m, 6H), 7.34-7.22 (m, 2H), 6.89 (t, J=52.2 Hz, 1H), 5.61-5.37 (m, 1H), 5.11-4.99 (m, 1H), 4.70 (dd, J=11.1, 5.9 Hz, 1H), 2.31 (d, J=14.7 Hz, 1H), 1.99 (d, J=14.8 Hz, 1H), 1.14-1.11 (m, 2H) 1.06-1.02 (m, 2H), 0.96 (s, J=9H). For Compound 380: LCMS-ESI+: calc'd for $C_{34}H_{33}F_8N_9O_3$: 768.3 (M+H+). Found: 768.4 (M+H+). $^1$H NMR (400 MHz, Methanol-$d_4$) δ 8.38 (s, 1H), 8.06 (s, 1H), 8.03 (s, 1H), 7.67-7.33 (m, 6H), 7.29 (t, J=9.0 Hz, 2H), 6.80 (t, J=52.2 Hz, 1H), 5.50 (dd, J=8.9, 5.8 Hz, 1H), 5.05 (dd, J=11.0, 9.0 Hz, 1H), 4.65 (dd, J=11.1, 5.7 Hz, 1H), 2.30 (d, J=14.7 Hz, 1H), 1.95 (d, J=14.7 Hz, 1H), 1.04 (s, 2H), 0.99-0.88 (m, 11H).

Example 123: Preparation of Compound 381

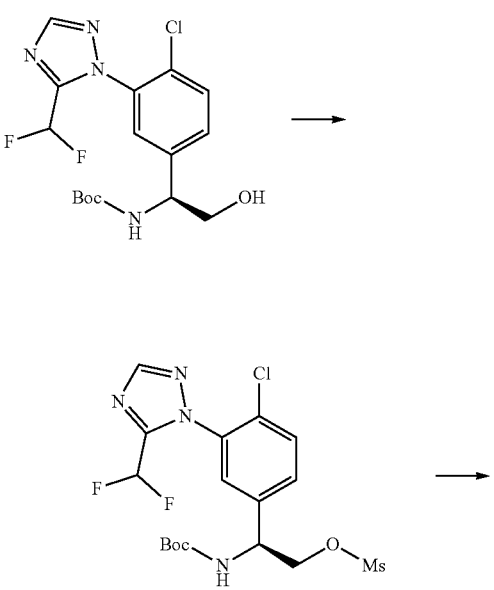

513
-continued

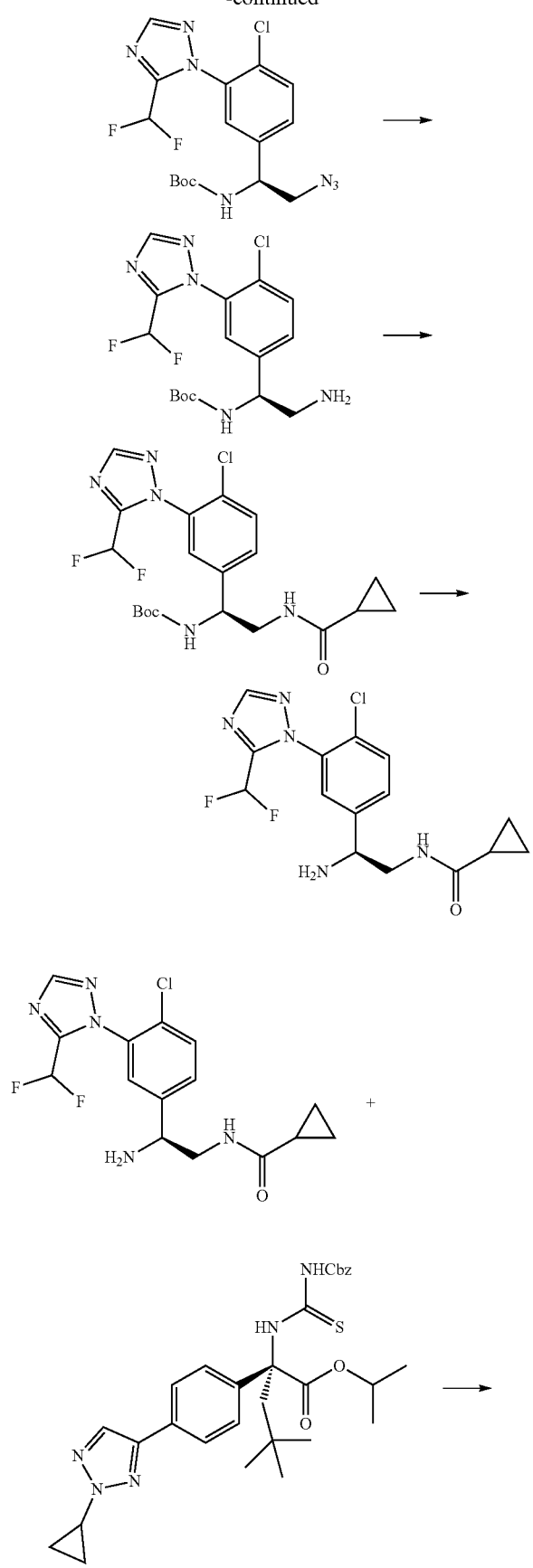

514
-continued

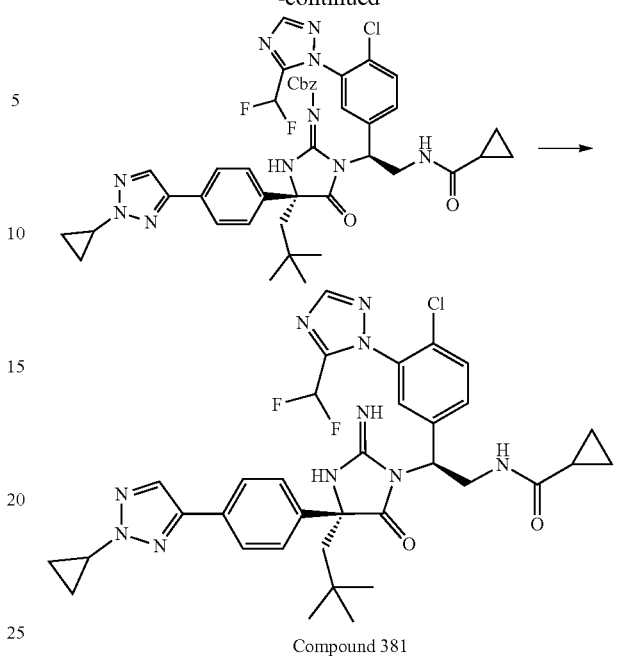

Compound 381

Preparation of (S)-2-((tert-butoxycarbonyl)amino)-2-(4-chloro-3-(5-(difluoromethyl)-1H-1,2,4-triazol-1-yl)phenyl) ethyl methanesulfonate: To a solution of tert-butyl (S)-(1-(4-chloro-3-(5-(difluoromethyl)-1H-1,2,4-triazol-1-yl) phenyl)-2-hydroxyethyl)carbamate (4.5 g, 11.6 mmol), Et₃N (1.75 mL, 12.7 mmol) in DCM (35 mL) at 0° C. was added methanesulfonyl chloride (0.90 mL, 11.6 mmol). The reaction mixture was allowed to slowly warm to rt and then heated at 40° C. After 16 h, the reaction mixture was cooled to rt, and treated with sat NH₄Cl and EtOAc. The layers were separated and the aqueous layer was further extracted with EtOAc. The combined organic layers were washed with brine, dried (over sodium sulfate), filtered, and concentrated in vacuo to afford the product.

Preparation of tert-butyl (S)-(2-azido-1-(4-chloro-3-(5-(difluoromethyl)-1H-1,2,4-triazol-1-yl)phenyl)ethyl)carbamate: (S)-2-((tert-butoxycarbonyl)amino)-2-(4-chloro-3-(5-(difluoromethyl)-1H-1,2,4-triazol-1-yl)phenyl)ethyl methanesulfonate (5.2 g, 11.1 mmol) and NaN₃ (2.17 g, 33.4 mmol) were combined in DMF (30 mL). The reaction mixture was stirred at 60° C. for 4 h (note: a blast shield was used to cover the reaction mixture and adequate venting was used to ensure minimal pressure build-up). The reaction mixture was cooled to rt, and quenched by addition of saturated NH₄Cl and EtOAc. The layers were separated and the aqueous layer was further extracted with EtOAc. The combined organic layers were washed with brine, dried (over sodium sulfate), filtered and concentrated in vacuo. The crude residue was purified by silica gel column chromatography (ISCO gold, 120 g column; 0-100% EtOAc/hexanes) to afford the product (4.0 g, 87%).

Preparation of tert-butyl (S)-(2-amino-1-(4-chloro-3-(5-(difluoromethyl)-1H-1,2,4-triazol-1-yl)phenyl)ethyl)carbamate: tert-Butyl (S)-(2-azido-1-(4-chloro-3-(5-(difluoromethyl)-1H-1,2,4-triazol-1-yl)phenyl)ethyl)carbamate (0.75 g, 1.81 mmol) and PPh₃ (0.59 g, 2.27 mmol) were mixed in THF (10 mL) and water (2 mL). The reaction mixture was stirred at 50° C. for 17 h. The reaction mixture was diluted with EtOAc and treated with 10% aqueous citric acid solution (30 mL). The aqueous layer was isolated and then was neutralized with saturated NaHCO₃ solution to pH=8. The mixture was then extracted with MTBE (2×50 mL). The organic layer was separated and drived over sodium sulfate. Evaporation of solvent from the organic layer afforded the product (0.42 g, 60%).

Preparation of tert-butyl (S)-(1-(4-chloro-3-(5-(difluoromethyl)-1H-1,2,4-triazol-1-yl)phenyl)-2-(cyclopropanecarboxamido)ethyl)carbamate: A solution of tert-butyl (S)-(2-amino-1-(4-chloro-3-(5-(difluoromethyl)-1H-1,2,4-triazol-1-yl)phenyl)ethyl)carbamate (100 mg, 0.26 mmol), cyclopropanecarboxylic acid (33.3 mg, 0.39 mmol), EDCI (74 mg, 0.39 mmol), DMAP (47 mg, 0.39 mmol) in DMF (1 mL) and DCM (1 mL) was stirred at rt. After 3 h, the reaction mixture was diluted with EtOAc and saturated aqueous NaHCO₃ solution. The organic layer was taken, and the aqueous layer was extracted with EtOAc. The organic layers were combined, washed with brine, and concentrated. The residue was purified on silica gel column eluted with EtOAc/hexanes to afford the product (95 mg, 80%).

Preparation of (S)—N-(2-amino-2-(4-chloro-3-(5-(difluoromethyl)-1H-1,2,4-triazol-1-yl)phenyl)ethyl)cyclopropanecarboxamide: To a solution of tert-butyl (S)-(1-(4-chloro-3-(5-(difluoromethyl)-1H-1,2,4-triazol-1-yl)phenyl)-2-(cyclopropanecarboxamido)ethyl)carbamate (100 mg, 0.22 mmol) in DCM (1 mL) was added TFA (0.3 mL). After 1 h, the reaction mixture was concentrated to dryness. The crude material was azeotroped with toluene to afford the product (78 mg, quantitative yield).

Preparation of benzyl ((R)-1-((S)-1-(4-chloro-3-(5-(difluoromethyl)-1H-1,2,4-triazol-1-yl)phenyl)-2-(cyclopropanecarboxamido)ethyl)-4-(4-(2-cyclopropyl-2H-1,2,3-triazol-4-yl)phenyl)-4-neopentyl-5-oxoimidazolidin-2-ylidene)carbamate: To a mixture of (S)—N-(2-amino-2-(4-chloro-3-(5-(difluoromethyl)-1H-1,2,4-triazol-1-yl)phenyl)ethyl)cyclopropanecarboxamide TFA salt (87.5 mg, 0.186 mmol) and isopropyl (R)-2-(3-((benzyloxy)carbonyl)thioureido)-2-(4-(2-cyclopropyl-2H-1,2,3-triazol-4-yl)phenyl)-4,4-dimethylpentanoate (70 mg, 0.124 mmol) in DMF (1.5 mL) were added DIEPA (0.11 mL, 0.62 mmol) and EDCI (71 mg, 0.37 mmol), and stirred at rt for 2 h and then heated at 50° C. for 17 h. The mixture was then diluted with EtOAc and treated with saturated aqueous NaHCO₃ solution. The organic layer was taken and the aqueous layer was extracted with EtOAc. The organic layers were combined, washed with brine, and concentrated. The residue was purified on silica gel column eluted with 0-100% gradient EtOAc/hexanes to afford the product.

Preparation of Compound 381: benzyl ((R)-1-((S)-1-(4-chloro-3-(5-(difluoromethyl)-1H-1,2,4-triazol-1-yl)phenyl)-2-(cyclopropanecarboxamido)ethyl)-4-(4-(2-cyclopropyl-2H-1,2,3-triazol-4-yl)phenyl)-4-neopentyl-5-oxoimidazolidin-2-ylidene)carbamate (86 mg, 0.10 mmol) was dissolved in TFA (1 mL) and was heated at 60° C. for 2 h. The mixture was concentrated and azeotroped with toluene. The residue was purified by reverse phase preparative HPLC with 10-90% MeCN/water containing 0.1% TFA to afford the product.

Similarly, the following examples were prepared.

| Compound # | Structures | Mass data | NMR data |
|---|---|---|---|
| 381 | 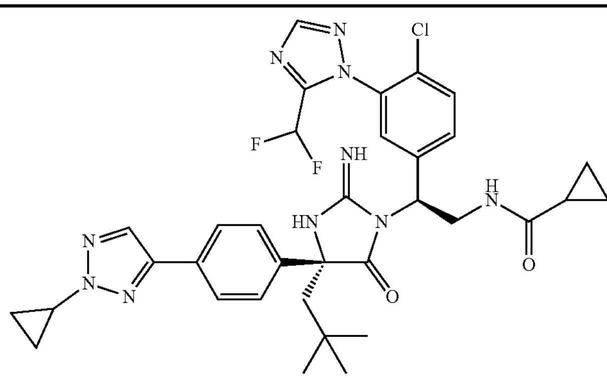 | LCMS-ESI+: calc'd for C₃₄H₃₈ClF₂N₁₀O₂: 691.3 (M + H); Found: 691.2 (M + H) | 1H NMR (400 MHz, Methanol-d₄) δ 8.05 (s, 1H), 8.00 (s, 1H), 7.82-7.76 (m, 2H)J = , 7.66-7.52 (m, 3H), 7.52-7.47 (m, 2H), 7.24 (s, 1H), 7.13-6.62 (m, 1H), 5.62 (t, J = 7.6 Hz, 1H), 4.30-4.15 (m, 1H), 4.11 (tt, J = 7.5, 3.8 Hz, 1H), 3.99 (dt, J = 14.0, 5.2 Hz, 1H), 2.47 (d, J = 15.1 Hz, 1H), 2.22 (d, J = 15.1 Hz, 1H), 1.49 (ddt, J = 15.7, 12.4, 3.6 Hz, 1H), 1.39-1.30 (m, 2H), 1.19-1.10 (m, 2H), 0.99 (s, 9H), 0.83-0.71 (J = m, 5H). |
| 382 | 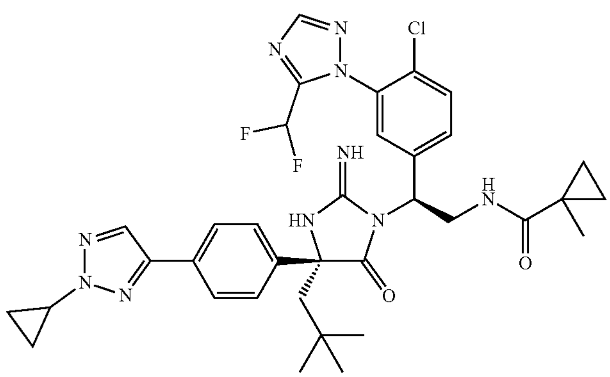 [SMILES: CC(C)(C)C[C@]1(c2ccc(-c3cnn(C4CC4)n3)cc2)NC(=N)N([C@H](CNC(=O)C2(C)CC2)c2ccc(Cl)c(-n3ncnc3C(F)F)c2)C1=O] | LCMS-ESI+: calc'd for C₃₅H₄₀ClF₂N₁₀O₂: 705.3 (M + H); Found: 705.4 (M + H) | 1H NMR (400 MHz, Methanol-d₄) δ 8.09 (s, 1H), 8.00 (s, 1H), 7.83-7.78 (m, 2H), 7.69-7.59 (m, 1H), 7.56 (dd, J = 8.6, 2.2 Hz, 1H), 7.54-7.49 (m, 2H), 7.31 (s, 1H), 6.83 (t, J = 52.2 Hz, 1H), 5.63 (dd, J = 8.4, 6.1 Hz, 1H), 4.27 (dd, J = 14.0, 8.5 Hz, 1H), 4.11 (tt, J = 7.5, 3.8 Hz, 1H), 3.94 (dd, J = 14.0, 6.1 Hz, 1H), 2.44 (d, J = 15.1 Hz, 1H), 2.24 (d, J = 15.1 Hz, 1H), 1.38-1.32 (m, 2H), 1.19-1.11 (m, 4H), 0.98 (s, 9H), 0.59-0.44 (m, 2H). |

| Compound # | Structures | Mass data | NMR data |
|---|---|---|---|
| 383 | 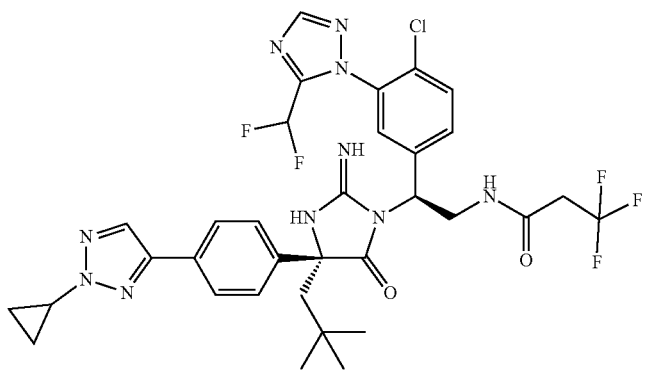 [SMILES: CC(C)(C)C[C@]1(c2ccc(-c3cnn(C4CC4)n3)cc2)NC(=N)N([C@H](CNC(=O)CC(F)(F)F)c2ccc(Cl)c(-n3ncnc3C(F)F)c2)C1=O] | LCMS-ESI+: calc'd for $C_{33}H_{35}ClF_5N_{10}O_2$: 733.3 (M + H); Found: 733.3 (M + H) | 1H NMR (400 MHz, Methanol-$d_4$) δ 8.05 (s, 1H), 7.99 (s, 1H), 7.83-7.75 (m, 2H), 7.62 (d, J = 8.4 Hz, 1H), 7.56 (dd, J = 8.5, 2.2 Hz, 1H), 7.53-7.43 (m, 2H), 7.33-7.19 (m, 1H), 6.80 (t, J = 52.2 Hz, 1H), 5.62 (dd, J = 8.8, 6.1 Hz, 1H), 4.31 (dd, J = 14.0, 8.9 Hz, 1H), 4.11 (tt, J = 7.5, 3.8 Hz, 1H), 4.02 (dd, J = 14.0, 6.1 Hz, 1H), 3.05 (dt, J = 17.4, 10.8 Hz, 2H), 2.42 (d, J = 15.1 Hz, 1H), 2.27 (d, J = 15.1 Hz, 1H), 1.35 (qd, J = 5.3, 3.8 Hz, 2H), 1.19-1.10 (m, 2H), 0.96 (s, 9H). |
| 384 | 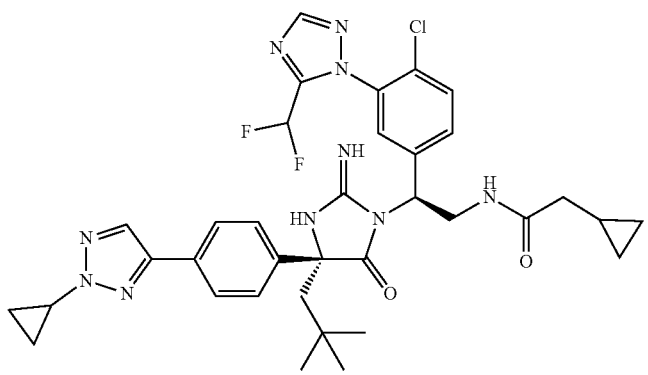 [SMILES: CC(C)(C)C[C@]1(c2ccc(-c3cnn(C4CC4)n3)cc2)NC(=N)N([C@H](CNC(=O)CC2CC2)c2ccc(Cl)c(-n3ncnc3C(F)F)c2)C1=O] | LCMS-ESI+: calc'd for $C_{35}H_{40}ClF_2N_{10}O_2$: 705.3 (M + H); Found: 705.4 (M + H) | 1H NMR (400 MHz, Methanol-$d_4$) δ 8.10 (s, 1H), 8.00 (s, 1H), 7.82-7.76 (m, 2H), 7.65 (d, J = 8.5 Hz, 1H), 7.59 (dd, J = 8.5, 2.2 Hz, 1H), 7.55-7.47 (m, 2H), 7.33 (s, 1H), 6.84 (t, J = 52.1 Hz, 1H), 5.63 (dd, J = 8.7, 6.1 Hz, 1H), 4.28 (dd, J = 14.0, 8.9 Hz, 1H), 4.11 (tt, J = 7.5, 3.8 Hz, 1H), 3.96 (dd, J = 14.0, 6.1 Hz, 1H), 2.44 (d, J = 15.1 Hz, 1H), 2.24 (d, J = 15.1 Hz, 1H), 1.34 (td, J = 5.1, 4.4, 3.1 Hz, 2H), 1.18-1.10 (m, 2H), 0.96 (s, 9H), 0.85-0.70 (m, 1H), 0.47-0.36 (m, 2H), 0.05--0.04 (m, 2H). |
| 385 | 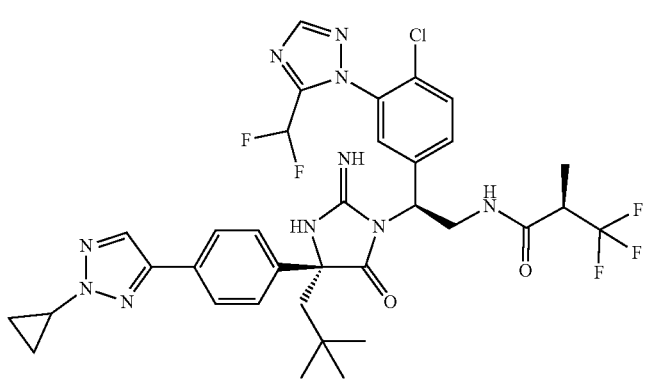 [SMILES: C[C@H](C(=O)NC[C@H](c1ccc(Cl)c(-n2ncnc2C(F)F)c1)N1C(=N)N[C@](CC(C)(C)C)(c2ccc(-c3cnn(C4CC4)n3)cc2)C1=O)C(F)(F)F] | LCMS-ESI+: calc'd for $C_{35}H_{36}ClF_5N_{10}O_2$: 747.3 (M + H); Found: 747.4 (M + H) | 1H NMR (400 MHz, Methanol-$d_4$) δ 8.03 (s, 1H), 7.99 (s, 1H), 7.80-7.76 (m, 2H), 7.61 (d, J = 8.5 Hz, 1H), 7.56 (dd, J = 8.6, 2.2 Hz, 1H), 7.53-7.48 (m, 2H), 7.22 (d, J = 2.1 Hz, 1H), 6.79 (t, J = 52.2 Hz, 1H), 5.64 (dd, J = 9.0, 6.0 Hz, 1H), 4.29 (dd, J = 14.0, 9.0 Hz, 1H), 4.13-3.97 (m, 2H), 3.24-3.08 (m, 1H), 2.39 (d, J = 15.1 Hz, 1H), 2.32 (d, J = 15.1 Hz, 1H), 1.39-1.30 (m, 2H), 1.27 (d, J = 7.1 Hz, 3H), 1.18-1.11 (m, 2H), 0.96 (s, 9H). |

| Compound # | Structures | Mass data | NMR data |
|---|---|---|---|
| 386 | 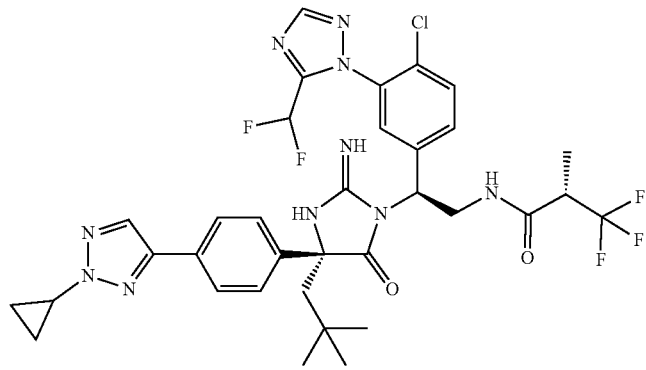 [SMILES: C[C@@H](C(=O)NC[C@H](c1ccc(Cl)c(-n2ncnc2C(F)F)c1)N1C(=N)N[C@](CC(C)(C)C)(c2ccc(-c3cnn(C4CC4)n3)cc2)C1=O)C(F)(F)F] | LCMS-ESI+: calc'd for $C_{35}H_{36}ClF_5N_{10}O_2$: 747.3 (M + H); Found: 747.4 (M + H) | 1H NMR (400 MHz, Methanol-$d_4$) δ 8.06 (s, 1H), 7.99 (s, 1H), 7.82-7.74 (m, 2H), 7.61 (d, J = 8.5 Hz, 1H), 7.56 (dd, J = 8.5, 2.1 Hz, 1H), 7.53-7.46 (m, 2H), 7.28 (d, J = 2.1 Hz, 1H), 6.78 (t, J = 52.2 Hz, 1H), 5.56 (dd, J = 8.3, 6.4 Hz, 1H), 4.34 (dd, J = 14.0, 8.4 Hz, 1H), 4.11 (hept, J = 3.8 Hz, 1H), 4.04 (dd, J = 14.0, 6.4 Hz, 1H), 3.20-3.03 (m, 1H), 2.43 (d, J = 15.2 Hz, 1H), 2.28 (d, J = 15.1 Hz, 1H), 1.38-1.31 (m, 2H), 1.26 (d, J = 7.1 Hz, 3H), 1.18-1.11 (m, 2H), 0.96 (s, 9H). |
| 387 | 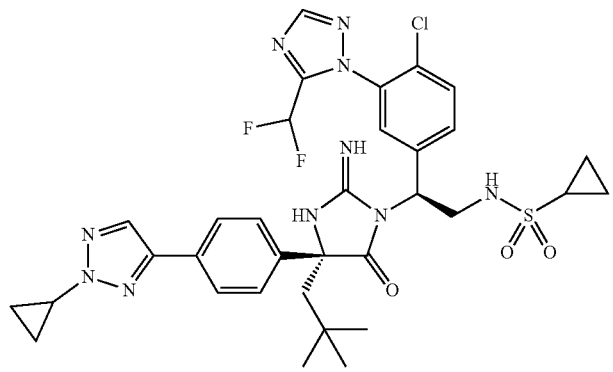 [SMILES: CC(C)(C)C[C@]1(c2ccc(-c3cnn(C4CC4)n3)cc2)NC(=N)N([C@H](CNS(=O)(=O)C2CC2)c2ccc(Cl)c(-n3ncnc3C(F)F)c2)C1=O] | LCMS-ESI+: calc'd for $C_{33}H_{38}ClF_2N_{10}O_3S$: 727.2 (M + H); Found: 727.3 (M + H) | 1H NMR (400 MHz, Methanol-$d_4$) δ 8.02 (s, 1H), 8.00 (s, 1H), 7.81-7.76 (m, 2H), 7.61 (d, J = 8.5 Hz, 1H), 7.55 (ddd, J = 8.5, 2.3, 0.6 Hz, 1H), 7.53-7.48 (m, 2H), 7.21 (d, J = 2.2 Hz, 1H), 6.79 (t, J = 52.2 Hz, 1H), 5.54 (dd, J = 10.0, 5.5 Hz, 1H), 4.21 (dd, J = 14.5, 10.1 Hz, 1H), 4.11 (dt, J = 7.5, 3.7 Hz, 1H), 3.93 (dd, J = 14.5, 5.5 Hz, 1H), 2.63 (tt, J = 7.5, 5.4 Hz, 1H), 2.47 (d, J = 15.1 Hz, 1H), 2.28 (d, J = 15.1 Hz, 1H), 1.40-1.32 (m, 2H), 1.18-1.00 (m, 6H), 0.98 (s, 9H). |
| 388 | 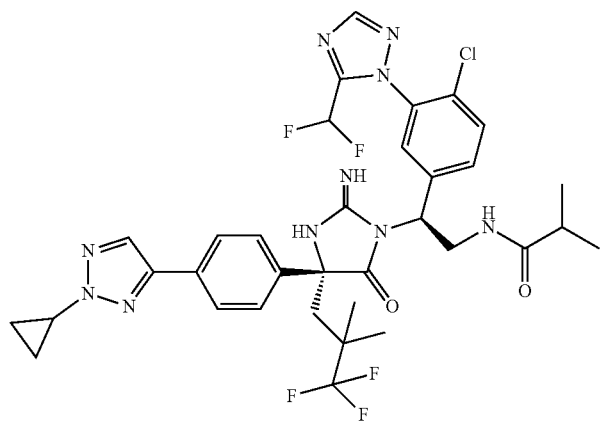 [SMILES: CC(C)C(=O)NC[C@H](c1ccc(Cl)c(-n2ncnc2C(F)F)c1)N1C(=N)N[C@](CC(C)(C)C(F)(F)F)(c2ccc(-c3cnn(C4CC4)n3)cc2)C1=O] | LCMS-ESI+: calc'd for $C_{34}H_{36}ClF_5N_{10}O_2$, 747.3 (M + H); Found 747.3 (M + H) | $^1$H NMR (400 MHz, Methanol-$d_4$) δ 8.05 (s, 1H), 8.00 (s, 1H), 7.84-7.76 (m, 2H), 7.64-7.47 (m, 4H), 7.26 (s, 1H), 6.79 (t, J = 52.2 Hz, 1H), 5.58-5.46 (m, 1H), 4.23 (dd, J = 13.9, 8.6 Hz, 1H), 4.11 (tt, J = 7.5, 3.8 Hz, 1H), 3.94 (dd, J = 14.0, 6.1 Hz, 1H), 2.68 (d, J = 15.4 Hz, 1H), 2.52 (d, J = 15.4 Hz, 1H), 2.33 (p, J = 6.9 Hz, 1H), 1.39-1.32 (m, 2H), 1.18-1.12 (m, 2H), 1.16 (s, 3H) 1.09 (s, 3H), 1.02 (dd, J = 6.9, 1.8 Hz, 6H). |

-continued

| Compound # | Structures | Mass data | NMR data |
|---|---|---|---|
| 389 | 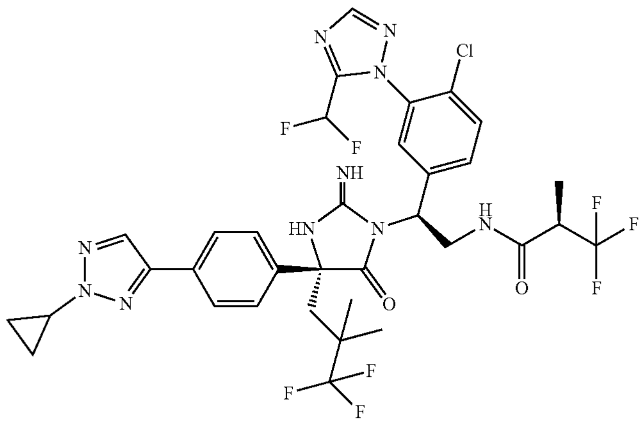 [SMILES: C[C@H](C(=O)NC[C@H](c1ccc(Cl)c(-n2ncnc2C(F)F)c1)N1C(=N)N[C@](CC(C)(C)C(F)(F)F)(c2ccc(-c3cnn(C4CC4)n3)cc2)C1=O)C(F)(F)F] | LCMS-ESI+: calc'd for C$_{34}$H$_{33}$ClF$_8$N$_{10}$O$_2$, 801.3 (M + H); Found 801.4 (M + H) | $^1$H NMR (400 MHz, Methanol-d$_4$) δ 8.02 (d, J = 7.2 Hz, 1H), 7.96 (s, 1H), 7.69 (s, 2H), 7.60-7.44 (m, 4H), 7.17 (s, 1H), 6.74 (t, J = 52.2 Hz, 1H), 5.40-5.35 (m, 1H), 4.37-4.20 (m, 1H), 4.10 (tt, J = 7.5, 3.8 Hz, 1H), 3.96 (dd, J = 13.9, 5.9 Hz, 1H), 3.21-3.02 (m, 1H), 2.40-2.35 (m, 2H), 1.38 (tdd, J = 5.2, 4.3, 2.0 Hz, 2H), 1.24 (d, J = 7.1 Hz, 3H), 1.21-1.07 (m, 6H), 1.02 (s, 3H). |
| 390 | 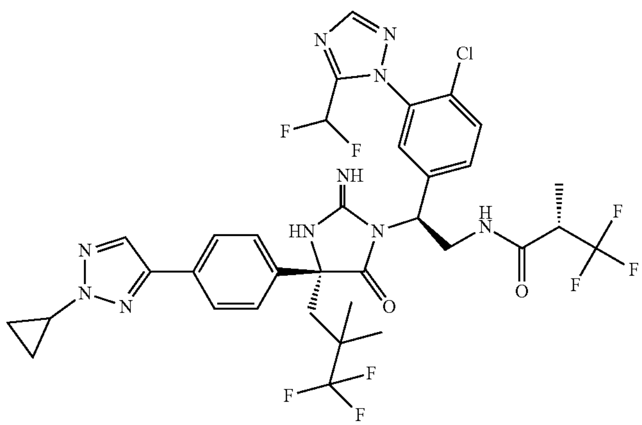 [SMILES: C[C@@H](C(=O)NC[C@H](c1ccc(Cl)c(-n2ncnc2C(F)F)c1)N1C(=N)N[C@](CC(C)(C)C(F)(F)F)(c2ccc(-c3cnn(C4CC4)n3)cc2)C1=O)C(F)(F)F] | LCMS-ESI+: calc'd for C$_{34}$H$_{33}$ClF$_8$N$_{10}$O$_2$, 801.3 (M + H); Found 801.4 (M + H) | $^1$H NMR (400 MHz, Methanol-d$_4$) δ 8.05 (s, 1H), 7.96 (s, 1H), 7.73-7.69 (m, 2H), 7.63-7.46 (m, 4H), 7.25-7.20 (m, 1H), 6.75 (t, J = 52.1 Hz, 1H), 5.41-5.38 (m, 1H), 4.20-4.15 (m, 1H), 4.10 (tt, J = 7.5, 3.8 Hz, 1H), 4.03 (dd, J = 13.8, 6.3 Hz, 1H), 3.05-2.95 (m, 1H), 2.35-2.30 (m, 2H), 1.38-1.30 (m, 2H), 1.27-1.07 (m, 8H), 1.04 (s, 3H). |
| 391 | 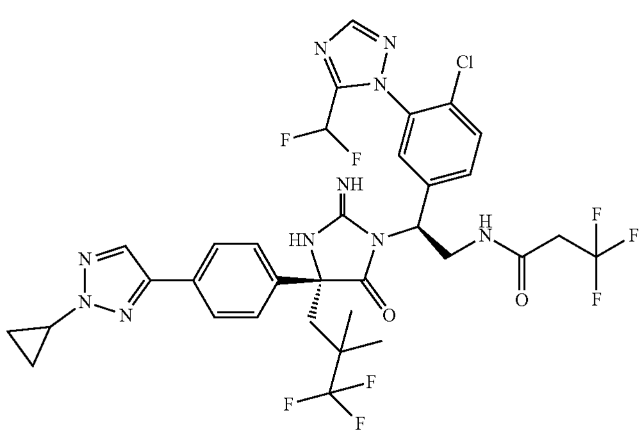 [SMILES: CC(C)(C[C@]1(c2ccc(-c3cnn(C4CC4)n3)cc2)NC(=N)N([C@H](CNC(=O)CC(F)(F)F)c2ccc(Cl)c(-n3ncnc3C(F)F)c2)C1=O)C(F)(F)F] | LCMS-ESI+: calc'd for C$_{33}$H$_{31}$ClF$_8$N$_{10}$O$_2$, 787.2 (M + H); Found 787.3 (M + H) | $^1$H NMR (400 MHz, Methanol-d$_4$) δ 8.04 (s, 1H), 8.00 (s, 1H), 7.84-7.75 (m, 2H), 7.65-7.48 (m, 4H), 7.22 (d, J = 2.1 Hz, 1H), 6.79 (t, J = 52.2 Hz, 1H), 5.58 (dd, J = 8.9, 5.9 Hz, 1H), 4.33 (dd, J = 14.0, 9.0 Hz, 1H), 4.12 (tt, J = 7.5, 3.8 Hz, 1H), 3.99 (dd, J = 14.1, 6.0 Hz, 1H), 3.19-2.95 (m, 2H), 2.76-2.49 (m, 2H), 1.39-1.32 (m, 2H), 1.20-1.12 (m, 6H), 1.07 (s, 3H). |

Example 124: Preparation of Compound 392

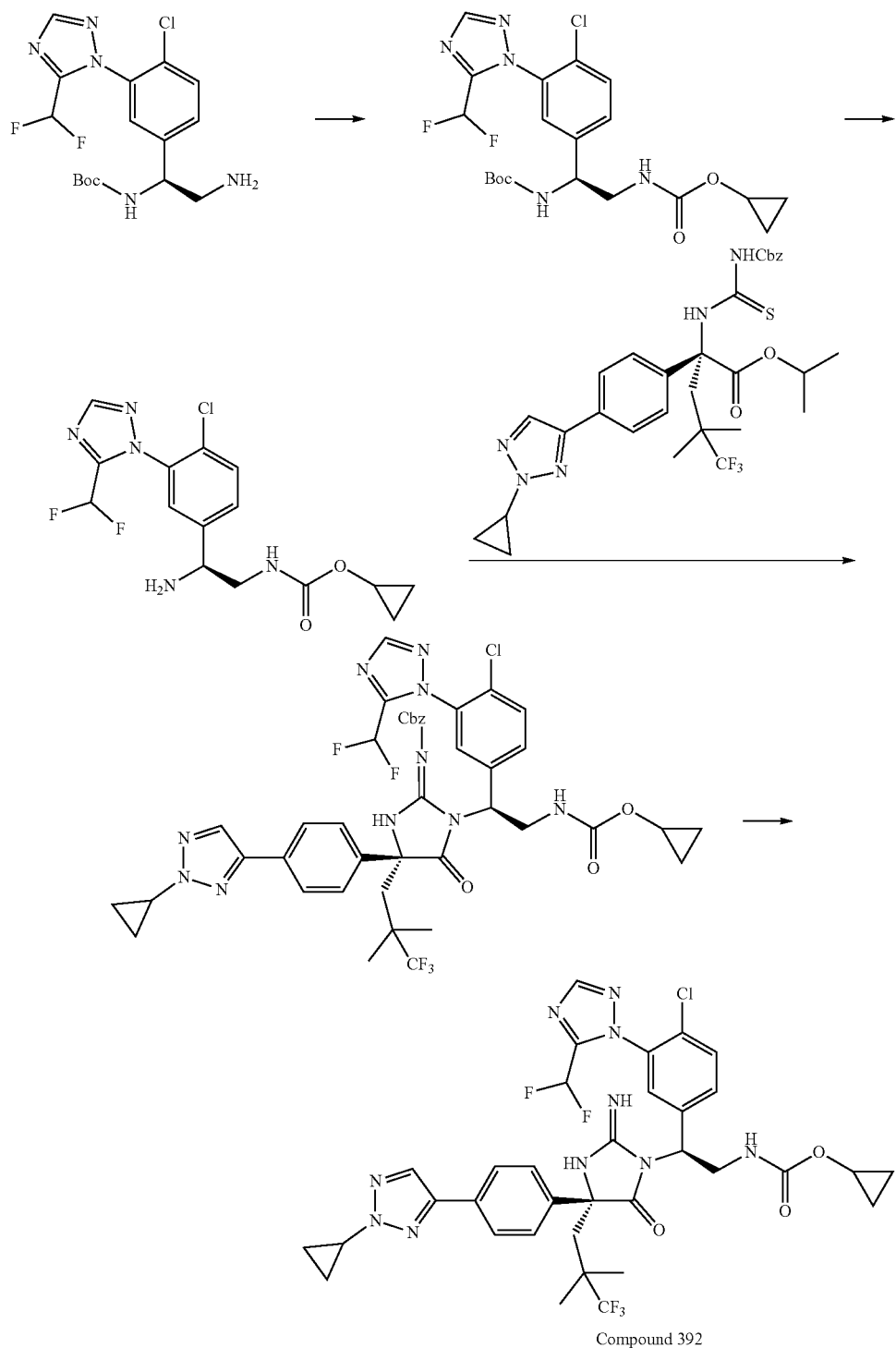

Compound 392

Preparation of tert-butyl cyclopropyl (1-(4-chloro-3-(5-(difluoromethyl)-1H-1,2,4-triazol-1-yl)phenyl)ethane-1,2-diyl)(S)-dicarbamate: Cyclopropyl alcohol (29.7 mg, 0.511 mmol) was dissolved in DCM (3 mL) at rt. To this solution, DIEA (0.16 mL, 0.93 mmol) and CDI (75 mg, 0.46 mmol) were added sequentially, and stirred for 25 min. A solution of tert-butyl (S)-(2-amino-1-(4-chloro-3-(5-(difluoromethyl)-1H-1,2,4-triazol-1-yl)phenyl)ethyl)carbamate (180 mg, 0.46 mmol) in DCM (2 mL) was added. After one hour, another portion of DIEA (0.16 mL, 0.93 mmol), cyclopropyl alcohol (60 mg, 1.0 mmol) and CDI (75 mg, 0.46 mmol) were added. After 17 h, the reaction mixture was concentrated, and the residue was partitioned between saturated aqueous NaHCO$_3$ and EtOAc. The organic phase was separated, concentrated, and purified by silica gel column chromatography 0-100% gradient EtOAc/hexanes to afford the product.

Compound 392 was then prepared according to the similar procedure as Example 123. LCMS-ESI+: calc'd for C$_{34}$H$_{34}$ClF$_5$N$_{10}$O$_3$, 761.3 (M+H). Found 761.4 (M+H). $^1$H NMR (400 MHz, Methanol-d$_4$) δ 8.04 (s, 1H), 8.00 (s, 1H), 7.84-7.75 (m, 2H), 7.65-7.48 (m, 4H), 7.22 (s, 1H), 6.79 (t, J=52.2 Hz, 1H), 5.54 (dd, J=9.1, 5.7 Hz, 1H), 4.24-4.05 (m, 1H), 3.89 (dt, J=14.3, 6.8 Hz, 1H), 2.72 (d, J=15.4 Hz, 1H), 2.51 (d, J=15.4 Hz, 1H), 1.39-1.32 (m, 2H), 1.17 (s, 3H), 1.16-1.12 (m, 2H), 1.10 (s, 3H), 0.70-0.55 (m, 5H).

Example 125: Preparation of Compound 393

Compound 393

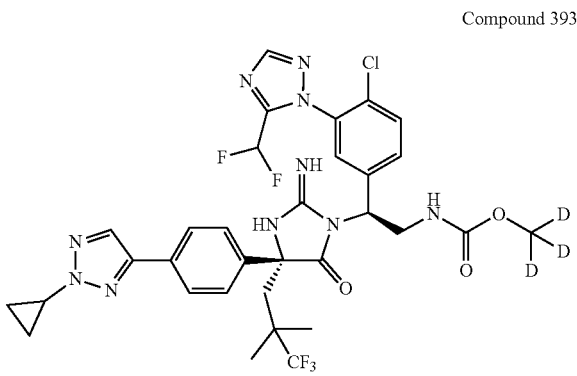 [SMILES: [2H]C([2H])([2H])OC(=O)NC[C@H](c1ccc(Cl)c(-n2ncnc2C(F)F)c1)N1C(=N)N[C@](CC(C)(C)C(F)(F)F)(c2ccc(-c3cnn(C4CC4)n3)cc2)C1=O]

Compound 393 was prepared according to the same procedure as that for preparing Compound 392, except that CD3OH was used to prepare tert-butyl (methyl-d$_3$) (1-(4-chloro-3-(5-(difluoromethyl)-1H-1,2,4-triazol-1-yl)phenyl)ethane-1,2-diyl) (S)-dicarbamate. LCMS-ESI+: calc'd for C$_{32}$H$_{29}$D$_3$ClF$_5$N$_{10}$O$_3$, 738.3 (M+W). Found 738.5 (M+W). $^1$H NMR (400 MHz, Methanol-d$_4$) δ 8.04 (s, 1H), 8.01 (s, 1H), 7.82 (d, J=1.9 Hz, 1H), 7.81 (d, J=2.0 Hz, 1H), 7.64-7.47 (m, 4H), 7.23 (s, 1H), 6.80 (t, J=52.2 Hz, 1H), 5.61-5.50 (m, 1H), 4.19-4.15 (m, 1H), 4.15-4.09 (m, 1H), 3.89 (dd, J=14.3, 5.8 Hz, 1H), 2.75 (d, J=15.5 Hz, 1H), 2.54 (d, J=15.5 Hz, 1H), 1.38-1.33 (m, 2H), 1.18 (s, 3H), 1.19-1.12 (m, 2H), 1.10 (s, 3H).

2. Biological Assays

MT-4 HIV Assay.

Compounds were tested in a high-throughput 384-well assay format for their ability to inhibit the replication of HIV-1 (IIIB) in MT-4 cells. Compounds were serially diluted (1:3) in DMSO on 384-well polypropylene plates and further diluted 200-fold into complete RPMI media (10% FBS, 1% P/S) using the Biotek Micro Flow and Agilent ECHO acoustic dispenser. Each plate contained up to 8 test compounds, with negative (No Drug Control) and 5 uM AZT positive controls. MT-4 cells were pre-infected with 10 uL of either RPMI (mock-infected) or a fresh 1:250 dilution of an HIV-1 (TIM) concentrated virus stock. Infected and uninfected MT-4 cells were further diluted in complete RPMI media and added to each plate using a Micro Flow dispenser. After 5 days incubation in a humidified and temperature controlled incubator (37° C.), Cell Titer Glo (Promega) was added to the assay plates to quantify the amount of luciferase. EC$_{50}$ and CC$_{50}$ values were defined as the compound concentration that causes a 50% decrease in luminescence signal, and were calculated using a sigmoidal dose-response model to generate curve fits. Data for certain compounds are reported in Table 1 below.

MT-4 HIV High Resolution Antiviral Assay

Assay protocol is identical to that described for the MT-4 antiviral assay with the following changes: Each drug is run in 2 series of quadruplicates with different starting concentrations for each series and 19 1.5 fold dilutions performed across the plate. This results in an inhibition curve with 40 data points for each compound. Data is analyzed and Hill coefficients determined in Graph Pad Prism (San Diego, Calif.). EC$_{95}$s were determined by the formula EC$_{95}$=(19)$^{1/hill\ coefficient}$×EC$_{50}$. HD values were determined for certain compounds and reported in Table 1 below as an illustrative example.

Liver Microsomal Stability Protocol

Test compounds and one control compound (verapamil) were tested in 3 different species in duplicate sets.

General Conditions:

Test compound concentration: 1 uM; Protein concentration: 0.5 mg/mL (for dog, rat, and human liver microsomes); Cofactor: NADPH-Regenerating system (NRS) solution; Time-points: 2, 12, 25, 45, and 65 minutes.

Reaction Composition (in Each Incubation Well) Contains:

| |
|---|
| 5 uL compound (50 uM stock solution, 50:50 ACN:H2O) |
| 25 uL NRS solution |
| 6.25 uL 20 mg/mL liver microsomes |
| 213.75 uL 100 mM KPO4, pH 7.4 |
| 250 uL total volume |

At an incubation temperature of 37° C., the reaction was started with addition of NADPH Regeneration System, at each time point, 25 uL of the reaction mixture was removed and added to a plate with 225 uL quenching solution (50% MeOH, 25% ACN, 25% H$_2$O, and 200 nM labetalol as internal standard). After plates were vortexed, they were centrifuged for 30 minutes to remove proteins. About 100 μL supernatant was removed to a new plate and diluted with 150 μL water. About 20 μL of the mixture was injected into LC/MS/MS system to monitor the compound's response. In vitro measured t½ was used to calculate Clint values.

Half-lives of atazanavir and darunavir measured in this assay using human liver microsomes were 26-107 min and 16-32 min, respectively. The following compounds were ≥395 min: Compounds 17, 20, 34, 72, 78, 89, 91, 97, 105, 110, 129, 131, 134, 135, 146, 152, 153, 154, 155, 160, 163, 179, 182, 194, 195, 217, 223, 224, 236, 242, 270, 278, 289, 290, 291, 295, 303, 308, 311, 312, 317, 331, 336, 339, 344, 345, 350, 351, 352, 359, 360, 361, 363, 372, 380, 387, 389, 391, and 392.

HIV Protease Enzyme Inhibition (PI) Activity

Inhibitor potency against HIV protease was measured using an enzymatic assay with a fluorogenic readout. To a reaction buffer containing 100 mM ammonium acetate at pH 5.3, 100 mM NaCl, 1 mM EDTA, 1 mM DTT, 0.25 mg/mL BSA and 1% DMSO were added 10 nM of recombinant HIV protease (concentration based on protein monomer) and test compound at one of various concentrations. After a 10-minute pre-incubation, the enzymatic reaction was initiated by the addition of the fluorogenic substrate (2-aminobenzoyl)Thr-Ile-Nle-(p-nitro)Phe-Gln-Arg (Bachem) (SEQ ID NO:

1) to a final concentration of 40 μM. The total volume of the assay solution was 100 μL. The reaction was measured over 10 minutes on a Tecan Infinite M1000 plate reader using an excitation wavelength of 320 nm and a detection wavelength of 420 nm. The slopes of the progress curves were the measure of reaction rates. Reaction rates were plotted as a function of inhibitor concentration, and the data were fit with a four-parameter logistic fit using Graphpad PRISM software to yield $IC_{50}$ values. Data for certain compounds are reported in Table 1 below.

Compounds were screened according to the Biological Assays. Activity is listed in Table 1.

TABLE 1

| COMPD # | STRUCTURE | HIV PI $IC_{50}$ (nM) | MT4 $EC_{50}$ (nM) |
|---|---|---|---|
| 1 | 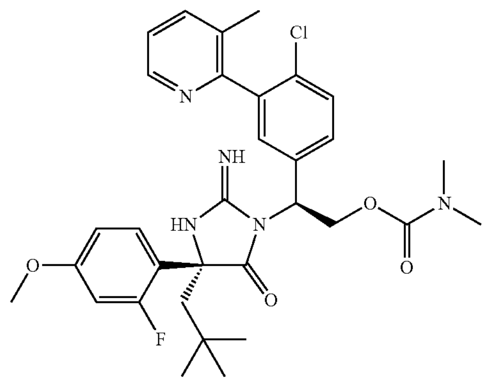 | 2.8 | 64.573 |
| 2 | 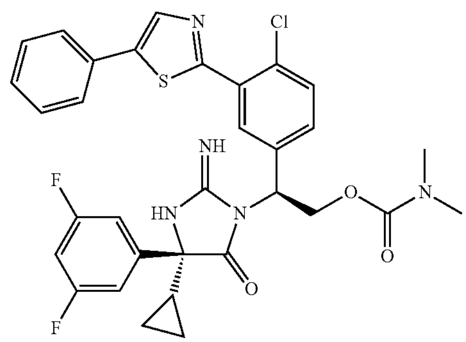 [SMILES: CN(C)C(=O)OC[C@H](c1ccc(Cl)c(-c2ncc(-c3ccccc3)s2)c1)N1C(=N)N[C@@](c2cc(F)cc(F)c2)(C2CC2)C1=O] | 276.5 | 3004.3 |
| 3 | 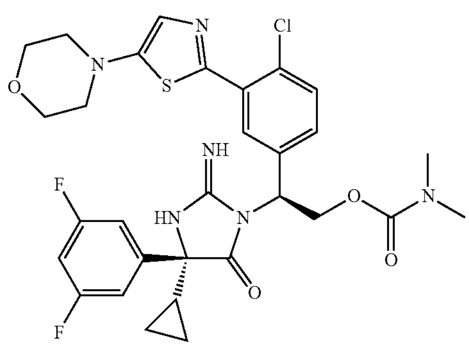 [SMILES: CN(C)C(=O)OC[C@H](c1ccc(Cl)c(-c2ncc(N3CCOCC3)s2)c1)N1C(=N)N[C@@](c2cc(F)cc(F)c2)(C2CC2)C1=O] | 640.9 | 5714.3 |
| 4 | 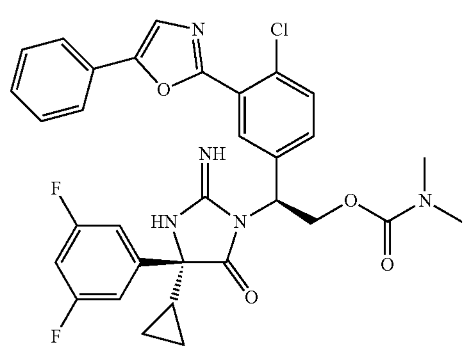 | 436.5 | 3620.3 |

TABLE 1-continued

| COMPD # | STRUCTURE | HIV PI IC$_{50}$ (nM) | MT4 EC$_{50}$ (nM) |
|---|---|---|---|
| 5 | 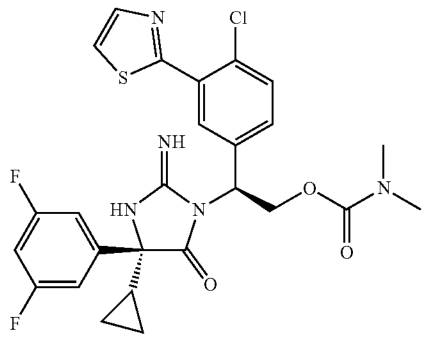 [SMILES: CN(C)C(=O)OC[C@H](c1ccc(Cl)c(-c2nccs2)c1)N1C(=N)N[C@@](c2cc(F)cc(F)c2)(C2CC2)C1=O] | 2139.4 | 5714.3 |
| 6 | 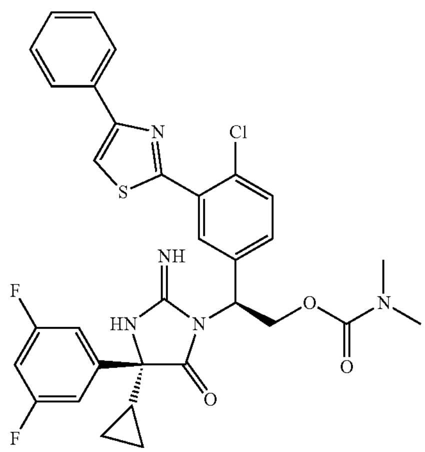 [SMILES: CN(C)C(=O)OC[C@H](c1ccc(Cl)c(-c2nc(-c3ccccc3)cs2)c1)N1C(=N)N[C@@](c2cc(F)cc(F)c2)(C2CC2)C1=O] | 8971.1 | 5714.3 |
| 7 | 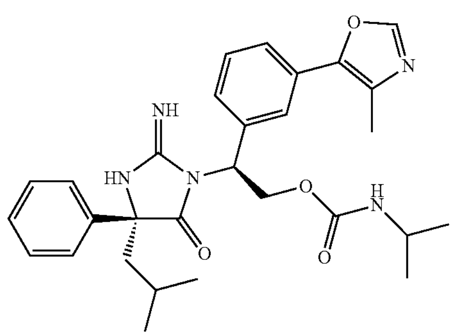 [SMILES: Cc1ncoc1-c1cccc([C@@H](COC(=O)NC(C)C)N2C(=N)N[C@](CC(C)C)(c3ccccc3)C2=O)c1] | 894.4 | 57143 |
| 8 | 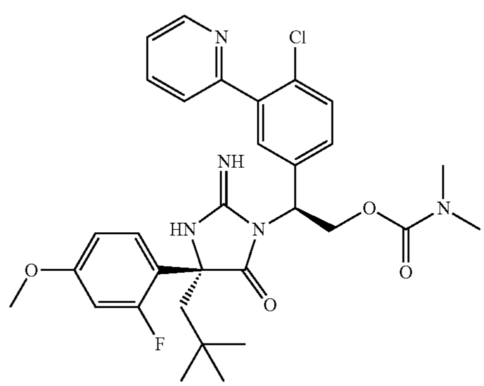 | 3.6 | 277.33 |

TABLE 1-continued
| COMPD # | STRUCTURE | HIV PI IC$_{50}$ (nM) | MT4 EC$_{50}$ (nM) |
|---|---|---|---|
| 9 | 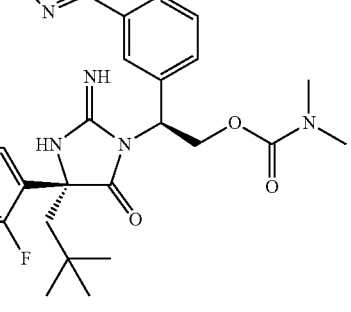 | 226.6 | 1690.4 |
| 10 | 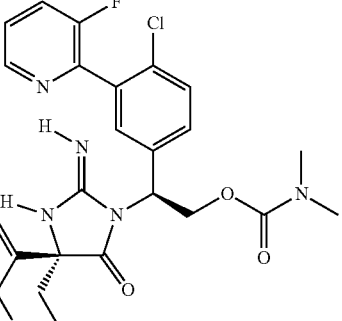 | 1.7 | 91.926 |
| 11 | 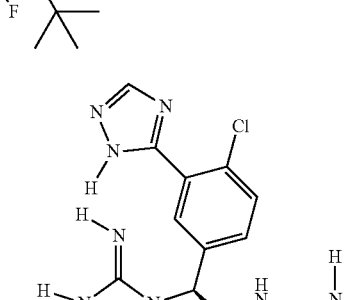 | 2.3 | 35.514 |
| 12 | 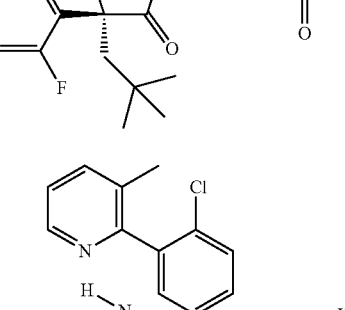 | 1.7 | 22.227 |

TABLE 1-continued

| COMPD # | STRUCTURE | HIV PI IC$_{50}$ (nM) | MT4 EC$_{50}$ (nM) |
|---|---|---|---|
| 13 | 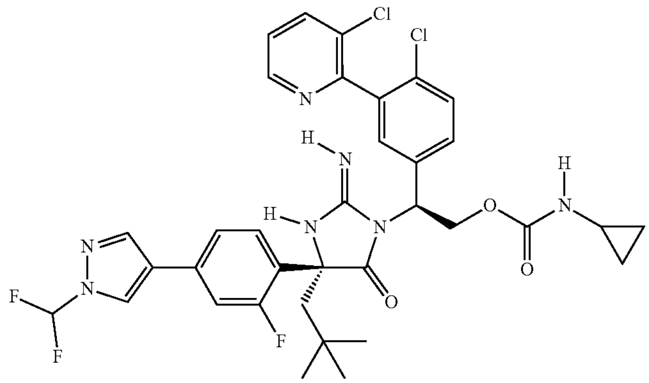 | 11.8 | 310.07 |
| 14 | 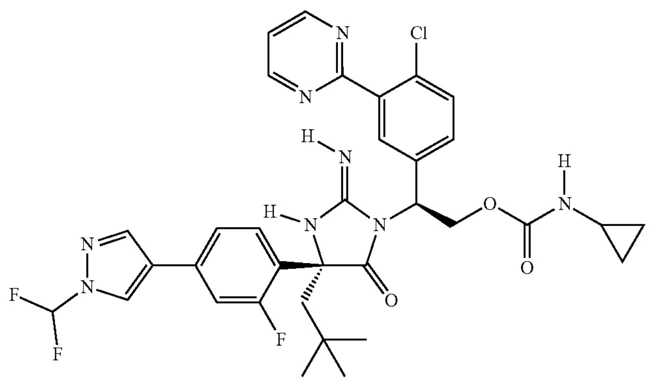 [SMILES: [H]/N=C1\N[C@](CC(C)(C)C)(c2ccc(-c3cnn(C(F)F)c3)cc2F)C(=O)N1[C@H](COC(=O)NC1CC1)c1ccc(Cl)c(-c2ncccc2C)c1] | 3.1 | 68.587 |
| 15 | 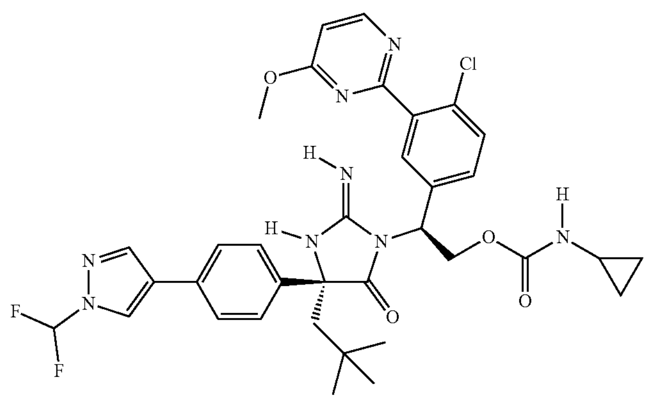 [SMILES: [H]/N=C1\N[C@](CC(C)(C)C)(c2ccc(-c3cnn(C(F)F)c3)cc2)C(=O)N1[C@H](COC(=O)NC1CC1)c1ccc(Cl)c(-c2nccc(OC)n2)c1] | 4.3 | 229.6 |
| 16 | 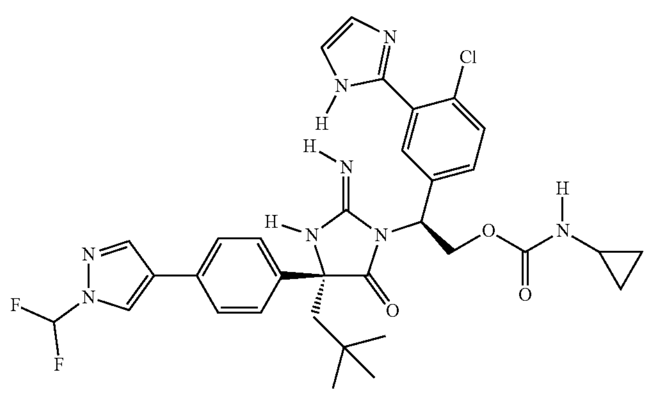 [SMILES: [H]/N=C1\N[C@](CC(C)(C)C)(c2ccc(-c3cnn(C(F)F)c3)cc2)C(=O)N1[C@H](COC(=O)NC1CC1)c1ccc(Cl)c(-c2ncc[nH]2)c1] | 2.1 | 11.411 |

TABLE 1-continued

| COMPD # | STRUCTURE | HIV PI IC$_{50}$ (nM) | MT4 EC$_{50}$ (nM) |
|---|---|---|---|
| 17 | 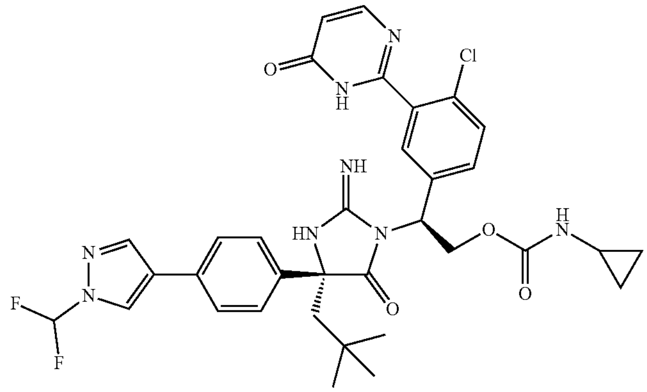 [SMILES: CC(C)(C)C[C@]1(c2ccc(-c3cnn(C(F)F)c3)cc2)NC(=N)N([C@H](COC(=O)NC2CC2)c2ccc(Cl)c(-c3nccc(=O)[nH]3)c2)C1=O] | 1.7 | 556.33 |
| 18 | 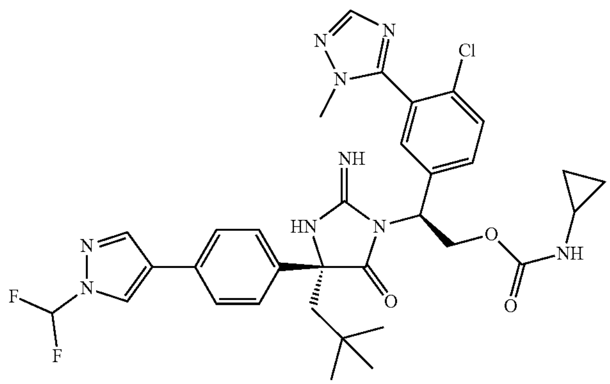 [SMILES: Cn1ncnc1-c1cc([C@@H](COC(=O)NC2CC2)N2C(=N)N[C@](CC(C)(C)C)(c3ccc(-c4cnn(C(F)F)c4)cc3)C2=O)ccc1Cl] | 1.7 | 9.56 |
| 19 | 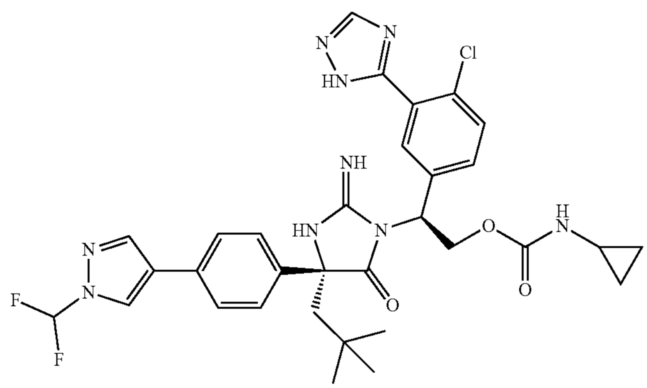 [SMILES: CC(C)(C)C[C@]1(c2ccc(-c3cnn(C(F)F)c3)cc2)NC(=N)N([C@H](COC(=O)NC2CC2)c2ccc(Cl)c(-c3ncn[nH]3)c2)C1=O] | 1.8 | 49.945 |
| 20 | 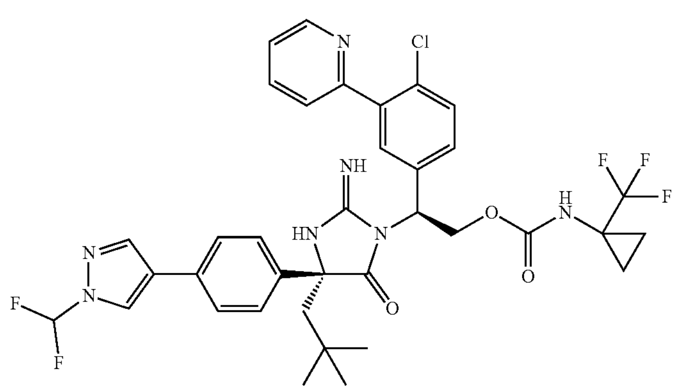 [SMILES: CC(C)(C)C[C@]1(c2ccc(-c3cnn(C(F)F)c3)cc2)NC(=N)N([C@H](COC(=O)NC2(C(F)(F)F)CC2)c2ccc(Cl)c(-c3ccccn3)c2)C1=O] | 3.4 | 76.709 |

TABLE 1-continued
| COMPD # | STRUCTURE | HIV PI IC$_{50}$ (nM) | MT4 EC$_{50}$ (nM) |
|---|---|---|---|
| 21 | 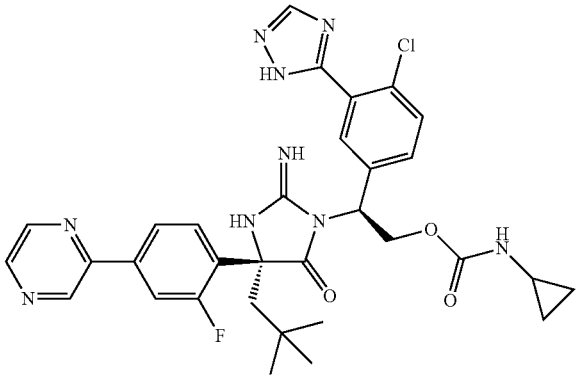 [SMILES: CC(C)(C)C[C@]1(c2ccc(-c3cnccn3)cc2F)NC(=N)N([C@H](COC(=O)NC2CC2)c2ccc(Cl)c(-c3ncn[nH]3)c2)C1=O] | 2.2 | 63.756 |
| 22 | 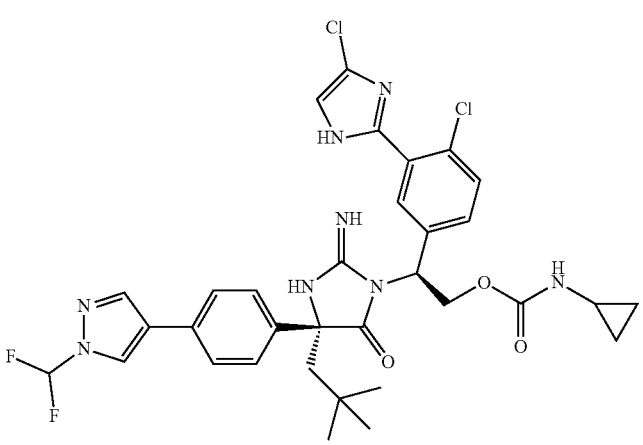 [SMILES: CC(C)(C)C[C@]1(c2ccc(-c3cnn(C(F)F)c3)cc2)NC(=N)N([C@H](COC(=O)NC2CC2)c2ccc(Cl)c(-c3nc(Cl)c[nH]3)c2)C1=O] | 4.6 | |
| 23 | 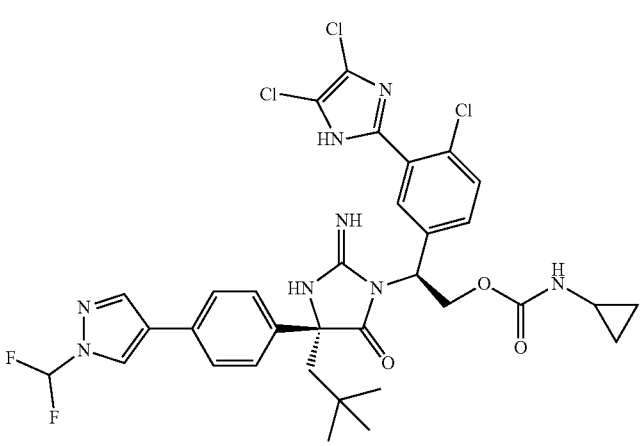 [SMILES: CC(C)(C)C[C@]1(c2ccc(-c3cnn(C(F)F)c3)cc2)NC(=N)N([C@H](COC(=O)NC2CC2)c2ccc(Cl)c(-c3nc(Cl)c(Cl)[nH]3)c2)C1=O] | 7.4 | 70.351 |

| COMPD # | STRUCTURE | HIV PI IC$_{50}$ (nM) | MT4 EC$_{50}$ (nM) |
|---|---|---|---|
| 24 | 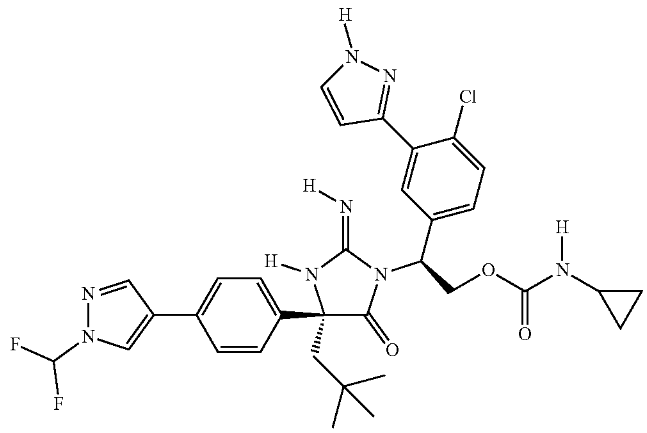 [SMILES: [H]/N=C1\N[C@](CC(C)(C)C)(c2ccc(-c3cnn(C(F)F)c3)cc2)C(=O)N1[C@H](COC(=O)NC1CC1)c1ccc(Cl)c(-c2cc[nH]n2)c1] | 1.7 | 68.172 |
| 25 | 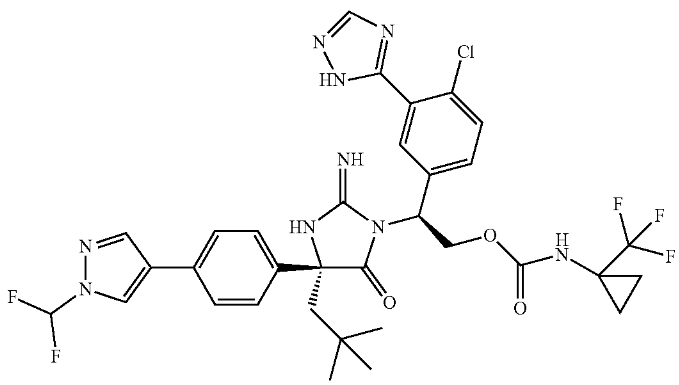 [SMILES: CC(C)(C)C[C@]1(c2ccc(-c3cnn(C(F)F)c3)cc2)NC(=N)N([C@H](COC(=O)NC2(C(F)(F)F)CC2)c2ccc(Cl)c(-c3ncn[nH]3)c2)C1=O] | 2.0 | 52.704 |
| 26 | 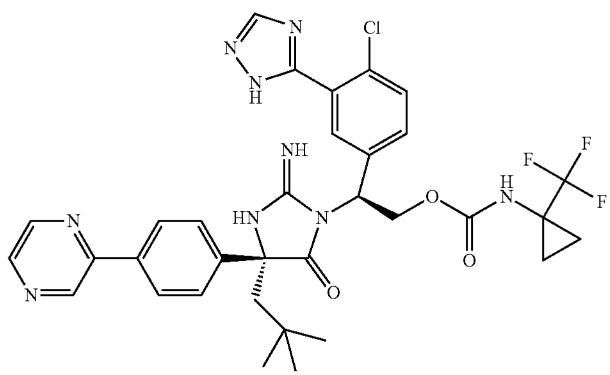 [SMILES: CC(C)(C)C[C@]1(c2ccc(-c3cnccn3)cc2)NC(=N)N([C@H](COC(=O)NC2(C(F)(F)F)CC2)c2ccc(Cl)c(-c3ncn[nH]3)c2)C1=O] | 3.1 | 101.5 |
| 27 | 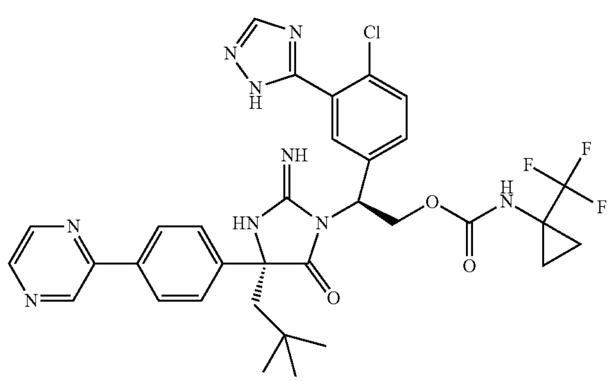 [SMILES: CC(C)(C)C[C@]1(c2ccc(-c3cnccn3)cc2)NC(=N)N([C@H](COC(=O)NC2(C(F)(F)F)CC2)c2ccc(Cl)c(-c3ncn[nH]3)c2)C1=O] | 1.8 | 80.431 |

TABLE 1-continued

| COMPD # | STRUCTURE | HIV PI IC$_{50}$ (nM) | MT4 EC$_{50}$ (nM) |
|---|---|---|---|
| 28 | 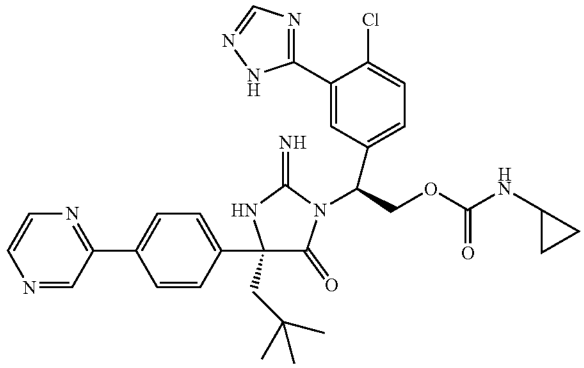 [SMILES: CC(C)(C)C[C@]1(c2ccc(-c3cnccn3)cc2)NC(=N)N([C@H](COC(=O)NC2CC2)c2ccc(Cl)c(-c3ncn[nH]3)c2)C1=O] | 1.7 | 91.697 |
| 29 | 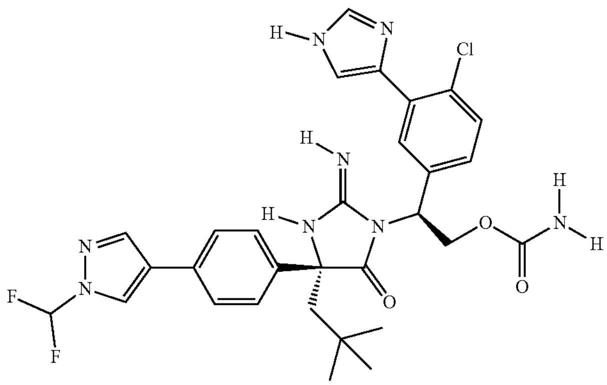 [SMILES: [H]/N=C1\N[C@](CC(C)(C)C)(c2ccc(-c3cnn(C(F)F)c3)cc2)C(=O)N1[C@H](COC(N)=O)c1ccc(Cl)c(-c2c[nH]cn2)c1] | 6.4 | 228.46 |
| 30 | 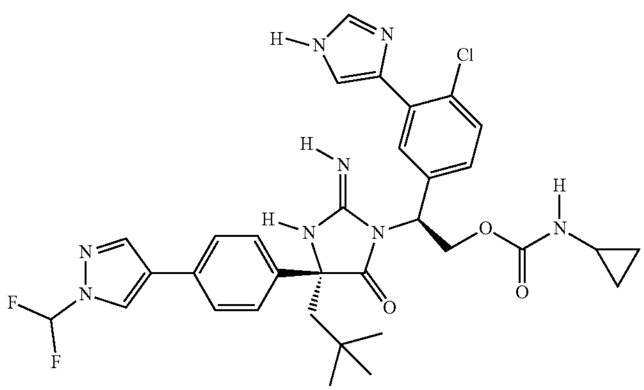 [SMILES: [H]/N=C1\N[C@](CC(C)(C)C)(c2ccc(-c3cnn(C(F)F)c3)cc2)C(=O)N1[C@H](COC(=O)NC1CC1)c1ccc(Cl)c(-c2c[nH]cn2)c1] | 3.3 | 120.2 |
| 31 | 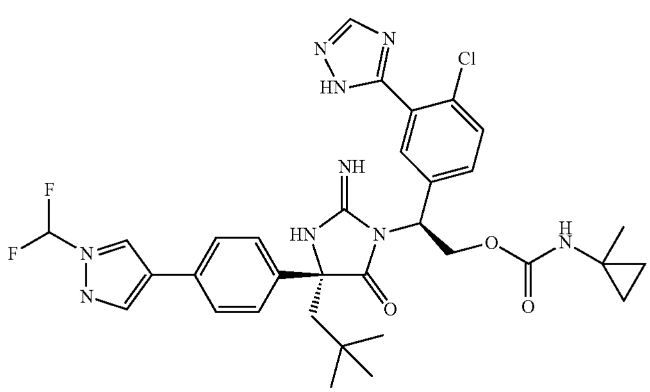 | 1.7 | 50.96 |

TABLE 1-continued
| COMPD # | STRUCTURE | HIV PI IC$_{50}$ (nM) | MT4 EC$_{50}$ (nM) |
|---|---|---|---|
| 32 | 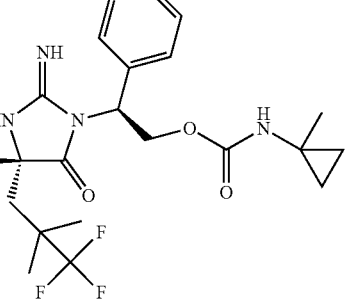 | 1.7 | 69.177 |
| 33 | 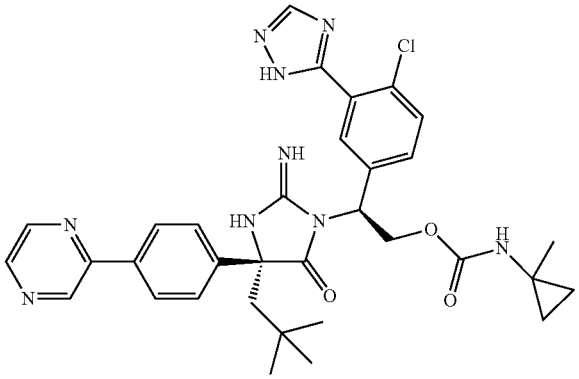 [SMILES: CC(C)(C)C[C@]1(c2ccc(-c3cnccn3)cc2)NC(=N)N([C@H](COC(=O)NC2(C)CC2)c2ccc(Cl)c(-c3ncn[nH]3)c2)C1=O] | 1.8 | 37.162 |
| 34 | 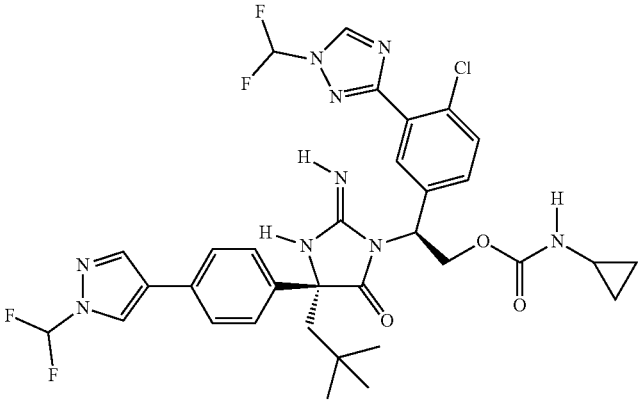 [SMILES: [H]/N=C1\N[C@](CC(C)(C)C)(c2ccc(-c3cnn(C(F)F)c3)cc2)C(=O)N1[C@H](COC(=O)NC1CC1)c1ccc(Cl)c(-c2ncn(C(F)F)n2)c1] | 3.4 | 38.727 |
| 35 | 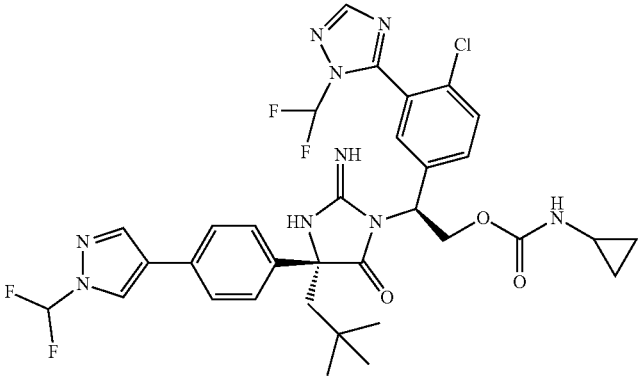 [SMILES: CC(C)(C)C[C@]1(c2ccc(-c3cnn(C(F)F)c3)cc2)NC(=N)N([C@H](COC(=O)NC2CC2)c2ccc(Cl)c(-c3ncnn3C(F)F)c2)C1=O] | 4.1 | 98.1 |

TABLE 1-continued
| COMPD # | STRUCTURE | HIV PI IC$_{50}$ (nM) | MT4 EC$_{50}$ (nM) |
|---|---|---|---|
| 36 | 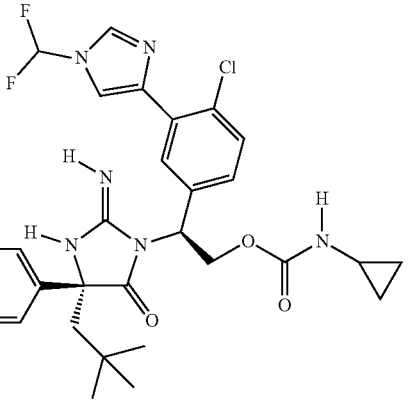 | 1.7 | 89.3 |
| 37 | 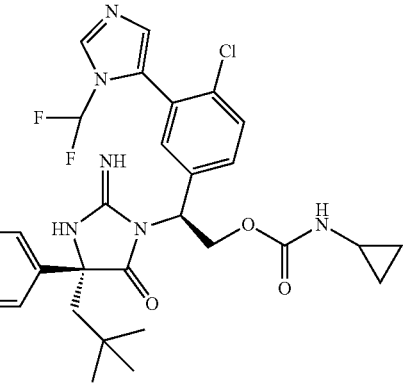 | 15.3 | 218.97 |
| 38 | 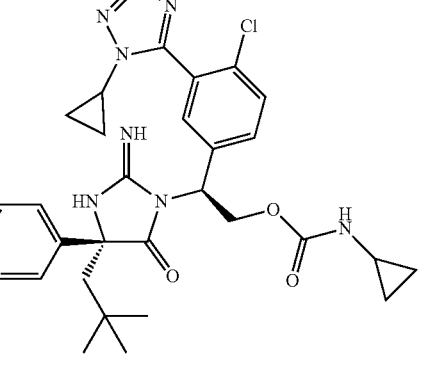 | 1.7 | 9.829 |
| 39 | 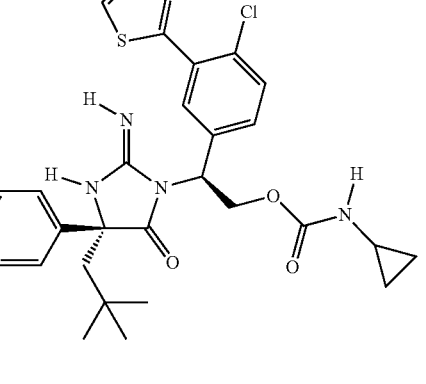 | 1.7 | 29.779 |

TABLE 1-continued

| COMPD # | STRUCTURE | HIV PI IC$_{50}$ (nM) | MT4 EC$_{50}$ (nM) |
|---|---|---|---|
| 40 | 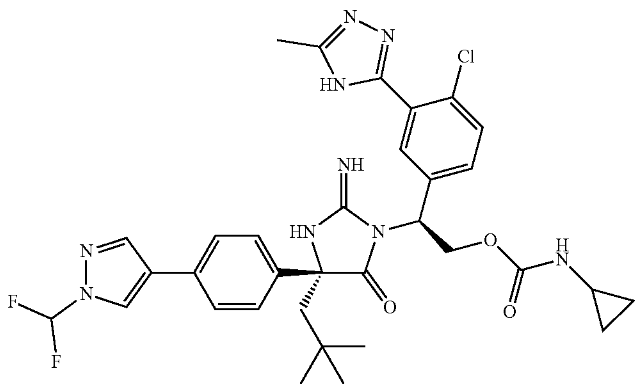 [SMILES: Cc1nnc(-c2cc([C@@H](COC(=O)NC3CC3)N3C(=N)N[C@](CC(C)(C)C)(c4ccc(-c5cnn(C(F)F)c5)cc4)C3=O)ccc2Cl)[nH]1] | 2.3 | 84.148 |
| 41 | 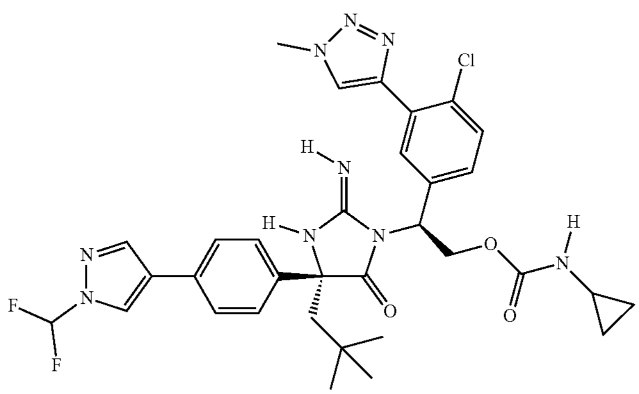 [SMILES: [H]/N=C1\N[C@](CC(C)(C)C)(c2ccc(-c3cnn(C(F)F)c3)cc2)C(=O)N1[C@H](COC(=O)NC1CC1)c1ccc(Cl)c(-c2cn(C)nn2)c1] | 1.8 | 18.075 |
| 42 | 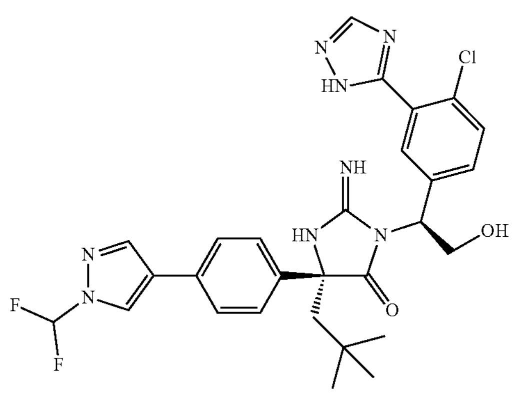 [SMILES: CC(C)(C)C[C@]1(c2ccc(-c3cnn(C(F)F)c3)cc2)NC(=N)N([C@H](CO)c2ccc(Cl)c(-c3ncn[nH]3)c2)C1=O] | 3.5 | 102.68 |
| 43 | 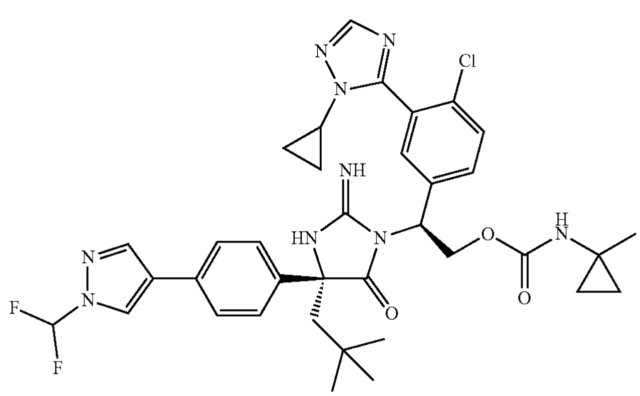 [SMILES: CC(C)(C)C[C@]1(c2ccc(-c3cnn(C(F)F)c3)cc2)NC(=N)N([C@H](COC(=O)NC2(C)CC2)c2ccc(Cl)c(-c3ncnn3C3CC3)c2)C1=O] | 1.7 | 8.178 |

TABLE 1-continued
| COMPD # | STRUCTURE | HIV PI IC$_{50}$ (nM) | MT4 EC$_{50}$ (nM) |
|---|---|---|---|
| 44 | 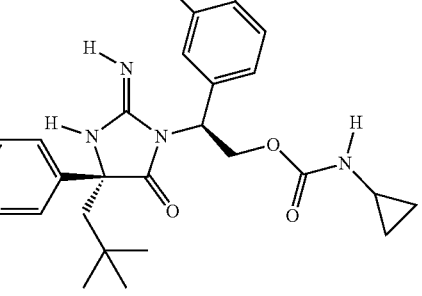 | 2.9 | 246.47 |
| 45 | 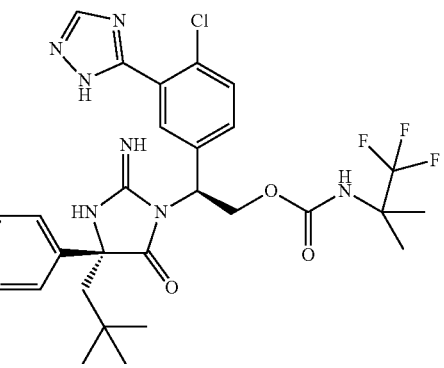 | 1.7 | 31.722 |
| 46 | 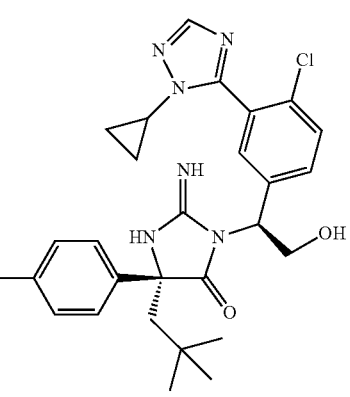 | 10.7 | 37.627 |
| 47 | 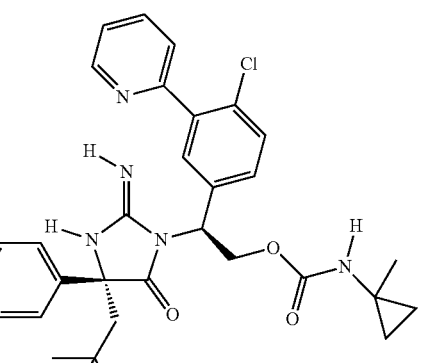 | 3.5 | 60.914 |

TABLE 1-continued
| COMPD # | STRUCTURE | HIV PI IC$_{50}$ (nM) | MT4 EC$_{50}$ (nM) |
|---|---|---|---|
| 48 | 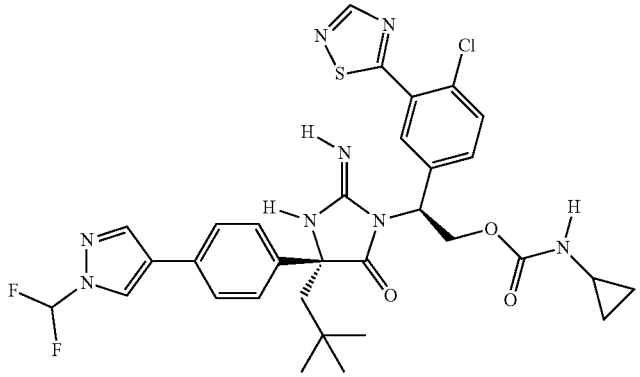 [SMILES: [H]/N=C1\N[C@](CC(C)(C)C)(c2ccc(-c3cnn(C(F)F)c3)cc2)C(=O)N1[C@H](COC(=O)NC1CC1)c1ccc(Cl)c(-c2ncns2)c1] | 10.5 | 80.001 |
| 49 | 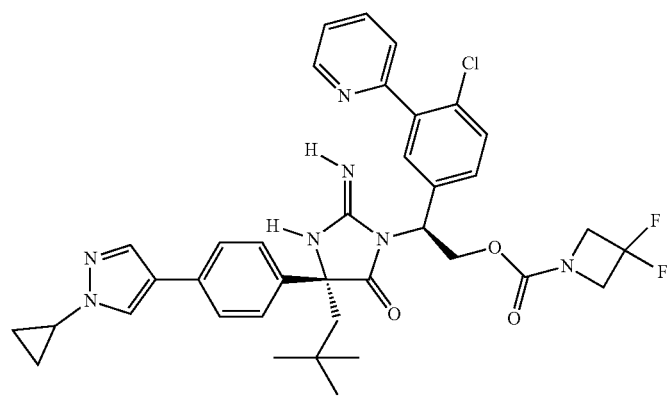 [SMILES: [H]/N=C1\N[C@](CC(C)(C)C)(c2ccc(-c3cnn(C4CC4)c3)cc2)C(=O)N1[C@H](COC(=O)N1CC(F)(F)C1)c1ccc(Cl)c(-c2ccccn2)c1] | 1.7 | 68.123 |
| 50 | 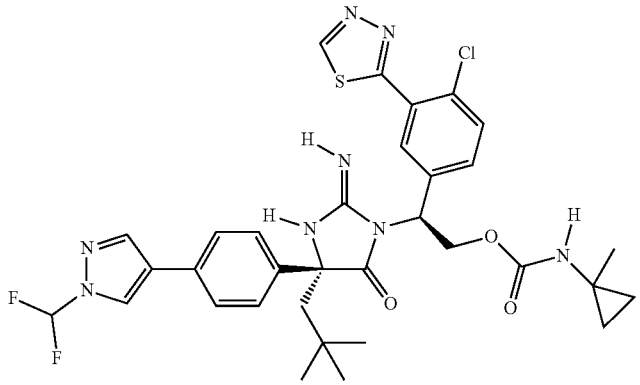 [SMILES: [H]/N=C1\N[C@](CC(C)(C)C)(c2ccc(-c3cnn(C(F)F)c3)cc2)C(=O)N1[C@H](COC(=O)NC1(C)CC1)c1ccc(Cl)c(-c2nncs2)c1] | 27.7 | 27.652 |
| 51 | 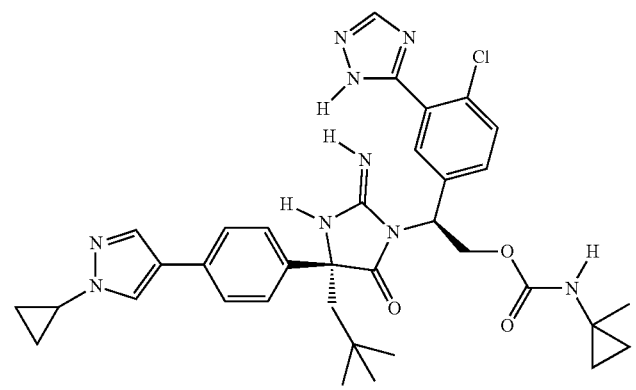 [SMILES: [H]/N=C1\N[C@](CC(C)(C)C)(c2ccc(-c3cnn(C4CC4)c3)cc2)C(=O)N1[C@H](COC(=O)NC1(C)CC1)c1ccc(Cl)c(-c2ncn[nH]2)c1] | 33.6 | 33.594 |

TABLE 1-continued

| COMPD # | STRUCTURE | HIV PI IC$_{50}$ (nM) | MT4 EC$_{50}$ (nM) |
|---|---|---|---|
| 52 | 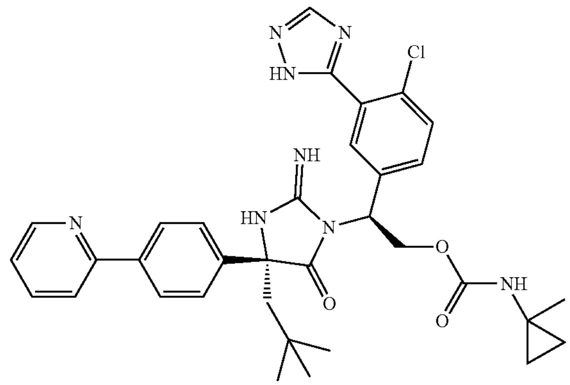 [SMILES: CC(C)(C)C[C@]1(c2ccc(-c3ccccn3)cc2)NC(=N)N([C@H](COC(=O)NC2(C)CC2)c2ccc(Cl)c(-c3ncn[nH]3)c2)C1=O] | 41.9 | 41.931 |
| 53 | 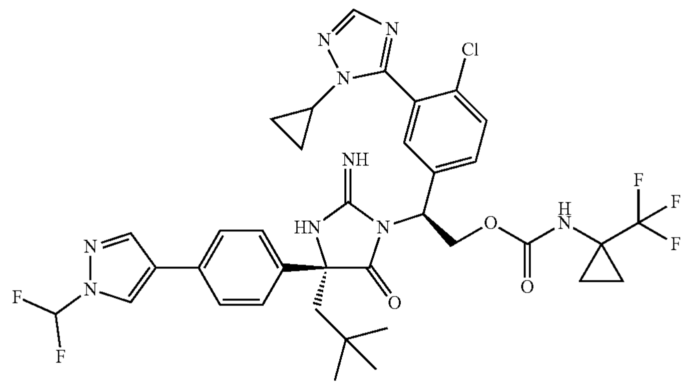 [SMILES: CC(C)(C)C[C@]1(c2ccc(-c3cnn(C(F)F)c3)cc2)NC(=N)N([C@H](COC(=O)NC2(C(F)(F)F)CC2)c2ccc(Cl)c(-c3ncnn3C3CC3)c2)C1=O] | 16.2 | 16.222 |
| 54 | 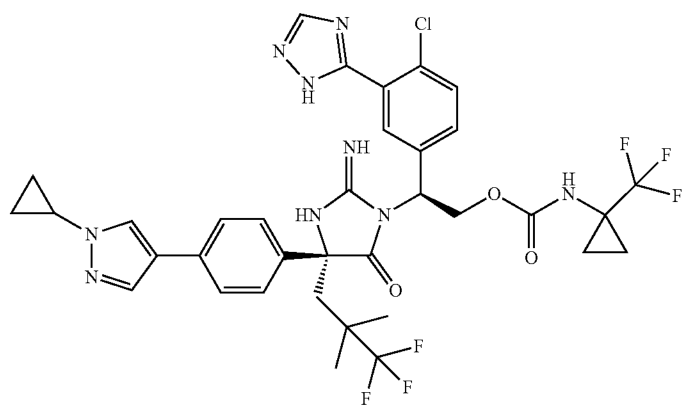 [SMILES: CC(C)(C[C@]1(c2ccc(-c3cnn(C4CC4)c3)cc2)NC(=N)N([C@H](COC(=O)NC2(C(F)(F)F)CC2)c2ccc(Cl)c(-c3ncn[nH]3)c2)C1=O)C(F)(F)F] | 83.2 | 83.226 |
| 55 | 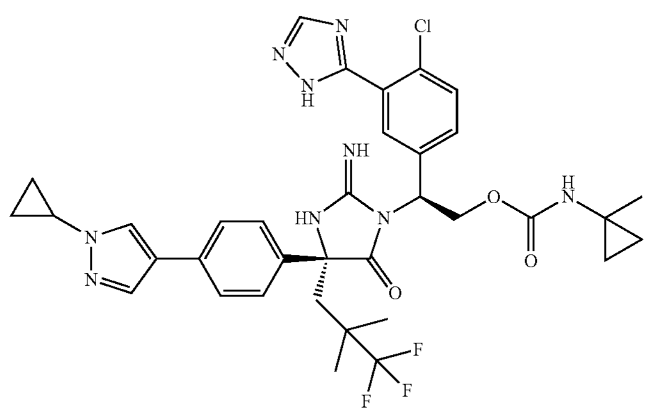 [SMILES: CC1(NC(=O)OC[C@H](c2ccc(Cl)c(-c3ncn[nH]3)c2)N2C(=N)N[C@](CC(C)(C)C(F)(F)F)(c3ccc(-c4cnn(C5CC5)c4)cc3)C2=O)CC1] | 50.4 | 50.4 |

TABLE 1-continued

| COMPD # | STRUCTURE | HIV PI IC$_{50}$ (nM) | MT4 EC$_{50}$ (nM) |
|---|---|---|---|
| 56 | 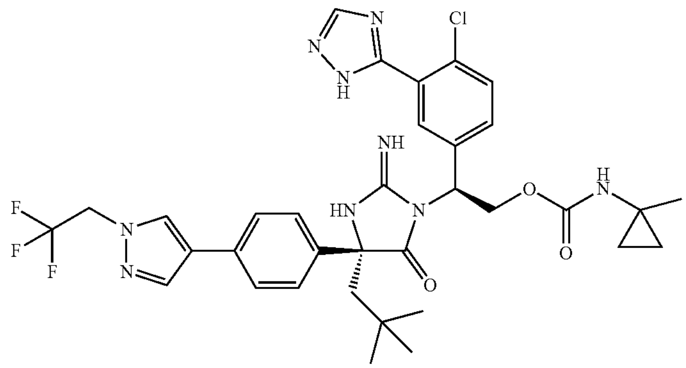 [SMILES: CC(C)(C)C[C@]1(c2ccc(-c3cnn(CC(F)(F)F)c3)cc2)NC(=N)N([C@H](COC(=O)NC2(C)CC2)c2ccc(Cl)c(-c3ncn[nH]3)c2)C1=O] | 62.9 | 62.919 |
| 57 | 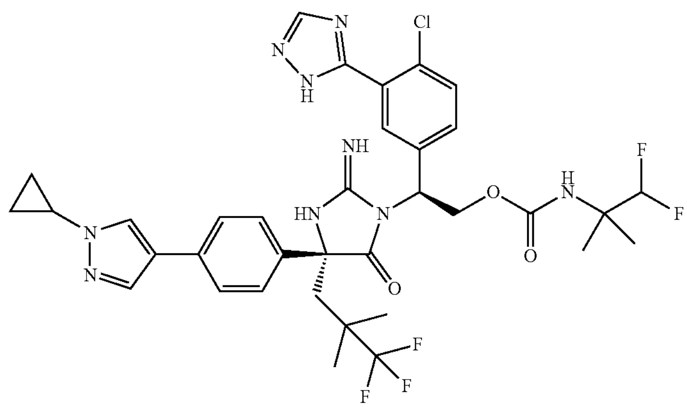 [SMILES: CC(C)(NC(=O)OC[C@H](c1ccc(Cl)c(-c2ncn[nH]2)c1)N1C(=N)N[C@](CC(C)(C)C(F)(F)F)(c2ccc(-c3cnn(C4CC4)c3)cc2)C1=O)C(F)F] | 37.2 | 37.237 |
| 58 | 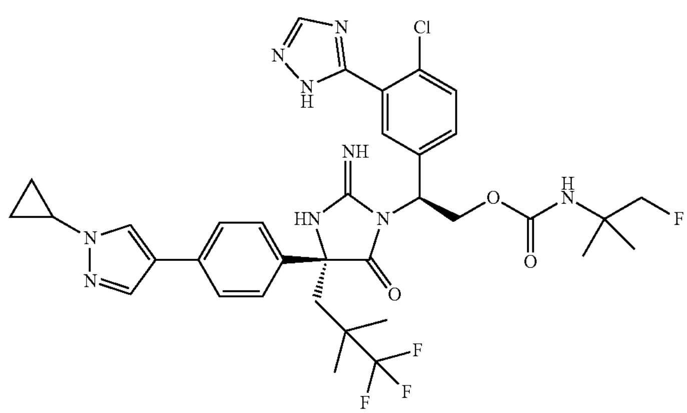 [SMILES: CC(C)(CF)NC(=O)OC[C@H](c1ccc(Cl)c(-c2ncn[nH]2)c1)N1C(=N)N[C@](CC(C)(C)C(F)(F)F)(c2ccc(-c3cnn(C4CC4)c3)cc2)C1=O] | 35.4 | 35.376 |
| 59 | 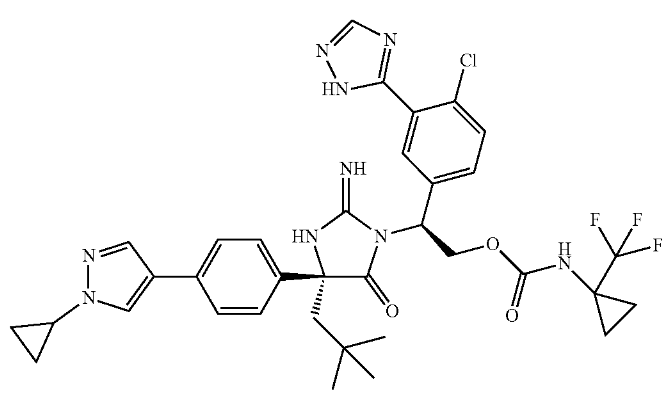 [SMILES: CC(C)(C)C[C@]1(c2ccc(-c3cnn(C4CC4)c3)cc2)NC(=N)N([C@H](COC(=O)NC2(C(F)(F)F)CC2)c2ccc(Cl)c(-c3ncn[nH]3)c2)C1=O] | 31.6 | 31.554 |

TABLE 1-continued

| COMPD # | STRUCTURE | HIV PI IC$_{50}$ (nM) | MT4 EC$_{50}$ (nM) |
|---|---|---|---|
| 60 | 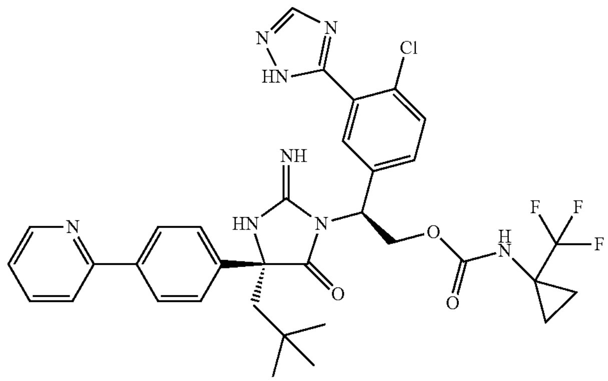 [SMILES: CC(C)(C)C[C@]1(c2ccc(-c3ccccn3)cc2)NC(=N)N([C@H](COC(=O)NC2(C(F)(F)F)CC2)c2ccc(Cl)c(-c3ncn[nH]3)c2)C1=O] | 2.8 | 28.497 |
| 67 | 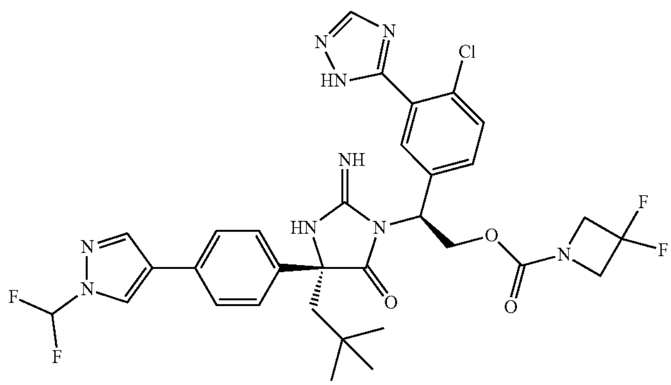 [SMILES: CC(C)(C)C[C@]1(c2ccc(-c3cnn(C(F)F)c3)cc2)NC(=N)N([C@H](COC(=O)N2CC(F)(F)C2)c2ccc(Cl)c(-c3ncn[nH]3)c2)C1=O] | 2.0 | 20.825 |
| 68 | 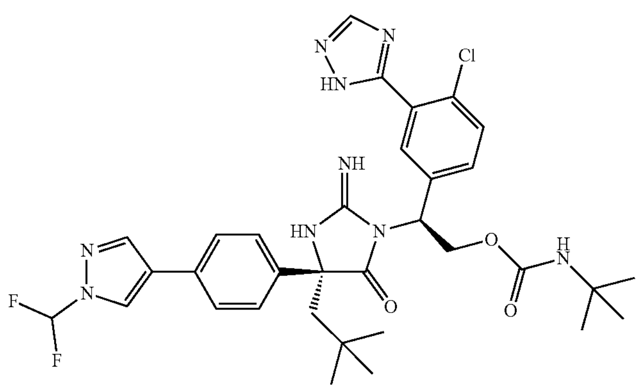 [SMILES: CC(C)(C)C[C@]1(c2ccc(-c3cnn(C(F)F)c3)cc2)NC(=N)N([C@H](COC(=O)NC(C)(C)C)c2ccc(Cl)c(-c3ncn[nH]3)c2)C1=O] | 2.2 | 21.609 |
| 69 | 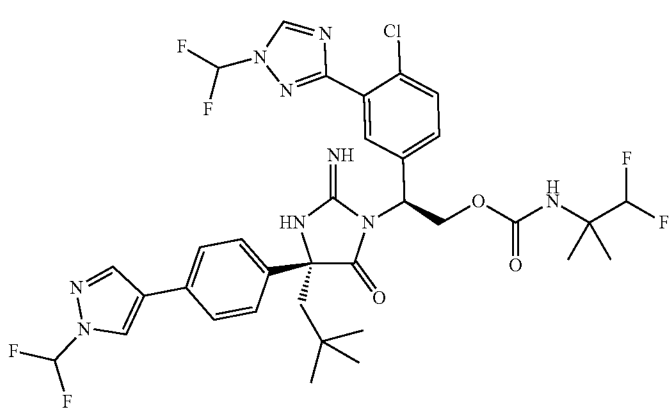 [SMILES: CC(C)(C)C[C@]1(c2ccc(-c3cnn(C(F)F)c3)cc2)NC(=N)N([C@H](COC(=O)NC(C)(C)C(F)F)c2ccc(Cl)c(-c3ncn(C(F)F)n3)c2)C1=O] | 2.6 | 32.568 |

TABLE 1-continued

| COMPD # | STRUCTURE | HIV PI IC$_{50}$ (nM) | MT4 EC$_{50}$ (nM) |
|---|---|---|---|
| 70 | 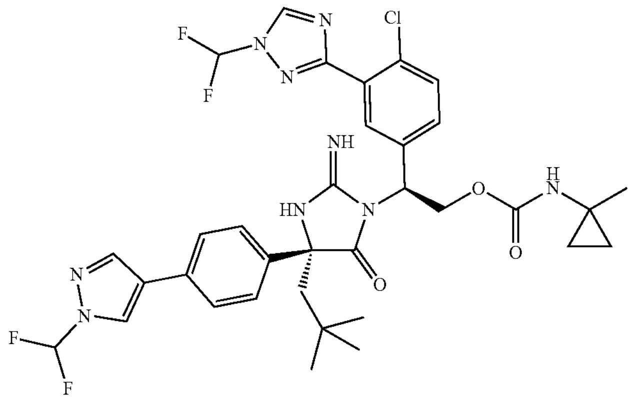 [SMILES: CC(C)(C)C[C@]1(c2ccc(-c3cnn(C(F)F)c3)cc2)NC(=N)N([C@H](COC(=O)NC2(C)CC2)c2ccc(Cl)c(-c3ncn(C(F)F)n3)c2)C1=O] | 5.1 | 29.399 |
| 71 | 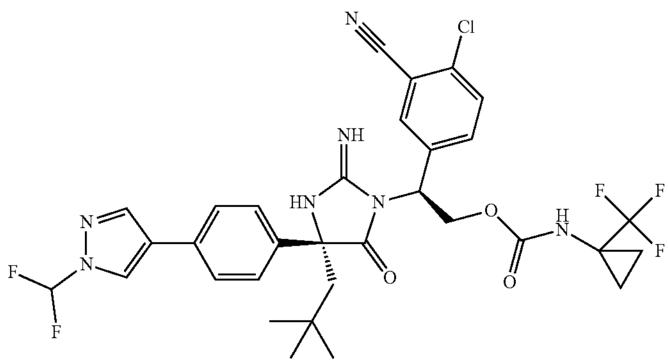 [SMILES: CC(C)(C)C[C@]1(c2ccc(-c3cnn(C(F)F)c3)cc2)NC(=N)N([C@H](COC(=O)NC2(C(F)(F)F)CC2)c2ccc(Cl)c(C#N)c2)C1=O] | 40.4 | 323.93 |
| 72 | 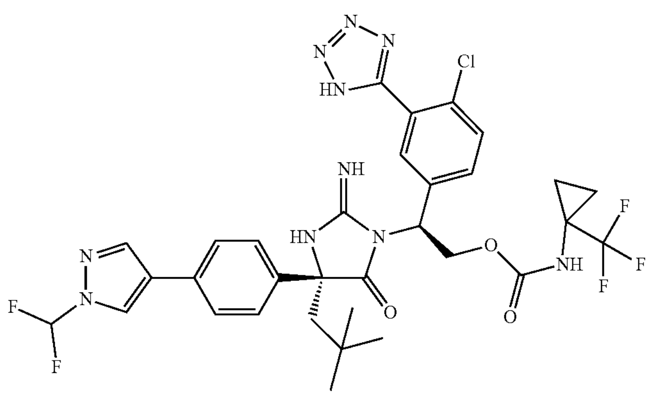 [SMILES: CC(C)(C)C[C@]1(c2ccc(-c3cnn(C(F)F)c3)cc2)NC(=N)N([C@H](COC(=O)NC2(C(F)(F)F)CC2)c2ccc(Cl)c(-c3nnn[nH]3)c2)C1=O] | 59.2 | 5714.3 |
| 75 | 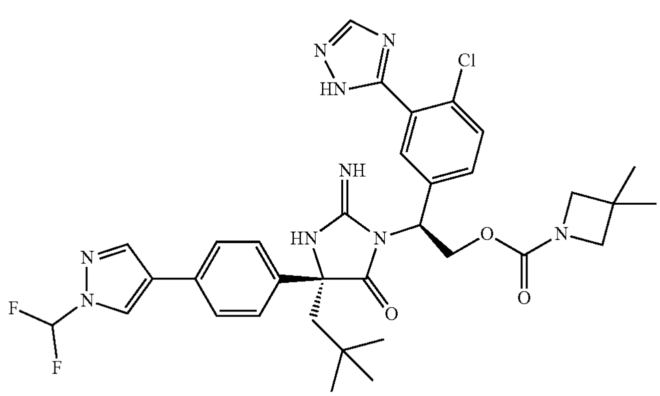 [SMILES: CC(C)(C)C[C@]1(c2ccc(-c3cnn(C(F)F)c3)cc2)NC(=N)N([C@H](COC(=O)N2CC(C)(C)C2)c2ccc(Cl)c(-c3ncn[nH]3)c2)C1=O] | 2.0 | 30.478 |

TABLE 1-continued

| COMPD # | STRUCTURE | HIV PI IC$_{50}$ (nM) | MT4 EC$_{50}$ (nM) |
|---|---|---|---|
| 76 | 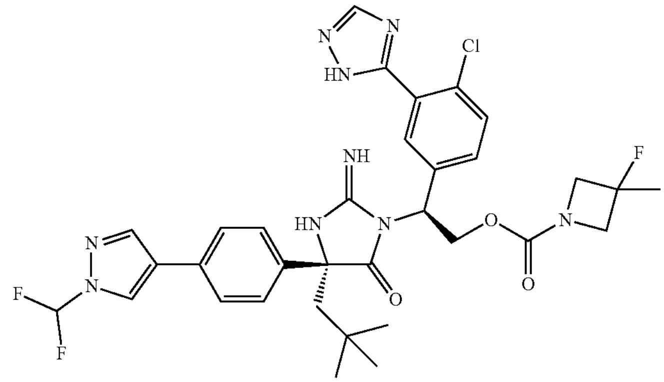 | 2.2 | 34.827 |
| 77 | 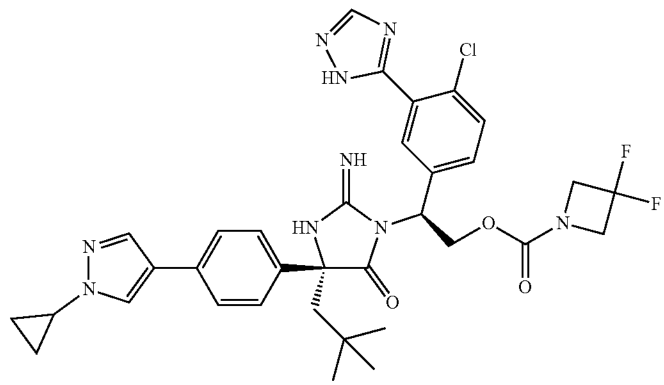 [SMILES: CC(C)(C)C[C@]1(c2ccc(-c3cnn(C4CC4)c3)cc2)NC(=N)N([C@H](COC(=O)N2CC(F)(F)C2)c2ccc(Cl)c(-c3ncn[nH]3)c2)C1=O] | 2.2 | 38.942 |
| 78 | 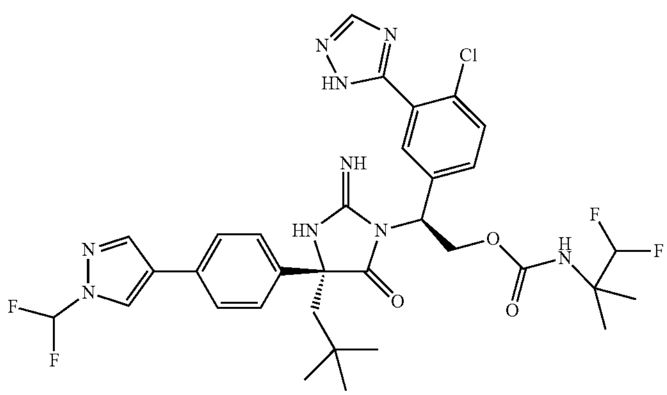 [SMILES: CC(C)(C)C[C@]1(c2ccc(-c3cnn(C(F)F)c3)cc2)NC(=N)N([C@H](COC(=O)NC(C)(C)C(F)F)c2ccc(Cl)c(-c3ncn[nH]3)c2)C1=O] | 3.1 | 74.865 |
| 79 | 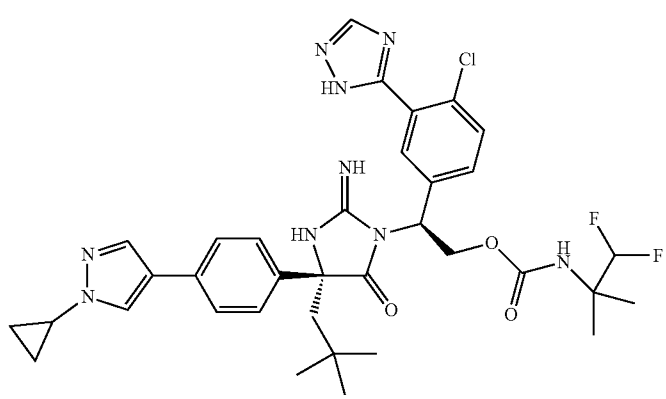 [SMILES: CC(C)(C)C[C@]1(c2ccc(-c3cnn(C4CC4)c3)cc2)NC(=N)N([C@H](COC(=O)NC(C)(C)C(F)F)c2ccc(Cl)c(-c3ncn[nH]3)c2)C1=O] | 3.2 | 64.485 |

TABLE 1-continued

| COMPD # | STRUCTURE | HIV PI IC$_{50}$ (nM) | MT4 EC$_{50}$ (nM) |
|---|---|---|---|
| 80 | 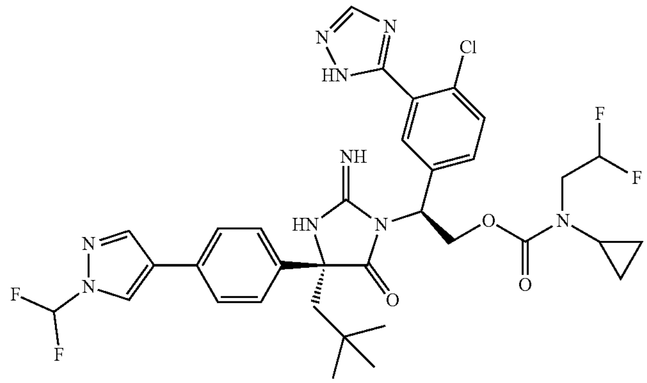 [SMILES: CC(C)(C)C[C@]1(c2ccc(-c3cnn(C(F)F)c3)cc2)NC(=N)N([C@H](COC(=O)N(CC(F)F)C2CC2)c2ccc(Cl)c(-c3ncn[nH]3)c2)C1=O] | 3.2 | 28.822 |
| 81 | 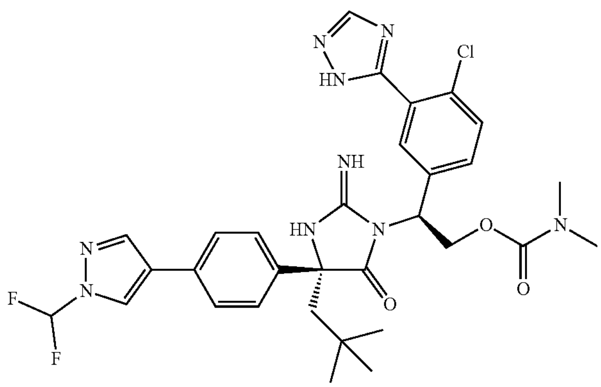 [SMILES: CN(C)C(=O)OC[C@H](c1ccc(Cl)c(-c2ncn[nH]2)c1)N1C(=N)N[C@](CC(C)(C)C)(c2ccc(-c3cnn(C(F)F)c3)cc2)C1=O] | 1.8 | 31.554 |
| 82 | 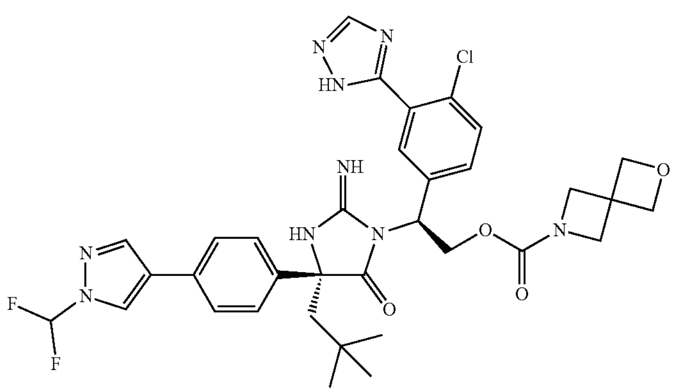 [SMILES: CC(C)(C)C[C@]1(c2ccc(-c3cnn(C(F)F)c3)cc2)NC(=N)N([C@H](COC(=O)N2CC3(COC3)C2)c2ccc(Cl)c(-c3ncn[nH]3)c2)C1=O] | 2.2 | 180.16 |
| 83 | 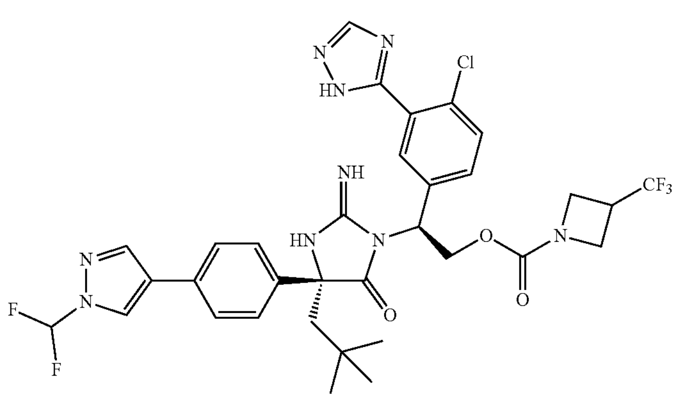 [SMILES: CC(C)(C)C[C@]1(c2ccc(-c3cnn(C(F)F)c3)cc2)NC(=N)N([C@H](COC(=O)N2CC(C(F)(F)F)C2)c2ccc(Cl)c(-c3ncn[nH]3)c2)C1=O] | 2.2 | 33.356 |

TABLE 1-continued

| COMPD # | STRUCTURE | HIV PI IC$_{50}$ (nM) | MT4 EC$_{50}$ (nM) |
|---|---|---|---|
| 84 | 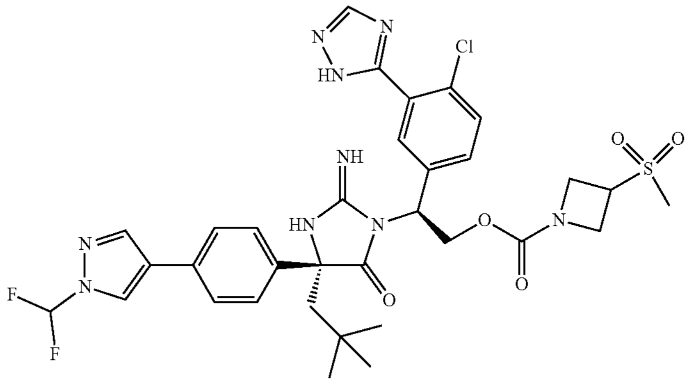 [SMILES: CC(C)(C)C[C@]1(c2ccc(-c3cnn(C(F)F)c3)cc2)NC(=N)N([C@H](COC(=O)N2CC(S(C)(=O)=O)C2)c2ccc(Cl)c(-c3ncn[nH]3)c2)C1=O] | 2.0 | 1053 |
| 85 | 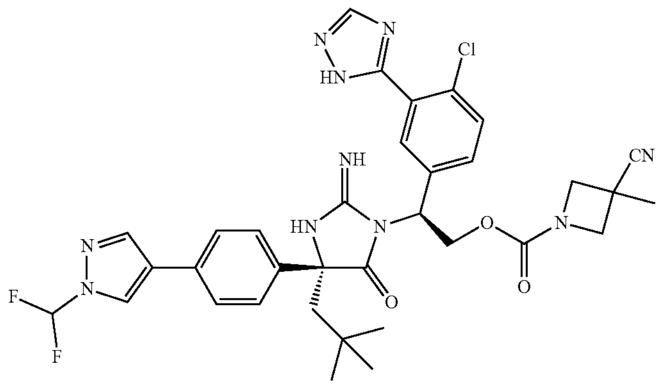 [SMILES: CC(C)(C)C[C@]1(c2ccc(-c3cnn(C(F)F)c3)cc2)NC(=N)N([C@H](COC(=O)N2CC(C)(C#N)C2)c2ccc(Cl)c(-c3ncn[nH]3)c2)C1=O] | 1.7 | 112.2 |
| 86 | 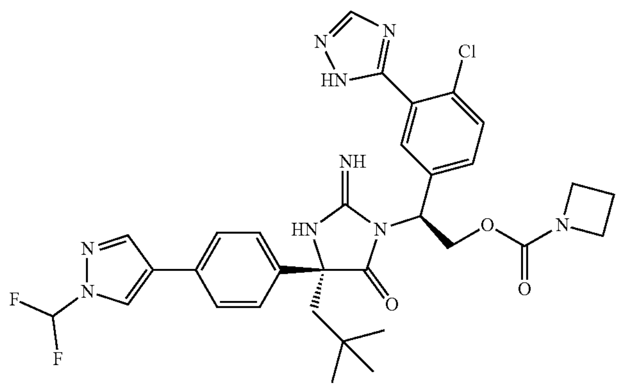 [SMILES: CC(C)(C)C[C@]1(c2ccc(-c3cnn(C(F)F)c3)cc2)NC(=N)N([C@H](COC(=O)N2CCC2)c2ccc(Cl)c(-c3ncn[nH]3)c2)C1=O] | 2.0 | 35.407 |
| 87 | 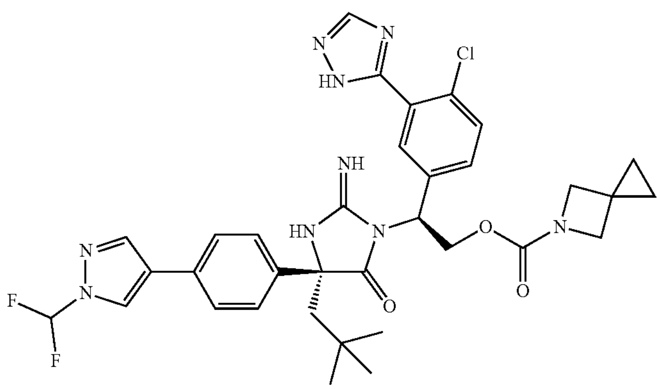 [SMILES: CC(C)(C)C[C@]1(c2ccc(-c3cnn(C(F)F)c3)cc2)NC(=N)N([C@H](COC(=O)N2CC3(CC3)C2)c2ccc(Cl)c(-c3ncn[nH]3)c2)C1=O] | 1.8 | 38.484 |

TABLE 1-continued
| COMPD # | STRUCTURE | HIV PI IC$_{50}$ (nM) | MT4 EC$_{50}$ (nM) |
|---|---|---|---|
| 88 | 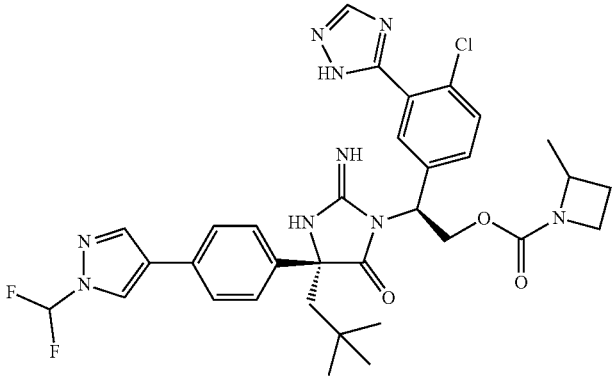 [SMILES: CC1CCN1C(=O)OC[C@H](c1ccc(Cl)c(-c2ncn[nH]2)c1)N1C(=N)N[C@](CC(C)(C)C)(c2ccc(-c3cnn(C(F)F)c3)cc2)C1=O] | 2.0 | 24.265 |
| 89 | 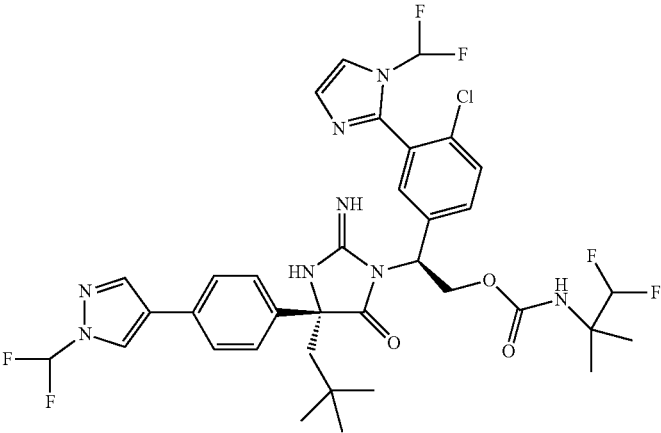 [SMILES: CC(C)(C)C[C@]1(c2ccc(-c3cnn(C(F)F)c3)cc2)NC(=N)N([C@H](COC(=O)NC(C)(C)C(F)F)c2ccc(Cl)c(-c3nccn3C(F)F)c2)C1=O] | 3.0 | 34.369 |
| 90 | 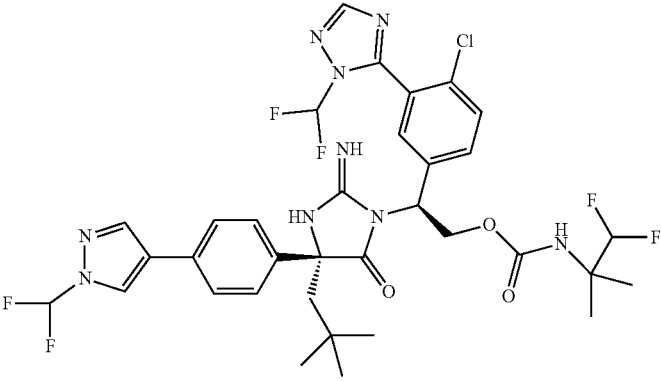 [SMILES: CC(C)(C)C[C@]1(c2ccc(-c3cnn(C(F)F)c3)cc2)NC(=N)N([C@H](COC(=O)NC(C)(C)C(F)F)c2ccc(Cl)c(-c3ncnn3C(F)F)c2)C1=O] | 2.0 | 12.208 |

TABLE 1-continued

| COMPD # | STRUCTURE | HIV PI IC$_{50}$ (nM) | MT4 EC$_{50}$ (nM) |
|---|---|---|---|
| 91 | 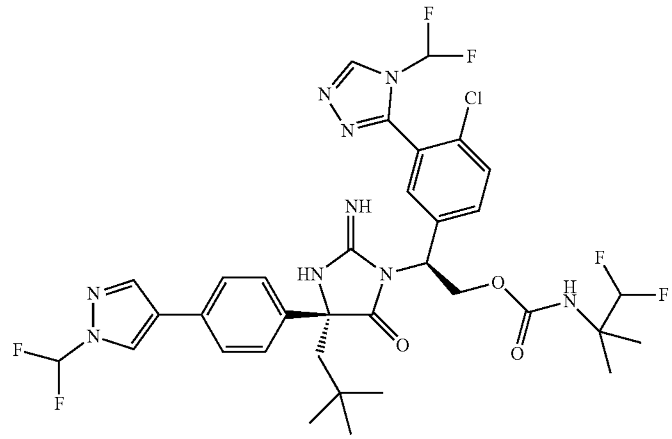 [SMILES: CC(C)(C)C[C@]1(c2ccc(-c3cnn(C(F)F)c3)cc2)NC(=N)N([C@H](COC(=O)NC(C)(C)C(F)F)c2ccc(Cl)c(-c3nncn3C(F)F)c2)C1=O] | 23.8 | 200.45 |
| 92 | 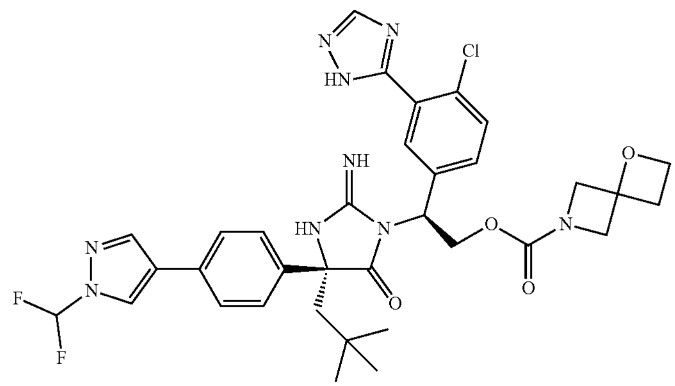 [SMILES: CC(C)(C)C[C@]1(c2ccc(-c3cnn(C(F)F)c3)cc2)NC(=N)N([C@H](COC(=O)N2CC3(CCO3)C2)c2ccc(Cl)c(-c3ncn[nH]3)c2)C1=O] | 1.9 | 112.63 |
| 93 | 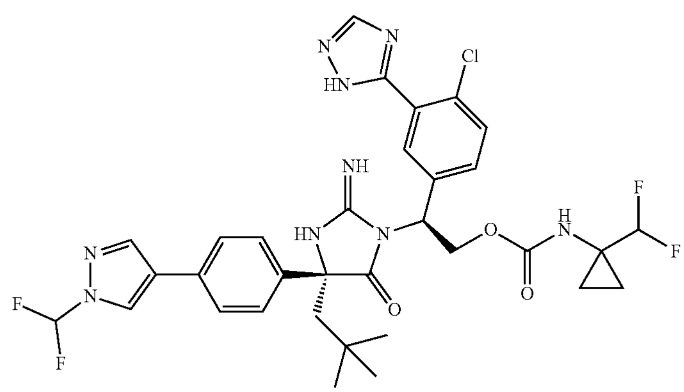 [SMILES: CC(C)(C)C[C@]1(c2ccc(-c3cnn(C(F)F)c3)cc2)NC(=N)N([C@H](COC(=O)NC2(C(F)F)CC2)c2ccc(Cl)c(-c3ncn[nH]3)c2)C1=O] | 3.0 | 104.73 |
| 94 | 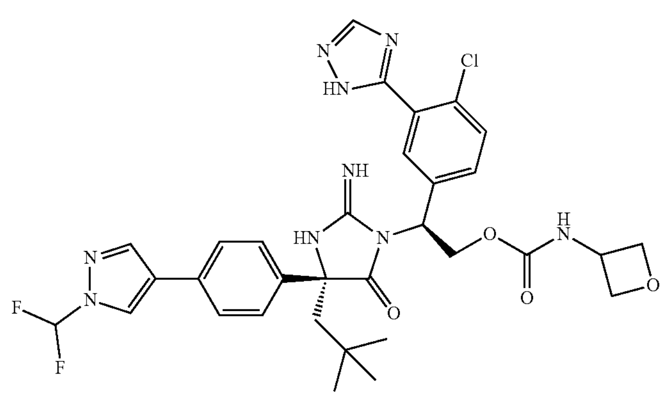 [SMILES: CC(C)(C)C[C@]1(c2ccc(-c3cnn(C(F)F)c3)cc2)NC(=N)N([C@H](COC(=O)NC2COC2)c2ccc(Cl)c(-c3ncn[nH]3)c2)C1=O] | 1.8 | 341.45 |

TABLE 1-continued

| COMPD # | STRUCTURE | HIV PI IC$_{50}$ (nM) | MT4 EC$_{50}$ (nM) |
|---|---|---|---|
| 95 | 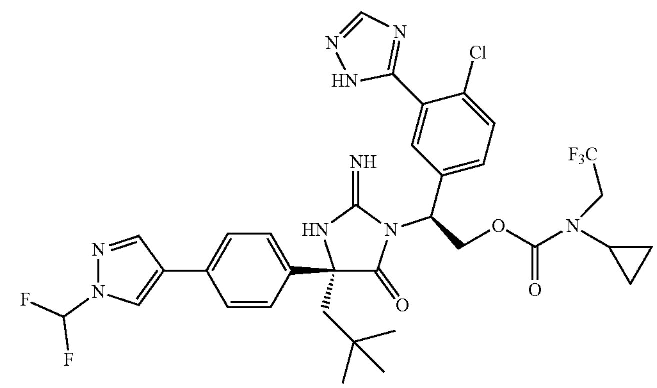 [SMILES: CC(C)(C)C[C@]1(c2ccc(-c3cnn(C(F)F)c3)cc2)NC(=N)N([C@H](COC(=O)N(CC(F)(F)F)C2CC2)c2ccc(Cl)c(-c3ncn[nH]3)c2)C1=O] | 2.8 | 30.408 |
| 96 | 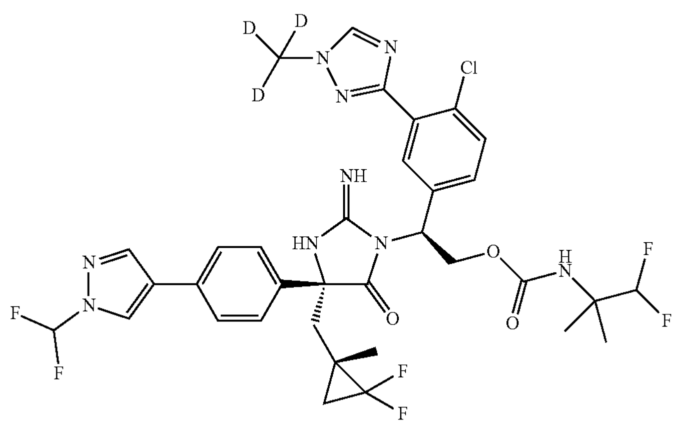 [SMILES: [2H]C([2H])([2H])n1cnc(-c2cc([C@@H](COC(=O)NC(C)(C)C(F)F)N3C(=N)N[C@](C[C@@]4(C)CC4(F)F)(c4ccc(-c5cnn(C(F)F)c5)cc4)C3=O)ccc2Cl)n1] | | 83.674 |
| 97 | 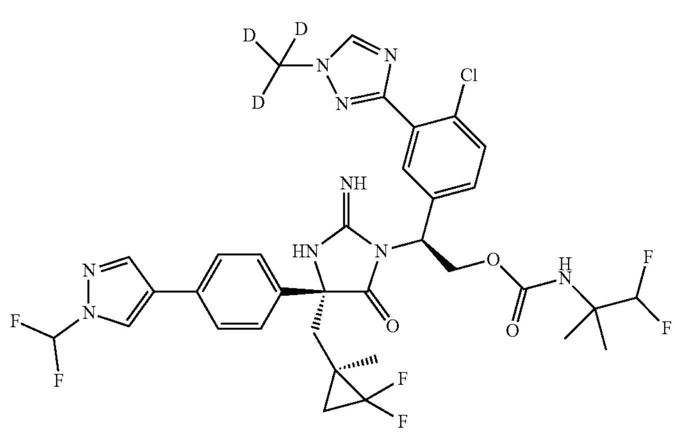 [SMILES: [2H]C([2H])([2H])n1cnc(-c2cc([C@@H](COC(=O)NC(C)(C)C(F)F)N3C(=N)N[C@](C[C@]4(C)CC4(F)F)(c4ccc(-c5cnn(C(F)F)c5)cc4)C3=O)ccc2Cl)n1] | | 18.897 |

TABLE 1-continued

| COMPD # | STRUCTURE | HIV PI IC$_{50}$ (nM) | MT4 EC$_{50}$ (nM) |
|---|---|---|---|
| 98 | 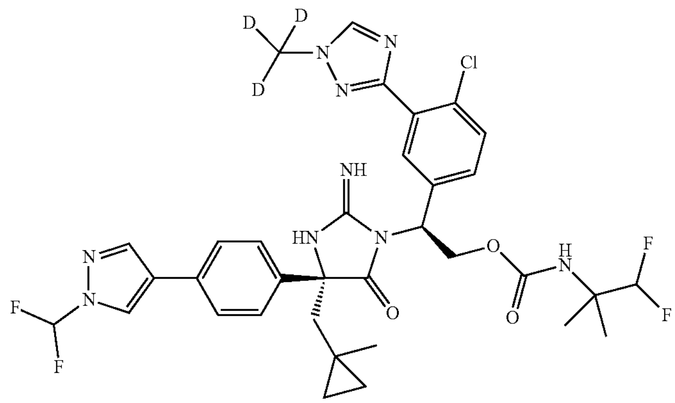 [SMILES: [2H]C([2H])([2H])n1cnc(-c2cc([C@@H](COC(=O)NC(C)(C)C(F)F)N3C(=N)N[C@](CC4(C)CC4)(c4ccc(-c5cnn(C(F)F)c5)cc4)C3=O)ccc2Cl)n1] | | 51.971 |
| 99 | 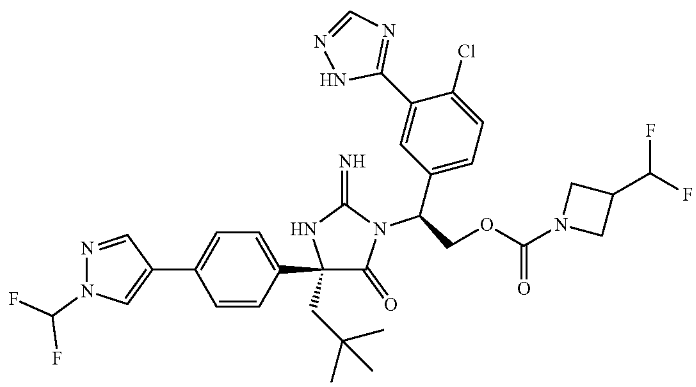 [SMILES: CC(C)(C)C[C@]1(c2ccc(-c3cnn(C(F)F)c3)cc2)NC(=N)N([C@H](COC(=O)N2CC(C(F)F)C2)c2ccc(Cl)c(-c3ncn[nH]3)c2)C1=O] | 2.0 | 65.662 |
| 100 | 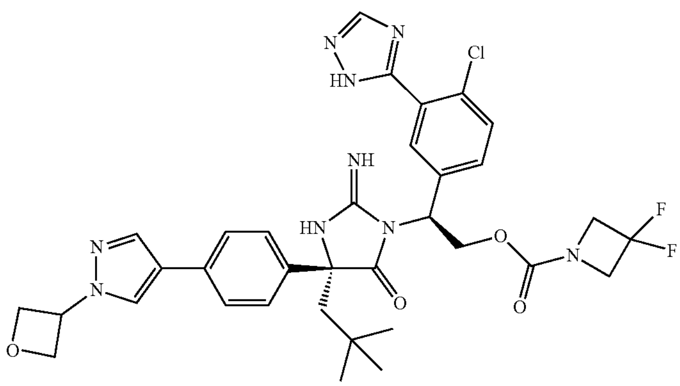 [SMILES: CC(C)(C)C[C@]1(c2ccc(-c3cnn(C4COC4)c3)cc2)NC(=N)N([C@H](COC(=O)N2CC(F)(F)C2)c2ccc(Cl)c(-c3ncn[nH]3)c2)C1=O] | 2.5 | 170.91 |
| 101 | 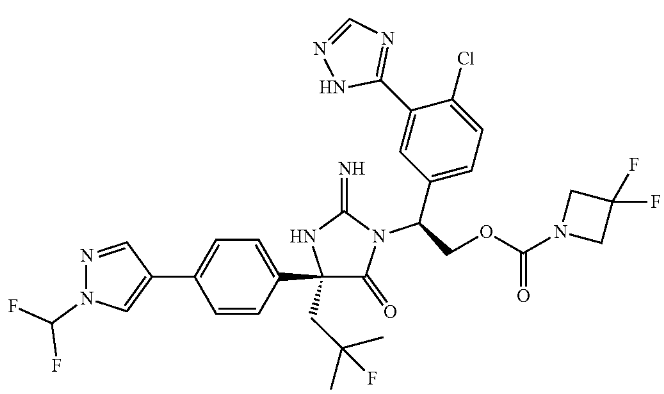 [SMILES: CC(C)(F)C[C@]1(c2ccc(-c3cnn(C(F)F)c3)cc2)NC(=N)N([C@H](COC(=O)N2CC(F)(F)C2)c2ccc(Cl)c(-c3ncn[nH]3)c2)C1=O] | 2.8 | 65.927 |

TABLE 1-continued

| COMPD # | STRUCTURE | HIV PI IC$_{50}$ (nM) | MT4 EC$_{50}$ (nM) |
|---|---|---|---|
| 102 | 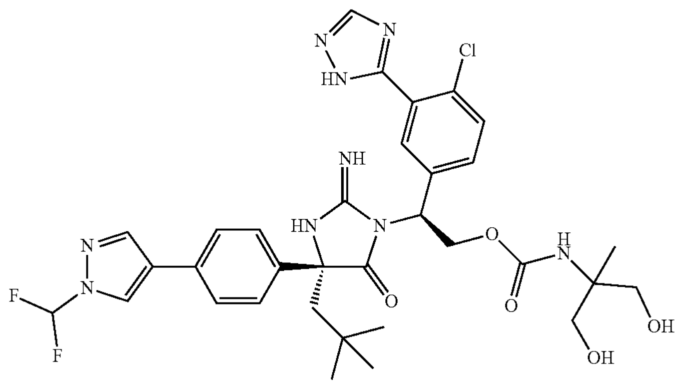 [SMILES: CC(C)(C)C[C@]1(c2ccc(-c3cnn(C(F)F)c3)cc2)NC(=N)N([C@H](COC(=O)NC(C)(CO)CO)c2ccc(Cl)c(-c3ncn[nH]3)c2)C1=O] | 14.3 | 196.01 |
| 104 | 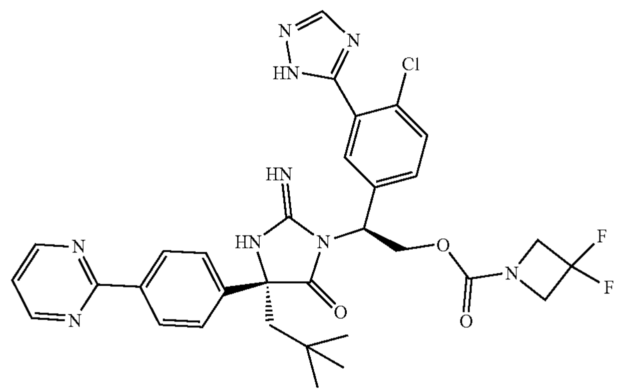 [SMILES: CC(C)(C)C[C@]1(c2ccc(-c3ncccn3)cc2)NC(=N)N([C@H](COC(=O)N2CC(F)(F)C2)c2ccc(Cl)c(-c3ncn[nH]3)c2)C1=O] | 2.5 | 33.528 |
| 105 | 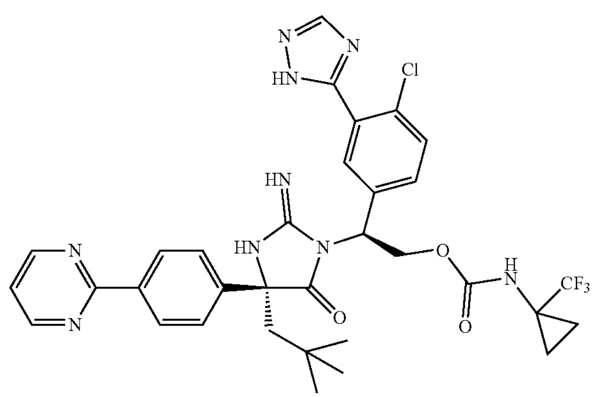 [SMILES: CC(C)(C)C[C@]1(c2ccc(-c3ncccn3)cc2)NC(=N)N([C@H](COC(=O)NC2(C(F)(F)F)CC2)c2ccc(Cl)c(-c3ncn[nH]3)c2)C1=O] | 2.0 | 36.676 |
| 106 | 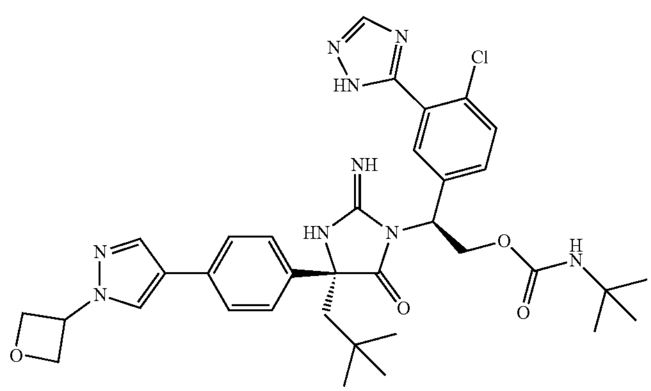 [SMILES: CC(C)(C)C[C@]1(c2ccc(-c3cnn(C4COC4)c3)cc2)NC(=N)N([C@H](COC(=O)NC(C)(C)C)c2ccc(Cl)c(-c3ncn[nH]3)c2)C1=O] | 2.3 | 100.91 |

TABLE 1-continued

| COMPD # | STRUCTURE | HIV PI IC$_{50}$ (nM) | MT4 EC$_{50}$ (nM) |
|---|---|---|---|
| 107 | 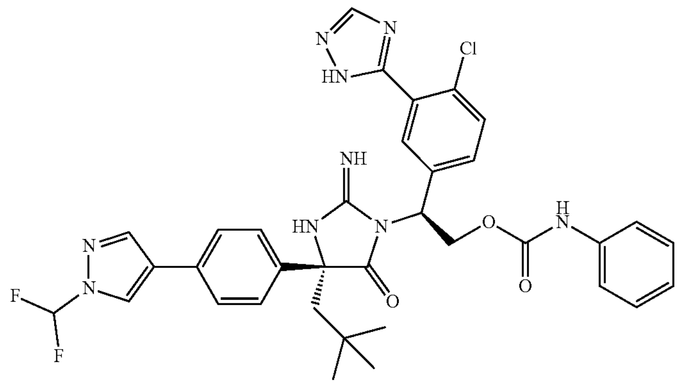 [SMILES: CC(C)(C)C[C@]1(c2ccc(-c3cnn(C(F)F)c3)cc2)NC(=N)N([C@H](COC(=O)Nc2ccccc2)c2ccc(Cl)c(-c3ncn[nH]3)c2)C1=O] | 2.9 | 49.098 |
| 108 | 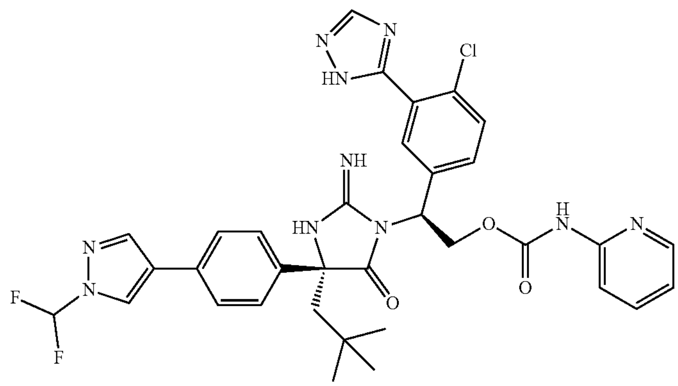 [SMILES: CC(C)(C)C[C@]1(c2ccc(-c3cnn(C(F)F)c3)cc2)NC(=N)N([C@H](COC(=O)Nc2ccccn2)c2ccc(Cl)c(-c3ncn[nH]3)c2)C1=O] | 3.5 | 85.78 |
| 110 | 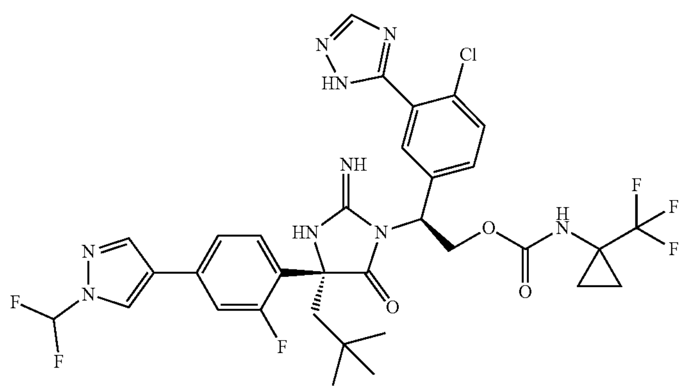 [SMILES: CC(C)(C)C[C@]1(c2ccc(-c3cnn(C(F)F)c3)cc2F)NC(=N)N([C@H](COC(=O)NC2(C(F)(F)F)CC2)c2ccc(Cl)c(-c3ncn[nH]3)c2)C1=O] | 2.8 | 96.036 |
| 111 | 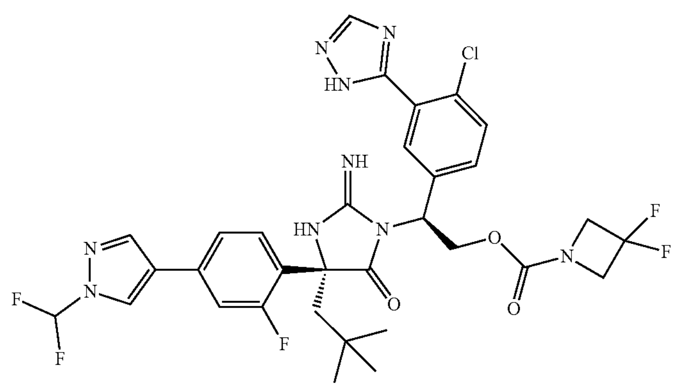 [SMILES: CC(C)(C)C[C@]1(c2ccc(-c3cnn(C(F)F)c3)cc2F)NC(=N)N([C@H](COC(=O)N2CC(F)(F)C2)c2ccc(Cl)c(-c3ncn[nH]3)c2)C1=O] | 2.0 | 40.397 |

TABLE 1-continued
| COMPD # | STRUCTURE | HIV PI IC$_{50}$ (nM) | MT4 EC$_{50}$ (nM) |
|---|---|---|---|
| 112 | 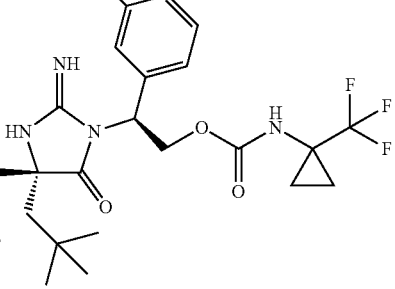 | 3.4 | 40.401 |
| 113 | 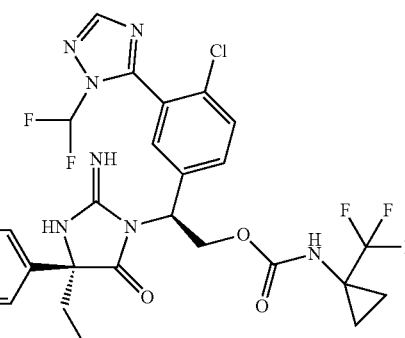 | 2.1 | 7.751 |
| 114 | 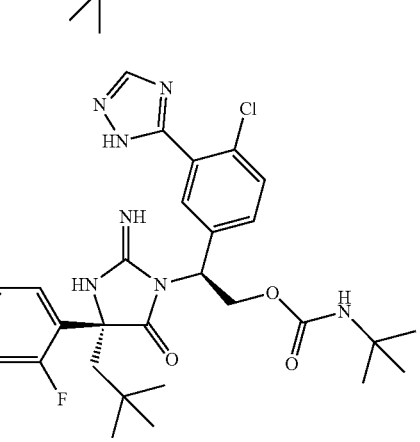 | 2.5 | 40.582 |
| 115 | 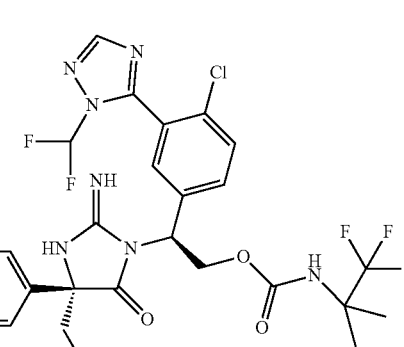 | 2.4 | 11.729 |

TABLE 1-continued

| COMPD # | STRUCTURE | HIV PI IC$_{50}$ (nM) | MT4 EC$_{50}$ (nM) |
|---|---|---|---|
| 116 | 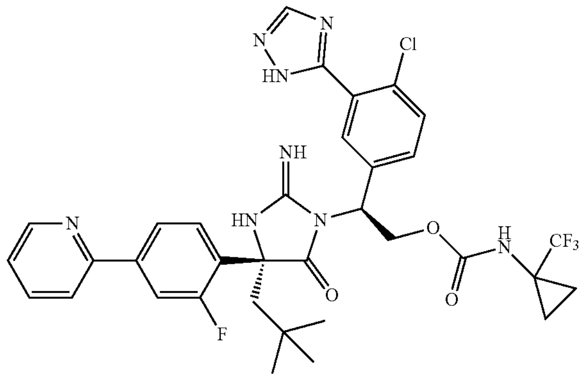 [SMILES: CC(C)(C)C[C@]1(c2ccc(-c3ccccn3)cc2F)NC(=N)N([C@H](COC(=O)NC2(C(F)(F)F)CC2)c2ccc(Cl)c(-c3ncn[nH]3)c2)C1=O] | 2.7 | 42.627 |
| 117 | 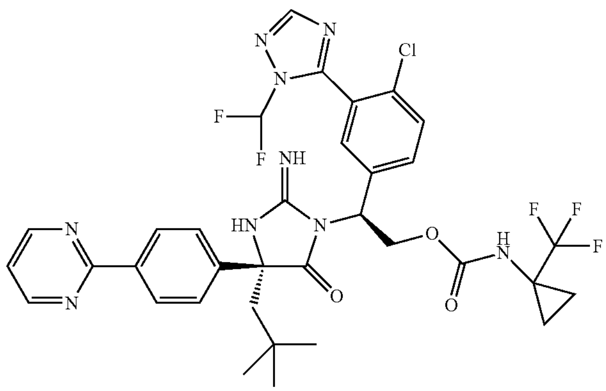 [SMILES: CC(C)(C)C[C@]1(c2ccc(-c3ncccn3)cc2)NC(=N)N([C@H](COC(=O)NC2(C(F)(F)F)CC2)c2ccc(Cl)c(-c3ncnn3C(F)F)c2)C1=O] | 2.1 | 6.812 |
| 118 | 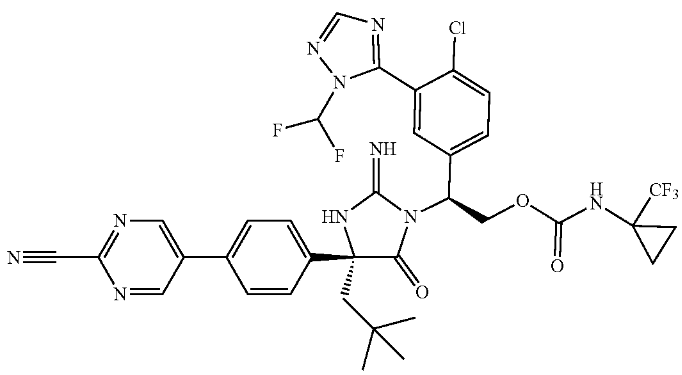 [SMILES: CC(C)(C)C[C@]1(c2ccc(-c3cnc(C#N)nc3)cc2)NC(=N)N([C@H](COC(=O)NC2(C(F)(F)F)CC2)c2ccc(Cl)c(-c3ncnn3C(F)F)c2)C1=O] | 3.1 | 16.367 |
| 119 | 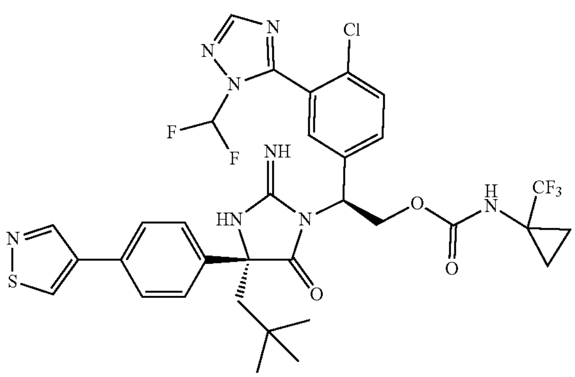 [SMILES: CC(C)(C)C[C@]1(c2ccc(-c3cnsc3)cc2)NC(=N)N([C@H](COC(=O)NC2(C(F)(F)F)CC2)c2ccc(Cl)c(-c3ncnn3C(F)F)c2)C1=O] | 2.4 | 10.311 |

TABLE 1-continued

| COMPD # | STRUCTURE | HIV PI IC$_{50}$ (nM) | MT4 EC$_{50}$ (nM) |
|---|---|---|---|
| 120 | 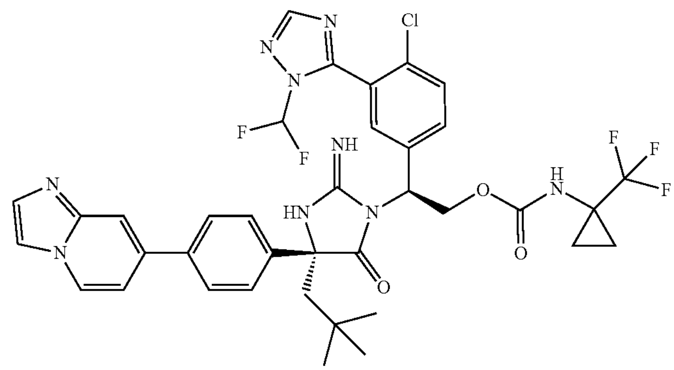 [SMILES: CC(C)(C)C[C@]1(c2ccc(-c3ccn4ccnc4c3)cc2)NC(=N)N([C@H](COC(=O)NC2(C(F)(F)F)CC2)c2ccc(Cl)c(-c3ncnn3C(F)F)c2)C1=O] | 2.9 | 27.759 |
| 121 | 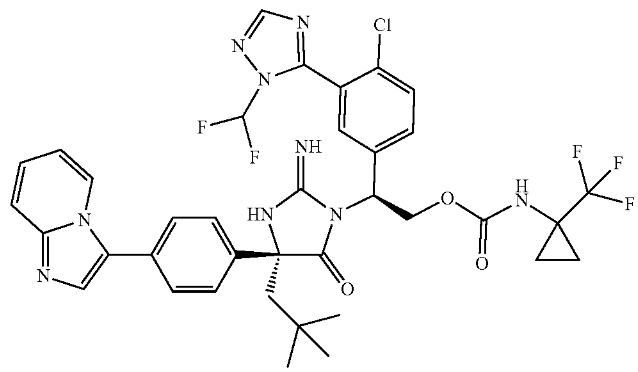 [SMILES: CC(C)(C)C[C@]1(c2ccc(-c3cnc4ccccn34)cc2)NC(=N)N([C@H](COC(=O)NC2(C(F)(F)F)CC2)c2ccc(Cl)c(-c3ncnn3C(F)F)c2)C1=O] | 2.7 | 21.045 |
| 122 | 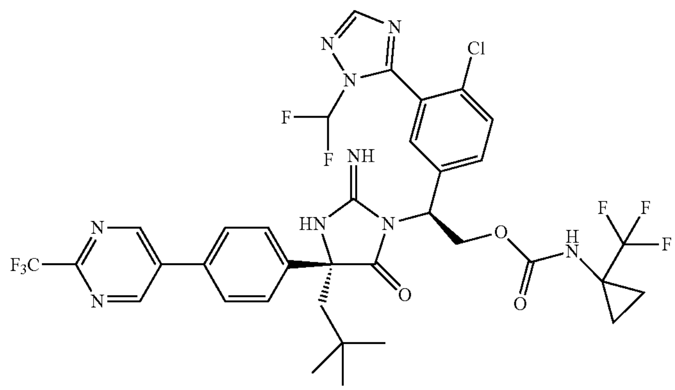 [SMILES: CC(C)(C)C[C@]1(c2ccc(-c3cnc(C(F)(F)F)nc3)cc2)NC(=N)N([C@H](COC(=O)NC2(C(F)(F)F)CC2)c2ccc(Cl)c(-c3ncnn3C(F)F)c2)C1=O] | 3.5 | 25.405 |
| 123 | 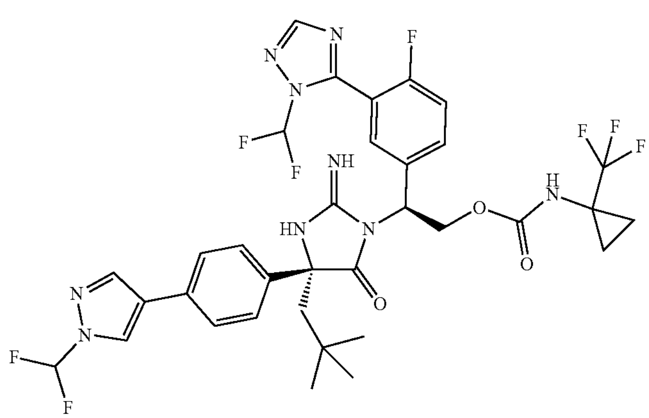 [SMILES: CC(C)(C)C[C@]1(c2ccc(-c3cnn(C(F)F)c3)cc2)NC(=N)N([C@H](COC(=O)NC2(C(F)(F)F)CC2)c2ccc(F)c(-c3ncnn3C(F)F)c2)C1=O] | 5.9 | 28.13 |

TABLE 1-continued

| COMPD # | STRUCTURE | HIV PI IC$_{50}$ (nM) | MT4 EC$_{50}$ (nM) |
|---|---|---|---|
| 124 | 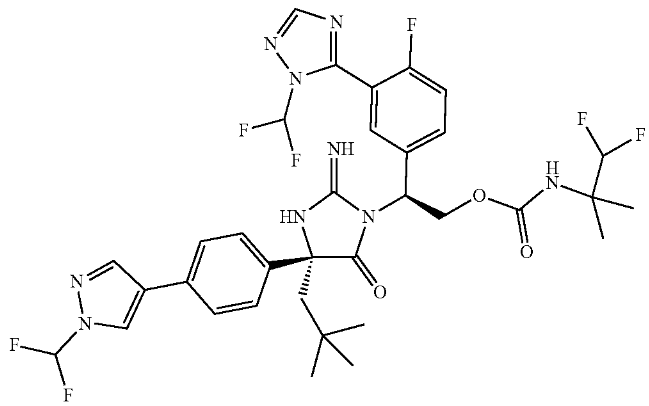 [SMILES: CC(C)(C)C[C@]1(c2ccc(-c3cnn(C(F)F)c3)cc2)NC(=N)N([C@H](COC(=O)NC(C)(C)C(F)F)c2ccc(F)c(-c3ncnn3C(F)F)c2)C1=O] | 6.9 | 65.302 |
| 125 | 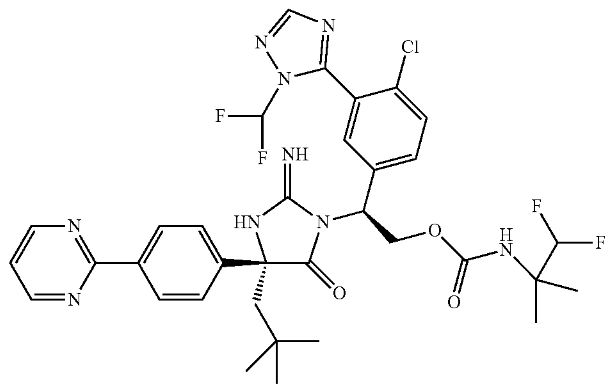 [SMILES: CC(C)(C)C[C@]1(c2ccc(-c3ncccn3)cc2)NC(=N)N([C@H](COC(=O)NC(C)(C)C(F)F)c2ccc(Cl)c(-c3ncnn3C(F)F)c2)C1=O] | 2.8 | 12.012 |
| 126 | 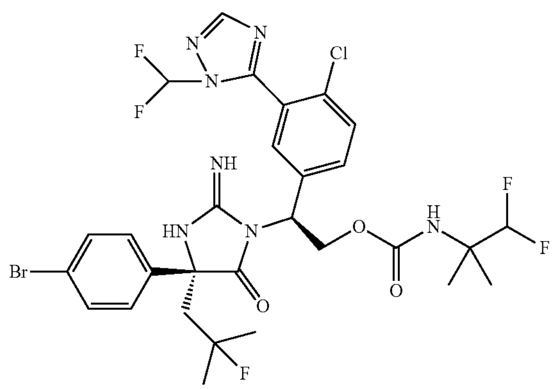 [SMILES: CC(C)(F)C[C@]1(c2ccc(Br)cc2)NC(=N)N([C@H](COC(=O)NC(C)(C)C(F)F)c2ccc(Cl)c(-c3ncnn3C(F)F)c2)C1=O] | 11.6 | 242.17 |
| 127 | 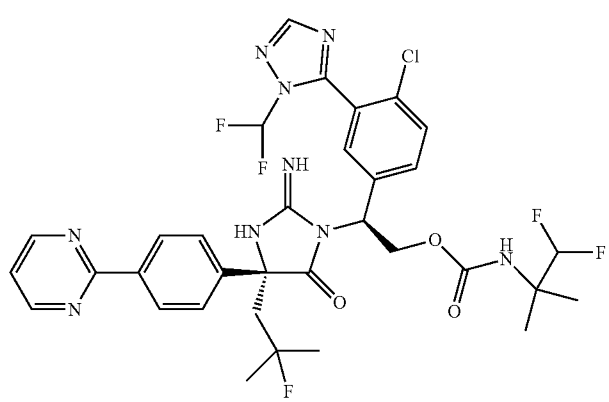 [SMILES: CC(C)(F)C[C@]1(c2ccc(-c3ncccn3)cc2)NC(=N)N([C@H](COC(=O)NC(C)(C)C(F)F)c2ccc(Cl)c(-c3ncnn3C(F)F)c2)C1=O] | 3.7 | 27.544 |

TABLE 1-continued

| COMPD # | STRUCTURE | HIV PI IC$_{50}$ (nM) | MT4 EC$_{50}$ (nM) |
|---|---|---|---|
| 128 | 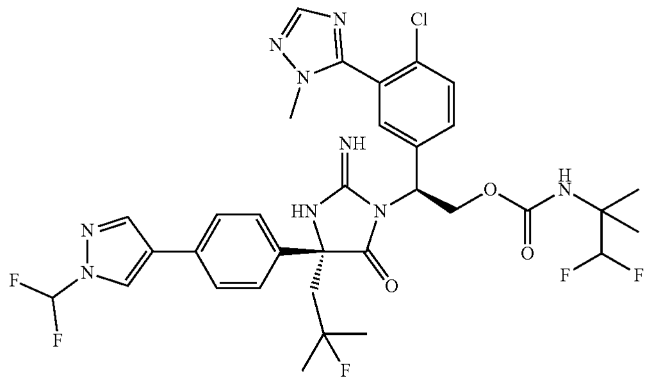 [SMILES: Cn1ncnc1-c1cc([C@@H](COC(=O)NC(C)(C)C(F)F)N2C(=N)N[C@](CC(C)(C)F)(c3ccc(-c4cnn(C(F)F)c4)cc3)C2=O)ccc1Cl] | 13.7 | 85.01 |
| 129 | 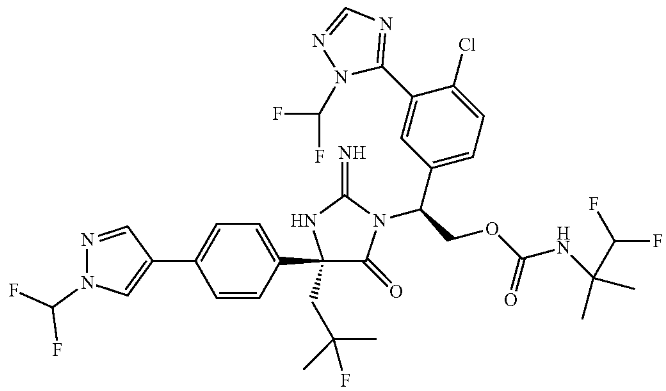 [SMILES: CC(C)(F)C[C@]1(c2ccc(-c3cnn(C(F)F)c3)cc2)NC(=N)N([C@H](COC(=O)NC(C)(C)C(F)F)c2ccc(Cl)c(-c3ncnn3C(F)F)c2)C1=O] | 4.8 | 27.31 |
| 130 | 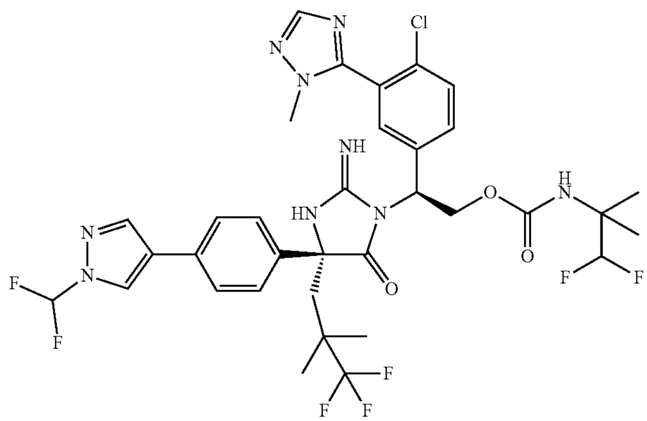 [SMILES: Cn1ncnc1-c1cc([C@@H](COC(=O)NC(C)(C)C(F)F)N2C(=N)N[C@](CC(C)(C)C(F)(F)F)(c3ccc(-c4cnn(C(F)F)c4)cc3)C2=O)ccc1Cl] | 5.4 | 18.656 |
| 131 | 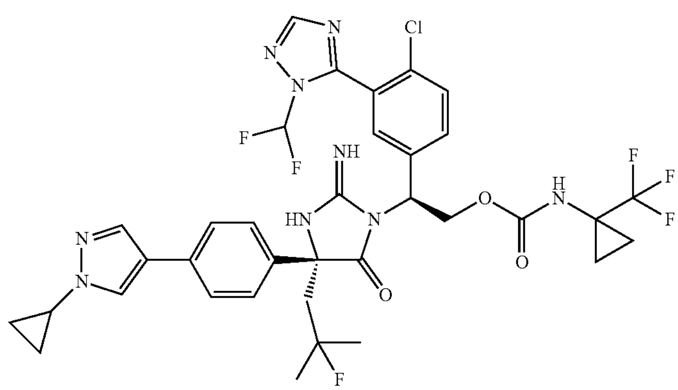 [SMILES: CC(C)(F)C[C@]1(c2ccc(-c3cnn(C4CC4)c3)cc2)NC(=N)N([C@H](COC(=O)NC2(C(F)(F)F)CC2)c2ccc(Cl)c(-c3ncnn3C(F)F)c2)C1=O] | 2.8 | 20.8 |

TABLE 1-continued

| COMPD # | STRUCTURE | HIV PI IC$_{50}$ (nM) | MT4 EC$_{50}$ (nM) |
|---|---|---|---|
| 132 | 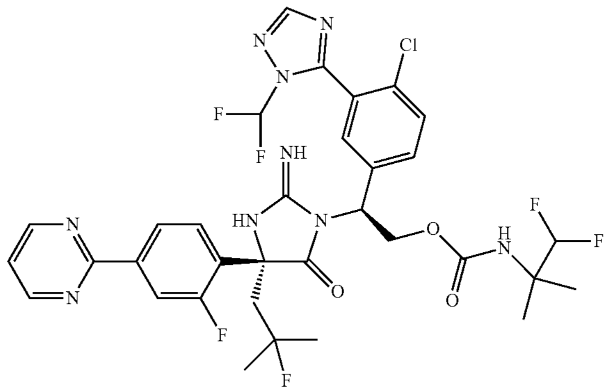 [SMILES: CC(C)(F)C[C@]1(c2ccc(-c3ncccn3)cc2F)NC(=N)N([C@H](COC(=O)NC(C)(C)C(F)F)c2ccc(Cl)c(-c3ncnn3C(F)F)c2)C1=O] | 3.2 | 48.038 |
| 133 | 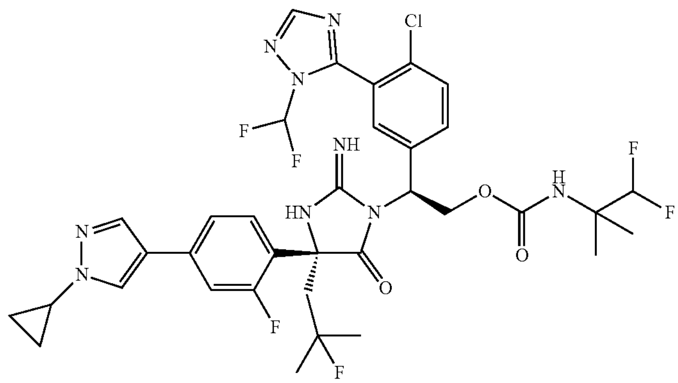 [SMILES: CC(C)(F)C[C@]1(c2ccc(-c3cnn(C4CC4)c3)cc2F)NC(=N)N([C@H](COC(=O)NC(C)(C)C(F)F)c2ccc(Cl)c(-c3ncnn3C(F)F)c2)C1=O] | 3.6 | 35.051 |
| 134 | 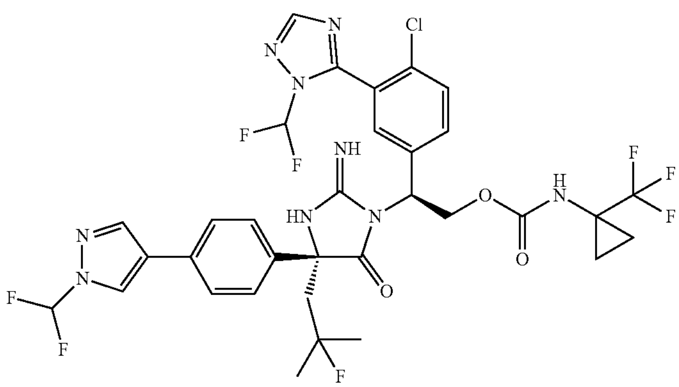 [SMILES: CC(C)(F)C[C@]1(c2ccc(-c3cnn(C(F)F)c3)cc2)NC(=N)N([C@H](COC(=O)NC2(C(F)(F)F)CC2)c2ccc(Cl)c(-c3ncnn3C(F)F)c2)C1=O] | 3.5 | 18.503 |
| 135 | 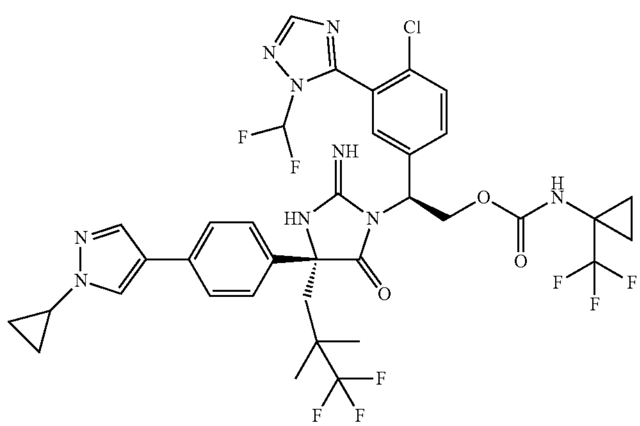 [SMILES: CC(C)(C[C@]1(c2ccc(-c3cnn(C4CC4)c3)cc2)NC(=N)N([C@H](COC(=O)NC2(C(F)(F)F)CC2)c2ccc(Cl)c(-c3ncnn3C(F)F)c2)C1=O)C(F)(F)F] | 2.8 | 13.593 |

TABLE 1-continued

| COMPD # | STRUCTURE | HIV PI IC$_{50}$ (nM) | MT4 EC$_{50}$ (nM) |
|---|---|---|---|
| 136 | 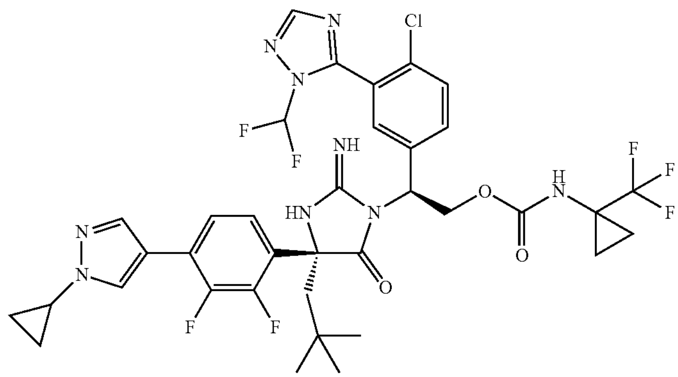 [SMILES: CC(C)(C)C[C@]1(c2ccc(-c3cnn(C4CC4)c3)c(F)c2F)NC(=N)N([C@H](COC(=O)NC2(C(F)(F)F)CC2)c2ccc(Cl)c(-c3ncnn3C(F)F)c2)C1=O] | 2.7 | 7.906 |
| 137 | 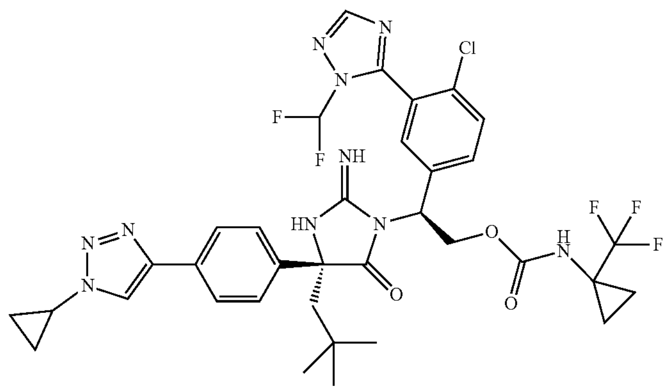 [SMILES: CC(C)(C)C[C@]1(c2ccc(-c3cn(C4CC4)nn3)cc2)NC(=N)N([C@H](COC(=O)NC2(C(F)(F)F)CC2)c2ccc(Cl)c(-c3ncnn3C(F)F)c2)C1=O] | 2.3 | 19.533 |
| 138 | 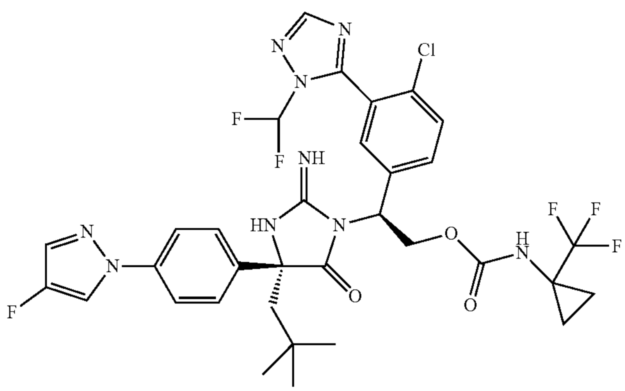 [SMILES: CC(C)(C)C[C@]1(c2ccc(-n3cc(F)cn3)cc2)NC(=N)N([C@H](COC(=O)NC2(C(F)(F)F)CC2)c2ccc(Cl)c(-c3ncnn3C(F)F)c2)C1=O] | 2.5 | 11.528 |
| 139 | 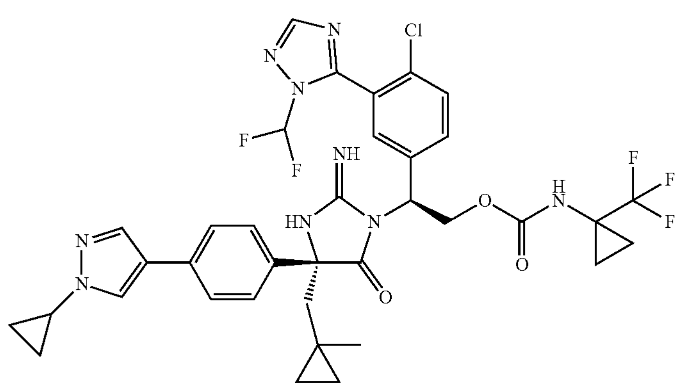 [SMILES: CC1(C[C@]2(c3ccc(-c4cnn(C5CC5)c4)cc3)NC(=N)N([C@H](COC(=O)NC3(C(F)(F)F)CC3)c3ccc(Cl)c(-c4ncnn4C(F)F)c3)C2=O)CC1] | 3.6 | 28.073 |

TABLE 1-continued

| COMPD # | STRUCTURE | HIV PI IC$_{50}$ (nM) | MT4 EC$_{50}$ (nM) |
|---|---|---|---|
| 140 | 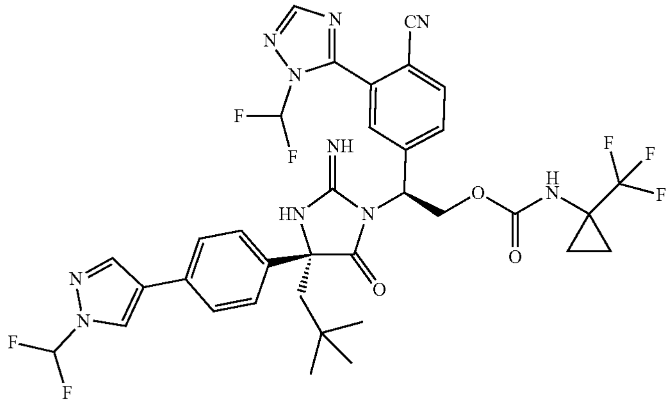 [SMILES: CC(C)(C)C[C@]1(c2ccc(-c3cnn(C(F)F)c3)cc2)NC(=N)N([C@H](COC(=O)NC2(C(F)(F)F)CC2)c2ccc(C#N)c(-c3ncnn3C(F)F)c2)C1=O] | 3.2 | 265.53 |
| 141 | 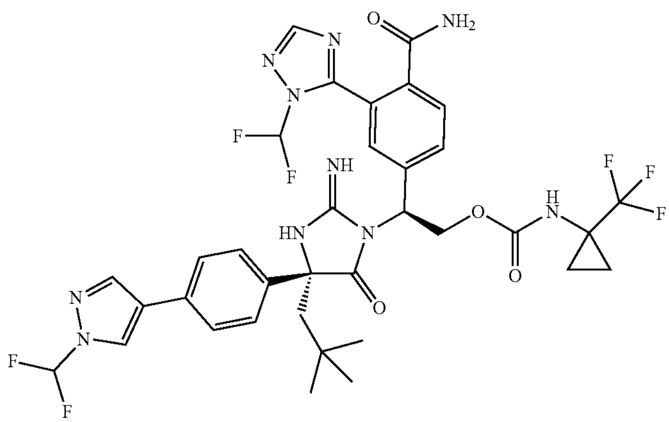 [SMILES: CC(C)(C)C[C@]1(c2ccc(-c3cnn(C(F)F)c3)cc2)NC(=N)N([C@H](COC(=O)NC2(C(F)(F)F)CC2)c2ccc(C(N)=O)c(-c3ncnn3C(F)F)c2)C1=O] | 3.7 | 1023.1 |
| 142 | 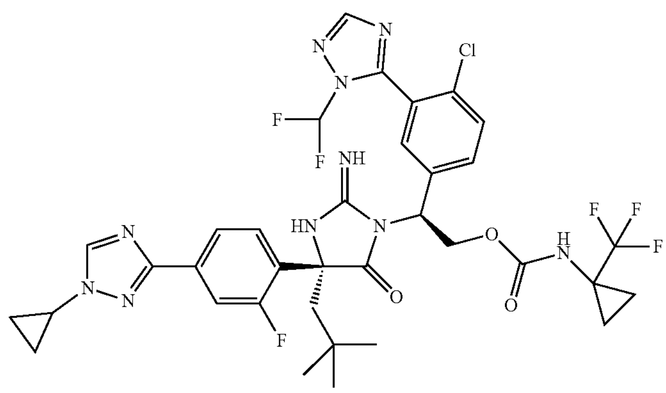 [SMILES: CC(C)(C)C[C@]1(c2ccc(-c3ncn(C4CC4)n3)cc2F)NC(=N)N([C@H](COC(=O)NC2(C(F)(F)F)CC2)c2ccc(Cl)c(-c3ncnn3C(F)F)c2)C1=O] | 2.1 | 10.102 |
| 143 | 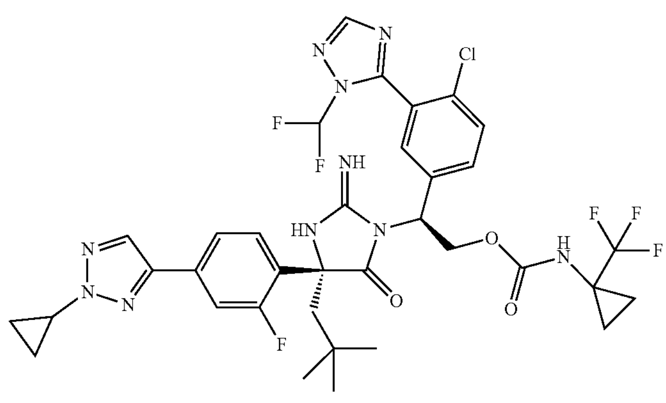 | 2.3 | 9.593 |

TABLE 1-continued

| COMPD # | STRUCTURE | HIV PI IC$_{50}$ (nM) | MT4 EC$_{50}$ (nM) |
|---|---|---|---|
| 144 | 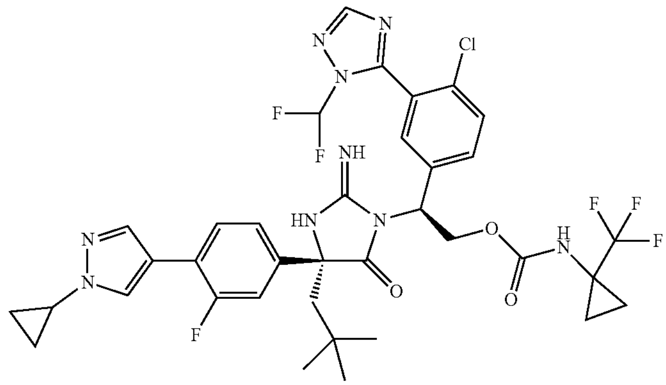 [SMILES: CC(C)(C)C[C@]1(c2ccc(-c3cnn(C4CC4)c3)c(F)c2)NC(=N)N([C@H](COC(=O)NC2(C(F)(F)F)CC2)c2ccc(Cl)c(-c3ncnn3C(F)F)c2)C1=O] | 2.1 | 7.924 |
| 145 | 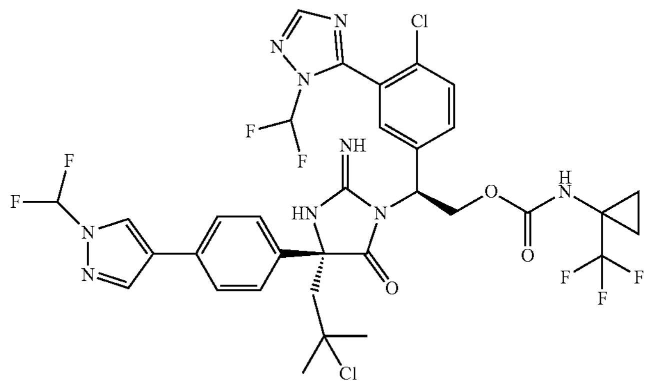 [SMILES: CC(C)(Cl)C[C@]1(c2ccc(-c3cnn(C(F)F)c3)cc2)NC(=N)N([C@H](COC(=O)NC2(C(F)(F)F)CC2)c2ccc(Cl)c(-c3ncnn3C(F)F)c2)C1=O] | 7.9 | 228.1 |
| 146 | 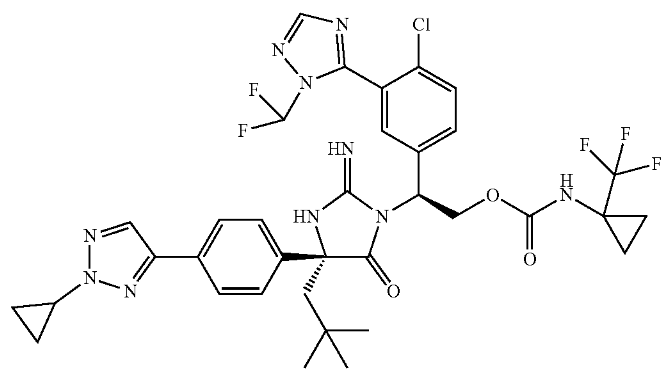 [SMILES: CC(C)(C)C[C@]1(c2ccc(-c3cnn(C4CC4)n3)cc2)NC(=N)N([C@H](COC(=O)NC2(C(F)(F)F)CC2)c2ccc(Cl)c(-c3ncnn3C(F)F)c2)C1=O] | 3.5 | 10.319 |
| 147 | 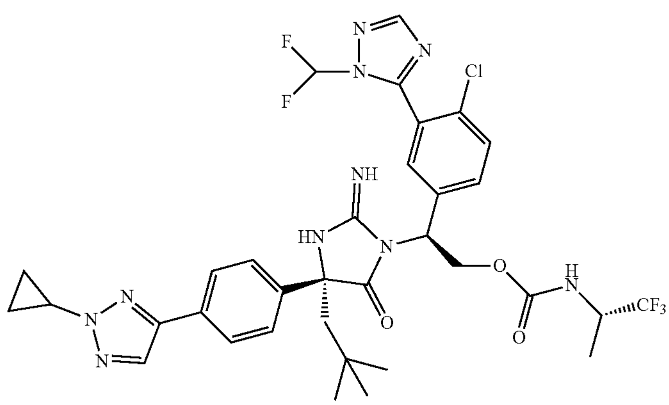 [SMILES: C[C@H](NC(=O)OC[C@H](c1ccc(Cl)c(-c2ncnn2C(F)F)c1)N1C(=N)N[C@](CC(C)(C)C)(c2ccc(-c3cnn(C4CC4)n3)cc2)C1=O)C(F)(F)F] | 2.3 | 7.929 |

TABLE 1-continued

| COMPD # | STRUCTURE | HIV PI IC₅₀ (nM) | MT4 EC₅₀ (nM) |
|---|---|---|---|
| 148 | 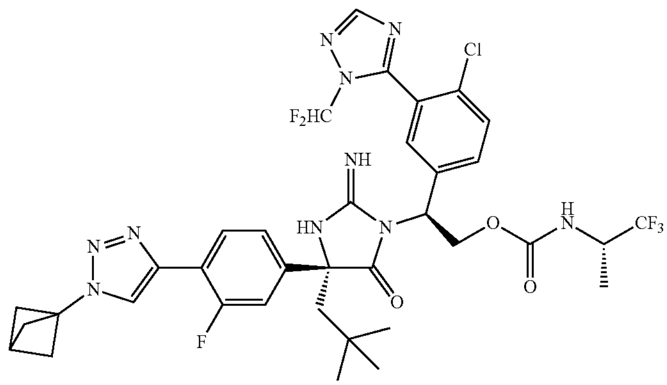 [SMILES: C[C@H](NC(=O)OC[C@H](c1ccc(Cl)c(-c2ncnn2C(F)F)c1)N1C(=N)N[C@](CC(C)(C)C)(c2ccc(-c3cn(C45CC(C4)C5)nn3)c(F)c2)C1=O)C(F)(F)F] | 1.7 | 13.832 |
| 149 | 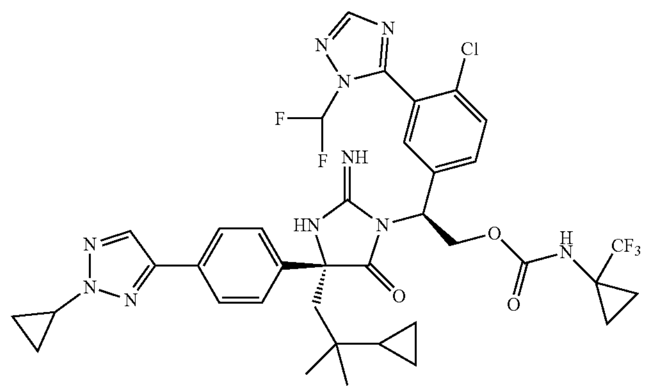 [SMILES: CC(C)(C[C@]1(c2ccc(-c3cnn(C4CC4)n3)cc2)NC(=N)N([C@H](COC(=O)NC2(C(F)(F)F)CC2)c2ccc(Cl)c(-c3ncnn3C(F)F)c2)C1=O)C1CC1] | 2.6 | 11.936 |
| 150 | 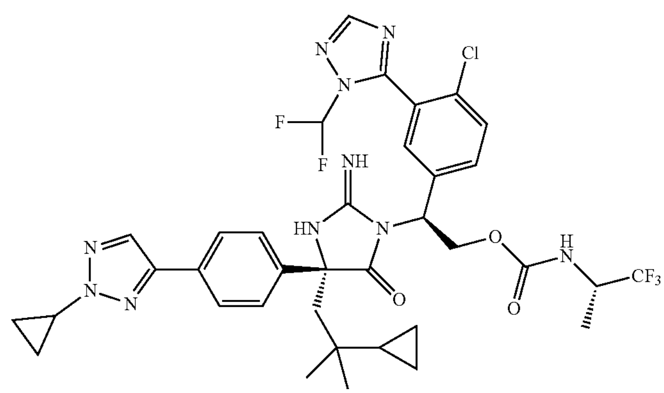 [SMILES: C[C@H](NC(=O)OC[C@H](c1ccc(Cl)c(-c2ncnn2C(F)F)c1)N1C(=N)N[C@](CC(C)(C)C2CC2)(c2ccc(-c3cnn(C4CC4)n3)cc2)C1=O)C(F)(F)F] | 2.7 | 9.92 |
| 151 | 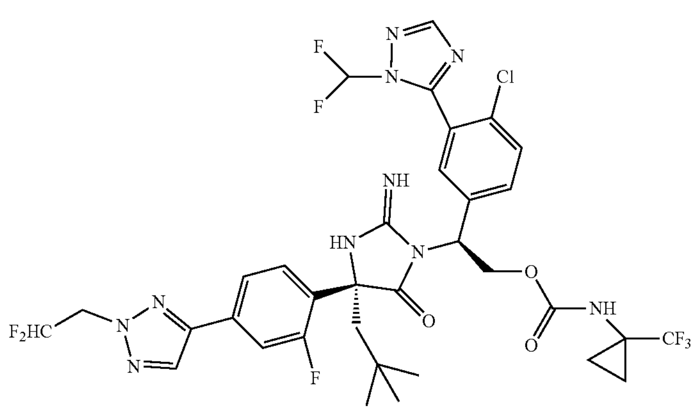 [SMILES: CC(C)(C)C[C@]1(c2ccc(-c3cnn(CC(F)F)n3)cc2F)NC(=N)N([C@H](COC(=O)NC2(C(F)(F)F)CC2)c2ccc(Cl)c(-c3ncnn3C(F)F)c2)C1=O] | 1.8 | 7.552 |

TABLE 1-continued

| COMPD # | STRUCTURE | HIV PI IC$_{50}$ (nM) | MT4 EC$_{50}$ (nM) |
|---|---|---|---|
| 152 | 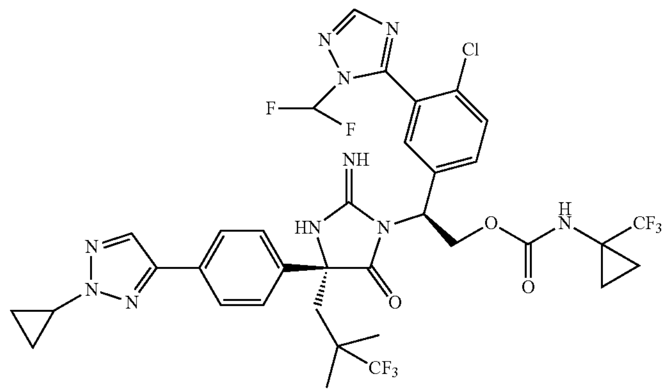 [SMILES: CC(C)(C[C@]1(c2ccc(-c3cnn(C4CC4)n3)cc2)NC(=N)N([C@H](COC(=O)NC2(C(F)(F)F)CC2)c2ccc(Cl)c(-c3ncnn3C(F)F)c2)C1=O)C(F)(F)F] | 2.4 | 12.976 |
| 153 | 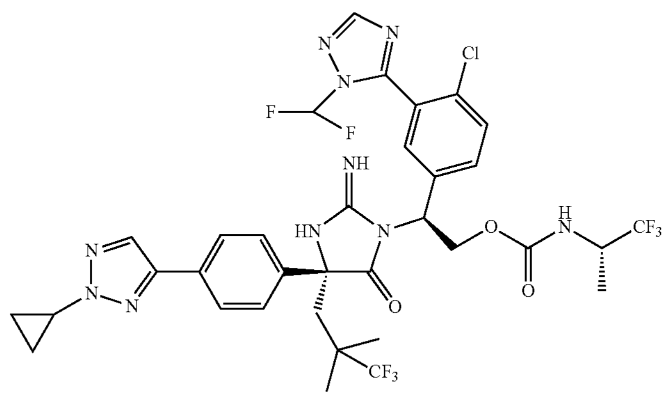 [SMILES: C[C@H](NC(=O)OC[C@H](c1ccc(Cl)c(-c2ncnn2C(F)F)c1)N1C(=N)N[C@](CC(C)(C)C(F)(F)F)(c2ccc(-c3cnn(C4CC4)n3)cc2)C1=O)C(F)(F)F] | 2.1 | 14.014 |
| 154 | 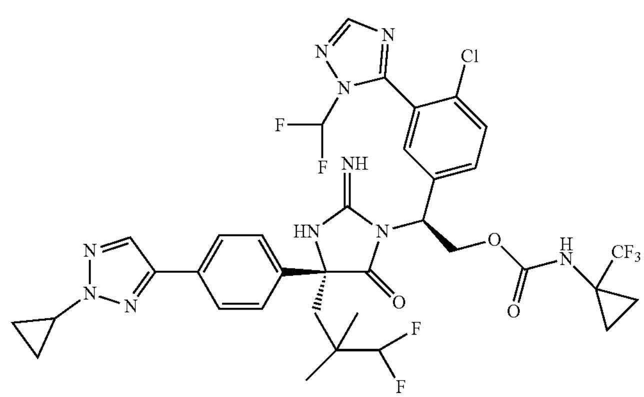 [SMILES: CC(C)(C[C@]1(c2ccc(-c3cnn(C4CC4)n3)cc2)NC(=N)N([C@H](COC(=O)NC2(C(F)(F)F)CC2)c2ccc(Cl)c(-c3ncnn3C(F)F)c2)C1=O)C(F)F] | 3.9 | 19.732 |

TABLE 1-continued

| COMPD # | STRUCTURE | HIV PI IC$_{50}$ (nM) | MT4 EC$_{50}$ (nM) |
|---|---|---|---|
| 155 | 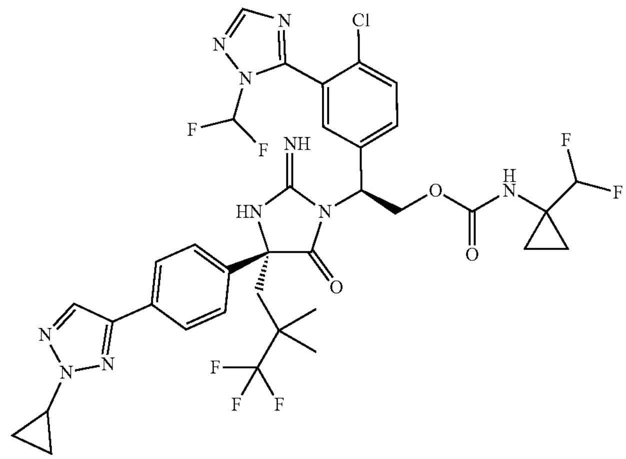 [SMILES: CC(C)(C[C@]1(c2ccc(-c3cnn(C4CC4)n3)cc2)NC(=N)N([C@H](COC(=O)NC2(C(F)F)CC2)c2ccc(Cl)c(-c3ncnn3C(F)F)c2)C1=O)C(F)(F)F] | 2.0 | 9.87 |
| 156 | 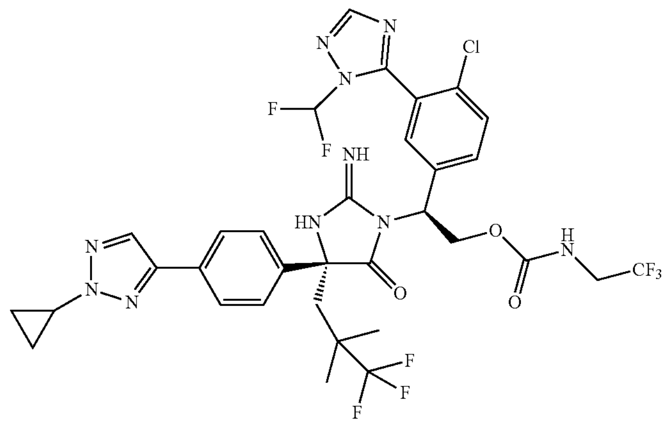 [SMILES: CC(C)(C[C@]1(c2ccc(-c3cnn(C4CC4)n3)cc2)NC(=N)N([C@H](COC(=O)NCC(F)(F)F)c2ccc(Cl)c(-c3ncnn3C(F)F)c2)C1=O)C(F)(F)F] | 2.7 | 11.051 |
| 157 | 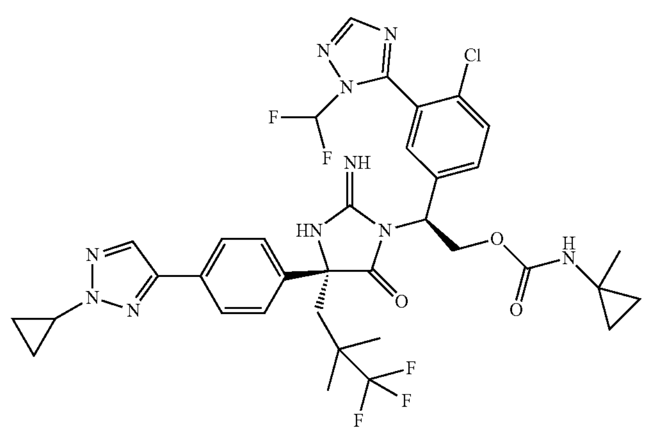 [SMILES: CC1(NC(=O)OC[C@H](c2ccc(Cl)c(-c3ncnn3C(F)F)c2)N2C(=N)N[C@](CC(C)(C)C(F)(F)F)(c3ccc(-c4cnn(C5CC5)n4)cc3)C2=O)CC1] | 2.4 | 7.641 |

TABLE 1-continued

| COMPD # | STRUCTURE | HIV PI IC$_{50}$ (nM) | MT4 EC$_{50}$ (nM) |
|---|---|---|---|
| 159 | 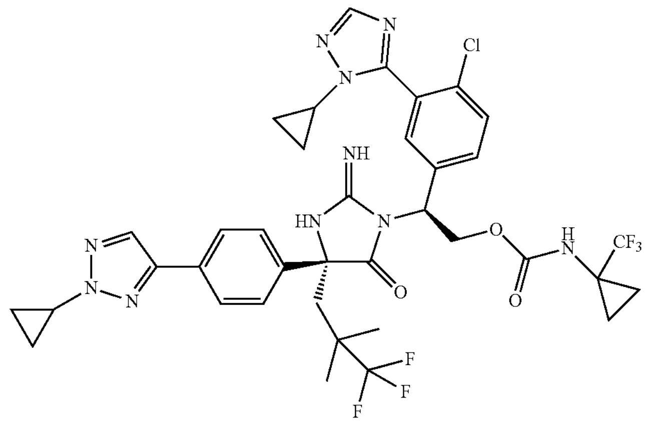 [SMILES: CC(C)(C[C@]1(c2ccc(-c3cnn(C4CC4)n3)cc2)NC(=N)N([C@H](COC(=O)NC2(C(F)(F)F)CC2)c2ccc(Cl)c(-c3ncnn3C3CC3)c2)C1=O)C(F)(F)F] | 2.8 | 10.926 |
| 160 | 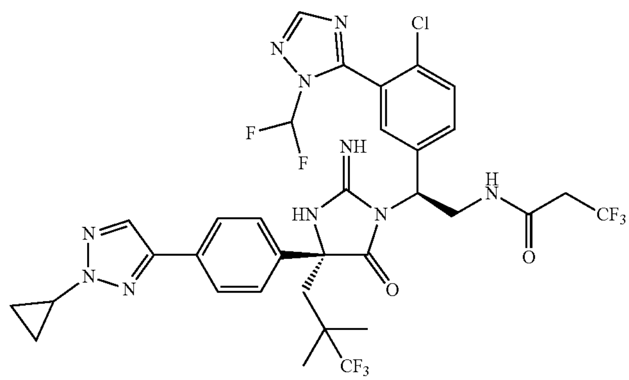 [SMILES: CC(C)(C[C@]1(c2ccc(-c3cnn(C4CC4)n3)cc2)NC(=N)N([C@H](CNC(=O)CC(F)(F)F)c2ccc(Cl)c(-c3ncnn3C(F)F)c2)C1=O)C(F)(F)F] | 3.4 | 12.575 |
| 161 | 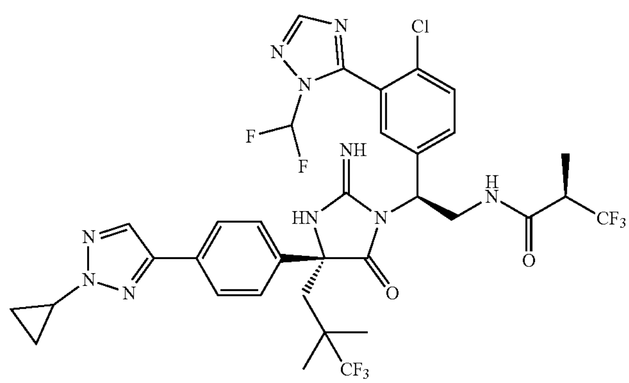 [SMILES: C[C@H](C(=O)NC[C@H](c1ccc(Cl)c(-c2ncnn2C(F)F)c1)N1C(=N)N[C@](CC(C)(C)C(F)(F)F)(c2ccc(-c3cnn(C4CC4)n3)cc2)C1=O)C(F)(F)F] | 4.4 | 14.272 |
| 162 | 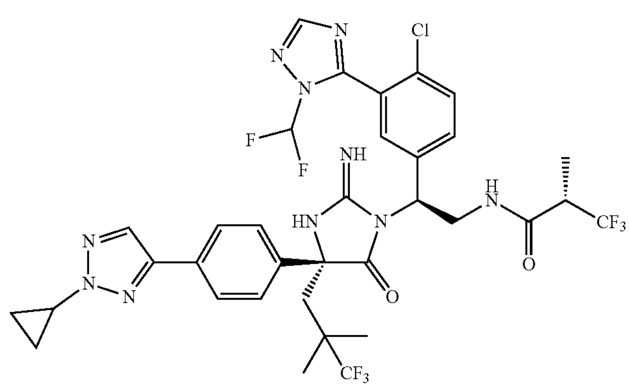 [SMILES: C[C@@H](C(=O)NC[C@H](c1ccc(Cl)c(-c2ncnn2C(F)F)c1)N1C(=N)N[C@](CC(C)(C)C(F)(F)F)(c2ccc(-c3cnn(C4CC4)n3)cc2)C1=O)C(F)(F)F] | 4.4 | 20.977 |

TABLE 1-continued

| COMPD # | STRUCTURE | HIV PI IC$_{50}$ (nM) | MT4 EC$_{50}$ (nM) |
|---|---|---|---|
| 163 | 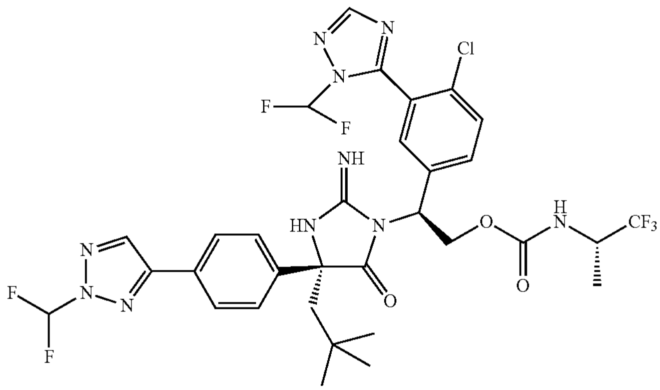 [SMILES: C[C@H](NC(=O)OC[C@H](c1ccc(Cl)c(-c2ncnn2C(F)F)c1)N1C(=N)N[C@](CC(C)(C)C)(c2ccc(-c3cnn(C(F)F)n3)cc2)C1=O)C(F)(F)F] | 2.5 | 9.061 |
| 164 | 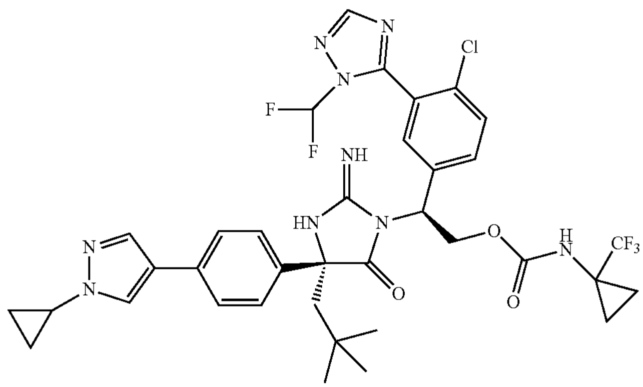 [SMILES: CC(C)(C)C[C@]1(c2ccc(-c3cnn(C4CC4)c3)cc2)NC(=N)N([C@H](COC(=O)NC2(C(F)(F)F)CC2)c2ccc(Cl)c(-c3ncnn3C(F)F)c2)C1=O] | 2.6 | 16.521 |
| 177 | 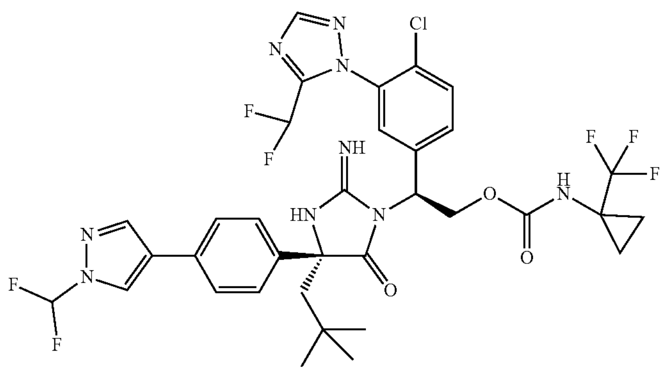 | 1.9 | 9.813 |
| 178 | 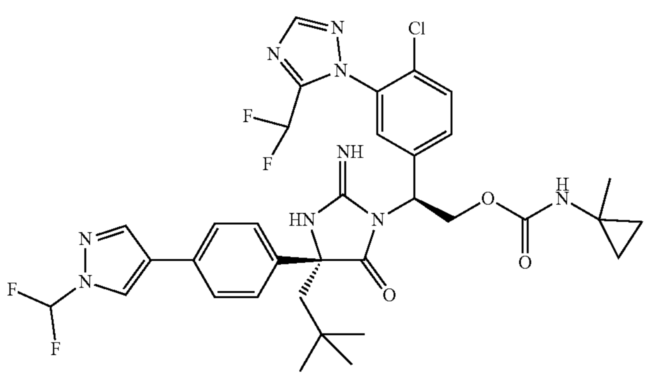 [SMILES: CC(C)(C)C[C@]1(c2ccc(-c3cnn(C(F)F)c3)cc2)NC(=N)N([C@H](COC(=O)NC2(C)CC2)c2ccc(Cl)c(-n3ncnc3C(F)F)c2)C1=O] | 1.9 | 9.995 |

TABLE 1-continued

| COMPD # | STRUCTURE | HIV PI IC$_{50}$ (nM) | MT4 EC$_{50}$ (nM) |
|---|---|---|---|
| 179 | 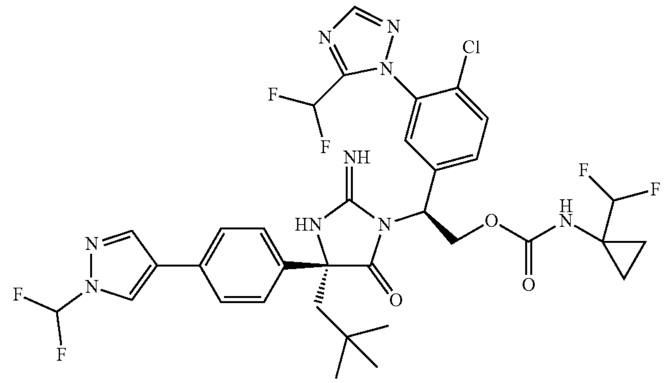 [SMILES: CC(C)(C)C[C@]1(c2ccc(-c3cnn(C(F)F)c3)cc2)NC(=N)N([C@H](COC(=O)NC2(C(F)F)CC2)c2ccc(Cl)c(-n3ncnc3C(F)F)c2)C1=O] | 2.3 | 9.367 |
| 180 | 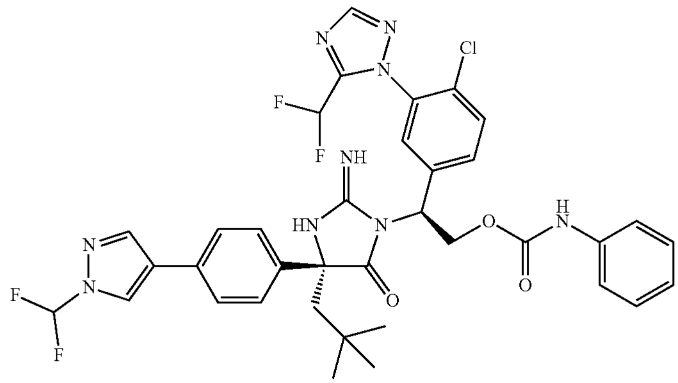 [SMILES: CC(C)(C)C[C@]1(c2ccc(-c3cnn(C(F)F)c3)cc2)NC(=N)N([C@H](COC(=O)Nc2ccccc2)c2ccc(Cl)c(-n3ncnc3C(F)F)c2)C1=O] | 2.6 | 23.665 |
| 181 | 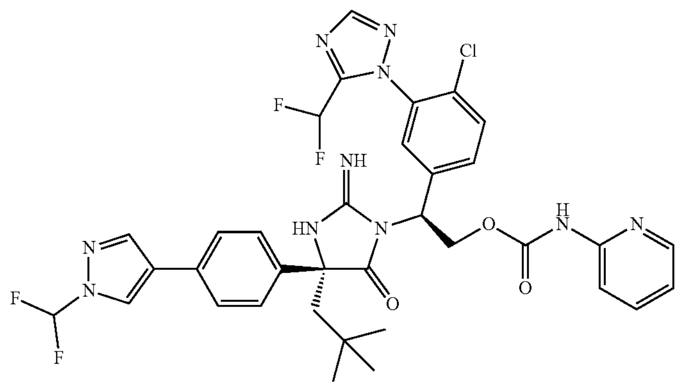 [SMILES: CC(C)(C)C[C@]1(c2ccc(-c3cnn(C(F)F)c3)cc2)NC(=N)N([C@H](COC(=O)Nc2ccccn2)c2ccc(Cl)c(-n3ncnc3C(F)F)c2)C1=O] | 3.2 | 28.956 |
| 182 | 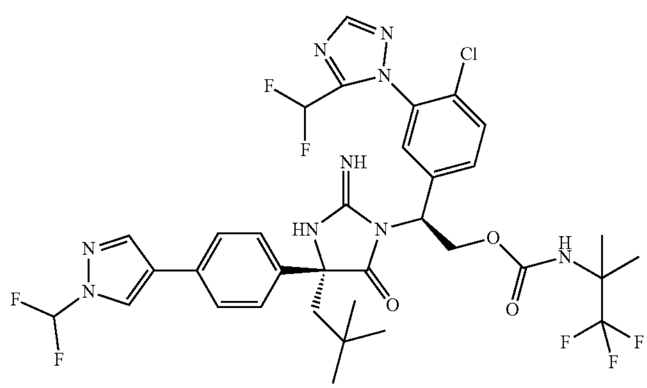 [SMILES: CC(C)(C)C[C@]1(c2ccc(-c3cnn(C(F)F)c3)cc2)NC(=N)N([C@H](COC(=O)NC(C)(C)C(F)(F)F)c2ccc(Cl)c(-n3ncnc3C(F)F)c2)C1=O] | 2.0 | 12.044 |

TABLE 1-continued

| COMPD # | STRUCTURE | HIV PI IC$_{50}$ (nM) | MT4 EC$_{50}$ (nM) |
|---|---|---|---|
| 183 | 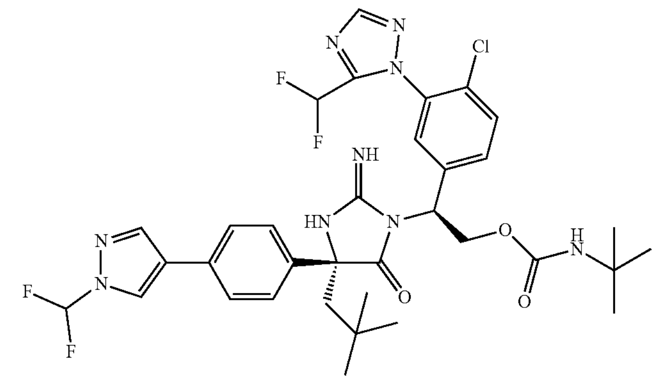 [SMILES: CC(C)(C)C[C@]1(c2ccc(-c3cnn(C(F)F)c3)cc2)NC(=N)N([C@H](COC(=O)NC(C)(C)C)c2ccc(Cl)c(-n3ncnc3C(F)F)c2)C1=O] | 2.0 | 12.002 |
| 184 | 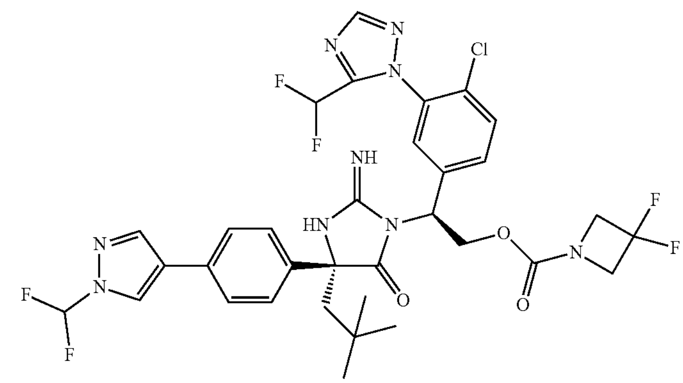 [SMILES: CC(C)(C)C[C@]1(c2ccc(-c3cnn(C(F)F)c3)cc2)NC(=N)N([C@H](COC(=O)N2CC(F)(F)C2)c2ccc(Cl)c(-n3ncnc3C(F)F)c2)C1=O] | 2.0 | 9.928 |
| 185 | 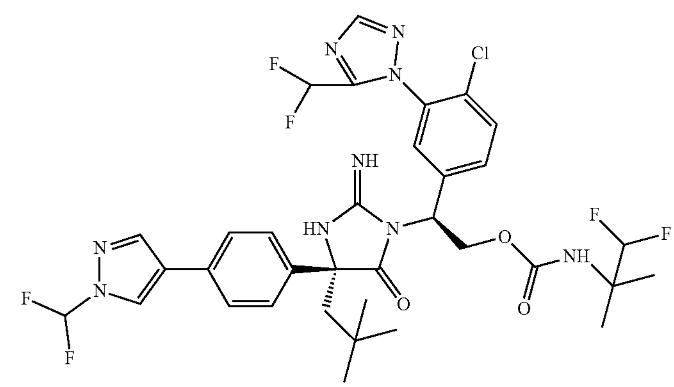 [SMILES: CC(C)(C)C[C@]1(c2ccc(-c3cnn(C(F)F)c3)cc2)NC(=N)N([C@H](COC(=O)NC(C)(C)C(F)F)c2ccc(Cl)c(-n3ncnc3C(F)F)c2)C1=O] | 1.8 | 12.64 |
| 186 | 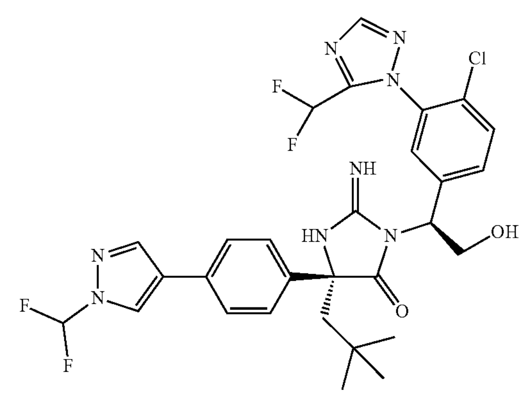 [SMILES: CC(C)(C)C[C@]1(c2ccc(-c3cnn(C(F)F)c3)cc2)NC(=N)N([C@H](CO)c2ccc(Cl)c(-n3ncnc3C(F)F)c2)C1=O] | 10.2 | 80.195 |

TABLE 1-continued

| COMPD # | STRUCTURE | HIV PI IC$_{50}$ (nM) | MT4 EC$_{50}$ (nM) |
|---|---|---|---|
| 187 | 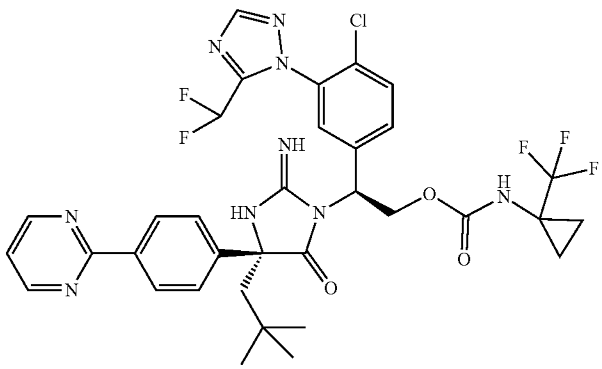 [SMILES: CC(C)(C)C[C@]1(c2ccc(-c3ncccn3)cc2)NC(=N)N([C@H](COC(=O)NC2(C(F)(F)F)CC2)c2ccc(Cl)c(-n3ncnc3C(F)F)c2)C1=O] | 2.2 | 11.591 |
| 188 | 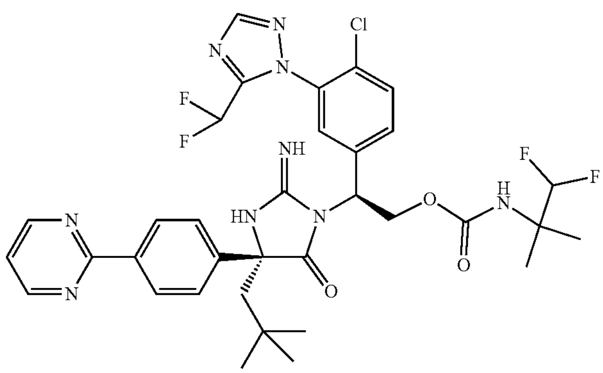 [SMILES: CC(C)(C)C[C@]1(c2ccc(-c3ncccn3)cc2)NC(=N)N([C@H](COC(=O)NC(C)(C)C(F)F)c2ccc(Cl)c(-n3ncnc3C(F)F)c2)C1=O] | 2.2 | 9.904 |
| 189 | 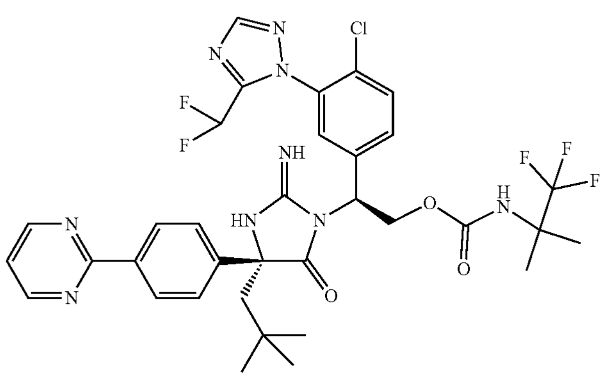 [SMILES: CC(C)(C)C[C@]1(c2ccc(-c3ncccn3)cc2)NC(=N)N([C@H](COC(=O)NC(C)(C)C(F)(F)F)c2ccc(Cl)c(-n3ncnc3C(F)F)c2)C1=O] | 2.0 | 9.12 |
| 190 | 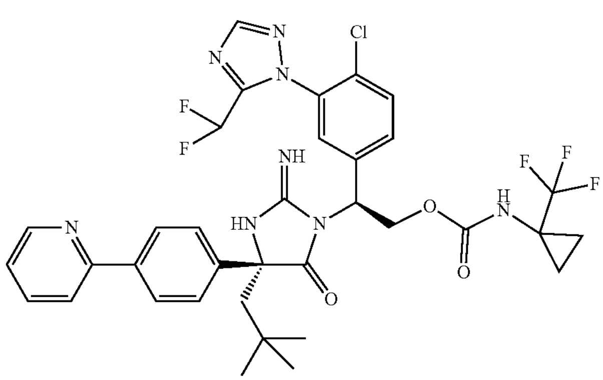 [SMILES: CC(C)(C)C[C@]1(c2ccc(-c3ccccn3)cc2)NC(=N)N([C@H](COC(=O)NC2(C(F)(F)F)CC2)c2ccc(Cl)c(-n3ncnc3C(F)F)c2)C1=O] | 2.6 | 22.568 |

TABLE 1-continued

| COMPD # | STRUCTURE | HIV PI IC$_{50}$ (nM) | MT4 EC$_{50}$ (nM) |
|---|---|---|---|
| 191 | 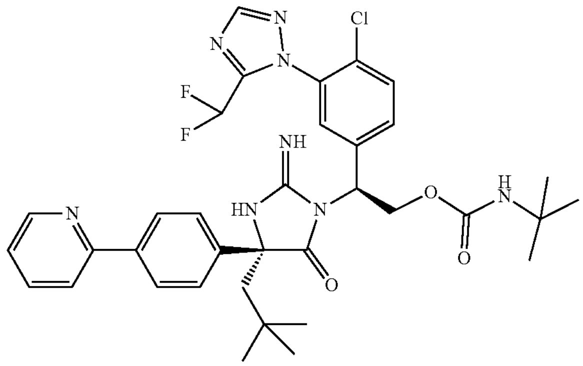 [SMILES: CC(C)(C)C[C@]1(c2ccc(-c3ccccn3)cc2)NC(=N)N([C@H](COC(=O)NC(C)(C)C)c2ccc(Cl)c(-n3ncnc3C(F)F)c2)C1=O] | 2.3 | 9.69 |
| 192 | 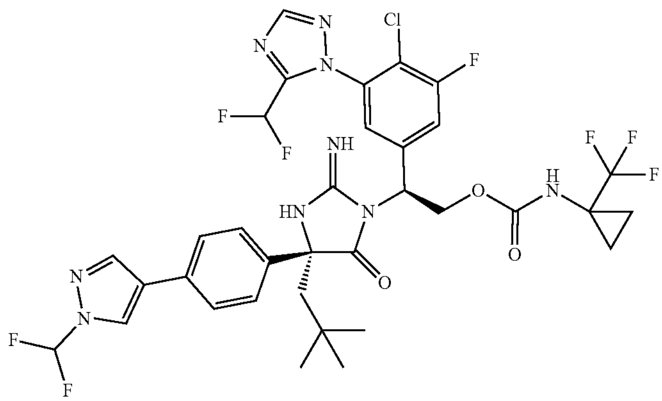 [SMILES: CC(C)(C)C[C@]1(c2ccc(-c3cnn(C(F)F)c3)cc2)NC(=N)N([C@H](COC(=O)NC2(C(F)(F)F)CC2)c2cc(F)c(Cl)c(-n3ncnc3C(F)F)c2)C1=O] | 3.4 | 61.926 |
| 193 | 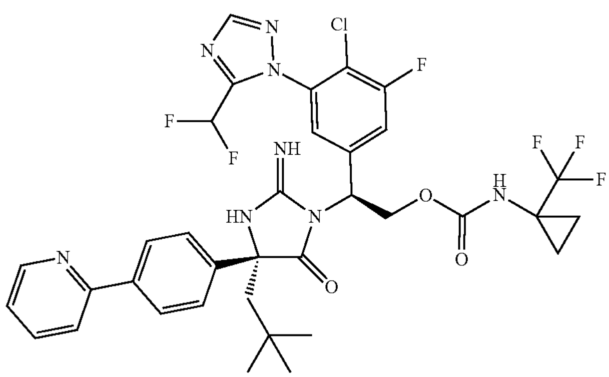 [SMILES: CC(C)(C)C[C@]1(c2ccc(-c3ccccn3)cc2)NC(=N)N([C@H](COC(=O)NC2(C(F)(F)F)CC2)c2cc(F)c(Cl)c(-n3ncnc3C(F)F)c2)C1=O] | 4.5 | 88.272 |
| 194 | 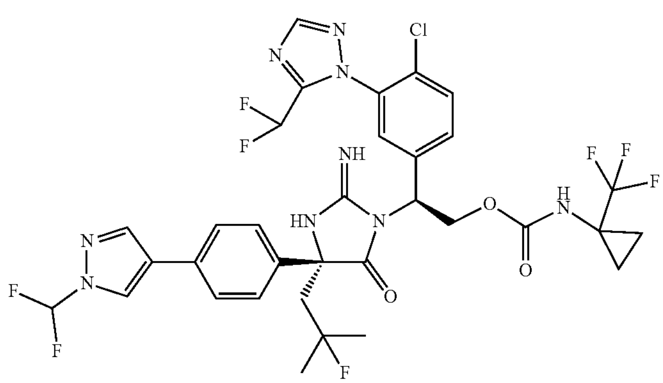 [SMILES: CC(C)(F)C[C@]1(c2ccc(-c3cnn(C(F)F)c3)cc2)NC(=N)N([C@H](COC(=O)NC2(C(F)(F)F)CC2)c2ccc(Cl)c(-n3ncnc3C(F)F)c2)C1=O] | 2.3 | 14.819 |

TABLE 1-continued

| COMPD # | STRUCTURE | HIV PI IC$_{50}$ (nM) | MT4 EC$_{50}$ (nM) |
|---|---|---|---|
| 195 | 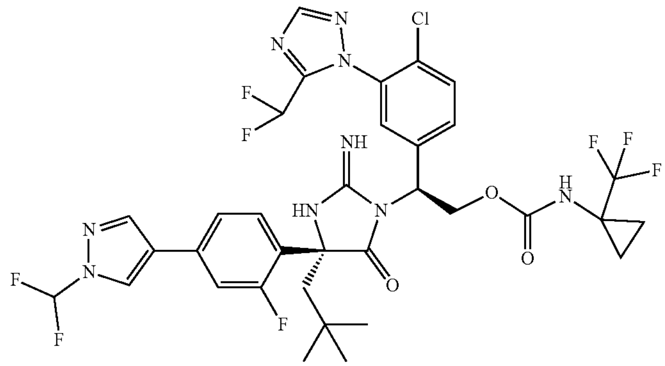 [SMILES: CC(C)(C)C[C@]1(c2ccc(-c3cnn(C(F)F)c3)cc2F)NC(=N)N([C@H](COC(=O)NC2(C(F)(F)F)CC2)c2ccc(Cl)c(-n3ncnc3C(F)F)c2)C1=O] | 2.5 | 10.503 |
| 196 | 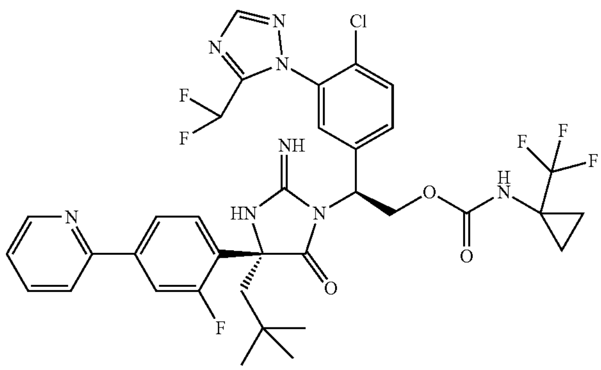 [SMILES: CC(C)(C)C[C@]1(c2ccc(-c3ncccn3)cc2F)NC(=N)N([C@H](COC(=O)NC2(C(F)(F)F)CC2)c2ccc(Cl)c(-n3ncnc3C(F)F)c2)C1=O] | 2.5 | 12.708 |
| 197 | 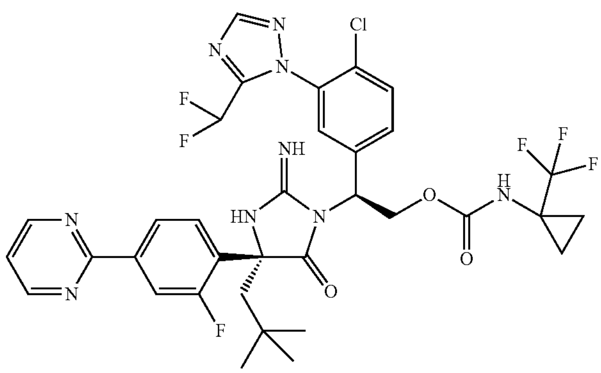 | 2.3 | 11.166 |
| 198 | 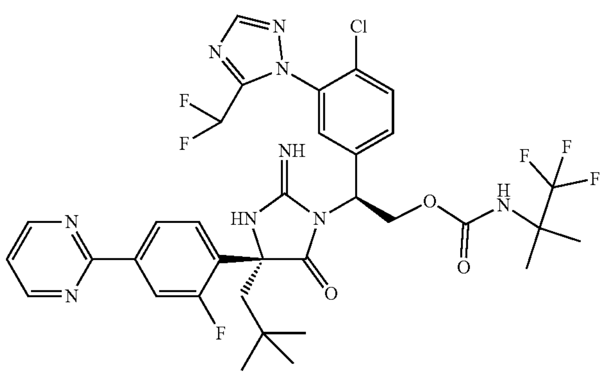 [SMILES: CC(C)(C)C[C@]1(c2ccc(-c3ncccn3)cc2F)NC(=N)N([C@H](COC(=O)NC(C)(C)C(F)(F)F)c2ccc(Cl)c(-n3ncnc3C(F)F)c2)C1=O] | 2.1 | 11.529 |

TABLE 1-continued

| COMPD # | STRUCTURE | HIV PI IC$_{50}$ (nM) | MT4 EC$_{50}$ (nM) |
| --- | --- | --- | --- |
| 199 | 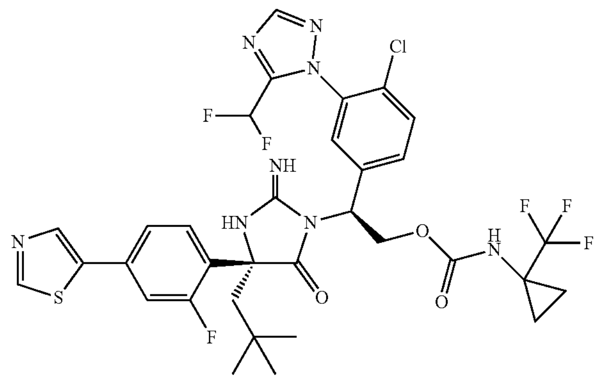 [SMILES: CC(C)(C)C[C@]1(c2ccc(-c3cncs3)cc2F)NC(=N)N([C@H](COC(=O)NC2(C(F)(F)F)CC2)c2ccc(Cl)c(-n3ncnc3C(F)F)c2)C1=O] | 2.2 | 7.596 |
| 200 | 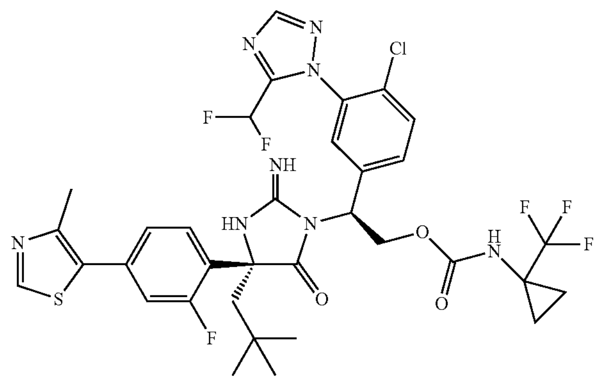 [SMILES: Cc1ncsc1-c1ccc([C@@]2(CC(C)(C)C)NC(=N)N([C@H](COC(=O)NC3(C(F)(F)F)CC3)c3ccc(Cl)c(-n4ncnc4C(F)F)c3)C2=O)c(F)c1] | 2.8 | 26.166 |
| 201 | 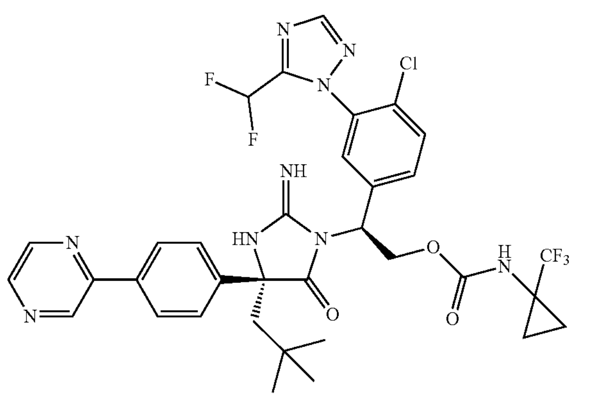 [SMILES: CC(C)(C)C[C@]1(c2ccc(-c3cnccn3)cc2)NC(=N)N([C@H](COC(=O)NC2(C(F)(F)F)CC2)c2ccc(Cl)c(-n3ncnc3C(F)F)c2)C1=O] | 9.3 | 9.263 |
| 202 | 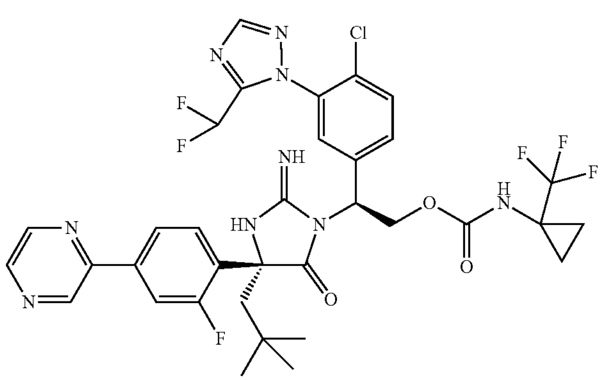 [SMILES: CC(C)(C)C[C@]1(c2ccc(-c3cnccn3)cc2F)NC(=N)N([C@H](COC(=O)NC2(C(F)(F)F)CC2)c2ccc(Cl)c(-n3ncnc3C(F)F)c2)C1=O] | 8.7 | 8.67 |

TABLE 1-continued

| COMPD # | STRUCTURE | HIV PI IC$_{50}$ (nM) | MT4 EC$_{50}$ (nM) |
|---|---|---|---|
| 203 | 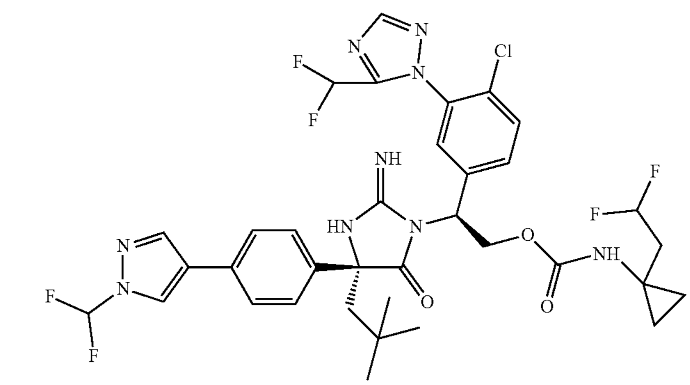 [SMILES: CC(C)(C)C[C@]1(c2ccc(-c3cnn(C(F)F)c3)cc2)NC(=N)N([C@H](COC(=O)NC2(CC(F)F)CC2)c2ccc(Cl)c(-n3ncnc3C(F)F)c2)C1=O] | 8.8 | 8.786 |
| 204 | 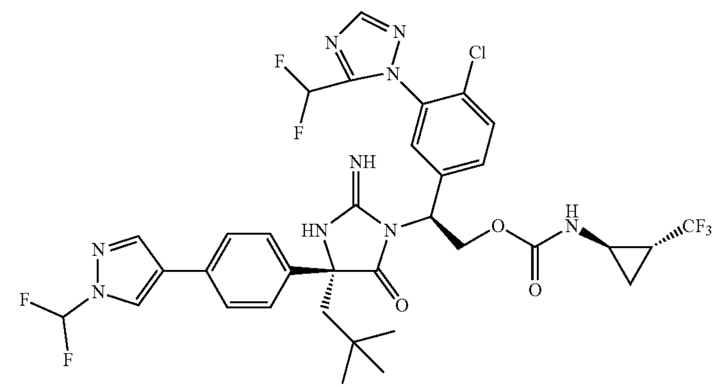 [SMILES: CC(C)(C)C[C@]1(c2ccc(-c3cnn(C(F)F)c3)cc2)NC(=N)N([C@H](COC(=O)N[C@@H]2C[C@H]2C(F)(F)F)c2ccc(Cl)c(-n3ncnc3C(F)F)c2)C1=O] | 9.3 | 9.261 |
| 330 | 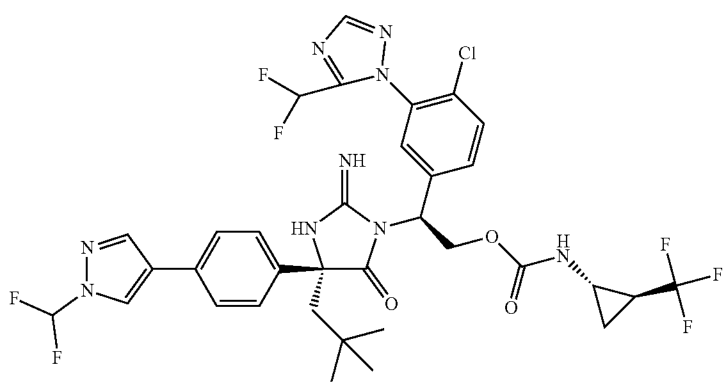 [SMILES: CC(C)(C)C[C@]1(c2ccc(-c3cnn(C(F)F)c3)cc2)NC(=N)N([C@H](COC(=O)N[C@H]2C[C@@H]2C(F)(F)F)c2ccc(Cl)c(-n3ncnc3C(F)F)c2)C1=O] | 22.2 | 22.182 |
| 331 | 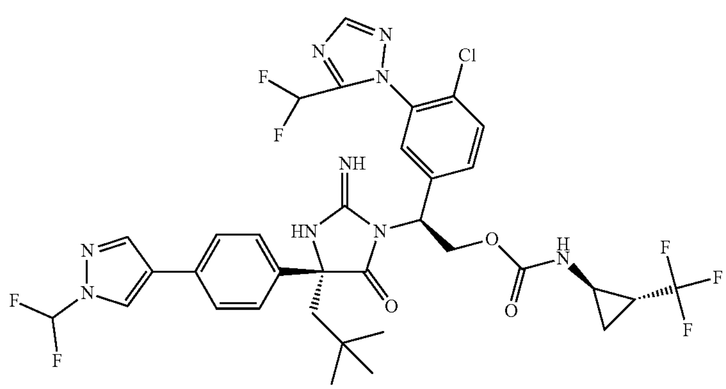 [SMILES: CC(C)(C)C[C@]1(c2ccc(-c3cnn(C(F)F)c3)cc2)NC(=N)N([C@H](COC(=O)N[C@@H]2C[C@H]2C(F)(F)F)c2ccc(Cl)c(-n3ncnc3C(F)F)c2)C1=O] | 2.7 | 16.447 |

TABLE 1-continued

| COMPD # | STRUCTURE | HIV PI IC$_{50}$ (nM) | MT4 EC$_{50}$ (nM) |
|---|---|---|---|
| 332 | 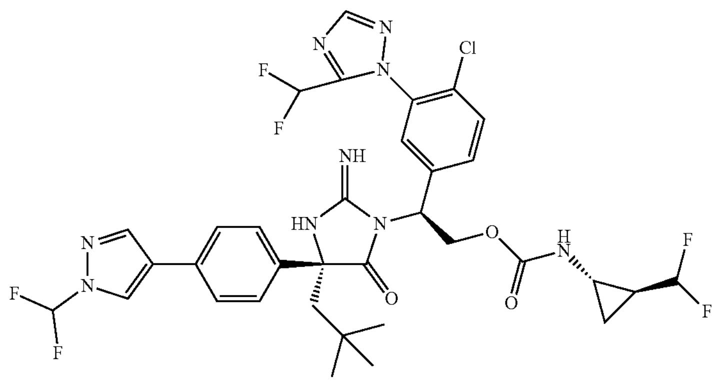 [SMILES: CC(C)(C)C[C@]1(c2ccc(-c3cnn(C(F)F)c3)cc2)NC(=N)N([C@H](COC(=O)N[C@H]2C[C@@H]2C(F)F)c2ccc(Cl)c(-n3ncnc3C(F)F)c2)C1=O] | 3.6 | 12.255 |
| 333 | 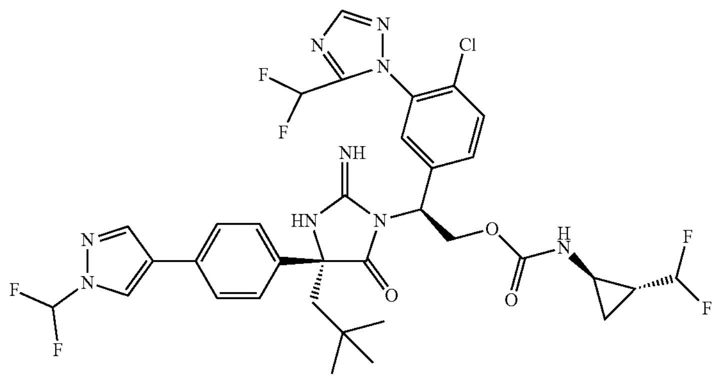 [SMILES: CC(C)(C)C[C@]1(c2ccc(-c3cnn(C(F)F)c3)cc2)NC(=N)N([C@H](COC(=O)N[C@@H]2C[C@H]2C(F)F)c2ccc(Cl)c(-n3ncnc3C(F)F)c2)C1=O] | 2.7 | 10.507 |
| 205 | 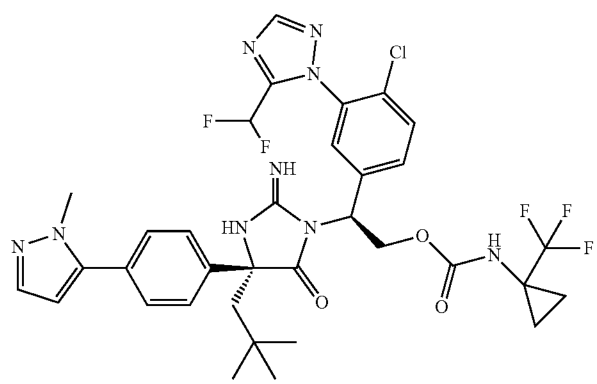 [SMILES: Cn1nccc1-c1ccc([C@@]2(CC(C)(C)C)NC(=N)N([C@H](COC(=O)NC3(C(F)(F)F)CC3)c3ccc(Cl)c(-n4ncnc4C(F)F)c3)C2=O)cc1] | 2.5 | 20.179 |
| 206 | 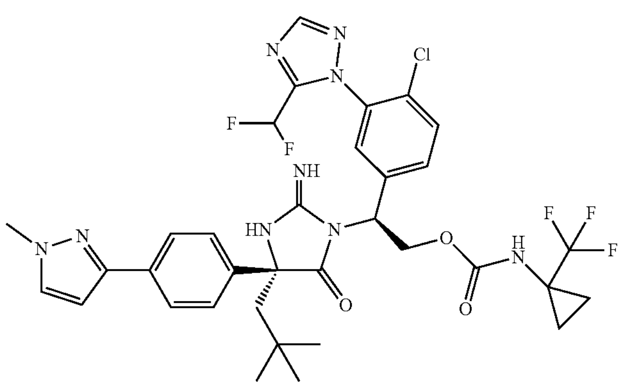 [SMILES: Cn1ccc(-c2ccc([C@@]3(CC(C)(C)C)NC(=N)N([C@H](COC(=O)NC4(C(F)(F)F)CC4)c4ccc(Cl)c(-n5ncnc5C(F)F)c4)C3=O)cc2)n1] | 2.1 | 6.737 |

TABLE 1-continued

| COMPD # | STRUCTURE | HIV PI IC$_{50}$ (nM) | MT4 EC$_{50}$ (nM) |
|---|---|---|---|
| 207 | 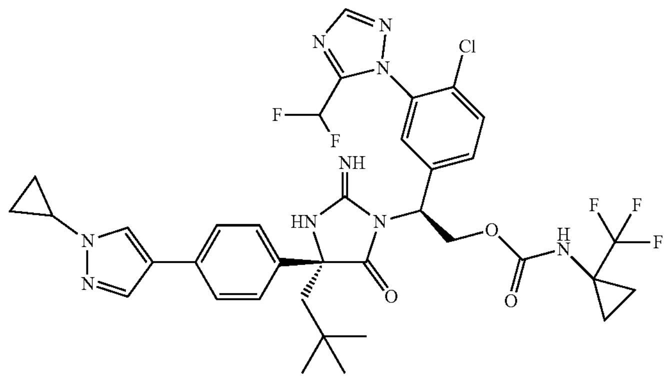 | 2.2 | 13.931 |
| 209 | 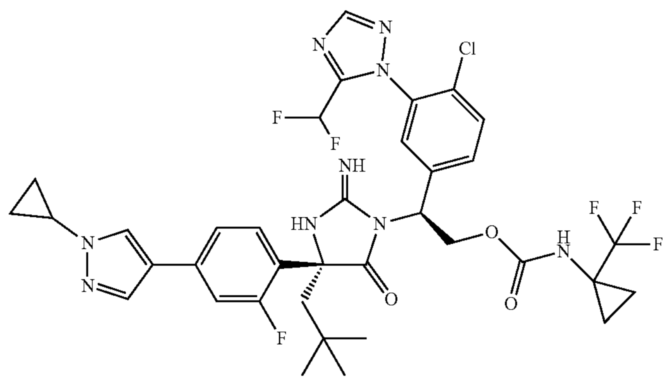 [SMILES: CC(C)(C)C[C@]1(c2ccc(-c3cnn(C4CC4)c3)cc2F)NC(=N)N([C@H](COC(=O)NC2(C(F)(F)F)CC2)c2ccc(Cl)c(-n3ncnc3C(F)F)c2)C1=O] | 2.6 | 14.716 |
| 210 | 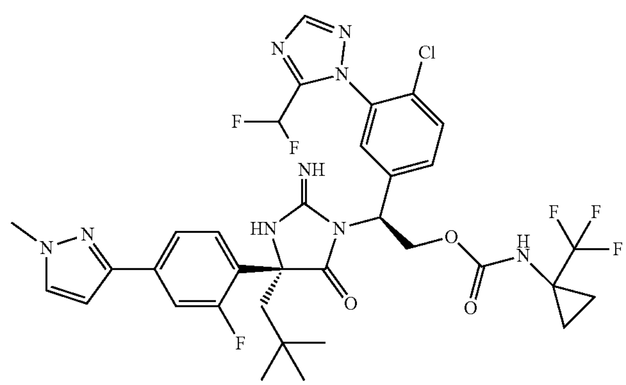 | 2.5 | 6.941 |
| 274 | 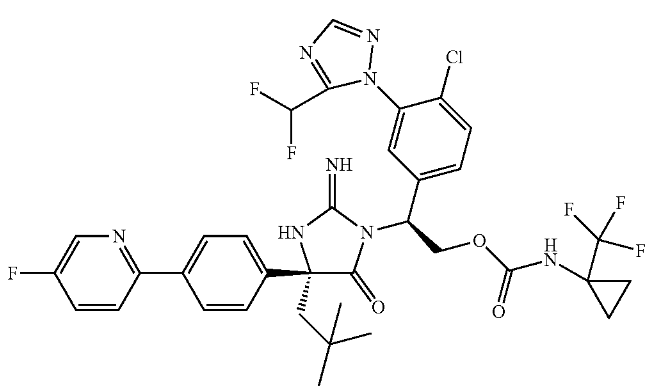 [SMILES: CC(C)(C)C[C@]1(c2ccc(-c3ccc(F)cn3)cc2)NC(=N)N([C@H](COC(=O)NC2(C(F)(F)F)CC2)c2ccc(Cl)c(-n3ncnc3C(F)F)c2)C1=O] | 2.9 | 11.125 |

TABLE 1-continued

| COMPD # | STRUCTURE | HIV PI IC$_{50}$ (nM) | MT4 EC$_{50}$ (nM) |
|---|---|---|---|
| 275 | 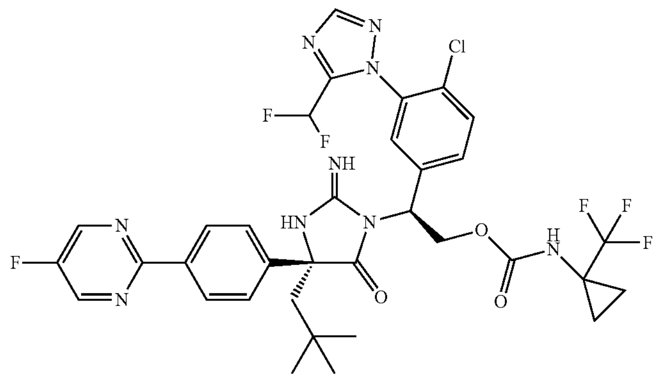 [SMILES: CC(C)(C)C[C@]1(c2ccc(-c3ncc(F)cn3)cc2)NC(=N)N([C@H](COC(=O)NC2(C(F)(F)F)CC2)c2ccc(Cl)c(-n3ncnc3C(F)F)c2)C1=O] | 2.0 | 12.839 |
| 276 | 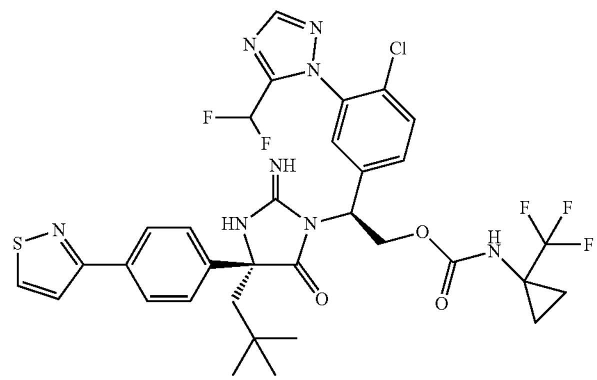 [SMILES: CC(C)(C)C[C@]1(c2ccc(-c3ccsn3)cc2)NC(=N)N([C@H](COC(=O)NC2(C(F)(F)F)CC2)c2ccc(Cl)c(-n3ncnc3C(F)F)c2)C1=O] | 4.9 | 12.503 |
| 277 | 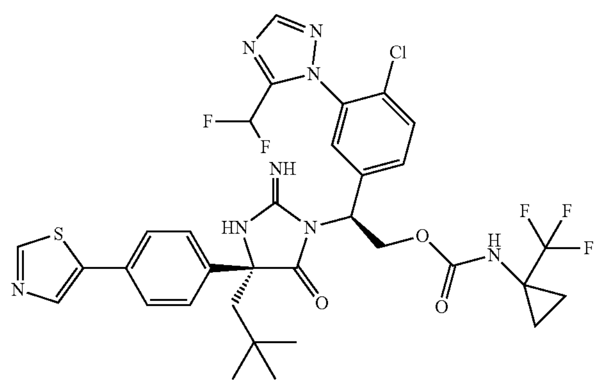 [SMILES: CC(C)(C)C[C@]1(c2ccc(-c3cncs3)cc2)NC(=N)N([C@H](COC(=O)NC2(C(F)(F)F)CC2)c2ccc(Cl)c(-n3ncnc3C(F)F)c2)C1=O] | 3.0 | 6.991 |
| 278 | 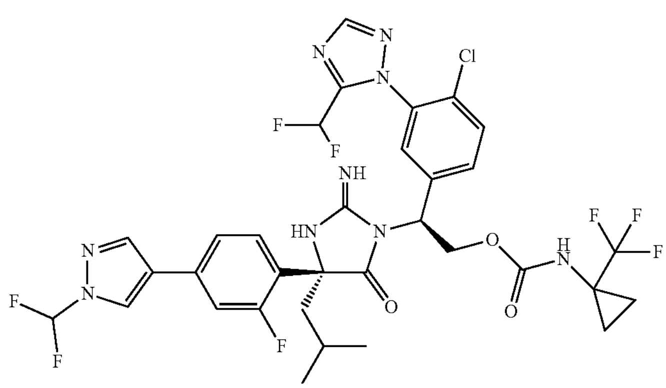 [SMILES: CC(C)C[C@]1(c2ccc(-c3cnn(C(F)F)c3)cc2F)NC(=N)N([C@H](COC(=O)NC2(C(F)(F)F)CC2)c2ccc(Cl)c(-n3ncnc3C(F)F)c2)C1=O] | 2.5 | 23.618 |

TABLE 1-continued
| COMPD # | STRUCTURE | HIV PI IC$_{50}$ (nM) | MT4 EC$_{50}$ (nM) |
|---|---|---|---|
| 279 | 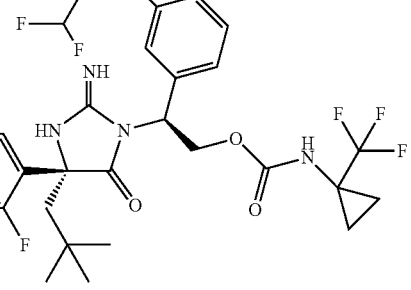 | 3.4 | 23.544 |
| 280 | 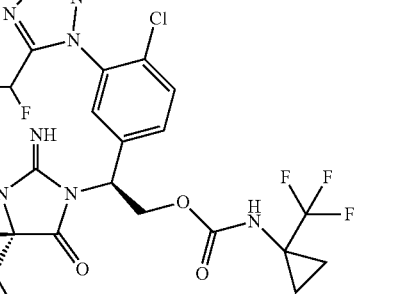 | 3.3 | 20.68 |
| 281 | 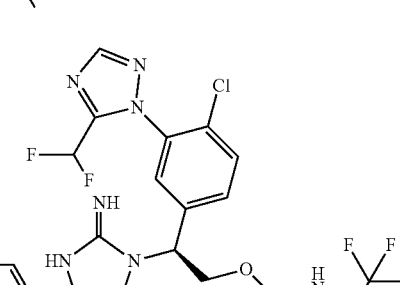 | 1.7 | 22.22 |
| 282 | 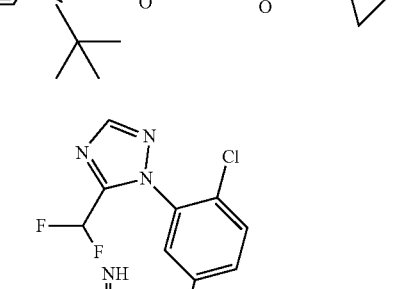 | 3.7 | 62.021 |

TABLE 1-continued

| COMPD # | STRUCTURE | HIV PI IC$_{50}$ (nM) | MT4 EC$_{50}$ (nM) |
|---|---|---|---|
| 283 | 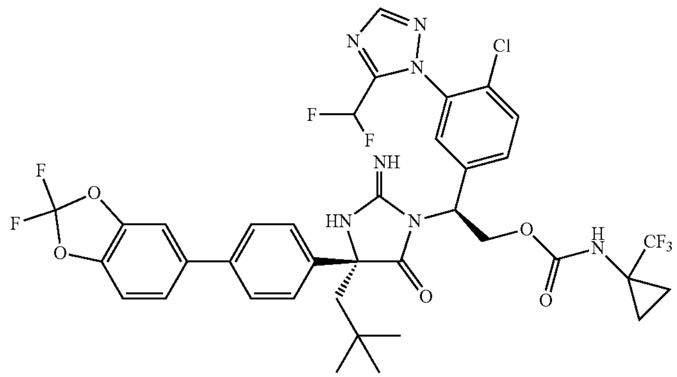 [SMILES: CC(C)(C)C[C@]1(c2ccc(-c3ccc4c(c3)OC(F)(F)O4)cc2)NC(=N)N([C@H](COC(=O)NC2(C(F)(F)F)CC2)c2ccc(Cl)c(-n3ncnc3C(F)F)c2)C1=O] | 5.8 | 113.43 |
| 326 | 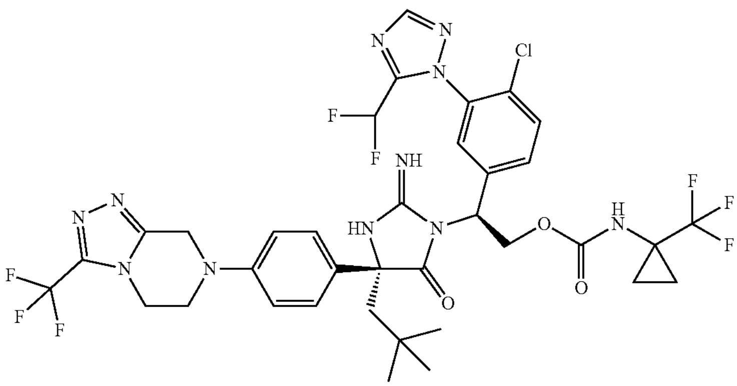 [SMILES: CC(C)(C)C[C@]1(c2ccc(N3CCn4c(nnc4C(F)(F)F)C3)cc2)NC(=N)N([C@H](COC(=O)NC2(C(F)(F)F)CC2)c2ccc(Cl)c(-n3ncnc3C(F)F)c2)C1=O] | 2.8 | 52.935 |
| 327 | 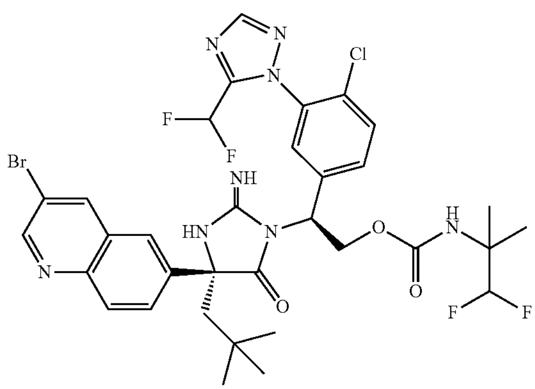 [SMILES: CC(C)(C)C[C@]1(c2ccc3ncc(Br)cc3c2)NC(=N)N([C@H](COC(=O)NC(C)(C)C(F)F)c2ccc(Cl)c(-n3ncnc3C(F)F)c2)C1=O] | 3.8 | 30.749 |
| 284 | 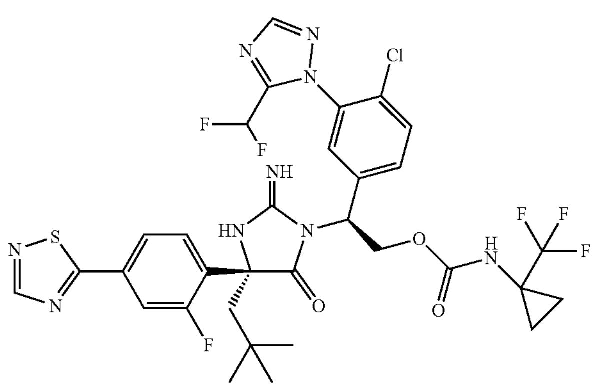 [SMILES: CC(C)(C)C[C@]1(c2ccc(-c3ncns3)cc2F)NC(=N)N([C@H](COC(=O)NC2(C(F)(F)F)CC2)c2ccc(Cl)c(-n3ncnc3C(F)F)c2)C1=O] | 4.2 | 11.366 |

TABLE 1-continued

| COMPD # | STRUCTURE | HIV PI IC$_{50}$ (nM) | MT4 EC$_{50}$ (nM) |
|---|---|---|---|
| 328 | 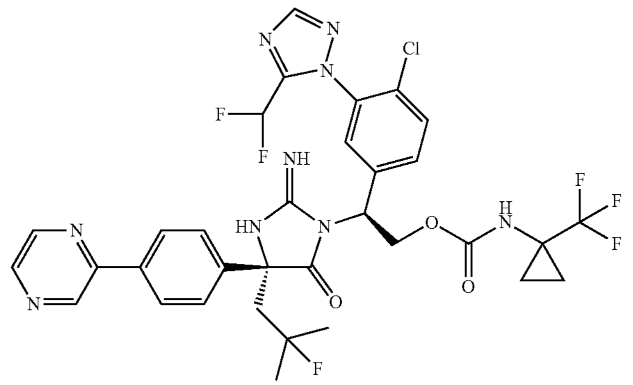 [SMILES: CC(C)(F)C[C@]1(c2ccc(-c3cnccn3)cc2)NC(=N)N([C@H](COC(=O)NC2(C(F)(F)F)CC2)c2ccc(Cl)c(-n3ncnc3C(F)F)c2)C1=O] | 3.1 | 22.435 |
| 329 | 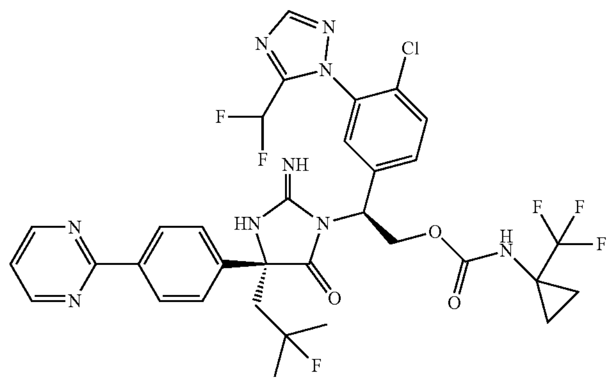 [SMILES: CC(C)(F)C[C@]1(c2ccc(-c3ncccn3)cc2)NC(=N)N([C@H](COC(=O)NC2(C(F)(F)F)CC2)c2ccc(Cl)c(-n3ncnc3C(F)F)c2)C1=O] | 2.9 | 23.02 |
| 211 | 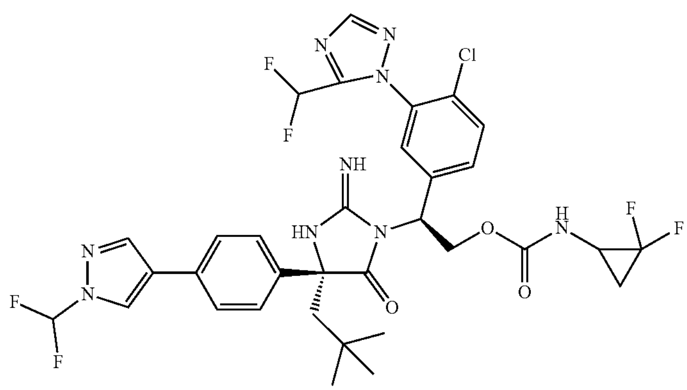 [SMILES: CC(C)(C)C[C@]1(c2ccc(-c3cnn(C(F)F)c3)cc2)NC(=N)N([C@H](COC(=O)NC2CC2(F)F)c2ccc(Cl)c(-n3ncnc3C(F)F)c2)C1=O] | 2.5 | 10.822 |
| 334 | 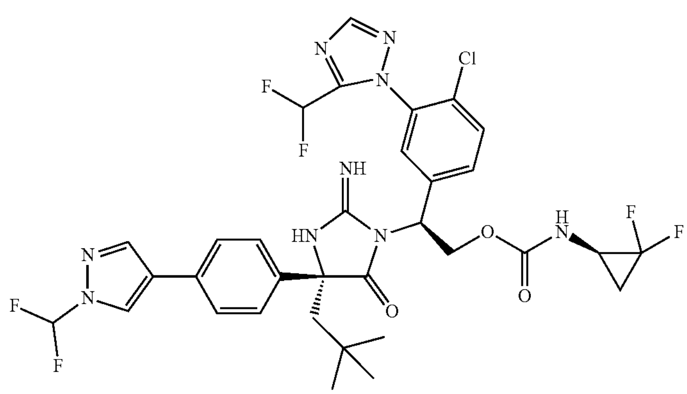 [SMILES: CC(C)(C)C[C@]1(c2ccc(-c3cnn(C(F)F)c3)cc2)NC(=N)N([C@H](COC(=O)N[C@@H]2CC2(F)F)c2ccc(Cl)c(-n3ncnc3C(F)F)c2)C1=O] | 2.4 | 8.978 |

TABLE 1-continued

| COMPD # | STRUCTURE | HIV PI IC₅₀ (nM) | MT4 EC₅₀ (nM) |
|---|---|---|---|
| 335 | 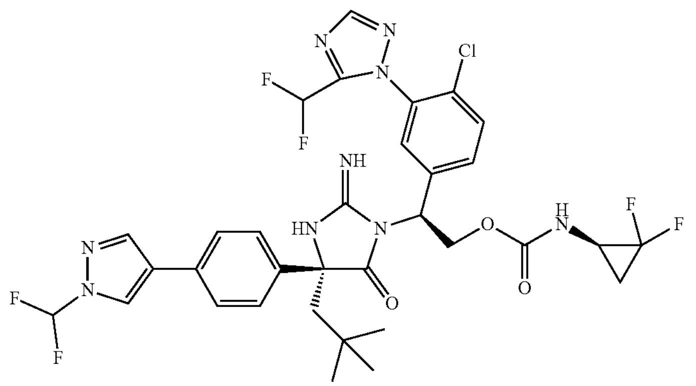 [SMILES: CC(C)(C)C[C@]1(c2ccc(-c3cnn(C(F)F)c3)cc2)NC(=N)N([C@H](COC(=O)N[C@@H]2CC2(F)F)c2ccc(Cl)c(-n3ncnc3C(F)F)c2)C1=O] | 2.1 | 5.594 |
| 212 | | 2.8 | 11.884 |
| 213 | 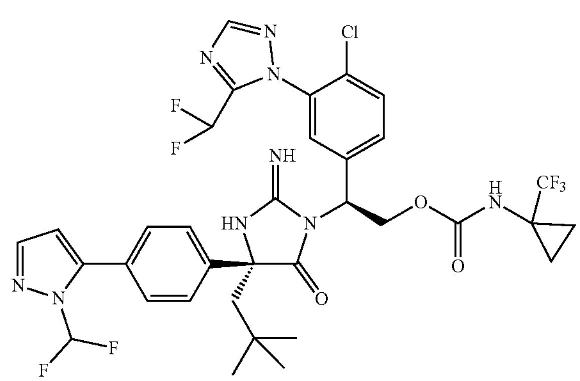 | 3.0 | 25.525 |

TABLE 1-continued

| COMPD # | STRUCTURE | HIV PI IC$_{50}$ (nM) | MT4 EC$_{50}$ (nM) |
|---|---|---|---|
| 214 | 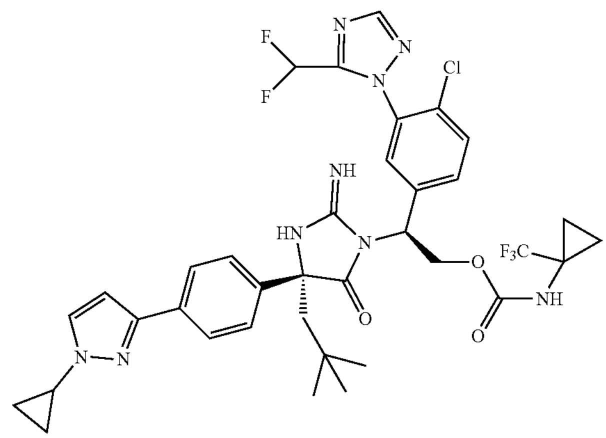 [SMILES: CC(C)(C)C[C@]1(c2ccc(-c3ccn(C4CC4)n3)cc2)NC(=N)N([C@H](COC(=O)NC2(C(F)(F)F)CC2)c2ccc(Cl)c(-n3ncnc3C(F)F)c2)C1=O] | 3.0 | 11.482 |
| 285 | 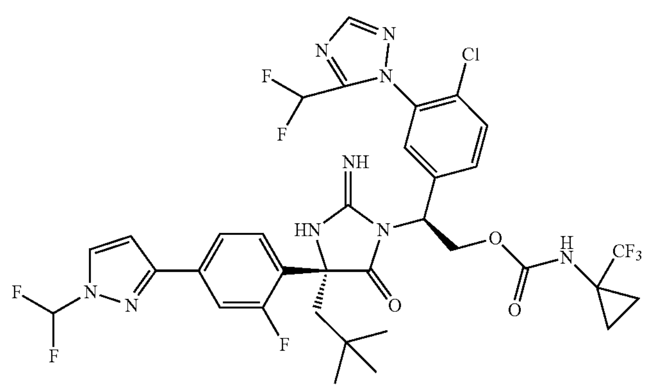 [SMILES: CC(C)(C)C[C@]1(c2ccc(-c3ccn(C(F)F)n3)cc2F)NC(=N)N([C@H](COC(=O)NC2(C(F)(F)F)CC2)c2ccc(Cl)c(-n3ncnc3C(F)F)c2)C1=O] | 5.3 | 16.751 |

TABLE 1-continued

| COMPD # | STRUCTURE | HIV PI IC$_{50}$ (nM) | MT4 EC$_{50}$ (nM) |
|---|---|---|---|
| 215 | 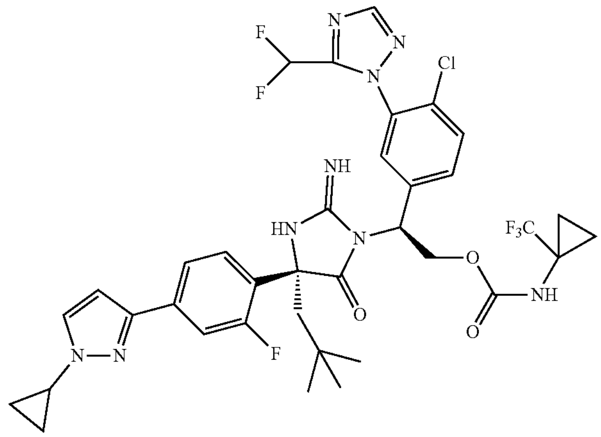 [SMILES: CC(C)(C)C[C@]1(c2ccc(-c3ccn(C4CC4)n3)cc2F)NC(=N)N([C@H](COC(=O)NC2(C(F)(F)F)CC2)c2ccc(Cl)c(-n3ncnc3C(F)F)c2)C1=O] | 3.3 | 18.454 |
| 336 | 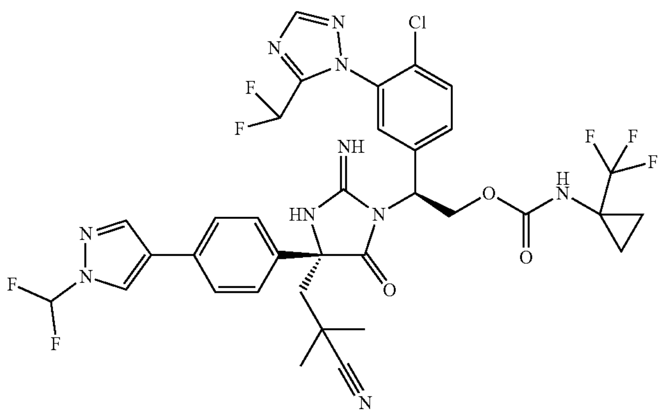 [SMILES: CC(C)(C#N)C[C@]1(c2ccc(-c3cnn(C(F)F)c3)cc2)NC(=N)N([C@H](COC(=O)NC2(C(F)(F)F)CC2)c2ccc(Cl)c(-n3ncnc3C(F)F)c2)C1=O] | 3.1 | 74.7 |
| 216 | 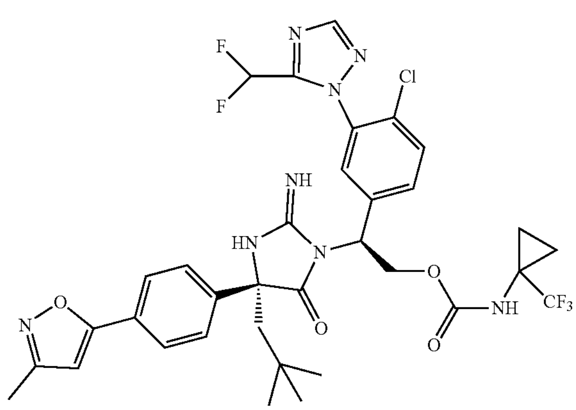 [SMILES: Cc1cc(-c2ccc([C@@]3(CC(C)(C)C)NC(=N)N([C@H](COC(=O)NC4(C(F)(F)F)CC4)c4ccc(Cl)c(-n5ncnc5C(F)F)c4)C3=O)cc2)on1] | 2.9 | 9.74 |

TABLE 1-continued

| COMPD # | STRUCTURE | HIV PI IC$_{50}$ (nM) | MT4 EC$_{50}$ (nM) |
|---|---|---|---|
| 286 | 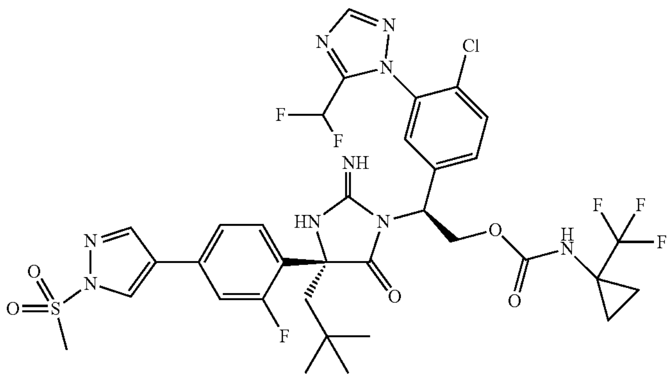 [SMILES: CC(C)(C)C[C@]1(c2ccc(-c3cnn(S(C)(=O)=O)c3)cc2F)NC(=N)N([C@H](COC(=O)NC2(C(F)(F)F)CC2)c2ccc(Cl)c(-n3ncnc3C(F)F)c2)C1=O] | 2.4 | 9.611 |
| 287 | 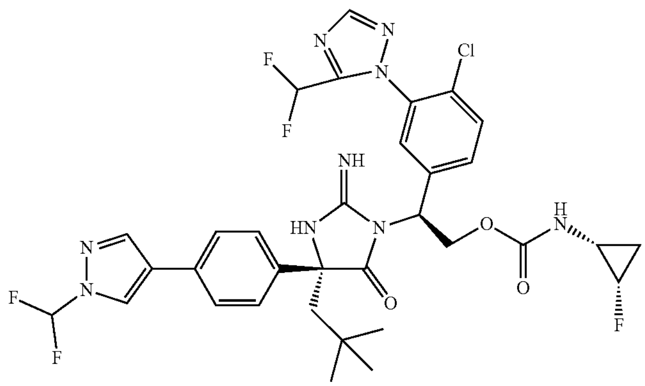 [SMILES: CC(C)(C)C[C@]1(c2ccc(-c3cnn(C(F)F)c3)cc2)NC(=N)N([C@H](COC(=O)N[C@@H]2C[C@@H]2F)c2ccc(Cl)c(-n3ncnc3C(F)F)c2)C1=O] | 2.1 | 7.548 |
| 288 | 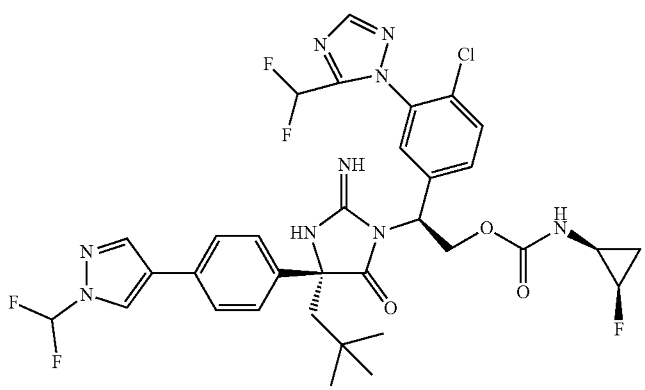 [SMILES: CC(C)(C)C[C@]1(c2ccc(-c3cnn(C(F)F)c3)cc2)NC(=N)N([C@H](COC(=O)N[C@H]2C[C@H]2F)c2ccc(Cl)c(-n3ncnc3C(F)F)c2)C1=O] | 2.0 | 6.069 |
| 217 | 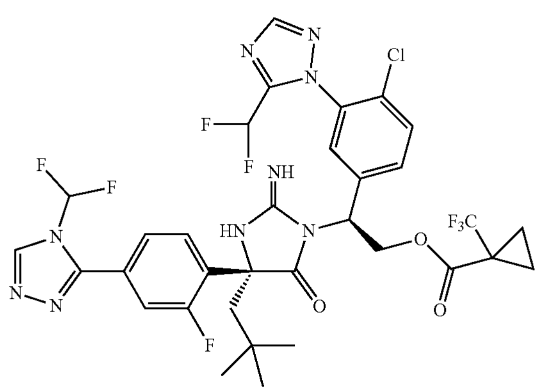 [SMILES: CC(C)(C)C[C@]1(c2ccc(-c3nncn3C(F)F)cc2F)NC(=N)N([C@H](COC(=O)C2(C(F)(F)F)CC2)c2ccc(Cl)c(-n3ncnc3C(F)F)c2)C1=O] | 5.0 | 76.711 |

TABLE 1-continued

| COMPD # | STRUCTURE | HIV PI IC$_{50}$ (nM) | MT4 EC$_{50}$ (nM) |
|---|---|---|---|
| 337 | 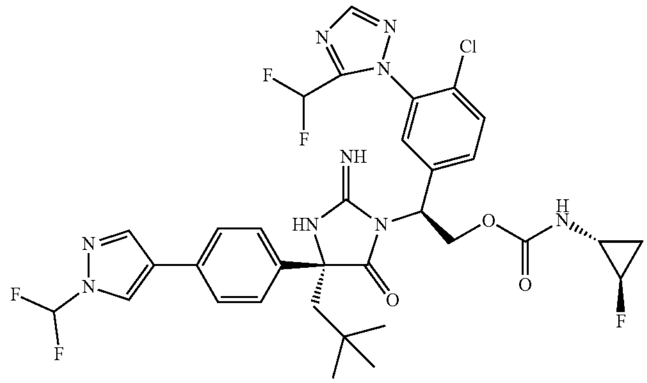 [SMILES: CC(C)(C)C[C@]1(c2ccc(-c3cnn(C(F)F)c3)cc2)NC(=N)N([C@H](COC(=O)N[C@@H]2C[C@H]2F)c2ccc(Cl)c(-n3ncnc3C(F)F)c2)C1=O] | 2.1 | 9.751 |
| 338 | 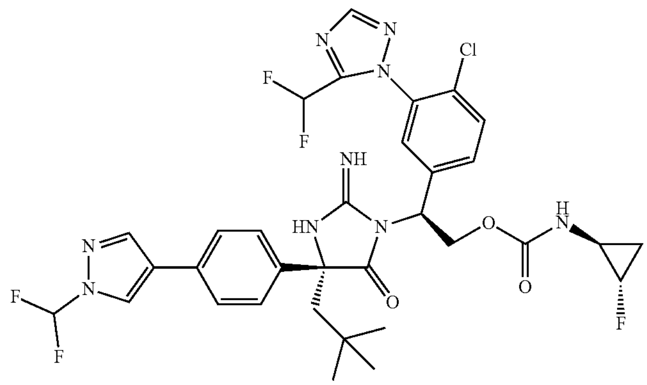 [SMILES: CC(C)(C)C[C@]1(c2ccc(-c3cnn(C(F)F)c3)cc2)NC(=N)N([C@H](COC(=O)N[C@H]2C[C@@H]2F)c2ccc(Cl)c(-n3ncnc3C(F)F)c2)C1=O] | 2.0 | 9.941 |
| 218 | 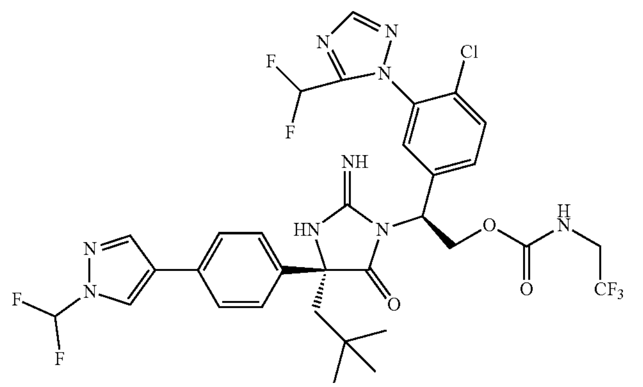 [SMILES: CC(C)(C)C[C@]1(c2ccc(-c3cnn(C(F)F)c3)cc2)NC(=N)N([C@H](COC(=O)NCC(F)(F)F)c2ccc(Cl)c(-n3ncnc3C(F)F)c2)C1=O] | 2.3 | 9.886 |
| 219 | 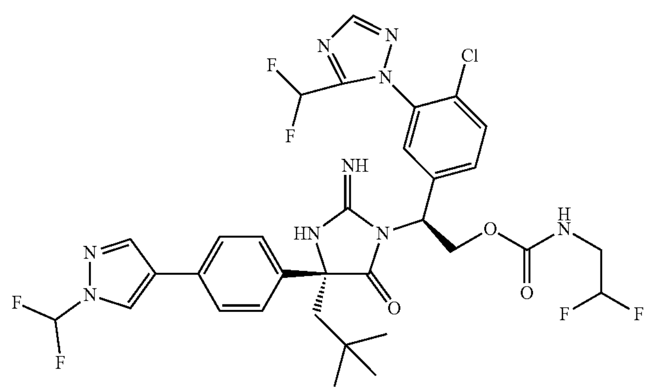 [SMILES: CC(C)(C)C[C@]1(c2ccc(-c3cnn(C(F)F)c3)cc2)NC(=N)N([C@H](COC(=O)NCC(F)F)c2ccc(Cl)c(-n3ncnc3C(F)F)c2)C1=O] | 2.2 | 8.801 |

TABLE 1-continued

| COMPD # | STRUCTURE | HIV PI IC$_{50}$ (nM) | MT4 EC$_{50}$ (nM) |
|---|---|---|---|
| 339 | 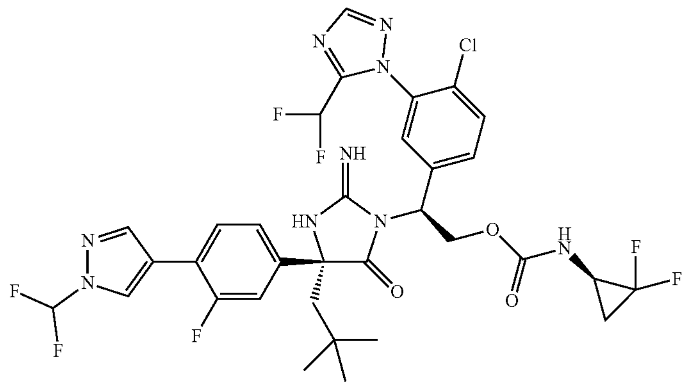 [SMILES: CC(C)(C)C[C@]1(c2ccc(-c3cnn(C(F)F)c3)c(F)c2)NC(=N)N([C@H](COC(=O)N[C@@H]2CC2(F)F)c2ccc(Cl)c(-n3ncnc3C(F)F)c2)C1=O] | 1.8 | 9.092 |
| 340 | 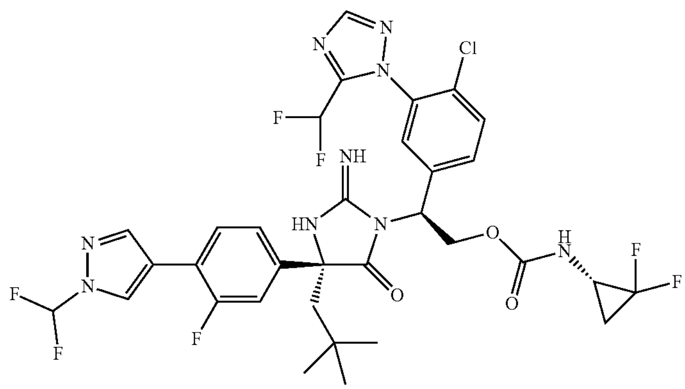 [SMILES: CC(C)(C)C[C@]1(c2ccc(-c3cnn(C(F)F)c3)c(F)c2)NC(=N)N([C@H](COC(=O)N[C@H]2CC2(F)F)c2ccc(Cl)c(-n3ncnc3C(F)F)c2)C1=O] | 1.7 | 6.674 |
| 289 | 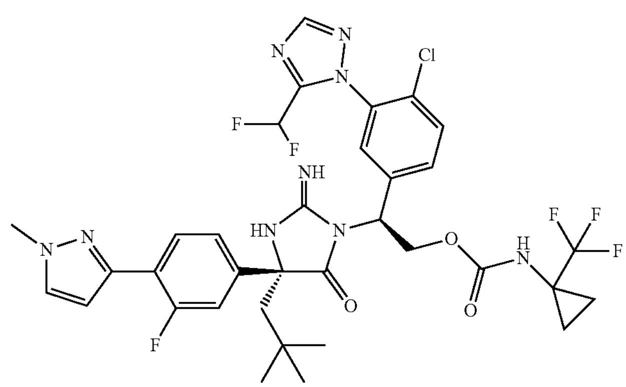 [SMILES: Cn1ccc(-c2ccc([C@@]3(CC(C)(C)C)NC(=N)N([C@H](COC(=O)NC4(C(F)(F)F)CC4)c4ccc(Cl)c(-n5ncnc5C(F)F)c4)C3=O)cc2F)n1] | 1.7 | 8.255 |
| 290 | 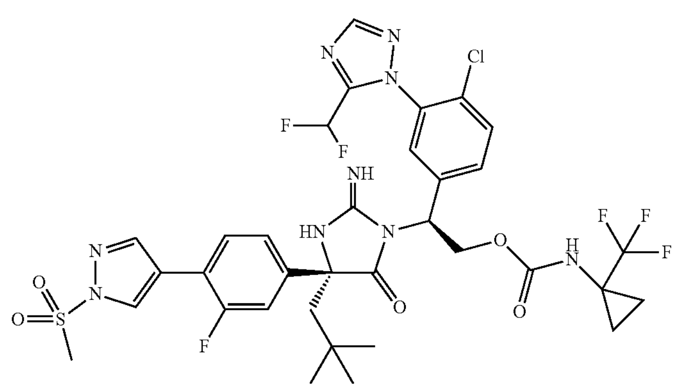 [SMILES: CC(C)(C)C[C@]1(c2ccc(-c3cnn(S(C)(=O)=O)c3)c(F)c2)NC(=N)N([C@H](COC(=O)NC2(C(F)(F)F)CC2)c2ccc(Cl)c(-n3ncnc3C(F)F)c2)C1=O] | 3.2 | 11.647 |

TABLE 1-continued
| COMPD # | STRUCTURE | HIV PI IC$_{50}$ (nM) | MT4 EC$_{50}$ (nM) |
|---|---|---|---|
| 291 | 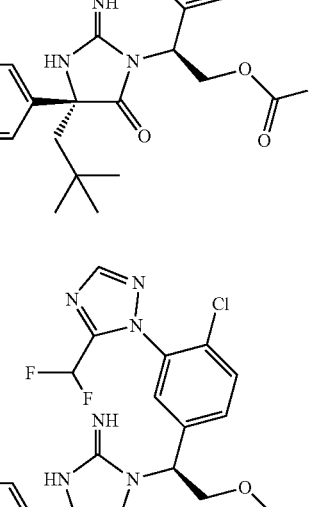 | 3.2 | 11.751 |
| 292 | 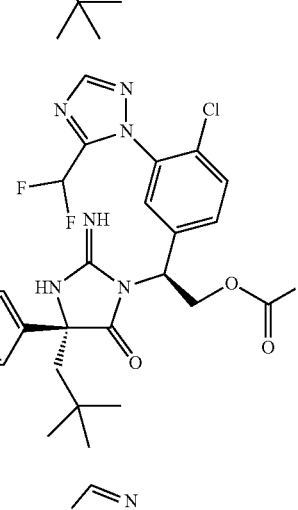 | 2.0 | 14.223 |
| 293 | 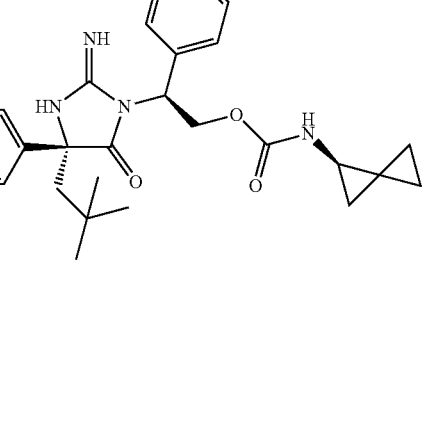 | 3.4 | 10.5 |
| 341 | 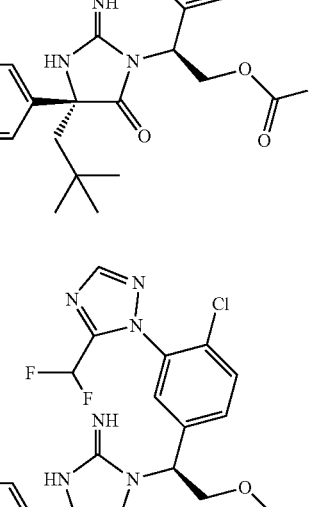 | 3.2 | 8.538 |

TABLE 1-continued

| COMPD # | STRUCTURE | HIV PI IC$_{50}$ (nM) | MT4 EC$_{50}$ (nM) |
|---|---|---|---|
| 342 | 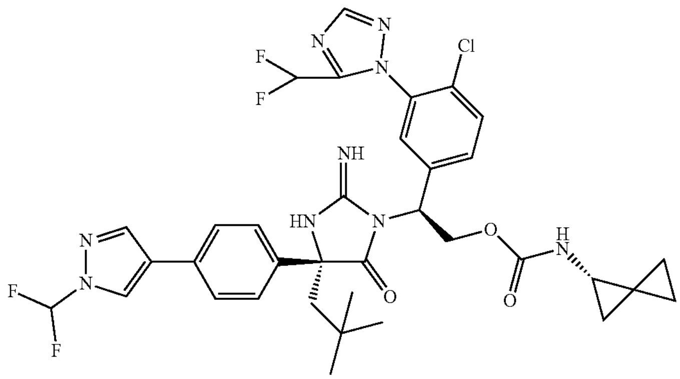 [SMILES: CC(C)(C)C[C@]1(c2ccc(-c3cnn(C(F)F)c3)cc2)NC(=N)N([C@H](COC(=O)N[C@H]2CC23CC3)c2ccc(Cl)c(-n3ncnc3C(F)F)c2)C1=O] | 3.0 | 8.921 |
| 294 | 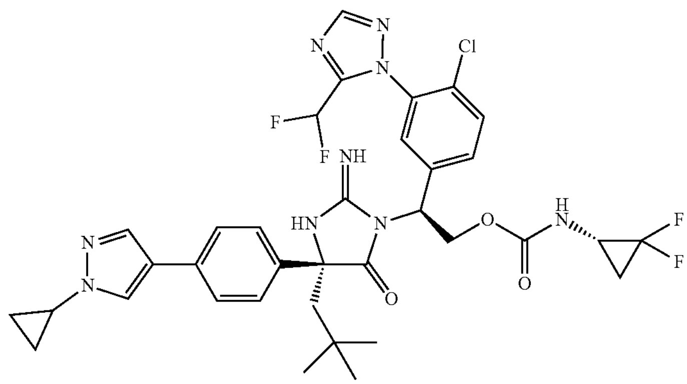 [SMILES: CC(C)(C)C[C@]1(c2ccc(-c3cnn(C4CC4)c3)cc2)NC(=N)N([C@H](COC(=O)N[C@H]2CC2(F)F)c2ccc(Cl)c(-n3ncnc3C(F)F)c2)C1=O] | 2.8 | 8.739 |
| 295 | 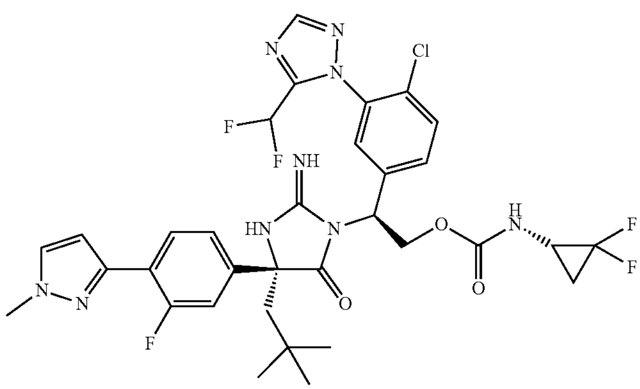 | 2.8 | 7.33 |
| 345 | 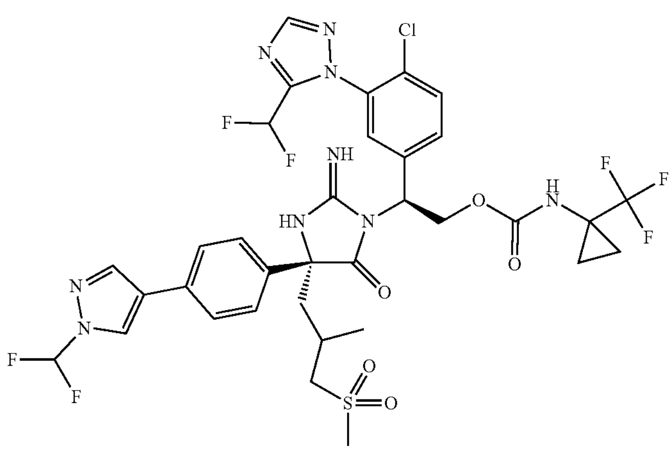 [SMILES: CC(C[C@]1(c2ccc(-c3cnn(C(F)F)c3)cc2)NC(=N)N([C@H](COC(=O)NC2(C(F)(F)F)CC2)c2ccc(Cl)c(-n3ncnc3C(F)F)c2)C1=O)CS(C)(=O)=O] | 13.2 | 133.96 |

TABLE 1-continued

| COMPD # | STRUCTURE | HIV PI IC$_{50}$ (nM) | MT4 EC$_{50}$ (nM) |
|---|---|---|---|
| 296 | 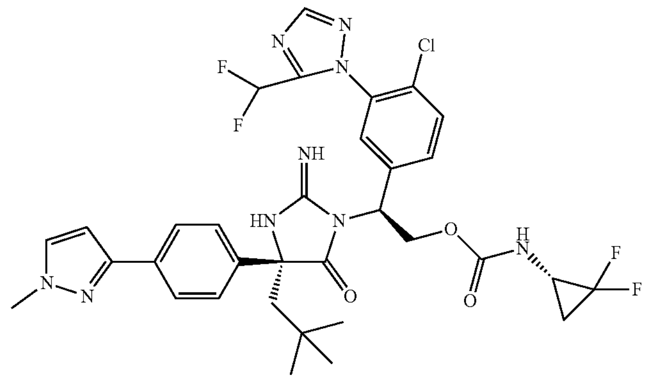 [SMILES: Cn1ccc(-c2ccc([C@@]3(CC(C)(C)C)NC(=N)N([C@H](COC(=O)N[C@H]4CC4(F)F)c4ccc(Cl)c(-n5ncnc5C(F)F)c4)C3=O)cc2)n1] | 2.3 | 8.575 |
| 297 | 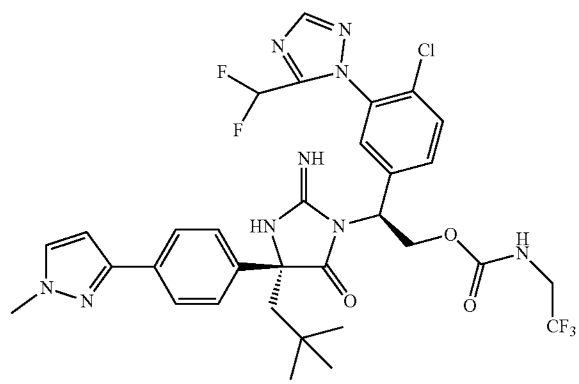 [SMILES: Cn1ccc(-c2ccc([C@@]3(CC(C)(C)C)NC(=N)N([C@H](COC(=O)NCC(F)(F)F)c4ccc(Cl)c(-n5ncnc5C(F)F)c4)C3=O)cc2)n1] | 2.7 | 10.338 |
| 346 | 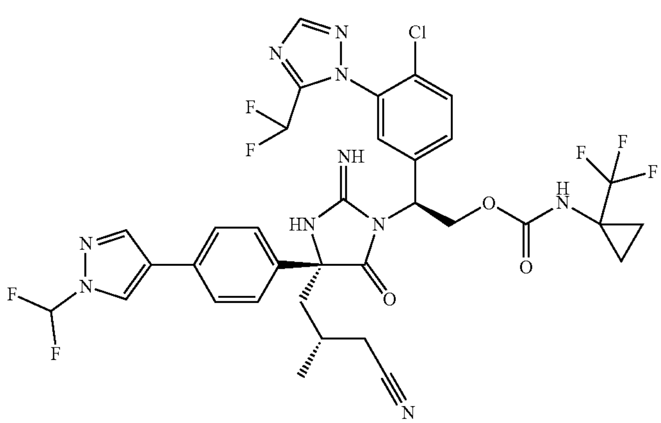 [SMILES: C[C@@H](CC#N)C[C@]1(c2ccc(-c3cnn(C(F)F)c3)cc2)NC(=N)N([C@H](COC(=O)NC2(C(F)(F)F)CC2)c2ccc(Cl)c(-n3ncnc3C(F)F)c2)C1=O] | 4.7 | 31.866 |

TABLE 1-continued

| COMPD # | STRUCTURE | HIV PI IC$_{50}$ (nM) | MT4 EC$_{50}$ (nM) |
|---|---|---|---|
| 347 | 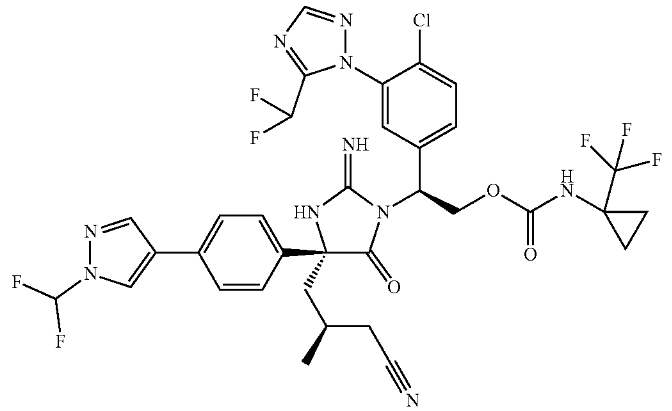 [SMILES: C[C@H](CC#N)C[C@]1(c2ccc(-c3cnn(C(F)F)c3)cc2)NC(=N)N([C@H](COC(=O)NC2(C(F)(F)F)CC2)c2ccc(Cl)c(-n3ncnc3C(F)F)c2)C1=O] | 4.3 | 31.975 |
| 298 | 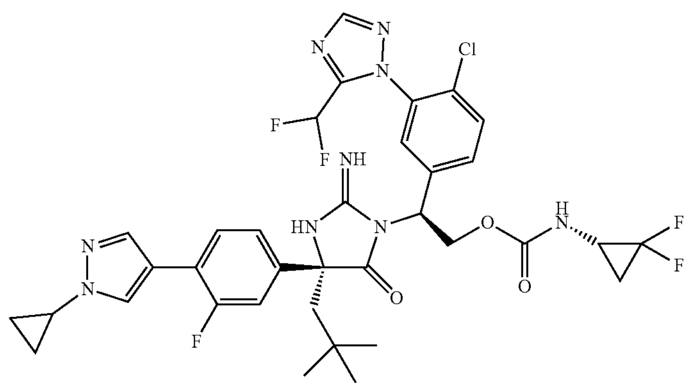 | 2.9 | 7.83 |
| 221 | 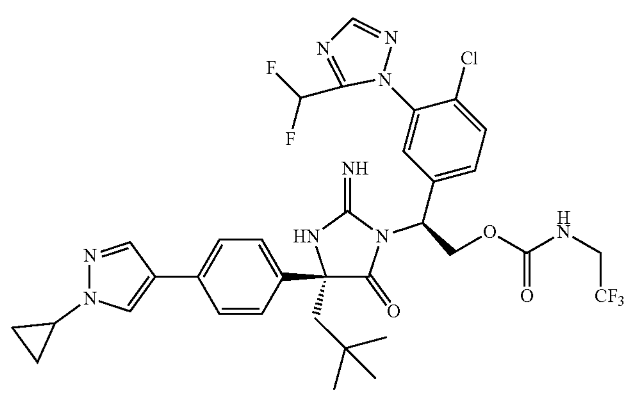 [SMILES: CC(C)(C)C[C@]1(c2ccc(-c3cnn(C4CC4)c3)cc2)NC(=N)N([C@H](COC(=O)NCC(F)(F)F)c2ccc(Cl)c(-n3ncnc3C(F)F)c2)C1=O] | 3.6 | 15.45 |
| 299 | 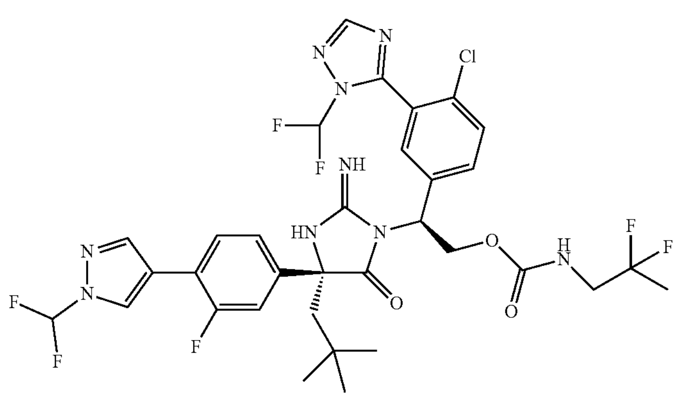 [SMILES: CC(C)(C)C[C@]1(c2ccc(-c3cnn(C(F)F)c3)c(F)c2)NC(=N)N([C@H](COC(=O)NCC(C)(F)F)c2ccc(Cl)c(-c3ncnn3C(F)F)c2)C1=O] | 3.4 | 13.03 |

TABLE 1-continued

| COMPD # | STRUCTURE | HIV PI IC$_{50}$ (nM) | MT4 EC$_{50}$ (nM) |
|---|---|---|---|
| 300 | 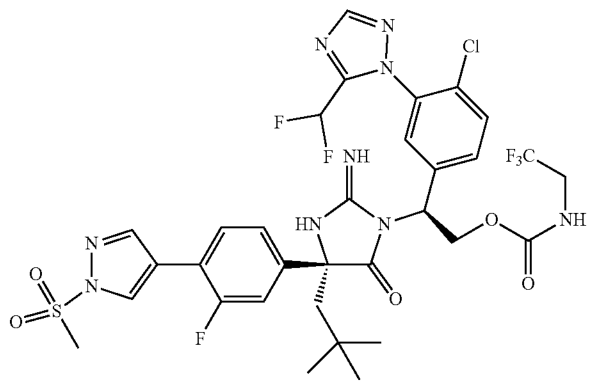 [SMILES: CC(C)(C)C[C@]1(c2ccc(-c3cnn(S(C)(=O)=O)c3)c(F)c2)NC(=N)N([C@H](COC(=O)NCC(F)(F)F)c2ccc(Cl)c(-n3ncnc3C(F)F)c2)C1=O] | 2.9 | 12.52 |
| 302 | 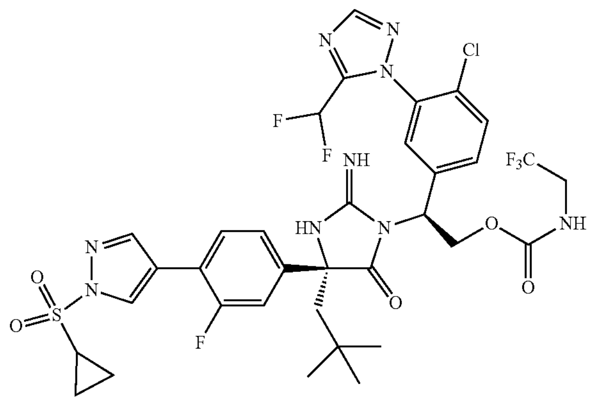 [SMILES: CC(C)(C)C[C@]1(c2ccc(-c3cnn(S(=O)(=O)C4CC4)c3)c(F)c2)NC(=N)N([C@H](COC(=O)NCC(F)(F)F)c2ccc(Cl)c(-n3ncnc3C(F)F)c2)C1=O] | 2.8 | 18.137 |
| 303 | 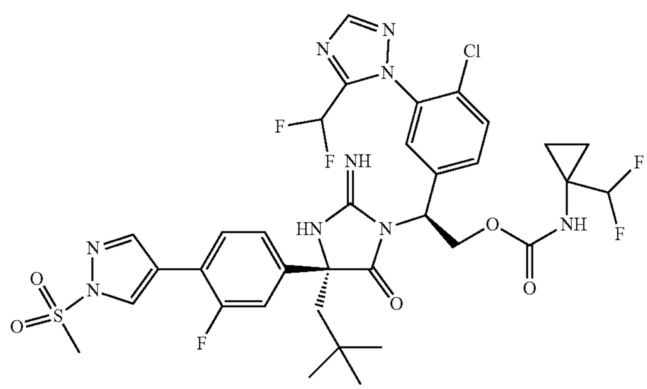 [SMILES: CC(C)(C)C[C@]1(c2ccc(-c3cnn(S(C)(=O)=O)c3)c(F)c2)NC(=N)N([C@H](COC(=O)NC2(C(F)F)CC2)c2ccc(Cl)c(-n3ncnc3C(F)F)c2)C1=O] | | 11.173 |
| 306 | 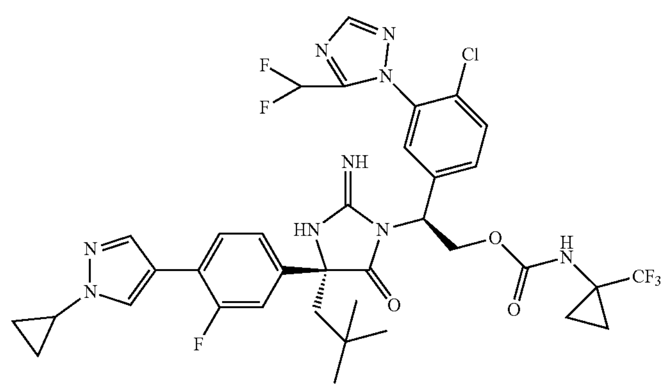 [SMILES: CC(C)(C)C[C@]1(c2ccc(-c3cnn(C4CC4)c3)c(F)c2)NC(=N)N([C@H](COC(=O)NC2(C(F)(F)F)CC2)c2ccc(Cl)c(-n3ncnc3C(F)F)c2)C1=O] | | 10.915 |

TABLE 1-continued
| COMPD # | STRUCTURE | HIV PI IC$_{50}$ (nM) | MT4 EC$_{50}$ (nM) |
|---|---|---|---|
| 307 | 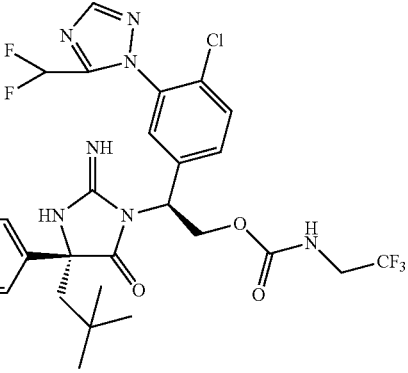 | 3.2 | 12.65 |
| 308 | 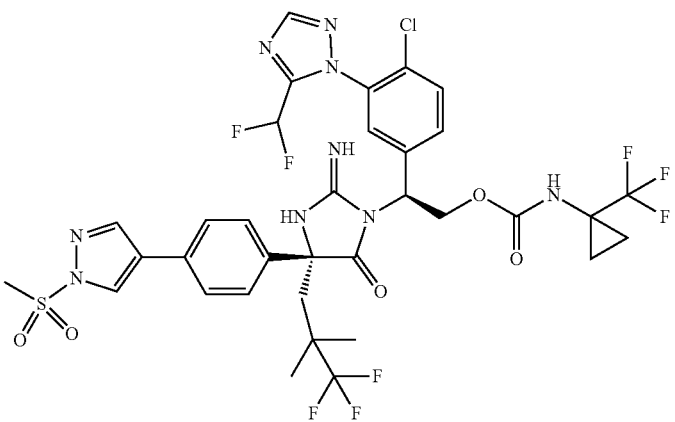 [SMILES: CC(C)(C[C@]1(c2ccc(-c3cnn(S(C)(=O)=O)c3)cc2)NC(=N)N([C@H](COC(=O)NC2(C(F)(F)F)CC2)c2ccc(Cl)c(-n3ncnc3C(F)F)c2)C1=O)C(F)(F)F] | 3.2 | 16.344 |
| 223 | 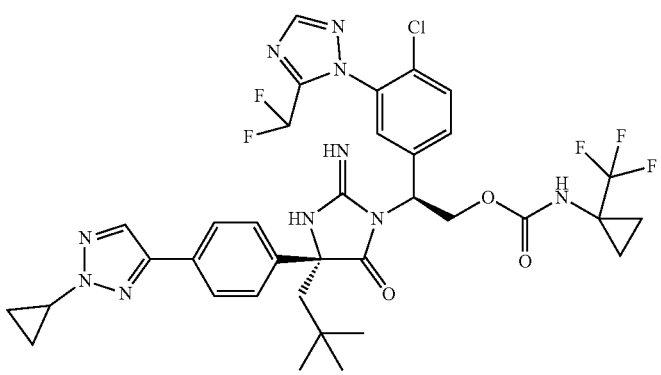 [SMILES: CC(C)(C)C[C@]1(c2ccc(-c3cnn(C4CC4)n3)cc2)NC(=N)N([C@H](COC(=O)NC2(C(F)(F)F)CC2)c2ccc(Cl)c(-n3ncnc3C(F)F)c2)C1=O] | 3.3 | 13.13 |
| 224 | 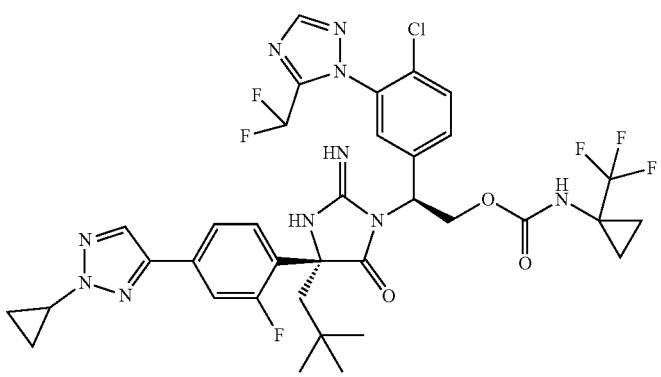 [SMILES: CC(C)(C)C[C@]1(c2ccc(-c3cnn(C4CC4)n3)cc2F)NC(=N)N([C@H](COC(=O)NC2(C(F)(F)F)CC2)c2ccc(Cl)c(-n3ncnc3C(F)F)c2)C1=O] | 3.9 | 19.538 |

TABLE 1-continued

| COMPD # | STRUCTURE | HIV PI IC$_{50}$ (nM) | MT4 EC$_{50}$ (nM) |
|---|---|---|---|
| 225 | 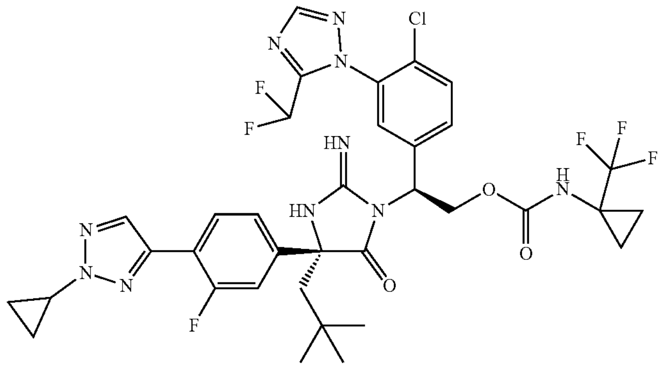 [SMILES: CC(C)(C)C[C@]1(c2ccc(-c3cnn(C4CC4)n3)c(F)c2)NC(=N)N([C@H](COC(=O)NC2(C(F)(F)F)CC2)c2ccc(Cl)c(-n3ncnc3C(F)F)c2)C1=O] | 2.8 | 17.417 |
| 309 | 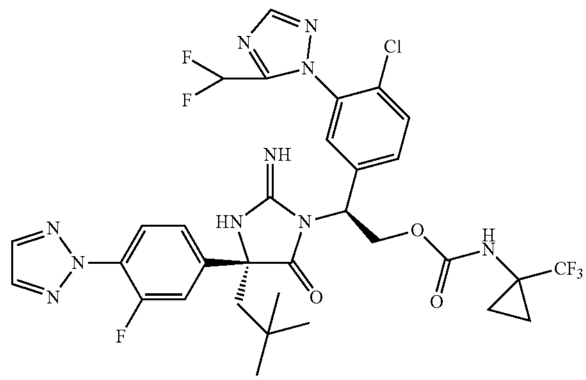 [SMILES: CC(C)(C)C[C@]1(c2ccc(-n3nccn3)c(F)c2)NC(=N)N([C@H](COC(=O)NC2(C(F)(F)F)CC2)c2ccc(Cl)c(-n3ncnc3C(F)F)c2)C1=O] | 3.4 | 13.367 |
| 348 | 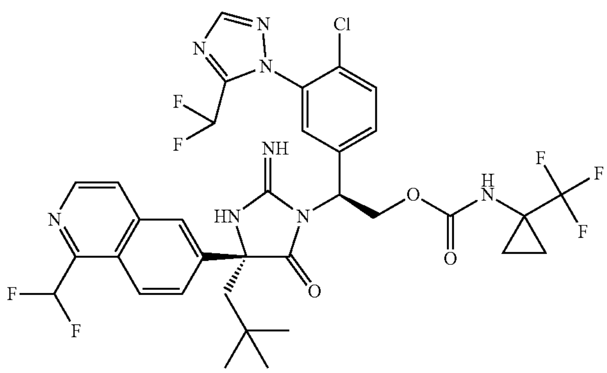 [SMILES: CC(C)(C)C[C@]1(c2ccc3c(C(F)F)nccc3c2)NC(=N)N([C@H](COC(=O)NC2(C(F)(F)F)CC2)c2ccc(Cl)c(-n3ncnc3C(F)F)c2)C1=O] | 4.7 | 7.458 |
| 226 | 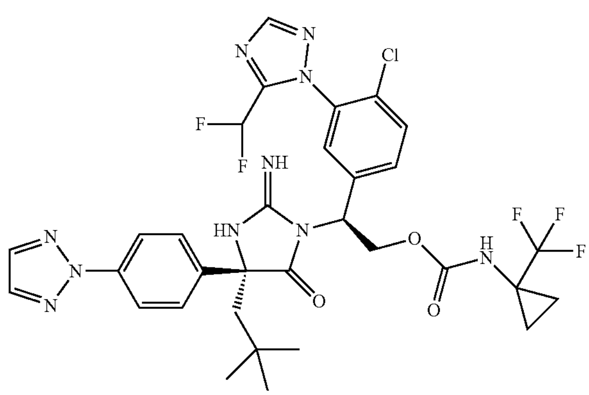 [SMILES: CC(C)(C)C[C@]1(c2ccc(-n3nccn3)cc2)NC(=N)N([C@H](COC(=O)NC2(C(F)(F)F)CC2)c2ccc(Cl)c(-n3ncnc3C(F)F)c2)C1=O] | 4.4 | 10.558 |

TABLE 1-continued

| COMPD # | STRUCTURE | HIV PI IC₅₀ (nM) | MT4 EC₅₀ (nM) |
|---|---|---|---|
| 349 | 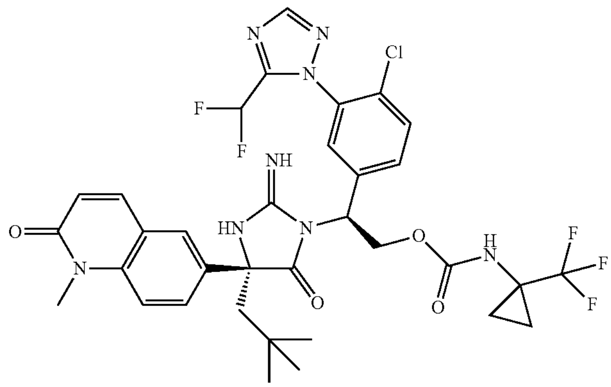 [SMILES: Cn1c(=O)ccc2cc([C@@]3(CC(C)(C)C)NC(=N)N([C@H](COC(=O)NC4(C(F)(F)F)CC4)c4ccc(Cl)c(-n5ncnc5C(F)F)c4)C3=O)ccc21] | 3.2 | 36.043 |
| 310 | 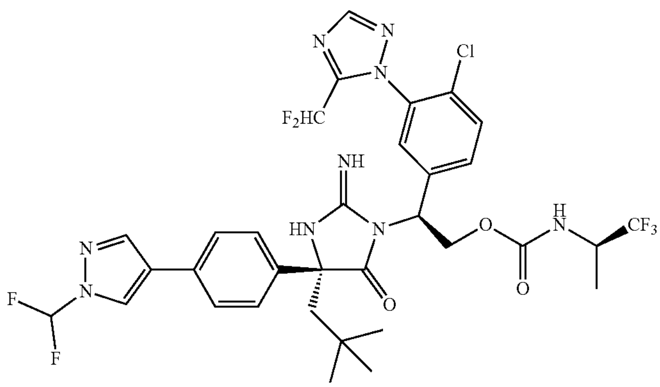 [SMILES: C[C@@H](NC(=O)OC[C@H](c1ccc(Cl)c(-n2ncnc2C(F)F)c1)N1C(=N)N[C@](CC(C)(C)C)(c2ccc(-c3cnn(C(F)F)c3)cc2)C1=O)C(F)(F)F] | 3.9 | 20.251 |
| 311 | 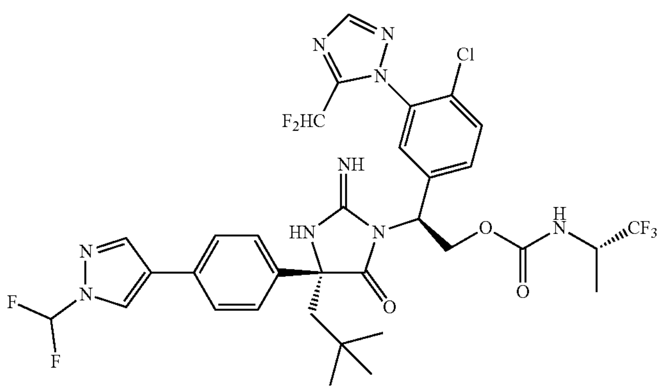 [SMILES: C[C@H](NC(=O)OC[C@H](c1ccc(Cl)c(-n2ncnc2C(F)F)c1)N1C(=N)N[C@](CC(C)(C)C)(c2ccc(-c3cnn(C(F)F)c3)cc2)C1=O)C(F)(F)F] | 3.3 | 7.013 |
| 227 | 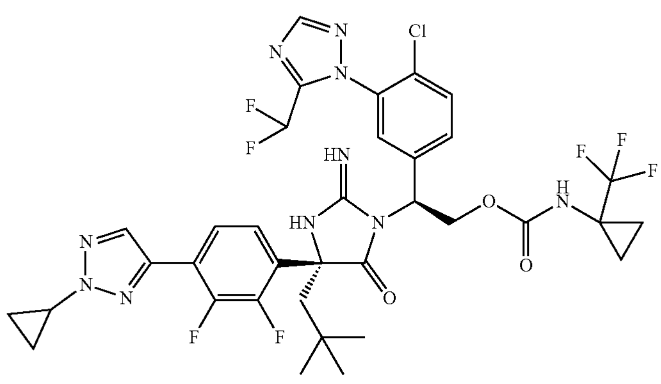 [SMILES: CC(C)(C)C[C@]1(c2ccc(-c3cnn(C4CC4)n3)c(F)c2F)NC(=N)N([C@H](COC(=O)NC2(C(F)(F)F)CC2)c2ccc(Cl)c(-n3ncnc3C(F)F)c2)C1=O] | 4.2 | 25.408 |

TABLE 1-continued

| COMPD # | STRUCTURE | HIV PI IC$_{50}$ (nM) | MT4 EC$_{50}$ (nM) |
|---|---|---|---|
| 228 | 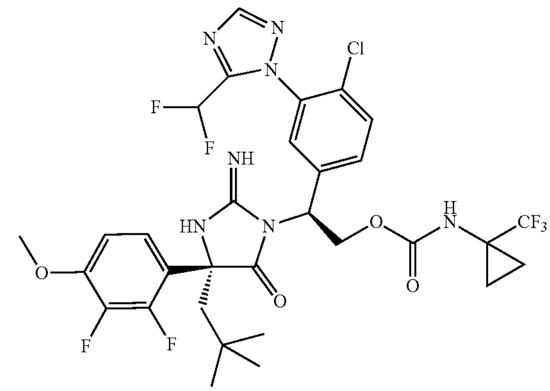 [SMILES: COc1ccc([C@@]2(CC(C)(C)C)NC(=N)N([C@H](COC(=O)NC3(C(F)(F)F)CC3)c3ccc(Cl)c(-n4ncnc4C(F)F)c3)C2=O)c(F)c1F] | 4.8 | 14.313 |
| 350 | 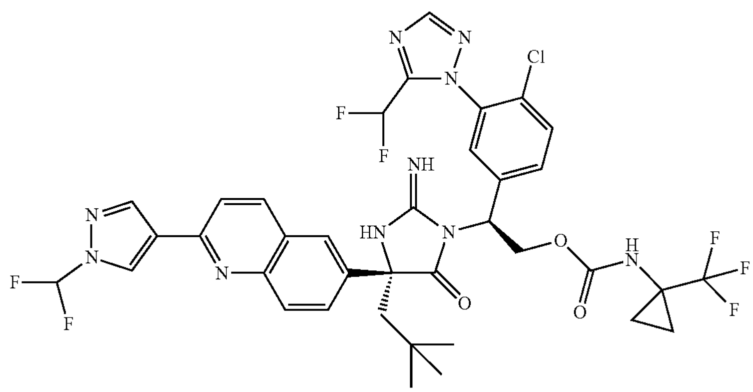 [SMILES: CC(C)(C)C[C@]1(c2ccc3nc(-c4cnn(C(F)F)c4)ccc3c2)NC(=N)N([C@H](COC(=O)NC2(C(F)(F)F)CC2)c2ccc(Cl)c(-n3ncnc3C(F)F)c2)C1=O] | 3.2 | 8.902 |
| 351 | 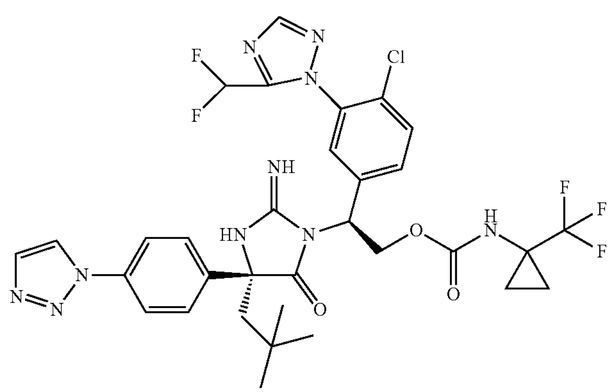 [SMILES: CC(C)(C)C[C@]1(c2ccc(-n3ccnn3)cc2)NC(=N)N([C@H](COC(=O)NC2(C(F)(F)F)CC2)c2ccc(Cl)c(-n3ncnc3C(F)F)c2)C1=O] | 2.4 | 17.867 |
| 352 | 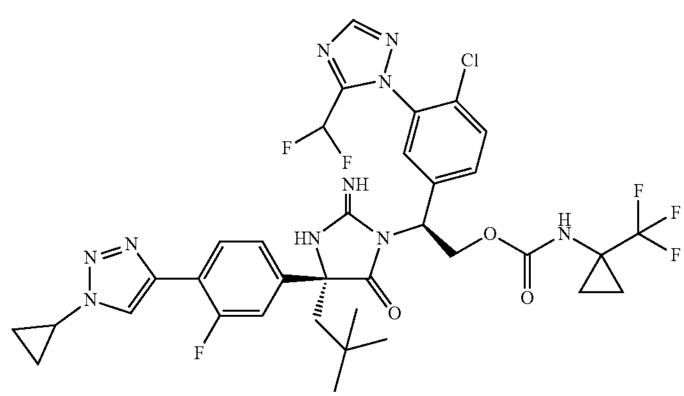 [SMILES: CC(C)(C)C[C@]1(c2ccc(-c3cn(C4CC4)nn3)c(F)c2)NC(=N)N([C@H](COC(=O)NC2(C(F)(F)F)CC2)c2ccc(Cl)c(-n3ncnc3C(F)F)c2)C1=O] | 2.8 | 10.911 |

TABLE 1-continued

| COMPD # | STRUCTURE | HIV PI IC$_{50}$ (nM) | MT4 EC$_{50}$ (nM) |
|---|---|---|---|
| 353 | 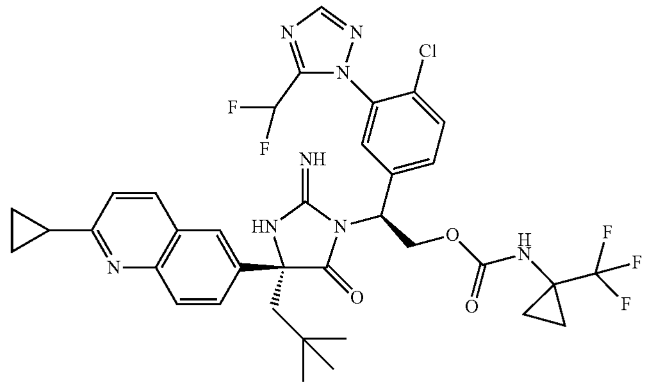 [SMILES: CC(C)(C)C[C@]1(c2ccc3nc(C4CC4)ccc3c2)NC(=N)N([C@H](COC(=O)NC2(C(F)(F)F)CC2)c2ccc(Cl)c(-n3ncnc3C(F)F)c2)C1=O] | 2.4 | 8.594 |
| 354 | 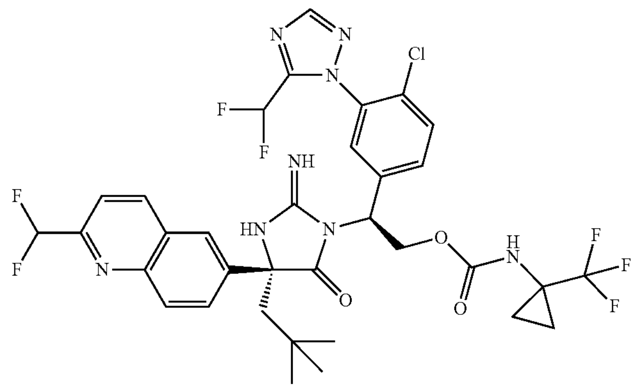 [SMILES: CC(C)(C)C[C@]1(c2ccc3nc(C(F)F)ccc3c2)NC(=N)N([C@H](COC(=O)NC2(C(F)(F)F)CC2)c2ccc(Cl)c(-n3ncnc3C(F)F)c2)C1=O] | 2.4 | 5.057 |
| 229 | 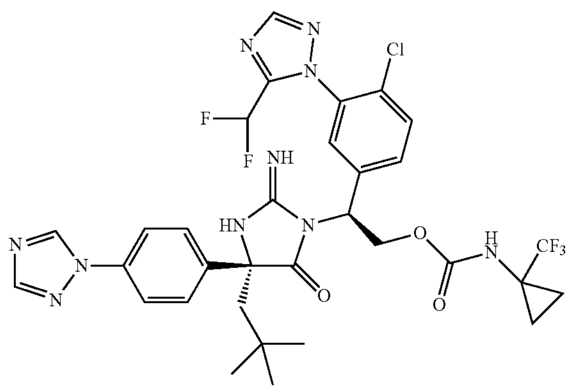 [SMILES: CC(C)(C)C[C@]1(c2ccc(-n3cncn3)cc2)NC(=N)N([C@H](COC(=O)NC2(C(F)(F)F)CC2)c2ccc(Cl)c(-n3ncnc3C(F)F)c2)C1=O] | 3.5 | 27.626 |
| 343 | 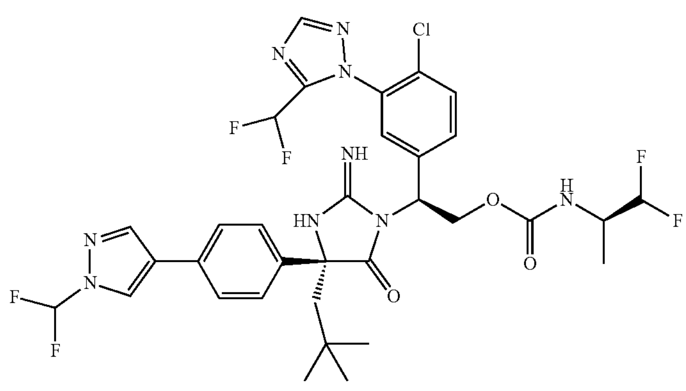 [SMILES: C[C@@H](NC(=O)OC[C@H](c1ccc(Cl)c(-n2ncnc2C(F)F)c1)N1C(=N)N[C@](CC(C)(C)C)(c2ccc(-c3cnn(C(F)F)c3)cc2)C1=O)C(F)F] | 3.3 | 17.022 |

TABLE 1-continued

| COMPD # | STRUCTURE | HIV PI IC$_{50}$ (nM) | MT4 EC$_{50}$ (nM) |
|---|---|---|---|
| 344 | 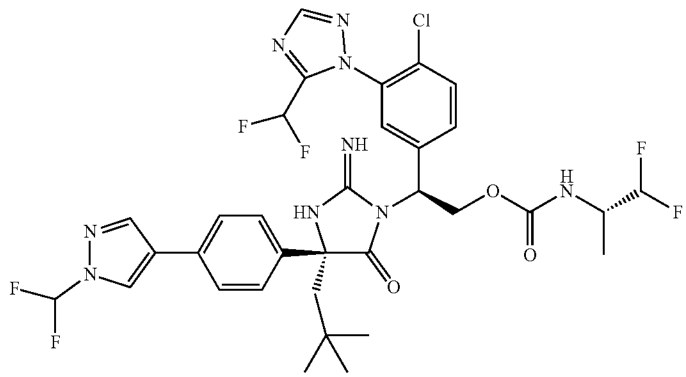 [SMILES: C[C@H](NC(=O)OC[C@H](c1ccc(Cl)c(-n2ncnc2C(F)F)c1)N1C(=N)N[C@](CC(C)(C)C)(c2ccc(-c3cnn(C(F)F)c3)cc2)C1=O)C(F)F] | 2.9 | 12.061 |
| 355 | 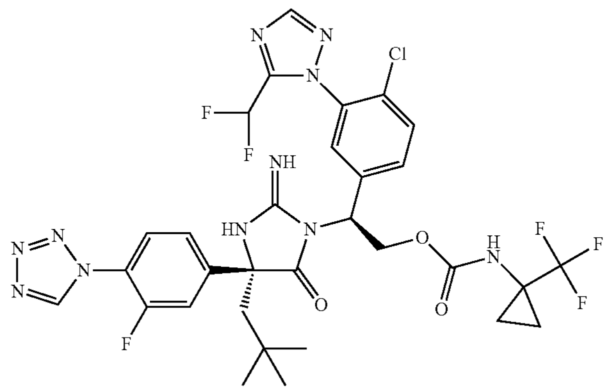 [SMILES: CC(C)(C)C[C@]1(c2ccc(-n3cnnn3)c(F)c2)NC(=N)N([C@H](COC(=O)NC2(C(F)(F)F)CC2)c2ccc(Cl)c(-n3ncnc3C(F)F)c2)C1=O] | 3.2 | 24.641 |
| 356 | 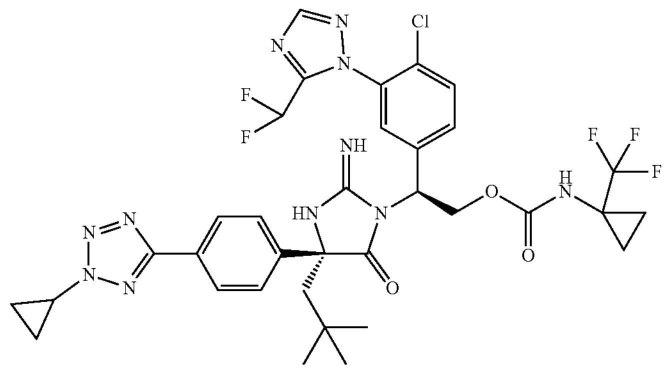 [SMILES: CC(C)(C)C[C@]1(c2ccc(-c3nnn(C4CC4)n3)cc2)NC(=N)N([C@H](COC(=O)NC2(C(F)(F)F)CC2)c2ccc(Cl)c(-n3ncnc3C(F)F)c2)C1=O] | 2.5 | 19.493 |
| 357 | 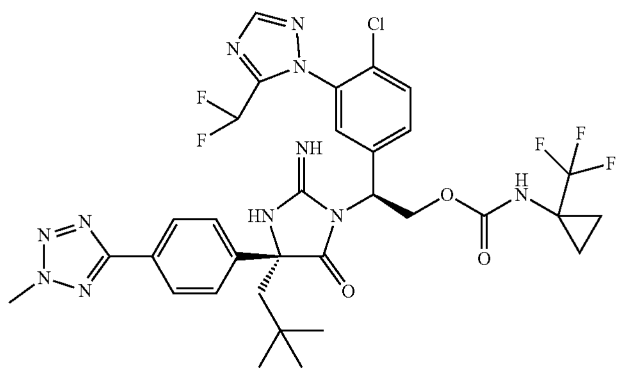 [SMILES: Cn1nnc(-c2ccc([C@@]3(CC(C)(C)C)NC(=N)N([C@H](COC(=O)NC4(C(F)(F)F)CC4)c4ccc(Cl)c(-n5ncnc5C(F)F)c4)C3=O)cc2)n1] | 2.5 | 10.575 |

TABLE 1-continued
| COMPD # | STRUCTURE | HIV PI IC$_{50}$ (nM) | MT4 EC$_{50}$ (nM) |
|---|---|---|---|
| 358 | 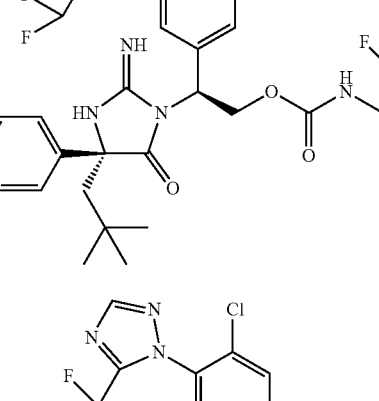 | 4.4 | 76.2 |
| 230 | 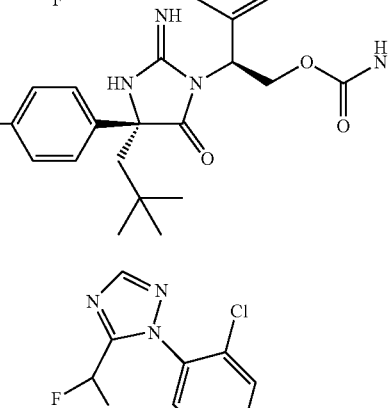 | 2.1 | 7.623 |
| 359 | 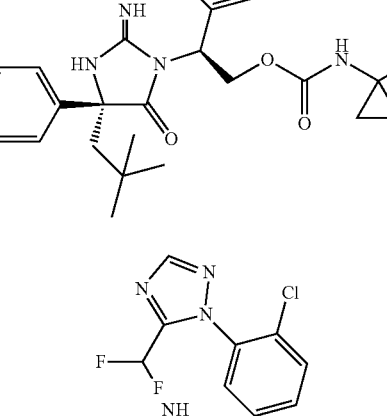 | 3.1 | 424.08 |
| 231 | 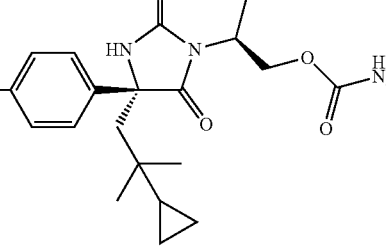 | 2.2 | 12.197 |

TABLE 1-continued

| COMPD # | STRUCTURE | HIV PI IC$_{50}$ (nM) | MT4 EC$_{50}$ (nM) |
|---|---|---|---|
| 360 | 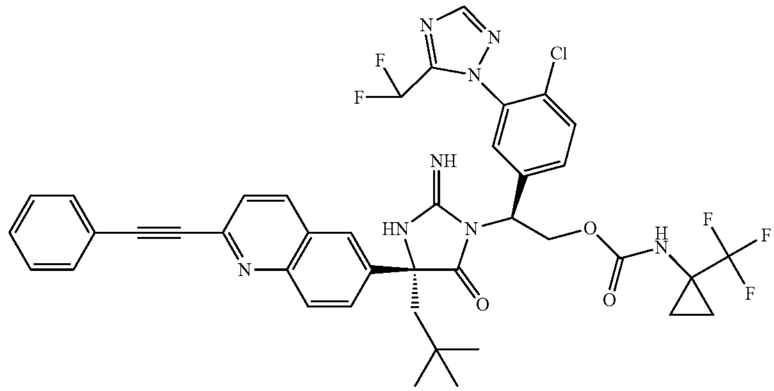 [SMILES: CC(C)(C)C[C@]1(c2ccc3nc(C#Cc4ccccc4)ccc3c2)NC(=N)N([C@H](COC(=O)NC2(C(F)(F)F)CC2)c2ccc(Cl)c(-n3ncnc3C(F)F)c2)C1=O] | 3.6 | 79.869 |
| 312 | 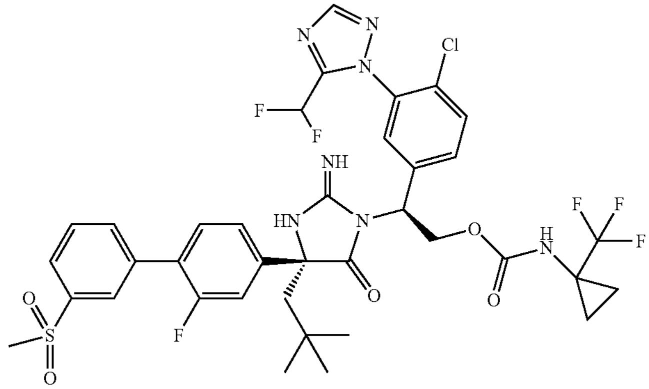 [SMILES: CC(C)(C)C[C@]1(c2ccc(-c3cccc(S(C)(=O)=O)c3)c(F)c2)NC(=N)N([C@H](COC(=O)NC2(C(F)(F)F)CC2)c2ccc(Cl)c(-n3ncnc3C(F)F)c2)C1=O] | 2.7 | 27.755 |
| 361 | 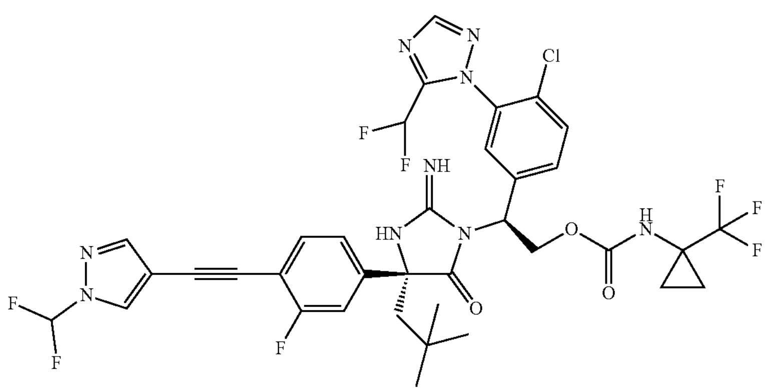 [SMILES: CC(C)(C)C[C@]1(c2ccc(C#Cc3cnn(C(F)F)c3)c(F)c2)NC(=N)N([C@H](COC(=O)NC2(C(F)(F)F)CC2)c2ccc(Cl)c(-n3ncnc3C(F)F)c2)C1=O] | 6.4 | 81.987 |
| 313 | 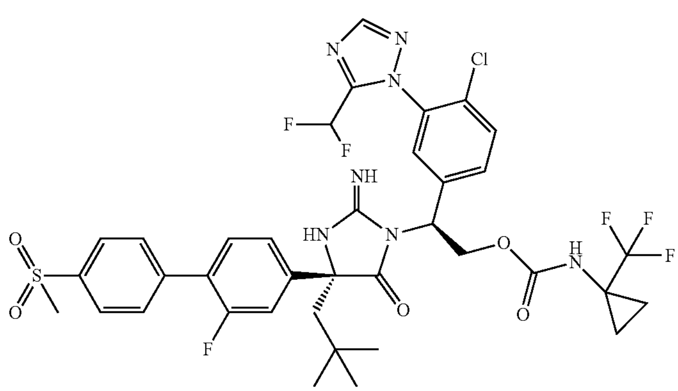 [SMILES: CC(C)(C)C[C@]1(c2ccc(-c3ccc(S(C)(=O)=O)cc3)c(F)c2)NC(=N)N([C@H](COC(=O)NC2(C(F)(F)F)CC2)c2ccc(Cl)c(-n3ncnc3C(F)F)c2)C1=O] | 2.5 | 19.502 |

TABLE 1-continued

| COMPD # | STRUCTURE | HIV PI IC$_{50}$ (nM) | MT4 EC$_{50}$ (nM) |
|---|---|---|---|
| 232 | 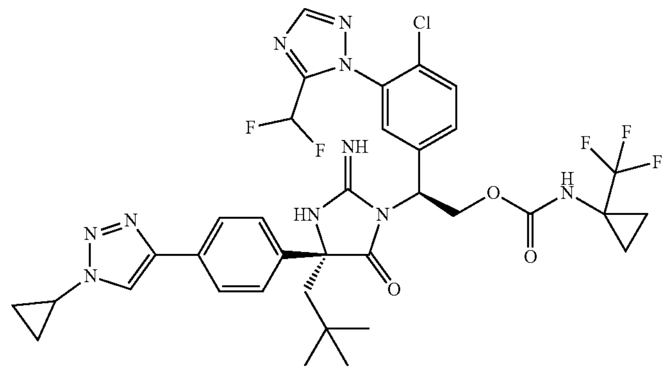 [SMILES: CC(C)(C)C[C@]1(c2ccc(-c3cn(C4CC4)nn3)cc2)NC(=N)N([C@H](COC(=O)NC2(C(F)(F)F)CC2)c2ccc(Cl)c(-n3ncnc3C(F)F)c2)C1=O] | 2.9 | 18.175 |
| 233 | 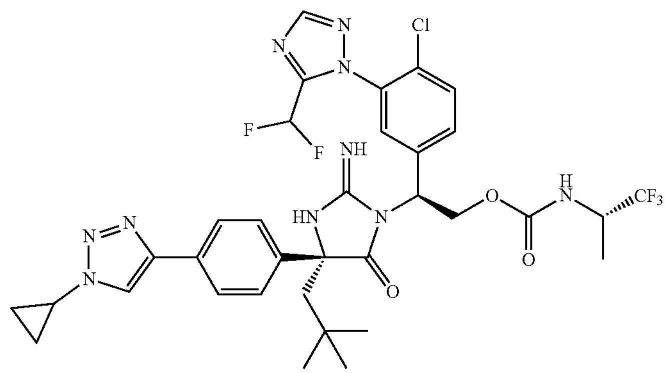 [SMILES: C[C@H](NC(=O)OC[C@H](c1ccc(Cl)c(-n2ncnc2C(F)F)c1)N1C(=N)N[C@](CC(C)(C)C)(c2ccc(-c3cn(C4CC4)nn3)cc2)C1=O)C(F)(F)F] | 2.6 | 13.617 |
| 234 | 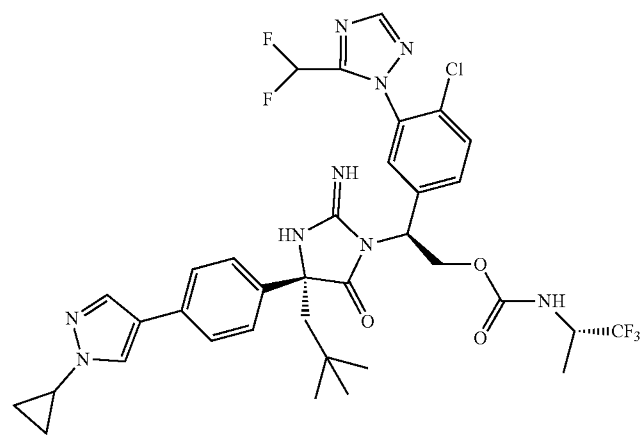 [SMILES: C[C@H](NC(=O)OC[C@H](c1ccc(Cl)c(-n2ncnc2C(F)F)c1)N1C(=N)N[C@](CC(C)(C)C)(c2ccc(-c3cnn(C4CC4)c3)cc2)C1=O)C(F)(F)F] | 2.2 | 9.276 |
| 314 | 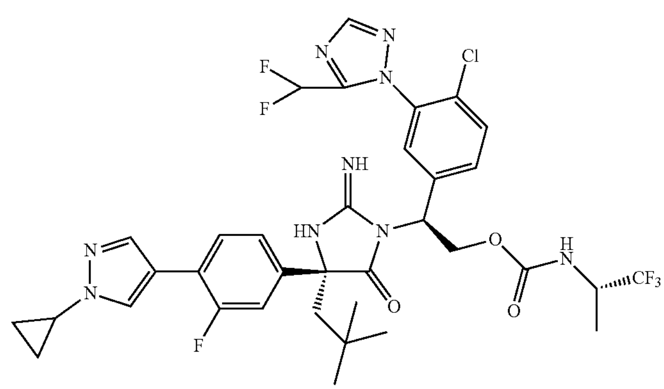 [SMILES: C[C@H](NC(=O)OC[C@H](c1ccc(Cl)c(-n2ncnc2C(F)F)c1)N1C(=N)N[C@](CC(C)(C)C)(c2ccc(-c3cnn(C4CC4)c3)c(F)c2)C1=O)C(F)(F)F] | 2.5 | 8.191 |

TABLE 1-continued

| COMPD # | STRUCTURE | HIV PI IC$_{50}$ (nM) | MT4 EC$_{50}$ (nM) |
|---|---|---|---|
| 315 | 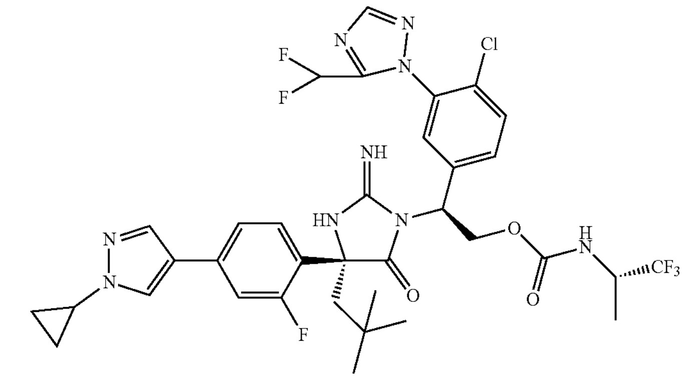 [SMILES: C[C@H](NC(=O)OC[C@H](c1ccc(Cl)c(-n2ncnc2C(F)F)c1)N1C(=N)N[C@](CC(C)(C)C)(c2ccc(-c3cnn(C4CC4)c3)cc2F)C1=O)C(F)(F)F] | 2.8 | 9.966 |
| 362 | 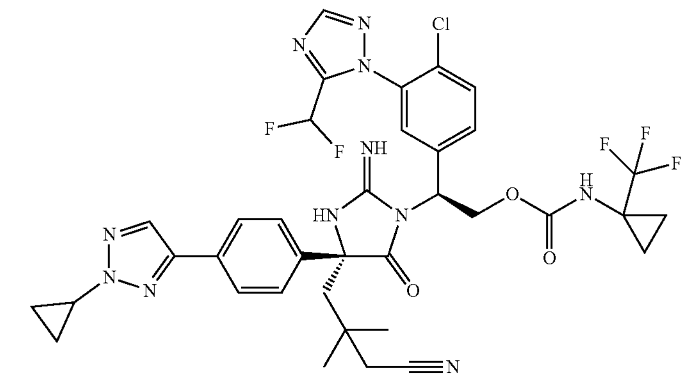 [SMILES: CC(C)(CC#N)C[C@]1(c2ccc(-c3cnn(C4CC4)n3)cc2)NC(=N)N([C@H](COC(=O)NC2(C(F)(F)F)CC2)c2ccc(Cl)c(-n3ncnc3C(F)F)c2)C1=O] | 3.0 | 36.359 |
| 363 | 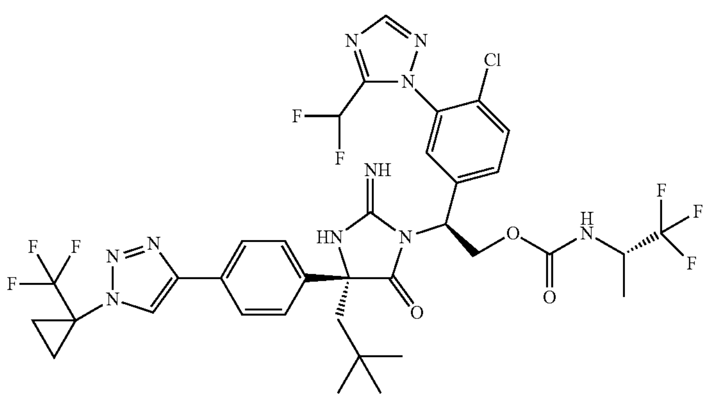 [SMILES: C[C@H](NC(=O)OC[C@H](c1ccc(Cl)c(-n2ncnc2C(F)F)c1)N1C(=N)N[C@](CC(C)(C)C)(c2ccc(-c3cn(C4(C(F)(F)F)CC4)nn3)cc2)C1=O)C(F)(F)F] | 2.2 | 11.69 |
| 364 | 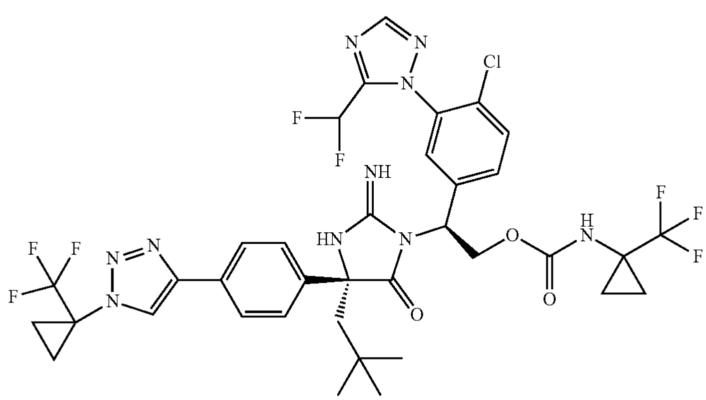 [SMILES: CC(C)(C)C[C@]1(c2ccc(-c3cn(C4(C(F)(F)F)CC4)nn3)cc2)NC(=N)N([C@H](COC(=O)NC2(C(F)(F)F)CC2)c2ccc(Cl)c(-n3ncnc3C(F)F)c2)C1=O] | 2.8 | 21.588 |

TABLE 1-continued

| COMPD # | STRUCTURE | HIV PI IC$_{50}$ (nM) | MT4 EC$_{50}$ (nM) |
|---|---|---|---|
| 365 | 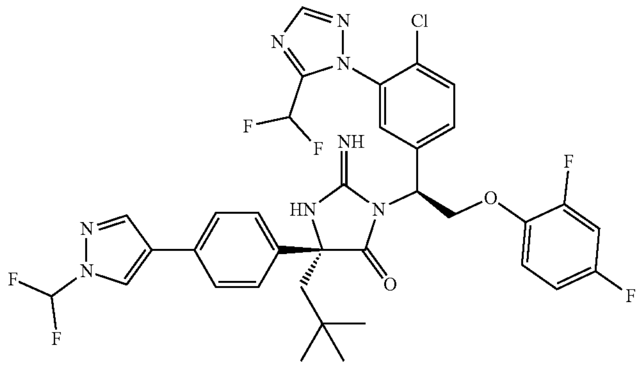 [SMILES: CC(C)(C)C[C@]1(c2ccc(-c3cnn(C(F)F)c3)cc2)NC(=N)N([C@H](COc2ccc(F)cc2F)c2ccc(Cl)c(-n3ncnc3C(F)F)c2)C1=O] | 6.5 | 142.87 |
| 367 | 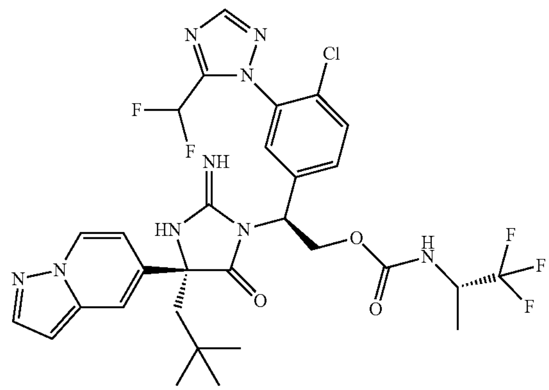 [SMILES: C[C@H](NC(=O)OC[C@H](c1ccc(Cl)c(-n2ncnc2C(F)F)c1)N1C(=N)N[C@](CC(C)(C)C)(c2ccn3nccc3c2)C1=O)C(F)(F)F] | 2.5 | 18.967 |
| 316 | 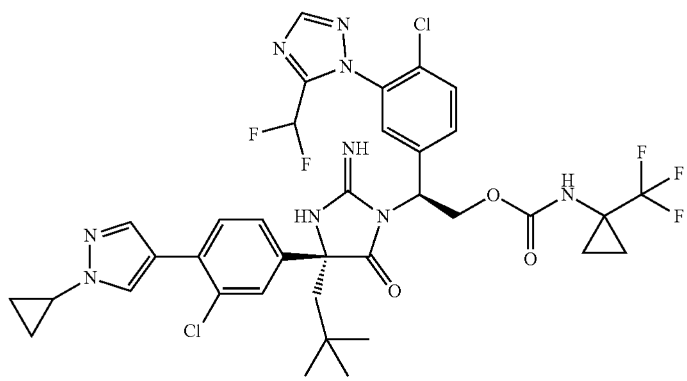 [SMILES: CC(C)(C)C[C@]1(c2ccc(-c3cnn(C4CC4)c3)c(Cl)c2)NC(=N)N([C@H](COC(=O)NC2(C(F)(F)F)CC2)c2ccc(Cl)c(-n3ncnc3C(F)F)c2)C1=O] | 2.4 | 13.335 |
| 317 | 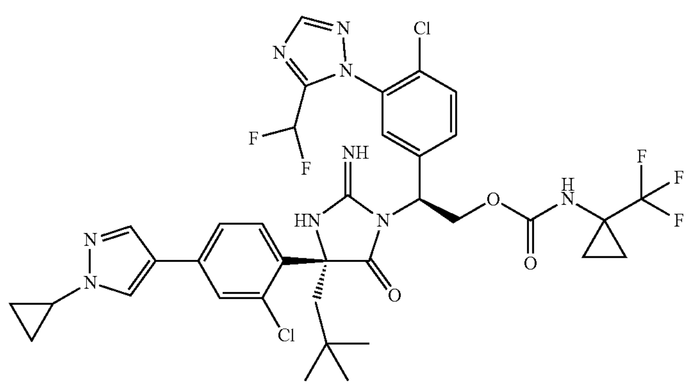 [SMILES: CC(C)(C)C[C@]1(c2ccc(-c3cnn(C4CC4)c3)cc2Cl)NC(=N)N([C@H](COC(=O)NC2(C(F)(F)F)CC2)c2ccc(Cl)c(-n3ncnc3C(F)F)c2)C1=O] | 5.8 | 99.058 |

TABLE 1-continued

| COMPD # | STRUCTURE | HIV PI IC$_{50}$ (nM) | MT4 EC$_{50}$ (nM) |
|---|---|---|---|
| 318 | 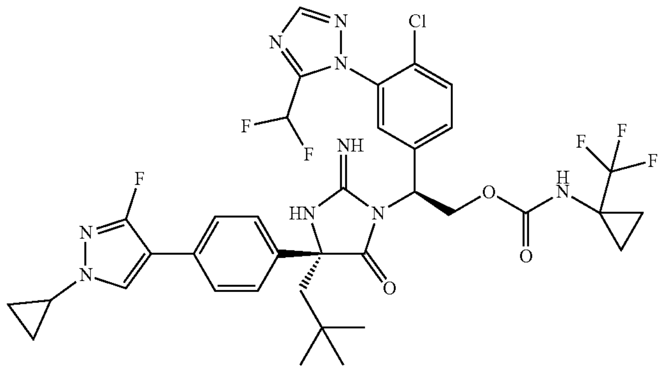 [SMILES: CC(C)(C)C[C@]1(c2ccc(-c3cn(C4CC4)nc3F)cc2)NC(=N)N([C@H](COC(=O)NC2(C(F)(F)F)CC2)c2ccc(Cl)c(-n3ncnc3C(F)F)c2)C1=O] | 2.4 | 13.225 |
| 371 | 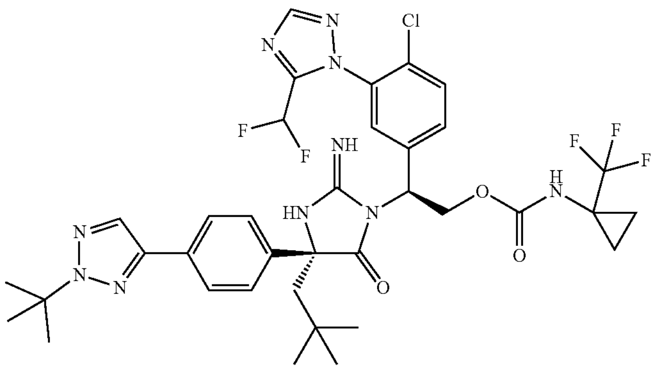 [SMILES: CC(C)(C)C[C@]1(c2ccc(-c3cnn(C(C)(C)C)n3)cc2)NC(=N)N([C@H](COC(=O)NC2(C(F)(F)F)CC2)c2ccc(Cl)c(-n3ncnc3C(F)F)c2)C1=O] | 2.8 | 26.671 |
| 372 | 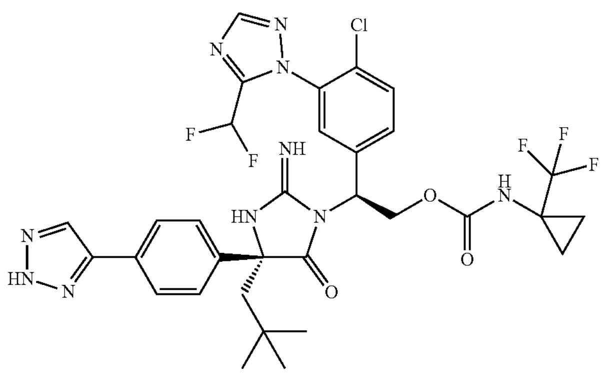 [SMILES: CC(C)(C)C[C@]1(c2ccc(-c3cn[nH]n3)cc2)NC(=N)N([C@H](COC(=O)NC2(C(F)(F)F)CC2)c2ccc(Cl)c(-n3ncnc3C(F)F)c2)C1=O] | 2.6 | 47.302 |
| 373 | 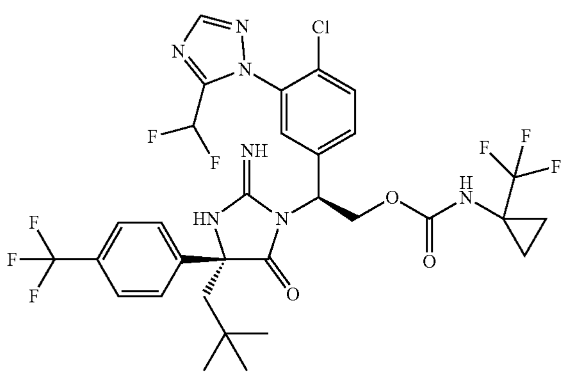 [SMILES: CC(C)(C)C[C@]1(c2ccc(C(F)(F)F)cc2)NC(=N)N([C@H](COC(=O)NC2(C(F)(F)F)CC2)c2ccc(Cl)c(-n3ncnc3C(F)F)c2)C1=O] | 5.9 | 49.748 |

TABLE 1-continued

| COMPD # | STRUCTURE | HIV PI IC$_{50}$ (nM) | MT4 EC$_{50}$ (nM) |
|---|---|---|---|
| 235 | 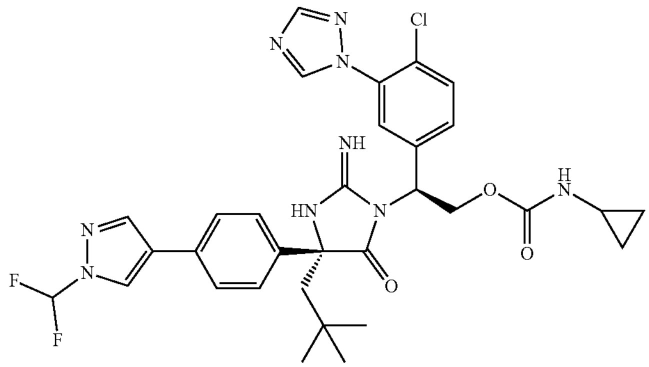 [SMILES: CC(C)(C)C[C@]1(c2ccc(-c3cnn(C(F)F)c3)cc2)NC(=N)N([C@H](COC(=O)NC2CC2)c2ccc(Cl)c(-n3cncn3)c2)C1=O] | 1.7 | 9.611 |
| 236 | 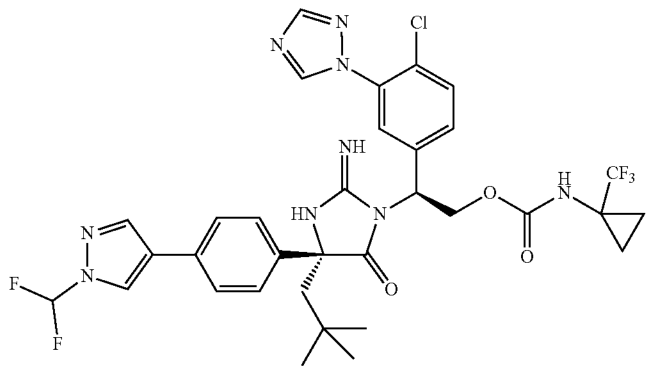 [SMILES: CC(C)(C)C[C@]1(c2ccc(-c3cnn(C(F)F)c3)cc2)NC(=N)N([C@H](COC(=O)NC2(C(F)(F)F)CC2)c2ccc(Cl)c(-n3cncn3)c2)C1=O] | 1.9 | 10.558 |
| 237 | 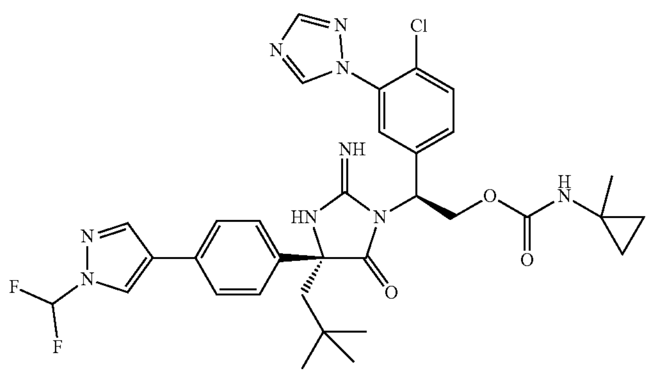 [SMILES: CC(C)(C)C[C@]1(c2ccc(-c3cnn(C(F)F)c3)cc2)NC(=N)N([C@H](COC(=O)NC2(C)CC2)c2ccc(Cl)c(-n3cncn3)c2)C1=O] | 2.1 | 8.793 |
| 375 | 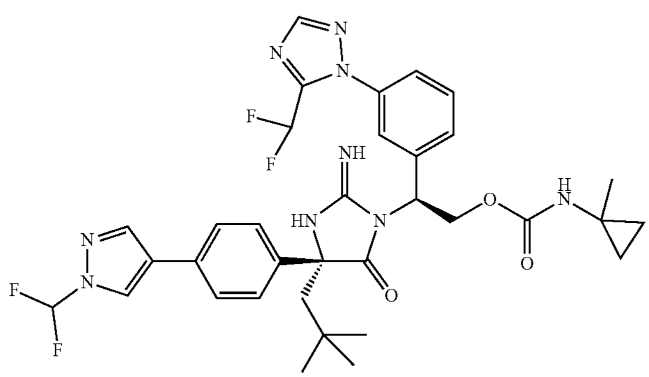 [SMILES: CC(C)(C)C[C@]1(c2ccc(-c3cnn(C(F)F)c3)cc2)NC(=N)N([C@H](COC(=O)NC2(C)CC2)c2cccc(-n3ncnc3C(F)F)c2)C1=O] | 7.5 | 30.773 |

TABLE 1-continued
| COMPD # | STRUCTURE | HIV PI IC$_{50}$ (nM) | MT4 EC$_{50}$ (nM) |
|---|---|---|---|
| 238 | 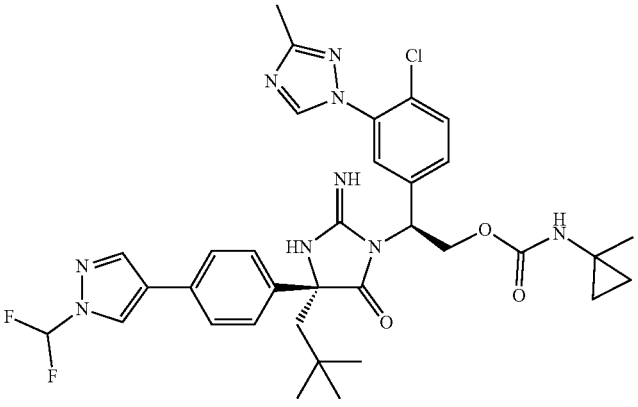 [SMILES: Cc1ncn(-c2cc([C@@H](COC(=O)NC3(C)CC3)N3C(=N)N[C@](CC(C)(C)C)(c4ccc(-c5cnn(C(F)F)c5)cc4)C3=O)ccc2Cl)n1] | 15.7 | 156.23 |
| 239 | 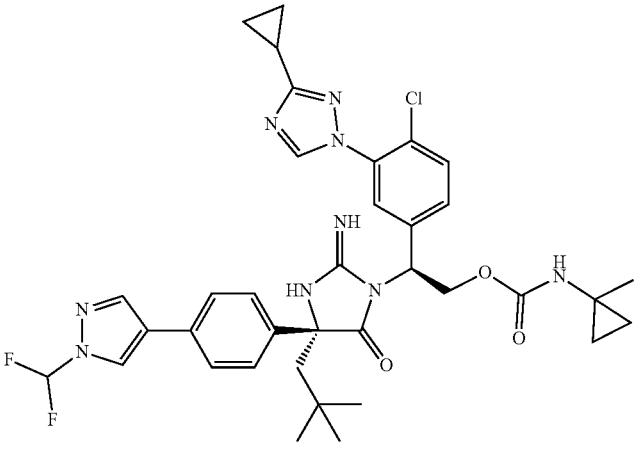 [SMILES: CC(C)(C)C[C@]1(c2ccc(-c3cnn(C(F)F)c3)cc2)NC(=N)N([C@H](COC(=O)NC2(C)CC2)c2ccc(Cl)c(-n3cnc(C4CC4)n3)c2)C1=O] | 48.0 | 604.2 |
| 319 | 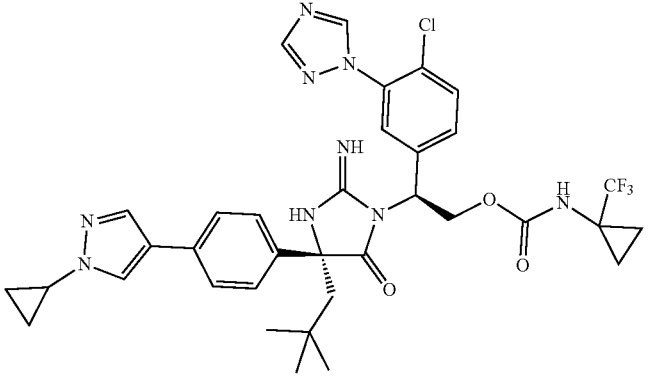 [SMILES: CC(C)(C)C[C@]1(c2ccc(-c3cnn(C4CC4)c3)cc2)NC(=N)N([C@H](COC(=O)NC2(C(F)(F)F)CC2)c2ccc(Cl)c(-n3cncn3)c2)C1=O] | 2.7 | 17.78 |

TABLE 1-continued

| COMPD # | STRUCTURE | HIV PI IC$_{50}$ (nM) | MT4 EC$_{50}$ (nM) |
|---|---|---|---|
| 320 | 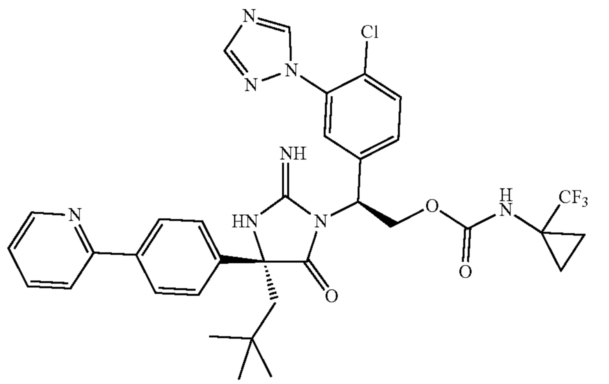 [SMILES: CC(C)(C)C[C@]1(c2ccc(-c3ccccn3)cc2)NC(=N)N([C@H](COC(=O)NC2(C(F)(F)F)CC2)c2ccc(Cl)c(-n3cncn3)c2)C1=O] | 5.4 | 22.538 |
| 240 | 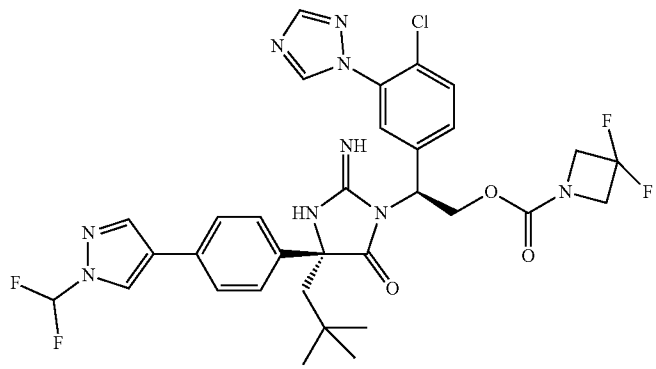 [SMILES: CC(C)(C)C[C@]1(c2ccc(-c3cnn(C(F)F)c3)cc2)NC(=N)N([C@H](COC(=O)N2CC(F)(F)C2)c2ccc(Cl)c(-n3cncn3)c2)C1=O] | 1.7 | 5.058 |
| 241 | 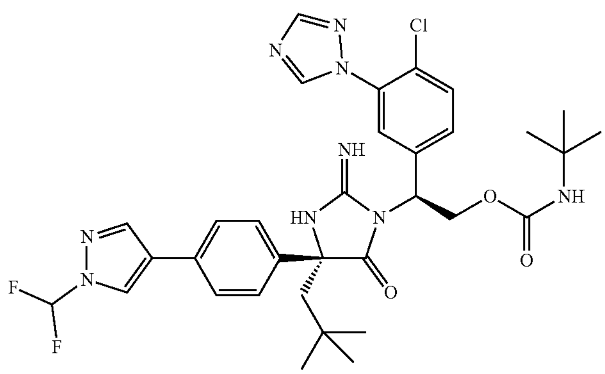 [SMILES: CC(C)(C)C[C@]1(c2ccc(-c3cnn(C(F)F)c3)cc2)NC(=N)N([C@H](COC(=O)NC(C)(C)C)c2ccc(Cl)c(-n3cncn3)c2)C1=O] | 1.7 | 8.362 |
| 242 | 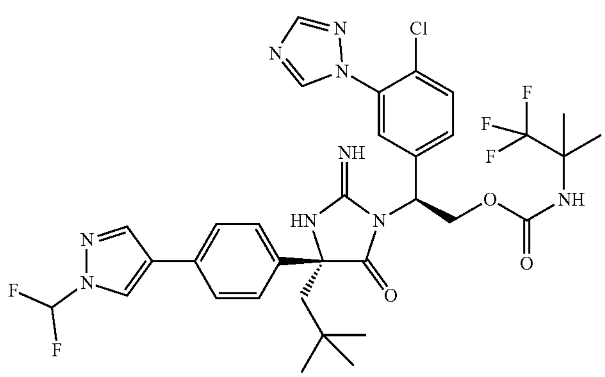 [SMILES: CC(C)(C)C[C@]1(c2ccc(-c3cnn(C(F)F)c3)cc2)NC(=N)N([C@H](COC(=O)NC(C)(C)C(F)(F)F)c2ccc(Cl)c(-n3cncn3)c2)C1=O] | 1.9 | 6.832 |

TABLE 1-continued

| COMPD # | STRUCTURE | HIV PI IC$_{50}$ (nM) | MT4 EC$_{50}$ (nM) |
|---|---|---|---|
| 243 | 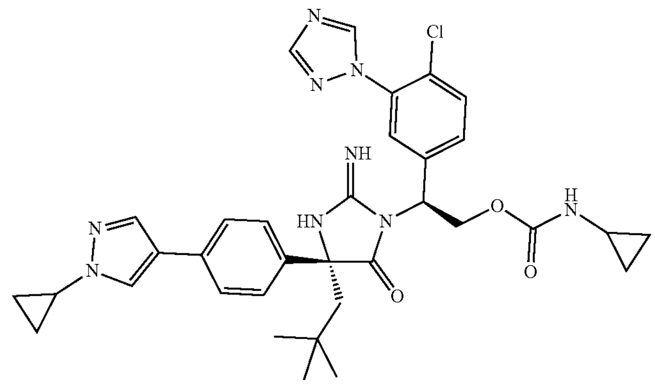 [SMILES: CC(C)(C)C[C@]1(c2ccc(-c3cnn(C4CC4)c3)cc2)NC(=N)N([C@H](COC(=O)NC2CC2)c2ccc(Cl)c(-n3cncn3)c2)C1=O] | 2.1 | 9.109 |
| 244 | 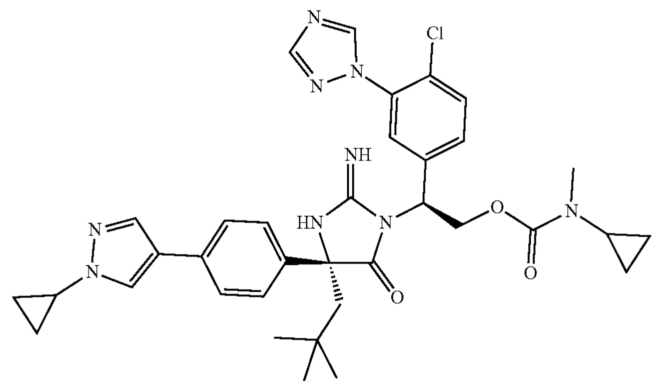 [SMILES: CN(C(=O)OC[C@H](c1ccc(Cl)c(-n2cncn2)c1)N1C(=N)N[C@](CC(C)(C)C)(c2ccc(-c3cnn(C4CC4)c3)cc2)C1=O)C1CC1] | 2.6 | 7.656 |
| 245 | 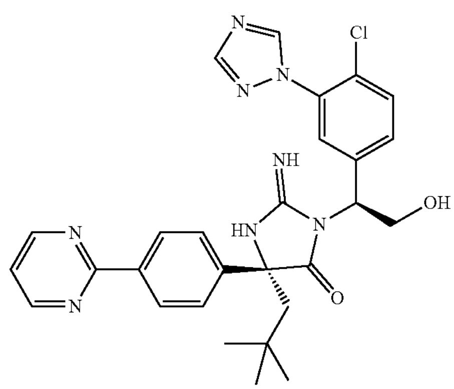 [SMILES: CC(C)(C)C[C@]1(c2ccc(-c3ncccn3)cc2)NC(=N)N([C@H](CO)c2ccc(Cl)c(-n3cncn3)c2)C1=O] | 23.5 | 239.46 |
| 246 | 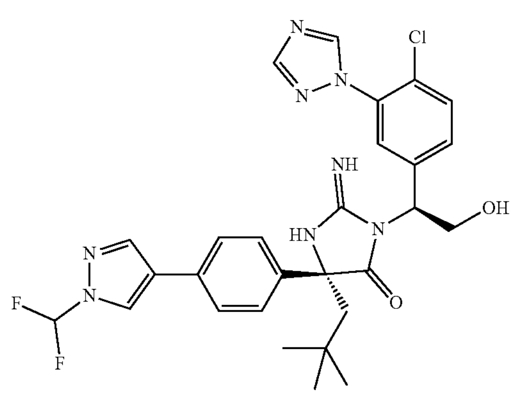 [SMILES: CC(C)(C)C[C@]1(c2ccc(-c3cnn(C(F)F)c3)cc2)NC(=N)N([C@H](CO)c2ccc(Cl)c(-n3cncn3)c2)C1=O] | 16.4 | 84.263 |

TABLE 1-continued

| COMPD # | STRUCTURE | HIV PI IC$_{50}$ (nM) | MT4 EC$_{50}$ (nM) |
|---|---|---|---|
| 247 | 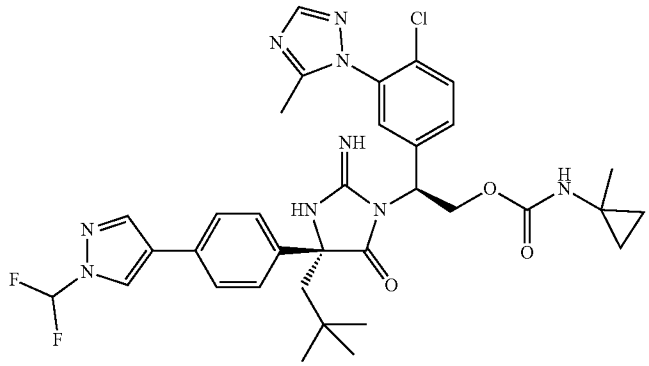 [SMILES: Cc1ncnn1-c1cc([C@@H](COC(=O)NC2(C)CC2)N2C(=N)N[C@](CC(C)(C)C)(c3ccc(-c4cnn(C(F)F)c4)cc3)C2=O)ccc1Cl] | 2.3 | 7.514 |
| 248 | 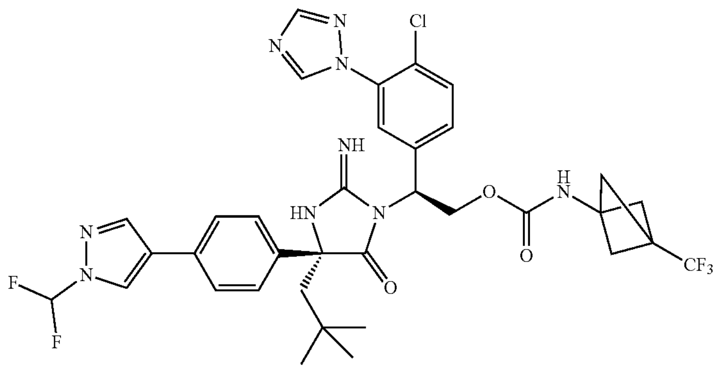 [SMILES: CC(C)(C)C[C@]1(c2ccc(-c3cnn(C(F)F)c3)cc2)NC(=N)N([C@H](COC(=O)NC23CC(C(F)(F)F)(C2)C3)c2ccc(Cl)c(-n3cncn3)c2)C1=O] | 7.0 | 70.254 |
| 376 | 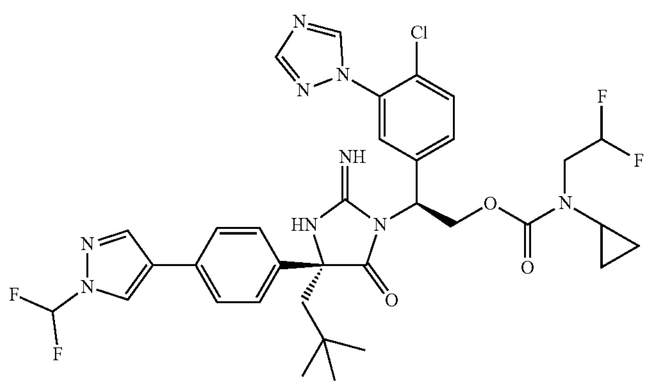 [SMILES: CC(C)(C)C[C@]1(c2ccc(-c3cnn(C(F)F)c3)cc2)NC(=N)N([C@H](COC(=O)N(CC(F)F)C2CC2)c2ccc(Cl)c(-n3cncn3)c2)C1=O] | 2.3 | 11.991 |
| 249 | 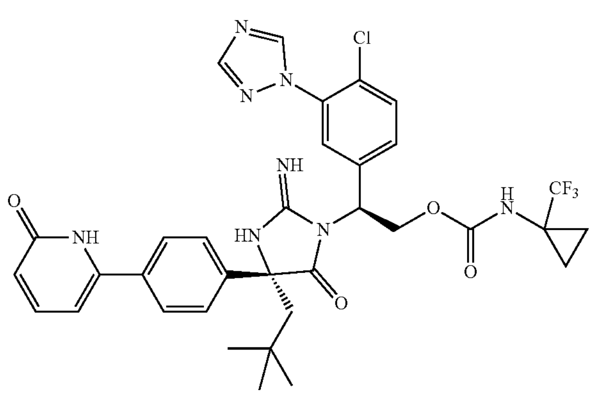 [SMILES: CC(C)(C)C[C@]1(c2ccc(-c3cccc(=O)[nH]3)cc2)NC(=N)N([C@H](COC(=O)NC2(C(F)(F)F)CC2)c2ccc(Cl)c(-n3cncn3)c2)C1=O] | 3.8 | 325.01 |

TABLE 1-continued

| COMPD # | STRUCTURE | HIV PI IC$_{50}$ (nM) | MT4 EC$_{50}$ (nM) |
|---|---|---|---|
| 250 | 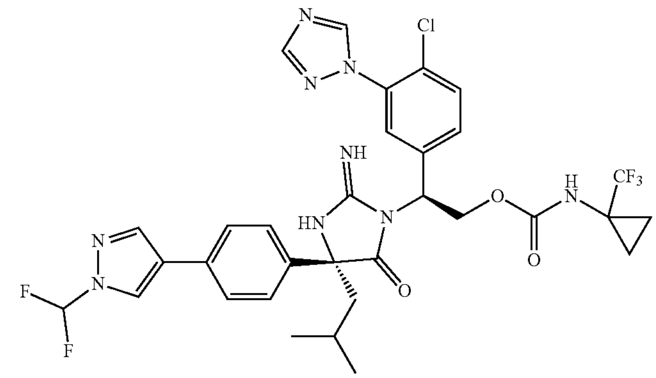 [SMILES: CC(C)C[C@]1(c2ccc(-c3cnn(C(F)F)c3)cc2)NC(=N)N([C@H](COC(=O)NC2(C(F)(F)F)CC2)c2ccc(Cl)c(-n3cncn3)c2)C1=O] | 3.0 | 29.8 |
| 377 | 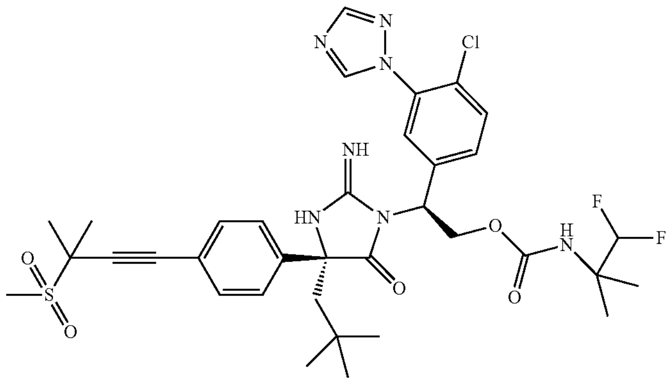 [SMILES: CC(C)(C)C[C@]1(c2ccc(C#CC(C)(C)S(C)(=O)=O)cc2)NC(=N)N([C@H](COC(=O)NC(C)(C)C(F)F)c2ccc(Cl)c(-n3cncn3)c2)C1=O] | 4.7 | 90.729 |
| 321 | 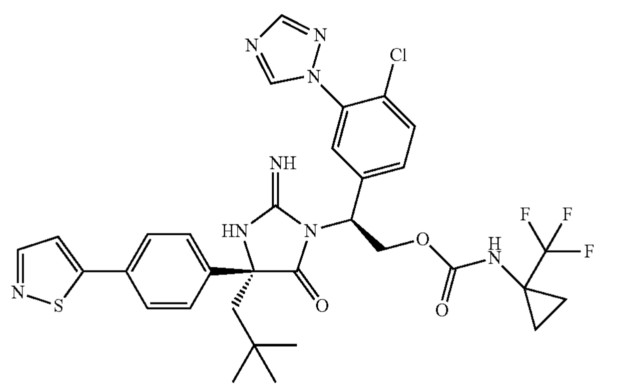 [SMILES: CC(C)(C)C[C@]1(c2ccc(-c3ccns3)cc2)NC(=N)N([C@H](COC(=O)NC2(C(F)(F)F)CC2)c2ccc(Cl)c(-n3cncn3)c2)C1=O] | 2.6 | 20.804 |
| 251 | 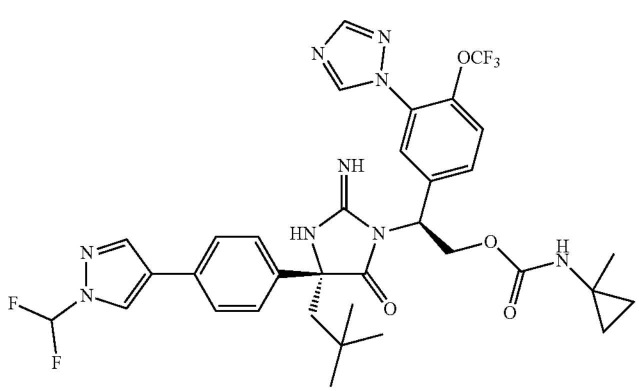 [SMILES: CC(C)(C)C[C@]1(c2ccc(-c3cnn(C(F)F)c3)cc2)NC(=N)N([C@H](COC(=O)NC2(C)CC2)c2ccc(OC(F)(F)F)c(-n3cncn3)c2)C1=O] | 3.2 | 85.707 |

TABLE 1-continued

| COMPD # | STRUCTURE | HIV PI IC$_{50}$ (nM) | MT4 EC$_{50}$ (nM) |
|---|---|---|---|
| 252 | 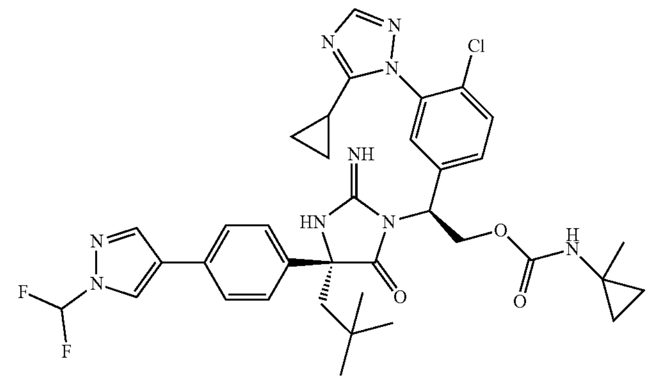 [SMILES: CC(C)(C)C[C@]1(c2ccc(-c3cnn(C(F)F)c3)cc2)NC(=N)N([C@H](COC(=O)NC2(C)CC2)c2ccc(Cl)c(-n3ncnc3C3CC3)c2)C1=O] | 1.7 | 20.703 |
| 253 | 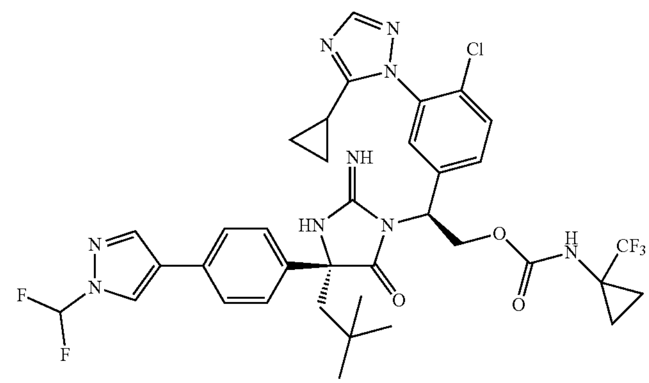 [SMILES: CC(C)(C)C[C@]1(c2ccc(-c3cnn(C(F)F)c3)cc2)NC(=N)N([C@H](COC(=O)NC2(C(F)(F)F)CC2)c2ccc(Cl)c(-n3ncnc3C3CC3)c2)C1=O] | 2.4 | 28.115 |
| 254 | 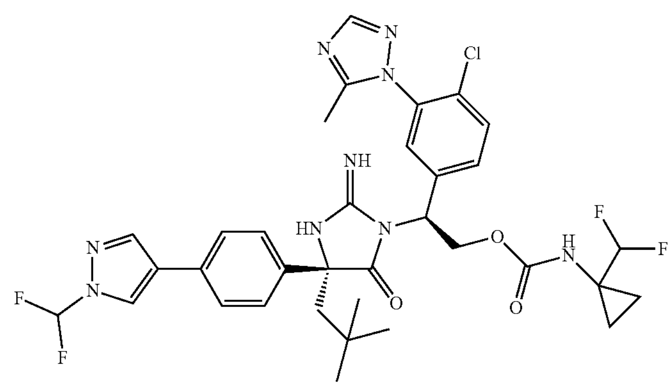 [SMILES: Cc1ncnn1-c1cc([C@@H](COC(=O)NC2(C(F)F)CC2)N2C(=N)N[C@](CC(C)(C)C)(c3ccc(-c4cnn(C(F)F)c4)cc3)C2=O)ccc1Cl] | 2.6 | 17.993 |
| 378 | 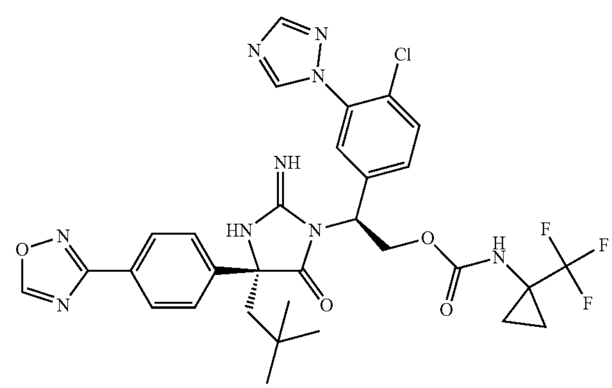 [SMILES: CC(C)(C)C[C@]1(c2ccc(-c3ncon3)cc2)NC(=N)N([C@H](COC(=O)NC2(C(F)(F)F)CC2)c2ccc(Cl)c(-n3cncn3)c2)C1=O] | 3.0 | 35.608 |

TABLE 1-continued
| COMPD # | STRUCTURE | HIV PI IC$_{50}$ (nM) | MT4 EC$_{50}$ (nM) |
|---|---|---|---|
| 379 | 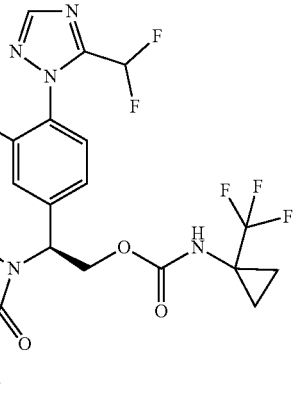 | 22.8 | 133.84 |
| 380 | 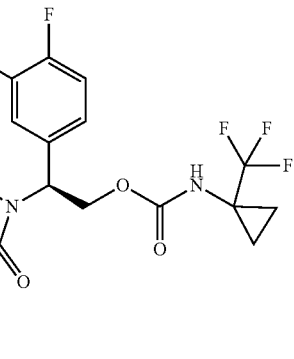 | 3.5 | 29.232 |
| 322 | 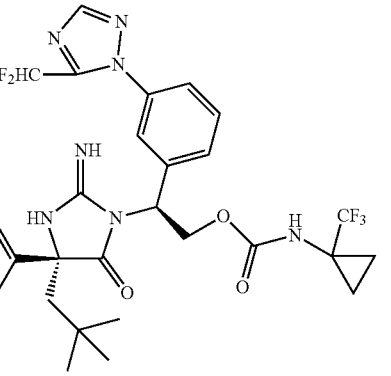 | 7.3 | 38.993 |
| 255 | 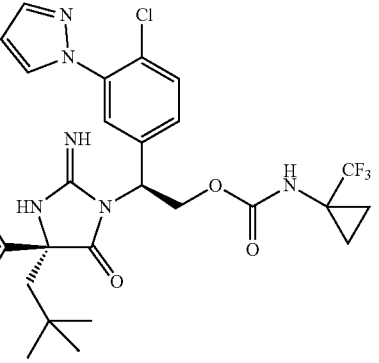 | 2.1 | 22.693 |

TABLE 1-continued

| COMPD # | STRUCTURE | HIV PI IC$_{50}$ (nM) | MT4 EC$_{50}$ (nM) |
|---|---|---|---|
| 256 | 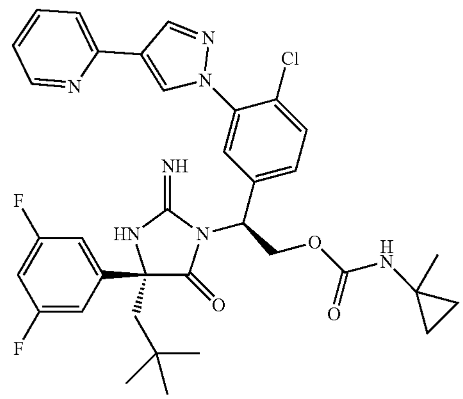 [SMILES: CC(C)(C)C[C@]1(c2cc(F)cc(F)c2)NC(=N)N([C@H](COC(=O)NC2(C)CC2)c2ccc(Cl)c(-n3cc(-c4ccccn4)cn3)c2)C1=O] | 2.0 | 553.88 |
| 257 | 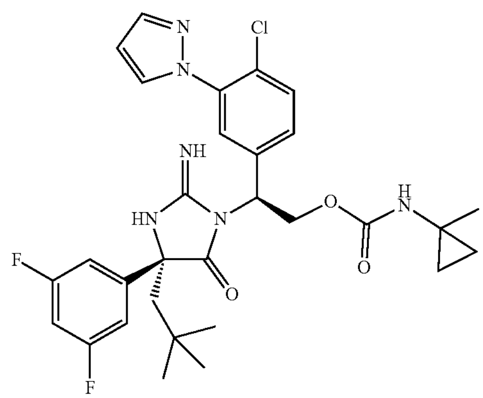 [SMILES: CC(C)(C)C[C@]1(c2cc(F)cc(F)c2)NC(=N)N([C@H](COC(=O)NC2(C)CC2)c2ccc(Cl)c(-n3cccn3)c2)C1=O] | 4.0 | 4175.2 |
| 258 | 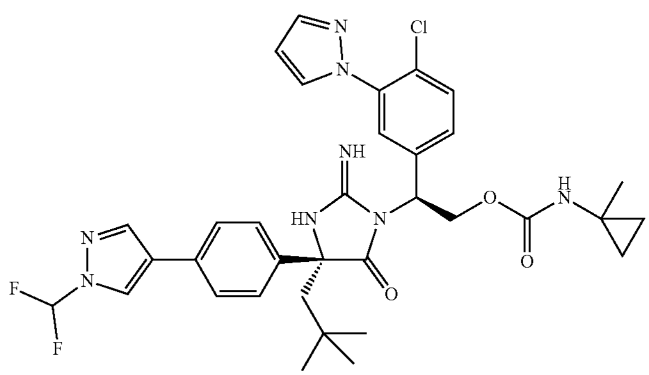 [SMILES: CC(C)(C)C[C@]1(c2ccc(-c3cnn(C(F)F)c3)cc2)NC(=N)N([C@H](COC(=O)NC2(C)CC2)c2ccc(Cl)c(-n3cccn3)c2)C1=O] | 2.6 | 28.503 |
| 259 | 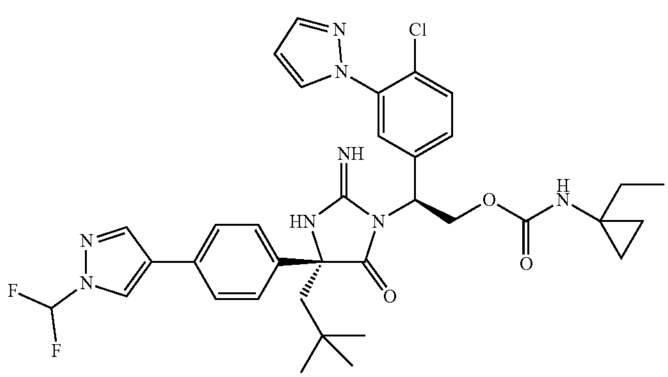 [SMILES: CCC1(NC(=O)OC[C@H](c2ccc(Cl)c(-n3cccn3)c2)N2C(=N)N[C@](CC(C)(C)C)(c3ccc(-c4cnn(C(F)F)c4)cc3)C2=O)CC1] | 2.7 | 65.443 |

TABLE 1-continued

| COMPD # | STRUCTURE | HIV PI IC$_{50}$ (nM) | MT4 EC$_{50}$ (nM) |
|---|---|---|---|
| 260 | 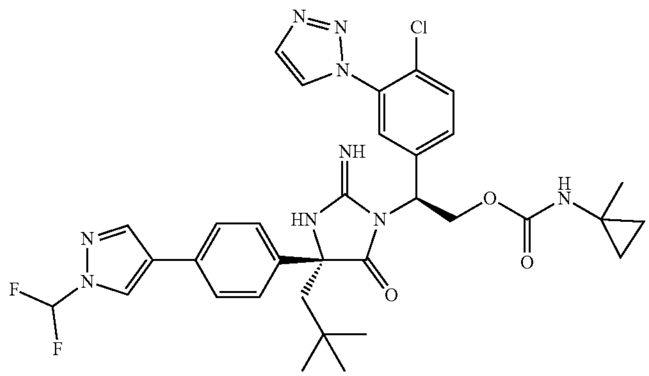 [SMILES: CC(C)(C)C[C@]1(c2ccc(-c3cnn(C(F)F)c3)cc2)NC(=N)N([C@H](COC(=O)NC2(C)CC2)c2ccc(Cl)c(-n3ccnn3)c2)C1=O] | 2.8 | 32.413 |
| 261 | 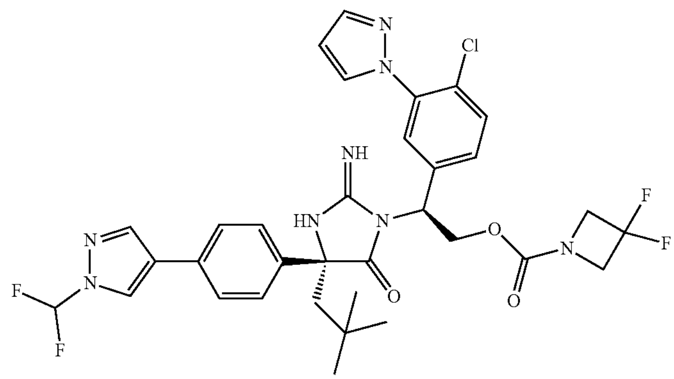 [SMILES: CC(C)(C)C[C@]1(c2ccc(-c3cnn(C(F)F)c3)cc2)NC(=N)N([C@H](COC(=O)N2CC(F)(F)C2)c2ccc(Cl)c(-n3cccn3)c2)C1=O] | 2.1 | 29.036 |
| 262 | 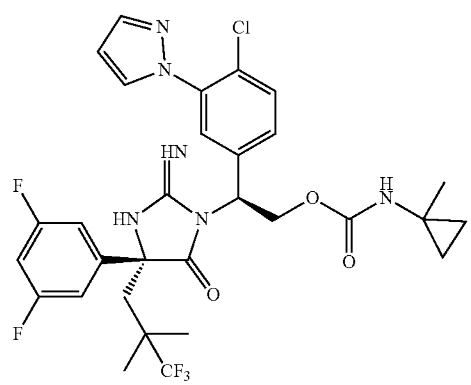 [SMILES: CC1(NC(=O)OC[C@H](c2ccc(Cl)c(-n3cccn3)c2)N2C(=N)N[C@](CC(C)(C)C(F)(F)F)(c3cc(F)cc(F)c3)C2=O)CC1] | 2.9 | 1802.7 |
| 263 | 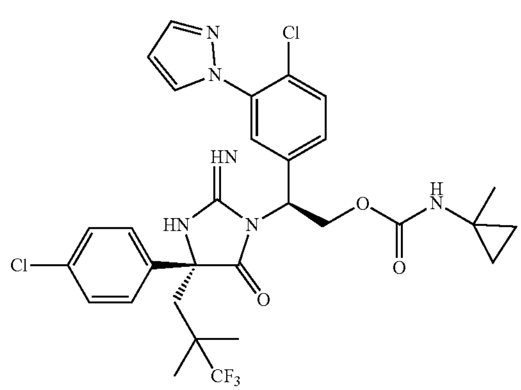 [SMILES: CC1(NC(=O)OC[C@H](c2ccc(Cl)c(-n3cccn3)c2)N2C(=N)N[C@](CC(C)(C)C(F)(F)F)(c3ccc(Cl)cc3)C2=O)CC1] | 2.8 | 747.62 |

TABLE 1-continued

| COMPD # | STRUCTURE | HIV PI IC$_{50}$ (nM) | MT4 EC$_{50}$ (nM) |
|---|---|---|---|
| 323 | 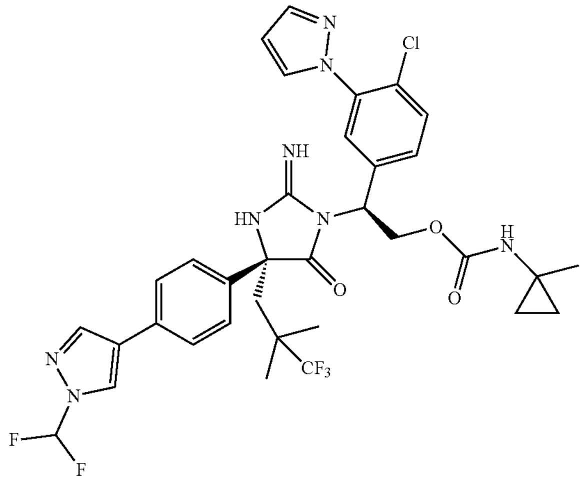 [SMILES: CC1(NC(=O)OC[C@H](c2ccc(Cl)c(-n3cccn3)c2)N2C(=N)N[C@](CC(C)(C)C(F)(F)F)(c3ccc(-c4cnn(C(F)F)c4)cc3)C2=O)CC1] | 3.1 | 50.67 |
| 324 | 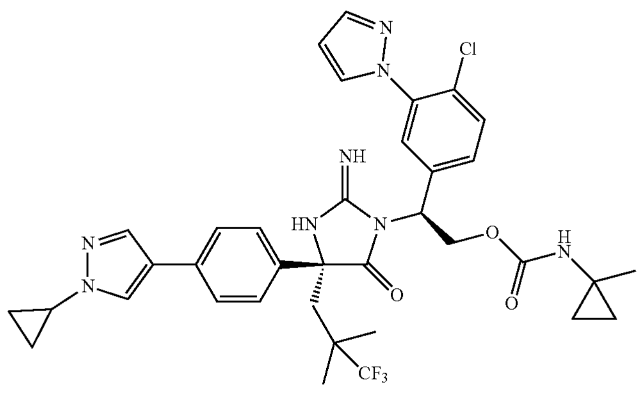 [SMILES: CC1(NC(=O)OC[C@H](c2ccc(Cl)c(-n3cccn3)c2)N2C(=N)N[C@](CC(C)(C)C(F)(F)F)(c3ccc(-c4cnn(C5CC5)c4)cc3)C2=O)CC1] | 2.3 | 27.768 |
| 264 | 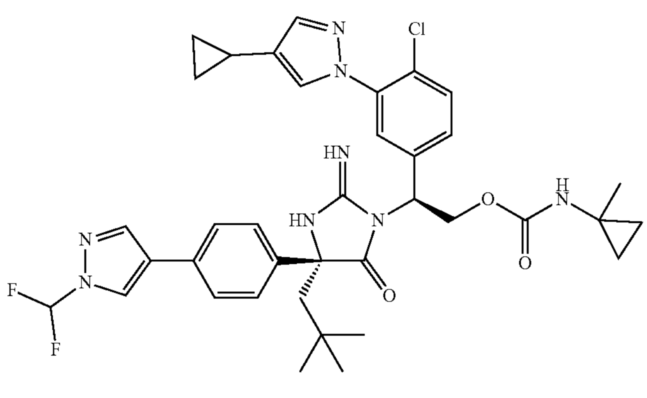 [SMILES: CC(C)(C)C[C@]1(c2ccc(-c3cnn(C(F)F)c3)cc2)NC(=N)N([C@H](COC(=O)NC2(C)CC2)c2ccc(Cl)c(-n3cc(C4CC4)cn3)c2)C1=O] | 3.9 | 227.58 |

TABLE 1-continued

| COMPD # | STRUCTURE | HIV PI IC$_{50}$ (nM) | MT4 EC$_{50}$ (nM) |
|---|---|---|---|
| 265 | 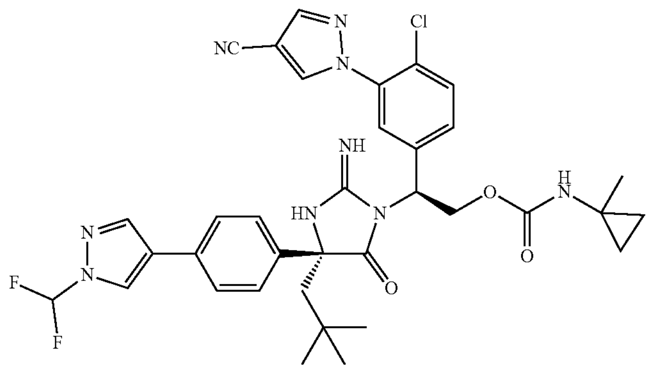 [SMILES: CC(C)(C)C[C@]1(c2ccc(-c3cnn(C(F)F)c3)cc2)NC(=N)N([C@H](COC(=O)NC2(C)CC2)c2ccc(Cl)c(-n3cc(C#N)cn3)c2)C1=O] | 1.7 | 17.873 |
| 266 | 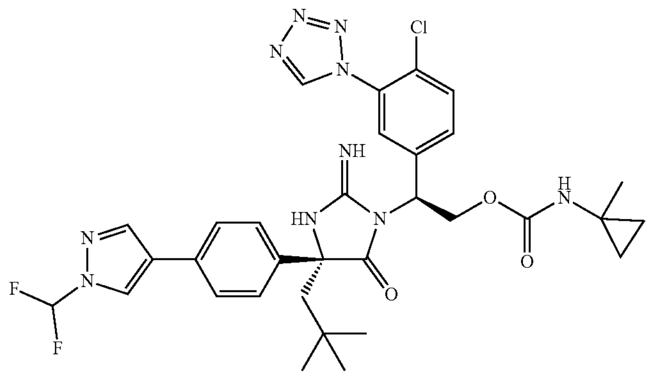 [SMILES: CC(C)(C)C[C@]1(c2ccc(-c3cnn(C(F)F)c3)cc2)NC(=N)N([C@H](COC(=O)NC2(C)CC2)c2ccc(Cl)c(-n3cnnn3)c2)C1=O] | 3.7 | 57.446 |
| 267 | 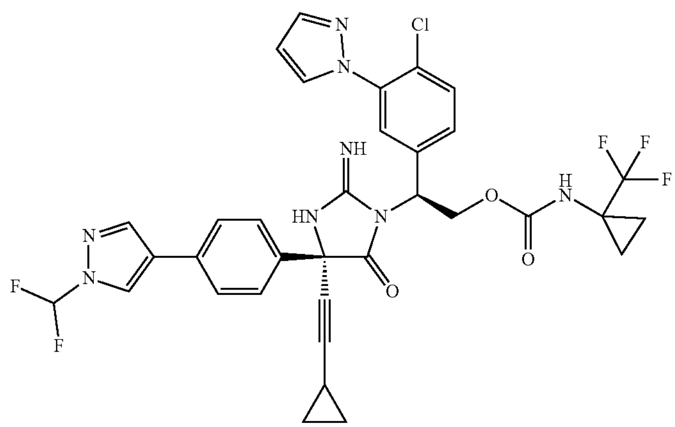 [SMILES: N=C1N[C@](C#CC2CC2)(c2ccc(-c3cnn(C(F)F)c3)cc2)C(=O)N1[C@H](COC(=O)NC1(C(F)(F)F)CC1)c1ccc(Cl)c(-n2cccn2)c1] | 9.1 | 243.03 |
| 268 | 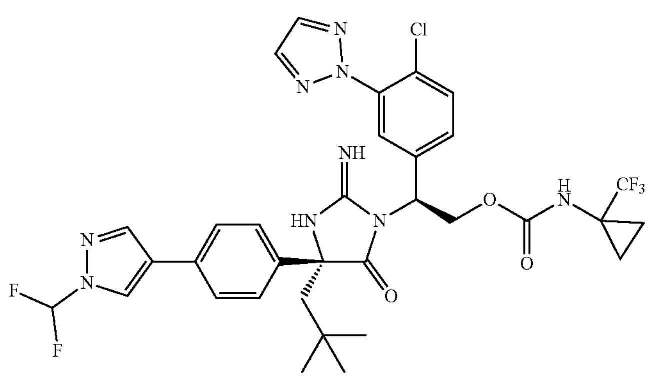 [SMILES: CC(C)(C)C[C@]1(c2ccc(-c3cnn(C(F)F)c3)cc2)NC(=N)N([C@H](COC(=O)NC2(C(F)(F)F)CC2)c2ccc(Cl)c(-n3nccn3)c2)C1=O] | 5.2 | 37.751 |

TABLE 1-continued

| COMPD # | STRUCTURE | HIV PI IC$_{50}$ (nM) | MT4 EC$_{50}$ (nM) |
|---|---|---|---|
| 269 | 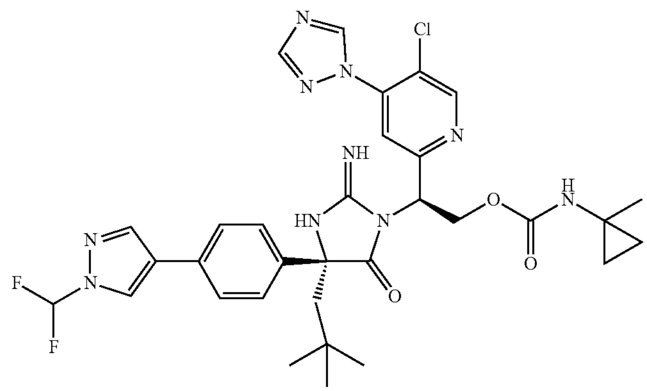 [SMILES: CC(C)(C)C[C@]1(c2ccc(-c3cnn(C(F)F)c3)cc2)NC(=N)N([C@H](COC(=O)NC2(C)CC2)c2cc(-n3cncn3)c(Cl)cn2)C1=O] | 3.4 | 62.351 |
| 270 | 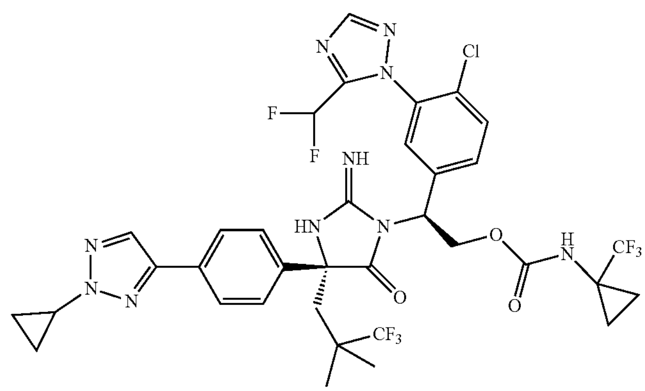 [SMILES: CC(C)(C[C@]1(c2ccc(-c3cnn(C4CC4)n3)cc2)NC(=N)N([C@H](COC(=O)NC2(C(F)(F)F)CC2)c2ccc(Cl)c(-n3ncnc3C(F)F)c2)C1=O)C(F)(F)F] | 2.9 | 19.136 |
| 381 | 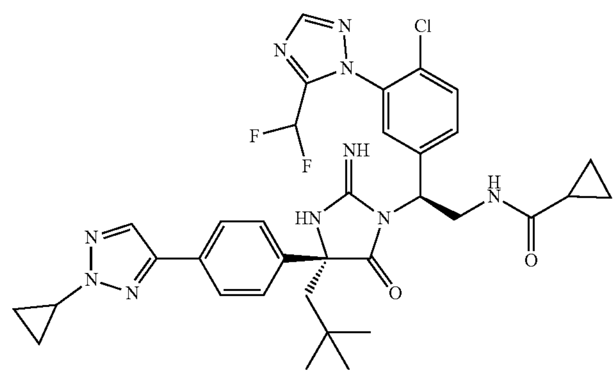 [SMILES: CC(C)(C)C[C@]1(c2ccc(-c3cnn(C4CC4)n3)cc2)NC(=N)N([C@H](CNC(=O)C2CC2)c2ccc(Cl)c(-n3ncnc3C(F)F)c2)C1=O] | 2.8 | 24.755 |
| 382 | 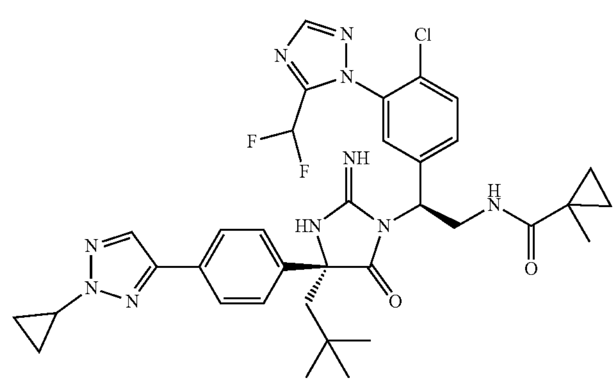 [SMILES: CC(C)(C)C[C@]1(c2ccc(-c3cnn(C4CC4)n3)cc2)NC(=N)N([C@H](CNC(=O)C2(C)CC2)c2ccc(Cl)c(-n3ncnc3C(F)F)c2)C1=O] | 3.4 | 36.506 |

TABLE 1-continued

| COMPD # | STRUCTURE | HIV PI IC$_{50}$ (nM) | MT4 EC$_{50}$ (nM) |
|---|---|---|---|
| 383 | 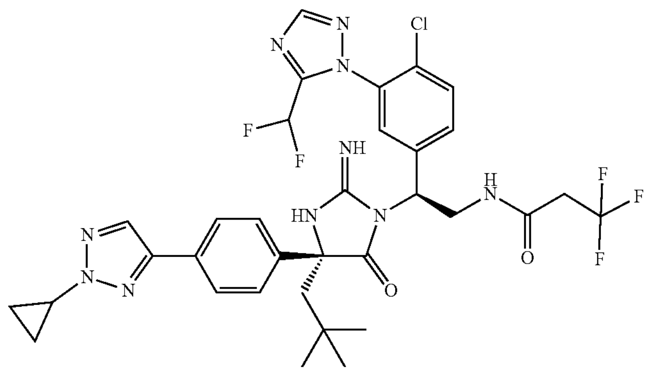 [SMILES: CC(C)(C)C[C@]1(c2ccc(-c3cnn(C4CC4)n3)cc2)NC(=N)N([C@H](CNC(=O)CC(F)(F)F)c2ccc(Cl)c(-n3ncnc3C(F)F)c2)C1=O] | 2.4 | 9.699 |
| 384 | 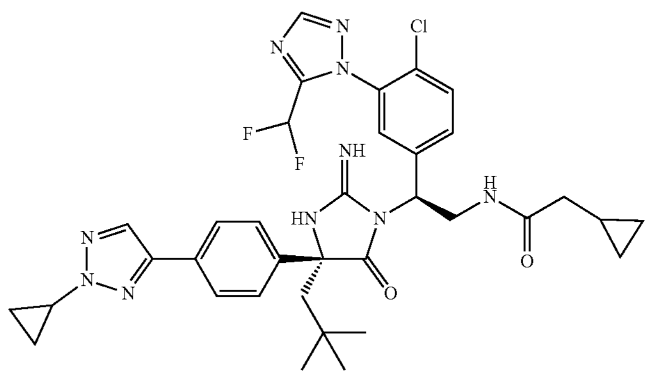 [SMILES: CC(C)(C)C[C@]1(c2ccc(-c3cnn(C4CC4)n3)cc2)NC(=N)N([C@H](CNC(=O)CC2CC2)c2ccc(Cl)c(-n3ncnc3C(F)F)c2)C1=O] | 2.6 | 18.024 |
| 385 | 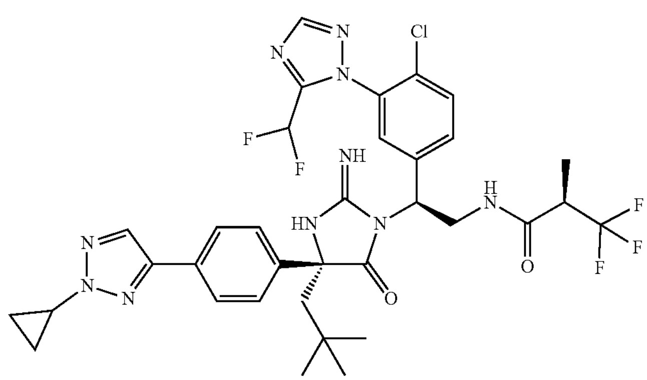 [SMILES: C[C@H](C(=O)NC[C@H](c1ccc(Cl)c(-n2ncnc2C(F)F)c1)N1C(=N)N[C@](CC(C)(C)C)(c2ccc(-c3cnn(C4CC4)n3)cc2)C1=O)C(F)(F)F] | 2.6 | 12.776 |
| 386 | 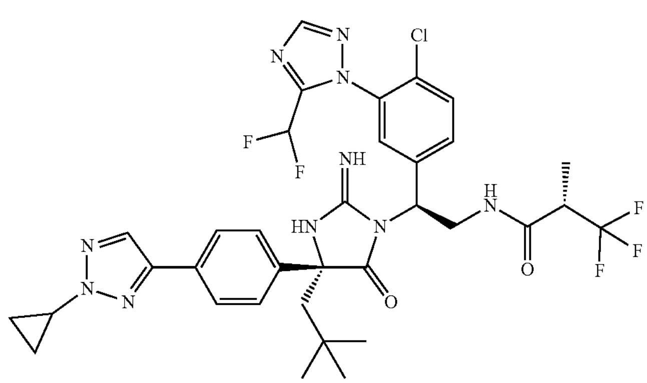 [SMILES: C[C@@H](C(=O)NC[C@H](c1ccc(Cl)c(-n2ncnc2C(F)F)c1)N1C(=N)N[C@](CC(C)(C)C)(c2ccc(-c3cnn(C4CC4)n3)cc2)C1=O)C(F)(F)F] | 2.8 | 23.421 |

TABLE 1-continued

| COMPD # | STRUCTURE | HIV PI IC$_{50}$ (nM) | MT4 EC$_{50}$ (nM) |
|---|---|---|---|
| 387 | 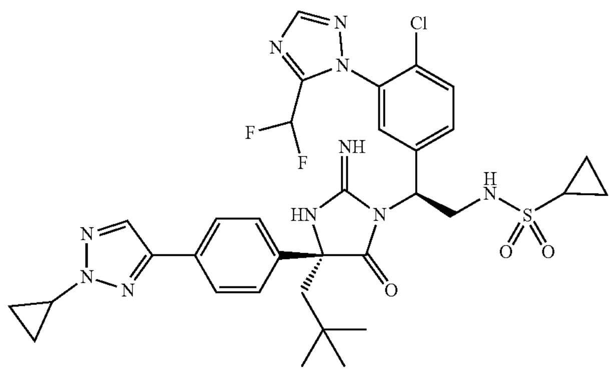 [SMILES: CC(C)(C)C[C@]1(c2ccc(-c3cnn(C4CC4)n3)cc2)NC(=N)N([C@H](CNS(=O)(=O)C2CC2)c2ccc(Cl)c(-n3ncnc3C(F)F)c2)C1=O] | 3.7 | 47.9 |
| 388 | 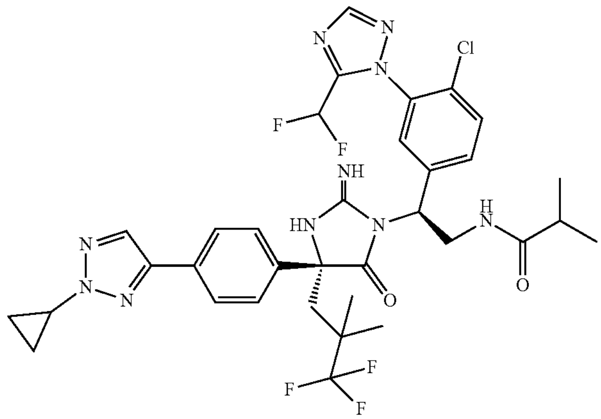 [SMILES: CC(C)C(=O)NC[C@H](c1ccc(Cl)c(-n2ncnc2C(F)F)c1)N1C(=N)N[C@](CC(C)(C)C(F)(F)F)(c2ccc(-c3cnn(C4CC4)n3)cc2)C1=O] | 2.8 | 16.879 |
| 389 | 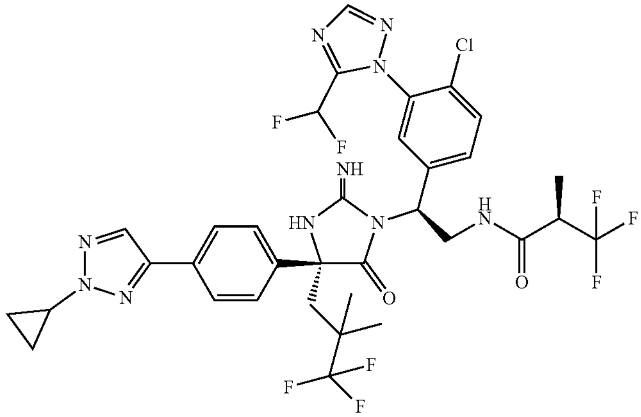 [SMILES: C[C@H](C(=O)NC[C@H](c1ccc(Cl)c(-n2ncnc2C(F)F)c1)N1C(=N)N[C@](CC(C)(C)C(F)(F)F)(c2ccc(-c3cnn(C4CC4)n3)cc2)C1=O)C(F)(F)F] | 2.8 | 12.163 |

TABLE 1-continued

| COMPD # | STRUCTURE | HIV PI IC$_{50}$ (nM) | MT4 EC$_{50}$ (nM) |
|---|---|---|---|
| 390 | 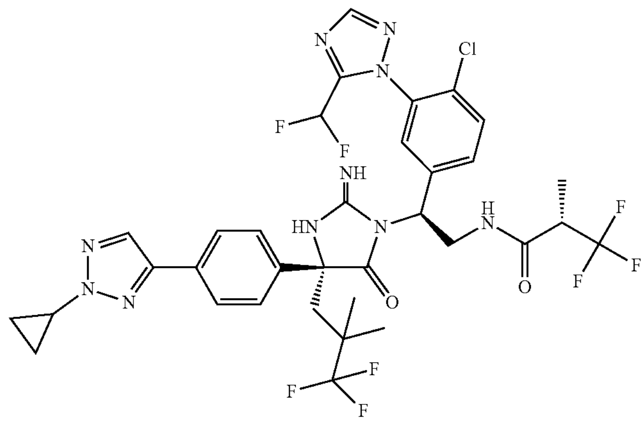 [SMILES: C[C@@H](C(=O)NC[C@H](c1ccc(Cl)c(-n2ncnc2C(F)F)c1)N1C(=N)N[C@](CC(C)(C)C(F)(F)F)(c2ccc(-c3cnn(C4CC4)n3)cc2)C1=O)C(F)(F)F] | 3.4 | 20.922 |
| 391 | 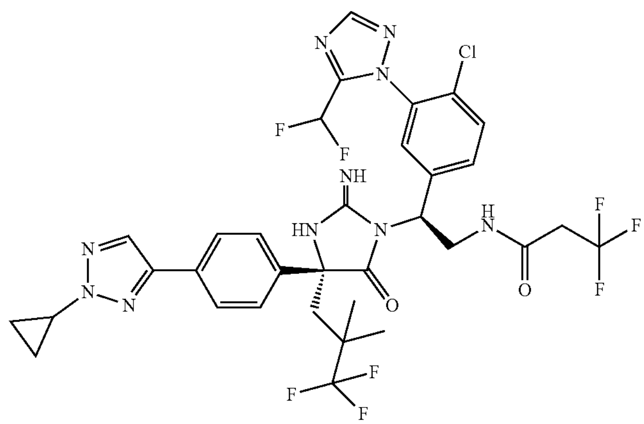 [SMILES: CC(C)(C[C@]1(c2ccc(-c3cnn(C4CC4)n3)cc2)NC(=N)N([C@H](CNC(=O)CC(F)(F)F)c2ccc(Cl)c(-n3ncnc3C(F)F)c2)C1=O)C(F)(F)F] | 3.3 | 12.477 |
| 271 | 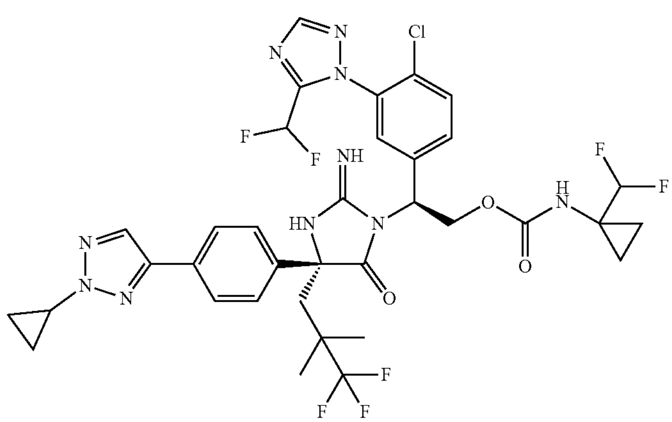 [SMILES: CC(C)(C[C@]1(c2ccc(-c3cnn(C4CC4)n3)cc2)NC(=N)N([C@H](COC(=O)NC2(C(F)F)CC2)c2ccc(Cl)c(-n3ncnc3C(F)F)c2)C1=O)C(F)(F)F] | 2.5 | 12.613 |

TABLE 1-continued

| COMPD # | STRUCTURE | HIV PI IC$_{50}$ (nM) | MT4 EC$_{50}$ (nM) |
|---|---|---|---|
| 392 | (structure) | 3.7 | 24.289 |
| 393 | (structure) | 2.5 | 27.039 |

Beta-Secretase (BACE) Inhibition Assay

Inhibitory potency against β-secretase (BACE) was measured using an enzymatic assay with a fluorogenic readout. 50 nM of recombinant human BACE-1 (R&D Systems) and test compound at one of various concentrations were added to a reaction buffer containing 20 mM sodium acetate at pH 4.8, with 0.06% Triton X-100, and 1% DMSO. After a 15-minute pre-incubation, the enzymatic reaction was initiated by the addition of the fluorogenic substrate Mca-SEVNLDAEFRK(Dnp)RR-NH2 (R&D Systems) (SEQ ID NO: 2) to a final concentration of 1.0 μM. The total volume of the assay solution was 100 μL. The reaction was measured over 10 minutes on a Tecan Infinite M1000 plate reader using an excitation wavelength of 320 nm and a detection wavelength of 405 nm. The slopes of the progress curves were the measure of reaction rates. Reaction rates were plotted as a function of inhibitor concentration, and the data were fit with a four-parameter logistic fit using Graphpad PRISM software to yield IC$_{50}$ values. A positive control compound used in this assay is a beta-secretase inhibitor IV (commercially available, CAS #797035-11-1) described as compound 3 in J Med Chem 2004, 47(26), 6447-6450, which showed an average IC$_{50}$ of 37 nM.

For a subset of the compounds disclosed herein, BACE inhibitory activity was determined. For compounds 32, 90, 113, 131, 146, 152, 155, 177, 185, 194, 195, 212, 218, 223, 236, 242, 244, 270, 271, 286, 311, 335, 348, 349, and 389, the corresponding BACE IC$_{50}$ values were all greater than 100,000 nM. Accordingly, the compounds are inactive in BACE and demonstrate selective inhibitors of HIV protease.

Resistance Profiling

Resistance testing was done by Monogram Biosciences using their proprietary PhenoSense HIV assay. This assay evaluates drug susceptibility by using a single replication cycle recombinant virus containing the protease (amino acids 1-99 plus p7/p1/p6 gag cleavage sites) and reverse transcriptase (amino acids 1-304) coding regions of HIV-1 from a patient blood sample. Fold changes in EC$_{50}$ were reported in Table 2.

TABLE 2

| | Fold change in EC$_{50}$ | | | | |
|---|---|---|---|---|---|
| Resistance Mutations | Atazanavir | Darunavir | Compound 155 | Compound 307 | Compound 146 |
| L10F M46I I47V I50V I54V G73S I84V L90M | 30.0 | >615 | 4.59 | 3.4 | 10 |
| L10I V32I L33F M46L I54L I84V L89V | 97.0 | >615 | 0.74 | 0.96 | 0.98 |
| L10I V32I IM46I 47V I50V I54L L90M | 36.0 | >615 | 4.45 | 4.47 | 4.31 |

TABLE 2-continued

| Resistance Mutations | Fold change in EC$_{50}$ | | | | |
|---|---|---|---|---|---|
| | Atazanavir | Darunavir | Compound 155 | Compound 307 | Compound 146 |
| L10F V32I M46I I47V I50V I54L I84V | 5.67 | 383 | 1.11 | 0.86 | 1.83 |
| L33F M46I I50V L76V | 1.91 | 37.0 | 1.52 | 2.1 | 1.49 |
| L10I M46I I50V | 1.99 | 11.0 | 1.79 | 3.39 | 3.05 |
| L10F M46L I54V V82A I84V | >101 | 9.02 | 1.11 | 1.4 | 1.8 |
| L10I V32I M46I I47V G48V I54M V82T L90M | 11.0 | 6.92 | 3.15 | 1.65 | 2.75 |
| L10I L33F/L G48V G73S V82A | >101 | 2.28 | 2.57 | 2.87 | 2.37 |
| L10V/L M46I I50L V82A | >101 | 1.96 | 8.43 | 6.4 | 6.47 |
| L10I L33F G48V I50L I54V/I V82A | 87.0 | 1.13 | 0.70 | 0.73 | 0.66 |
| D30N L33F N88D L90M | 5.27 | 0.87 | 6.74 | 3.8 | 5.88 |

What is claimed is:

1. A compound of the formula

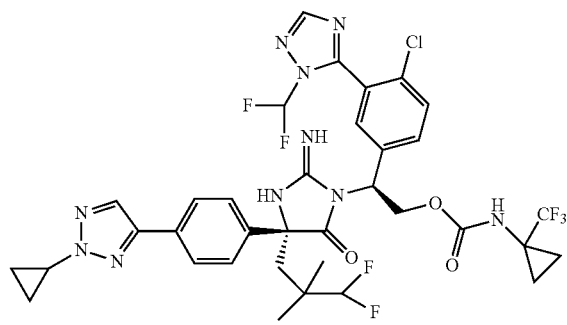 [SMILES: CC(C)(C[C@]1(c2ccc(-c3cnn(C4CC4)n3)cc2)NC(=N)N([C@H](COC(=O)NC2(C(F)(F)F)CC2)c2ccc(Cl)c(-c3ncnn3C(F)F)c2)C1=O)C(F)F]

or a pharmaceutically acceptable salt thereof.

2. A compound of the formula

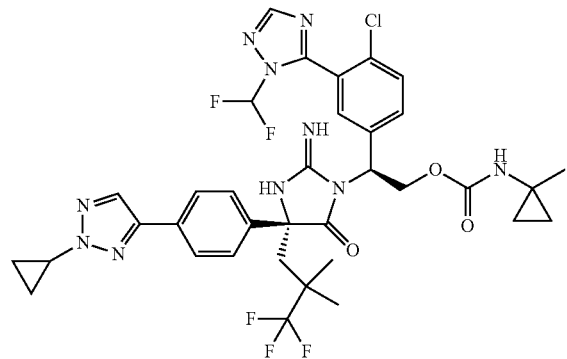 [SMILES: CC1(NC(=O)OC[C@H](c2ccc(Cl)c(-c3ncnn3C(F)F)c2)N2C(=N)N[C@](CC(C)(C)C(F)(F)F)(c3ccc(-c4cnn(C5CC5)n4)cc3)C2=O)CC1]

or a pharmaceutically acceptable salt thereof.

3. A compound of the formula

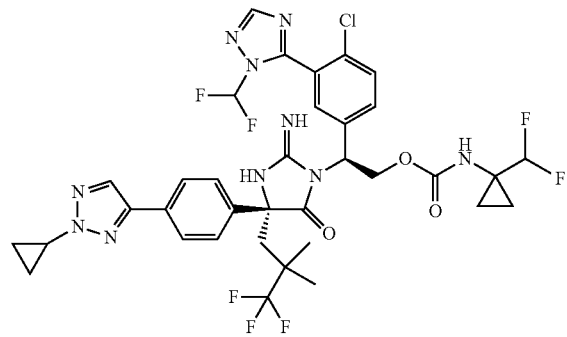 [SMILES: CC(C)(C[C@]1(c2ccc(-c3cnn(C4CC4)n3)cc2)NC(=N)N([C@H](COC(=O)NC2(C(F)F)CC2)c2ccc(Cl)c(-c3ncnn3C(F)F)c2)C1=O)C(F)(F)F]

or a pharmaceutically acceptable salt thereof.

4. A compound of the formula

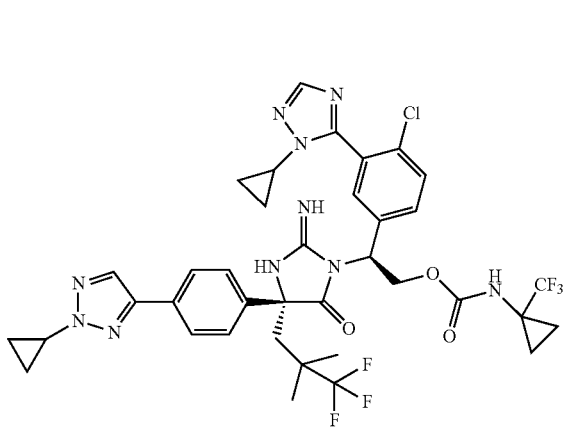 [SMILES: CC(C)(C[C@]1(c2ccc(-c3cnn(C4CC4)n3)cc2)NC(=N)N([C@H](COC(=O)NC2(C(F)(F)F)CC2)c2ccc(Cl)c(-c3ncnn3C3CC3)c2)C1=O)C(F)(F)F]

or a pharmaceutically acceptable salt thereof.

5. A compound of the formula

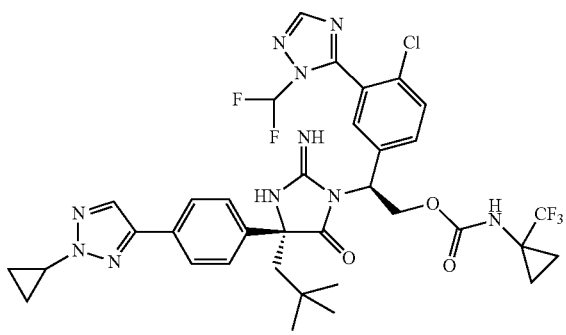 [SMILES: CC(C)(C)C[C@]1(c2ccc(-c3cnn(C4CC4)n3)cc2)NC(=N)N([C@H](COC(=O)NC2(C(F)(F)F)CC2)c2ccc(Cl)c(-c3ncnn3C(F)F)c2)C1=O]

or a pharmaceutically acceptable salt thereof.

* * * * *